US010793568B2

(12) United States Patent
Chao et al.

(10) Patent No.: US 10,793,568 B2
(45) Date of Patent: Oct. 6, 2020

(54) HORMONE RECEPTOR MODULATORS FOR TREATING METABOLIC CONDITIONS AND DISORDERS

(71) Applicant: ARDELYX, INC., Fremont, CA (US)

(72) Inventors: Jianhua Chao, Fremont, CA (US); Rakesh Jain, Fremont, CA (US); Lily Hu, Fremont, CA (US); Jason Gustaf Lewis, Fremont, CA (US); Helene Baribault, Fremont, CA (US); Jeremy Caldwell, Fremont, CA (US)

(73) Assignee: ARDELYX, INC., Fremont, CA (US)

( * ) Notice: Subject to any disclaimer, the term of this patent is extended or adjusted under 35 U.S.C. 154(b) by 0 days.

(21) Appl. No.: 16/327,791

(22) PCT Filed: Aug. 23, 2017

(86) PCT No.: PCT/US2017/048281

§ 371 (c)(1),
(2) Date: Feb. 22, 2019

(87) PCT Pub. No.: WO2018/039386

PCT Pub. Date: Mar. 1, 2018

(65) Prior Publication Data

US 2019/0233420 A1 Aug. 1, 2019

Related U.S. Application Data

(60) Provisional application No. 62/532,983, filed on Jul. 14, 2017, provisional application No. 62/378,625, filed on Aug. 23, 2016.

(51) Int. Cl.

| | |
|---|---|
| *C07D 471/08* | (2006.01) |
| *C07D 493/08* | (2006.01) |
| *C07D 413/14* | (2006.01) |
| *C07F 9/6558* | (2006.01) |
| *C07D 417/14* | (2006.01) |
| *C07D 413/12* | (2006.01) |

(52) U.S. Cl.

CPC ......... *C07D 471/08* (2013.01); *C07D 413/12* (2013.01); *C07D 413/14* (2013.01); *C07D 417/14* (2013.01); *C07D 493/08* (2013.01); *C07F 9/65583* (2013.01)

(58) Field of Classification Search

CPC .................................................. C07D 471/08

See application file for complete search history.

(56) References Cited

FOREIGN PATENT DOCUMENTS

| | | | | | |
|---|---|---|---|---|---|
| WO | 2012087519 | A1 | | 6/2012 | |
| WO | 2016127924 | A1 | | 8/2016 | |
| WO | WO-2018039386 | A1 | * | 3/2018 | ................ A61P 3/10 |
| WO | WO-2019007418 | A1 | * | 1/2019 | ................ A61P 1/00 |

OTHER PUBLICATIONS

Han, H. "Targeted Prodrug Design to Optimize Drug Delivery." AAPS Pharmsci. (2000), vol. 2 (1) article 6, pp. 1-11. (Year: 2000).*

Ettmayer, P., et al. "Lessons Learned from Marketed and Investigational Prodrugs." J. Med. Chem. (2004) 47(10), pp. 2393-2404. (Year: 2004).*

Testa, B. "Prodrug research: futile or fertile?" Biochem. Pharm. (2004) 68, pp. 2097-2106. (Year: 2004).*

Huang, W , et al., "FXR a metabolie regulator and cell protector", Cell Res 18, 1087-1095 (2008).

Matsubara, T , et al., "FXR signaling in the enterohepatic system", Mol Cell Endocrinol 368, 17-29 (2013).

Moschetta, A , "Deciphering the nuclear bile acid receptor FXR paradigm", Nucl Recept Signal 8, e005, 28 pages (2010).

Patent Cooperation Treaty , International Searching Authority, Search Report and Written Opinion for PCT/US2017/048281, 9 pages, dated Nov. 2, 2017.

Shaik, F , et al., "Role of farnesoid X receptor in inflammation and resolution", Inflamm Res 64, 9-20 (2015).

Vavassori, P , "The bile acid receptor FXR is a modulator of intestinal innate immunity", J Immunol 183, 6251-6261 (2009).

Verbeke, L , "The FXR agonist obeticholic acid prevents gut barrier dysfunction and bacterial translocation in cholestatic rats", Am J Pathol 185, 409-419 (2015).

* cited by examiner

*Primary Examiner* — John S Kenyon

(74) *Attorney, Agent, or Firm* — Viksnins Harris Padys Malen LLP

(57) ABSTRACT

The invention relates to activators of FXR useful in the treatment of autoimmune disorders, liver disease, intestinal disease, kidney disease, cancer, and other diseases in which FXR plays a role, having the Formula (I): (I), wherein $L_1$, A, $X_1$, $X_2$, $R^1$, $R^2$, and $R^3$ are described herein.

(I)

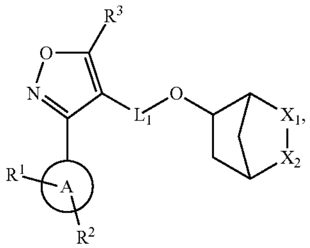

1 Claim, 6 Drawing Sheets

Specification includes a Sequence Listing.

SEQUENCE LISTING

```
<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Artificial Polypeptide
```

-continued
```
<400> SEQUENCE: 1
Leu Lys Glu Lys His Lys Ile Leu His Arg Leu Leu Gln Asp Ser Ser
1               5                   10                  15
Ser Pro Val
```

HORMONE RECEPTOR MODULATORS FOR TREATING METABOLIC CONDITIONS AND DISORDERS

CROSS-REFERENCE TO RELATED APPLICATION(S)

This application is a 35 U.S.C § 371 application of International Application No. PCT/US2017/048281, filed on Aug. 23, 2017, which claims priority to U.S. Provisional Application No. 62/532,983, filed Jul. 14, 2017 and U.S. Provisional Application No. 62/378,625, filed Aug. 23, 2016. The contents of each of these applications are incorporated by reference herein.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ARDE_024_02WO_SeqList.txt, date recorded: Aug. 23, 2017, file size: 4 kilobyte).

FIELD OF INVENTION

The present invention is directed to modulators of a nuclear hormone receptor, farnesoid X receptor (FXR), useful in the treatment of diseases or disorders associated with FXR proteins. Specifically, the invention is related to compounds and compositions which modulate FXR, methods of treating diseases or disorders associated with FXR, and methods of synthesis of these compounds.

BACKGROUND OF THE INVENTION

FXR is a ligand-activated transcription factor. Upon binding of a ligand. FXR either binds to DNA at the FXR response elements (FXREs) as a monomer, or forms a heterodimer with retinoid X receptor (RXR) and then binds to FXREs, regulating the transcription of a variety of target genes. To date, more than 40 FXR target genes have been identified that are involved in a wide range of physiological functions including bile acid homeostasis (i.e., BACS, BAAT, BSEP, FGF15/19, etc.), cholesterol and lipoprotein metabolism (i.e., Apolipoprotein C-I, II, IV, Apolipoprotein E, MDR3, Human complement C3, ApoA-1, hepatic lipase, SREPB-1c), glucose metabolism (i.e., PEPCK, GSK3, AKR1B7, GLUT4, G6Pase), and xenobiotics metabolism (i.e., GSTα3, GSTα4, GSTμ1, GSTμ3, SULT1A1, SULT1A2). In addition to the regulation of metabolic related genes, recent results have identified FXR as a regulator of cellular inflammatory and immune responses. Activation of FXR can provide anti-inflammatory effects by negative regulation of nuclear factor κB (NFκB) pathway, reducing the expression of NFκB and the many pro-inflammatory cytokines associated with this pathway (Matsubara, T, et al., "FXR signaling in the enterohepatic system," *Mol. Cell Endocrinol.* 2013, 368, 17-29; Moschetta, A., "Deciphering the nuclear bile acid receptor FXR paradigm," *Nucl. Recept. Signal.,* 2010, 8, e005; Huang, W., et al., "FXR: a metabolic regulator and cell protector," *Cell Res.,* 2008, 1087-1095).

FXR plays a key role in the synthesis, transport and metabolism of bile acids (BAs) and the many physiological and pathophysiological conditions that involve BAs. In the liver, activation of FXR has been shown to lead to the increased expression of short heterodimer partner (SHP), which in turn inactivates liver receptor homolog-1 (LRH-1) and inhibits the cholesterol 7-alpha-hydroxylase (CYP7A1), the rate-limiting enzyme in the first step of biosynthesis of primary bile acids from cholesterol, thereby reduces the production of bile acids. Activation of FXR in the liver has also been shown to downregulate transporters like Na-taurocholate co-transporting polypeptide (NTCP) and organic anion-transporting peptides (OATPs) preventing the uptake of bile acids to liver. The accumulation of BAs in the liver plays a pivotal role in cholestasis-associated liver damage, pharmacological activation of FXR by synthetic ligands can provide therapeutic intervention.

FXR has also been shown to play an important role in the inflammation control of various liver and intestinal diseases (Shaik, F. B., et al., "Role of farnesoid X receptor in inflammation and resolution." *Inflamm. Res.* 2015, 64, 9-20). Activation of FXR has been shown to repress the NFκB pathway, a prototypical proinflammatory signaling pathway, and inhibit the expression of key cytokines such as TNFα, IL-1β, and IL-6. In the colon of FXR knockout mice, increased expression of both proinflammatory cytokines (e.g., TNFα, IL-1β, IFNγ) and profibrotic genes (i.e., Collagen α1, TIMP-1, and αSMA) has been observed, indicative of dysregulation in intestinal immunity and tissue remodeling. Activation of FXR with FXR activators in the TNBS induced murine inflammatory bowel disease model has been shown to inhibit the above cytokines and provide protection against inflammation and fibrosis, subsequently against the development of colitis (Vavassori, P., "The bile acid receptor FXR is a modulator of intestinal innate immunity," *J. Immunol.* 2009, 183, 6251-6261). Moreover, treatment with an FXR agonist in a rat model of cholestatic liver injury (bile-duct ligation) reduced NK cells and INFγ expression, leading to reduction in intestinal inflammation, reduction in bacterial translocation, and overall improvement in gut barrier function (Verbeke, L., "The FXR agonist obeticholic acid prevents gut barrier dysfunction and bacterial translocation in cholestatic rats," *Am. J. Pathol.* 2015, 185, 409-419).

Activation of FXR with small molecule activators has the potential to be a treatment for a range of diseases including bile acid related disorders, metabolic syndrome, type-2-diabetes, hyperlipidemia, hypertriglyceridemia, primary biliary cirrhosis (PBC), fatty liver disease, nonalcoholic steatohepatitis (NASH), inflammatory autoimmune diseases, Crohn's disease, multiple sclerosis, atherosclerosis, hepatic and colon cancers, and other disorders. However, known FXR activators have demonstrated toxicities, treatment limiting adverse effects, and other issues. For these reasons, there remains a need for novel and potent small molecule FXR activators.

SUMMARY OF THE INVENTION

In an aspect of the invention, there is provided a compound of Formula I:

(I)

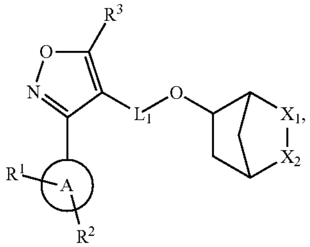

or a salt thereof, wherein:

one of $X_1$ or $X_2$ is $NR_x$ or $N^+(O^-)R_x$ and the other is $CHR_y$ or C(O);

$R_x$ is

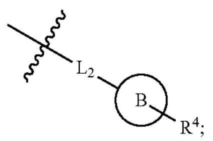

$R_y$ is H, alkyl, cycloalkyl or cycloalkylalkyl wherein said alkyl, cycloalkyl and cycloalkylalkyl are optionally substituted with halogen or alkoxy;

$L_1$ is $-(CH_2)_m(C{=}O)-$ or $-(CH_2)_p-$;

$L_2$ is a bond or $-S(O)_2-$;

A is cycloalkyl, aryl, heterocycloalkyl or heteroaryl, wherein the cycloalkyl, aryl, heterocycloalkyl, or heteroaryl is optionally substituted with one or more $R^7$;

B is aryl or heteroaryl, wherein the aryl or heteroaryl is optionally substituted with one or more $R^5$;

$R^1$ and $R^2$ are each independently H, alkyl, alkoxy, haloalkyl, haloalkoxy, halogen, cycloalkyl, or CN, wherein the cycloalkyl is optionally substituted with one or more $R^9$;

or when A is cycloalkyl or heterocycloalkyl, $R^1$ and $R^2$ together when attached to the same carbon atom form a spirocycloalkyl ring optionally substituted with one or more $R^8$; or when A is cycloalkyl or heterocycloalkyl, $R^1$ and $R^2$ together when attached to the same atom form a spiroheterocycloalkyl ring optionally substituted with one or more $R^8$; or $R^1$ and $R^2$ when on adjacent atoms together with the atoms to which they are attached form a cycloalkyl ring optionally substituted with one or more $R^8$; or $R^1$ and $R^2$ when on adjacent atoms together with the atoms to which they are attached form a heterocycloalkyl ring optionally substituted with one or more $R^8$; or $R^1$ and $R^2$ when on adjacent atoms together with the atoms to which they are attached form an aryl ring optionally substituted with one or more $R^8$; or $R^1$ and $R^2$ when on adjacent atoms together with the atoms to which they are attached form a heteroaryl ring optionally substituted with one or more $R^8$; or when A is cycloalkyl or heterocycloalkyl, $R^1$ and $R^2$ when on non-adjacent atoms, together with the atoms to which they are attached form a cycloalkyl ring optionally substituted with one or more $R^8$; or when cycloalkyl or heterocycloalkyl, $R^1$ and $R^2$ when on non-adjacent atoms, together with the atoms to which they are attached form a heterocycloalkyl ring optionally substituted with one or more $R^8$;

$R^3$ is alkyl, alkoxy, haloalkyl, haloalkoxy, hydroxyalkyl, or cycloalkyl optionally substituted with one or more substituents each independently selected from the group consisting of halogen, alkyl, alkoxy, haloalkyl, haloalkoxy, and —OH;

$R^4$ is $COOR^{6a}$, $-(CH_2)_n-COOR^{6a}$, $CONR^{6b}OH$, $CONR^{6b}R^{6c}$, $CONH(CH_2)_nCOOR^{6a}$, $CONH(CH_2)_nR^{6a}$, $-(CH_2)_nCONH(CH_2)_nR^{6a}$, $CONR^{6b}SO_2R^{6d}$, $CONR^{6b}SO_2(CH_2)_nR^{6d}$, $-(CH_2)_n-CONR^{6b}SO_2R^{6d}$, $CONR^{6b}SO_2(CH_2)_nN(CO)R^{6d}$, $CONH(CH_2)_nSO_2R^{6e}$, $COR^{6f}$, $(CH_2)_nPO(OR^{6g})_2$, $CONR^{6b}(CH_2)_nPO(OR^{6g})_2$, $CONR^{6b}SO_2(CH_2)_nN^+(R^{6f})_3$, $COO(CH_2)_nPO(OR^{6g})_2$, $SO_2NR^{6b}(CH_2)_nCOOR^{6a}$, $SO_2R^{6e}$, CN, $-(CH_2)-NR^{6b}C(O)R^{6c}$, $-(CH_2)_n-N(OH)-C(O)R^{6c}$, oxo, alkyl, cycloalkyl, $-(CH_2)_n$-cycloalkyl, heterocycloalkyl, $-(CH_2)_n$-heterocycloalkyl, heteroaryl or $-(CH_2)_n$-heteroaryl; wherein said alkyl, cycloalkyl, $-(CH_2)_n$-cycloalkyl, heterocycloalkyl, $-(CH_2)_n$-heterocycloalkyl, heteroaryl and $-(CH_2)_n$-heteroaryl are optionally substituted with $COOR^{6a}$, $-(CH_2)_n-COOR^{6a}$, $CONR^{6b}OH$, $CONR^{6b}R^{6c}$, $CONH(CH_2)_nCOOR^{6a}$, $CONH(CH_2)_nR^{6a}$, $-(CH_2)_nCONH(CH_2)_nR^{6a}$, $CONR^{6b}SO_2R^{6d}$, $CONR^{6b}SO_2(CH_2)_nR^{6d}$, $-(CH_2)_n-CONR^{6b}SO_2R^{6d}$, $CONR^{6b}SO_2(CH_2)_nN(CO)R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, CN, $-(CH_2)_n-NR^{6b}C(O)R^6$, or $-(CH_2)_n-N(OH)-C(O)R^{6c}$;

each $R^5$ is independently at each occurrence halogen, alkyl, haloalkyl, alkoxy, haloalkoxy, CN, cycloalkyl, spiroheterocycloalkyl, —O-cycloalkyl, —O-heterocycloalkyl, aryl, heterocycloalkyl, or heteroaryl wherein the cycloalkyl, aryl, heterocycloalkyl or heteroaryl are optionally substituted with one or more substituents each independently selected from the group consisting of halogen, alkyl, haloalkyl, alkoxy, and haloalkoxy;

$R^{6a}$ is H, alkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, $NR^{6b}R^{6c}$, $SO_2NR^{6b}R^{6c}$, and —OH;

$R^{6b}$ and $R^{6c}$ are each independently H, alkyl, haloalkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6d}$ is alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, COOH, alkyl, haloalkyl, alkoxy, haloalkoxy, alkoxyalkoxy, —O—CO-alkyl, —O—COcycloalkyl, —O—CO-alkyl-COOH, $NR^{6b}R^{6c}$, $NR^{6f}$CO-alkyl, $NR^{6f}$CO-alkoxy, cycloalkyl, heterocycloalkyl and —OH;

$R^{6e}$ is —OH, alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6f}$ is alkyl or haloalkyl;

$R^{6g}$ is H or alkyl optionally substituted with —O—CO-alkyl;

each $R^7$ is independently at each occurrence OH, alkyl, alkoxy, haloalkyl, haloalkoxy, halogen, or CN;

each $R^8$ is independently at each occurrence alkyl, alkoxy, haloalkyl, haloalkoxy, halogen, or —OH;

each $R^9$ is independently at each occurrence alkyl, alkoxy, haloalkyl, haloalkoxy, halogen, or —OH;

m is 0, 1, or 2;

n is 1, 2, 3, 4, 5, 6, 7, 8, 9, 10, 11, or 12; and p is 1 or 2.

Another aspect of the invention relates to a method of treating a disease or disorder in which FXR plays a role. The method comprises administering to a patient in need of a treatment for diseases or disorders in which FXR plays a role an effective amount of a compound of Formula (I), or a pharmaceutically acceptable salt, hydrate, solvate, prodrug, stereoisomer, or tautomer thereof.

Another aspect of the invention is directed to a method of modulating FXR. The method involves administering to a patient in need thereof an effective amount of a compound of Formula (I), or a pharmaceutically acceptable salt, hydrate, solvate, prodrug, stereoisomer, or tautomer thereof.

Another aspect of the invention is directed to a method of activating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a liver disease. The method comprises administering to a patient in need of a treatment for a liver disease an effective amount of a compound of Formula (I), or a pharmaceutically acceptable salt, hydrate, solvate, prodrug, stereoisomer, or tautomer thereof.

Another aspect of the invention relates to a method of treating an intestinal disease. The method comprises administering to a patient in need of a treatment for an intestinal disease an effective amount of a compound of Formula (I), or a pharmaceutically acceptable salt, hydrate, solvate, prodrug, stereoisomer, or tautomer thereof.

Another aspect of the invention relates to a method of treating a kidney disease. The method comprises administering to a patient in need of a treatment for a kidney disease an effective amount of a compound of Formula (I), or a pharmaceutically acceptable salt, hydrate, solvate, prodrug, stereoisomer, or tautomer thereof.

Another aspect of the invention relates to a method of treating an autoimmune disorder. The method comprises administering to a patient in need of a treatment for an autoimmune disorder an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need of a treatment for cancer an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with activating FXR.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease in which FXR plays a role.

Another aspect of the present invention relates to a compound of Formula (I), or a pharmaceutically acceptable salt, hydrate, solvate, prodrug, stereoisomer, or tautomer thereof, for use in the manufacture of a medicament for treating a liver disease.

Another aspect of the present invention relates to a compound of Formula (I), or a pharmaceutically acceptable salt, hydrate, solvate, prodrug, stereoisomer, or tautomer thereof, for use in the manufacture of a medicament for treating an intestinal disease.

Another aspect of the present invention relates to a compound of Formula (I), or a pharmaceutically acceptable salt, hydrate, solvate, prodrug, stereoisomer, or tautomer thereof, for use in the manufacture of a medicament for treating a kidney disease.

Another aspect of the present invention relates to a compound of Formula (I), or a pharmaceutically acceptable salt, hydrate, solvate, prodrug, stereoisomer, or tautomer thereof, for use in the manufacture of a medicament for treating an autoimmune disorder.

Another aspect of the present invention relates to a compound of Formula (I), or a pharmaceutically acceptable salt, hydrate, solvate, prodrug, stereoisomer, or tautomer thereof, for use in the manufacture of a medicament for treating cancer.

Another aspect of the present invention relates to a compound of Formula (I), or a pharmaceutically acceptable salt, hydrate, solvate, prodrug, stereoisomer, or tautomer thereof, for use in the treatment of a disease associated with activating FXR.

Another aspect of the present invention relates to a compound of Formula (I), or a pharmaceutically acceptable salt, hydrate, solvate, prodrug, stereoisomer, or tautomer thereof, for use in the treatment of a disease in which FXR plays a role.

Another aspect of the present invention relates to a compound of Formula (I), or a pharmaceutically acceptable salt, hydrate, solvate, prodrug, stereoisomer, or tautomer thereof, for use in the treatment of a liver disease.

Another aspect of the present invention relates to a compound of Formula (I), or a pharmaceutically acceptable salt, hydrate, solvate, prodrug, stereoisomer, or tautomer thereof, for use in the treatment of an intestinal disease.

Another aspect of the present invention relates to a compound of Formula (I), or a pharmaceutically acceptable salt, hydrate, solvate, prodrug, stereoisomer, or tautomer thereof, for use in the treatment of a kidney disease.

Another aspect of the present invention relates to a compound of Formula (I), or a pharmaceutically acceptable salt, hydrate, solvate, prodrug, stereoisomer, or tautomer thereof, for use in the treatment of an autoimmune disorder.

Another aspect of the present invention relates to a compound of Formula (I), or a pharmaceutically acceptable salt, hydrate, solvate, prodrug, stereoisomer, or tautomer thereof, for use in the treatment of cancer.

The present invention further provides methods of treating a disease or disorder associated with modulation of FXR including, but not limited to, liver diseases, intestinal diseases, kidney disease, autoimmune disorders, or cancer, comprising administering to a patient suffering from at least one of said diseases or disorder a compound of Formula (I), or a pharmaceutically acceptable salt, hydrate, solvate, prodrug, stereoisomer, or tautomer thereof.

The present invention provides activators of FXR that are therapeutic agents in the treatment of diseases, such as liver diseases, intestinal diseases, kidney disease, autoimmune disorders, and cancer. Ultimately the present invention provides the medical community with a novel pharmacological strategy for the treatment of diseases and disorders associated with the modulation of FXR.

DETAILED DESCRIPTION OF THE INVENTION

Figure 1:
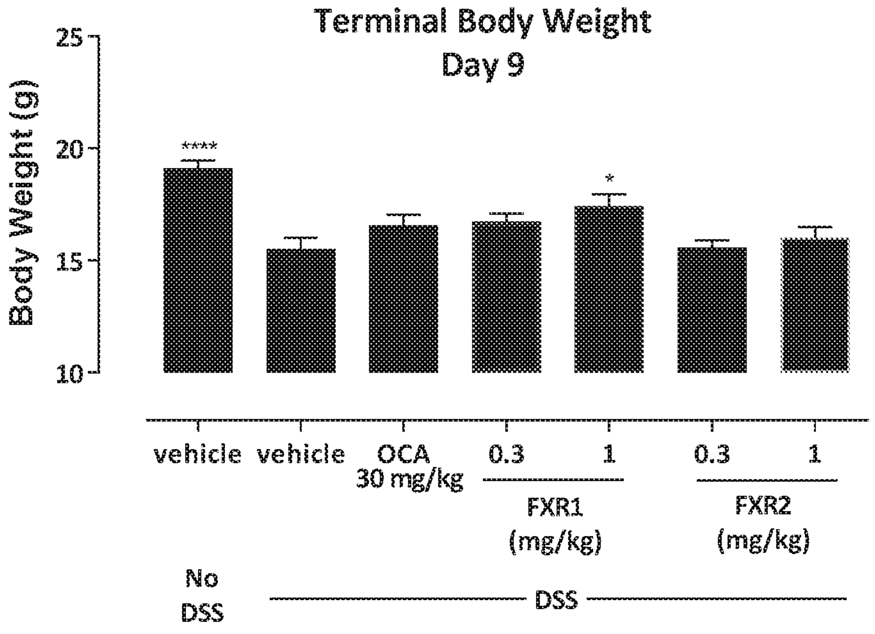
FIG. 1: Body weight of DSS colitis model mice measured on Day 9 immediately prior to terminal necropsy. Mice were administered vehicle with and without DSS and FXR agonist compounds OCA, FXR1 and FXR2.

The present invention relates to compounds and compositions that are capable of modulating the activity of FXR. The invention features methods of treating, preventing or ameliorating a disease or disorder in which FXR plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of FXR dependent diseases and disorders by increasing the activity of nuclear receptor FXR. Activation or modulation of FXR provides a novel approach to the treatment, prevention, or amelioration of diseases including, but not limited to, liver diseases, intestinal diseases, kidney diseases, autoimmune disorders, and cancer.

In a first aspect of the invention, the compounds of Formula (I) are described:

(I)

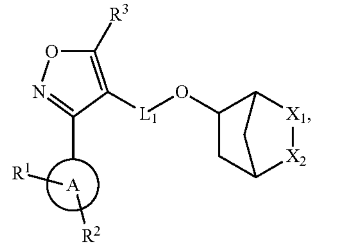

and pharmaceutically acceptable salts, hydrates, solvates, prodrugs, stereoisomers, and tautomers thereof, wherein $L_1$, A, $X_1$, $X_2$, $R^1$, $R^2$, and $R^3$ are as described herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used herein to refer to one or more than one (e.g., to at least one) of the grammatical object of the article. By way of example, "an element" means one element or more than one element.

The term "and/or" is used herein to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —$CH_2$CN, —O—($C_1$-$C_6$) alkyl, ($C_1$-$C_6$) alkyl, ($C_1$-$C_6$) alkenyl, ($C_1$-$C_6$) alkynyl, ($C_1$-$C_6$) hydroxyalkyl, ($C_1$-$C_6$)alkoxy, ($C_1$-$C_6$) haloalkyl, ($C_1$-$C_6$)haloalkoxy, ($C_3$-$C_7$) cycloalkyl, aryl, heterocycloalkyl, heteroaryl, —O—($C_2$-$C_6$) alkenyl, —O—($C_2$-$C_6$) alkynyl, ($C_2$-$C_6$) alkenyl, ($C_2$-$C_6$) alkynyl, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)$_2$NH($C_1$-$C_6$) alkyl, and S(O)$_2$N(($C_1$-$C_6$) alkyl)$_2$. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, NH(($C_1$-$C_6$) alkyl), N(($C_1$-$C_6$) alkyl)$_2$, —$S(O)_2$—($C_1$-$C_6$) alkyl, —$S(O)_2$NH($C_1$-$C_6$) alkyl, and —$S(O)_2$N(($C_1$-$C_6$) alkyl)$_2$. Furthermore when containing two fused rings an aryl group herein defined may be fused to an unsaturated or partially saturated ring, or fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from the group consisting of N, O, and S, the remaining ring atoms being C. Heteroaryl as herein defined also means a bicyclic heteroaromatic group wherein the heteroatom is selected from the group consisting of N, O, and S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may be fused to an unsaturated or partially saturated ring containing a heteroatom selected from N, O and S; or fused with a fully saturated ring containing a heteroatom selected from N, O and S. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

"Alkyl", either alone or in combination with other groups (e.g, alkoxy, haloalkyl and the like) refers to a straight or branched chain saturated, unsaturated (fully or partially) hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl. In an embodiment, "alkyl" is fully saturated.

"Alkoxy" refers to a straight or branched chain saturated or unsaturated (fully or partially) hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups. In an embodiment, "alkoxy" is fully saturated.

"Alkoxyalkoxy" refers to an alkoxy group as defined herein which is substituted with an alkoxy group e.g., —O(alkyl)-O-(alkyl). Examples of alkoxyalkoxy groups include without limitation, methoxymethoxy, ethoxyethoxy, propoxymethoxy, or ethoxymethoxy.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkynyl groups include ethynyl, propanyl, n-butynyl, iso-butynyl, pentynyl, or hexynyl. An alkynyl group can be unsubstituted or substituted.

"Cycloalkyl" or "carbocyclyl" means monocyclic or polycyclic saturated or unsaturated (fully or partially) non-aromatic carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane). In an embodiment, "cycloalkyl" is fully saturated.

"Heterocyclyl" or "heterocycloalkyl" monocyclic or polycyclic rings containing carbon and heteroatoms taken from oxygen, nitrogen, or sulfur and wherein there is not delocalized $\pi$ electrons (aromaticity) shared among the ring carbon or heteroatoms. In an embodiment, heterocycloalkyl comprises one or two 4- to 7-membered rings and 1-4 heteroatoms selected from the group consisting of N, O and S, or heteroaryl. The heterocycloalkyl ring structure may be substituted by one or more substituents. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl. In an embodiment, "heterocycle" or "heterocycloalkyl" is fully saturated.

The term "hydroxyalkyl" means an alkyl group as defined above, where the alkyl group is substituted with one or more —OH groups. Examples of hydroxyalkyl groups include HO—$CH_2$—, HO—$CH_2$—$CH_2$— and $CH_3$—CH(OH)—. In an embodiment, "hydroxyalkyl" is fully saturated.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc. In an embodiment, "haloalkyl" is fully saturated.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc. In an embodiment, "haloalkoxy" is fully saturated.

The term "cyano" as used herein means a substituent having a carbon atom joined to a nitrogen atom by a triple bond, e.g., C≡N.

The term "oxo" as used herein refers to an "=O" group.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom. In an embodiment, "spirocycloalkyl" or "spirocyclyl" is fully saturated.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl). In an embodiment, "spiroheterocycloalkyl" or "spiroheterocyclyl is fully saturated.

As defined herein, "GW4064" is an FXR agonist compound having the following structure.

GW4064

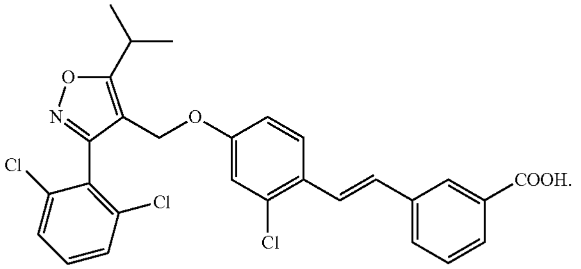

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The invention also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used herein, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used herein to mean, and is used interchangeably with, the terms disease, condition, or illness, unless otherwise indicated.

The term "administer". "administering", or "administration" as used herein refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used herein, means a compound which is convertible in vivo by metabolic means (e.g., by hydrolysis) to a disclosed compound.

The term "autoimmune disease" includes, but is not limited to, the following autoimmune diseases: Amyotrophic Lateral Sclerosis (ALS). Autoimmune Atherosclerosis, Autoimmune Diabetes Insipidus, Autoimmune Gastritis, Autoimmune Hepatitis, Autoimmune Interstitial Cystitis, Autoimmune Uveitis, Autoimmune Vasculitis, Behcet's Disease, Celiac Disease, Chronic Fatigue Syndrome, Crohn's Disease, chronic active hepatitis, Diabetes Mellitus, Multiple Sclerosis, PBC, Primary Biliary Cirrhosis, Primary Glomerulonephritis, Primary Sclerosing Cholangitis, Psoriasis, Psoriatic Arthritis, Scleroderma, Sjogren's Syndrome, Systemic Lupus Erythematosus, Ulcerative Colitis, and Vasculitis.

The term "kidney disease" includes, but is not limited to the following kidney diseases: fibrotic renal disease and diabetic nephrophathy.

The term "liver disease" includes, but is not limited to, the following liver diseases: primary biliary cirrhosis (PBC), primary sclerosing cholangitis (PSC), non-alcoholic fatty liver disease (NAFLD), non-alcoholic steatohepatitis (NASH), alcoholic liver disease, intra- and extra-cholestasis, portal vein hypertension (PAH), obesity and Type 2 Diabetes.

The term "intestinal disease" includes, but is not limited to the following intestinal diseases: inflammatory bowel disease, Crohn's disease, ulcerative colitis, proctitis, pouchitis, Celiac's disease and bile acid diarrhea.

The term "cancer" includes, but is not limited to, the following cancers: hepatocellular carcinoma, hepatocellular adenoma, cholangiocarcinoma, colorectal cancer, colorectal adenoma, ileal adenoma, renal cancer, oesophageal cancer, gastric cancer, gastric carcinoma, colon carcinoma, gastrointestinal stromal carcinoma, bile duct carcinoma, renal carcinoma, breast cancer, and Barett's esophagus, and combinations thereof.

The present invention relates to compounds or pharmaceutically acceptable salts, hydrates, solvates, prodrugs, stereoisomers, or tautomers thereof, capable of activating FXR, which are useful for the treatment of diseases and disorders associated with modulation of a FXR protein or receptor. The invention further relates to compounds, or pharmaceutically acceptable salts, hydrates, solvates, prodrugs, stereoisomers, or tautomers thereof, which are useful for activating FXR.

The present invention relates to compounds or pharmaceutically acceptable salts, hydrates, solvates, prodrugs, stereoisomers, or tautomers thereof, capable of activating FXR, which are useful for the treatment of diseases and disorders associated with modulation of a FXR protein. The invention further relates to compounds, or pharmaceutically acceptable salts, hydrates, solvates, prodrugs, stereoisomers, or tautomers thereof, which are useful for activating FXR.

In one embodiment, compounds of the invention have the structure of Formula (I):

(I)

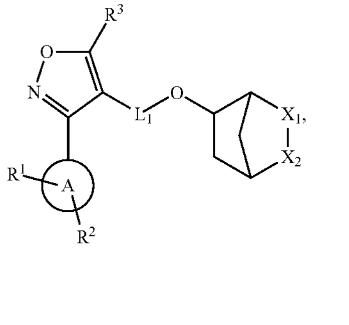

or a salt thereof, wherein:

one of $X_1$ or $X_2$ is $NR_x$ or $N^+(O^-)R_x$ and the other is $CHR_y$ or C(O);

$R_x$ is

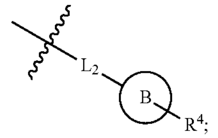

$R_y$ is H, alkyl, cycloalkyl or cycloalkylalkyl wherein said alkyl, cycloalkyl and cycloalkylalkyl are optionally substituted with halogen or alkoxy;

$L_1$ is $—(CH_2)_m(C{=}O)—$ or $—(CH_2)_p—$;

$L_2$ is a bond or $—S(O)_2—$;

A is cycloalkyl, aryl, heterocycloalkyl or heteroaryl, wherein the cycloalkyl, aryl, heterocycloalkyl, or heteroaryl is optionally substituted with one or more $R^7$;

B is aryl or heteroaryl, wherein the aryl or heteroaryl is optionally substituted with one or more $R^5$;

$R^1$ and $R^2$ are each independently H, alkyl, alkoxy, haloalkyl, haloalkoxy, halogen, cycloalkyl, or CN, wherein the cycloalkyl is optionally substituted with one or more $R^9$;

or when A is cycloalkyl or heterocycloalkyl, $R^1$ and $R^2$ together when attached to the same carbon atom form a spirocycloalkyl ring optionally substituted with one or more $R^8$; or when A is cycloalkyl or heterocycloalkyl. $R^1$ and $R^2$ together when attached to the same atom form a spiroheterocycloalkyl ring optionally substituted with one or more $R^8$; or $R^1$ and $R^2$ when on adjacent atoms together with the atoms to which they are attached form a cycloalkyl ring optionally substituted with one or more $R^8$; or $R^1$ and $R^2$ when on adjacent atoms together with the atoms to which they are attached form a heterocycloalkyl ring optionally substituted with one or more $R^8$; or $R^1$ and $R^2$ when on adjacent atoms together with the atoms to which they are attached form an aryl ring optionally substituted with one or more $R^8$; or $R^1$ and $R^2$ when on adjacent atoms together with the atoms to which they are attached form a heteroaryl ring optionally substituted with one or more $R^8$; or when A is cycloalkyl or heterocycloalkyl, $R^1$ and $R^2$ when on non-adjacent atoms, together with the atoms to which they are attached form a cycloalkyl ring optionally substituted with one or more $R^8$; or when cycloalkyl or heterocycloalkyl, $R^1$ and $R^2$ when on non-adjacent atoms, together with the atoms to which they are attached form a heterocycloalkyl ring optionally substituted with one or more $R^8$; cycloalkyl ring optionally substituted with one or more $R^8$; or when cycloalkyl or heterocycloalkyl, $R^1$ and $R^2$ together with the atoms to which they are attached form a heterocycloalkyl ring optionally substituted with one or more $R^8$;

$R^3$ is alkyl, alkoxy, haloalkyl, haloalkoxy, hydroxyalkyl, or cycloalkyl optionally substituted with one or more substituents each independently selected from the group consisting of halogen, alkyl, alkoxy, haloalkyl, haloalkoxy, and —OH;

$R^4$ is $COOR^{6a}$, $—(CH_2)_n—COOR^{6a}$, $CONR^{6b}OH$, $CONR^{6b}R^{6c}$, $CONH(CH_2)_nCOOR^{6a}$, $CONH(CH_2)_nR^{6a}$, $—(CH_2)_nCONH(CH_2)_nR^{6a}$, $CONR^{6b}SO_2R^{6d}$, $CONR^{6b}SO_2(CH_2)_nR^{6d}$, $—(CH_2)_n—CONR^{6b}SO_2R^{6d}$, $CONR^{6b}SO_2(CH_2)_nN(CO)R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, CN, $—(CH_2)_n—NR^{6b}C(O)R^{6c}$, $—(CH_2)_n—N(OH)—C(O)R^{6c}$, oxo, alkyl, cycloalkyl, $—(CH_2)_n$-cycloalkyl, heterocycloalkyl, $—(CH_2)_n$-heterocycloalkyl, heteroaryl and $-(CH_2)_n$-heteroaryl; wherein said alkyl, cycloalkyl, $-(CH_2)_n$-cycloalkyl, heterocycloalkyl, $-(CH_2)_n$-heterocycloalkyl, heteroaryl and $-(CH_2)_n$-heteroaryl are optionally substituted with $COOR^{6a}$, $-(CH_2)_n-COOR^{6a}$, $CONR^{6b}OH$, $CONR^{6b}R^{6c}$, $CONH(CH_2)_nCOOR^{6a}$, $CONH(CH_2)_nR^{6a}$, $-(CH_2)_nCONH(CH_2)_nR^{6a}$, $CONR^{6b}SO_2R^{6d}$, $CONR^{6b}SO_2(CH_2)_nR^{6d}$, $-(CH_2)_n-CONR^{6b}SO_2R^{6d}$, $CONR^{6b}SO_2(CH_2)_nN(CO)R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, CN, $-(CH_2)_n-NR^{6b}C(O)R^{6c}$, $-(CH_2)_n-N(OH)-C(O)R^{6c}$;

each $R^5$ is independently at each occurrence halogen, alkyl, haloalkyl, alkoxy, haloalkoxy, CN, cycloalkyl, aryl, heterocycloalkyl, or heteroaryl wherein the cycloalkyl, aryl, heterocycloalkyl or heteroaryl are optionally substituted with one or more substituents each independently selected from the group consisting of halogen, alkyl, haloalkyl, alkoxy, and haloalkoxy;

$R^{6a}$ is H, alkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, $NR^{6b}R^{6c}$ and —OH;

$R^{6b}$ and $R^{6c}$ are each independently H, alkyl, haloalkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6d}$ is alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, COOH, alkyl, haloalkyl, alkoxy, haloalkoxy, alkoxyalkoxy, —O—CO-alkyl, —O—COcycloalkyl, —O—CO-alkyl-COOH, $NR^{6b}R^{6c}$, $NR^{6f}$CO-alkyl, $NR^{6f}$CO-alkoxy, cycloalkyl, heterocycloalkyl and —OH;

$R^{6e}$ is —OH, alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6f}$ is alkyl or haloalkyl;

$R^{6g}$ is H or alkyl optionally substituted with —O—CO-alkyl;

each $R^7$ is independently at each occurrence alkyl, alkoxy, haloalkyl, haloalkoxy, halogen, or CN;

each $R^8$ is independently at each occurrence alkyl, alkoxy, haloalkyl, haloalkoxy, halogen, or —OH;

each $R^9$ is independently at each occurrence alkyl, alkoxy, haloalkyl, haloalkoxy, halogen, or —OH;

m is 0, 1, or 2;

n is 1, 2, 3, or 4; and p is 1 or 2.

In another embodiment, compounds of the invention have the Formula (I)

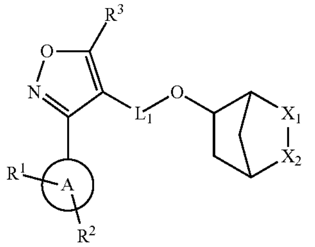

wherein:

one of $X_1$ or $X_2$ is $NR_x$ and the other is $CH_2$;

$R_x$ is

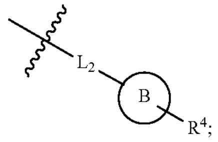

$L_1$ is $-(CH_2)_m(C{=}O)-$ or $-(CH_2)_p-$;

$L_2$ is a bond or $-S(O)_2-$;

A is $(C_3$-$C_8)$ cycloalkyl, $(C_6$-$C_{10})$ aryl, heterocycloalkyl, wherein the heterocycloalkyl comprises one or two 5- to 7-membered rings and 1-4 heteroatoms selected from the group consisting of N, O and S, or heteroaryl, wherein the heteroaryl comprises one or two 5- or 6-membered rings and 1-4 heteroatoms selected from the group consisting of N, O and S, and wherein the cycloalkyl, aryl, heterocycloalkyl, or heteroaryl is optionally substituted with one or more $R^7$;

B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$;

$R^1$ and $R^2$ are each independently H, $(C_1$-$C_6)$ alkyl, $(C_2$-$C_6)$ alkenyl, $(C_2$-$C_6)$ alkynyl. $(C_1$-$C_6)$ alkoxy. $(C_1$-$C_6)$ haloalkyl, $(C_1$-$C_6)$ haloalkoxy, halogen, $(C_3$-$C_7)$ cycloalkyl, or CN, wherein the cycloalkyl is optionally substituted with one or more $R^9$;

or $R^1$ and $R^2$ together when attached to the same carbon atom form a $(C_3$-$C_8)$ spirocycloalkyl ring optionally substituted with one or more $R^8$; or $R^1$ and $R^2$ together when attached to the same atom form a $(C_3$-$C_8)$ spiroheterocycloalkyl ring optionally substituted with one or more $R^8$; or $R^1$ and $R^2$ on adjacent atoms together with the atoms to which they are attached form a $(C_3$-$C_8)$ cycloalkyl ring optionally substituted with one or more $R^8$; or $R^1$ and $R^2$ on adjacent atoms together with the atoms to which they are attached form a heterocycloalkyl ring optionally substituted with one or more $R^8$; or $R^1$ and $R^2$ on adjacent atoms together with the atoms to which they are attached form an aryl ring optionally substituted with one or more $R^8$; or $R^1$ and $R^2$ on adjacent atoms together with the atoms to which they are attached form a heteroaryl ring optionally substituted with one or more $R^8$; or when A is cycloalkyl or heterocycloalkyl, $R^1$ and $R^2$ together with the atoms to which they are attached form a $(C_3$-$C_8)$ cycloalkyl ring optionally substituted with one or more $R^8$; or when cycloalkyl or heterocycloalkyl, $R^1$ and $R^2$ together with the atoms to which they are attached form a heterocycloalkyl ring optionally substituted with one or more $R^8$;

$R^3$ is ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, ($C_1$-$C_6$) hydroxyalkyl, or ($C_3$-$C_7$) cycloalkyl optionally substituted with one or more substituents each independently selected from the group consisting of halogen, ($C_1$-$C_6$) alkyl, ($C_1$-$C_6$) alkoxy, ($C_1$-$C_6$) haloalkyl, ($C_1$-$C_6$) haloalkoxy, and —OH;

$R^4$ is $COOR^{6a}$, $CONR^{6b}R^{6c}$, $CONH(CH_2)_nCOOR^{6a}$, $CONR^{6b}SO_2R^{6d}$, $CONH(CH_2)_nSO_2R^{6e}$, CN, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S;

each $R^5$ is independently at each occurrence halogen, ($C_1$-$C_6$) alkyl, ($C_1$-$C_6$) haloalkyl, ($C_1$-$C_6$) alkoxy, ($C_1$-$C_6$) haloalkoxy, CN, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of halogen, ($C_1$-$C_6$) alkyl, ($C_1$-$C_6$) haloalkyl, ($C_1$-$C_6$) alkoxy, and ($C_1$-$C_6$) haloalkoxy;

$R^{6a}$ is H, ($C_1$-$C_6$) alkyl, ($C_1$-$C_6$) haloalkyl, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen. ($C_1$-$C_6$) alkyl, ($C_1$-$C_6$) haloalkyl, ($C_1$-$C_6$) alkoxy, ($C_1$-$C_6$) haloalkoxy, and —OH;

$R^{6b}$ and $R^{6c}$ are each independently H, ($C_1$-$C_6$) alkyl, ($C_1$-$C_6$) haloalkyl, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH;

$R^{6d}$ is ($C_1$-$C_6$) alkyl, ($C_1$-$C_6$) haloalkyl, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH;

$R^{6e}$ is —OH, ($C_1$-$C_6$) alkyl, ($C_1$-$C_6$) haloalkyl, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen. ($C_1$-$C_6$) alkyl, ($C_1$-$C_6$) haloalkyl, ($C_1$-$C_6$) alkoxy, ($C_1$-$C_6$) haloalkoxy, and —OH;

each $R^7$ is independently at each occurrence ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl. ($C_1$-$C_6$) haloalkoxy, halogen, or CN;

each $R^8$ is independently at each occurrence ($C_1$-$C_6$) alkyl, ($C_1$-$C_6$) alkoxy, ($C_1$-$C_6$) haloalkyl, ($C_1$-$C_6$) haloalkoxy, halogen, or —OH;

each $R^9$ is independently at each occurrence ($C_1$-$C_6$) alkyl, ($C_1$-$C_6$) alkoxy, ($C_1$-$C_6$) haloalkyl, ($C_1$-$C_6$) haloalkoxy, halogen, or —OH;

m is 0, 1, or 2; and p is 1 or 2.

In one embodiment, the compounds of Formula (I) have the structure of Formula (Ia) or (Ib):

(Ia)

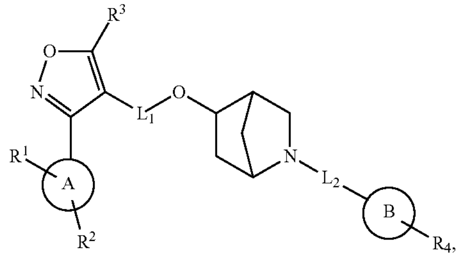

or (Ib)

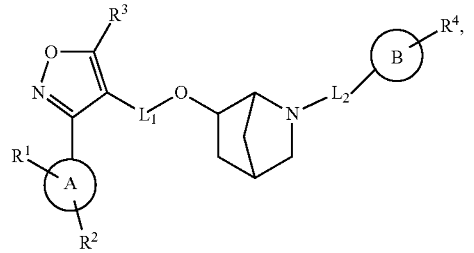

and pharmaceutically acceptable salts, hydrates, solvates, prodrugs, stereoisomers, and tautomers thereof.

In another embodiment, the compounds of Formula (I) have the structure of Formula (Ic) or (Id):

(Ic)

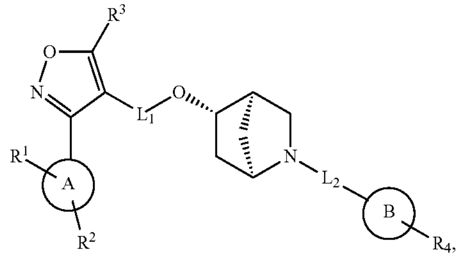

or

-continued (Id)

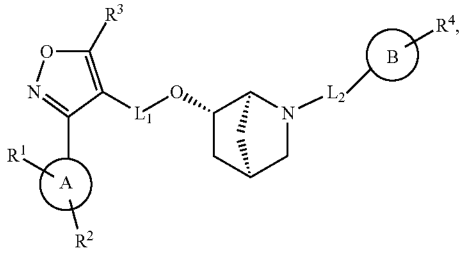

and pharmaceutically acceptable salts, hydrates, solvates, prodrugs, stereoisomers, and tautomers thereof.

In another embodiment, the compounds of Formula (I) have the structure of Formula (Ie) or (If):

(Ie)

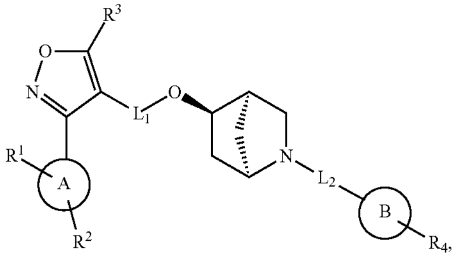

or (If)

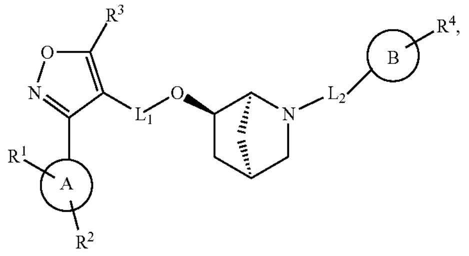

and pharmaceutically acceptable salts, hydrates, solvates, prodrugs, stereoisomers, and tautomers thereof.

In another embodiment, the compounds of Formula (I) have the structure of Formula (Ig) or (Ih):

(Ig)

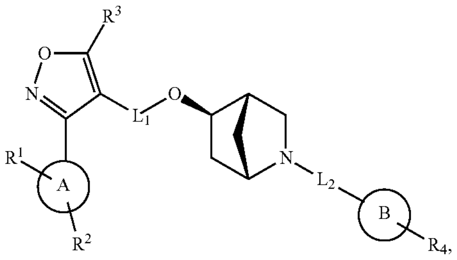

or

-continued (Ih)

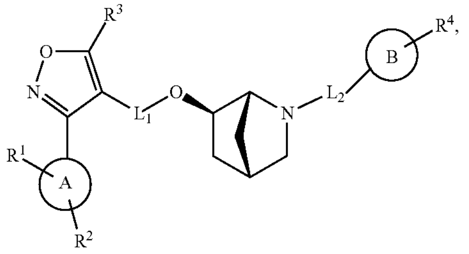

and pharmaceutically acceptable salts, hydrates, solvates, prodrugs, stereoisomers, and tautomers thereof.

In another embodiment, the compounds of Formula (I) have the structure of Formula (Ii) or (Ij).

(Ii)

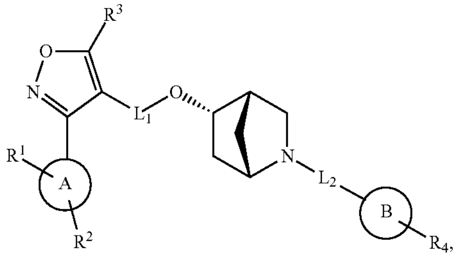

or (Ij)

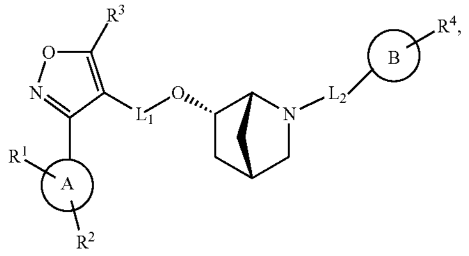

and pharmaceutically acceptable salts, hydrates, solvates, prodrugs, stereoisomers, and tautomers thereof.

In another embodiment, the compounds of Formula (I) have the structure of Formula (Ik) or (Il):

(Ik)

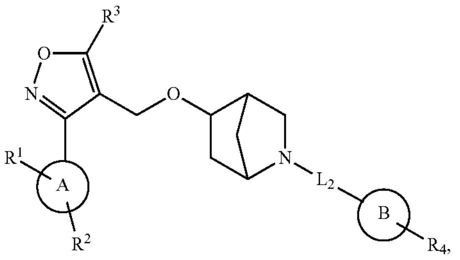

or

-continued (Il)

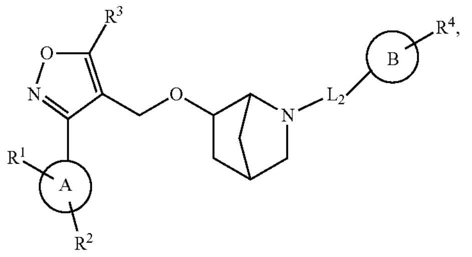

and pharmaceutically acceptable salts, hydrates, solvates, prodrugs, stereoisomers, and tautomers thereof.

In another embodiment, the compounds of Formula (I) have the structure of Formula (Im) or (In):

(Im)

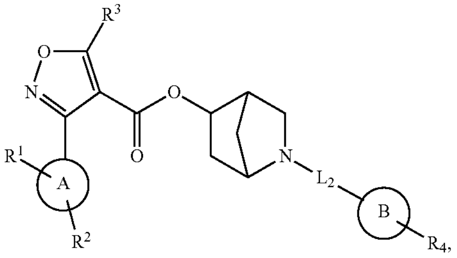

or (In)

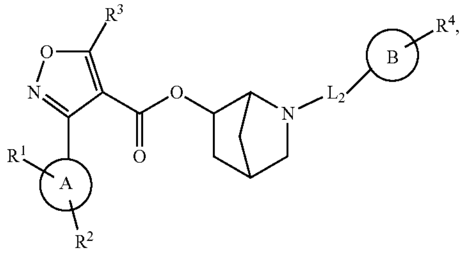

and pharmaceutically acceptable salts, hydrates, solvates, prodrugs, stereoisomers, and tautomers thereof.

In another embodiment, the compounds of Formula (I) have the structure of Formula (Io) or (Ip):

(Io)

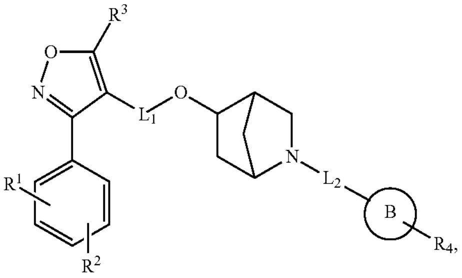

or

-continued (Ip)

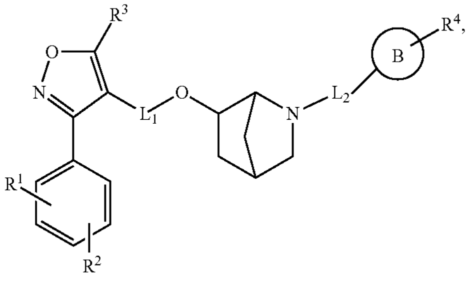

and pharmaceutically acceptable salts, hydrates, solvates, prodrugs, stereoisomers, and tautomers thereof.

In another embodiment, the compounds of Formula (I) have the structure of Formula (Iq) or (Ir):

(Iq)

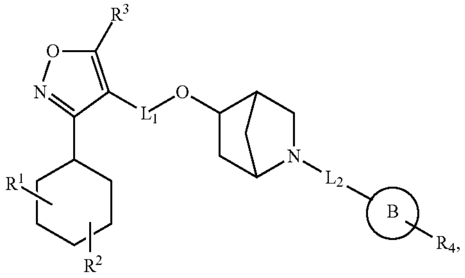

or (Ir)

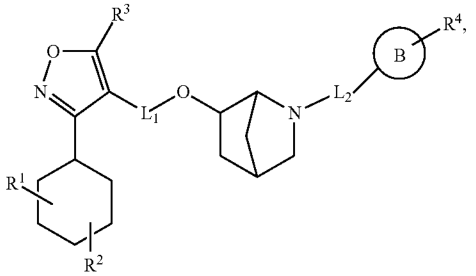

and pharmaceutically acceptable salts, hydrates, solvates, prodrugs, stereoisomers, and tautomers thereof.

In another embodiment, the compounds of Formula (I) have the structure of Formula (Is) or (It):

(Is)

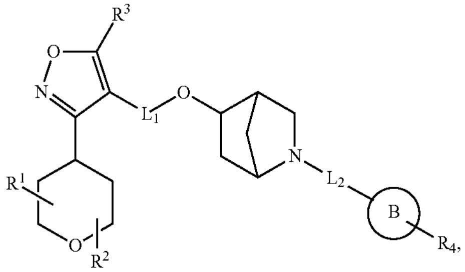

or

-continued (It)

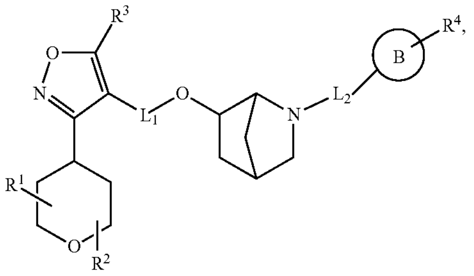

and pharmaceutically acceptable salts, hydrates, solvates, prodrugs, stereoisomers, and tautomers thereof.

In another embodiment, the compounds of Formula (I) have the structure of Formula (Iu) or (Iv):

(Iu)

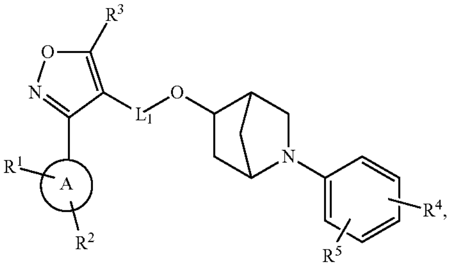

or (Iv)

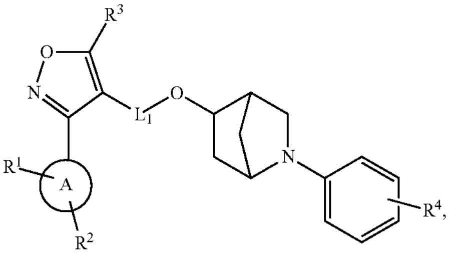

and pharmaceutically acceptable salts, hydrates, solvates, prodrugs, stereoisomers, and tautomers thereof.

In another embodiment, the compounds of Formula (I) have the structure of Formula (Iw) or (Ix):

(Iw)

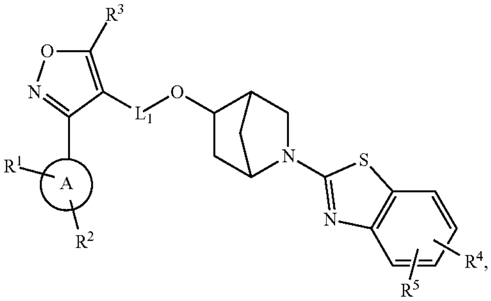

or

-continued (Ix)

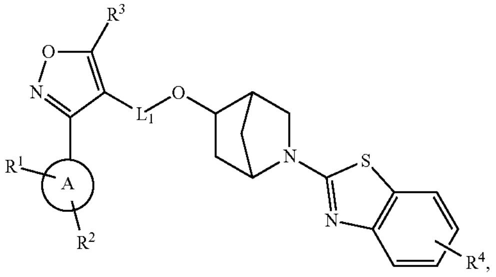

and pharmaceutically acceptable salts, hydrates, solvates, prodrugs, stereoisomers, and tautomers thereof.

In another embodiment, the compounds of Formula (I) have the structure of Formula (Iy) or (Iz):

(Iy)

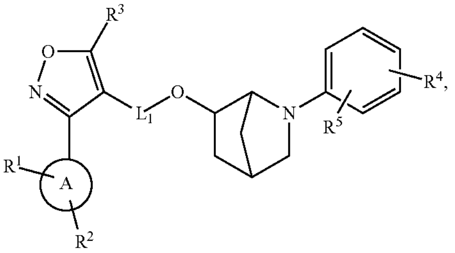

or (Iz)

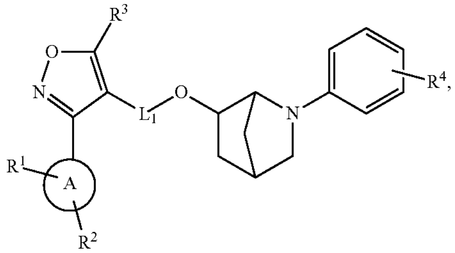

and pharmaceutically acceptable salts, hydrates, solvates, prodrugs, stereoisomers, and tautomers thereof.

In another embodiment, the compounds of Formula (I) have the structure of Formula (Iaa) or (Ibb):

(Iaa)

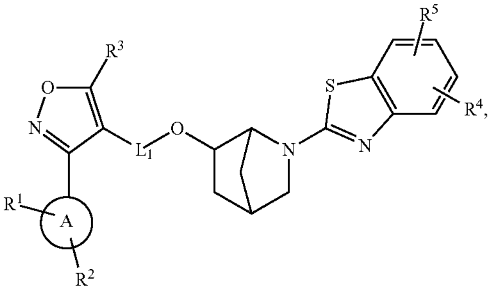

or

-continued (Ibb)

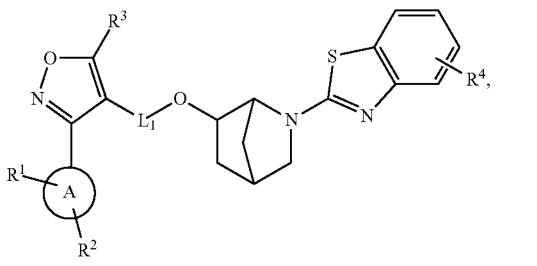

and pharmaceutically acceptable salts, hydrates, solvates, prodrugs, stereoisomers, and tautomers thereof.

In some embodiments of the Formulae above, $X_1$ is $CHR_y$ or C(O) and $X_2$ is $NR_x$ or $N^+(O^-)R_x$. In an embodiment, $X^1$ is $CHR_y$ and $X_2$ is $NR_x$ or $N^+(O^-)R_x$. In an embodiment, $X_1$ is C(O) and $X_2$ is $NR_x$ or $N^+(O^-)R_x$. In an embodiment, $X_1$ is $CHR_y$ and $X_2$ is $NR_x$. In an embodiment, $X_1$ is C(O) and $X_2$ is $NR_x$. In an embodiment, $X_1$ is $CHR_y$ and $X_2$ is $N^+(O^-)R_x$. In an embodiment, $X_1$ is C(O) and $X_2$ is $N^+(O^-)R_x$. In an embodiment, $X_1$ is $CH_2$ and $X_2$ is $NR_x$. In another embodiment, $X_1$ is $NR_x$ or $N^+(O^-)R_x$ and $X_2$ is $CHR_y$ or C(O). In another embodiment, $X_1$ is $NR_x$ and $X_2$ is $CHR_y$ or C(O). In another embodiment, $X_1$ is $N^+(O^-)R_x$ and $X_2$ is $CHR_y$ or C(O). In another embodiment, $X_1$ is $NR_x$ and $X_2$ is $CHR_y$. In another embodiment, $X_1$ is $NR_x$ and $X_2$ is C(O). In another embodiment, $X_1$ is $N^+(O^-)R_x$ and $X_2$ is $CHR_y$. In another embodiment, $X_1$ is $N^+(O^-)R_x$ and $X_2$ is C(O). In another embodiment, $X_1$ is $NR_x$ and $X_2$ is $CH_2$.

In some embodiments of the Formulae above, $L_1$ is $—(CH_2)_m(C{=}O)—$. In another embodiment $L_1$ is $—(CH_2)_p$. In another embodiment $L_1$ is $—CH_2$. In another embodiment $L_1$ is $—CH_2C(O)—$. In another embodiment $L_1$ is —C(O)—.

In some embodiments of the Formulae above, $L_2$ is a bond. In another embodiment $L_2$ is $—S(O)_2—$.

In some embodiments of the Formulae above. A is ($C_3$-$C_8$) cycloalkyl optionally substituted with one or more $R^7$. In another embodiment, A is ($C_3$-$C_8$) cycloalkyl. In yet another embodiment, A is ($C_3$-$C_8$) cycloalkyl substituted with one or more $R^7$. In another embodiment, ($C_6$-$C_{10}$) aryl optionally substituted with one or more $R^7$. In yet another embodiment, A is ($C_6$-$C_{10}$) aryl. In another embodiment, A is ($C_6$-$C_{10}$) aryl substituted with one or more $R^7$. In an embodiment, A is phenyl optionally substituted with one or more $R^7$. In another embodiment, A is phenyl unsubstituted by $R^7$ while $R^1$ and $R^2$ are both a halogen. In another embodiment, A is phenyl unsubstituted by $R^7$ while $R^1$ and $R^2$ are both a Cl at the ortho positions relative to the isoxazole ring. In yet another embodiment, A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, A is heterocycloalkyl comprising one or two 5- to 7-membered rings and 1-4 heteroatoms selected from the group consisting of N, O and S. In yet another embodiment, A is heterocycloalkyl wherein the heterocycloalkyl comprises one or two 5- to 7-membered rings and 1-4 heteroatoms selected from the group consisting of N, O and S, substituted with one or more $R^7$. In another embodiment, A is heteroaryl wherein the heteroaryl comprises one or two 5- or 6-membered rings and 1-4 heteroatoms selected from the group consisting of N, O and S, optionally substituted with one or more $R^7$. In yet another embodiment, A is heteroaryl wherein the heteroaryl comprises one or two 5- or 6-membered rings and 1-4 heteroatoms selected from the group consisting of N, O and S.

In another embodiment, A is heteroaryl wherein the heteroaryl comprises one or two 5- or 6-membered rings and 1-4 heteroatoms selected from the group consisting of N, O and S, substituted with one or more $R^7$. In yet another embodiment. A is ($C_3$-$C_8$) cycloalkyl or heterocycloalkyl wherein the heterocycloalkyl comprises one or two 5- to 7-membered rings and 1-4 heteroatoms selected from the group consisting of N, O and S, wherein the cycloalkyl or heterocycloalkyl are optionally substituted with one or more $R^7$. In another embodiment, A is ($C_6$-$C_{10}$) aryl or heteroaryl wherein the heteroaryl comprises one or two 5- or 6-membered rings and 1-4 heteroatoms selected from the group consisting of N, O and S, wherein the aryl or heteroaryl is optionally substituted with one or more $R^7$. In yet another embodiment, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, A is ($C_3$-$C_8$) cycloalkyl or ($C_6$-$C_{10}$) aryl, wherein the cycloalkyl or aryl are optionally substituted with one or more $R^7$. In yet another embodiment, A is ($C_6$-$C_{10}$) aryl or heterocycloalkyl wherein the heterocycloalkyl comprises one or two 5- to 7-membered rings and 1-4 heteroatoms selected from the group consisting of N, O and S, wherein the aryl or heterocycloalkyl are optionally substituted with one or more $R^7$.

In some embodiments of the Formulae above, B is ($C_6$-$C_{10}$) aryl optionally substituted with one or more $R^5$. In another embodiment, B is heteroaryl comprising one or two 5- or 6-member rings and 1-4 heteroatoms selected from the group consisting of N, O and S, optionally substituted with one or more $R^5$. In yet another embodiment, B is ($C_6$-$C_{10}$) aryl. In another embodiment, B is ($C_6$-$C_{10}$) aryl substituted with one or more $R^5$. In yet another embodiment, B is heteroaryl. In another embodiment, B is heteroaryl comprising one or two 5- or 6-member rings and 1-4 heteroatoms selected from the group consisting of N, O and S, substituted with one or more $R^5$. In another embodiment, B is ($C_6$-$C_{10}$) aryl or heteroaryl wherein the heteroaryl comprises one or two 5- or 6-member rings and 1-4 heteroatoms selected from the group consisting of N, O and S. In another embodiment, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl are substituted with one or more $R^5$.

In some embodiments of the Formulae above, $R^1$ is H, ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, or halogen. In another embodiment, $R^1$ is halogen, CN, or ($C_3$-$C_7$) cycloalkyl optionally substituted with one or more $R^9$. In yet another embodiment, $R^1$ is H, ($C_1$-$C_6$) alkyl, ($C_1$-$C_6$) alkoxy, ($C_1$-$C_6$) haloalkyl, ($C_1$-$C_6$) haloalkoxy, halogen, or ($C_3$-$C_7$) cycloalkyl optionally substituted with one or more $R^9$. In another embodiment, $R^1$ is H, ($C_1$-$C_6$) alkyl, ($C_1$-$C_6$) alkoxy, halogen, or ($C_3$-$C_7$) cycloalkyl optionally substituted with one or more $R^9$. In yet another embodiment, $R^1$ is ($C_1$-$C_6$) alkyl, ($C_1$-$C_6$) alkoxy, halogen, or ($C_3$-$C_7$) cycloalkyl optionally substituted with one or more $R^9$. In another embodiment, $R^1$ is H, ($C_1$-$C_6$) alkoxy, ($C_1$-$C_6$) haloalkyl, ($C_1$-$C_6$) haloalkoxy, or halogen. In yet another embodiment, $R^1$ is ($C_1$-$C_6$) alkoxy, ($C_1$-$C_6$) haloalkyl, ($C_1$-$C_6$) haloalkoxy, or halogen. In another embodiment, $R^1$ is H, $(C_1-C_6)$ alkoxy, $(C_1-C_6)$ haloalkoxy, or halogen. In yet another embodiment, $R^1$ is $(C_1-C_6)$ alkoxy, $(C_1-C_6)$ haloalkoxy, or halogen. In another embodiment, $R^1$ is H, $(C_1-C_6)$ haloalkyl, $(C_1-C_6)$ haloalkoxy, or halogen. In yet another embodiment, $R^1$ is $(C_1-C_6)$ haloalkyl, $(C_1-C_6)$ haloalkoxy, or halogen. In another embodiment. $R^1$ is $(C_1-C_6)$ alkyl, $(C_1-C_6)$ alkoxy, $(C_1-C_6)$ haloalkyl, $(C_1-C_6)$ haloalkoxy, halogen, or $(C_3-C_7)$ cycloalkyl optionally substituted with one or more $R^9$. In yet another embodiment, $R^1$ is H, $(C_1-C_6)$ haloalkyl, or halogen. In another embodiment, $R^1$ is $(C_1-C_6)$ haloalkyl or halogen.

In some embodiments of the Formulae above, $R^2$ is H, $(C_1-C_6)$ alkyl. $(C_2-C_6)$ alkenyl, $(C_2-C_6)$ alkynyl, $(C_1-C_6)$ alkoxy, $(C_1-C_6)$ haloalkyl. $(C_1-C_6)$ haloalkoxy, or halogen. In another embodiment, $R^2$ is halogen, CN, or $(C_3-C_7)$ cycloalkyl optionally substituted with one or more $R^9$. In yet another embodiment, $R^2$ is H, $(C_1-C_6)$ alkyl, $(C_1-C_6)$ alkoxy, $(C_1-C_6)$ haloalkyl, $(C_1-C_6)$ haloalkoxy, halogen, or $(C_3-C_7)$ cycloalkyl optionally substituted with one or more $R^9$. In another embodiment, $R^2$ is H, $(C_1-C_6)$ alkyl, $(C_1-C_6)$ alkoxy, halogen, or $(C_3-C_7)$ cycloalkyl optionally substituted with one or more $R^9$. In yet another embodiment, $R^2$ is $(C_1-C_6)$ alkyl, $(C_1-C_6)$ alkoxy, halogen, or $(C_3-C_7)$ cycloalkyl optionally substituted with one or more $R^9$. In another embodiment, $R^2$ is H, $(C_1-C_6)$ alkoxy, $(C_1-C_6)$ haloalkyl, $(C_1-C_6)$ haloalkoxy, or halogen. In yet another embodiment, $R^2$ is $(C_1-C_6)$ alkoxy, $(C_1-C_6)$ haloalkyl, $(C_1-C_6)$ haloalkoxy, or halogen. In another embodiment, $R^2$ is H, $(C_1-C_6)$ alkoxy, $(C_1-C_6)$ haloalkoxy, or halogen. In yet another embodiment, $R^2$ is $(C_1-C_6)$ alkoxy. $(C_1-C_6)$ haloalkoxy, or halogen. In another embodiment, $R^2$ is H, $(C_1-C_6)$ haloalkyl, $(C_1-C_6)$ haloalkoxy, or halogen. In yet another embodiment, $R^2$ is $(C_1-C_6)$ haloalkyl, $(C_1-C_6)$ haloalkoxy, or halogen. In another embodiment, $R^2$ is $(C_1-C_6)$ alkyl, $(C_1-C_6)$ alkoxy, $(C_1-C_6)$ haloalkyl, $(C_1-C_6)$ haloalkoxy, halogen, or $(C_3-C_7)$ cycloalkyl optionally substituted with one or more $R^9$. In yet another embodiment, $R^2$ is H, $(C_1-C_6)$ haloalkyl, or halogen. In another embodiment, $R^2$ is $(C_1-C_6)$ haloalkyl or halogen.

In some embodiments of the Formulae above, $R^1$ and $R^2$ together when attached to the same carbon atom form a $(C_3-C_8)$ spirocycloalkyl ring optionally substituted with one or more $R^8$. In another embodiment, $R^1$ and $R^2$ together when attached to the same carbon atom form a $(C_3-C_8)$ spirocycloalkyl ring optionally substituted with one to three $R^8$. In yet another embodiment, $R^1$ and $R^2$ together when attached to the same carbon atom form a $(C_3-C_8)$ spirocycloalkyl ring. In another embodiment, $R^1$ and $R^2$ together when attached to the same carbon atom form a $(C_3-C_8)$ spirocycloalkyl ring substituted with one to three $R^8$.

In some embodiments of the Formulae above, $R^1$ and $R^2$ together when attached to the same atom form a $(C_3-C_8)$ spiroheterocycloalkyl ring optionally substituted with one or more $R^8$. In another embodiment, $R^1$ and $R^2$ together when attached to the same atom form a $(C_3-C_8)$ spiroheterocycloalkyl ring optionally substituted with one to three $R^8$. In yet another embodiment, $R^1$ and $R^2$ together when attached to the same atom form a $(C_3-C_8)$ spiroheterocycloalkyl ring. In another embodiment, $R^1$ and $R^2$ together when attached to the same atom form a $(C_3-C_8)$ spiroheterocycloalkyl ring substituted with one to three $R^8$.

In some embodiments of the Formulae above, $R^1$ and $R^2$ on adjacent atoms together with the atoms to which they are attached form a $(C_3-C_8)$ cycloalkyl ring optionally substituted with one or more $R^8$. In another embodiment, $R^1$ and $R^2$ on adjacent atoms together with the atoms to which they are attached form a $(C_3-C_8)$ cycloalkyl ring optionally substituted with one to three $R^8$. In yet another embodiment, $R^1$ and $R^2$ on adjacent atoms together with the atoms to which they are attached form a $(C_3-C_8)$ cycloalkyl ring. In another embodiment, $R^1$ and $R^2$ on adjacent atoms together with the atoms to which they are attached form a $(C_3-C_8)$ cycloalkyl ring substituted with one to three $R^8$.

In some embodiments of the Formulae above, $R^1$ and $R^2$ on adjacent atoms together with the atoms to which they are attached form a heterocycloalkyl ring optionally substituted with one or more $R^8$. In another embodiment, $R^1$ and $R^2$ on adjacent atoms together with the atoms to which they are attached form a heterocycloalkyl ring optionally substituted with one to three $R^8$. In yet another embodiment, $R^1$ and $R^2$ on adjacent atoms together with the atoms to which they are attached form a heterocycloalkyl ring. In another embodiment, $R^1$ and $R^2$ on adjacent atoms together with the atoms to which they are attached form a heterocycloalkyl ring substituted with one to three $R^8$.

In some embodiments of the Formulae above. $R^1$ and $R^2$ on adjacent atoms together with the atoms to which they are attached form an aryl ring optionally substituted with one or more $R^8$. In another embodiment, $R^1$ and $R^2$ on adjacent atoms together with the atoms to which they are attached form an aryl ring optionally substituted with one to three $R^8$. In yet another embodiment, $R^1$ and $R^2$ on adjacent atoms together with the atoms to which they are attached form an aryl ring. In another embodiment, $R^1$ and $R^2$ on adjacent atoms together with the atoms to which they are attached form an aryl ring substituted with one to three $R^8$.

In some embodiments of the Formulae above, $R^1$ and $R^2$ on adjacent atoms together with the atoms to which they are attached form a heteroaryl ring optionally substituted with one or more $R^8$. In another embodiment, $R^1$ and $R^2$ on adjacent atoms together with the atoms to which they are attached form a heteroaryl ring optionally substituted with one to three $R^8$. In yet another embodiment, $R^1$ and $R^2$ on adjacent atoms together with the atoms to which they are attached form a heteroaryl ring. In another embodiment, $R^1$ and $R^2$ on adjacent atoms together with the atoms to which they are attached form a heteroaryl ring substituted with one to three $R^8$.

In some embodiments of the Formulae above, when A is cycloalkyl or heterocycloalkyl, $R^1$ and $R^2$ together with the atoms to which they are attached form a $(C_4-C_8)$ cycloalkyl ring optionally substituted with one or more $R^8$. In another embodiment, when A is cycloalkyl or heterocycloalkyl, $R^1$ and $R^2$ together with the atoms to which they are attached form a $(C_4-C_8)$ cycloalkyl ring optionally substituted with one to three $R^5$. In yet another embodiment, when A is cycloalkyl or heterocycloalkyl, $R^1$ and $R^2$ together with the atoms to which they are attached form a $(C_4-C_8)$ cycloalkyl ring. In another embodiment, when A is cycloalkyl or heterocycloalkyl, $R^1$ and $R^2$ together with the atoms to which they are attached form a $(C_4-C_8)$ cycloalkyl ring substituted with one to three $R^8$.

In some embodiments of the Formulae above, when cycloalkyl or heterocycloalkyl. $R^1$ and $R^2$ together with the atoms to which they are attached form a heterocycloalkyl ring optionally substituted with one or more $R^8$. In another embodiment, when cycloalkyl or heterocycloalkyl, $R^1$ and $R^2$ together with the atoms to which they are attached form a heterocycloalkyl ring optionally substituted with one to three $R^8$. In yet another embodiment, when cycloalkyl or heterocycloalkyl, $R^1$ and $R^2$ together with the atoms to which they are attached form a heterocycloalkyl ring. In another embodiment, when cycloalkyl or heterocycloalkyl, $R^1$ and $R^2$ together with the atoms to which they are attached form a heterocycloalkyl ring substituted with one to three $R^8$.

In some embodiments of the Formulae above, $R^3$ is $(C_1\text{-}C_4)$ alkyl, $(C_2\text{-}C_4)$ alkenyl, $(C_2\text{-}C_4)$ alkynyl, $(C_1\text{-}C_4)$ alkoxy, $(C_1\text{-}C_4)$ haloalkyl, $(C_1\text{-}C_4)$ haloalkoxy, $(C_1\text{-}C_4)$ hydroxyalkyl, or $(C_3\text{-}C_7)$ cycloalkyl optionally substituted with one or more substituents each independently selected from the group consisting of halogen, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, and —OH. In another embodiment, $R^3$ is $(C_1\text{-}C_4)$ alkyl, $(C_2\text{-}C_4)$ alkenyl, $(C_2\text{-}C_4)$ alkynyl, or. $(C_1\text{-}C_4)$ alkoxy. In yet another embodiment, $R^3$ is $(C_1\text{-}C_4)$ haloalkyl, $(C_1\text{-}C_4)$ haloalkoxy, or $(C_1\text{-}C_4)$ hydroxyalkyl. In another embodiment, $R^3$ is $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, $(C_1\text{-}C_4)$ hydroxyalkyl, or $(C_3\text{-}C_7)$ cycloalkyl optionally substituted with one or more substituents each independently selected from the group consisting of halogen, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, and —OH. In yet another embodiment, $R^3$ is $(C_1\text{-}C_4)$ alkyl or $(C_3\text{-}C_7)$ cycloalkyl optionally substituted with one or more substituents each independently selected from the group consisting of halogen, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, and —OH. In another embodiment, $R^3$ is $(C_1\text{-}C_4)$ alkyl or $(C_3\text{-}C_7)$ cycloalkyl optionally substituted with one or more substituents each independently selected from the group consisting of halogen and $(C_1\text{-}C_6)$ alkyl. In yet another embodiment, $R^3$ is $(C_3\text{-}C_7)$ cycloalkyl optionally substituted with one or more substituents each independently selected from the group consisting of halogen, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, and —OH. In another embodiment, $R^3$ is $(C_3\text{-}C_7)$ cycloalkyl optionally substituted with one or more substituents each independently selected from the group consisting of halogen or $(C_1\text{-}C_6)$ alkyl.

In some embodiments of the Formulae above, $R^4$ is $COOR^{6a}$, $-(CH_2)_n-COOR^{6a}$, $CONR^{6b}OH$, $CONR^{6b}R^{6c}$, $CONH(CH_2)_nCOOR^{6a}$, $CONH(CH_2)_nR^{6a}$, $-(CH_2)_nCONH(CH_2)_nR^{6a}$, $CONR^{6b}SO_2R^{6d}$, $CONR^{6b}SO_2(CH_2)_nR^{6d}$, $-(CH_2)_n-CONR^{6b}SO_2R^{6d}$, $CONR^{6b}SO_2(CH_2)_nN(CO)R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, CN, $-(CH_2)_n-NR^{6b}C(O)R^{6c}$, $-(CH_2)_n-N(OH)-C(O)R^{6c}$, oxo, alkyl, cycloalkyl, $-(CH_2)_n$-cycloalkyl, heterocycloalkyl, $-(CH_2)_n$-heterocycloalkyl, heteroaryl and $-(CH_2)_n$-heteroaryl; wherein the heterocycloalkyl and $-(CH_2)_n-$ heterocycloalkyl independently comprise one or two 5- to 7-membered rings and 1-4 heteroatoms selected from the group consisting of N, O and S, or heteroaryl wherein the heteroaryl and $-(CH_2)_n$-heteroaryl comprises one or two 5- or 6-membered rings and 1-4 heteroatoms selected from the group consisting of N, O and S; and said alkyl, cycloalkyl, $-(CH_2)_n$-cycloalkyl, heterocycloalkyl, $-(CH_2)_n$-heterocycloalkyl, heteroaryl and $-(CH_2)_n$-heteroaryl are optionally substituted with $COOR^6$, $-(CH_2)_n-COOR^{6a}$, $CONR^{6b}OH$, $CONR^{6b}R^{6C}$, $CONH(CH_2)COOR^{6a}$, $CONH(CH_2)_nR^{6a}$, $-(CH_2)_nCONH(CH_2)_nR^{6a}$, $CONR^{6b}SO_2R^{6d}$, $CONR^{6b}SO_2(CH_2)_nR^{6d}$, $-(CH_2)_n-CONR^{6b}SO_2R^{6d}$, $CONR^{6b}SO_2(CH_2)_nN(CO)R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6d}(CH_2)_nCOOR^{6a}$, $SO_2R^{6e}$, CN, $-(CH_2)_n-NR^6C(O)R^{6c}$, $-(CH_2)_n-N(OH)-C(O)R^{6c}$.

In an embodiment, $R^4$ is $COOR^{6a}$. In an embodiment, $R^4$ is -alkyl-$COOR^{6a}$. In another embodiment, $R^4$ is $-(CH_2)_n-COOR^{6a}$. In an embodiment, $R^4$ is $CONR^{6b}OH$. In another embodiment, $R^4$ is $CONR^{6b}R^{6c}$. In yet another embodiment, $R^4$ is $-CONH(CH_2)_nCOOR^{6a}$. In another embodiment, $R^4$ is $CONH(CH_2)_nSO_2R^{6e}$. In yet another embodiment, $R^4$ is $CONH(CH_2)_nCOOR^{6a}$, $CONH(CH_2)_nR^{6a}$, $-(CH_2)_nCONH(CH_2)_nR^{6a}$. In yet another embodiment, $R^4$ is $CONH(CH_2)_nR^{6a}$. In yet another embodiment, $R^4$ is $-(CH_2)_nCONH(CH_2)_nR^{6a}$. In yet another embodiment, $R^4$ is $CONR^{6b}SO_2R^{6d}$. In yet another embodiment, $R^4$ is $-(CH_2)_n-NR^{6b}C(O)R^{6c}$. In yet another embodiment, $R^4$ is $-(CH_2)_n-N(OH)-C(O)R^{6c}$. In yet another embodiment, $R^4$ is -alkyl-$CONR^{6b}SO_2R^{6d}$. In yet another embodiment, $R^4$ is $COR^{6f}$, $(CH_2)_nPO(OR^{6g})_2$. In yet another embodiment, $R^4$ is $COO(CH_2)_nPO(OR^{6g})_2$. In yet another embodiment, $R^4$ is $SO_2NR^{6b}(CH_2)_nCOOR^{6a}$. In yet another embodiment, $R^4$ is $SO_2R^{6e}$. In yet another embodiment, $R^4$ is oxo. In yet another embodiment, $R^4$ is $(C_3\text{-}C_8)$ cycloalkyl optionally substituted with $(CH_2)_nCOOR^{6a}$, $COOR^{6a}$, $CONR^{6b}OH$, $CONR^6R^{6c}$, $CONH(CH_2)_nCOOR^{6a}$, $CONR^{6b}SO_2R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$. In another embodiment, $R^4$ is heterocycloalkyl comprising one or two 5- to 7-membered rings and 1-4 heteroatoms selected from the group consisting of N, O and S; and said heterocycloalkyl is optionally substituted with $(CH_2)_nCOOR^{6a}$, $COOR^{6a}$, $CONR^{6b}OH$, $CONR^{6b}R^{6c}$, $CONH(CH_2)COOR^{6a}$, $CONR^{6b}SO_2R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^6$, $SO_2R^{6e}$. In yet another embodiment, $R^4$ is or heteroaryl wherein the heteroaryl comprises one or two 5- or 6-membered rings and 1-4 heteroatoms selected from the group consisting of N, O and S; and said said heterary1 is optionally substituted with $(CH_2)_nCOOR^{6a}$, $COOR^{6a}$, $CONR^{6b}OH$, $CONR^{6b}R^{6c}$, $CONH(CH_2)_nCOOR^{6a}$, $CONR^{6b}SO_2R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^6$. In another embodiment, $R^4$ is $COOR^{6a}$, $CONR^{6b}SO_2R^{6d}$, or $CONR^{6b}R^{6c}$. In yet another embodiment, $R^4$ is $COOR^{6a}$, $CONR^{6b}SO_2R^{6d}$, or $CONH(CH_2)_nSO_2R^{6e}$. In another embodiment. $R^4$ is $COOR^{6a}$, $CONR^{6b}SO_2R^{6d}$, or $CONH(CH_2)_nCOOR^{6a}$. In yet another embodiment, $R^4$ is $COOR^{6a}$, $CONR^{6b}SO_2R^{6d}$, or heterocycloalkyl comprising one or two 5- to 7-membered rings and 1-4 heteroatoms selected from the group consisting of N, O and S. In another embodiment, $R^4$ is $COOR^{6a}$, $CONR^{6b}SO_2R^{6d}$, $CONR^{6b}R^{6c}$, or heterocycloalkyl comprising one 5- to 7-membered ring and 1-4 heteroatoms selected from the group consisting of N, O and S. In another embodiment, $R^4$ is $COOR^{6a}$, $CONR^{6b}SO_2R^{6d}$, or heterocycloalkyl comprising one 5- to 7-membered ring and 1-4 heteroatoms selected from the group consisting of N, O and S. In another embodiment, $R^4$ is $CONH(CH_2)_nCOOR^{6a}$ or $CONH(CH_2)_nSO_2R^{6e}$. In yet another embodiment, $R^4$ is $CONR^{6b}R^{6c}$ or $CONH(CH_2)_nCOOR^{6a}$. In another embodiment, $R^4$ is $CONR^{6b}SO_2R^{6d}$ or $CONH(CH_2)_nSO_2R^{6e}$.

In some embodiments, n is 1. In another embodiment, n is 2. In another embodiment, n is 3. In another embodiment, n is 4.

In some embodiments of the Formulae above, $R^5$ is halogen, $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, CN, $(C_3\text{-}C_8)$ cycloalkyl, $(C_6\text{-}C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl or heteroaryl are optionally substituted with one or more substituents each independently selected from the group consisting of halogen, ($C_1$-$C_6$) alkyl, ($C_1$-$C_6$) haloalkyl, ($C_1$-$C_6$) alkoxy, and ($C_1$-$C_6$) haloalkoxy. In another embodiment, $R^5$ is halogen, ($C_1$-$C_4$) alkyl, ($C_1$-$C_4$) haloalkyl, ($C_1$-$C_4$) alkoxy, ($C_1$-$C_4$) haloalkoxy, or ($C_3$-$C_8$) cycloalkyl optionally substituted with one or more substituents each independently selected from the group consisting of halogen, ($C_1$-$C_6$) alkyl, ($C_1$-$C_6$) haloalkyl, ($C_1$-$C_6$) alkoxy, and ($C_1$-$C_6$) haloalkoxy. In another embodiment, $R^5$ is ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl or heteroaryl are optionally substituted with one or more substituents each independently selected from the group consisting of halogen, ($C_1$-$C_6$) alkyl, ($C_1$-$C_6$) haloalkyl, ($C_1$-$C_6$) alkoxy, and ($C_1$-$C_6$) haloalkoxy. In another embodiment, $R^5$ is halogen, ($C_1$-$C_4$) alkyl, ($C_1$-$C_4$) haloalkyl, ($C_1$-$C_4$) alkoxy, ($C_1$-$C_4$) haloalkoxy, or ($C_3$-$C_8$) cycloalkyl. In another embodiment, $R^5$ is halogen, ($C_1$-$C_4$) alkyl, ($C_1$-$C_4$) haloalkyl, ($C_1$-$C_4$) alkoxy, or ($C_1$-$C_4$) haloalkoxy.

In some embodiments of the Formulae above, $R_y$ is H, ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy or halogen. In an embodiment $R_y$ is H. In an embodiment $R_y$ is methyl. In an embodiment $R_y$ is ethyl. In an embodiment $R_y$ is $CF_3$. In an embodiment $R_y$ is ($C_1$-$C_6$) alkyl. In an embodiment $R_y$ is ($C_1$-$C_6$) haloalkyl. In an embodiment $R_y$ is alkoxyalkyl. In some embodiments of the Formulae above. $R^{6a}$ is H, ($C_1$-$C_4$) alkyl, ($C_1$-$C_4$) haloalkyl, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, $NR^{6b}R^{6c}$ and —OH. In another embodiment, $R^{6a}$ is H, ($C_1$-$C_4$) alkyl, or ($C_1$-$C_4$) haloalkyl. In yet another embodiment, $R^{6a}$ is H, ($C_1$-$C_4$) haloalkyl, or ($C_1$-$C_4$) alkyl optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH. In another embodiment, $R^{6a}$ is ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH. In yet another embodiment, $R^{6a}$ is H or ($C_1$-$C_4$) alkyl.

In some embodiments of the Formulae above, $R^{6b}$ is H, ($C_1$-$C_4$) alkyl, ($C_1$-$C_4$) haloalkyl, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH. In yet another embodiment, $R^6$ is H. ($C_1$-$C_4$) alkyl, or ($C_1$-$C_4$) haloalkyl. In another embodiment, R is H, ($C_1$-$C_4$) haloalkyl, or ($C_1$-$C_4$) alkyl optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH. In yet another embodiment, $R^{6b}$ is ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH. In another embodiment, $R^{6b}$ is H or ($C_1$-$C_4$) alkyl. In yet another embodiment, $R^{6b}$ is H.

In some embodiments of the Formulae above, $R^{6c}$ is H, ($C_1$-$C_4$) alkyl, ($C_1$-$C_4$) haloalkyl, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH. In another embodiment, $R^{6c}$ is H, ($C_1$-$C_4$) alkyl, or ($C_1$-$C_4$) haloalkyl. In yet another embodiment, $R^{6c}$ is H, ($C_1$-$C_4$) haloalkyl, or ($C_1$-$C_4$) alkyl optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH. In another embodiment, $R^{6c}$ is ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, ($C_1$-$C_6$) alkyl, ($C_1$-$C_6$) haloalkyl, ($C_1$-$C_6$) alkoxy, ($C_1$-$C_6$) haloalkoxy, and —OH. In yet another embodiment, $R^{6c}$ is H or ($C_1$-$C_4$) alkyl. In another embodiment, $R^1$ is H.

In some embodiments of the Formulae above, $R^{6d}$ is ($C_1$-$C_6$) alkyl, ($C_1$-$C_6$) haloalkyl, ($C_3$-$C_8$) cycloalkyl, ($C_6$-$C_{10}$) aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen, COOH, $(C_1-C_6)$ alkyl, $(C_1-C_6)$ haloalkyl, $(C_1-C_6)$ alkoxy, $(C_1-C_6)$ haloalkoxy, $(C_1-C_6)$ alkoxyalkoxy, —O—CO—$(C_1-C_6)$ alkyl, —O—CO—$(C_3-C_8)$ cycloalkyl, —O—CO—$(C_1-C_6)$ alkyl-COOH, $NR^{6b}R^{6c}$, $NR^{6f}CO$—$(C_1-C_6)$ alkyl, $NR^{6f}CO$—$(C_1-C_6)$ alkoxy, cycloalkyl, heterocycloalkyl and —OH. In an embodiment, $R^{6d}$ is $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6d}$ is $(C_1-C_4)$ alkyl, or $(C_1-C_4)$ haloalkyl. In yet another embodiment. $R^{6d}$ is $(C_1-C_4)$ haloalkyl, or $(C_1-C_4)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In yet another embodiment, $R^{6d}$ is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6d}$ is $(C_1-C_4)$ alkyl or $(C_3-C_8)$ cycloalkyl, wherein the alkyl or cycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In yet another embodiment, $R^{6d}$ is $(C_1-C_4)$ alkyl or $(C_3-C_8)$ cycloalkyl, wherein the alkyl or cycloalkyl are optionally substituted with one or more —OH. In another embodiment, $R^{6d}$ is $(C_1-C_4)$ alkyl or $(C_3-C_8)$ cycloalkyl.

In some embodiments of the Formulae above, $R^{6e}$ is —OH, $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is —OH, $(C_1-C_4)$ haloalkyl, $(C_1-C_4)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is $(C_3-C_8)$ cycloalkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^6$ is $(C_6-C_{10})$ aryl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6c}$ is heterocycloalkyl wherein the heterocycloalkyl comprises one or two 5- to 7-membered rings and 1-4 heteroatoms selected from the group consisting of N, O and S, optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is heteroaryl wherein the heteroaryl comprises one or two 5- or 6-membered rings and 1-4 heteroatoms selected from the group consisting of N, O and S, optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH.

In another embodiment, $R^{6e}$ is $(C_3-C_8)$ cycloalkyl or heterocycloalkyl wherein the heterocycloalkyl comprises one or two 5- to 7-membered rings and 1-4 heteroatoms selected from the group consisting of N, O and S, wherein the cycloalkyl or heterocycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^6$ is $(C_6-C_{10})$ aryl or heteroaryl wherein the heteroaryl comprises one or two 5- or 6-membered rings and 1-4 heteroatoms selected from the group consisting of N, O and S, wherein the aryl or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^6$ is $(C_1-C_4)$ alkyl or $(C_3-C_8)$ cycloalkyl, wherein the alkyl or cycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In yet another embodiment, $R^{6e}$ is $(C_1-C_4)$ alkyl or $(C_3-C_8)$ cycloalkyl, wherein the alkyl or cycloalkyl are optionally substituted with one or more —OH. In another embodiment, $R^{6e}$ is $(C_1-C_4)$ alkyl or $(C_3-C_8)$ cycloalkyl. In another embodiment, $R^{6e}$ is —OH, $(C_1-C_4)$ alkyl or $(C_3-C_8)$ cycloalkyl.

In some embodiments, $R^{6f}$ is $(C_1-C_6)$ alkyl or $(C_1-C_6)$ haloalkyl. In another embodiment, $R^{6f}$ is $(C_1-C_6)$ alkyl. In another embodiment, $R^{6f}$ is methyl. In another embodiment, $R^{6f}$ is $(C_1-C_6)$ haloalkyl. In another embodiment, $R^{6f}$ trifluoromethyl.

In some embodiments, $R^{6g}$ is H or $(C_1-C_6)$ alkyl optionally substituted with —O—CO—$(C_1-C_6)$ alkyl. In an embodiment, $R^{6g}$ is H. In an embodiment, $R^{6g}$ is $(C_1-C_6)$ alkyl optionally substituted with —O—CO—$(C_1-C_6)$ alkyl. In an embodiment. $R^{6g}$ is —$CH_2$—O—C(O)—$C(CH_3)_3$.

In some embodiments of the Formulae above, $R^7$ is $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, halogen, or CN. In another embodiment, $R^7$ is $(C_1-C_4)$ alkyl, $(C_1-C_4)$ alkoxy, $(C_1-C_4)$ haloalkyl, $(C_1-C_4)$ haloalkoxy, halogen, or CN. In yet another embodiment, $R^7$ is $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, or $(C_1-C_4)$ haloalkoxy. In another embodiment, $R^7$ is $(C_1-C_4)$ alkyl, $(C_2-C_4)$ alkenyl, $(C_2-C_4)$ alkynyl, or $(C_1-C_4)$ alkoxy. In yet another embodiment, $R^7$ is $(C_1-C_4)$ alkyl, $(C_2-C_4)$ alkenyl, $(C_2-C_4)$ alkynyl, $(C_1-C_4)$ alkoxy, or halogen. In another embodiment, $R^7$ is $(C_1-C_4)$ alkyl, $(C_1-C_4)$ alkoxy, $(C_1-C_4)$ haloalkyl, $(C_1-C_4)$ haloalkoxy, or halogen. In yet another embodiment, $R^7$ is $(C_1-C_4)$ alkoxy, $(C_1-C_4)$ haloalkyl, $(C_1-C_4)$ haloalkoxy, or halogen. In another embodiment. $R^7$ is $(C_1-C_4)$ haloalkyl, $(C_1-C_4)$ haloalkoxy, or halogen.

In some embodiments of the Formulae above, $R^8$ is $(C_1-C_4)$ alkyl, $(C_1-C_4)$ alkoxy, $(C_1-C_4)$ haloalkyl, $(C_1-C_4)$ haloalkoxy, halogen, or —OH. In another embodiment, $R^8$ is $(C_1-C_4)$ alkyl, $(C_1-C_4)$ alkoxy, $(C_1-C_4)$ haloalkyl, $(C_1-C_4)$ haloalkoxy, or halogen. In yet another embodiment, $R^8$ is $(C_1-C_4)$ alkyl, $(C_1-C_4)$ alkoxy, $(C_1-C_4)$ haloalkyl, or $(C_1-C_4)$ haloalkoxy. In another embodiment, $R^8$ is $(C_1-C_4)$ haloalkyl, $(C_1-C_4)$ haloalkoxy, halogen, or —OH. In yet another embodiment, $R^8$ is $(C_1-C_4)$ alkyl, $(C_1-C_4)$ alkoxy, halogen, or —OH. In another embodiment, $R^8$ is halogen, or —OH. In yet another embodiment, $R^8$ is $(C_1-C_4)$ alkoxy, $(C_1-C_4)$ haloalkyl, $(C_1-C_4)$ haloalkoxy, halogen, or —OH. In another embodiment, $R^8$ is $(C_1-C_4)$ alkyl, $(C_1-C_4)$ haloalkyl, $(C_1-C_4)$ haloalkoxy, halogen, or —OH. In yet another embodiment, $R^8$ is $(C_1-C_4)$ alkyl, $(C_1-C_4)$ alkoxy, $(C_1-C_4)$ haloalkoxy, halogen, or —OH. In another embodiment, $R^8$ is $(C_1-C_4)$ alkyl, $(C_1-C_4)$ alkoxy, $(C_1-C_4)$ haloalkyl, halogen, or —OH. In yet another embodiment, $R^8$ is $(C_1-C_4)$ alkyl, $(C_1-C_4)$ alkoxy, $(C_1-C_4)$ haloalkyl, $(C_1-C_4)$ haloalkoxy, or —OH.

In some embodiments of the Formulae above, $R^9$ is $(C_1-C_4)$ alkyl, $(C_1-C_4)$ alkoxy, $(C_1-C_4)$ haloalkyl, $(C_1-C_4)$ haloalkoxy, halogen, or —OH. In another embodiment. $R^9$ is $(C_1-C_4)$ alkyl, $(C_1-C_4)$ alkoxy, $(C_1-C_4)$ haloalkyl, $(C_1-C_4)$ haloalkoxy, or halogen. In yet another embodiment, $R^9$ is $(C_1-C_4)$ alkyl, $(C_1-C_4)$ alkoxy, $(C_1-C_4)$ haloalkyl, or $(C_1-C_4)$ haloalkoxy. In another embodiment, $R^9$ is $(C_1-C_4)$ haloalkyl, $(C_1-C_4)$ haloalkoxy, halogen, or —OH. In yet another embodiment, $R^9$ is $(C_1-C_4)$ alkyl, $(C_1-C_4)$ alkoxy, halogen, or —OH. In another embodiment, $R^9$ is halogen, or —OH. In yet another embodiment, $R^9$ is $(C_1-C_4)$ alkoxy. $(C_1-C_4)$ haloalkyl, $(C_1-C_4)$ haloalkoxy, halogen, or —OH. In another embodiment, $R^9$ is $(C_1-C_4)$ alkyl, $(C_1-C_4)$ haloalkyl, $(C_1-C_4)$ haloalkoxy, halogen, or —OH. In yet another embodiment, $R^9$ is $(C_1-C_4)$ alkyl, $(C_1-C_4)$ alkoxy, $(C_1-C_4)$ haloalkoxy, halogen, or —OH. In another embodiment, $R^9$ is $(C_1-C_4)$ alkyl, $(C_1-C_4)$ alkoxy, $(C_1-C_4)$ haloalkyl, halogen, or —OH. In yet another embodiment, $R^9$ is $(C_1-C_4)$ alkyl, $(C_1-C_4)$ alkoxy, $(C_1-C_4)$ haloalkyl, $(C_1-C_4)$ haloalkoxy, or —OH.

In some embodiments of the Formulae above, m is 0. In another embodiment, m is 1. In another embodiment, m is 2. In another embodiment, m is 1 or 2. In another embodiment, m is 0 or 1.

In some embodiments of the Formulae above, p is 1. In another embodiment, p is 2.

In some embodiments of the Formulae above, A is $(C_6-C_{10})$ aryl, $(C_3-C_8)$ cycloalkyl or heterocycloalkyl wherein the heterocycloalkyl comprises one or two 5- to 7-membered rings and 1-4 heteroatoms selected from the group consisting of N, O and S. In another embodiment, A is $(C_6-C_{10})$ aryl or $(C_3-C_8)$ cycloalkyl. In yet another embodiment, A is $(C_6-C_{10})$ aryl or heterocycloalkyl wherein the heterocycloalkyl comprises one or two 5- to 7-membered rings and 1-4 heteroatoms selected from the group consisting of N, O and S. In another embodiment, A is $(C_3-C_8)$ cycloalkyl or heterocycloalkyl wherein the heterocycloalkyl comprises one or two 5- to 7-membered rings and 1-4 heteroatoms selected from the group consisting of N, O and S. In yet another embodiment, A is phenyl or $(C_3-C_8)$ cycloalkyl. In another embodiment, A is phenyl or heterocycloalkyl wherein the heterocycloalkyl comprises one or two 5- to 7-membered rings and 1-4 heteroatoms selected from the group consisting of N, O and S. In yet another embodiment, A is phenyl. In another embodiment, A is cyclohexyl, bicyclo[2.2.2.]octanyl, or spiro[2.5]octanyl. In yet another embodiment, A is cyclohexyl or bicyclo[2.2.2.]octanyl. In another embodiment, A is bicyclo[2.2.2.]octanyl, or spiro[2.5]octanyl. In yet another embodiment, A is cyclohexyl, bicyclo[2.2.2.]octanyl, or tetrahydropyranyl. In another embodiment, A is cyclohexyl. In yet another embodiment, A is bicyclo[2.2.2.]octanyl. In another embodiment, A is tetrahydropyranyl.

In some embodiments of the Formulae above, $R^1$ and $R^2$ are each independently H, halogen, $(C_1-C_6)$ alkoxy, or $(C_1-C_6)$ haloalkoxy. In another embodiment, $R^1$ and $R^2$ are each independently H, halogen, or $(C_1-C_6)$ haloalkyl. In yet another embodiment, $R^1$ and $R^2$ are each independently halogen or $(C_1-C_6)$ haloalkyl. In another embodiment, $R^1$ is H and $R^2$ is halogen, $(C_1-C_6)$ haloalkyl, or $(C_1-C_6)$ haloalkoxy. In yet another embodiment, $R^1$ is H and $R^2$ is $(C_1-C_6)$ haloalkyl or $(C_1-C_6)$ haloalkoxy. In another embodiment, $R^1$ is H and $R^2$ is $(C_1-C_6)$ haloalkyl. In yet another embodiment, $R^1$ is H and $R^2$ is $(C_1-C_6)$ haloalkoxy. In another embodiment, $R^1$ is halogen and $R^2$ is halogen, $(C_1-C_6)$ haloalkyl, or $(C_1-C_6)$ haloalkoxy. In yet another embodiment, $R^1$ is halogen and $R^2$ is $(C_1-C_6)$ haloalkoxy. In another embodiment, $R^1$ is halogen and $R^2$ is $(C_1-C_6)$ haloalkyl. In yet another embodiment, $R^1$ is halogen and $R^2$ is halogen.

In some embodiments of the Formulae above. B is unsubstituted heteroaryl comprising one or two 5- or 6-member rings and 1-4 heteroatoms selected from the group consisting of N, O and S.

In some embodiments of the Formulae above, B is heteroaryl comprising one or two 5- or 6-member rings and 1-4 heteroatoms selected from the group consisting of N, O and S, substituted with one or more halogen, $(C_1-C_6)$ alkyl, $(C_1-C_6)$ alkoxy, $(C_1-C_6)$ haloalkoxy, or $(C_3-C_8)$ cycloalkyl.

In some embodiments of the Formulae above, B is unsubstituted $(C_6-C_{10})$ aryl. In some embodiments of the Formulae above, B is $(C_6-C_{10})$ aryl optionally substituted with $(C_1-C_6)$ alkyl, halogen, $(C_1-C_6)$ alkoxy, $(C_1-C_6)$ haloalkoxy, or $(C_3-C_8)$ cycloalkyl.

In some embodiments of the Formulae above, B is pyrimidinyl, furanyl, benzo[d]thiazolyl, 1-methyl-1H-benzo[d]imidazolyl, 1-methyl-1H-indolyl, benzo[d]isoxazolyl, 2,2-difluoro-1-methylindolin-3-onyl, or 7-fluoro-1-methyl-1H-benzo[d]imidazolyl, wherein each B is optionally substituted with one or more halogen, $(C_1-C_6)$ alkyl, $(C_1-C_6)$ alkoxy, or $(C_1-C_6)$ haloalkyl.

In some embodiments of the Formulae above, $R^3$ is $(C_3-C_8)$ cycloalkyl optionally substituted with halogen or $(C_1-C_6)$ alkyl. In another embodiment, $R^3$ is $(C_3-C_8)$ cycloalkyl optionally substituted with halogen. In another embodiment, $R^3$ is unsubstituted $(C_3-C_8)$ cycloalkyl.

In some embodiments of the Formulae above, $L_1$ is $-(CH_2)_m(C{=}O)-$ and $L_2$ is a bond. In another embodiment, $L_1$ is $-(CH_2)_m(C{=}O)-$, $L_2$ is a bond and A is ($C_3$-$C_8$) cycloalkyl, ($C_6$-$C_{10}$) aryl or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, $L_1$ is —$(CH_2)_m$(C═O)—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is —$(CH_2)_m$(C═O)—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^1$ is H, halogen, or ($C_1$-$C_4$) haloalkyl. In another embodiment, $L_1$ is —$(CH_2)_m$(C═O)—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is a —$(CH_2)_m$(C═O)—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_m$(C═O)—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C═O)— and $L_2$ is a bond. In another embodiment, $L_1$ is —$(CH_2)_m$(C═O)—, $L_2$ is a bond and A is ($C_3$-$C_8$) cycloalkyl or ($C_6$-$C_{10}$) aryl wherein the cycloalkyl or aryl are optionally substituted with one or more $R^7$. In another embodiment, $L_1$ is —$(CH_2)_m$(C═O)—, $L_2$ is a bond, A is ($C_3$-$C_8$) cycloalkyl or ($C_6$-$C_{10}$) aryl wherein the cycloalkyl or aryl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is a —$(CH_2)_m$(C═O)—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_m$(C═O)—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_m$(C═O)—, $L_2$ is a bond, A is ($C_3$-$C_8$) cycloalkyl or ($C_6$-$C_{10}$) aryl, wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl, or ($C_1$-$C_4$) haloalkoxy. In another embodiment, $L_1$ is —$(CH_2)_m$ (C═O)—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C═O)—, $L_2$ is a bond and A is ($C_3$-$C_8$) cycloalkyl optionally substituted with one or more $R^7$. In another embodiment, $L_1$ is —$(CH_2)_m$(C═O)—, $L_2$ is a bond, A is ($C_3$-$C_8$) cycloalkyl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and H, halogen, or ($C_1$-$C_4$) haloalkyl.

In another embodiment, $L_1$ is —$(CH_2)_m$(C═O)—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_m$(C═O)—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_m$(C═O)—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_m$(C═O)—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C═O)—, $L_2$ is a bond, and A is ($C_6$-$C_{10}$) aryl optionally substituted with one or more $R^7$. In another embodiment, $L_1$ is —$(CH_2)_m$(C═O)—, $L_2$ is a bond, A is ($C_6$-$C_{10}$) aryl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is a bond, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is —$(CH_2)_m$(C═O)—, $L_2$ is a bond, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is —$(CH_2)_m$(C═O)—, $L_2$ is a bond, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_m$(C═O)—, $L_2$ is a bond, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is —$(CH_2)_m$(C═O)—, $L_2$ is a bond, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen. ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C═O)—, $L_2$ is a bond, and A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, $L_1$ is —$(CH_2)_m$(C═O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is —$(CH_2)_m$(C═O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is —$(CH_2)_m$(C═O)—, $L_2$ is a bond. A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_m$(C═O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is —$(CH_2)_m$(C═O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$— and $L_2$ is a bond. In another embodiment, $L_1$ is —$(CH_2)_p$—. $L_2$ is a bond and A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is a —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$— and $L_2$ is a bond. In another embodiment, $L_1$ is —$(CH_2)_p$—, $L_2$ is a bond and A is ($C_3$-$C_8$) cycloalkyl or ($C_6$-$C_{10}$) aryl wherein the cycloalkyl or aryl are optionally substituted with one or more $R^7$. In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or ($C_6$-$C_{10}$) aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is a —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment. $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl, or ($C_1$-$C_4$) haloalkoxy. In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$—, $L_2$ is a bond and A is ($C_3$-$C_8$) cycloalkyl optionally substituted with one or more $R^7$. In another embodiment, $L_1$ is —$(CH_2)_p$—, $L_2$ is a bond, A is ($C_3$-$C_8$) cycloalkyl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and H, halogen, or ($C_1$-$C_4$) haloalkyl.

In another embodiment, $L_1$ is —$(CH_2)_p$—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_p$—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_p$—, $L_2$ is a bond, A is ($C_3$-$C_8$) cycloalkyl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, $R^2$ is halogen or $(C_1-C_4)$ haloalkyl, and $R^3$ is $(C_3-C_7)$ cycloalkyl optionally substituted with one or more substituents each independently selected from the group consisting of halogen or $(C_1-C_4)$ alkyl.

In some embodiments of the Formulae above, $L_1$ is $-(CH_2)_p-$, $L_2$ is a bond, and A is $(C_6-C_{10})$ aryl optionally substituted with one or more $R^7$. In another embodiment, $L_1$ is $-(CH_2)_p-$, $L_2$ is a bond, A is $(C_6-C_{10})$ aryl optionally substituted with one or more $R^7$, and B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is $-(CH_2)_p-$, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is $-(CH_2)_p-$, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is $-(CH_2)_p-$, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is $-(CH_2)_p-$, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkoxy, $(C_1-C_4)$ haloalkyl, or $(C_1-C_4)$ haloalkoxy. In another embodiment, $L_1$ is $-(CH_2)_p-$, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is $-(CH_2)_p-$, $L_2$ is a bond, and A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, $L_1$ is $-(CH_2)_p-$, $L_2$ is a bond. A is heterocycloalkyl wherein the heterocycloalkyl comprises one or two 5- to 7-membered rings and 1-4 heteroatoms selected from the group consisting of N, O and S, optionally substituted with one or more $R^7$, and B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is $-(CH_2)_p-$, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is $-(CH_2)_p-$, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is $-(CH_2)_p-$, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is $-(CH_2)_p-$, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkoxy, $(C_1-C_4)$ haloalkyl, or $(C_1-C_4)$ haloalkoxy. In another embodiment, $L_1$ is $-(CH_2)_p-$, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C═O)— and $L_2$ is —$S(O)_2$—. In another embodiment, $L_1$ is —$(CH_2)_m$(C═O)—, $L_2$ is —$S(O)_2$— and A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, $L_1$ is —$(CH_2)_m$(C═O)—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is —$(CH_2)_m$(C═O)—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_m$(C═O)—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is a —$(CH_2)_m$(C═O)—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_m$(C═O)—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C═O)—, $L_2$ is —$S(O)_2$— and A is ($C_3$-$C_8$) cycloalkyl or ($C_6$-$C_{10}$) aryl wherein the cycloalkyl or aryl are optionally substituted with one or more $R^7$. In another embodiment, $L_1$ is —$(CH_2)_m$(C═O)—. $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is a —$(CH_2)_m$(C═O)—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_m$(C═O)—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_m$(C═O)—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl, or ($C_1$-$C_4$) haloalkoxy. In another embodiment, $L_1$ is —$(CH_2)_m$(C═O)—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C═O)—, $L_2$ is —$S(O)_2$—, and A is ($C_3$-$C_8$) cycloalkyl optionally substituted with one or more $R^7$. In another embodiment, $L_1$ is —$(CH_2)_m$(C═O)—, $L_2$ is —$S(O)_2$—, A is ($C_3$-$C_8$) cycloalkyl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and H, halogen, or ($C_1$-$C_4$) haloalkyl.

In another embodiment, $L_1$ is —$(CH_2)_m$(C═O)—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_m$(C═O)—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_m$(C═O)—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_m$(C═O)—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C═O)—, $L_2$ is —$S(O)_2$—, and A is ($C_6$-$C_{10}$) aryl optionally substituted with one or more $R^7$. In another embodiment, $L_1$ is —$(CH_2)_m$(C═O)—, $L_2$ is —$S(O)_2$—, A is ($C_6$-$C_{10}$) aryl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C═O)—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is —$(CH_2)_m$(C═O)—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is —$(CH_2)_m$(C═O)—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_m$(C═O)—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, $(C_1\text{-}C_4)$ alkoxy, $(C_1\text{-}C_4)$ haloalkyl, or $(C_1\text{-}C_4)$ haloalkoxy. In another embodiment, $L_1$ is $-(CH_2)_m(C{=}O)-$. $L_2$ is $-S(O)_2-$, A is $(C_6\text{-}C_{10})$ aryl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, $R^2$ is halogen, $(C_1\text{-}C_4)$ alkoxy, $(C_1\text{-}C_4)$ haloalkyl, or $(C_1\text{-}C_4)$ haloalkoxy, and $R^3$ is $(C_1\text{-}C_4)$ alkyl or $(C_3\text{-}C_7)$ cycloalkyl optionally substituted with one or more substituents each independently selected from the group consisting of halogen or $(C_1\text{-}C_4)$ alkyl.

In some embodiments of the Formulae above, $L_1$ is $-(CH_2)_m(C{=}O)-$, $L_2$ is $-S(O)_2-$, and A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, $L_1$ is $-(CH_2)_m(C{=}O)-$, $L_2$ is $-S(O)_2-$, A is heterocycloalkyl wherein the heterocycloalkyl comprises one or two 5- to 7-membered rings and 1-4 heteroatoms selected from the group consisting of N, O and S, optionally substituted with one or more $R^7$, and B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is $-(CH_2)_m(C{=}O)-$, $L_2$ is $-S(O)_2-$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1\text{-}C_4)$ alkoxy, $(C_1\text{-}C_4)$ haloalkyl, or $(C_1\text{-}C_4)$ haloalkoxy.

In another embodiment, $L_1$ is $-(CH_2)_m(C{=}O)-$, $L_2$ is $-S(O)_2-$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, and $R^2$ is H, halogen, $(C_1\text{-}C_4)$ alkoxy, $(C_1\text{-}C_4)$ haloalkyl, or $(C_1\text{-}C_4)$ haloalkoxy. In another embodiment, $L_1$ is $-(CH_2)_m(C{=}O)-$, $L_2$ is $-S(O)_2-$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, $R^2$ is H, halogen, $(C_1\text{-}C_4)$ alkoxy, $(C_1\text{-}C_4)$ haloalkyl, or $(C_1\text{-}C_4)$ haloalkoxy, and $R^3$ is $(C_1\text{-}C_4)$ alkyl or $(C_3\text{-}C_7)$ cycloalkyl optionally substituted with one or more substituents each independently selected from the group consisting of halogen or $(C_1\text{-}C_4)$ alkyl.

In another embodiment, $L_1$ is $-(CH_2)_m(C{=}O)-$, $L_2$ is $-S(O)_2-$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy. $(C_1\text{-}C_4)$ haloalkyl, or $(C_1\text{-}C_4)$ haloalkoxy, and R is halogen, $(C_1\text{-}C_4)$ alkoxy, $(C_1\text{-}C_4)$ haloalkyl, or $(C_1\text{-}C_4)$ haloalkoxy. In another embodiment, $L_1$ is $-(CH_2)_m(C{=}O)-$, $L_2$ is $-S(O)_2-$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, $R^2$ is halogen, $(C_1\text{-}C_4)$ alkoxy, $(C_1\text{-}C_4)$ haloalkyl, or $(C_1\text{-}C_4)$ haloalkoxy, and $R^3$ is $(C_1\text{-}C_4)$ alkyl or $(C_3\text{-}C_7)$ cycloalkyl optionally substituted with one or more substituents each independently selected from the group consisting of halogen or $(C_1\text{-}C_4)$ alkyl.

In some embodiments of the Formulae above, $L_1$ is $-(CH_2)_p-$ and $L_2$ is $-S(O)_2-$. In another embodiment, $L_1$ is $-(CH_2)_p-$, $L_2$ is $-S(O)_2-$ and A is $(C_3\text{-}C_8)$ cycloalkyl, $(C_6\text{-}C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, alkyl, or heterocycloalkyl are optionally substituted with one or more $R^7$. In another embodiment, $L_1$ is $-(CH_2)_p-$, $L_2$ is $-S(O)_2-$, A is $(C_3\text{-}C_8)$ cycloalkyl, $(C_6\text{-}C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, and B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is $-(CH_2)_p-$, $L_2$ is $-S(O)_2-$, A is $(C_3\text{-}C_8)$ cycloalkyl, $(C_6\text{-}C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or $(C_1\text{-}C_4)$ haloalkyl.

In another embodiment, $L_1$ is $-(CH_2)_p-$, $L_2$ is $-S(O)_2-$, A is $(C_3\text{-}C_8)$ cycloalkyl, $(C_6\text{-}C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is a —$(CH_2)_p$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment. $L_1$ is —$(CH_2)_p$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$— and $L_2$ is —$S(O)_2$—. In another embodiment, $L_1$ is —$(CH_2)_p$—, $L_2$ is —$S(O)_2$—, and A is ($C_3$-$C_8$) cycloalkyl or ($C_6$-$C_{10}$) aryl wherein the cycloalkyl or aryl are optionally substituted with one or more $R^7$. In another embodiment, $L_1$ is —$(CH_2)_p$—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is a —$(CH_2)_p$—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_p$—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl, or ($C_1$-$C_4$) haloalkoxy. In another embodiment, $L_1$ is —$(CH_2)_p$—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$—, $L_2$ is —$S(O)_2$—, and A is ($C_3$-$C_8$) cycloalkyl optionally substituted with one or more $R^7$. In another embodiment, $L_1$ is —$(CH_2)_p$—, $L_2$ is —$S(O)_2$—, A is ($C_3$-$C_8$) cycloalkyl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and H, halogen, or ($C_1$-$C_4$) haloalkyl.

In another embodiment, $L_1$ is —$(CH_2)_p$—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_p$—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_p$—, $L_2$ is —$S(O)_2$—, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$—, $L_2$ is —$S(O)_2$—, and A is ($C_6$-$C_{10}$) aryl optionally substituted with one or more $R^7$. In another embodiment, $L_1$ is —$(CH_2)_p$—, $L_2$ is —$S(O)_2$—, A is ($C_6$-$C_{10}$) aryl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is —$(CH_2)_p$—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is —$(CH_2)_p$—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_p$—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is —$(CH_2)_p$—, $L_2$ is —$S(O)_2$—, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen. ($C_1$-$C_4$) alkoxy, ($C_1$-$C_4$) haloalkyl, or ($C_1$-$C_4$) haloalkoxy, $R^1$ is halogen, ($C_1$-$C_4$) alkoxy, ($C_1$-$C_4$) haloalkyl, or ($C_1$-$C_4$) haloalkoxy, and $R^2$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$—, $L_2$ is —$S(O)_2$—, and A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, $L_1$ is —$(CH_2)_p$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is —$(CH_2)_p$—, $L_2$ is —$S(O)_2$—. A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is —$(CH_2)_p$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, $R^2$ is H, halogen, $(C_1\text{-}C_4)$ alkoxy, $(C_1\text{-}C_4)$ haloalkyl, or $(C_1\text{-}C_4)$ haloalkoxy, and $R^3$ is $(C_1\text{-}C_4)$ alkyl or $(C_3\text{-}C_7)$ cycloalkyl optionally substituted with one or more substituents each independently selected from the group consisting of halogen or $(C_1\text{-}C_4)$ alkyl.

In another embodiment, $L_1$ is $—(CH_2)_p—$, $L_2$ is $—S(O)_2—$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, and $R^2$ is halogen, $(C_1\text{-}C_4)$ alkoxy, $(C_1\text{-}C_4)$ haloalkyl, or $(C_1\text{-}C_4)$ haloalkoxy. In another embodiment. $L_1$ is $—(CH_2)_p—$, $L_2$ is $—S(O)_2—$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, $R^2$ is halogen, $(C_1\text{-}C_4)$ alkoxy, $(C_1\text{-}C_4)$ haloalkyl, or $(C_1\text{-}C_4)$ haloalkoxy, and $R^3$ is $(C_1\text{-}C_4)$ alkyl or $(C_3\text{-}C_7)$ cycloalkyl optionally substituted with one or more substituents each independently selected from the group consisting of halogen or $(C_1\text{-}C_4)$ alkyl.

Non-limiting illustrative compounds of the invention include:

2-[(1S,4S,5R)-5-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic acid (I-1);

2-[(1S,4S,5R)-5-[5-cyclopropyl-3-(2,6-dichlorophenyl)-1,2-oxazole-4-carbonyloxy]-2-azabicyclo[2.2.1]heptan-2-yl]-1,3-benzothiazole-6-carboxylic acid (I-2);

2-[(1S,4S,5R)-5-[5-cyclopropyl-3-(2,6-dichlorophenyl)-1,2-oxazole-4-carbonyloxy]-2-azabicyclo[2.2.1]heptan-2-yl]-4-methyl-1,3-benzothiazole-6-carboxylic acid (I-3);

4-cyclopropyl-2-[(1S,4S,5R)-5-[5-cyclopropyl-3-(2,6-dichlorophenyl)-1,2-oxazole-4-carbonyloxy]-2-azabicyclo[2.2.1]heptan-2-yl]-1,3-benzothiazole-6-carboxylic acid (I-4);

2-[(1S,4S,5R)-5-[5-cyclopropyl-3-(2,6-dichlorophenyl)-1,2-oxazole-4-carbonyloxy]-2-azabicyclo[2.2.1]heptan-2-yl]-4-(trifluoromethyl)-1,3-benzothiazole-6-carboxylic acid (I-5);

2-[(1S,4S,5R)-5-[5-cyclopropyl-3-(2,6-dichlorophenyl)-1,2-oxazole-4-carbonyloxy]-2-azabicyclo[2.2.1]heptan-2-yl]-4-(trifluoromethoxy)-1,3-benzothiazole-(6-carboxylic acid (I-6);

2-[(1S,4S,5R)-5-[5-cyclopropyl-3-(2,6-dichlorophenyl)-1,2-oxazole-4-carbonyloxy]-2-azabicyclo[2.2.1]heptan-2-yl]-4-(2,2,2-trifluoroethoxy)-1,3-benzothiazole-6-carboxylic acid (I-7);

2-[(1S,4S,5R)-5-[5-cyclopropyl-3-(2,6-dichlorophenyl)-1,2-oxazole-4-carbonyloxy]-2-azabicyclo[2.2.1]heptan-2-yl]-4-ethoxy-1,3-benzothiazole-6-carboxylic acid (I-8);

2-[(1S,4S,5R)-5-{5-cyclopropyl-3-[2-(trifluoromethyl)phenyl]-1,2-oxazole-4-carbonyloxy}-2-azabicyclo[2.2.1]heptan-2-yl]-4-(trifluoromethoxy)-1,3-benzothiazole-6-carboxylic acid (I-9);

2-[(1S,4S,5R)-5-[3-(2,6-dichlorophenyl)-5-(1-fluorocyclopropyl)-1,2-oxazole-4-carbonyloxy]-2-azabicyclo[2.2.1]heptan-2-yl]-4-fluoro-1,3-benzothiazole-6-carboxylic acid (I-10);

2-[(1S,4S,5R)-5-(3-{bicyclo[2.2.2]octan-1-yl}-5-cyclopropyl-1,2-oxazole-4-carbonyloxy)-2-azabicyclo[2.2.1]heptan-2-yl]-4-fluoro-1,3-benzothiazole-6-carboxylic acid (I-11);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic acid (I-12);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-methyl-1,3-benzothiazole-6-carboxylic acid (I-13);

4-cyclopropyl-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic acid (I-14);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(trifluoromethyl)-1,3-benzothiazole-6-carboxylic acid (I-15);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(trifluoromethoxy)-1,3-benzothiazole-(6-carboxylic acid (I-16);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(2,2,2-trifluoroethoxy)-1,3-benzothiazole-6-carboxylic acid (I-17);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-ethoxy-1,3-benzothiazole-6-carboxylic acid (I-18);

2-[(1S,4S,5R)-5-({5-cyclopropyl-3-[2-(trifluoromethyl)phenyl]-1,2-oxazol-4-yl}methoxy)-2-azabicyclo[2.2.1]heptan-2-yl]-4-fluoro-1,3-benzothiazole-6-carboxylic acid (I-19);

2-[(1S,4S,5R)-5-({5-cyclopropyl-3-[2-(trifluoromethyl)phenyl]-1,2-oxazol-4-yl}methoxy)-2-azabicyclo[2.2.1]heptan-2-yl]-4-(trifluoromethoxy)-1,3-benzothiazole-6-carboxylic acid (I-20);

2-[(1S,4S,5R)-5-[(3-cyclohexyl-5-cyclopropyl-1,2-oxazol-4-yl)methoxy]-2-azabicyclo[2.2.1]heptan-2-yl]-4-(trifluoromethoxy)-1,3-benzothiazole-6-carboxylic acid (I-21);

2-[(1S,4S,5R)-5-[(3-cyclohexyl-5-cyclopropyl-1,2-oxazol-4-yl)methoxy]-2-azabicyclo[2.2.1]heptan-2-yl]-4-fluoro-1,3-benzothiazole-6-carboxylic acid (I-22);

2-[(1S,4S,5R)-5-{[5-cyclopropyl-3-(oxan-4-yl)-1,2-oxazol-4-yl]methoxy}-2-azabicyclo[2.2.1]heptan-2-yl]-4-(trifluoromethoxy)-1,3-benzothiazole-6-carboxylic acid (I-23);

2-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-4-fluoro-1,3-benzothiazole-6-carboxylic acid (I-24);

2-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-4-(trifluoromethoxy)-1,3-benzothiazole-6-carboxylic acid (I-25);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-6-(2H-1,2,3,4-tetrazol-5-yl)-1,3-benzothiazole (I-26);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-6-(2H-1,2,3,4-tetrazol-5-yl)-4-(trifluoromethoxy)-1,3-benzothiazole (I-27);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-N-methanesulfonyl-1,3-benzothiazole-6-carboxamide (I-28);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-N-(propane-1-sulfonyl)-1,3-benzothiazole-6-carboxamide (I-29);

N-(cyclopropanesulfonyl)-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxamide (I-30);

(1S,4S,5R)-2-[4-fluoro-6-(methanesulfonylcarbamoyl)-1,3-benzothiazol-2-yl]-2-azabicyclo[2.2.1]heptan-5-yl 5-cyclopropyl-3-(2,6-dichlorophenyl)-1,2-oxazole-4-carboxylate (I-31);

(1S,4S,5R)-2-{4-fluoro-6-[(propane-1-sulfonyl)carbamoyl]-1,3-benzothiazol-2-yl}-2-azabicyclo[2.2.1]heptan-5-yl 5-cyclopropyl-3-(2,6-dichlorophenyl)-1,2-oxazole-4-carboxylate (I-32);

(1S,4S,5R)-2-{6-[(cyclopropanesulfonyl)carbamoyl]-4-fluoro-1,3-benzothiazol-2-yl}-2-azabicyclo[2.2.1]heptan-5-yl 5-cyclopropyl-3-(2,6-dichlorophenyl)-1,2-oxazole-4-carboxylate (I-33);

2-[(1S,4S,5S)-5-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic acid (I-34);

2-[(1S,4S,5S)-5-[5-cyclopropyl-3-(2,6-dichlorophenyl)-1,2-oxazole-4-carbonyloxy]-2-azabicyclo[2.2.1]heptan-2-yl]-1,3-benzothiazole-6-carboxylic acid (I-35);

methyl 2-[(1S,4S,5S)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylate (I-36);

2-[(1S,4S,5S)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic acid (I-37);

2-[(1R,4R,5S)-5-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic acid (I-38);

2-[(1R,4R,5S)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic acid (I-39);

2-[(1R,4R,5R)-5-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic acid (I-40);

2-[(1R,4R,5R)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic acid (I-41);

4-[(1S,4S,5R)-5-[5-cyclopropyl-3-(2,6-dichlorophenyl)-1,2-oxazole-4-carbonyloxy]-2-azabicyclo[2.2.1]heptan-2-yl]benzoic acid (I-42);

4-[(1S,4S,5R)-5-[5-cyclopropyl-3-(2,6-dichlorophenyl)-1,2-oxazole-4-carbonyloxy]-2-azabicyclo[2.2.1]heptan-2-yl]-3-fluorobenzoic acid (I-43);

4-[(1S,4S,5R)-5-[3-(2,6-dichlorophenyl)-5-(1-fluorocyclopropyl)-1,2-oxazole-4-carbonyloxy]-2-azabicyclo[2.2.1]heptan-2-yl]-3-fluorobenzoic acid (I-44);

(1S,4S,5R)-2-[4-(methanesulfonylcarbamoyl)phenyl]-2-azabicyclo[2.2.1]heptan-5-yl 5-cyclopropyl-3-(2,6-dichlorophenyl)-1,2-oxazole-4-carboxylate (I-45);

(1S,4S,5R)-2-{4-[(propane-1-sulfonyl)carbamoyl]phenyl}-2-azabicyclo[2.2.1]heptan-5-yl 5-cyclopropyl-3-(2,6-dichlorophenyl)-1,2-oxazole-4-carboxylate (I-46);

(1S,4S,5R)-2-{4-[(cyclopropanesulfonyl)carbamoyl]phenyl}-2-azabicyclo[2.2.1]heptan-5-yl 5-cyclopropyl-3-(2,6-dichlorophenyl)-1,2-oxazole-4-carboxylate (I-47);

(1S,4S,5R)-2-[2-fluoro-4-(methanesulfonylcarbamoyl)phenyl]-2-azabicyclo[2.2.1]heptan-5-yl 5-cyclopropyl-3-(2,6-dichlorophenyl)-1,2-oxazole-4-carboxylate (I-48);

(1S,4S,5R)-2-{2-fluoro-4-[(propane-1-sulfonyl)carbamoyl]phenyl}-2-azabicyclo[2.2.1]heptan-5-yl 5-cyclopropyl-3-(2,6-dichlorophenyl)-1,2-oxazole-4-carboxylate (I-49);

(1S,4S,5R)-2-[4-(2H-1,2,3,4-tetrazol-5-yl)phenyl]-2-azabicyclo[2.2.1]heptan-5-yl 5-cyclopropyl-3-(2,6-dichlorophenyl)-1,2-oxazole-4-carboxylate (I-50);

(1S,4S,5R)-2-[2-fluoro-4-(2H-1,2,3,4-tetrazol-5-yl)phenyl]-2-azabicyclo[2.2.1]heptan-5-yl 5-cyclopropyl-3-(2,6-dichlorophenyl)-1,2-oxazole-4-carboxylate (I-51);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoic acid (I-52);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorobenzoic acid (I-53);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3,5-difluorobenzoic acid (I-54);

6-[(1S,4S,5R)-5-{[5-cyclopropyl-3-(2,6-dichlorophenyl)-1,2-oxazol-4-yl]methoxy}-2-azabicyclo[2.2.1]heptan-2-yl]pyridine-3-carboxylic acid (I-55);

4-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]benzoic acid (I-56);

4-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-3-fluorobenzoic acid (I-57);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-methanesulfonylbenzamide (I-58);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(propane-1-sulfonyl)benzamide (I-59);

N-(cyclopropanesulfonyl)-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzamide (I-60);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluoro-N-(propane-1-sulfonyl)benzamide (I-61);

N-(cyclopropanesulfonyl)-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorobenzamide (I-62);

2-[(1R,4S,6R)-6-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic acid (I-63);

2-[(1R,4S,6S)-6-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic acid (I-64);

2-[(1R,4S,6R)-6-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic acid (I-65);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3,5-difluorobenzonitrile (I-54a)

2-Cyano-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoic acid (I-101);

3-cyano-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoic acid (I-102);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorobenzoic acid (I-103);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,6-difluorobenzoic acid (I-104);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,5-difluorobenzoic acid (I-105);

4-((1S,4S,5R)-5-((5-cyclopropyl-3-(2,6-dichlorophenyl)isoxazol-4-yl)methoxy)-2-azabicyclo[2.2.1]heptan-2-yl)-3-(trifluoromethyl)benzoic acid (I-106);

4-((1S,4S,5R)-5-((5-cyclopropyl-3-(2,6-dichlorophenyl)isoxazol-4-yl)methoxy)-2-azabicyclo[2.2.1]heptan-2-yl)-3-methylbenzoic acid (I-107);

3-cyclopropyl-4-((1S,4S,5R)-5-((5-cyclopropyl-3-(2,6-dichlorophenyl)isoxazol-4-yl)methoxy)-2-azabicyclo[2.2.1]heptan-2-yl)benzoic acid (I-108);

4-((1S,4S,5R)-5-((5-cyclopropyl-3-(2,6-dichlorophenyl)isoxazol-4-yl)methoxy)-2-azabicyclo[2.2.1]heptan-2-yl)-3-ethylbenzoic acid (I-109);

4-((1S,4S,5R)-5-((5-cyclopropyl-3-(2,6-dichlorophenyl)isoxazol-4-yl)methoxy)-2-azabicyclo[2.2.1]heptan-2-yl)-2,3-difluorobenzoic acid (I-110);

4-((1S,4S,5R)-5-((5-cyclopropyl-3-(2,6-dichlorophenyl)isoxazol-4-yl)methoxy)-2-azabicyclo[2.2.1]heptan-2-yl)-2-methylbenzoic acid (I-111);

4-((1S,4S,5R)-5-((5-cyclopropyl-3-(2,6-dichlorophenyl)isoxazol-4-yl)methoxy)-2-azabicyclo[2.2.1]heptan-2-yl)-2-methoxybenzoic acid (I-112);

4-[(1S,4S,5R)-5-{([3-(2-chloro-6-methylphenyl)-5-cyclopropyl-1,2-oxazol-4-yl]methoxy}-2-azabicyclo[2.2.1]heptan-2-yl]-3-fluorobenzoic acid (I-113);

4-[(1S,4S,5R)-5-{[3-(2-chloro-(6-methylphenyl)-5-cyclopropyl-1,2-oxazol-4-yl]methoxy}-2-azabicyclo[2.2.1]heptan-2-yl]-benzoic acid (I-114);

4-[(1S,4S,5R)-5-{[3-(2-chloro-6-methylphenyl)-5-cyclopropyl-1,2-oxazol-4-yl]methoxy}-2-azabicyclo[2.2.1]heptan-2-yl]-2-fluorobenzoic acid (I-115);

4-[(1S,4S,5R)-5-{[5-cyclopropyl-3-(2,6-dimethylphenyl)-1,2-oxazol-4-yl]methoxy}-2-azabicyclo[2.2.1]heptan-2-yl]-3-fluorobenzoic acid (I-116);

4-[(1S,4S,5R)-5-{[5-cyclopropyl-3-(2,6-dimethylphenyl)-1,2-oxazol-4-yl]methoxy}-2-azabicyclo[2.2.1]heptan-2-yl]benzoic acid (I-117);

4-[(1S,4S,5R)-5-{[3-(2-chloro-6-fluorophenyl)-5-cyclopropyl-1,2-oxazol-4-yl]methoxy}-2-azabicyclo[2.2.1]heptan-2-yl]benzoic acid (I-118);

4-[(1S,4S,5R)-5-{[3-(2-chloro-6-fluorophenyl)-5-cyclopropyl-1,2-oxazol-4-yl]methoxy}-2-azabicyclo[2.2.1]heptan-2-yl]-3-fluorobenzoic acid (I-119);

4-[(1S,4S,5R)-5-({5-cyclopropyl-3-[2-(trifluoromethyl)phenyl]-1,2-oxazol-4-yl}methoxy)-2-azabicyclo[2.2.1]heptan-2-yl]benzoic acid (I-120);

4-[(1S,4S,5R)-5-({5-cyclopropyl-3-[2-(trifluoromethyl)phenyl]-1,2-oxazol-4-yl}methoxy)-2-azabicyclo[2.2.1]heptan-2-yl]-3-fluorobenzoic acid (I-121);

4-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-2-fluorobenzoic acid (I-122);

2-cyano-4-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]benzoic acid (I-123);

4-[(1S,4S,5R)-5-{[3-(2-chloro-6-methylphenyl)-5-(1-fluorocyclopropyl)-1,2-oxazol-4-yl]methoxy}-2-azabicyclo[2.2.1]heptan-2-yl]-2-fluorobenzoic acid (I-124);

4-[(1S,4S,5R)-5-[(5-cyclopropyl-3-{spiro[2.5]octan-6-yl}-1,2-oxazol-4-yl)methoxy]-2-azabicyclo[2.2.1]heptan-2-yl]benzoic acid (I-125);

4-[(1S,4S,5R)-5-[(5-cyclopropyl-3-{spiro[2.5]octan-(6-yl}-1,2-oxazol-4-yl)methoxy]-2-azabicyclo[2.2.1]heptan-2-yl]-3-fluorobenzoic acid (I-126);

(1S,4S,5R)-2-(4-carboxyphenyl)-5-{[5-cyclopropyl-3-(2,6-dichlorophenyl)-1,2-oxazol-4-yl]methoxy}-2-azabicyclo[2.2.1]heptan-2-ium-2-olate (I-127);

5-[(1S,4S,5R)-5-{[5-cyclopropyl-3-(2,6-dichlorophenyl)-1,2-oxazol-4-yl]methoxy}-2-azabicyclo[2.2.1]heptan-2-yl]pyridine-2-carboxylic acid (I-128);

6-[(1S,4S,5R)-5-{([5-cyclopropyl-3-(2,6-dichlorophenyl)-1,2-oxazol-4-yl]methoxy}-2-azabicyclo[2.2.1]heptan-2-yl]-5-fluoropyridine-3-carboxylic Acid (I-129);

6-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-5-fluoropyridine-3-carboxylic acid (I-130);

4-[(1R,4R,5S)-5-{[5-cyclopropyl-3-(2,6-dichlorophenyl)-1,2-oxazol-4-yl]methoxy}-2-azabicyclo[2.2.1]heptan-2-yl]-3-fluorobenzoic acid (I-131);

4-[(1R,4R,5S)-5-{[5-cyclopropyl-3-(2,6-dichlorophenyl)-1,2-oxazol-4-yl]methoxy}-2-azabicyclo[2.2.1]heptan-2-yl]benzoic acid (I-132);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,6-difluorobenzonitrile (I-133) (1S,4S,5R)-5-{[5-cyclopropyl-3-(2,6-dichlorophenyl)-1,2-oxazol-4-yl]methoxy}-2-[2-fluoro-4-(2H-1,2,3,4-tetrazol-5-yl)phenyl]-2-azabicyclo[2.2.1]heptane (I-134);

5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,3-dihydro-1H-isoindol-1-one (I-135);

6-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,2,3,4-tetrahydroisoquinolin-1-one (I-136);

(2R)-6-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,2,3,4-tetrahydronaphthalene-2-carboxylic acid (I-137) and (2S)-6-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,2,3,4-tetrahydronaphthalene-2-carboxylic acid (I-138);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-hydroxy-3-methylbenzamide (I-139);

5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,3-dihydro-1,3-benzoxazol-2-one (I-140);

5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-dihydro-2-benzofuran-1-one (I-141);

1-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}-2,2,2-trifluoroethan-1-one (I-142);

2-{N-methyl4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzenesulfonamido}acetic acid (I-143);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzene-1-sulfonic acid (I-144);

2-[(1S,4S,5R)-5-{([5-cyclopropyl-3-(2,6-dichlorophenyl)-1,2-oxazol-4-yl]methoxy}-2-azabicyclo[2.2.1]heptan-2-yl]pyrimidine-5-carboxylic acid (I-145);

2-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}acetic acid (I-146);

3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}propanoic acid (I-147);

4-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}butanoic acid (I-148);

1-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}cyclopropane-1-carboxylic acid (I-149);

1-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}cyclobutane-1-carboxylic acid (I-150);

3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}cyclobutane-1-carboxylic acid (I-151);

3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}butanoic acid (I-152);

2-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}acetic acid (I-153);

3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}propanoic acid (I-154);

3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorophenyl}propanoic acid (I-155);

3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorophenyl}-2,2-dimethylpropanoic acid (I-156);

4-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}-butanoic acid (I-157);

3-{3-cyano-4-[(1S,4S,5R)-5-{[5-cyclopropyl-3-(2,6-dichlorophenyl)-1,2-oxazol-4-yl]methoxy)}-2-azabicyclo[2.2.1]heptan-2-yl]phenyl}propanoic acid (I-158);

3-{4-[(1S,4S,5R)-5-{[3-(2-chloro-6-methylphenyl)-5-cyclopropyl-1,2-oxazol-4-yl]methoxy}-2-azabicyclo[2.2.1]heptan-2-yl]-3-fluorophenyl}propanoic acid (I-159);

1-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}methyl)azetidine-3-carboxylic acid (I-160);

N-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}methyl)-N-hydroxyformamide (I-161);

(1S,4S,5R)-5-{[5-cyclopropyl-3-(2,6-dichlorophenyl)-1,2-oxazol-4-yl]methoxy}-2-{2-fluoro-4-[2-(2H-1,2,3,4-tetrazol-5-yl)ethyl]phenyl}-2-azabicyclo[2.2.1]heptane (I-162);

2-[bis(2-hydroxyethyl)amino]ethyl 3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}propanoate (I-163);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(2H-1,2,3,4-tetrazol-5-ylmethyl)benzamide (I-164);

2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)acetic acid (I-165);

2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)ethane-1-sulfonic acid (I-166);

2-({(4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorophenyl}formamido)acetic acid (I-167);

2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorophenyl}formamido)ethane-1-sulfonic acid (I-168);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(2-methanesulfonylethyl)benzamide (I-169);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluoro-N-(2-methanesulfonylethyl)benzamide (I-170);

N-[2-(cyclopropanesulfonyl)ethyl]-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorobenzamide (I-171);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluoro-N-[2-(oxane-4-sulfonyl)ethyl]benzamide (I-172);

[2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-methylphenyl}formamido)ethyl]phosphonic acid (I-173);

({[2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-methylphenyl}formamido)ethyl]({[(2,2-dimethylpropanoyl)oxy]methoxy})phosphoryl}oxy)methyl 2,2-dimethylpropanoate (I-174);

(2-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}ethyl)phosphonic acid (I-175);

({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}methyl)phosphonic acid (I-176);

methyl 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorobenzoate (I-177);

5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3,4-thiadiazole-2-carboxylic acid (I-178);

3-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,2-oxazole-5-carboxylic acid (I-179);

5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1-methyl-1H-pyrazole-3-carboxylic acid (I-180);

N-(cyclohexanesulfonyl)-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzamide (I-181);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(oxane-4-sulfonyl)benzamide (I-182);

N-(cyclobutylsulfonyl)-4-((1S,4S,5R)-5-((5-cyclopropyl-3-(2,6-dichlorophenyl)isoxazol-4-yl)methoxy)-2-azabicyclo[2.2.1]heptan-2-yl)benzamide (I-183);

4-((1S,4S,5R)-5-((5-cyclopropyl-3-(2,6-dichlorophenyl)isoxazol-4-yl)methoxy)-2-azabicyclo[2.2.1]heptan-2-yl)-N-(oxetan-3-ylsulfonyl)benzamide (I-184);

4-((1S,4S,5R)-5-((5-cyclopropyl-3-(2,6-dichlorophenyl)isoxazol-4-yl)methoxy)-2-azabicyclo[2.2.1]heptan-2-yl)-N-((tetrahydrofuran-3-yl)sulfonyl)benzamide (I-185);

4-((1S,4S,5R)-5-((5-cyclopropyl-3-(2,6-dichlorophenyl)isoxazol-4-yl)methoxy)-2-azabicyclo[2.2.1]heptan-2-yl)-N-(((tetrahydrofuran-3-yl)methyl)sulfonyl)benzamide (I-186);

4-((1S,4S,5R)-5-((5-cyclopropyl-3-(2,6-dichlorophenyl)isoxazol-4-yl)methoxy)-2-azabicyclo[2.2.1]heptan-2-yl)-N-((1-methylpiperidin-4-yl)sulfonyl)benzamide (I-187);

N-((1H-pyrazol-4-yl)sulfonyl)-4-((1S,4S,5R)-5-((5-cyclopropyl-3-(2,6-dichlorophenyl)isoxazol-4-yl)methoxy)-2-azabicyclo[2.2.1]heptan-2-yl)benzamide (I-188);

4-((1S,4S,5R)-5-((5-cyclopropyl-3-(2,6-dichlorophenyl)isoxazol-4-yl)methoxy)-2-azabicyclo[2.2.1]heptan-2-yl)-N-(phenylsulfonyl)benzamide (I-189);

4-((1S,4S,5R)-5-((5-cyclopropyl-3-(2,6-dichlorophenyl)isoxazol-4-yl)methoxy)-2-azabicyclo[2.2.1]heptan-2-yl)-3-fluoro-N-(isopentylsulfonyl)benzamide (I-190);

4-((1S,4S,5R)-5-((5-cyclopropyl-3-(2,6-dichlorophenyl)isoxazol-4-yl)methoxy)-2-azabicyclo[2.2.1]heptan-2-yl)-3-fluoro-N-(pentylsulfonyl)benzamide (I-191);

4-((1S,4S,5R)-5-((5-cyclopropyl-3-(2,6-dichlorophenyl)isoxazol-4-yl)methoxy)-2-azabicyclo[2.2.1]heptan-2-yl)-3-fluoro-N-(octylsulfonyl)benzamide (I-192);

4-((1S,4S,5R)-5-((5-cyclopropyl-3-(2,6-dichlorophenyl)isoxazol-4-yl)methoxy)-2-azabicyclo[2.2.1]heptan-2-yl)-N-((2-(2-ethoxyethoxy)ethyl)sulfonyl)-3-fluorobenzamide (I-193);

4-((1S,4S,5R)-5-((5-cyclopropyl-3-(2,6-dichlorophenyl)isoxazol-4-yl)methoxy)-2-azabicyclo[2.2.1]heptan-2-yl)-2-fluoro-N-(propylsulfonyl)benzamide (I-194);

4-((1S,4S,5R)-5-((5-cyclopropyl-3-(2,6-dichlorophenyl)isoxazol-4-yl)methoxy)-2-azabicyclo[2.2.1]heptan-2-yl)-N-(cyclopropylsulfonyl)-2-fluorobenzamide (I-195);

N-(cyclopropylsulfonyl)-4-((1S,4S,5R)-5-((3-(2,6-dichlorophenyl)-5-(1-fluorocyclopropyl)isoxazol-4-yl)methoxy)-2-azabicyclo[2.2.1]heptan-2-yl)benzamide (I-196);

N-(cyclopropylsulfonyl)-4-((1S,4S,5R)-5-((3-(2,6-dichlorophenyl)-5-(1-fluorocyclopropyl)isoxazol-4-yl)methoxy)-2-azabicyclo[2.2.1]heptan-2-yl)-3-fluorobenzamide (I-197);

4-((1S,4S,5R)-5-((3-(2,6-dichlorophenyl)-5-(1-fluorocyclopropyl)isoxazol-4-yl)methoxy)-2-azabicyclo[2.2.1]heptan-2-yl)-3-fluoro-N-(propylsulfonyl)benzamide (I-198);

(1S,4S,5R)-2-(4-((cyclopropylsulfonyl)carbamoyl)-2-fluorophenyl)-2-azabicyclo[2.2.1]heptan-5-yl 3-(2,6-dichlorophenyl)-5-(1-fluorocyclopropyl)isoxazole-4-carboxylate (I-199);

4-((1S,4S,5R)-5-((5-cyclopropyl-3-(2-(trifluoromethyl)phenyl)isoxazol-4-yl)methoxy)-2-azabicyclo[2.2.1]heptan-2-yl)-3-fluoro-N-(propylsulfonyl)benzamide (I-200);

N-(butylsulfonyl)-4-((1S,4S,5R)-5-((5-cyclopropyl-3-(2-(trifluoromethyl)phenyl)isoxazol-4-yl)methoxy)-2-azabicyclo[2.2.1]heptan-2-yl)-3-fluorobenzamide (I-201);

4-((1S,4S,5R)-5-((5-cyclopropyl-3-(2-(trifluoromethyl)phenyl)isoxazol-4-yl)methoxy)-2-azabicyclo[2.2.1]heptan-2-yl)-N-(cyclopropylsulfonyl)-3-fluorobenzamide (I-202);

4-((1S,4S,5R)-5-((3-(2-chloro-6-methylphenyl)-5-cyclopropylisoxazol-4-yl)methoxy)-2-azabicyclo[2.2.1]heptan-2-yl)-N-((tetrahydro-2H-pyran-4-yl)sulfonyl)benzamide (I-203);

6-((1S,4S,5R)-5-((5-cyclopropyl-3-(2,6-dichlorophenyl)isoxazol-4-yl)methoxy)-2-azabicyclo[2.2.1]heptan-2-yl)-N-(propylsulfonyl)nicotinamide (I-204);

6-((1S,4S,5R)-5-((5-cyclopropyl-3-(2,6-dichlorophenyl)isoxazol-4-yl)methoxy)-2-azabicyclo[2.2.1]heptan-2-yl)-N-(cyclopropylsulfonyl)nicotinamide (I-205);

6-((1S,4S,5R)-5-((5-cyclopropyl-3-(2,6-dichlorophenyl)isoxazol-4-yl)methoxy)-2-azabicyclo[2.2.1]heptan-2-yl)-5-fluoro-N-(propylsulfonyl)nicotinamide (I-206);

6-((1S,4S,5R)-5-((5-cyclopropyl-3-(2,6-dichlorophenyl)isoxazol-4-yl)methoxy)-2-azabicyclo[2.2.1]heptan-2-yl)-N-(cyclopropylsulfonyl)-5-fluoronicotinamide (I-207);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(oxane-4-sulfonyl)benzamide (I-208);

N-(cyclopropanesulfonyl)-6-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]pyridine-3-carboxamide (I-209);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(2-hydroxyethanesulfonyl)benzamide (I-210);

2-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]ethyl acetate (I-211);

2-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]ethyl cyclopropanecarboxylate (I-212);

2-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]ethyl 2-methylpropanoate (I-213);

3-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]propyl acetate (I-214);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(3-hydroxypropanesulfonyl)benzamide (I-215);

4-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]butan-2-yl acetate (I-216);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(3-hydroxybutanesulfonyl)benzamide (I-217);

4-({4-[({4-[(1S,4S,5R)-5-{[5-cyclopropyl-3-(2,3-dichlorophenyl)-1,2-oxazol-4-yl]methoxy}-2-azabicyclo[2.2.1]heptan-2-yl]phenyl}formamido)sulfonyl]butan-2-yl}oxy)-4-oxobutanoic acid (I-218);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(3,4-dihydroxybutanesulfonyl)benzamide (I-219);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-{[(1s,4s)-4-hydroxycyclohexyl]sulfonyl}benzamide (I-220) and 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-{[(1r,4r)-4-hydroxycyclohexyl]sulfonyl}benzamide (I-221);

4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(dodecane-1-sulfonyl)-3-fluorobenzamide (I-222);

(2R,3S,4R,5R)—N-{(10-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}formamido)sulfonyl]decyl}-2,3,4,5,6-pentahydroxyhexanamide (I-223);

N-{10-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}formamido)sulfonyl]decyl}acetamide (I-224);

N-{10-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}formamido)sulfonyl]decyl}-2-methoxyacetamide (I-225);

{10-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}formamido)sulfonyl]decyl}diethylmethylazanium (I-226);

N-[10-(azetidin-1-yl)decanesulfonyl]-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorobenzamide (I-227);

4-((1S,4S,5R)-5-((5-cyclopropyl-3-(spiro[2.5]octan-6-yl)isoxazol-4-yl)methoxy)-2-azabicyclo[2.2.1]heptan-2-yl)-N-(cyclopropylsulfonyl)benzamide (I-228);

4-((1S,4S,5R)-5-((5-cyclopropyl-3-(spiro[2.5]octan-6-yl)isoxazol-4-yl)methoxy)-2-azabicyclo[2.2.1]heptan-2-yl)-N-(cyclopropylsulfonyl)-3-fluorobenzamide (I-229);

4-((1S,4S,5R)-5-((5-cyclopropyl-3-(spiro[2.5]octan-6-yl)isoxazol-4-yl)methoxy)-2-azabicyclo[2.2.1]heptan-2-yl)-3-fluoro-N-((tetrahydro-2H-pyran-4-yl)sulfonyl)benzamide (I-230);

4-((1R,4R,5S)-5-((5-cyclopropyl-3-(2,6-dichlorophenyl)isoxazol-4-yl)methoxy)-2-azabicyclo[2.2.1]heptan-2-yl)-N-(cyclopropylsulfonyl)-3-fluorobenzamide (I-231);

4-((1R,4R,5S)-5-((5-cyclopropyl-3-(2,6-dichlorophenyl)isoxazol-4-yl)methoxy)-2-azabicyclo[2.2.1]heptan-2-yl)-N-(cyclopropylsulfonyl)benzamide (I-232);

N-(cyclopropanesulfonyl)-5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1-methyl-1H-pyrazole-3-carboxamide (I-233);

(1S,4S,5R)-2-{4-[(cyclopropanesulfonyl)carbamoyl]phenyl}-5-{[5-cyclopropyl-3-(2,6-dichlorophenyl)-1,2-oxazol-4-yl]methoxy}-2-azabicyclo[2.2.1]heptan-2-ium-2-olate (I-234);

3-{4-[(1S,4S,5R)-5-{[3-(2-chloro-6-fluorophenyl)-5-cyclopropyl-1,2-oxazol-4-yl]methoxy}-2-azabicyclo[2.2.1]heptan-2-yl]-3-fluorophenyl}-N-(oxane-4-sulfonyl)propanamide (I-235);

3-(4-((1S,4S,5R)-5-((5-cyclopropyl-3-(2,6-dichlorophenyl)isoxazol-4-yl)methoxy)-2-azabicyclo[2.2.1]heptan-2-yl)-3-fluorophenyl)-N-(methylsulfonyl)propanamide (I-236);

3-(4-((1S,4S,5R)-5-((5-cyclopropyl-3-(2,6-dichlorophenyl)isoxazol-4-yl)methoxy)-2-azabicyclo[2.2.1]heptan-2-yl)-3-fluorophenyl)-N-(cyclopropylsulfonyl)propanamide (I-237);

3-(4-((1S,4S,5R)-5-((5-cyclopropyl-3-(2,6-dichlorophenyl)isoxazol-4-yl)methoxy)-2-azabicyclo[2.2.1]heptan-2-yl)-3-fluorophenyl)-N-((tetrahydro-2H-pyran-4-yl)sulfonyl)propanamide (I-238);

3-(4-((1S,4S,5R)-5-((3-(2-chloro-6-fluorophenyl)-5-cyclopropylisoxazol-4-yl)methoxy)-2-azabicyclo[2.2.1]heptan-2-yl)-3-fluorophenyl)-N-(methylsulfonyl)propanamide (I-239);

3-(4-((1S,4S,5R)-5-((3-(2-chloro-6-fluorophenyl)-5-cyclopropylisoxazol-4-yl)methoxy)-2-azabicyclo[2.2.1]heptan-2-yl)-3-fluorophenyl)-N-(cyclopropylsulfonyl)propanamide (I-240);

3-(4-((1S,4S,5R)-5-((3-(2-chloro-6-methylphenyl)-5-cyclopropylisoxazol-4-yl)methoxy)-2-azabicyclo[2.2.1]heptan-2-yl)-3-fluorophenyl)-N-(methylsulfonyl)propanamide (I-241);

3-(4-((1S,4S,5R)-5-((3-(2-chloro-6-methylphenyl)-5-cyclopropylisoxazol-4-yl)methoxy)-2-azabicyclo[2.2.1]heptan-2-yl)-3-fluorophenyl)-N-(cyclopropylsulfonyl)propanamide (I-242);

3-(4-((1S,4S,5R)-5-((3-(2-chloro-6-methylphenyl)-5-cyclopropylisoxazol-4-1)methoxy)-2-azabicyclo[2.2.1]heptan-2-yl)-3-fluorophenyl)-N-((tetrahydro-2H-pyran-4-yl)sulfonyl)propanamide (I-243);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic acid (I-244);

4-[(1S,4R,5S)-5-{[5-cyclopropyl-3-(2,6-dichlorophenyl)-1,2-oxazol-4-yl]methoxy}-3-oxo-2-azabicyclo[2.2.1]heptan-2-yl]benzoic acid (I-245);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-ethyl-1,3-benzothiazole-6-carboxylic acid (I-246);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(propan-2-yl)-1,3-benzothiazole-6-carboxylic acid (I-247);

4-tert-butyl-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic acid (I-248);

4-cyclobutyl-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic acid (I-249);

4-cyclopentyl-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic acid (I-250);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(oxolan-3-yl)-1,3-benzothiazole-6-carboxylic acid (I-251);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(3S)-oxolan-3-yl]-1,3-benzothiazole-6-carboxylic acid (I-252);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(3R)-oxolan-3-yl]-1,3-benzothiazole-6-carboxylic acid (I-253);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(oxan-4-yl)-1,3-benzothiazole-6-carboxylic acid (I-254);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(1R,3R,5S)-8-oxabicyclo[3.2.1]octan-3-yl]-1,3-benzothiazole-6-carboxylic acid (I-255);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(1R,3S,5S)-8-oxabicyclo[3.2.1]octan-3-yl]-1,3-benzothiazole-6-carboxylic acid (I-256);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-{7-oxaspiro[3.5]nonan-2-yl}-1,3-benzothiazole-6-carboxylic acid (I-257);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(oxepan-4-yl)-1,3-benzothiazole-6-carboxylic acid (I-258);

4-cyclopropoxy-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic acid (I-259);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(3S)-oxolan-3-yloxy]-1,3-benzothiazole-6-carboxylic Acid (I-260);

2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(3R)-oxolan-3-yloxy]-1,3-benzothiazole-6-carboxylic Acid (I-261);

2-[(1S,4S,5R)-5-{[3-(2-chloro-6-fluorophenyl)-5-cyclopropyl-1,2-oxazol-4-yl]methoxy}-2-azabicyclo[2.2.1]heptan-2-yl]-4-methyl-1,3-benzothiazole-6-carboxylic acid (I-262);

2-((1S,4S,5R)-5-((3-(2-chloro-6-fluorophenyl)-5-cyclopropylisoxazol-4-yl)methoxy)-2-azabicyclo[2.2.1]heptan-2-yl)-4-cyclopropoxybenzo[d]thiazole-6-carboxylic acid (I-263);

2-((1S,4S,5R)-5-((3-(2-chloro-6-fluorophenyl)-5-cyclopropylisoxazol-4-yl)methoxy)-2-azabicyclo[2.2.1]heptan-2-yl)-4-(tetrahydro-2H-pyran-4-yl)benzo[d]thiazole-6-carboxylic acid (I-264);

2-((1S,4S,5R)-5-((3-(2-chloro-6-fluorophenyl)-5-cyclopropylisoxazol-4-yl)methoxy)-2-azabicyclo[2.2.1]heptan-2-yl)-4-((R)-tetrahydrofuran-3-yl)benzo[d]thiazole-(6-carboxylic Acid (I-265);

2-((1S,4S,5R)-5-((3-(2-chloro-6-fluorophenyl)-5-cyclopropylisoxazol-4-yl)methoxy)-2-azabicyclo[2.2.1]heptan-2-yl)-4-((S)-tetrahydrofuran-3-yl)benzo[d]thiazole-6-carboxylic Acid (I-266);

2-((1S,4S,5R)-5-((3-(2-chloro-6-fluorophenyl)-5-cyclopropylisoxazol-4-yl)methoxy)-2-azabicyclo[2.2.1]heptan-2-yl)-4-(((S)-tetrahydrofuran-3-yl)oxy)benzo[d]thiazole-6-carboxylic acid (I-267);

2-((1S,4S,5R)-5-((3-(2-chloro-6-fluorophenyl)-5-cyclopropylisoxazol-4-yl)methoxy)-2-azabicyclo[2.2.1]heptan-2-yl)-4-(((R)-tetrahydrofuran-3-yl)oxy)benzo[d]thiazole-6-carboxylic acid (I-268);

2-((1S,4S,5R)-5-((3-(2-chloro-(6-methylphenyl)-5-cyclopropylisoxazol-4-yl)methoxy)-2-azabicyclo[2.2.1]heptan-2-yl)-4-methylbenzo[d]thiazole-6-carboxylic acid (I-269);

2-((1S,4S,5R)-5-((3-(2-chloro-6-methylphenyl)-5-cyclopropylisoxazol-4-yl)methoxy)-2-azabicyclo[2.2.1]heptan-2-yl)-4-cyclopropoxybenzo[d]thiazole-6-carboxylic acid (I-270);

2-((1S,4S,5R)-5-((3-(2-chloro-6-methylphenyl)-5-cyclopropylisoxazol-4-yl)methoxy)-2-azabicyclo[2.2.1]heptan-2-yl)-4-(tetrahydro-2H-pyran-4-yl)benzo[d]thiazole-6-carboxylic acid (I-271);

2-((1S,4S,5R)-5-((3-(2-chloro-6-methylphenyl)-5-cyclopropylisoxazol-4-yl)methoxy)-2-azabicyclo[2.2.1]heptan-2-yl)-4-((R)-tetrahydrofuran-3-yl)benzo[d]thiazole-6-carboxylic Acid (I-272);

2-((1S,4S,5R)-5-((3-(2-chloro-6-methylphenyl)-5-cyclopropylisoxazol-4-yl)methoxy)-2-azabicyclo[2.2.1]heptan-2-yl)-4-((S)-tetrahydrofuran-3-yl)benzo[d]thiazole-6-carboxylic Acid (I-273);

2-((1S,4S,5R)-5-((3-(2-chloro-6-methylphenyl)-5-cyclopropylisoxazol-4-yl)methoxy)-2-azabicyclo[2.2.1]heptan-2-yl)-4-(((S)-tetrahydrofuran-3-yl)oxy)benzo[d]thiazole-6-carboxylic acid (I-274);

2-((1S,4S,5R)-5-((3-(2-chloro-6-methylphenyl)-5-cyclopropylisoxazol-4-yl)methoxy)-2-azabicyclo[2.2.1]heptan-2-yl)-4-(((R)-tetrahydrofuran-3-yl)oxy)benzo[d]thiazole-6-carboxylic acid (I-275);

2-[(1S,4S,5R)-5-{[5-cyclopropyl-3-(2,6-dimethylphenyl)-1,2-oxazol-4-yl]methoxy}-2-azabicyclo[2.2.1]heptan-2-yl]-4-methyl-1,3-benzothiazole-6-carboxylic acid (I-276);

2-[(1S,4S,5R)-5-[(5-cyclopropyl-3-{spiro[2.5]octan-6-yl}-1,2-oxazol-4-yl)methoxy]-2-azabicyclo[2.2.1]heptan-2-yl]-4-fluoro-1,3-benzothiazole-6-carboxylic acid (I-277);

4-cyclopropoxy-2-((1S,4S,5R)-5-((5-cyclopropyl-3-(spiro[2.5]octan-6-yl)isoxazol-4-yl)methoxy)-2-azabicyclo[2.2.1]heptan-2-yl)benzo[d]thiazole-6-carboxylic acid (I-278);

2-((1S,4S,5R)-5-((5-cyclopropyl-3-(spiro[2.5]octan-(6-yl)isoxazol-4-yl)methoxy)-2-azabicyclo[2.2.1]heptan-2-yl)-4-(tetrahydro-2H-pyran-4-yl)benzo[d]thiazole-6-carboxylic acid (I-279);

2-((1S,4S,5R)-5-((5-cyclopropyl-3-(spiro[2.5]octan-6-yl)isoxazol-4-yl)methoxy)-2-azabicyclo[2.2.1]heptan-2-yl)-4-((R)-tetrahydrofuran-3-yl)benzo[d]thiazole-6-carboxylic acid (I-280);

2-((1S,4S,5R)-5-((5-cyclopropyl-3-(spiro[2.5]octan-6-yl)isoxazol-4-yl)methoxy)-2-azabicyclo[2.2.1]heptan-2-yl)-4-((S)-tetrahydrofuran-3-yl)benzo[d]thiazole-6-carboxylic acid (I-281);

4-cyclobutyl-2-((1S,4S,5R)-5-((5-cyclopropyl-3-(spiro[2.5]octan-6-yl)isoxazol-4-yl)methoxy)-2-azabicyclo[2.2.1]heptan-2-yl)benzo[d]thiazole-6-carboxylic acid (I-282);

4-cyclopentyl-2-((1S,4S,5R)-5-((5-cyclopropyl-3-(spiro[2.5]octan-6-yl)isoxazol-4-yl)methoxy)-2-azabicyclo[2.2.1]heptan-2-yl)benzo[d]thiazole-6-carboxylic acid (I-283);

4-cyclobutyl-2-[(1R,4R,5S)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic acid (I-284);

4-cyclopentyl-2-[(1R,4R,5S)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic acid (I-285);

2-[(1S,4S,5R)-5-{[5-cyclopropyl-3-(2,6-dichloro-4-methoxyphenyl)-1,2-oxazol-4-yl]methoxy}-2-azabicyclo[2.2.1]heptan-2-yl]-4-fluoro-1,3-benzothiazole-6-carboxylic acid (I-286);

2-[(1S,4S,5R)-5-{[5-cyclopropyl-3-(2,6-dichloro-4-hydroxyphenyl)-1,2-oxazol-4-yl]methoxy}-2-azabicyclo[2.2.1]heptan-2-yl]-4-fluoro-1,3-benzothiazole-6-carboxylic acid (I-287);

2-((1S,4S,5R)-5-((5-cyclopropyl-3-(2-methoxyphenyl)isoxazol-4-yl)methoxy)-2-azabicyclo[2.2.1]heptan-2-yl)-4-fluorobenzo[d]thiazole-6-carboxylic acid (I-288);

2-((1S,4S,5R)-5-((5-cyclopropyl-3-(3-methoxyphenyl)isoxazol-4-yl)methoxy)-2-azabicyclo[2.2.1]heptan-2-yl)-4-fluorobenzo[d]thiazole-6-carboxylic acid (I-289);

2-((1S,4S,5R)-5-((5-cyclopropyl-3-(4-methoxyphenyl)isoxazol-4-yl)methoxy)-2-azabicyclo[2.2.1]heptan-2-yl)-4-fluorobenzo[d]thiazole-6-carboxylic acid (I-290);

2-((1S,4S,5R)-5-((5-cyclopropyl-3-(2-hydroxyphenyl)isoxazol-4-yl)methoxy)-2-azabicyclo[2.2.1]heptan-2-yl)-4-fluorobenzo[d]thiazole-6-carboxylic acid (I-291);

2-((1S,4S,5R)-5-((5-cyclopropyl-3-(3-hydroxyphenyl)isoxazol-4-yl)methoxy)-2-azabicyclo[2.2.1]heptan-2-yl)-4-fluorobenzo[d]thiazole-6-carboxylic acid (I-292);

2-((1S,4S,5R)-5-((5-cyclopropyl-3-(4-hydroxyphenyl)isoxazol-4-yl)methoxy)-2-azabicyclo[2.2.1]heptan-2-yl)-4-fluorobenzo[d]thiazole-6-carboxylic acid (I-293);

2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-4-ethyl-1,3-benzothiazole-6-carboxylic acid (I-294);

4-cyclopropyl-2-((1S,4R,5R)-5-((5-cyclopropyl-3-(2,6-dichlorophenyl)isoxazol-4-yl)methoxy)-3-oxo-2-azabicyclo[2.2.1]heptan-2-yl)benzo[d]thiazole-6-carboxylic acid (I-295);

4-cyclobutyl-2-((1S,4R,5R)-5-((5-cyclopropyl-3-(2,6-dichlorophenyl)isoxazol-4-yl)methoxy)-3-oxo-2-azabicyclo[2.2.1]heptan-2-yl)benzo[d]thiazole-6-carboxylic acid (I-296);

4-cyclopropoxy-2-((1S,4R,5R)-5-((5-cyclopropyl-3-(2,6-dichlorophenyl)isoxazol-4-yl)methoxy)-3-oxo-2-azabicyclo[2.2.1]heptan-2-yl)benzo[d]thiazole-6-carboxylic acid (I-297);

2-((1S,4R,5R)-5-((5-cyclopropyl-3-(2,6-dichlorophenyl)isoxazol-4-yl)methoxy)-3-oxo-2-azabicyclo[2.2.1]heptan-2-yl)-4-(tetrahydro-2H-pyran-4-yl)benzo[d]thiazole-6-carboxylic acid (I-298);

2-((1S,4R,5R)-5-((5-cyclopropyl-3-(2,6-dichlorophenyl)isoxazol-4-yl)methoxy)-3-oxo-2-azabicyclo[2.2.1]heptan-2-yl)-4-(tetrahydrofuran-3-yl)benzo[d]thiazole-6-carboxylic acid (I-299);

2-((1S,4R,5R)-5-((5-cyclopropyl-3-(2,6-dichlorophenyl)isoxazol-4-yl)methoxy)-3-oxo-2-azabicyclo[2.2.1]heptan-2-yl)-4-(7-oxaspiro[3.5]nonan-2-yl)benzo[d]thiazole-6-carboxylic acid (I-300);

2-((1S,4S,5R)-5-((3-(2-chloro-6-methylphenyl)-5-cyclopropylisoxazol-4-yl)methoxy)-2-azabicyclo[2.2.1]heptan-2-yl)-4-(((R)-tetrahydrofuran-3-yl)oxy)benzo[d]thiazole-6-carboxylic acid (I-301);

2-((1S,4R,5R)-5-((5-cyclopropyl-3-(2,6-dichlorophenyl)isoxazol-4-yl)methoxy)-3-oxo-2-azabicyclo[2.2.1]heptan-2-yl)-4-(((S)-tetrahydrofuran-3-yl)oxy)benzo[d]thiazole-6-carboxylic acid (I-302);

3-{4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]phenyl}propanoic acid (I-303);

3-{4-[1 S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluorophenyl}propanoic acid (I-304);

3-{4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorophenyl}propanoic acid (I-305);

4-[(1S,4R,5R)-5-{[3-(2-chloro-6-fluorophenyl)-5-cyclopropyl-1,2-oxazol-4-yl]methoxy}-3-oxo-2-azabicyclo[2.2.1]heptan-2-yl]benzoic acid (I-306);

4-[(1S,4R,5R)-5-{[5-cyclopropyl-3-(2-fluoro-6-methylphenyl)-1,2-oxazol-4-yl]methoxy}-3-oxo-2-azabicyclo[2.2.1]heptan-2-yl]benzoic acid (I-307);

4-[(1S,4R,5R)-5-{[5-cyclopropyl-3-(2,6-dimethylphenyl)-1,2-oxazol-4-yl]methoxy}-3-oxo-2-azabicyclo[2.2.1]heptan-2-yl]benzoic acid (I-308);

4-[(1S,4R,5R)-5-{[3-(2-chloro-6-methylphenyl)-5-cyclopropyl-1,2-oxazol-4-yl]methoxy}-3-oxo-2-azabicyclo[2.2.1]heptan-2-yl]benzoic acid (I-309);

4-[(1S,4R,5R)-5-({5-cyclopropyl-3-[2-fluoro-6-(propan-2-yl)phenyl]-1,2-oxazol-4-yl}methoxy}-3-oxo-2-azabicyclo[2.2.1]heptan-2-yl]benzoic acid (I-310);

4-[(1S,4R,5R)-5-{[5-cyclopropyl-3-(2-cyclopropyl-6-fluorophenyl)-1,2-oxazol-4-yl]methoxy}-3-oxo-2-azabicyclo[2.2.1]heptan-2-yl]benzoic acid (I-311);

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2,3-dihydro-1H-indene-1-carboxylic acid (I-312)

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2,3-dihydro-1H-indene-2-carboxylic acid (I-313);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorobenzoic acid (I-314);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluorobenzoic acid (I-315);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-methylbenzoic acid (I-316);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-methylbenzoic acid (I-317);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-ethylbenzoic acid (I-318);

2-cyclopropyl-4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic acid (I-319);

4-cyclopropyl-2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic acid (I-320);

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridine-2-carboxylic acid (I-321);

6-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridine-3-carboxylic acid (I-322);

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyrimidine-2-carboxylic acid (I-323);

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyrazine-2-carboxylic acid (I-324);

6-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridazine-3-carboxylic acid (I-325);

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluoropyridine-2-carboxylic acid (I-326);

3-{5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridin-2-yl}propanoic acid (I-327);

3-{5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluoropyridin-2-yl}propanoic acid (I-328);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[(2,2-dimethyloxan-4-yl)sulfonyl]benzamide (I-329);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[(2,2-dimethyloxan-4-yl)sulfonyl]-2-fluorobenzamide (I-330);

4-((1S,4R,5R)-5-((5-cyclopropyl-3-(2,6-chlorophenyl)isoxazol-4-yl)methoxy)-3-oxo-2-azabicyclo[2.2.1]heptan-2-yl)-N-(cyclopropylsulfonyl)-2-fluorobenzamiide (I-331);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-2-fluoro-N-((tetrahydro-2H-pyran-4-yl)sulfonyl)benzamide (I-332);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-2-fluoro-N-(((tetrahydro-2H-pyran-4-yl)methyl)sulfonyl)benzamide (I-333);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-2-fluoro-N-((tetrahydrofuran-3-yl)sulfonyl)benzamide (I-334);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-2-fluoro-N-(((tetrahydrofuran-3-yl)methyl)sulfonyl)benzamide (I-335);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-2-fluoro-N-((2-(tetrahydrofuran-3-yl)ethyl)sulfonyl)benzamide (I-336);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-(cyclopropylsulfonyl)benzamide (I-337);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-((tetrahydro-2H-pyran-4-ylsulfonyl)benzamide (I-338);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-(((tetrahydro-2H-pyran-4-yl)methyl)sulfonyl)benzamide (I-339);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-((tetrahydrofuran-3-yl)sulfonyl)benzamide (I-340);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-(((tetrahydrofuran-3-yl)methyl)sulfonyl)benzamide (I-341);

4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-((2-(tetrahydrofuran-3-yl)ethyl)sulfonyl)benzamide (I-342);

N-(cyclopentylsulfonyl)-4-((1S,4R,5R)-5-((5-cyclopropyl-3-(2,6-dichlorophenyl)isoxazol-4-yl)methoxy)-3-oxo-2-azabicyclo[2.2.1]heptan-2-yl)benzamide (I-343);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-{[(1R,2R)-2-hydroxycyclopentyl]sulfonyl}benzamide (I-344)

(1R,2R)-2-sulfamoylcyclopentyl 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoate (I-345);

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-{[(1R,2R)-2-hydroxycyclopentyl]sulfonyl}benzamide (I-346);

(1R,2R)-2-sulfamoylcyclopentyl 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorobenzoate (I-347)

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluoro-N-{[(1R,2R)-2-methoxycyclopentyl]sulfonyl}pyridine-2-carboxamide (I-348);

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluoro-N-{[(1R,2R)-2-hydroxycyclopentyl]sulfonyl}pyridine-2-carboxamide (I-349);

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-{[(1R,2R)-2-hydroxycyclopentyl]sulfonyl}pyridine-2-carboxamide (I-350);

5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-(cyclopropylsulfonyl)picolinamide (I-351);

5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-((tetrahydro-2H-pyran-4-yl)sulfonyl)picolinamide (I-352);

N-(cyclopentylsulfonyl)-5-((1S,4R,5R)-5-((5-cyclopropyl-3-(2,6-dichlorophenyl)isoxazol-4-yl)methoxy)-3-oxo-2-azabicyclo[2.2.1]heptan-2-yl)picolinamide (I-353);

5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-((2,2-dimethyltetrahydro-2H-pyran-4-yl)sulfonyl)picolinamide (I-354);

5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-(cyclopropylsulfonyl)-3-fluoropicolinamide (I-355);

N-(cyclopentylsulfonyl)-5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoropicolinamide (I-356);

5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-((2,2-dimethyltetrahydro-2H-pyran-4-yl)sulfonyl)-3-fluoropicolinamide (I-357);

2-({4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]phenyl}formamido)acetic acid (I-358);

2-({4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]phenyl}formamido)ethane-1-sulfonic acid (I-359);

4-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]benzoic acid (I-360);

4-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]benzoic acid (I-361);

4-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]-2-fluorobenzoic acid (I-362);

4-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]-3-fluorobenzoic acid (I-363);

4-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]-3-fluorobenzoic acid (I-364);

4-[(1S,3R,4S,5R)-5-{[5-cyclopropyl-3-(2,6-dichlorophenyl)-1,2-oxazol-4-yl]methoxy}-3-ethyl-2-azabicyclo[2.2.1]heptan-2-yl]-benzoic acid (I-365);

-[(1R,3S,4R,5S)-5-{[5-cyclopropyl-3-(2,6-dichlorophenyl)-1,2-oxazol-4-yl]methoxy}-3-ethyl-2-azabicyclo[2.2.1]heptan-2-yl]benzoic acid (I-366);

5-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]pyridine-2-carboxylic acid (I-367);

5-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]pyridine-2-carboxylic acid (I-368);

6-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]pyridine-3-carboxylic acid (I-369);

6-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]pyridine-3-carboxylic acid (I-370);

5-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]-N-(oxane-4-sulfonyl)pyridine-2-carboxamide (I-371);

5-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]-N-(oxane-4-sulfonyl)pyridine-2-carboxamide (I-372);

6-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]-N-(oxane-4-sulfonyl)pyridine-3-carboxamide (I-373); and 6-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]-N-(oxane-4-sulfonyl)pyridine-3-carboxamide (I-374).

In another embodiment, the compound is selected from the group consisting of the group consisting of:

6-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridazine-3-carboxylic acid;

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-2-fluoro-N-(oxane-4-sulfonyl)benzamide;

3-{4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-3-fluorophenyl}propanoic acid;

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyrazine-2-carboxylic acid;

3-{5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridin-2-yl}propanoic acid;

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]benzoic acid;

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-2-fluorobenzoic acid;

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-(oxane-4-sulfonyl)pyridine-2-carboxamide;

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyrimidine-2-carboxylic acid;

6-[(1S,4R,5R)-5-{[(5-cyclopropyl-3-(2,6-dichlorophenyl)-1,2-oxazol-4-yl]methoxy}-3-oxo-2-azabicyclo[2.2.1]heptan-2-yl]pyridine-3-carboxylic acid;

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridine-2-carboxylic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-{[(1R,2R)-2-hydroxycyclopentyl]sulfonyl}benzamide;

(1R,2R)-2-sulfamoylcyclopentyl 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorobenzoate;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-{[(1R,2R)-2-hydroxycyclopentyl]sulfonyl}benzamide;

(1R,2R)-2-sulfamoylcyclopentyl 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoate;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-[2-(oxolan-3-yl)ethanesulfonyl]benzamide;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[2-(oxolan-3-yl)ethanesulfonyl]benzamide;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[(oxan-4-yl)methanesulfonyl]benzamide;

4-cyclopropyl-2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic acid;

2-cyclopropyl-4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-[(oxan-4-yl)methanesulfonyl]benzamide;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-methylbenzoic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[(2,2-dimethyloxan-4-yl)sulfonyl]-2-fluorobenzamide;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[(2,2-dimethyloxan-4-yl)sulfonyl]benzamide;

2-({4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]phenyl}formamido)ethane-1-sulfonic acid;

2-({4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]phenyl}formamido)acetic acid;

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2,3-dihydro-1H-indene-2-carboxylic acid;

4-[(1S,4R,5R)-5-({5-cyclopropyl-3-[2-fluoro-6-(propan-2-yl)phenyl]-1,2-oxazol-4-yl}methoxy)-3-oxo-2-azabicyclo[2.2.1]heptan-2-yl]benzoic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-ethylbenzoic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-methylbenzoic acid;

5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2,3-dihydro-1H-indene-1-carboxylic acid;

4-cyclopropoxy-2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-1,3-benzothiazole-6-carboxylic acid;

2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-4-{7-oxaspiro[3.5]nonan-2-yl}-1,3-benzothiazole-6-carboxylic acid;

4-[(1S,4R,5R)-5-{[5-cyclopropyl-3-(2-cyclopropyl-6-fluorophenyl)-1,2-oxazol-4-yl]methoxy}-3-oxo-2-azabicyclo[2.2.1]heptan-2-yl]benzoic acid;

N-(cyclopropanesulfonyl)-4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzamide; 2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-4-(oxolan-3-yl)-1,3-benzothiazole-6-carboxylic acid;

2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-4-ethyl-1,3-benzothiazole-6-carboxylic acid;

4-[(1S,4R,5R)-5-{[3-(2-chloro-6-methylphenyl)-5-cyclopropyl-1,2-oxazol-4-yl]methoxy}-3-oxo-2-azabicyclo[2.2.1]heptan-2-yl]benzoic acid;

4-[(1S,4R,5R)-5-{[5-cyclopropyl-3-(2,6-dimethylphenyl)-1,2-oxazol-4-yl]methoxy}-3-oxo-2-azabicyclo[2.2.1]heptan-2-yl]benzoic acid;

4-[(1S,4R,5R)-5-{[5-cyclopropyl-3-(2-fluoro-6-methylphenyl)-1,2-oxazol-4-yl]methoxy}-3-oxo-2-azabicyclo[2.2.1]heptan-2-yl]benzoic acid;

N-(cyclopropanesulfonyl)-4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorobenzamide;

4-[(1S,4R,5R)-5-{[3-(2-chloro-6-fluorophenyl)-5-cyclopropyl-1,2-oxazol-4-yl]methoxy}-3-oxo-2-azabicyclo[2.2.1]heptan-2-yl]benzoic acid;

N-(cyclopentanesulfonyl)-4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzamide;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-[(oxolan-3-yl)methanesulfonyl]benzamide;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-(oxolane-3-sulfonyl)benzamide;

4-cyclobutyl-2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-1,3-benzothiazole-6-carboxylic acid;

4-cyclopropyl-2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-1,3-benzothiazole-6-carboxylic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluorobenzoic acid;

2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-4-(oxan-4-yl)-1,3-benzothiazole-6-carboxylic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[(oxolan-3-yl)methanesulfonyl]benzamide;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-(oxolane-3-sulfonyl)benzamide;

3-{4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorophenyl}propanoic acid;

2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-4-[(3S)-oxolan-3-yloxy]-1,3-benzothiazole-6-carboxylic acid;

2-[(1S,4R,5R)-5-{([5-cyclopropyl-3-(2,6-dichlorophenyl)-1,2-oxazol-4-yl]methoxy}-3-oxo-2-azabicyclo[22.1]heptan-2-yl]-4-[(3R)-oxolan-3-yloxy]-1,3-benzothiazole-6-carboxylic acid;

3-{4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluorophenyl}propanoic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-(oxane-4-sulfonyl)benzamide;

3-{4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]phenyl}propanoic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-(oxane-4-sulfonyl)benzamide;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorobenzoic acid;

4-[(1S,4R,5S)-5-{[5-cyclopropyl-3-(2,6-dichlorophenyl)-1,2-oxazol-4-yl]methoxy}-3-oxo-2-azabicyclo[2.2.1]heptan-2-yl]benzoic acid;

4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic acid;

In another embodiment of the invention, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

In another embodiment of the invention, the compounds of Formula (I) are diastereomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of FXR. In one embodiment, the compounds of the present invention are activators (agonists) of FXR.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereof as appreciated by those skilled in the art. These methods include, but are not limited to, those described below. Compounds of the present invention can be synthesized by following the steps outlined in General Schemes 1, 2, 3, and 4 which comprise different sequences of assembling intermediates. Starting materials are either commercially available or made by known procedures in the reported literature or as illustrated.

General Scheme 1

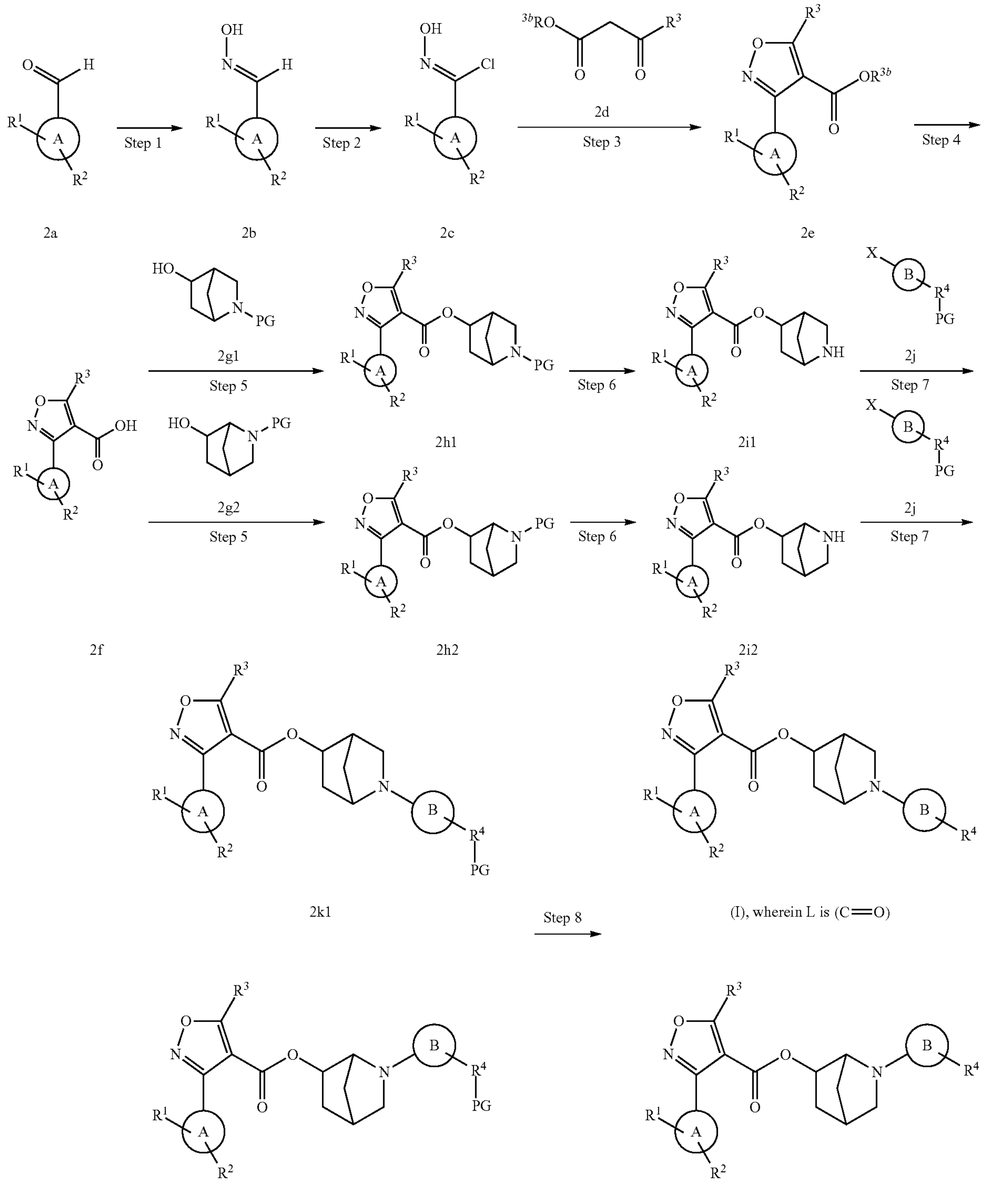

2a 2b 2c 2e 2f 2h1 2i1 2h2 2i2

2k1 (I), wherein L is (C═O)

2k2 (I), wherein L is (C═O)

wherein A, B, and $R^1$-$R^4$, are defined as in Formula (I), $R^{3b}$ is an alkyl group, X is halogen (i.e., Cl, F, etc.) or another suitable leaving group (i.e., mesylate), and PG is a protecting group (i.e., tert-butyl carbonate (BOC)).

The general manner of preparing target compounds of Formula (I) by using intermediates 2a-2f, 2g1, 2g2, 2h1, 2h2, 2i1, 2i2, 2j, 2k1, and 2k2, is outlined above in General Scheme 1. Condensation of aldehyde 2a, with hydroxylamine hydrochloride in the presence of a base (i.e., sodium hydroxide (NaOH)) and in a solvent (i.e., water ($H_2O$) and/or ethanol (EtOH)) optionally at elevated temperature provides intermediate 2b. Intermediate 2c is then prepared by treatment of 2b with a chlorinating agent, i.e. N-chlorosuccinimide in a solvent (i.e., N,N-dimethylformamide (DMF)). Cyclization of 2c with beta-keto ester 2d in the presence of a base (i.e., $NEt_3$, NaOMe, and or tBuOK) and in a solvent (i.e., dichloromethane) yields intermediate 2e. Hydrolysis of 2e in the presence of a base (i.e., lithium hydroxide monohydrate) and in a solvent (i.e., EtOH—$H_2O$) optionally at elevated temperature generates the acid 2f. Acid 2f is treated with activating agent (i.e., 1,1'-Carbonyldiimidazole (CDI)) and then reacted with protected 3-hydroxyl-aza-bicycloheptane intermediate 2g1 or 2g2 in a solvent (i.e., DMF) optionally at elevated temperature to form ester 2h1 or 2h2. Alternatively, acid 2f can be converted to an acid chloride using a chlorinating agent (i.e., thienyl chloride) in a solvent (i.e., DMF) and then reacted with protected 3-hydroxyl-aza-bicycloheptane intermediate 2g1 or 2g2 in the presence of DMAP and a base (i.e., triethylamine ($Et_3N$)) and in a solvent (i.e., DMF) to form ester 2h1 or 2h2.

Deprotection of intermediate 2h1 or 2h2 (i.e., when PG is an acid labile group, i.e., BOC) in the presence of a strong acid (i.e., trifluoroacetic acid (TFA)) and in a solvent (i.e., dichloromethane (DCM)) affords the intermediate 2i1 or 2i2. Coupling of 2i1 or 2i2 with 2j, wherein $R^4$ in reagent 2j is optionally protected, using a catalytic amount of a palladium catalyst and ligand (i.e., palladium (II) acetate ($Pd(OAc)_2$) and 1,1'-Ferrocenediyl-bis(diphenylphosphine) (dppf)) and acetic anhydride in a solvent, e.g., DMF, at elevated temperature affords the desired product of Formula (I) when $R^4$ is unprotected, or advanced intermediate 2k1 or 2k2 when $R^4$ is protected. Alternatively, 2i1 or 2i2 and 2j, wherein $R^4$ in reagent 2j is optionally protected, are treated with a base in a solvent and optionally at elevated temperature to afford the desired product of Formula (I) when $R^4$ is unprotected, or advanced intermediate 2k1 or 2k2 when $R^4$ is protected. Deprotection intermediate 2k1 or 2k2 provides the desired product of Formula (I).

General Scheme 2

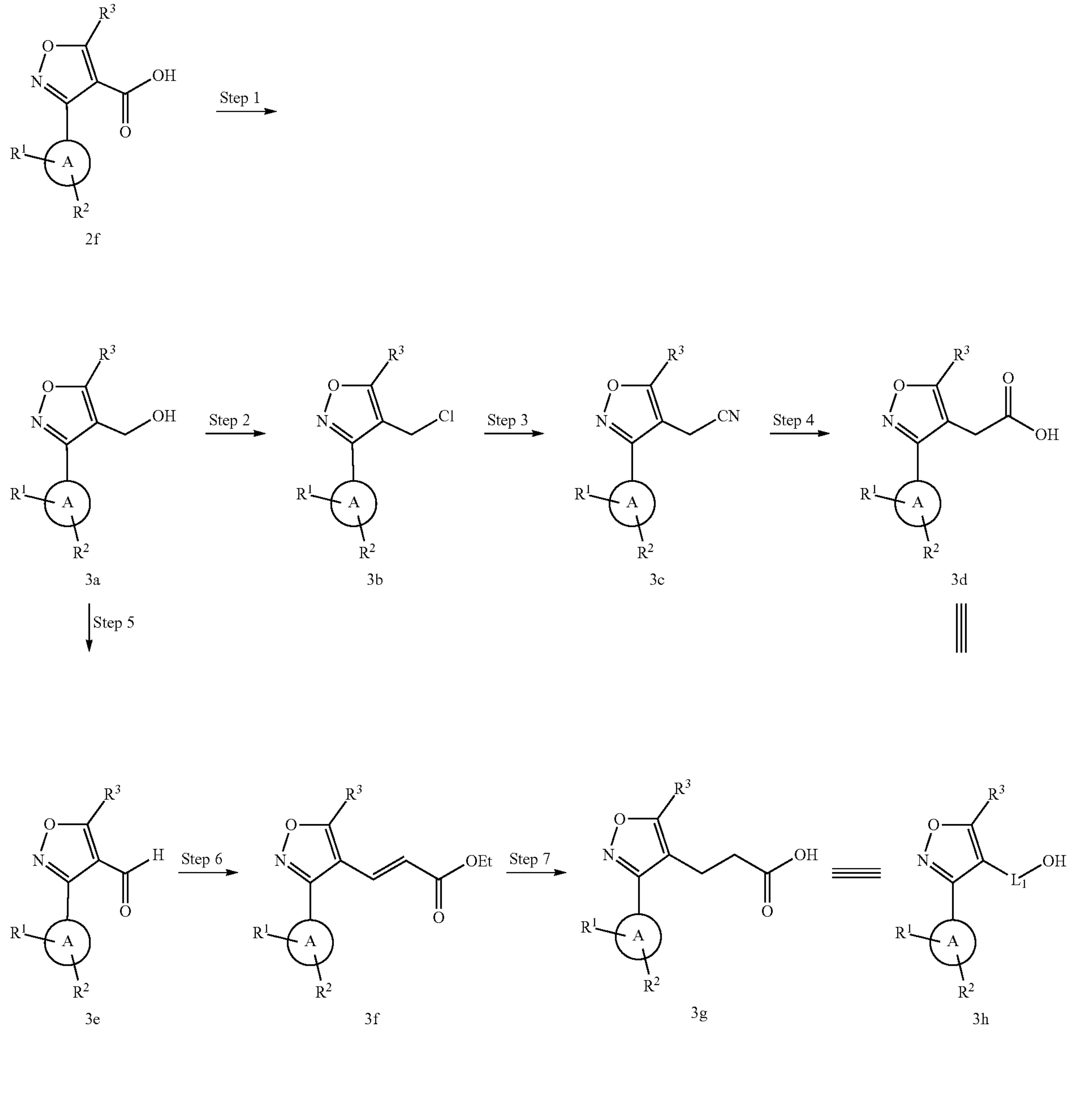

2f, 3a, 3b, 3c, 3d, 3e, 3f, 3g, 3h

-continued

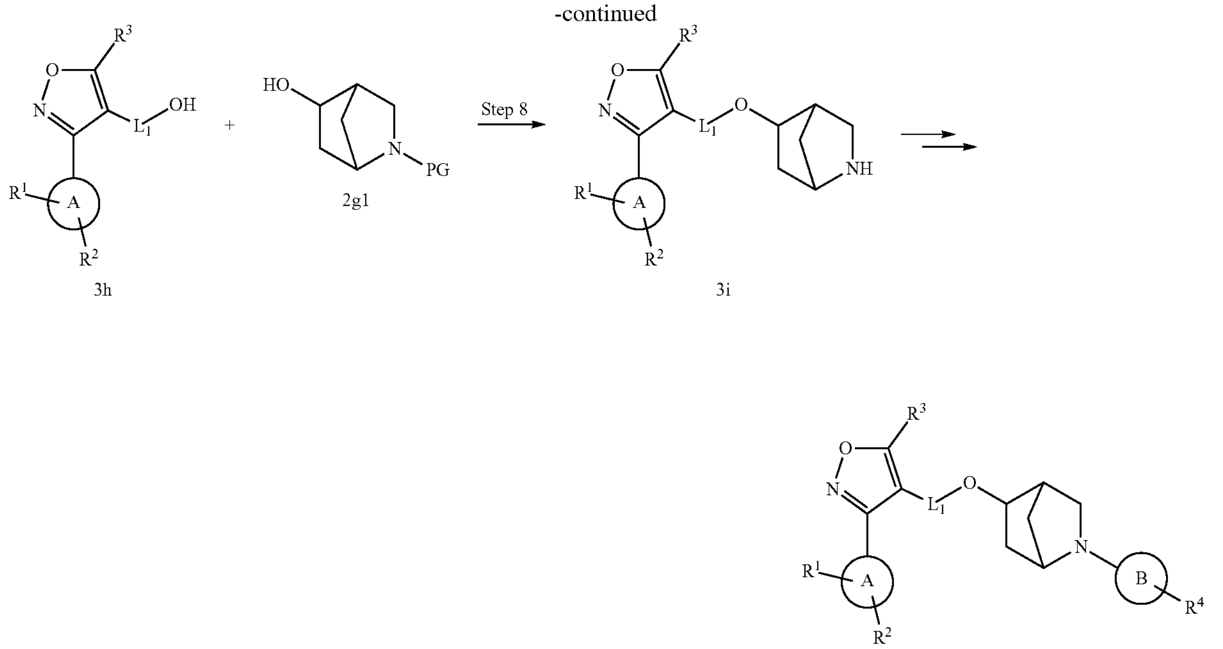

3h

2gl

3i (I),
wherein $L_1$ is $-(CH_2)_m(C{=}O)-$
$X_1$ is $CH_2$, $X_2$ is $NR_x$ and m is 1 or 2 wherein A, B, $R^1$-$R^4$ and $L_1$ are defined as in Formula (I).

The general manner of preparing target compounds of Formula (I) wherein $L_1$ is $-(CH_2)_m(C{=}O)-$, $X_1$ is $CH_2$, and $X_2$ is $NR_x$, by using intermediates 2f and 3a through 3i, is outlined above in General Scheme 2 Reduction of intermediate 2f using a reducing agent (i.e., lithium aluminum hydride (LAH)) in a solvent (i.e., tetrahydrofuran (THF)) provides alcohol 3a. Treatment of alcohol 3a with thienyl chloride in a solvent (i.e., DCM) provides chloride 3b. Cyanation of 3b in the presence of potassium cyanide or sodium cyanide in a solvent (i.e., water) optionally at elevated temperature affords intermediate 3c. Hydrolysis of nitrile 3c using a base (i.e., sodium hydroxide (NaOH)) in a solvent (i.e., $H_2O$ and/or EtOH) and optionally at elevated temperature provides 3d. Alternatively, Alcohol 3a can be oxidized to the aldehyde 3e, which is further converted to the two carbon elongated α,β-unsaturated ester 3f via a standard Wittig reaction conditions (i.e., (Carboxymethyl) triphenylphosphonium bromide ethyl ester, a base (i.e., potassium tert-butoxide) and a solvent (i.e., THF)). Hydrogenation of 3f in the presence of a metal catalyst (i.e., palladium on carbon), hydrogen gas and in a solvent (i.e., DCM) and subsequent hydrolysis of the resulting ester in the presence of a base (i.e., lithium hydroxide monohydrate) and in a solvent (i.e., EtOH/$H_2O$) optionally at elevated temperature provides acid 3g. 3d or 3h and 3-hydroxyl-aza-bicycloheptane intermediate 2g1 are coupled using standard acylation conditions (i.e., treatment of 3h and 2g1 with DMAP and 1-ethyl-3-(3-dimethylaminopropyl)carbodiimide in a solvent (i.e., DCM)) to form the ester 3i. Intermediate 3i can be converted to the desired product of Formula (I) as described above in steps 6 to 8 of General Scheme 1. Compounds of Formula (I) can also be synthesized as described above in steps 1 to 8 of General Scheme 2 and steps 6 to 8 of General Scheme 1 from hydroxyl-aza-bicycloheptane intermediate 2g2.

General Scheme 3

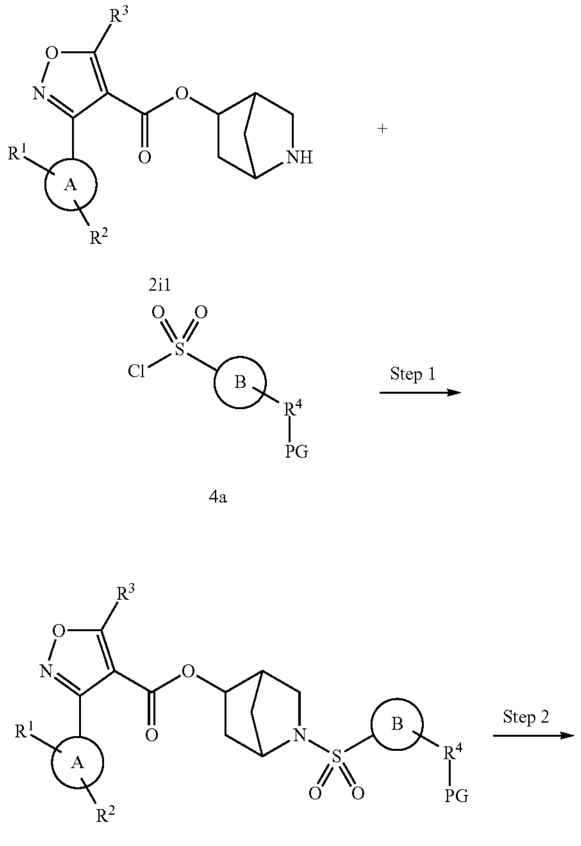

2i1

4a

4b1

-continued

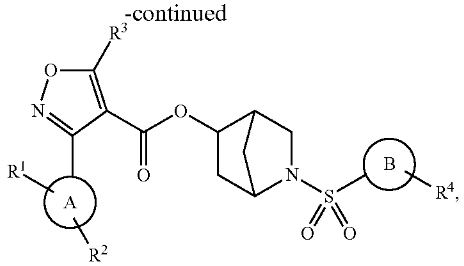

(I)

wherein $L_1$ is (C═O) and $L_2$ is —$S(O)_2$—, $X_1$ is $CH_2$ and $X_2$ is $NR_x$

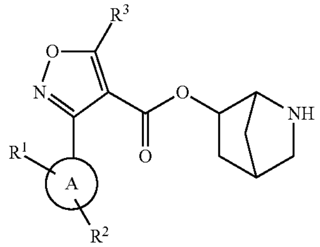

+

2i2

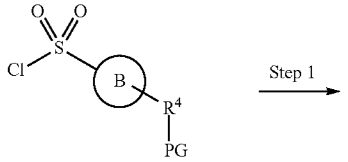

4a

-continued

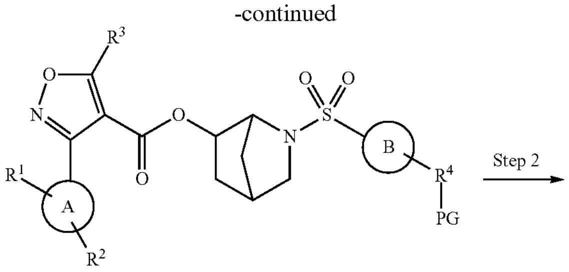

4b2

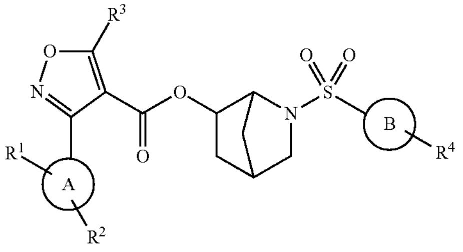

(I)

wherein $L_1$ is (C═O) and $L_2$ is —$S(O)_2$—, $X_1$ is $CH_2$ and $X_2$ is $NR_x$ wherein A, B, and $R^1$-$R^4$ are defined as in Formula (I)

Alternatively compounds of Formula (I) wherein $L_1$ is (C═O) and $L_2$ is —$S(O)_2$—, $X_1$ is $CH_2$ and $X_2$ is $NR_x$ can be prepared using intermediates 2i1, 2i2, 4a, 4b1, and 4b2, as outlined above in General Scheme 3. Sulfonation of the ester-substituted intermediate 2i1 or 2i2 with a substituted sulfonyl chloride 4a in the presence of a base (i.e., N,N-diisopropylethylamine (DIEA)) and in a solvent (i.e., DCM) affords the sulfonamide compound intermediate 4b1 or 4b2. Deprotection of intermediate 4b1 provides the desired product of Formula (I). Alternatively, deprotection of intermediate 4b2 provides the desired product of Formula (I).

General Scheme 4

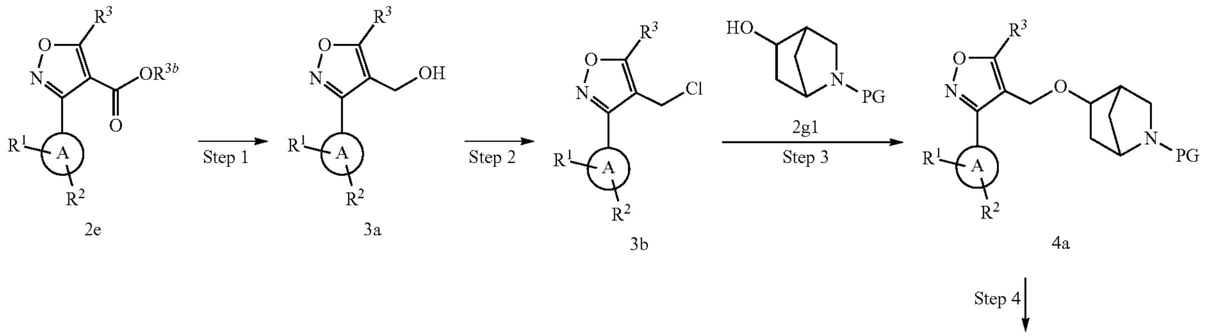

2e 3a 3b 4a

-continued

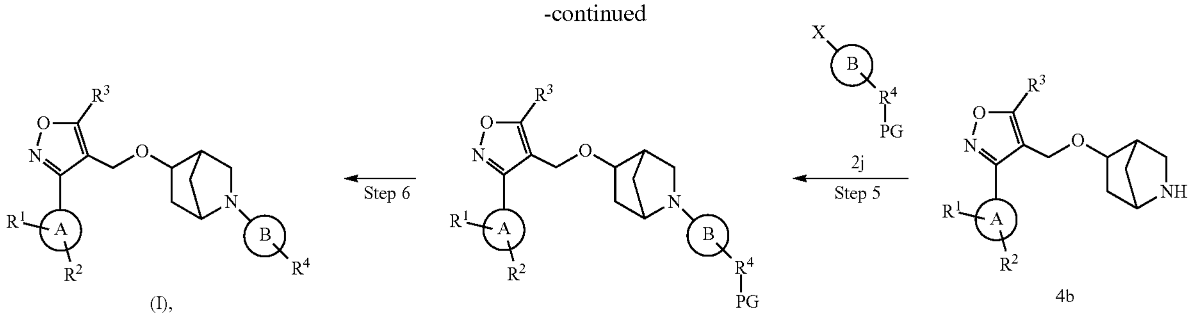

(I), wherein $L_1$ is $CH_2$

4c

4b wherein A, B, and $R^1$-$R^4$ are defined as in Formula (I)

Alternatively compounds of Formula (I) wherein $L_1$ is $-(CH_2)_p-$ can be prepared using intermediates 2e, 2g2, 2j, 3a, 3b, 4a, 4b, and 4c, as outlined above in General Scheme 4. Reduction of intermediate 2e using a reducing agent (i.e., lithium aluminum hydride (LAH)) in a solvent (i.e., tetrahydrofuran (THF)) provides alcohol 3a. Treatment of alcohol 3a with thienyl chloride in a solvent (i.e., DCM) provides chloride 3b. Nucleophilic addition of 2g1 to 3b in the presence of a base (i.e., sodium hydride (NaH)) and in a solvent (i.e., THF) provides 4a. Deprotection of intermediate 4a (i.e., when PG is an acid labile group, i.e., BOC) in the presence of a strong acid (i.e., trifluoroacetic acid (TFA)) and in a solvent (i.e., dichloromethane (DCM)) affords the intermediate 4b. Alternatively deprotection of intermediate 4a when PG is benzyloxycarbamate (Cbz) in the presence of a palladium catalyst (i.e., palladium on carbon), hydrogen gas, and in a solvent (i.e., dichloromethane (DCM)) also affords the intermediate 4b. Coupling of 4b with 2j, wherein $R^4$ in reagent 2j is optionally protected, using a catalytic amount of a palladium catalyst and ligand (i.e., palladium (II) acetate ($Pd(OAc)_2$) and 1,1'-Ferrocenediyl-bis(diphenylphosphine) (dppf)) and acetic anhydride in a solvent, e.g., DMF, at elevated temperature provides intermediate 4c. Deprotection intermediate 4c provides the desired product of Formula (I). Compounds of Formula (I) can also be synthesized as described above in steps 1 to 6 of General Scheme 4 from hydroxyl-aza-bicycloheptane intermediate 2g2.

It should be understood that in the description and formula shown above, the various groups $L_1$, $L_2$, A, B, $R^1$, $R^2$, $R^3$, $R^4$, $R^5$, $R^{6a}$, $R^{6b}$, $R^{6c}$, $R^{6d}$, $R^{6e}$, $R^7$, $R^8$, $R^9$, m, and n, and other variables are as defined above, except where otherwise indicated. Furthermore, for synthetic purposes, the compounds of General Schemes 1, 2 and 3 are mere representative with elected radicals to illustrate the general synthetic methodology of the compounds of Formula (I) as defined herein.

Methods of Using the Disclosed Compounds

Another aspect of the invention is directed to a method of modulating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the invention is directed to a method of modulating FXR. The method comprises administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the invention is directed to a method of activating FXR. The method involves administering to a patient in need thereof an effective amount of a compound of Formula (I), or a pharmaceutically acceptable salt, hydrate, solvate, prodrug, stereoisomer, or tautomer thereof.

In another aspect, the invention is directed to a method of activating FXR. The method involves administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the invention relates to a method of treating, preventing, inhibiting, or eliminating a disease or disorder in which FXR plays a role. The method comprises administering to a patient in need of a treatment for diseases or disorders in which FXR plays a role an effective amount of a compound of Formula (I), or a pharmaceutically acceptable salt, hydrate, solvate, prodrug, stereoisomer, or tautomer thereof. In one embodiment, the disease or disorder is a liver disease, an intestinal disease, a kidney disease, an autoimmune disorder, or cancer.

Another aspect of the invention relates to a method of treating, preventing, inhibiting, or eliminating a disease or disorder in which FXR plays a role. The method comprises administering to a patient in need of a treatment for diseases or disorders in which FXR plays a role an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier. In one embodiment, the disease or disorder is a liver disease, an intestinal disease, a kidney disease, an autoimmune disorder, or cancer.

Another aspect of the invention relates to a method of modulating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of modulating FXR. The method comprises administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the present invention relates to a method of treating, preventing, inhibiting, or eliminating a disease or disorder in a patient associated with the activation of FXR, the method comprising administering to a patient in need thereof an effective amount of a compound of Formula (I), or a pharmaceutically acceptable salt, hydrate, solvate, prodrug, stereoisomer, or tautomer thereof. In one embodiment, the disease or disorder is a liver disease, an intestinal disease, a kidney disease, an autoimmune disorder, or cancer.

Another aspect of the present invention relates to a method of treating, preventing, inhibiting, or eliminating a disease or disorder in a patient associated with the activation of FXR, the method comprising administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier. In one embodiment, the disease or disorder is a liver disease, an intestinal disease, a kidney disease, an autoimmune disorder, or cancer.

In another aspect, the present invention relates to a method of treating, preventing, inhibiting, or eliminating a liver disease. The method comprises administering to a patient in need of a treatment for a liver disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating a liver disease. The method comprises administering to a patient in need of a treatment for a liver disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating an intestinal disease. The method comprises administering to a patient in need of a treatment for an intestinal disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an intestinal disease. The method comprises administering to a patient in need of a treatment for an intestinal disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating a kidney disease. The method comprises administering to a patient in need of a treatment for a kidney disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating a kidney disease. The method comprises administering to a patient in need of a treatment for a kidney disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating an autoimmune disease. The method comprises administering to a patient in need of a treatment for an autoimmune disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an autoimmune disease. The method comprises administering to a patient in need of a treatment for an autoimmune disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating cancer. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating cancer. The method comprises administering to a patient in need of a treatment for cancer an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the present invention relates to a compound of Formula (I), or a pharmaceutically acceptable salt, hydrate, solvate, prodrug, stereoisomer, or tautomer thereof, for use in the treatment, prevention, inhibition, or elimination of a disease or disorder in which FXR plays a role. In one embodiment, the disease or disorder is a liver disease, an intestinal disease, a kidney disease, an autoimmune disorder, or cancer.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a disease or disorder in which FXR plays a role. In one embodiment, the disease or disorder is a liver disease, an intestinal disease, a kidney disease, an autoimmune disorder, or cancer.

In another aspect, the present invention relates to a compound of Formula (I), or a pharmaceutically acceptable salt, hydrate, solvate, prodrug, stereoisomer, or tautomer thereof, for use in the treatment, prevention, inhibition, or elimination of a liver disease.

Another aspect of the present invention relates to a compound of Formula (I), or a pharmaceutically acceptable salt, hydrate, solvate, prodrug, stereoisomer, or tautomer thereof, for use in the treatment, prevention, inhibition, or elimination of a disease associated with activating FXR.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a liver disease.

In another aspect, the present invention relates to a compound of Formula (I) or (Ia), or a pharmaceutically acceptable salt, hydrate, solvate, prodrug, stereoisomer, or tautomer thereof, for use in the treatment, prevention, inhibition, or elimination of an intestinal disease.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of an intestinal disease.

In another aspect, the present invention relates to a compound of Formula (I), or a pharmaceutically acceptable salt, hydrate, solvate, prodrug, stereoisomer, or tautomer thereof, for use in the treatment, prevention, inhibition, or elimination of a kidney disease.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a kidney disease.

In another aspect, the present invention relates to a compound of Formula (I) or (Ia), or a pharmaceutically acceptable salt, hydrate, solvate, prodrug, stereoisomer, or tautomer thereof, for use in the treatment, prevention, inhibition, or elimination of an autoimmune disorder.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of an autoimmune disorder.

In another aspect, the present invention relates to a compound of Formula (I) or (Ia), or a pharmaceutically acceptable salt, hydrate, solvate, prodrug, stereoisomer, or tautomer thereof, for use in the treatment, prevention, inhibition, or elimination of cancer.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of cancer.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder in which FXR plays a role. In one embodiment, the disease or disorder is a liver disease, an intestinal disease, a kidney disease, an autoimmune disorder or cancer.

Another aspect of the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a disease or disorder in which FXR plays a role. In one embodiment, the disease or disorder is a liver disease, an intestinal disease, a kidney disease, an autoimmune disorder or cancer.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a liver disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a liver disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating an intestinal disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating an intestinal disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a kidney disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a kidney disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating an autoimmune disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating an autoimmune disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a cancer.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a cancer.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with activating FXR.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a disease associated with activating FXR.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease in which FXR plays a role.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a disease in which FXR plays a role.

Another aspect of the present invention relates to a compound of Formula (I), or a pharmaceutically acceptable salt, hydrate, solvate, prodrug, stereoisomer, or tautomer thereof, for use in the manufacture of a medicament for treating a liver disease.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a liver disease.

Another aspect of the present invention relates to a compound of Formula (I), or a pharmaceutically acceptable salt, hydrate, solvate, prodrug, stereoisomer, or tautomer thereof, for use in the manufacture of a medicament for treating an intestinal disease.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating an intestinal disease.

Another aspect of the present invention relates to a compound of Formula (I), or a pharmaceutically acceptable salt, hydrate, solvate, prodrug, stereoisomer, or tautomer thereof, for use in the manufacture of a medicament for treating a kidney disease.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a kidney disease.

Another aspect of the present invention relates to a compound of Formula (I), or a pharmaceutically acceptable salt, hydrate, solvate, prodrug, stereoisomer, or tautomer thereof, for use in the manufacture of a medicament for treating an autoimmune disorder.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating an autoimmune disorder.

Another aspect of the present invention relates to a compound of Formula (I), or a pharmaceutically acceptable salt, hydrate, solvate, prodrug, stereoisomer, or tautomer thereof, for use in the manufacture of a medicament for treating cancer.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating cancer.

In other embodiments, the present invention relates to the use of an activator of FXR for the preparation of a medicament used in the treatment, prevention, inhibition or elimination of a liver disease.

In other embodiments, the present invention relates to the use of an activator of FXR for the preparation of a medicament used in the treatment, prevention, inhibition or elimination of an intestinal disease.

In other embodiments, the present invention relates to the use of an activator of FXR for the preparation of a medicament used in the treatment, prevention, inhibition or elimination of a kidney disease.

In other embodiments, the present invention relates to the use of an activator of FXR for the preparation of a medicament used in the treatment, prevention, inhibition or elimination of an autoimmune disorder.

In other embodiments, the present invention relates to the use of an activator of FXR for the preparation of a medicament used in the treatment, prevention, inhibition or elimination of a cancer.

The present invention also relates to the use of an activator of FXR for the preparation of a medicament used in the treatment, prevention, inhibition, or elimination of a disease or condition in which FXR plays a role, wherein the medicament comprises a compound of Formula (I).

In another aspect, the present invention relates to a method for the manufacture of a medicament for treating, preventing, inhibiting, or eliminating a disease or condition mediated by FXR, wherein the medicament comprises a compound of Formula (I), or a pharmaceutically acceptable salt, hydrate, solvate, prodrug, stereoisomer, or tautomer thereof.

In some embodiments of the methods described herein, the disease or condition is selected from the group consisting of liver disease, intestinal disease, kidney disease, an autoimmune disorder, or cancer. In other embodiments, the disease can be any disease including, but not limited to, Alagille syndrome (ALGS), atherosclerosis, biliary atresia, Byler disease, gallstone disease, hyperlipidemia, hepatocellular carcinoma, hepatocellular adenoma, cholangiocarcinoma, colorectal cancer, colorectal adenoma, ileal adenoma, renal cancer, oesophageal cancer, obesity, type-2 diabetes mellitus, and gastric cancer.

In any of the embodiments of the invention, the liver disease can be any liver diseases, including, but not limited to, primary biliary cirrhosis (PBC), primary sclerosing cholangitis (PSC), non-alcoholic fatty liver disease (NAFLD), non-alcoholic steatohepatitis (NASH), alcoholic liver disease, intra- and extra-cholestasis, biliary atresia, portal vein hypertension (PAH), spontaneous bacterial peritonitis (SBP), acute decompensation liver failure, hepatorenal syndrome and hepatic encephalopathy. In an embodiment, the liver disease is NASH. In an embodiment, the liver disease is NAFLD. In an embodiment, the liver disease is NASH and the compound of the invention is administered in combination with an anti-inflammatory agent or anti-fibrotic agent.

In any of the embodiments of the invention, the intestinal disease can be any intestinal disease, including, but not limited to, inflammatory bowel disease, Crohn's disease, ulcerative colitis, proctitis, pouchitis, Celiac's disease and bile acid diarrhea.

In an embodiment, the disease is an intestinal permeability disease, disorder or condition mediated by tight junction dysfunction. In an embodiment the disease, disorder or condition is gastric ulcers, infectious diarrhea, irritable bowel syndrome, functional GI diseases (IBS, IBS-C, IBS- D, IBS-M, post infectious IBS), inflammatory bowel disease (CD, UC), Celiac's, cancer (colorectal), Leaky Gut Syndrome, cystic fibrosis GI manifestations, multi-organ failure, microscopic colitis or necrotizing enterocolitis.

In another embodiment, compounds of the invention are used to treat one of the following disease, disorder or condition: allergy e.g, atopy, food allergy; infections e.g, respiratory infections; acute inflammation e.g, sepsis, SIRS, MOF); chronic inflammation e.g, arthritis; obesity-induced metabolic diseases e.g. NASH, diabetes, T1D/T2D, CVD; kidney disease e.g, chronic kidney disease, diabetic kidney disease; heart disease e.g, heart failure, congestive heart failure; liver disease e.g, cirrhosis, NASH, NAFLD, steatosis, PSC, PBC, portal hypertension; autoimmune disease e.g, type 1 diabetes, celiac disease, multiple sclerosis, IBD, ankylosing spondylitis. RA, lupus, alopecia areata, rheumatoid arthritis, polymyalgia rheumatica, multiple sclerosis, fibromyalgia, chronic fatigue syndrome, Sjogren's syndrome, vitiligo, thyroiditis, vasculitis, Crohn's disease, ulcerative colitis, urticaria (hives) and Raynaud's syndrome; neurological e.g, schizophrenia, autism spectrum disorders, multiple sclerosis, hepatic encephlopathy; and chronic alcoholism.

In any of the embodiments of the invention, the kidney disease can be any kidney disease, including, but not limited to, fibrotic renal disease and diabetic nephrophathy.

In any of the embodiments of the invention, the autoimmune disorder can be any autoimmune disorder, including, but not limited to, inflammatory bowel disease, autoimmune hepatitis, autoimmune liver disease (primary biliary cirrhosis (PBC) and primary sclerosing cholangitis (PSC)), and multiple sclerosis.

In any of the embodiments of the invention, the cancer can be any cancer including, but not limited to, a cancer is selected from the group consisting of hepatocellular carcinoma, hepatocellular adenoma, cholangiocarcinoma, colorectal cancer, colorectal adenoma, ileal adenoma, renal cancer, oesophageal cancer, or gastric cancer.

In another embodiment, the present invention relates to a compound of Formula (I), or a pharmaceutically acceptable salt, hydrate, solvate, prodrug, stereoisomer, or tautomer thereof, or a pharmaceutical composition comprising a compound, or a pharmaceutically acceptable salt, hydrate, solvate, prodrug, stereoisomer, or tautomer thereof, of the present invention and a pharmaceutically acceptable carrier used for the treatment of diseases including, but not limited to liver diseases, intestinal diseases, kidney diseases, autoimmune disorders or cancer.

Another aspect of the invention is directed to pharmaceutical compositions comprising a compound of Formula (I), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

In one embodiment, are provided methods of treating a disease or disorder in which FXR plays a role including a liver disease, an intestinal disease, a kidney disease or an autoimmune disorder comprising administering to a patient suffering from at least one of said diseases or disorder a compound of Formula (I).

One therapeutic use of the compounds or compositions of the present invention which activate FXR is to provide treatment to patients or subjects suffering from a liver disease, an intestinal disease, a kidney disease, an autoimmune disorder, or cancer.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The invention is further illustrated by the following examples and synthesis schemes, which are not to be construed as limiting this invention in scope or spirit to the specific procedures herein described. It is to be understood that the examples are provided to illustrate certain embodiments and that no limitation to the scope of the invention is intended thereby. It is to be further understood that resort may be had to various other embodiments, modifications, and equivalents thereof which may suggest themselves to those skilled in the art without departing from the spirit of the present invention and/or scope of the appended claims.

Analytical Methods, Materials, and Instrumentation

Unless otherwise noted, reagents and solvents were used as received from commercial suppliers. Proton nuclear magnetic resonance (NMR) spectra were obtained with a Varian spectrometer at 400 MHz, a Bruker spectrometer at 300 MHz or 400 MHz. Spectra are given in ppm (δ) and coupling constants, J, are reported in Hertz. Tetramethylsilane (TMS) or the solvent peak was used as an internal standard. If not otherwise specified, purity and low resolution mass spectral data were measured using a Thermo Finnigan Surveyor HPLC system with Surveyor photo diode array (PDA) detection and a Thermo LCQ Fleet™ ion trap mass spectrometer. Column: Synergi 4 micron, hydro-RP80A, 30×2.0 mm, Flow rate: 0.500 mL/min; Solvent A (water+0.1% formic acid), Solvent B (acetonitrile+0.1% formic acid); Gradient: 2% B at t=0 to 95% B at 3 min to 95% B at 3.3 min.

Abbreviations used in the following examples and elsewhere herein are:

AcOH acetic acid
ACN acetonitrile
aq. Aqueous
BINAP 2,2'-Bis(diphenylphosphino)-1,1'-binaphthyl
Boc tert-butyl carbonate
tert-BuONO tert-butyl nitrite
CbzCl benzyl chloroformate
CDI carbonyldiimidazole
$Cs_2CO_3$ cesium carbonate
$CuBr_2$ copper(II)bromide
DCM dichloromethane
DIAD diisopropyl azodicarboxylate
DIEA N,N-diisopropylethylamine
DMA dimethylacetamide
DMAP 4-dimethylaminopyridine
DMF N,N-dimethylformamide
DMSO dimethylsulfoxide
dppf bis(diphenylphosphino)ferrocene
EDCI 1-ethyl-3-(3-dimethylaminopropyl)carbodiimide
equiv, equivalents
ESI electrospray ionization
$Et_2O$ diethylether
EtOAc ethyl acetate
EtOH ethanol
h hours
HATU 1-[bis(dimethylamino)methylene]-1H-1,2,3-triazolo[4,5-b]pyridinium 3-oxid hexafluorophosphate
HCl hydrogen chloride
HPLC high performance liquid chromatography
LCMS liquid chromatography-mass spectrometry
LAH lithium aluminium hydride
LiOH lithium hydroxide
MeOH methanol
min minutes
MeCN acetonitrile
MeI methyl iodide
MS mass spectrometry
NaOMe sodium methoxide
NaOH sodium hydroxide
NaSCN sodium thiocyanate
$NEt_3$ triethylamine
$NH_2OH.HCl$ hydroxylamine hydrochloride
NCS N-chlorosuccinimide
NIS N-Iodosuccinimide
$Pd(OAc)_2$ palladium (II) acetate $Pd_2(dba)_3$ tris(dibenzylideneacetone)dipalladium
PE petroleum ether
$P(Cy)_3$ tricyclohexyl phosphine
$PPh_3$ triphenyl phosphine
RT room temperature
TEA triethylamine
$TMSCH_2N_2$ trimethylsilyldiazomethane
THF tetrahydrofuran
TFA trifluoroacetic acid Example 1: Intermediate. Benzyl (1S,4S,5R)-5-hydroxy-2-azabicyclo[2.2.1]heptane-2-carboxylate (C-1) and (1S,4R,6S)-Benzyl 6-hydroxy-2-aza-bicyclo[2.2.1]heptane-2-carboxylate (C-2)

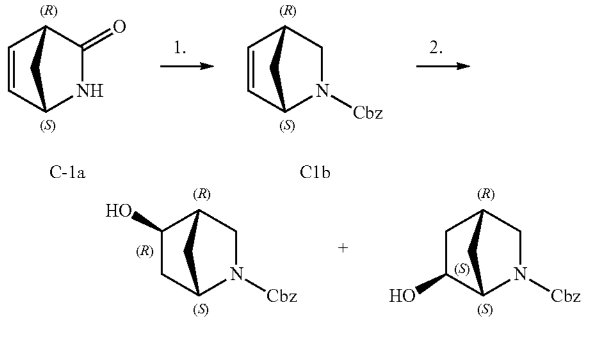

C-1a C1b C-1 C-2

Step 1. Benzyl (1S,4R)-2-azabicyclo[2.2.1]hept-5-ene-2-carboxylate (C-1b)

To a 250-mL 3-necked round-bottom flask purged and maintained under an inert atmosphere of nitrogen was added a solution of $LiAlH_4$ (2.15 g, 56.65 mmol, 1.25 equiv.) in tetrahydrofuran (80 mL). A solution of (1S,4R)-2-azabicyclo[2.2.1]hept-5-en-3-one C-1a (5 g, 45.82 mmol, 1.0 equiv.) in tetrahydrofuran (45 mL) was added dropwise with stirring at 0° C. The mixture was stirred at 23° C., for 3 h, and then continued at 60° C., for 24 h. After cooling to room temperature, water (5 mL) was added. The resulting mixture was diluted with 250 mL of tetrahydrofuran, and the solids were removed by filtration. The filtrate was cooled to 0° C., and TEA was added (9.1 g, 89.93 mmol, 2.0 equiv.) dropwise followed by the dropwise addition of benzyl chloroformate (11.75 g, 68.88 mmol, 1.50 equiv.). The reaction mixture was stirred at 23° C., for 48 h and concentrated under reduced pressure. The crude product was purified by Flash-Prep-HPLC using the following conditions: Column, C18 silica gel; mobile phase, $CH_3CN:H_2O=0:100$ increasing to $CH_3CN:H_2O=30:70$ within 30 min; Detector, UV 254 nm. Removal of solvents provided benzyl (1S,4R)-2-azabicyclo[2.2.1]hept-5-ene-2-carboxylate C-1b in 5.6 g (53%) as a light yellow oil.

Step 2. Benzyl (1S,4S,5R)-5-hydroxy-2-azabicyclo[2.2.1]heptane-2-carboxylate (C-1) (1S,4R,6S)-Benzyl 6-hydroxy-2-aza-bicyclo[2.2.1]heptane-2-carboxylate (C-2)

To a 500-mL round-bottom flask purged and maintained under an inert atmosphere of nitrogen, was added a solution of benzyl (1S,4R)-2-azabicyclo[2.2.1]hept-5-ene-2-carboxylate (8.6 g, 24.42 mmol, 1.0 equiv.) C-1b in tetrahydrofuran (60 mL). $NaBH_4$ (1.17 g, 30.93 mmol, 0.80 equiv.) was added. The mixture was stirred 23° C., for 30 min then cooled in an ice bath. A solution of $Me_2SO_4$ (2.93 mL, 0.80 equiv.) in tetrahydrofuran (2 mL) was added dropwise with stirring at 0° C. Reaction was continued at 35° C., for 4 h. The mixture was cooled again at 0° C., a 1M sodium hydroxide aqueous solution (80 mL) was added dropwise with stirring followed by the dropwise addition of $H_2O_2$ (30%) (5 mL). The resulting mixture was stirred at 23° C., for 1 h. 250 mL of ethyl acetate was added. The mixture was washed with brine (150 mL), dried over anhydrous sodium sulfate, filtered, and concentrated under reduced pressure. The residue was purified by silica gel column chromatography eluting with ethyl acetate/petroleum ether (0-60% in 1 h, 100 mL/min). Removal of solvents provided 3.7 g (40%) of benzyl (1S,4S,5R)-5-hydroxy-2-azabicyclo[2.2.1]heptane-2-carboxylate C-1 as a colorless oil and 3.5 g (38%) its isomer (1S,4R,6S)-benzyl 6-hydroxy-2-aza-bicyclo[2.2.1]heptane-2-carboxylate C-2 also a colorless oil. Rf(C1)<Rf(C2).

C-1: $^1H$ NMR (400 MHz, Methanol-$d_4$) δ 7.40-7.24 (m, 5H), 5.15-5.01 (m, 2H), 4.30-4.19 (m, 1H), 3.98-3.89 (m, 1H), 3.25 (ddd, J=18.3, 10.2, 4.0 Hz, 1H), 2.97-2.84 (m, 1H), 2.48-2.37 (m, 1H), 2.10-1.79 (m, 2H), 1.56 (ddt, J=9.9, 7.5, 2.1 Hz, 1H), 1.44 (dq, J=13.6, 2.9 Hz, 1H). Rf(C1)<Rf(C2).

C-2: $^1H$ NMR (400 MHz, Methanol-$d_4$) δ 7.42-7.24 (m, 5H), 5.10 (dd, J=11.7, 3.1 Hz, 2H), 4.03 (d, J=9.9 Hz, 1H), 3.87 (tdt, J=8.4, 2.5, 1.3 Hz, 1H), 3.20 (ddt, J=15.2, 9.4, 2.8 Hz, 1H), 2.88 (ddd, J=20.8, 9.4, 1.6 Hz, 1H), 2.58-2.51 (m, 1H), 1.88-1.73 (m, 2H), 1.61-1.49 (m, 1H), 1.42 (ddt, J=13.4, 4.7, 2.4 Hz, 1H).

Example 2: Intermediate. Benzyl (1R,4R,5S)-5-hydroxy-2-azabicyclo[2.2.1]heptane-2-carboxylate (C-4) and Benzyl (1R,4S,6R)-6-hydroxy-2-azabicyclo[2.2.1]heptane-2-carboxylate (C-5)

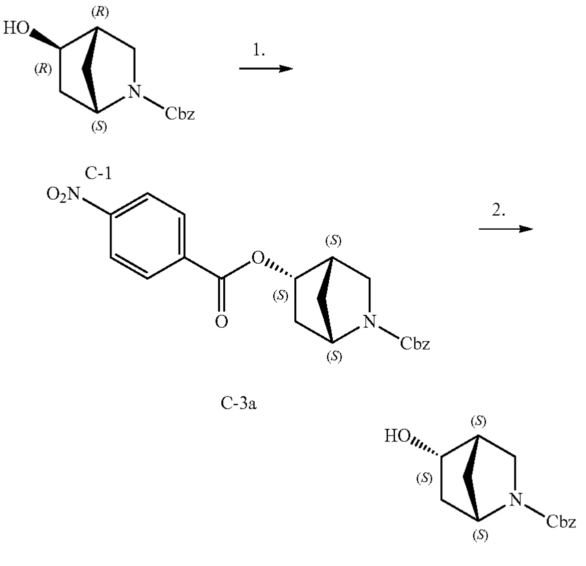

C-1 C-3a C-3

Step 1. Benzyl (1S,4S,5S)-5-[(4-nitrophenyl)carbonyloxy]-2-azabicyclo[2.2.1]heptane-2-carboxylate (C-3a)

To a 250-mL round-bottom flask was added a solution of benzyl (1S,4S,5R)-5-hydroxy-2-azabicyclo[2.2.1]heptane-2-carboxylate C-1 (1.03 g, 4.17 mmol, 1.0 equiv.) in tetrahydrofuran (50 mL) and 4-nitrobenzoic acid (1.05 g, 6.28 mmol, 1.50 equiv.). The reaction mixture was cooled to 0° C., and $PPh_3$ was added (1.64 g, 6.25 mmol, 1.50 equiv) in several batches followed by dropwise addition of DIAD (1.26 g, 6.23 mmol, 1.50 equiv). The resulting mixture was stirred at room temperature overnight and then concentrated under reduced pressure. The residue was purified by silica gel column chromatography eluting with ethyl acetate/petroleum ether (25:75) to give 1.6 g (97%) of benzyl (1S,4S,5S)-5-[(4-nitrophenyl)carbonyloxy]-2-azabicyclo[2.2.1]heptane-2-carboxylate C-3a as a colorless oil.

Step 2. Benzyl (1S,4S,5S)-5-hydroxy-2-azabicyclo[2.2.1]heptane-2-carboxylate (C-3)

To a 250-mL round-bottom flask was added a solution of benzyl (1S,4S,5S)-5-[(4-nitrophenyl)carbonyloxy]-2-azabicyclo[2.2.1]heptane-2-carboxylate C-3a (1.6 g, 4.04 mmol, 1.0 equiv.) in methanol/$H_2O$ (20 mL/2 mL) and $LiOH.H_2O$ (1.69 g, 40.28 mmol, 10.0 equiv.). The resulting mixture was stirred at 60° C., for 1 h, and then concentrated under reduced pressure. The crude product was purified by Flash-Prep-HPLC using the following conditions: Column, C18 silica gel; mobile phase, $CH_3CN:H_2O$=0:100 increasing to $CH_3CN:H_2O$=30:70 within 20 min; Detector, UV 254 nm. 0.6 g product was obtained. Removal of solvents afforded 0.6 g (60%) of benzyl (1S,4S,5S)-5-hydroxy-2-azabicyclo[2.2.1]heptane-2-carboxylate C-3 as a light yellow oil. $^1H$ NMR (400 MHz, Methanol-$d_4$) δ 7.40-7.24 (m, 5H), 5.10 (t, J=2.5 Hz, 2H), 4.33 (dq, J=7.8, 3.6 Hz, 1H), 4.16 (dt, J=14.9, 2.5 Hz, 1H), 3.73 (ddd, J=19.9, 9.9, 1.4 Hz, 1H), 3.24-3.12 (m, 1H), 2.57 (t, J=3.7 Hz, 1H), 2.02 (dddd, J=12.9, 9.9, 4.7, 2.8 Hz, 1H), 1.76-1.65 (m, 1H), 1.58 (d, J=10.3 Hz, 1H), 1.31 (ddt, J=17.0, 12.9, 3.3 Hz, 1H).

Example 3: Intermediates. Benzyl (1R,4R,5S)-5-hydroxy-2-azabicyclo[2.2.1]heptane-2-carboxylate (C-4) and Benzyl (1R,4S,6R)-6-hydroxy-2-azabicyclo[2.2.1]heptane-2-carboxylate (C-5)

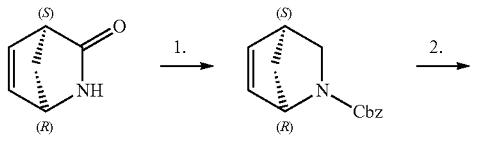

C-4a C4b

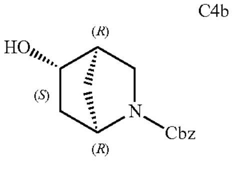

+

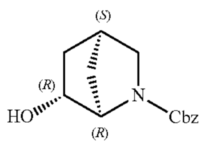

C-4 C-5

Step 1. Benzyl (1R,4S)-2-azabicyclo[2.2.1]hept-5-ene-2-carboxylate (C-2)

A solution of (1R,4S)-2-azabicyclo[2.2.1]hept-5-en-3-one C-4a (5.0 g, 45.8 mmol) in anhydrous THF (50 mL) was added slowly to a solution of LAH (28.7 mL, 57.3 mmol, 2M solution in THF) in anhydrous THF (50 mL) under a nitrogen atmosphere at 0° C. The resulting mixture was then stirred at room temperature for 3 h and then heated at 60° C., for 24 h. The mixture was cooled to 0° C., and $H_2O$ (5.0 mL) was added carefully to the mixture. The resulting white suspension was filtered through a Celite pad and the pad was washed with anhydrous THF (250.0 mL). The clear filtrate was cooled to 0° C., and then treated with trimethylamine (12.8 mL, 91.6 mmol) and CbzCl (10.3 mL, 68.7 mmol). The reaction mixture was slowly warmed to room temperature and stirred for 48 hours. The white precipitate was filtered and the resulting clear filtrate solution was concentrated to dryness. The crude material was purified by column chromatography (hexane:EtOAc 4:1) to give benzyl (1R,4S)-2-azabicyclo[2.2.1]hept-5-ene-2-carboxylate C-4b (7.06 g, 63%) as a clear oil. MS (ES, m/z): [M+1]=230.

Step 2. Benzyl (1R,4R,5S)-5-hydroxy-2-azabicyclo[2.2.1]heptane-2-carboxylate (C-4), Benzyl (1R,4S,6R)-6-hydroxy-2-azabicyclo[2.2.1]heptane-2-carboxylate (C-5)

A mixture of benzyl (1R,4S)-2-azabicyclo[2.2.1]hept-5-ene-2-carboxylate C-4b (7.0 g, 30.8 mmol) and sodium borohydride (0.95 g, 25.1 mmol) in THF (50 mL) was stirred at 23° C., for 30 minutes under nitrogen atmosphere. The mixture was warmed to 35° C., and then dimethylsulfate (2.37 mL, 25.1 mmol) dissolved in THF (2.0 mL) was added dropwise. The resulting mixture was stirred at 35° C., for 4 hours, and then cooled to 0° C., and quenched by dropwise addition of $H_2O$ (4.0 mL). A 1M aqueous solution of sodium hydroxide (70 mL, 70.0 mmol) was added at 0 (C followed by addition of hydrogen peroxide (4.0 mL, 30 wt % in $H_2O$). The mixture was warmed to room temperature and stirred for an additional hour. The resulting mixture was diluted with ethyl acetate (250 mL) and the organic layer was separated, washed with brine, and dried over $MgSO_4$, filtered and concentrated. The crude product was purified by column chromatography (hexane:ethyl acetate 1:1 v/v) to provide both benzyl (1R,4R,5S)-5-hydroxy-2-azabicyclo[2.2.1]heptane-2-carboxylate C-4 (3.0 g, Rf=0.22, clear oil) and Benzyl (1R,4S,6R)-6-hydroxy-2-azabicyclo[2.2.1]heptane-2-carboxylate C-5 (2.9 g, Rf=0.36, clear oil).

C-4: $^1H$ NMR (400 MHz, $CDCl_3$) δ: 7.41-7.27 (m, 5H), 5.14-5.06 (m, 2H), 4.29 (d, J=21.5 Hz, 1H), 4.02 (d, J=6.6 Hz, 1H), 3.26 (dt, J=13.1, 6.5 Hz, 1H), 2.91 (t, J=9.8 Hz, 1H), 2.47 (s, 1H), 2.20-2.01 (m, 2H), 1.85 (t, J=10.8 Hz, 1H), 1.62-1.39 (m, 2H)

C-5: $^1H$ NMR (400 MHz, $CDCl_3$) δ: 7.40-7.28 (m, 5H), 5.20-5.02 (m, 2H), 4.16-3.94 (m, 2H), 3.22 (ddd, J=9.5, 6.9, 2.9 Hz, 1H), 2.90 (dd, J=16.0, 6.1 Hz, 1H), 2.54 (s, 1H), 1.90-1.73 (m, 2H), 1.61-1.37 (m, 2H).

Example 4: Intermediate. Benzyl (1R,4R,5R)-5-hydroxy-2-azabicyclo[2.2.1]heptane-2-carboxylate (C-6)

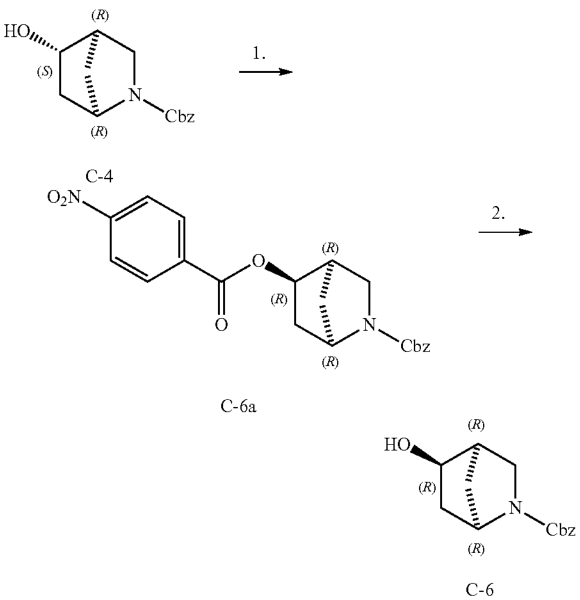

C-4

C-6a

C-6

Step 1. Benzyl (1R,4R,5R)-5-((4-nitrobenzoyl)oxy)-2-azabicyclo[2.2.1]heptane-2-carboxylate (C-6a)

To a mixture of benzyl (1R,4R,5S)-5-hydroxy-2-azabicyclo[2.2.1]heptane-2-carboxylate C-4 (0.4 g, 2.4 mmol) and 4-nitrobenzoic acid (0.6 g, 2.4 mmol) in THF (10 mL) was added DIAD (1.0 mL, 4.8 mmol) and $PPh_3$ (1.28 g, 4.8 mmol) and the resulting mixture was stirred at room temperature overnight. The mixture was then partitioned between EtOAc and water. The organic layer was washed with brine, dried, filtered, concentrated, and purified by column chromatography (20-40% EtOAc in hexanes) to give benzyl (1R,4R,5R)-5-((4-nitrobenzoyl)oxy)-2-azabicyclo[2.2.1]heptane-2-carboxylate C-6a (0.85 g, 90%) as a yellow oil. MS (ES, m/z): [M+1]=397.

Step 2. Benzyl (1R,4R,5R)-5-hydroxy-2-azabicyclo[2.2.1]heptane-2-carboxylate (C-6)

To a solution of benzyl (1R,4R,5R)-5-((4-nitrobenzoyl)oxy)-2-azabicyclo[2.2.1]heptane-2-carboxylate C-6a (0.85 g, 2.1 mmol) in MeOH (6.0 mL) was added a 1M aqueous solution of NaOH (4.2 mL, 4.2 mmol) and the resulting mixture was heated at 50° C., for 2 hours. The reaction mixture was cooled to room temperature and partitioned between EtOAc and water. The organic layer was washed with 1M NaOH and brine, dried with $MgSO_4$, filtered, and concentrated. The crude product was purified by column chromatography (hexanes:EtOAc 1:1) to give benzyl (1R,4R,5R)-5-hydroxy-2-azabicyclo[2.2.1]heptane-2-carboxylate C-6 (0.32 g, 60%) as a clear oil. $^1H$ NMR (400 MHz, $CDCl_3$) δ 7.43-7.21 (m, 5H), 5.20-5.02 (m, 2H), 4.35 (dt, J=18.3, 9.2 Hz, 1H), 4.21 (d, J=22.8 Hz, 1H), 3.76 (dt, J=16.5, 8.1 Hz, 1H), 3.25-3.15 (m, 1H), 2.59 (s, 1H), 2.09-1.94 (m, 1H), 1.69 (t, J=9.6 Hz, 1H), 1.53-1.31 (m, 2H). MS (ES, m/z): [M+1]=248.

Example 5: Intermediate. Methyl 2-bromo-4-fluoro-1,3-benzothiazole-6-carboxylate (A-1)

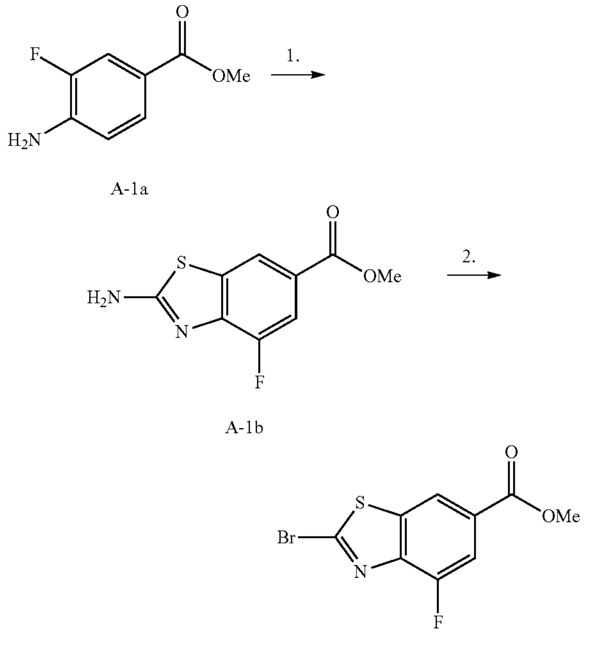

A-1a

A-1b

A-1

Step 1. Methyl 2-amino-4-fluoro-1,3-benzothiazole-6-carboxylate (A-1b)

To a 1 L round-bottom flask was added methyl 4-amino-3-fluorobenzoate A-1a (20 g, 118.24 mmol, 1.0 equiv.), AcOH (400 mL), and NaSCN (38.34 g, 473.33 mmol, 4.0 equiv.). The mixture was cooled at 0° C., and bromine (18.7 g, 117.01 mmol, 1.0 equiv) was added dropwise with stirring. The reaction mixture was stirred at 0° C., for 2 hours, then at 30° C., for 3 days. 400 mL of water was added, the pH value of the solution was adjusted to 9 using sodium hydroxide. Solids were collected by filtration and dried in an oven under reduced pressure, to give 28 g (crude) of methyl 2-amino-4-fluoro-1,3-benzothiazole-6-carboxylate A-1b as a yellow solid. The crude product was carried onto the next step without further purification.

Step 2. Methyl 2-bromo-4-fluoro-1,3-benzothiazole-6-carboxylate (A-1)

To a 250 mL round-bottom flask was added $CuBr_2$ (2.96 g, 1.50 equiv.) and MeCN (100 mL). The resulting mixture was cooled at 0° C., and t-BuONO (2.4 mL) was added dropwise followed by the batchwise addition of ethyl 2-amino-4-fluoro-1,3-benzothiazole-6-carboxylate A-1b (2 g, 8.84 mmol, 1.0 equiv.) at 0° C. The reaction mixture was stirred overnight at 30° C., and then concentrated under reduced pressure. The crude product was purified by Flash-Prep-HPLC, using the following conditions: Column, silica gel; mobile phase, eluting with PE:EA, 100:0 to 90:10 over 10 min; Detector, UV 254 nm, to afford 507.9 mg (20%) of methyl 2-bromo-4-fluoro-1,3-benzothiazole-6-carboxylate A-1 as a light yellow solid. $^{1}H$ NMR (300 MHz, DMSO-$d_6$) δ: 8.67 (d, J=1.4 Hz, 1H), 7.84 (dt, J=11.1, 1.2 Hz, 1H), 3.92 (s, 3H). MS (ES, m/z): [M+1]=290.

Example 6: Intermediate. Methyl 2-bromo-5-methoxy-1,3-benzothiazole-6-carboxylate (A-2)

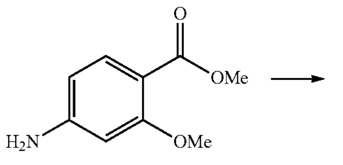

A-2a

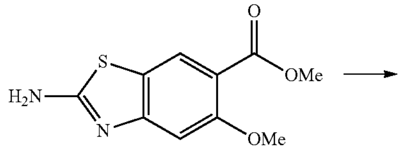

A-2b

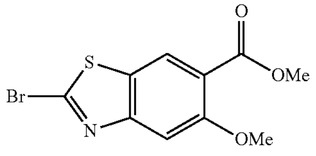

A-2

Step 1. Methyl 2-amino-5-methoxy-1,3-benzothiazole-6-carboxylate (A-2b)

To a 250-mL 3-necked round-bottom flask was added methyl 4-amino-2-methoxybenzoate A-2a (9.0 g, 49.67 mmol, 1.0 equiv.), AcOH (50 mL), and NaSCN (32.4 g, 399.65 mmol, 8.0 equiv.), followed by the dropwise addition of a solution of $Br_2$ (15.9 g, 99.49 mmol, 2.0 equiv) in AcOH (50 mL) over 1 h at 0° C. The resulting mixture was then stirred at 30° C., for 24 h. 200 mL of water was added and the pH of the solution was adjusted to 9 using sodium hydroxide pellets. The resulting solids were collected by filtration and dried in an oven under reduced pressure to give 10 g (84%) of methyl 2-amino-5-methoxy-1,3-benzothiazole-6-carboxylate A-2b as a brown solid. The crude product was carried onto the next step without further purification.

Step 2. Methyl 2-bromo-5-methoxy-1,3-benzothiazole-6-carboxylate (A-2)

To a 250-mL round-bottom flask was added methyl 2-amino-5-methoxy-1,3-benzothiazole-6-carboxylate A-2b (4.8 g, 20.15 mmol, 1.0 equiv.), MeCN (80 mL), and $CuBr_2$ (6.7 g, 30.0 mmol, 1.50 equiv.), followed by the dropwise addition of t-BuONO (6.2 g. 60.12 mmol, 3.0 equiv) at 0° C. The resulting mixture was stirred overnight at 30° C., and then concentrated under reduced pressure. The resulting residue was purified by silica gel column chromatography eluting with ethyl acetate/petroleum ether (1:10) to provide 1.5 g (25%) of methyl 2-bromo-5-methoxy-1,3-benzothiazole-6-carboxylate A-2 as a light yellow solid. This intermediate was 98% pure based on LCMS analysis. $^{1}H$ NMR (300 MHz, $CDCl_3$) δ: 8.424 (s, 1H), 7.547 (s, 1H), 3.974 (s, 3H), 3.931 (s, 3H). MS (ES, m/z): [M+1]=301.85.

Example 7: Intermediate. 2-Bromo-4-methoxy-1,3-benzothiazole-6-carboxylate (A-3)

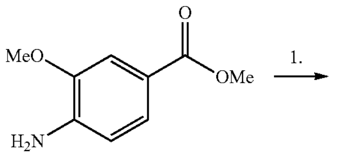

A-3a

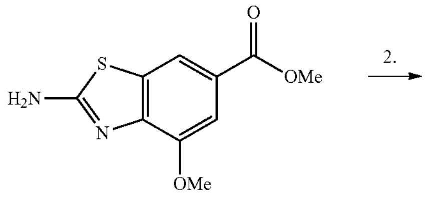

A-3b

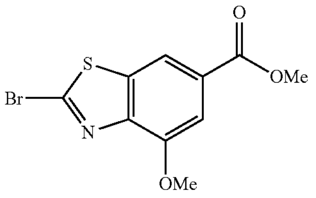

A-3

Step 1. Methyl 2-amino-4-methoxy-1,3-benzothiazole-6-carboxylate (A-3b)

To a 500 mL 3-necked round-bottom flask containing methyl 4-amino-3-methoxybenzoate A-3a (10 g, 55.19 mmol, 1.0 equiv.), AcOH (150 mL), and NaSCN (17.9 g) was added a solution of bromine (8.8 g, 55.07 mmol, 1.0 equiv.) in AcOH (50 mL) dropwise at 0-5° C. The resulting mixture was stirred at 30° C., overnight and poured into a 1000 mL $H_2O$ solution. The pH value of the aqueous solution was adjusted to 9 using potassium carbonate. The resulting solids were collected by filtration to give 12.5 g (95%) of methyl 2-amino-4-methoxy-1,3-benzothiazole-6-carboxylate A-3b as a yellow solid.

Step 2. 2-bromo-4-methoxy-1,3-benzothiazole-6-carboxylate (A-3)

To a 1000 mL round-bottom flask was added methyl 2-amino-4-methoxy-1,3-benzothiazole-6-carboxylate A-3b (9.2 g, 38.61 mmol, 1.0 equiv.), $CH_3CN$ (200 mL), $CuBr_2$ (12.9 g), and tert-butyl nitrite (9 g, 87.28 mmol, 2.26 equiv.) and the resulting mixture was stirred at 30° C., overnight. The solvent was removed under reduced pressure and the resulting crude residue purified via silica gel column eluting with ethyl acetate/petroleum ether (1:3) to give 4.7 g (40%) of 2-bromo-4-methoxy-1,3-benzothiazole-6-carboxylate A-3 as a light yellow solid.

Example 8: Intermediate. Methyl 2-bromo-4-(trifluoromethoxy)-1,3-benzothiazole-6-carboxylate (A-4)

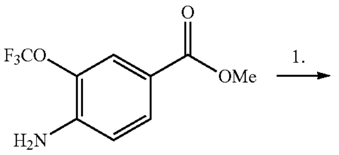

A-4a

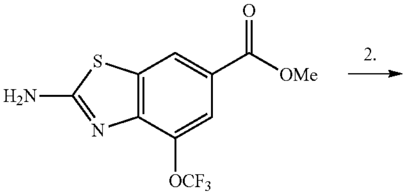

A-4b

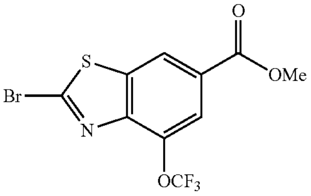

A-4

Step 1. Methyl 2-amino-4-(trifluoromethoxy)-1,3-benzothiazole-6-carboxylate (A-4b)

To a 500 mL round-bottom flask was added methyl 4-amino-3-(trifluoromethoxy) benzoate (7.1 g, 30.19 mmol, 1.0 equiv.), AcOH (100 mL), and NaSCN (12.1 g, 149.25 mmol, 5.0 equiv.), followed by the dropwise addition of a solution of bromine (9.6 g, 60.07 mmol, 2.0 equiv.) in AcOH (50 mL) at 0° C., over 1 hr. The mixture was stirred at 0° C., for 2 h, and then at 40° C., overnight. The reaction mixture was cooled to 0° C., and a second batch of NaSCN (12.2 g, 150.49 mmol, 5.0 equiv.) was added, followed by the dropwise addition of a solution of bromine (9.6 g, 60.07 mmol, 2.0 equiv.) in AcOH (50 mL) over 1 hr. Again, the reaction mixture was stirred at 0° C., for 2 h, and then at 40° C., for 3 days. The resulting mixture was diluted with 200 mL of water and the pH value of the aqueous solution was adjusted to 9 with sodium hydroxide. The resulting solids were collected by filtration, washed with water (20 mL×2), and dried in an oven at 60° C., for 6 h to provide of methyl 2-amino-4-(trifluoromethoxy)-1,3-benzothiazole-6-carboxylate A-4b (5.4 g, 61%) as a brown solid.

Step 2. Methyl 2-bromo-4-(trifluoromethoxy)-1,3-benzothiazole-6-carboxylate (A-4)

To a 250 mL round-bottom flask was added methyl 2-amino-4-(trifluoromethoxy)-1,3-benzothiazole-6-carboxylate A-4b (2.9 g, 9.92 mmol, 1.0 equiv.), MeCN (100 mL), and $CuBr_2$ (3.4 g, 15.22 mmol, 1.5 equiv.), followed by the dropwise addition of t-BuONO (3.1 g, 30.06 mmol, 3.0 equiv). The resulting mixture was stirred at 30° C., overnight, and then concentrated under reduced pressure. The resulting residue was purified via silica gel column eluting with ethyl acetate/petroleum ether (1:10) to provide of methyl 2-bromo-4-(trifluoromethoxy)-1,3-benzothiazole-6-carboxylate A-4 (1.8 g, 51%) as a white solid. $^1H$ NMR (300 MHz, $CD_3OD$) δ: 8.681 (s, 1H), 8.020 (s, 1H), 3.955 (s, 3H). MS (ES, m/z): [M+1]=356, [M+3]=358.

Example 9: Intermediate. Methyl 2-bromo-4-(trifluoromethyl)-1,3-benzothiazole-6-carboxylate (A-5)

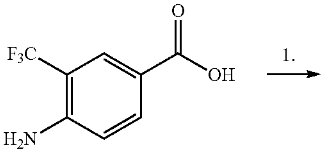

A-5a

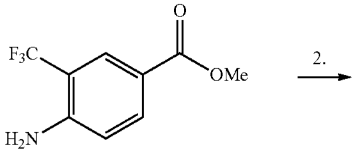

A-5b

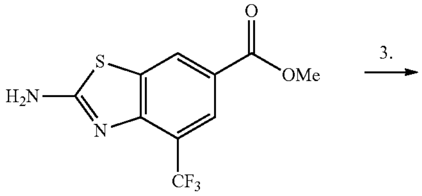

A-5c

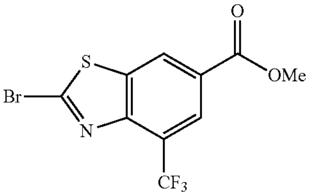

A-5

Step 1. Methyl 4-amino-3-(trifluoromethyl)benzoate (A-5b)

To a 250 mL round bottom flask was added 4-amino-3-(trifluoromethyl)benzoic acid A-5a (8 g, 39.0 mmol, 1.0 equiv.), tetrahydrofuran (40 mL), methanol (40 mL), and $TMSCHN_2$ (40 mL, 2.0 equiv.). The resulting mixture was stirred at room temperature overnight and then concentrated in vacuo. The resulting residue was purified via silica gel column eluting with ethyl acetate/petroleum ether (1:5) to give of methyl 4-amino-3-(trifluoromethyl)benzoate A-5b (7 g, 82%) as a colorless solid.

Step 2. Methyl 2-amino-4-(trifluoromethyl)-1,3-benzothiazole-6-carboxylate (A-5c)

To a 250 mL round-bottom flask was added methyl 4-amino-3-(trifluoromethyl) benzoate A-5b (2.2 g, 10.04 mmol, 1.0 equiv), NaSCN (4.0 g, 49.34 mmol, 5.0 equiv), and AcOH (50 mL), followed by the dropwise addition of a solution of bromine (3.2 g, 20.03 mmol, 2.0 equiv) in AcOH (20 mL) at 0° C., over 1 h. The reaction mixture was stirred for 1 h at 0° C., and then at 40° C., overnight. After cooling to 0° C., a second batch of NaSCN (4.1 g, 50.57 mmol, 5.0 equiv) was added, followed by the dropwise addition of a second batch of bromine (3.2 g, 20.03 mmol, 2.0 equiv.) in AcOH (20 mL) over 1 h. The reaction mixture was stirred at 0° C., for 1 h and then at 40° C., for 5 days. The reaction mixture was diluted with 100 mL of water and the pH of the aqueous solution was adjusted to 9 with sodium hydroxide pellets. The solids were collected by filtration, washed with water (20 mL×2), and dried in an oven at 60° C., for 6 h to provide 1.3 g (47%) of methyl 2-amino-4-(trifluoromethyl)-1,3-benzothiazole-6-carboxylate A-5c (1.3 g, 47%) as a brown solid.

Step 3. Methyl 2-bromo-4-(trifluoromethyl)-1,3-benzothiazole-6-carboxylate (A-5)

To a 100-mL round bottom flask was added methyl 2-amino-4-(trifluoromethyl)-1,3-benzothiazole-6-carboxylate A-5c (1.1 g, 3.98 mmol, 1.0 equiv.), MeCN (30 mL), and $CuBr_2$ (1.4 g, 6.27 mmol, 1.5 equiv.), followed by the dropwise addition oft-BuONO (1.2 g, 11.64 mmol, 3.0 equiv.). The resulting mixture was stirred at 30° C., overnight and concentrated in vacuo. The residue was purified via silica gel column eluting with ethyl acetate/petroleum ether (1:10) to give of methyl 2-bromo-4-(trifluoromethyl)-1,3-benzothiazole-6-carboxylate A-5 (560 mg, 41%) as a white solid. $^1$H NMR (300 MHz, $CDCl_3$) δ: 8.732 (s, 1H), 8.450 (s, 1H), 4.005 (s, 3H). MS (ES, m/z): [M+1]=340, [M+3]=342.

Example 10: Intermediate. Methyl 2-bromo-4-methyl-1,3-benzothiazole-6-carboxylate (A-6)

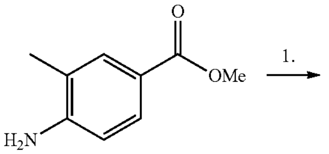

A-6a

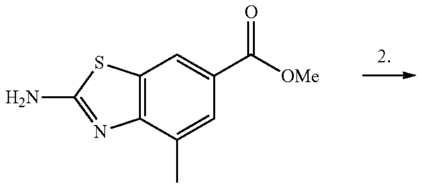

A-6b

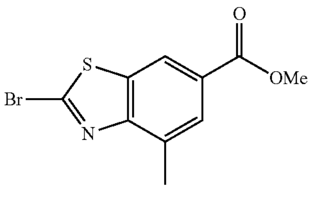

A-6

Step 1. Methyl 2-amino-4-methyl-1,3-benzothiazole-6-carboxylate (A-6a)

To a 500 mL round-bottom flask was added methyl 4-amino-3-methylbenzoate A-6a (10.0 g, 60.54 mmol, 1.0 equiv.), AcOH (200 mL), and NaSCN (19.6 g, 4.0 equiv.) followed by the dropwise addition of a solution of bromine (9.7 g, 60.70 mmol, 1.0 equiv.) in AcOH (100 mL) at 0° C. The resulting mixture was stirred at 30° C., for 16 h and then quenched by the addition of 500 mL of ice water. The pH value of the aqueous solution was adjusted to 9 using sodium hydroxide. The aqueous mixture was extracted with ethyl acetate (500 mL×3), and the combined organic layers were washed with brine (500 mL×3), dried over anhydrous sodium sulfate, filtered, and concentrated under reduced pressure to afford 15 g of methyl 2-amino-4-methyl-1,3-benzothiazole-6-carboxylate A-6a as a yellow solid (crude). The crude product was carried onto the next step without further purification.

Step 2. Methyl 2-bromo-4-methyl-1,3-benzothiazole-6-carboxylate (A-6)

To a 500 mL round-bottom flask was added methyl 2-amino-4-methyl-1,3-benzothiazole-6-carboxylate A-6a (15 g, 67.49 mmol, 1.0 equiv.), $CH_3CN$ (200 mL), t-BuONO (20 g, 2.26 equiv.), and $CuBr_2$ (22.4 g, 1.5 equiv.) and the resulting mixture was heated at 50° C., for 16 h. The solvent was removed in vacuo and the resulting residue was purified by silica gel column chromatography eluting with ethyl acetate/petroleum ether (1:3) to yield of methyl 2-bromo-4-methyl-1,3-benzothiazole-6-carboxylate A-6 (15.2 g, 79%) as a yellow solid.

Example 11: Intermediate. Methyl 2-bromo-4-cyclopropyl-1,3-benzothiazole-6-carboxylate (A-7)

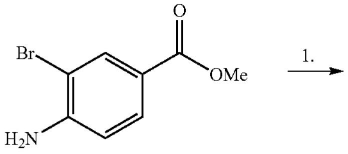

A-7a

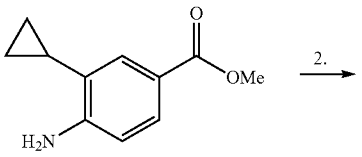

A-7b

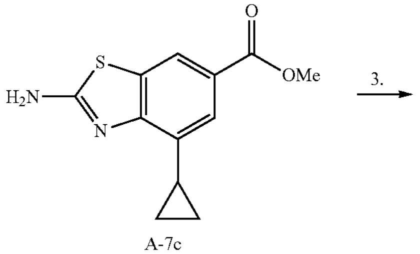

A-7c

-continued

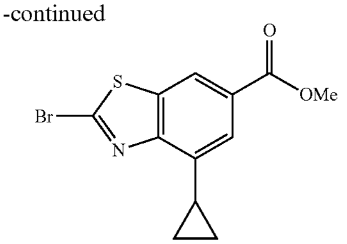

A-7

Step 1. Methyl 4-amino-3-cyclopropylbenzoate (A-7b)

To a 1000 mL round-bottom flask, purged and maintained under an inert atmosphere of nitrogen, was added methyl 4-amino-3-bromobenzoate A-7a (25 g, 108.67 mmol, 1.0 equiv.), $K_3PO_4$ (65 g, 306.21 mmol, 2.82 equiv.), toluene (50 mL), water (100 mL), $P(Cy)_3$ (2.8 g, 0.05 equiv.), $Pd(OAc)_2$ (2.25 g, 10.02 mmol, 0.09 equiv.), and cyclopropyl boronic acid (26 g, 302.69 mmol, 2.79 equiv.) and the resulting mixture was heated at 100° C., overnight. The resulting solids were filtered off and the filtrate was diluted with 200 mL of $H_2O$ and extracted with ethyl acetate (200 mL×3). The combined organic layers were concentrated in vacuo and the resulting residue was purified by silica gel column chromatography eluting with ethyl acetate/petroleum ether (1:20 to 1:10 and then to 1:5) to provide 19.9 g (96%) of methyl 4-amino-3-cyclopropylbenzoate A-7b as a light brown solid.

Step 2. Methyl 2-amino-4-cyclopropyl-1,3-benzothiazole-6-carboxylate (A-7c)

To a 500 mL round-bottom flask containing methyl 4-amino-3-cyclopropylbenzoate A-7b (16 g, 83.67 mmol, 1.0 equiv.) and AcOH (200 mL) was added sodium thiocyanate (27.13 g, 334.64 mmol, 4.0 equiv.) and the resulting mixture was stirred for 0.5 h at 5-10° C. A solution of bromine (13.3 g, 83.22 mmol, 0.99 equiv.) in AcOH (100 mL) was then added dropwise with at 0-5° C., and the resulting mixture was stirred at 0-5° C., for 10 min and then at 30° C., overnight. 1500 mL of $H_2O$ was then added and the pH of the aqueous solution was adjusted to 8-9 using potassium carbonate. The resulting solids were collected by filtration and dried in an oven under reduced pressure to afford 24 g (crude) of methyl 2-amino-4-cyclopropyl-1,3-benzothiazole-6-carboxylate A-7c as an orange colored solid. The crude product was carried onto the next step without further purification.

Step 3. Methyl 2-bromo-4-cyclopropyl-1,3-benzothiazole-6-carboxylate (A-7)

To a 500-mL round-bottom flask containing methyl 2-amino-4-cyclopropyl-1,3-benzothiazole-6-carboxylate A-7c (12 g, 48.33 mmol, 1.0 equiv.), $CH_3CN$ (200 mL), and $CuBr_2$ (16.19 g) was added t-BuONO (11.26 g) dropwise. The resulting mixture was stirred at 30° C., for 12 h and concentrated under reduced pressure. The residue was purified via silica gel column eluting with ethyl acetate/petroleum ether (1:20 to 1:10, and then to 1:5) to provide 11.2 g (74%) of methyl 2-bromo-4-cyclopropyl-1,3-benzothiazole-6-carboxylate A-7 as a light yellow solid. $^1H$ NMR (300 MHz, $CDCl_3$) δ: 8.33 (d, J=1.6 Hz, 1H), 7.60 (d, J=1.6 Hz, 1H), 3.97 (s, 3H), 2.82 (tt, J=8.5, 5.2 Hz, 1H), 1.32-1.12 (m, 2H), 1.05-0.93 (m, 2H). MS (ES, m/z): [M+1]=312.

Example 12: Intermediate. Tert-butyl 6-bromo-1-methyl-1H-indole-3-carboxylate (A-8)

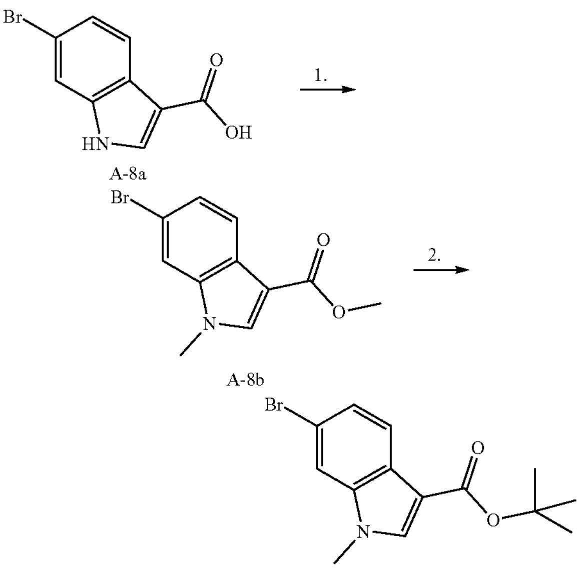

A-8a

A-8b

A-8

Step 1. Methyl 6-bromo-1-methyl-1H-indole-3-carboxylate (A-8b)

To a 250 mL round bottom flask was added 6-bromo-1H-indole-3-carboxylic acid A-8a (5 g, 20.83 mmol, 1.0 equiv.), N,N-dimethylformamide (150 mL), MeI (5.9 g), and sodium hydride (3.5 g, 145.83 mmol, 7.0 equiv.). The resulting mixture was stirred at 10-25° C., for 1 h, and then diluted with 1500 mL of $H_2O$. The aqueous mixture was extracted with ethyl acetate (200 mL×3) and the combined organic layers were dried over anhydrous magnesium sulfate, filtered, and concentrated in vacuo. The crude product was purified by re-crystallization from PE. The solids were collected by filtration to yield 3.5 g (63%) of methyl 6-bromo-1-methyl-1H-indole-3-carboxylate A-8b as a light yellow solid.

Step 2. Tert-butyl 6-bromo-1-methyl-1H-indole-3-carboxylate (A-8)

To a 250 mL round-bottom flask was added methyl 6-bromo-1-methyl-1H-indole-3-carboxylate (2 g, 7.46 mmol, 1.0 equiv.), toluene (100 mL), and sodium-tert-butoxide (3.6 g, 37.46 mmol, 5.02 equiv.) and the resulting mixture was stirred at 110° C., overnight. The reaction mixture was cooled to RT, diluted with 200 mL of $H_2O$, and extracted with ethyl acetate (200 mL×3). The combined organic extracts were dried over anhydrous sodium sulfate, filtered, and concentrated in vacuo to provide 2.1 g (91%) of tert-butyl 6-bromo-1-methyl-1H-indole-3-carboxylate A-8 as a light yellow solid.

Example 13: Intermediate. Tert-butyl 4-bromo-3-fluorobenzoate (A-9)

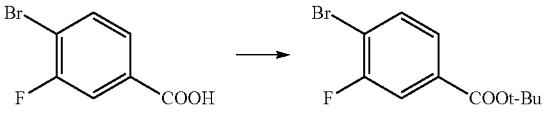

A-9a A-9

To a 250 round-bottom flask was added 4-bromo-3-fluorobenzoic acid A-9a (10 g, 45.66 mmol, 1.0 equiv), 4-dimethylaminopyridine (560 mg, 4.58 mmol, 0.10 equiv), di-tert-butyl dicarbonate (14.9 g, 68.27 mmol, 1.5 equiv), and tert-butanol (100 mL). The resulting mixture was stirred at 50° C., overnight and 200 mL of $H_2O$ was then added. The aqueous mixture was extracted with ethyl acetate (200 mL×2) and the combined organic extracts were washed with brine (200 mL×2), dried over anhydrous sodium sulfate, filtered, and concentrated under reduced pressure. The crude product was purified by Flash-Prep-HPLC using the following conditions: Column, silica gel; mobile phase, PE:EA=100:0 increasing to 92:8 over 5 min; Detector, UV 254 nm, to provide 6.5 g (52%) of tert-butyl 4-bromo-3-fluorobenzoate A-9 as colorless oil. $^1$H NMR (300 MHz, DMSO-$d_6$) δ: 7.94-7.81 (m, 1H), 7.82-7.61 (m, 2H), 1.56 (s, 9H).

Example 14: Intermediates A-10-A-15

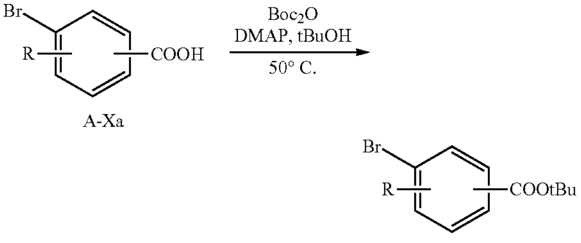

A-Xa

A-X

Intermediates A10-A15 listed in the Table 1 below were made according to the procedure described in Example 13 for the preparation of Intermediate A-9.

TABLE 1

| Preparation of Intermediates A-10 to A-14. | | |
|---|---|---|
| A-Xa | | $^1$H NMR |
| 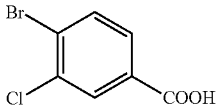 | A-10 | $^1$H NMR (400 MHz, Methanol-$d_4$) δ: 8.01 (q, J = 2.2 Hz, 1H), 7.76 (dddd, J = 10.7, 8.4, 4.4, 2.5 Hz, 2H), 1.59 (s, 9H). |
| 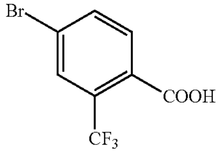 | A-11 | $^1$H NMR (400 MHz, DMSO-$d_6$) δ: 7.85-7.76 (m, 2H), 7.60 (ddd, J = 9.0, 2.4, 1.3 Hz, 1H), 1.52 (s, 9H). |
| 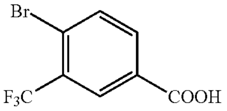 | A-12 | $^1$H NMR (300 MHz, DMSO-$d_6$) δ: 8.13 (d, J = 2.0 Hz, 1H), 8.02 (dt, J = 2.6, 1.2 Hz, 2H), 1.55 (d, J = 1.1 Hz, 9H). |
| 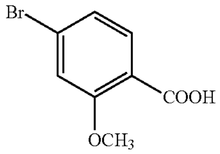 | A-13 | $^1$H NMR (300 MHz, DMSO-$d_6$) δ: 7.51 (d, J = 8.2 Hz, 1H), 7.33 (d, J = 1.8 Hz, 1H), 7.20 (dd, J = 8.2, 1.8 Hz, 1H), 3.85 (s, 3H), 1.51 (s, 9H). |
| 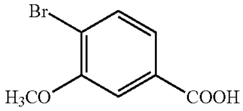 | A-14 | $^1$H NMR (300 MHz, DMSO-$d_6$) δ: 7.72 (d, J = 8.2 Hz, 1H), 7.57-7.33 (m, 2H), 3.92 (s, 3H), 1.55 (s, 9H). |
| 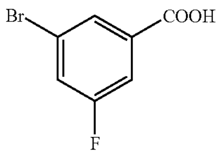 | A-15 | |

Example 15: Intermediate. Methyl 2-bromo-1,3-benzothiazole-6-carboxylate (A-16)

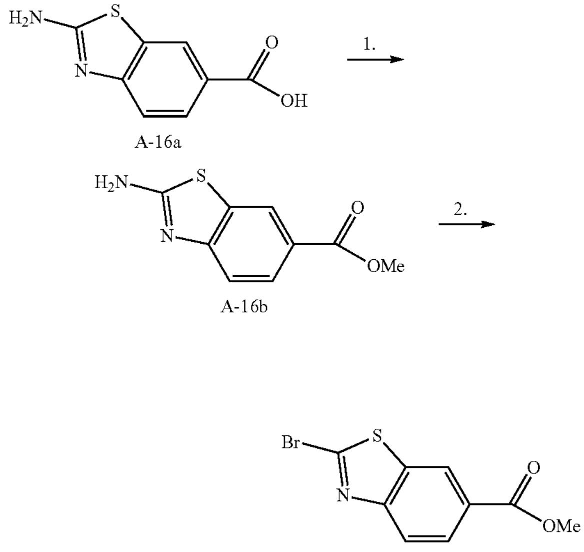

A-16a

A-16b

A-16

Step 1. Methyl 2-amino-1,3-benzothiazole-6-carboxylate (A-16)

To a 500 mL round-bottom flask containing a solution of 2-amino-1,3-benzothiazole-6-carboxylic acid A-16a (5 g, 25.75 mmol, 1.0 equiv.) in tetrahydrofuran/MeOH (200/200 mL) was added $TMSCHN_2$ (2M in hexane) (25.8 mL, 2.0 equiv.) dropwise. The resulting mixture was stirred at room temperature overnight and then concentrated in vacuo. The resulting residue was diluted with 200 mL of PE:EA (1:1), and the resulting solids were collected by filtration and dried in an oven under reduced pressure to give 4 g of (75%) of methyl 2-amino-1,3-benzothiazole-6-carboxylate A-16b as an off-white solid.

Step 2. Methyl 2-bromo-1,3-benzothiazole-6-carboxylate (A-16)

To a 250 mL round-bottom flask, purged and maintained under an inert atmosphere of nitrogen, was added methyl 2-amino-1,3-benzothiazole-6-carboxylate A-16b (2 g, 9.60 mmol, 1.0 equiv.), $CH_3CN$ (50 mL), t-BuONO (2.6 mL, 2.26 equiv.), and $CuBr_2$ (3.22 g, 14.44 mmol, 1.5 equiv.). The resulting mixture was stirred at 30° C., overnight, and then concentrated under reduced pressure. The resulting residue was purified by silica gel column chromatography eluting with PE:EA (93:7) to give 0.7 g (27%) of methyl 2-bromo-1,3-benzothiazole-6-carboxylate A-16 as an off-white solid. $^1H$ NMR (300 MHz, $CDCl_3$) δ: 8.55 (dd, J=1.7, 0.7 Hz, 4H), 8.16 (dd, J=8.6, 1.7 Hz, 4H), 8.03 (dd, J=8.6, 0.7 Hz, 4H), 3.98 (s, 13H), 1.25 (d, J=9.6 Hz, 1H). MS (ES, m/z): [M+1]=274.

Example 16: Intermediate. Methyl 2-bromo-4-(2,2,2-trifluoroethoxy)-1,3-benzothiazole-6-carboxylate (A-17)

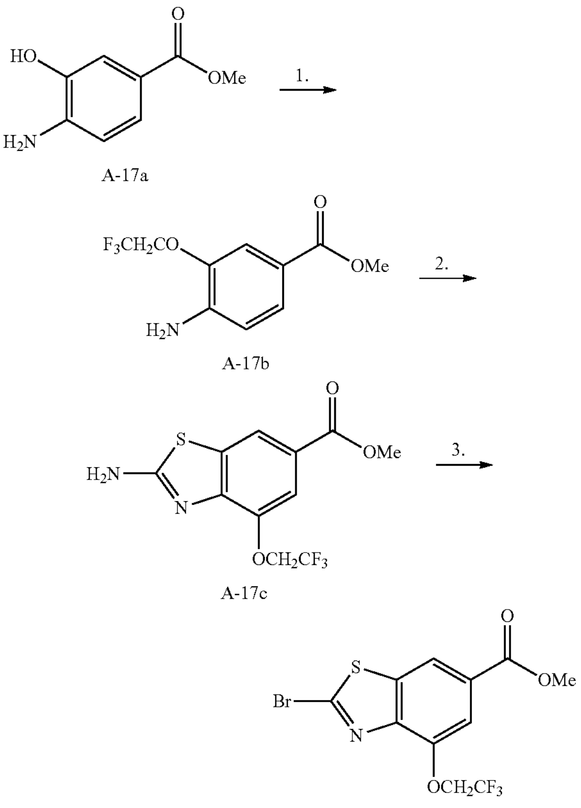

A-17a

A-17b

A-17c

A-17

Step 1. Methyl 4-amino-3-(2,2,2-trifluoroethoxy)benzoate (A-17b)

To a 100-mL round-bottom flask was added methyl 4-amino-3-hydroxybenzoate A-17a (1.0 g, 5.98 mmol, 1.0 equiv.), 2,2,2-trifluoroethyl trifluoromethanesulfonate (1.67 g, 7.2 mmol, 1.2 equiv.), potassium carbonate (1.24 g, 8.97 mmol, 1.5 equiv), and N,N-dimethylformamide (10 mL) and the resulting mixture was stirred at room temperature overnight. The reaction mixture was diluted with 100 mL of $H_2O$, and extracted with ethyl acetate (100 mL×2). The combined organic extracts were washed with brine (100 mL×2), dried over anhydrous sodium sulfate, filtered, and concentrated in vacuo. The resulting crude product was purified by Flash-Prep-HPLC using the following conditions (IntelFlash-1): Column, silica gel; mobile phase, PE:EA=100:0 increasing to PE:EA=65:35 over 15 min; Detector, UV 254 nm to provide 0.7 g (47%) of methyl 4-amino-3-(2,2,2-trifluoroethoxy)benzoate A-17b as an off-white solid.

Step 2. Methyl 2-amino-4-(2,2,2-trifluoroethoxy)-1,3-benzothiazole-6-carboxylate (A-17c)

To a 250-mL round-bottom flask was added methyl 4-amino-3-(2,2,2-trifluoroethoxy)benzoate A-17b (700 mg, 2.81 mmol, 1.0 equiv.), AcOH (150 mL), $Br_2$ (488 mg, 3.05 mmol, 1.10 equiv.), and NaSCN (0.911 g, 4.0 equiv.) and the resulting mixture was stirred at room temperature overnight. The reaction mixture was then diluted with 100 mL of $H_2O$/ice and the pH value of the aqueous solution was adjusted to 10.0 with sodium hydroxide pellets. The resulting solids were collected by filtration to provide 0.78 g (91%) of methyl 2-amino-4-(2,2,2-trifluoroethoxy)-1,3-benzothiazole-6-carboxylate A-17c as a yellow solid.

Step 3. Methyl 2-bromo-4-(2,2,2-trifluoroethoxy)-1,3-benzothiazole-6-carboxylate (A-17)

To a 100-mL round-bottom flask containing methyl 2-amino-4-(2,2,2-trifluoroethoxy)-1,3-benzothiazole-6-carboxylate A-17c (780 mg, 2.55 mmol, 1.0 equiv.) and $CH_3CN$ (10 mL), was added $CuBr_2$ (0.84 g, 1.5 equiv.) and t-BuONO (0.75 g, 2.26 equiv.), The resulting mixture was stirred at room temperature overnight and concentrated in vacuo. The resulting residue was purified by silica gel column chromatography eluting with ethyl acetate/petroleum ether (0%-8%) to afford 0.678 g (72%) of methyl 2-bromo-4-(2,2,2-trifluoroethoxy)-1,3-benzothiazole-6-carboxylate A-17 as a light yellow solid.

Example 17: Intermediate. Methyl 2-bromo-4-ethoxy-1,3-benzothiazole-6-carboxylate (A-18)

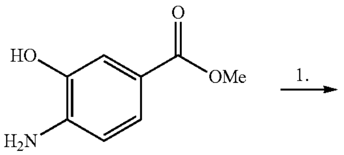

A-17a

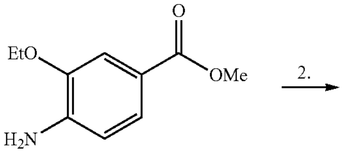

A-18a

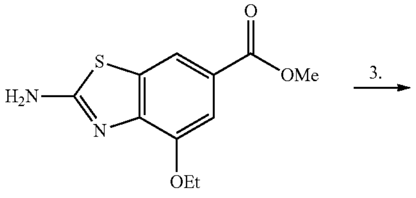

A-18b

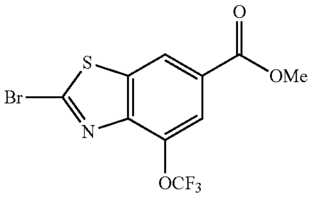

A-18

Step 1. Methyl 4-amino-3-ethoxybenzoate (A-18a)

To a 250-mL round-bottom flask was added methyl 4-amino-3-hydroxybenzoate A-17a (5 g, 29.91 mmol, 1.0 equiv.), N,N-dimethylformamide (100 mL), iodoethane (5.56 g, 35.65 mmol, 1.2 equiv.), and potassium carbonate (6.2 g, 44.86 mmol, 2.0 equiv.) and the resulting mixture was stirred at room temperature for 16 h. 500 mL of water was then added, the aqueous mixture was extracted with ethyl acetate (500 mL×3). The combined organic extracts were washed with brine (1500 mL×2), dried over anhydrous sodium sulfate, filtered, and concentrated in vacuo. The residue was purified by silica gel column chromatography eluting with ethyl acetate/petroleum ether (1:5) to give 4.2 g (72%) of methyl 4-amino-3-ethoxybenzoate A-18a as a yellow solid.

Step 2. Methyl 2-amino-4-ethoxy-1,3-benzothiazole-6-carboxylate (A-18b)

To a 500-mL round-bottom flask containing methyl 4-amino-3-ethoxybenzoate A-18a (2 g, 10.25 mmol, 1.0 equiv.), AcOH (100 mL), and NaSCN (3.3 g, 40.74 mmol, 4.0 equiv) was added $Br_2$ (2.4 g, 15.02 mmol, 1.5 equiv) in AcOH (100 mL) dropwise at 0° C. The resulting mixture was stirred at 30° C., for 16 h and then quenched by the addition of 500 mL of water/ice. The pH value of the aqueous solution was adjusted to 10 using sodium hydroxide pellets. The resulting solids were collected by filtration and dried in an oven under reduced pressure to afford 3.1 g (crude) of methyl 2-amino-4-ethoxy-1,3-benzothiazole-6-carboxylate A-18b as a yellow solid.

Step 3. Methyl 2-bromo-4-ethoxy-1,3-benzothiazole-6-carboxylate (A-18)

To a 250-mL round-bottom flask was added methyl 2-amino-4-ethoxy-1,3-benzothiazole-6-carboxylate A-18b (3 g, 11.89 mmol, 1.0 equiv.). MeCN (100 mL), $CuBr_2$ (3.95 g, 1.5 equiv.), and t-BuONO (3.52 g, 2.26 equiv.) and the resulting mixture was stirred at 30° C., for 16 h. The crude product was purified by silica gel column chromatography eluting with ethyl acetate/petroleum ether (1:10) to yield 2.2 g (59%) of methyl 2-bromo-4-ethoxy-1,3-benzothiazole-6-carboxylate A-18 as a light yellow solid.

PREPARATIVE EXAMPLES

Example 18: 2-[(1S,4S,5R)-5-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic Acid (I-1)

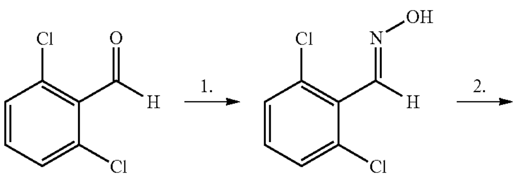

1a 1b

-continued

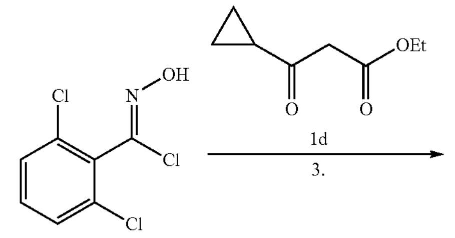

1c

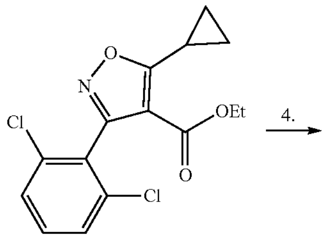

1e

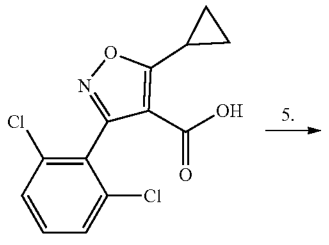

1f

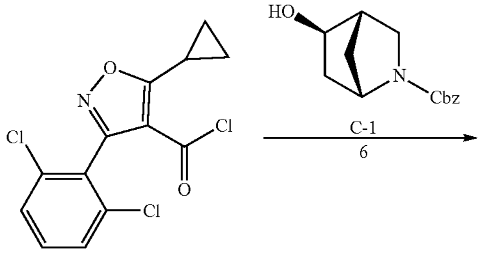

1g

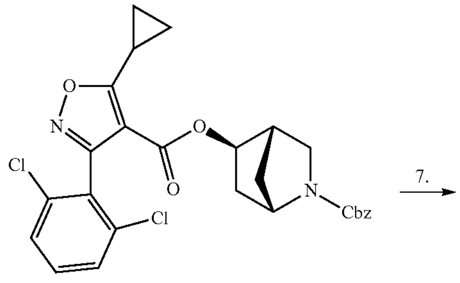

1i

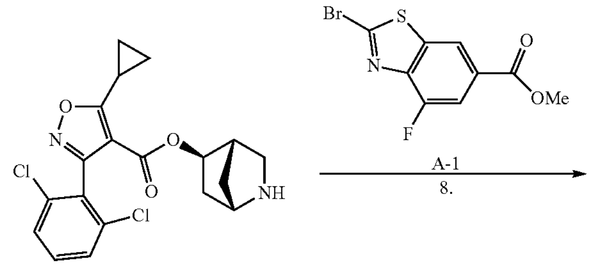

1j

-continued

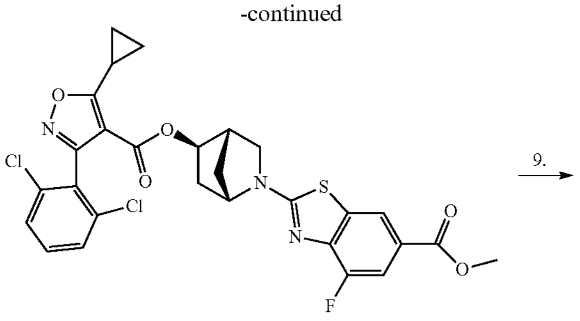

1k

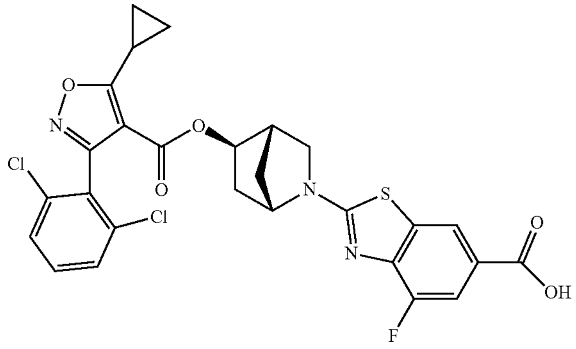

I-1

Step 1. N-[(2,6-dichlorophenyl)methylidene]-hydroxylamine (1b)

To a 2 L round-bottom flask containing hydroxylamine hydrochloride (108 g, 1.55 mol, 1.3 equiv.), sodium hydroxide (60 g, 1.50 mol, 1.3 equiv.), and water (200 mL) was added 2,6-Dichlorobenzaldehyde 1a (200 g, 1.14 mol, 1.0 equiv.) dropwise at 0° C., followed by ethanol (500 mL). The resulting mixture was heated at 90° C., overnight, and then concentrated under reduced pressure. The resulting solids were collected by filtration and dried in an oven under reduced pressure, to provide 210 g (97%) of N-[(2,6-dichlorophenyl)methylidene]-hydroxylamine 1b as an off-white solid.

Step 2. 2,6-dichloro-N-hydroxylbenzene-1-carbonimidoyl chloride (1c)

To a 1 L round-bottom flask was added N-[(2,6-dichlorophenyl) methylidene]hydroxylamine 1b (60 g, 315.74 mmol, 1.0 equiv.), N,N-dimethylformamide (250 mL), and N-chlorosuccinimide (NCS, 42.5 g, 318.28 mmol, 1.0 equiv.). The resulting mixture was stirred for 2 h at room temperature, and then quenched by the addition of 500 mL of ice/salt. The aqueous mixture was extracted with ethyl acetate (1 L×3) and the combined organic layers were washed with brine (1 L×3), dried with sodium sulfate, filtered and concentrated in vacuo to give result 68 g (96%) of 2,6-dichloro-N-hydroxylbenzene-1-carbonimidoyl chloride 1c as a white solid.

Step 3. Ethyl 5-cyclopropyl-3-(2,6-dichlorophenyl)-1,2-oxazole-4-carboxylate (1e)

To a 1 L round bottom flask was added 2,6-dichloro-N-hydroxybenzene-1-carbonimidoyl chloride 1c (68 g, 302.93 mmol, 1.0 equiv.), triethylamine (500 mL), and ethyl 3-cyclopropyl-3-oxopropanoate 1d (71.3 g, 456.53 mmol, 1.5 equiv.) and the resulting mixture was stirred for 16 h at room temperature. 1 L of ice/brine was then added and the aqueous mixture was extracted with ethyl acetate (1 L×3). The combined organic extracts were washed with brine (1 L×3), dried over anhydrous sodium sulfate, filtered, and concentrated in vacuo to afford 118 g of ethyl 5-cyclopropyl-3-(2,6-dichlorophenyl)-1,2-oxazole-4-carboxylate 1e as a yellow oil. This material was used without purification in the next step. MS (ES, m/z): [M+1]=325.90.

Step 4. 5-cyclopropyl-3-(2,6-dichlorophenyl)-1,2-oxazole-4-carboxylic Acid (1f)

To a 1 L round-bottom flask was added ethyl 5-cyclopropyl-3-(2,6-dichlorophenyl)-1,2-oxazole-4-carboxylate 1e (52 g, 159.42 mmol, 1.0 equiv.), ethanol (300 mL), water (150 mL), and LiOH (67 g, 2.80 mol, 10 equiv.). The resulting mixture was heated at 50° C., for 16 h, concentrated in vacuo, and the resulting residue was dissolved in 500 mL of $H_2O$. The pH of the aqueous solution was adjusted to 9 using a 3M HCl solution. The aqueous mixture was extracted with ethyl acetate (500 mL×5), and the combined organic layers were dried over anhydrous sodium sulfate, filtered and concentrated. The crude product was purified by silica gel column chromatography eluting with ethyl acetate/petroleum ether (1:1, v/v) to afford 26 g (55%) of 5-cyclopropyl-3-(2,6-dichlorophenyl)-1,2-oxazole-4-carboxylic acid if as a yellow solid. $^1$H NMR (300 MHz, $CDCl_3$) δ: 13.09 (s, 1H), 7.69-7.47 (m, 3H), 2.91 (tt, J=8.2, 5.1 Hz, 1H), 1.41-1.14 (m, 4H). MS (ES, m/z): [M+1]=297.90.

Step 5. 5-cyclopropyl-3-(2,6-dichlorophenyl)-1,2-oxazole-4-carbonyl chloride (1g)

To a 250-mL round-bottom flask was added 5-cyclopropyl-3-(2,6-dichlorophenyl)-1,2-oxazole-4-carboxylic acid 1f (3 g, 10.06 mmol), thionyl chloride (20 mL), and N,N-dimethylformamide (0.06 mL) and the resulting mixture was stirred overnight at 60° C. The reaction mixture was concentrated in vacuo to yield 3.1 g (97%) of 5-cyclopropyl-3-(2,6-dichlorophenyl)-1,2-oxazole-4-carbonyl chloride 1g as a light yellow oil.

Step 6. Benzyl (1S,4S,5R)-5-[[5-cyclopropyl-3-(2,6-dichlorophenyl)-1,2-oxazol-4-yl]carbonyloxy]-2-azabicyclo[2.2.1]heptane-2-carboxylate (1i)

To a 250-mL round bottom flask purged with and maintained under an inert atmosphere of nitrogen was added 5-cyclopropyl-3-(2,6-dichlorophenyl)-1,2-oxazole-4-carbonyl chloride 1g (2.72 g, 8.59 mmol, 1.0 equiv.), dichloromethane (100 mL), 4-dimethylaminopyridine (420 mg, 3.44 mmol, 0.4 equiv.), and TEA (2.62 g, 25.89 mmol, 3.0 equiv.). The resulting mixture was cooled to 0° C., and benzyl (1S,4S,5R)-5-hydroxy-2-azabicyclo[2.2.1]heptane-2-carboxylate C-1 (2.13 g, 8.61 mmol, 1.0 equiv.) in dichloromethane (10 mL) was added dropwise and the resulting mixture was stirred at 30° C., for 2 days. 50 mL of $H_2O$ was then added and the aqueous mixture was extracted with dichloromethane (30 mL×3). The combined organic extracts were dried over anhydrous sodium sulfate, filtered and concentrated in vacuo The crude product was purified by silica gel column chromatography eluting with ethyl acetate/petroleum ether (1:5) to give 3.5 g (77%) of benzyl (1S,4S,5R)-5-[[5-cyclopropyl-3-(2,6-dichlorophenyl)-1,2-oxazol-4-yl]carbonyloxy]-2-azabicyclo[2.2.1]heptane-2-carboxylate (1i) as a brown oil.

Step 7. (1S,4S,5R)-2-azabicyclo[2.2.1]heptan-5-yl 5-cyclopropyl-3-(2,6-dichlorophenyl)-1,2-oxazole-4-carboxylate (1j)

To a 250-mL round-bottom flask containing benzyl (1S,4S,5R)-5-[[5-cyclopropyl-3-(2,6-dichlorophenyl)-1,2-oxazol-4-yl]carbonyloxy]-2-azabicyclo[2.2.1]heptane-2-carboxylate (1i) (3.5 g, 6.64 mmol, 1.0 equiv.) and dichloromethane (50 mL) was added trimethylsilyl iodide (6.65 g, 33.25 mmol, 5.0 equiv.) and the resulting mixture was stirred at room temperature for 10 min. Hydrogen chloride (1M, aq) was then added to adjust the pH to 3-4 and the resulting mixture was concentrated in vacuo. The crude product was purified by Flash-Prep-HPLC with the following conditions: Column, silica gel; mobile phase, $CH_3CN$:$H_2O$=0:100 increasing to 30:70 over 30 min; Detector, UV 254 nm to provide 2.6 g (100%) of (1S,4S,5R)-2-azabicyclo[2.2.1]heptan-5-yl 5-cyclopropyl-3-(2,6-dichlorophenyl)-1,2-oxazole-4-carboxylate (1j) as a light-yellow oil.

Step 8. Methyl 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylate (1k)

To a 50 mL round-bottom flask purged and maintained under an inert atmosphere of nitrogen was added methyl 2-bromo-4-fluoro-1,3-benzothiazole-6-carboxylate A-1 (300 mg, 1.03 mmol, 1.0 equiv.), DMA (10 mL), (1S,4S,5R)-2-azabicyclo[2.2.1]heptan-5-yl 5-cyclopropyl-3-(2,6-dichlorophenyl)-1,2-oxazole-4-carboxylate (1j) (267 mg, 0.68 mmol, 1.2 equiv), and $Cs_2CO_3$ (747 mg, 2.29 mmol, 3.0 equiv.) and the resulting mixture was stirred at 60° C., overnight. After cooling to room temperature, 200 mL of EA was added and the mixture was washed with brine (30 mL×3), dried over anhydrous sodium sulfate, filtered, and concentrated in vacuo. The crude product was purified by a silica gel column with ethyl acetate/petroleum ether (1:5) to afford 300 mg (48%) of methyl 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylate (1k) as an off-white solid.

Step 9. 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylic Acid (I-1)

To a 50 mL round-bottom flask purged and maintained under an inert atmosphere of nitrogen was added methyl 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylate (1k) (100 mg, 0.17 mmol, 1.0 equiv.) in pyridine (3 mL) and LiI (233 mg, 10.0 equiv.) and the resulting mixture was stirred at 125° C., overnight. Upon cooling, 30 mL of EA was added and the resulting mixture was washed with a 1 M hydrogen chloride solution (10 mL) and brine (30 mL×3). The organic layer was dried over anhydrous sodium sulfate, filtered and concentrated in vacuo. The crude product was purified by Prep-HPLC using the following conditions: Column, XBridge C18 OBD Prep Column: 5 μm, 19 mm×250 mm; mobile phase, Water (0.05% TFA) and ACN (62.0% ACN to 80.0% over 8 min); Detector, UV 254 nm to provide 21.7 mg (22%) of 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylic acid (I-1) was obtained as an off-white solid. $^{1}$H-NMR (300 MHz, $CD_3OD$) δ: 8.14 (d, J=1.5 Hz, 1H), 7.72-7.48 (m, 4H), 4.99 (d, J=6.9 Hz, 1H), 4.39 (s, 1H), 3.20 (d, J=10.4 Hz, 1H), 2.98 (q, J=6.7 Hz, 1H), 2.59 (s, 1H), 2.24 (dd, J=14.8, 6.3 Hz, 1H), 1.69 (d, J=10.3 Hz, 1H), 1.40-1.27 (m, 8H). MS (ES, m/z): [M+1]=588.0.

Example 19: Synthesis of Compounds I-2 to I-8

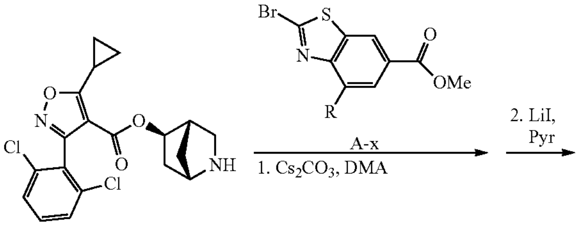

1j

-continued

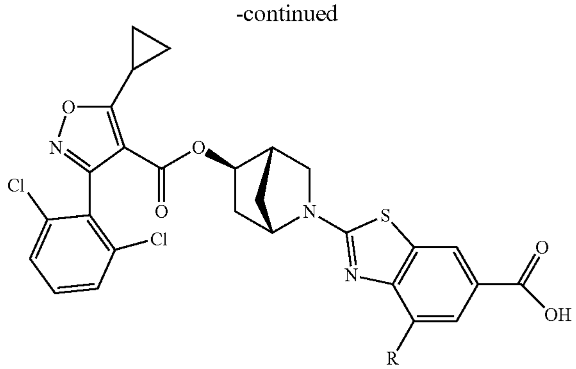

I-2 to I-8

I-2 to I-8 in table 2 below were synthesized according to the procedures described in Preparative Example 1, steps 8 and 9, from intermediate 1j and substituted bromo-benzothiazole esters A-x.

TABLE 2

Compounds I-2 to I-8.

| Cmpd Structure | Cmpd No. | MS/$^{1}$H NMR |
| --- | --- | --- |
| 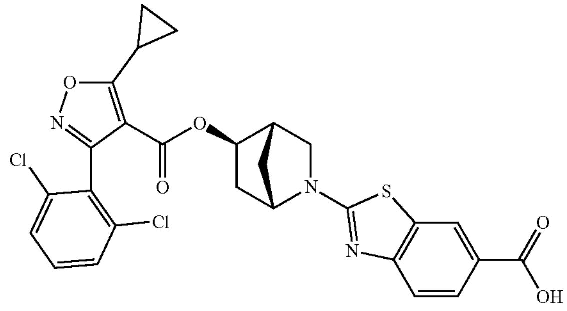 [SMILES: O=C(O)c1ccc2nc(N3C[C@@H]4C[C@H]3C[C@H]4OC(=O)c3c(-c4c(Cl)cccc4Cl)noc3C3CC3)sc2c1] | I-2 | MS (ES, m/z): [M + 1] = 570. $^{1}$H NMR (400 MHz, $CD_3OD$) δ: 8.38 (d, J = 1.7 Hz, 1H), 8.04 (dd, J = 8.5, 1.7 Hz, 1H), 7.64-7.46 (m, 4H), 5.05-4.99 (m, 1H), 4.39 (s, 1H), 3.60 (dd, J = 10.3, 4.0 Hz, 1H), 3.26 (d, J = 10.4 Hz, 1H), 3.00 (p, J = 6.7 Hz, 1H), 2.64 (d, J = 3.6 Hz, 1H), 2.34-2.23 (m, 1H), 1.75 (d, J = 10.6 Hz, 1H), 1.40-1.28 (m, 6H). |
| 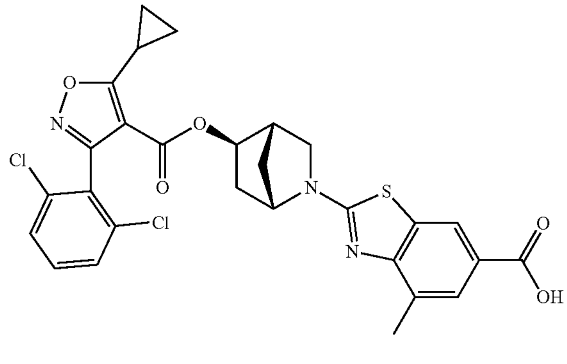 [SMILES: Cc1cc(C(=O)O)cc2sc(N3C[C@@H]4C[C@H]3C[C@H]4OC(=O)c3c(-c4c(Cl)cccc4Cl)noc3C3CC3)nc12] | I-3 | MS (ES, m/z): [M + 1] = 584.10. $^{1}$H NMR (300 MHz, $CD_3OD$) δ: 8.17 (dd, J = 1.6, 0.7 Hz, 1H), 7.81 (dd, J = 1.6, 0.9 Hz, 1H), 7.64-7.48 (m, 3H), 4.99 (d, J = 6.6 Hz, 1H), 4.42 (s, 1H), 3.57 (dd, J = 10.3, 4.0 Hz, 1H), 3.24 (d, J = 10.2 Hz, 1H), 2.99 (p, J = 6.7 Hz, 1H), 2.61 (d, J = 2.0 Hz, 1H), 2.54 (s, 3H), 2.33-2.19 (m, 1H), 1.76-1.65 (m, 1H), 1.40-1.26 (m, 6H). |

TABLE 2-continued

Compounds I-2 to I-8.

| Cmpd Structure | Cmpd No. | MS/$^1$H NMR |
|---|---|---|
| 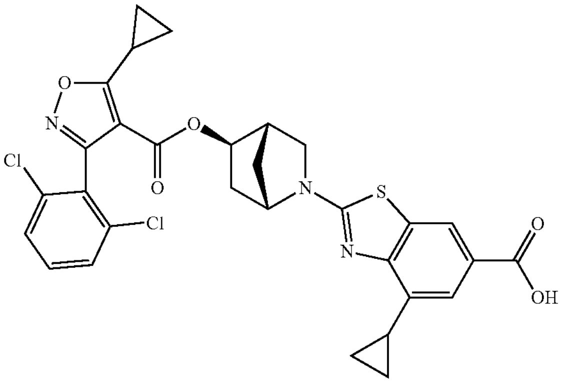 [SMILES: O=C(O)c1cc(C2CC2)c2nc(N3C[C@@H]4C[C@H]3C[C@H]4OC(=O)c3c(-c4c(Cl)cccc4Cl)noc3C3CC3)sc2c1] | I-4 | MS (ES, m/z): [M + 1] = 610.2. $^1$H NMR (300 MHz, DMSO-$d_6$) δ 8.12 (d, J = 1.6 Hz, 1H), 7.75-7.57 (m, 3H), 7.30 (d, J = 1.7 Hz, 1H), 4.99 (d, J = 6.0 Hz, 1H), 4.30 (s, 1H), 3.47 (dd, J = 9.9, 3.9 Hz, 1H), 3.17 (d, J = 10.1 Hz, 1H), 2.98-2.82 (m, 1H), 2.51 (dd, J = 22.6, 4.7 Hz, 1H), 2.15 (dd, J = 13.5, 6.8 Hz, 1H), 1.64 (d, J = 10.3 Hz, 1H), 1.44-1.20 (m, 6H), 1.15 (d, J = 10.1 Hz, 1H), 1.08-0.93 (m, 2H), 0.89-0.73 (m, 2H). |
| 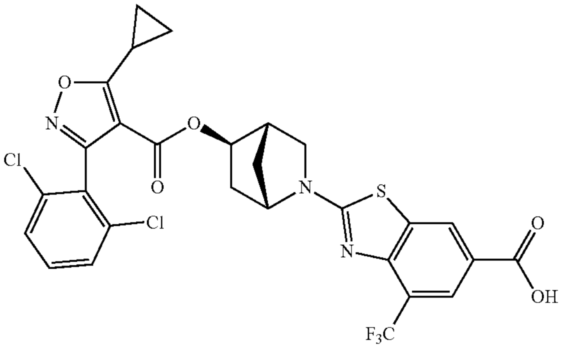 | I-5 | MS (ES, m/z): [M + 1] = 638.10. $^1$H NMR (400 MHz, $CD_3OD$) δ: 8.48 (d, J = 1.6 Hz, 1H), 8.19-8.14 (m, 1H), 7.62-7.49 (m, 3H), 4.98 (d, J = 6.8 Hz, 1H), 4.41 (s, 1H), 3.53 (s, 1H), 3.21 (s, 1H), 3.04-2.92 (m, 1H), 2.57 (d, J = 3.6 Hz, 1H), 2.27-2.16 (m, 1H), 1.67 (d, J = 10.5 Hz, 1H), 1.38-1.26 (m, 6H). |
| 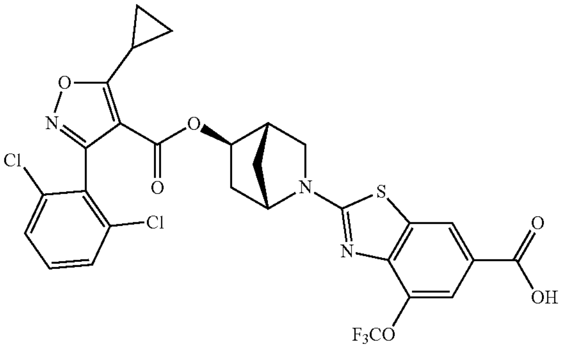 [SMILES: O=C(O)c1cc(OC(F)(F)F)c2nc(N3C[C@@H]4C[C@H]3C[C@H]4OC(=O)c3c(-c4c(Cl)cccc4Cl)noc3C3CC3)sc2c1] | I-6 | MS (ES, m/z/): [M + 1] = 654.0. $^1$H NMR (400 MHz, $CD_3OD$) δ: 8.28 (d, J = 1.5 Hz, 1H), 7.82 (p, J = 1.4 Hz, 1H), 7.62-7.49 (m, 3H), 4.98 (d, J = 6.8 Hz, 1H), 4.42 (s, 2H), 3.54 (s, 1H), 3.20 (s, 1H), 2.98 (p, J = 6.7 Hz, 1H), 2.58 (s, 1H), 2.28-2.18 (m, 1H), 1.68 (d, J = 10.6 Hz, 1H), 1.38-1.27 (m, 6H). |
| 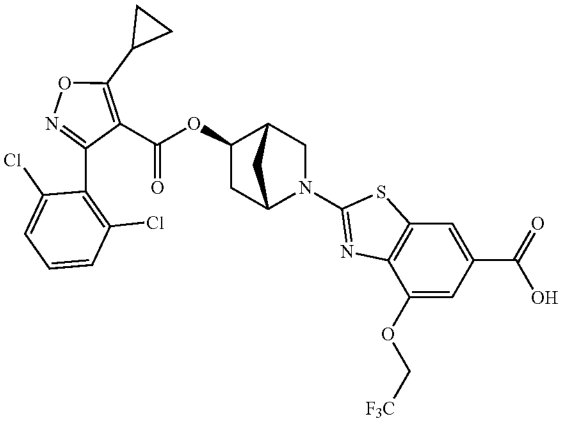 [SMILES: O=C(O)c1cc(OCC(F)(F)F)c2nc(N3C[C@@H]4C[C@H]3C[C@H]4OC(=O)c3c(-c4c(Cl)cccc4Cl)noc3C3CC3)sc2c1] | I-7 | MS (ES, m/z): [M + 1] = 668.0. $^1$H NMR (400 MHz, $CD_3OD$) δ: 8.09 (q, J = 1.2 Hz, 1H), 7.66-7.51 (m, 4H), 5.04-4.97 (m, 1H), 4.83 (q, J = 8.7 Hz, 2H), 4.42 (s, 1H), 3.57 (dd, J = 10.3, 4.0 Hz, 1H), 3.23 (d, J = 10.2 Hz, 1H), 3.06-2.95 (m, 1H), 2.60 (d, J = 3.3 Hz, 1H), 2.26 (dd, J = 14.3, 7.1 Hz, 1H), 1.71 (d, J = 10.6 Hz, 1H), 1.40-1.29 (m, 6H). |

TABLE 2-continued
| Compounds I-2 to I-8. | | |
|---|---|---|
| Cmpd Structure | Cmpd No. | MS/$^1$H NMR |
| 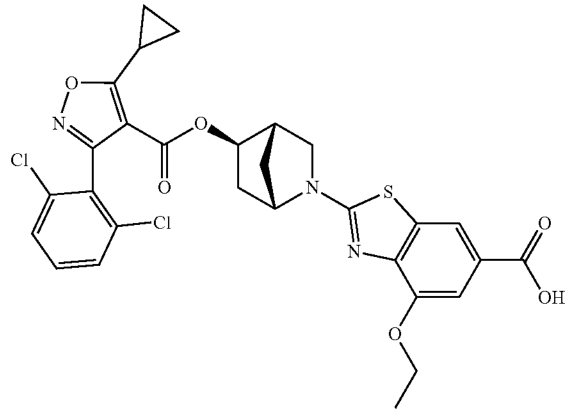 [SMILES: CCOc1cc(C(=O)O)cc2sc(N3C[C@@H]4C[C@H]3C[C@H]4OC(=O)c3c(-c4c(Cl)cccc4Cl)noc3C3CC3)nc12] | I-8 | MS (ES, m/z): [M + 1] = 614.15. $^1$H NMR (300 MHz, $CD_3OD$) δ: 8.01 (d, J = 1.4 Hz, 1H), 7.66-7.49 (m, 4H), 5.01 (d, J = 6.8 Hz, 1H), 4.49 (s, 1H), 4.30 (q, J = 7.0 Hz, 2H), 3.61 (dd, J = 10.5, 4.0 Hz, 1H), 3.27 (d, J = 10.1 Hz, 1H), 3.00 (p, J = 6.7 Hz, 1H), 2.63 (s, 1H), 2.28 (dd, J = 13.5, 6.6 Hz, 1H), 1.74 (d, J = 10.8 Hz, 1H), 1.53 (t, J = 7.0 Hz, 3H), 1.42-1.30 (m, 6H). |
Example 20: 2-[(1S,4S,5R)-5-{5-cyclopropyl-3-[2-(trifluoromethyl)phenyl]-1,2-oxazole-4-carbonyloxy}-2-azabicyclo[2.2.1]heptan-2-yl]-4-(trifluoromethoxy)-1,3-benzothiazole-6-carboxylic Acid (I-9)
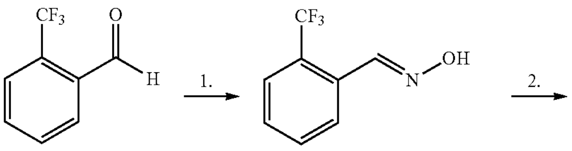
9a 9b
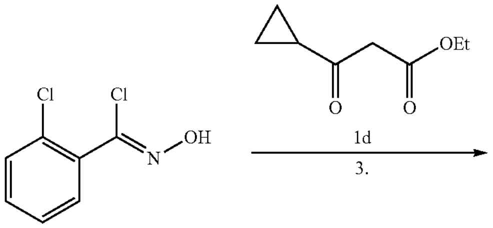
9c
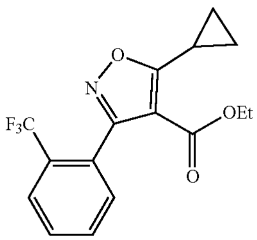
9d
-continued
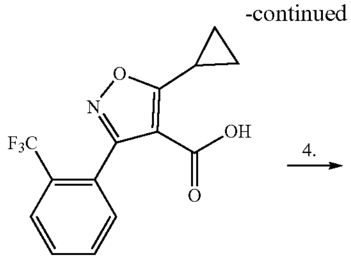
9e
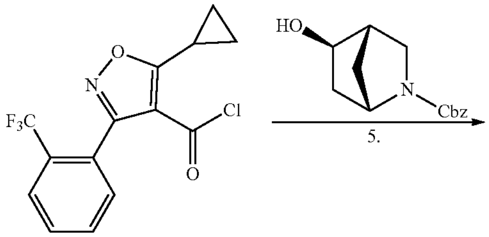
9f
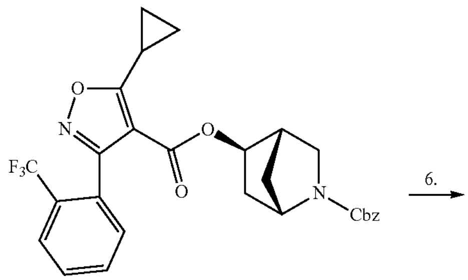
9g -continued

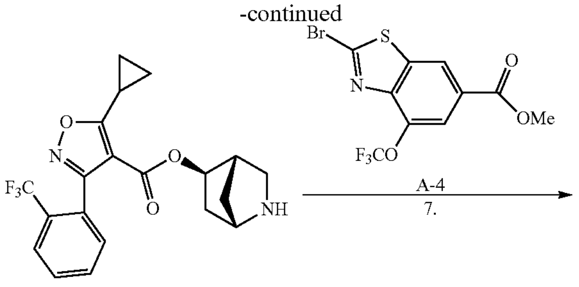

9h

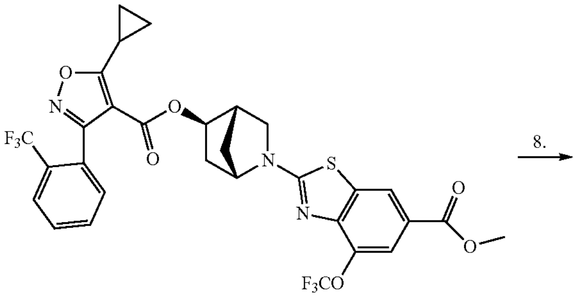

9i

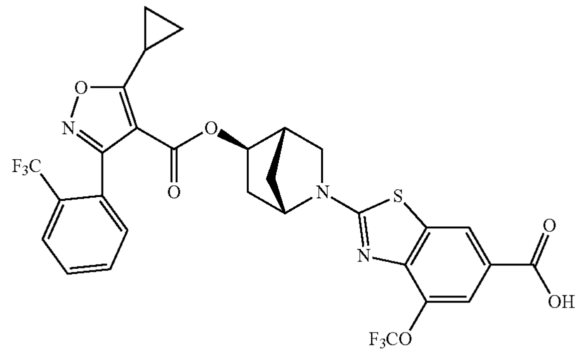

I-9

Step 1. (N-[[2-(trifluoromethyl)phenyl]methylidene] hydroxylamine (9b)

To a 500-mL round-bottom flask was added 2-(trifluoromethyl)benzaldehyde 9a (20 g, 114.86 mmol, 1.0 equiv.), ethanol (120 mL), water (60 mL), $NH_2OH.HCl$ (12 g), and sodium hydroxide (7 g, 175 mmol, 1.52 equiv.). The resulting mixture was stirred at 80° C., for 4 h and then concentrated in vacuo. 200 mL of $H_2O$ was added and the aqueous mixture was extracted with dichloromethane (100 mL×3). The combined organic extracts were dried over anhydrous sodium sulfate, filtered and concentrated in vacuo to give 22 g (crude) of (N-[[2-(trifluoromethyl)phenyl]methylidene] hydroxylamine (9b) as a white solid.

Step 2. N-hydroxy-2-(trifluoromethyl)benzene-1-carbonimidoyl chloride (9c)

To a 250-mL round-bottom flask was added N-[[2-(trifluoromethyl) phenyl]methylidene]-hydroxylamine 9b (10 g, 52.87 mmol, 1.0 equiv.), N,N-dimethylformamide (50 mL), and NCS (7.5 g, 56.17 mmol, 1.06 equiv.). The resulting mixture was stirred at 10-25° C., for 2 h, and then diluted with 200 mL of $H_2O$. The aqueous mixture was extracted with ethyl acetate (200 mL×3) and the combined organic extracts were dried over anhydrous sodium sulfate, filtered, and concentrated in vacuo to provide 11.5 g (97%) of N-hydroxy-2-(trifluoromethyl)benzene-1-carbonimidoyl chloride (9c) as colorless crude oil.

Step 3. Ethyl 5-cyclopropyl-3-[2-(trifluoromethyl) phenyl]-1,2-oxazole-4-carboxylate (9d)

To a 250-mL round-bottom flask was added N-hydroxy-2-(trifluoromethyl)benzene-1-carbonimidoyl chloride 9c (11.5 g, 51.44 mmol, 1.0 equiv.), ethyl 3-cyclopropyl-3-oxopropanoate 1d (12 g, 76.83 mmol, 1.49 equiv.), and TEA (50 mL) and the resulting mixture was stirred at 10-25° C., overnight. The reaction mixture was diluted with 200 mL of $H_2O$ and the pH of the aqueous solution was adjusted to 5-6 using a hydrogen chloride (aq.). The aqueous mixture was extracted with ethyl acetate (150 mL×3) and the combined organic layers were dried over anhydrous sodium sulfate, filtered, concentrated in vacuo to give 16 g (96%) of ethyl 5-cyclopropyl-3-[2-(trifluoromethyl)phenyl]-1,2-oxazole-4-carboxylate (9d) as a light brown crude oil. The crude product was carried on to the next step without further purification.

Step 4. 5-cyclopropyl-3-(2-methylphenyl)-1,2-oxazole-4-carboxylic Acid (9e)

To a 250-mL round-bottom flask was added ethyl 5-cyclopropyl-3-(2-methylphenyl)-1,2-oxazole-4-carboxylate 9d (17 g, 62.66 mmol, 1.0 equiv.), water (100 mL), ethanol (20 mL), and sodium hydroxide (5.2 g, 130.00 mmol, 2.07 equiv.). The resulting mixture was stirred at 60° C., overnight and then concentrated in vacuo. The resulting residue was diluted with 200 mL of $H_2O$, and washed with dichloromethane (100 mL×2). The pH value of aqueous layer was adjusted to 5-6 using a hydrogen chloride (aq.), and then extracted with ethyl acetate (100 mL×3). The combined organic extracts were dried over anhydrous sodium sulfate, filtered, and concentrated in vacuo to afford 11 g (72%) of 5-cyclopropyl-3-(2-methylphenyl)-1,2-oxazole-4-carboxylic acid (9e) as an off-white solid. The crude product was carried on to the next step without further purification.

Step 5. 5-cyclopropyl-3-[2-(trifluoromethyl)phenyl]-1,2-oxazole-4-carbonyl chloride (9f)

To a 100-mL round-bottom flask was added 5-cyclopropyl-3-[2-(trifluoromethyl) phenyl]-1,2-oxazole-4-carboxylic acid 9e (1.6 g, 5.38 mmol, 1.0 equiv.) and thionyl chloride (20 mL). The resulting mixture was stirred at 60° C., for 2 h and then concentrated in vacuo to give 1.7 g (100%) of 5-cyclopropyl-3-[2-(trifluoromethyl)phenyl]-1,2-oxazole-4-carbonyl chloride (9f) as a light brown crude oil. The crude product was carried on to the next step without further purification.

Step 6. Benzyl (1S,4S,5R)-5-([5-cyclopropyl-3-[2-(trifluoromethyl)phenyl]-1,2-oxazol-4-yl]carbonyloxy)-2-azabicyclo[2.2.1]heptane-2-carboxylate (9g)

To a 50-mL round-bottom flask was added 5-cyclopropyl-3-[2-(trifluoromethyl) phenyl]-1,2-oxazole-4-carbonyl chloride 9f (350 mg, 1.11 mmol, 1.0 equiv.), dichloromethane (20 mL), benzyl (1S,4S,5R)-5-hydroxy-2-azabicyclo[2.2.1] heptane-2-carboxylate C-1 (328.1 mg, 1.33 mmol, 1.2 equiv.), 4-dimethylaminopyridine (13.5 mg, 0.11 mmol, 0.1 equiv.), and TEA (335.6 mg, 3.32 mmol, 2.99 equiv.). The resulting mixture was stirred at 10-25° C., overnight, and then diluted with 50 mL of $H_2O$. The aqueous mixture was extracted with dichloromethane (50 mL×3) and the combined organic layers were concentrated in vacuo. The crude residue was purified by silica gel column chromatography eluting with ethyl acetate/petroleum ether (1:10-1:5) to afford 450 mg (77%) of benzyl (1S,4S,5R)-5-([5-cyclopropyl-3-[2-(trifluoromethyl)phenyl]-1,2-oxazol-4-yl]carbonyloxy)-2-azabicyclo[2.2.1]heptane-2-carboxylate (9g) as a light brown oil.

Step 7. (1S,4S,5R)-2-azabicyclo[2.2.1]heptan-5-yl 5-cyclopropyl-3-[2-(trifluoromethyl) phenyl]-1,2-oxazole-4-carboxylate (9h)

To a 100-mL round-bottom flask was added benzyl (1S,4S,5R)-5-([5-cyclopropyl-3-[2-(trifluoromethyl)phenyl]-1,2-oxazol-4-yl]carbonyloxy)-2-azabicyclo[2.2.1]heptane-2-carboxylate 9g (450 mg, 0.85 mmol, 1.0 equiv.), dichloromethane (10 mL), and TMSI (900 mg). The resulting mixture was stirred at 10-25° C., for 1 h, and then quenched by the addition of 10 mL of hydrogen chloride (1M, aq.). The mixture was concentrated in vacuo. The crude residue was purified by silica gel column chromatography eluting with dichloromethane/methanol (15:1) to provide 185 mg (55%) of (1S,4S,5R)-2-azabicyclo[2.2.1]heptan-5-yl 5-cyclopropyl-3-[2-(trifluoromethyl)phenyl]-1,2-oxazole-4-carboxylate (9h) as a light brown oil.

Step 8. Methyl 2-[(1S,4S,5R)-5-([5-cyclopropyl-3-[2-(trifluoromethyl)phenyl]-1,2-oxazol-4-yl]carbonyloxy)-2-azabicyclo[2.2.1]heptan-2-yl]-4-(trifluoromethoxy)-1,3-benzothiazole-6-carboxylate (9i)

To a 100-mL round-bottom flask was added (1S,4S,5R)-2-azabicyclo[2.2.1]heptan-5-yl 5-cyclopropyl-3-[2-(trifluoromethyl)phenyl]-1,2-oxazole-4-carboxylate 9h (130 mg, 0.33 mmol, 1.0 equiv.), DMA (20 mL), methyl 2-bromo-4-(trifluoromethoxy)-1,3-benzothiazole-6-carboxylate A-4 (100 mg, 0.28 mmol, 0.85 equiv), and $Cs_2CO_3$ (183.1 mg, 0.56 mmol, 1.70 equiv) and the resulting mixture was stirred at 60° C., overnight. After cooling to room temperature, 100 mL of $H_2O$ was added. The aqueous mixture was extracted with ethyl acetate (100 mL×3) and the combined organic extracts were concentrated in vacuo. The crude residue was purified by silica gel column chromatography eluting with ethyl acetate/petroleum ether (from 1:10 to 1:5) to provide 120 mg (54%) of methyl 2-[(1S,4S,5R)-5-([5-cyclopropyl-3-[2-(trifluoromethyl)phenyl]-1,2-oxazol-4-yl]carbonyloxy)-2-azabicyclo[2.2.1]heptan-2-yl]-4-(trifluoromethoxy)-1,3-benzothiazole-6-carboxylate (9i) as an off-white solid.

Step 9. 2-[(1S,4S,5S)-5-([5-cyclopropyl-3-[2-(trifluoromethyl)phenyl]-1,2-oxazol-4-yl]carbonyloxy)-2-azabicyclo[2.2.1]heptan-2-yl]-4-(trifluoromethoxy)-1,3-benzothiazole-6-carboxylic Acid (I-9)

To a 100-mL round-bottom flask was added methyl 2-[(1S,4S,5S)-5-([5-cyclopropyl-3-[2-(trifluoromethyl)phenyl]-1,2-oxazol-4-yl]carbonyloxy)-2-azabicyclo[2.2.1]heptan-2-yl]-4-(trifluoromethoxy)-1,3-benzothiazole-6-carboxylate 9i (120 mg, 0.18 mmol, 1.0 equiv.), pyridine (3 mL), and LiI (240.6 mg). The resulting mixture was stirred at 125° C., overnight, and concentrated in vacuo. The crude residue was purified by Prep-HPLC using the following conditions: Column, XSelect CSH Prep C18 OBD Column, 5 μm, 19×150 mm; mobile phase. Water (0.05% TFA) and ACN (70.0% ACN to 85.0% over 8 min); Detector, UV 254 nm to provide 85 mg (72%) of 2-[(1S,4S,5S)-5-([5-cyclopropyl-3-[2-(trifluoromethyl)phenyl]-1,2-oxazol-4-yl]carbonyloxy)-2-azabicyclo[2.2.1]heptan-2-yl]-4-(trifluoromethoxy)-1,3-benzothiazole-6-carboxylic acid (I-9) was obtained as a light yellow solid. $^1$H-NMR (300 MHz, DMSO-$d_6$) δ: 13.11 (s, 1H), 8.40 (d, J=1.5 Hz, 1H), 8.00-7.90 (m, 1H), 7.88-7.69 (m, 3H), 7.69-7.59 (m, 1H), 4.94 (d, J=6.6 Hz, 1H), 3.44 (s, 5H), 3.15 (s, 1H), 2.87 (ddd, J=13.1, 8.4, 5.0 Hz, 1H), 2.42 (s, 1H), 1.60 (d, J=10.2 Hz, 1H), 1.43-1.17 (m, 6H), 1.03 (d, J=10.1 Hz, 1H). MS (ES, m/z): [M+1]=654.2.

Example 21: 2-[(1S,4S,5R)-5-[3-(2,6-dichlorophenyl)-5-(1-fluorocyclopropyl)-1,2-oxazole-4-carbonyloxy]-2-azabicyclo[2.2.1]heptan-2-yl]-4-fluoro-1,3-benzothiazole-6-carboxylic Acid (I-10)

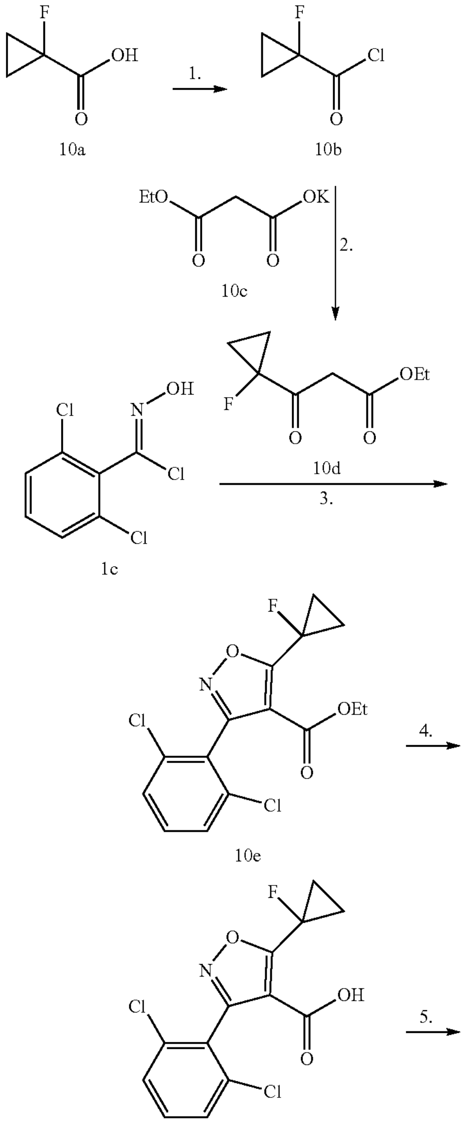

10a 10b 10c 10d 1c 10e 10f

-continued

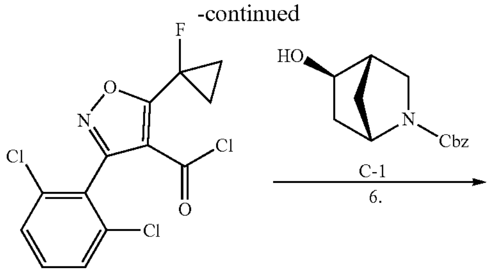

10g

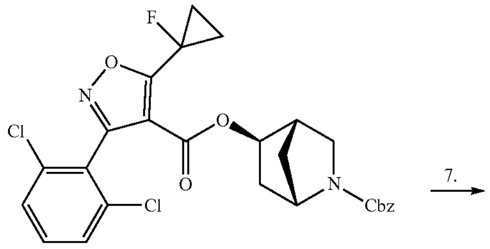

10h

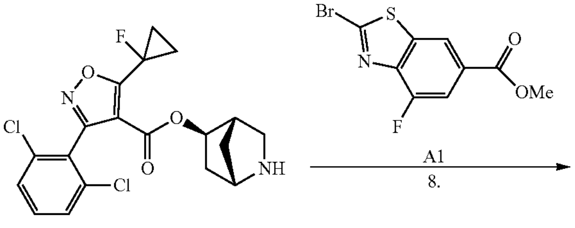

10i

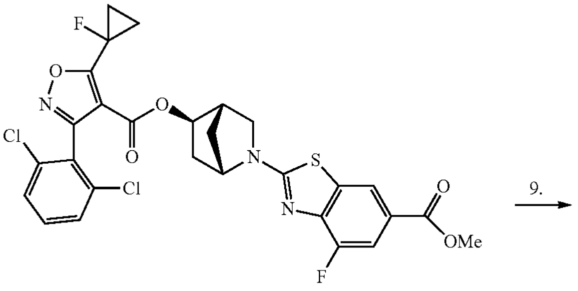

10j

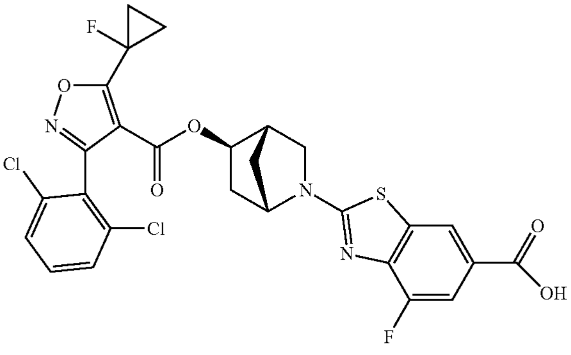

I-10

Step 1. 1-Fluorocyclopropane-1-carbonyl Chloride (10b)

To a 50 mL round-bottom flask purged and maintained under an inert atmosphere of nitrogen was added 1-fluoro-cyclopropane-1-carboxylic acid 10a (2.96 g, 28.48 mmol, 1.0 equiv.), THF (30 mL), and oxalyl chloride (2.52 mL, 1.0 equiv.), followed by DMF (2 mg, 0.03 mmol) at 0° C. The reaction mixture was stirred at 0° C., for 1 h and then at room temperature for 1 h. This mixture was used in the next step directly without workup or further purification.

Step 2. Ethyl 3-(1-fluorocyclopropyl)-3-oxopropanoate (10d)

To a 250 mL round-bottom flask purged and maintained under an inert atmosphere of nitrogen was added 1-ethyl 3-potassium propanedioate 10c (9.81 g, 57.64 mmol, 2.0 equiv.) and ethyl acetate (60 mL) and the resulting mixture was cooled to 0° C. $MgCl_2$ (8.13 g, 3.0 equiv.) was then added at 0° C., followed by TEA (14.6 g, 144.28 mmol, 5.0 equiv.). The reaction mixture was stirred at 40° C., overnight and then cooled to 0° C. A solution of 1-fluorocyclopropane-1-carbonyl chloride 10b (3.49 g, 28.48 mmol, 1.0 equiv.) in THF (30 mL) was added and the resulting mixture was stirred overnight at 25° C. The reaction mixture was quenched with 300 mL of a citric acid solution (10% aq.). The aqueous mixture was extracted with dichloromethane (500 mL×2) and the combined organic extracts were washed with a sodium bicarbonate aqueous solution (100 mL×2), brine (200 mL×2), dried over anhydrous sodium sulfate, filtered, and concentrated in vacuo. The crude product was purified by silica gel column chromatography eluting with PE:EA (0%-5%) to provide (75%) of ethyl 3-(1-fluorocyclopropyl)-3-oxopropanoate 10d as a yellow oil (volatile product, removal of solvents on rotavap should be done at low temperature).

Step 3. Ethyl 3-(2,6-dichlorophenyl)-5-(1-fluorocyclopropyl)-1,2-oxazole-4-carboxylate (10e)

To a 100-mL round-bottom flask was added ethyl 3-(1-fluorocyclopropyl)-3-oxopropanoate 10d (380 mg, 2.18 mmol, 1.0 equiv.), tetrahydrofuran (10 mL), KO$^t$Bu (290 mg, 2.59 mmol, 1.20 equiv.), and 2,6-dichloro-N-hydroxy-benzene-1-carbonimidoyl chloride 1c (580 mg, 2.58 mmol, 1.20 equiv.) in tetrahydrofuran (5 mL). The resulting mixture was stirred at room temperature overnight. The mixture was then diluted with 100 mL of EA and washed with brine (30 mL×3). The organic layer was dried over sodium sulfate, filtered, and concentrated in vacuo to give 700 mg (93%) of ethyl 3-(2,6-dichlorophenyl)-5-(1-fluorocyclopropyl)-1,2-oxazole-4-carboxylate (10e) as a pale-yellow oil. The crude product was carried on to the next without further purification.

Step 4. 3-(2,6-dichlorophenyl)-5-(1-fluorocyclopropyl)-1,2-oxazole-4-carboxylic Acid (10f)

To a 25 mL round-bottom flask was added ethyl 3-(2,6-dichlorophenyl)-5-(1-fluorocyclopropyl)-1,2-oxazole-4-carboxylate 10e (700 mg, 2.03 mmol, 1.0 equiv.), ethanol/$H_2O$ (20/2 mL), followed by $LiOH.H_2O$ (860 mg, 20.5 mmol, 10.0 equiv). The resulting mixture was stirred at 50° C., for 2 h, and then quenched with 50 mL of $H_2O$. The pH of the aqueous solution was adjusted to 3-4 using a hydrogen chloride (1M aq.). The aqueous mixture was extracted with ethyl acetate (30 mL×3), and the combined organic extracts were dried over sodium sulfate, filtered, and concentrated under reduced pressure. The residue was purified by silica gel column chromatography eluting with PE:EA (5:1) to give 200 mg (31%) of 3-(2,6-dichlorophenyl)-5-(1-fluorocyclopropyl)-1,2-oxazole-4-carboxylic acid (10f) as a pale-yellow solid.

Step 5. 3-(2,6-dichlorophenyl)-5-(1-fluorocyclopropyl)-1,2-oxazole-4-carbonyl chloride (10g)

To a 250 mL round-bottom flask was added 3-(2,6-dichlorophenyl)-5-(1-fluorocyclopropyl)-1,2-oxazole-4-carboxylic acid 10f (200 mg, 0.63 mmol, 1.0 equiv.) and thionyl chloride (10 mL). The resulting mixture was stirred at 80° C., overnight, and then concentrated in vacuo to provide 200 mg (94%) of 3-(2,6-dichlorophenyl)-5-(1-fluorocyclopropyl)-1,2-oxazole-4-carbonyl chloride 10g as a light yellow oil. The crude product was carried on to the next without further purification.

Step 6. Benzyl (1S,4S,5R)-5-[[3-(2,6-dichlorophenyl)-5-(1-fluorocyclopropyl)-1,2-oxazol-4-yl]carbonyloxy]-2-azabicyclo[2.2.1]heptane-2-carboxylate (10h)

To a 100 mL round-bottom flask was added benzyl (1S,4S,5R)-5-hydroxy-2-azabicyclo[2.2.1]heptane-2-carboxylate C-1 (235 mg, 0.95 mmol, 1.0 equiv.), dichloromethane (10 mL), 4-dimethylaminopyridine (46 mg, 0.38 mmol, 0.40 equiv), and TEA (288 mg, 2.85 mmol, 3.0 equiv.), followed by 3-(2,6-dichlorophenyl)-5-(1-fluorocyclopropyl)-1,2-oxazole-4-carbonyl chloride 10g (300 mg, 0.9 mmol, 1.0 equiv.) in dichloromethane (5 mL) dropwise at 0° C. The resulting mixture was stirred at 35° C., overnight. $H_2O$ was added and the aqueous mixture was extracted with ethyl acetate (100 mL×2). The combined organic extracts were washed with brine (30 mL×3), dried over anhydrous sodium sulfate, filtered, and concentrated under reduced pressure. The crude product was purified by silica gel column chromatography eluting with PE:EA (5:1) to give 320 mg (65%) of benzyl (1S,4S,5R)-5-[[3-(2,6-dichlorophenyl)-5-(1-fluorocyclopropyl)-1,2-oxazol-4-yl]carbonyloxy]-2-azabicyclo[2.2.1]heptane-2-carboxylate (10h) as a yellow solid.

Step 7. (1S,4S,5R)-2-azabicyclo[2.2.1]heptan-5-yl 3-(2,6-dichlorophenyl)-5-(1-fluorocyclopropyl)-1,2-oxazole-4-carboxylate (10i)

To a 50 mL round-bottom flask was added benzyl (1S,4S,5R)-5-[[3-(2,6-dichlorophenyl)-5-(1-fluorocyclopropyl)-1,2-oxazol-4-yl]carbonyloxy]-2-azabicyclo[2.2.1]heptane-2-carboxylate 10h (270 mg, 0.50 mmol, 1.0 equiv.), dichloromethane (4 mL) and TMSI (500 mg, 2.50 mmol, 5.0 equiv.) and the resulting mixture was stirred at room temperature for 10 min. The pH of the solution was adjusted to 4-5 using hydrogen chloride (1M aq.). The mixture was concentrated in vacuo and the crude product was purified by silica gel column chromatography eluting with ethyl acetate/petroleum ether (1:2) to provide 140 mg (69%) of (1S,4S,5R)-2-azabicyclo[2.2.1]heptan-5-yl 3-(2,6-dichlorophenyl)-5-(1-fluorocyclopropyl)-1,2-oxazole-4-carboxylate (10i) as a light yellow oil.

Step 8. Methyl 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylate (10j)

To a 25 mL round-bottom flask purged and maintained under an inert atmosphere of nitrogen was added (1S,4S,5R)-2-azabicyclo[2.2.1]heptan-5-yl 3-(2,6-dichlorophenyl)-5-(1-fluorocyclopropyl)-1,2-oxazole-4-carboxylate 10i (100 mg, 0.24 mmol, 1.0 equiv.), DMA (5 mL), methyl 2-bromo-4-fluoro-1,3-benzothiazole-6-carboxylate A-1 (78 mg, 0.27 mmol, 1.10 equiv), and $Cs_2CO_3$ (238 mg, 0.73 mmol, 3.0 equiv.) and the resulting mixture was stirred at 60° C., overnight. 100 mL of $H_2O$ was then added, the aqueous mixture was extracted with ethyl acetate (100 mL×2). The combined organic extracts were washed with brine (20 mL×2), dried over sodium sulfate, filtered, and concentrated in vacuo. The crude product was purified by silica gel column chromatography eluting with PE:EA (3:1) to give 80 mg (55%) of methyl 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylate (10j) as a light yellow oil.

Step 9. 2-[(1S,4S,5R)-5-[[3-(2,6-dichlorophenyl)-5-(1-fluorocyclopropyl)-1,2-oxazol-4-yl]carbonyloxy]-2-azabicyclo[2.2.1]heptan-2-yl]-4-fluoro-1,3-benzothiazole-6-carboxylic Acid (I-10)

To a 50-mL round-bottom flask purged and maintained under an inert atmosphere of nitrogen was added methyl 2-[(1S,4S,5R)-5-[[3-(2,6-dichlorophenyl)-5-(1-fluorocyclopropyl)-1,2-oxazol-4-yl]carbonyloxy]-2-azabicyclo[2.2.1]heptan-2-yl]-4-fluoro-1,3-benzothiazole-6-carboxylate 10j (60 mg, 0.10 mmol, 1.0 equiv.), pyridine (1 mL), and LiI (134 mg, 10.0 equiv) and the resulting mixture was stirred at 120° C., overnight. After cooling to room temperature, the mixture was diluted with 100 mL of EA and washed with a 1M hydrogen chloride aqueous solution (50 mL×2), $H_2O$ (30 mL×2), and brine (30 mL×1). The organic layer was dried over anhydrous sodium sulfate, filtered, and concentrated under reduced pressure. The residue was purified by Prep-HPLC using the following conditions: Column, XSelect CSH Prep C18 OBD Column, 5 μm, 19×150 mm; mobile phase, water (0.1% FA) and ACN (66.0% ACN to 82.0% over 8 min); Detector, UV 254 nm to provide 25.2 mg (43%) of 2-[(1S,4S,5R)-5-[[3-(2,6-dichlorophenyl)-5-(1-fluorocyclopropyl)-1,2-oxazol-4-yl]carbonyloxy]-2-azabicyclo[2.2.1]heptan-2-yl]-4-fluoro-1,3-benzothiazole-6-carboxylic acid (I-10) was obtained as an off-white solid. $^1$H-NMR (300 MHz, DMSO-$d_6$) δ: 12.90 (s, 1H), 8.18 (d, J=1.5 Hz, 1H), 7.73-7.49 (m, 4H), 4.98 (d, J=6.3 Hz, 1H), 4.33 (s, 1H), 3.50-3.40 (m, 1H), 3.15 (s, 1H), 2.52 (s, 1H), 2.13 (dd, J=14.4, 6.8 Hz, 1H), 1.77-1.47 (m, 5H), 1.39-1.16 (m, 3H). MS (ES, m/z): [M+1]=606.0.

Example 22: 2-[(1S,4S,5R)-5-(3-{bicyclo[2.2.2]octan-1-yl}-5-cyclopropyl-1,2-oxazole-4-carbonyloxy)-2-azabicyclo[2.2.1]heptan-2-yl]-4-fluoro-1,3-benzothiazole-6-carboxylic Acid (I-11)

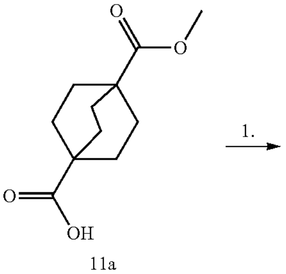

11a

-continued

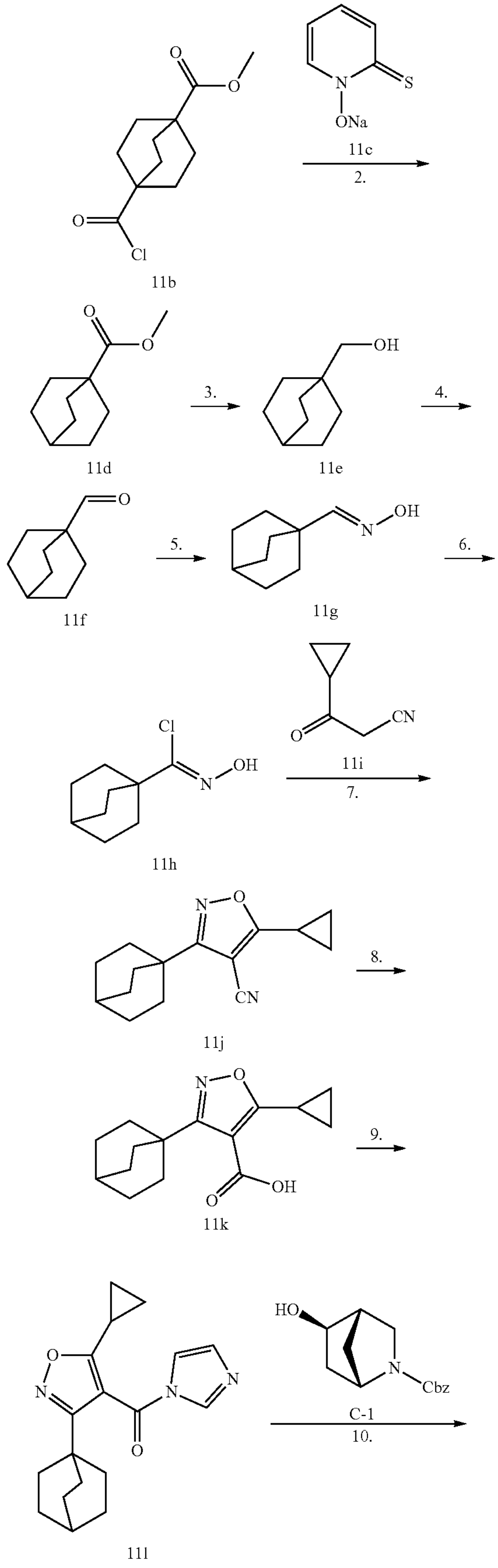

-continued

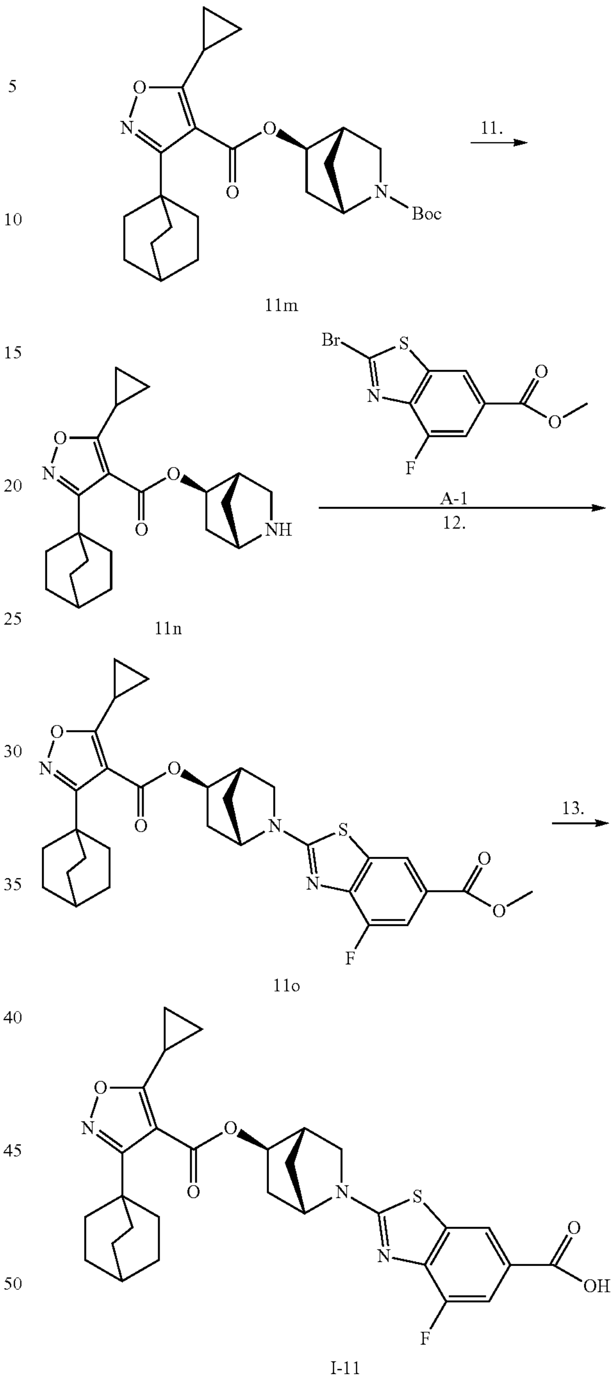

Step 1. Methyl 4-(carbonochloridoyl)bicyclo[2.2.2]octane-1-carboxylate (11b)

To a 250 mL round-bottom flask was added 4-(methoxycarbonyl)bicyclo[2.2.2]octane-1-carboxylic acid 11a (20 g, 94.23 mmol, 1.0 equiv.) and thionyl chloride (100 mL). The resulting mixture was stirred at room temperature overnight and concentrated under reduced pressure to give 21 g (97%) of methyl 4-(carbonochloridoyl)bicyclo[2.2.2]octane-1-carboxylate 11b as a white solid.

Step 2. Methyl bicyclo[2.2.2]octane-1-carboxylate (11d)

To a 500 mL 3-necked round-bottom flask containing 1-(sodiooxy)-1,2-dihydropyridine-2-thione 11c (16.3 g, 109.29 mmol, 1.20 equiv.), chloroform (150 mL), and 4-dimethylaminopyridine (112 mg, 0.92 mmol, 0.01 equiv.) was added methyl 4-(carbonochloridoyl)bicyclo[2.2.2]-octane-1-carboxylate 11b (21 g, 91.03 mmol, 1.0 equiv.) in chloroform (50 mL) dropwise over 30 min with concomitant irradiation from a tungsten lamp (120V, 150 W). The resulting mixture was stirred at 80° C., for 120 min. Upon cooling to room temperature, 300 mL of a 1M hydrogen chloride solution was added and the resulting aqueous mixture was extracted with dichloromethane (300 mL×3). The organic layers were combined, dried over anhydrous sodium sulfate, filtered, and concentrated under reduced pressure. The crude product (15 g), was purified by Flash-Prep-HPLC using the following conditions: Column, silica gel; mobile phase, PE:EA=100:0 to 100:10 over 20 min; Detector, UV 254 nm, to provide 13 g (85%) of methyl bicyclo[2.2.2]octane-1-carboxylate 11d as a light yellow oil.

Step 3. Bicyclo[2.2.2]octan-1-ylmethanol (11e)

To a 500 mL round-bottom flask containing methyl bicyclo[2.2.2]octane-1-carboxylate 11d (13 g, 77.27 mmol, 1.0 equiv.) and tetrahydrofuran (150 mL) was add lithium aluminum hydride (5.9 g, 155.47 mmol, 2.0 equiv.) at 0° C. After 5 min, the cooling bath was removed and reaction was stirred at room temperature for 1 h. The reaction was quenched by the addition of 300 mL of $H_2O$. The resulting mixture was extracted with ethyl acetate (500 mL×3) and the combined organic layers were dried over anhydrous sodium sulfate, filtered, and concentrated. The crude product (12 g) was purified by Flash-Prep-HPLC using the following conditions: Column, silica gel; mobile phase, PE:EA=100:0 to 90:10 over 30 min; Detector. UV 254 nm, to provide 8.0 g (74%) of bicyclo[2.2.2]octan-1-ylmethanol 11e was obtained as a colorless oil.

Step 4. Bicyclo[2.2.2]octane-1-carbaldehyde (11f)

To a 500 mL round-bottom flask was added bicyclo[2.2.2]octan-1-ylmethanol 11e (8.0 g, 57.05 mmol, 1.0 equiv.), dichloromethane (240 mL), and Dess-martin periodinate (1,1,1-Tris(acetyloxy)-1,1-dihydro-1,2-benziodoxol-3-(1H)-one, 37 g, 87.26 mmol, 1.50 equiv.) and the resulting mixture was stirred at room temperature overnight. The solvent was removed under reduced pressure and the resulting residue was purified by silica gel column chromatography eluting with ethyl acetate/petroleum ether (10%-90%) to provide 5.6 g (71%) of bicyclo[2.2.2]octane-1-carbaldehyde 11f as a light yellow oil.

Step 5. N-[bicyclo[2.2.2]octan-1-ylmethylidene] hydroxylamine (11g)

To a 250 mL vial was added $NH_2OH$.HCl (4.2 g, 60.87 mmol, 1.50 equiv), water (60 mL), sodium carbonate (2.2 g, 20.76 mmol, 0.50 equiv.), and a solution of bicyclo[2.2.2]octane-1-carbaldehyde 11f (5.6 g, 40.52 mmol, 1.0 equiv.) in ethanol (30 mL). The resulting mixture was stirred at room temperature for 2 h and then extracted with ethyl acetate (600 mL). The organic extract was washed with brine (300 mL×3), dried over anhydrous sodium sulfate, filtered, and concentrated under reduced pressure. The resulting residue was purified by silica gel column chromatography eluting with PE:EA (90:10) to give 4.3 g (69%) of N-[bicyclo[2.2.2]octan-1-ylmethylidene]hydroxylamine 11g as a white solid.

Step 6. N-hydroxybicyclo[2.2.2]oct-1-carbonimidoyl chloride (11h)

To a 50 mL round-bottom flask was added N-[bicyclo[2.2.2]octan-1-ylmethylidene]-hydroxylamine 11g (2.3 g, 15.01 mmol, 1.0 equiv.) and N,N-dimethylformamide (20 mL). NCS (3.1 g, 23.13 mmol, 1.50 equiv.). The reaction mixture was stirred for 2 h at room temperature and then 300 mL of ethyl acetate was added. The resulting mixture was washed with brine (200 mL×3), dried over anhydrous sodium sulfate, filtered, and concentrated under reduced pressure to provide 2.8 g (99%) of N-hydroxybicyclo[2.2.2]oct-1-carbonimidoyl chloride 11h as a white solid.

Step 7. 3-[bicyclo[2.2.2]octan-1-yl]-5-cyclopropyl-1,2-oxazole-4-carbonitrile (11j)

To a 50 mL round-bottom flask containing 3-cyclopropyl-3-oxopropanenitrile 11i (1.63 g, 14.94 mmol, 1.0 equiv.), ethanol (20 mL), and TEA (1.51 g, 14.92 mmol, 1.0 equiv.) was added N-hydroxybicyclo[2.2.2]oct-1-carbonimidoyl chloride 11h (2.8 g, 14.92 mmol, 1.0 equiv.). The reaction mixture was stirred for 5 min at 0° C., and then for 2 h at room temperature. The resulting mixture was diluted with 300 mL of ethyl acetate, washed with brine (100 mL×2), dried over anhydrous sodium sulfate, filtered, and concentrated under reduced pressure. The crude product was purified by Flash-Prep-HPLC using the following conditions: Column, silica gel; mobile phase, PE:EA=100:0 to 80:20 over 30 min; Detector, UV 254 nm to provide 1.7 g (47%) of 3-[bicyclo[2.2.2]octan-1-yl]-5-cyclopropyl-1,2-oxazole-4-carbonitrile 11j as a light yellow oil.

Step 8. 3-[bicyclo[2.2.2]octan-1-yl]-5-cyclopropyl-1,2-oxazole-4-carboxylic Acid (11k)

To a 25 mL round-bottom flask purged and maintained under an inert atmosphere of nitrogen was added 3-[bicyclo[2.2.2]octan-1-yl]-5-cyclopropyl-1,2-oxazole-4-carbonitrile 11j (200 mg, 0.83 mmol, 1.0 equiv.), ethylene glycol (2 mL), and potassium hydroxide (462 mg, 8.23 mmol, 10.0 equiv.). The resulting mixture was stirred at 140° C., overnight. The mixture was diluted with 100 mL of $H_2O$ and the pH of the solution was adjusted to 3-4 using a 1M HCl aqueous solution. The aqueous mixture was extracted with 200 mL of ethyl acetate and the organic layer was washed with brine (50 mL×2), filtered, and concentrated. The crude product was purified by silica gel column chromatography eluting with dichloromethane/methanol (10:1) to afford 150 mg (70%) of 3-[bicyclo[2.2.2]octan-1-yl]-5-cyclopropyl-1,2-oxazole-4-carboxylic acid 11k as a light yellow solid.

Step 9. 3-[bicyclo[2.2.2]octan-1-yl]-5-cyclopropyl-4-[(1H-imidazol-1-yl)carbonyl]-1,2-oxazole (11l)

To a 50 mL round-bottom flask purged and maintained under an inert atmosphere of nitrogen was added 3-[bicyclo[2.2.2]octan-1-yl]-5-cyclopropyl-1,2-oxazole-4-carboxylic acid 11k (100 mg, 0.38 mmol, 1.0 equiv.), N,N-dimethylformamide (1 mL), and CDI (75 mg, 0.46 mmol, 1.20 equiv.). The resulting mixture was stirred at 40° C., for 2 h, then concentrated under reduced pressure to give 100 mg (84%) of 3-[bicyclo[2.2.2]octan-1-yl]-5-cyclopropyl-4-[(1H-imidazol-1-yl)carbonyl]-1,2-oxazole 11l as a yellow oil.

Step 10. Benzyl (1S,4S,5R)-5-[(3-[bicyclo[2.2.22]octan-1-yl]-5-cyclopropyl-1,2-oxazol-4-yl)carbonyloxy]-2-azabicyclo[2.2.1]heptane-2-carboxylate (11m)

To a 25-mL round-bottom flask purged and maintained under an inert atmosphere of nitrogen was added 3-[bicyclo[2.2.2]octan-1-yl]-5-cyclopropyl-4-[(1H-imidazol-1-yl)carbonyl]-1,2-oxazole 11l (118 mg, 0.38 mmol, 1.0 equiv.), N,N-dimethylformamide (1 mL), benzyl (1S,4S,5R)-5-hydroxy-2-azabicyclo[22.1]heptane-2-carboxylate C-1 (188 mg, 0.76 mmol, 2.0 equiv), and DBU (58 mg, 0.38 mmol, 1.0 equiv). The resulting solution was stirred for at 50° C., overnight. $H_2O$ was then added and the resulting aqueous mixture was extracted with 100 mL of ethyl acetate. The organic extract was washed with brine (10 mL×5), dried over anhydrous sodium sulfate, filtered, and concentrated under reduced pressure. The residue was purified by silica gel column chromatography eluting with ethyl acetate/petroleum ether (1:4) to give 90 mg (48%) of benzyl (1S,4S,5R)-5-[(3-[bicyclo[2.2.2]octan-1-yl]-5-cyclopropyl-1,2-oxazol-4-yl)carbonyloxy]-2-azabicyclo[2.2.1]heptane-2-carboxylate 11m as a light yellow oil.

Step 11. (1S,4S,5R)-2-azabicyclo[2.2.1]heptan-5-yl 3-[bicyclo[2.2.2]octan-1-yl]-5-cyclopropyl-1,2-oxazole-4-carboxylate (11n)

To a 25-mL round-bottom flask was added benzyl (1S,4S,5R)-5-[(3-[bicyclo[2.2.2]octan-1-yl]-5-cyclopropyl-1,2-oxazol-4-yl)carbonyloxy]-2-azabicyclo[2.2.1]heptane-2-carboxylate 11m (90 mg, 0.18 mmol, 1.0 equiv.), dichloromethane (2 mL), and TMSI (183 mg, 5.0 equiv.) and the resulting mixture was stirred at room temperature for 10 min. The reaction mixture was quenched by the addition of a dimethylaniline (2M in THF, 1 mL) and then concentrated under reduced pressure. The residue was purified by a silica gel column chromatography eluting with dichloromethane/methanol (15:1) to give 50 mg (76%) of (1S,4S,5R)-2-azabicyclo[2.2.1]heptan-5-yl 3-[bicyclo[2.2.2]octan-1-yl]-5-cyclopropyl-1,2-oxazole-4-carboxylate 11n as a light yellow oil.

Step 12. Methyl-2-[(1S,4S,5R)-5-[(3-[bicyclo[2.2.2]octan-1-yl]-5-cyclopropyl-1,2-oxazol-4-yl)carbonyloxy]-2-azabicyclo[2.2.1]heptan-2-yl]-4-fluoro-1,3-benzothiazole-6-carboxylate (11o)

To a 25-mL round-bottom flask purged and maintained under an inert atmosphere of nitrogen was added (1S,4S,5R)-2-azabicyclo[2.2.1]heptan-5-yl 3-[bicyclo[2.2.2]octan-1-yl]-5-cyclopropyl-1,2-oxazole-4-carboxylate 11n (80 mg, 0.22 mmol, 1.0 equiv.), methyl 2-bromo-4-fluoro-1,3-benzothiazole-6-carboxylate A-1 (78 mg, 0.27 mmol, 1.20 equiv.), DMA (1.5 mL), and $Cs_2CO_3$ (143 mg, 0.44 mmol, 2.0 equiv.) and the resulting mixture was stirred at 60° C., overnight. $H_2O$ was added and the mixture was extracted with 200 mL of ethyl acetate. The organic extract was washed with brine (20 mL×4), dried over anhydrous sodium sulfate, filtered, and concentrated under reduced pressure. The residue was purified by silica gel column chromatography eluting with ethyl acetate/petroleum ether (1:5) to provide 90 mg (71%) of methyl-2-[(1S,4S,5R)-5-[(3-[bicyclo[2.2.2]octan-1-yl]-5-cyclopropyl-1,2-oxazol-4-yl)carbonyloxy]-2-azabicyclo[2.2.1]heptan-2-yl]-4-fluoro-1,3-benzothiazole-6-carboxylate 11o as a light yellow oil.

Step 13. 2-[(1S,4S,5R)-5-[(3-[bicyclo[2.2.2]octan-1-yl]-5-cyclopropyl-1,2-oxazol-4-yl)carbonyloxy]-2-azabicyclo[2.2.1]heptan-2-yl]-4-fluoro-1,3-benzothiazole-6-carboxylic Acid (I-11)

To a 25-mL round-bottom flask purged and maintained under an inert atmosphere of nitrogen was added methyl 2-[(1S,4S,5R)-5-[(3-[bicyclo[2.2.2]octan-1-yl]-5-cyclopropyl-1,2-oxazol-4-yl)carbonyloxy]-2-azabicyclo[2.2.1]heptan-2-yl]-4-fluoro-1,3-benzothiazole-6-carboxylate 11o (80 mg, 0.14 mmol, 1.0 equiv.), pyridine (1.5 mL) and LiI (189 mg, 10.0 equiv.). The resulting mixture was stirred at 125° C., overnight and concentrated under reduced pressure. $H_2O$ was added and the aqueous mixture was extracted with 100 mL of ethyl acetate. The organic extract was washed with brine (20 mL×3), dried over anhydrous sodium sulfate, filtered, and concentrated under reduced pressure. The crude product was purified by Prep-HPLC using the following conditions: Column, XBridge C18 OBD Prep Column 5 μm, 19 mm×250 mm; mobile phase, water (0.05% TFA) and ACN (82.0% ACN to 90.0% over 8 min); Detector, UV 254 nm, to provide 19.7 mg (25%) of 2-[(1S,4S,5R)-5-[(3-[bicyclo[2.2.2]octan-1-yl]-5-cyclopropyl-1,2-oxazol-4-yl)carbonyloxy]-2-azabicyclo[2.2.1]heptan-2-yl]-4-fluoro-1,3-benzothiazole-6-carboxylic acid I-11 was obtained as an off-white solid. $^1H$ NMR (300 MHz, $CD_3OD$) δ: 8.19 (d, J=1.5 Hz, 1H), 7.71 (dd, J=11.5, 1.5 Hz, 1H), 5.19 (d, J=6.9 Hz, 1H), 4.63 (s, 1H), 3.77-3.67 (m, 1H), 3.03 (d, J=4.8 Hz, 1H), 2.80-2.68 (m, 1H), 2.50 (dd, J=14.5, 7.1 Hz, 1H), 2.12-1.90 (m, 10H), 1.78-1.66 (m, 8H), 1.32 (s, 1H), 1.27-1.13 (m, 4H), 0.92 (s, 1H). MS (ES, m/z): [M+1]=552.25.

Example 23: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic Acid (I-12)

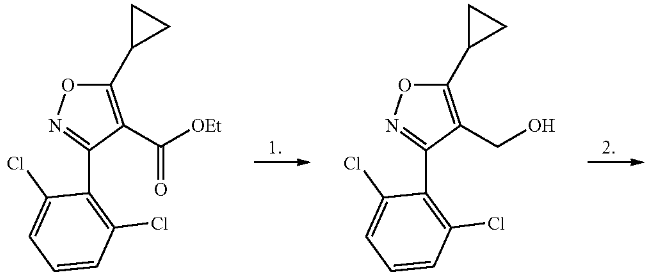

1e 12a

-continued

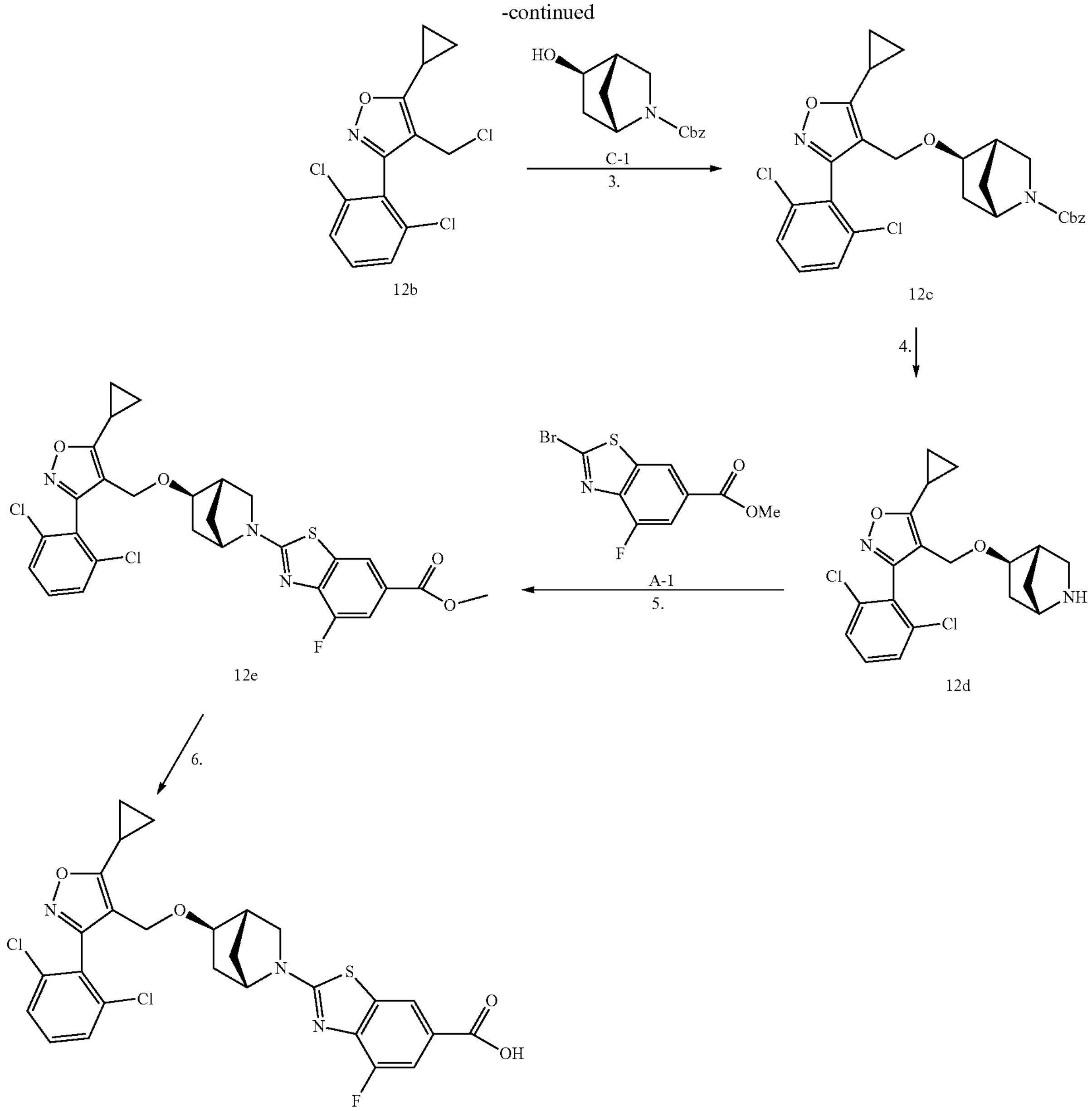

12b 12c 12d 12e I-12

Step 1. [5-cyclopropyl-3-(2,6-dichlorophenyl)-1,2-oxazol-4-yl]methanol (12a)

To a 100 mL round-bottom flask containing ethyl 5-cyclopropyl-3-(2,6-dichlorophenyl)-1,2-oxazole-4-carboxylate 1e (12.5 g, 38.32 mmol, 1.0 equiv.) and tetrahydrofuran (100 mL) was added $LiAlH_4$ (2.9 g, 76.42 mmol, 2.0 equiv.) batchwise at 0° C. The resulting mixture was stirred at room temperature for 2 h and then quenched by the addition of 50 mL of water/ice. The aqueous mixture was extracted with ethyl acetate (200 mL×2), and the combined organic extracts were washed with brine (200 mL×2) and concentrated. The crude product was purified by Flash-Prep-HPLC using the following conditions: Column, silica gel; mobile phase, PE:EA=100:0 increasing to 70:30 over 35 min; Detector, UV 254 nm, to provide 3.9 g (36%) of [5-cyclopropyl-3-(2,6-dichlorophenyl)-1,2-oxazol-4-yl]methanol 12a as a light yellow oil. $^1H$ NMR (400 MHz, $CD_3OD$) δ: 7.56-7.42 (m, 3H), 4.36 (s, 2H), 2.36-2.25 (m, 1H), 1.21-1.10 (m, 4H). MS (ES, m/z): [M+1]=284.05.

Step 2. 4-(chloromethyl)-5-cyclopropyl-3-(2,6-dichlorophenyl)-1,2-oxazole (12b)

To a 250 mL round-bottom flask containing 1H-1,2,3-benzotriazole (1 g, 8.39 mmol, 1.0 equiv.) and dichloromethane (50 mL) at 0° C., was added $SOCl_2$ (1 g, 8.41 mmol, 1.0 equiv.) dropwise. After 1 h, [5-cyclopropyl-3-(2,6-dichlorophenyl)-1,2-oxazol-4-yl]methanol 12a (2.5 g, 8.80 mmol, 1.0 equiv.) in dichloromethane (50 mL) was added dropwise at 0° C. The resulting mixture was stirred at room temperature overnight and then quenched by the addition of 50 mL of water/ice. The aqueous mixture was extracted with 100 mL of dichloromethane. The organic layer was washed with brine (100 mL), dried over anhydrous sodium sulfate, filtered, and concentrated under reduced pressure. The residue was purified by silica gel column chromatography eluting with ethyl acetate/petroleum ether (0-10%) to give 2.11 g (79%) of 4-(chloromethyl)-5-cyclopropyl-3-(2,6-dichlorophenyl)-1,2-oxazole 12b as an off-white solid. $^1$H NMR (300 MHz; $CDCl_3$) δ: 7.46-7.28 (m, 3H), 4.33 (s, 2H), 2.11 (tt, J=8.3, 5.1 Hz, 1H), 1.32-1.08 (m, 4H). MS (ES, m/z): [M+1]=301.75.

Step 3. Benzyl (1S,4S,5R)-5-[[5-cyclopropyl-3-(2,6-dichlorophenyl)-1,2-oxazol-4-yl]methoxy]-2-azabicyclo[2.2.1]heptane-2-carboxylate (12c)

To a 250-mL round-bottom flask containing benzyl (1S,4S,5R)-5-hydroxy-2-azabicyclo[2.2.1]heptane-2-carboxylate C-1 (1 g, 4.04 mmol, 1.0 equiv.) and N,N-dimethylformamide (20 mL) was added 4-(chloromethyl)-5-cyclopropyl-3-(2,6-dichlorophenyl)-1,2-oxazole 12b (1.41 g, 4.06 mmol, 1.0 equiv.). Sodium hydride (60% in mineral oil) (320 mg, 13.33 mmol, 2.0 equiv.) was then added batchwise at 0° C., and the resulting mixture was stirred at room temperature for 2 h. The mixture was diluted with 200 mL of ethyl acetate, washed with brine (50 mL×3), dried over sodium sulfate, and concentrated under reduced pressure. The residue was purified by silica gel column chromatography eluting with PE:EA (5:1) to give 1.7 g (82%) of benzyl (1S,4S,5R)-5-[[5-cyclopropyl-3-(2,6-dichlorophenyl)-1,2-oxazol-4-yl]methoxy]-2-azabicyclo[2.2.1]heptane-2-carboxylate 12c as a light-yellow oil.

Step 4. (1S,4S,5R)-5-[[5-cyclopropyl-3-(2,6-dichlorophenyl)-1,2-oxazol-4-yl]methoxy]-2-azabicyclo[2.2.1]heptane (12d)

To a 250-mL round-bottom flask was added benzyl (1S,4S,5R)-5-[[5-cyclopropyl-3-(2,6-dichlorophenyl)-1,2-oxazol-4-yl]methoxy]-2-azabicyclo[2.2.1]heptane-2-carboxylate 12c (1.7 g, 3.31 mmol, 1.0 equiv.), dichloromethane (30 mL) and TMSI (3.32 g, 16.60 mmol, 5.0 equiv.) and the resulting mixture was stirred at room temperature for 10 min. 1M hydrogen chloride aqueous solution was then added until the pH value of solution reached 3-4 and the resulting mixture was concentrated under reduced pressure. The crude product (5 g) was purified by Flash-Prep-HPLC using the following conditions: Column, silica gel; mobile phase, $CH_3CN$:$H_2O$=0:100 increasing to 20:80 over 30 min; Detector, UV 254 nm, to provide 1 g (80%) of (1S,4S,5R)-5-[[5-cyclopropyl-3-(2,6-dichlorophenyl)-1,2-oxazol-4-yl]methoxy]-2-azabicyclo[2.2.1]heptane 12d as a light-yellow solid.

Step 5. Methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylate (12e)

To a 100-mL round-bottom flask purged and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane 12d (300 mg, 0.79 mmol, 1.0 equiv.), DMA (10 mL), methyl 2-bromo-4-fluoro-1,3-benzothiazole-6-carboxylate A-1 (253 mg, 0.87 mmol, 1.1 equiv), and $Cs_2CO_3$ (775 mg, 2.38 mmol, 3.0 equiv.) and the reaction mixture was stirred at 60° C., overnight. The resulting mixture was diluted with 200 mL of ethyl acetate, washed with brine (30 mL×3), dried over sodium sulfate, filtered, and concentrated under reduced pressure. The residue was purified by silica gel column chromatography eluting with PE:EA (5:1) to provide 350 mg (75%) of methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylate 12e as a light-yellow oil.

Step 6. 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylic Acid (I-12)

To a 250-mL round-bottom flask purged and maintained under an inert atmosphere of nitrogen was added methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylate 12e (400 mg, 0.68 mmol, 1.0 equiv.), methanol/$H_2O$ (10/1 mL), and $LiOH.H_2O$ (286 mg, 6.82 mmol, 10.0 equiv) and the resulting mixture was stirred at 50° C., for 2 h. The reaction was then quenched by the addition of 50 mL of $H_2O$ and the pH value of the solution was adjusted to 3-4 using aqueous hydrogen chloride (1M). The aqueous mixture was extracted with ethyl acetate (30 mL×3) and the combined organic layers were dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, Water (0.05% TFA) and ACN (56% ACN to 78% over 8 min); Detector, UV 254 nm, to provide 50.5 mg (13%) of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylic acid I-12 as an off-white solid. $^1$H NMR (400 MHz, $CD_3OD$) δ: 8.15 (d, J=1.5 Hz, 1H), 7.68 (dd, J=11.5, 1.5 Hz, 1H), 7.61-7.46 (m, 3H), 4.42-4.30 (m, 4H), 3.67 (dd, J=6.9, 2.4 Hz, 1H), 3.56-3.49 (m, 1H), 3.04 (s, 1H), 2.63 (d, J=3.9 Hz, 1H), 2.29 (p, J=6.9 Hz, 1H), 2.08-1.96 (m, 1H), 1.70 (s, 2H), 1.47-1.37 (m, 1H), 1.24-1.16 (m, 4H). MS (ES, m/z): [M+1]=574.0.

Example 24: Synthesis of I-13 to I-18

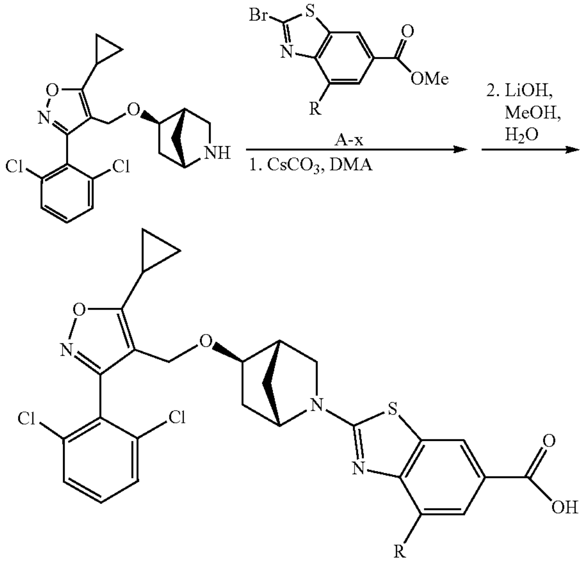

I-13 to I-18

Compounds I-13 to I-18 were prepared in two steps from intermediate 12d and substituted bromo-benzothiazole esters A-x following the procedures described in Preparative Example 23 steps 5 and 6. Data for Compounds I-13 to I-18 is shown herein below in Table 3.

TABLE 3

| Cmpd Structure | Cmpd No. | MS/$^1$H NMR |
|---|---|---|
| 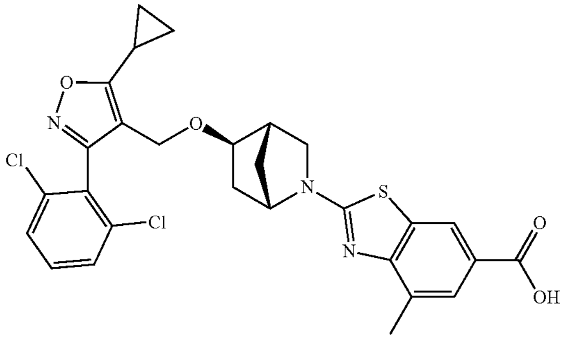 [SMILES: Cc1cc(C(=O)O)cc2sc(N3C[C@@H]4C[C@H]3C[C@H]4OCc3c(-c4c(Cl)cccc4Cl)noc3C3CC3)nc12] | I-13 | MS (ES, m/z): [M + 1] = 570.0. $^1$H NMR (300 MHz, $CD_3OD$) δ: 8.18 (dd, J = 1.7, 0.7 Hz, 2H), 7.82 (dd, J = 1.7, 0.9 Hz, 2H), 7.63-7.44 (m, 6H), 4.37 (d, J = 2.0 Hz, 4H), 3.68 (d, J = 4.7 Hz, 1H), 3.53 (d, J = 4.0 Hz, 1H), 3.06 (s, 1H), 2.64 (s, 2H), 2.59-2.52 (m, 6H), 2.30 (p, J = 6.7 Hz, 2H), 2.03 (dd, J = 13.5, 6.7 Hz, 2H), 1.71 (s, 4H), 1.43 (d, J = 13.5 Hz, 2H), 1.20 (d, J = 6.7 Hz, 8H). |
| 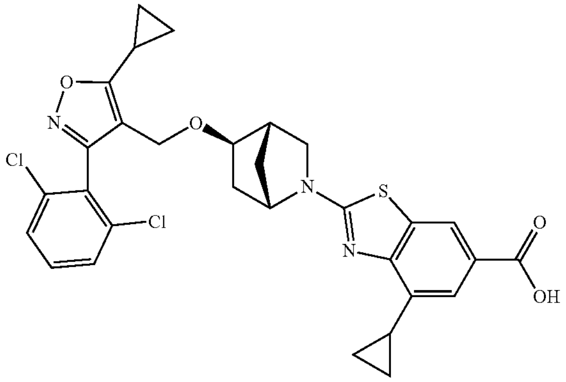 [SMILES: O=C(O)c1cc(C2CC2)c2nc(N3C[C@@H]4C[C@H]3C[C@H]4OCc3c(-c4c(Cl)cccc4Cl)noc3C3CC3)sc2c1] | I-14 | MS (ES, m/z): [M + 1] = 596.0. $^1$H NMR (300 MHz, $CD_3OD$) δ: 8.16 (d, J = 1.6 Hz, 1H), 7.64-7.44 (m, 4H), 4.38 (d, J = 1.7 Hz, 2H), 3.70 (dd, J = 6.9, 2.4 Hz, 1H), 3.57 (dd, J = 10.1, 3.9 Hz, 1H), 3.13 (s, 1H), 2.67 (s, 1H), 2.51 (ddd, J = 13.7, 8.5, 5.2 Hz, 1H), 2.30 (p, J = 6.8 Hz, 1H), 2.06 (dd, J = 13.6, 6.8 Hz, 1H), 1.73 (d, J = 2.0 Hz, 2H), 1.44 (d, J = 13.6 Hz, 1H), 1.21 (d, J = 6.7 Hz, 4H), 1.16-1.03 (m, 2H), 0.93-0.82 (m, 2H) |
| 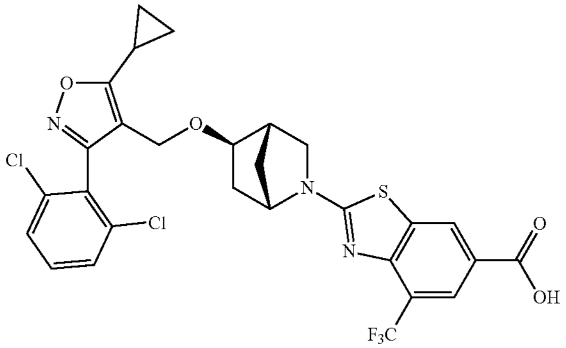 [SMILES: O=C(O)c1cc(C(F)(F)F)c2nc(N3C[C@@H]4C[C@H]3C[C@H]4OCc3c(-c4c(Cl)cccc4Cl)noc3C3CC3)sc2c1] | I-15 | MS (ES, m/z): [M + 1] = 624.0. $^1$H NMR (400 MHz, $CD_3OD$) δ: 8.47 (d, J = 1.6 Hz, 1H), 8.21-8.14 (m, 1H), 7.59-7.43 (m, 3H), 4.33 (d, J = 1.9 Hz, 2H), 3.65 (dd, J = 6.9, 2.4 Hz, 1H), 3.49 (s, 1H), 3.01 (d, J = 18.6 Hz, 1H), 2.63-2.57 (m, 1H), 2.33-2.21 (m, 1H), 2.03-1.93 (m, 1H), 1.67 (s, 2H), 1.40 (dt, J = 13.6, 2.8 Hz, 1H), 1.21-1.13 (m, 4H). |
| 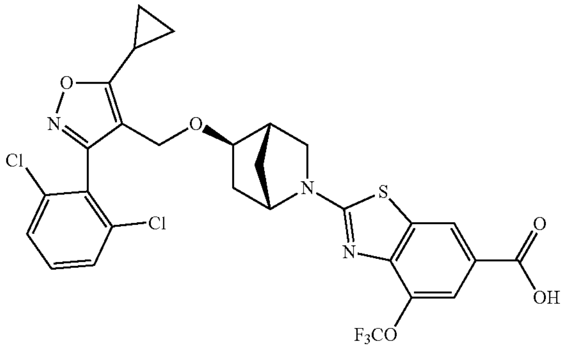 | I-16 | MS (ES, m/z): [M + 1] = 640.0. $^1$H NMR (400 MHz, $CD_3OD$) δ: 8.28 (d, J = 1.5 Hz, 1H), 7.82 (p, J = 1.4 Hz, 1H), 7.59-7.44 (m, 3H), 4.34 (d, J = 2.4 Hz, 2H), 3.65 (dd, J = 7.0, 2.4 Hz, 1H), 3.03 (s, 2H), 2.60 (s, 1H), 2.27 (p, J = 6.8 Hz, 1H), 1.99 (dd, J = 13.7, 7.0 Hz, 1H), 1.67 (d, J = 1.9 Hz, 2H), 1.40 (d, J = 13.6 Hz, 1H), 1.21-1.14 (m, 4H). |

TABLE 3-continued

| Cmpd Structure | Cmpd No. | MS/$^1$H NMR |
|---|---|---|
| 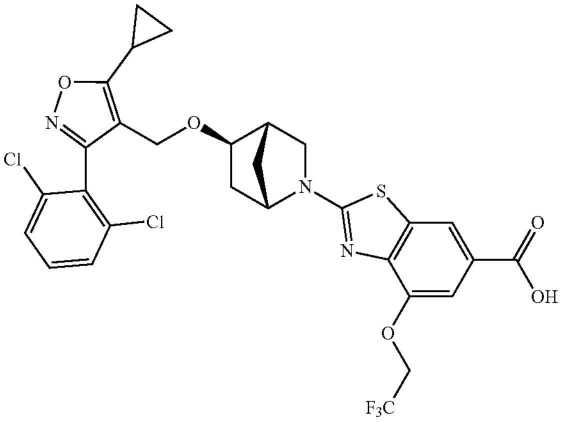 [SMILES: O=C(O)c1cc(OCC(F)(F)F)c2nc(N3C[C@@H]4C[C@H]3C[C@H]4OCc3c(-c4c(Cl)cccc4Cl)noc3C3CC3)sc2c1] | I-17 | MS (ES, m/z): [M + 1] = 654.0. $^1$H NMR (400 MHz, DMSO-$d_6$) δ: 8.09 (d, J = 1.5 Hz, 1H), 7.70-7.53 (m, 3H), 7.49 (d, J = 1.5 Hz, 1H), 4.97 (q, J = 9.0 Hz, 2H), 4.34-4.22 (m, 2H), 3.64-3.58 (m, 1H), 3.43 (d, J = 9.3 Hz, 1H), 2.96 (s, 1H), 2.54 (d, J = 4.3 Hz, 2H), 2.41-2.33 (m, 1H), 1.95-1.84 (m, 1H), 1.59 (d, J = 9.7 Hz, 1H), 1.47 (d, J = 9.8 Hz, 1H), 1.27 (dd, J = 16.2, 5.5 Hz, 1H), 1.20-1.05 (m, 4H). |
| 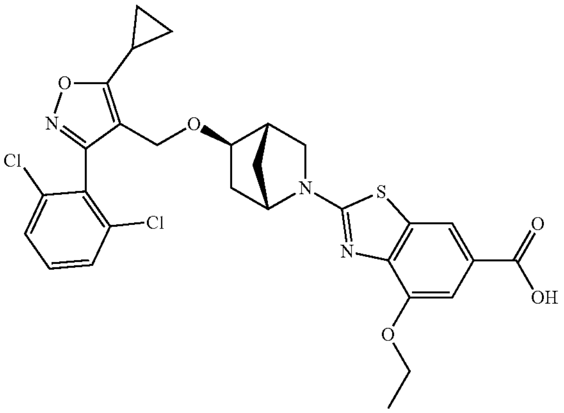 [SMILES: CCOc1cc(C(=O)O)cc2sc(N3C[C@@H]4C[C@H]3C[C@H]4OCc3c(-c4c(Cl)cccc4Cl)noc3C3CC3)nc12] | I-18 | MS (ES, m/z): [M + 1] = 600.10. $^1$H NMR (400 MHz, DMSO-$d_6$) δ: 7.94 (d, J = 1.5 Hz, 1H), 7.67-7.50 (m, 3H), 7.34 (d, J = 1.5 Hz, 1H), 4.31-4.10 (m, 5H), 3.61-3.54 (m, 1H), 3.39 (dd, J = 10.1, 4.0 Hz, 1H), 2.90 (d, J = 9.6 Hz, 1H), 2.51 (d, J = 3.7 Hz, 1H), 2.32 (tt, J = 8.3, 5.2 Hz, 1H), 1.91-1.81 (m, 1H), 1.56 (d, J = 9.7 Hz, 1H), 1.44 (d, J = 9.8 Hz, 1H), 1.36 (t, J = 6.9 Hz, 3H), 1.24 (dt, J = 15.2, 3.5 Hz, 1H), 1.18-1.03 (m, 4H) |

Example 25: 2-[(1S,4S,5R)-5-({5-cyclopropyl-3-[2-(trifluoromethyl)phenyl]-1,2-oxazol-4-yl}methoxy)-2-azabicyclo[2.2.1]heptan-2-yl]-4-fluoro-1,3-benzothiazole-6-carboxylic Acid

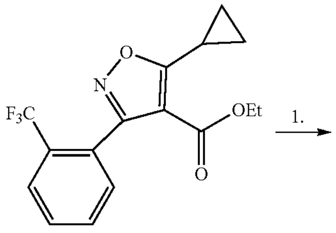

9d

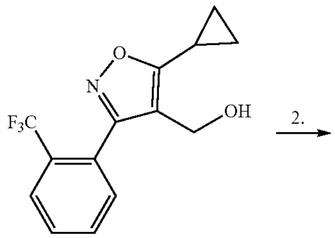

19a

-continued

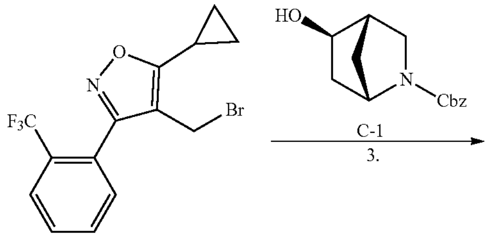

19b

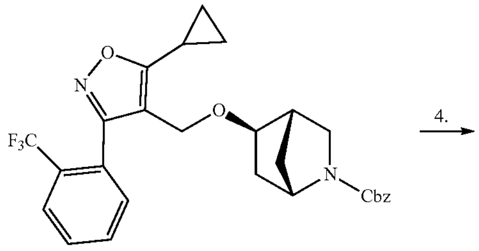

19c

-continued

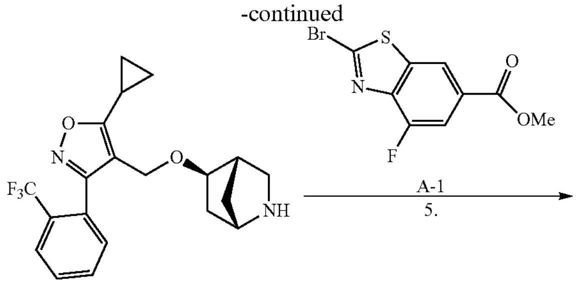

19d

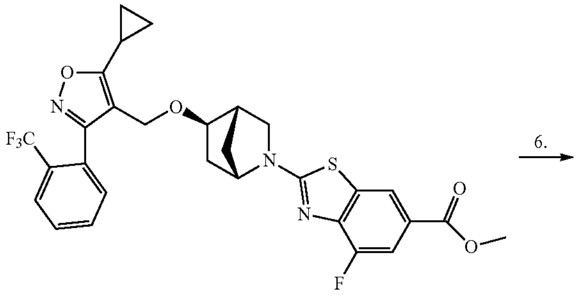

19e

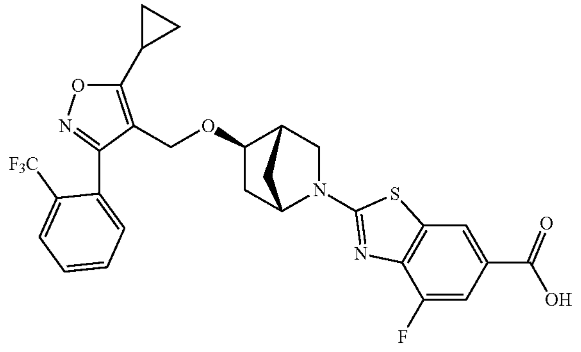

I-19

Step 1. [5-cyclopropyl-3-[2-(trifluoromethyl)phenyl]-1,2-oxazol-4-yl]methanol (19a)

To a 500-mL round-bottom flask containing ethyl 5-cyclopropyl-3-[2-(trifluoromethyl)phenyl]-1,2-oxazole-4-carboxylate 9d (15 g, 46.11 mmol, 1.0 equiv.) and tetrahydrofuran (300 mL) at 0° C., was added $LiAlH_4$ (3.5 g, 92.23 mmol, 2.0 equiv) in several batches and the resulting mixture was warmed to room temperature and stirred for 3 h. 100 mL of ethyl acetate was then added followed by 200 mL of water/ice. The mixture was extracted with ethyl acetate (200 mL×2), and the combined organic extracts were washed with brine (300 mL), dried over anhydrous sodium sulfate, filtered, and concentrated under reduced pressure. The residue was purified by column chromatography eluting with ethyl acetate/petroleum ether (0-50%) to provide 10 g (77%) of [5-cyclopropyl-3-[2-(trifluoromethyl)phenyl]-1,2-oxazol-4-yl]methanol 19a as a light yellow solid.

Step 2. 4-(bromomethyl)-5-cyclopropyl-3-[2-(trifluoromethyl)phenyl]-1,2-oxazole (19b)

To a 500-mL round-bottom flask containing [5-cyclopropyl-3-[2-(trifluoromethyl)phenyl]-1,2-oxazol-4-yl]methanol 19a (5 g, 17.65 mmol, 1.0 equiv.) and dichloromethane (100 mL) was added $CBr_4$ (9.27 g, 28.26 mmol, 1.60 equiv) batchwise followed by $PPh_3$ (6.94 g, 26.46 mmol, 1.50 equiv) batchwise. The resulting mixture was stirred at room temperature overnight and then diluted with 100 mL of DCM. The organic layer was washed with 200 mL of water and 200 mL of brine, dried over anhydrous sodium sulfate, filtered, and concentrated under reduced pressure. The residue was purified by silica gel column chromatography eluting with ethyl acetate/petroleum ether (0%-10%) to give 3.2 g (52%) of 4-(bromomethyl)-5-cyclopropyl-3-[2-(trifluoromethyl)phenyl]-1,2-oxazole 19b as a colorless oil.

Step 3. Benzyl (1S,4S,5R)-5-([5-cyclopropyl-3-[2-(trifluoromethyl)phenyl]-1,2-oxazol-4-yl]methoxy)-2-azabicyclo[2.2.1]heptane-2-carboxylate (19c)

To a 8-mL sealed tube containing 4-(bromomethyl)-5-cyclopropyl-3-[2-(trifluoromethyl)phenyl]-1,2-oxazole 19b (345 mg, 1.0 mmol, 1.0 equiv.), benzyl (1S,4S,5R)-5-hydroxy-2-azabicyclo[2.2.1]heptane-2-carboxylate C-1 (247 mg, 1.0 mmol, 1.0 equiv.), and N,N-dimethylformamide (5 mL) was added sodium hydride (80 mg, 2.0 mmol, 2.0 equiv., 60% in mineral oil) batchwise at 0° C., and the reaction mixture was stirred at room temperature overnight. The resulting mixture was diluted with 30 mL of ethyl acetate, and 30 mL of water/ice was then added. The aqueous mixture was extracted with ethyl acetate (30 mL×2) and the combined organic extracts were washed with brine (60 mL), dried over anhydrous sodium sulfate, filtered, and concentrated under reduced pressure. The residue was purified by silica gel column chromatography eluting with ethyl acetate/petroleum ether (1:1.5) to afford 420 mg (82%) of benzyl (1S,4S,5R)-5-([5-cyclopropyl-3-[2-(trifluoromethyl)phenyl]-1,2-oxazol-4-yl]methoxy)-2-azabicyclo[2.2.1]heptane-2-carboxylate 19c as a colorless oil.

Step 4. (1S,4S,5R)-5-([5-cyclopropyl-3-[2-(trifluoromethyl)phenyl]-1,2-oxazol-4-yl]methoxy)-2-azabicyclo[2.2.1]heptane (19d)

To a 50-mL round-bottom flask containing a solution of benzyl (1S,4S,5R)-5-([5-cyclopropyl-3-[2-(trifluoromethyl)phenyl]-1,2-oxazol-4-yl]methoxy)-2-azabicyclo[2.2.1]heptane-2-carboxylate 19c (500 mg, 0.98 mmol, 1.0 equiv.) in dichloromethane (5 mL) was added iodotrimethylsilane (977 mg, 4.88 mmol, 5.0 equiv.) dropwise at room temperature. The resulting mixture was stirred for 10 min and then quenched by the addition of 10 mL a 1M HCl aqueous solution. The mixture was concentrated under reduced pressure and the resulting residue was purified by silica gel column chromatography eluting with $CH_3CN:H_2O$ (0%-100%) to give 350 mg (95%) of (1S,4S,5R)-5-([5-cyclopropyl-3-[2-(trifluoromethyl)phenyl]-1,2-oxazol-4-yl]methoxy)-2-azabicyclo[2.2.1]heptane 19d as a colorless oil.

Step 5. Methyl 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-fluoro-1,3-benzothiazole-6-carboxylate (19e)

To a 100-mL round-bottom flask was added (1S,4S,5R)-5-([5-cyclopropyl-3-[2-(trifluoromethyl)phenyl]-1,2-oxazol-4-yl]methoxy)-2-azabicyclo[2.2.1]heptane 19d (125 mg, 0.33 mmol, 1.0 equiv.), methyl 2-bromo-4-fluoro-1,3-benzothiazole-6-carboxylate A-1 (115 mg, 0.40 mmol, 1.20 equiv.), DMA (5 mL), and $Cs_2CO_3$ (323 mg, 0.99 mmol, 3.0 equiv.). The resulting mixture was stirred at 60° C., overnight. The mixture was then diluted with $H_2O$ and extracted with ethyl acetate (30 mL×3). The combined organic extracts were washed with brine (30 mL×2), dried over anhydrous sodium sulfate, filtered, and concentrated under reduced pressure. The residue was purified by silica gel column chromatography eluting with ethyl acetate/petroleum ether (1:3) to afford 160 mg (82%) of methyl 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-fluoro-1,3-benzothiazole-6-carboxylate 19e as a light yellow oil.

Step 6. 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-fluoro-1,3-benzothiazole-6-carboxylic Acid (I-19)

To a 50-mL round-bottom flask containing methyl 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-fluoro-1,3-benzothiazole-6-carboxylate 19e (160 mg, 0.27 mmol, 1.0 equiv.), methanol (3 mg, 0.09 mmol, 0.34 equiv.), and tetrahydrofuran (1 mL) was added $H_2O$ dropwise (1 mL) followed by LiOH (66 mg, 10.0 equiv.). The resulting mixture was stirred at 50° C., for 2 h. Upon cooling to room temperature, 5 mL of $H_2O$ was added and the pH value of the solution was adjusted to 2 using a aqueous hydrogen chloride (1M). The aqueous mixture was extracted with 50 mL of ethyl acetate and the organic extract was washed with brine (100 mL×2), dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, Water (0.05% TFA) and ACN (63.0% to 78.0% over 8 min); Detector, UV 254 nm, to provide 80.3 mg (51%) of 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-fluoro-1,3-benzothiazole-6-carboxylic acid I-19 as a colorless solid. $^1H$ NMR (400 MHz, $CD_3OD$) δ: 8.13 (q, J=1.7 Hz, 1H), 7.87 (d, J=7.5 Hz, 1H), 7.79-7.62 (m, 3H), 7.56-7.49 (m, 1H), 4.36-4.22 (m, 3H), 3.65 (d, J=6.2 Hz, 1H), 3.51 (d, J=8.6 Hz, 1H), 3.03 (s, 1H), 2.64 (s, 1H), 2.25 (p, J=7.1 Hz, 1H), 2.04 (dd, J=13.7, 6.8 Hz, 1H), 1.70 (s, 2H), 1.45 (d, J=13.9 Hz, 1H), 1.21-1.13 (m, 4H). MS (ES, m/z): [M+1]=574.20.

Example 26: 2-[(1S,4S,5R)-5-({5-cyclopropyl-3-[2-(trifluoromethyl)phenyl]-1,2-oxazol-4-yl}methoxy)-2-azabicyclo[2.2.1]heptan-2-yl]-4-(trifluoromethoxy)-1,3-benzothiazole-6-carboxylic Acid (I-20)

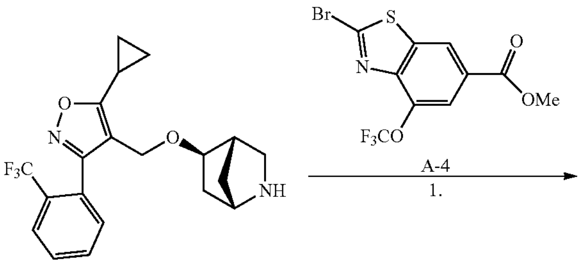

19d

-continued

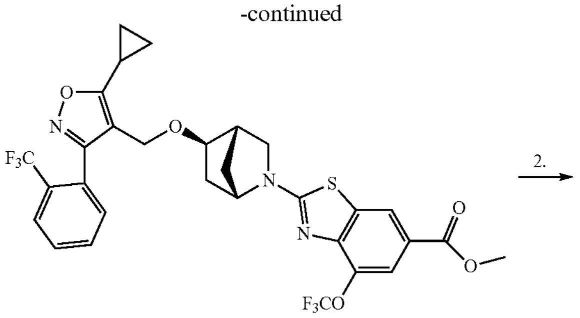

20a

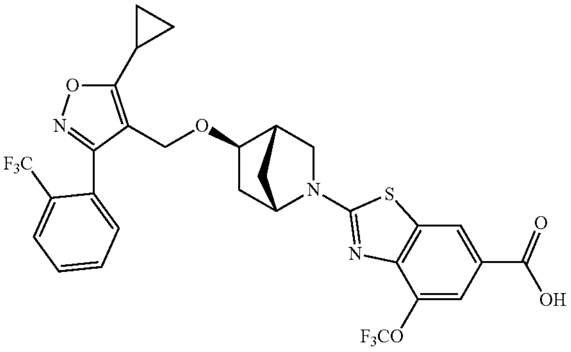

I-20

Step 1. Methyl 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-(trifluoromethoxy)-1,3-benzothiazole-6-carboxylate (20a)

To a 100-mL round-bottom flask was added a solution of (1S,4S,5R)-5-([5-cyclopropyl-3-[2-(trifluoromethyl)phenyl]-1,2-oxazol-4-yl]methoxy)-2-azabicyclo[2.2.1]heptane 19d (117 mg, 0.31 mmol, 1.10 equiv.) in DMA (5 mL), methyl 2-bromo-4-(trifluoromethoxy)-1,3-benzothiazole-6-carboxylate A-4 (100 mg, 0.28 mmol, 1.0 equiv.), and $Cs_2CO_3$ (275 mg, 0.84 mmol, 3.0 equiv.) and the resulting mixture was stirred at 60° C., overnight. After cooling to room temperature, the mixture was diluted with $H_2O$ and extracted with ethyl acetate (30 mL×3). The combined organic extracts were washed with brine (30 mL×2), dried over anhydrous sodium sulfate, filtered, and concentrated under reduced pressure. The residue was purified by silica gel column chromatography eluting with ethyl acetate/petroleum ether (1:3) to provide 167 mg (91%) of methyl 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-(trifluoromethoxy)-1,3-benzothiazole-6-carboxylate 20a as a light yellow oil.

Step 2. 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-(trifluoromethoxy)-1,3-benzothiazole-6-carboxylic Acid (I-20)

To a 50-mL round-bottom flask containing a solution of methyl 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-(trifluoromethoxy)-1,3-benzothiazole-6-carboxylate 20a (167 mg, 0.26 mmol, 1.0 equiv) in tetrahydrofuran (1.5 mL) was added methanol (3 mL), water (1.5 mL), and LiOH (61.37 mg, 2.56 mmol, 10.0 equiv.)

successively. The resulting mixture was stirred at room temperature for 2 h and then diluted with 10 mL of $H_2O$. The pH value of the solution was adjusted to 2 using aqueous HCl (1M). The aqueous mixture was extracted with ethyl acetate (50 mL×2) and the combined organic extracts were washed with brine (100 mL), dried over anhydrous sodium sulfate, filtered, and concentrated under reduced pressure. The crude product was purified by Prep-HPLC using the following conditions: Column, XBridge BEH130 Prep C18 OBD Column, 150 mm×5 um 13 nm; mobile phase, Water (0.05% TFA) and ACN (70.0% to 85.0% over 8 min); Detector, UV 254 nm, to provide 33.8 mg (21%) of 2-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-4-(trifluoromethoxy)-1,3-benzothiazole-6-carboxylic acid I-20 as a colorless solid. $^1H$ NMR (400 MHz, $CD_3OD$) δ: 8.27 (d, J=1.5 Hz, 1H), 7.90-7.79 (m, 2H), 7.79-7.66 (m, 2H), 7.53 (d, J=7.3 Hz, 1H), 4.29 (d, J=8.2 Hz, 2H), 3.65 (d, J=6.0 Hz, 1H), 3.50 (s, 1H), 2.64 (s, 1H), 2.30-2.22 (m, 1H), 2.04 (dd, J=13.6, 6.7 Hz, 1H), 1.70 (s, 2H), 1.45 (d, J=13.7 Hz, 1H), 1.20-1.13 (m, 5H). MS (ES, m/z): [M+1]=640.10.

Example 27: 2-[(1S,4S,5R)-5-[(3-cyclohexyl-5-cyclopropyl-1,2-oxazol-4-yl)methoxy]-2-azabicyclo[2.2.1]heptan-2-yl]-4-fluoro-1,3-benzothiazole-6-carboxylic Acid (I-21)

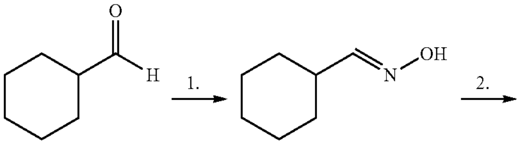

21a

21b

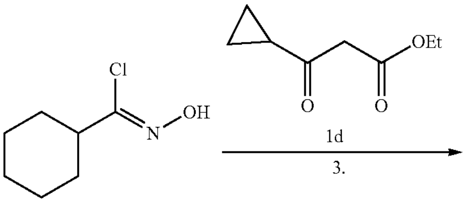

21c

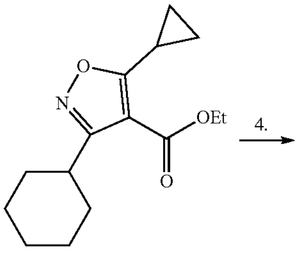

21d

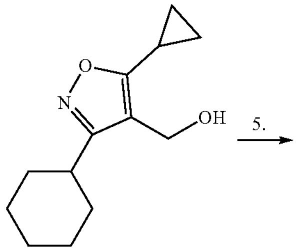

21e

-continued

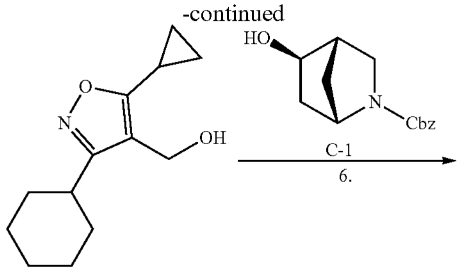

21e

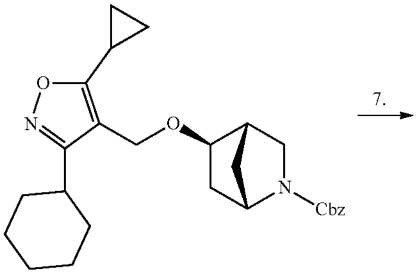

21g

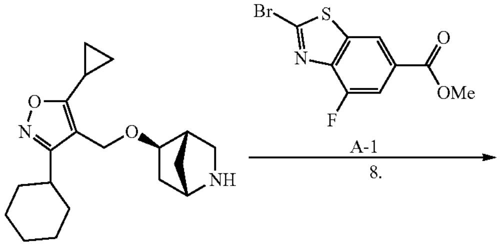

21h

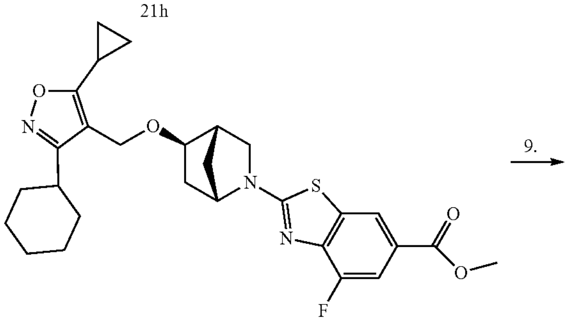

21i

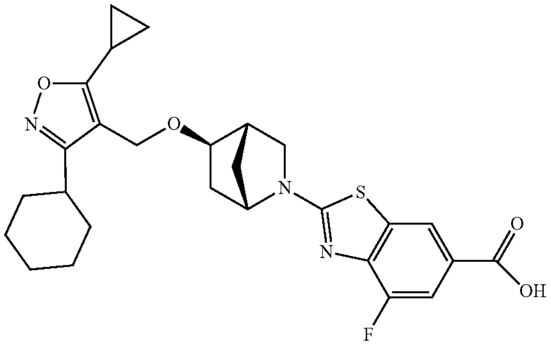

I-21

Step 1. N-(Cyclohexylmethylidene)hydroxylamine (21b)

To a 250-mL round-bottom flask was added $NH_2OH$ HCl (9.26 g, 1.50 equiv.), water (80 mL), sodium carbonate (4.74 g, 44.72 mmol, 0.5 equiv.), and a solution of cyclohexanecarboxaldehyde 21a (10 g, 89.15 mmol, 1.0 equiv.) in ethanol (80 mL) and the reaction mixture was stirred at room temperature for 2 h. The mixture was extracted with ethyl acetate (300 mL×3) and the combined organic extracts were washed with brine (300 mL×3), dried over anhydrous sodium sulfate, filtered, and concentrated under reduced pressure. The crude product (13.0 g) was purified by Flash-Prep-HPLC using the following conditions: Column, silica gel; mobile phase, PE:EA=100:0 increasing to 50:50 over 30 min; Detector, UV 254 nm, to provide 10.8 g (95%) of N-(cyclohexylmethylidene)hydroxylamine 21b as colorless oil.

Step 2. N-hydroxycyclohex-1-carbonimidoyl chloride (21c)

To a 100-mL round-bottom flask was added a solution of N-(cyclohexylmethylidene)-hydroxylamine 21b (2.5 g, 19.66 mmol, 1.0 equiv.) in N,N-dimethylformamide (25 mL), and NCS (3.96 g, 29.66 mmol, 1.50 equiv.). The resulting mixture was stirred for 2 h at room temperature. $H_2O$ was added, the mixture was extracted with ethyl acetate (50 mL×3). The combined organic extracts were washed with brine (50 mL×4), dried over anhydrous sodium sulfate, filtered, and concentrated under reduced pressure to provide 3.1 g (98%) of N-hydroxycyclohex-1-carbonimidoyl chloride 21c as a colorless solid.

Step 3. Ethyl 3-cyclohexyl-5-cyclopropyl-1,2-oxazole-4-carboxylate (21d)

To a 100-mL round-bottom flask was added ethyl 3-cyclopropyl-3-oxopropanoate 1d (3.0 g, 19.21 mmol, 1.0 equiv) and tetrahydrofuran (30 mL), t-BuOK (3.3 g, 29.41 mmol, 1.50 equiv) was added. The mixture was stirred for 5 minutes. The mixture was cooled to 0° C., and a solution of N-hydroxycyclohex-1-carbonimidoyl chloride 21c (3.1 g, 19.18 mmol, 1.0 equiv) in tetrahydrofuran (10 mL) was added. The resulting mixture was stirred at room temperature overnight. 100 mL of $H_2O$ was added. The aqueous mixture was extracted with ethyl acetate (100 mL×3). The combined organic extracts were washed with brine, dried over anhydrous sodium sulfate, filtered, and concentrated under reduced pressure. The crude product was purified by Flash-Prep-HPLC using the following conditions: Column, silica gel; mobile phase, PE:EA=100:0 increasing to PE:EA=90:10 within 30 min; Detector, UV 254 nm. Removal of solvents afforded 3.5 g (69%) of ethyl 3-cyclohexyl-5-cyclopropyl-1,2-oxazole-4-carboxylate 21d as a colorless oil.

Step 4. (3-cyclohexyl-5-cyclopropyl-1,2-oxazol-4-yl)methanol (21e)

To a 100-mL round-bottom flask was added ethyl 3-cyclohexyl-5-cyclopropyl-1,2-oxazole-4-carboxylate 21d (546 mg, 2.07 mmol, 1.0 equiv.), $LiAlH_4$ (158 mg, 4.16 mmol, 2.0 equiv.), and tetrahydrofuran (10 mL). The resulting mixture was stirred at room temperature for 1 h. A 1 N hydrogen chloride solution was added (60 mL), the aqueous mixture was extracted with dichloromethane (50 mL×3). The combined organic extracts were dried over anhydrous sodium sulfate, filtered, and concentrated under reduced pressure to a residue, which was purified by silica gel column chromatography eluting with ethyl acetate/petroleum ether (1:3) to provide 404 mg (88%) of (3-cyclohexyl-5-cyclopropyl-1,2-oxazol-4-yl)methanol 21e as a light yellow oil.

Step 5. 4-(chloromethyl)-3-cyclohexyl-5-cyclopropyl-1,2-oxazole (21f)

To a 8-mL round-bottom flask was added 1H-1,2,3-benzotriazole (215 mg, 1.80 mmol, 1.60 equiv.) and dichloromethane (5 mL). Thionyl chloride (0.140 mL, 1.60 equiv.) was added dropwise with stirring at 0° C. The reaction mixture was stirred at 0° C., for 30 min. (3-cyclohexyl-5-cyclopropyl-1,2-oxazol-4-yl)methanol 21e (250 mg, 1.13 mmol, 1.0 equiv.) was added. Reaction was continued at room temperature overnight and concentrated under reduced pressure. The residue was purified by silica gel column chromatography eluting with ethyl acetate/petroleum ether (1:5) to give 219 mg (65%) of 4-(chloromethyl)-3-cyclohexyl-5-cyclopropyl-1,2-oxazole 21f as a light yellow crude oil.

Step 6. Benzyl (1S,4S,5R)-5-((3-cyclohexyl-5-cyclopropylisoxazol-4-yl)methoxy)-2-azabicyclo[2.2.1]heptane-2-carboxylate (21g)

To a 25-mL round-bottom flask was added benzyl (1S,4S,5R)-5-hydroxy-2-azabicyclo[2.2.1]heptane-2-carboxylate C-1 (322 mg, 1.30 mmol, 1.50 equiv.), N,N-dimethylformamide (10 mL), and 4-(chloromethyl)-3-cyclohexyl-5-cyclopropyl-1,2-oxazole 21f (208 mg, 0.87 mmol, 1.0 equiv). Sodium hydride (70 mg, 1.75 mmol, 2.0 equiv., 60% in mineral oil) was added in small portions at 0° C. The resulting mixture was stirred at room temperature overnight, and then diluted with of $H_2O$. The aqueous mixture was extracted with ethyl acetate (50 mL×3); and the combined organic extracts were washed with brine, dried over anhydrous sodium sulfate, filtered, and concentrated under reduced pressure. The residue was purified by silica gel column chromatography eluting with ethyl acetate/petroleum ether (1:5) to give 167 mg (43%) of benzyl (1S,4S,5R)-5-((3-cyclohexyl-5-cyclopropylisoxazol-4-yl)methoxy)-2-azabicyclo[2.2.1]heptane-2-carboxylate 21g as a light yellow oil.

Step 7. (1S,4S,5R)-5-[(3-cyclohexyl-5-cyclopropyl-1,2-oxazol-4-yl)methoxy]-2-azabicyclo[2.2.1]heptane (21h)

To a 50-mL round-bottom flask was added benzyl (1S,4S,5R)-5-((3-cyclohexyl-5-cyclopropylisoxazol-4-yl)methoxy)-2-azabicyclo[2.2.1]heptane-2-carboxylate 21g (167 mg, 0.37 mmol, 1.0 equiv.), dichloromethane (3 mL), and TMSI (372 mg, 5.0 equiv.). The resulting mixture was stirred at room temperature for 1 h. A 1M HCl aqueous solution was added until pH value is around 3-4. The mixture was concentrated to a residue, which was purified by silica gel column chromatography eluting with dichloromethane/methanol (10:1). Removal of solvents gave 166 mg (111%) of (1S,4S,5R)-5-[(3-cyclohexyl-5-cyclopropyl-1,2-oxazol-4-yl)methoxy]-2-azabicyclo[2.2.1]heptane 21h as a yellow crude oil.

Step 8. Methyl 2-[(1S,4S,5R)-5-[(3-cyclohexyl-5-cyclopropyl-1,2-oxazol-4-yl)methoxy]-2-azabicyclo[2.2.1]heptan-2-yl]-4-fluoro-1,3-benzothiazole-6-carboxylate (21i)

To a 50-mL round-bottom flask was added (1S,4S,5R)-5-[(3-cyclohexyl-5-cyclopropyl-1,2-oxazol-4-yl)methoxy]-

2-azabicyclo[2.2.1]heptane 21h (166 mg, 0.52 mmol, 1.0 equiv.), methyl 2-bromo-4-fluoro-1,3-benzothiazole-6-carboxylate A-1 (183 mg, 0.63 mmol, 1.20 equiv.), DMA (5 mL), $Cs_2CO_3$ (343 mg, 1.05 mmol, 2.0 equiv.). The resulting mixture was stirred at 60° C., for 2 h. The mixture was diluted with of $H_2O$. The aqueous mixture was extracted with of ethyl acetate (50 mL×3); the combined organic layers were washed with brine, dried over anhydrous sodium sulfate, filtered, and concentrated under reduced pressure. The residue was purified by silica gel column chromatography eluting with ethyl acetate/petroleum ether (1:5) to afford 131 mg (48%) of methyl 2-[(1S,4S,5R)-5-[(3-cyclohexyl-5-cyclopropyl-1,2-oxazol-4-yl)methoxy]-2-azabicyclo[2.2.1]heptan-2-yl]-4-fluoro-1,3-benzothiazole-6-carboxylate 21i as a white oil.

Step 9. 2-[(1S,4S,5R)-5-[(3-cyclohexyl-5-cyclopropyl-1,2-oxazol-4-yl)methoxy]-2-azabicyclo[2.2.1]heptan-2-yl]-4-fluoro-1,3-benzothiazole-6-carboxylic Acid (I-21)

To a 50-mL round-bottom flask was added methyl 2-[(1S,4S,5R)-5-[(3-cyclohexyl-5-cyclopropyl-1,2-oxazol-4-yl)methoxy]-2-azabicyclo[2.2.1]heptan-2-yl]-4-fluoro-1,3-benzothiazole-6-carboxylate 21i (131 mg, 0.25 mmol, 1.0 equiv.), methanol (2 mL), water (1 mL), and lithium hydroxide monohydrate (105 mg, 2.50 mmol, 10.0 equiv.). The resulting mixture was stirred at room temperature overnight. The pH value of the solution was adjusted to 3.0 using a 1M hydrogen chloride solution. The aqueous mixture was extracted with dichloromethane (50 mL×3); the combined organic layers were dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, Water (0.05% TFA) and ACN (67.0% ACN up to 83.0% in 8 min); Detector, UV 254 nm. After purification, 43.6 mg (34%) of 2-[(1S,4S,5R)-5-[(3-cyclohexyl-5-cyclopropyl-1,2-oxazol-4-yl)methoxy]-2-azabicyclo[2.2.1]heptan-2-yl]-4-fluoro-1,3-benzothiazole-6-carboxylic acid I-21 was obtained as a colorless solid. $^1$H-NMR (400 MHz, $CD_3OD$) δ: 8.14 (d, J=1.5 Hz, 1H), 7.66 (dd, J=11.5, 1.5 Hz, 1H), 4.54-4.38 (m, 3H), 3.87 (dd, J=6.5, 2.1 Hz, 1H), 3.62 (dd, J=10.1, 4.1 Hz, 1H), 3.16 (s, 1H), 2.95 (d, J=2.1 Hz, 1H), 2.72 (tt, J=11.7, 3.3 Hz, 1H), 2.28-2.09 (m, 2H), 1.96 (dd, J=11.8, 7.2 Hz, 3H), 1.89-1.80 (m, 3H), 1.80-1.68 (m, 2H), 1.60-1.23 (m, 5H), 1.13-0.98 (m, 4H). MS (ES, m/z): [M+1]=512.0.

Example 28: 2-[(1S,4S,5R)-5-[(3-cyclohexyl-5-cyclopropyl-1,2-oxazol-4-yl)methoxy]-2-azabicyclo[2.2.1]heptan-2-yl]-4-(trifluoromethoxy)-1,3-benzothiazole-6-carboxylic Acid (I-22)

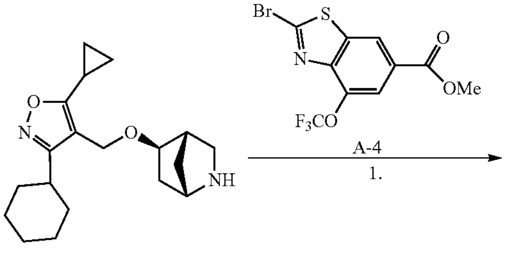

21h

-continued

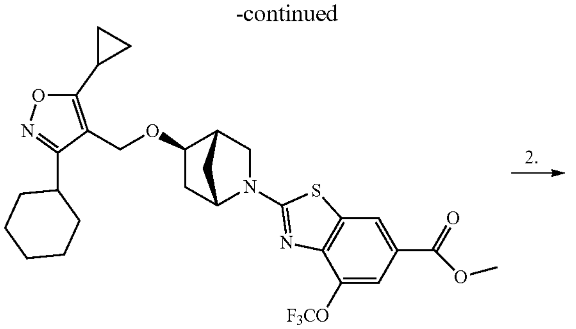

22a

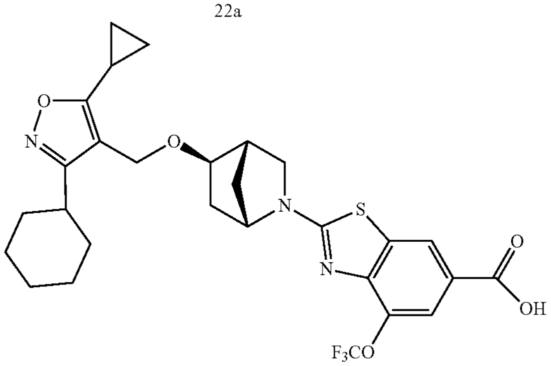

I-22

Step 1. Methyl 2-[(1S,4S,5R)-5-[(3-cyclohexyl-5-cyclopropyl-1,2-oxazol-4-yl)methoxy]-2-azabicyclo[2.2.1]heptan-2-yl]-4-(trifluoromethoxy)-1,3-benzothiazole-6-carboxylate (22a)

To a 50-mL round-bottom flask was added (1S,4S,5R)-5-[(3-cyclohexyl-5-cyclopropyl-1,2-oxazol-4-yl)methoxy]-2-azabicyclo[2.2.1]heptane 21h (149 mg, 0.47 mmol, 1.0 equiv.), methyl 2-bromo-4-(trifluoromethoxy)-1,3-benzothiazole-6-carboxylate (202 mg, 0.57 mmol, 1.20 equiv), $Cs_2CO_3$ (308 mg, 0.95 mmol, 2.0 equiv), and DMA (5 mL) and the resulting mixture was stirred at 60° C., overnight. 100 mL of $H_2O$ was added and the aqueous mixture was extracted with ethyl acetate (50 mL×2). The combined organic extracts were dried over anhydrous sodium sulfate, filtered, and concentrated under reduced pressure. The residue was purified by silica gel column chromatography eluting with ethyl acetate/petroleum ether (1:5) to give 171 mg (61%) of methyl 2-[(1S,4S,5R)-5-[(3-cyclohexyl-5-cyclopropyl-1,2-oxazol-4-yl)methoxy]-2-azabicyclo[2.2.1]heptan-2-yl]-4-(trifluoromethoxy)-1,3-benzothiazole-6-carboxylate 22a as a white foam.

Step 2. 2-[(1S,4S,5R)-5-[(3-cyclohexyl-5-cyclopropyl-1,2-oxazol-4-yl)methoxy]-2-azabicyclo[2.2.1]heptan-2-yl]-4-(trifluoromethoxy)-1,3-benzothiazole-6-carboxylic Acid (1-22)

To a 25-mL round-bottom flask was added methyl 2-[(1S,4S,5R)-5-[(3-cyclohexyl-5-cyclopropyl-1,2-oxazol-4-yl)methoxy]-2-azabicyclo[2.2.1]heptan-2-yl]-4-(trifluoromethoxy)-1,3-benzothiazole-6-carboxylate 22a (171 mg, 0.29 mmol, 1.0 equiv.), methanol (3 mL), $H_2O$ (1 mL), $LiOH—H_2O$ (122 mg, 10.0 equiv.), and tetrahydrofuran (1 mL). The resulting mixture was stirred at room temperature overnight and then concentrated under reduced pressure. The crude product was purified by Prep-HPLC with the following conditions: Column, XSelect CSH Prep C18 OBD Column, 5 um, 19×150 mm; mobile phase, Water (0.05% TFA) and ACN (80% to 90%/o over 8 min); Detector, UV 254 nm, to provide 52.6 mg (32%) of 2-[(1S,4S,5R)-5-[(3-cyclohexyl-5-cyclopropyl-1,2-oxazol-4-yl)methoxy]-2-azabicyclo[2.2.1]heptan-2-yl]-4-(trifluoromethoxy)-1,3-benzothiazole-6-carboxylic acid I-22 as a colorless solid. $^1$H NMR (300 MHz, $CD_3OD$) δ: 1.034 (4H, m), 1.318 (5H, m), 1.682 (2H, m), 1.806 (3H, m), 1.948 (3H, m), 2.101 (1H, m), 2.196 (1H, m), 2.684 (1H, m), 2.918 (1H, m), 3.284 (1H, m), 3.593 (1H, m), 3.855 (1H, m), 4.414 (2H, m), 7.808 (1H, s), 8.271 (1H, s). MS (ES, m/z): [M+1]=578.0.

Example 29: 2-[(1S,4S,5R)-5-{[5-cyclopropyl-3-(oxan-4-yl)-1,2-oxazol-4-yl]methoxy}-2-azabicyclo[2.2.1]heptan-2-yl]-4-(trifluoromethoxy)-1,3-benzothiazole-6-carboxylic Acid (I-23)

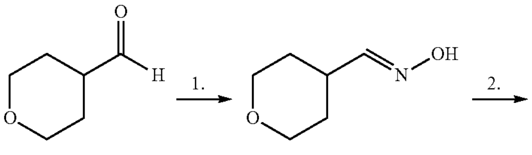

23a 23b

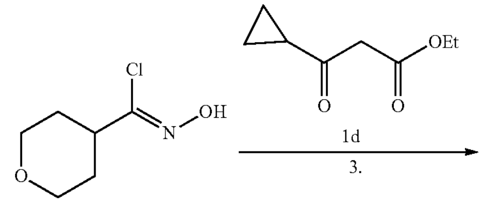

23c

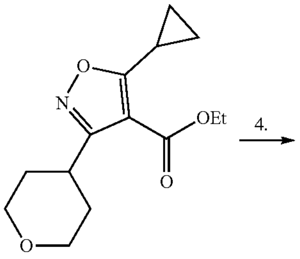

23d

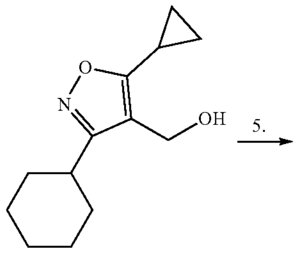

23e

-continued

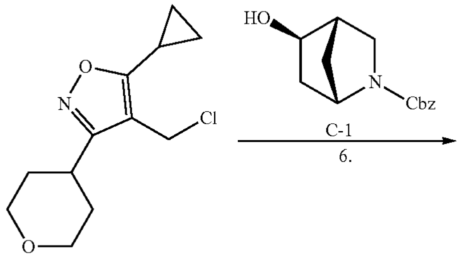

23f

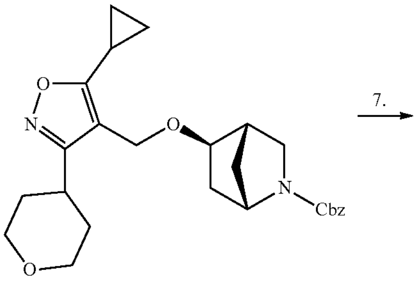

23g

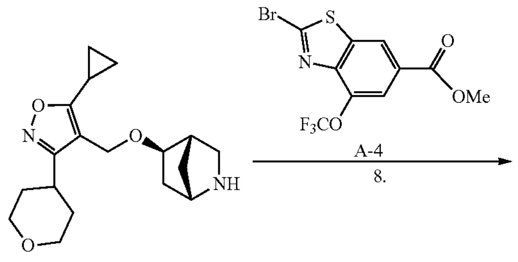

23h

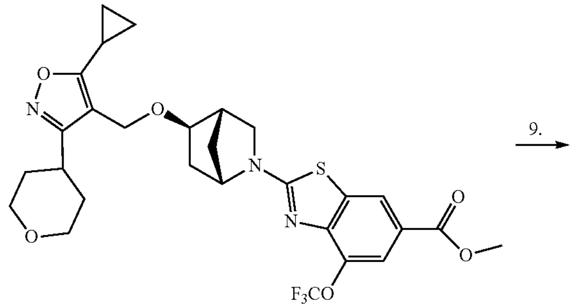

23i

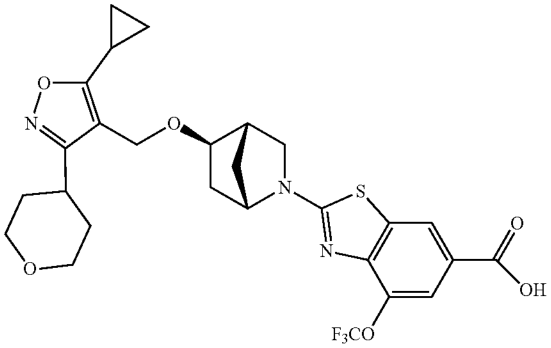

I-23

Step 1. N-(tetrahydropyran-4-ylmethylidene)hydroxylamine (23b)

To a 250-mL round-bottom flask containing a solution of $NH_2OH.HCl$ (1.8 g, 26.09 mmol, 1.50 equiv) in water (30 mL) and sodium carbonate (930 mg, 8.77 mmol, 0.50 equiv.) was added a solution of tetrahydropyran-4-carbaldehyde 23a (2 g, 17.52 mmol, 1.0 equiv) in ethanol (30 mL) dropwise and the resulting mixture was stirred at room temperature for 3 h. The mixture was diluted with 100 mL of brine and extracted with ethyl acetate (100 mL×2). The combined organic extracts were dried over anhydrous sodium sulfate, filtered, and concentrated under reduced pressure to give 2.1 g (93%) of N-(tetrahydropyran-4-ylmethylidene) hydroxylamine 23b as a white solid.

Step 2. N-hydroxyoxy-4-carbonimidoyl chloride (23c)

To a 50-mL round-bottom flask was added a solution of N-(tetrahydropyran-4-ylmethylidene)-hydroxylamine 23b (200 mg, 1.55 mmol, 1.0 equiv.) in N,N-dimethylformamide (2 mL). NCS (200 mg, 1.50 mmol, 1.0 equiv.) batchwise. The resulting mixture was stirred at room temperature for 2 h and then diluted with ethyl acetate. The mixture was washed with brine, dried over anhydrous sodium sulfate, filtered, and concentrated under reduced pressure to yield 200 mg (79%) of N-hydroxyoxy-4-carbonimidoyl chloride 23c as a colorless oil.

Step 3. Ethyl 5-cyclopropyl-3-(oxan-4-yl)-1,2-oxazole-4-carboxylate (23d)

To a 250-mL round-bottom flask containing ethyl 3-cyclopropyl-3-oxopropanoate 1d (3.44 g, 22.03 mmol, 1.50 equiv.) and tetrahydrofuran (30 mL) was added potassium tert-butoxide (2.47 g, 22.01 mmol, 1.50 equiv.) and the reaction mixture was stirred for 20 min at room temperature. A solution of N-hydroxyoxy-4-carbonimidoyl chloride 23c (2.4 g, 14.67 mmol, 1.0 equiv.) in tetrahydrofuran (20 mL) was then added dropwise at 0° C., and the resulting mixture was stirred at room temperature for 3 h. The mixture was diluted with 100 mL of ethyl acetate and the organic extract was washed with brine (100 mL) and concentrated under reduced pressure. The resulting solid was dried in an oven under reduced pressure to afford 3 g (77%) of ethyl 5-cyclopropyl-3-(oxan-4-yl)-1,2-oxazole-4-carboxylate 23d as a crude yellow oil. The crude product was carried onto the next step without further purification.

Step 4. [5-cyclopropyl-3-(oxan-4-yl)-1,2-oxazol-4-yl]methanol (23e)

To a 50-mL round-bottom flask containing a solution of ethyl 5-cyclopropyl-3-(oxan-4-yl)-1,2-oxazole-4-carboxylate 23d (240 mg, 0.90 mmol, 1.0 equiv) in tetrahydrofuran (4 mL) at 0° C., was added $LiAlH_4$ (68.8 mg, 1.81 mmol, 2.0 equiv.) the resulting mixture was stirred for 2 h at 0° C. The reaction was quenched by the addition of water/ice and diluted with 10 mL of ethyl acetate. The organic extract was washed with brine (30 mL×2) and the combined aqueous washings were back extracted with ethyl acetate (30 mL×2). The combined organic extracts were concentrated under reduced pressure to a residue, which was purified by silica gel column chromatography eluting with ethyl acetate/petroleum ether (1:1) to afford 65 mg (32%) of [5-cyclopropyl-3-(oxan-4-yl)-1,2-oxazol-4-yl]methanol 23e as a light yellow oil.

Step 5. 4-(chloromethyl)-5-cyclopropyl-3-(oxan-4-yl)-1,2-oxazole (23f)

To a 100-mL round-bottom flask containing a solution of 1H-1,2,3-benzotriazole (533.6 mg, 4.48 mmol, 2.0 equiv.) in dichloromethane (10 mL) was added thionyl chloride (533.6 mg, 4.49 mmol, 2.0 equiv.) dropwise at 0° C., followed by a solution of [5-cyclopropyl-3-(oxan-4-yl)-1,2-oxazol-4-yl] methanol 23e (500 mg, 2.24 mmol, 1.0 equiv.) in dichloromethane (2 mL). The resulting mixture was stirred at room temperature for 2 h, and then diluted with 10 mL of dichloromethane. $H_2O$ was added, the aqueous mixture was extracted with 50 mL of dichloromethane. The combined organic extracts were washed with brine (100 mL×2), dried over anhydrous sodium sulfate, filtered, and concentrated under reduced pressure. The residue was purified by silica gel column chromatography eluting with ethyl acetate/petroleum ether (5:1) to give 394 mg (73%) of 4-(chloromethyl)-5-cyclopropyl-3-(oxan-4-yl)-1,2-oxazole 23f as a yellow oil.

Step 6. Benzyl (1S,4S,5R)-5-[[5-cyclopropyl-3-(oxan-4-yl)-1,2-oxazol-4-yl]methoxy]-2-azabicyclo[2.2.1]heptane-2-carboxylate (23g)

To a 100-mL round-bottom flask containing benzyl (1S,4S,5R)-5-hydroxy-2-azabicyclo[2.2.1]heptane-2-carboxylate C-1 (350 mg, 1.42 mmol, 1.0 equiv.), N,N-dimethylformamide (15 mL), and 4-(chloromethyl)-5-cyclopropyl-3-(oxan-4-yl)-1,2-oxazole 23f (376 mg, 1.56 mmol, 1.10 equiv.) was added sodium hydride (113 mg, 4.71 mmol, 2.0 equiv., 60% in mineral oil) batchwise at 0° C. The resulting mixture was stirred at room temperature for 1 h, and then quenched by the addition of water/ice. The aqueous mixture was diluted with 20 mL of ethyl acetate, and further extracted with ethyl acetate (50 mL×2). The combined organic extracts were washed with brine (100 mL×2), dried over anhydrous sodium sulfate, filtered, and concentrated under reduced pressure. The residue was purified by silica gel column chromatography eluting with ethyl acetate/petroleum ether (1:3) to give 400 mg (62%) of benzyl (1S,4S,5R)-5-[[5-cyclopropyl-3-(oxan-4-yl)-1,2-oxazol-4-yl] methoxy]-2-azabicyclo[2.2.1]heptane-2-carboxylate 23g as a yellow oil.

Step 7. (1S,4S,5R)-5-[[5-cyclopropyl-3-(oxan-4-yl)-1,2-oxazol-4-yl]methoxy]-2-azabicyclo[2.2.1]heptane (23h)

To a 50-mL round-bottom flask was added benzyl (1S,4S,5R)-5-[[5-cyclopropyl-3-(oxan-4-yl)-1,2-oxazol-4-yl] methoxy]-2-azabicyclo[2.2.1]heptane-2-carboxylate 23g (270 mg, 0.60 mmol, 1.0 equiv.), dichloromethane (10 mL), and iodotrimethylsilane (600 mg, 3.00 mmol, 5.03 equiv.). The resulting mixture was stirred at room temperature for 30 min, and then quenched with 10 mL of water. The aqueous mixture was extracted with dichloromethane (100 mL×2) and the combined organic extracts were washed with brine (100 mL×2), dried over anhydrous sodium sulfate, filtered, and concentrated under reduced pressure. The residue was purified by silica gel column chromatography eluting with dichloromethane/methanol (15:1) to provide 120 mg (63%)

of (1S,4S,5R)-5-[[5-cyclopropyl-3-(oxan-4-yl)-1,2-oxazol-4-yl]methoxy]-2-azabicyclo[2.2.1]heptane 23h as a colorless oil.

Step 8. Methyl 2-[(1S,4S,5R)-5-[[5-cyclopropyl-3-(oxan-4-yl)-1,2-oxazol-4-yl]methoxy]-2-azabicyclo[2.2.1]heptan-2-yl]-4-(trifluoromethoxy)-1,3-benzothiazole-6-carboxylate (23i)

To a 50-mL round-bottom flask was added (1S,4S,5R)-5-[[5-cyclopropyl-3-(oxan-4-yl)-1,2-oxazol-4-yl]methoxy]-2-azabicyclo[2.2.1]heptane 23h (105 mg, 0.33 mmol, 1.0 equiv.), DMA (3 mL), $Cs_2CO_3$ (323 mg, 0.99 mmol, 3.0 equiv.), and methyl 2-bromo-4-(trifluoromethoxy)-1,3-benzothiazole-6-carboxylate A-4 (1.2 mg, 1.20 equiv.) and the resulting mixture was stirred at 60° C., overnight. The mixture was diluted with of ethyl acetate and washed with brine (50 mL×2). The organic extract was dried over anhydrous sodium sulfate, filtered, and concentrated under reduced pressure. The residue was purified by silica gel column chromatography eluting with ethyl acetate/petroleum ether (1:1) to afford 60 mg (31%) of methyl 2-[(1S,4S,5R)-5-[[5-cyclopropyl-3-(oxan-4-yl)-1,2-oxazol-4-yl]methoxy]-2-azabicyclo[2.2.1]heptan-2-yl]-4-(trifluoromethoxy)-1,3-benzothiazole-6-carboxylate 23i as a yellow oil.

Step 9. 2-[(1S,4S,5R)-5-[[5-cyclopropyl-3-(oxan-4-yl)-1,2-oxazol-4-yl]methoxy]-2-azabicyclo[2.2.1]heptan-2-yl]-4-(trifluoromethoxy)-1,3-benzothiazole-6-carboxylic Acid (I-23)

To a 50-mL round-bottom flask was added a solution of methyl 2-[(1S,4S,5R)-5-[[5-cyclopropyl-3-(oxan-4-yl)-1,2-oxazol-4-yl]methoxy]-2-azabicyclo[2.2.1]heptan-2-yl]-4-(trifluoromethoxy)-1,3-benzothiazole-6-carboxylate 23i (70 mg, 0.12 mmol, 1.0 equiv.) in tetrahydrofuran (0.5 mL), methanol (1 mL), water (0.5 mL), and LiOH (49.5 mg, 2.07 mmol, 10.0 equiv.). The resulting mixture was stirred at 25° C., overnight, and then diluted with 2 mL of $H_2O$. The pH of the aqueous mixture was adjusted to 2 using aqueous HCl (1M). The aqueous mixture was extracted with ethyl acetate (50 mL) and the organic extract was washed with brine (50 mL), dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, Water (0.05% TFA) and ACN (50.0% 70.0% over 8 min); Detector, UV 254 nm, to provide 36.6 mg (54%) of 2-[(1S,4S,5R)-5-[[5-cyclopropyl-3-(oxan-4-yl)-1,2-oxazol-4-yl]methoxy]-2-azabicyclo[2.2.1]heptan-2-yl]-4-(trifluoromethoxy)-1,3-benzothiazole-6-carboxylic acid I-23 as a colorless solid. $^1H$ NMR (400 MHz, $CD_3OD$) δ: 8.13 (q, J=1.7 Hz, 1H), 7.87 (d, J=7.5 Hz, 1H), 7.79-7.62 (m, 3H), 7.56-7.49 (m, 1H), 4.36-4.22 (m, 2H), 3.65 (d, J=6.2 Hz, 1H), 3.51 (d, J=8.6 Hz, 1H), 3.03 (s, 1H), 2.64 (s, 1H), 2.25 (p, J=7.1 Hz, 1H), 2.04 (dd, J=13.7, 6.8 Hz, 1H), 1.70 (s, 2H), 1.45 (d, J=13.9 Hz, 1H), 1.21-1.13 (m, 4H). MS (ES, m/z): [M+1]=580.15.

Example 30: 2-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-4-fluoro-1,3-benzothiazole-6-carboxylic Acid (I-24)

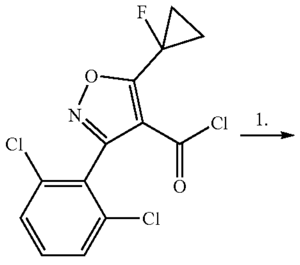

10g

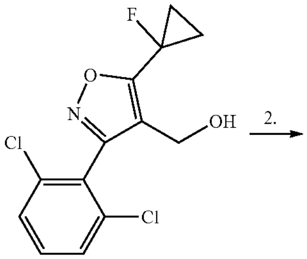

24a

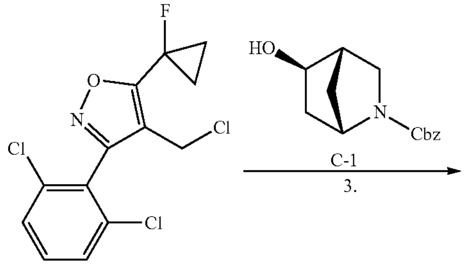

24b

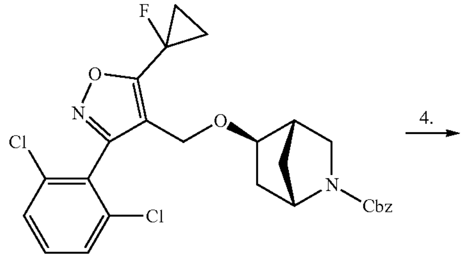

24c

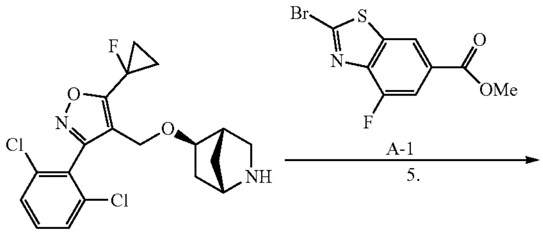

24d

-continued

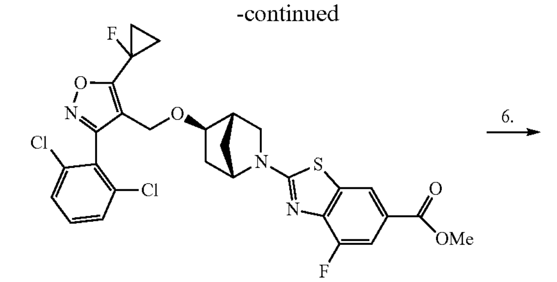

24e

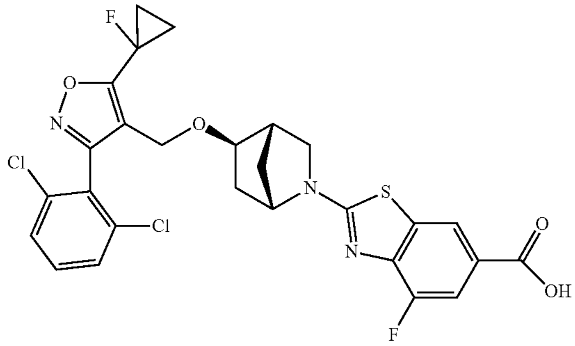

I-24

Step 1. [3-(2,6-dichlorophenyl)-5-(1-fluorocyclopropyl)-1,2-oxazol-4-yl]methanol (24a)

To a 100-mL round-bottom flask containing a solution of 3-(2,6-dichlorophenyl)-5-(1-fluorocyclopropyl)-1,2-oxazole-4-carbonyl chloride 10g (900 mg, 2.69 mmol, 1.0 equiv.) in tetrahydrofuran (15 mL) was added $NaBH_4$ (307 mg, 8.12 mmol, 3.0 equiv) batchwise at 0° C. The resulting mixture was stirred at room temperature for 6 h, and then quenched by the addition of methanol. The mixture was concentrated under reduced pressure and the resulting residue was purified by silica gel column chromatography eluting with ethyl acetate/petroleum ether (1/4) to give 650 mg (81%) of [3-(2,6-dichlorophenyl)-5-(1-fluorocyclopropyl)-1,2-oxazol-4-yl]methanol 24a as a colorless oil.

Step 2. 4-(chloromethyl)-3-(2,6-dichlorophenyl)-5-(1-fluorocyclopropyl)-1,2-oxazole (24b)

To a 50-mL round-bottom flask containing a solution of benzotriazole (198 mg, 1.0 equiv.) in dichloromethane (5 mL) was added thionyl chloride (392 mg, 2.0 equiv.) at 0° C., and the resulting mixture was stirred 0° C., for 30 min. A solution of [3-(2,6-dichlorophenyl)-5-(1-fluorocyclopropyl)-1,2-oxazol-4-yl]methanol 24a (500 mg, 1.65 mmol, 1.0 equiv.) in dichloromethane (2 mL) was then added and the resulting mixture was stirred at room temperature overnight. The reaction was quenched by the addition of water/ice and the resulting aqueous mixture was extracted with ethyl acetate (100 mL×2). The combined organic extracts were washed with brine (100 mL×3), dried over anhydrous sodium sulfate, filtered, and concentrated under reduced pressure. The residue was purified by silica gel column chromatography eluting with ethyl acetate/petroleum ether (1/5) to afford 450 mg (85%) of 4-(chloromethyl)-3-(2,6-dichlorophenyl)-5-(1-fluorocyclopropyl)-1,2-oxazole 24b as an off-white solid.

Step 3. Benzyl (1S,4S,5R)-5-[[3-(2,6-dichlorophenyl)-5-(1-fluorocyclopropyl)-1,2-oxazol-4-yl]methoxy]-2-azabicyclo[2.2.1]heptane-2-carboxylate (24c)

To a 25-mL round-bottom flask containing 4-(chloromethyl)-3-(2,6-dichlorophenyl)-5-(1-fluorocyclopropyl)-1,2-oxazole 24b (110 mg, 0.34 mmol, 1.0 equiv), benzyl (1S,4S,5R)-5-hydroxy-2-azabicyclo[2.2.1]heptane-2-carboxylate C-1 (86 mg, 0.35 mmol, 1.0 equiv.), and N,N-dimethylformamide (5 mL) was added sodium hydride (30 mg, 1.25 mmol, 2.0 equiv., 60% in mineral oil) batchwise at 0° C. The resulting mixture was stirred at room temperature for 2 h and then quenched by the addition of 5 mL of water/ice. The aqueous mixture was extracted with 200 mL of ethyl acetate and the organic extract was washed with brine (30 mL×4), dried over anhydrous sodium sulfate, filtered, and concentrated under reduced pressure. The residue was purified by silica gel column chromatography eluting with ethyl acetate/petroleum ether (1:5) to provide 100 mg (55%) of benzyl (1S,4S,5R)-5-[[3-(2,6-dichlorophenyl)-5-(1-fluorocyclopropyl)-1,2-oxazol-4-yl]methoxy]-2-azabicyclo[2.2.1]heptane-2-carboxylate 24c a as light yellow oil.

Step 4. (1S,4S,5R)-5-[[3-(2,6-dichlorophenyl)-5-(1-fluorocyclopropyl)-1,2-oxazol-4-yl]methoxy]-2-azabicyclo[2.2.1]heptane (24d)

To a 25-mL round-bottom flask purged and maintained under an inert atmosphere of nitrogen was added benzyl (1S,4S,5R)-5-[[3-(2,6-dichlorophenyl)-5-(1-fluorocyclopropyl)-1,2-oxazol-4-yl]methoxy]-2-azabicyclo[2.2.1]heptane-2-carboxylate 24c (100 mg, 0.19 mmol, 1.0 equiv.), dichloromethane (1 mL), and TMSI (188 mg, 0.94 mmol, 5.0 equiv.). The resulting mixture was stirred at room temperature for 10 min and then quenched by the addition of 1 mL of dimethylamine. The mixture was concentrated under reduced pressure and the resulting residue was purified by silica gel column chromatography eluting with dichloromethane/methanol (15:1) to give 50 mg (67%) of (1S,4S,5R)-5-[[3-(2,6-dichlorophenyl)-5-(1-fluorocyclopropyl)-1,2-oxazol-4-yl]methoxy]-2-azabicyclo[2.2.1]heptane 24d as a light yellow oil.

Step 5. Methyl 2-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-4-fluoro-1,3-benzothiazole-6-carboxylate (24e)

To a 25-mL round-bottom flask purged and maintained under an inert atmosphere of nitrogen was added (1S,4S,5R)-5-[[3-(2,6-dichlorophenyl)-5-(1-fluorocyclopropyl)-1,2-oxazol-4-yl]methoxy]-2-azabicyclo[2.2.1]heptane 24d (40 mg, 0.10 mmol, 1.0 equiv.), $Cs_2CO_3$ (65 mg, 0.20 mmol, 2.0 equiv.), methyl 2-bromo-4-fluoro-1,3-benzothiazole-6-carboxylate A-1 (35 mg, 0.12 mmol, 1.20 equiv.), and DMA (1 mL) and the resulting mixture was stirred at 60° C., for 6 h. $H_2O$ was added and the aqueous mixture was extracted with ethyl acetate (200 mL). The organic extract was washed with brine (30 mL×4), dried over anhydrous sodium sulfate, filtered, and concentrated under reduced pressure. The residue was purified by silica gel column chromatography eluting with ethyl acetate/petroleum ether (1:5) to yield 40 mg (66%) of methyl 2-[(1S,4S,5R)-5-[[3-(2,6-dichlorophenyl)-5-(1-fluorocyclopropyl)-1,2-oxazol-4-yl]methoxy]-2- azabicyclo[2.2.1]heptan-2-yl]-4-fluoro-1,3-benzothiazole-6-carboxylate 24e as a light yellow oil.

Step 6. 2-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-4-fluoro-1,3-benzothiazole-6-carboxylic Acid (I-24)

To a 25-mL round-bottom flask purged and maintained under an inert atmosphere of nitrogen was added methyl 2-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-4-fluoro-1,3-benzothiazole-6-carboxylate 24e (40 mg, 0.07 mmol, 1.0 equiv.). LiI (88 mg, 0.66 mmol, 10.0 equiv.), and pyridine (1 mL) and the resulting mixture was stirred at 120° C., overnight. $H_2O$ was then added at room temperature and the aqueous mixture was extracted with ethyl acetate (50 mL×3). The combined organic extracts were washed with brine (30 mL×3), dried over anhydrous sodium sulfate, filtered, and concentrated under reduced pressure. The crude product was purified by Prep-HPLC using the following conditions: Column, XBridge C18 OBD Prep Column 5 μm, 19 mm×250 mm; mobile phase, water (0.05% TFA) and ACN (60.0% to 80.0% over 8 min); Detector, UV 254 nm, to provide 9.5 mg (24%) of 2-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-4-fluoro-1,3-benzothiazole-6-carboxylic acid I-24 was obtained as an off-white solid. $^1$H NMR (300 MHz, DMSO-$d_6$) δ: 8.21 (d, J=1.5 Hz, 1H), 7.75-7.53 (m, 4H), 4.51-4.28 (m, 2H), 3.69-3.59 (m, 3H), 2.95 (d, J=10.3 Hz, 1H), 1.96-1.83 (m, 1H), 1.80-1.51 (m, 3H), 1.54-1.36 (m, 3H), 1.35-1.17 (m, 2H). MS (ES, m/z): [M+1]=592.20.

Example 31: 2-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-4-(trifluoromethoxy)-1,3-benzothiazole-6-carboxylic Acid (I-25)

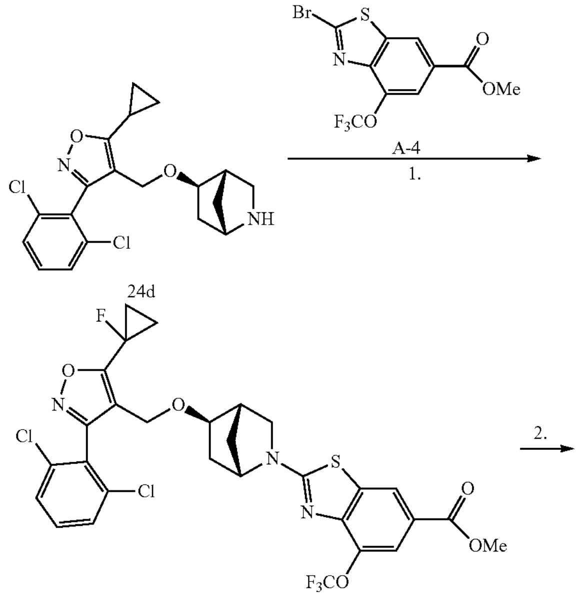

24d

25a

-continued

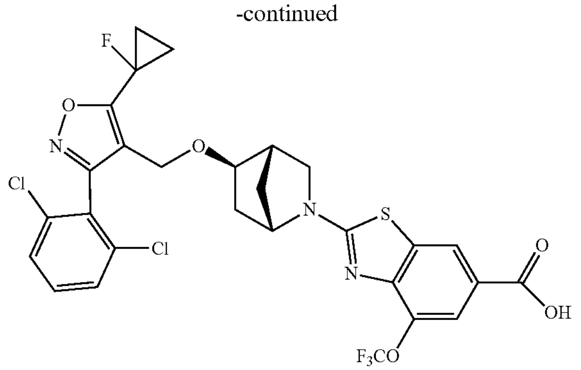

I-25

Step 1. Methyl 2-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-4-(trifluoromethoxy)-1,3-benzothiazole-6-carboxylate (25a)

To a 50-mL round-bottom flask purged and maintained under an inert atmosphere of nitrogen was added (1S,4S,5R)-5-[[3-(2,6-dichlorophenyl)-5-(1-fluorocyclopropyl)-1,2-oxazol-4-yl]methoxy]-2-azabicyclo[2.2.1]heptane 24d (50 mg, 0.13 mmol, 1.0 equiv.), DMA (2 mL), methyl 2-bromo-4-(trifluoromethoxy)-1,3-benzothiazole-6-carboxylate A-4 (54 mg, 0.15 mmol, 1.20 equiv.), and $Cs_2CO_3$ (82 mg, 0.25 mmol, 2.0 equiv.) and the resulting mixture was stirred at 60° C., overnight. After cooling to room temperature, 20 mL water was added, and the aqueous mixture was extracted with 100 mL of ethyl acetate. The organic layer was washed with brine (20 mL×2), dried over anhydrous sodium sulfate, filtered, and concentrated under reduced pressure. The resulting residue was purified by silica gel column chromatography eluting with ethyl acetate/petroleum ether (1:3) to give 30 mg (35%) of methyl 2-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-4-(trifluoromethoxy)-1,3-benzothiazole-6-carboxylate 25a as a light yellow oil.

Step 2. 2-[(1S,4S,5R)-5-[[5-(2,6-dichlorophenyl)-3-(1-fluorocyclopropyl)-2H-pyrrol-4-yl]methoxy]-2-azabicyclo[2.2.1]heptan-2-yl]-4-(trifluoromethoxy)-1,3-benzothiazole-6-carboxylic Acid (I-25)

To a 50-mL round-bottom flask purged and maintained under an inert atmosphere of nitrogen was added methyl 2-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-4-(trifluoromethoxy)-1,3-benzothiazole-6-carboxylate 25a (30 mg, 0.04 mmol, 1.0 equiv.), pyridine (2 mL), and LiI (60 mg, 10.0 equiv.). The resulting mixture was stirred at 120° C., overnight and concentrated under reduced pressure. The residue was suspended in 100 mL water, and extracted with ethyl acetate (100 mL×2). The combined organic extracts were washed with brine (50 mL×3), dried over anhydrous sodium sulfate, filtered, and concentrated under reduced pressure. The resulting residue was purified by Prep-HPLC using the following conditions: Column, XBridge C18 OBD Prep Column: 5 μm, 19 mm×250 mm; mobile phase, water (0.05% TFA) and ACN (75.0% to 85.0% over 7 min); Detector, UV 254 nm, to provide 19.3 mg (66%) of 2-[(1S,4S,5R)-5-[[5-(2,6-dichlorophenyl)-3-

(1-fluorocyclopropyl)-2H-pyrrol-4-yl]methoxy]-2-azabicyclo[2.2.1]heptan-2-yl]-4-(trifluoromethoxy)-1,3-benzothiazole-6-carboxylic acid I-25 was obtained as an off-white solid. $^1$H NMR (300 MHz, DMSO-$d_6$) δ: 8.36 (d, J=1.6 Hz, 1H), 7.73-7.53 (m, 5H), 4.43-4.26 (m, 3H), 3.61 (d, J=6.3 Hz, 1H), 2.93 (s, 1H), 2.40 (s, 3H), 1.87 (dd, J=13.7, 6.7 Hz, 1H), 1.75-1.53 (m, 4H), 1.48-1.33 (m, 4H), 1.27-1.16 (m, 2H). MS (ES, m/z): [M+1]=658.4.

Example 32: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-6-(2H-1,2,3,4-tetrazol-5-yl)-1,3-benzothiazole (I-26)

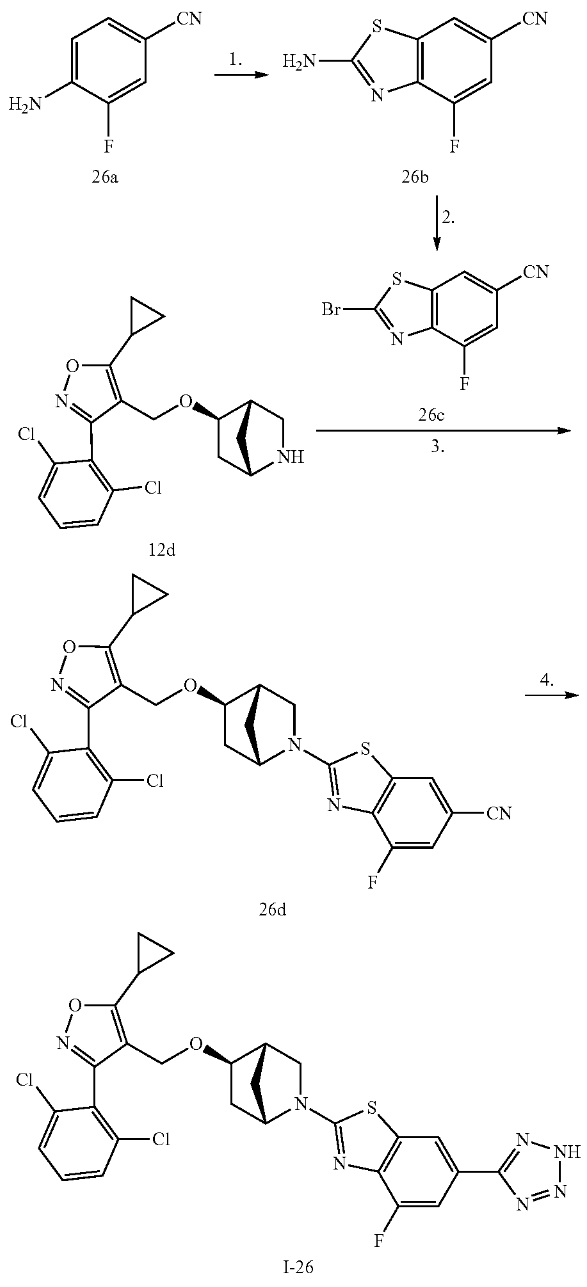

26a 26b 26c 12d 26d I-26

Step 1. 2-amino-4-fluoro-1,3-benzothiazole-6-carbonitrile (26b)

To a 250 mL round-bottom flask was added 4-amino-3-fluorobenzonitrile 26a (650 mg, 4.77 mmol, 1.0 equiv.), AcOH (50 mL), NaSCN (1.548 g, 4.0 equiv), and $Br_2$ (1.132 g, 7.08 mmol, 1.50 equiv) and the resulting mixture was stirred at 30° C., for 16 h. 100 mL of water was then added and the pH of the mixture was adjusted to 10 using sodium hydroxide. The solids were collected by filtration and further dried in an oven under reduced pressure to give 600 mg (65%) of 2-amino-4-fluoro-1,3-benzothiazole-6-carbonitrile 26b as a yellow solid. The crude product was carried onto the next step without further purification.

Step 2. 2-bromo-4-fluoro-1,3-benzothiazole-6-carbonitrile (26c)

To a 100-mL round-bottom flask was added 2-amino-4-fluoro-1,3-benzothiazole-6-carbonitrile 26b (600 mg, 3.11 mmol, 1.0 equiv.), MeCN (20 mL), $CuBr_2$ (1.03 g, 1.50 equiv), and t-BuONO (920 mg, 2.26 equiv.). The resulting mixture was stirred for at 30° C., for 3 days and then concentrated under reduced pressure. The resulting residue was purified by silica gel column chromatography eluting with ethyl acetate/petroleum ether (1:10) to give 150 mg (19%) of 2-bromo-4-fluoro-1,3-benzothiazole-6-carbonitrile 26c as a colorless solid.

Step 3. 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carbonitrile (26d)

To a 100-mL round-bottom flask was added 2-bromo-4-fluoro-1,3-benzothiazole-6-carbonitrile 26c (150 mg, 0.58 mmol, 1.0 equiv.), DMA (10 mL), (1S,4S,5R)-5-[[5-cyclopropyl-3-(2,6-dichlorophenyl)-1,2-oxazol-4-yl]methoxy]-2-azabicyclo[2.2.1]heptane 12d (122 mg, 0.32 mmol, 1.20 equiv.), and $Cs_2CO_3$ (388 mg, 1.19 mmol, 3.0 equiv.) and the resulting mixture was stirred at 60° C., for 16 h. The reaction was then quenched by the addition of 100 mL of ice/salt and the aqueous mixture was extracted with ethyl acetate (100 mL×3). The combined organic extracts were washed with brine (100 mL×3), dried over anhydrous sodium sulfate, filtered, and concentrated. The resulting residue was purified by silica gel column chromatography eluting with ethyl acetate/petroleum ether (1:5) to provide 210 mg (65%) of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carbonitrile 26d as a colorless solid.

Step 4. 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-6-(2H-1,2,3,4-tetrazol-5-yl)-1,3-benzothiazole (I-26)

To a 50-mL round-bottom flask was added 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carbonitrile 26d (100 mg, 0.18 mmol, 1.0 equiv.), m-xylene (5 mL), and n-$Bu_3SnN_3$ (101 mg, 1.40 equiv.) and the resulting mixture was stirred at 140° C., for 16 h. After cooling to room temperature, 50 mL of ice/salt was added and the aqueous mixture was extracted with ethyl acetate (50 mL×3). The combined organic extracts were washed with brine (150 mL×2), dried over anhydrous sodium sulfate, filtered, and concentrated under reduced pressure. The resulting residue was dissolved in 3 mL of DMF and purified by Prep-HPLC using the following conditions: Column, XSelect CSH Prep C18 OBD Column, 5 um, 19×150 mm; mobile phase, water (0.05% TFA) and ACN (52.0% to 70.0% over 8 min); Detector. UV 254 nm to provide 27.8 mg (26%) of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-6-(2H-1,2,3,4-tetrazol-5-yl)-1,3-benzothiazole I-26 as a colorless solid. $^1$H NMR (300 MHz, DMSO-$d_6$) δ: 8.31 (d, J=1.6 Hz, 1H), 7.81-7.53 (m, 4H), 4.37-4.21 (m, 1H), 3.63 (d, J=5.9 Hz, 1H), 3.46 (dd, J=10.0, 3.9 Hz, 1H), 2.98 (s, 1H), 2.61-2.52 (m, 1H), 2.36 (tt, J=8.3, 4.0 Hz, 1H), 1.99-1.85 (m, 1H), 1.62 (d, J=9.7 Hz, 1H), 1.50 (d, J=10.1 Hz, 2H), 1.39-1.05 (m, 6H), 0.89 (t, J=7.3 Hz, 1H). MS (ES, m/z): [M+1]=598.15.

Example 33: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-trifluoromethoxy-6-(2H-1,2,3,4-tetrazol-5-yl)-1,3-benzothiazole (I-27)

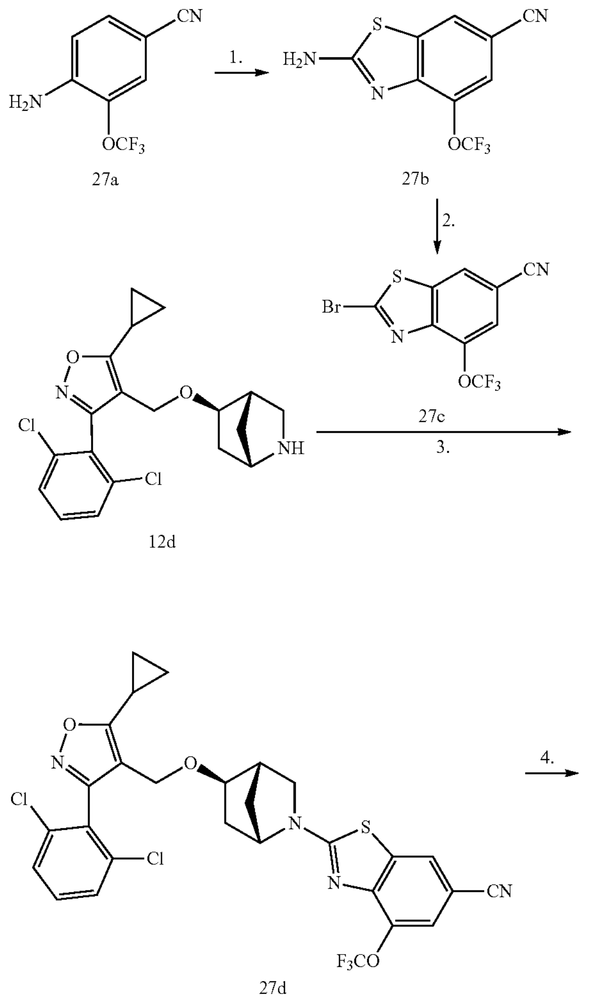

27a
27b
27c
12d
27d

-continued

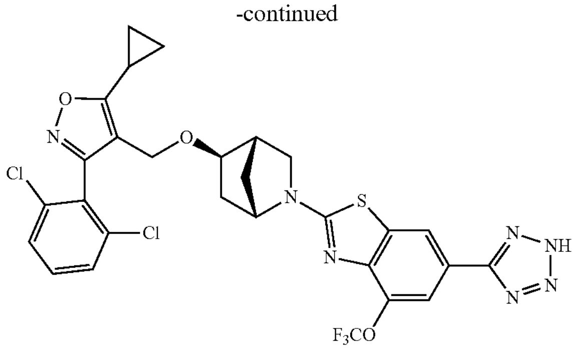

I-27

Step 1. 2-amino-4-(trifluoromethoxy)-1,3-benzothiazole-6-carbonitrile (27b)

To a 1000 mL 3-necked round-bottom flask containing 4-amino-3-(trifluoromethoxy) benzonitrile 27a (10 g, 49.47 mmol, 1.0 equiv.), AcOH (180 mL), and KSCN (5 g, 1.0 equiv.) was added a solution of $Br_2$ (3 mL, 1.15 equiv.) in AcOH dropwise with stirring at 13° C. The resulting mixture was stirred at room temperature overnight, and then quenched by the addition of 200 mL of water/ice. The pH of the solution was adjusted to 9 using sodium hydroxide. The solids were collected by filtration to give 2.5 g (19%) of 2-amino-4-(trifluoromethoxy)-1,3-benzothiazole-6-carbonitrile 27b as a yellow solid. The crude product was carried onto the next step without further purification.

Step 2. 2-bromo-4-(trifluoromethoxy)-1,3-benzothiazole-6-carbonitrile (27c)

To a 250-mL round-bottom flask was added 2-amino-4-(trifluoromethoxy)-1,3-benzothiazole-6-carbonitrile 27b (2.5 g, 9.64 mmol, 1.0 equiv.), $CH_3CN$ (50 mL), $CuBr_2$ (3.231 g, 1.50 equiv.), and t-BuONO (2.6 mL, 2.26 equiv). The resulting mixture was stirred at 30° C., overnight and then concentrated under reduced pressure. The resulting residue was purified by silica gel column chromatography eluting with ethyl acetate/petroleum ether (0%-5%) to give 400 mg (13%) of 2-bromo-4-(trifluoromethoxy)-1,3-benzothiazole-6-carbonitrile 27c as a yellow solid.

Step 3. 2-[(1S,4S,5R)-5-[[5-cyclopropyl-3-(2,6-dichlorophenyl)-2-oxazol-4-yl]methoxy]-2-azabicyclo[2.2.1]heptan-2-yl]-4-(trifluoromethoxy)-1,3-benzothiazole-6-carbonitrile (27d)

To a 100-mL round-bottom flask was added 2-bromo-4-(trifluoromethoxy)-1,3-benzothiazole-6-carbonitrile 27c (112 mg, 0.35 mmol, 1.10 equiv.), (1S,4S,5R)-5-[[5-cyclopropyl-3-(2,6-dichlorophenyl)-1,2-oxazol-4-yl]methoxy]-2-azabicyclo[2.2.1]heptane 12d (120 mg, 0.32 mmol, 1.0 equiv), DMA (10 mL), and $Cs_2CO_3$ (206 mg, 0.63 mmol, 2.0 equiv) and the resulting mixture was stirred at 60° C., overnight. $H_2O$ was then added and the aqueous mixture was extracted with ethyl acetate (50 mL×4). The combined organic extracts were dried with anhydrous sodium sulfate, filtered, and concentrated under reduced pressure. The residue was purified by silica gel column chromatography eluting with ethyl acetate/petroleum ether (1:2) to afford 180 mg (92%) of 2-[(1S,4S,5R)-5-[[5-cyclopropyl-3-(2,6-dichlorophenyl)-1,2-oxazol-4-yl]methoxy]-2-azabicyclo

[2.2.1]heptan-2-yl]-4-(trifluoromethoxy)-1,3-benzothiazole-6-carbonitrile 27d as a white solid.

Step 4. 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-6-(2H-1,2,3,4-tetrazol-5-yl)-4-(trifluoromethoxy)-1,3-benzothiazole (I-27)

To a 50-mL round-bottom flask was added 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(trifluoromethoxy)-1,3-benzothiazole-6-carbonitrile 27d (180 mg, 0.29 mmol, 1.0 equiv.), m-xylene (10 mL), and n-$Bu_3SnN_3$ (0.16 mL, 2.0 equiv) and the resulting mixture was stirred at 140° C., overnight. The mixture was cooled to room temperature and 50 mL water was added. The aqueous mixture was extracted with ethyl acetate (50 mL×4) and the combined organic extracts were concentrated under reduced pressure. The resulting crude product was purified by Prep-HPLC using the following conditions: Column, XSelect CSH Prep C18 OBD Column, 5 um, 19×150 mm; mobile phase, water (0.05% TFA) and ACN (63.0% to 78.0% over 8 min); Detector, UV 254 nm, to provide 28 mg (15%) of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-6-(2H-1,2,3,4-tetrazol-5-yl)-4-(trifluoromethoxy)-1,3-benzothiazole I-27 as a light yellow solid. $^1H$ NMR (400 MHz, DMSO-$d_6$) δ: 8.46 (d, J=1.6 Hz, 1H), 7.88 (s, 1H), 7.51-7.68 (m, 3H), 4.26 (d, J=2.3 Hz, 2H), 2.54 (d, J=3.9 Hz, 2H), 2.34 (dt, J=8.5, 5.1 Hz, 1H), 1.84-1.94 (m, 1H), 1.58 (q. J=9.4, 8.6 Hz, 2H), 1.48 (t, J=9.4 Hz, 1H), 1.19-1.38 (m, 3H), 1.03-1.18 (m, 4H), 0.86 (td, J=7.3, 5.7 Hz, 1H). MS (ES, m/z): [M+1]=665.0.

Example 34: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-N-methanesulfonyl-1,3-benzothiazole-6-carboxamide (I-28)

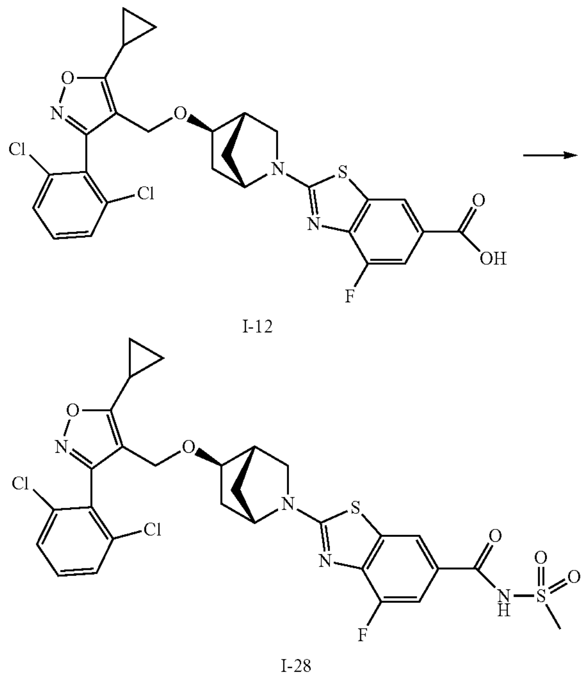

I-12

I-28

To a 25 mL round-bottom flask purged and maintained under an inert atmosphere of nitrogen containing a solution of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylic acid I-12 (200 mg, 0.35 mmol, 1.0 equiv.) in N,N-dimethylformamide (3 mL) was added methanesulfonamide (40 mg, 0.42 mmol, 1.20 equiv.) and EDCI (100 mg, 0.52 mmol, 1.50 equiv.), followed by 4-dimethylaminopyridine (64 mg, 0.52 mmol, 1.50 equiv.). The resulting mixture was stirred at room temperature overnight and then concentrated under reduced pressure. The crude product was purified by Prep-HPLC using the following conditions: Column, XBridge C18 OBD Prep Column, 19 mm×250 mm; mobile phase, water (0.05% TFA) and ACN (60% to 75% over 10 min); Detector, UV 254 nm to provide 57 mg (25%) of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-N-methanesulfonyl-1,3-benzothiazole-6-carboxamide I-28 as an off-white solid. $^1H$ NMR (400 MHz, $CD_3OD$) δ: 8.07 (d, J=1.7 Hz, 1H), 7.69-7.46 (m, 5H), 4.42-4.30 (m, 4H), 3.67 (dd, J=6.9, 2.4 Hz, 1H), 3.52 (d, J=6.9 Hz, 1H), 3.38 (s, 3H), 3.04 (s, 2H), 2.63 (d, J=3.8 Hz, 1H), 2.29 (p, J=6.9 Hz, 1H), 2.01 (dd, J=13.6, 6.7 Hz, 1H), 1.70 (s, 2H), 1.42 (d, J=13.7 Hz; 1H), 1.19 (d, J=6.2 Hz, 4H). MS (ES, m/z): [M+1]=651.0.

Example 35: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-N-(propane-1-sulfonyl)-1,3-benzothiazole-6-carboxamide (I-29)

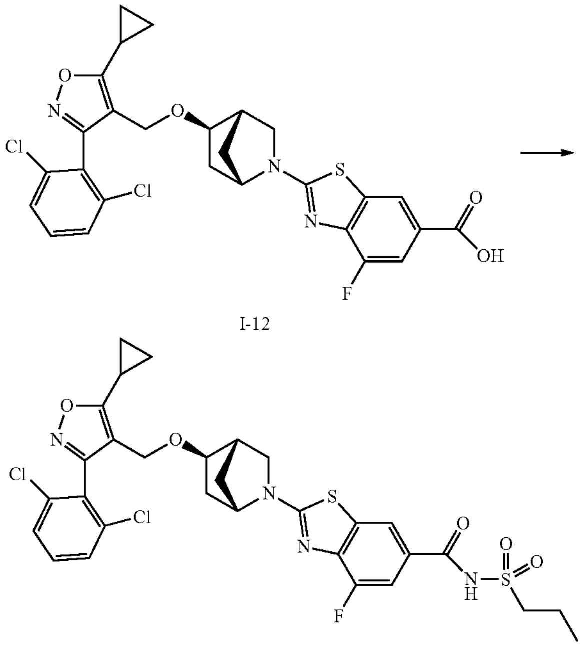

I-12

I-29

To a 50-mL round-bottom flask was added a solution of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylic acid I-12 (100 mg, 0.17 mmol, 1.0 equiv.) in N,N-dimethylformamide (2 mL), propane-1-sulfonamide (32 mg, 0.26 mmol, 1.50 equiv.), EDCI (50 mg, 0.26 mmol, 1.50 equiv.), and 4-dimethylaminopyridine (32 mg, 0.26 mmol, 1.50 equiv.) and the resulting mixture was stirred at room temperature overnight. The solids were filtered off and the filtrate was concentrated to provide crude product which was purified by Prep-HPLC using the following conditions: Column, XBridge C18 OBD Prep Column, 19 mm×250 mm; mobile phase, water (0.05% TFA) and ACN (66.0% to 80.0% over 8 min); Detector, UV 254 nm. Removal of solvents afforded 40.2 mg (34%) of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-N-(propane-1-sulfonyl)-1,3-benzothiazole-6-carboxamide I-29 as an off-white solid. $^1$H NMR (300 MHz, $CD_3OD$) δ: 8.08 (d, J=1.7 Hz, 1H), 7.70-7.44 (m, 4H), 4.91 (d, J=2.4 Hz, 1H), 4.36 (d, J=2.2 Hz, 2H), 3.72-3.63 (m, 1H), 3.57-3.48 (m, 2H), 3.04 (s, 1H), 2.64 (s, 1H), 2.29 (p, J=6.8 Hz; 1H), 2.09-1.78 (m, 3H), 1.70 (s, 2H), 1.42 (d, J=13.5 Hz, 1H), 1.24-1.04 (m, 7H). MS (ES, m/z): [M+1]=679.0.

Example 36: N-(cyclopropanesulfonyl)-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxamide (I-30)

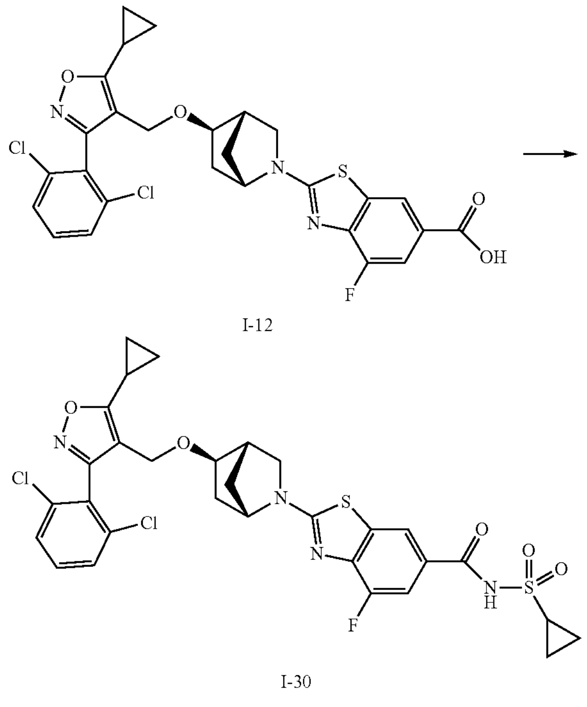

I-12

I-30

To a 50-mL round-bottom flask was added a solution of 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylic acid I-12 (100 mg, 0.17 mmol, 1.0 equiv) in N,N-dimethylformamide (2 mL), cyclopropanesulfonamide (32 mg, 0.26 mmol, 1.50 equiv.). EDCI (50 mg, 0.26 mmol, 1.50 equiv.), and 4-dimethylaminopyridine (32 mg, 0.26 mmol, 1.50 equiv.) and the resulting mixture was stirred at room temperature overnight. The solids were filtered off and the filtrate was concentrated to provide a crude product which was purified by Prep-HPLC with the following conditions: Column. XBridge C18 OBD Prep Column, 19 mm×250 mm; mobile phase, water (0.05% TFA) and ACN (55.0% to 78.0% over 8 min); Detector, UV 254 nm. After purification, 47.2 mg (40%) of N-(cyclopropanesulfonyl)-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxamide I-30 was obtained as an off-white solid. $^1$H NMR (300 MHz, $CD_3OD$) δ: 8.07 (d, J=1.6 Hz, 1H), 7.70-7.44 (m, 4H), 4.36 (d, J=2.1 Hz, 2H), 3.67 (dd, J=6.8, 2.4 Hz, 1H), 3.52 (dd, J=10.1, 4.0 Hz, 1H), 3.16 (tt, J=8.0, 4.8 Hz, 1H), 3.04 (s, 1H), 2.64 (s, 1H), 2.29 (p, J=6.8 Hz, 1H), 2.09-1.94 (m, 1H), 1.70 (s, 2H), 1.48-1.08 (m, 10H). MS (ES, m/z): [M+1]=677.0.

Example 37: (1S,4S,5R)-2-[4-fluoro-6-(methanesulfonylcarbamoyl)-1,3-benzothiazol-2-yl]-2-azabicyclo[2.2.1]heptan-5-yl 5-cyclopropyl-3-(2,6-dichlorophenyl)-1,2-oxazole-4-carboxylate (I-31)

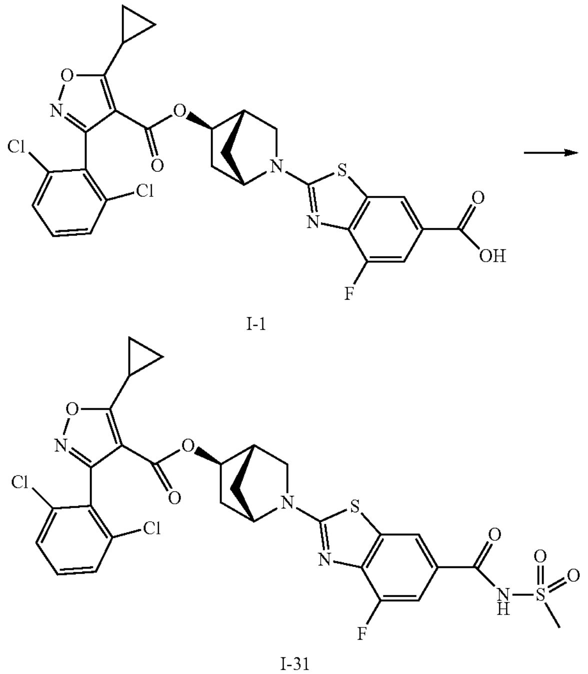

I-1

I-31

To a 25-mL round-bottom flask was added a solution of 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylic acid I-1 (200 mg, 0.34 mmol, 1.0 equiv.) in N,N-dimethylformamide (3 mL), methanesulfonamide (39 mg, 0.41 mmol, 1.20 equiv.), EDCI (98 mg, 0.51 mmol, 1.50 equiv.), and 4-dimethylaminopyridine (62 mg, 0.51 mmol, 1.50 equiv.) and the resulting mixture was stirred at room temperature overnight. The solids were filtered off and the filtrate was concentrated. The crude product was purified by Prep-HPLC using the following conditions: Column, XBridge C18 OBD Prep Column, 19 mm×250 mm; mobile phase, water (0.05% TFA) and ACN (58% to 90% over 10 min); Detector, UV 254 nm, to provide 34 mg (15%) of (1S,4S,5R)-2-[4-fluoro-6-(methanesulfonylcarbamoyl)-1,3-benzothiazol-2-yl]-2-azabicyclo[2.2.1]heptan-5-yl 5-cyclopropyl-3-(2,6-dichlorophenyl)-1,2-oxazole-4-carboxylate I-31 as an off-white solid. $^1$H NMR (400 MHz, $CD_3OD$) δ: 8.08 (d, J=1.7 Hz, 1H), 7.69-7.51 (m, 4H), 5.00 (d, J=6.7 Hz, 1H), 4.41 (s, 1H), 3.60-3.52 (m, 1H), 3.38 (s, 3H), 3.00 (p, J=6.8 Hz, 1H), 2.60 (s, 1H), 2.25 (ddd, J=14.2, 7.2, 2.7 Hz, 1H), 1.71 (d, J=10.5 Hz, 1H), 1.40-1.29 (m, 7H). MS (ES, m/z): [M+1]=665.0

Example 38: (1S,4S,5R)-2-{4-fluoro-6-[(propane-1-sulfonyl)carbamoyl]-1,3-benzothiazol-2-yl}-2-azabicyclo[2.2.1]heptan-5-yl 5-cyclopropyl-3-(2,6-dichlorophenyl)-1,2-oxazole-4-carboxylate (I-32)

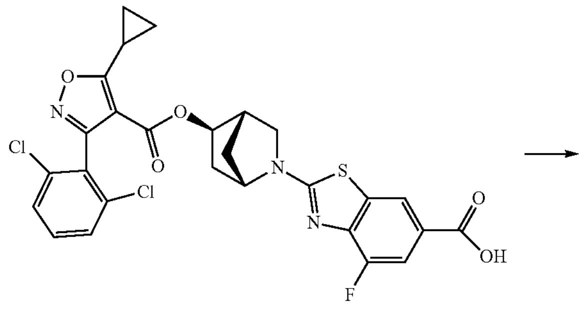

I-1

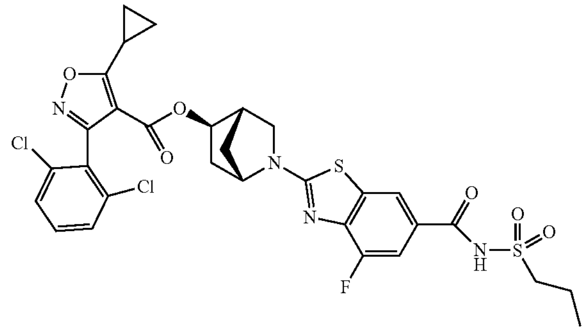

I-32

To a 100-mL round-bottom flask was added 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylic acid I-1 (150 mg, 0.25 mmol, 1.0 equiv), dichloromethane (15 mL), propane-1-sulfonamide (47 mg, 0.38 mmol, 1.5 equiv.), 4-dimethylaminopyridine (47 mg, 0.38 mmol, 1.5 equiv), and EDCI (73 mg, 0.38 mmol, 1.5 equiv) and the resulting mixture was stirred at room temperature for 16 h. 100 mL of brine was added and the aqueous mixture was extracted with dichloromethane (100 mL×5). The combined organic extracts were dried over anhydrous sodium sulfate, filtered, and concentrated under reduced pressure. The residue was dissolved in 2 mL of DMF and purified by Prep-HPLC using the following conditions: Column, XBridge C18 OBD Prep Column, 19 mm×250 mm; mobile phase, water (0.05% TFA) and ACN (68% to 84% over 8 min); Detector, UV 254 nm, to provide 48.9 mg (28%) of (1S,4S,5R)-2-[4-fluoro-6-[(propane-1-sulfonyl)carbamoyl]-1,3-benzothiazol-2-yl]-2-azabicyclo[2.2.1]heptan-5-yl 5-cyclopropyl-3-(2,6-dichlorophenyl)-1,2-oxazole-4-carboxylate I-32 as a white solid. $^1$H NMR (300 MHz, $CD_3OD$) δ: 8.08 (d, J=1.7 Hz, 1H), 7.70-7.49 (m, 4H), 5.00 (d, J=6.6 Hz, 1H), 4.41 (s, 1H), 3.62-3.47 (m, 3H), 3.23 (s, 1H), 3.00 (p, J=6.7 Hz, 1H), 2.60 (s, 1H), 2.25 (ddd, J=14.1, 7.1, 2.5 Hz, 1H), 1.99-1.78 (m, 2H), 1.71 (d, J=10.6 Hz, 1H), 1.41-1.28 (m, 6H), 1.10 (t, J=7.5 Hz, 3H). MS (ES, m/z): [M+1]=693.25.

Example 39: (1S,4S,5R)-2-{6-[(cyclopropanesulfonyl)carbamoyl]-4-fluoro-1,3-benzothiazol-2-yl}-2-azabicyclo[2.2.1]heptan-5-yl 5-cyclopropyl-3-(2,6-dichlorophenyl)-1,2-oxazole-4-carboxylate (I-33)

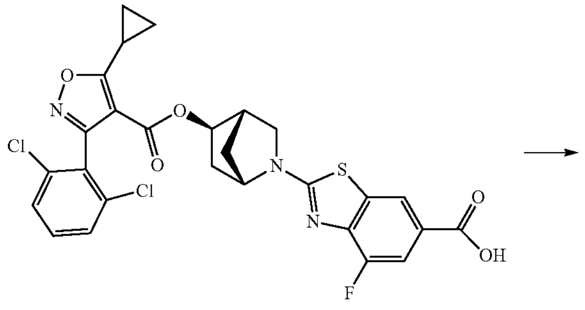

I-1

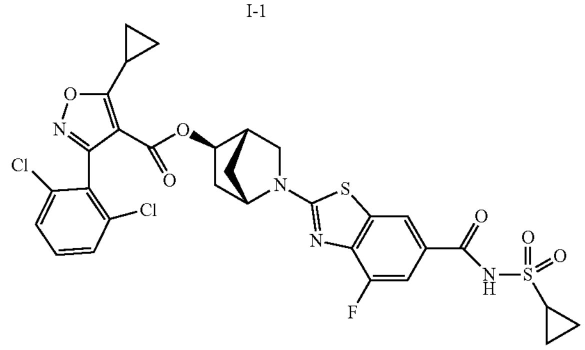

I-33

To a 100-mL round-bottom flask was added 2-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylic acid I-1 (150 mg, 0.25 mmol, 1.0 equiv.), dichloromethane (15 mL), cyclopropanesulfonamide (47 mg, 0.39 mmol, 1.50 equiv.), EDCI (73 mg, 0.38 mmol, 1.50 equiv.), and 4-dimethylaminopyridine (47 mg, 0.38 mmol, 1.50 equiv.) and the resulting mixture was stirred at room temperature for 16 h. The reaction was quenched by the addition of 100 mL of water and the aqueous mixture was extracted with dichloromethane (100 mL×5). The combined organic extracts were dried over anhydrous sodium sulfate, filtered, and concentrated under reduced pressure. The residue was dissolved in 2 mL of DMF and purified by Prep-HPLC using the following conditions: Column, XBridge C18 OBD Prep Column, 19 mm×250 mm; mobile phase, water (0.05% TFA) and ACN (68% to 84% over 8 min); Detector, UV 254 nm, to provide 51.3 mg (29%) of (1S,4S,5R)-2-[6-[(cyclopropanesulfonyl)carbamoyl]-4-fluoro-1,3-benzothiazol-2-yl]-2-azabicyclo[2.2.1]heptan-5-yl 5-cyclopropyl-3-(2,6-dichlorophenyl)-1,2-oxazole-4-carboxylate I-33 as a colorless solid. $^1$H NMR (300 MHz, DMSO-$d_6$) δ: 12.00 (s, 1H), 8.25 (d, J=1.6 Hz, 1H), 7.77-7.57 (m, 4H), 5.04-4.94 (m, 1H), 3.49 (d, J=9.1 Hz, 1H), 3.13 (tt, J=7.7, 5.1 Hz, 1H), 2.97-2.82 (m, 1H), 2.47 (d, J=3.3 Hz, 1H), 2.22-2.09 (m, 1H), 1.65 (d, J=10.2 Hz, 1H), 1.45-1.04 (m, 11H). MS (ES, m/z): [M+1]=691.25.

Example 40: 2-[(1S,4S,5S)-5-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic Acid (I-34)

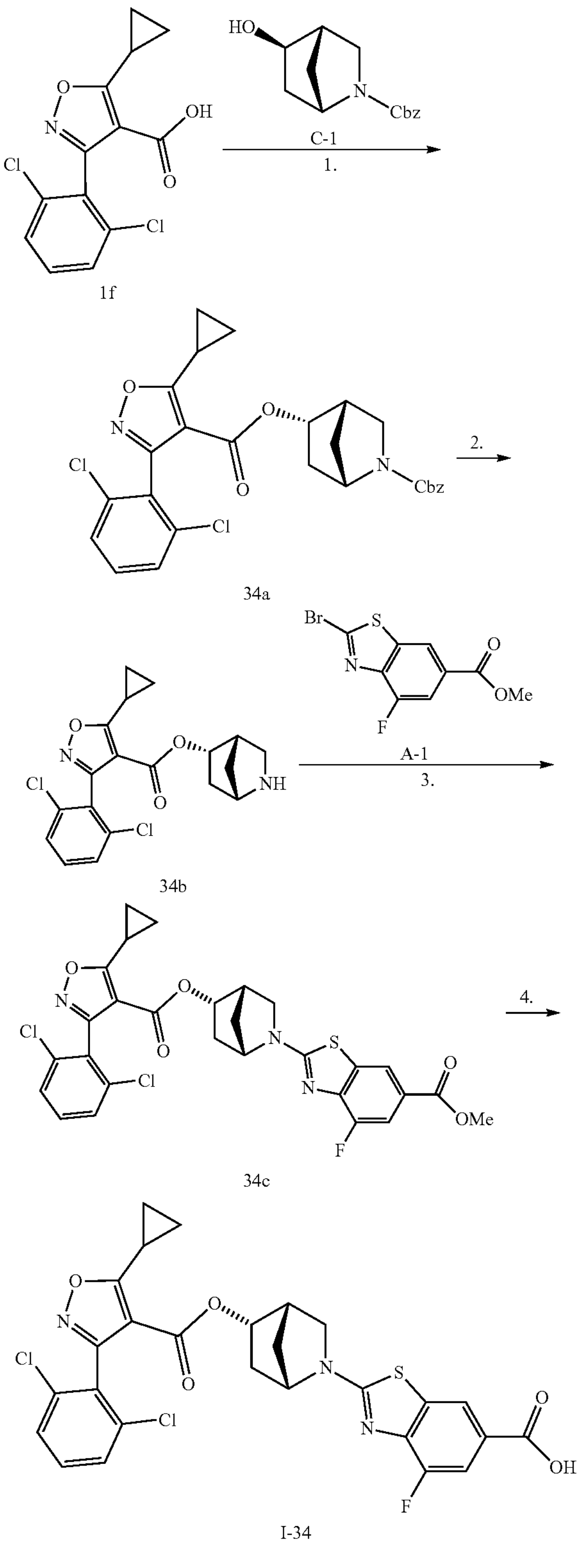

1f

34a

34b

34c

I-34

Step 1. Benzyl (1S,4S,5S)-5-[[5-cyclopropyl-3-(2,6-dichlorophenyl)-1,2-oxazol-4-yl]carbonyloxy]-2-azabicyclo[2.2.1]heptane-2-carboxylate (34a)

To a 250-mL round-bottom flask containing a solution of benzyl (1S,4S,5R)-5-hydroxy-2-azabicyclo[2.2.1]heptane-2-carboxylate C-1 (608 mg, 2.46 mmol, 1.0 equiv.) in tetrahydrofuran (30 mL) was added 5-cyclopropyl-3-(2,6-dichlorophenyl)-1,2-oxazole-4-carboxylic acid if (1.1 g, 3.69 mmol, 1.50 equiv.). The resulting mixture was cooled to 0° C., and $PPh_3$ (967 mg, 3.69 mmol, 1.50 equiv) was added followed by the dropwise addition of a solution of DIAD (746 mg, 3.69 mmol, 1.50 equiv.). The resulting mixture was stirred at room temperature overnight and then concentrated under reduced pressure. The residue was purified by silica gel column chromatography eluting with PE:EA (5:1) to give 1.2 g (93%) of benzyl (1S,4S,5S)-5-[[5-cyclopropyl-3-(2,6-dichlorophenyl)-1,2-oxazol-4-yl] carbonyloxy]-2-azabicyclo[2.2.1]heptane-2-carboxylate 34a as a light-yellow oil.

Step 2. (1S,4S,5S)-2-azabicyclo[2.2.1]heptan-5-yl 5-cyclopropyl-3-(2,6-dichlorophenyl)-1,2-oxazole-4-carboxylate (34b)

To a 250-mL round-bottom flask was added a solution of benzyl (1S,4S,5S)-5-[[5-cyclopropyl-3-(2,6-dichlorophenyl)-1,2-oxazol-4-yl]carbonyloxy]-2-azabicyclo[2.2.1]heptane-2-carboxylate 34a (1.2 g, 2.28 mmol, 1.0 equiv.) in dichloromethane (30 mL) followed by TMSI (2.28 g, 11.40 mmol, 5.0 equiv.) and the resulting mixture was stirred at room temperature for 10 min. A 1M hydrogen chloride solution was added until the pH of the solution was adjusted to 3-4 and the mixture was concentrated under reduced pressure. The crude product was purified by Flash-Prep-HPLC using the following conditions (IntelFlash-1): Column, C18 silica gel; mobile phase, $CH_3CN:H_2O=0:100$ increasing to 20:80 over 30 min; Detector, UV 254 nm, to provide 800 mg (89%) of (1S,4S,5S)-2-azabicyclo[2.2.1] heptan-5-yl 5-cyclopropyl-3-(2,6-dichlorophenyl)-1,2-oxazole-4-carboxylate 34b as a pale-yellow solid.

Step 3. Methyl 2-[(1S,4S,5S)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylate (34c)

To a 100-mL round-bottom flask purged and maintained under an inert atmosphere of nitrogen was added a solution of (1S,4S,5S)-2-azabicyclo[2.2.1]heptan-5-yl 5-cyclopropyl-3-(2,6-dichlorophenyl)-1,2-oxazole-4-carboxylate 34b (200 mg, 0.51 mmol, 1.0 equiv.) in DMA (10 mL), methyl 2-bromo-4-fluoro-1,3-benzothiazole-6-carboxylate A-1 (178 mg, 0.61 mmol, 1.20 equiv), and $Cs_2CO_3$ (498 mg, 1.53 mmol, 3.0 equiv.) and the resulting mixture was stirred at 60° C., overnight. The mixture was then diluted with 200 mL of ethyl acetate and the organic extract was washed with brine (30 mL×3), dried over anhydrous sodium sulfate, filtered, and concentrated under reduced pressure. The residue was purified by silica gel column chromatography eluting with ethyl acetate/petroleum ether (1:3) to afford 230 mg (75%) of methyl 2-[(1S,4S,5S)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylate 34c as a light yellow solid.

Step 4. 2-[(1S,4S,5S)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylic Acid (I-34)

To a 50-mL round-bottom flask purged and maintained under an inert atmosphere of nitrogen containing a solution of methyl 2-[(1S,4S,5S)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylate 34c (230 mg, 0.38 mmol, 1.0 equiv.) in pyridine (5 mL) was added LiI (513 mg, 10.0 equiv.) and the resulting mixture was stirred at 125° C., overnight. The mixture was then diluted with 200 mL of ethyl acetate and the organic extract was washed with a 1M hydrogen chloride aqueous solution (30 mL×3) and brine (30 mL×3), dried over anhydrous sodium sulfate, filtered, and concentrated under reduced pressure. The crude product was purified by Prep-HPLC using the following conditions: Column, XBridge C18 OBD Prep Column; 5 μm, 19 mm×250 mm; mobile phase, water (0.05% TFA) and ACN (20% to 35% over 8 min); Detector, UV 220 nm, to provide 30.3 mg (13%) of 2-[(1S,4S,5S)-5-[[5-cyclopropyl-3-(2,6-dichlorophenyl)-1,2-oxazol-4-yl]carbonyloxy]-2-azabicyclo[2.2.1]heptan-2-yl]-4-fluoro-1,3-benzothiazole-6-carboxylic acid I-34 as a light yellow solid. $^1H$ NMR (400 MHz, $CD_3OD$) δ: 8.24 (d, J=1.5 Hz, 1H), 7.75 (dd, J=11.5, 1.5 Hz, 1H), 7.47-7.40 (m, 1H), 7.03 (t, J=8.1 Hz, 1H), 6.79 (d, J=8.2 Hz, 1H), 5.26 (dd, J=9.2, 4.8 Hz, 1H), 3.39 (s, 1H), 3.04-2.91 (m, 2H), 2.17 (ddd, J=13.3, 10.1, 2.7 Hz, 1H), 1.95 (d, J=10.8 Hz, 1H), 1.83 (d, J=10.7 Hz, 1H), 1.37-1.26 (m, 4H), 1.07 (dt, J=14.1, 3.5 Hz, 1H). MS (ES, m/z): [M+1]=588.0.

Example 41: 2-[(1S,4S,5S)-5-[5-cyclopropyl-3-(2,6-dichlorophenyl)-1,2-oxazole-4-carbonyloxy]-2-azabicyclo[2.2.1]heptan-2-yl]-1,3-benzothiazole-6-carboxylic Acid (I-35)

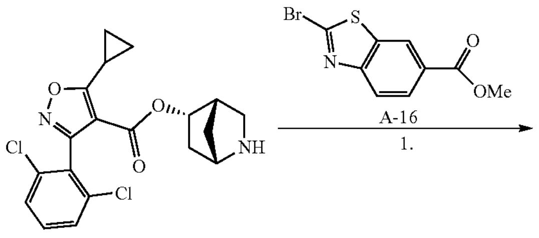

34b

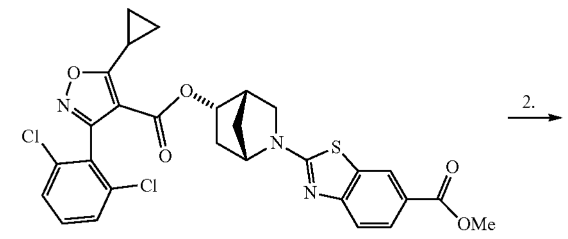

34c

-continued

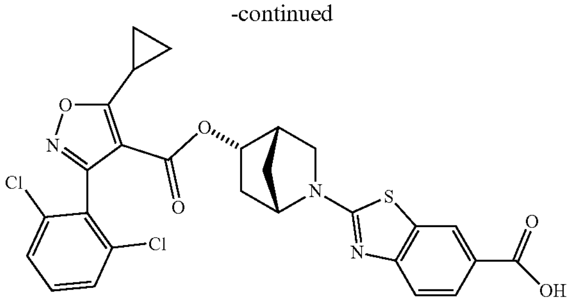

I-35

The title compound I-35 (8.9 mg, 9%) was prepared in two steps and as a light yellow solid following the procedures described in Preparative Example 40 steps 3 and 4, from (1S,4S,5S)-2-azabicyclo[2.2.1]heptan-5-yl 5-cyclopropyl-3-(2,6-dichlorophenyl)-1,2-oxazole-4-carboxylate 34b (200 g, 0.51 mmol, 1.0 equiv.) and methyl 2-bromo-1,3-benzothiazole-6-carboxylate A-16 (167 mg, 0.61 mmol, 1.20 equiv.). H NMR (400) MHz, $CD_3OD$) 8.46 (d, J=1.8 Hz 1H), 8.10 (dd, J=8.5, 1.9 Hz, 1H), 7.57 (d, J=8.4 Hz, 1H) 7.41 (d, J=8.2 Hz, 1H), 6.98 (t, J=8.1 Hz, 1H), 6.68 (s, 1H), 5.30-5.22 (m, 1H), 4.26 (s, 2H), 3.45 (s, 1H), 3.08 (s, 1H), 3.03-2.91 (m, 1H), 2.23-2.11 (m, 1H), 1.97 (s, 1H), 1.86 (d, J=10.9 Hz, 1H), 1.36-1.27 (m, 4H), 1.01 (d, J=13.9 Hz, 1H). MS (ES, m/z): [M+1]=570.0.

Example 42: Methyl 2-[(1S,4S,5S)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylate (I-36)

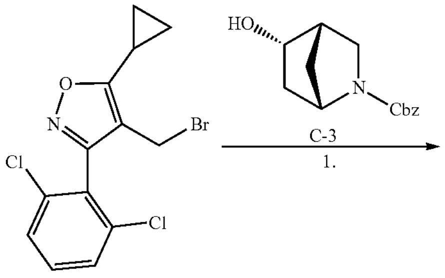

36a

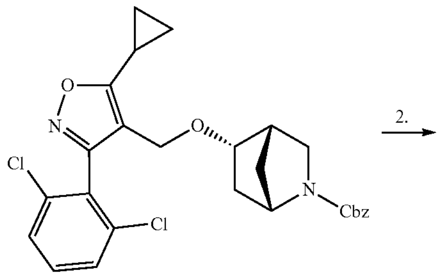

36b

-continued

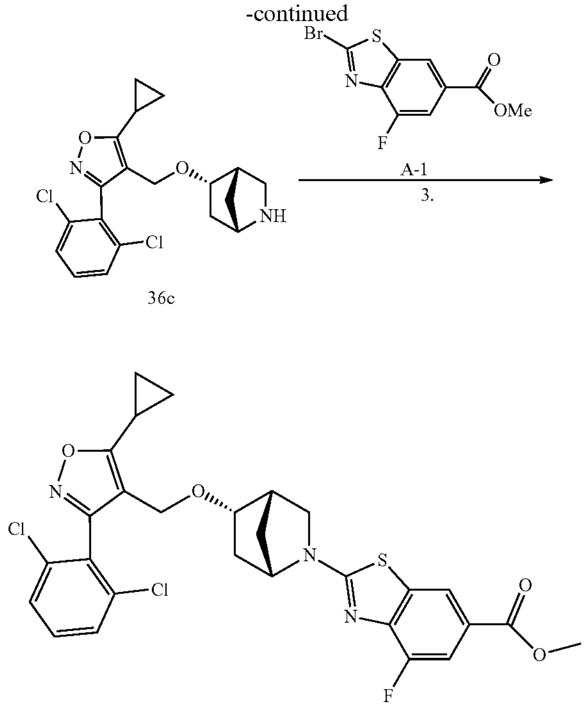

36c

I-36

Step 1. Benzyl (1S,4S,5S)-5-[[5-cyclopropyl-3-(2,6-dichlorophenyl)-1,2-oxazol-4-yl]methoxy]-2-azabicyclo[2.2.1]heptane-2-carboxylate (36b)

To a 250-mL round-bottom flask containing a solution of benzyl (1S,4S,5S)-5-hydroxy-2-azabicyclo[2.2.1]heptane-2-carboxylate C3 (600 mg, 2.43 mmol, 1.0 equiv.) in N,N-dimethylformamide (30 mL) was added 4-(bromomethyl)-5-cyclopropyl-3-(2,6-dichlorophenyl)-1,2-oxazole 36a (930 mg, 2.68 mmol, 1.10 equiv., prepared from 12a) followed by the batchwise addition of sodium hydride (190 mg, 7.92 mmol, 2.0 equiv., 60% in mineral oil) at 0° C. The resulting mixture was stirred at room temperature for 3 h. 200 mL of ethyl acetate was then added followed by 1 mL of $H_2O$. The resulting mixture was washed with brine (30 mL×3), dried over anhydrous sodium sulfate, filtered, and concentrated under reduced pressure. The residue was purified by a silica gel column chromatography eluting with PE:EA (5:1) to give 0.8 g (64%) of benzyl (1S,4S,5S)-5-[[5-cyclopropyl-3-(2,6-dichlorophenyl)-1,2-oxazol-4-yl]methoxy]-2-azabicyclo[2.2.1]heptane-2-carboxylate 36b as a light yellow oil.

Step 2. (1S,4S,5S)-5-[[5-cyclopropyl-3-(2,6-dichlorophenyl)-1,2-oxazol-4-yl]methoxy]-2-azabicyclo[2.2.1]heptane (36c)

To a 100-mL round-bottom flask containing a solution of benzyl (1S,4S,5S)-5-[[5-cyclopropyl-3-(2,6-dichlorophenyl)-1,2-oxazol-4-yl]methoxy]-2-azabicyclo[2.2.1]heptane-2-carboxylate 36b (800 mg, 1.56 mmol, 1.0 equiv.) in dichloromethane (10 mL) was added TMSI (1.56 g, 7.80 mmol, 5.0 equiv.) and the resulting mixture was stirred at room temperature for 10 min. A 1M hydrogen chloride aqueous solution was then added until the pH of the solution was adjusted to 4-5 and the resulting mixture was concentrated under reduced pressure. The crude product (0.8 g) was purified by Flash-Prep-HPLC using the following conditions: Column, silica gel; mobile phase, $CH_3CN$:$H_2O$=0:100 increasing to 25:75 over 30 min; Detector, UV 254 nm, to provide 0.4 g (68%) of (1S,4S,5S)-5-[[5-cyclopropyl-3-(2,6-dichlorophenyl)-1,2-oxazol-4-yl]methoxy]-2-azabicyclo[2.2.1]heptane 36c as a light yellow solid.

Step 3. Methyl 2-[(1S,4S,5S)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylate (I-36)

To a 100-mL round-bottom flask purged and maintained under an inert atmosphere of nitrogen was added a solution of (1S,4S,5S)-5-[[5-cyclopropyl-3-(2,6-dichlorophenyl)-1,2-oxazol-4-yl]methoxy]-2-azabicyclo[2.2.1]heptane 36c (50 mg, 0.13 mmol, 1.0 equiv.) in DMA (5 mL), methyl 2-bromo-4-fluoro-1,3-benzothiazole-6-carboxylate A-1 (46 mg, 0.16 mmol, 1.2 equiv.), and $Cs_2CO_3$ (129 mg, 0.40 mmol, 3.0 equiv.) and the resulting mixture was stirred at 60° C., overnight. The resulting solids were filtered off and the filtrate was concentrated under reduced pressure to provide a crude product which was purified by Prep-HPLC using the following conditions: Column. XBridge C18 OBD Prep Column, 5 μm, 19 mm×250 mm; mobile phase, water (0.05% TFA) and ACN (70% to 87% over 8 min); Detector, UV 254 nm. After purification, 32.3 mg (42%) of methyl 2-[(1S,4S,5S)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylate I-36 was obtained as an off-white solid. $^1$H NMR (400 MHz, $CD_3OD$) δ: 8.19 (d, J=1.5 Hz, 1H), 7.71 (dd, J=11.6, 1.5 Hz, 1H), 7.45 (dd, J=8.1, 1.2 Hz, 1H), 7.29-7.14 (m, 2H), 4.88 (s, 14H), 4.35 (d, J=11.9 Hz, 1H), 4.20 (d, J=11.9 Hz, 1H), 4.07 (dt, J=8.2, 3.6 Hz, 1H), 3.92 (s, 3H), 2.82 (d, J=3.8 Hz, 1H), 2.29-2.18 (m, 1H), 1.89 (d, J=10.1 Hz, 1H), 1.70 (d, J=10.6 Hz; 1H), 1.23-1.07 (m, 5H). MS (ES, m/z): [M+1]=588.0.

Example 43: 2-[(1S,4S,5S)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic Acid (I-37)

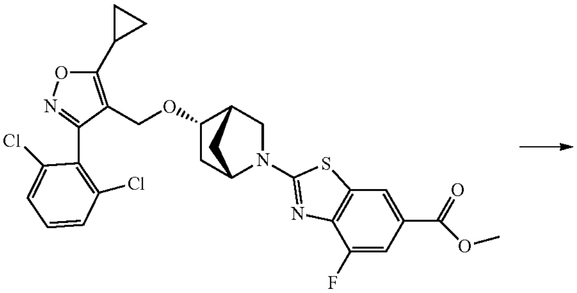

I-36

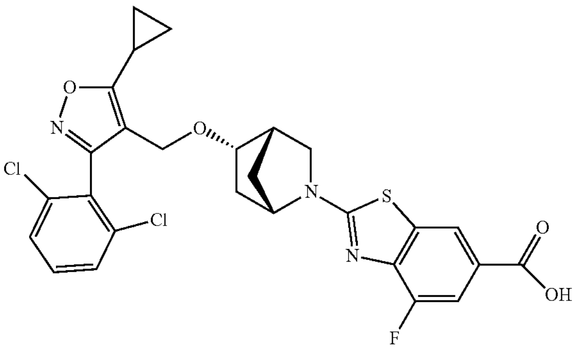

I-37

To a 250-mL round-bottom flask containing a solution of methyl 2-[(1S,4S,5S)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylate I-36 (260 mg, 0.44 mmol, 1.0 equiv.) in methanol/$H_2O$ (20/2 mL) was added $LiOH.H_2O$ (186 mg, 4.43 mmol, 10.0 equiv) and the resulting mixture was stirred at 125° C., overnight. The pH value of the mixture was adjusted to 4-5 using aqueous hydrogen chloride (1M) and the resulting aqueous mixture was extracted ethyl acetate (30 mL×3). The combined organic extracts were dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, water (0.05% TFA) and ACN (60.0% to 77.0% over 8 min); Detector, UV 254 nm, to provide 104.9 mg (41%) of 2-[(1S,4S,5S)-5-[[5-cyclopropyl-3-(2,6-dichlorophenyl)-1,2-oxazol-4-yl]methoxy]-2-azabicyclo[2.2.1]heptan-2-yl]-4-fluoro-1,3-benzothiazole-6-carboxylic acid I-37 as an off-white solid. $^1H$ NMR (400 MHz, $CD_3OD$) δ: 8.19 (d, J=1.5 Hz, 1H), 7.71 (dd, J=11.5, 1.5 Hz, 1H), 7.45 (dd, J=8.0, 1.2 Hz, 1H), 7.31-7.14 (m, 2H), 4.53 (s, 2H), 4.35 (d, J=11.9 Hz, 1H), 4.20 (d, J=11.9 Hz, 1H), 4.07 (dt, J=10.3, 3.8 Hz, 1H), 3.58 (s, 1H), 3.37 (s, 1H), 2.82 (t, J=3.6 Hz, 1H), 2.29-2.17 (m, 1H), 2.06-1.95 (m, 1H), 1.89 (d, J=10.6 Hz, 1H), 1.71 (d, J=10.4 Hz, 1H), 1.24-1.04 (m, 5H). MS (ES, m/z): [M+1]=574.0.

Example 44: 2-[(1R,4R,5S)-5-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic Acid) (I-38)

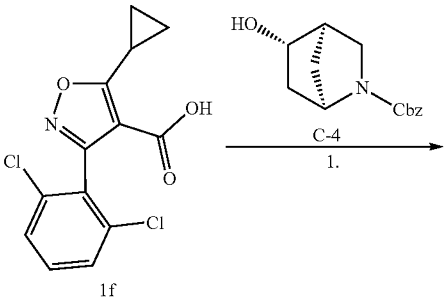

1f

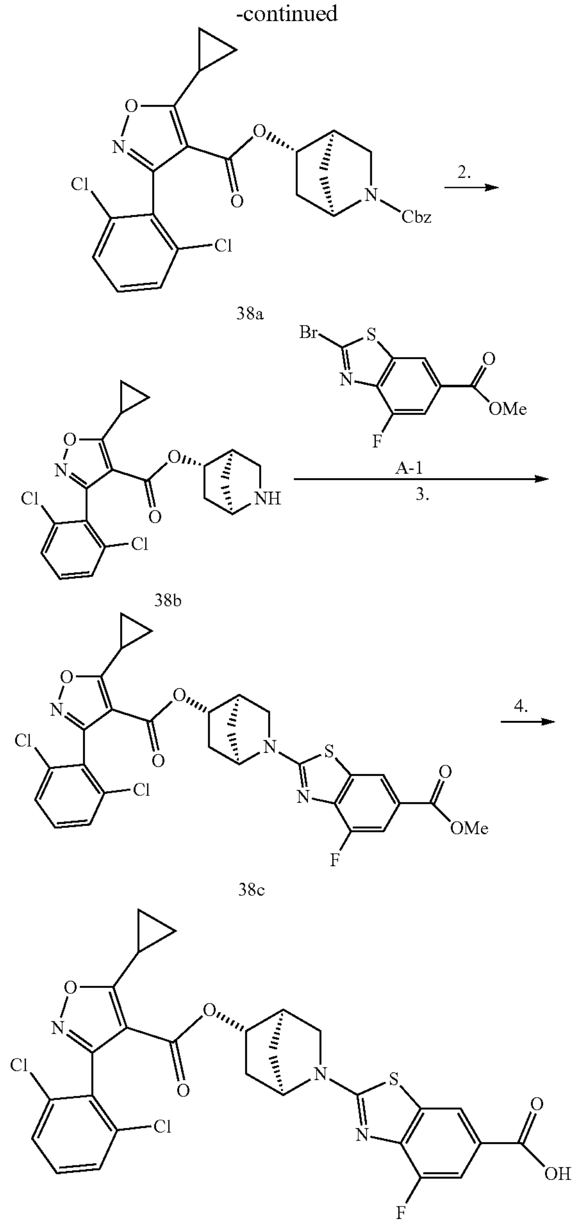

38a

38b

38c

I-38

Step 1. (1R,4R,5S)-2-((benzyloxy)carbonyl)-2-azabicyclo[2.2.1]heptan-5-yl 5-cyclopropyl-3-(2,6-dichlorophenyl)isoxazole-4-carboxylate (38a)

To a solution of 5-cyclopropyl-3-(2,6-dichlorophenyl) isoxazole-4-carboxylic Acid 1f (0.23 g, 0.77 mmol) in $CH_2Cl_2$ (5.0 mL) was added oxalyl chloride (0.13 mL, 1.54 mmol) followed by 3 drops of DMF through a syringe. The mixture was stirred at room temperature for 30 minutes. The mixture was concentrated to dryness. The residue was re-dissolved in $CH_2Cl_2$ (5.0 mL). Benzyl (1R,4R,5S)-5-hydroxy-2-azabicyclo[2.2.1]heptane-2-carboxylate C-4 (0.21 g, 0.85 mmol) was added followed by $Et_3N$ (0.32 mL, 2.31 mmol) and DMAP (9.4 mg, 0.07 mmol). The resulting mixture was stirred at room temperature overnight. The mixture was partitioned between EtOAc and water. The separated organic layer was washed with brine, dried, filtered and concentrated. The residue was purified with column chromatography (20-30% EtOAc in hexanes) to give (1R,4R,5S)-2-((benzyloxy)carbonyl)-2-azabicyclo[2.2.1]heptan-5-yl 5-cyclopropyl-3-(2,6-dichlorophenyl)isoxazole-4-carboxylate 38a (0.165 g, 40%) as a clear oil. Yield: 0.165 g, 40%. MS (ES, m/z): [M+1]=527.

Step 2. (1R,4R,5S)-2-azabicyclo[2.2.1]heptan-5-yl 5-cyclopropyl-3-(2,6-dichlorophenyl)isoxazole-4-carboxylate HCl salt (38b)

To a solution of (1R,4R,5S)-2-((benzyloxy)carbonyl)-2-azabicyclo[2.2.1]heptan-5-yl 5-cyclopropyl-3-(2,6-dichlorophenyl)isoxazole-4-carboxylate 38a (0.165 g, 0.31 mmol) in $CH_2Cl_2$ (6 mL) was added iodotrimethylsilane (0.62 mL, 0.62 mmol, 1M solution in $CH_2Cl_2$). After the mixture was stirred at room temperature for 30 minutes, it was concentrated to dryness. A solution of HCl in $Et_2O$ (5.0 mL, 2M HCl in $Et_2O$) was added and the resulting mixture was stirred at room temperature for 10 min. A light brown solid formed at the bottom of the flask and the clear $Et_2O$ solution was discarded. The solid was triturated with $Et_2O$ twice then dried to give the (1R,4R,5S)-2-azabicyclo[2.2.1]heptan-5-yl 5-cyclopropyl-3-(2,6-dichlorophenyl) isoxazole-4-carboxylate HCl salt 38b (0.13 g, 100%) as a yellow solid. MS (ES, m/z): [M+1]=393.

Step 3. (1R,4R,5S)-2-(4-fluoro-6-(methoxycarbonyl)benzo[d]thiazol-2-yl)-2-azabicyclo[2.2.1]heptan-5-yl 5-cyclopropyl-3-(2,6-dichlorophenyl)isoxazole-4-carboxylate (38c)

A mixture of (1R,4R,5S)-2-azabicyclo[2.2.1]heptan-5-yl 5-cyclopropyl-3-(2,6-dichlorophenyl)isoxazole-4-carboxylate HCl salt 38b (0.13 g, 0.30 mmol), methyl 2-bromo-4-fluorobenzo[d]thiazole-6-carboxylate A-1 (0.087 g, 0.30 mmol) and $Cs_2CO_3$ (0.20 g, 0.60 mmol) in DMA (5.0 mL) was heated at 80° C., with stirring overnight. The reaction mixture was cooled to room temperature and partitioned between EtOAc and water. The organic layer was washed with brine, dried with anhydrous sodium sulfate, filtered, and concentrated. The residue was purified with column chromatography (20-30% EtOAc in hexanes) to give (1R,4R,5S)-2-(4-fluoro-6-(methoxycarbonyl)benzo[d]thiazol-2-yl)-2-azabicyclo[2.2.1]heptan-5-yl 5-cyclopropyl-3-(2,6-dichlorophenyl)isoxazole-4-carboxylate 38c (0.16 g, 89%) as a white foam. MS (ES, m/z): [M+1]=602.

Step 4. 2-((1R,4R,5S)-5-((5-cyclopropyl-3-(2,6-dichlorophenyl)isoxazole-4-carbonyl)oxy)-2-azabicyclo[2.2.1]heptan-2-yl)-4-fluorobenzo[d]thiazole-6-carboxylic Acid (I-38)

To a solution of (1R,4R,5S)-2-(4-fluoro-6-(methoxycarbonyl)benzo[d]thiazol-2-yl)-2-azabicyclo[2.2.1]heptan-5-yl 5-cyclopropyl-3-(2,6-dichlorophenyl)isoxazole-4-carboxylate 38c (0.16 g, 0.26 mmol) in pyridine (3 mL) was added lithium iodide (0.21 g, 1.57 mmol). The mixture was heated at 100° C., for 48 h. Pyridine was then removed under reduced pressure. The resulting residue was dissolved in $CH_2Cl_2$ (100 mL) and washed with aqueous HCl (1M, 15 mL) and brine, dried with anhydrous $MgSO_4$, filtered, and concentrated. The residue was purified with prep HPLC using 40 to 90% acetonitrile/water with 0.1% TFA gradient to yield 2-((1R,4R,5S)-5-((5-cyclopropyl-3-(2,6-dichlorophenyl)isoxazole-4-carbonyl)oxy)-2-azabicyclo[2.2.1]heptan-2-yl)-4-fluorobenzo[d]thiazole-6-carboxylic acid I-38 as a TFA salt (117.1 mg), an off-white solid. $^1$H NMR (400 MHz, DMSO-$d_6$) δ: 12.96 (br, 1H), 8.21 (d, J=1.5 Hz, 1H), 7.73-7.53 (m, 4H), 4.98 (d, J=6.5 Hz, 1H), 3.48 (d, J=5.9 Hz, 1H), 3.17 (s, 1H), 2.89 (dq, J=8.3, 5.1 Hz, 1H), 2.47 (s, 1H), 2.20-2.09 (m, 1H), 1.64 (d, J=10.4 Hz, 1H), 1.41-1.22 (m, 6H), 1.17 (d, J=10.0 Hz, 1H). MS (ES, m/z): [M+1]=588.

Example 45: 2-[(1R,4R,5S)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic Acid (I-39)

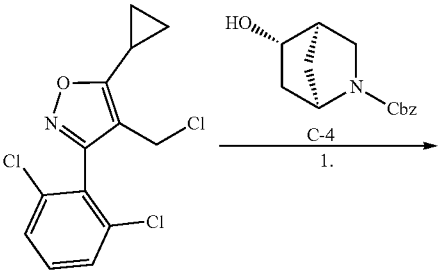

12b

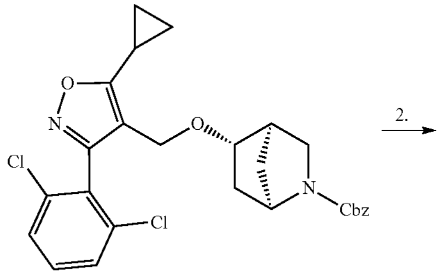

39a

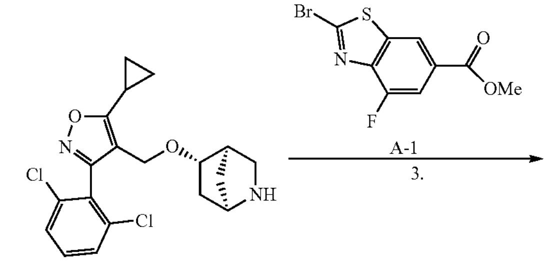

39b

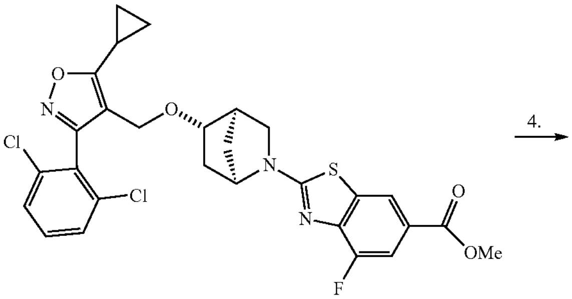

39c

-continued

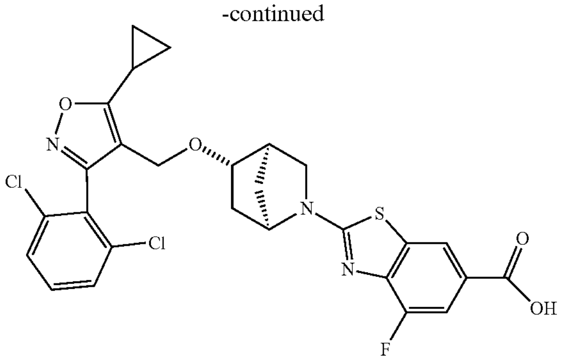

I-39

Step 1. Benzyl (1R,4R,5S)-5-((5-cyclopropyl-3-(2,6-dichlorophenyl)isoxazol-4-yl)methoxy)-2-azabicyclo[2.2.1]heptane-2-carboxylate (39a)

To a solution of benzyl (1R,4R,5S)-5-hydroxy-2-azabicyclo[2.2.1]heptane-2-carboxylate C-4 (0.164 g, 0.66 mmol) in DMF (5.0 mL) at 0° C., was added NaH (0.026 g, 0.73 mmol, 60% in mineral oil). After the mixture was stirred at 0° C., for 30 minutes, 4-(chloromethyl)-5-cyclopropyl-3-(2,6-dichlorophenyl)isoxazole 12b (0.2 g, 0.66 mmol) was added and the resulting mixture was heated at 60° C., overnight. The mixture was cooled to 0° C., quenched with water, and partitioned between EtOAc and water. The organic layer was washed with brine, dried with anhydrous $MgSO_4$, filtered, and concentrated under reduced pressure. The residue was purified by column chromatography (eluting with 20-30% EtOAc in hexanes) to give benzyl (1R,4R,5S)-5-((5-cyclopropyl-3-(2,6-dichlorophenyl)isoxazol-4-yl)methoxy)-2-azabicyclo[2.2.1]heptane-2-carboxylate 39a (0.14 g, 42%). MS (ES, m/z): [M+1]=513.

Step 2. 4-((((1R,4R,5S)-2-azabicyclo[2.2.1]heptan-5-yl)oxy)methyl)-5-cyclopropyl-3-(2,6-dichlorophenyl)isoxazole HCl Salt (39b)

Following the procedure described in Preparative Example 44 step 2. (1R,4R,5S)-5-((5-cyclopropyl-3-(2,6-dichlorophenyl)isoxazol-4-yl)methoxy)-2-azabicyclo[2.2.1]heptane-2-carboxylate 39a was converted to 4-((((1R,4R,5S)-2-azabicyclo[2.2.1]heptan-5-yl)oxy)methyl)-5-cyclopropyl-3-(2,6-dichlorophenyl)isoxazole HCl salt 39b upon treatment with iodotrimethylsilane. MS (ES, m/z): [M+1]=379.0.

Step 3. Methyl 2-((1R,4R,5S)-5-((5-cyclopropyl-3-(2,6-dichlorophenyl)isoxazol-4-yl)methoxy)-2-azabicyclo[2.2.1]heptan-2-yl)-4-fluorobenzo[d]thiazole-6-carboxylate (39c)

Following the procedure described in Preparative Example 44 step 3, 4-((((1R,4R,5S)-2-azabicyclo[2.2.1]heptan-5-yl)oxy)methyl)-5-cyclopropyl-3-(2,6-dichlorophenyl) isoxazole HCl salt 39b was coupled with methyl 2-bromo-4-fluorobenzo[d]thiazole-6-carboxylate A-1 to provide methyl 2-((1R,4R,5S)-5-((5-cyclopropyl-3-(2,6-dichlorophenyl)isoxazol-4-yl)methoxy)-2-azabicyclo[2.2.1]heptan-2-yl)-4-fluorobenzo[d]thiazole-6-carboxylate 39c. MS (ES, m/z): [M+1]=588.0.

Step 4. 2-((1R,4R,5S)-5-((5-cyclopropyl-3-(2,6-dichlorophenyl)isoxazol-4-yl)methoxy)-2-azabicyclo[2.2.1]heptan-2-yl)-4-fluorobenzo[d]thiazole-6-carboxylic Acid as TFA Salt (I-39)

To a solution of methyl 2-((1R,4R,5S)-5-((5-cyclopropyl-3-(2,6-dichlorophenyl)isoxazol-4-yl)methoxy)-2-azabicyclo[2.2.1]heptan-2-yl)-4-fluorobenzo[d]thiazole-6-carboxylate 39c (0.1 g, 0.17 mmol) in MeOH (3 mL) and THF (1 mL) was added NaOH (0.34 mL, 0.34 mmol, 1M in water) and the reaction mixture was heated at 60° C., overnight. The mixture was then acidified with aqueous HCl (1M) to a pH of 5-6 at 0° C. The aqueous mixture was extracted with $CH_2Cl_2$ (100 mL×2) and the combined organic extracts were dried over $MgSO_4$, filtered, and concentrated. The residue was purified with prep-HPLC using a 40 to 90% acetonitrile/water with 0.1% TFA gradient to yield 2-((1R,4R,5S)-5-((5-cyclopropyl-3-(2,6-dichlorophenyl)isoxazol-4-yl) methoxy)-2-azabicyclo[2.2.1]heptan-2-yl)-4-fluorobenzo [d]thiazole-6-carboxylic Acid as TFA salt I-39 (65.7 mg) as a white solid. $^1H$ NMR (400 MHz, DMSO-$d_6$) δ: 13.00 (br, 1H), 8.20 (d, J=1.5 Hz, 1H), 7.68-7.54 (m, 4H), 4.60-4.33 (m, 1H), 4.32-4.21 (m, 2H), 3.61 (d, J=5.8 Hz, 1H), 3.43 (s, 1H), 3.03-2.88 (m, 1H), 2.55 (s, 1H), 2.35 (ddd. J=16.8, 8.3, 5.2 Hz, 1H), 1.90 (dd, J=13.6 Hz, 1H), 1.60 (d, J=10.3 Hz, 1H), 1.48 (d, J=9.4 Hz, 1H), 1.26 (d, J=13.7 Hz, 1H), 1.18-1.06 (m, 4H). MS (ES, m/z): [M+1]=574.

Example 46: 2-[(1R,4R,5R)-5-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic Acid (I-40)

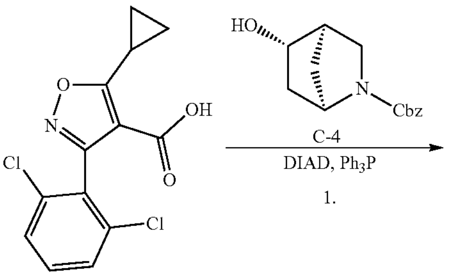

1f

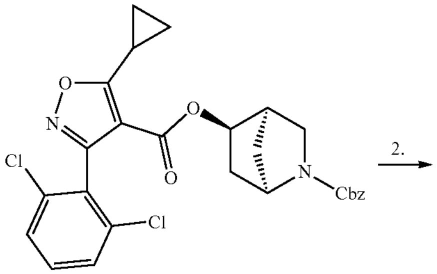

40a

-continued

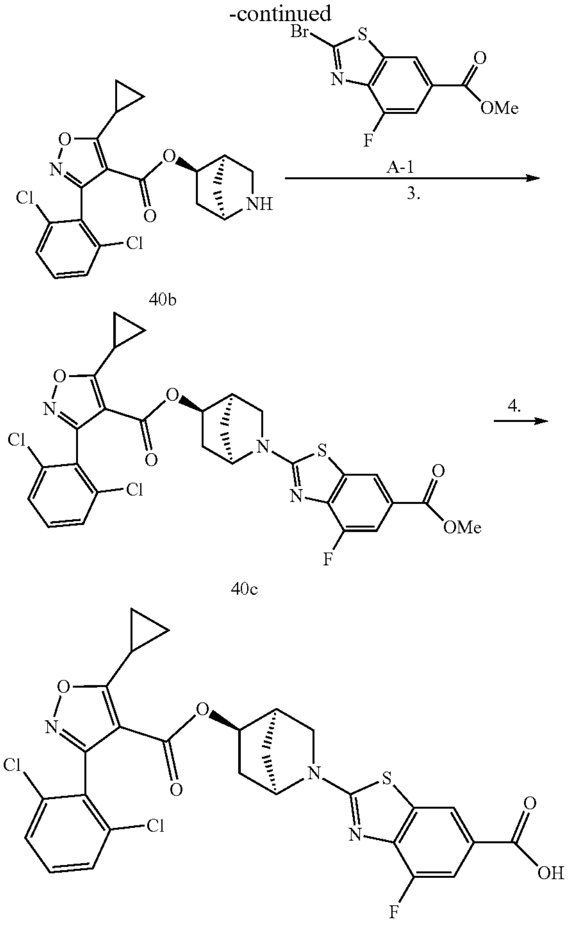

40b

40c

I-40

Step 1. (1R,4R,5R)-2-((benzyloxy)carbonyl)-2-azabicyclo[2.2.1]heptan-5-yl 5-cyclopropyl-3-(2,6-dichlorophenyl)isoxazole-4-carboxylate (40a)

To a mixture of 5-cyclopropyl-3-(2,6-dichlorophenyl) isoxazole-4-carboxylic acid 1f (0.2 g, 0.67 mmol), benzyl (1R,4R,5S)-5-hydroxy-2-azabicyclo[2.2.1]heptane-2-carboxylate C-4 (0.2 g, 0.8 mmol) and $PPh_3$ (0.35 g, 1.30 mmol) in THF (5 mL) was added diisopropyl azodicarboxylate (0.26 mL, 1.30 mmol). The resulting mixture was stirred at room temperature overnight, and then partitioned between EtOAc and water. The organic layer was washed with brine, dried over $MgSO_4$, filtered, and concentrated. The residue was purified by column chromatography (eluting with 30% EtOAc in hexanes) to give (1R,4R,5R)-2-((benzyloxy)carbonyl)-2-azabicyclo[22.1]heptan-5-yl 5-cyclopropyl-3-(2,6-dichlorophenyl)isoxazole-4-carboxylate 40a (0.35 g) as a clear oil. MS (ES, m/z): [M+1]=527.

Step 2. (1R,4R,5R)-2-azabicyclo[2.2.1]heptan-5-yl 5-cyclopropyl-3-(2,6-dichlorophenyl) isoxazole-4-carboxylate HCl Salt (40b)

Following the procedure described in Preparative Example 44 step 2, (1R,4R,5R)-2-((benzyloxy)carbonyl)-2-azabicyclo[2.2.1]heptan-5-yl 5-cyclopropyl-3-(2,6-dichlorophenyl)isoxazole-4-carboxylate 40a was converted to (1R,4R,5R)-2-azabicyclo[2.2.1]heptan-5-yl 5-cyclopropyl-3-(2,6-dichlorophenyl)isoxazole-4-carboxylate HCl salt 40b upon treatment with TMSI. MS (ES, m/z): [M+1]=393.

Step 3. (1R,4R,5R)-2-(4-fluoro-6-(methoxycarbonyl)benzo[d]thiazol-2-yl)-2-azabicyclo[2.2.1]heptan-5-yl 5-cyclopropyl-3-(2,6-dichlorophenyl)isoxazole-4-carboxylate (40c)

(1R,4R,5R)-2-(4-fluoro-6-(methoxycarbonyl)benzo[d] thiazol-2-yl)-2-azabicyclo[2.2.1]heptan-5-yl 5-cyclopropyl-3-(2,6-dichlorophenyl)isoxazole-4-carboxylate 40c was obtained by following the procedure described in Preparative Example 44 step 3, from (1R,4R,5R)-2-azabicyclo [2.2.1]heptan-5-yl 5-cyclopropyl-3-(2,6-dichlorophenyl) isoxazole-4-carboxylate HCl salt 40b and methyl 2-bromo-4-fluorobenzo[d]thiazole-6-carboxylate A-1. MS (ES, m/z): [M+1]=602.

Step 4. 2-((1R,4R,5R)-5-((5-cyclopropyl-3-(2,6-dichlorophenyl)isoxazole-4-carbonyl)oxy)-2-azabicyclo[2.2.1]heptan-2-yl)-4-fluorobenzo[d]thiazole-6-carboxylic Acid (I-40)

Following the procedure described in Preparative Example 44 step 4, (1R,4R,5R)-2-(4-fluoro-6-(methoxycarbonyl)benzo[d]thiazol-2-yl)-2-azabicyclo[2.2.1]heptan-5-yl 5-cyclopropyl-3-(2,6-dichlorophenyl)isoxazole-4-carboxylate 40c was converted to 2-((1R,4R,5R)-5-((5-cyclopropyl-3-(2,6-dichlorophenyl)isoxazole-4-carbonyl)oxy)-2-azabicyclo[2.2.1]heptan-2-yl)-4-fluorobenzo[d]thiazole-6-carboxylic acid I-40. $^1$H NMR (400 MHz, DMSO-$d_6$) δ: 12.97 (br, 1H), 8.29 (d, J=1.4 Hz, 1H), 7.66 (dd, J=11.5, 1.5 HZ, 1H), 7.58 (d, J=8.1 HZ, 1H), 7.18 (t, J=8.1 Hz, 1H), 7.00 (s, 1H), 5.30-5.16 (m, 1H), 5.16-4.87 (m, 1H), 2.94-2.77 (m, 3H), 2.18 (td, J=10.3, 5.0 Hz, 1H), 1.88 (d, J=10.7 Hz, 1H), 1.78 (d, J=11.2 Hz, 1H), 1.38-1.19 (m, 5H), 0.99 (d, J=13.6 Hz, 1H). MS (ES, m/z): [M+1]=588.

Example 47: 2-[(1R,4R,5R)-5-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic Acid (I-41)

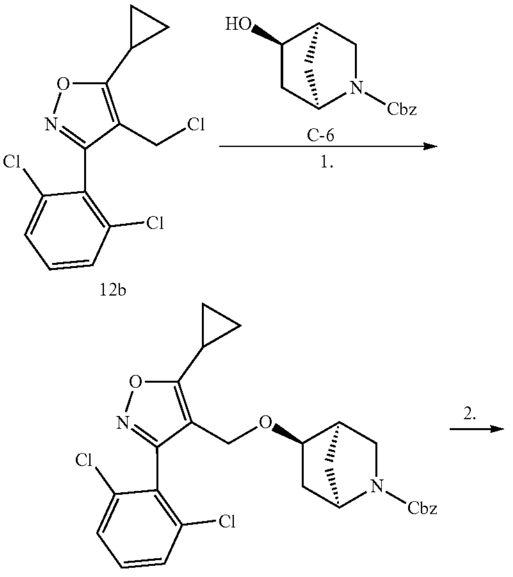

12b

41a

-continued

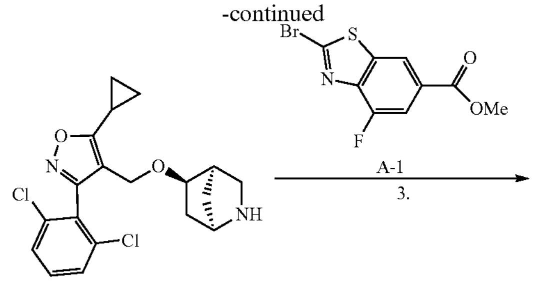

41b

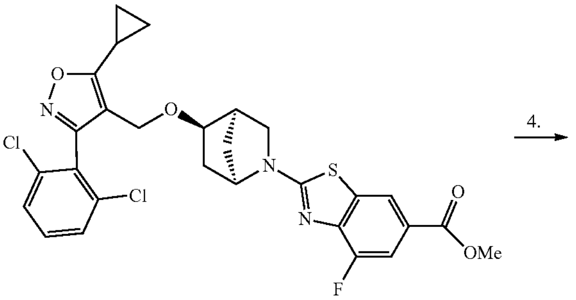

41c

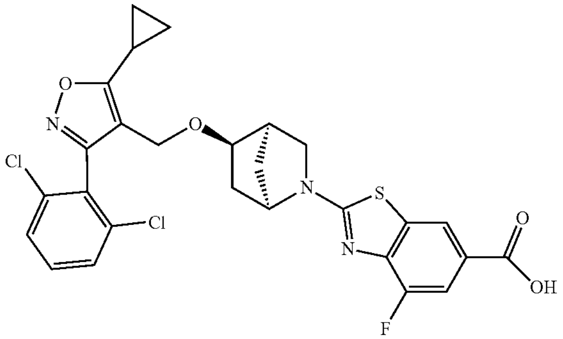

I-41

Step 1. Benzyl (1R,4R,5R)-5-((5-cyclopropyl-3-(2,6-dichlorophenyl)isoxazol-4-yl)methoxy)-2-azabicyclo[2.2.1]heptane-2-carboxylate (41a)

Benzyl (1R,4R,5R)-5-((5-cyclopropyl-3-(2,6-dichlorophenyl)isoxazol-4-yl)methoxy)-2-azabicyclo[2.2.1]heptane-2-carboxylate 41a was obtained by following the procedure described in Preparative Example 45 step 1, from intermediate benzyl (1R,4R,5R)-5-hydroxy-2-azabicyclo[2.2.1]heptane-2-carboxylate C-6 and 4-(chloromethyl)-5-cyclopropyl-3-(2,6-dichlorophenyl)isoxazole 12b. MS (ES, m/z): [M+1]=513.

Steps 2 to 4: 2-((1R,4R,5R)-5-((5-cyclopropyl-3-(2,6-dichlorophenyl)isoxazol-4-yl)methoxy)-2-azabicyclo[2.2.1]heptan-2-yl)-4-fluorobenzo[d]thiazole-6-carboxylic Acid (I-41)

2-((1R,4R,5R)-5-((5-cyclopropyl-3-(2,6-dichlorophenyl)isoxazol-4-yl)methoxy)-2-azabicyclo[2.2.1]heptan-2-yl)-4-fluorobenzo[d]thiazole-6-carboxylic acid I-41 was obtain by following the procedure set forth in Preparative Example 45 steps 2, 3, and 4, from benzyl (1R,4R,5R)-5-((5-cyclopropyl-3-(2,6-dichlorophenyl)isoxazol-4-yl)methoxy)-2-azabicyclo[2.2.1]heptane-2-carboxylate 41a. $^1$H NMR (400 MHz, DMSO-$d_6$) δ: 12.69 (br, 1H), 8.23 (s, 1H), 7.62-7.59 (m, 2H), 7.38-7.35 (m, 2H), 4.22 (dd, J=45.7, 12.1 Hz, 2H), 4.00 (m, 2H), 3.29 (m, 1H), 2.77 (s, 1H), 2.32 (dt, J=13.2, 6.2 Hz, 1H), 1.97 (t, J=11.9 Hz, 1H), 1.97 (t, J=11.9 Hz, 1H), 1.81 (s, 1H), 1.62 (d, J=9.9 Hz, 1H), 1.18-1.02 (m, 6H). MS (ES, m/z): [M+1]=574.

Example 48: 4-[(1S,4S,5R)-5-[5-cyclopropyl-3-(2,6-dichlorophenyl)-1,2-oxazole-4-carbonyloxy]-2-azabicyclo[2.2.1]heptan-2-yl]benzoic Acid (I-42)

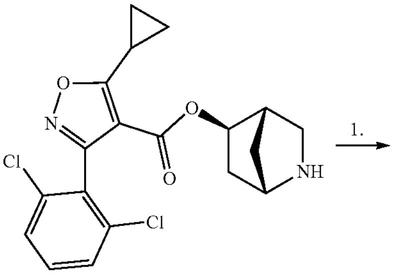

1j

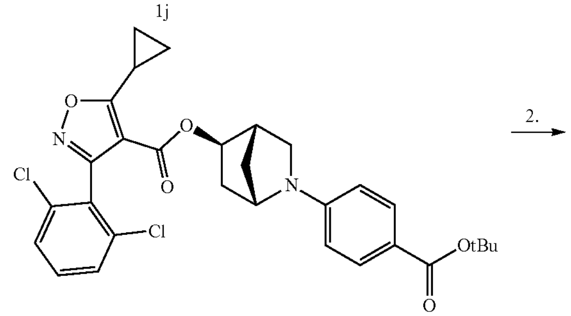

42a

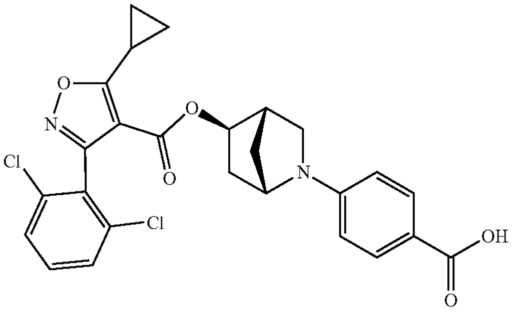

I-42

Step 1. (1S,4S,5R)-2-[4-[(tert-butoxy)carbonyl]phenyl]-2-azabicyclo[2.2.1]heptan-5-yl 5-cyclopropyl-3-(2,6-dichlorophenyl)-1,2-oxazole-4-carboxylate (42a)

To a 250-mL round-bottom flask purged and maintained under an inert atmosphere of nitrogen was added a solution of (1S,4S,5R)-2-azabicyclo[2.2.2.1]heptan-5-yl 5-cyclopropyl-3-(2,6-dichlorophenyl)-1,2-oxazole-4-carboxylate 1j (800 mg, 2.03 mmol, 1.0 equiv.) in toluene (60 mL), tert-butyl 4-bromobenzoate (573 mg, 2.23 mmol, 1.10 equiv.), $Cs_2CO_3$ (929 mg, 2.85 mmol, 1.40 equiv). BINAP (127 mg, 0.20 mmol, 0.10 equiv), and $Pd_2(dba)_3$ (186 mg, 0.20 mmol, 0.10 equiv.) and the resulting mixture was stirred at 110° C., overnight. The mixture was concentrated under reduced pressure and the residue was purified by silica gel column chromatography eluting with ethyl acetate/petroleum ether (15:85) to give 1.2 g (crude) of (1S,4S,5R)-2-[4-[(tert-butoxy)carbonyl]phenyl]-2-azabicyclo[2.2.1]heptan-5-yl 5-cyclopropyl-3-(2,6-dichlorophenyl)-1,2-oxazole-4-carboxylate 42a as a light yellow solid.

Step 2. 4-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]benzoic Acid (I-42)

To a 250-mL round-bottom flask purged and maintained under an inert atmosphere of nitrogen was added a solution of (1S,4S,5R)-2-[4-[(tert-butoxy)carbonyl]phenyl]-2-azabicyclo[2.2.1]heptan-5-yl 5-cyclopropyl-3-(2,6-dichlorophenyl)-1,2-oxazole-4-carboxylate 42a (1.2 g, 2.11 mmol, 1.0 equiv) in dichloromethane (10 mL), and trifluoroacetic acid (3 mL). The resulting mixture was stirred at room temperature for 1 h, and then quenched by the addition of 50 mL of $H_2O$. The pH of the solution was adjusted to 7 using aqueous sodium bicarbonate. The resulting aqueous mixture was extracted with ethyl acetate (30 mL×3) and the combined organic extracts were dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, water (0.05% TFA) and ACN (66.0% to 78.0% over 8 min); Detector, UV 254 nm, to provide 700 mg (65%) of 4-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]benzoic acid I-42 as a light yellow solid. $^1$H NMR (300 MHz, $CD_3OD$) δ: 7.85-7.75 (m, 2H), 7.63-7.47 (m, 3H), 6.56-6.47 (m, 2H), 4.83 (d, J=6.5 Hz, 1H), 4.19 (d, J=2.5 Hz, 1H), 3.42 (dd, J=9.6, 4.1 Hz, 1H), 2.98 (d, J=6.7 Hz, 1H), 2.77 (d, J=9.7 Hz, 1H), 2.46 (d, J=3.8 Hz, 1H), 2.13-1.99 (m, 1H), 1.57 (d, J=9.7 Hz, 1H), 1.39-1.16 (m, 7H). MS (ES, m/z): [M+1]=513.0.

Example 49: 4-[(1S,4S,5R)-5-[5-cyclopropyl-3-(2,6-dichlorophenyl)-1,2-oxazole-4-carbonyloxy]-2-azabicyclo[2.2.1]heptan-2-yl]-3-fluorobenzoic Acid (I-43)

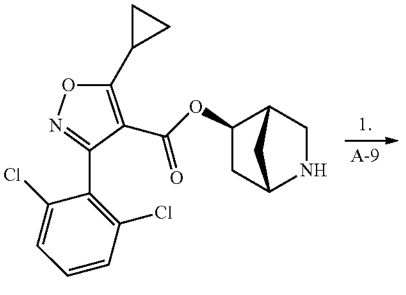

1j

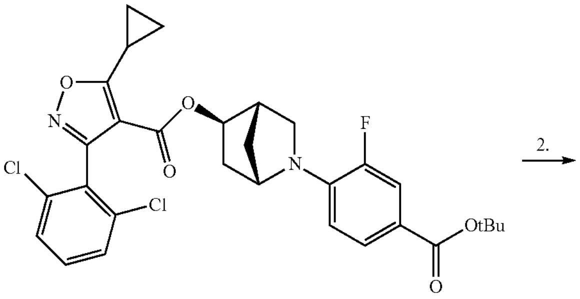

43a

-continued

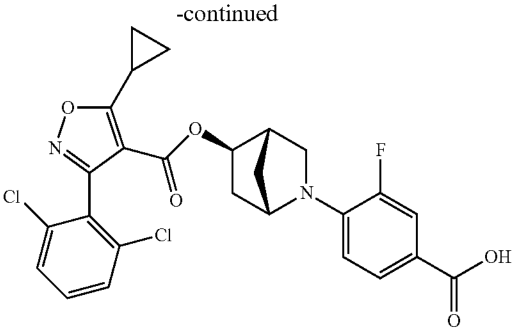

I-43

Step 1. (1S,4S,5R)-2-[4-[(tert-butoxy)carbonyl]-2-fluorophenyl]-2-azabicyclo[2.2.1]heptan-5-yl 5-cyclopropyl-3-(2,6-dichlorophenyl)-1,2-oxazole-4-carboxylate (43a)

To a 50-mL round-bottom flask purged and maintained under an inert atmosphere of nitrogen was added a solution of (1S,4S,5R)-2-azabicyclo[2.2.1]heptan-5-yl 5-cyclopropyl-3-(2,6-dichlorophenyl)-1,2-oxazole-4-carboxylate 1j (200 mg, 0.51 mmol, 1.0 equiv.) in toluene (5 mL), tert-butyl 4-bromo-3-fluorobenzoate A-9 (140 mg, 0.51 mmol, 1.0 equiv.), $Cs_2CO_3$ (233 mg, 0.72 mmol, 1.40 equiv.), BINAP (32 mg, 0.05 mmol, 0.10 equiv.), and $Pd_2(dba)_3$ (47 mg, 0.05 mmol, 0.10 equiv.). The resulting mixture was stirred at 110° C., overnight and concentrated under reduced pressure. The residue was purified by silica gel column chromatography eluting with ethyl acetate/petroleum ether (1/5) to give 165 mg (55%) of (1S,4S,5R)-2-[4-[(tert-butoxy)carbonyl]-2-fluorophenyl]-2-azabicyclo[2.2.1]heptan-5-yl 5-cyclopropyl-3-(2,6-dichlorophenyl)-1,2-oxazole-4-carboxylate 43a as a yellow solid.

Step 2. 4-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-3-fluorobenzoic Acid (I-43)

To a 50-mL round-bottom flask was added a solution of (1S,4S,5R)-2-[4-[(tert-butoxy)carbonyl]-2-fluorophenyl]-2-azabicyclo[2.2.1]heptan-5-yl 5-cyclopropyl-3-(2,6-dichlorophenyl)-1,2-oxazole-4-carboxylate 43a (165 mg, 0.28 mmol, 1.0 equiv.) in dichloromethane (2 mL) and trifluoroacetic acid (1 mL). The resulting mixture was stirred at room temperature for 2 h, and then quenched by the addition of 50 mL of $H_2O$. The pH of the solution was adjusted to 7 using aqueous sodium bicarbonate. The resulting aqueous mixture was extracted ethyl acetate (40 mL×3) and the combined organic extracts were washed with brine (50 mL), dried over anhydrous sodium sulfate, filtered, and concentrated under reduced pressure. The residue was purified by Prep-HPLC using the following conditions: Column, XBridge C18 OBD Prep Column, 19 mm×250 mm; mobile phase, water (0.05% TFA) and ACN (68.0% to 88.0% over 8 min); Detector, UV 254 nm, to provide 82.3 mg (55%) of 4-[(1S,4S,5R)-5-[[5-cyclopropyl-3-(2,6-dichlorophenyl)-1,2-oxazol-4-yl]carbonyloxy]-2-azabicyclo[2.2.1]heptan-2-yl]-3-fluorobenzoic acid I-43 as an off-white solid. $^1$H NMR (400 MHz, $CD_3OD$) δ: 7.69-7.50 (m, 5H), 6.65 (t, 0.1=8.8 Hz, 1H), 4.28 (s, 1H), 3.65-3.57 (m, 1H), 3.03-2.87 (m, 2H), 2.44 (d, J=3.6

Hz, 1H), 2.18 (ddd, J=14.1, 7.2, 2.7 Hz, 1H), 1.58 (d, J=10.1 Hz, 1H), 1.36 (d, J=6.9 Hz, 4H), 1.29-1.19 (m, 2H). MS (ES, m/z): [M+1]=531.0.

Example 50: 4-[(1S,4S,5R)-5-[3-(2,6-dichlorophenyl)-5-(1-fluorocyclopropyl)-1,2-oxazole-4-carbonyloxy]-2-azabicyclo[2.2.1]heptan-2-yl]-3-fluorobenzoic Acid (I-44)

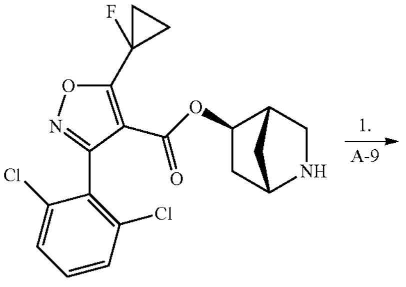

10i

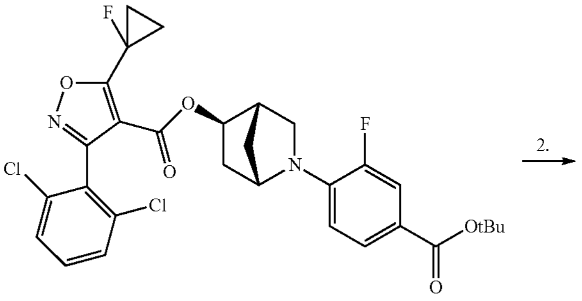

44a

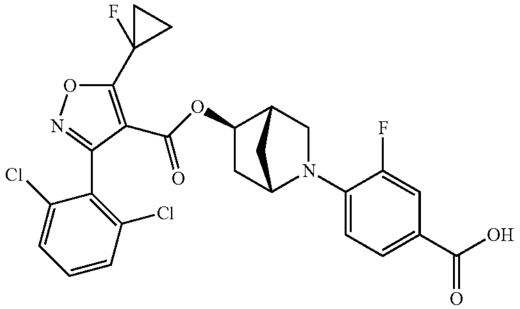

I-44

Step 1. (1S,4S,5R)-2-[4-[(tert-butoxy)carbonyl]-2-fluorophenyl]-2-azabicyclo[2.2.1]heptan-5-yl 3-(2,6-dichlorophenyl)-5-(1-fluorocyclopropyl)-1,2-oxazole-4-carboxylate (44a)

To a 25-mL round-bottom flask purged and maintained under an inert atmosphere of nitrogen was added (1S,4S,5R)-2-azabicyclo[2.2.1]heptan-5-yl 3-(2,6-dichlorophenyl)-5-(1-fluorocyclopropyl)-1,2-oxazole-4-carboxylate 10i (480 mg, 1.17 mmol, 1.0 equiv.), tert-butyl 4-bromo-3-fluorobenzoate A-9 (396 mg, 1.44 mmol, 1.20 equiv.), $Cs_2CO_3$ (552 mg, 1.69 mmol, 1.4 equiv), toluene (5 mL), BINAP (74 mg, 0.12 mmol, 0.10 equiv.), and $Pd_2(dba)_3$ (108 mg, 0.12 mmol, 0.10 equiv.) and the resulting mixture was stirred at 110° C., overnight. $H_2O$ was added and the mixture was extracted with ethyl acetate (100 mL×2). The combined organic extracts were washed with brine (50 mL×3), dried over anhydrous sodium sulfate, filtered, and concentrated under reduced pressure. The residue was purified by silica gel column chromatography eluting with ethyl acetate/petroleum ether (1:5) to provide 540 mg (76%) of (1S,4S,5R)-2-[4-[(tert-butoxy)carbonyl]-2-fluorophenyl]-2-azabicyclo[2.2.1]heptan-5-yl 3-(2,6-dichlorophenyl)-5-(1-fluorocyclopropyl)-1,2-oxazole-4-carboxylate 44a as a light yellow solid.

Step 2. 4-[(1S,4S,5R)-5-[[3-(2,6-dichlorophenyl)-5-(1-fluorocyclopropyl)-1,2-oxazol-4-yl]carbonyloxy]-2-azabicyclo[2.2.1]heptan-2-yl]-3-fluorobenzoic Acid (I-44)

To a 25-mL round-bottom flask purged and maintained under an inert atmosphere of nitrogen, was added (1S,4S,5R)-2-[4-[(tert-butoxy)carbonyl]-2-fluorophenyl]-2-azabicyclo[2.2.1]heptan-5-yl 3-(2,6-dichlorophenyl)-5-(1-fluorocyclopropyl)-1,2-oxazole-4-carboxylate 44a (110 mg, 0.18 mmol, 1.0 equiv), dichloromethane (2 mL), and trifluoroacetic acid (1 mL) and the resulting mixture was stirred at room temperature for 0.5 h. The mixture was diluted with 50 mL of $H_2O$ and extracted with ethyl acetate (50 mL×3). The combined organic extracts were washed with brine (20 mL×3), dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, water (0.05% TFA) and ACN (68.0% to 83.0% over 8 min); Detector, UV 254 nm, to provide 56 mg (56%) of 4-[(1S,4S,5R)-5-[[3-(2,6-dichlorophenyl)-5-(1-fluorocyclopropyl)-1,2-oxazol-4-yl]carbonyloxy]-2-azabicyclo[2.2.1]heptan-2-yl]-3-fluorobenzoic acid I-44 as an off-white solid. $^1H$ NMR (300 MHz, DMSO-$d_6$) δ: 12.49 (s, 1H), 7.78-7.42 (m, 5H), 6.70 (t, J=8.8 Hz, 1H), 4.93-4.83 (m, 1H), 4.27 (s, 1H), 3.55 (dd, J=9.1, 4.8 Hz, 1H), 2.93 (dd, J=9.9, 3.5 Hz, 1H), 2.44 (d, J=3.9 Hz, 1H), 2.19-2.05 (m, 1H), 1.81-1.52 (m, 5H), 1.24 (dd, J=22.8, 12.2 Hz, 2H. MS (ES, m/z): [M+1]=549.2.

Example 51: Synthesis of Compounds I-45 to I-47

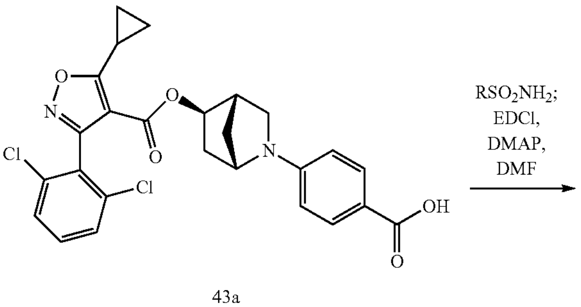

43a

-continued

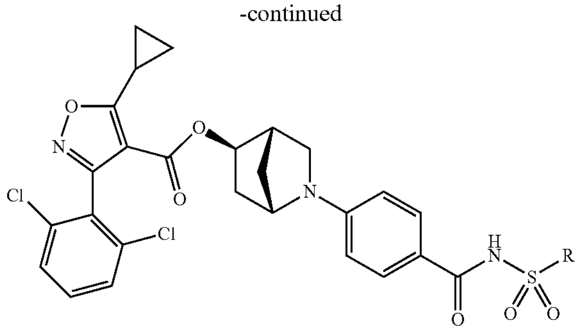

I-x

I-45, I-46, and I-47 were prepared from I-42 following the procedure described in Preparative Example 34. The data is summarized in Table 4.

Example 52: Synthesis of I-48 and I-49

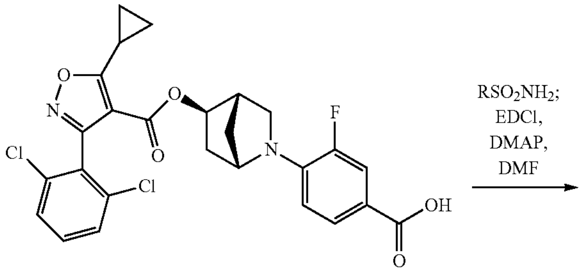

I-43

TABLE 4

| Cmpd Structure | Cmpd No. | MS/$^1$H NMR |
|---|---|---|
| 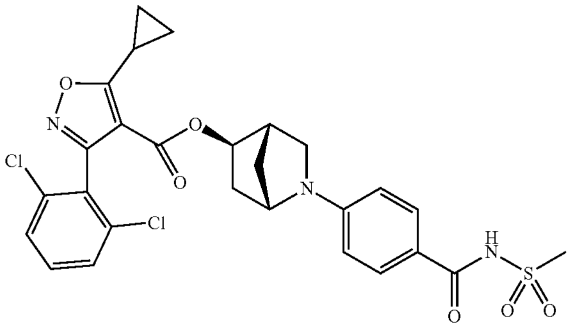 [SMILES: CS(=O)(=O)NC(=O)c1ccc(N2C[C@@H]3C[C@H]2C[C@H]3OC(=O)c2c(-c3c(Cl)cccc3Cl)noc2C2CC2)cc1] | I-45 | MS (ES, m/z): [M + 1] = 590.0. $^1$H NMR (400 MHz, $CD_3OD$) δ: 7.73 (d, J = 8.9 Hz, 2H), 7.61-7.48 (m, 3H), 6.59-6.51 (m, 2H), 4.90 (s, 1H), 4.83 (d, J = 6.8 Hz, 1H), 4.21 (s, 1H), 3.41 (dd, J = 9.7, 4.1 Hz, 1H), 3.32 (s, 2H), 2.97 (p, J = 6.8 Hz, 1H), 2.80 (d, J = 9.7 Hz, 1H), 2.47 (s, 1H), 2.10-1.99 (m, 1H), 1.57 (d, J = 10.1 Hz, 1H), 1.37-1.19 (m, 6H). |
| 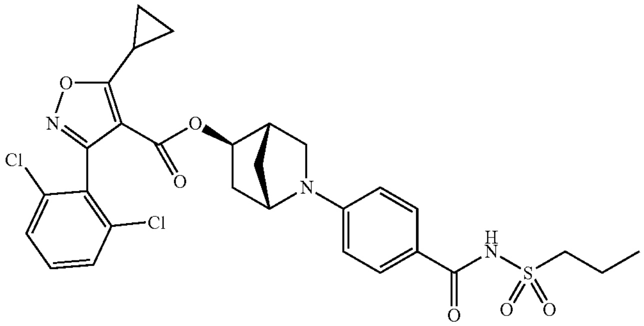 [SMILES: CCCS(=O)(=O)NC(=O)c1ccc(N2C[C@@H]3C[C@H]2C[C@H]3OC(=O)c2c(-c3c(Cl)cccc3Cl)noc2C2CC2)cc1] | I-46 | MS (ES, m/z): [M + 1] = 618.0. $^1$H NMR (400 MHz, $CD_3OD$) δ: 7.73 (d, J = 8.9 Hz, 2H), 7.61-7.48 (m, 3H), 6.59-6.51 (m, 2H), 4.83 (d, J = 6.8 Hz, 1H), 4.21 (s, 1H), 3.52-3.37 (m, 3H), 2.97 (p, J = 6.8 Hz, 1H), 2.84-2.76 (m, 1H), 2.47 (s, 1H), 2.05 (ddd, J = 13.9, 7.2, 2.6 Hz, 1H), 1.90-1.76 (m, 2H), 1.57 (d, J = 10.3 Hz, 1H), 1.37-1.19 (m, 7H), 1.06 (t, J = 7.5 Hz, 3H). |
| 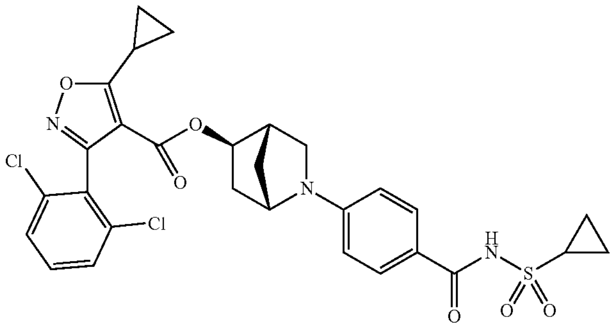 [SMILES: O=C(NS(=O)(=O)C1CC1)c1ccc(N2C[C@@H]3C[C@H]2C[C@H]3OC(=O)c2c(-c3c(Cl)cccc3Cl)noc2C2CC2)cc1] | I-47 | MS (ES, m/z): [M + 1] = 616.0. $^1$H NMR (400 MHz, $CD_3OD$) δ:) 7.76-7.69 (m, 2H), 7.61-7.48 (m, 3H), 6.59-6.51 (m, 2H), 4.88 (s, 1H), 4.21 (s, 1H), 3.41 (dd, J = 9.7, 4.1 Hz, 1H), 3.16-3.07 (m, 1H), 2.97 (p, J = 6.8 Hz, 1H), 2.80 (d, J = 9.8 Hz, 1H), 2.47 (s, 1H), 2.09-2.00 (m, 1H), 1.57 (d, J = 10.1 Hz, 1H), 1.37-1.19 (m, 8H), 1.15-1.04 (m, 2H). |

-continued

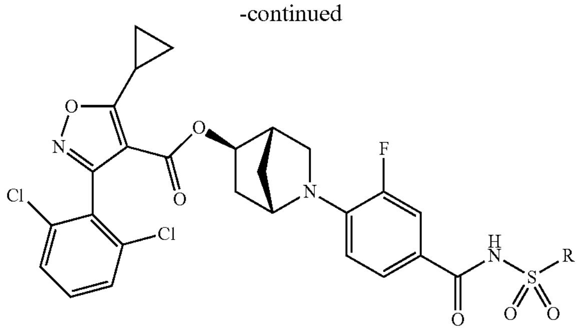

I-x

I-48 and I-49 were prepared from I-43 following the procedure described in Preparative Example 34. The data is summarized in Table 5.

TABLE 5

| Cmpd Structure | Cmpd No. | MS/$^1$H NMR |
| --- | --- | --- |
| 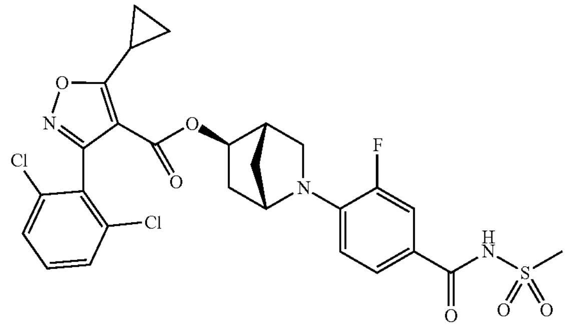 [SMILES: CS(=O)(=O)NC(=O)c1ccc(N2C[C@@H]3C[C@H]2C[C@H]3OC(=O)c2c(-c3c(Cl)cccc3Cl)noc2C2CC2)c(F)c1] | I-48 | MS (ES, m/z): [M + 1] = 608.0. $^1$H NMR (400 MHz, $CD_3OD$) δ: 7.73 (d, J = 8.9 Hz, 2H), 7.61-7.48 (m, 5H), 6.66 (t, J = 8.8 Hz, 1H), 4.84 (d, J = 6.8 Hz, 1H), 4.29 (s, 1H), 3.65-3.55 (m, 1H), 3.32 (s, 3H), 3.01-2.89 (m, 2H), 2.43 (s, 1H), 2.16 (ddd, J = 14.1, 7.1, 2.5 Hz, 1H), 1.57 (d, J = 10.4 Hz, 1H), 1.34 (d, J = 6.7 Hz, 4H), 1.28-1.18 (m, 2H). |
| 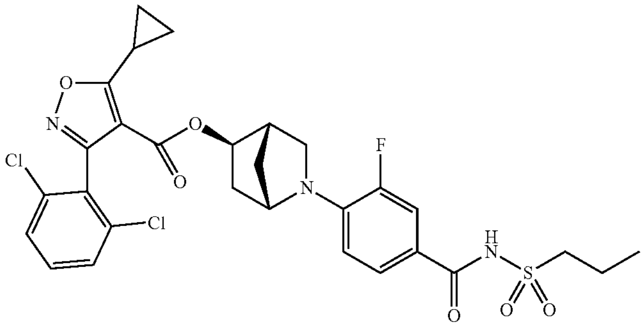 [SMILES: CCCS(=O)(=O)NC(=O)c1ccc(N2C[C@@H]3C[C@H]2C[C@H]3OC(=O)c2c(-c3c(Cl)cccc3Cl)noc2C2CC2)c(F)c1] | I-49 | MS (ES, m/z): [M + 1] = 636.0. $^1$H NMR (400 MHz, $CD_3OD$) δ: 7.64-7.50 (m, 5H), 6.69 (t, J = 8.8 Hz, 1H), 4.90 (s, 12H), 4.31 (s, 1H), 3.67-3.57 (m, 1H), 3.54-3.45 (m, 2H), 3.04-2.91 (m, 2H), 2.45 (d, J = 3.8 Hz, 1H), 2.18 (ddd, J = 13.9, 7.3, 2.5 Hz, 1H), 1.92-1.78 (m, 2H), 1.59 (d, J = 10.3 Hz, 1H), 1.36 (d, J = 6.7 Hz, 4H), 1.30-1.20 (m, 2H), 1.08 (t, J = 7.5 Hz, 3H). |

Example 53: (1S,4S,5R)-2-[4-(2H-1,2,3,4-tetrazol-5-yl)phenyl]-2-azabicyclo[2.2.1]heptan-5-yl 5-cyclopropyl-3-(2,6-dichlorophenyl)-1,2-oxazole-4-carboxylate (I-50)

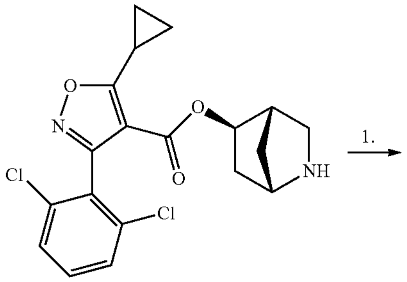

1j

-continued

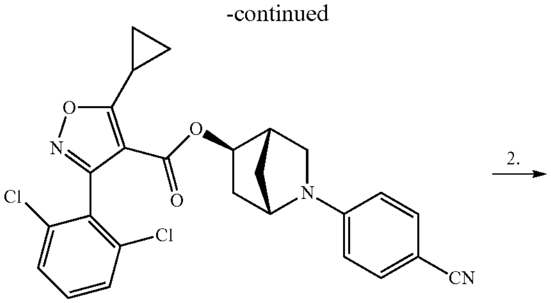

50a

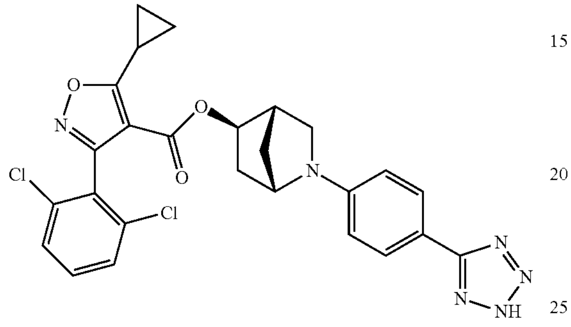

I-50

Step 1. (1S,4S,5R)-2-(4-cyanophenyl)-2-azabicyclo[2.2.1]heptan-5-yl 5-cyclopropyl-3-(2,6-dichlorophenyl)-1,2-oxazole-4-carboxylate (50a)

To a 250-mL round-bottom flask purged and maintained under an inert atmosphere of nitrogen was added a solution of (1S,4S,5R)-2-azabicyclo[2.2.1]heptan-5-yl 5-cyclopropyl-3-(2,6-dichlorophenyl)-1,2-oxazole-4-carboxylate 1j (200 mg, 0.51 mmol, 1.0 equiv.) in toluene (20 mL), 4-bromobenzonitrile (101 mg, 0.55 mmol, 1.10 equiv.), $Cs_2CO_3$ (232 mg, 0.71 mmol, 1.40 equiv.), BINAP (623 mg, 1.00 mmol, 0.10 equiv.), and $Pd_2(dba)_3$ (916 mg, 1.00 mmol, 0.10 equiv.) and the resulting mixture was stirred at 110° C., overnight. The mixture was concentrated under reduced pressure and the resulting residue was purified by silica gel column chromatography eluting with ethyl acetate/petroleum ether (1:5) to give 220 mg (88%) of (1S,4S,5R)-2-(4-cyanophenyl)-2-azabicyclo[2.2.1]heptan-5-yl 5-cyclopropyl-3-(2,6-dichlorophenyl)-1,2-oxazole-4-carboxylate 50a as a light yellow solid.

Step 2. (1S,4S,5R)-2-[4-(2H-1,2,3,4-tetrazol-5-yl)phenyl]-2-azabicyclo[2.2.1]heptan-5-yl 5-cyclopropyl-3-(2,6-dichlorophenyl)-1,2-oxazole-4-carboxylate (I-50)

To a 25-mL round-bottom flask was added (1S,4S,5R)-2-(4-cyanophenyl)-2-azabicyclo[2.2.1]heptan-5-yl 5-cyclopropyl-3-(2,6-dichlorophenyl)-1,2-oxazole-4-carboxylate 50a (50 mg, 0.10 mmol, 1.0 equiv.), m-xylene (5 mL), and n-$Bu_3SnN_3$ (47 mg, 0.14 mmol, 1.40 equiv.) and the resulting mixture was stirred at 140° C., for 1 d. The mixture was diluted with 50 mL of $H_2O$ and extracted with ethyl acetate (50 mL×2). The combined organic extracts were washed with brine (50 mL×2), dried over anhydrous sodium sulfate, filtered, and concentrated under reduced pressure. The crude product was purified by Prep-HPLC using the following conditions: Column, XBridge C18 OBD Prep Column, up to 75.0% in 8 min); Detector, UV 254 nm, to provide 10.0 mg (18%) of (1S,4S,5R)-2-[4-(2H-1,2,3,4-tetrazol-5-yl)phenyl]-2-azabicyclo[2.2.1]heptan-5-yl 5-cyclopropyl-3-(2,6-dichlorophenyl)-1,2-oxazole-4-carboxylate I-50 as a white solid. $^1H$ NMR (300 MHz, $CD_3OD$) δ: 7.85-7.73 (m, 2H), 7.65-7.49 (m, 3H), 6.74-6.62 (m, 2H), 4.85 (d, J=6.6 Hz, 1H), 4.21 (s, 1H), 3.46 (dd, J=9.6, 4.1 Hz, 1H), 2.99 (p, J=6.8 Hz, 1H), 2.79 (d, J=9.7 Hz, 1H), 2.49 (s, 1H), 2.17-2.02 (m, 1H), 1.61 (d, J=10.1 Hz, 1H), 1.41-1.19 (m, 7H). MS (ES, m/z): [M+1]=537.0.

Example 54: (1S,4S,5R)-2-[2-fluoro-4-(2H-1,2,3,4-tetrazol-5-yl)phenyl]-2-azabicyclo[2.2.1]heptan-5-yl 5-cyclopropyl-3-(2,6-dichlorophenyl)-1,2-oxazole-4-carboxylate (I-51)

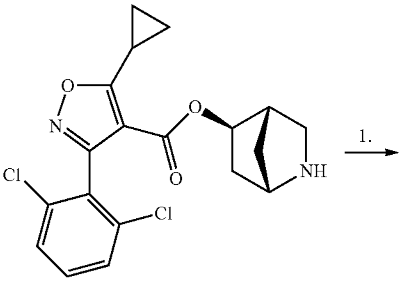

1j

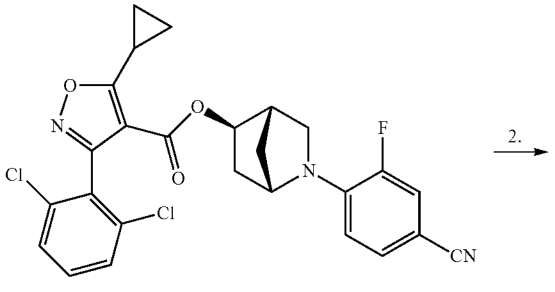

51a

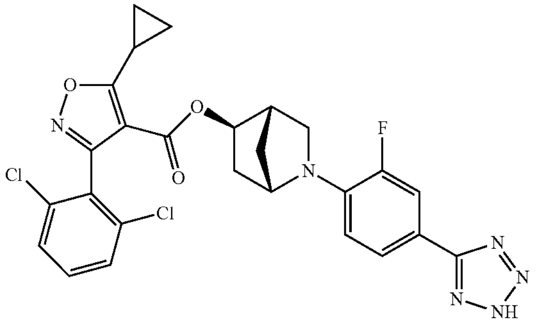

I-51

Step 1. (1S,4S,5R)-2-(4-cyano-2-fluorophenyl)-2-azabicyclo[2.2.1]heptan-5-yl 5-cyclopropyl-3-(2,6-dichlorophenyl)-1,2-oxazole-4-carboxylate (51a)

To a 50-mL round-bottom flask purged and maintained under an inert atmosphere of nitrogen was added (1S,4S,5R)-2-azabicyclo[2.2.1]heptan-5-yl 5-cyclopropyl-3-(2,6-dichlorophenyl)-1,2-oxazole-4-carboxylate 1j (300 mg, 0.76 mmol, 1.0 equiv.), toluene (6 mL), $Cs_2CO_3$ (348 mg, 1.07 mmol, 1.40 equiv.), 4-bromo-3-fluorobenzonitrile (182 mg, 0.91 mmol, 1.20 equiv), $Pd_2(dba)_3$ (70 mg, 0.08 mmol, 0.10 equiv.), and BINAP (48 mg, 0.08 mmol, 0.10 equiv.) and the resulting mixture was stirred at 110° C., for 16 h. The reaction was quenched by the addition of 50 mL of ice/salt and the aqueous mixture was extracted with ethyl acetate (50 mL×3). The combined organic extracts were washed with salt/water (100 mL×3), dried over anhydrous sodium sulfate, filtered, and concentrated under reduced pressure to give 250 mg (64%) of (1S,4S,5R)-2-(4-cyano-2-fluorophenyl)-2-azabicyclo[2.2.1]heptan-5-yl 5-cyclopropyl-3-(2,6-dichlorophenyl)-1,2-oxazole-4-carboxylate 51a as a colorless solid. The crude product was carried onto the next step without further purification.

Step 2. (1S,4S,5R)-2-[2-fluoro-4-(2H-1,2,3,4-tetrazol-5-yl)phenyl]-2-azabicyclo[2.2.1]heptan-5-yl 5-cyclopropyl-3-(2,6-dichlorophenyl)-1,2-oxazole-4-carboxylate (I-51)

To a 50-mL round-bottom flask was added (1S,4S,5R)-2-(4-cyano-2-fluorophenyl)-2-azabicyclo[2.2.1]heptan-5-yl 5-cyclopropyl-3-(2,6-dichlorophenyl)-1,2-oxazole-4-carboxylate 51a (100 mg, 0.20 mmol, 1.0 equiv.), m-xylene (6 mL), and $n\text{-}Bu_3SnN_3$ (91 mg, 1.40 equiv.) and the resulting mixture was stirred at 140° C., for 16 h. The reaction was quenched by the addition of 100 mL of water and the aqueous mixture was extracted with ethyl acetate (100 mL×3). The combined organic extracts were dried over anhydrous sodium sulfate and concentrated under reduced pressure. The residue was dissolved in 2 mL of DMF and purified by Prep-HPLC using the following conditions: Column, XBridge C18 OBD Prep Column, 19 mm×250 mm; mobile phase, water (0.05% TFA) and ACN (68.0% to 82.0% over 8 min); Detector, UV 254 nm, to provide 24.2 mg (22%) of (1S,4S,5R)-2-[2-fluoro-4-(2H-1,2,3,4-tetrazol-5-yl)phenyl]-2-azabicyclo[2.2.1]heptan-5-yl 5-cyclopropyl-3-(2,6-dichlorophenyl)-1,2-oxazole-4-carboxylate I-51 as a colorless solid. $^1H$ NMR (400 MHz. DMSO-$d_6$) δ: 7.74-7.59 (m, 5H), 6.85 (t, J=8.9 Hz, 1H), 4.88-4.82 (m, 1H), 4.22 (s, 1H), 3.55 (dt, J=10.0, 4.1 Hz, 1H), 2.95-2.83 (m, 2H), 2.39-2.32 (m, 1H), 2.17-2.06 (m, 1H), 1.53 (d, J=10.1 Hz, 1H), 1.42-1.13 (m, 6H), 1.08 (d, J=9.9 Hz, 1H), 0.87 (dt, J=11.6, 7.2 Hz, 1H). MS (ES, m/z): [M+1]=555.20.

Example 55: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoic Acid (I-52)

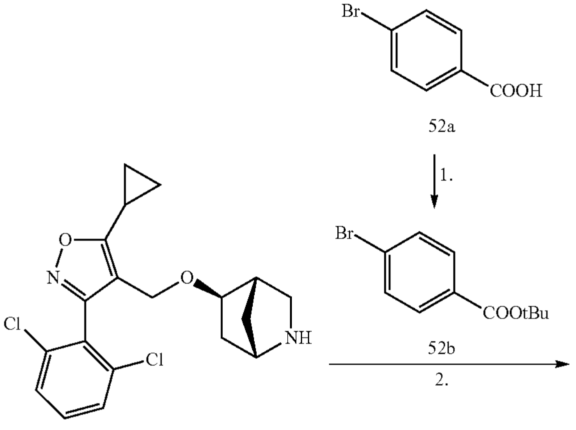

52a

52b

12d

-continued

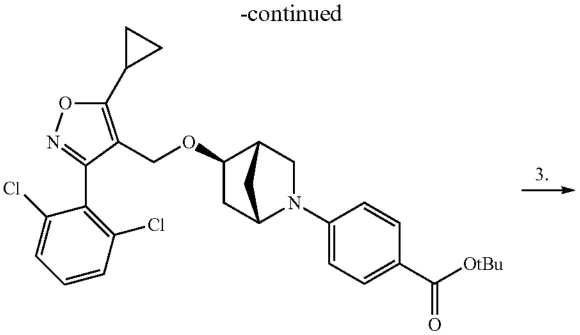

52c

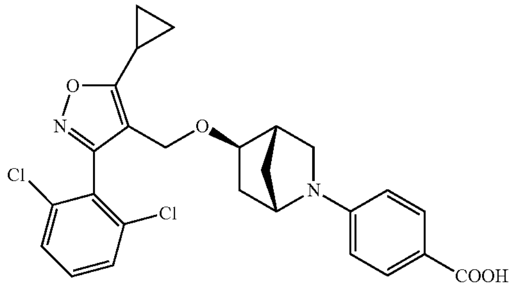

I-52

Step 1. Tert-butyl 4-bromobenzoate (52b)

To a 1000-mL round-bottom flask was added 4-bromobenzoic acid 52a (20 g, 99.49 mmol, 1.0 equiv.), tert-butanol (200 mL), 4-dimethylaminopyridine (1.22 g, 9.99 mmol, 0.10 equiv.), and $Boc_2O$ (32.7 g, 149.83 mmol, 1.50 equiv.) and the resulting mixture was stirred at 50° C., overnight. The mixture was diluted with 200 mL of $H_2O$ and extracted with ethyl acetate (300 mL×2). The combined organic extracts were washed with brine (300 mL×2), dried over anhydrous sodium sulfate, filtered, and concentrated under reduced pressure. The crude product was purified by Flash-Prep-HPLC using the following conditions: Column, silica gel; mobile phase, PE:EA=100:0 increasing to 90:10 over 5 min; Detector, UV 254 nm, to provide 5.43 g (21%) of tert-butyl 4-bromobenzoate 52b as a colorless oil.

Step 2. Tert-butyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoate (52c)

To a 50-mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane 12d (800 mg, 2.11 mmol, 1.0 equiv.), tert-butyl 4-bromobenzoate 52b (650 mg, 2.53 mmol, 1.20 equiv.), $Pd_2(dba)_3$ (190 mg, 0.21 mmol, 0.10 equiv.), BINAP (130 mg, 0.21 mmol, 0.10 equiv), $Cs_2CO_3$ (960 mg, 2.95 mmol, 1.40 equiv.), and toluene (5 mL) and the resulting mixture was stirred at 110° C., overnight. After cooling to room temperature, 100 mL of $H_2O$ was added and the aqueous mixture was extracted with ethyl acetate (100 mL×2). The combined organic extracts were washed with brine (100 mL×2), dried over anhydrous sodium sulfate, filtered, and concentrated under reduced pressure. The residue was purified by silica gel column chromatography eluting with ethyl acetate/petroleum ether (1:6) to give 0.55 g (47%) of tert-butyl 4-[(1S,4S,5R)-5-[[5- cyclopropyl-3-(2,6-dichlorophenyl)-1,2-oxazol-4-yl]methoxy]-2-azabicyclo[2.2.1]heptan-2-yl]benzoate 52c as a light green solid.

Step 3. 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic Acid (I-52)

To a 100-mL round-bottom flask was added tert-butyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoate 52c (550 mg, 0.99 mmol, 1.0 equiv), dichloromethane (10 mL), and trifluoroacetic acid (5 mL). The resulting mixture was stirred at room temperature for 1 h and then quenched with 50 mL of brine. The pH of the solution was adjusted to 7 using aqueous sodium bicarbonate and the aqueous mixture was extracted with ethyl acetate (100 mL×2). The combined organic extracts were washed with brine, dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, water (0.05% TFA) and ACN (hold 67.0% ACN for 8 min); Detector, UV 254 nm, to provide 34.5 mg (7%) of 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-52 as an off-white solid. $^1$H NMR (300 MHz, $CD_3OD$) δ: 7.86-7.75 (m, 2H), 7.61-7.45 (m, 3H), 6.55-6.45 (m, 2H), 4.91 (s, 9H), 4.32 (s, 2H), 4.17 (s, 1H), 3.51 (d, J=6.2 Hz; 1H), 3.39 (dd, J=9.4, 4.1 Hz, 1H), 2.60 (d, J=9.4 Hz, 1H), 2.52 (s, 1H), 2.36-2.20 (m, 1H), 1.82 (dd, J=14.1, 5.9 Hz, 1H), 1.61 (t, J=8.4 Hz, 2H), 1.31 (d, J=13.1 Hz, 2H), 1.23-1.14 (m, 4H). MS (ES, m/z): [M+1]=499.0.

Example 56: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorobenzoic Acid (I-53)

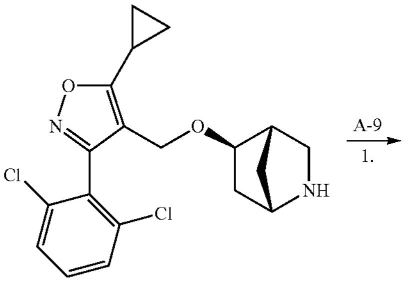

12d

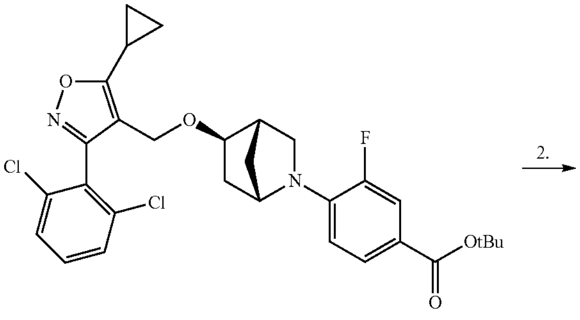

53a

-continued

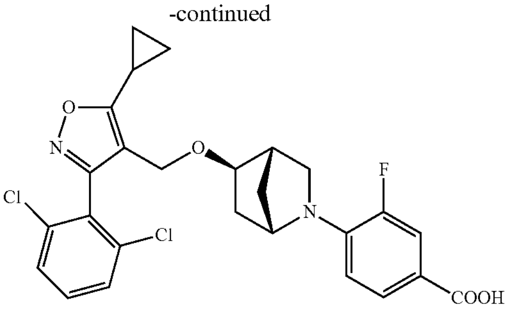

I-53

Step 1. Tert-butyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzoate (53a)

To a 50-mL round-bottom flask purged and maintained under an inert atmosphere of nitrogen was added a solution of (1S,4S,5R)-5-[[5-cyclopropyl-3-(2,6-dichlorophenyl)-1,2-oxazol-4-yl]methoxy]-2-azabicyclo[2.2.1]heptane 12d (100 mg, 0.26 mmol, 1.0 equiv.) in toluene (3 mL), tert-butyl 4-bromo-3-fluorobenzoate A-9 (85 mg, 0.31 mmol, 1.10 equiv.), $Cs_2CO_3$ (120 mg, 0.37 mmol, 1.40 equiv.), BINAP (16 mg, 0.03 mmol, 0.10 equiv.), and $Pd_2(dba)_3$ (24 mg, 0.03 mmol, 0.10 equiv.). The resulting mixture was stirred at 110° C., for 2 d and then concentrated under reduced pressure. The residue was purified by silica gel column chromatography eluting with ethyl acetate/petroleum ether (1:5) to give 100 mg (66%) of tert-butyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzoate 53a as a yellow solid.

Step 2. 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzoic Acid (I-53)

To a 50-mL round-bottom flask containing a solution of tert-butyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzoate 53a (100 mg, 0.17 mmol, 1.0 equiv.) in dichloromethane (4 mL), was added trifluoroacetic acid (2 mL). The resulting mixture was stirred at room temperature for 2 h and then diluted with 30 mL of ethyl acetate. The organic extract was washed with brine (30 mL×3), dried over anhydrous sodium sulfate, filtered, and concentrated under reduced pressure. The crude product was purified by Prep-HPLC using the following conditions: Column, XBridge C18 OBD Prep Column, 19 mm×250 mm; mobile phase, water (0.05% TFA) and ACN (68.0% to 75.0% over 9 min); Detector, UV 254 nm to provide 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzoic acid I-53 as an off-white solid (30.7 mg, 34%). $^1$H NMR (300 MHz. $CD_3OD$) δ: 7.69-7.43 (m, 5H), 6.62 (t, J=8.8 Hz, 1H), 4.32 (s, 2H), 4.25 (s, 1H), 3.63-3.47 (m, 2H), 2.73 (dd, J=9.8, 3.4 Hz, 1H), 2.48 (s, 1H), 2.28 (p, J=6.8 Hz, 1H), 1.93 (dd, J=13.6, 7.0 Hz, 1H), 1.59 (s, 2H), 1.32 (d, J=13.4 Hz, 1H), 1.18 (d, J=6.7 Hz, 4H). MS (ES, m/z): [M+1]=517.0.

Example 57: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3,5-difluorobenzoic Acid (I-54)

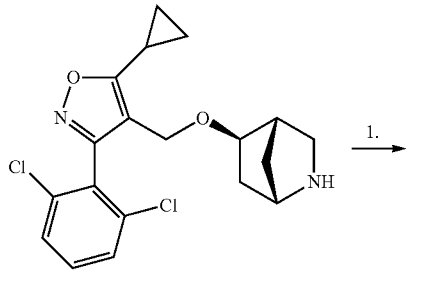

12d

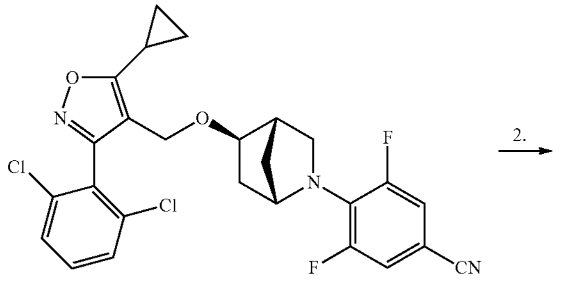

I-54a

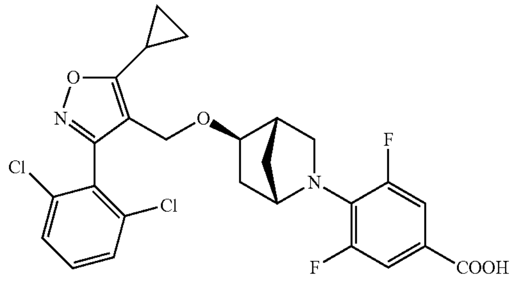

I-54

Step 1. 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3,5-difluorobenzonitrile (I-54a)

To a 50-mL round-bottom flask was added a solution of (1S,4S,5R)-5-[[5-cyclopropyl-3-(2,6-dichlorophenyl)-1,2-oxazol-4-yl]methoxy]-2-azabicyclo[2.2.1]heptane 12d (100 mg, 0.26 mmol, 1.0 equiv.) in toluene (5 mL), $Pd_2(dba)_3$ (24 mg, 0.03 mmol, 0.10 equiv.), $Cs_2CO_3$ (340 mg, 1.04 mmol, 4.0 equiv.), BINAP (16 mg, 0.03 mmol, 0.10 equiv.), and 4-bromo-3,5-difluorobenzonitrile (69 mg, 0.32 mmol, 1.20 equiv.) and the resulting mixture was stirred at 110° C., overnight. Upon cooling to room temperature, 100 mL of $H_2O$ was added and the aqueous mixture was extracted with ethyl acetate (100 mL×2). The combined organic extracts were washed with brine (100 mL×2), dried over anhydrous sodium sulfate, filtered, and concentrated under reduced pressure. The residue was purified by silica gel column chromatography eluting with ethyl acetate/petroleum ether (1:6) to give 55 mg (40%) of 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3,5-difluorobenzonitrile I-54a as a yellow green oil.

Step 2. 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3,5-difluorobenzoic Acid (I-54)

To a 50-mL round-bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3,5-difluorobenzonitrile I-54a (60 mg, 0.12 mmol, 1.0 equiv.), ethylene glycol (5 mL), and potassium hydroxide (65 mg, 1.16 mmol, 10.0 equiv.) and the resulting mixture was stirred at 140° C., overnight. After cooling to room temperature, 50 mL of $H_2O$ was added and the pH of the solution was adjusted to 3-4 with aqueous HCl (1M) and the resulting aqueous mixture was extracted with ethyl acetate (100 mL×2). The combined organic extracts were washed with brine (100 mL×2), dried over anhydrous sodium sulfate, filtered, and concentrated under reduced pressure. The resulting crude product was purified by Prep-HPLC using the following conditions: Column, XBridge C18 OBD Prep Column, 19 mm×250 mm; mobile phase, water (0.05% TFA) and ACN (hold 80.0% for 10 min); Detector, UV 254 nm, to provide 25.6 mg (41%) of 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3,5-difluorobenzoic acid I-54 as an off-white solid). $^1H$ NMR (300 MHz, $CD_3OD$) δ: 7.63-7.34 (m, 5H), 4.37-4.25 (m, 3H), 3.77 (dq, J=7.9, 4.0 Hz, 1H), 3.55 (d, J=6.5 Hz, 1H), 2.82 (d, J=10.2 Hz, 1H), 2.45 (s, 1H), 2.29 (p, J=6.8 Hz, 1H), 2.10-1.93 (m, 1H), 1.65-1.49 (m, 2H), 1.42-1.28 (m, 2H), 1.20 (d, J=6.7 Hz, 4H). MS (ES, m/z): [M+1]=535.0.

Example 58: 6-[(1S,4S,5R)-5-{[5-cyclopropyl-3-(2,6-dichlorophenyl)-1,2-oxazol-4-yl]methoxy}-2-azabicyclo[2.2.1]heptan-2-yl]pyridine-3-carboxylic Acid (I-55)

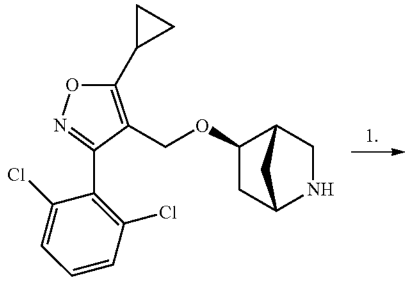

12d

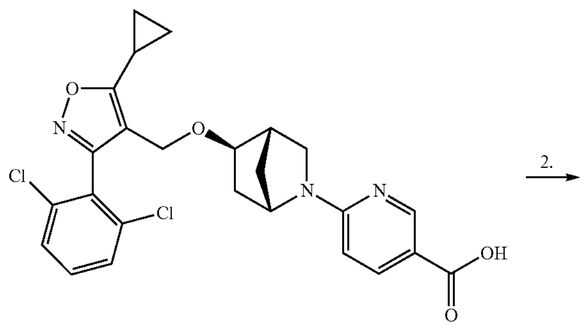

55a

-continued

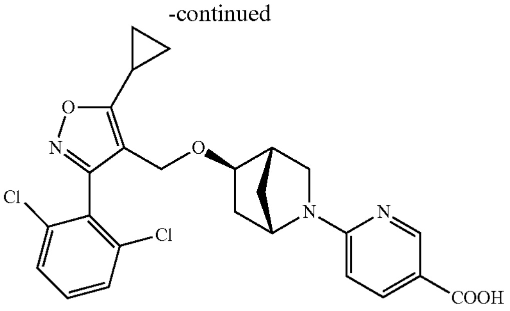

I-55

Step 1. Methyl 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyridine-3-carboxylate (55a)

To a 50-mL round-bottom flask was added a solution of (1S,4S,5R)-5-[[5-cyclopropyl-3-(2,6-dichlorophenyl)-1,2-oxazol-4-yl]methoxy]-2-azabicyclo[2.2.1]heptane 12d (100 mg, 0.26 mmol, 1.0 equiv.) in toluene (5 mL), methyl-6-bromopyridine-3-carboxylate (68 mg, 0.31 mmol, 1.2 equiv), $Cs_2CO_3$ (120 mg, 0.37 mmol, 1.4 equiv), BINAP (160 mg, 0.26 mmol, 0.1 equiv), and $Pd_2(dba)_3$ (24 mg, 0.03 mmol, 0.10 equiv.) and the resulting mixture was stirred at 110° C., overnight. After cooling to room temperature, 100 mL of $H_2O$ was added and the resulting aqueous mixture was extracted with ethyl acetate (100 mL×2). The combined organic extracts were washed with brine (100 mL×2), dried over anhydrous sodium sulfate, filtered, and concentrated under reduced pressure. The residue was purified by silica gel column chromatography eluting with ethyl acetate/petroleum ether (1:8) to provide 40 mg (29%) of methyl 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyridine-3-carboxylate 55a as a red oil.

Step 2. 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyridine-3-carboxylic Acid (I-55)

To a 25-mL round-bottom flask was added a solution of methyl 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyridine-3-carboxylate 55a (40 mg, 0.08 mmol, 1.0 equiv.) in methanol/$H_2O$ (4/1 mL) followed by LiOH (33 mg, 1.38 mmol, 10.0 equiv.) and the resulting mixture was stirred at 50° C., overnight. 20 mL of $H_2O$ was then added and the pH of the solution was adjusted to 3-4 with aqueous HCl (1M) and the resulting aqueous mixture was extracted with ethyl acetate (100 mL×2). The combined organic extracts were washed with brine (100 mL×2), dried over anhydrous sodium sulfate, filtered, and concentrated under reduced pressure. The crude product was purified by Prep-HPLC using the following conditions: Column, XSelect CSH Prep C18 OBD Column, 5 um, 19×150 mm; mobile phase, water (0.05% TFA) and ACN (24.0% to 45.0% over 8 min); Detector, UV 254 nm, to provide 13.2 mg (34%) of 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyridine-3-carboxylic Acid I-55 as a colorless solid. $^1H$ NMR (400 MHz, DMSO-$d_6$) δ: 8.48 (d, J=2.5 Hz, 1H), 7.89 (d, J=8.1 Hz, 1H), 7.67-7.51 (m, 3H), 6.47 (s, 1H), 4.31-4.18 (m, 2H), 3.50 (d, J=6.4 Hz, 1H), 3.31 (d, J=9.9 Hz, 1H), 2.83 (s, 1H), 2.38-2.26 (m, 1H), 1.72 (s, 1H), 1.44 (q, J=9.9 Hz, 2H), 1.21-1.03 (m, 5H). MS (ES, m/z): [M+1]=500.0.

Example 59: 4-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]benzoic Acid (I-56)

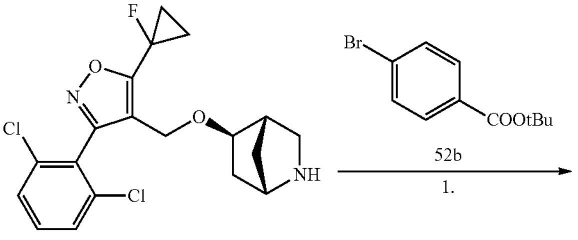

24d

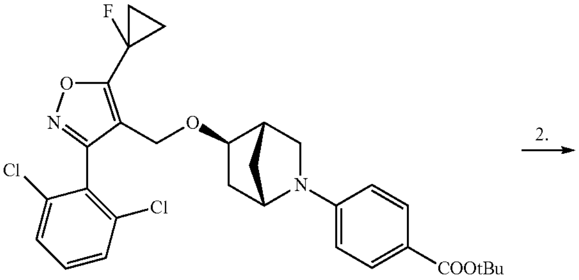

56a

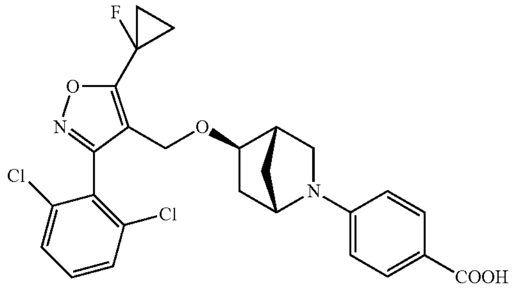

I-56

Step 1. Tert-butyl 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]benzoate (56a)

To a 100-mL round-bottom flask purged and maintained under an inert atmosphere of nitrogen was added (1S,4S,5R)-5-[[3-(2,6-dichlorophenyl)-5-(1-fluorocyclopropyl)-1,2-oxazol-4-yl]methoxy]-2-azabicyclo[2.2.1]heptane 24d (200 mg, 0.5 mmol, 1.0 equiv.), tert-butyl 4-bromobenzoate (155 mg, 0.6 mmol, 1.2 equiv.), $Cs_2CO_3$ (491 mg, 1.51 mmol, 3.0 equiv.), Toluene (3 mL), BINAP (63 mg, 0.10 mmol, 0.20 equiv.), and $Pd_2(dba)_3$ (92 mg, 0.1 mmol, 0.20 equiv.) and the resulting mixture was stirred at 110° C., for 2 d. The resulting mixture was diluted with 100 mL water at room temperature, and extracted with ethyl acetate (100 mL×3). The combined organic extracts were washed with brine (50 mL×3), dried over anhydrous sodium sulfate, filtered, and concentrated under reduced pressure. The residue was purified by silica gel column chromatography eluting with ethyl acetate/petroleum ether (1/5) to afford 90 mg (31%) of tert-butyl 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]benzoate 56a as a light yellow solid Step 2. 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]benzoic Acid (I-56)

To a 25-mL round-bottom flask was added tert-butyl 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]benzoate 56a (90 mg, 0.16 mmol, 1.0 equiv.), dichloromethane (2 mL), and trifluoroacetic acid (1 mL) and the resulting mixture was stirred at room temperature for 1 h. $H_2O$ was added and the pH of the solution was adjusted to 9 using aqueous sodium bicarbonate (10%). The aqueous mixture was extracted with ethyl acetate (50 mL×3) and the combined organic extracts were washed with brine (30 mL×3), dried over anhydrous sodium sulfate, filtered, and concentrated under reduced pressure. The residue was purified by Prep-HPLC using the following conditions: Column, XBridge C18 OBD Prep Column: 5 μm, 19 mm×250 mm; mobile phase, water (0.05% TFA) and ACN (60.0% to 85.0% over 8 min); Detector, UV 254 nm, to provide 37.6 mg (46%) of 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]benzoic acid I-56 as an off-white solid. $^1$H NMR (400 MHz, $CD_3OD$) δ: 7.82-7.74 (m, 2H), 7.61-7.45 (m, 3H), 6.52-6.43 (m, 2H), 4.42 (t, 0.1=1.2 Hz, 2H), 4.13 (d, J=2.1 Hz, 1H), 3.36 (dd, J=9.4, 4.1 Hz, 1H), 2.57 (d, J=9.4 Hz, 1H), 2.48 (s, 1H), 1.80 (dd, J=13.4, 6.7 Hz, 1H), 1.68-1.51 (m, 4H), 1.47-1.36 (m, 2H), 1.25 (dt, J=13.2, 2.7 Hz, 1H). MS (ES, m/z): [M+1]=517.15.

Example 60: 4-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-3-fluorobenzoic Acid (I-57)

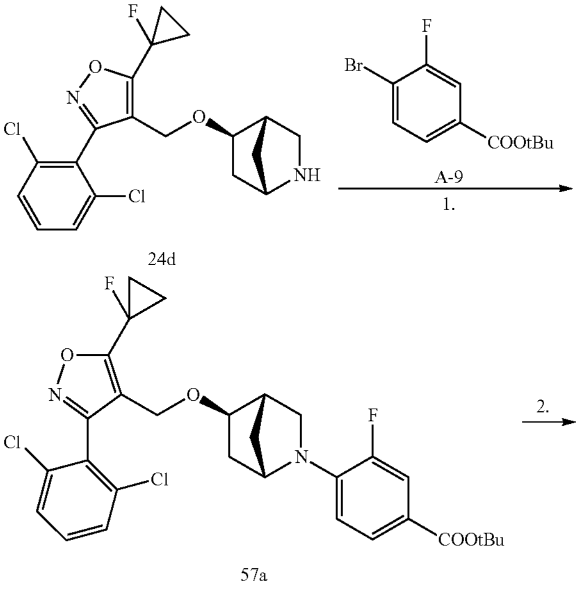

-continued

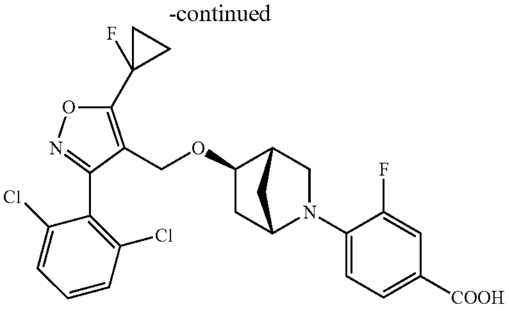

I-57

Step 1. Tert-butyl 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-3-fluorobenzoate (57a)

To a 100-mL round-bottom flask purged and maintained under an inert atmosphere of nitrogen was added (1S,4S,5R)-5-[[3-(2,6-dichlorophenyl)-5-(1-fluorocyclopropyl)-1,2-oxazol-4-yl]methoxy]-2-azabicyclo[2.2.]heptane 24d (600 mg, 1.51 mmol, 1.0 equiv.), tert-butyl 4-bromo-3-fluorobenzoate A-9 (396 mg, 1.44 mmol, 1.20 equiv.), $Cs_2CO_3$ (1.49 g, 4.57 mmol, 3.0 equiv.), toluene (6 mL), BINAP (189 mg, 0.30 mmol, 0.20 equiv.), and $Pd_2(dba)_3$ (304 mg, 0.33 mmol, 0.20 equiv.) and the resulting mixture was stirred at 110° C., for 2 d. The mixture was cooled to room temperature and then diluted with water (100 mL). The aqueous mixture was extracted with ethyl acetate (100 mL×3) and the combined organic extracts were washed with brine (50 mL×3), dried over anhydrous sodium sulfate, filtered, and concentrated under reduced pressure. The residue was purified by silica gel column chromatography eluting with ethyl acetate/petroleum ether (1/5) to give 300 mg (34%) of tert-butyl 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-3-fluorobenzoate 57a as a light yellow oil.

Step 2. 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-3-fluorobenzoic Acid (I-57)

To a 25-mL round-bottom flask was added tert-butyl 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-3-fluorobenzoate 57a (50 mg, 0.08 mmol, 1.0 equiv.), dichloromethane (2 mL), and trifluoroacetic acid (1 mL). The resulting mixture was stirred at room temperature for 1 h and then diluted with 20 mL of DCM. 10 mL of water was added and the pH value of the solution was adjusted to 9 using aqueous sodium bicarbonate (10%) and the resulting aqueous mixture was extracted ethyl acetate (80 mL×2). The combined organic extracts were washed with brine (30 mL×2), dried over anhydrous sodium sulfate, filtered, and concentrated under reduced pressure. The crude product was purified by Prep-HPLC using the following conditions: Column, XBridge C18 OBD Prep Column, 5 μm, 19 mm×250 mm; mobile phase. Water (0.05% TFA) and ACN (58.0% to 88.0% over 8 min); Detector, UV 220 nm, to provide 9.3 mg (21%) of 4-[(1S,4S,5R)-5-[[3-(2,6-dichlorophenyl)-5-(1-fluorocyclopropyl)-1,2-oxazol-4-yl]

methoxy]-2-azabicyclo[2.2.1]heptan-2-yl]-3-fluorobenzoic acid I-57 an off-white solid. $^1$H NMR (300 MHz, DMSO-do) δ: 7.76-7.39 (m, 6H), 6.65 (t, J=8.9 Hz, 1H), 4.43-4.26 (m, 2H), 4.17 (s, 1H), 3.49 (t, J=5.9 Hz, 3H), 2.73-2.63 (m, 1H), 2.55 (s, 1H), 2.49-2.35 (m, 2H), 1.89-1.58 (m, 3H), 1.52-1.29 (m, 4H), 1.13 (d, J=13.8 Hz, 1H). MS (ES, m/z): [M+1]=535.2.

Example 61: Synthesis of I-58 to I-60

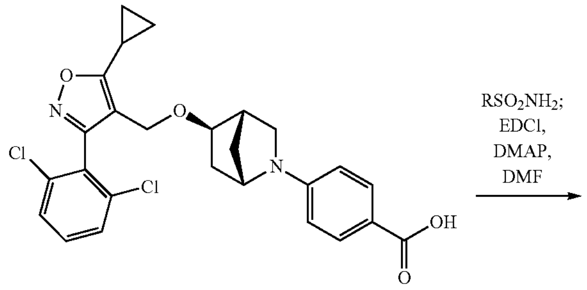

I-52

-continued

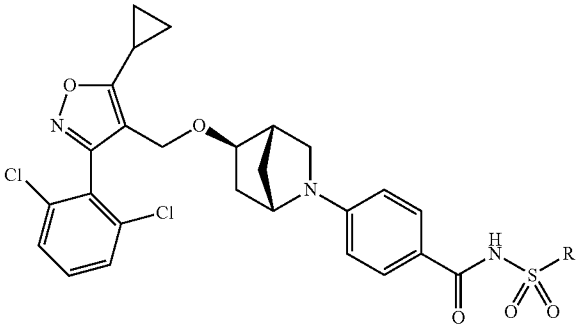

I-x

I-58, I-59 and I-60 were prepared from I-52 following the procedure described in Preparative Example 34. The data for compounds I-58, I-59 and I-60 is summarized in Table 6.

TABLE 6

| Cmpd Structure | Cmpd No. | MS/$^1$H NMR |
|---|---|---|
| 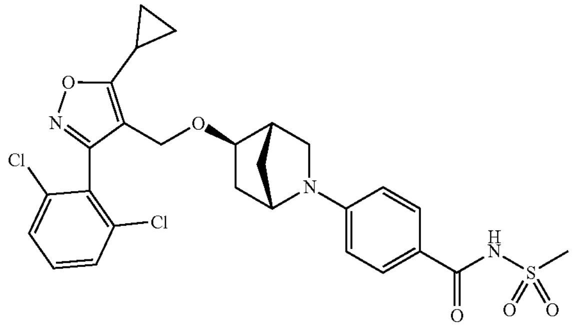 [SMILES: CS(=O)(=O)NC(=O)c1ccc(N2C[C@@H]3C[C@H]2C[C@H]3OCc2c(-c3c(Cl)cccc3Cl)noc2C2CC2)cc1] | I-58 | MS (ES, m/z): [M + 1] = 576.0. $^1$H NMR (400 MHz, $CD_3OD$) δ: 7.75 (d, J = 8.7 Hz, 2H), 7.60-7.47 (m, 3H), 6.54 (d, J = 8.7 Hz, 2H), 4.33 (s, 2H), 4.19 (d, J = 2.6 Hz, 1H), 3.53 (s, 1H), 3.39 (dd, J = 9.7, 4.3 Hz, 4H), 2.63 (d, J = 9.7 Hz, 1H), 2.53 (s, 1H), 2.29 (q, J = 6.7 Hz, 1H), 1.87-1.78 (m, 1H), 1.67-1.54 (m, 2H), 1.33 (d, J = 14.0 Hz, 2H), 1.22-1.15 (m, 4H). |
| 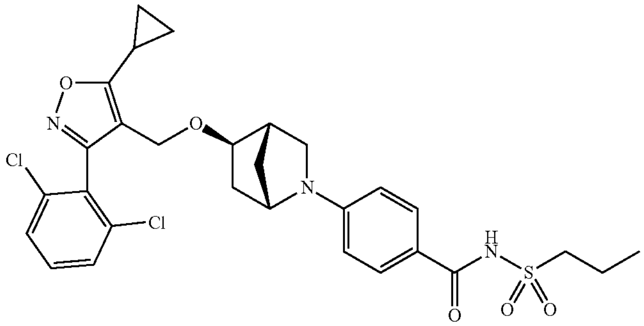 [SMILES: CCCS(=O)(=O)NC(=O)c1ccc(N2C[C@@H]3C[C@H]2C[C@H]3OCc2c(-c3c(Cl)cccc3Cl)noc2C2CC2)cc1] | I-59 | MS (ES, m/z): [M + 1] = 604.0. $^1$H NMR (300 MHz, $CD_3OD$) δ: 7.75 (d, J = 8.9 Hz, 2H), 7.62-7.46 (m, 3H), 6.59-6.49 (m, 2H), 4.92 (s, 15H), 4.33 (s, 2H), 4.20 (s, 1H), 3.56-3.33 (m, 5H), 2.68-2.58 (m, 1H), 2.54 (s, 1H), 2.28 (p, J = 6.7 Hz, 1H), 1.95-1.75 (m, 3H), 1.61 (q, J = 9.9 Hz, 2H), 1.39-1.27 (m, 1H), 1.23-1.03 (m, 7H). |

TABLE 6-continued

| Cmpd Structure | Cmpd No. | MS/$^1$H NMR |
|---|---|---|
| 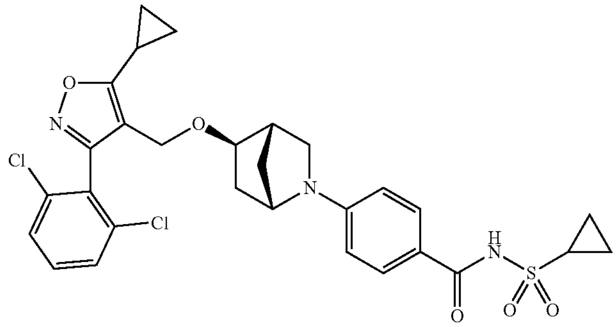 [SMILES: O=C(NS(=O)(=O)C1CC1)c1ccc(N2C[C@@H]3C[C@H]2C[C@H]3OCc2c(-c3c(Cl)cccc3Cl)noc2C2CC2)cc1] | I-60 | MS (ES, m/z): [M + 1] = 602.0. $^1$H NMR (300 MHz, CDC13) δ: 7.76-7.67 (m, 2H), 7.59-7.43 (m, 3H), 6.57-6.47 (m, 2H), 4.30 (s, 2H), 4.17 (s, 1H), 3.54-3.45 (m, 1H), 3.18-3.05 (m, 1H), 2.66-2.56 (m, 1H), 2.51 (s, 1H), 2.33-2.18 (m, 1H), 1.86-1.73 (m, 1H), 1.58 (q, J = 9.9 Hz, 2H), 1.37-1.21 (m, 3H), 1.21-1.03 (m, 6H), -0.00 (s, 6H) |

Example 62: Synthesis of I-61 and I-62

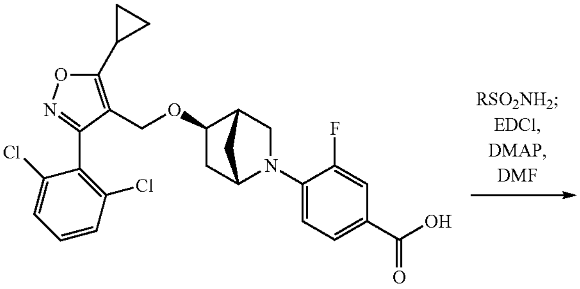

I-53

-continued

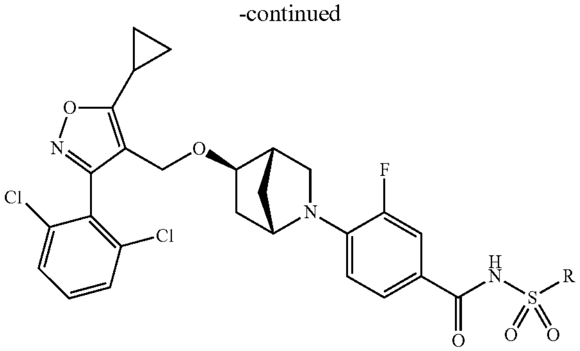

I-x

I-61 and I-62 were prepared from I-53 following the procedure described in Preparative Example 28, I-61 and I-62 were prepared from I-53. The data for compounds I-61 and I-62 is summarized in Table 7.

TABLE 7

| Cmpd Structure | Cmpd No. | MS/$^1$H NMR |
|---|---|---|
| 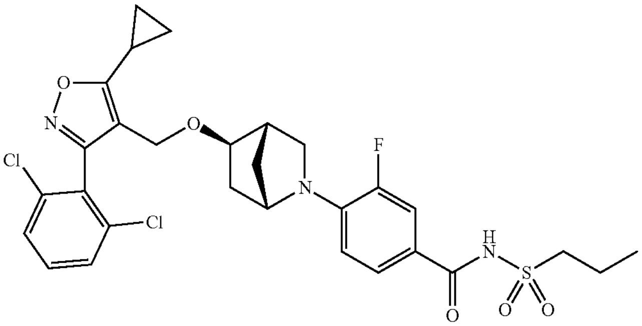 [SMILES: CCCS(=O)(=O)NC(=O)c1ccc(N2C[C@@H]3C[C@H]2C[C@H]3OCc2c(-c3c(Cl)cccc3Cl)noc2C2CC2)c(F)c1] | I-61 | MS (ES, m/z): [M + 1] = 622.0. $^1$H NMR (300 MHz, $CD_3OD$) δ: 7.64-7.43 (m, 5H), 6.65 (t, J = 8.7 Hz, 1H), 4.36-4.25 (m, 3H), 3.64-3.44 (m, 4H), 2.76 (dd, J = 9.9, 3.4 Hz, 1H), 2.49 (s, 1H), 2.28 (p, J = 6.7 Hz, 1H), 1.99-1.76 (m, 3H), 1.61 (t, J = 7.6 Hz, 2H), 1.33 (dt, J = 13.5, 2.8 Hz, 1H), 1.24-1.03 (m, 7H). |

TABLE 7-continued

| Cmpd Structure | Cmpd No. | MS/$^1$H NMR |
|---|---|---|
| 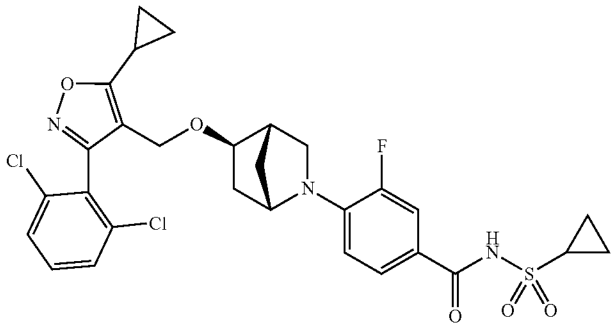 [SMILES: O=C(NS(=O)(=O)C1CC1)c1ccc(N2C[C@@H]3C[C@H]2C[C@H]3OCc2c(-c3c(Cl)cccc3Cl)noc2C2CC2)c(F)c1] | I-62 | MS (ES, m/z): [M + 1] = 620.0. $^1$H NMR (300 MHz, $CD_3OD$) δ: 7.63-7.43 (m, 5H), 6.66 (t, J = 8.7 Hz, 1H), 4.90 (s, 1H), 4.39-4.25 (m, 3H), 3.64-3.48 (m, 2H), 3.21-3.08 (m, 1H), 2.76 (dd, J = 9.9, 3.4 Hz, 1H), 2.49 (s, 1H), 2.36-2.20 (m, 1H), 1.93 (dd, J = 13.1, 6.6 Hz, 1H), 1.67-1.52 (m, 2H), 1.40-1.06 (m, 10H). |

Example 63: 2-[(1R,4S,6R)-6-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic Acid (I-63)

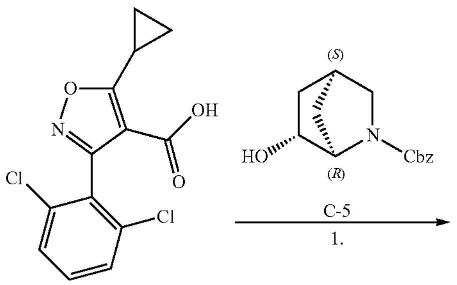

1f

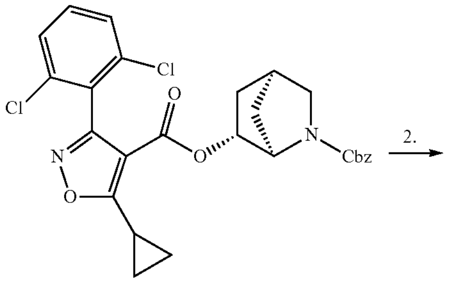

63a

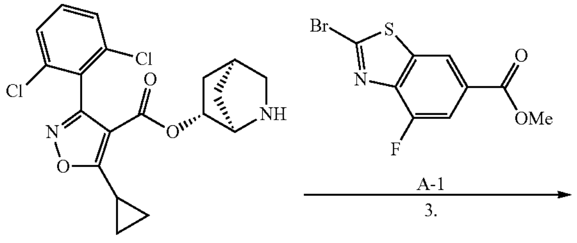

63b

-continued

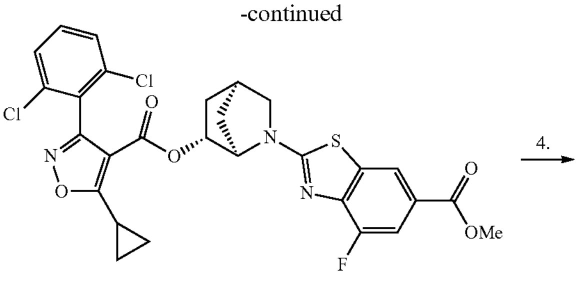

63c

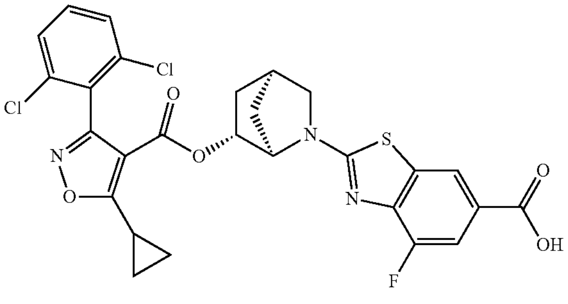

I-63

Compound I-63 was prepared in four steps following the procedures set forth in the Preparative Example 44 steps 1 to 4, from 5-cyclopropyl-3-(2,6-dichlorophenyl)isoxazole-4-carboxylic acid 1f and intermediate Benzyl (1R,4S,6R)-6-hydroxy-2-azabicyclo[2.2.1]heptane-2-carboxylate C-5. $^1$H NMR (400 MHz, DMSO-$d_6$) δ: 12.96 (s, 1H), 8.24 (d, J=1.5 Hz, 1H), 7.79-7.47 (m, 4H), 4.85 (d, J=6.4 Hz, 1H), 3.39 (m, 2H), 3.10 (s, 1H), 2.97-2.85 (m, 1H), 2.61 (s, 1H), 1.98 (d, J=5.7 Hz, 1H), 1.65 (d, J=10.2 Hz, 1H), 1.45-1.27 (m, 4H), 1.08 (dd, J=25.2, 11.5 Hz; 2H). MS (ES, m/z): [M+1]=588.0.

Example 64: 2-[(1R,4S,6S)-6-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic Acid (I-64)

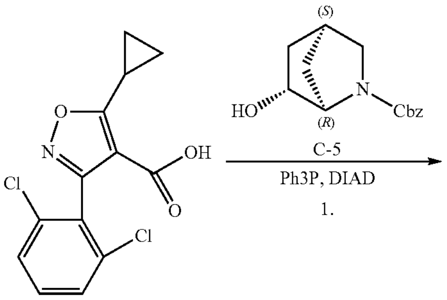

1f

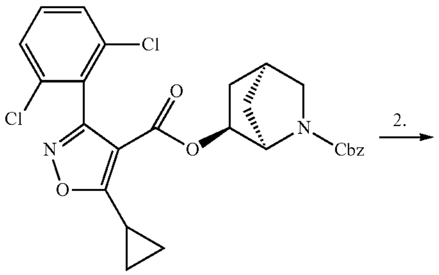

64a

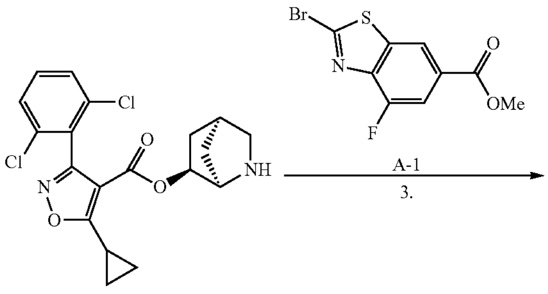

64b

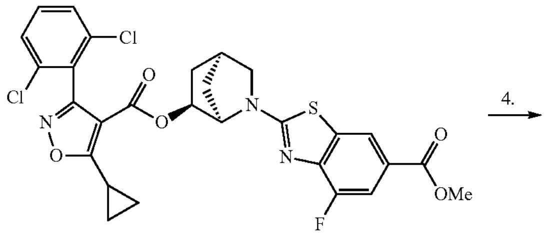

64c

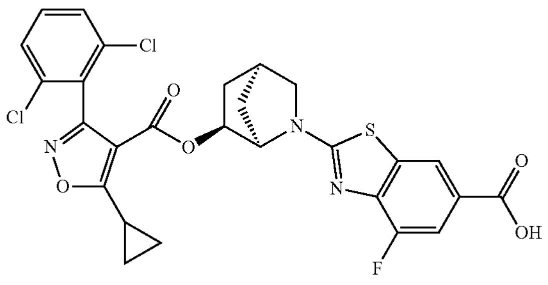

I-64

Compound 2-[(1R,4S,6S)-6-[5-cyclopropyl-3-(2,6-dichlorophenyl)-1,2-oxazole-4-carbonyloxy]-2-azabicyclo[2.2.1]heptan-2-yl]-4-fluoro-1,3-benzothiazole-6-carboxylic acid (I-64) was prepared in four steps following the procedures set forth in the Preparative Example 46 steps 1 to 4, from 5-cyclopropyl-3-(2,6-dichlorophenyl)isoxazole-4-carboxylic acid 1f, intermediate Benzyl (1R,4S,6R)-6-hydroxy-2-azabicyclo[2.2.1]heptane-2-carboxylate C-5, using triphenylphosphine and DIAD. $^1$H NMR (400 MHz, DMSO-$d_6$) δ: 13.00 (br, 1H), 8.25 (d, J=1.5 Hz, 1H), 7.76-7.55 (m, 4H), 4.85 (d, J=6.4 Hz, 1H), 3.39 (s, 1H), 3.10 (s, 1H), 2.91 (dq, J=8.3, 5.1 Hz, 1H), 2.61 (s, 1H), 1.99 (dd, J=12.4, 6.3 Hz, 1H), 1.65 (d, J=10.1 Hz, 1H), 1.45-1.27 (m, 5H), 1.08 (dd, J=25.1, 11.5 Hz, 2H). MS (ES, m/z): [M+1]=588.0.

Example 65: 2-[(1R,4S,6R)-6-{[5-cyclopropyl-3-(2,6-dichlorophenyl)-1,2-oxazol-4-yl]methoxy}-2-azabicyclo[2.2.1]heptan-2-yl]-4-fluoro-1,3-benzothiazole-6-carboxylic Acid (I-65)

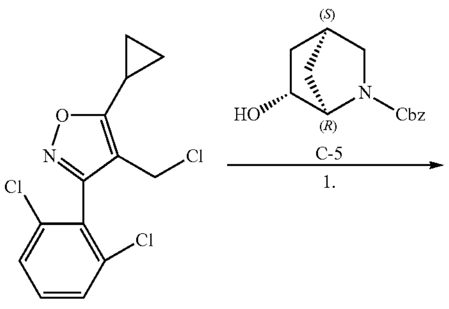

12b

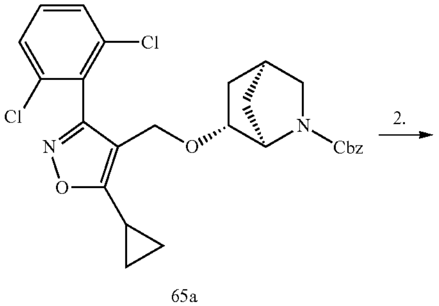

65a

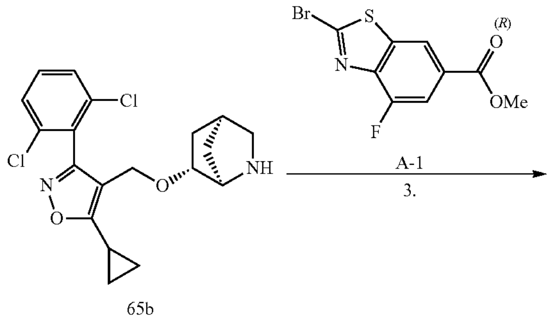

65b

-continued

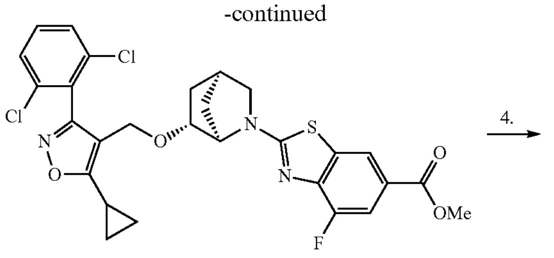

65c

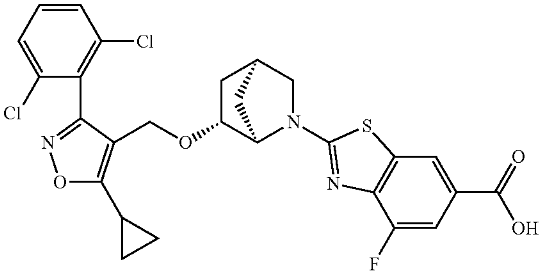

I-65

Compound 2-((1R,4S,6R)-6-((5-cyclopropyl-3-(2,6-dichlorophenyl)isoxazol-4-yl)methoxy)-2-azabicyclo[2.2.1]heptan-2-yl)-4-fluorobenzo[d]thiazole-6-carboxylic acid (I-65) was prepared in four steps following the procedures set forth in the Preparative Example 45 steps 1 to 4, from 4-(chloromethyl)-5-cyclopropyl-3-(2,6-dichlorophenyl)isoxazole 12b and intermediate benzyl (1R,4S,6R)-6-hydroxy-2-azabicyclo[2.2.1]heptane-2-carboxylate C-5. $^1H$ NMR (400 MHz, DMSO-$d_6$) δ: 12.95 (s, 1H), 8.23 (d, J=1.5 Hz, 1H), 7.67-7.51 (m, 4H), 4.43-4.26 (m, 2H), 3.52 (d, J=6.3 Hz, 1H), 3.37 (d, J=8.4 Hz, 2H), 3.00 (m, 1H), 2.57 (s, 1H), 2.42 (s, 1H), 1.74 (dd, J=12.3, 6.1 Hz, 1H), 1.61 (d, J=9.6 Hz, 1H), 1.43 (d, J=10.0 Hz, 1H), 1.26-0.94 (m, 5H). MS (ES, m/z): [M+1]=574.0.

Example 101: 2-Cyano-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoic Acid (I-101)

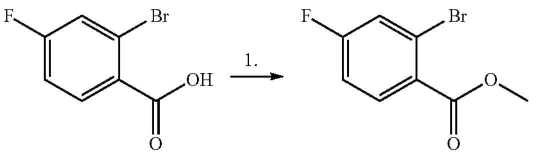

101a

101b

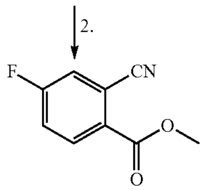

101c

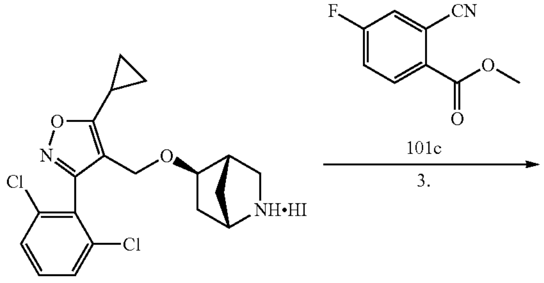

12dd

-continued

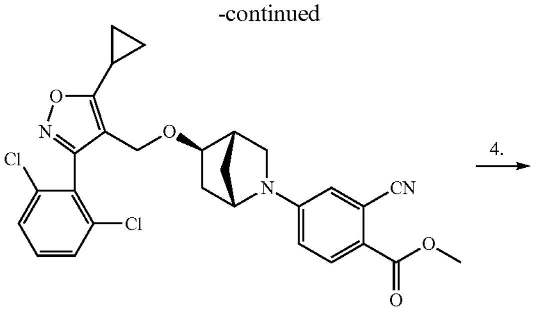

101d

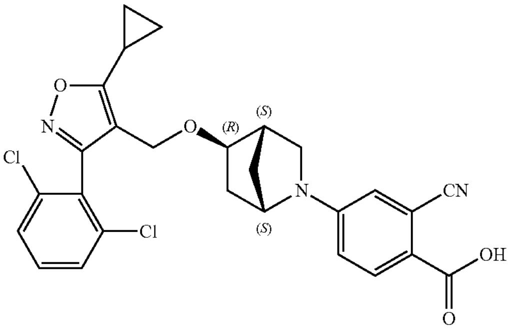

I-101

Step 1. Methyl 2-bromo-4-fluorobenzoate (101b)

To a 250-mL round-bottom flask was added a solution of 2-bromo-4-fluorobenzoic acid 101a (10 g, 45.66 mmol, 1.0 equiv.) in methanol (100 mL). Thionyl chloride (16.2 g, 137.29 mmol, 3.0 equiv.) was added dropwise. The resulting mixture was stirred at 70° C., for 2 h, and then quenched with the addition of water/ice. The aqueous mixture was extracted with ethyl acetate (100 mL×2). The combined organic extracts were washed brine (50 mL×2), concentrated to a crude solid, which was further purified by silica gel column chromatography eluting with ethyl acetate/petroleum ether (0%-8%). Removal of solvents afforded methyl 2-bromo-4-fluorobenzoate 101b (9.4 g, 88%) as a colorless solid.

Step 2. Methyl 2-cyano-4-fluorobenzoate (101c)

To a 250-mL round-bottom flask purged and maintained under an inert atmosphere of nitrogen, was added methyl 2-bromo-4-fluorobenzoate 101b (4 g, 17.16 mmol, 1.0 equiv.) and N,N-dimethylformamide (20 mL). Solid CuCN (2.3 g, 25.84 mmol, 1.5 equiv.) was added in several batches. The resulting mixture was stirred at 140° C., overnight. Upon cooling to room temperature, the mixture was quenched with water. The aqueous mixture was extracted with ethyl acetate (100 mL×3), and the combined organic extracts were washed with $H_2O$ (50 mL×2) and brine (80 mL×2). Removal of solvents gave a residue which was purified by silica gel column chromatography eluting with ethyl acetate/petroleum ether (10%) to provide methyl 2-cyano-4-fluorobenzoate 101c (1.2 g, 39%) as a white solid.

Step 3

Methyl 2-cyano-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoate (101d)

To a 8 mL sealed tube was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.394 mmol, 1.0 equiv.), methyl 2-cyano-4-fluorobenzoate 101c (104 mg, 0.58 mmol, 1.49 equiv.), potassium carbonate (144 mg, 1.04 mmol, 2.67 equiv.) and DMSO (2 mL). The resulting mixture was stirred at 120° C., overnight. After cooling, water was added, the mixture was extracted with ethyl acetate (150 mL×2). The combined organic extracts were washed with brine (100 mL×5), dried over anhydrous sodium sulfate and concentrated under vacuum to afford methyl 2-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoate 101d (250 mg) as a greenish yellow solid.

Step 4. 2-Cyano-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoic Acid (I-101)

To a 50 mL round-bottom flask purged with and maintained under an inert atmosphere of nitrogen was added methyl 2-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoate 101d (250 mg, ~0.39 mmol, 1.0 equiv.), methanol (3 mL), water (0.3 mL), and LiOH (195 mg, 8.14 mmol, 21 equiv.). The resulting mixture was stirred at 40° C., for 3 h. After cooling, the pH value of the solution was adjusted to 6 using a 1M hydrogen chloride aqueous solution. The resulting mixture was extracted with ethyl acetate (100 mL×3). The combined organic extracts were washed with brine (100 mL×3), dried over anhydrous sodium sulfate and concentrated under vacuum. The residue was dissolved in 2 mL of DMF and purified by Prep-HPLC using the following conditions: Column, XBridge Shield RP18 OBD Column, 5 um, 19*150 mm; mobile phase, Water (0.05% TFA) and ACN (58.0% ACN up to 74.0% in 10 min); Detector, uv 254 nm. Removal of solvents afforded 2-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-101 (19.5 mg, 9.5%) as a light yellow solid. $^1$H NMR (300 MHz, $CD_3OD$) δ 7.89 (d, J=8.8 Hz, 1H), 7.62-7.46 (m, 3H), 6.82 (d, J=2.5 Hz, 1H), 6.73 (dd, J=8.8, 2.5 Hz, 1H), 4.33 (s, 2H), 4.20 (s, 1H), 3.53 (d, J=6.4 Hz, 1H), 3.39 (dd, J=9.5, 3.7 Hz, 1H), 2.62 (d, J=9.6 Hz, 1H), 2.53 (s, 1H), 2.28 (p, J=6.8 Hz, 1H), 1.88-1.74 (min, 1H), 1.61 (q, J=10.1 Hz, 2H), 1.34 (d, J=13.8 Hz, 1H), 1.19 (d, J=6.9 Hz, 4H). MS (ES, m/z): [M+1]=524.

Example 102: 3-cyano-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoic Acid (I-102)

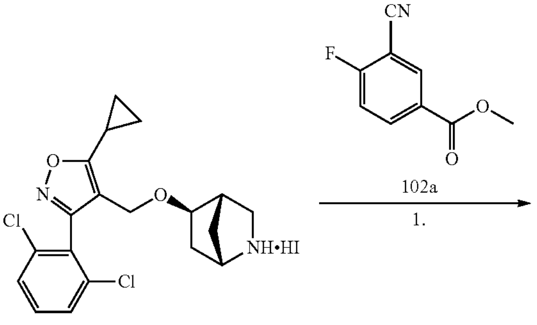

12dd

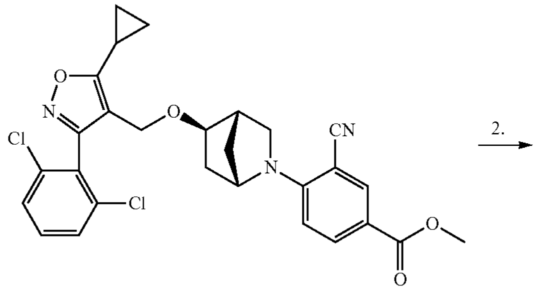

102b

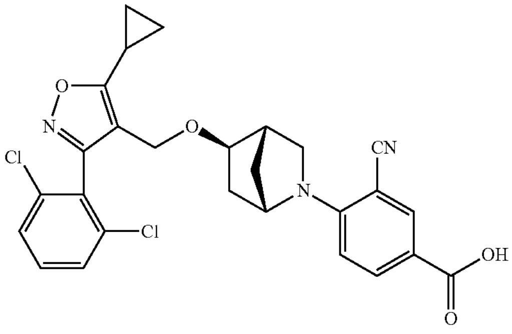

I-102

Step 1. Methyl 3-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoate (102b)

To a 100 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.394 mmol, 1.0 equiv.), methyl 3-cyano-4-fluorobenzoate 102a (110 mg, 0.61 mmol, 1.56 equiv.), DMSO (3 mL), and potassium carbonate (146 mg, 1.06 mmol, 2.72 equiv.). The resulting mixture was stirred at 120° C., overnight. After cooling to room temperature, 50 mL of $H_2O$ was added. The aqueous mixture was extracted with ethyl acetate (200 mL×2), the combined organic extracts were washed with brine (200 mL×3), dried over anhydrous sodium sulfate, and concentrated under vacuum to a residue which was purified by silica gel column chromatography eluting with ethyl acetate/petroleum ether (1:3). Removal of solvents gave methyl 3-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoate 102b (0.176 g, 84%) as a greenish oil.

Step 2. 3-cyano-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzoic Acid (I-102)

To a 50 mL round-bottom flask was added methyl 3-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoate 102b (176 mg, 0.33 mmol, 1.0 equiv.), methanol (5 mL), water (1 mL), and LiOH (138 mg, 5.76 mmol, 10.0 equiv.). The resulting mixture was stirred at room temperature overnight, then diluted with 20 mL of $H_2O$, and adjusted the pH value to 3-4 using a 1M HCl aqueous solution. The aqueous mixture was extracted with ethyl acetate (100 mL×2); the combined organic layers were washed with brine (100 mL×2), dried over anhydrous sodium sulfate, and concentrated under vacuum. The crude product was purified by Prep-HPLC using the following conditions: Column, XBridge Shield RP18 OBD Column, 5 um, 19*150 mm; mobile phase, Water (0.05% TFA) and ACN (50.0% ACN up to 68.0% in 8 min); Detector, UV 254 nm. After purification, 3-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-102 (37.6 mg, 22%) was obtained as an off-white solid. $^1H$ NMR (300 MHz, $CD_3OD$) δ 8.06 (t, J=1.9 Hz, 1H), 7.91 (dt, J=9.2, 1.9 Hz, 1H), 7.64-7.44 (m, 3H), 6.73 (dd, J=9.4, 2.6 Hz, 1H), 4.56 (s, 1H), 4.34 (d, J=2.1 Hz, 2H), 3.80 (dd, J=9.9, 4.1 Hz, 1H), 3.58 (dd, J=6.8, 2.4 Hz, 1H), 2.94 (d, J=9.8 Hz, 1H), 2.60-2.51 (m, 1H), 2.29 (p, J=6.8 Hz, 1H), 2.05-1.90 (m, 1H), 1.72-1.57 (m, 2H), 1.44-1.28 (m, 1H), 1.19 (d, J=6.7 Hz, 4H). MS (ES, m/z): [M+1]=524.

Example 103: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorobenzoic Acid (I-103)

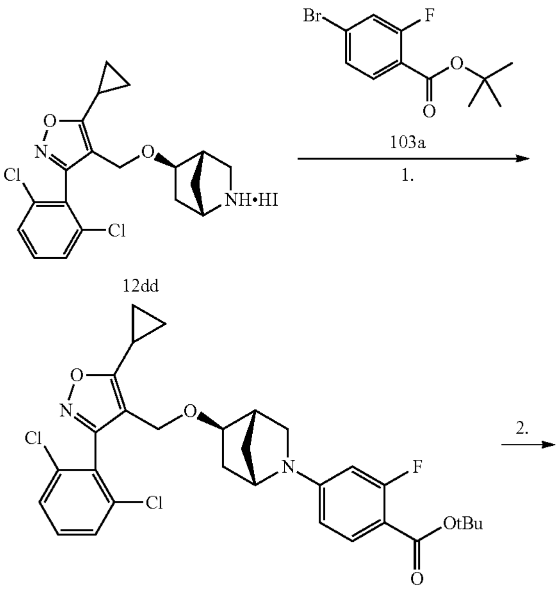

12dd
103b

-continued

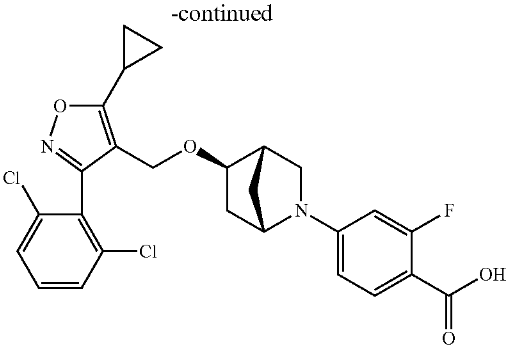

I-103

Step 1, tert-Butyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoate (103b)

To a 250 mL round-bottom flask purged with and maintained under an inert atmosphere of nitrogen was added a solution of (1S,4S,5R)-5-[[5-cyclopropyl-3-(2,6-dichlorophenyl)-1,2-oxazol-4-yl]methoxy]-2-azabicyclo[2.2.1]heptane hydroiodide 12dd (2 g, 3.94 mmol, 1.0 equiv.) in toluene (20 mL), tert-butyl 4-bromo-2-fluorobenzoate 103a (2.2 g, 8.00 mmol, 2.03 equiv.), cesium carbonate (5.2 g, 15.91 mmol, 4.04 equiv.), $Pd(OAc)_2$ (237 mg, 1.06 mmol, 0.27 equiv.), and XantPhos (612 mg, 1.06 mmol, 0.27 equiv.). The resulting mixture was stirred at 90° C. overnight. The solids were filtered out, the filtrate was diluted with 200 mL of EA and washed with $H_2O$ (200 mL×2) followed by brine (200 mL×2). The organic layer was dried over anhydrous sodium sulfate and concentrated under vacuum to a residue which was purified by silica gel column chromatography eluting with ethyl acetate/petroleum ether (0-30%). Removal of solvents afforded tert-butyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoate 103b (2.3 g, Q) as a yellow solid.

Step 2. 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorobenzoic Acid (I-103)

To a 1 L round-bottom flask was added tert-butyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoate 103b (12 g, 20.92 mmol, 1.0 equiv.), dioxane (400 mL), and hydrogen chloride (200 mL). The resulting mixture was stirred at room temperature overnight and then diluted with 1 L of EA. The mixture was washed with $H_2O$ (500 mL×3) and brine (500 mL×2), dried over anhydrous sodium sulfate, and concentrated under vacuum to a crude oily product. This crude product (10 mL) was purified by Flash-Prep-HPLC using the following conditions: Column, silica gel; mobile phase, $CH_3CN:H_2O$ (0.1%6 FA)=55% increasing to $CH_3CN:H_2O$ (0.1% FA)=70% within 50 min; Detector, UV 254 nm. Evaporation of solvents afforded 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoic acid I-103 (4.1353 g, 38%) as a colorless solid. $^1H$ NMR (300 MHz, $CD_3OD$) δ 7.73 (t, J=8.8 Hz, 1H), 7.61-7.43 (m, 3H), 6.32 (dd, J=8.9, 2.3 Hz, 1H), 6.20 (dd, J=14.6, 2.3 Hz, 1H), 4.33 (s, 2H), 4.15 (s, 1H), 3.53 (d, J=6.1 Hz, 1H), 2.61 (d, J=9.4 Hz, 1H), 2.52 (d, J=3.7 Hz, 1H), 2.28 (p, J=6.8 Hz, 1H), 1.89-1.75 (m, 1H), 1.60 (q, J=10.1 Hz, 2H), 1.33 (dt, J=13.4, 2.6 Hz, 1H), 1.24-1.14 (m, 4H). MS (ES, m/z): [M+1]=517.10.

Example 104: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,6-difluorobenzoic Acid (I-104)

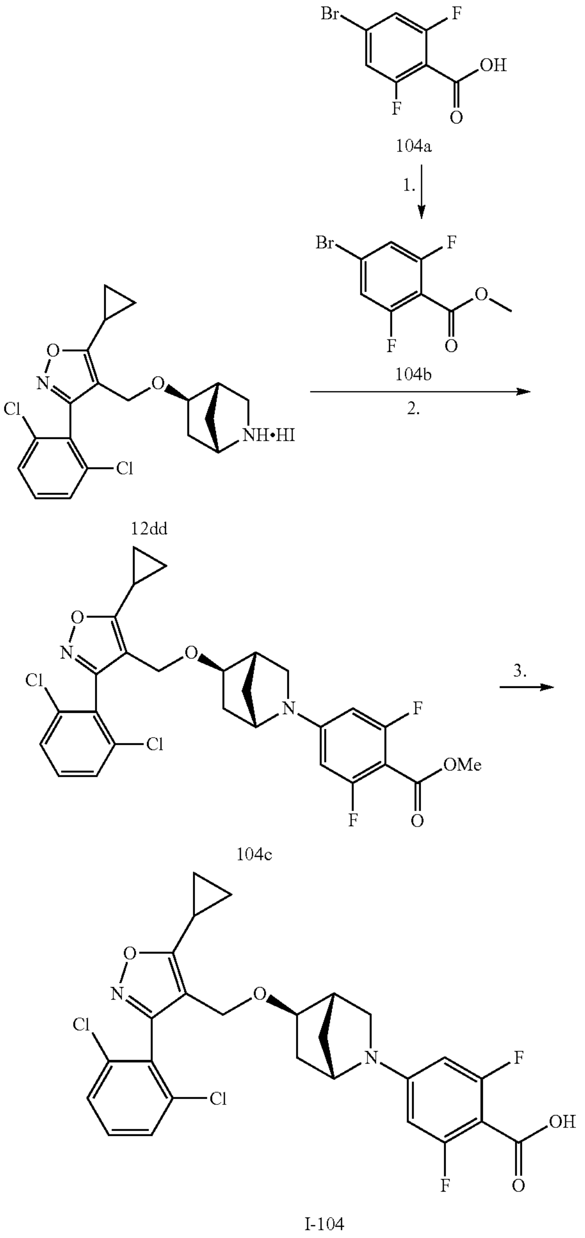

104a
104b
12dd
104c
I-104

Step 1

To a 100-mL round-bottom flask was added 4-bromo-2,6-difluorobenzoic acid 104a (3.5 g, 14.77 mmol, 1.0 equiv.) and methanol (10 mL). Thionyl chloride (3.3 g, 2.0 equiv.) was added dropwise at 0° C., with stirring. The resulting mixture was stirred at room temperature overnight. 100 mL of water/ice was added to quench the reaction. The aqueous mixture was extracted with ethyl acetate (200 mL×2), and the combined organic layers were washed with brine (200 mL×2), dried over anhydrous sodium sulfate, and concentrated under vacuum to a residue which was purified by silica gel column chromatography eluting with ethyl acetate/petroleum ether (0%-4%). Removal of solvents afforded methyl 4-bromo-2,6-difluorobenzoate 104b (1.2 g, 32%) as a colorless oil.

Step 2

To a 25 mL round-bottom flask was added methyl 4-bromo-2,6-difluorobenzoate 104b (160 mg, 0.64 mmol, 1.2 equiv.), (1S,4S,5R)-5-[5-cyclopropyl-3-(2,6-dichlorophenyl)-1,2-oxazol-4-yl]methoxy-2-azabicyclo[2.2.1]heptane 12dd (200 mg, 0.394 mmol, 1.0 equiv.), $Pd(OAc)_2$ (60 mg, 0.27 mmol, 0.69 equiv.), Xantphos (150 mg, 0.26 mmol, 0.66 equiv.), $Cs_2CO_3$ (340 mg, 1.04 mmol, 2.64 equiv.), and toluene (4 mL). The resulting mixture was stirred at 90° C., overnight. Upon cooling, the mixture was diluted with 20 mL of $H_2O$ and extracted with ethyl acetate (20 mL×2). The combined organic extracts were washed with water (20 mL×2), dried over anhydrous sodium sulfate and concentrated under vacuum. The residue was purified by silica gel column chromatography eluting with ethyl acetate/petroleum ether (1:5) to give 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2,6-difluorobenzoate 104c (26 mg, 12.3%) as a yellow oil.

Step 3

To a 50 mL round-bottom flask was added methyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2,6-difluorobenzoate 104c (70 mg, 0.13 mmol, 1.0 equiv.), methanol (5 mL), water (2 mL), and LiOH (54 mg, 2.25 mmol, 10.0 equiv.). The resulting solution was stirred at room temperature overnight, then diluted with 30 mL of $H_2O$. The pH of the solution was adjusted to 3-4 with a hydrogen chloride aqueous solution, and the mixture was extracted with ethyl acetate (50 mL×2). The combined organic extracts were washed with brine (50 mL×2), dried over anhydrous sodium sulfate and concentrated under vacuum. The crude product (5 mL) was purified by Prep-HPLC using the following conditions (2#-AnalyseHPLC-SHIMADZU(HPLC-10)): Column, XBridge Prep OBD C18 Column, 19*250 mm, 5 um; mobile phase. Water (0.05% TFA) and ACN (59.0% ACN up to 70.0% in 10 min); Detector, UV 220 nm. After purification, 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2,6-difluorobenzoic acid I-104 (14.7 mg, 22%) was obtained as a colorless oil. $^1H$ NMR (300 MHz, $CD_3OD$) S 7.62-7.44 (m, 3H), 6.10 (d, J=12.9 Hz, 2H), 4.33 (s, 2H), 4.12 (s, 1H), 3.54 (d, J=6.4 Hz, 1H), 2.65-2.49 (m, 2H), 2.28 (p, J=6.7 Hz, 1H), 1.88-1.74 (m, 1H), 1.59 (q, J=10.1 Hz, 2H), 1.39-1.27 (m, 2H), 1.24-1.14 (m, 4H). MS (ES, m/z): [M+1]=535.

Example 105: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,5-difluorobenzoic Acid (I-105)

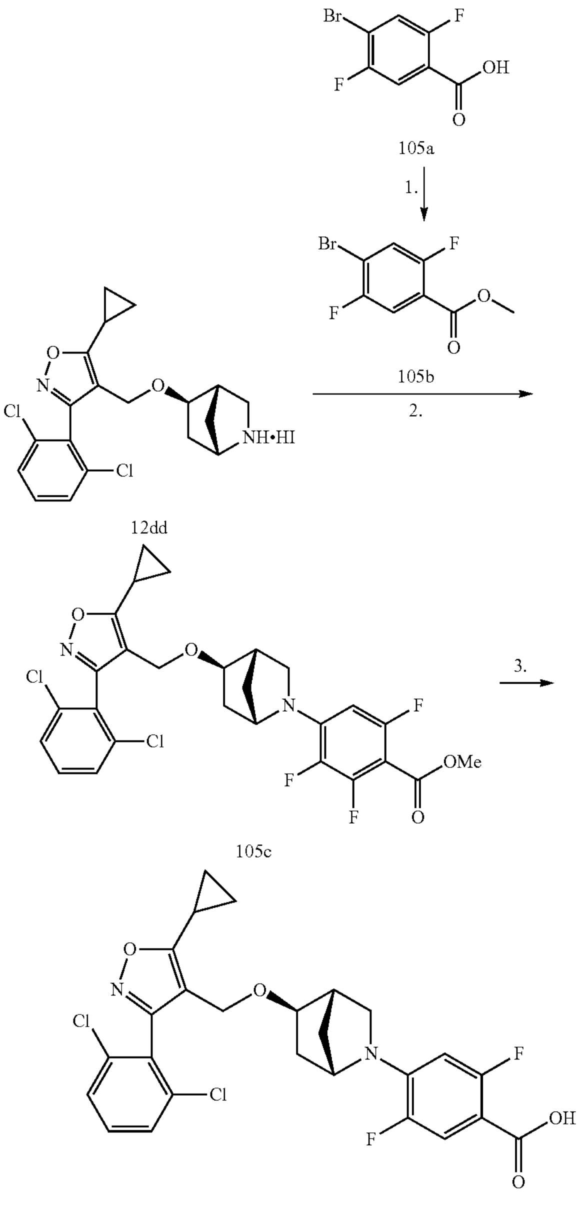

105a, 105b, 12dd, 105c, I-105

Steps 1 to 3

Following similar procedures described in Example 104, 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2,5-difluorobenzoic acid I-105 (118.3 mg, 61%) was obtained as an off-white solid starting from (1S,4S,5R)-5-[[5-cyclopropyl-3-(2,6-dichlorophenyl)-1,2-oxazol-4-yl]methoxy]-2-azabicyclo[2.2.1]heptane 12dd (400 mg, 0.789 mmol, 1.47 equiv.), methyl 4-bromo-2,5-difluorobenzoate 105b (292 mg, 1.16 mmol, 1.47 equiv.). $^1$H NMR (300 MHz, $CD_3OD$)

δ 7.59-7.39 (m, 4H), 6.31 (dd, J=13.6, 7.2 Hz, 1H), 4.30 (s, 2H), 4.24 (s, 1H), 3.51 (dt, J=9.5, 4.3 Hz, 2H), 2.77-2.69 (m, 1H), 2.49-2.43 (m, 1H), 2.25 (p, J=6.8 Hz, 1H), 1.94-1.83 (m, 1H), 1.62-1.50 (m, 2H), 1.31 (dt, J=13.4, 2.7 Hz, 1H), 1.20-1.12 (m, 4H). MS (ES, m/z): [M+1]=535.05.

Example 106: Synthesis of I-106 to I-112

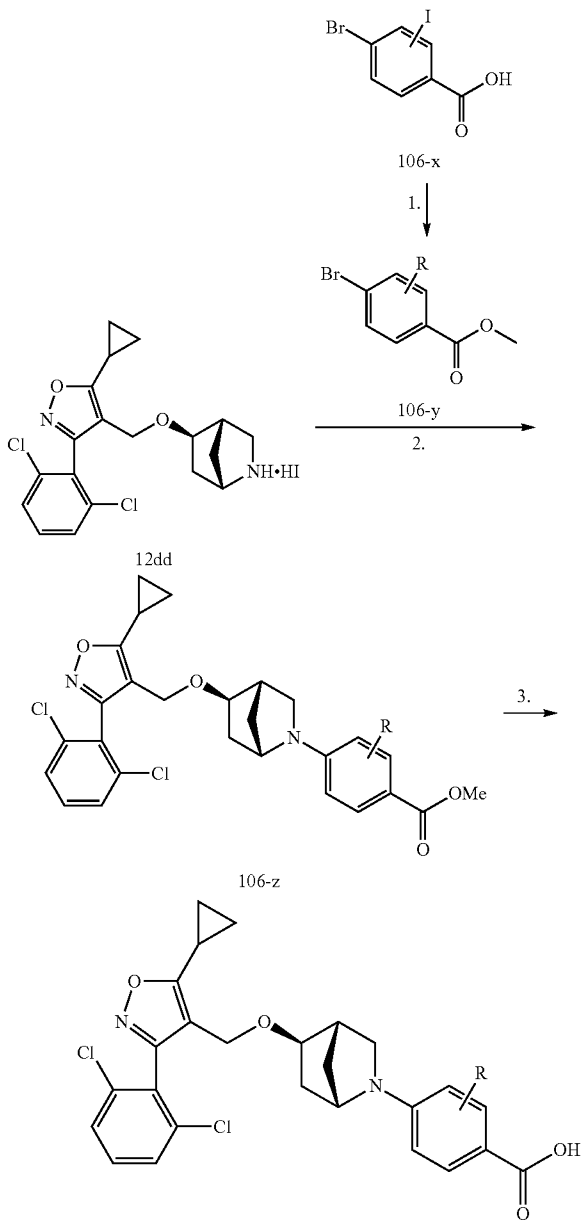

106-x, 106-y, 12dd, 106-z

I-106 to I-112

Compounds I-106 to I-112 were prepared in two to three steps following the general procedures described below. Data for Compounds I-106 to I-112 is summarized in Table 8 below.

Step 1

Non-commercially available 3R or 2R substituted esters 106-y were prepared from the corresponding 3-iodo or 2-iodo substituted methyl 4-bromo-phenyl esters 106-x. A mixture of methyl 4-bromo-3-iodobenzoate (1 mmol, 1 equiv.), alkyl boronic acid (1.5 mmol, 1.5 equiv.), potassium phosphate tribasic (1.5 mmol, 1.5 equiv.), $PdCl_2$(dppf) $.CH_2Cl_2$ (0.1 mmol, 0.1 equiv.) in 20 mL of Toluene and 10 mL of water was heated at 90° C., under nitrogen for 5 hr. The mixture was cooled to room temperature and diluted with ethyl acetate. The organic solution was washed with aq, sodium bicarbonate and brine, dried over anhydrous sodium sulfate, filtered and concentrated in vacuo to provide the desired 106-y after silica gel column chromatography using 2-5% ethyl acetate in hexane as eluent.

Step 2

A suspension of 4-(((1S,4S,5R)-2-azabicyclo[2.2.1]heptan-5-yloxy)methyl)-5-cyclopropyl-3-(2,6-dichlorophenyl) isoxazole hydroiodide salt 12dd (0.52 mmol, 1 equiv.), methyl 4-bromo-2/3-substituted benzoate 106-y (0.68 mmol, 1.3 equiv.), $Cs_2CO_3$ (1.3 mmol, 2.5 equiv.), $Pd_2(dba)_3$ (0.15 equiv.), BINAP (0.2 equiv.) in Toluene (10.0 mL) was heated under a nitrogen atmosphere at 110° C., for 16 h. The reaction mixture was cooled to room temperature, diluted with ethyl acetate and filtered through a pad of Celite. The organic layer was washed with brine, dried over anhydrous $Na_2SO_4$, filtered and concentrated under reduced pressure. The crude material was purified on ISCO silica gel column chromatography using hexane/ethyl acetate as eluents to give the desired methyl ester 106z which was used as such in the next step.

Step 3

The above residue 106z was dissolved in methanol (5 mL) and treated with a 1N-NaOH solution (1.0 mL, 2.0 equiv.) and heated at 70° C., for 16 to 48 h. After cooling to room temperature, the mixture was neutralized with a 1N HCl aqueous solution and concentrated under the reduced pressure. The residue was purified on Semi-prep HPLC using 40-95% acetonitrile (0.1% TFA) in 30 min method. The fractions were collected monitoring UV absorbance at 215 nm and lyophilized to give the desired Compounds I-106 to I-112.

TABLE 8

Compounds I-106 to I-112.

| Cmpd Structure | Cmpd No. | MS/$^1$H NMR |
|---|---|---|
| 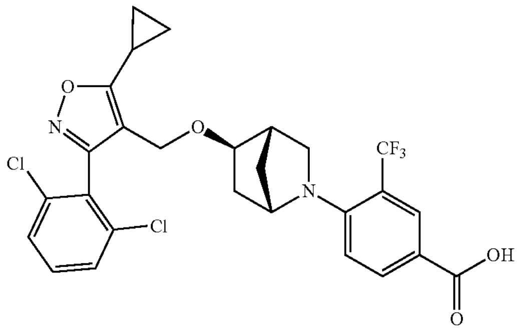 [SMILES: O=C(O)c1ccc(N2C[C@@H]3C[C@H]2C[C@H]3OCc2c(-c3c(Cl)cccc3Cl)noc2C2CC2)c(C(F)(F)F)c1] | I-106 | MS (ES, m/z): [M + 1] = 567.19. $^1$H NMR (400 MHz, DMSO-d6) δ: 8.04 (d, J = 1.9 Hz, 1H), 7.91-7.75 (m, 1H), 7.65-7.54 (m, 3H), 6.89 (d, J = 9.0 Hz, 1H), 4.24 (s, 2H), 4.16 (s, 1H), 3.51 (t, J = 7.7 Hz, 2H), 2.66 (d, J = 9.4 Hz, 1H), 2.45 (s, 1H), 2.37-2.25 (m, 1H), 1.95 (dd, J = 13.5 & 6.1 Hz, 1H), 1.45 (dd, J = 23.6 & 9.7 Hz, 2H), 1.28-1.15 (m, 1H), 1.15-1.01 (m, 5H). |
| 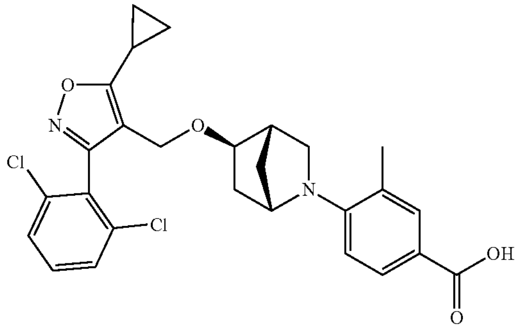 [SMILES: Cc1cc(C(=O)O)ccc1N1C[C@@H]2C[C@H]1C[C@H]2OCc1c(-c2c(Cl)cccc2Cl)noc1C1CC1] | I-107 | MS (ES, m/z): [M + 1] = 513.26. $^1$H NMR (400 MHz, DMSO-d6) δ: 7.65-7.54 (m, 5H), 6.59 (d, J = 9.2 Hz, 1H), 4.23 (s, 2H), 3.97 (s, 1H), 3.59-3.33 (m, 2H), 2.57 (d, J = 9.2 Hz, 1H), 2.42-2.26 (m, 2H), 2.20 (s, 3H), 1.96 (dd, J = 13.4 & 4.9 Hz, 1H), 1.41 (dd, J = 29.2 & 9.4 Hz, 2H), 1.26-1.03 (m, 5H). |

TABLE 8-continued

| Compounds I-106 to I-112. | | |
|---|---|---|
| Cmpd Structure | Cmpd No. | MS/$^{1}$H NMR |
| 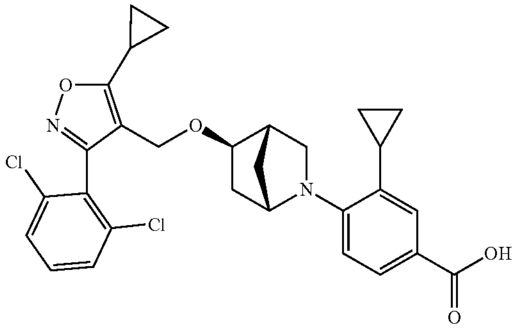 [SMILES: O=C(O)c1ccc(N2C[C@@H]3C[C@H]2C[C@H]3OCc2c(-c3c(Cl)cccc3Cl)noc2C2CC2)c(C2CC2)c1] | I-108 | MS (ES, m/z): [M + 1] = 539.28. $^{1}$H NMR (400 MHz, DMSO-d6) δ: 7.74-7.40 (m, 5H), 6.56 (d, J = 8.5 Hz, 1H), 4.26 (bs, 2H), 4.14 (bs, 1H), 3.72 (bs, 1H), 3.43 (bs, 1H), 2.72 (d, J = 8.9 Hz, 1H), 2.43-2.25 (m, 2H), 1.92 (dd, J = 13.4 & 4.9 Hz, 1H), 1.43 (dd, J = 29.2 & 9.4 Hz, 2H), 1.29-1.01 (m, 6H), 0.93 (bs, 1H), 0.82 (bs, 1H), 0.56 (bs, 2H). |
| 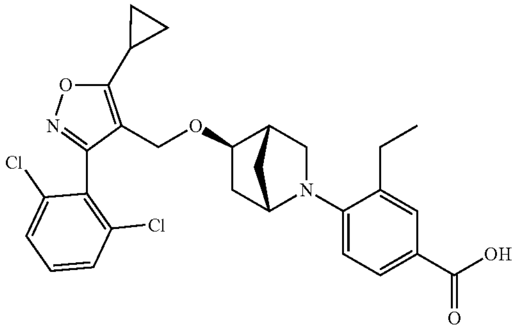 [SMILES: CCc1cc(C(=O)O)ccc1N1C[C@@H]2C[C@H]1C[C@H]2OCc1c(-c2c(Cl)cccc2Cl)noc1C1CC1] | I-109 | MS (ES, m/z): [M + 1] = 527.24. $^{1}$H NMR (400 MHz, DMSO-d6) δ: 7.74-7.40 (m, 5H), 6.65 (d, J = 6.5 Hz, 1H), 4.24 (bs, 2H), 3.94 (bs, 1H), 3.44 (bs, 2H), 2.63-2.50 (m, 5H), 2.01-1.96 (m, 1H), 1.52-1.30 (m, 2H), 1.21-1.07 (m, 8H). |
| 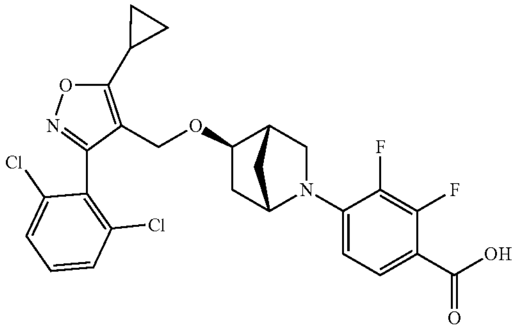 [SMILES: O=C(O)c1ccc(N2C[C@@H]3C[C@H]2C[C@H]3OCc2c(-c3c(Cl)cccc3Cl)noc2C2CC2)c(F)c1F] | I-110 | MS (ES, m/z): [M + 1] = 535.12. $^{1}$H NMR (400 MHz, DMSO-d6) δ: 7.64-7.59 (m, 3H), 7.55-7.44 (m, 1H), 6.46 (d, J = 9.2 Hz, 1H), 4.25 (s, 2H), 4.20 (s, 1H), 3.54-3.49 (m, 2H), 2.72 (bs, 1H), 2.43 (s, 1H), 2.32 (bs, 1H), 1.80 (bs, 1H), 1.46-1.41 (m, 2H), 1.01-1.03 (m, 5H). |
| 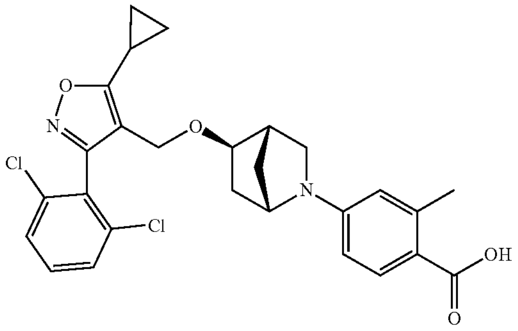 [SMILES: Cc1cc(N2C[C@@H]3C[C@H]2C[C@H]3OCc2c(-c3c(Cl)cccc3Cl)noc2C2CC2)ccc1C(=O)O] | I-111 | MS (ES, m/z): [M + 1] = 513.12. $^{1}$H NMR (400 MHz, DMSO-d6) δ: 7.74-7.48 (m, 4H), 6.30 (d, J = 9.6 Hz, 2H), 4.24 (s, 2H), 4.13 (s, 1H), 3.41 (d, J = 5.9 Hz, 1H), 3.27 (dd, J = 9.5 & 4.1 Hz, 1H), 2.44 (s, 5H), 2.35-2.27 (m, 1H), 1.68 (dd, J = 13.1 & 6.7 Hz, 1H), 1.41 (dd, J = 24.7 & 9.6 Hz, 2H), 1.19-1.01 (m, 5H). |

TABLE 8-continued
| Compounds I-106 to I-112. | | |
|---|---|---|
| Cmpd Structure | Cmpd No. | MS/$^1$H NMR |
| 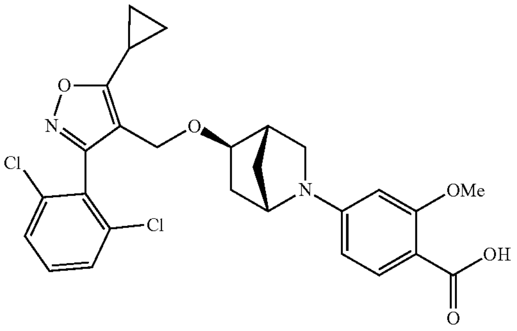 [SMILES: COc1cc(N2C[C@@H]3C[C@H]2C[C@H]3OCc2c(-c3c(Cl)cccc3Cl)noc2C2CC2)ccc1C(=O)O] | I-112 | MS (ES, m/z): [M + 1] = 529.22. $^1$H NMR (400 MHz, DMSO-d6) δ: 7.68-7.49 (m, 4H), 6.04 (d, J = 9.6 Hz, 2H), 4.25 (bs, 2H), 4.18 (bs, 1H), 3.77 (bs, 2H), 3.34 (s, 3H), 2.44 (bs, 5H), 2.38-2.29 (m, 1H), 1.72 (bs, 1H), 1.40 (dd, J = 24.7 & 9.6 Hz, 2H), 1.19-1.01 (m, 5H). |
Example 107: 4-[(1S,4S,5R)-5-{[3-(2-chloro-6-methylphenyl)-5-cyclopropyl-1,2-oxazol-4-yl]methoxy}-2-azabicyclo[2.2.1]heptan-2-yl]-3-fluorobenzoic Acid (I-113)
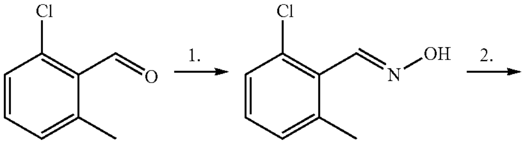
113a 113b
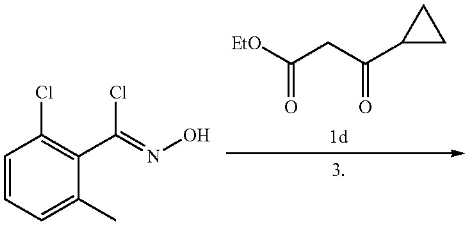
113c
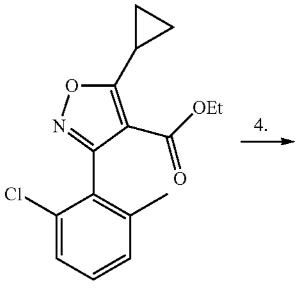
113d
-continued
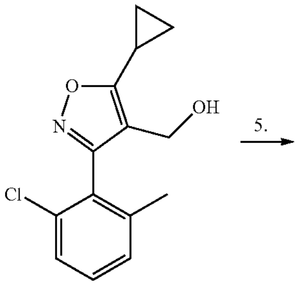
113e
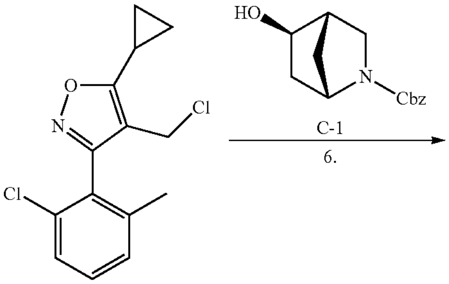
113f
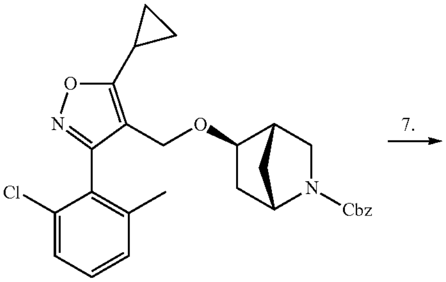
113g -continued

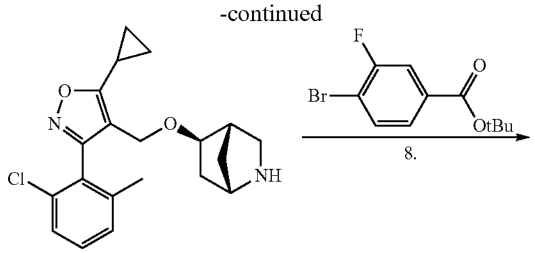

113h

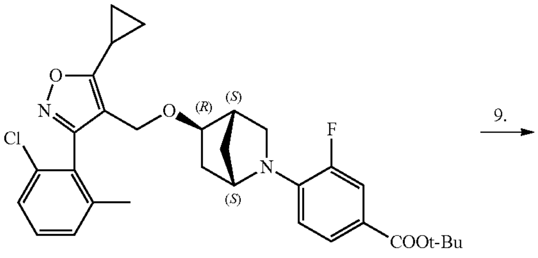

113i

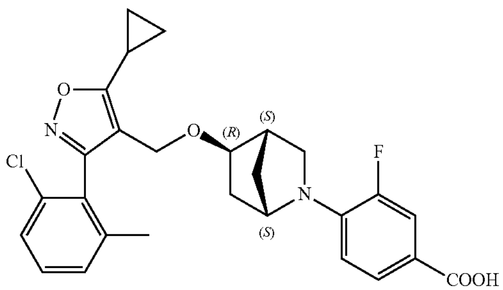

I-113

Step 1

To a 500 mL round-bottom flask was added 2-chloro-6-methylbenzaldehyde 113a (12 g, 77.62 mmol, 1.00 equiv.), ethanol (120 mL), water (60 mL), $NH_2OH$ hydrogen chloride salt (16.18 g), and sodium hydroxide (9.31 g, 232.75 mmol, 3.00 equiv.). The resulting mixture was stirred at 80° C., overnight. The mixture was concentrated under vacuum, the residue was diluted with 200 mL of $H_2O$ and extracted with dichloromethane (150 mL×3). The organic layers were combined and concentrated under vacuum. The crude product was recrystallized from PE to provide N-[(2-chloro-6-methylphenyl)methylidene]hydroxylamine 113b (12 g, 91%) as a white solid.

Step 2

To a 250 mL round-bottom flask was added N-[(2-chloro-6-methylphenyl)methylidene]hydroxylamine 113b (12 g, 70.75 mmol, 1.0 equiv.), N,N-dimethylformamide (100 mL), and NCS (10.5 g, 78.63 mmol, 1.11 equiv.). The resulting mixture was stirred at 10-25° C., for 2 h. 500 mL of $H_2O$ was added. The aqueous mixture was extracted with ethyl acetate (150 mL×3); the combined organic extracts were dried over anhydrous sodium sulfate, concentrated under vacuum to afford 2-chloro-N-hydroxy-6-methylbenzene-1-carbonimidoyl chloride 113c (16g, Q) as a light brown crude oil.

Step 3

To a 500 mL round-bottom flask was added tetrahydrofuran (300 mL) and potassium tert-butoxide (9 g, 80.21 mmol, 1.0 equiv.). Ethyl 3-cyclopropyl-3-oxopropanoate 1d (12.5 g, 80.04 mmol, 1.0 equiv.) was added dropwise at 0-5° C., with stirring. The resulting mixture was stirred at 15-25° C., for 0.5 h, and a solution of (Z)-2-chloro-N-hydroxy-6-methylbenzene-1-carbonimidoyl chloride 113c (16.34 g, 80.08 mmol, 1.0 equiv.) in tetrahydrofuran (25 mL) was added dropwise. Reaction was continued at 10-25° C., overnight, then quenched by the addition of 200 mL of water/ice. The aqueous mixture was extracted with ethyl acetate (150 mL×3). The organic layers were combined, dried over sodium sulfate, and concentrated under vacuum to give ethyl 3-(2-chloro-6-methylphenyl)-5-cyclopropyl-1,2-oxazole-4-carboxylate 113d (12 g, 49%) as a light yellow oil (crude).

Step 4

To a 250 mL round-bottom flask was added ethyl 3-(2-chloro-6-methylphenyl)-5-cyclopropyl-1,2-oxazole-4-carboxylate 113d (4.8 g, 15.70 mmol, 1.0 equiv.) and tetrahydrofuran (150 mL). Solid $LiAlH_4$ (1.2 g, 31.62 mmol, 2.01 equiv.) was added in several batches at 0-5° C. The resulting mixture was stirred at 10-25° C., for 1 h. The reaction was quenched by the addition of sodium sulfate. $10H_2O$ (3.6 g). The solids were filtered out, the filtrate was concentrated under vacuum to give [3-(2-chloro-6-methylphenyl)-5-cyclopropyl-1,2-oxazol-4-yl]methanol 113e (4.1 g, 99%) as an off-white solid (crude).

Step 5

To a 250 mL round-bottom flask was added benzotriazole (2.4 g) and dichloromethane (100 mL). A solution of $SO_2Cl_2$ (5.5 g) was added dropwise with stirring at 0-5° C. The resulting mixture was stirred at 10-25° C., for 0.5 h. A solution of [3-(2-chloro-6-methylphenyl)-5-cyclopropyl-1,2-oxazol-4-yl]methanol 113e (5.4 g, 20.48 mmol, 1.00 equiv.) in dichloromethane (10 mL) was added dropwise at 15-25° C., with stirring. Reaction was continued at 10-25° C., for 30 min. 200 mL of water/ice was added, the pH value of the solution was adjusted to 7 with sodium carbonate. The resulting mixture was extracted with dichloromethane (100 mL×3), and the combined organic extracts were dried and concentrated under vacuum. The residue was purified by silica gel column chromatography eluting with ethyl acetate/petroleum ether (0:1 to 1:20). Removal of solvents gave 3-(2-chloro-6-methylphenyl)-4-(chloromethyl)-5-cyclopropyl-1,2-oxazole 113f (4.2 g, 73%) as a light brown oil.

Step 6

To a 250-mL round-bottom flask was added 3-(2-chloro-6-methylphenyl)-4-(chloromethyl)-5-cyclopropyl-1,2-oxazole 113f (2.56 g, 9.07 mmol, 1.0 equiv), N,N-dimethylformamide (50 mL), benzyl (1S,4S,5R)-5-hydroxy-2-azabicyclo[2.2.1]heptane-2-carboxylate C-1 (2.3 g, 9.30 mmol, 1.03 equiv.), and sodium hydride (725 mg, 30.21 mmol, 3.33 equiv.). The resulting mixture was stirred at 10-25° C., overnight. 200 mL of water/ice was added, the aqueous mixture was extracted with ethyl acetate (100 mL×3) and the combined organic extracts were concentrated under vacuum to a residue, which was purified by silica gel column chromatography eluting with ethyl acetate/petroleum ether (0:1 to 1:4). Removal of solvents provided benzyl (1S,4S,5R)-5-[[3-(2-chloro-6-methylphenyl)-5-cyclopropyl-1,2-oxazol-4-yl]methoxy]-2-azabicyclo[2.2.1]heptane-2-carboxylate 113g (2.6 g, 58%) as a light brown oil.

Step 7

To a 100 mL round-bottom flask was added benzyl (1S,4S,5R)-5-[[3-(2-chloro-6-methylphenyl)-5-cyclopropyl-1,2-oxazol-4-yl]methoxy]-2-azabicyclo[2.2.1]heptane-2-carboxylate 113g (450 mg, 0.91 mmol, 1.0 equiv.), dichloromethane (5 mL), and iodotrimethylsilane (365.28 mg, 1.83 mmol, 2.0 equiv.). The reaction mixture was stirred at 10-25° C., for 2 h, then quenched by the addition of 2 mL of a 2M HCl in ether solution. The mixture was diluted with 50 mL of DCM and concentrated under vacuum. The residue was purified by silica gel column chromatography eluting with a gradient mixture of ethyl acetate in petroleum ether (from 1:10 to 1:0). Removal of solvents afforded (1S,4S,5R)-5-[[3-(2-chloro-6-methylphenyl)-5-cyclopropyl-1,2-oxazol-4-yl]methoxy]-2-azabicyclo[2.2.1]heptane 113h (300 mg, 90%) as a light brown oil.

Step 8

To a 100 mL round-bottom flask purged and maintained under an inert atmosphere of nitrogen was added (1S,4S,5R)-5-[[3-(2-chloro-6-methylphenyl)-5-cyclopropyl-1,2-oxazol-4-yl]methoxy]-2-azabicyclo[2.2.1]heptane 113h (300 mg, 0.84 mmol, 1.0 equiv.), tert-butyl 4-bromo-3-fluorobenzoate (345 mg, 1.25 mmol, 1.5 equiv.), Tol (50 mL), $Cs_2CO_3$ (817.5 mg, 2.51 mmol, 3.0 equiv.). BIANP (26.3 mg), and $Pd_2(dba)_3$ (38.25 mg, 0.042 mmol, 0.05 equiv.). The resulting mixture was stirred at 110° C., overnight. Solids were filtered out, the filtrate was concentrated under vacuum to a residue, which was purified by silica gel column chromatography eluting with a gradient mixture of ethyl acetate/petroleum ether (1:10, 1:5, 3:1). Removal of solvents afforded tert-butyl 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-3-fluorobenzoate 113i (210, 45%) as a light brown oil.

Step 9

To a 100 mL round-bottom flask was added tert-butyl 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-3-fluorobenzoate 113i (210 mg, 0.38 mmol, 1.0 equiv.), dichloromethane (3 mL), and trifluoroacetic acid (3 mL). The reaction mixture was stirred at 10-25° C., for 3 h, then diluted with 100 mL of $H_2O$. The pH value of the solution was adjusted to 7 using sodium bicarbonate. The aqueous mixture was extracted with dichloromethane (50 mL×3). The combined organic extracts were concentrated under vacuum. The crude product was purified by Prep-HPLC using the following conditions: Column, XBridge Shield RP18 OBD Column, 5 um, 19*150 mm; mobile phase, Water (0.05% TFA) and ACN (5.0% ACN up to 60.0% in 1 min, up to 76.0% in 7 min); Detector, UV 254 nm. After purification, 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-3-fluorobenzoic acid I-113 (130 mg, 69%) was obtained as a colorless solid. $^1H$ NMR (300 MHz. DMSO-d6): δ 13.33-11.36 (m, 1H), 7.55 (dd, J=8.6, 2.0 Hz, 1H), 7.50-7.39 (m, 3H), 7.33 (td, J=6.4, 3.2 Hz, 1H), 6.65 (t, J=8.8 Hz, 1H), 4.29 (dd, J=11.7, 1.7 Hz, 1H), 4.21-4.00 (m, 2H), 3.48 (tt, J=8.5, 4.3 Hz, 2H), 2.68 (dt, J=8.8, 4.1 Hz, 1H), 2.49 (d, J=7.2 Hz, 1H), 2.33 (ddd, J=13.4, 8.0, 5.0 Hz, 2H), 2.10 (d, J=4.0 Hz, 3H), 1.84 (td, J=14.4, 7.0 Hz, 1H), 1.57-1.21 (m, 3H), 1.12 (ddt, J=10.0, 7.8, 2.8 Hz, 4H). MS (ES, m/z): [M+1]=497.1.

Example 108: 4-[(1S,4S,5R)-5-{[3-(2-chloro-6-methylphenyl)-5-cyclopropyl-1,2-oxazol-4-yl]methoxy}-2-azabicyclo[2.2.1]heptan-2-yl]-benzoic Acid (I-114)

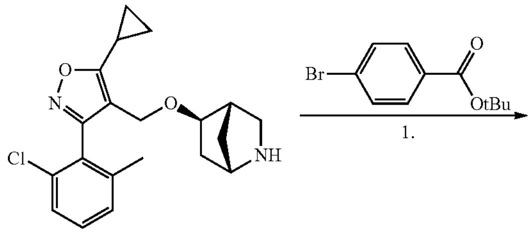

113h

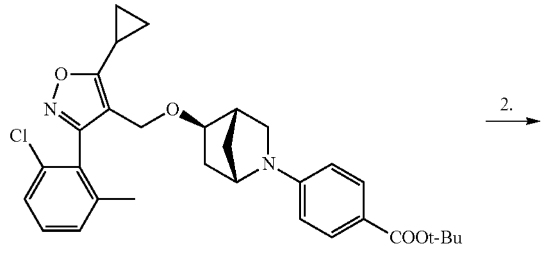

114a

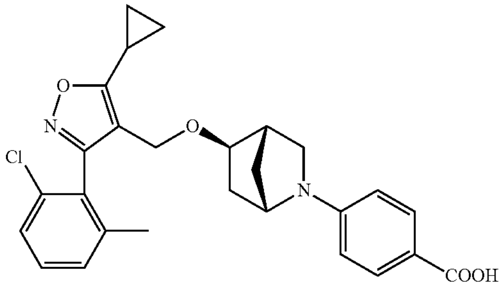

I-114

Step 1

To a 100 mL round-bottom flask purged and maintained under an inert atmosphere of nitrogen was added (1S,4S,5R)-5-[[3-(2-chloro-6-methylphenyl)-5-cyclopropyl-1,2-oxazol-4-yl]methoxy]-2-azabicyclo[2.2.1]heptane 113h (150 mg, 0.42 mmol, 1.0 equiv.), Tol (20 mL), tert-butyl 4-bromobenzoate (161.2 mg, 0.63 mmol, 1.50 equiv.), $Cs_2CO_3$ (408.8 mg, 1.25 mmol, 3.0 equiv.), BIANP (13 mg), and $Pd_2(dba)_3$ (19 mg, 0.02 mmol, 0.05 equiv.). The resulting mixture was stirred at 110° C., overnight. Solids were filtered out. The filtrate was concentrated under vacuum to a residue which was purified by silica gel column chromatography eluting with ethyl acetate/petroleum ether (1:10 to 1:5). Removal of solvents gave tert-butyl 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]benzoate 114a (100 mg, 45%) as a light yellow oil.

Step 2

To a 100 mL round-bottom flask was added tert-butyl 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]benzoate 114a (100 mg, 0.19 mmol, 1.0 equiv.), dichloromethane (2 mL), and trifluoroacetic acid (2 mL). The resulting mixture was stirred at 10-25° C., for 2 h. The mixture was diluted with 100 mL of $H_2O$, and extracted with dichloromethane (50 mL×3). The combined organic extracts were concentrated under vacuum to a crude product, which was purified by Prep-HPLC using the following conditions Column, XBridge Shield RP18 OBD Column, 5 um, 19*150 mm; mobile phase, Water (0.05% TFA) and ACN (54.0% ACN up to 69.0% in 8 min); Detector, UV 220 nm. After purification, 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]benzoic acid was obtained as a grayish solid I-114 (25 mg, 28%). $^1$H NMR (300 MHz, $CD_3OD$): δ 7.92-7.72 (m, 2H), 7.46-7.35 (m, 2H), 7.33-7.23 (m, 1H), 6.50 (dd, J=9.0, 2.1 Hz, 2H), 4.36 (d, J=11.7 Hz, 1H), 4.26-4.06 (m, 2H), 3.35 (d, J=1.7 Hz, 3H), 2.70-2.52 (m, 1H), 2.42-2.28 (d, J=0.9 Hz, 0H), 2.17 (d, J=3.0 Hz, 3H), 1.84 (td, J=12.7, 6.6 Hz, 1H), 1.64-1.48 (m, 2H), 1.37 (d, J=13.0 Hz, 1H), 1.22-1.10 (m, 4H). MS (ES, m/z): [M+1]=479.2.

Example 109: 4-[(1S,4S,5R)-5-{[3-(2-chloro-6-methylphenyl)-5-cyclopropyl-1,2-oxazol-4-yl]methoxy}-2-azabicyclo[2.2.1]heptan-2-yl]-2-fluorobenzoic Acid (I-115)

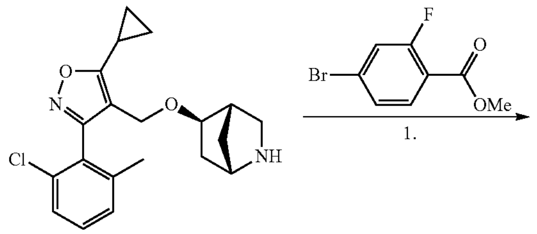

113h

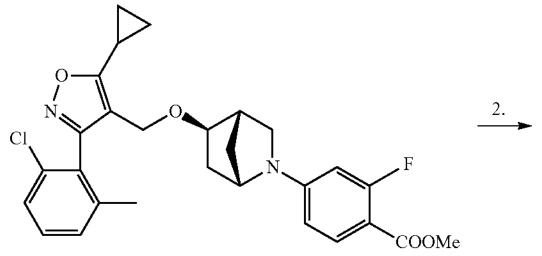

115a

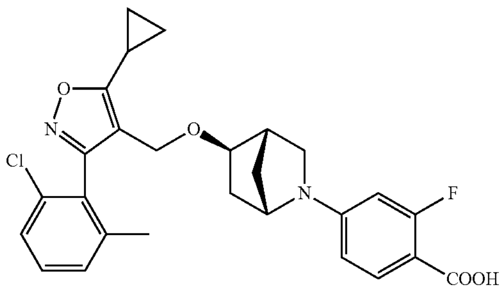

I-115

Step 1

To a 5 mL sealed tube purged and maintained under an inert atmosphere of nitrogen was added a solution of (1S,4S,5R)-5-[[3-(2-chloro-6-methylphenyl)-5-cyclopropyl-1,2-oxazol-4-yl]methoxy]-2-azabicyclo[2.2.1]heptane 113h (150 mg, 0.42 mmol, 1.0 equiv.) in toluene (3 mL), methyl 4-bromo-2-fluorobenzoate (106 mg, 0.45 mmol, 1.1 equiv.), $Pd(OAc)_2$ (19 mg, 0.08 mmol, 0.2 equiv.), Xantphos (48 mg, 0.08 mmol, 0.2 equiv.), and $Cs_2CO_3$ (410 mg, 1.26 mmol, 3.0 equiv.). The resulting mixture was stirred at 90° C., overnight. The reaction mixture was diluted with 100 mL of EA, washed with $H_2O$ (100 mL) and brine (100 mL), dried over anhydrous sodium sulfate and concentrated to a residue. The residue was purified by silica gel column chromatography eluting with ethyl acetate/petroleum ether (1:5). Removal of solvents provided methyl 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-2-fluorobenzoate 115a (70 mg, 33%) as a yellow oil.

Step 2

To a 50-mL round-bottom flask was added a solution of methyl 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-2-fluorobenzoate 115a (100 mg, 0.20 mmol, 1.0 equiv.) in methanol (1.5 mL), and a solution of LiOH (82 mg, 3.42 mmol, 10.0 equiv.) in water (0.5 mL). The resulting mixture was stirred at 50° C. overnight. The mixture was diluted with 10 mL of EA, washed with brine (10 mL×2), dried over anhydrous sodium sulfate, and concentrated under vacuum. The crude product was purified by Prep-HPLC using the following conditions (mobile phase, Water (0.05% TFA) and ACN (65% ACN up to 84% in 8 min). Detector, uv 220 nm. 20 mg product was obtained. After purification 4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-2-fluorobenzoic acid I-115 (17.3 mg, 18%) as a white solid. $^1$H NMR (300 MHz, $CD_3OD$): δ 7.73 (t, J=8.8 Hz, 1H), 7.43-7.35 (m, 2H), 7.29 (ddd, J=11.1, 6.3, 2.6 Hz, 1H), 6.32 (dt, J=9.0, 2.2 Hz, 1H), 6.20 (dt, J=14.6, 2.6 Hz, 1H), 4.35 (d, J=11.7 Hz, 1H), 4.25-4.10 (m, 2H), 3.50 (ddd, J=8.6, 6.1, 2.1 Hz, 1H), 3.39-3.29 (m, 1H), 2.63-2.40 (m, 2H), 2.31-2.23 (m, 1H), 2.17 (d, J=2.5 Hz, 3H), 1.92-1.75 (m, 1H), 1.61 (q, J=9.8 Hz, 1H), 1.52 (s, 1H), 1.41-1.21 (m, 1H), 1.20-1.17 (m, 4H). MS (ES, m/z): [M+1]=497.30.

Example 110: 4-[(1S,4S,5R)-5-{[5-cyclopropyl-3-(2,6-dimethylphenyl)-1,2-oxazol-4-yl]methoxy}-2-azabicyclo[2.2.1]heptan-2-yl]-3-fluorobenzoic Acid (I-116)

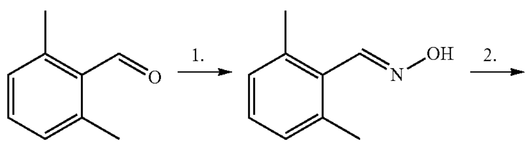

116a 116b

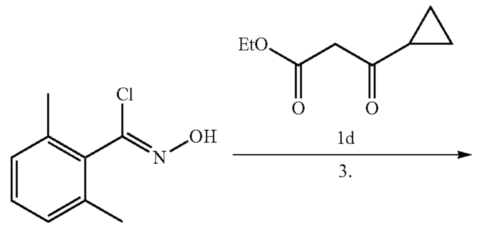

116c

-continued

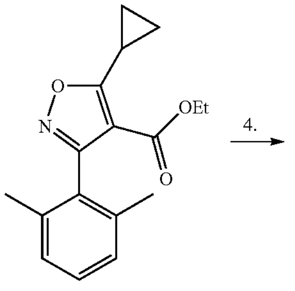

116d

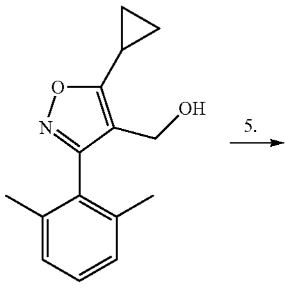

116e

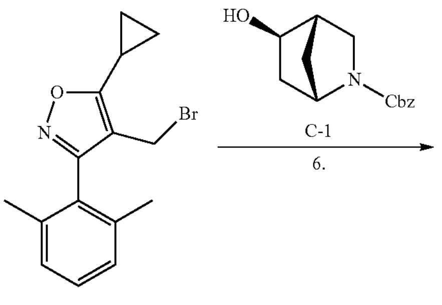

116f

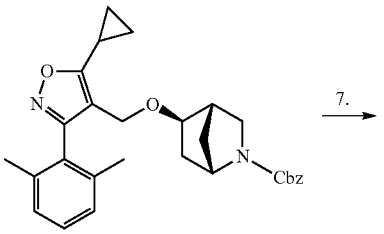

116g

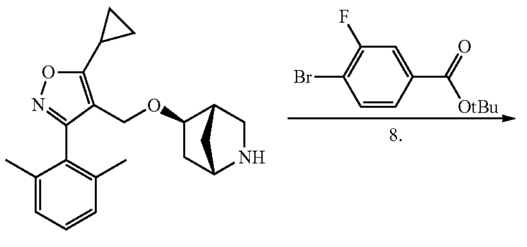

116h

-continued

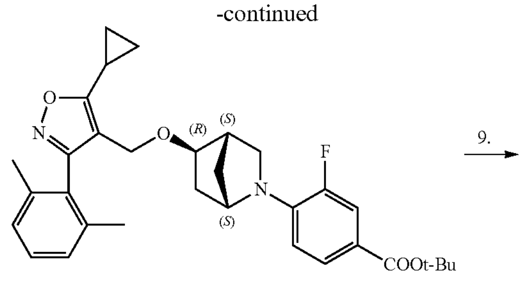

116i

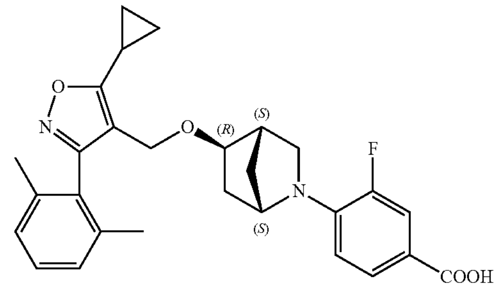

I-116

Step 1

To a 500 mL round-bottom flask was added $NH_2OH$ hydrochloride (13.388 g, 192.66 mmol, 1.3 equiv.), water (70 mL), sodium hydroxide (7.761 g, 194.03 mmol, 1.30 equiv.), a solution of 2,6-dimethylbenzaldehyde 116a (20 g, 149.06 mmol, 1.0 equiv.) in ethanol (60 mL), and ethanol (100 mL). The resulting mixture was stirred at 90° C., overnight. EtOH was removed under vacuum. The solids precipitated were collected by filtration, dried under vacuum to give N-[(2,6-dimethylphenyl)methylidene]hydroxylamine 116b (8.89 g, 85%) as a white solid.

Step 2

To a 1-L round-bottom flask was added N-[(2,6-dimethylphenyl)methylidene]-hydroxylamine 116b (18.89 g, 126.62 mmol, 1.0 equiv.) and N,N-dimethylformamide (300 mL). This was followed by the addition of NCS (16.91 g, 126.62 mmol, 1.0 equiv.) at 0° C. The resulting mixture was stirred at room temperature for 2 h, then diluted with 100 mL of $H_2O$. The mixture was extracted with 800 mL of ethyl acetate, the organic layer was washed with $H_2O$ (800 mL×3) and dried. Removal of solvents gave N-hydroxy-2,6-dimethylbenzene-1-carbonimidoyl chloride 116c (20 g, 86%) as a yellow oil.

Step 3

To a 250 mL round-bottom flask was added ethyl 3-cyclopropyl-3-oxopropanoate 1d (1.69 g, 10.82 mmol, 2.0 equiv.), tetrahydrofuran (15 mL) and t-BuOK (1.22 g, 10.87 mmol, 2.0 equiv.). N-hydroxy-2,6-dimethylbenzene-1-carbonimidoyl chloride 116c (1 g, 5.45 mmol, 1.0 equiv.) was added. The resulting mixture was stirred at room temperature for 2 h. 20 mL of $H_2O$ was added. The aqueous mixture was extracted with ethyl acetate (50 mL×3); the combined organic extracts were washed with brine (100 mL×1), dried over anhydrous sodium sulfate and concentrated under vacuum to provide ethyl 5-cyclopropyl-3-(2,6-dimethylphenyl)-1,2-oxazole-4-carboxylate 116d (1.26 g, 81%) of as an orange oil.

Step 4

To a 250 mL round-bottom flask was added ethyl 5-cyclopropyl-3-(2,6-dimethylphenyl)-1,2-oxazole-4-carboxylate 116d (1.26 g, 4.42 mmol, 1.0 equiv.) and tetrahydrofuran (15 mL). Solid $LiAlH_4$ (335 mg, 8.83 mmol, 2.0 equiv.) was added in several batches. The resulting mixture was stirred at room temperature for 2 h. The mixture was diluted with 50 mL of EA, washed with $H_2O$ (50 mL×2) and brine (50 mL×2), and dried over anhydrous sodium sulfate. Removal of solvents yielded a crude product which was purified by Flash-Prep-HPLC using the following conditions (IntelFlash-1): Column, silica gel; mobile phase, EA/PE=0.12 increasing to EA/PE=0.2 within 1 min; Detector, UV 254 nm. After purification, [5-cyclopropyl-3-(2,6-dimethylphenyl)-1,2-oxazol-4-yl]methanol 116e (0.72 g, 67%) was obtained as an orange color solid.

Step 5

To a 1 L round-bottom flask was added [5-cyclopropyl-3-(2,6-dimethylphenyl)-1,2-oxazol-4-yl]methanol 116e (5.7 g, 23.43 mmol, 1.0 equiv.), dichloromethane (300 mL), CBr4 (12.24 g, 37.36 mmol, 1.60 equiv.), and $PPh_3$ (9.18 g, 35.00 mmol, 1.5 equiv.). The resulting mixture was stirred at room temperature for 4 h and diluted with 100 mL of DCM. The mixture was washed with $H_2O$ (500 mL×2), dried over anhydrous sodium sulfate and concentrated under vacuum. The crude product was purified by Flash-Prep-HPLC with the following conditions (IntelFlash-1): Column, silica gel; mobile phase, H2O/MeCN=1/9 increasing to H2O/MeCN=1/9 within 2 min; Detector, UV 254 nm. This afforded 4-(bromomethyl)-5-cyclopropyl-3-(2,6-dimethylphenyl)-1,2-oxazole 116f (3.6 g, 50%) as a light yellow oil.

Step 6

To a 100 mL round-bottom flask was added a solution of 4-(bromomethyl)-5-cyclopropyl-3-(2,6-dimethylphenyl)-1,2-oxazole 116f (401 mg, 1.31 mmol, 1.30 equiv.) in dichloromethane (10 mL), a solution of benzyl (1S,4S,5R)-5-hydroxy-2-azabicyclo[2.2.1]heptane-2-carboxylate C-1 (250 mg, 1.01 mmol, 1.0 equiv.) in dichloromethane (5 mL), and sodium hydride (40.48 mg, 2.0 equiv.). The resulting mixture was stirred at room temperature overnight, then quenched by the addition of water/ice. The aqueous mixture was diluted with 50 mL of EA and extracted with ethyl acetate (50 mL×2). The combined organic extracts were brine (100 mL×2), dried over anhydrous sodium sulfate, and concentrated under vacuum. The residue was purified by silica gel column chromatography eluting with ethyl acetate/petroleum ether (1:4) to give benzyl (1S,4S,5R)-5-[[5-cyclopropyl-3-(2,6-dimethylphenyl)-1,2-oxazol-4-yl]methoxy]-2-azabicyclo[2.2.1]heptane-2-carboxylate 116g (337 mg, 71%) as a yellow oil.

Step 7

To a 50 mL round-bottom flask was added a solution of benzyl (1S,4S,5R)-5-[[5-cyclopropyl-3-(2,6-dimethylphenyl)-1,2-oxazol-4-yl]methoxy]-2-azabicyclo[2.2.1]heptane-2-carboxylate 116g (337 mg, 0.71 mmol, 1.0 equiv.) in dichloromethane (10 mL), and TMSI (713.9 g, 3.57 mol, 5.0 equiv.). The resulting mixture was stirred for 0.5 h at room temperature and then quenched by the addition of a hydrogen chloride solution. The mixture was extracted with dichloromethane (50 mL×3). The combined organic extracts were washed with brine (100 mL), dried over anhydrous sodium sulfate, and concentrated under vacuum. The residue was purified by silica gel column chromatography eluting with dichloromethane/methanol (10:1) to afford (1S,4S,5R)-5-[[5-cyclopropyl-3-(2,6-dimethylphenyl)-1,2-oxazol-4-yl]methoxy]-2-azabicyclo[22.21]heptane 116h (120 mg, 50%) as a yellow oil.

Step 8

To a 50-mL round-bottom flask was added (1S,4S,5R)-5-[[5-cyclopropyl-3-(2,6-dimethylphenyl)-1,2-oxazol-4-yl]methoxy]-2-azabicyclo[2.2.1]heptane 116h (200 mg, 0.59 mmol, 1.0 equiv.), a solution of tert-butyl 4-bromo-3-fluorobenzoate (194 mg, 0.71 mmol, 1.20 equiv.) in toluene (5 mL), $Cs_2CO_3$ (385 mg, 1.18 mmol, 2.0 equiv.), BINAP (78 mg, 0.13 mmol, 0.20 equiv.), and $Pd_2(dba)_3$ (108 mg, 0.12 mmol, 0.2 equiv.). The resulting mixture was stirred at 110° C., overnight. The reaction mixture was cooled, diluted with 20 mL of $H_2O$, and extracted with ethyl acetate (50 mL×2). The organic extracts were washed with brine (50 mL×2), dried over anhydrous sodium sulfate, and concentrated under vacuum. The residue was purified by silica gel column chromatography eluting with ethyl acetate/petroleum ether (1:5) to provide tert-butyl 4-[(1S,4S,5R)-5-[[5-cyclopropyl-3-(2,6-di methylphenyl)-1,2-oxazol-4-yl]methoxy]-2-azabicyclo[2.2.1]heptan-2-yl]-3-fluorobenzoate 116i (120 mg, 38%) as a yellow oil.

Step 9

To a 50 mL round-bottom flask was added a solution of tert-butyl 4-[(1S,4S,5R)-5-[[5-cyclopropyl-3-(2,6-dimethylphenyl)-1,2-oxazol-4-yl]methoxy]-2-azabicyclo[2.2.1]heptan-2-yl]-3-fluorobenzoate 116i (180 mg, 0.34 mmol, 1.0 equiv.) in dichloromethane (4 mL) and trifluoroacetic acid (2 mL). The resulting mixture was stirred at room temperature for 1 h. $H_2O$ (20 mL) was added, the mixture was extracted with dichloromethane (30 mL×3). The combined organic layers were washed with brine (50 mL×2), dried over anhydrous sodium sulfate and concentrated under vacuum. The crude product was purified by Prep-HPLC using the following conditions (mobile phase, Water (0.05% TFA) and ACN (55.0% ACN up to 75.0% in 8 min). Detector, uv 254 nm. After purification 4-[(1S,4S,5R)-5-[[5-cyclopropyl-3-(2,6-dimethylphenyl)-1,2-oxazol-4-yl]methoxy]-2-azabicyclo[2.2.1]heptan-2-yl]-3-fluorobenzoic acid I-116 (119.1 mg, 74%) was obtained as a colorless solid. $^1H$ NMR (300 MHz, $CD_3OD$): δ 7.62 (dd, J=8.7, 2.0 Hz, 1H), 7.51 (dd, J=15.0, 2.0 Hz, 1H), 7.27 (t, J=7.6 Hz, 1H), 7.13 (dd, J=7.5, 3.8 Hz, 2H), 6.60 (t, J=8.8 Hz, 1H), 4.26-4.07 (m, 3H), 3.54 (dt. J=10.0, 3.9 Hz, 1H), 3.45 (dd, J=6.6, 2.4 Hz, 1H), 2.69 (dd, J=9.8, 3.4 Hz, 1H), 2.47-2.39 (m, 1H), 2.26 (p, J=6.6 Hz, 1H), 2.09 (d, J=1.5 Hz, 6H), 2.00-1.84 (m, 1H), 1.56 (s, 2H), 1.35-1.20 (m, 1H), 1.16 (d, J=6.7 Hz, 4H). MS (ES, m/z): [M+1]=477.2.

Example 111: 4-[(1S,4S,5R)-5-{[5-cyclopropyl-3-(2,6-dimethylphenyl)-1,2-oxazol-4-yl]methoxy}-2-azabicyclo[2.2.1]heptan-2-yl]benzoic Acid (I-117)

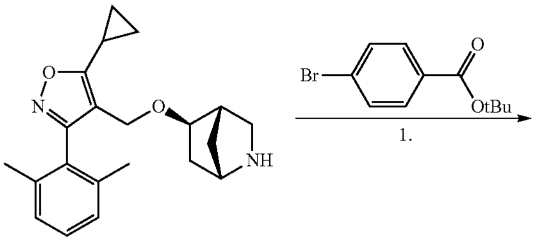

116h

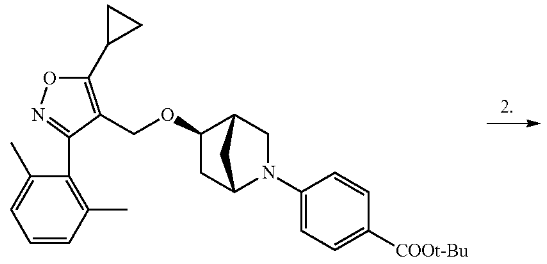

117a

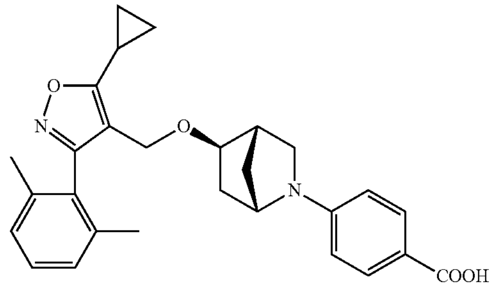

I-117

Step 1

To a 50 mL round-bottom flask was added (1S,4S,5R)-5-[[5-cyclopropyl-3-(2,6-dimethylphenyl)-1,2-oxazol-4-yl]methoxy]-2-azabicyclo[2.2.1]heptane 116h (200 mg, 0.59 mmol, 1.0 equiv.), tert-butyl 4-bromobenzoate (182 mg, 0.71 mmol, 1.2 equiv.), a solution of $Cs_2CO_3$ (384 mg, 1.18 mmol, 2.0 equiv.) in toluene (5 mL), BINAP (74 mg, 0.12 mmol, 0.20 equiv), and $Pd_2(dba)_3$ (108 mg, 0.12 mmol, 0.2 equiv.). The resulting mixture was stirred at 110° C., overnight. The reaction mixture was cooled, diluted with 50 mL of $H_2O$, and extracted with ethyl acetate (50 mL×2). The combined organic extracts were washed with brine (100 mL×2), dried over anhydrous sodium sulfate, and concentrated under vacuum. The residue was purified by silica gel column chromatography eluting with ethyl acetate/petroleum ether (1:5) to give tert-butyl 4-[(1S,4S,5R)-5-[[5-cyclopropyl-3-(2,6-dimethylphenyl)-1,2-oxazol-4-yl]methoxy]-2-azabicyclo[2.2.1]heptan-2-yl]benzoate 117a (59 mg, 19%) as a yellow oil.

Step 2

To a 50 mL round-bottom flask was added a solution of tert-butyl 4-[(1S,4S,5R)-5-[[5-cyclopropyl-3-(2,6-dimethylphenyl)-1,2-oxazol-4-yl]methoxy]-2-azabicyclo[2.2.1]heptan-2-yl]benzoate 117a (59 mg, 0.11 mmol, 1.0 equiv.) in dichloromethane (2 mL), and trifluoroacetic acid (1 mL). The resulting mixture was stirred at room temperature for 1 h and added with 10 mL of $H_2O$. The aqueous mixture was extracted with dichloromethane (50 mL×2). The organic layers were combined and washed with brine (50 mL×2), dried over anhydrous sodium sulfate and concentrated under vacuum. The crude product was purified by Prep-HPLC using the following conditions (Column. XBridge Shield RP18 OBD Column, 5 um, 19*150 mm; mobile phase, Water (0.05% TFA) and ACN (50.0% ACN up to 70.0% in 9 min); Detector, UV 220 nm. After purification 4-[(1S,4S,5R)-5-[[5-cyclopropyl-3-(2,6-dimethylphenyl)-1,2-oxazol-4-yl]methoxy]-2-azabicyclo[2.2.1]heptan-2-yl]benzoic acid I-117 (8 mg, 15%) was obtained as a white solid. $^1H$ NMR (300 MHz, $CD_3OD$): δ 7.82-7.74 (m, 2H), 7.26 (t, J=7.6 Hz, 1H), 7.12 (t, J=7.3 Hz, 2H), 6.51-6.44 (m, 2H), 4.20-4.08 (m, 3H), 3.47-3.40 (m, 1H), 3.35 (dd, J=9.4, 4.1 Hz, 1H), 2.56 (d, J=9.4 Hz, 1H), 2.46 (d, J=3.8 Hz, 1H), 2.31-2.19 (m, 1H), 2.08 (d, J=2.7 Hz, 6H), 1.83 (ddd, J=13.2, 6.9, 2.3 Hz, 1H), 1.63-1.51 (m, 2H), 1.31-1.20 (m, 1H), 1.16 (d, J=6.7 Hz, 4H). MS (ES, m/z): [M+1]=459.4.

Example 112: 4-[(1S,4S,5R)-5-{[3-(2-chloro-6-fluorophenyl)-5-cyclopropyl-1,2-oxazol-4-yl]methoxy}-2-azabicyclo[2.2.1]heptan-2-yl]benzoic Acid (I-118)

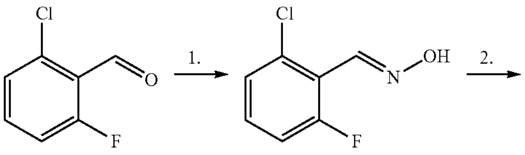

118a

118b

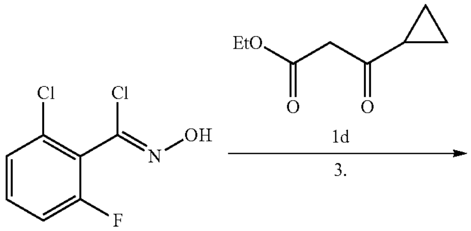

118c

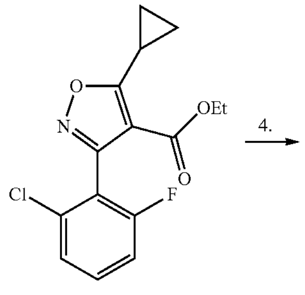

118d

-continued

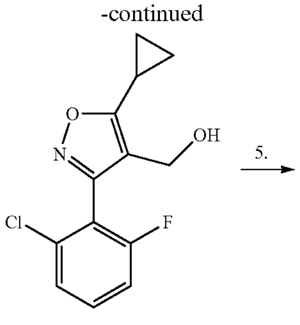

118e

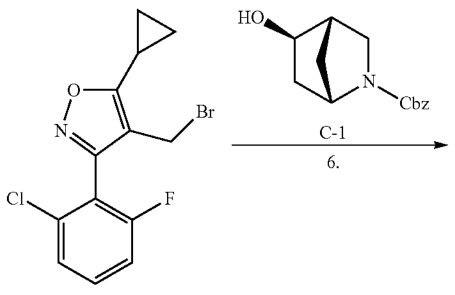

118f

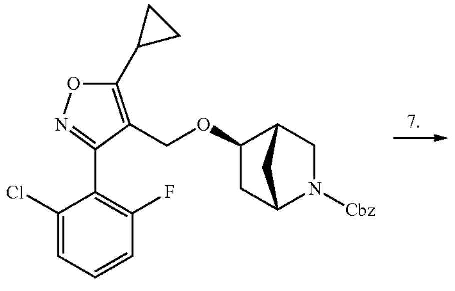

118g

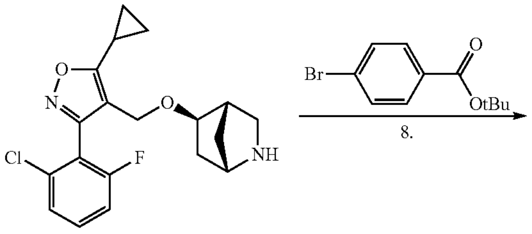

118h

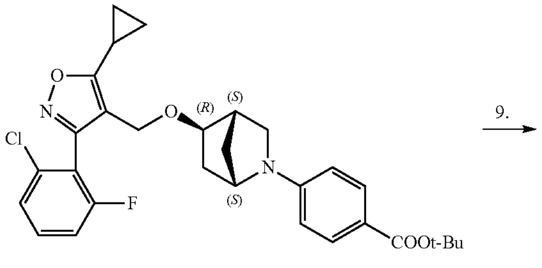

118i

-continued

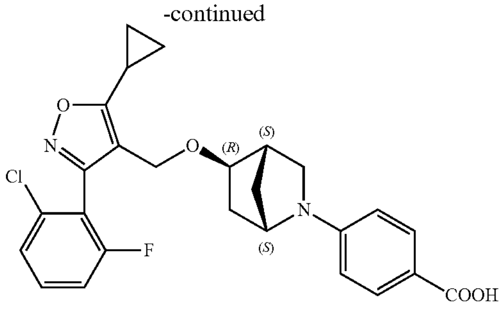

I-118

Step 1

To a 1 L round-bottom flask was added hydroxylamine hydrochloride (11.35 g, 163.33 mmol, 1.30 equiv.) and a solution of sodium hydroxide (6.58 g, 164.50 mmol, 1.30 equiv.) in water (200 mL). A solution of 2-chloro-6-fluorobenzaldehyde 118a (20 g, 126.14 mmol, 1.0 equiv.) in ethanol (200 mL) was added at 0° C., with stirring. The resulting mixture was stirred at 90° C., overnight. EtOH was removed under vacuum. The precipitations were collected by filtration to afford N-[(2-chloro-6-fluorophenyl) methylidene]hydroxylamine 118b (18 g, 82%) as a colorless solid.

Step 2

To a 500-mL round-bottom flask was added N-[(2-chloro-6-fluorophenyl)-methylidene]hydroxylamine 118b (19.1 g, 110.04 mmol, 1.0 equiv.), N,N-dimethylformamide (200 mL), and NCS (14.8 g, 110.84 mmol, 1.0 equiv.). The resulting mixture was stirred at room temperature for 2 h. The mixture was diluted with 300 mL of $H_2O$ and extracted with ethyl acetate (300 mL×2). The combined organic extracts were washed with brine (300 mL×2), dried over anhydrous sodium sulfate, and concentrated under vacuum to give 2-chloro-6-fluoro-N-hydroxybenzene-1-carbonimidoyl chloride 118-c (20 g, 87%) as a colorless oil.

Step 3

To a 1000 mL round-bottom flask was added TEA (300 mL) and ethyl 3-cyclopropyl-3-oxopropanoate 1d (22.6 g, 144.71 mmol, 1.5 equiv.). 2-Chloro-6-fluoro-N-hydroxybenzene-1-carbonimidoyl chloride 118-c (20 g, 96.15 mmol, 1.0 equiv.) was added. The resulting mixture was stirred at room temperature overnight and then diluted with 500 mL of $H_2O$. The aqueous mixture was extracted with ethyl acetate (500 mL×2) the combined organic extracts were washed with brine (500 mL×2) and dried over anhydrous sodium sulfate and concentrated under vacuum to give ethyl 3-(2-chloro-6-fluorophenyl)-5-cyclopropyl-1,2-oxazole-4-carboxylate 118d (30 g, Q) as a reddish oil.

Step 4

To a 500 mL round-bottom flask was added ethyl 3-(2-chloro-6-fluorophenyl)-5-cyclopropyl-1,2-oxazole-4-carboxylate 118d (15 g, 48.43 mmol, 1.0 equiv.) and tetrahydrofuran (150 mL). $LiAlH_4$ (3.7 g, 97.50 mmol, 2.00 equiv.) was added in small portion. The resulting mixture was stirred at room temperature for 2 h. The reaction was quenched by the addition of an aqueous solution of sodium potassium tartrate tetrahydrate (Rochelle salt, $KNaC_4H_4O_6.4H_2O$). The mixture was extracted with ethyl acetate (500 mL×2). The combined organic extracts were washed with brine (500 mL×2), dried over anhydrous sodium sulfate, and concentrated under vacuum. The residue was purified by silica gel column chromatography eluting with ethyl acetate/petroleum ether (0% to 15%). Removal of solvents gave [3-(2-chloro-6-fluorophenyl)-5-cyclopropyl-1,2-oxazol-4-yl]methanol 118e (9.7 g, 75%) as a red color oil.

Step 5

To a 500 mL round-bottom flask was added a solution of [3-(2-chloro-6-fluorophenyl)-5-cyclopropyl-1,2-oxazol-4-yl]methanol 118e (9.7 g, 36.24 mmol, 1.0 equiv.) in dichloromethane (150 mL). $CBr_4$ (19.0 g, 1.6 equiv.) and $PPh_3$ (14.3 g, 54.52 mmol, 1.5 equiv.) were added. The resulting mixture was stirred at room temperature for 4 h. The mixture was washed with $H_2O$ (300 mL) and brine (300 mL), dried over anhydrous sodium sulfate, and concentrated under vacuum. The residue was purified by silica gel column chromatography eluting with ethyl acetate/petroleum ether (0% to 8%) to afford 4-(bromomethyl)-3-(2-chloro-6-fluorophenyl)-5-cyclopropyl-1,2-oxazole 118f (8.2 g, 68%) as a yellow oil.

Step 6

To a 100 mL round-bottom flask was added a solution of 4-(bromomethyl)-3-(2-chloro-6-fluorophenyl)-5-cyclopropyl-1,2-oxazole 118f (1.46 g, 4.42 mmol, 1.1 equiv.) in N,N-dimethylformamide (25 mL), benzyl (1S,4S,5R)-5-hydroxy-2-azabicyclo[2.2.1]heptane-2-carboxylate C-1 (1 g, 4.04 mmol, 1.0 equiv.), and sodium hydride (324 mg, 13.50 mmol, 2.0 equiv.). The resulting mixture was stirred at room temperature for 2 h and quenched by the addition of 15 mL of water. The aqueous mixture was further diluted with 10 mL of EA, and extracted with 100 mL of ethyl acetate. The organic layer was washed with brine (100 mL), dried over anhydrous sodium sulfate and concentrated under vacuum to give benzyl (1S,4S,5R)-5-[[3-(2-chloro-6-fluorophenyl)-5-cyclopropyl-1,2-oxazol-4-yl]methoxy]-2-azabicyclo[2.2.1]heptane-2-carboxylate 118g (1.8 g, 90%) as a yellow oil.

Step 7

To a 100 mL round-bottom flask was added a solution of benzyl (1S,4S,5R)-5-[[3-(2-chloro-6-fluorophenyl)-5-cyclopropyl-1,2-oxazol-4-yl]methoxy]-2-azabicyclo[2.2.1]heptane-2-carboxylate 118g (1.8 g, 3.62 mmol, 1.0 equiv.) in dichloromethane (20 mL) and TMSI (1.45 g, 7.25 mmol, 2.0 equiv.). The resulting mixture was stirred at room temperature for 2 h, diluted with 20 mL of $CH_2Cl_2$, and quenched by the addition of 15 mL of water. The aqueous mixture was extracted with $CH_2Cl_2$ (150 mL), the organic extract was washed with brine (200 mL×2). The mixture was dried over anhydrous sodium sulfate and concentrated under vacuum. The residue was applied onto a silica gel column with dichloromethane/methanol (10:1). This resulted in 1.13 g (86%) of (1S,4S,5R)-5-[[3-(2-chloro-6-fluorophenyl)-5-cyclopropyl-1,2-oxazol-4-yl]methoxy]-2-azabicyclo[2.2.1]heptane 118h as a light yellow solid.

Step 8

To a 25-mL round-bottom flask purged with and maintained under an inert atmosphere of nitrogen was added (1S,4S,5R)-5-[[3-(2-chloro-6-fluorophenyl)-5-cyclopropyl-1,2-oxazol-4-yl]methoxy]-2-azabicyclo[2.2.1]heptane 118h (150 mg, 0.41 mmol, 1.0 equiv.), a solution of tert-butyl 4-bromobenzoate (127 mg, 0.49 mmol, 1.2 equiv.) in toluene (3 mL), BINAP (52 mg, 0.08 mmol, 0.2 equiv.), $Pd_2(dba)_3$ (76 mg, 0.08 mmol, 0.2 equiv.), and $Cs_2CO_3$ (270 mg, 0.83 mmol, 2.0 equiv.). The resulting mixture was stirred at 110° C., overnight. Upon cooling to room temperature, the mixture was diluted with 20 mL of water and extracted with ethyl acetate (20 mL×2). The combined organic extracts were washed with brine (50 mL), dried over anhydrous sodium sulfate, and concentrated under vacuum. The residue was purified by silica gel column chromatography eluting with ethyl acetate/petroleum ether (1:5). Removal of solvents afforded tert-butyl 4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]benzoate 118i (100 mg, 45%) as a light yellow oil.

Step 9

To a 50 mL round-bottom flask was added tert-butyl 4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]benzoate 118i (100 mg, 0.19 mmol, 1.0 equiv.), dichloromethane (4 mL), and trifluoroacetic acid (2 mL, 5.0 equiv.). The resulting mixture was stirred at room temperature for 1 h and then diluted with 10 mL of dichloromethane. The pH value of the solution was adjusted to 2 using an aqueous hydrogen chloride solution (1 N). The aqueous mixture was extracted with 100 mL of ethyl acetate; and the organic extract was washed with brine (100 mL×2), dried over anhydrous sodium sulfate and concentrated under vacuum. The crude product (5 mL) was purified by Prep-HPLC using the following conditions (mobile phase, Water (0.05% TFA) and ACN (65.0% ACN up to 78.0% in 7 min); Detector, uv 254 nm. After purification 4-[(1S,4S,5R)-5-[[3-(2-chloro-6-fluorophenyl)-5-cyclopropyl-1,2-oxazol-4-yl]methoxy]-2-azabicyclo[2.2.2.1]heptan-2-yl]benzoic acid I-118 (55.3 mg, 63%) was obtained as a colorless solid. $^1H$ NMR (300 MHz, $CD_3OD$): δ 7.82-7.70 (m, 2H), 7.49 (td, J=8.3, 5.9 Hz, 1H), 7.36 (d, J=8.2 Hz, 1H), 7.19 (t, J=8.7 Hz, 1H), 6.55-6.39 (m, 2H), 4.29 (s, 2H), 4.11 (d, J=2.6 Hz, 1H), 3.43 (dd, J=7.1, 2.4 Hz, 1H), 3.32 (dd, J=9.5, 4.1 Hz, 1H), 2.58-2.41 (m, 2H), 2.29-2.10 (m, 1H), 1.83-1.69 (m, 1H), 1.53 (d, J=3.4 Hz, 2H), 1.33-1.20 (m, 1H), 1.13 (d, J=6.7 Hz, 4H). MS (ES, m/z): [M+1]=483.15.

Example 113: 4-[(1S,4S,5R)-5-{[3-(2-chloro-6-fluorophenyl)-5-cyclopropyl-1,2-oxazol-4-yl]methoxy}-2-azabicyclo[2.2.1]heptan-2-yl]-3-fluorobenzoic Acid (I-119)

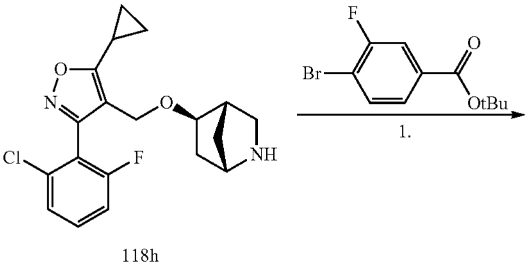

118h

-continued

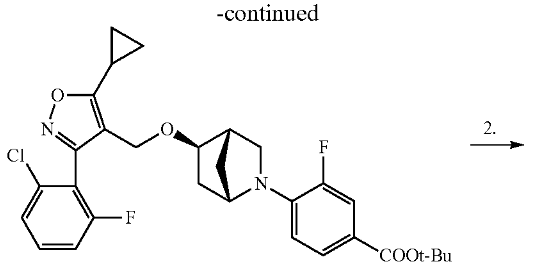

119a

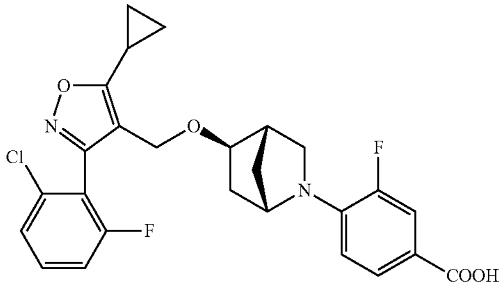

I-119

Step 1

To a 50 mL round-bottom flask was added (1S,4S,5R)-5-[[3-(2-chloro-6-fluorophenyl)-5-cyclopropyl-1,2-oxazol-4-yl]methoxy]-2-azabicyclo[2.2.1]heptane 118h (150 mg, 0.41 mmol, 1.00 equiv.), tert-butyl 4-bromo-3-fluorobenzoate (136 mg, 0.49 mmol, 1.2 equiv.), a solution of $Cs_2CO_3$ (269 mg, 0.83 mmol, 2.0 equiv.) in toluene (5 mL), BINAP (55 mg, 0.09 mmol, 0.20 equiv.), and $Pd_2(dba)_3$ (76 mg, 0.08 mmol, 0.2 equiv.). The resulting mixture was stirred at 110° C., overnight. After cooling to room temperature, the mixture was diluted with 20 mL of $H_2O$ and extracted with ethyl acetate (50 mL×2). The combined organic extracts were washed with brine (100 mL×2), dried over anhydrous sodium sulfate, and concentrated under vacuum. The residue was purified by silica gel column chromatography eluting with ethyl acetate/petroleum ether (1:5) to give tert-butyl 4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-3-fluorobenzoate 119a (127 mg, 55%) as a yellow solid.

Step 2

To a 50 mL round-bottom flask was added tert-butyl 4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-3-fluorobenzoate 119a (127 mg, 0.23 mmol, 1.0 equiv.) in DCM (4 mL). Trifluoroacetic acid (2 mL, 2.0 equiv.) was added dropwise. The resulting mixture was stirred at room temperature for 2 h. 10 mL of water was added. The aqueous mixture was extracted with dichloromethane (30 mL×3). The combined organic extracts were washed with brine, dried over anhydrous sodium sulfate, and concentrated under vacuum. The crude product was purified by Prep-HPLC using the following conditions (mobile phase, Water (0.05% TFA) and methanol—(35.0% methanol-up to 65.0% in 10 min); Detector, uv 254 nm. After purification 4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-3-fluorobenzoic acid I-119 (47.3 mg, 41%) was obtained as a colorless solid. $^1H$ NMR (300 MHz, $CD_3OD$): δ 7.62 (dd, J=8.6, 2.0 Hz, 1H), 7.57-7.48 (m, 2H), 7.40 (d, J=8.1 Hz, 1H), 7.23 (t, J=8.7 Hz, 1H), 6.61 (t, J=8.8 Hz, 1H), 4.33 (s, 2H), 4.24 (s, 1H), 3.62-3.43 (m, 2H), 2.70 (dd, J=9.9, 3.4 Hz, 1H), 2.45 (d, J=4.0 Hz, 1H), 2.33-2.18 (m, 1H), 2.04 (s, OH), 1.91 (dd, J=13.5, 6.8 Hz, 1H), 1.56 (s, 2H), 1.36-1.24 (m, 1H), 1.20-1.14 (m, 4H). MS (ES, m/z): [M+1]=501.3.

Example 114: 4-[(1S,4S,5R)-5-({5-cyclopropyl-3-[2-(trifluoromethyl)phenyl]-1,2-oxazol-4-yl}methoxy)-2-azabicyclo[2.2.1]heptan-2-yl]benzoic Acid (I-120)

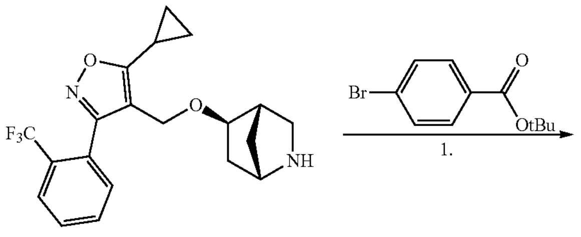

19d

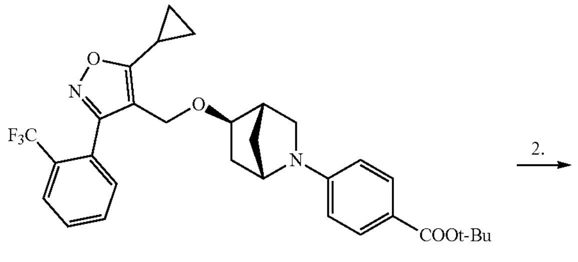

120a

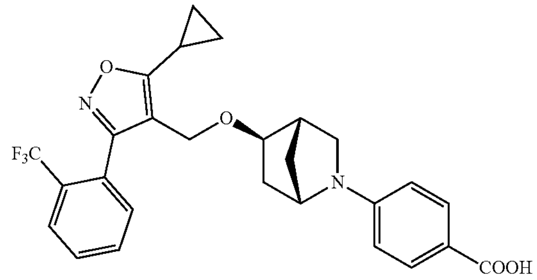

I-120

Step 1

To a 100 mL round-bottom flask purged with and maintained under an inert atmosphere of nitrogen was added (1S,4S,5R)-5-([5-cyclopropyl-3-[2-(trifluoromethyl)phenyl]-1,2-oxazol-4-yl]methoxy)-2-azabicyclo[2.2.1]heptane 19d (160 mg, 0.42 mmol, 1.0 equiv.), toluene (20 mL), tert-butyl 4-bromobenzoate (163 mg, 0.63 mmol, 1.5 equiv.), $Cs_2CO_3$ (413.5 mg, 1.27 mmol, 3.0 equiv.), BINAP (13.2 mg, 0.02 mmol, 0.05 equiv.), and $Pd_2(dba)_3$ (19.3 mg, 0.02 mmol, 0.05 equiv.). The resulting mixture was stirred at 110° C., overnight. Solids were filtered out, the filtrate was concentrated under vacuum to give tert-butyl 4-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]benzoate 120a (200 mg, 85%, crude) as a light brown oil.

Step 2

To a 100 mL round-bottom flask was added tert-butyl 4-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]benzoate 120b (150 mg, 0.27 mmol, 1.0 equiv.), dichloromethane (2 mL), and trifluoroacetic acid (2 mL). The resulting mixture was stirred at 10-25° C., for 2 h, then diluted with 100 mL of $H_2O$. The pH value of the solution was adjusted to 7 using sodium carbonate. The aqueous mixture was extracted with dichloromethane (50 mL×3), the combined organic extracts were concentrated under vacuum. The residue was purified by Prep-HPLC using the following conditions: Column, XBridge C18 OBD Prep Column, 19 mm×250 mm; mobile phase, Water (0.05% TFA) and ACN (65.0% ACN up to 73.0% in 8 min); Detector, uv 254 nm. After purification 4-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]benzoic acid I-120 (60 mg, 45%) was obtained as a colorless solid. $^1$H NMR (300 MHz, $CD_3OD$): δ 7.91-7.64 (m, 5H), 7.58-7.47 (m, 1H), 6.49 (d, J=8.9 Hz, 2H), 4.26 (d, J=4.4 Hz, 2H), 4.17 (s, 1H), 3.53-3.44 (m, 1H), 3.37 (dd, J=9.5, 4.0 Hz, 1H), 2.58 (d, J=9.4 Hz, 1H), 2.53 (d, J=2.6 Hz, 1H), 2.24 (p, J=6.9 Hz, 1H), 1.87 (dd, J=13.2, 7.1 Hz, 1H), 1.62 (t, J=8.5 Hz, 2H), 1.40-1.26 (m, 1H), 1.21-1.11 (m, 4H). MS (ES, m/z): [M+1]=499.5.

Example 115: 4-[(1S,4S,5R)-5-({5-cyclopropyl-3-[2-(trifluoromethyl)phenyl]-1,2-oxazol-4-yl}methoxy)-2-azabicyclo[2.2.1]heptan-2-yl]-3-fluorobenzoic Acid (I-121)

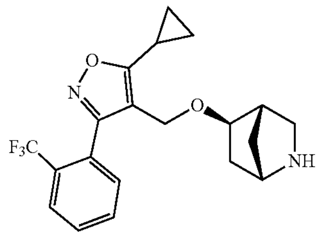

19d

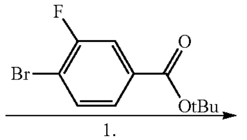

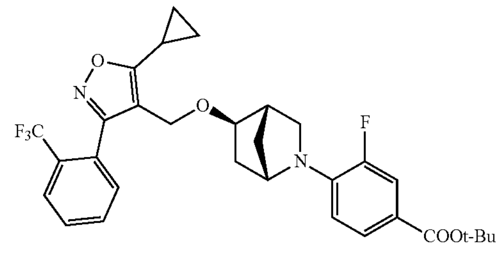

121a

-continued

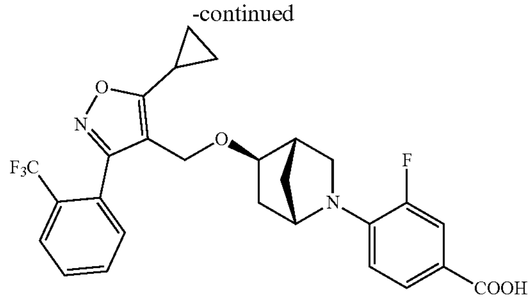

I-121

Step 1

To a 250 mL round-bottom flask purged with and maintained under an inert atmosphere of nitrogen was added (1S,4S,5R)-5-([5-cyclopropyl-3-[2-(trifluoromethyl)phenyl]-1,2-oxazol-4-yl]methoxy)-2-azabicyclo[2.2.1]heptane 19d (670 mg, 1.77 mmol, 1.0 equiv.), toluene (50 mL), tert-butyl 4-bromo-3-fluorobenzoate (731 mg, 2.66 mmol, 1.5 equiv.), $Cs_2CO_3$ (1.73 g, 5.31 mmol, 3.0 equiv.), BINAP (53.5 mg, 0.09 mmol, 0.05 equiv.), and $Pd_2(dba)_3$ (81 mg, 0.09 mmol, 0.05 equiv.). The resulting mixture was stirred at 110° C., overnight. Solids were filtered out, the filtrate was concentrated under vacuum to a residue which was purified by silica gel column chromatography eluting with ethyl acetate/petroleum ether (1:10-1:5-1:3). Removal of solvents gave tert-butyl 4-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-3-fluorobenzoate 121a (750 mg, 74%) as a light yellow oil.

Step 2

To a 100 mL round-bottom flask was added tert-butyl 4-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-3-fluorobenzoate 121a (750 mg, 1.31 mmol, 1.0 equiv.), dichloromethane (3 mL), and trifluoroacetic acid (3 mL). The resulting mixture was stirred at 10-25° C., for 2 h, then diluted with 100 mL of $H_2O$. The pH value of the solution was adjusted to 7 using sodium carbonate. The aqueous mixture was extracted with dichloromethane (50 mL×3), and the combined organic extracts were dried over anhydrous sodium sulfate and concentrated. The crude product was purified by Prep-HPLC using the following conditions Column, XBridge Prep C18 OBD Column, 19??150 mm 5 um mobile phase, Water (0.05% TFA) and ACN (35.0% ACN up to 65.0% in 8 min); Detector, uv 254 nm. After purification 4-[(1S,4S,5R)-5-([5-cyclopropyl-3-[2-(trifluoromethyl)phenyl]-1,2-oxazol-4-yl]methoxy)-2-azabicyclo[2.2.1]heptan-2-yl]-3-fluorobenzoic acid I-121 (300 mg, 44%) was obtained as a colorless solid. $^1$H NMR (300 MHz. $CD_3OD$): δ 7.87 (dd, J=7.0, 2.1 Hz, 1H), 7.73 (td, J=5.3, 4.7, 2.3 Hz, 2H), 7.62 (dd, J=8.6, 2.0 Hz, 1H), 7.52 (ddd, J=11.2, 4.2, 2.0 Hz, 2H), 6.61 (t, J=8.7 Hz, 1H), 4.34-4.18 (m, 3H), 3.67-3.53 (m, 1H), 3.50 (dd, J=6.8, 2.3 Hz, 1H), 2.71 (dd, J=9.9, 3.4 Hz, 1H), 2.52-2.44 (m, 1H), 2.33-2.17 (m, 1H), 2.04-1.90 (m, 1H), 1.60 (s, 2H), 1.41-1.26 (m, 1H), 1.24-1.10 (m, 4H). MS (ES, m/z): [M+1]=517.5.

Example 116: 4-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-2-fluorobenzoic Acid (I-122)

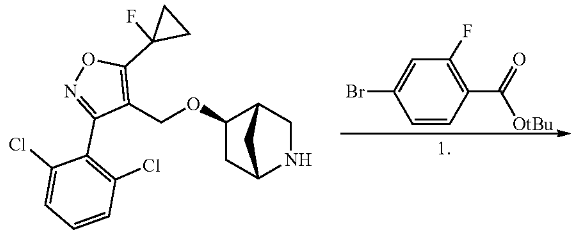

24d

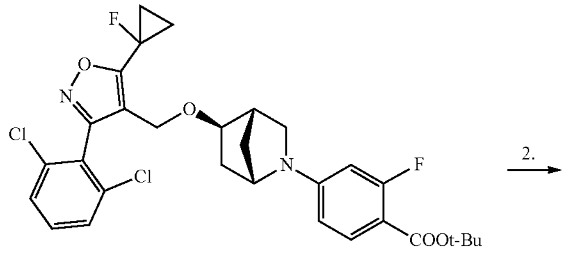

122a

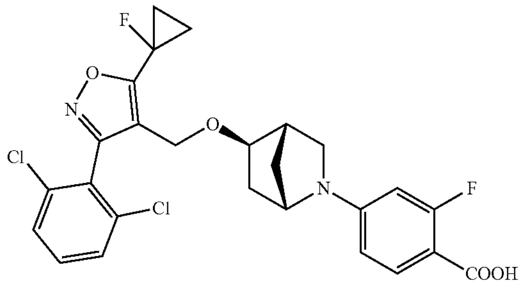

I-122

Step 1

To a 250 mL round-bottom flask was added (1S,4S,5R)-5-[[3-(2,6-dichlorophenyl)-5-(1-fluorocyclopropyl)-1,2-oxazol-4-yl]methoxy]-2-azabicyclo[2.2.1]heptane 24d (3.48 g, 8.76 mmol, 1.0 equiv.), toluene (50 mL), tert-butyl 4-bromo-2-fluorobenzoate (3.61 g, 13.12 mmol, 1.1 equiv.), $Pd(OAc)_2$ (393 mg, 1.75 mmol, 0.20 equiv.), Xantphos (1.02 g, 1.76 mmol, 0.2 equiv.), and $Cs_2CO_3$ (8.6 g, 26.39 mmol, 3.0 equiv.). The resulting mixture was stirred at 90° C. overnight. Solids were filtered out, the filtrate was concentrated under vacuum. The residue was purified by Flash-Prep-HPLC using the following conditions (IntelFlash-1): Column, silica gel; mobile phase, EA/PE=0:0 increasing to EA/PE=20:80 within 20 min; Detector, UV 254 nm. Removal of solvents gave tert-butyl 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-2-fluorobenzoate 122a (2.45 g, 47%) as a light yellow solid.

Step 2

To a 500 mL round-bottom flask was added tert-butyl 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-2-fluorobenzoate 122a (3 g, 5.07 mmol, 1.00 equiv) and a solution of hydrogen chloride (60 mL) in dioxane (200 mL). The resulting mixture was stirred at room temperature overnight. $H_2O$ (200 mL) was added and the pH value of the mixture was adjusted to 7 using sodium carbonate. The aqueous mixture was extracted with ethyl acetate (200 mL×2). The combined organic extracts were washed with brine (100 mL×3), dried over anhydrous sodium sulfate, and concentrated under vacuum to a residue, which was purified by Prep-HPLC using the following conditions: Column, XBridge Prep OBD C18 Column, 19*250 mm, 5 um; mobile phase, Water (0.05% TFA) and ACN (55.0% ACN up to 68.0% in 8 min); Detector, UV 220 nm. After purification 4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-2-fluorobenzoic acid I-122 (1.912 g, 70%) as a light pinkish solid. $^1H$ NMR (400 MHz, $CD_3OD$): δ 7.73 (t, J=8.8 Hz, 1H), 7.63-7.48 (m, 3H), 6.32 (dd, J=8.9, 2.3 Hz, 1H), 6.19 (dd, J=14.5, 2.4 Hz, 1H), 4.44 (t, J=1.3 Hz, 2H), 4.13 (s, 1H), 3.52 (dd, J=6.8, 2.5 Hz, 1H), 2.61 (d, J=9.5 Hz, 1H), 2.54-2.47 (m, 1H), 1.87-1.77 (m, 1H), 1.71-1.49 (m, 4H), 1.51-1.36 (m, 2H), 1.29 (dt, J=13.2, 2.6 Hz, 1H). MS (ES, m/z): [M+1]=535.0.

Example 117: 2-cyano-4-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]benzoic Acid (I-123)

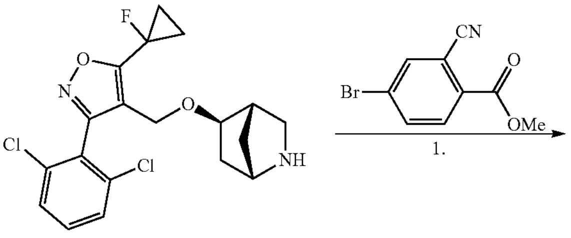

24d

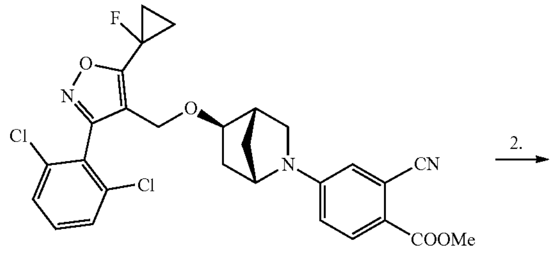

123a

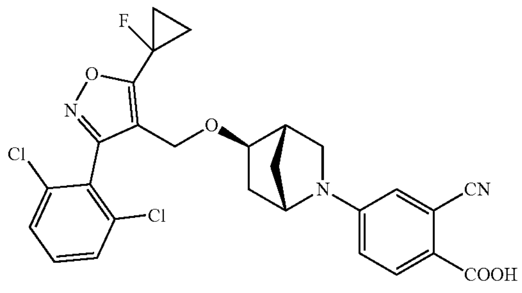

I-123

Step 1

To a 50 mL round-bottom flask was added (1S,4S,5R)-5-[[3-(2,6-dichlorophenyl)-5-(1-fluorocyclopropyl)-1,2-oxazol-4-yl]methoxy]-2-azabicyclo[2.2.1]heptane 24d (120 mg, 0.30 mmol, 1.0 equiv.), methyl 4-bromo-2-cyanobenzoate (55 mg, 0.23 mmol, 1.0 equiv.), potassium carbonate (83 mg, 0.60 mmol, 2.0 equiv.), and DMSO (1 mL). The resulting mixture was stirred at 110° C., overnight. After cooling to room temperature, the mixture was diluted with of ethyl acetate and added with $H_2O$. The pH value of the solution was adjusted to 6 using a 1M hydrogen chloride aqueous solution. The aqueous mixture was extracted with ethyl acetate (100 mL×2). The combined organic extracts were washed with brine (50 mL×4), dried over anhydrous sodium sulfate, and concentrated under vacuum. The residue was purified by silica gel column chromatography eluting with ethyl acetate/petroleum ether (1:3) to give methyl 2-cyano-4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]benzoate 123a (90 mg, 54%) as an off-white solid.

Step 2

To a 50 mL round-bottom flask was added methyl 2-cyano-4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]benzoate 123a (90 mg, 0.16 mmol, 1.0 equiv.), methanol (1 mL), LiOH (65 mg, 2.71 mmol, 10.0 equiv.), and water (0.1 mL). The resulting mixture was stirred at 35° C., overnight. The mixture was diluted with ethyl acetate. The pH value of the solution was adjusted to 6 using a 1M hydrogen chloride aqueous solution, and the aqueous mixture was extracted with ethyl acetate (100 mL×2). The combined organic extracts were washed with brine (50 mL×2), dried over anhydrous sodium sulfate, and concentrated under vacuum. The crude product was purified by Prep-HPLC using the following conditions: Column, XBridge C18 OBD Prep Column, 100� 10 μm, 19 mm×250 mm; mobile phase, Water (10 mmol/L $NH_4HCO_3$) and ACN (33.0% ACN up to 51.0% in 8 min); Detector, UV 254 nm. After purification 2-cyano-4-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]benzoic acid I-123 (48.9 mg, 56%) as a colorless solid. $^1H$ NMR (400 MHz, $CD_3OD$): δ 7.86 (d, J=8.8 Hz, 1H), 7.60-7.53 (m, 1H), 7.51 (d, J=3.7 Hz, 2H), 6.78 (d, J=2.6 Hz, 1H), 6.69 (dd, J=8.9, 2.6 Hz, 1H), 4.42 (d, J=1.4 Hz, 2H), 4.16 (s, 1H), 3.49 (s, 1H), 3.36 (dd, J=9.4, 4.0 Hz, 1H), 2.58 (d, J=9.6 Hz, 1H), 2.49 (s, 1H), 1.78 (dd, J=13.3, 6.7 Hz, 1H), 1.68-1.53 (m, 4H), 1.41 (dt, J=8.6, 2.2 Hz, 2H), 1.27 (d, J=13.6 Hz, 1H). MS (ES, m/z): [M+1]=542.0.

Example 118: 4-[(1S,4S,5R)-5-{[3-(2-chloro-6-methylphenyl)-5-(1-fluorocyclopropyl)-1,2-oxazol-4-yl]methoxy}-2-azabicyclo[2.2.1]heptan-2-yl]-2-fluorobenzoic Acid (I-124)

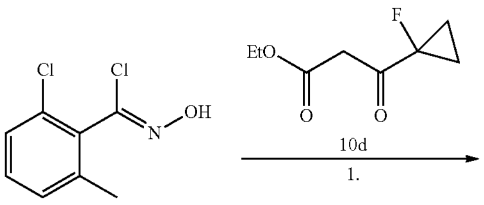

113c

-continued

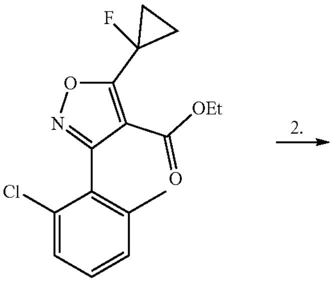

124a

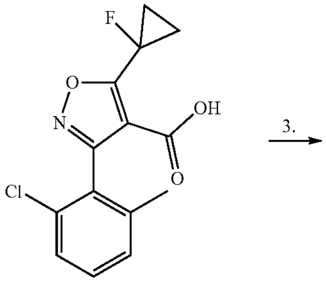

124b

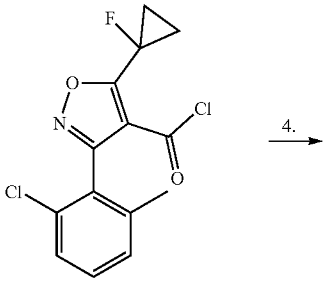

124c

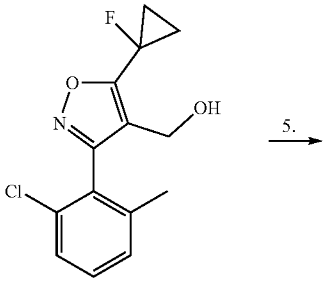

124d

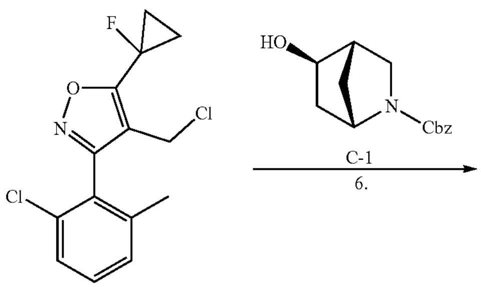

124e

-continued

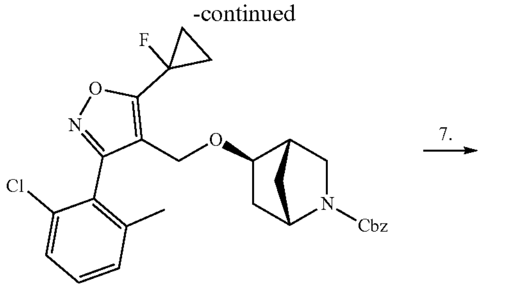

124f

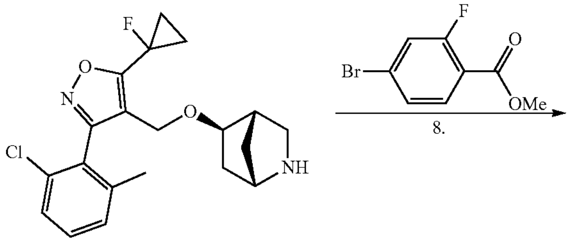

124g

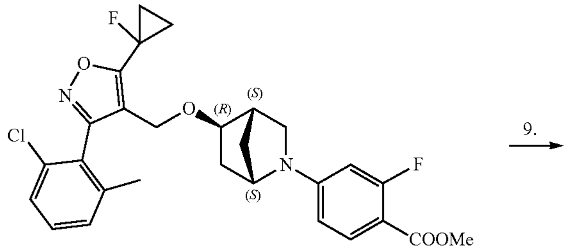

124h

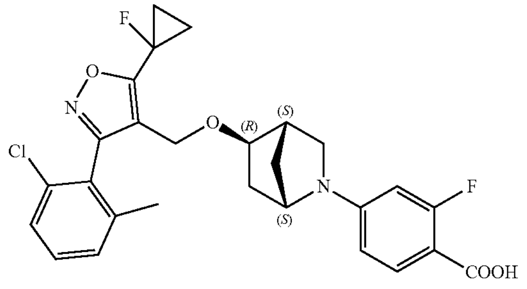

I-124

Step 1

To a 250 mL round-bottom flask was added ethyl 3-(1-fluorocyclopropyl)-3-oxopropanoate 10d (1.03 g, 5.91 mmol, 1.0 equiv.) and tetrahydrofuran (5 mL). The solution was cooled at 0° C. Solid t-BuOK (663 mg, 5.91 mmol, 1.0 equiv.) was added with stirring. The reaction mixture was stirred for 30 min at 0° C., and then treated with a solution of 2-chloro-N-hydroxy-6-methylbenzene-1-carbonimidoyl chloride 113c (1.0 g, 4.90 mmol, 1.0 equiv.) in tetrahydrofuran (5 mL). The resulting mixture was stirred overnight while temperature was increased to room temperature. 50 mL of $H_2O$ was added, the aqueous mixture was extracted with ethyl acetate (100 mL×2); the combined organic extracts were dried over anhydrous sodium sulfate and concentrated under vacuum. The residue was purified by silica gel column chromatography eluting with ethyl acetate/petroleum ether (1:5) to afford ethyl 3-(2-chloro-6-methylphenyl)-5-(1-fluorocyclopropyl)-1,2-oxazole-4-carboxylate 124a (1.2 g, 63%) as a light yellow crude oil.

Step 2

To a 250 mL round-bottom flask was added ethyl 3-(2-chloro-6-methylphenyl)-5-(1-fluorocyclopropyl)-1,2-oxazole-4-carboxylate 124a (1.2 g, 3.71 mmol, 1.0 equiv.) followed by a solution of sulfuric acid (5.16 mL) in AcOH (11.36 mL). The resulting mixture was stirred at 100° C., overnight. After cooling to room temperature, the mixture was diluted with 20 mL of $H_2O$, and extracted with ethyl acetate (100 mL×2). The combined organic extracts were washed with brine (50 mL×5), dried over anhydrous sodium sulfate and concentrated under vacuum. The residue was purified by silica gel column chromatography eluting with ethyl acetate/petroleum ether (1:3) to yield 3-(2-chloro-6-methylphenyl)-5-(1-fluorocyclopropyl)-1,2-oxazole-4-carboxylic acid 124b (935 mg, 85%) as a light yellow oil.

Step 3

To a 100 mL round-bottom flask was added 3-(2-chloro-6-methylphenyl)-5-(1-fluorocyclopropyl)-1,2-oxazole-4-carboxylic acid 124b (935 mg, 3.16 mmol, 1.0 equiv.) and thionyl chloride (5 mL, 2.0 equiv.). The reaction mixture was stirred at 60° C., overnight, and concentrated under vacuum to yield 3-(2-chloro-6-methylphenyl)-5-(1-fluorocyclopropyl)-1,2-oxazole-4-carbonyl chloride 124c (992 mg, Q, crude) as a yellow oil.

Step 4

To a 100 mL round-bottom flask was added 3-(2-chloro-6-methylphenyl)-5-(1-fluorocyclopropyl)-1,2-oxazole-4-carbonyl chloride 124c (992 mg, 3.16 mmol, 1.0 equiv.) and tetrahydrofuran (8 mL). Solid $NaBH_4$ (241 mg, 6.37 mmol, 2.0 equiv.) was added in portions at 0° C., during a 2 h period. The resulting mixture was stirred at room temperature for 4 h. The mixture was diluted with 50 mL of water, and extracted with ethyl acetate (150 mL×2). The combined organic extracts were washed with brine (50 mL×2), dried over anhydrous sodium sulfate, and concentrated under vacuum. The residue was purified by silica gel column chromatography eluting with ethyl acetate/petroleum ether (1:3) to give [3-(2-chloro-6-methylphenyl)-5-(1-fluorocyclopropyl)-1,2-oxazol-4-yl]methanol 124d (570 mg, 64%) as a light yellow solid.

Step 5

To a 250 mL round-bottom flask was added a solution of benzotriazole (610 mg, 1.00 equiv) in dichloromethane (15 mL) followed by thionyl chloride (1.228 g, 10.41 mmol, 2.0 equiv.) at 0° C. The mixture was stirred 0° C., for 30 min. A solution of [3-(2-chloro-6-methylphenyl)-5-(1-fluorocyclopropyl)-1,2-oxazol-4-yl]methanol 124d (1.447 g, 5.14 mmol, 1.0 equiv.) in dichloromethane (15 mL) was added dropwise with stirring at 0° C. The resulting mixture was stirred at room temperature overnight. 10 mL of water/ice was added to quench the reaction. The aqueous mixture was extracted with ethyl acetate (100 mL×2); the combined organic extracts were washed with brine (30 mL×2), dried over anhydrous sodium sulfate, and concentrated under vacuum. The crude product was purified by Flash-Prep-HPLC using the following conditions (IntelFlash-1): Column, silica gel; mobile phase, ethyl acetate/petroleum ether=0% increasing to ethyl acetate/petroleum ether=30% within 20 min; Detector, UV 254 nm. Removal of solvents afforded 3-(2-chloro-6-methylphenyl)-4-(chloromethyl)-5-(1-fluorocyclopropyl)-1,2-oxazole 124e (1 g, 65%) as a light yellow solid.

Step 6

To a 100 mL round-bottom flask was added 3-(2-chloro-6-methylphenyl)-4-(chloromethyl)-5-(1-fluorocyclopropyl)-1,2-oxazole 124e (1 g, 3.33 mmol, 1.0 equiv.) and N,N-dimethylformamide (10 mL). Benzyl (1S,4S,5R)-5-hydroxy-2-azabicyclo[2.2.1]heptane-2-carboxylate C-1 (990 mg, 4.00 mmol, 1.2 equiv.) was added. The mixture was stirred for 5 min at 0° C. Sodium hydride (267 mg, 6.67 mmol, 2.0 equiv., 60% in mineral oil) was added in portions at 0° C. The resulting mixture was stirred at room temperature overnight. The reaction was quenched by the addition of 10 mL of water/ice. The aqueous mixture was extracted with ethyl acetate (150 mL×2), and the combined organic extracts were washed with brine (50 mL×2), dried over anhydrous sodium sulfate, and concentrated under vacuum. The crude product was purified by Flash-Prep-HPLC using the following conditions (IntelFlash-1): Column, silica gel; mobile phase, ethyl acetate/petroleum ether=0% increasing to ethyl acetate/petroleum ether=30% within 20 min; Detector, UV 254 nm. Removal of solvents afforded benzyl (1S,4S,5R)-5-[[3-(2-chloro-6-methylphenyl)-5-(1-fluorocyclopropyl)-1,2-oxazol-4-yl]methoxy]-2-azabicyclo[2.2.1]heptane-2-carboxylate 124f (1.3 g, 76%) as a light yellow oil.

Step 7

To a 100 mL round-bottom flask was added benzyl (1S,4S,5R)-5-[[3-(2-chloro-6-methylphenyl)-5-(1-fluorocyclopropyl)-1,2-oxazol-4-yl]methoxy]-2-azabicyclo[2.2.1]heptane-2-carboxylate 124f (1.3 g, 2.54 mmol, 1.0 equiv.), dichloromethane (10 mL), and TMSI (1.34 g, 2.0 equiv.). The resulting mixture was stirred at room temperature for 30 min and diluted with 10 mL of methylene chloride. A 1 M hydrogen chloride aqueous solution (10 mL) was added, the mixture was extracted with dichloromethane (100 mL×2). The combined organic extracts were dried over anhydrous sodium sulfate and concentrated under vacuum. The residue was purified by silica gel column chromatography eluting with dichloromethane/methanol (10:1) to give (1S,4S,5R)-5-[[3-(2-chloro-6-methylphenyl)-5-(1-fluorocyclopropyl)-1,2-oxazol-4-yl]methoxy]-2-azabicyclo[2.2.1]heptane 124g (886 mg, 92%) as a light yellow solid.

Step 8

To a 250 mL round-bottom flask purged with and maintained under a dry nitrogen atmosphere was added (1S,4S,5R)-5-[[3-(2-chloro-6-methylphenyl)-5-(1-fluorocyclopropyl)-1,2-oxazol-4-yl]methoxy]-2-azabicyclo[2.2.1]heptane 124g (500 mg, 1.33 mmol, 1.0 equiv.), toluene (10 mL), methyl 4-bromo-2-fluorobenzoate (340 mg, 1.46 mmol, 1.10 equiv), $Pd(OAc)_2$ (60 mg, 0.27 mmol, 0.2 equiv.), Xantphos (154 mg, 0.27 mmol, 0.2 equiv.), and $Cs_2CO_3$ (1.3 g, 3.99 mmol, 3.0 equiv.). The resulting mixture was stirred at 90° C., overnight. Solids were filtered off, and filtrate was concentrated under vacuum. The residue was purified by silica gel column chromatography eluting with ethyl acetate/petroleum ether (1:5) to give methyl 4-[(1S,4S,5R)-5-[[3-(2-chloro-6-methylphenyl)-5-(1-fluorocyclopropyl)-1,2-oxazol-4-yl]methoxy]-2-azabicyclo[2.2.1]heptan-2-yl]-2-fluorobenzoate 124h (300 mg, 43%) as a light yellow solid.

Step 9

To a 50 mL round-bottom flask was added methyl 4-[(1S,4S,5R)-5-[[3-(2-chloro-6-methylphenyl)-5-(1-fluorocyclopropyl)-1,2-oxazol-4-yl]methoxy]-2-azabicyclo[2.2.1]heptan-2-yl]-2-fluorobenzoate 124h (300 mg, 0.57 mmol, 1.0 equiv.), methanol (3 mL), LiOH (227 mg, 5.69 mmol, 10.0 equiv.), and water (0.2 mL). The resulting mixture was stirred at 35° C., overnight. The mixture was diluted with 10 mL of water. The pH value of the solution was adjusted to 6 using a 1M hydrogen chloride aqueous solution. The aqueous mixture was extracted with ethyl acetate (100 mL×2); the combined organic extracts were washed with (30 mL×2), dried over anhydrous sodium sulfate, and concentrated under vacuum. The crude product (5 mL) was purified by Prep-HPLC using the following conditions: Column, XBridge Prep OBD C18 Column, 19*250 mm, 5 um; mobile phase, Water (0.05% TFA) and ACN (58.0% ACN up to 69.0% in 11 min); Detector, UV 220 nm. After purification 4-[(1S,4S,5R)-5-[[3-(2-chloro-6-methylphenyl)-5-(1-fluorocyclopropyl)-1,2-oxazol-4-yl]methoxy]-2-azabicyclo[2.2.1]heptan-2-yl]-2-fluorobenzoic acid I-124 (154.2 mg, 53%) as a colorless solid. $^1H$ NMR (400 MHz, $CD_3OD$): δ 7.70 (t, J=8.8 Hz, 1H), 7.44-7.34 (m, 2H), 7.34-7.25 (m, 1H), 6.29 (d, J=9.3 Hz, 1H), 6.17 (d, J=15.2 Hz, 1H), 4.47 (d, J=11.6 Hz, 1H), 4.22 (ddd, J=25.6, 11.5, 1.6 Hz, 1H), 4.11 (d, J=11.0 Hz, 1H), 3.37-3.35 (m, 1H), 3.34 (s, 1H), 2.62-2.34 (mi 2H), 2.16 (d, J=3.0 Hz; 3H), 1.88-1.54 (m, 1H), 1.50-1.36 (m, 3H), 1.37-1.26 (m, 3H), 1.15 (d, J=13.7 Hz, 1H). MS (ES, m/z): [M+1]=515.0.

Example 119: 4-[(1S,4S,5R)-5-[(5-cyclopropyl-3-{spiro[2.5]octan-6-yl}-1,2-oxazol-4-yl)methoxy]-2-azabicyclo[2.2.1]heptan-2-yl]benzoic Acid (I-125)

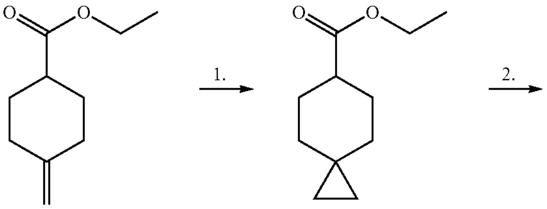

125a 125b

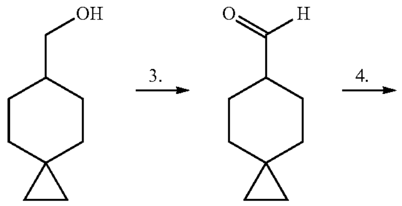

125c 125d

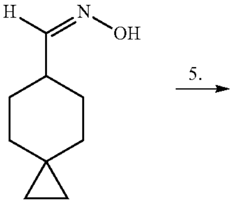

125e

-continued

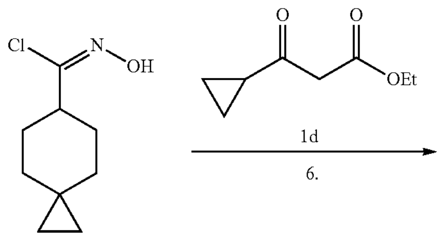

125f

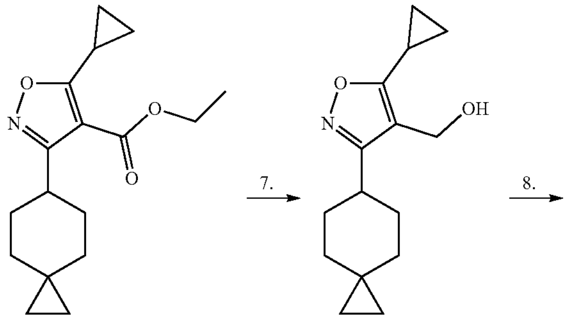

125g

125h

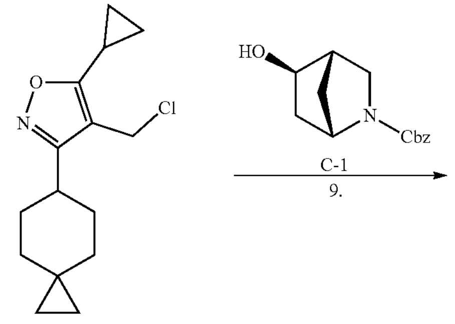

125i

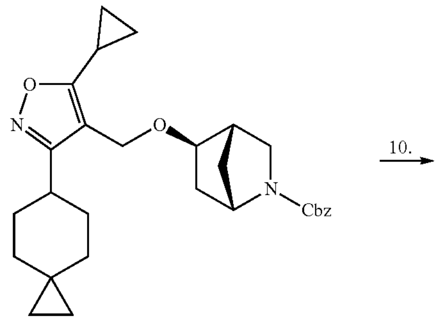

125j

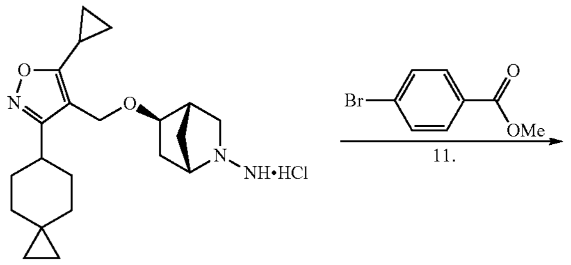

125k

-continued

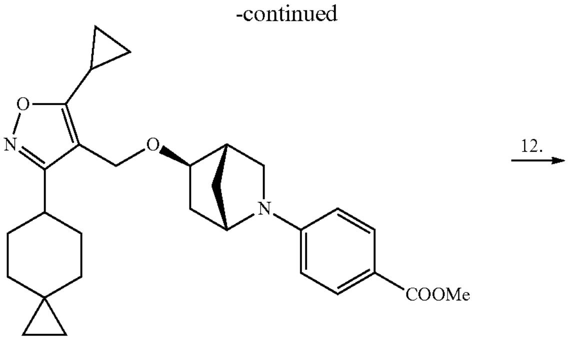

1251

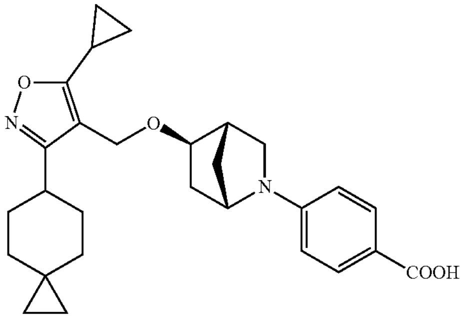

I-125

Step 1

To a solution of diethyl zinc (67 mL of a 1M solution in hexane) in DCM (55 mL) TFA (5.12 mL, 66.87 mmol) in DCM (25 mL) was added dropwise at 0° C. The reaction mixture was stirred for 1 h at 0° C. A solution of $CH_2I_2$ (5.38 mL, 66.87 mmol) in DCM (20 mL) was added slowly, and the resulting mixture was stirred for an additional 40 min, followed by the dropwise addition of ethyl 4-methylenecyclohexane-1-carboxylate 125a (4.5 g, 26.75 mmol) in DCM (15 mL) The reaction was continued for 2 h, then the mixture was diluted with DCM (200 mL), washed with a saturated aqueous $NH_4Cl$ solution and brine, dried over $MgSO_4$, and concentrated in vacuo to give ethyl spiro[2.5]octane-6-carboxylate 125b (4.9 g, 100%) as a clear oil.

Step 2

To a solution of ethyl spiro[2.5]octane-6-carboxylate 125b (4.90 g, 26.74 mmol) in 50 mL of dry THF was added LAH solution (17.38 mL, 2 M in THF) at (PC. The reaction mixture was stirred overnight while being allowed to come to RT. The mixture was cooled again to 0° C., quenched with water (1.5 mL), NaOH (1.5 mL, 1N in water), and a second batch of water (3.0 mL). The aqueous mixture was diluted with EtOAc (200 mL), dried over $MgSO_4$, filtered, and concentrated in vacuo to give spiro[2.5]octan-6-ylmethanol 125c (3.43 g, 91%) as a clear oil.

Step 3

To a solution of spiro[2.5]octan-6-ylmethanol 125c (3.43 g, 24.33 mmol) in DCM (50 mL) at 0° C. was added Dess-Martin reagent (10.32 g, 24.33 mmol) portionwise. The mixture was stirred for 2 h while gradually being warmed to RT. The mixture was diluted with DCM (200 mL), washed with brine, dried over $MgSO_4$, filtered, concentrated and purified with column chromatography to give spiro[2.5]octane-6-carbaldehyde 125d (1.61 g, 47.6%) as a clear oil.

Step 4

To a solution of spiro[2.5]octane-6-carbaldehyde 125d (1.60 g, 11.51 mmol) in EtOH (30 mL) at 0° C., was added hydroxylamine hydrochloride (0.96 g, 13.81 mmol) and pyridine. The mixture was stirred at 0° C. for 3 h. EtOH was removed and the residue was partitioned between EtOAc and water. The organic layer was dried over $MgSO_4$, filtered and concentrated to give spiro[2.5]octane-6-carbaldehyde oxime 125e (1.77 g) as a sticky solid. The product was carried on to the next step without further purification.

Step 5

To a solution of spiro[2.5]octane-6-carbaldehyde oxime 125e (1.77 g, 11.49 mmol) in DMF (20 mL) at 0° C., was added N-chlorosuccinimide (1.69 g, 12.66 mmol). The reaction mixture was slowly warmed to RT and stirred overnight, then quenched with brine and extracted with $Et_2O$. The combined organic layers were washed with water and brine, dried over $MgSO_4$, filtered and concentrated in vacuo. The residue was purified via silica gel chromatography eluting with hexane-EtOAc (20% EtOAc) to give N-hydroxyspiro [2.5]octane-6-carbimidoyl chloride 125f (1.22 g, 56%) as a clear oil.

Step 6

A solution of ethyl 3-cyclopropyl-3-oxopropanoate 1d (1.0 g, 6.40 mmol) in THF (20 mL) at 0° C., was treated with potassium tert-butoxide (7.59 mL, 1M in THF). After stirring for 30 minutes at 0° C., N-hydroxyspiro[2.5]octane-6-carbimidoyl chloride 125f (1.10 g, 5.84 mmol) in THF (10 mL) was added dropwise. The reaction mixture was stirred for 1.5 h at 0° C., then quenched with water (5 mL) at 0° C. THF was removed and the residue was partitioned between EtOAc and water. The organic layer was dried over $MgSO_4$, filtered, concentrated and purified via silica gel chromatography to give ethyl 5-cyclopropyl-3-(spiro[2.5]octan-6-yl) isoxazole-4-carboxylate 125g (0.84 g, 50%) as a light oil. $^1$HNMR (400 MHz, $CDCl_3$): δ 4.43-4.25 (m, 2H), 3.14 (tt, J=11.7, 3.2 Hz, 1H), 2.81 (tt, J=8.4, 5.1 Hz, 1H), 2.03-1.93 (m, 2H), 1.85 (tt, J=13.7, 7.0 Hz, 2H), 1.79-1.64 (m, 2H), 1.43-1.34 (m, 3H), 1.31-1.21 (m, 2H), 1.20-1.09 (m, 2H), 0.98 (d, J=13.2 Hz, 2H), 0.37-0.18 (m, 4H).

Step 7

To a solution of ethyl 5-cyclopropyl-3-(spiro[2.5]octan-6-yl)isoxazole-4-carboxylate 125g (1.85 g, 6.40 mmol) in THF (40.0 mL) at −40° C. was added LAH solution (2M in THF, 4.8 mL, 9.60 mmol) dropwise. The mixture was stirred for 3 hours while it was slowly warmed to RT. The mixture was cooled to 0° C., and quenched with the addition of water (1.0 mL), 1M NaOH (1.0 mL), and water (1.0 mL) successively. The mixture was diluted with EtOAc (200 mL), dried over $MgSO_4$, filtered, and the filtrate was concentrated to a crude material which was purified by silica gel column chromatography eluting with EtOAc in hexanes (20-30%) to give 4-(chloromethyl)-5-cyclopropyl-3-(spiro[2.5]octan-6-yl)isoxazole 125h (1.10 g) as a clear oil. Yield: 1.10 g. MS (ES, m/z): [M+1]=248.

Step 8

To a solution of benzotriazole (0.64 g, 5.34 mmol) in DCM (40 mL) at 0° C. was added $SOCl_2$ (0.39 mL, 5.34 mmol) dropwise. The mixture was stirred at 0° C. for 30 minutes. A solution of 4-(chloromethyl)-5-cyclopropyl-3-(spiro[2.5]octan-6-yl)isoxazole 125h (1.10 g, 4.45 mmol) in DCM (10 mL) was added slowly. The resulting mixture was stirred at 0° C., for 2 hours. Solids were filtered and washed with DCM (10 mL×2). The combined filtrate was concentrated and purified by silica gel column chromatography eluting with EtOAc in hexanes (10-20%) to yield 4-(chloromethyl)-5-cyclopropyl-3-(spiro[2.5]octan-6-yl)isoxazole 125i (1.0 g) as a clear oil.

Step 9

To a solution of benzyl (1S,4S,5R)-5-hydroxy-2-azabicyclo[2.2.1]heptane-2-carboxylate C-1 (1.12 g, 3.76 mmol) in DMF (20 mL) at 0° C. was added NaH (60% in mineral oil, 0.23 g, 5.64 mmol). The mixture was stirred at 0° C., for 30 minutes. A solution of 4-(chloromethyl)-5-cyclopropyl-3-(spiro[2.5]octan-6-yl)isoxazole 125i (1.0 g, 3.76 mmol) in DMF (10 mL) was added at 0° C. The reaction mixture was stirred for 16 hours while it was warmed to RT slowly. The mixture was cooled to 0° C., again and quenched with water carefully. The mixture was partitioned between EtOAc and water. The organic layer was separated, washed with brine, dried with $MgSO_4$, filtered and concentrated. The residue was purified by silica gel column chromatography eluting with EtOAc in hexanes (20-30%) to give Benzyl (1S,4S,5R)-5-((5-cyclopropyl-3-(spiro[2.5]octan-6-yl)isoxazol-4-yl)methoxy)-2-azabicyclo[2.2.1]heptane-2-carboxylate 125j (1.46 g) as a clear oil. MS (ES, m/z): [M+1]=477.0.

Step 10

To a solution of benzyl (1S,4S,5R)-5-((5-cyclopropyl-3-(spiro[2.5]octan-6-yl)isoxazol-4-yl)methoxy)-2-azabicyclo [2.2.1]heptane-2-carboxylate 125j (1.0 g, 2.10 mmol) in DCM (15 mL) at 0° C., was added TMSI solution (4.2 mL, 4.2 mmol). The mixture was stirred at RT for 2 hours. The solvent was removed under vacuum. The residue was suspended in $Et_2O$ (20 mL), then HCl in $Et_2O$ solution (5 mL, 1 M in $Et_2O$) was added. The mixture was stirred for 30 minutes and brown solids were formed. The solids were filtered and dried to give 4-((((1S,4S,5R)-2-Azabicyclo [2.2.1]heptan-5-yl)oxy)methyl)-5-cyclopropyl-3-(spiro[2.5] octan-6-yl)isoxazole hydrochloride 125k (0.837 g) as a brown solid. MS (ES, m/z): [M+1]=343.

Step 11

Following a similar procedure described in Example 114 step 1, by using $Pd_2(dba)_3$ (0.2 equiv.), BINAP (0.3 equiv.), $Cs_2CO_3$ (2.5 equiv.), and in toluene with heating at 110° C., overnight, 4-((((1S,4S,5R)-2-Azabicyclo[2.2.1]heptan-5-yl) oxy)methyl)-5-cyclopropyl-3-(spiro[2.5]octan-6-yl)isoxazole hydrochloride 125k (0.11 g, 0.291 mmol, 1 equiv.) was reacted with methyl-4-bromobenzoate (0.094 g, 0.437 mmol, 1.5 equiv.) to provide methyl 4-((1S,4S,5R)-5-((5-cyclopropyl-3-(spiro[2.5]octan-6-yl)isoxazol-4-yl) methoxy)-2-azabicyclo[2.2.1]heptan-2-yl)benzoate 125l (0.1 g, 72%) as a light yellow oil. MS (ES, m/z): [M+1]= 477.

Step 12

Following a similar procedure described in Example 120 step 9, methyl 4-((1S,4S,5R)-5-((5-cyclopropyl-3-(spiro

[2.5]octan-6-yl)isoxazol-4-yl)methoxy)-2-azabicyclo[2.2.1]heptan-2-yl)benzoate 125l (0.1 g, 0.21 mmol, 1 equiv.) was hydrolyzed, under the conditions of NaOH (0.53 mL, 1 M aq.), MeOH (3 mL), THF (1 mL) and heating at 70° C., overnight, to afford 4-((1S,4S,5R)-5-((5-Cyclopropyl-3-(spiro[2.5]octan-6-yl)isoxazol-4-yl)methoxy)-2-azabicyclo[2.2.1]heptan-2-yl)benzoic acid I-125 (0.08 g, 80%) as a colorless solid. $^1$HNMR (400 MHz, $CDCl_3$): δ 7.93 (d, J=9.0 Hz, 2H), 6.49 (d, J=9.0 Hz, 2H), 4.36 (q, J=11.6 Hz, 2H), 4.24 (s, 1H), 3.67 (d, J=6.1 Hz, 1H), 3.50 (dd, J=9.3, 4.0 Hz, 1H), 2.80 (s, 1H), 2.75-2.60 (m, 2H), 2.17-2.07 (m, 1H), 2.02-1.88 (m, 4H), 1.87-1.71 (m, 5H), 1.66 (d, J=13.2 Hz, 1H), 1.15-1.07 (m, 2H), 1.05-0.94 (m, 4H), 0.37-0.19 (m, 4H); MS (ES, m/z): [M+1]=463.

Example 120: 4-[(1S,4S,5R)-5-[(5-cyclopropyl-3-{spiro[2.5]octan-6-yl}-1,2-oxazol-4-yl)methoxy]-2-azabicyclo[2.2.1]heptan-2-yl]-3-fluorobenzoic Acid (I-126)

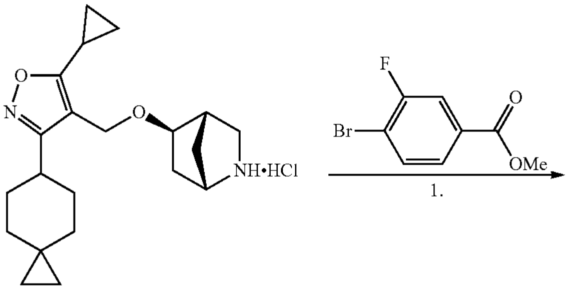

125k

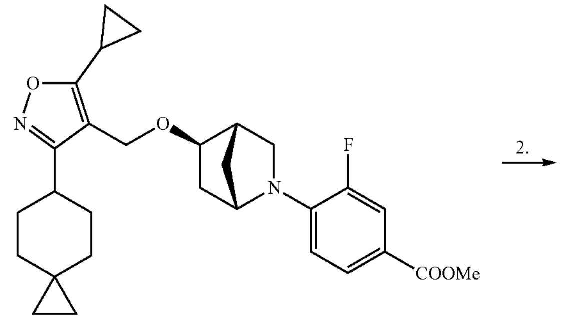

126a

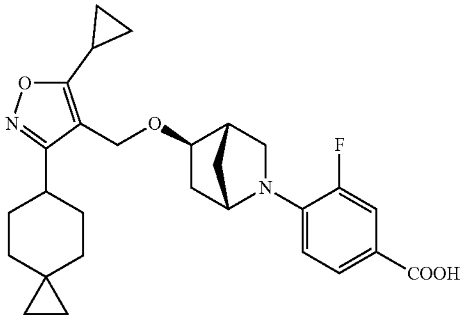

I-126

Step 1

Following a similar procedure described in Example 114 step 1, by using $Pd_2(dba)_3$ (0.2 equiv.), BINAP (0.3 equiv.), $Cs_2CO_3$ (2.5 equiv.), and in toluene with heating at 110° C., overnight, 4-((((1S,4S,5R)-2-Azabicyclo[2.2.1]heptan-5-yl)oxy)methyl)-5-cyclopropyl-3-(spiro[2.5]octan-6-yl)isoxazole hydrochloride 125k (0.15 g, 0.396 mmol, 1 equiv.) was reacted with methyl-4-bromo-3-fluoro-benzoate (0.14 g, 0.6 mmol, 1.5 equiv.) to provide methyl 4-((1S,4S,5R)-5-((5-cyclopropyl-3-(spiro[2.5]octan-6-yl)isoxazol-4-yl)methoxy)-2-azabicyclo[2.2.1]heptan-2-yl)-3-fluorobenzoate 126a (0.167 g, 85%) as a light yellow oil. MS (ES, m/z): [M+1]=495.

Step 2

Following a similar procedure described in Example 106 step 3, methyl 4-((1S,4S,5R)-5-((5-cyclopropyl-3-(spiro[2.5]octan-6-yl)isoxazol-4-yl)methoxy)-2-azabicyclo[2.2.1]heptan-2-yl)-3-fluorobenzoate 126a (0.167 g, 0.338 mmol, 1 equiv.) was hydrolyzed, under the conditions of NaOH (0.53 mL, 1 M aq.), MeOH (3 mL), THF (1 mL) and heating at 60° C., overnight, to afford 4-((1S,4S,5R)-5-((5-cyclopropyl-3-(spiro[2.5]octan-6-yl)isoxazol-4-yl)methoxy)-2-azabicyclo[2.2.1]heptan-2-yl)-3-fluorobenzoic acid I-126 (0.12 g, 73.8%) as a colorless solid. $^1$HNMR (400 MHz, $CDCl_3$): δ 7.77-7.60 (m, 2H), 6.54 (t, J=8.8 Hz, 1H), 4.36 (dd, J=17.7, 11.6 Hz, 3H), 3.74-3.60 (m, 2H), 2.84 (dd, J=9.8, 2.8 Hz, 1H), 2.75 (d, J=2.8 Hz, 1H), 2.73-2.58 (m, 1H), 2.26-2.13 (m, 1H), 2.04-1.84 (m, 4H), 1.84-1.71 (m, 5H), 1.67 (d, J=13.4 Hz, 1H), 1.16-1.07 (m, 2H), 1.06-0.93 (m, 4H), 0.36-0.19 (m, 4H); MS (ES, m/z): [M+1]=481.0.

Example 121: (1S,4S,5R)-2-(4-carboxyphenyl)-5-{[5-cyclopropyl-3-(2,6-dichlorophenyl)-1,2-oxazol-4-yl]methoxy}-2-azabicyclo[2.2.1]heptan-2-ium-2-olate (I-127)

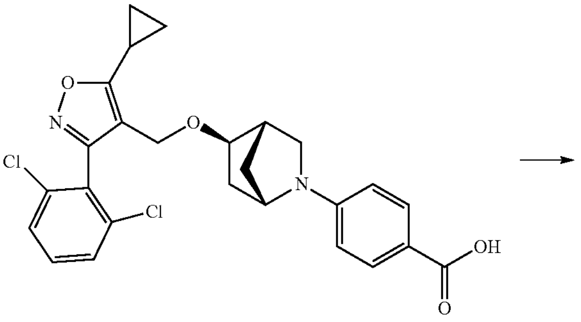

I-52

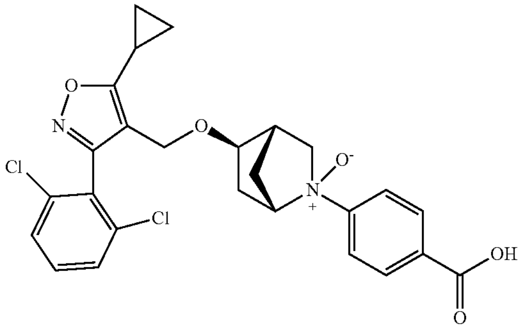

I-127

To a 8 mL vial was added 4-[(1S,4S,5R)-5-[[5-cyclopropyl-3-(2,6-dichlorophenyl)-1,2-oxazol-4-yl]methoxy]-2- azabicyclo[2.2.1]heptan-2-yl]benzoic acid I-52 (180 mg, 0.36 mmol, 1.0 equiv.), methanol (3 mL), water (1.5 mL), and Oxone (445 mg, 0.72 mmol, 2.0 equiv). The resulting mixture was stirred at room temperature for 6 h. Solids were filtered out, the filtrate was concentrated to a residue, which was purified by Flash-Prep-HPLC using the following conditions (IntelFlash-1): Column, silica gel; mobile phase, $CH_3CN:H_2O=0:100$ increasing to $CH_3CN:H_2O=50:50$ within 20 min; Detector, UV 254 nm. Removal of solvents furnished (1S,4S,5R)-2-(4-carboxyphenyl)-5-[[5-cyclopropyl-3-(2,6-dichlorophenyl)-1,2-oxazol-4-yl]methoxy]-2-azabicyclo[0.2.1]heptan-2-ium-2-olate I-127 (170 mg, 92%) as a light yellow solid. $^1$H NMR (400 MHz, $CDCl_3$): δ 0.869 (4H, m), 1.126 (3H, m), 1.517 (1H, m), 1.665 (2H, m), 1.986 (1H, m), 2.077 (1H, m), 2.663 (1H, m), 2.906 (1H, m), 3.447 (1H, m), 3.844 (1H, m), 4.257 (2H, m), 4.51 (1H, m), 5.013 (1H, m), 7.284 (2H, m), 7.343 (3H, m), 7.903 (2H, m). MS (ES, m/z): [M+1]=515.0.

Example 122: 5-[(1S,4S,5R)-5-{[5-cyclopropyl-3-(2,6-dichlorophenyl)-1,2-oxazol-4-yl]methoxy}-2-azabicyclo[2.2.1]heptan-2-yl]pyridine-2-carboxylic Acid (I-128)

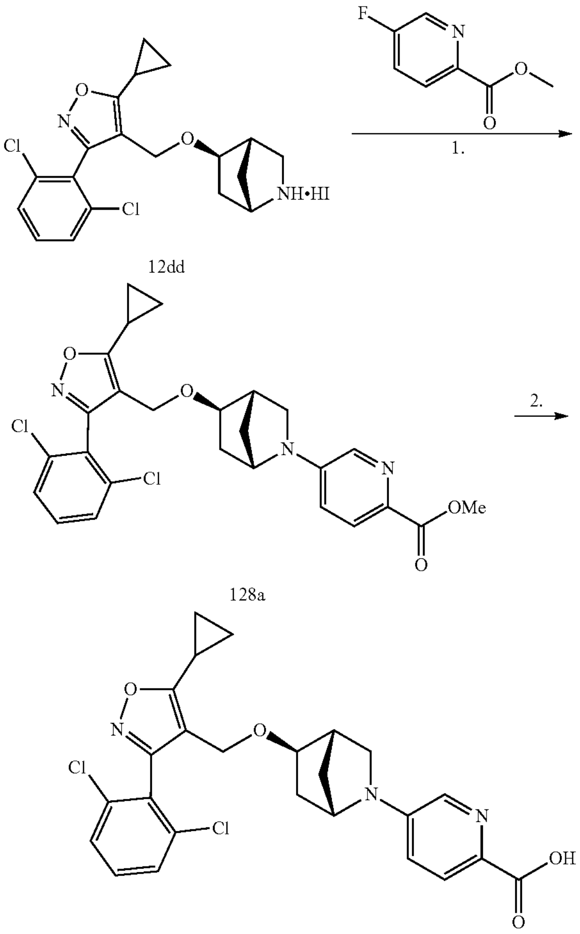

12dd

128a

I-128

Step 1

To a 10 mL vial was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.3943 mmol, 1.00 equiv.), DMSO (2 mL), methyl 5-fluoropyridine-2-carboxylate (123 mg, 0.79 mmol, 2.0 equiv.), and potassium carbonate (146 mg, 1.06 mmol, 2.00 equiv.). The resulting mixture was stirred at 120° C., for 16 h. After cooling to room temperature, 50 mL of ice/salt was added. The aqueous mixture was extracted with ethyl acetate (50 mL×3). The combined organic layers were washed with brine (100 mL×3), dried over anhydrous sodium sulfate, and concentrated under vacuum. The residue was purified by silica gel column chromatography eluting with ethyl acetate/petroleum ether (1:2) to yield methyl 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyridine-2-carboxylate 128a (130 mg, 48%) as a light yellow solid.

Step 2

To a 250 mL round-bottom flask was added methyl 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyridine-2-carboxylate 128a (130 mg, 0.25 mmol, 1.0 equiv.). LiOH (61 mg, 2.55 mmol, 10.0 equiv.), methanol (2 mL), and water (2 mL). The resulting mixture was stirred at room temperature overnight. The mixture was diluted with 10 mL of $H_2O$. The pH value of the solution was adjusted to ~7 using a 1M hydrogen chloride aqueous solution. The aqueous mixture was extracted with ethyl acetate (50 mL×3), and the combined organic extracts were washed with brine (20 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (42.0% ACN up to 60.0% in 8 min); Detector, UV 254 nm. After purification 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyridine-2-carboxylic acid I-128 (66 mg, 52%) was obtained as a yellow solid. $^1$H NMR (300 MHz, DMSO-$d_6$): δ 07.94-7.81 (m, 2H), 7.71-7.49 (m, 3H), 7.04 (dd, J=9.0, 2.8 Hz, 1H), 4.32 (d, J=2.4 Hz, 3H), 3.51-3.42 (m, 1H), 3.35 (dd, J=9.9, 4.1 Hz, 1H), 2.64 (d, J=9.8 Hz, 1H), 2.50 (p, J=1.9 Hz, 2H), 2.33 (tt, J=8.2, 5.3 Hz, 1H), 1.78-1.64 (m, 1H), 1.45 (q, J=9.8 Hz, 2H), 1.25-1.01 (m, 5H). MS (ES, m/z): [M+1]=500.0.

Example 123: 6-[(1S,4S,5R)-5-{[5-cyclopropyl-3-(2,6-dichlorophenyl)-1,2-oxazol-4-yl]methoxy}-2-azabicyclo[2.2.1]heptan-2-yl]-5-fluoropyridine-3-carboxylic Acid (I-129)

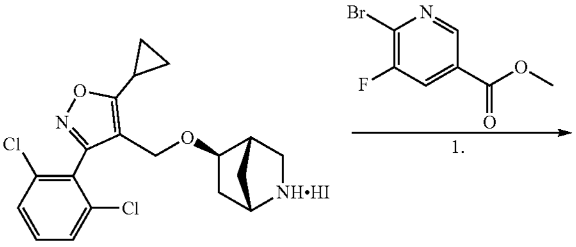

12dd

-continued

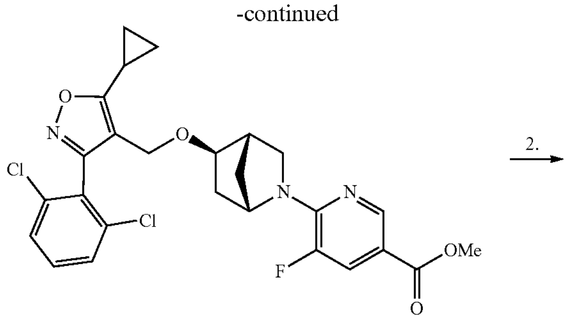

129a

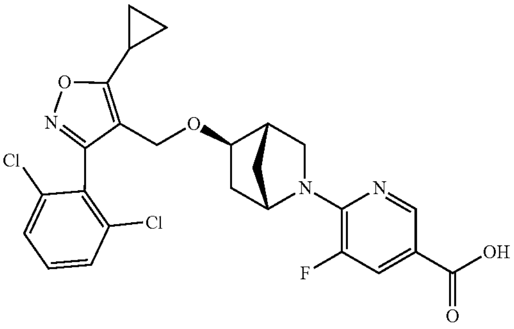

I-129

Step 1

To a 25 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (300 mg, 0.591 mmol, 1.0 equiv.), MeCN (4 mL), methyl 6-chloro-5-fluoropyridine-3-carboxylate (165 mg, 0.87 mmol, 1.47 equiv), and TEA (160 mg, 1.58 mmol, 2.67 equiv.). The resulting mixture was stirred at 80° C., overnight. The mixture was concentrated under vacuum. The residue was dissolved in 1 mL of DCM and purified by silica gel column chromatography eluting with ethyl acetate/petroleum ether (1:3) to afford methyl 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-5-fluoropyridine-3-carboxylate 129a (210 mg, 50%) as a light yellow solid.

Step 2

To a 50 mL round-bottom flask was added tert-butyl 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-5-fluoropyridine-3-carboxylate 129a (100 mg, 0.17 mmol, 1.0 equiv.), methanol (2 mL), water (0.2 mL), and LiOH (74 mg, 3.09 mmol, 10.0 equiv.). The resulting mixture was stirred at room temperature overnight. The mixture was diluted with 10 mL of $H_2O$. The pH value of the solution was adjusted to 6 using a 1M hydrogen chloride aqueous solution. The aqueous mixture was extracted with ethyl acetate (100 mL×2); the combined organic layers resulting mixture were washed with brine (50 mL×2), dried over anhydrous sodium sulfate, and concentrated under vacuum. The crude product was purified by Prep-HPLC using the following conditions: Column, XBridge C18 OBD Prep Column, 19 mm×250 mm; mobile phase, water (0.05% TFA) and ACN (51.0% ACN up to 68.0% in 8 min); Detector, uv 254 nm. After purification 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-5-fluoropyridine-3-carboxylic acid I-129 (46.5 mg, 52%) was obtained as an off-white solid. $^1H$ NMR (300 MHz, $CD_3OD$): δ 8.40 (d, J=1.6 Hz, 1H), 7.74 (dd, J=13.8, 1.9 Hz, 1H), 7.61-7.43 (m, 3H), 4.65 (s, 1H), 4.41-4.25 (m, 2H), 3.61 (t, J=7.7 Hz, 2H), 3.12 (dd, J=10.5, 3.4 Hz, 1H), 2.54 (s, 1H), 2.26 (q. J=6.7 Hz, 1H), 1.94 (dd, J=13.7, 6.8 Hz, 1H), 1.61 (q, J=10.2 Hz, 2H), 1.36 (d, J=13.5 Hz, 1H), 1.18 (d, J=6.7 Hz, 4H). MS (ES, m/z): [M+1]=518.25.

Example 124: 6-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]-5-fluoropyridine-3-carboxylic Acid (I-130)

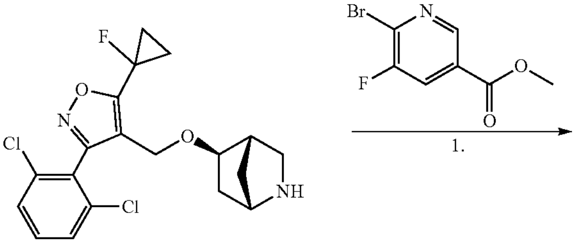

24d

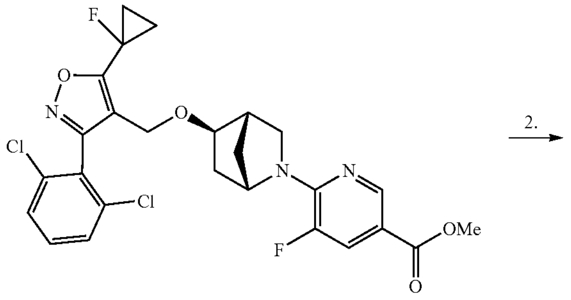

130a

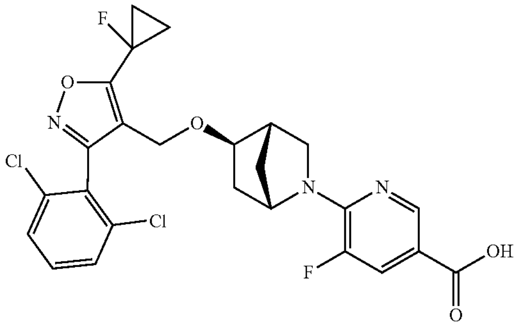

I-130

Step 1

To a 100 mL round-bottom flask purged with and maintained under an inert atmosphere of nitrogen was added (1S,4S,5R)-5-[[3-(2,6-dichlorophenyl)-5-(1-fluorocyclopropyl)-1,2-oxazol-4-yl]methoxy]-2-azabicyclo[2.2.1]heptane 24d (100 mg, 0.25 mmol, 1.0 equiv.), MeCN (2 mL), TEA (50.5 mg, 0.50 mmol, 2.0 equiv.), and methyl 6-bromo-4-fluoropyridine-3-carboxylate (70 mg, 0.30 mmol, 1.1 equiv.). The resulting mixture was stirred at 80° C., overnight. The mixture was then concentrated under vacuum to a residue which was dissolved in 2 mL of DCM and purified by silica gel column chromatography eluting with ethyl acetate/petroleum ether (1/3). Removal of solvents afforded methyl 6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-4-fluoropyridine-3-carboxylate 130a (100 mg, 72%) as a light yellow solid.

Step 2

To a 50 mL round-bottom flask was added methyl 6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-5-fluoropyridine-3-carboxylate 130a (100 mg, 0.18 mmol, 1.0 equiv.), methanol (2.0 mL). LiOH (76 mg, 3.17 mmol, 10.0 equiv.), and water (0.2 mL). The resulting mixture was stirred overnight at room temperature. 20 mL of $H_2O$ was added, the pH value of the solution was adjusted to 6 using a 1M hydrogen chloride aqueous solution. The aqueous mixture was extracted with ethyl acetate (100 mL×2). The combined organic extracts were washed with brine (20 mL×2), dried over anhydrous sodium sulfate and concentrated under vacuum. The residue was dissolved in 2 mL of DMF and purified by Prep-HPLC using the following conditions: Column, XBridge C18 OBD Prep Column, 19 mm×250 mm; mobile phase, Water (0.05% TFA) and ACN (52.0% ACN up to 70.0% in 8 min); Detector, uv 254 nm. After purification 6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]-5-fluoropyridine-3-carboxylic acid I-130 (41.2 mg, 42%) was obtained as an off-white solid. $^1H$ NMR (300 MHz, $CD_3OD$): δ 8.39 (s, 1H), 7.74 (dd, J=13.8, 1.8 Hz, 1H), 7.63-7.46 (m, 3H), 4.88 (s, 10H), 4.64 (s, 1H), 4.44 (dd, J=3.4, 1.4 Hz, 2H), 3.60 (dq, J=9.8, 3.0, 2.6 Hz, 2H), 3.12 (dd, J=10.9, 3.4 Hz, 1H), 2.53 (d, J=2.6 Hz, 1H), 1.94 (dd, J=13.5, 6.8 Hz, 1H), 1.72-1.54 (m, 4H), 1.53-1.26 (m, 3H). MS (ES, m/z): [M+1]=536.20.

Example 125: 4-[(1R,4R,5S)-5-{[5-cyclopropyl-3-(2,6-dichlorophenyl)-1,2-oxazol-4-yl]methoxy}-2-azabicyclo[2.2.1]heptan-2-yl]-3-fluorobenzoic Acid (I-131)

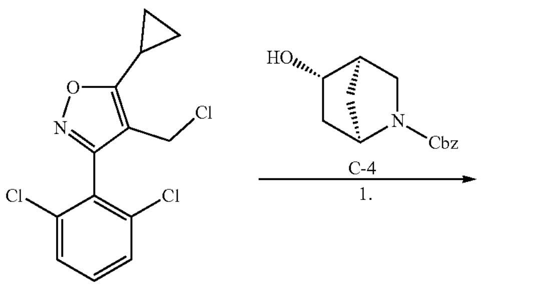

12b

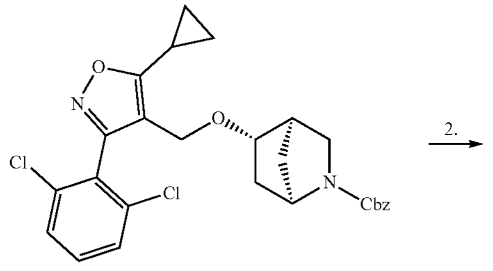

131a

-continued

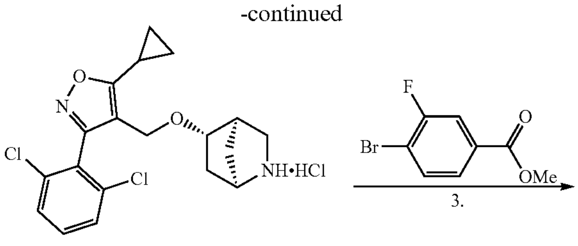

131b

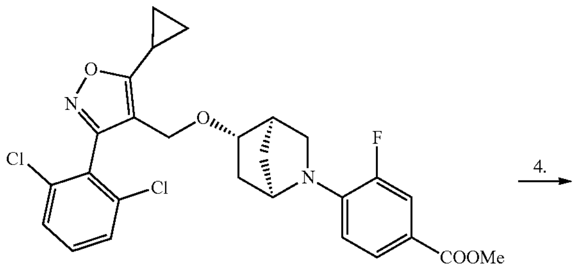

131c

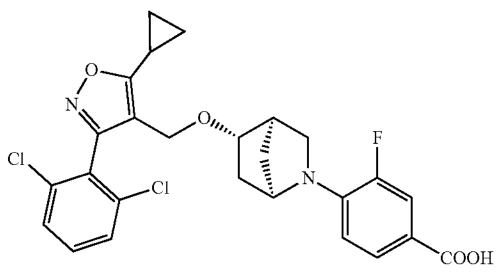

I-131

Step 1

To a solution of benzyl (1R,4R,5S)-5-hydroxy-2-azabicyclo[2.2.2.1]heptane-2-carboxylate (0.164 g, 0.66 mmol) C-4 in DMF (5.0 mL) at 0° C., was added NaH (0.026 g, 0.73 mmol, 60% in mineral oil). After the mixture was stirred for 30 minutes, 4-(chloromethyl)-5-cyclopropyl-3-(2,6-dichlorophenyl)isoxazole 12b (0.2 g, 0.66 mmol) was added. Cooling bath was removed. The resulting mixture was heated at 60° C. overnight. Upon cooling to 0° C., again. $H_2O$ was added, the mixture was partitioned between EtOAc and water. The EtOAc layer was washed with brine, dried with $MgSO_4$, filtered and concentrated. The residue was purified by silica gel column chromatography eluting with EtOAc in hexanes (20-30%) to give benzyl (1R,4R,5S)-5-((5-cyclopropyl-3-(2,6-dichlorophenyl)isoxazol-4-yl)methoxy)-2-azabicyclo[2.2.1]heptane-2-carboxylate 131a (0.14 g, 42%). MS (ES, m/z): [M+1]=513.0.

Step 2

To a solution of benzyl (1R,4R,5S)-5-((5-cyclopropyl-3-(2,6-dichlorophenyl)isoxazol-4-yl)methoxy)-2-azabicyclo[2.2.1]heptane-2-carboxylate 131a (0.8 g, 1.56 mmol) in DCM (10 mL) at 0° C. was added TMSI solution (1M in DCM, 3.12 mL, 3.12 mmol). The mixture was stirred at RT for 2 hours. The solvent was removed under vacuo and the residue was suspended in $Et_2O$ (20 mL). A 1M solution of HCl in $Et_2O$ (5 mL) was added and a brown solid was formed. The solid was filtered and dried to give 4-((((1R,4R,5S)-2-azabicyclo[2.2.1]heptan-5-yl)oxy)methyl)-5-cyclopropyl-3-(2,6-dichlorophenyl)isoxazole HCl salt 131b (0.45 g, 69.4%). MS (ES, m/z): [M+1]=379.0.

Step 3

To a solution of 4-((((1R,4R,5S)-2-azabicyclo[2.2.1]heptan-5-yl)oxy)methyl)-5-cyclopropyl-3-(2,6-dichlorophenyl) isoxazole HCl salt 131b (0.2 g, 0.481 mmol) and methyl 4-bromo-3-fluorobenzoate (0.15 g, 0.648 mmol) in toluene (3.0 mL) was added $Pd_2(dba)_3$ (0.044 g, 0.048 mmol), BINAP (0.046 g, 0.074 mmol) and $Cs_2CO_3$ (0.392 g, 1.203 mmol). The mixture was heated at 110° C., under $N_2$ for 16 hours. The mixture was cooled to RT and partitioned between water and EtOAc. The EtOAc layer was dried with $MgSO_4$, filtered and concentrated. The residue was purified by silica gel column chromatography eluting with EtOAc in hexanes (20-30%) to give methyl 4-((1R,4R,5S)-5-((5-cyclopropyl-3-(2,6-dichlorophenyl)isoxazol-4-yl)methoxy)-2-azabicyclo[2.2.1]heptan-2-yl)-3-fluorobenzoate 131c (0.065 g, 26%) as a yellow oil. MS (ES, m/z): [M+1]=531.

Step 4

To a solution of methyl 4-((1R,4R,5S)-5-((5-cyclopropyl-3-(2,6-dichlorophenyl)isoxazol-4-yl)methoxy)-2-azabicyclo[2.2.1]heptan-2-yl)-3-fluorobenzoate 131c (0.065 g, 0.122 mmol) in MeOH (2.0 mL) and THF (1.0 mL) was added NaOH (1M in water, 0.24 mL, 0.240 mmol). The mixture was heated at 60° C., for 2 days. The mixture was cooled to 0° C. and acidified with a 1M aqueous HCl solution. The solvent was removed under vacuum and the crude product was purified with HPLC to afford 4-((1R,4R,5S)-5-((5-cyclopropyl-3-(2,6-dichlorophenyl)isoxazol-4-yl)methoxy)-2-azabicyclo[2.2.1]heptan-2-yl)-3-fluorobenzoic acid I-131 (0.040 g, 63.4%) as an off-white solid. $^1$HNMR (400 MHz, $CD_3OD$): δ 7.62 (dd, J=8.6, 2.0 Hz, 2H), 7.56-7.52 (m, 1H), 7.50-7.46 (m, 2H), 6.60 (t, J=8.8 Hz, 1H), 4.30 (d, J=0.9 Hz, 2H), 4.23 (s, 1H), 3.55 (dt, J=9.7, 3.8 Hz, 1H), 3.49 (d, J=4.7 Hz, 1H), 2.70 (dd, J=9.8, 3.1 Hz, 1H), 2.45 (s, 1H), 2.29-2.20 (m, 1H), 1.90 (dd, J=14.0, 7.6 Hz, 1H), 1.56 (q, J=9.8 Hz, 2H), 1.29 (d, J=13.4 Hz, 1H), 1.19-1.13 (m, 4H). MS (ES, m/z): [M+1]=517.0.

Example 126: 4-[(1R,4R,5S)-5-{([5-cyclopropyl-3-(2,6-dichlorophenyl)-1,2-oxazol-4-yl]methoxy}-2-azabicyclo[2.2.1]heptan-2-yl]benzoic Acid (I-132)

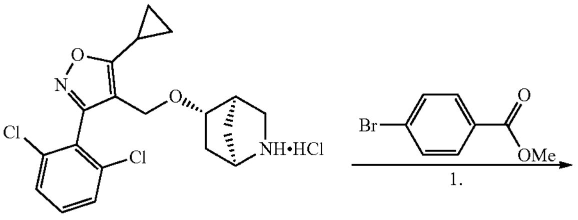

131b

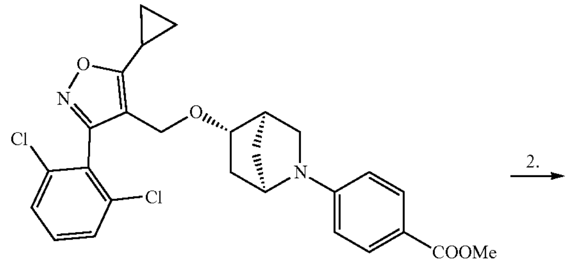

132a

-continued

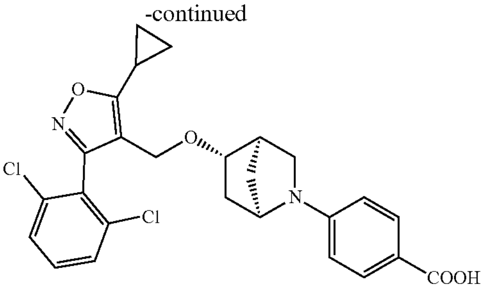

I-132

Step 1

Following a similar procedure described in Example 125 step 3, under the conditions of $Pd_2(dba)_3$ (0.1 equiv.), BINAP (0.15 equiv.), $Cs_2CO_3$ (2.5 equiv.), in toluene (10 mL) and dioxane (5 mL) with heating at 110° C., overnight, 4-((((1R,4R,5S)-2-azabicyclo[2.2.1]heptan-5-yl)oxy) methyl)-5-cyclopropyl-3-(2,6-dichlorophenyl)isoxazole hydrochloride 131b (0.6 g, 1.44 mmol, 1 equiv.) was reacted with methyl 4-bromobenzoate (0.40 g, 1.86 mmol, 1.3 equiv.) to afford methyl 4-((1R,4R,5S)-5-((5-cyclopropyl-3-(2,6-dichlorophenyl)isoxazol-4-yl)methoxy)-2-azabicyclo [2.2.1]heptan-2-yl)benzoate 132a (0.135 g, 19%). MS (ES, m/z): [M+1]=513.0.

Step 2

Following a similar procedure described in Example 125 step 4, under the conditions of NaOH (0.53 mL, 1 M in $H_2O$), MeOH (3 mL), THF (1 mL), and heating at 70° C., overnight, methyl 4-((1R,4R,5S)-5-((5-cyclopropyl-3-(2,6-dichlorophenyl)isoxazol-4-yl)methoxy)-2-azabicyclo[2.2.1] heptan-2-yl)benzoate 132a (0.135 g, 0.263 mmol) was hydrolyzed to furnish 4-((1R,4R,5S)-5-((5-cyclopropyl-3-(2,6-dichlorophenyl)isoxazol-4-yl)methoxy)-2-azabicyclo [2.2.1]heptan-2-yl)benzoic acid I-132 (0.11 g, 83.8%) as a colorless solid. $^1$HNMR (400 MHz, $CD_3OD$): δ 7.83-7.75 (m, 2H), 7.57-7.50 (m, 1H), 7.50-7.45 (m, 2H), 6.51-6.44 (m, 2H), 4.31 (d, J=12.4 Hz, 2H), 4.14 (s, 1H), 3.48 (d, J=5.1 Hz, 1H), 3.36 (dd, J=9.5, 4.1 Hz, 1H), 2.58 (d, J=9.3 Hz, 1H), 2.49 (s, 1H), 2.30-2.19 (m, 1H), 1.85-1.74 (m, 1H), 1.58 (q, J=9.9 Hz, 2H), 1.29 (d, J=13.7 Hz, 1H), 1.16 (dd, J=4.2, 3.4 Hz, 4H). MS (ES, m/z): [M+1]=499.

Example 127: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,6-difluorobenzonitrile (I-133)

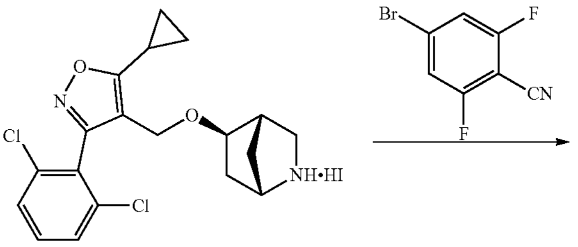

12dd

-continued

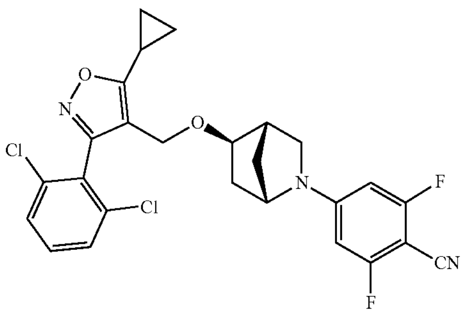

I-133

To a 250 mL round-bottom flask purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (100 mg, 0.197 mmol, 1.0 equiv.), $Pd(OAc)_2$ (30 mg, 0.13 mmol, 0.66 equiv.). Xantphos (75 mg, 0.13 mmol, 0.66 equiv.), $Cs_2CO_3$ (172 mg, 0.53 mmol, 2.7 equiv.), tol (4 mL), and 4-bromo-2,6-difluorobenzonitrile (69 mg, 0.32 mmol, 1.6 equiv.). The resulting mixture was stirred at 80° C., overnight. After cooling to room temperature, the mixture was diluted with 20 mL of $H_2O$ and extracted with ethyl acetate (20 mL×2). The combined organic extracts were dried over anhydrous sodium sulfate and concentrated under vacuum. The residue was purified by silica gel column chromatography eluting with ethyl acetate/petroleum ether (5:1) to afford 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2,6-difluorobenzonitrile I-133 (9.5 mg) as a colorless solid. $^1$HNMR (300 MHz, $CD_3OD$): δ 7.60-7.43 (m, 3H), 6.24 (s, 2H), 4.32 (s, 2H), 4.17 (s, 1H), 3.56 (s, 1H), 2.69-2.59 (m, 1H), 2.54 (d, J=3.3 Hz, 1H), 2.26 (p, J=6.9 Hz, 1H), 1.87-1.74 (m, 1H), 1.59 (q, J=10.2 Hz, 2H), 1.41-1.26 (m, 2H), 1.17 (d, J=6.7 Hz, 4H), 0.90 (s, 1H). MS (ES, m/z): [M+1]=516.1.

Example 128: (1S,4S,5R)-5-{[5-cyclopropyl-3-(2,6-dichlorophenyl)-1,2-oxazol-4-yl]methoxy}-2-[2-fluoro-4-(2H-1,2,3,4-tetrazol-5-yl)phenyl]-2-azabicyclo[2.2.1]heptane (1-134)

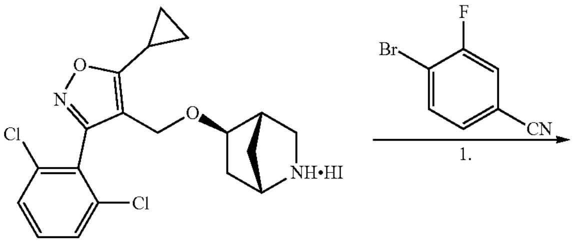

12dd

-continued

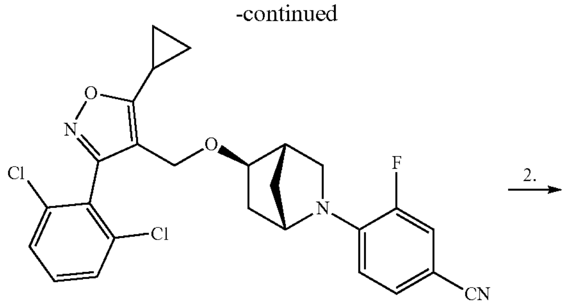

134a

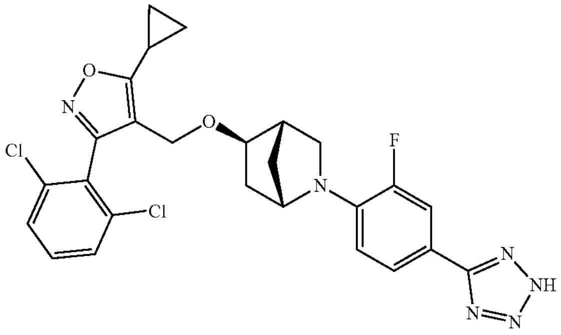

I-134

Step 1

To a 100 mL round-bottom flask, purged with and maintained under an inert atmosphere of nitrogen, was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.394 mmol, 1.00 equiv.), $Pd_2(dba)_3$ (48 mg, 0.05 mmol, 0.13 equiv.), BINAP (33 mg, 0.05 mmol, 0.13 equiv), $Cs_2CO_3$ (690 mg, 2.12 mmol, 5.4 equiv.), 4-bromo-3-fluorobenzonitrile (126 mg, 0.63 mmol, 1.6 equiv.), and tol (10 mL). The resulting mixture was stirred at 110° C., overnight. Upon cooling to room temperature, 100 mL of $H_2O$ was added. The aqueous mixture was extracted with ethyl acetate (100 mL×2), and the combined organic extracts were washed brine (100 mL×2), dried over anhydrous sodium sulfate and concentrated under vacuum. The residue was purified by silica gel column chromatography eluting with ethyl acetate/petroleum ether (1:2) to give 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzonitrile 134a (0.1 g, 51%) as a yellow oil.

Step 2

To a 50 mL round-bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzonitrile 134a (100 mg, 0.20 mmol, 1.0 equiv.), n-$Bu_3SnN_3$ (94 mg, 1.4 equiv.), and m-xylene (5 mL). The resulting mixture was heated at 140° C., with stirring for 1 day. Upon cooling to room temperature, 50 mL of $H_2O$ was added, and aqueous mixture was extracted with ethyl acetate (100 mL×2). The combined organic extracts were washed with brine (100 mL×2), dried over anhydrous sodium sulfate and concentrated under vacuum. The crude product was purified by Prep-HPLC using the following conditions: Column, XBridge C18 OBD Prep Column, 19 mm×250 mm; mobile phase, Water (0.05% TFA) and ACN (43.0% ACN up to 63.0% in 8 min); Detector, uv 254 nm. After purification (1S,4S,5R)-5-[[5-cyclopropyl-3-(2,6-dichlorophenyl)-1,2-oxazol-4-yl]methoxy]-2-[2-fluoro-4-(2H-1,2,3,4-tetrazol-5-yl)phenyl]-2-azabicyclo[2.2.1]heptane I-134 (25.7 mg, 24%) was obtained as a colorless solid. $^1$HNMR (400 MHz. $CD_3OD$): δ 7.67-7.45 (m, 5H), 6.75 (t, J=8.9 Hz, 2H), 4.33 (s, 2H), 4.22 (s, 1H), 3.64-3.49 (m, 2H), 2.71 (dd, J=9.8, 3.3 Hz, 1H), 2.47 (s, 1H), 2.28 (p, J=6.9 Hz, 1H), 1.96 (dd, J=13.4, 7.0 Hz, 1H), 1.73-1.54 (m, 2H), 1.26 (dd, J=54.6, 8.3 Hz, 8H), 1.00-0.88 (m, 1H). MS (ES, m/z): [M+1]=541.

Example 129: 5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,3-dihydro-1H-isoindol-1-one (I-135)

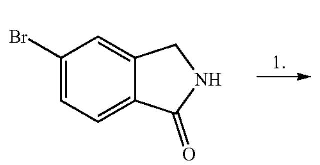

135a

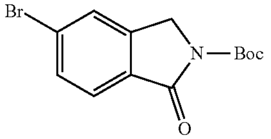

135b

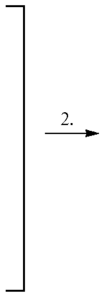

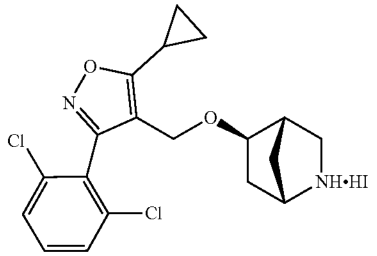

12dd

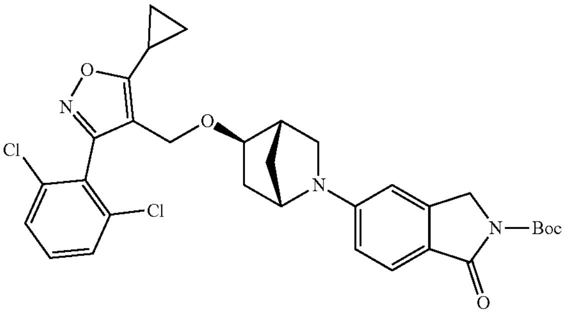

135c

-continued

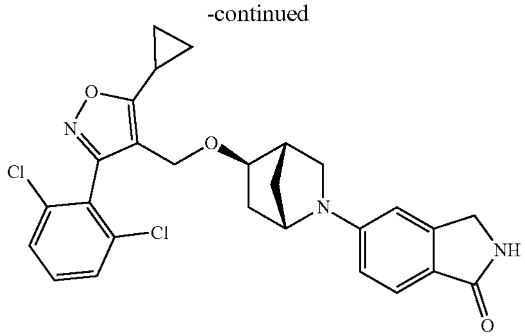

I-135

Step 1

To a 25 mL round-bottom flask was added 5-bromo-2,3-dihydro-1H-isoindol-1-one 135a (500 mg, 2.36 mmol, 1.0 equiv.), di-tert-butyl dicarbonate (800 mg, 3.67 mmol, 1.5 equiv.), 4-dimethylaminopyridine (30 mg, 0.25 mmol, 0.1 equiv.), and tetrahydrofuran (5 mL). The resulting mixture was stirred at room temperature overnight. The mixture was diluted with 500 mL of brine and extracted with ethyl acetate (250 mL×3). The organic extracts were combined, dried over anhydrous sodium sulfate, and concentrated under vacuum. The residue was purified by Flash-Prep-HPLC using the following conditions (IntelFlash-1): Column, silica gel; mobile phase: EA:PE=0:100 increasing to EA:PE=20:80 within 25 min; Detector, UV 254 nm. Removal of solvents gave tert-butyl 5-bromo-1-oxo-2,3-dihydro-1H-isoindole-2-carboxylate 135b (659 mg, 90%) as a light yellow solid.

Step 2

To a 25 mL round-bottom flask was added a solution of (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (100 mg, 0.197 mmol, 1.0 equiv.) in toluene (2 mL), tert-butyl 5-bromo-1-oxo-2,3-dihydro-1H-isoindole-2-carboxylate 135b (124 mg, 0.40 mmol, 2.03 equiv), BINAP (33 mg, 0.05 mmol, 0.25 equiv.), $Pd_2(dba)_3$ (49 mg, 0.05 mmol, 0.25 equiv.), and $Cs_2CO_3$ (260 mg, 0.80 mmol, 4.0 equiv.). The resulting mixture was stirred at 110° C., overnight. After cooling to room temperature, the mixture was diluted with brine (200 mL), and extracted with ethyl acetate (150 mL×2). The combined organic extracts were dried over anhydrous sodium sulfate and concentrated under vacuum. The residue was purified by silica gel column chromatography eluting with ethyl acetate/petroleum ether (1:1.5) to yield tert-butyl 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1-oxo-2,3-dihydro-1H-isoindole-2-carboxylate 135c (64 mg, 40%) as a light yellow oil.

Step 3

To a 25 mL round-bottom flask was added tert-butyl 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1-oxo-2,3-dihydro-1H-isoindole-2-carboxylate 135c (64 mg, 0.10 mmol, 1.0 equiv.), dichloromethane (2 mL), and trifluoroacetic acid (1 mL). The resulting mixture was stirred for 15 min at room temperature. The pH value of the solution was adjusted to 7.0 using a 1M sodium hydroxide aqueous solution. The mixture was extracted with ethyl acetate (30 mL×3), the combined organic extracts were dried over anhydrous sodium sulfate and concentrated under vacuum. The crude product was purified by Prep-HPLC using the conditions: Mobile phase: Water (0.05% TFA) and ACN (51% ACN up to 66% in 8 min); Detector, UV 220 nm. After purification 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2,3-dihydro-1H-isoindol-1-one I-135 (21.2 mg, 40%) was obtained as a colorless solid. $^1$HNMR (300 MHz, $CD_3OD$): δ 7.58-7.37 (m, 4H), 6.55 (dq, J=3.9, 2.1 Hz, 2H), 4.29 (d, J=4.6 Hz, 4H), 4.13 (s, 1H), 3.50-3.29 (m, 2H), 2.60-2.42 (m, 2H), 2.23 (p, J=6.7 Hz, 1H), 1.87-1.73 (m, 1H), 1.58 (t, J=7.7 Hz, 2H), 1.33-1.21 (m, 1H), 1.13 (d, J=6.8 Hz, 4H). MS (ES, m/z): [M+1]=511.

Example 130: 6-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,2,3,4-tetrahydroisoquinolin-1-one (I-136)

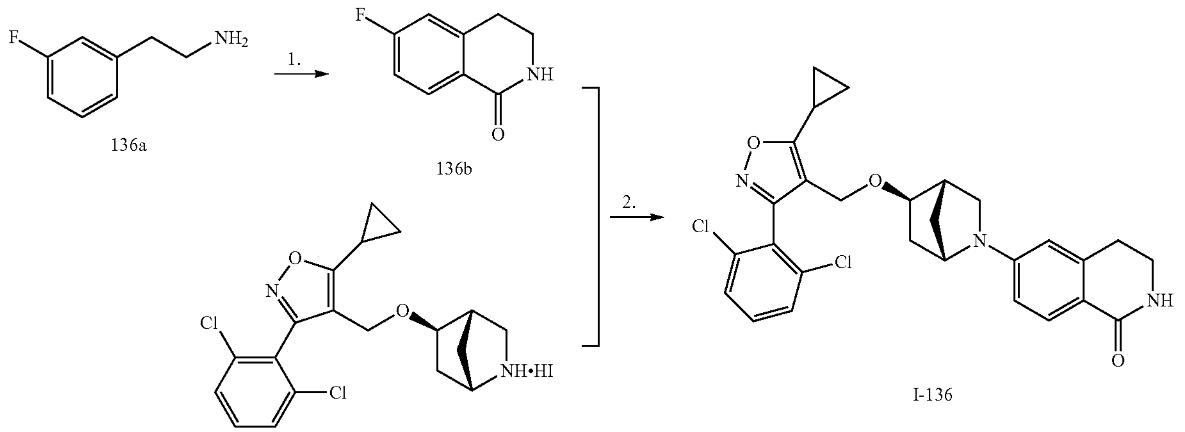

136a 136b 12dd I-136

Step 1

To a 25 mL round-bottom flask was added a solution of 2-(3-fluorophenyl)ethan-1-amine 136a (850 mg, 6.11 mmol, 1.0 equiv.) in dichloromethane (10 mL). A solution of triphosgene (1 g) in dichloromethane (5 mL) was added slowly followed by the addition of TEA (1.4 g, 13.84 mmol, 2.27 equiv.). The reaction mixture was stirred at room temperature for 2 h. A solution of $AlCl_3$ (3.8 g) in dichloromethane (25 mL) was dropwise with stirring at 0° C. The resulting mixture was stirred for 16 h at room temperature. The reaction was quenched by the addition of a 2.5% HCl aqueous solution (25 mL), and the mixture was further diluted with 300 mL of brine. The aqueous mixture was extracted with dichloromethane (200 mL×3); the combined organic layers were dried over anhydrous sodium sulfate and concentrated under vacuum. The crude product was purified by Flash-Prep-HPLC using the following conditions (Intel-Flash-1): Column, silica gel; mobile phase, EA:PE=0:100 increasing to EA:PE=50:50 within 20 min; Detector, UV 254 nm. Removal of solvents gave 6-fluoro-1,2,3,4-tetrahydroisoquinolin-1-one 136b (169 mg, 17%) as a colorless solid.

Step 2

To a 5 mL sealed tube was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (100 mg, 0.26 mmol, 1.0 equiv.), 6-fluoro-1,2,3,4-tetrahydroisoquinolin-1-one 136b (65 mg, 0.39 mmol, 1.5 equiv.), potassium carbonate (110 mg, 0.79 mmol, 3.0 equiv.), and DMSO (1.5 mL). The resulting mixture was stirred at 120° C., overnight. After cooling to room temperature, the mixture was diluted with EA (50 mL), washed with brine (30 mL×3), dried over anhydrous sodium sulfate, and concentrated under vacuum. The crude product was purified by Prep-HPLC using the following conditions: Column, XBridge Shield RP18 OBD Column, 5 um, 19*150 mm; mobile phase, Water (0.05% TFA) and ACN (46.0% ACN up to 64.0% in 8 min); Detector, uv 254 nm. After purification 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2,3,4-tetrahydroisoquinolin-1-one I-136 (35.7 mg, 26%) was obtained as a white solid. $^1$HNMR (300 MHz, $CD_3OD$): δ 7.649 (m, 1H), 7.510 (m, 1H), 7.438 (m, 2H), 6.418 (m, 1H), 6.282 (m, 1H), 4.274 (m, 2H), 4.116 (m, 1H), 3.411 (m, 3H), 3.285 (m, 1H), 2.858 (m, 2H), 2.540 (m, 2H), 2.201 (m, 1H), 1.717 (m, 1H), 1.593 (m, 2H), 1.289 (m, 1H), 1.121 (m, 4H). MS (ES, m/z): [M+1]=524.

Example 131: (2R)-6-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,2,3,4-tetrahydronaphthalene-2-carboxylic Acid (I-137) and (2S)-6-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,2,3,4-tetrahydronaphthalene-2-carboxylic Acid (I-138)

Step 1

To a 25 mL round-bottom flask was added 6-bromo-1,2,3,4-tetrahydronaphthalen-1-one 137a (100 mg, 0.44 mmol, 1.0 equiv.), a solution of sodium ethoxide (300 mg, 2.0 equiv.) in ethanol (2.4 mL), and dimethyl carbonate (160 mg, 1.78 mmol, 4.0 equiv.). The resulting mixture was stirred at 80° C., overnight. The mixture was diluted with 10

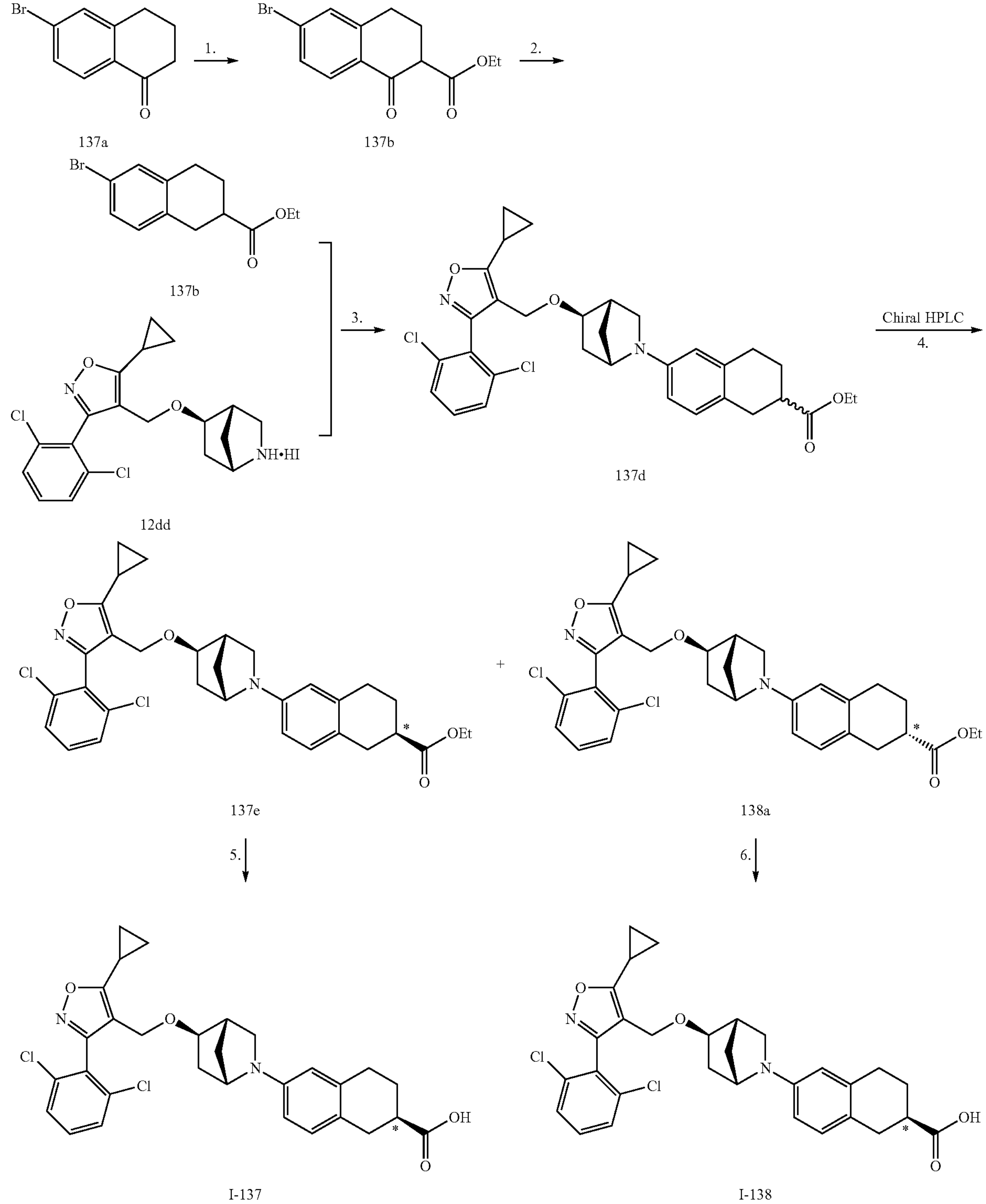

137a

137b

137b

12dd

137d

137e

138a

I-137

I-138 mL of methanol, solids were filtered out, and the filtrate was concentrated under vacuum. The residue was purified by silica gel column chromatography eluting with ethyl acetate/petroleum ether (1:8) to give methyl 6-bromo-1-oxo-1,2,3,4-tetrahydronaphthalene-2-carboxylate 137b (70 mg, 56%) as a colorless solid.

Step 2

To a 50 mL round-bottom flask was added ethyl 6-bromo-1-oxo-1,2,3,4-tetrahydronaphthalene-2-carboxylate 137b (1.4 g, 4.71 mmol, 1.0 equiv.), $Et_3SiH$ (4 mL), and trifluoroacetic acid (10 mL). The resulting mixture was stirred at room temperature overnight. The residue was applied onto a silica gel column and eluted with ethyl acetate/petroleum ether (1:10). Removal of solvents gave ethyl 6-bromo-1,2,3,4-tetrahydronaphthalene-2-carboxylate 137c (0.9 g, 67%) as a yellow oil.

Step 3

To a 25 mL round-bottom flask was added a solution of (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (500 mg, 0.9858 mmol, 1.0 equiv.) in toluene (4 mL), $Cs_2CO_3$ (860 mg, 2.64 mmol, 2.68 equiv.), Ru-Phos (30 mg), Ru-Phos Pre-catalyst (40 mg), and ethyl 6-bromo-1,2,3,4-tetrahydronaphthalene-2-carboxylate 137b (410 mg, 1.45 mmol, 1.47 equiv.). The resulting mixture was stirred at 1100° C., overnight. After cooling to room temperature 30 mL of $H_2O$ was added, the mixture was extracted with ethyl acetate (100 mL×2). The combined organic layers were washed with brine (100 mL×2), dried over anhydrous sodium sulfate and concentrated under vacuum. The residue was purified by silica gel column chromatography eluting with ethyl acetate/petroleum ether (1:5) to yield ethyl 6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2,3,4-tetrahydronaphthalene-2-carboxylate 137c (0.15 g, 26%) as a red color oil.

Step 4

6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2,3,4-tetrahydronaphthalene-2-carboxylate 137c (150 mg) was resolved by Chiral HPLC [Conditions: Column: (R,R) Whelk-01; Column size: 0.46*5 cm, 3.5 um; Mobile phase: hex (0.1% DEA):EtOH (50:50); Flow rate: 1.0 mL/min; Detector: 254 nm] to afford diastereomer 137e (44 mg, 29%, retention time=2.77 min), arbitrary assigned as (R)-ethyl 6-((1S,4S,5R)-5-((5-cyclopropyl-3-(2,6-dichlorophenyl)isoxazol-4-yl)methoxy)-2-aza-bicyclo[2.2.1]heptan-2-yl)-1,2,3,4-tetrahydronaphthalene-2-carboxylate, and diastereomer 138a (44 mg, 29%, retention time=4.02 min), arbitrary assigned as (S)-ethyl 6-((1S,4S,5R)-5-((5-cyclopropyl-3-(2,6-dichlorophenyl)isoxazol-4-yl)methoxy)-2-aza-bicyclo[2.2.1]heptan-2-yl)-1,2,3,4-tetrahydronaphthalene-2-carboxylate.

Step 5

To a 25 mL round-bottom flask was added ethyl (2R)-6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2,3,4-tetrahydronaphthalene-2-carboxylate 137e (110 mg, 0.19 mmol, 1.0 equiv.), ethanol (5 mL), water (1 mL), and $LiOH.H_2O$ (80 mg, 1.9 mmol, 10.0 equiv.). The resulting mixture was stirred at room temperature overnight. The mixture was diluted with 5 mL of $H_2O$, the pH value of the solution was adjusted to 3-4 using a 1M HCl aqueous solution, and the mixture was extracted with ethyl acetate (100 mL×2). The combined organic extracts were washed with brine (100 mL×2), dried over anhydrous sodium sulfate and concentrated under vacuum. The crude product was purified by Prep-HPLC using the following conditions Column, XBridge Shield RP18 OBD Column, 5 um, 19*150 mm; mobile phase, Water (0.05% TFA) and ACN (50.0% ACN up to 69.0% in 6 min); Detector, UV 254 nm. After purification (2R)-6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2,3,4-tetrahydronaphthalene-2-carboxylic acid I-137 (23.5 mg, 22%) was obtained as an off-white solid. $^1$HNMR (300 MHz, $CD_3OD$): δ 7.62-7.45 (m, 3H), 7.02 (d, J=8.0 Hz, 1H), 6.60 (s, 1H), 6.53 (s, 1H), 4.34 (s, 2H), 4.10 (s, 1H), 3.48 (dd, J=15.8, 5.4 Hz, 3H), 2.98-2.81 (m, 4H), 2.71 (d, J=9.3 Hz, 2H), 2.53 (s, 1H), 1.92-1.79 (m, 2H), 1.68 (s, 2H), 1.30 (d, J=14.1 Hz, 1H), 1.19 (d, J=6.9 Hz, 4H). MS (ES, m/z): [M+1]=553.

Step 6

To a 25 mL round-bottom flask was added ethyl (2S)-6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2,3,4-tetrahydronaphthalene-2-carboxylate 138a (100 mg, 0.17 mmol, 1.0 equiv.), ethanol (5 mL), water (1 mL), and LiOH (80 mg, 3.34 mmol, 10.0 equiv.). The resulting mixture was stirred at room temperature overnight. The mixture was diluted with 30 mL of $H_2O$, the pH value of the solution was adjusted to 3-4 using a 1 M HCl aqueous solution, and the mixture was extracted with ethyl acetate (100 mL×2). The combined organic extracts were washed with brine (100 mL×2), dried over anhydrous sodium sulfate and concentrated under vacuum. The crude product was purified by Prep-HPLC using the following conditions Column, XBridge Shield RP18 OBD Column, 5 um, 19*150 mm; mobile phase, Water (0.05% TFA) and ACN (50.0% ACN up to 70.0% in 8 min); Detector, uv 254 nm. After purification (2S)-6-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2,3,4-tetrahydronaphthalene-2-carboxylic acid I-138 (32.5 mg, 34%) was obtained as an off-white solid. $^1$HNMR (300 MHz, $CD_3OD$): δ 7.62-7.46 (m, 3H), 7.12 (d, J=8.3 Hz, 1H), 6.74 (s, 2H), 4.35 (s, 2H), 4.18 (s, 1H), 3.63-3.45 (m, 2H), 3.01-2.69 (m, 6H), 2.60 (s, 1H), 2.36-2.12 (m, 2H), 1.76 (s, 2H), 1.35 (d, J=14.7 Hz, 1H), 1.20 (d, J=6.8 Hz, 4H). MS (ES, m/z): [M+1]=553.

Example 132: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-hydroxy-3-methylbenzamide (I-139)

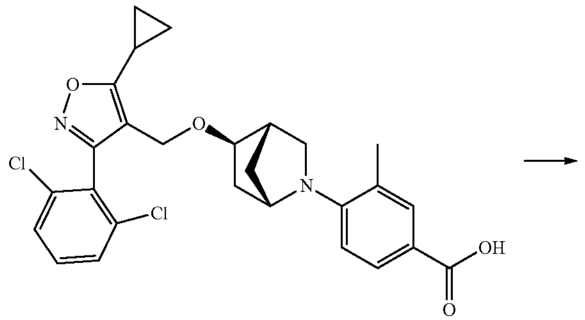

I-107

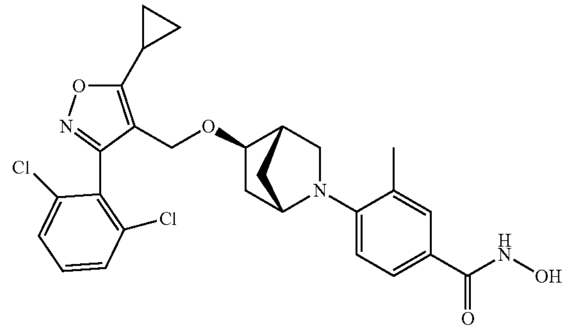

I-139

Reacting 4-((1S,4S,5R)-5-((5-cyclopropyl-3-(2,6-dichlorophenyl)isoxazol-4-yl)methoxy)-2-azabicyclo[2.2.1]heptan-2-yl)-3-methylbenzoic acid I-107 (75 mg, 0.15 mmol, 1 equiv.) with O-(tetrahydro-2H-pyran-2-yl)hydroxylamine (22 mg, 0.188 mmol, 1.2 equiv.) under the conditions of HATU (86 mg, 0.226 mmol, 1.5 equiv.)/DIEA (130 uL, 5 equiv.)/DMF (1 mL) at room temperature for 16 h. The mixture was diluted with ethyl acetate, washed with $H_2O$ and brine, dried over anhydrous sodium sulfate and concentrated to the O-THP protected hydroxyamide. This intermediate was dissolved in 10 mL of a mixed solution of methanol and trifluoroacetic acid (3:2, v/v), and heated at 50° C., for 1 h. The mixture was concentrated in vacuo to a residue, which was purified by Semi-prep HPLC purification to afford 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-hydroxy-3-methylbenzamide I-139 as a trifluoroacetate salt (36 mg, 38.2%) as an off-white solid. $^1$H-NMR (400 MHz, DMSO-$d_6$): δ 7.74-7.51 (m, 3H), 7.47-7.30 (m, 2H), 6.60 (d, J=8.4 Hz; 1H), 4.23 (s, 2H), 3.92 (s, 1H), 3.52-3.33 (m, 2H), 2.43-2.26 (m, 2H), 2.15 (s, 3H), 1.95 (dd, J=12.7 & 6.3 Hz, 1H), 1.40 (dd, J=29.4 & 9.4 Hz, 2H), 1.21-1.03 (m, 6H); MS (ES, m/z): [M+1]=528.09.

Example 133: 5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,3-dihydro-1,3-benzoxazol-2-one (I-140)

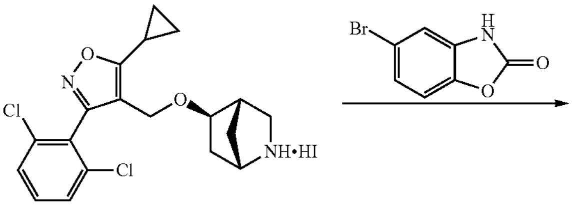

12dd

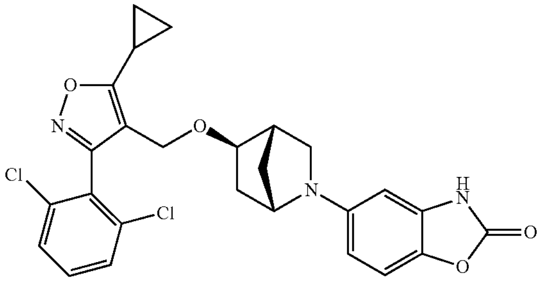

I-140

A suspension of 4-(((1S,4S,5R)-2-azabicyclo[2.2.1]heptan-5-yloxy)methyl)-5-cyclopropyl-3-(2,6-dichlorophenyl) isoxazole hydroiodide salt 12dd (124 mg, 0.3 mmol, 1 equiv.), 5-bromobenzo[d]oxazol-2(3H)-one (82 mg, 0.383, 1.3 equiv.), tert-BuOK (168 mg, 1.5 mmol, 5 equiv.), $Pd_2(dba)_3$ (58 mg, 0.06 mmol, 0.2 equiv.), 5-(di-t-butyl phosphino(1,3,5'-triphenyl-H-[1,4]bipyrazole (BippyPhos) (30 mg, 0.06 mmol, 0.2 equiv.) in t-Amyl alcohol (5.0 mL) was heated under nitrogen atmosphere at 60° C., for 16 h. The reaction mixture was cooled to room temperature, saturated ammonium chloride was added, diluted with ethyl acetate and filtered through a pad of Celite. The organic layer was washed with brine, dried over anhydrous $Na_2SO_4$, filtered and concentrated under reduced pressure. The crude material was purified by ISCO silica gel column chromatography using hexane/ethyl acetate as eluents to give the desired product, which was further purified by Semi-prep HPLC using 10-90% ACN (0.1% TFA) in 30 min, method to afford 5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2,3-dihydro-1,3-benzoxazol-2-one I-140 as a trifluoroacetate salt (18 mg, 9.6%) an off-white solid. $^1$H-NMR (400 MHz, DMSO-$d_6$): δ 7.59-7.48 (m, 3H), 7.01-6.59 (m, 1H), 6.36-6.25 (m, 2H), 4.26 (s, 2H), 3.96 (s, 1H), 3.49-3.33 (m, 2H), 2.37-2.33 (m, 2H), 1.75-1.72 (m, 1H), 1.41 (dd, J=29.2 & 9.4 Hz, 2H), 1.26-1.03 (m, 6H); MS (ES, m/z): [M+1]=512.26.

Example 134: 5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-dihydro-2-benzofuran-1-one (I-141)

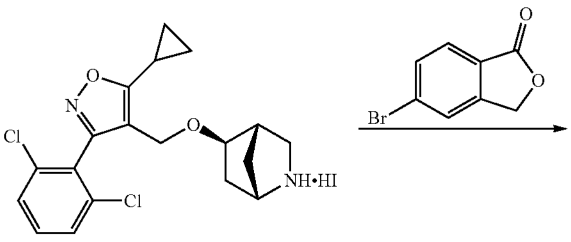

12dd

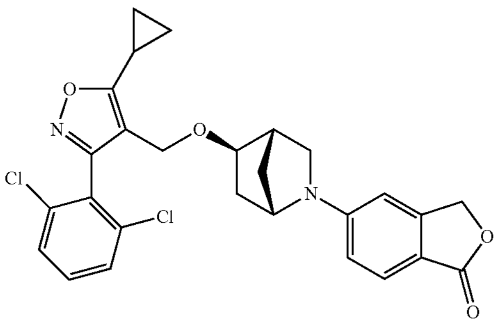

I-141

A suspension of 4-(((1S,4S,5R)-2-azabicyclo[2.2.1]heptan-5-yloxy)methyl)-5-cyclopropyl-3-(2,6-dichlorophenyl) isoxazole hydroiodide salt 12dd (0.124 g, 0.3 mmol, 1 equiv.), 5-bromoisobenzofuran-1(3H)-one (0.083 g, 0.4 mmol, 1.3 equiv.), $Cs_2CO_3$ (244 mg, 0.748 mmol, 2.5 equiv.). $Pd_2(dba)_3$ (58 mg, 0.06 mmol, 0.2 equiv.), BINAP (28 mg, 0.045 mmol, 0.2 equiv.) in Toluene (6 mL) was heated under nitrogen atmosphere at 110° C., for 16 h. The reaction mixture was cooled to room temperature, diluted with ethyl acetate and filtered through a pad of Celite. The organic layer was washed with saline, dried over anhydrous $Na_2SO_4$, filtered and concentrated under reduced pressure. The crude material was purified on Isco silica gel column chromatography using hexane/ethyl acetate as eluent to give the desired product, which was further purified by Semi-prep HPLC purification using 10-90% ACN (0.1% TFA) in 30 min, method to give 5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-dihydro-2-benzofuran-1-one I-141 as trifluoroacetate salt (36 mg, 19.2%) an off-white solid. $^1$H-NMR (400 MHz, DMSO-$d_6$): δ 7.72-7.45 (m, 4H), 6.69-6.48 (m, 2H), 5.18 (s, 2H), 4.28-4.18 (m, 3H), 3.46 (d, J=6.0 Hz, 1H), 3.33 (dd, J=9.8 & 4.0 Hz, 1H), 2.57 (d, J=9.7

Hz, 1H), 2.41-2.24 (m, 1H), 1.71 (dd, J=12.9 & 6.7 Hz, 1H), 1.45 (dd, J=26.8 & 9.5 Hz, 2H), 1.26-0.98 (m, 6H); MS (ES, m/z): [M+1]=511.23.

Example 135: 1-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}-2,2,2-trifluoroethan-1-one (I-142)

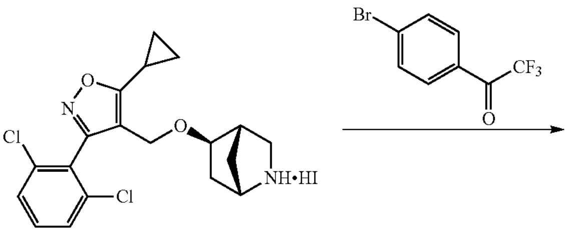

12dd

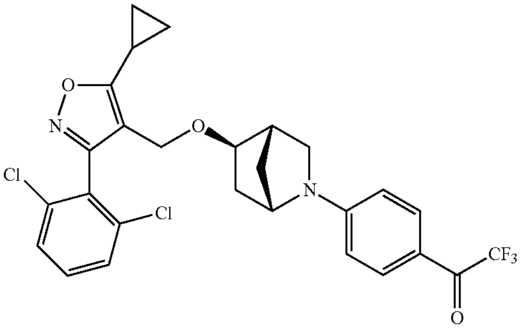

I-142

Following the procedure described in Example 134, 4-(((1S,4S,5R)-2-azabicyclo[2.2.1]heptan-5-yloxy)methyl)-5-cyclopropyl-3-(2,6-dichlorophenyl)isoxazole hydroiodide salt 12dd (0.124 g, 0.3 mmol, 1 equiv.) was reacted with 1-(4-bromophenyl)-2,2,2-trifluoroethanone (83 mg, 0.328 mmol, 1.1 equiv.) to provide the desired product, which was purified by Semi-prep HPLC using 40-95% ACN (0.1% TFA) in 30 min, method to afford the trifluoroacetate salt of 1-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}-2,2,2-trifluoroethan-1-one I-142 (78.0 mg, 47%) as an off-white solid. $^1$HNMR (400 MHz, DMSO-d6): δ 7.79 (d, J=8.6 Hz, 3H), 7.70-7.52 (m, 4H), 4.39-4.22 (m, 3H), 3.52 (d, J=5.4 Hz, 1H), 3.36 (dd, J=10.2 & 4.1 Hz, 1H), 2.72 (dd, J=23.9 & 9.8 Hz, 1H), 2.34 (dq, J=8.3&5.2 Hz 1H), 1.72 (dd, J=13.3 & 6.7 Hz, 1H), 1.47 (dd, J=23.9 & 9.8 Hz, 2H), 1.26-1.02 (m, 6H); MS (ES, m/z): [M+1]=551.14.

Example 136: 2-{N-methyl4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzenesulfonamido}acetic Acid (I-143)

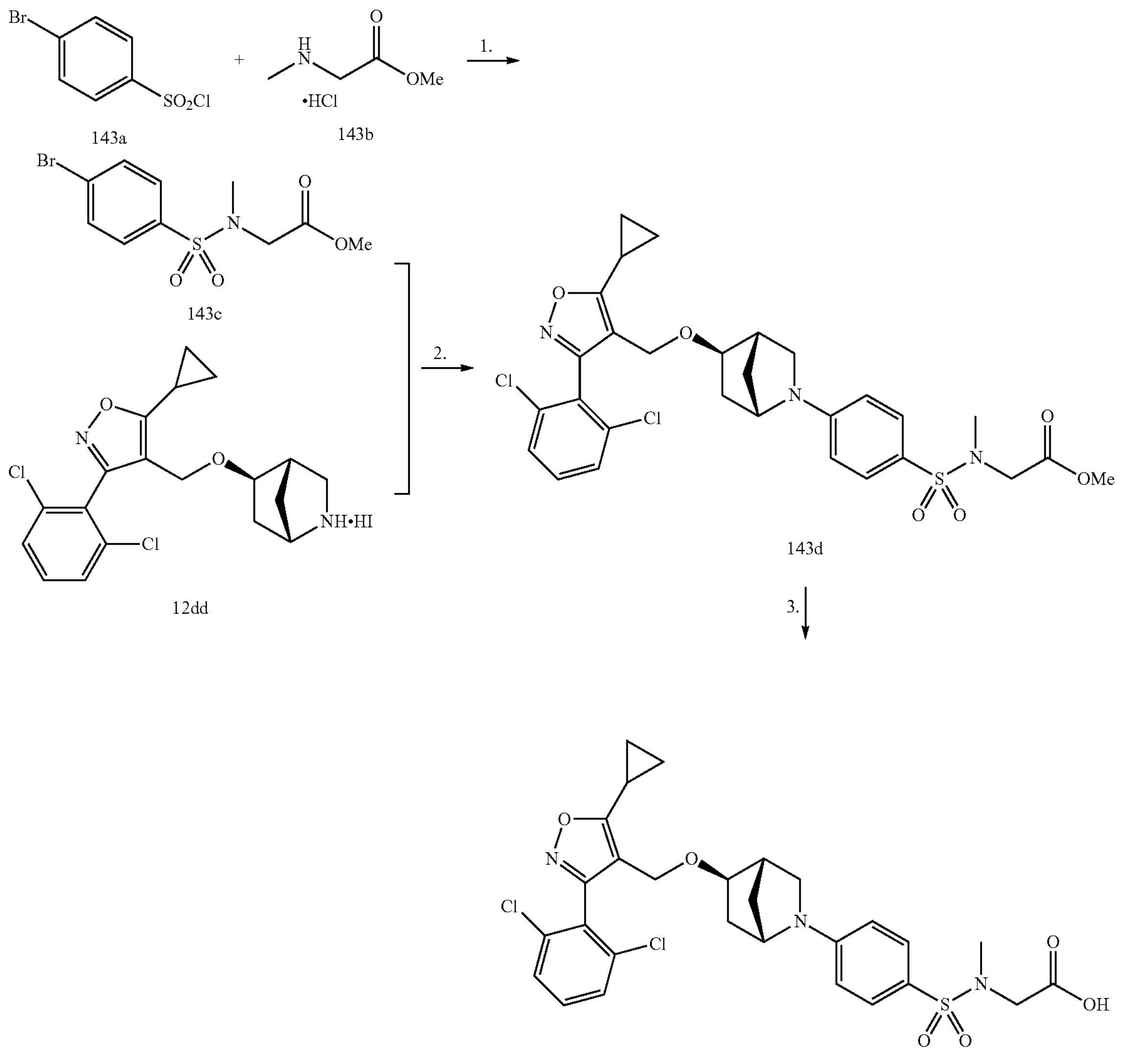

143a 143b 143c 12dd 143d I-143

Step 1

To a solution of methyl 2-(methylamino) acetate hydrochloride salt 143b (1.4 g, 10 mmol, 1 equiv.) and triethylamine (7.0 mL, 7 equiv.) in dichloromethane (20 mL) was added 4-bromobenzene-1-sulfonyl chloride 143a (3.0 g, 1.2 equiv.) dropwise at 0° C. The reaction mixture was warmed to room temperature and continued to stir for another 2 hr. The organic layer was washed with water, dried over sodium sulfate, filtered and concentrated in vacuo. The crude material was purified by silica gel chromatography using 20-30% ethyl acetate in hexane as eluent. Removal of solvents afforded methyl 2-(4-bromo-N-methylphenylsulfonamido)-acetate 143c (2.5 g). $^1$HNMR (400 MHz, DMSO-$d_6$): δ 7.84 (d, J=8.6 Hz, 2H), 7.73 (d, J=8.6 Hz, 2H), 4.05 (s, 2H), 3.59 (s, 3H), 2.80 (s, 3H).

Step 2 and 3

Following the procedure described in Example 134, 4-(((1S,4S,5R)-2-azabicyclo[2.2.1]heptan-5-yloxy)methyl)-5-cyclopropyl-3-(2,6-dichlorophenyl)isoxazole hydroiodide salt 12dd (0.124 g, 0.3 mmol, 1 equiv.) was reacted with methyl 2-(4-bromo-N-methylphenylsulfonamido)acetate (136 mg, 1.3 equiv.) to provide the desired product 143d which was hydrolyzed under the conditions of 1N NaOH aqueous/Methanol at 50° C., for 1 h and purified by Semi-prep HPLC using 40-95% ACN (0.1% TFA) in 30 min, method to afford trifluoroacetate salt of 2-{N-methyl4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzenesulfonamido}acetic acid I-143 (5.8 mg) as an off-white solid. $^1$HNMR (400 MHz, DMSO-d6) δ: 7.66-7.58 (m, 3H), 7.47 (d, J=8.9 Hz, 2H), 6.56 (d, J=8.5 Hz, 2H), 4.26 (s, 2H), 4.18 (s, 1H), 3.73 (s, 2H), 3.46 (d, J=6.3 Hz, 1H), 3.30 (dd, J=9.7 & 3.8 Hz, 1H), 2.66 (s, 3H), 2.32 (d, J=5.1 Hz, 1H), 1.76-1.69 (m, 1H), 1.44 (dd, J=24.6 & 9.8 Hz, 2H), 1.25-0.98 (m, 6H); MS (ES, m/z): [M+1]=605.82.

Example 137: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzene-1-sulfonic Acid (I-144)

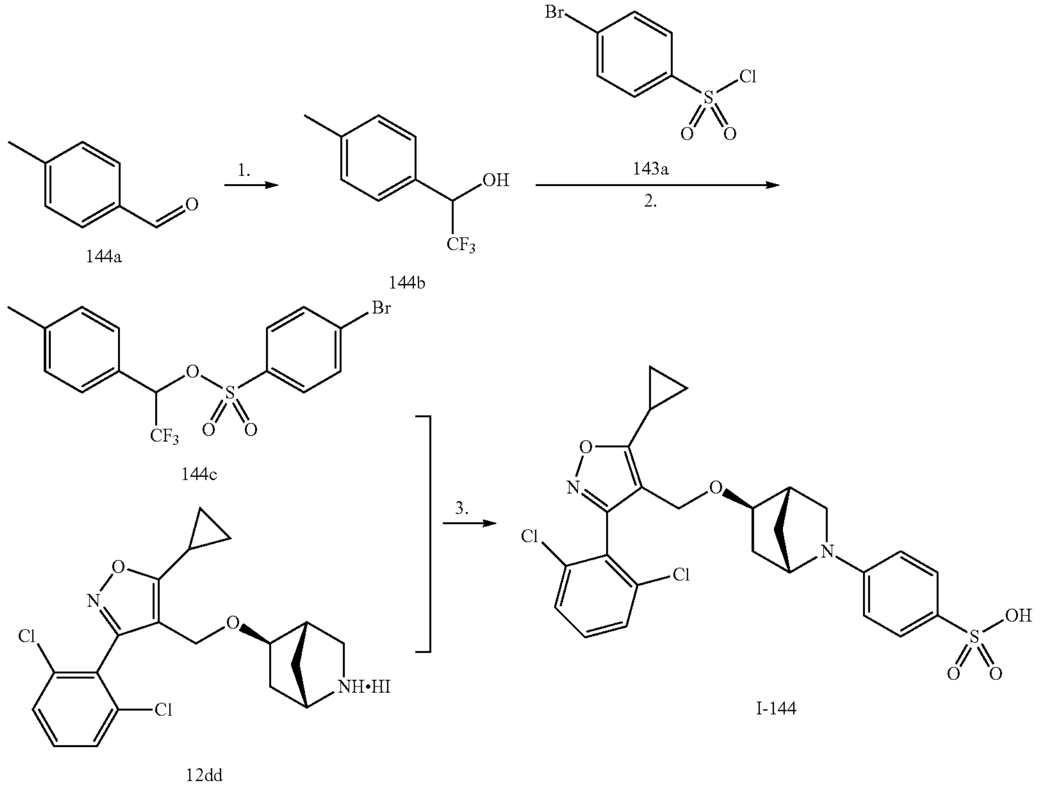

Step 1

A catalytic amount of 1M-tetrabutylammonium fluoride in THF (0.5 mL) was added to a solution of trimethyl (trifluoromethyl)silane (9.0 mL, 1.2 equiv.) and 4-methylbenzaldehyde 144a (6.0 g, 1 equiv.) in THF (50 mL) at 0° C., with stirring. Cooling bath was removed and the reaction was continued for 4 hr. The thin layer chromatography in hexane:ethylacetate (19:1; v/v) showed the completion of the reaction. A 1N HCl aqueous solution (60 mL) was added to the reaction mixture, and the reaction was continued for 16 hr. The mixture was diluted with ethyl acetate and washed with brine, dried over sodium sulfate, filtered and concentrated in vacuo to give the 2,2,2-trifluoro-1-p-tolylethanol 144b (5.5 g) which was used as such in the next step; $^{1}H$ NMR (400 MHz, DMSO-$d_6$): δ 7.37 (d, J=7.9 Hz, 2H), 7.21 (d, J=8.2 Hz, 2H), 6.74 (d, J=5.6 Hz, 1H), 5.18-4.99 (m, 1H), 2.31 (s, 3H).

Step 2

4-Bromobenzene-1-sulfonyl chloride 143a (5.1 g, 1 equiv.) and 2,2,2-trifluoro-1-p-tolylethanol 144b (3.8 g, 1 equiv.) were dissolved in dichloromethane (40 mL). A solution of DABCO (2.64 mL, 1.2 equiv.) in dichloromethane (10 mL) was added dropwise to the reaction mixture, resulting in precipitate formation. The mixture was stirred at room temperature for 16 h. The reaction was quenched by the addition of a 1N NaOH aqueous solution (5.0 mL). The organic layer was successively washed with aq, sodium bicarbonate solution, saline, 5% aq. Citric acid solution, saline, dried over sodium sulfate, filtered and concentrated under the reduced pressure to give 2,2,2-Trifluoro-1-p-tolylethyl 4-bromobenzenesulfonate 144c (4.5 g) as a white amorphous solid after precipitation with ether-hexane; $^{1}H$ NMR (400 MHz, DMSO-d6): δ 7.82-7.65 (m, 4H), 7.30 (d, J=8.1 Hz, 2H), 7.16 (d, J=8.3 Hz, 2H), 6.41 (q, J=6.6 Hz, 1H), 5.18-4.99 (m, 1H), 2.29 (s, 3H).

Step 3

Following the procedure described in Example 134, 4-(((1S,4S,5R)-2-azabicyclo[2.2.1]heptan-5-yloxy)methyl)-5-cyclopropyl-3-(2,6-dichlorophenyl)isoxazole hydroiodide salt 12dd (83 mg, 0.2 mmol, 1 equiv.) was reacted with 2,2,2-trifluoro-1-p-tolylethyl 4-bromobenzenesulfonate 144c (99 mg, 1.2 equiv.) to provide the desired intermediate, which was further hydrolyzed with TFA/water at room temperature for 4 h to give the desired crude product. Semi-prep HPLC purification of the crude using 40-95% ACN (0.1% TFA) in 30 min, method afforded the trifluoroacetate salt of 4-[(1S,4S,5R)-5-{[5-cyclopropyl-3-(2,6-dichlorophenyl)-1,2-oxazol-4-yl]methoxy}-2-azabicyclo [2.2.1]heptan-2-yl]benzene-1-sulfonic acid I-144 (9.0 mg) as an off-white solid. $^{1}$HNMR (400 MHz, DMSO-d6) δ: 7.65-7.57 (m, 3H), 7.36 (d, J=8.6 Hz, 2H), 6.39 (d, J=8.6 Hz, 2H), 4.24 (s, 2H), 4.05 (s, 1H), 3.33 (d, J=6.3 Hz, 1H), 3.27 (dd, J=9.7 & 3.8 Hz, 1H), 2.44-2.24 (m, 2H), 1.68 (dd, J=13.2 & 5.3 Hz, 1H), 1.43 (dd, J=33.5 & 9.5 Hz, 2H), 1.18-0.99 (m, 6H; MS (ES, m/z): [M+1]=535.02.

Example 138: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]pyrimidine-5-carboxylic Acid (I-145)

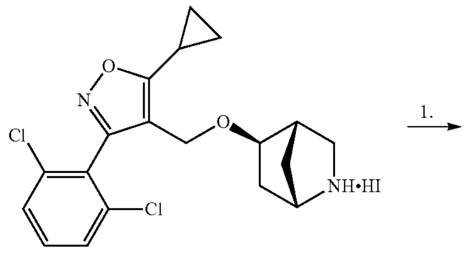

12dd

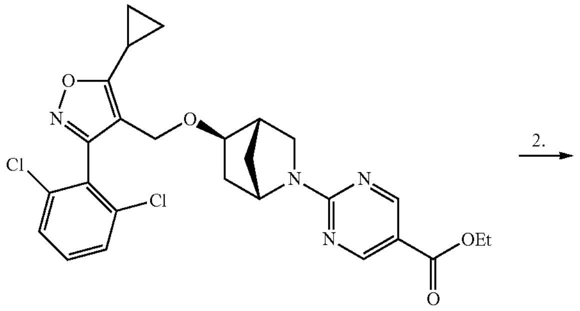

145a

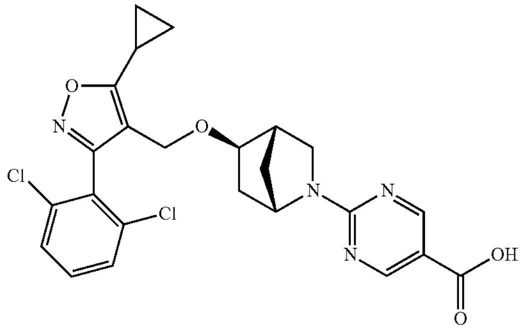

I-145

Step 1

To a 8 mL sealed tube was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.3943 mmol, 1.00 equiv.), ethyl 2-bromopyrimidine-5-carboxylate (120 mg, 0.52 mmol, 1.32 equiv.), DIEA (200 mg, 1.55 mmol, 3.93 equiv.), and dichloromethane (3 mL). The resulting mixture was stirred at room temperature overnight and concentrated. The residue was purified by silica gel column chromatography eluting with ethyl acetate/petroleum ether (1:4) to give ethyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyrimidine-5-carboxylate 145a (0.21 g, Q) as a yellow oil.

Step 2

To a 50 mL round-bottom flask was added ethyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyrimidine-5-carboxylate 145a (170 mg, 0.33 mmol, 1.00 equiv.), $LiOH.H_2O$ (130 mg, 3.3 mmol, 10.00 equiv.), methanol (15 mL) and water (3 mL). The resulting mixture was stirred at room temperature overnight. 20 mL of $H_2O$ was added, the pH value of the mixture was adjusted to <7 using a 1M hydrogen chloride aqueous solution. The aqueous mixture was extracted with ethyl acetate (100 mL×2). The combined organic extracts were washed with brine (100 mL×2), and concentrated to a crude product (5 mL) which was purified by Prep-HPLC using the following conditions: Column. XBridge Prep OBD C18 Column, 19*250 mm, 5 um; mobile phase, Water (0.05% TFA) and ACN (50.0% ACN up to 66.0% in 8 min); Detector, UV 220 nm. After purification, 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]pyrimidine-5-carboxylic acid I-145 (97.7 mg, 59%) was obtained as a colorless solid; $^1H$ NMR (300 MHz, $CD_3OD$): δ 8.75 (s, 2H), 7.61-7.43 (m, 3H), 4.66 (s, 1H), 4.41-4.25 (m, 2H), 3.65-3.55 (m, 1H), 3.41 (dd, J=11.2, 4.0 Hz, 1H), 3.01 (dd, J=11.2, 1.3 Hz, 1H), 2.56 (s, 1H), 2.35-2.19 (m, 1H), 2.04 (s, 1H), 1.84 (ddd. J=13.5, 6.8, 2.4 Hz, 1H), 1.68-1.49 (m, 2H), 1.34 (dt, J=13.7, 2.9 Hz, 1H), 1.18 (d, J=6.6 Hz, 4H); MS (ES, m/z): [M+1]=501.0.

Example 139: 2-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}acetic Acid (I-146)

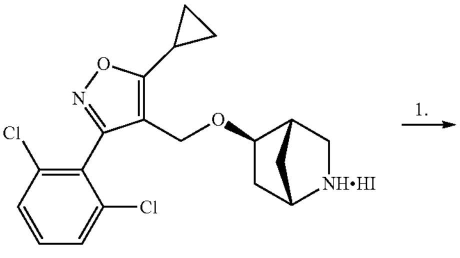

12dd

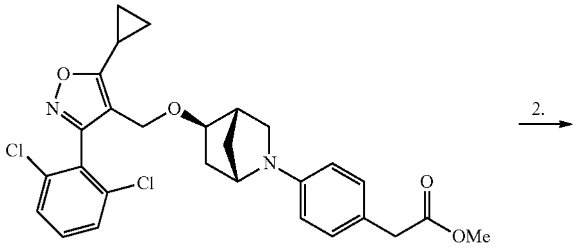

146a

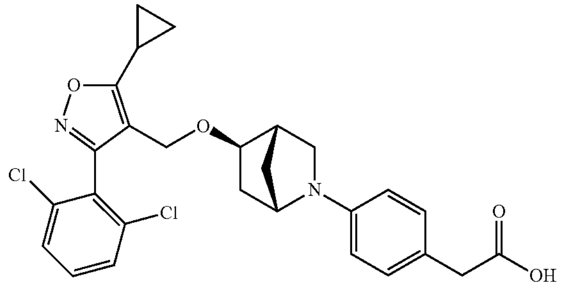

I-146

Step 1

To a 8 mL sealed tube purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.3943 mmol, 1.00 equiv.), methyl 2-(4-bromophenyl)acetate (240 mg, 1.05 mmol, 2.66 equiv.), a solution of $Cs_2CO_3$ (345 mg, 1.06 mmol, 2.66 equiv.) in toluene (5 mL), and RuPhos-Pd (100 mg, 0.12 mmol, 0.3 equiv.). The resulting mixture was stirred at 110° C., overnight. The mixture was cooled to room temperature and added with 10 mL of water. The aqueous mixture was extracted with ethyl acetate (50 mL×2), and the combined organic extracts were washed with brine (50 mL×2), dried over anhydrous sodium sulfate and concentrated under vacuum. The residue was purified by silica gel column chromatography eluting with ethyl acetate/petroleum ether (1:5) to afford methyl 2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]acetate 146a (171 mg, 81%) as a yellow oil.

Step 2

To a 50 mL round bottom flask was added methyl 2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]acetate 146a (171 mg, 0.32 mmol, 1.00 equiv.), methanol (2 mL), and LiOH (78 mg, 3.26 mmol, 10.00 equiv.) in water (0.2 mL). The resulting mixture was stirred at room temperature for 2 h. The mixture was diluted with 10 mL of $H_2O$, and the pH value of the mixture was adjusted to 2 using a 1M hydrogen chloride aqueous solution. The aqueous mixture was extracted with ethyl acetate (100 mL); the organic layer was washed with brine (100 mL×2), dried over anhydrous sodium sulfate, and concentrated under vacuum. The crude product was purified by Prep-HPLC using the following conditions (Column, XBridge Prep C18 OBD Column, 19×150 mm 5 um; mobile phase, Water (0.05% $NH_3$ in $H_2O$) and ACN (34.0% ACN up to 35.0% in 7 min); Detector, UV 254/220 nm. After purification 2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]acetic acid I-146 (30 mg, 18%) was obtained as a colorless solid. $^1H$ NMR (300 MHz, $CD_3OD$): δ 7.60-7.38 (m, 3H), 7.09 (d, J=8.4 Hz, 2H), 6.47 (d, J=8.5 Hz, 2H), 4.31 (d, J=1.8 Hz, 2H), 4.01 (s, 1H), 3.59-3.35 (m, 6H), 2.44 (d, J=8.7 Hz, 2H), 2.27 (q, J=6.7 Hz, 1H), 1.82-1.71 (m, 1H), 1.58 (s, 2H), 1.35-1.14 (m, 6H); MS (ES, m/z): [M+1]=530.0.

Example 140: 3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}propanoic Acid (I-147)

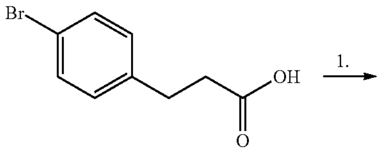

147a

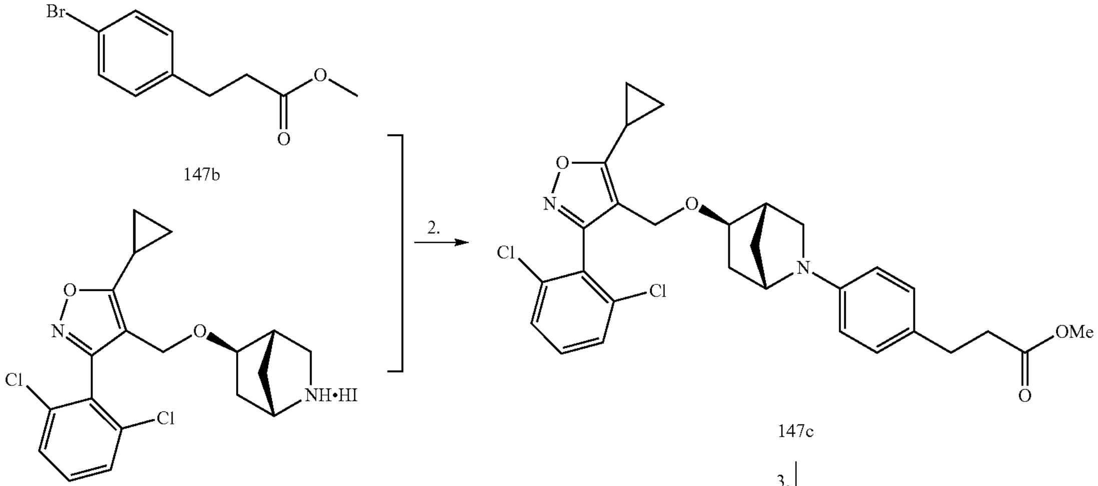

147b

12dd

147c

-continued

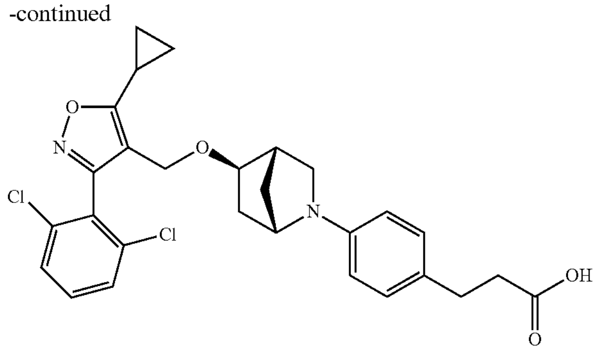

I-147

Step 1

To a 250 mL round bottom flask was added 3-(4-bromophenyl)propanoic acid 147a (5 g, 21.83 mmol, 1.00 equiv.) and methanol (50 mL). Thionyl chloride (7.76 g, 65.23 mmol, 3.00 equiv.) was added dropwise with stirring. The resulting mixture was stirred at 70° C., for 2 h. The reaction was quenched by the addition of water/ice. The aqueous mixture was extracted with ethyl acetate (200 mL×3), and the combined organic extracts were washed with brine (100 mL×2), dried over anhydrous sodium sulfate and concentrated. The residue was purified by silica gel column chromatography eluting with PE:EA (5.2%) to give methyl 3-(4-bromophenyl)propanoate 147b (4.84 g, 91%) as a colorless oil.

Step 2

To a 8 mL sealed tube was added a solution of (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.3943 mmol, 1.00 equiv.) in toluene (5 mL), methyl 3-(4-bromophenyl)propanoate 147b (256 mg, 1.05 mmol, 2.66 equiv.), Ru-phos-Pd (100 mg, 0.12 mmol, 0.3 equiv.), and cesium carbonate (345 mg, 1.06 mmol, 2.66 equiv.). The resulting mixture was stirred at 110° C., overnight. After cooling to room temperature, 40 mL of water was added, the mixture was extracted with ethyl acetate (40 mL×3). The combined organic extracts were washed with brine (30 mL×2), dried over anhydrous sodium sulfate and concentrated. The residue was purified by silica gel column chromatography eluting with ethyl acetate/petroleum ether (1:5) to afford methyl 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]propanoate 147c (110 mg, 51%) as yellow oil.

Step 3

To a 100 mL round-bottom flask was added methyl 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]propanoate 147c (110 mg, 0.20 mmol, 1.00 equiv.), methanol (10 mL), water (2 mL), and LiOH (50 mg, 2.09 mmol, 10.00 equiv.). The resulting mixture was stirred at 50° C., for 3 h, diluted with 30 mL of water after cooling to room temperature. The pH value of the mixture was adjusted to 2 using a 1M hydrogen chloride aqueous solution. The aqueous mixture was extracted with ethyl acetate (30 mL×2), and the combined organic extracts were washed with brine (30 mL×2), dried over anhydrous sodium sulfate and concentrated. The crude product was purified by Prep-HPLC using the following conditions: Column, XBridge Shield RP18 OBD Column, 5 um, 19*150 mm; mobile phase. Water (0.05% TFA) and ACN (46.0% ACN up to 64.0% in 8 min); Detector, UV 254 nm. After purification 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]propanoic acid I-147 (52.3 mg, 49%) was obtained as a gray solid. $^1H$ NMR (300 MHz, $CD_3OD$): δ 7.62-7.45 (m, 3H), 7.19 (s, 1H), 6.83 (s, 2H), 4.33 (s, 2H), 4.14 (s, 1H), 3.48 (s, 2H), 2.87 (t, J=7.6 Hz, 2H), 2.64-2.53 (m, 3H), 2.27 (p, J=6.8 Hz, 1H), 1.72 (s, 2H), 1.33 (d, J=11.0 Hz, 1H), 1.19 (d, J=7.0 Hz, 4H); MS (ES, m/z): [M+1]=527.25.

Example 141: 4-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}butanoic Acid (I-148)

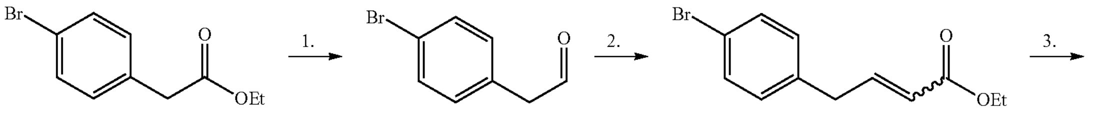

148a 148b 148c

-continued

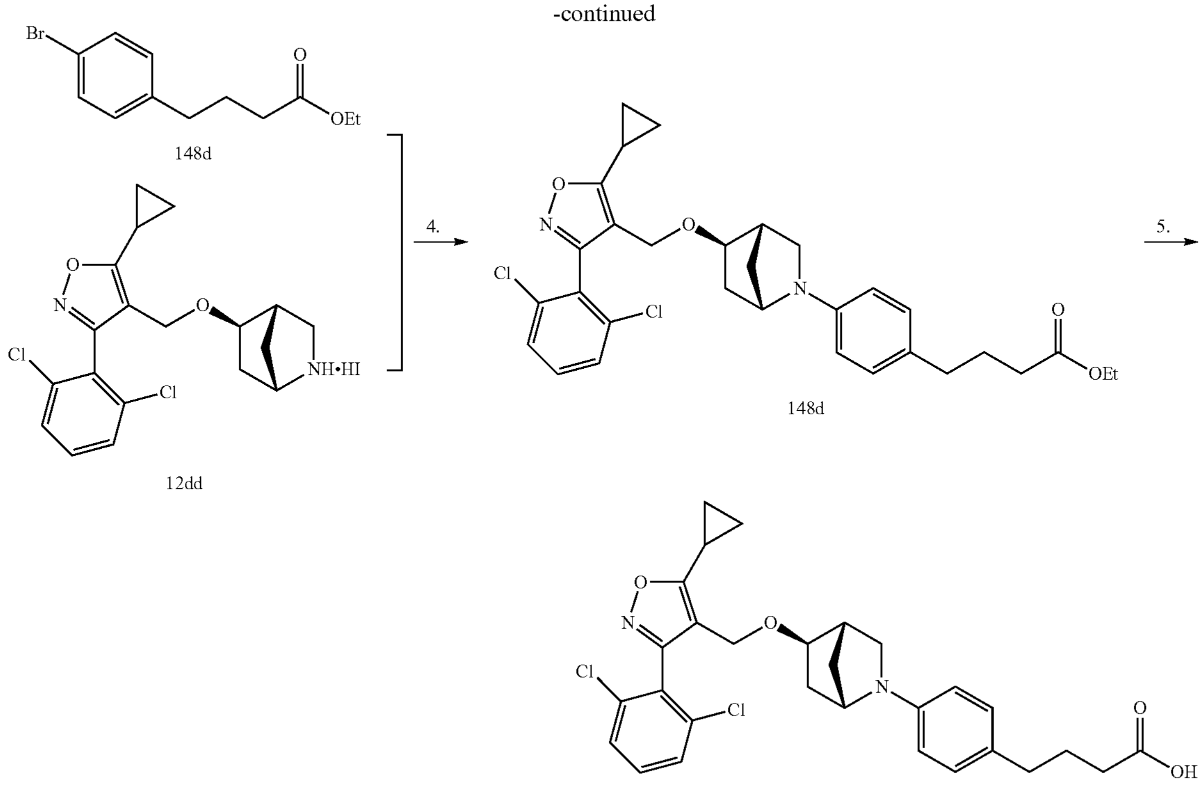

148d

12dd

148d

I-148

Step 1

To a solution of ethyl 2-(4-bromophenyl)acetate 148a (2.0 g, 8.22 mmol) in DCM (3 mL) cooled at −78° C., was added slowly a 1M solution of DIBAL-H in dichloromethane (8.63 mL, 8.63 mmol) over a period of 20 minutes. The mixture was stirred at −78° C., for 1 h. The reaction was quenched by the dropwise addition of methanol (1 mL), followed by water (1 mL) and then a 10% HCl aqueous solution (2 mL). The aqueous mixture was warmed to 0° C., stirred for 10 minutes, diluted with dichloromethane (50 mL), dried over $MgSO_4$ and filtered. Removal of solvent provided crude 2-(4-Bromophenyl)acetaldehyde 148b (1.63 g) as a clear oil, which was used as such in the next step.

Step 2

To a solution of 2-(4-bromophenyl)acetaldehyde 148b (1.63 g, 8.18 mmol) in DCM (20 mL) was added a solution of ethyl 2-(triphenylphosphoranylidene)acetate (2.84 g, 8.18 mmol) in DCM (10 mL) at 0° C. The mixture was stirred overnight while the temperature was slowly warmed up to RT. Solvent was removed and the residue was purified by silica gel chromatography eluting with 10% EtOAc in hexanes to give ethyl 4-(4-bromophenyl)but-2-enoate 148c (1.38 g) in a mixture of E and Z isomers as clear oil.

Step 3

Ethyl 4-(4-bromophenyl)but-2-enoate (1.38 g, 5.12 mmol) was dissolved in MeOH (20 mL) and cooled to 0° C. Cobalt (II) chloride hexahydrate (0.121 g, 0.512 mmol) was added followed by $NaBH_4$ (0.385 g, 10.2 mmol). The resulting mixture was stirred for 16 h while it was slowly warmed to RT. The reaction was quenched with ice, and the mixture was partitioned between water and EtOAc. The organic layer was washed with brine, dried with $MgSO_4$, filtered and concentrated in vacuo. The residue was purified by silica gel column chromatography eluting with 10% EtOAc in hexanes to afford ethyl 4-(4-bromophenyl)butanoate 148d (1.2 g, 86.9%) as a clear oil.

Step 4

4-(((1S,4S,5R)-2-Azabicyclo[2.2.1]heptan-5-yloxy)methyl)-5-cyclopropyl-3-(2,6-dichlorophenyl)isoxazole hydroiodide salt 12dd (120 mg, 0.2366 mmol) and ethyl 4-(4-bromophenyl)butanoate 148d (117 mg, 0.432 mmol) were mixed in toluene (3 mL). RuPhos (53.6 mg, 0.115 mmol) and RuPhos-Pd-precatalyst-3rd Generation (48.1 mg, 57.6 mmol) were added, followed by $Cs_2CO_3$ (234 mg, 0.720 mmol). The resulting mixture was heated at 110° C., under $N_2$ for 16 hours. After cooling to room temperature, the mixture was diluted with EtOAc, washed with water and brine. The organic layer was dried with $MgSO_4$, filtered and concentrated. The residue was purified by silica gel column chromatography (30-50% EtOAc in hexanes) to afford Ethyl 4-(4-((1S,4S,5R)-5-((5-cyclopropyl-3-(2,6-dichlorophenyl)isoxazol-4-yl)methoxy)-2-azabicyclo[2.2.1]heptan-2-yl)phenyl)butanoate 148e (32 mg) as a yellow oil.

Step 5

Ethyl 4-(4-((1S,4S,5R)-5-((5-cyclopropyl-3-(2,6-dichlorophenyl)isoxazol-4-yl)methoxy)-2-azabicyclo[2.2.1]heptan-2-yl)phenyl)butanoate 148e (32 mg, 0.056.1 mmol) was dissolved in THF (1.0 mL) and MeOH (1.0 mL). An aqueous solution of NaOH (112 μL, 0.112 mmol, 1.0 M in water) was added. The mixture was stirred at RT for 2 days. LCMS still showed some unreacted starting material. The mixture was heated at 60° C., for 4 hours. The reaction was complete. MeOH and THF were removed under vacuo. The residue was neutralized with a 1M HCl aqueous solution and purified with Prep-HPLC to give 4-(4-((1S,4S,5R)-5-((5-cyclopropyl-3-(2,6-dichlorophenyl)isoxazol-4-yl)methoxy)-2-azabicyclo[2.2.1]heptan-2-yl)phenyl)butanoic acid I-148 (9.4 mg) as a colorless solid. $^1$H NMR (400 MHz, $CD_3OD$): δ 77.53 (dd, J=6.6, 2.8 Hz, 1H), 7.51-7.44 (m, 2H), 7.20 (d, J=8.3 Hz, 2H), 6.93 (s, 2H), 4.37-4.28 (m, 3H), 4.17 (s, 1H), 3.57 (d, J=6.5 Hz, 1H), 3.48 (s, 1H), 2.91 (s, 1H), 2.61 (dd, J=14.2, 6.7 Hz, 4H), 2.33-2.21 (m, 4H), 1.93 (s, 1H), 1.92-1.82 (m, 3H), 1.74 (s, 2H), 1.34 (d, J=14.3 Hz, 1H), 1.16 (d, J=6.9 Hz, 4H); MS (ES, m/z): [M+1]=541.

Example 142: 1-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}cyclopropane-1-carboxylic Acid (I-149)

Step 1

To a 50 mL round-bottom flask was added 1-(4-bromophenyl)cyclopropane-1-carboxylic acid 149a (2 g, 8.30 mmol, 1.00 equiv.) and methanol (20 mL). Thionyl chloride (2.96 g, 24.88 mmol, 3.00 equiv.) was added dropwise with stirring at 0° C. The resulting mixture was stirred at 70° C., overnight. After cooling to room temperature, the reaction was quenched by the addition of water/ice. The aqueous mixture was extracted with ethyl acetate (50 mL×2). The combined organic extracts were washed with brine (50 mL×2, dried over anhydrous sodium sulfate, and concentrated under vacuum. The crude product was purified by Flash-Prep-HPLC eluting with EA/PE (from 0% to 10% within 20 min) to give methyl 1-(4-bromophenyl)cyclopropane-1-carboxylate 149b (1.7 g, 80%) as colorless oil.

Step 2

To a 50 mL round-bottom flask was added methyl 1-(4-bromophenyl)cyclopropane-1-carboxylate 149b (200 mg, 0.78 mmol, 2.4 equiv.), toluene (10 mL), and (1S,4S,5R)-

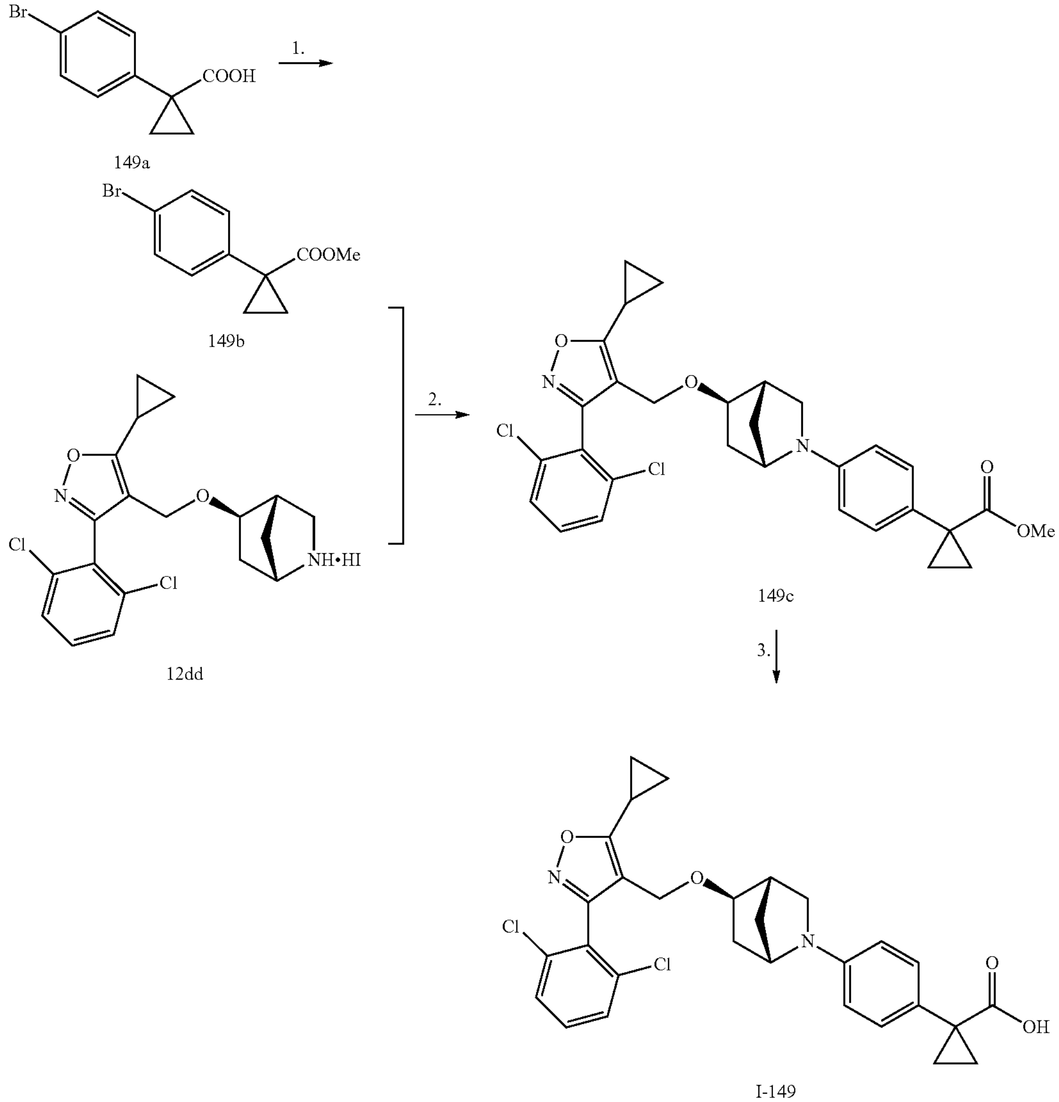

149a

149b

12dd

149c

I-149

5-[[5-cyclopropyl-3-(2,6-dichlorophenyl)-1,2-oxazol-4-yl]methoxy]-2-azabicyclo[2.2.1]heptane hydroiodide salt 12dd (164 mg, 0.3233 mmol, 1.0 equiv.), Rh-Phos-Precatalyst (50 mg, 0.62 equiv). Rh-Phos (92 mg, 0.62 equiv.), and $Cs_2CO_3$ (352 mg, 1.08 mmol, 3.3 equiv). The resulting mixture was stirred at 110° C., overnight. The mixture was concentrated under vacuum. The residue was purified by silica gel column chromatography eluting with ethyl acetate/petroleum ether (1:5). Removal of solvents gave methyl 1-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclopropane-1-carboxylate 149c (50 mg, 27.5%) as a light yellow solid.

Step 3

To a 50 mL round bottom flask purged with and maintained under an inert atmosphere of nitrogen was added methyl 1-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclopropane-1-carboxylate 149c (90 mg, 0.16 mmol, 1.00 equiv.), methanol (2 mL), LiOH (80 mg, 3.34 mmol, 10.00 equiv.), and water (0.2 mL). The resulting mixture was stirred at 50° C., overnight. The mixture was diluted with 10 mL of water, and the pH value of the solution was adjusted to 6 using a 1M hydrogen chloride aqueous solution. The aqueous mixture was extracted with ethyl acetate (50 mL×2), the combined organic extracts were washed with brine (50 mL×2), dried over anhydrous sodium sulfate, and concentrated under vacuum. The crude product was purified by Prep-HPLC using the following conditions: Column, XBridge Prep OBD C18 Column, 19*250 mm, 5 um, mobile phase, Water (0.05% TFA) and ACN (65.0% ACN up to 73.0% in 10 min); Detector, UV 254 nm. After purification 1-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclopropane-1-carboxylic Acid I-149 (16.9 mg, 19%) was obtained as an off-white solid. $^1H$ NMR (300 MHz, $CD_3OD$): δ 7.59-7.37 (m, 3H), 7.24-7.10 (m, 2H), 6.55-6.45 (m, 2H), 4.38-4.22 (m, 2H), 4.02 (d, J=2.8 Hz, 1H), 3.40 (td. J=9.2, 8.4, 3.2 Hz, 2H), 2.56-2.41 (m, 2H), 2.35-2.19 (m, 1H), 1.77 (dd, J=13.2, 7.0 Hz, 1H), 1.63-1.48 (m, 4H), 1.34-1.07 (m, 7H); MS (ES, m/z): [M+1]=539.

Example 143: 1-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}cyclobutane-1-carboxylic Acid (I-150)

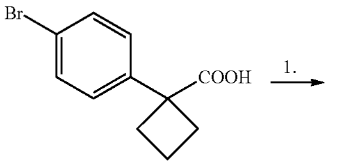

150a

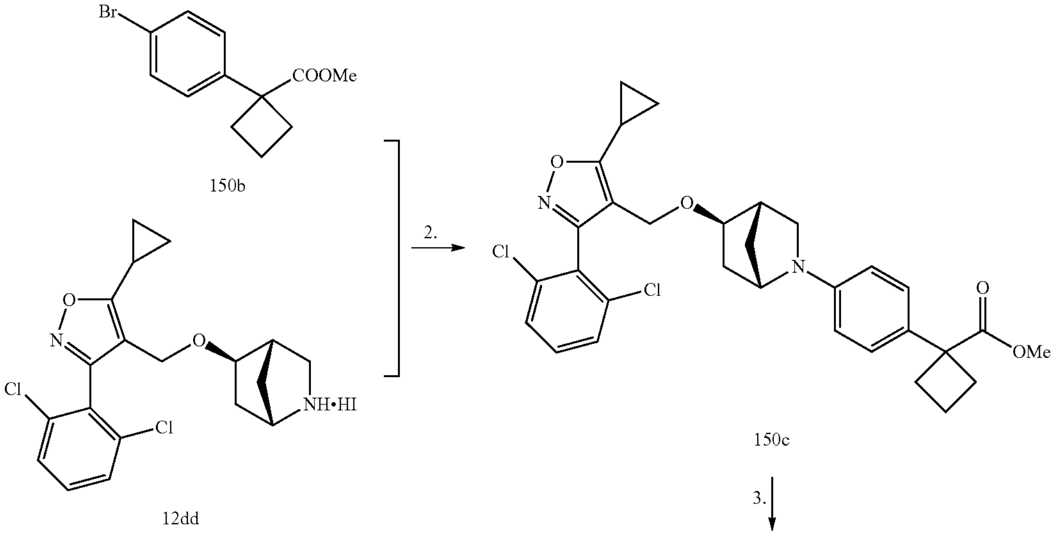

150b

12dd

150c

-continued

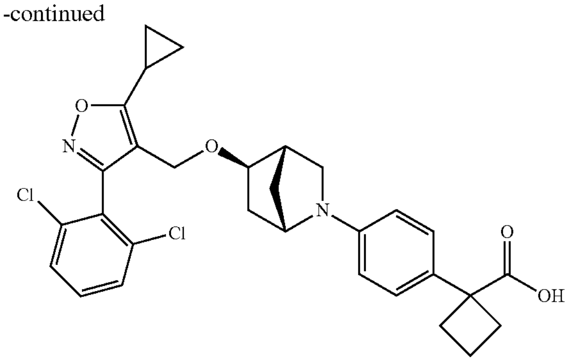

I-150

Step 1

To a 100 mL round bottom flask purged with and maintained under an inert atmosphere of nitrogen was added 1-(4-bromophenyl)cyclobutane-1-carboxylic Acid 150a (2 g, 7.84 mmol, 1.00 equiv.), methanol (20 mL). Thionyl chloride (2.78 g, 3.00 equiv.) was added dropwise. The resulting mixture was stirred at 70° C., overnight. Upon cooling to room temperature, the reaction was quenched by the addition of 20 mL of water/ice. The aqueous mixture was extracted with ethyl acetate (100 mL×2). The combined organic extracts were washed with brine (20 mL×2), dried over anhydrous sodium sulfate, and concentrated under vacuum to give methyl 1-(4-bromophenyl)cyclobutane-1-carboxylate 150b (2 g, 95%) as a light yellow oil.

Step 2

To a 25 mL round-bottom flask purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.3943 mmol, 1.00 equiv.), Tol (10 mL), methyl 1-(4-bromophenyl)cyclobutane-1-carboxylate 150b (212 mg, 0.79 mmol, 2.0 equiv.), Ru-Phos-Precatalyst (89 mg, 0.10 mmol, 0.25 equiv.), RuPhos (89 mg), and $Cs_2CO_3$ (516 mg, 1.58 mmol, 4.00 equiv.). The resulting mixture was stirred at 110° C., overnight, and concentrated under vacuum. The residue was purified by silica gel column chromatography eluting with ethyl acetate/petroleum ether (1/5) to afford methyl 1-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclobutane-1-carboxylate 150c (140 mg, 63%) as a light yellow oil.

Step 3

To a 25 mL round bottom flask was added methyl 1-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclobutane-1-carboxylate 150c (140 mg, 0.25 mmol, 1.00 equiv.), methanol (2 mL), LiOH (98 mg, 4.09 mmol, 10.00 equiv), and water (0.2 mL). The resulting mixture was stirred for at 50° C., for 2 h. After cooling to room temperature, the mixture was diluted with 10 mL of water, the pH value of the solution was adjusted to 7 using a 1M hydrogen chloride aqueous solution. The aqueous mixture was extracted with ethyl acetate (50 mL×2), the combined organic extracts were washed with brine (10 mL×3), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (58.0% ACN up to 74.0% in 8 min); Detector, UV 254 nm. After purification 1-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclobutane-1-carboxylic acid I-150 (53.9 mg, 39%) as an off-white solid. $^1H$ NMR (300 MHz, DMSO-$d_6$): δ 7.70-7.46 (m, 3H), 7.02 (d, J=8.5 Hz, 2H), 6.41 (d, J=8.4 Hz, 2H), 4.23 (s, 2H), 3.40-3.22 (m, 3H), 2.62 (ddd, J=11.3, 8.5, 5.6 Hz, 2H), 2.42-2.20 (m, 5H), 1.91-1.60 (m, 3H), 1.48-1.31 (m, 2H), 1.10 (ddt, J=14.4, 5.1, 2.7 Hz, 5H); MS (ES, m/z): [M+1]=553.25.

Example 144: 3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}cyclobutane-1-carboxylic Acid (I-151)

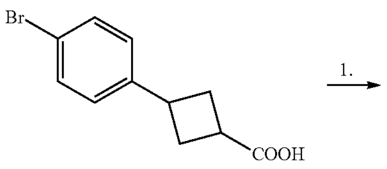

151a

-continued

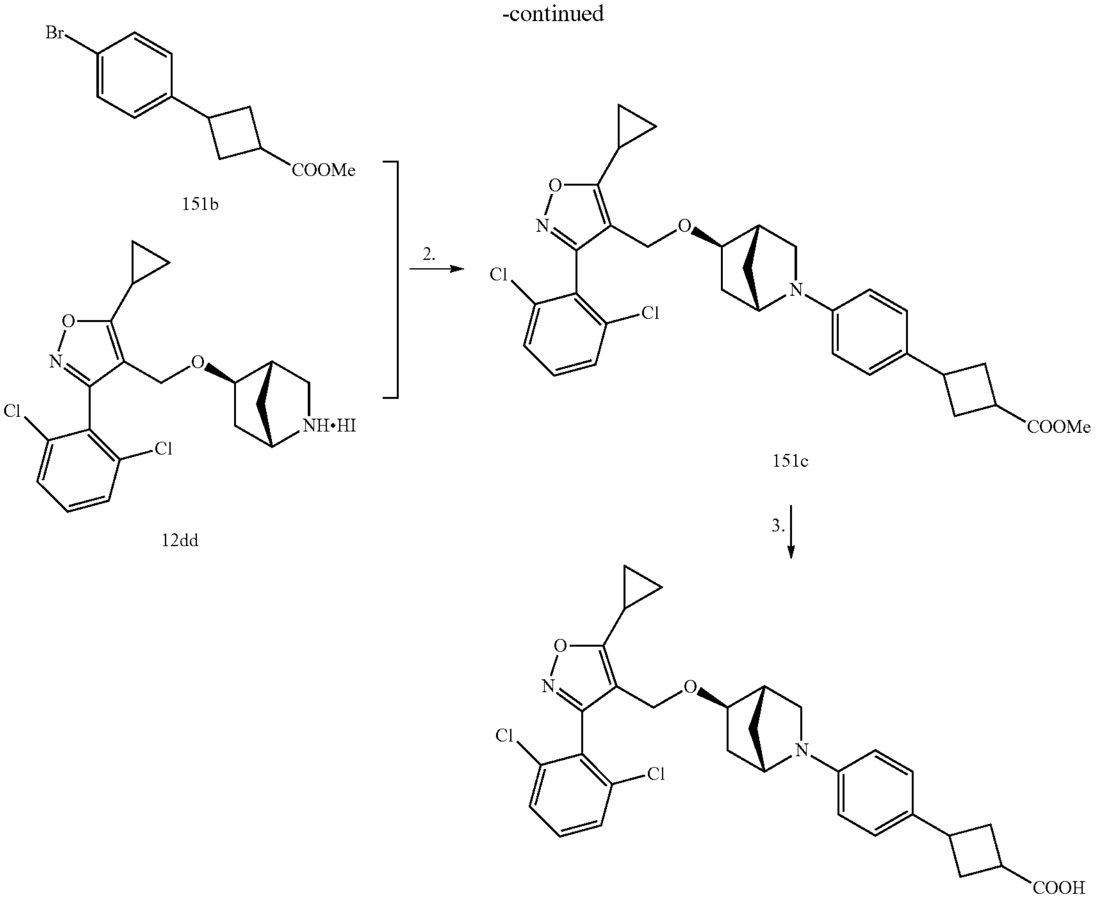

151b

12dd

151c

I-151

Step 1

To a 50 mL round-bottom flask was added 3-(4-bromophenyl)cyclobutane-1-carboxylic acid 151a (300 mg, 1.18 mmol, 1.00 equiv.) and methanol (8 mL). Thionyl chloride (418 mg, 3.00 equiv.) was added dropwise with stirring at 0° C. The resulting mixture was stirred at 70° C., overnight. After cooling to room temperature, water/ice was added to quench the reaction. The aqueous mixture was extracted with ethyl acetate (50 mL×2). The combined organic extracts were washed with brine (30 mL×2), dried over anhydrous sodium sulfate, and concentrated under vacuum. The residue was purified by silica gel column chromatography, eluting with ethyl acetate/petroleum ether (1:10) to give methyl 3-(4-bromophenyl)cyclobutane-1-carboxylate 151b (300 mg, 95%) as a colorless oil.

Step 2

To a 100 mL round-bottom flask purged with and maintained under an inert atmosphere of nitrogen, was added methyl 3-(4-bromophenyl)cyclobutane-1-carboxylate 151b (255 mg, 0.95 mmol, 1.60 equiv), (1S,4S,5R)-5-[5-cyclopropyl-3-(2,6-dichlorophenyl)-1,2-oxazol-4-yl]methoxy-2-azabicyclo[2.2.1]heptane hydroiodide salt 12dd (300 mg, 0.5915 mmol, 1.00 equiv.), Ru-Phos-Precatalyst (73 mg, 0.26 equiv), Ru-Phos (136 mg), $Cs_2CO_3$ (522 mg, 1.60 mmol, 2.7 equiv.), and toluene (10 mL). The resulting mixture was stirred at 110° C., overnight. The mixture was concentrated under vacuum and the residue was purified by silica gel column chromatography eluting with ethyl acetate/petroleum ether (1:5) to provide methyl 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclobutane-1-carboxylate 151c (107 mg, 32%) as an off-white solid.

Step 3

To a 50 mL round-bottom flask was added methyl 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclobutane-1-carboxylate 151c (107 mg, 0.19 mmol, 1.00 equiv.), methanol (2 mL), LiOH (90 mg, 3.76 mmol, 10.00 equiv) and water (0.2 mL). The resulting mixture was stirred at 35° C., overnight. The mixture was diluted with 10 mL of water. The pH value of the solution was adjusted to 6 using a 1M hydrogen chloride aqueous solution. The mixture was extracted with ethyl acetate (50 mL×2). The combined organic extracts were washed with brine (50 mL×2), dried over anhydrous sodium sulfate and concentrated under vacuum. The crude product was purified by Prep-HPLC using the following conditions: Column, XBridge Prep OBD C18 Column, 19*250 mm, 5 um; mobile phase. Water (0.05% TFA) and ACN (65.0% ACN up to 71.0% in 8 min); Detector, UV 254 nm. After the purification 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]cyclobutane-1-carboxylic Acid I-151 (40.4 mg, 39%) as an off-white solid. $^{1}$H NMR (300 MHz. $CD_3OD$): δ 7.63-7.38 (m, 3H), 7.09 (m, J=8.7, 2H), 6.56 (s, J=8.1 Hz, 2H), 4.28 (s, 2H), 4.01 (s, 1H), 3.39 (ddd, J=14.9, 8.8, 4.8 Hz, 3H), 3.07 (ddd, J=10.0, 8.0, 2.0 Hz, 1H), 2.65-2.37 (m, 4H), 2.36-2.16 (m, 3H), 1.82 (dd, J=13.6, 7.0 Hz, 1H), 1.58 (s, 2H), 1.15 (d, J=6.8 Hz, 5H); MS (ES, m/z): [M+1]=553.

Example 145: 3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}butanoic Acid (I-152)

showed about 50% conversion. Reaction was allowed to continue at 110° C., for 2 more days. TLC showed the reaction was complete. The mixture was concentrated to dryness and purified by silica gel column chromatography eluting with 10% EtOAc in hexanes to afford ethyl 3-(4-bromo-3-fluorophenyl)but-2-enoate 152b (1.02 g) a mixture of E and Z isomers as a clear oil.

Step 2

Ethyl 3-(4-bromo-3-fluorophenyl)but-2-enoate 152b (E and Z isomer mixture) (1.02 g, 3.55 mmol) was dissolved in MeOH (10 mL) and cooled to 0° C. Cobalt(II) chloride

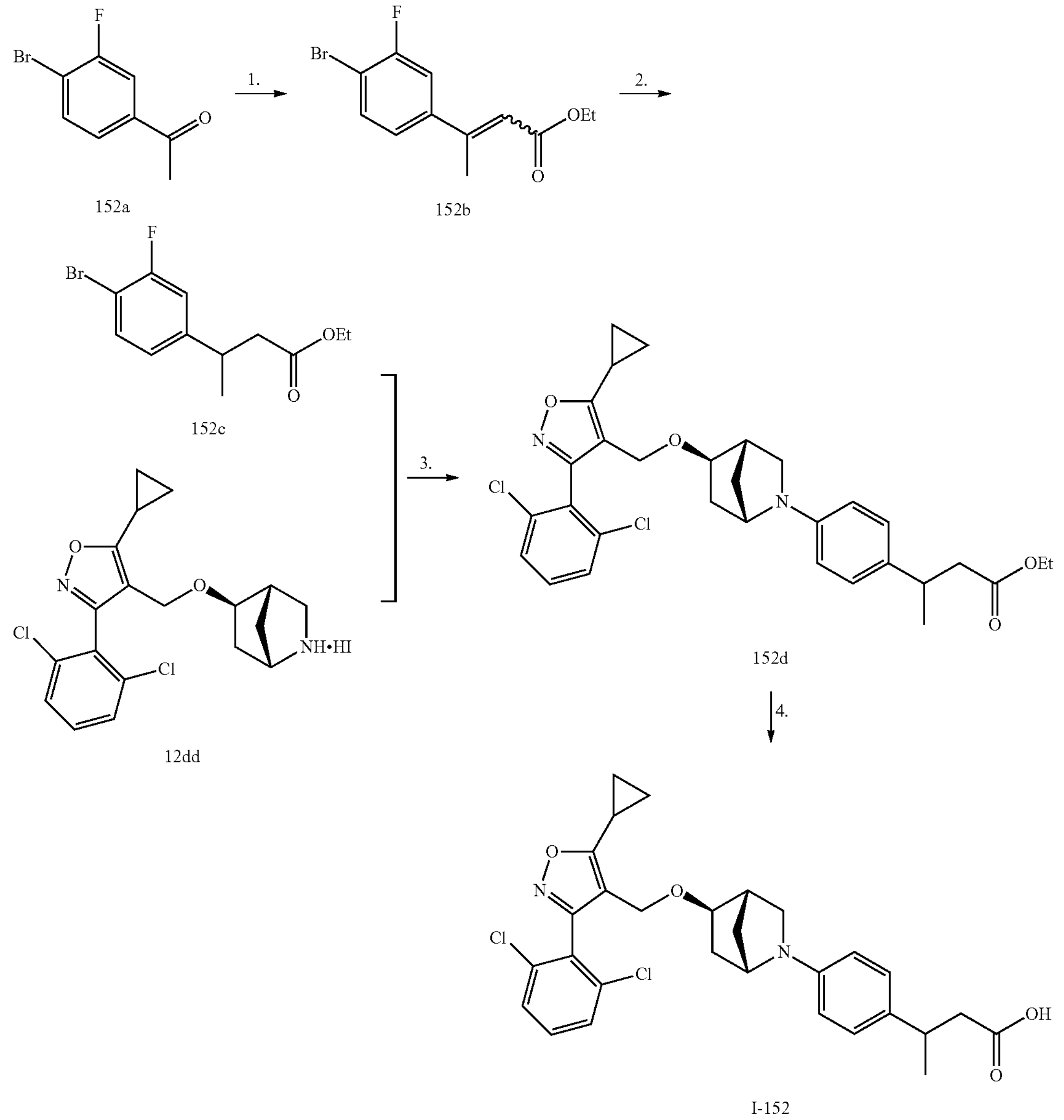

152a 152b 152c 12dd 152d I-152

Step 1

1-(4-Bromo-3-fluorophenyl)ethanone 152a (1.0 g, 4.60 mmol) and ethyl 2-(triphenylphosphoranylidene)acetate (1.60 g, 4.60 mmol) were dissolved in toluene (5.0 mL). The mixture was heated at 110° C., overnight with stirring. TLC hexahydrate (84.4 mg, 0.355 mmol) was added and followed by $NaBH_4$ (268 mg, 7.10 mmol). The mixture was stirred at RT overnight, quenched with the addition of ice, and partitioned between water and EtOAc. The organic layer was washed with brine, dried over $MgSO_4$, and concentrated. The residue was purified by silica gel column chromatography eluting with 10% EtOAc in hexanes to provide ethyl 3-(4-bromo-3-fluorophenyl)butanoate 152c (0.85 g) as a clear oil.

Step 3

4-(((1S,4S,5R)-2-azabicyclo[2.2.1]heptan-5-yloxy) methyl)-5-cyclopropyl-3-(2,6-dichlorophenyl)isoxazole hydroiodide salt 12dd (150 mg, 0.2957 mmol) and ethyl 3-(4-bromo-3-fluorophenyl)butanoate 152c (155 mg, 0.539 mmol) were mixed in toluene (3.0 mL). RuPhos (67.1 mg, 0.144 mmol) and RuPhos-Pd-precatalyst-3rd Gen (60.2 mg, 72.0 mmol) were added, followed by $Cs_2CO$ (293 mg, 900 mmol). The mixture was heated at 110° C., under $N_2$ for 2 days. After cooling to RT, EtOAc (50 mL) was added, the mixture was partitioned between water and EtOAc. The organic layer was separated, washed with brine, dried over $MgSO_4$, filtered and concentrated. The residue was purified by silica gel column chromatography eluting with 30-40% EtOAc in hexanes to give ethyl 3-(4-((1S,4S,5R)-5-((5-cyclopropyl-3-(2,6-dichlorophenyl)isoxazol-4-yl) methoxy)-2-azabicyclo[2.2.1]heptan-2-yl)-3-fluorophenyl) butanoate 152d (46.6 mg) as a light brown oil. MS (ES, m/z): [M+1]=587.

Step 4

Ethyl 3-(4-((1S,4S,5R)-5-((5-cyclopropyl-3-(2,6-dichlorophenyl)isoxazol-4-yl)methoxy)-2-azabicyclo[2.2.1]heptan-2-yl)-3-fluorophenyl)butanoate (46.4 mg, 0.0789 mmol) was dissolved in MeOH (1.0 mL) and THF (1.0 mL). A 1.0 M NaOH aqueous solution (157 μL, 0.157 mmol) was added. The mixture was heated at 50° C., overnight. LCMS showed the reaction was complete. MeOH and THF were removed in vacuo. The residue was neutralized with 1M HCl aqueous solution and purified by prep-HPLC to afford 3-(4-((1S,4S,5R)-5-((5-cyclopropyl-3-(2,6-dichlorophenyl) isoxazol-4-yl)methoxy)-2-azabicyclo[2.2.1]heptan-2-yl)-3-fluorophenyl)butanoic acid I-152 (30.0 mg) as a white solid. $^1$H NMR (400 MHz, $CD_3OD$): δ 7.56-7.50 (m, 1H), 7.50-7.44 (m, 2H), 6.95 (dt, J=9.1, 2.5 Hz, 2H), 6.76 (t, J=8.9 Hz, 1H), 4.30 (s, 2H), 4.10 (s, 1H), 3.54-3.44 (m, 2H), 3.15 (dd, J=14.4, 7.2 Hz, 1H), 2.71 (dd, J=10.1, 2.6 Hz, 1H), 2.51 (dt, J=9.3, 4.6 Hz, 2H), 2.46 (s, 1H), 2.30-2.20 (m, 1H), 1.94 (dd, J=14.1, 6.5 Hz, 1H), 1.61 (s, 2H), 1.30 (m, 1H), 1.25 (d, J=7.0 Hz, 3H), 1.16 (d, J=7.1 Hz, 4H); MS (ES, m/z): [M+1]=559.

Example 146: 2-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}acetic Acid (I-153)

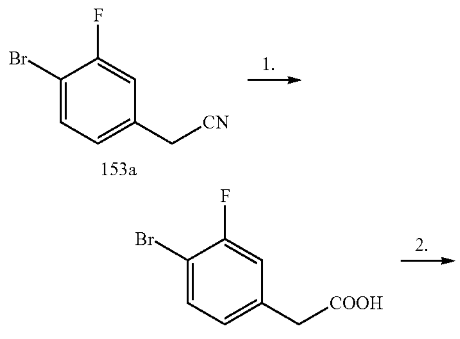

153a

153b

-continued

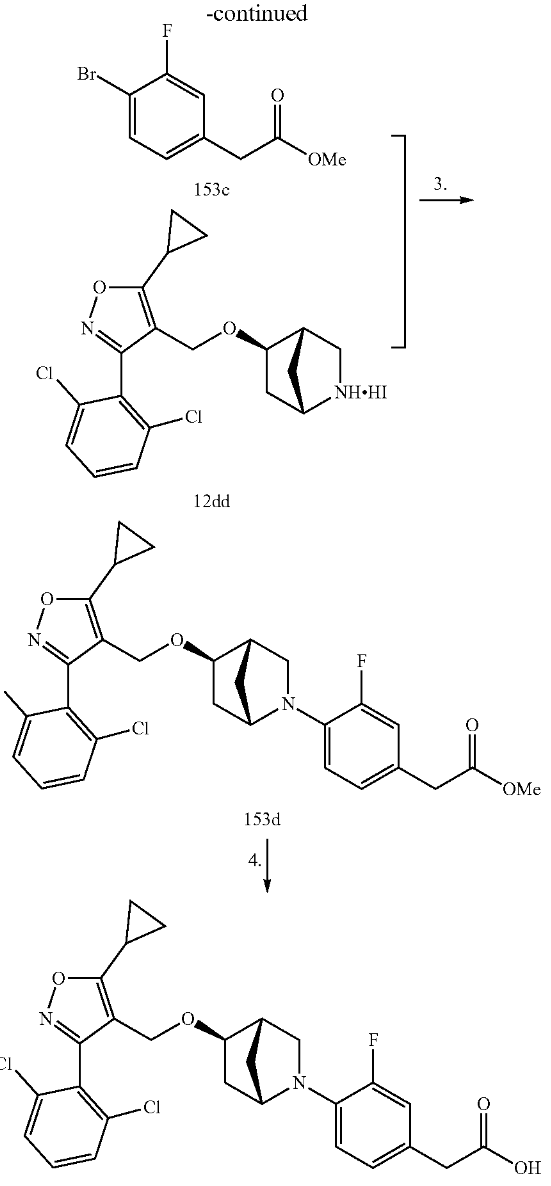

153c

12dd

153d

I-153

Step 1

To a 100 mL round bottom flask was added 2-(4-bromo-3-fluorophenyl)acetonitrile 153a (3.9 g, 18.22 mmol, 1.00 equiv.), water (3.75 mL), sulfuric acid (3.75 mL), and AcOH (3.75 mL). The resulting mixture was stirred at 105° C., for 2 h. After cooling to room temperature, solids were collected by filtration to give 2-(4-bromo-3-fluorophenyl)acetic acid 153b (4.05 g, 95%) as a white solid.

Step 2

To a 100 mL round-bottom flask was added 2-(4-bromo-3-fluorophenyl)acetic acid 153b (2 g, 8.58 mmol, 1.00 equiv.) and methanol (30 mL). Thionyl chloride (3 g) was added dropwise with stirring at 0° C. The resulting mixture was stirred at 50° C., for 4 h. After cooling to room temperature the reaction was quenched by the addition of water/ice. The aqueous mixture was extracted with ethyl acetate (200 mL×2); the combined organic extracts were washed with brine (400 mL), dried over anhydrous sodium sulfate, and concentrated under vacuum. The residue was purified by silica gel column chromatography eluting with ethyl acetate/petroleum ether (1:10) to give methyl 2-(4-bromo-3-fluorophenyl)acetate 153c (1.79 g, 84%) as a colorless oil.

Step 3

To a 5 mL sealed tube purged with and maintained under an inert atmosphere of nitrogen was added a solution of methyl 2-(4-bromo-3-fluorophenyl)acetate 153c (260 mg, 1.05 mmol, 2.66 equiv.) in toluene (3 mL), (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (200 mg, 0.3943 mmol, 1.00 equiv), $Cs_2CO_3$ (345 mg, 1.06 mmol, 2.69 equiv), and Ru-phos-precatalyst (89.9 mg, 0.11 mmol, 0.28 equiv). The resulting mixture was stirred at 110° C., overnight. The reaction mixture was cooled to room temperature, and added with 10 mL of water. The aqueous mixture was extracted with ethyl acetate (50 mL×2). The combined organic extracts were washed with brine (50 mL×2), dried over anhydrous sodium sulfate and concentrated under vacuum. The residue was purified by silica gel column chromatography eluting with ethyl acetate/petroleum ether (1:2) to yield methyl 2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]acetate 153d (30 mg, 14%) as yellow oil.

Step 4

To a 25 mL round-bottom flask was added a solution of methyl 2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]acetate 153d (150 mg, 0.28 mmol, 1.00 equiv.) in methanol (2.5 mL), and LiOH (115 mg, 4.80 mmol, 10.00 equiv.) in water (0.2 mL). The resulting mixture was stirred at 40° C., overnight. 10 mL of water was added, the pH value of the solution was adjusted to 3 using a 1M hydrogen chloride aqueous solution. The aqueous mixture was extracted with ethyl acetate (100 mL×2); and the combined organic extracts were washed with brine (200 mL), dried over anhydrous sodium sulfate and concentrated under vacuum. The crude product was purified by Prep-HPLC using the following conditions (mobile phase, Water (0.05% TFA) and ACN (hold 57.0% ACN in 9 min); Detector, UV 254 nm. After purification 2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]acetic acid I-153 (50.8 mg, 35%) was obtained as a colorless solid. $^1$H NMR (300 MHz, $CD_3OD$): δ 7.60-7.41 (m, 3H), 7.02-6.88 (m, 2H), 6.69 (t, J=8.4 Hz, 1H), 4.31 (s, 2H), 4.09 (s, 1H), 3.48 (d, J=17.1 Hz, 4H), 2.65 (d, J=8.5 Hz, 1H), 2.43 (s, 1H), 2.27 (p, J=6.8 Hz, 1H), 1.91 (dd, J=13.8, 6.8 Hz, 1H), 1.59 (s, 2H), 1.34-1.14 (m, 6H); MS (ES, m/z): [M+1]=531.15.

Example 147: 3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}propanoic Acid (I-154)

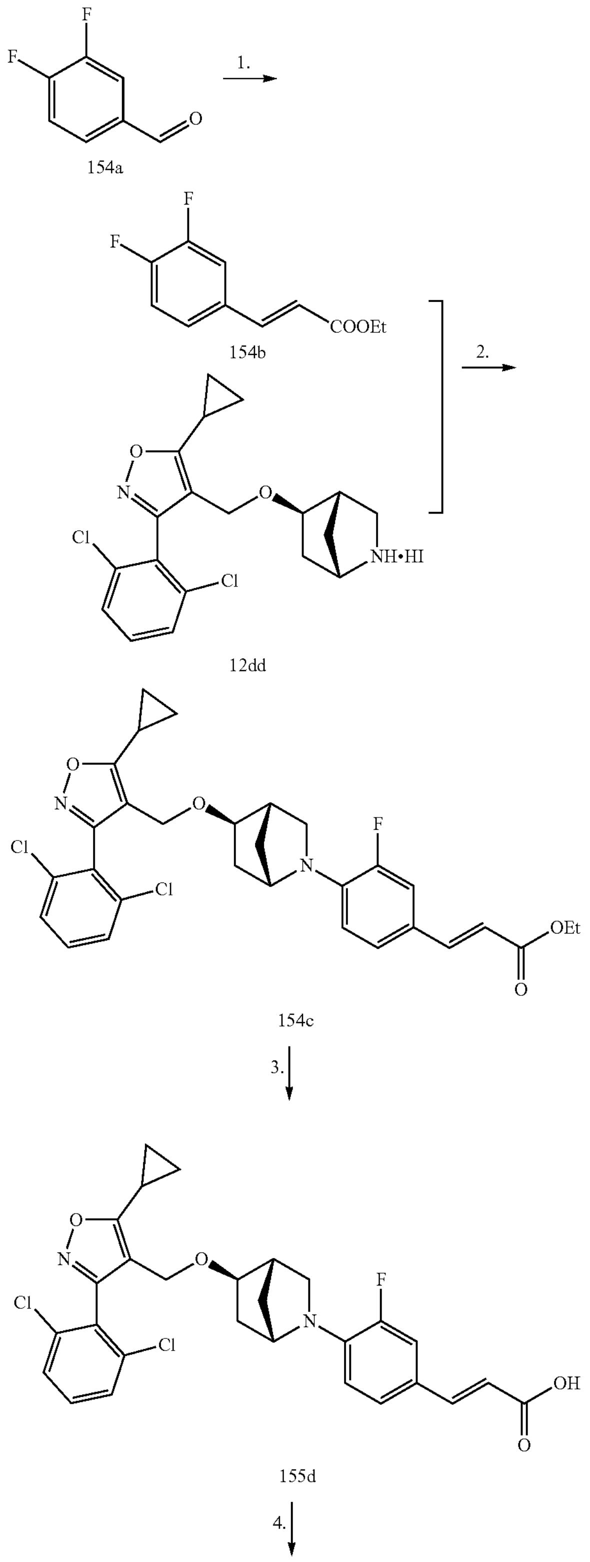

154a

154b

12dd

154c

155d

-continued

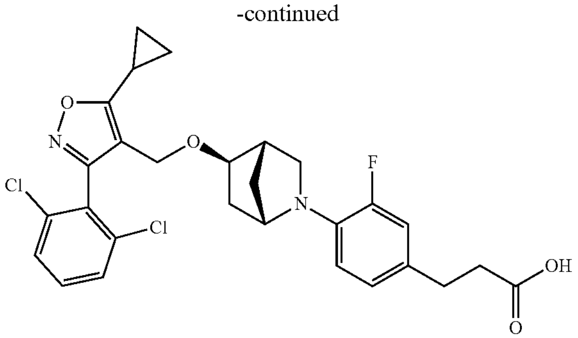

I-154

Step 1

To a 250 mL round-bottom flask was added 3,4-difluorobenzaldehyde 154a (10 g, 70.37 mmol, 1.00 equiv.), Toluene (91 mL), and ethyl (triphenylphosphoranylidene) acetate (29.4 g, 84.39 mmol, 1.20 equiv.). The resulting mixture was stirred at 80° C., for 1 h. The reaction was quenched by the addition of 20 mL of water upon cooling to room temperature. The aqueous mixture was extracted with ethyl acetate (200 mL×3). The combined organic extracts were washed with brine, dried over anhydrous sodium sulfate, and concentrated under vacuum. The residue was purified by silica gel column chromatography eluting with ethyl acetate/petroleum ether (0%-3%) to give ethyl (2E)-3-(3,4-difluorophenyl)prop-2-enoate 154b (10 g, 67%) as a colorless oil.

Step 2

To a 250 mL round-bottom flask purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (2 g, 3.934 mmol, 1.00 equiv.), ethyl 3-(3,4-difluorophenyl)prop-2-enoate 154b (2.2 g, 10.37 mmol, 2.64 equiv), potassium carbonate (1.6 g, 11.58 mmol, 2.94 equiv.), and DMSO (40 mL). The resulting mixture was stirred at 130° C., overnight. After cooling to room temperature 200 mL of EA was added, the mixture was washed with brine (50 mL×3), dried over sodium sulfate and concentrated under vacuum. The residue was purified by silica gel column chromatography eluting with ethyl acetate/petroleum ether (1/5) to afford ethyl (2E)-3-[4-[(1S,4S,5R)-5-[[5-cyclopropyl-3-(2,6-dichlorophenyl)-1,2-oxazol-4-yl] methoxy]-2-azabicyclo[2.2.1]heptan-2-yl]-3-fluorophenyl] prop-2-enoate 154c (1.55 g, 71.6%) as a light yellow solid.

Step 3

To a 25 mL round-bottom flask was added ethyl (2E)-3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]prop-2-enoate 154c (330 mg, 0.6 mmol, 1.00 equiv.), LiOH (240 mg, 5.7 mmol, 10.00 equiv.), ethanol (30 mL), and water (3 mL). The resulting mixture was stirred at 60° C. for 1 h. After cooling to room temperature, 100 mL of ethyl acetate was added, the pH value of the solution was adjusted to 7 using a hydrogen chloride aqueous solution (10% v/v aq). The mixture was separated, and the organic layer was washed with brine (10 mL×3), dried over sodium sulfate and concentrated under vacuum. The residue was purified by silica gel column chromatography eluting with dichloromethane/methanol (13/1) to provide (2E)-3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]prop-2-enoic acid 154d (300 mg, 96%) as a light yellow solid.

Step 4

To a 250 mL round-bottom flask was added (2E)-3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]prop-2-enoic acid 154d (3.6 g, 6.62 mmol, 1.00 equiv.), ethanol (60 mL), and $N_2H_4$ (2.64 g, 82.37 mmol, 8.00 equiv.). The resulting mixture was stirred at 80° C., overnight (note: in the presence of air). The mixture was diluted with 100 mL of water. The pH value of the solution was adjusted to 6 using a 1M hydrogen chloride (1 M). The aqueous mixture was extracted with ethyl acetate (200 mL×3). The combined organic extracts were washed with brine (100 mL×2), dried over anhydrous sodium sulfate and concentrated under vacuum. The crude product was purified by HP-flash using the following conditions: Column, C18; mobile phase, Water (0.05% TFA) and ACN (53.0% ACN up to 73.0% in 8 min); Detector, UV 254 nm. After purification 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]propanoic acid I-154 (2.1 g, 58%) was obtained as a light yellow solid. $^1H$ NMR (400 MHz, $CD_3OD$): δ 7.59-7.44 (m, 3H), 6.89-6.80 (m, 2H), 6.55 (t, J=8.5 Hz, 1H), 4.30 (d, J=0.8 Hz, 2H), 4.02 (s, 1H), 3.53-3.39 (m, 2H), 2.80 (t, J=7.5 Hz, 2H), 2.59-2.47 (m, 3H), 2.39 (d, J=3.9 Hz, 1H), 2.27 (dq, J=8.7, 6.8 Hz, 1H), 1.95-1.85 (m, 1H), 1.54 (d, J=2.2 Hz, 2H), 1.28-1.14 (m, 5H); MS (ES, m/z): [M+1]=545.2.

Example 148: 3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorophenyl}propanoic Acid (I-155)

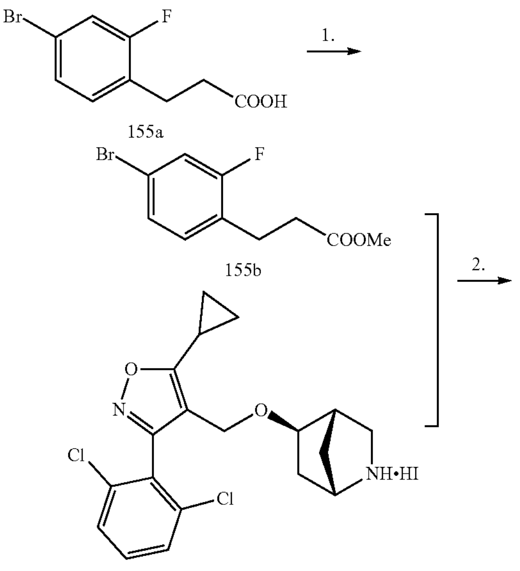

155a

155b

12dd

-continued

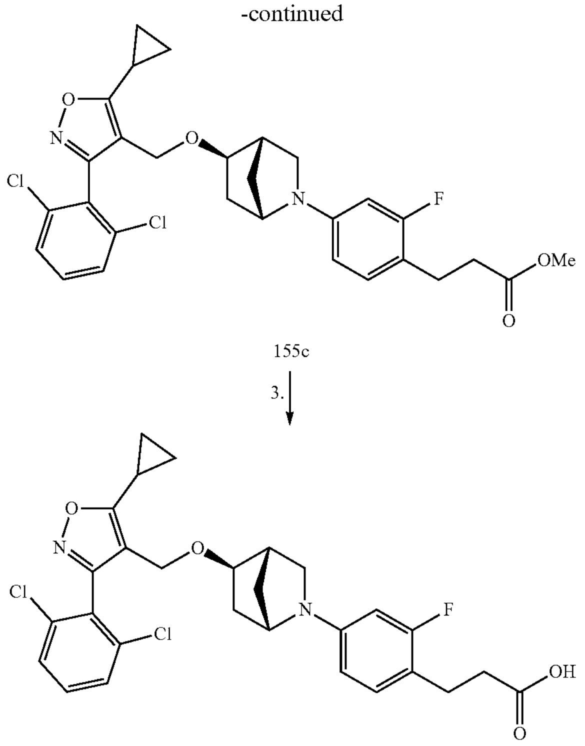

155c

I-155

Step 1

Acetyl chloride (5.0 mL) was added dropwise to methanol (50 mL) at 0° C., and stirred for another 0.5 h at the same temperature. 3-(4-Bromo-2-fluorophenyl)propanoic acid 155a (5.0 g) was added. The reaction mixture was allowed to reach room temperature and stirred for 3 h. The mixture was concentrated under reduced pressure and purified on Isco using 5-10% ethyl acetate in hexanes as eluents to give the methyl 3-(4-bromo-2-fluorophenyl)propanoate 155b (4.6 g) as an oil. $^1$H-NMR (400 MHz, DMSO-$d_6$): δ 7.48 (dd, J=9.8 & 1.9 Hz, 1H), 7.39-7.21 (m, 2H), 3.90-3.76 (m, 2H), 3.60 (s, 3H), 2.80 (t, J=7.5 Hz, 2H), 2.64 (t, J=7.5 Hz, 2H).

Step 2

A suspension of 4-(((1S,4S,5S)-2-azabicyclo[2.2.1]heptan-5-yloxy)methyl)-5-cyclopropyl-3-(2,6-dichlorophenyl) isoxazole hydrochloride 12dd (83 mg, 1 equiv.), methyl 3-(4-bromo-2-fluorophenyl)propanoate (78 mg, 1.5 equiv.), $Cs_2CO_3$ (163 mg, 2.5 equiv.), Ru-Phos (38 mg, 0.4 equiv.), and Ru-Phos-Pd (34 mg, 0.2 equiv.) in Toluene (2.0 mL) was heated under a nitrogen atmosphere at 110° C. for 16 h. The reaction mixture was cooled to RT and filtered through a pad of Celite. The filtrate was concentrated and purified on Isco silica gel column eluting with 20-30% ethyl acetate in hexanes to give methyl 3-(4-((1S,4S,5R)-5-((5-cyclopropyl-3-(2,6-dichlorophenyl)isoxazol-4-yl)methoxy)-2-azabicyclo[2.2.1]heptan-2-yl)-2-fluorophenyl)propanoate 155c (80 mg) and used as such in the next step. MS (ES, m/z): [M+1]=559.2.

Step 3

The above residue 155c (80 mg) was dissolved in methanol (5 mL) and treated with 1N-NaOH solution (300 ul) at 60° C., for 4 h. After cooling to RT, the mixture was neutralized with a 1N-HCl and concentrated under the reduced pressure. The residue was purified on Semi-prep HPLC using 40-95% acetonitrile in 30 min, method. The fractions corresponding to the desired product were lyophilized to give 3-(4-((1S,4S,5R)-5-((5-cyclopropyl-3-(2,6-dichlorophenyl)isoxazol-4-yl)methoxy)-2-azabicyclo[2.2.1]heptan-2-yl)-2-fluorophenyl)propanoic acid I-155 (20 mg). $^1$H NMR (400 MHz, DMSO-$d_6$): δ 7.76-7.44 (m, 3H), 6.99 (t, J=7.7 Hz, 1H), 6.33-6.08 (m, 2H), 4.24 (s, 2H), 3.99 (s, 1H), 3.36 (bs, 1H), 3.24 (d, J=8.1 Hz, 1H), 2.68-2.67 (m, 3H), 2.47-2.25 (m, 5H), 1.68-1.66 (m, 1H), 1.37 (d, J=10.7 Hz, 1H), 1.35 (d, J=10.8 Hz, 1H), 1.12-1.09 (m, 4H); MS (ES, m/z): [M+1]=545.32.

Example 149: 3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorophenyl}-2,2-dimethylpropanoic Acid (I-156)

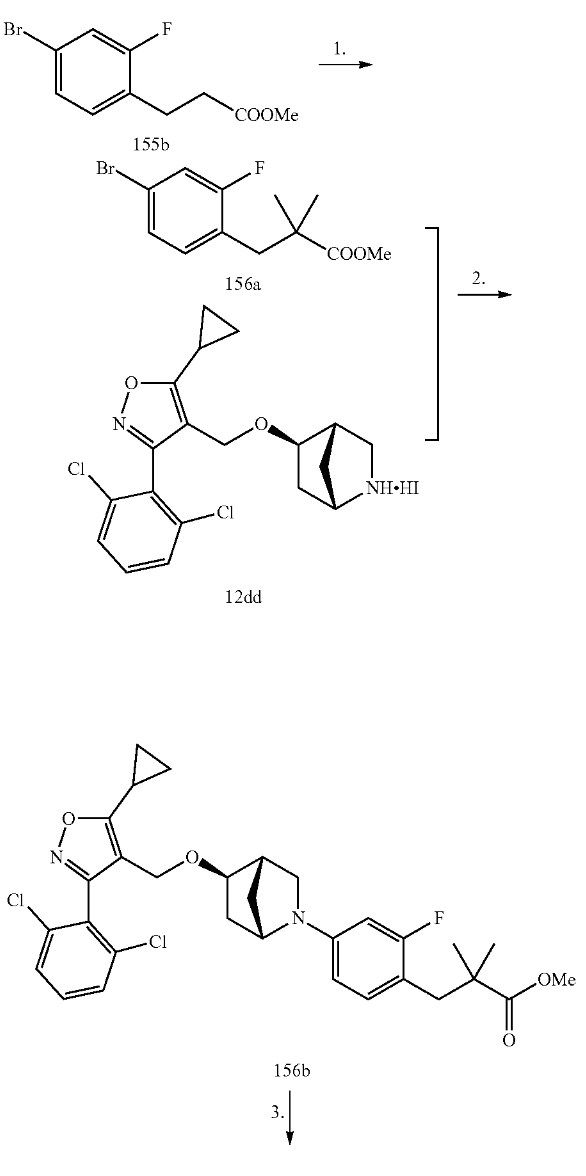

155b

156a

12dd

156b

-continued

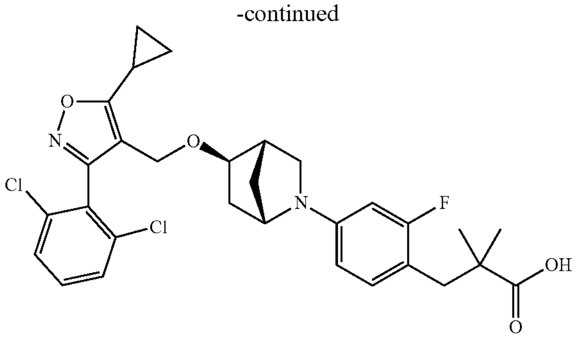

I-156

Step 1

A solution of methyl 3-(4-bromo-2-fluorophenyl)propanoate 155b (2.6 gm, 1 equiv.) in THF (50 mL) was added to a 2M solution of LDA in THF (8 mL) at −60° C., with stirring. The reaction mixture was stirred for 15 more min at the same temperature and then methyl iodide (3.45 mL, 2.75 equiv.) was added. Reaction was allowed to continue for 30 min at the same temperature. The mixture was poured into a 1M-HCl aqueous solution (150 mL) and extracted with ether (100 mL×2). The combined extracts were dried over $Na_2SO_4$ and concentrated under the reduced pressure to afford the crude mono-methylated product which was then subjected to a second methylation cycle as described above. The resulting residue was purified by flash chromatography using 5-10% ethyl acetate in hexanes as gradient to give methyl 3-(4-bromo-2-fluorophenyl)-2,2-dimethylpropanoate 156a (1.1 g) as an oil. $^1$H-NMR (400 MHz, DMSO-$d_6$): δ 7.36 (dd, J=8.2 & 3.1 Hz, 2H), 6.98-6.93 (m, 1H), 3.60 (s, 3H), 2.80 (d, J=2.0 Hz, 2H), 1.12 (s, 3H), 1.11 (s, 3H).

Step 2

A suspension of 4-(((1S,4S,5S)-2-azabicyclo[2.2.1]heptan-5-yloxy)methyl)-5-cyclopropyl-3-(2,6-dichlorophenyl) isoxazole hydrochloride 12dd (124.5 mg, 1 equiv.), methyl 3-(4-bromo-2-fluorophenyl)-2,2-dimethylpropanoate (130 mg, 1.5 equiv.), $Cs_2CO_3$ (245 mg, 2.5 equiv.), Ru-Phos (57 mg, 0.4 equiv.), and Ru-Phos-Pd (51 mg, 0.2 equiv.) in Toluene (4.0 mL) was heated under a nitrogen atmosphere at 110° C., for 16 h. The reaction mixture was cooled to RT and filtered through a pad of Celite. The filtrate was concentrated and purified on Isco silica gel column eluting with 15-20% ethyl acetate in hexanes to give the desired product 156b and used as such in the next step; MS (ES, m/z): [M+1]=587.35.

Step 3

The above residue 156b was dissolved in methanol (5 mL) and treated with a 1N NaOH aqueous solution (500 ul) and heated at 70° C., for 16 h. After cooling to RT, the mixture was neutralized with a 1N HCl aqueous solution and concentrated under the reduced pressure. The residue was purified on Semi-prep HPLC using 40-95% acetonitrile in 30 min, method. The fractions corresponding to the desired product were lyophilized to give 3-(4-((1S,4S,5R)-5-((5-cyclopropyl-3-(2,6-dichlorophenyl)isoxazol-4-yl) methoxy)-2-azabicyclo[2.2.1]heptan-2-yl)-2-fluorophenyl)-2,2-dimethylpropanoic acid I-156 (10 mg). $^1$H NMR (400 MHz, $CD_3OD$): δ 7.77-7.47 (m, 4H), 6.84 (t, J=8.7 Hz, 1H), 6.47 (d, J=8.4 Hz, 1H), 4.24 (s, 2H), 3.78 (s, 1H), 3.45 (d, J=6.0 Hz, 1H), 3.27 (dd, J=9.3 & 4.3 Hz, 1H), 2.70 (s, 2H), 2.62-2.50 (m, 2H), 2.35-2.32 (m, 2H), 1.92 (dd, J=13.1 & 6.6 Hz, 1H), 1.39 (dd, J=30.8 & 9.4 Hz. 2H), 1.15-1.04 (m, 10H); MS (ES, m/z): [M+1]=573.32.

Example 150: 4-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}butanoic Acid (I-157)

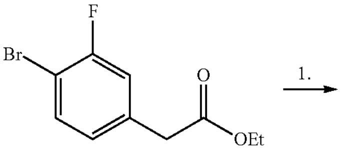

157a

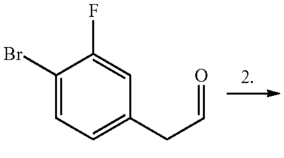

157b

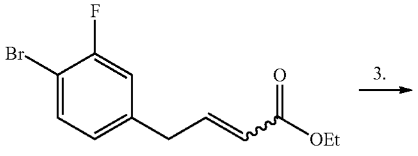

157c

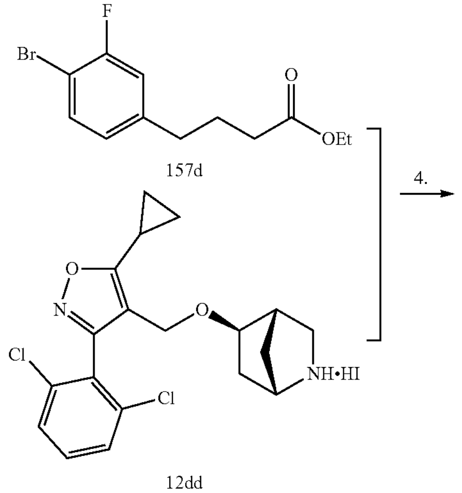

157d

12dd

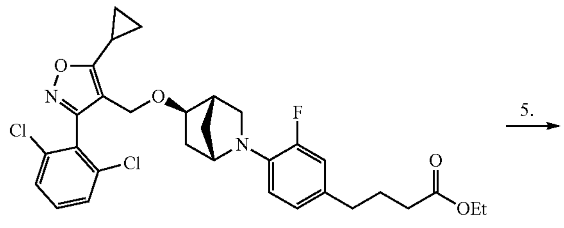

157e

-continued

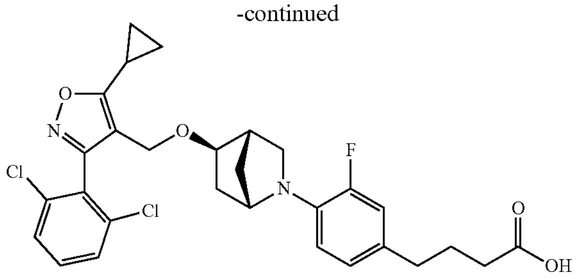

I-157

Step 1

A 1 M solution of DIBAL-H in dichloromethane (8.42 mL, 8.42 mmol) was added slowly to a solution of ethyl 2-(4-bromo-3-fluorophenyl)acetate 157a (2.0 g, 7.66 mmol) in DCM (30 mL) at −78° C. The mixture was stirred at −78° C., for 1 hour and quenched by the dropwise addition of MeOH (1 mL), followed by water (1 mL) and 10% HCl aqueous solution (2 mL). The mixture was then warmed to 0° C., stirred for 10 more minutes, diluted with dichloromethane (50 mL) and dried with $MgSO_4$. Removal of solvent gave 2-(4-Bromo-3-fluorophenyl)acetaldehyde 157b (1.62 g, crude) as a clear oil and used in the next step directly without further purification.

Step 2

2-(4-Bromo-3-fluorophenyl)acetaldehyde 157b (1.62 g, 7.46 mmol) and ethyl 2-(triphenylphosphoranylidene)acetate (2.59 g, 7.46 mmol) were dissolved in DCM (20 mL). The mixture was stirred at RT for 16 hours and then concentrated to dryness. The residue was purified by silica gel column chromatography eluting with 10% EtOAc in hexanes to give ethyl 4-(4-bromo-3-fluorophenyl)but-2-enoate 157c (0.85 g) as a clear oil.

Step 3

Ethyl 4-(4-bromo-3-fluorophenyl)but-2-enoate 157c (0.85 g, 2.96 mmol) was dissolved in MeOH (10 mL) and cooled to 0° C. Cobalt(II) chloride hexahydrate (70.4 mg, 0.296 mmol) was added followed by $NaBH_4$ (167 mg, 4.43 mmol). The mixture was stirred overnight while it was slowly warmed to RT. EtOAc (100 mL) was added, and the organic mixture was washed with water, dried over $MgSO_4$, filtered and concentrated to give ethyl 4-(4-bromo-3-fluorophenyl)butanoate 157d (0.75 g) as a clear oil.

Step 4

4-(((1S,4S,5R)-2-Azabicyclo[2.2.1]heptan-5-yloxy)methyl)-5-cyclopropyl-3-(2,6-dichlorophenyl)isoxazole hydroidodide 12dd (120 mg, 0.2366 mmol) and ethyl 4-(4-bromo-3-fluorophenyl)butanoate 157d (124 mg, 0.432 mmol) were suspended in toluene (2.0 mL). RuPhos (53.6 mg, 0.115 mmol), RuPhos-Pd precatalyst-Gen3 (48.1 mg, 0.0576 mmol) and $Cs_2CO_3$ (234 mg, 0.720 mmol) were added. The mixture was heated at 110° C., under $N_2$ for 16 hours. After cooling to room temperature, the mixture was partitioned between water and EtOAc. The organic layer was dried with $MgSO_4$, filtered and concentrated. The residue was purified by silica gel column chromatography eluting with 20 to 30% EtOAc in hexanes to give ethyl 4-(4-((1S,4S,5R)-5-((5-cyclopropyl-3-(2,6-dichlorophenyl)isoxazol-4-yl)methoxy)-2-azabicyclo[2.2.1]heptan-2-yl)-3-fluorophenyl)butanoate 157e (15 mg) as a clear oil. MS (ES, m/z): [M+1]=587.

Step 5

A 1 M NaOH aqueous solution (76.5 μL, 0.0765 mmol) was added to a solution of ethyl 4-(4-((1S,4S,5R)-5-((5-cyclopropyl-3-(2,6-dichlorophenyl)isoxazol-4-yl)methoxy)-2-azabicyclo[2.2.1]heptan-2-yl)-3-fluorophenyl)butanoate 157e (15.0 mg, 0.0255 mmol) in MeOH (2.0 mL). The mixture was heated at 60° C., for 16 hours. The mixture was cooled to 0° C., and acidified with a 1M HCl aqueous solution. The mixture was purified with prep-HPLC to afford 4-(4-((1S,4S,5R)-5-((5-cyclopropyl-3-(2,6-dichlorophenyl)isoxazol-4-yl)methoxy)-2-azabicyclo[2.2.1]heptan-2-yl)-3-fluorophenyl)butanoic acid I-157 (4.1 mg) as a colorless solid. $^1$H NMR (400 MHz, $CD_3OD$): δ 7.53 (dt, J=8.2, 4.1 Hz, 1H), 7.5-7.43 (m, 2H), 6.90-6.82 (m, 2H), 6.69 (t, J=8.9 Hz, 1H), 4.29 (s, 2H), 4.06 (s, 1H), 3.53-3.43 (m, 2H), 2.64 (dd, J=10.1, 2.8 Hz, 1H), 2.58-2.50 (m 2H), 2.43 (s, 1H), 2.25 (ddd, J=13.6, 10.0, 7.1 Hz, 3H), 1.94 (dd, J=13.8, 6.8 Hz, 1H), 1.89-1.79 (m, 2H), 1.58 (s, 2H), 1.26 (d, J=13.6 Hz, 1H), 1.16 (d, J=7.1 Hz, 4H); MS (ES, m/z): [M+1]=559.

Example 151: 3-{3-cyano-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}propanoic Acid (I-158)

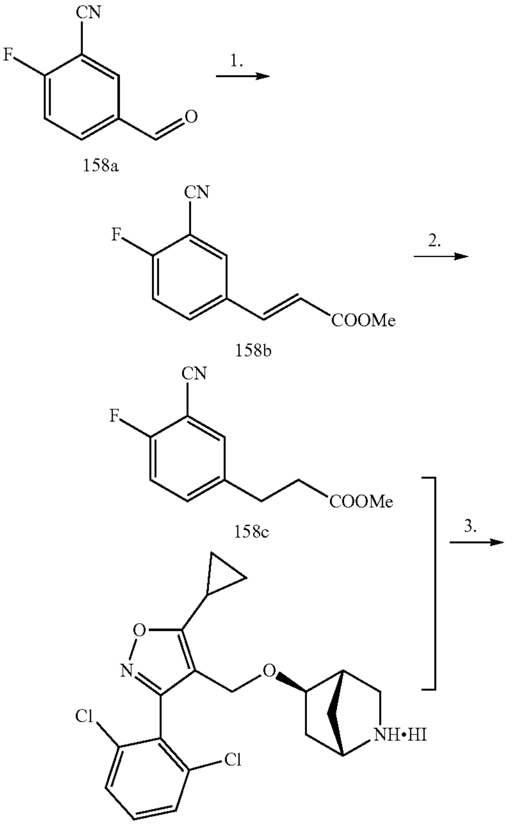

158a 158b 158c 12dd

-continued

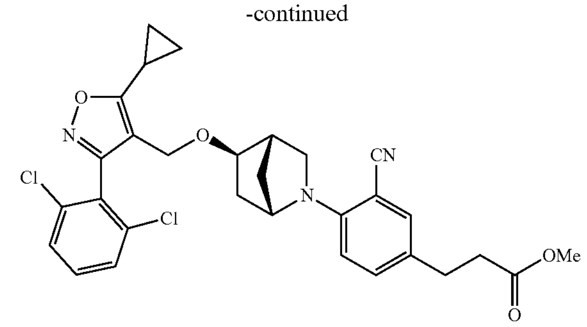

158d

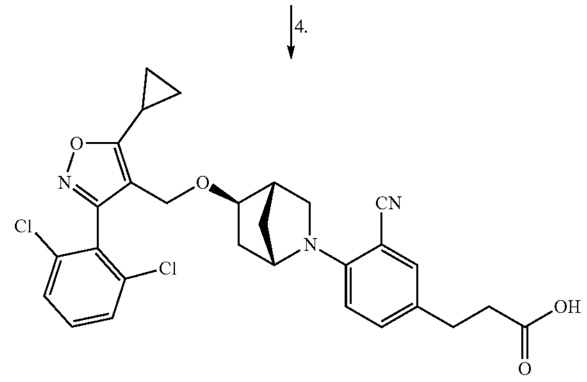

I-158

Step 1

To a 1 L round bottom flask was added methyl 2-(dimethoxyphosphoryl)acetate (8.33 g, 45.74 mmol, 1.50 equiv.), tetrahydrofuran (200 mL), sodium hydride (1.8 g, 75.00 mmol, 1.50 equiv.), and 2-fluoro-5-formylbenzonitrile 158a (4 g, 26.82 mmol, 1.00 equiv.). The resulting mixture was stirred at room temperature for 2 h. The reaction was quenched by the addition of water/ice. The aqueous mixture was extracted with ethyl acetate (400 mL×2); the combined organic extracts were washed with brine (300 mL×2), dried over anhydrous sodium sulfate and concentrated under vacuum. The residue was purified by silica gel column chromatography eluting with ethyl acetate/petroleum ether (0%-10%) to give methyl (2Z)-3-(3-cyano-4-fluorophenyl) prop-2-enoate 158b (4 g, 73%) as a light yellow solid.

Step 2

To a 250 mL round bottom flask was added methyl (2E)-3-(3-cyano-4-fluorophenyl)prop-2-enoate 158b (2 g, 9.75 mmol, 1.00 equiv.), methanol (30 mL), and $CoCl_2$-$6H_2O$ (0.23 g, 0.10 equiv.). The mixture was cooled at 0° C., sodium borohydride (820 mg, 21.68 mmol, 2.20 equiv.) was added in several batches. The resulting mixture was stirred at room temperature overnight. The reaction was quenched by the addition of water/ice. The aqueous mixture was extracted with ethyl acetate (200 mL×2); the combined organic extracts were washed with brine (200 mL×2), dried over anhydrous sodium sulfate and concentrated under vacuum. The residue was purified by silica gel column eluting with ethyl acetate/petroleum ether (1:2) to afford methyl 3-(3-cyano-4-fluorophenyl)propanoate 158c (0.49 g, 24%) as a light yellow oil.

Step 3

To a 100 mL round bottom flask was added (1S,4S,5R)-5-[[5-cyclopropyl-3-(2,6-dichlorophenyl)-1,2-oxazol-4-yl] methoxy]-2-azabicyclo[2.2.1]heptane hydroiodide salt 12dd (750 mg, 1.48 mmol, 1.00 equiv.), methyl 3-(3-cyano-4-fluorophenyl)propanoate 158c (50) mg, 2.41 mmol, 1.63 equiv.), potassium carbonate (550 mg, 3.98 mmol, 2.69 equiv.), and DMSO (10 mL). The resulting mixture was stirred at 120° C., overnight. After cooling to room temperature, 50 mL of $H_2O$ was added. The aqueous mixture was extracted with ethyl acetate (100 mL×2) and the combined organic extracts were washed with brine (100 mL×2), dried over anhydrous sodium sulfate and concentrated under vacuum. The residue was purified by silica gel column chromatography eluting with ethyl acetate/petroleum ether (1:2) to provide methyl 3-[3-cyano-4-[(1S,4S,5R)-5-[[5-cyclopropyl-3-(2,6-dichlorophenyl)-1,2-oxazol-4-yl] methoxy]-2-azabicyclo[2.2.1]heptan-2-yl]phenyl]propanoate 158d (0.1 g, 12%) as a yellow green solid.

Step 4

To a 25 mL round bottom flask was added methyl 3-[3-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]propanoate 158d (100 mg, 0.18 mmol, 1.00 equiv.), methanol (3 mL), water (0.8 mL), and LiOH (74 mg, 3.09 mmol, 10.00 equiv.). The resulting mixture was stirred overnight at room temperature and diluted with 20 mL of $H_2O$. The pH value of the solution was adjusted to 3-4 using a 1M HCl aqueous solution. The aqueous mixture was extracted with ethyl acetate (100 mL×2) and the combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (51.0/o ACN up to 69.0% in 8 min); Detector, UV 254 nm. After purification 3-[3-cyano-4-[(1S,4S,5R)-5-[[5-cyclopropyl-3-(2,6-dichlorophenyl)-1,2-oxazol-4-yl]methoxy]-2-azabicyclo[2.2.1]heptan-2-yl] phenyl]propanoic acid I-158 (13.5 mg, 14%) as grayish oil. $^1$H NMR (300 MHz, $CD_3OD$): δ 7.56-7.40 (m, 3H), 7.28-7.16 (m, 2H), 6.66-6.55 (m, 1H), 4.27 (t, J=4.1 Hz, 3H), 3.77-3.66 (m, 1H), 3.45 (s, 1H), 2.73 (dt, J=17.4, 8.1 Hz, 3H), 2.57-2.41 (m, 3H), 2.23 (t, J=6.7 Hz, 1H), 1.88 (s, 1H), 1.56 (s, 2H), 1.29 (d, J=4.7 Hz, 2H), 1.14 (dd, J=6.3, 2.5 Hz, 4H); MS (ES, m/z): [M+1]=552.

Example 152: 3-{4-[(1S,4S,5R)-5-{[3-(2-chloro-6-methylphenyl)-5-cyclopropyl-1,2-oxazol-4-yl] methoxy}-2-azabicyclo[2.2.1]heptan-2-yl]-3-fluorophenyl}propanoic Acid (I-159)

Step 1

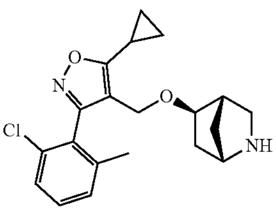

113h

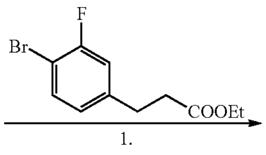

-continued

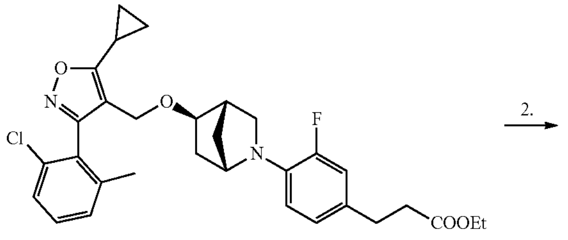

159a

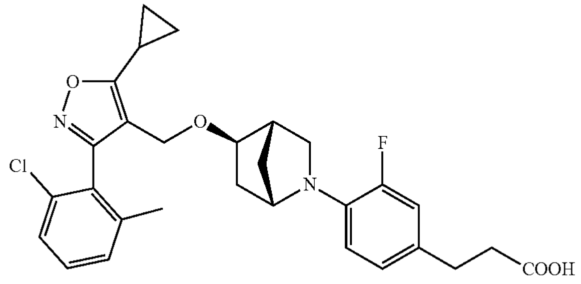

I-159

To a 250 mL round bottom flask purged with and maintained under an inert atmosphere of nitrogen was added (1S,4S,5R)-5-[[3-(2-chloro-6-methylphenyl)-5-cyclopropyl-1,2-oxazol-4-yl]methoxy]-2-azabicyclo[2.2.1]heptane 113h (1 g, 2.79 mmol, 1.00 equiv.), toluene (100 mL), ethyl 3-(4-bromo-3-fluorophenyl)propanoate (1.15 g, 4.18 mmol, 1.50 equiv.), $Cs_2CO_3$ (2.7 g, 8.29 mmol, 2.97 equiv.), Xant-Phos (322 mg), and $Pd(OAc)_2$ (125 mg, 0.56 mmol, 0.20 equiv.). The resulting mixture was stirred at 90° C., for 2 days. The solids were filtered out. The filtrate was concentrated under vacuum to a residue which was purified by silica gel column chromatography eluting with ethyl acetate/petroleum ether (1:10-1:5). Removal of solvents afforded ethyl 3-[4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-3-fluorophenyl]propanoate 159a (200 mg, 13%) as a light brown oil.

Step 2

To a 100 mL round bottom flask was added ethyl 3-[4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-3-fluorophenyl]propanoate 159a (65 mg, 0.12 mmol, 1.00 equiv.), ethanol (5 mL), water (1 mL), and LiOH (28 mg, 1.17 mmol, 9.95 equiv.). The resulting mixture was stirred at 60° C., for 2 h, then cooled to room temperature, and the pH value of the solution was adjusted to 7 using a 1M hydrogen chloride aqueous solution. The aqueous mixture was extracted with ethyl acetate (50 mL×2), and the combined organic extracts were washed with brine (50 mL), dried over anhydrous sodium sulfate and concentrated. The crude product was purified by Prep-HPLC using the following conditions Column, XBridge Shield RP18 OBD Column, 5 um, 19*150 mm; mobile phase, Water (0.05% TFA) and ACN (53.0% ACN up to 70.0% in 8 min); Detector, UV 254 nm. After purification 3-[4-[(1S,4S,5R)-5-[[3-(2-chloro-6-methylphenyl)-5-cyclopropyl-1,2-oxazol-4-yl]methoxy]-2-azabicyclo[2.2.1]heptan-2-yl]-3-fluorophenyl]propanoic acid I-159 (32.1 mg, 52%) was obtained as a colorless solid. $^1H$ NMR (300 MHz, $CD_3OD$): δ 7.46-7.35 (m, 2H), 7.29 (t, J=6.7 Hz, 1H), 6.98-6.86 (m, 2H), 6.76-6.64 (m, 1H), 4.35 (d, J=11.7 Hz, 1H), 4.26-4.03 (m, 2H), 3.48 (dt, J=14.7, 5.8 Hz, 1H), 2.83 (t, J=7.6 Hz, 2H), 2.70-2.47 (m, 4H), 2.41-2.20 (m, 1H), 2.17 (d, J=2.9 Hz, 3H), 1.97 (td, J=14.3, 6.1 Hz, 1H), 1.68-1.42 (m, 2H), 1.34 (d, J=13.3 Hz, 1H), 1.19 (d, J=6.9 Hz, 5H); MS (ES, m/z): [M+1]=525.2.

Example 153: 1-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}methyl)azetidine-3-carboxylic Acid (I-160)

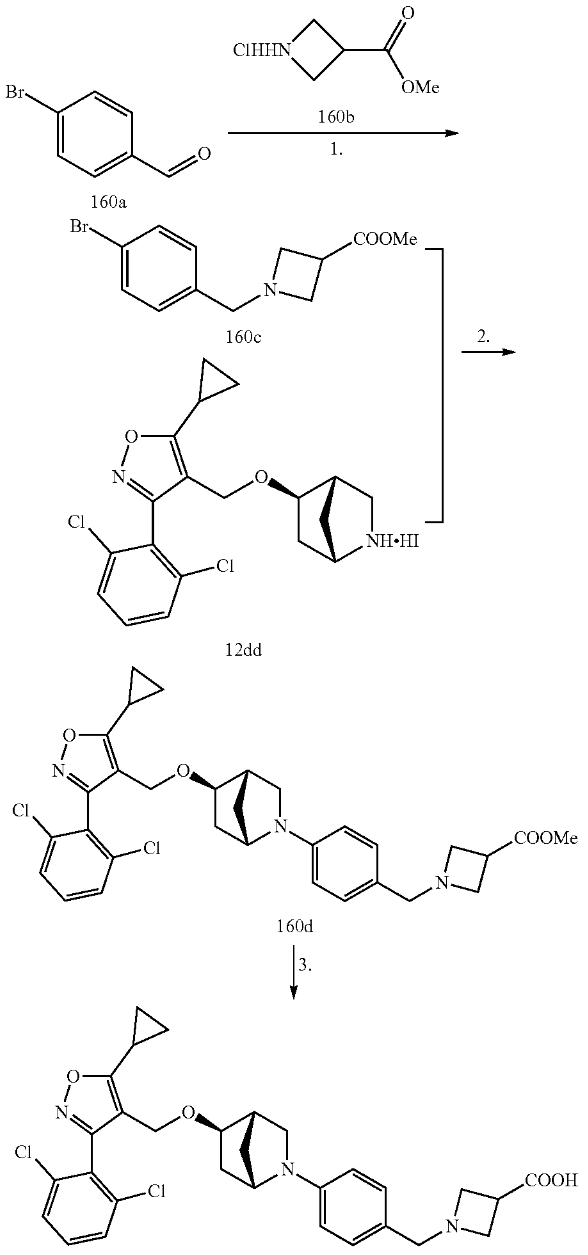

160b

160a

160c

12dd

160d

I-160

Step 1

To a 250 mL roundbottom flask was added 4-bromobenzaldehyde 160a (5.4 g, 29.19 mmol, 1.10 equiv.), sodium triacetoxyborohydride (34 g, 160.42 mmol, 6.00 equiv.), AcOH (1 mL), dichloromethane (80 mL), and methyl azetidine-3-carboxylate hydrochloride 160b (4 g, 34.74 mmol, 1.00 equiv.). The resulting mixture was stirred at 50° C., overnight. Upon cooling to room temperature, the mixture was diluted with 50 mL of $H_2O$ and extracted with ethyl acetate (100 mL×2). The combined organic extracts were washed with brine (100 mL×2), dried and concentrated. The residue was purified by silica gel column chromatography eluting with ethyl acetate/hexane (1:10) to give methyl 1-[(4-bromophenyl)methyl]azetidine-3-carboxylate 160c (4 g, 41%) as a yellow oil.

Step 2

To a 50 mL round-bottom flask was added methyl 1-[(4-bromophenyl)methyl]azetidine-3-carboxylate 160c (150 mg, 0.53 mmol, 1.34 equiv.), Ruphos (0.02 g, 0.13 equiv.), Ruphos precatalyst (0.04 g, 0.13 equiv.), $Cs_2CO_3$ (345 mg, 1.06 mmol, 2.66 equiv.), (1S,4S,5R)-5-[5-cyclopropyl-3-(2,6-dichlorophenyl)-1,2-oxazol-4-yl]methoxy-2-azabicyclo[2.2.1]heptane hydroiodide salt 12dd (200 mg, 0.3943 mmol, 1.00 equiv.), and toluene (3 mL). The resulting mixture was stirred at 110° C., overnight. After cooling to room temperature, 30 mL of $H_2O$ was added. The aqueous mixture was extracted ethyl acetate (100 mL×2) and the combined organic extracts were washed with brine (100 mL×2), dried over anhydrous sodium sulfate and concentrated under vacuum. The residue was purified by silica gel column chromatography eluting with ethyl acetate/petroleum ether (1:3) to afford methyl 1-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methyl)azetidine-3-carboxylate 160d (0.12 g, 53%) as a yellow oil.

Step 3

To a 50 mL round-bottom flask was added methyl 1-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methyl)azetidine-3-carboxylate 160d (120 mg, 0.21 mmol, 1.00 equiv.), LiOH (49 mg, 2.05 mmol, 10.00 equiv), methanol (2 mL), and water (0.4 L). The resulting mixture was stirred at 35° C., overnight. 20 mL of $H_2O$ was added, the aqueous mixture was extracted with ethyl acetate (20 mL×2), and the combined organic extracts were washed with brine (20 mL×2), dried and concentrated. The crude product was purified by Prep-HPLC using the following conditions: Column, XBridge Shield RP18 OBD Column, 5 um, 19*150 mm; mobile phase. Water (0.05% TFA) and ACN (30.0% ACN up to 50.0% in 8 min); Detector, UV 254 nm. After purification 1-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methyl)azetidine-3-carboxylic acid I-160 (29.9 mg, 26%) was obtained as a black solid. $^1H$ NMR (400 MHz, $CD_3OD$): δ 7.60-7.44 (m, 3H), 7.22 (d, J=8.3 Hz, 2H), 6.56 (d, J=8.6 Hz, 2H), 4.38-4.21 (m, 8H), 4.08 (s, 1H), 3.66 (s, 1H), 3.45 (d, J=6.5 Hz, 1H), 3.37 (dd, J=9.2, 4.2 Hz, 2H), 2.49 (d, J=8.4 Hz, 2H), 2.27 (p, J=6.8 Hz, 1H), 1.82 (dd, J=13.7, 7.1 Hz, 1H), 1.59 (q, J=9.9 Hz, 2H), 1.30 (d, J=13.2 Hz, 1H), 1.18 (d, J=6.6 Hz, 4H); MS (ES, m/z): [M+1]=568.49.

Example 154: N-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl)}methyl)-N-hydroxyformamide (I-161)

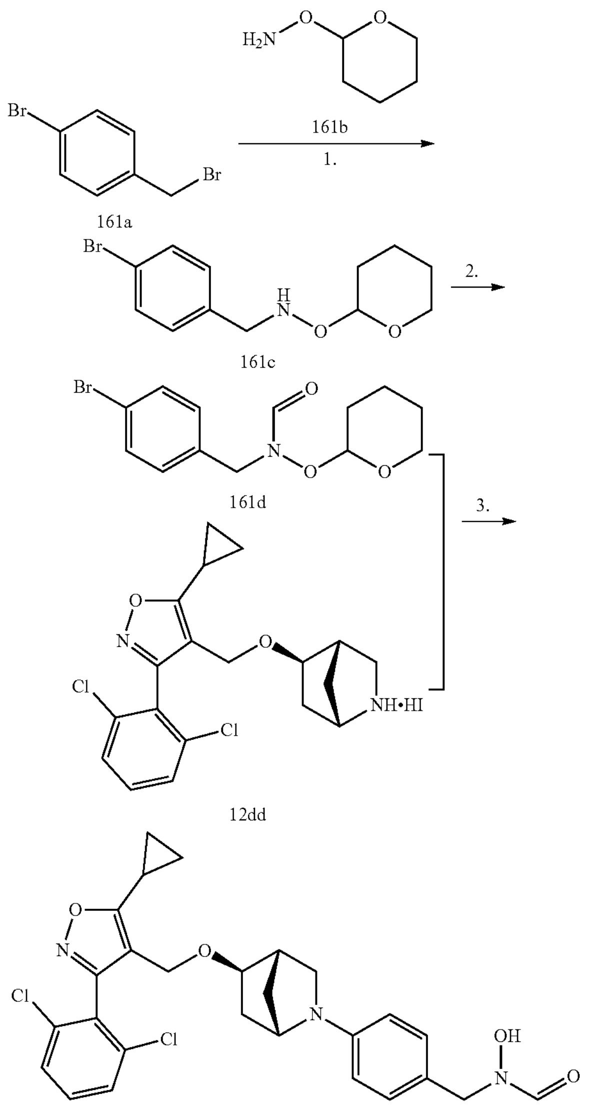

161a

161c

161d

12dd

I-161

Step 1

Potassium carbonate (12.5 g, 3 equiv.) and 4-bromobenzyl bromide 161a (7.5 g, 1.0 equiv.) were added to a DMF (70 mL) solution of O-(tetrahydro-2H-pyran-2-yl)hydroxylamine 161b (4.2 g, 1.2 equiv.). The mixture was heated at 70° C., for 3 h. The reaction mixture was cooled to room temperature, diluted with ethyl acetate and filtered. The resulting solution was washed with water, brine, dried over anhydrous sodium sulfate, filtered and concentrated in vacuo. The crude material was purified by flash column chromatography eluting with 5-10% ethyl acetate in dichloromethane to give N-(4-bromobenzyl)-O-(tetrahydro-2H-pyran-2-yl)hydroxylamine 161c (6.9 g). $^1H$ NMR (400 MHz, DMSO-$d_6$): δ 7.50 (d, J=8.3 Hz, 2H), 7.31 (d, J=8.3

Hz, 2H), 7.02 (t, J=5.9 Hz, 1H), 4.74-4.50 (m, 1H), 3.93 (d, J=5.9 Hz, 2H), 3.78-3.75 (m, 1H), 3.47-3.35 (m, 1H), 1.71-1.26 (m, 6H).

Step 2

To a solution of 4-methylmorpholine (1.65 mL, 1.5 equiv.) and formic acid (0.4 mL, 1.02 equiv.) in dichloromethane (20 mL), CDI (2.4 gm, 1.5 equiv.) was added at 0° C., followed by the addition of N-(4-bromobenzyl)-O-(tetrahydro-2H-pyran-2-yl)hydroxylamine 161c (3.1 g, 1.1 equiv.). The reaction mixture was stirred at the same temperature for 2 h, and then washed with water, saline, dried over sodium sulfate, filtered and concentrated in vacuo. The crude material was purified by flash column chromatography using 20-30% ethyl acetate in hexanes as eluent to provide N-(4-bromobenzyl)-N-(tetrahydro-2H-pyran-2-yloxy)formamide 161d (2.8 g); $^1$H-NMR (400 MHz, DMSO-D6): δ 8.42 (s, 1H), 7.56 (d, J=8.2 Hz, 2H), 7.26 (d, J=7.9 Hz, 2H), 5.02 (bs, 1H), 4.81 (d, J=14.6 Hz, 1H), 4.68 (d, J=14.2 Hz, 1H), 3.85 (bs, 1H), 3.54 (d, J=9.7 Hz, 1H), 1.70-1.37 (m, 6H).

Step 3

A suspension of 4-(((1S,4S,5S)-2-azabicyclo[2.2.1]heptan-5-yloxy)methyl)-5-cyclopropyl-3-(2,6-dichlorophenyl) isoxazole hydroiodide salt 12dd (124.5 mg, 1 equiv.), N-(4-bromobenzyl)-N-(tetrahydro-2H-pyran-2-yloxy)formamide 161d (230 mg, 1.5 equiv.), $Cs_2CO_3$ (245 mg, 2.5 equiv.), Ru-Phos (57 mg, 0.4 equiv.), Ru-Phos-Pd (51 mg, 0.2 equiv.) in Toluene (4.0 mL) was heated under a nitrogen atmosphere at 110° C. for 16 h. The reaction mixture was cooled to RT and filtered through a pad of Celite. The filtrate was concentrated and purified on Isco silica gel column using 40-60% ethyl acetate in hexane as eluent to give the desired intermediate which was used as such for the next step.

The above residue was dissolved in methanol (12 mL) and treated with TFA (8 mL) at RT for 2 h. Then, it was concentrated under the reduced pressure and the residue was purified on Semi-prep HPLC using 10-90% acetonitrile in 30 min, method. The fractions corresponding to the desired product were lyophilized to provide N-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}methyl)-N-hydroxyformamide I-161 as trifluoroacetate salt (11 mg); $^1$H-NMR (400 MHz, DMSO-$d_6$): δ 11.12 (bs, 2H), 7.67-7.47 (m, 3H), 7.18 (d, J=8.7 Hz, 2H), 6.47 (d, J=8.7 Hz, 2H), 4.27 (s, 2H), 4.13 (s, 2H), 4.05 (s, 1H), 3.37-3.35 (m, 1H), 3.28-3.26 (m, 1H), 2.42-2.39 (m, 2H), 2.37-2.30 (m, 1H), 1.64 (dd, J=13.4 & 6.9 Hz, 1H), 1.41 (dd, J=26.2 & 9.3 Hz, 2H), 1.15-1.07 (m, 4H).

Example 155: (1S,4S,5R)-5-{[5-cyclopropyl-3-(2,6-dichlorophenyl)-1,2-oxazol-4-yl]methoxy}-2-{2-fluoro-4-[2-(2H-1,2,3,4-tetrazol-5-yl)ethyl]phenyl}-2-azabicyclo[2.2.1]heptane (I-162)

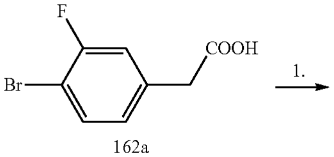

162a

-continued

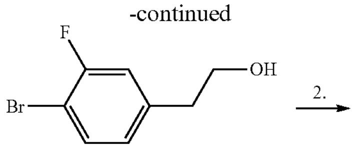

162b

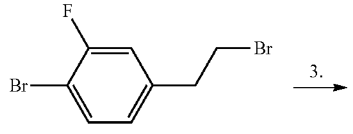

162c

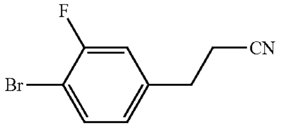

162d

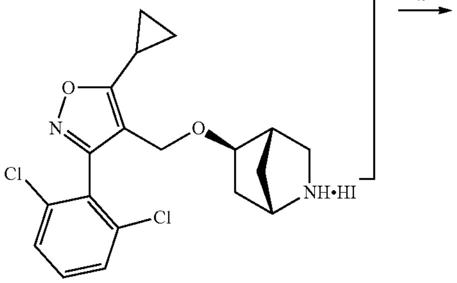

12dd

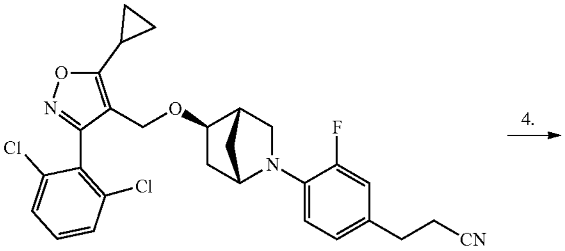

162e

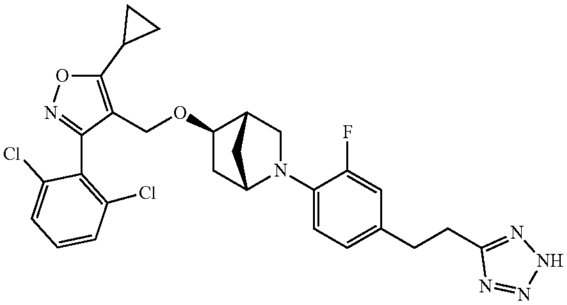

I-162

Step 1

To a 250 mL round bottom flask was added a solution of 2-(4-bromo-3-fluorophenyl)acetic acid 162a (5 g, 21.46 mmol, 1.00 equiv.) in tetrahydrofuran (50 mL). This was followed by the addition of $BH_3$ in tetrahydrofuran (43 mL, 2.00 equiv.) dropwise with stirring at 0° C. The resulting mixture was stirred at room temperature for 2 h, then diluted with 100 mL of EA. The mixture was washed with brine (100 mL×2), dried over anhydrous sodium sulfate and concentrated under vacuum. The residue was purified by silica gel column chromatography eluting with ethyl acetate/petroleum ether (0-50%) to give 2-(4-bromo-3-fluorophenyl)ethan-1-ol 162b (3 g, 64%) as a light yellow oil.

Step 2

To a 250 mL round-bottom flask was added a solution of 2-(4-bromo-3-fluorophenyl)ethan-1-ol 162b (1 g, 4.57 mmol, 1.00 equiv.) in dichloromethane (10 mL), cooled to 0° C. Triphenylphosphine (1.44 g, 5.49 mmol, 1.20 equiv.) was added in several batches followed by the addition of NBS (974 mg, 5.47 mmol, 1.20 equiv.) in several batches. The reaction was allowed to continue at room temperature for 1 h. The mixture was diluted with 50 mL of DCM, washed with a sat.sodium carbonate aqueous solution (t0 mL×2) and then brine (50 mL×2), dried over anhydrous sodium sulfate and concentrated under vacuum. The residue was purified by silica gel column chromatography eluting with ethyl acetate/petroleum ether to afford 1-bromo-4-(2-bromoethyl)-2-fluorobenzene 162c (1 g, 78%) as a colorless oil.

Step 3

To a 50 mL round bottom flask was added a solution of 1-bromo-4-(2-bromoethyl)-2-fluorobenzene 162c (500 mg, 1.77 mmol, 1.00 equiv.) in $CH_3CN$ (2 mL) followed by the addition of TBAF (2.7 mL, 1.50 equiv, 1M in THF) dropwise with stirring. TMSCN (265 mg, 2.68 mmol, 1.50 equiv.) was added dropwise. The reaction mixture was heated at 82° C., for 20 min, cooled to room temperature and concentrated in vacuo. The residue was purified by silica gel column chromatography eluting with EA:PE (1:5) to afford 3-(4-bromo-3-fluorophenyl)propanenitrile 162d (200 mg, 49%) as a light yellow oil.

Step 4

To a 8 mL sealed tube purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (400 mg, 0.7886 mmol, 0.9 equiv.), a solution of 3-(4-bromo-3-fluorophenyl)propanenitrile 162d (200 mg, 0.88 mmol, 1.00 equiv) in toluene (3 mL), RuPhos (82 mg, 0.18 mmol, 0.20 equiv.), RuPhos-precatalyst (150 mg, 0.18 mmol, 0.20 equiv.), and $Cs_2CO_3$ (574 mg, 1.76 mmol, 2.00 equiv.). The resulting mixture was stirred at 110° C., overnight. Upon cooling to room temperature, the mixture was diluted with 50 mL of EA, washed with brine (50 mL×2), dried and concentrated. The residue was purified by silica gel column chromatography eluting with EA:PE (1:3) to provide 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]propanenitrile 162e (100 mg, 22%) as a yellow oil.

Step 5

To a 8 mL sealed tube purged with and maintained under an inert atmosphere of nitrogen was added a solution of 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]propanenitrile 162e (100 mg, 0.19 mmol, 1.00 equiv.) in m-xylene (3 mL), and $Bu_3SnN_3$ (316 mg, 0.95 mmol, 5.00 equiv.). The resulting mixture was heated at 140° C., overnight with stirring. After cooling to room temperature, the mixture was diluted with 10 mL of EA, washed with brine (10 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (49.0% ACN up to 67.0% in 8 min); Detector, UV 254 nm. After purification (1S,4S,5R)-5-[[5-cyclopropyl-3-(2,6-dichlorophenyl)-1,2-oxazol-4-yl]methoxy]-2-[2-fluoro-4-[2-(2H-1,2,3,4-tetrazol-5-yl)ethyl]phenyl]-2-azabicyclo[2.2.1]heptane I-162 (28.7 mg, 27%) was obtained as a white solid. $^1$H-NMR (400 MHz, $CD_3OD$): δ 7.60-7.45 (m, 3H), 6.88-6.74 (m, 2H), 6.60 (t, J=8.8 Hz, 1H), 4.31 (s, 2H), 4.05 (s, 1H), 3.54-3.40 (m, 2H), 3.21 (t, J=7.5 Hz, 2H), 3.00 (t, J=7.6 Hz, 2H), 2.57 (dd, J=9.5, 3.2 Hz, 1H), 2.45-2.38 (m, 1H), 2.26 (p, J=6.7 Hz, 1H), 1.96-1.86 (m, 1H), 1.56 (s, 2H), 1.33-1.18 (m, J=6.8 Hz, 6H); MS (ES, m/z): [M+1]=569.15.

Example 156: 2-[bis(2-hydroxyethyl)amino]ethyl 3-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}propanoate (I-163)

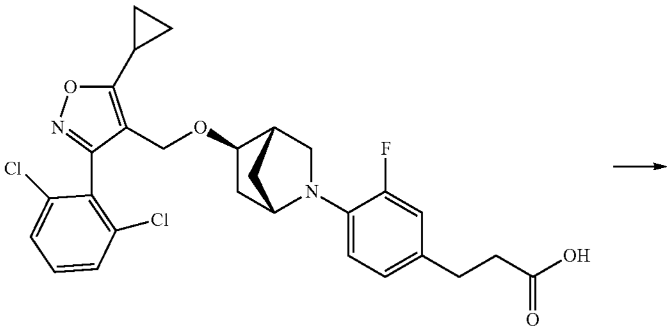

I-154

-continued

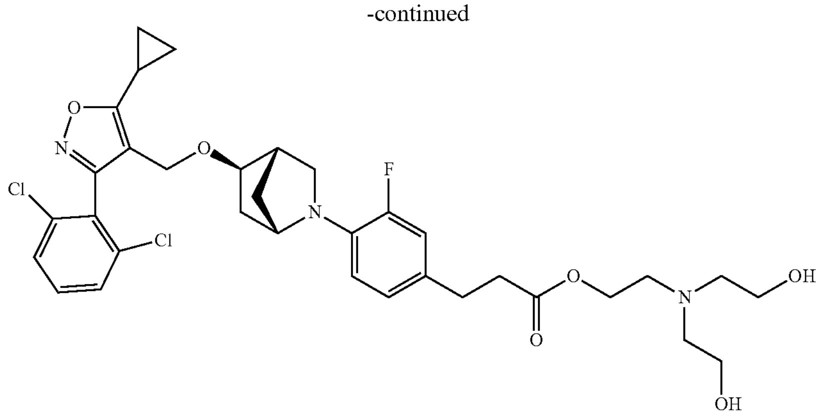

I-163

To a 25 mL round-bottom flask was added 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]propanoic acid I-154 (200 mg, 0.37 mmol, 1.00 equiv.), dichloromethane (3 mL), 2-[bis(2-hydroxyethyl)amino]ethan-1-ol (630 mg, 4.22 mmol, 10.00 equiv.), 4-dimethylaminopyridine (154 mg, 1.26 mmol, 3.00 equiv.), and EDCI (122 mg, 0.64 mmol, 1.50 equiv.). The resulting mixture was stirred at room temperature overnight, diluted with 10 mL of DCM, and quenched by the addition of 3 mL of water. The pH value of the solution was adjusted to 6 using a 1M hydrogen chloride aqueous solution. The aqueous mixture was extracted with ethyl acetate (50 mL×3), and the combined organic extracts were washed with brine (10 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (31.0% ACN up to 51.0% in 8 min); Detector, UV 254 nm. After purification 2-[bis(2-hydroxyethyl)amino]ethyl 3-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]propanoate 1-163 (34.2 mg, 14%) was obtained as a black oil. $^1$H-NMR (300 MHz, $CD_3OD$): δ 7.60-7.42 (m, 3H), 6.94-6.80 (m, 2H), 6.61 (t, J=9.0 Hz, 1H), 4.51-4.40 (m, 2H), 4.30 (s, 2H), 4.04 (s, 1H), 3.94-3.83 (m, 4H), 3.68-3.58 (m, 2H), 3.55-3.36 (m, 6H), 2.84 (t, J=7.6 Hz, 2H), 2.73-2.51 (m, 3H), 2.41 (d, J=4.0 Hz, 1H), 2.33-2.18 (m, 1H), 1.91 (dd, J=13.4, 6.7 Hz, 1H), 1.55 (s, 2H), 1.33-1.11 (m, 6H); MS (ES, m/z): [M+1]=676.25.

Example 157: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(2H-1,2,3,4-tetrazol-5-ylmethyl)benzamide (I-164)

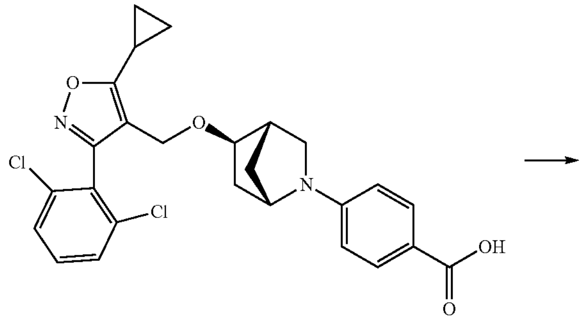

I-52

-continued

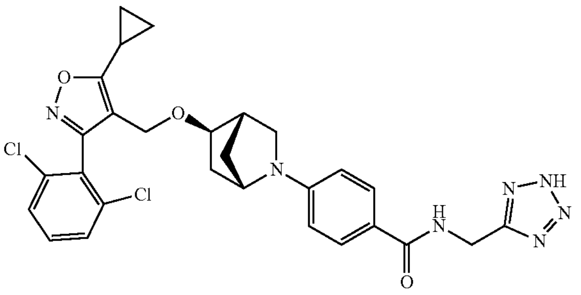

I-164

To a 8 mL sealed tube was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-52 (100 mg, 0.20 mmol, 1.00 equiv.), HATU (114 mg, 0.30 mmol, 1.50 equiv.), DIEA (100 mg, 0.77 mmol, 4.00 equiv.), 2H-1,2,3,4-tetrazol-5-ylmethanamine (20 mg, 0.20 mmol, 1.00 equiv.), and N,N-dimethylformamide (2 mL). The resulting mixture was stirred at room temperature for 3 h. The solids were filtered out and the filtrate was concentrated. The crude product was purified by Prep-HPLC using the following conditions: Column, XBridge Prep OBD C8 Column, 19*250 mm, 5 um; mobile phase, Water (0.05% TFA) and ACN (42.0% ACN up to 61.0% in 8 min); Detector, UV 254 nm. After purification 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-(2H-1,2,3,4-tetrazol-5-ylmethyl)benzamide I-164 (62.3 mg, 54%) was obtained as an off-white solid. $^1$H-NMR (300 MHz, $CD_3OD$): δ 7.78-7.68 (m, 2H), 7.63-7.46 (m 3H), 6.60-6.48 (m, 2H), 4.85 (s, 2H), 4.33 (s, 2H), 4.16 (s, 1H), 3.50 (d, J=6.1 Hz, 1H), 3.40 (dd, J=9.4, 4.1 Hz, 3H), 2.64-2.49 (m, 2H), 2.36-2.21 (m, 1H), 1.89-1.76 (m, 1H), 1.62 (t, J=8.4 Hz, 2H), 1.38-1.26 (m, 1H), 1.24-1.15 (m, 4H); MS (ES, m/z): [M+1]=580.

Example 158: 2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido) acetic Acid (I-165)

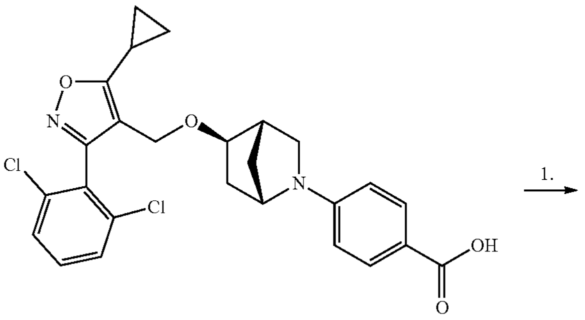

I-52

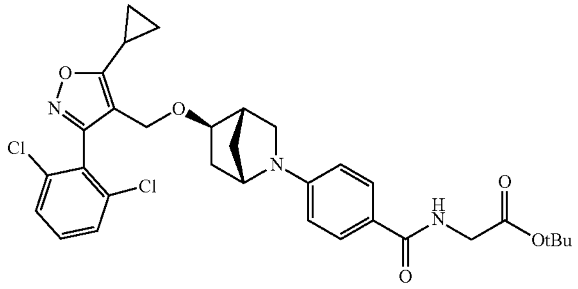

165a

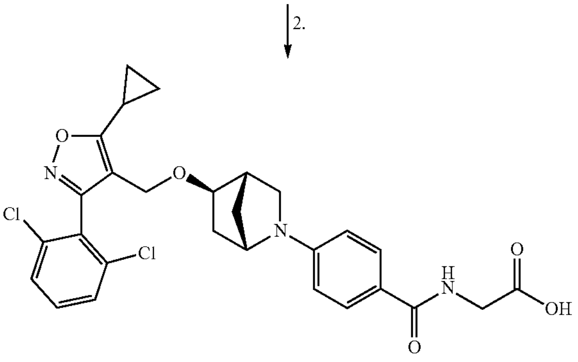

I-165

Step 1

To a 250 mL round bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-52 (100 mg, 0.20 mmol, 1.00 equiv.), HATU (153 mg, 0.40 mmol, 2.00 equiv.), DIEA (104 mg, 0.80 mmol, 4.00 equiv.), N,N-dimethylformamide (3 mL), and tert-butyl 2-aminoacetate (53 mg, 0.40 mmol, 2.00 equiv.). The resulting mixture was stirred at room temperature overnight. The mixture was diluted with 20 mL of $H_2O$, and extracted with ethyl acetate (20 mL×2). The combined organic extracts were washed with $H_2O$ (20 mL×2), dried over anhydrous sodium sulfate and concentrated under vacuum. The residue was purified by silica gel column chromatography eluting with ethyl acetate/petroleum ether (1:5) to give tert-butyl 2-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]formamido)acetate 165a (126 mg, Q) as a yellow oil.

Step 2

To a 250 mL round-bottom flask was added tert-butyl 2-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]formamido)acetate 165a (126 mg, 0.21 mmol, 1.00 equiv.), trifluoroacetic acid (2.5 mL), and dichloromethane (5 mL). The resulting mixture was stirred for 1 h at room temperature, diluted with dichloromethane (20 mL), washed with brine (20 mL×2). The organic fraction was dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (42.0% ACN up to 60.0% in 8 min); Detector. UV 254 nm. After purification 2-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]formamido)acetic acid I-165 (25.8 mg, 23%) was obtained as a gray solid. $^1H$-NMR (300 MHz, $CD_3OD$): δ 7.71 (d, J=8.8 Hz, 2H), 7.62-7.45 (m, 3H), 6.53 (d, J=8.8 Hz, 2H), 4.33 (s, 2H), 4.16 (s, 1H), 4.08 (s, 2H), 3.50 (d, J=6.0 Hz, 2H), 2.64-2.49 (m, 1H), 2.49-2.27 (m, 1H), 2.27 (q, J=6.7 Hz, 1H), 1.89-1.76 (m, 1H), 1.61 (d, J=6.0 Hz, 2H), 1.32 (d, J=13.2 Hz, 1H), 1.24-1.15 (m, 4H); MS (ES, m/z): [M+1]=556.2.

Example 159: 2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido) ethane-1-sulfonic Acid (I-166)

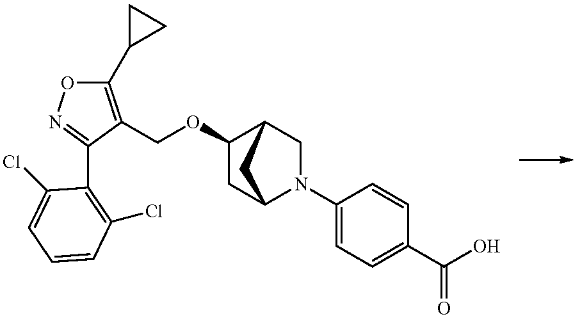

I-52

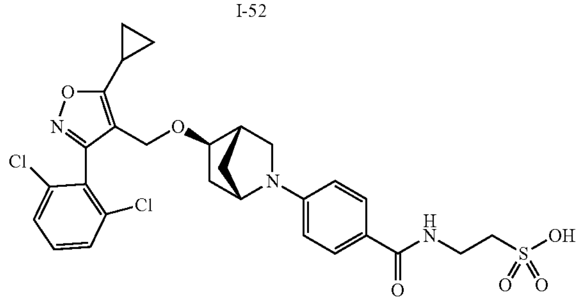

I-166

To a 50 mL round-bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-52

(200 mg, 0.40 mmol, 1.00 equiv.), DIEA (206 mg, 1.59 mmol, 4.00 equiv.), N,N-dimethylformamide (10 mL), PyBOP (312 mg, 1.30 equiv.), and 3-aminopropane-1-sulfonic acid (75 mg, 0.54 mmol, 1.50 equiv.). The resulting mixture was heated at 80° C., for 3 h with stirring. After cooling to room temperature, the mixture was diluted with 100 mL of EA, washed with brine (50 mL×2), dried over anhydrous sodium sulfate and concentrated under vacuum. The crude product was purified by Prep-HPLC using the following conditions: Column, XBridge Prep C18 OBD Column, $19_{i}$ Á150 mm 5 um 5umC-0013; mobile phase, Water (0.05% TFA) and ACN (48.0% ACN up to 62.0% in 8 min); Detector, UV 254 nm. After purification 2-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]formamido)ethane-1-sulfonic acid I-166 (79.4 mg, 33%) as a light yellow solid. $^{1}$H-NMR (300 MHz, $CD_3OD$): δ 7.69 (d, J=8.5 Hz, 2H), 7.60-7.44 (m, 3H), 6.68 (d, J=8.4 Hz, 2H), 4.32 (s, 2H), 4.19 (s, 1H), 3.80 (t, J=6.2 Hz, 2H), 3.52 (d, J=6.1 Hz, 1H), 3.42 (dd, J=9.8, 4.1 Hz, 1H), 3.08 (t, J=6.5 Hz, 2H), 2.71 (d, J=9.8 Hz, 1H), 2.53 (s, 1H), 2.26 (p, J=6.9 Hz, 1H), 1.92-1.78 (m, 1H), 1.64 (s, 2H), 1.32 (d, J=13.5 Hz, 1H), 1.22-1.11 (m, 4H); MS (ES, m/z): [M+1]=606.2.

Example 160: 2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorophenyl}formamido)acetic Acid (I-167)

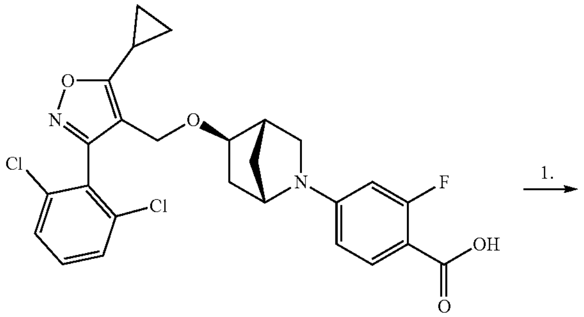

I-103

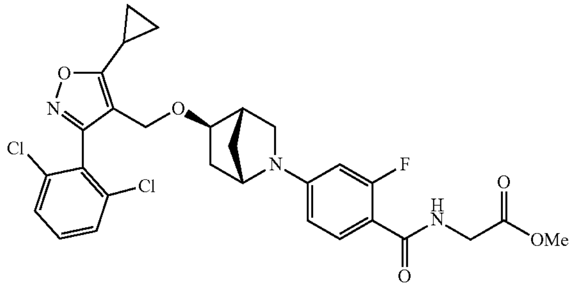

167a

2.

-continued

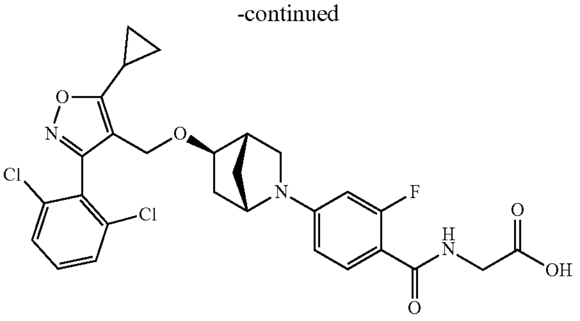

I-167

Step 1

To a 8 mL vial was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoic acid I-103 (100 mg, 0.19 mmol, 1.00 equiv.), methyl 2-aminoacetate hydrochloride (48 mg, 0.38 mmol, 2.00 equiv.), N,N-dimethylformamide (2 mL), HATU (147 mg, 0.39 mmol, 2.00 equiv), and DIEA (0.13 mL). The resulting mixture was stirred at room temperature overnight. The mixture was diluted with 100 mL of EA, washed with brine (50 mL×3), dried over anhydrous sodium sulfate and concentrated under vacuum to give methyl 2-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorophenyl]formamido)acetate 167a (200 mg, crude, Q) as a light yellow oil.

Step 2

To a 25 mL round-bottom flask was added methyl 2-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorophenyl]formamido) acetate 167a (200 mg, 1.00 equiv), methanol (2 mL), water (0.2 mL), and $LiOH.H_2O$ (144 mg, 3.43 mmol, 10.00 equiv.). The resulting mixture was stirred overnight at room temperature. The pH value of the solution was adjusted to 7.0 using a 1M hydrogen chloride aqueous solution. The aqueous mixture was extracted with ethyl acetate (30 mL×3), the combined organic extracts were dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (5% ACN up to 50% in 1 min, up to 62% in 7 min); Detector, UV 220 nm. After purification 2-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorophenyl]formamido)acetic acid I-167 (74 mg, 38%) was obtained as a light yellow solid. $^{1}$H-NMR (300 MHz, $CD_3OD$): δ 7.67 (t, J=9.0 Hz, 1H), 7.57-7.38 (m, 3H), 6.33 (dd, J=8.9, 2.3 Hz, 1H), 6.20 (dd, J=15.7, 2.3 Hz, 1H), 4.27 (s, 2H), 4.12-4.02 (m, 3H), 3.52-3.43 (m, 1H), 3.32 (d, J=4.1 Hz, 1H), 2.60-2.44 (m, 2H), 2.22 (p, J=6.7 Hz, 1H), 2.00 (s, 1H), 1.83-1.70 (m, 1H), 1.55 (q. J=10.1 Hz, 2H), 1.27 (d, J=13.3 Hz, 1H), 1.18-1.09 (m, 4H); MS (ES, m/z): [M+1]=574.43.

Example 161: 2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorophenyl}formamido)ethane-1-sulfonic Acid (I-168)

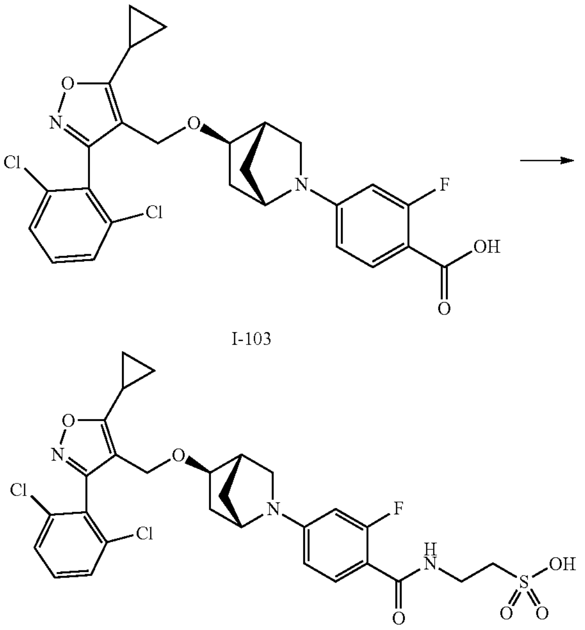

I-103

I-168

To a 25 mL round-bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoic acid I-103 (100 mg, 0.19 mmol, 1.00 equiv.). N,N-dimethylformamide (3 mL), PyBop (131 mg, 0.25 mmol, 1.30 equiv.), 2-aminoethane-1-sulfonic acid (36 mg, 0.29 mmol, 1.50 equiv.), and DIEA (0.13 mL). The resulting mixture was heated at 80° C., for 3 h. The solids were filtered out. The filtrate was concentrated to a crude product which was purified by Prep-HPLC using the following conditions: Column, XBridge Shield RP18 OBD Column, 5 um, 19*150 mm; mobile phase. Water (0.05% TFA) and ACN (40% ACN up to 60% in 8 min); Detector, UV 254 nm. 82.4 mg product was obtained. After purification 2-([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorophenyl]formamido) ethane-1-sulfonic acid I-168 (82.4 mg, 68%) was obtained as a light yellow solid. $^1$HNMR (300 MHz, $CD_3OD$): δ 7.65 (t, J=8.9 Hz, 1H), 7.56-7.38 (m, 3H), 6.34 (dd, J=8.9, 2.2 Hz, 1H), 6.20 (dd, J=15.4, 2.2 Hz, 1H), 4.27 (s, 2H), 4.09 (s, 1H), 3.79 (t, J=6.3 Hz, 2H), 3.47 (d, J=5.6 Hz, 1H), 3.32 (d, J=4.0 Hz, 1H), 3.03 (t, J=6.3 Hz, 2H), 2.56 (d, J=9.5 Hz, 1H), 2.46 (s, 1H), 2.22 (p, J=6.8 Hz, 1H), 1.77 (dd, J=13.7, 7.1 Hz, 1H), 1.56 (t, J=8.7 Hz, 2H), 1.27 (d, J=13.1 Hz, 1H), 1.18-1.08 (m, 4H); MS (ES, m/z): [M+1]=624.51.

Example 162: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(2-methanesulfonylethyl)benzamide (I-169)

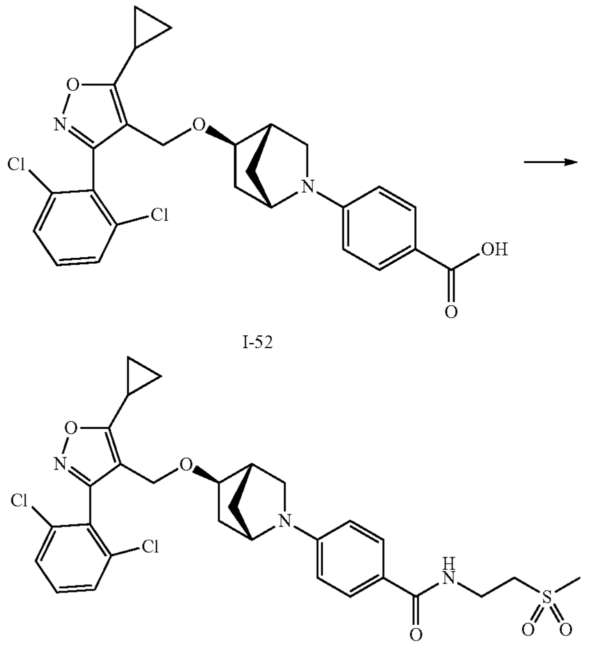

I-52

I-169

To a 25 mL round bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-52 (100 mg, 0.20 mmol, 1.00 equiv), HATU (114 mg, 0.30 mmol, 1.50 equiv), DIEA (104 mg, 0.80 mmol, 4.00 equiv), 2-methanesulfonylethan-1-amine (32 mg, 0.26 mmol, 1.00 equiv), and N,N-dimethylformamide (3 mL). The resulting mixture was stirred at room temperature overnight, then diluted with 50 mL of $H_2O$. The aqueous mixture was extracted with ethyl acetate (100 mL×2). The combined organic extracts were washed with brine (100 mL), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (43.0% ACN up to 61.0% in 8 min); Detector, UV 254 nm. After purification 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-(2-methanesulfonylethyl)benzamide I-169 (83.1 mg, 69%) was obtained as an off-white solid. $^1$H-NMR (300 MHz, $CD_3OD$): δ 7.67 (d, J=8.7 Hz, 2H), 7.62-7.45 (m, 3H), 6.53 (d, J=8.8 Hz, 2H), 4.33 (s, 2H), 4.15 (s, 1H), 3.83 (t, J=6.7 Hz, 2H), 3.44 (td, J=18.4, 18.0, 9.0 Hz, 6H), 3.04 (s, 3H), 2.63-2.48 (m, 2H), 2.28 (t, J=6.8 Hz, 1H), 1.81 (s, 1H), 1.61 (d, J=6.3 Hz, 2H), 1.31 (d, J=13.1 Hz, 1H), 1.19 (d, J=7.0 Hz, 4H); MS (ES, m/z): [M+1]=604.

Example 163: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluoro-N-(2-methanesulfonylethyl)benzamide (I-170)

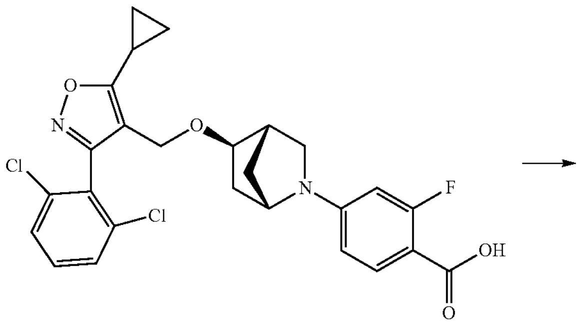

I-103

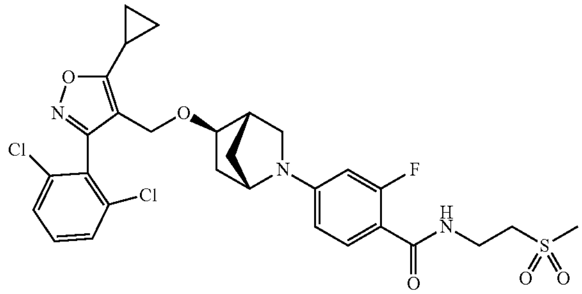

I-170

To a 50 mL round-bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoic acid (100 mg, 0.19 mmol, 1.00 equiv.), N,N-dimethylformamide (10 mL), 2-methanesulfonylethan-1-amine (60 mg, 0.49 mmol, 2.00 equiv.), HATU (110 mg, 0.29 mmol, 1.50 equiv.), and DIEA (73 mg, 0.56 mmol, 3.00 equiv.). The resulting mixture was stirred at room temperature overnight and quenched with the addition of water (100 mL). The aqueous mixture was extracted with ethyl acetate (100 mL×2) and the combined organic extracts were washed with brine (100 mL×5), dried over anhydrous sodium sulfate and concentrated under vacuum. The residue was dissolved in 2 mL of DMF and purified by Prep-HPLC using the following conditions: Column, XBridge Prep OBD C18 Column, 19*250 mm, 5 um; mobile phase, Water (0.05% TFA) and ACN (54.0% ACN up to 74.0% in 8 min); Detector, UV 220 nm. After purification 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluoro-N-(2-methanesulfonylethyl)benzamide I-170 (76.4 mg, 63%) was obtained as an off-white solid. $^1$H-NMR (400 MHz, $CD_3OD$): δ 7.69 (t, J=9.0 Hz, 1H), 7.60-7.47 (m, 3H), 6.38 (dd, J=9.1, 2.2 Hz, 1H), 6.24 (dd, J=15.6, 2.2 Hz, 1H), 4.33 (s, 2H), 4.14 (s, 1H), 3.91-3.82 (m, 2H), 3.52 (d, J=6.7 Hz, 1H), 3.46-3.33 (m, 3H), 3.05 (s, 3H), 2.60 (d, J=9.5 Hz, 1H), 2.52 (s, 1H), 2.28 (p, J=6.8 Hz, 1H), 1.81 (dd, J=12.6, 6.7 Hz, 1H), 1.60 (q, J=10.0 Hz, 2H), 1.32 (d, J=11.0 Hz, 2H), 1.22-1.15 (m, 4H); MS (ES, m/z): [M+1]=622.

Example 164: N-[2-(cyclopropanesulfonyl)ethyl]-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorobenzamide (I-171)

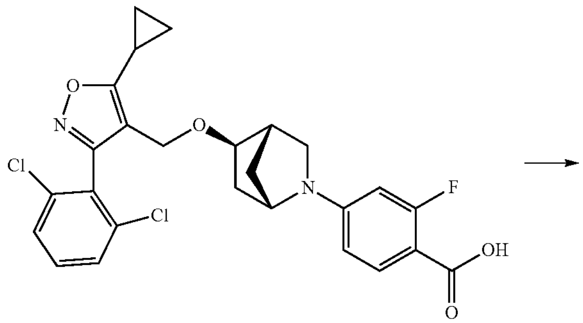

I-103

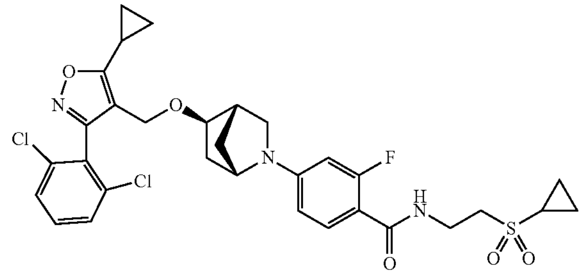

I-171

To a 25 mL round-bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoic acid I-103 (80 mg, 0.15 mmol, 1.00 equiv.), 2-(cyclopropanesulfonyl)ethan-1-amine hydrochloride (37 mg, 0.20 mmol, 1.30 equiv.), HATU (88 mg, 0.23 mmol, 1.50 equiv.), DIEA (80 mg, 0.62 mmol, 4.00 equiv.), and N,N-dimethylformamide (2 mL). The resulting mixture was stirred at room temperature for 2 h. The solids were filtered out. The filtrate was concentrated and purified by Prep-HPLC using the following conditions: Column, XBridge Shield RP18 OBD Column, 5 um, 19*150 mm; mobile phase, Water (0.05% TFA) and ACN (48.0% ACN up to 67.0% in 8 min); Detector, UV 254 nm. After purification N-[2-(cyclopropanesulfonyl)ethyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzamide I-171 (14.3 mg, 14%) was obtained as a white solid. $^1$H-NMR (300 MHz, $CD_3OD$): δ 7.68 (t, J=9.0 Hz, 1H), 7.60-7.44 (m, 3H), 6.37 (dd, J=8.9, 2.3 Hz, 1H), 6.23 (d, J=15.6 Hz, 1H), 4.31 (s, 2H), 4.12 (s, 1H), 3.88 (t, J=6.7 Hz, 2H), 3.55-3.38 (m, 4H), 2.74-2.47 (m, 3H), 2.32-2.21 (m, 1H), 1.79 (s, 1H), 1.60 (t, J=9.1 Hz, 2H), 1.31 (d, J=12.9 Hz, 1H), 1.22-1.03 (m, 8H), MS (ES, m/z): [M+1]=648.

Example 165: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluoro-N-[2-(oxane-4-sulfonyl)ethyl]benzamide (I-172)

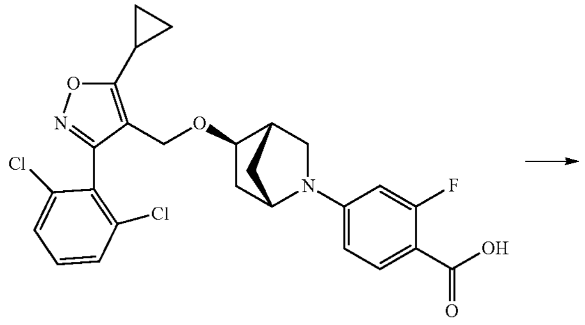

I-103

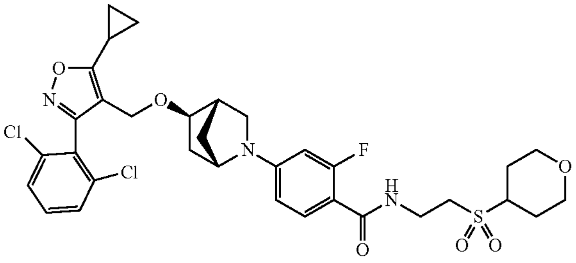

I-172

To a 50 mL round-bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoic acid I-103 (85 mg, 0.16 mmol, 1.00 equiv.), 2-(oxane-4-sulfonyl)ethan-1-amine hydrochloride (60 mg, 0.26 mmol, 1.30 equiv.), HATU (94 mg, 0.25 mmol, 1.50 equiv.), DIEA (85 mg, 0.66 mmol, 4.00 equiv.), and N,N-dimethylformamide (2 mL). The resulting mixture was stirred at room temperature for 3 h. The solids were filtered out. The filtrate was concentrated and purified by Prep-HPLC using the following conditions: Column, XBridge Shield RP18 OBD Column, 5 um, 19*150 mm; mobile phase, Water (0.05% TFA) and ACN (46% ACN up to 68% in 8 min); Detector, UV 254 nm. After purification 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluoro-N-[2-(oxane-4-sulfonyl)ethyl]benzamide I-171 (10.3 mg, 9%) was obtained as a white solid. $^{1}$H-NMR (300 MHz, $CD_3OD$): δ 7.68 (t, J=8.9 Hz, 1H), 7.60-7.44 (m, 3H), 6.37 (d, J=8.5 Hz, 1H), 6.23 (d, J=15.2 Hz, 1H), 4.31 (s, 2H), 4.16-4.00 (m, 1H), 3.85 (t, J=6.6 Hz, 2H), 3.49 (d, J=15.8 Hz, 2H), 3.41-3.34 (m, 5H), 2.59 (d, J=9.5 Hz, 1H), 2.51 (s, 1H), 2.26 (t, J=6.7 Hz, 1H), 2.00 (d, J=12.9 Hz, 2H), 1.87-1.73 (m, 3H), 1.59 (d, J=8.6 Hz, 2H), 1.31 (d, J=13.2 Hz, 1H), 1.17 (d, J=6.7 Hz, 4H); MS (ES, m/z): [M+1]=692.2.

Example 166: [2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-methylphenyl}formamido)ethyl]phosphonic Acid (I-173)

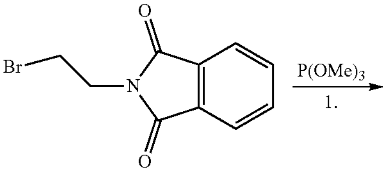

173a

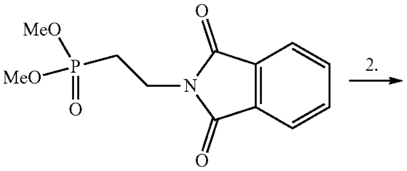

173b

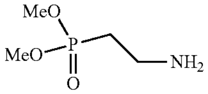

173c

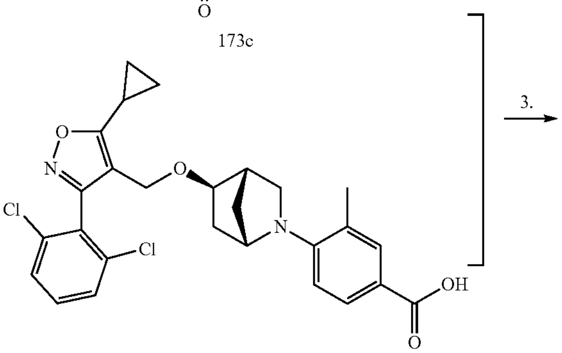

I-107

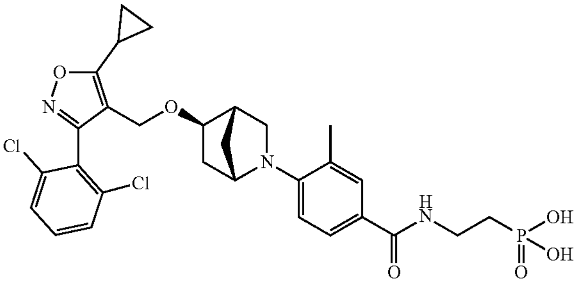

I-173

Step 1

A suspension of 2-(2-bromoethyl)isoindoline-1,3-dione 173a (7.62 g, 30 mmol) in trimethylphosphite (100 g) was heated under reflux (Bath temperature 130° C.) for 48 h. The reaction mixture was cooled to room temperature and diluted with ethyl acetate. It was washed with water, saline, dried over sodium sulfate, filtered and concentrated in vacuo. The crude material was purified by flash column chromatography using 5-10% methanol in dichloromethane as eluent to give dimethyl 2-(1,3-dioxoisoindolin-2-yl)ethylphosphonate 173b (1.5 g). $^{1}$H NMR (400 MHz. DMSO-d6): δ 8.01-7.71 (m, 4H), 3.90-3.76 (m, 2H), 3.64 (bs, 3H), 3.62 (bs, 3H), 2.28-2.10 (m, 2H); MS (ES, m/z): [M+1]=284.10.

Step 2

A solution of dimethyl 2-(1,3-dioxoisoindolin-2-yl)ethylphosphonate 173b (1.5 g, 5.3 mmol, 1 equiv.) and hydrazine hydrate (0.2 mL, 1 equiv.) in ethanol was refluxed for 3 h. The reaction mixture was cooled to room temperature and filtered. The filtrate was concentrated under the reduced pressure to give dimethyl 2-aminoethylphosphonate 173c (0.6 g). $^1$H-NMR (400 MHz, DMSO-$d_6$): δ 5.75 (s, 2H), 3.68 (bs, 3H), 3.65 (bs, 3H), 2.88-2.75 (m, 2H), 2.18-2.05 (m, 2H); MS (ES, m/z): [M+1]=154.07.

Step 3

HATU (114 mg; 2 equiv.) was added to a stirred mixture of dimethyl 2-aminoethylphosphonate 173c (60 mg, 2 equiv.), 4-((1S,4S,5R)-5-((5-cyclopropyl-3-(2,6-dichlorophenyl)isoxazol-4-yl)methoxy)-2-azabicyclo[2.2.1]heptan-2-yl)-3-methylbenzoic acid I-107 (102 mg, 1 equiv.) and DIEA (0.18 mL, 5 equiv.) in DMF (2.0 mL). The mixture was stirred at room temperature for 16 h, then diluted with ethyl acetate and washed successively with water, 5% aq. Citric acid, saline, and dried over sodium sulfate. Removal of solvents in vacuo gave a crude product which was purified by flash column chromatography using 5-10% methanol in dichloromethane as eluent to give desired intermediate (50 mg). MS (ES, m/z): [M+1]=648.05.

The above intermediate (50 mg) was dissolved in dichloromethane (4.0 mL) and treated with trimethylsilyl bromide (5.0 equiv.) at room temperature for 3 h. Then, it was concentrated under the reduced pressure. The residue was purified on Semi-prep HPLC using 30-90% acetonitrile in 30 min, method. The fractions corresponding to the desired product were lyophilized to provide Synthesis of 2-(4-((1S,4S,5R)-5-((5-cyclopropyl-3-(2,6-dichlorophenyl)isoxazol-4-yl)methoxy)-2-azabicyclo[2.2.1]heptan-2-yl)-3-methylbenzamido)ethylphosphonic acid I-173 as a trifluoroacetate salt (10.5 mg). $^1$H-NMR (400 MHz, $CD_3OD$) δ: 7.80-7.63 (m, 2H), 7.62-7.45 (m, 3H), 7.20 (d, J=8.5 Hz, 1H), 4.37 (s, 2H), 4.22 (s, 1H), 4.05 (s, 1H), 3.68-3.64 (m, 4H), 3.13 (d, J=10.6 Hz, 1H), 2.64 (s, 1H), 2.42 (s, 3H), 2.36-2.20 (m, 2H), 2.11 (dd, J=18.7 & 9.1 Hz, 2H), 1.84 (d, J=10.7 Hz, 1H), 1.74 (d, J=10.8 Hz, 1H), 1.43 (d, J=14.4 Hz, 1H), 1.45-1.23 (m, 4H); MS (ES, m/z): [M+1]=620.10.

Example 167: ({[2-({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-methylphenyl}formamido)ethyl]({[(2,2-dimethylpropanoyl)oxy]methoxy})phosphoryl}oxy)methyl 2,2-dimethylpropanoate (I-174)

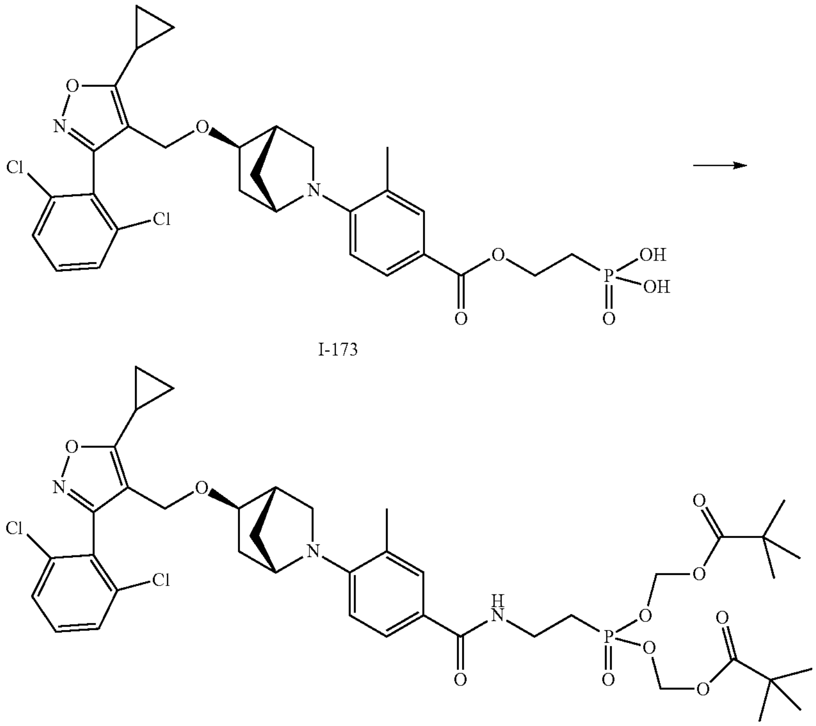

I-173

I-174

Iodomethyl pivalate (0.03 mL, 5 equiv.) was added to a solution of 2-(4-((1S,4S,5R)-5-((5-cyclopropyl-3-(2,6-dichlorophenyl)isoxazol-4-yl)methoxy)-2-azabicyclo[2.2.1]heptan-2-yl)-3-methylbenzamido)ethylphosphonic acid I-173 (15 mg, 1 equiv.) and DIEA (0.033, 7.5 equiv.) in DMF (1.0 mL). The reaction mixture was stirred for 16 h at room temperature, then diluted with ethyl acetate and washed with water, saline, dried over anhydrous sodium sulfate, filtered and concentrated in vacuo. The residue was purified on Semi-prep HPLC using 30-95% acetonitrile in 30 min, method. The fractions corresponding to the desired product were lyophilized to provide ({[2-({4-[(1S,4S,5R)-5-{([5-cyclopropyl-3-(2,6-dichlorophenyl)-1,2-oxazol-4-yl] methoxy}-2-azabicyclo[2.2.1]heptan-2-yl]-3-methylphenyl}formamido)ethyl]({[(2,2-dimethylpropanoyl)oxy]methoxy})phosphoryl}oxy)methyl 2,2-dimethylpropanoate I-174 (5.6 mg) as trifluoroacetate salt. $^{1}$H-NMR (400 MHz, DMSO-$d_6$): δ 7.62-7.39 (m, 5H), 6.79 (d, J=8.5 Hz, 1H), 4.32 (s, 2H), 4.05 (s, 1H), 3.70-3.41 (m, 8H), 2.81 (d, J=10.6 Hz, 1H), 2.64 (s, 1H), 2.36-2.21 (m, 5H), 2.11 (dd, J=18.7 & 9.1 Hz 2H), 1.64-1.62 (m, 2H), 1.27-1.20 (m, 23H); MS (ES, m/z): [M+1]=848.13.

Example 168: (2-{4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}ethyl)phosphonic Acid (I-175)

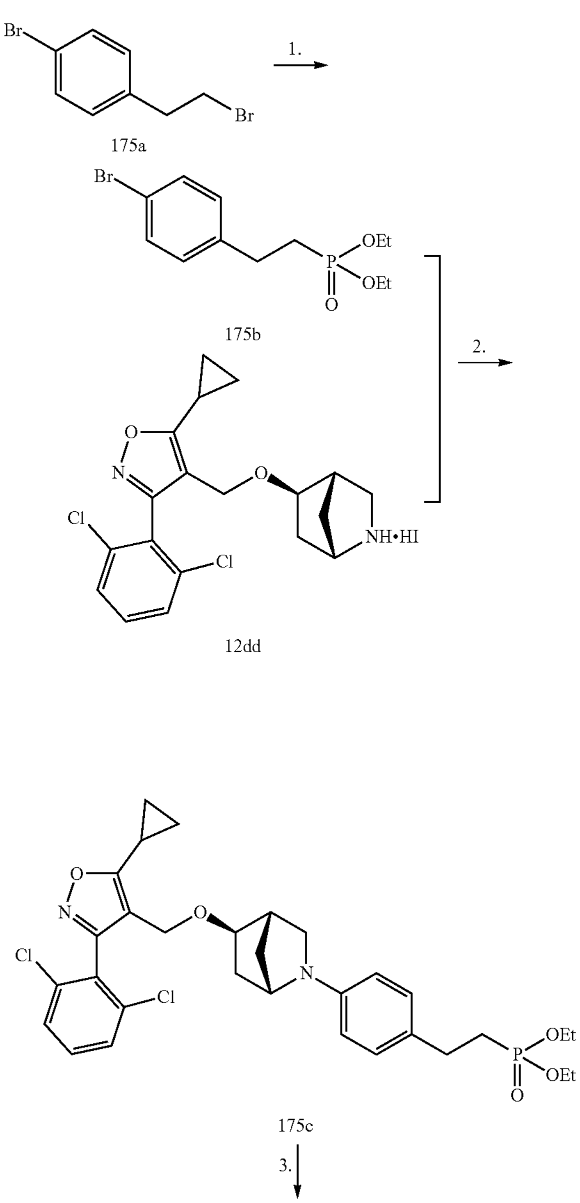

175a, 175b, 12dd, 175c

-continued

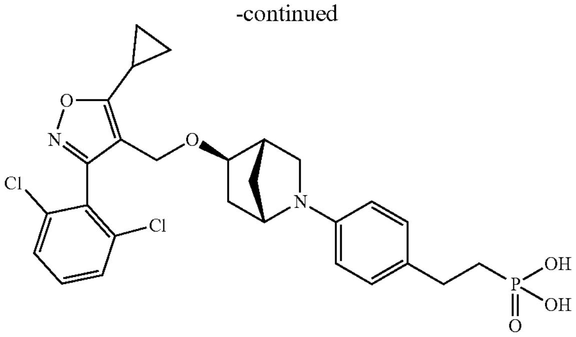

I-175

Step 1

To a 100 mL round bottom flask was added 1-bromo-4-(2-bromoethyl)benzene 175a (3.5 g, 13.26 mmol, 1.00 equiv.) and triethyl phosphite (10 mL). The mixture was heated at 135° C., overnight with stirring. After cooling to room temperature, the mixture was concentrated under vacuum and the residue was purified by silica gel column chromatography eluting with neat petroleum ether to give diethyl [2-(4-bromophenyl)ethyl]phosphonate 175b (3.5 g, 82%) as a light yellow oil.

Step 2

To a 500 mL round-bottom flask purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (500 mg, 0.986 mmol, 1.00 equiv.), toluene (150 mL), diethyl [2-(4-bromophenyl)ethyl]phosphonate 175b (465.7 mg, 1.45 mmol, 1.47 equiv.), $Cs_2CO_3$ (1.315 g, 4.04 mmol, 4.1 equiv.), RuPhos (114.3 mg), and Ru-Phos-Precatalyst (62.8 mg). The resulting mixture was heated at 100° C., overnight with stirring. After cooling to room temperature the mixture was concentrated under vacuum. The residue was treated with 150 mL of $H_2O$ and extracted with dichloromethane (50 mL×3). The combined organic extracts were washed with brine, dried over sodium sulfate, and concentrated under vacuum. The residue was purified by silica gel column chromatography eluting with ethyl acetate/petroleum ether (1:5-1:3-1:1) to afford diethyl (2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]ethyl)phosphonate 175c (400 mg, 65%) as a light brown solid.

Step 3

To a 100 mL round bottom flask was added diethyl (2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]ethyl)phosphonate 175c (200 mg, 0.32 mmol, 1.00 equiv.), dichloromethane (10 mL), and TMSBr (247 mg, 1.61 mmol, 5.0 equiv.). The resulting mixture was stirred at 10 to 25° C. for 2 h. 100 mL of DCM was added followed by 100 mL of water. The mixture was separated, and the aqueous layer was extracted with dichloromethane (50 mL×3). The combined organic extracts were washed with brine, dried and concentrated under vacuum. The crude product was purified by Prep-HPLC using the following conditions Column, XBridge Shield RP18 OBD Column, 5 um, 19*150 mm; mobile phase, Water (0.05% $NH_3H_2O$) and ACN (20.0% ACN up to 41.0% in 8 min); Detector, UV 254 nm. After purification (2-[4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]ethyl)phosphonic acid I-175 (35 mg, 19%) was obtained as an off-white solid. $^1$H-NMR (300 MHz, $CDCl_3$): δ 7.35 (s, 3H), 6.92 (s, 2H), 6.44 (s, 2H), 4.23 (s, 3H), 3.88 (s, 1H), 3.37 (s, 3H), 2.79 (s, 1H), 2.08 (s, 5H), 1.57 (s, 3H), 1.16 (d, J=38.8 Hz, 6H); MS (ES, m/z): [M+1]=563.15.

Example 169: ({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}methyl)phosphonic Acid (I-176)

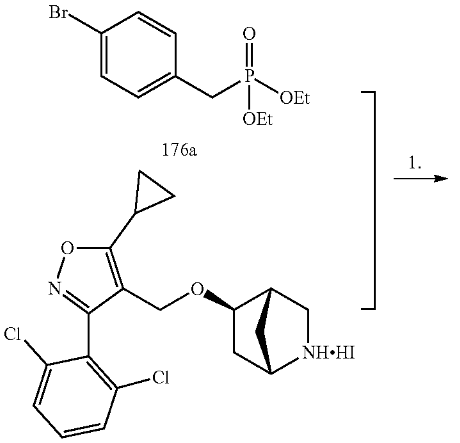

176a

12dd

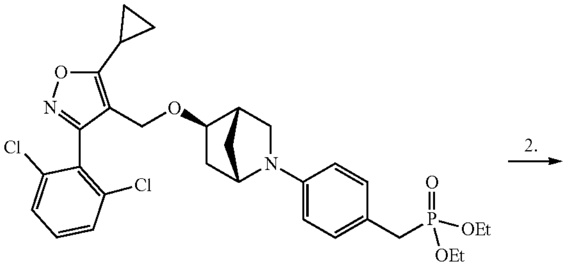

176b

-continued

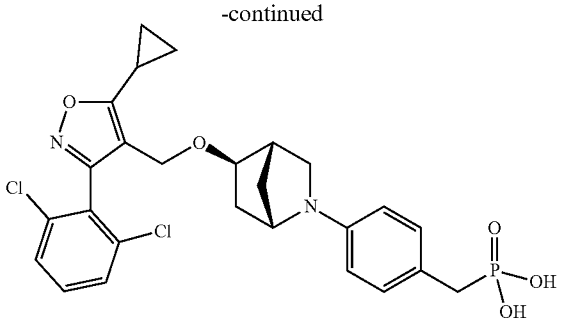

I-176

Step 1

To a 100 mL round bottom flask purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (300 mg, 0.5915 mmol, 1.00 equiv.), diethyl [(4-bromophenyl)methyl]phosphonate 176a (267.2 mg, 0.87 mmol, 1.47 equiv.), toluene (50 mL), RuPhos (67.23 mg), Rh-Phos-Precatalyst (36.9 mg), and $Cs_2CO_3$ (773.5 mg, 2.37 mmol, 3.00 equiv.). The resulting mixture was heated at 100° C., overnight with stirring. After cooling to room temperature, the solids were filtered out, and the filtrate was concentrated under vacuum. The residue was purified by silica gel column chromatography eluting with ethyl acetate/petroleum ether (1:10-1:5-1:3-1:1) to furnish diethyl ([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methyl)phosphonate 176b (267 mg, 75%) as a white solid.

Step 2

To a 100 mL round-bottom flask was added diethyl ([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methyl)phosphonate 176b (300 mg, 0.50 mmol, 1.00 equiv.), dichloromethane (5 mL), and TMSBr (380 mg). The resulting mixture was stirred at 10-25° C., for 1 h. 100 mL of $H_2O$ was added, the aqueous mixture was extracted with dichloromethane (50 mL×3), and the combined organic extracts were washed with brine, dried over anhydrous sodium sulfate, then concentrated under vacuum. The crude product was purified by Prep-HPLC using the following conditions Column, XBridge Shield RP18 OBD Column, 5 um, 19*150 mm; mobile phase, Water (0.05% NH3H2O) and ACN (20.0% ACN up to 33.0% in 11 min); Detector, UV 254 nm. After purification ([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methyl)phosphonic acid I-176 (106 mg, 39%) as a white solid. $^1$H-NMR (300 MHz, $CDCl_3$): δ 7.36 (s, 3H), 7.13 (s, 2H), 6.44 (s, 2H), 4.20 (s, 4H), 3.27 (s, 3H), 2.82 (s, 1H), 2.35 (s, 2H), 2.11 (s, 1H), 1.72 (s, 1H), 1.28 (s, 2H), 1.24 (s, 2H), 1.12 (d, J=9.2 Hz, 4H); MS (ES, m/z): [M+1]=549.1.

Example 170: methyl 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-2-fluorobenzoate (I-177)

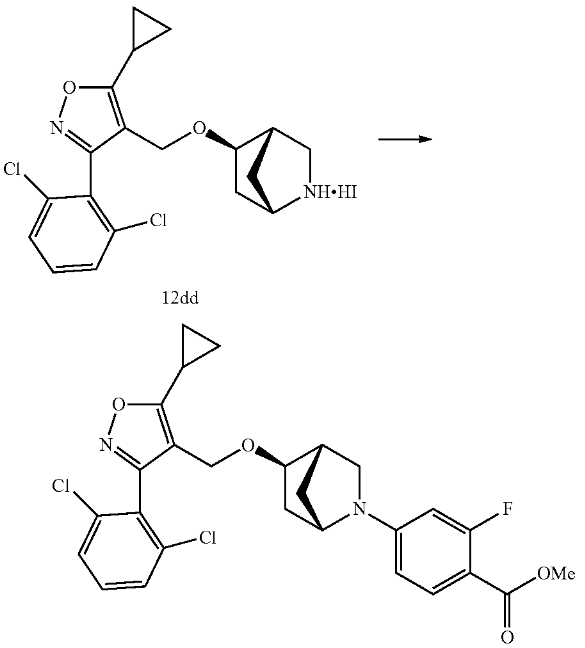

12dd

I-177

To a 50 mL round bottom flask purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (250 mg, 0.49 mmol, 1.00 equiv.), methyl 2,4-difluorobenzoate (225 mg, 1.31 mmol, 2.67 equiv.), CsF (298 mg, 1.96 mmol, 4.00 equiv.), and 1-Ethyl-3-methylimidazolium dimethyl phosphate (3 mL). The resulting mixture was heated at 90° C., overnight. After cooling to room temperature, the mixture was diluted with 20 mL of $H_2O$ and extracted with ethyl acetate (30 mL×2). The combined organic extracts were washed with brine (30 mL×3), dried over anhydrous sodium sulfate and concentrated under vacuum. The residue was purified by silica gel column chromatography eluting with ethyl acetate/petroleum ether (1:3). Removal of solvents afforded methyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-fluorobenzoate I-177 (158.6 mg, 50%) as an off-white solid. $^1$H-NMR (300 MHz, $CDCl_3$): δ 7.77 (t, J=8.7 Hz, 1H), 7.49-7.29 (m, 3H), 6.22 (dd, J=8.8, 2.4 Hz, 1H), 6.10 (dd, J=14.3, 2.3 Hz, 1H), 4.28 (s, 2H), 4.04 (s, 1H), 3.87 (s, 3H), 3.54-3.44 (m, 1H), 3.35 (dd, J=9.3, 4.0 Hz, 1H), 2.63-2.49 (m, 2H), 2.12 (ddt, J=12.9, 9.6, 4.8 Hz, 1H), 1.85 (ddd, J=13.3, 6.8, 2.4 Hz, 1H), 1.71-1.54 (m, 2H), 1.41-1.22 (m, 3H), 1.27-1.03 (m, 2H); MS (ES, m/z): [M+1]=531.05.

Example 171: 5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3,4-thiadiazole-2-carboxylic Acid (I-178)

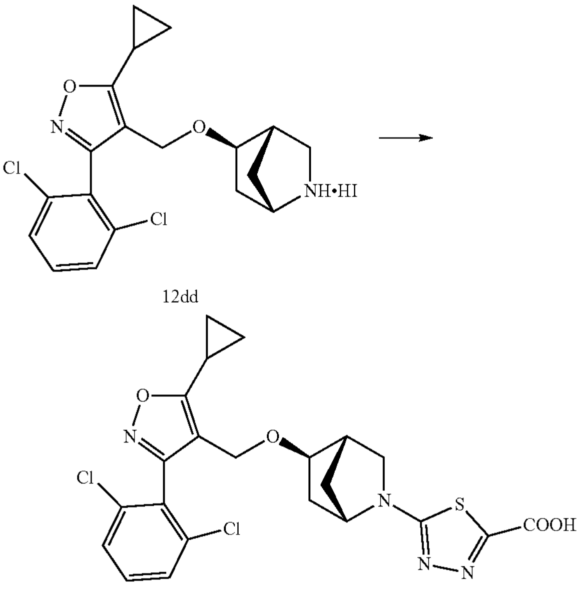

12dd

I-178

A mixture of 4-(((1S,4S,5R)-2-azabicyclo[2.2.1]heptan-5-yloxy)methyl)-5-cyclopropyl-3-(2,6-dichlorophenyl)isoxazole hydroiodide salt 12dd (214 mg, 0.52 mmol, 1 equiv.), ethyl 5-bromo-1,3,4-thiadiazole-2-carboxylate (136 mg, 1.3 equiv.), Cesium carbonate (440 mg, 2.5 equiv.), in N,N-dimethylacetamide (5.0 mL) was heated at 100° C. for 16 h with stirring. After cooling to room temperature, water (15 mL) was added, the mixture was further diluted with ethyl acetate (60 mL) and separated. The organic layer was washed with saline, dried over anhydrous $Na_2SO_4$, filtered and concentrated under reduced pressure. The crude material was purified on Isco silica gel column chromatography using 10-20% ethyl acetate in dichloromethane as eluent to give the desired intermediate and used as such in the next step (MS (ES, m/z): [M+1]=535.20).

The above residue (80 mg) was dissolved in ethanol (5.0 mL) and treated with a 1N NaOH aqueous solution (0.5 mL) at 60° C., for 4 h. After cooling to room temperature, the mixture was neutralized with glacial acetic acid and concentrated in vacuo to a residue, which was purified by Semi-prep HPLC using 30-90% ACN (0.1% TFA) in 30 min, method to give 5-((1S,4S,5R)-5-((5-cyclopropyl-3-(2,6-dichlorophenyl)isoxazol-4-yl)methoxy)-2-azabicyclo[2.2.1]heptan-2-yl)-1,3,4-thiadiazole-2-carboxylic acid I-178 as a trifluoroacetate salt (24 mg). $^1$H-NMR (400 MHz, DMSO-$d_6$): δ 7.66-7.55 (m, 3H), 4.26 (s, 2H), 4.01 (s, 1H), 3.53 (bs, 1H), 3.38-3.36 (m, 1H), 2.81 (d, J=8.1 Hz, 1H), 2.33-2.32 (m, 1H), 1.83-1.82 (m, 1H), 1.51 (dd, J=29.2 & 9.4 Hz, 2H), 1.21-1.09 (m, 6H); MS (ES, m/z): [M+1]=507.15.

Example 172: 3-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,2-oxazole-5-carboxylic Acid (I-179)

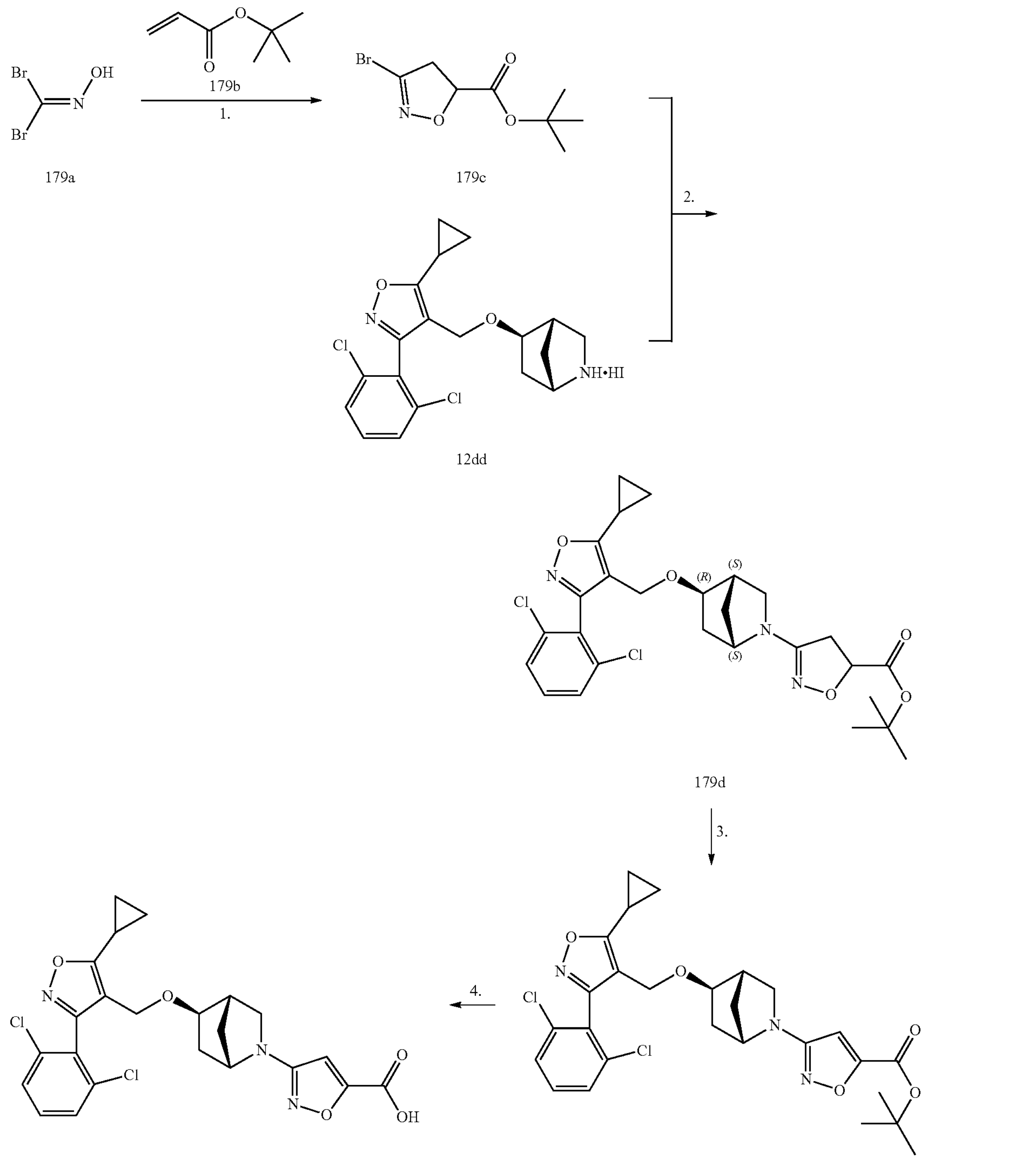

179a 179c 12dd 179d 179e I-179

Step 1

To a 25 mL round-bottom flask was added 1-bromo-N-hydroxymethanecarbonimidoyl bromide 179a (3 g, 14.79 mmol, 1.00 equiv.) and N,N-dimethylformamide (15 mL). The solution was cooled to −10° C., and added with tert-Butyl acrylate (2.3 g, 17.95 mmol, 1.20 equiv.) dropwise. An aqueous solution of $KHCO_3$ (3.8 g, 2.50 equiv.) in water (23 mL) was added dropwise with stirring in 1.5 hr. The resulting mixture was stirred for another 1.5 h at room temperature. The pH value of the solution was adjusted to 5 using a 0.5 M HCl aqueous solution. The reaction mixture was diluted with 400 mL of methyl tert-butyl ether, and washed with brine (200 mL×3). The organic layer was dried over anhydrous sodium sulfate and concentrated under vacuum. The crude product was purified by Flash-Prep-HPLC using the following conditions (IntelFlash-1): Column, silica gel; mobile phase: EA:PE=0:100 increasing to EA:PE=10:90 within 15 min; Detector, UV 254 nm. Removal of solvents gave tert-butyl 3-bromo-4,5-dihydro-1,2-oxazole-5-carboxylate 179c (3.47 g, 94%) as a colorless oil.

Step 2

To a 8 mL sealed tube was added (1S,4S,5R)-5-[[5-cyclopropyl-3-(2,6-dichlorophenyl)-1,2-oxazol-4-yl]methoxy]-2-azabicyclo[2.2.1]heptane hydroiodide 12dd (300 mg, 0.5915 mmol, 1.00 equiv.), n-BuOH (5 mL), tert-butyl 3-bromo-4,5-dihydro-1,2-oxazole-5-carboxylate 179c (450 mg, 1.80 mmol, 3.0 equiv.), and DIEA (600 mg, 4.64 mmol, 7.8 equiv.). The resulting mixture was stirred at ! 10° C., overnight. After cooling to room temperature, the mixture was diluted with 100 mL of EA and washed with brine (50 mL), dried over sodium sulfate and concentrated under vacuum. The residue was purified by silica gel column chromatography eluting with PE:EA (1:1) to afford tert-butyl 3-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4,5-dihydro-1,2-oxazole-5-carboxylate 179d (250 mg, 77.5%) as a brownish oil.

Step 3

To a 5 mL sealed tube was added tert-butyl 3-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4,5-dihydro-1,2-oxazole-5-carboxylate 179d (300 mg, 0.55 mmol, 1.00 equiv.), toluene (1.2 mL), imidazole (112 mg, 1.50 equiv.), and iodine (210 mg, 3.00 equiv.). The resulting mixture was stirred at 110° C., overnight and concentrated under vacuum. The residue was purified by silica gel column chromatography eluting with ethyl acetate/petroleum ether (1:3) to provide tert-butyl 3-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2-oxazole-5-carboxylate 179e (56 mg, 19%) as light yellow oil.

Step 4

To a 25 mL vial was added tert-butyl 3-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2-oxazole-5-carboxylate 179e (56 mg, 0.10 mmol, 1.00 equiv.), dichloromethane (2 mL), and trifluoroacetic acid (1 mL). The resulting mixture was stirred at room temperature for 2 h. The pH value of the solution was adjusted to 7.0 using a 1 M sodium carbonate aqueous solution. The aqueous mixture was extracted with ethyl acetate (20 mL×3); the combined organic extracts wee washed with brine, dried over sodium sulfate, and concentrated under vacuum. The crude product was purified by Flash HPLC using the following conditions: Column, silica gel; mobile phase: EA:PE increasing to EA:PE=100 within 25 min; Detector, UV 254 nm. After purification 3-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,2-oxazole-5-carboxylic acid I-179 (9.5 mg, 19%) as a colorless oil. $^1$H-NMR (300 MHz, $CD_3OD$): δ 7.56-7.39 (m, 3H), 6.54-6.44 (m, 1H), 4.27 (d, J=1.0 Hz, 2H), 3.91 (s, 1H), 3.46 (d, J=5.3 Hz, 1H), 3.22 (dd, J=9.5, 4.1 Hz, 1H), 2.62 (d, J=9.6 Hz, 1H), 2.44 (d, J=2.3 Hz, 1H), 2.30-2.10 (m, 1H), 1.85-1.72 (m, 1H), 1.52 (d, J=2.2 Hz, 2H), 1.34-1.19 (m, 2H), 1.14 (d, J=6.7 Hz, 4H); MS (ES, m/z): [M+1]=491.

Example 173: 5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1-methyl-1H-pyrazole-3-carboxylic Acid (I-180)

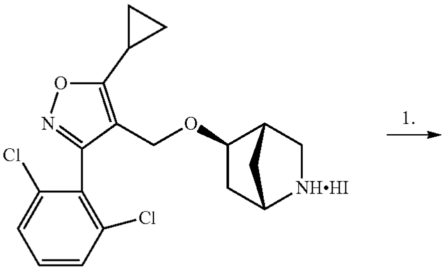

12dd

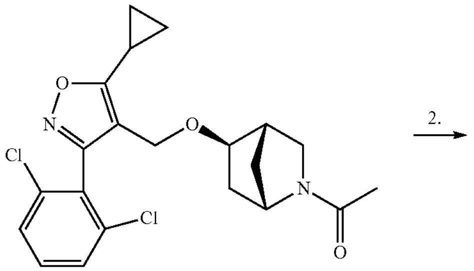

180a

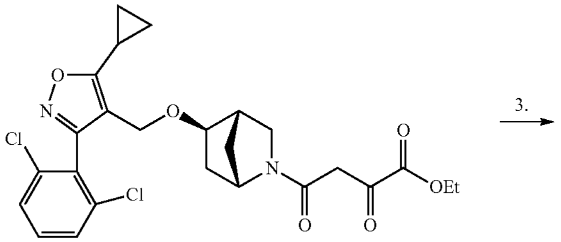

180b

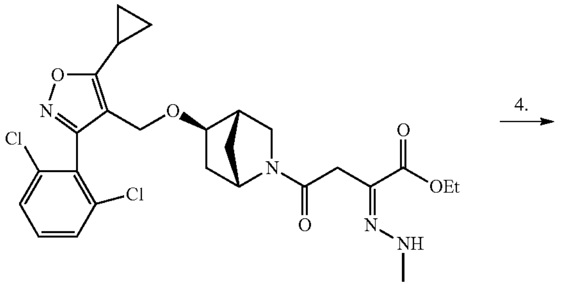

180c

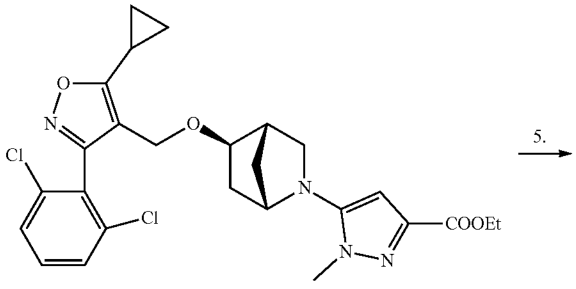

180d

-continued

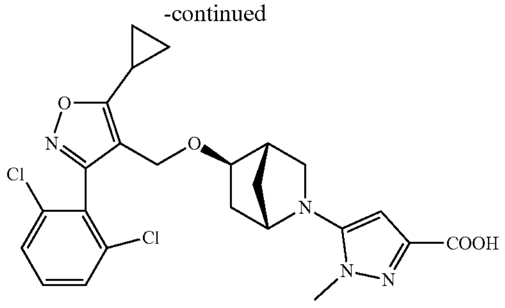

I-180

Step 1

To a 250 mL round bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide 12dd (600 mg, 1.183 mmol, 1.00 equiv.), dichloromethane (50 mL) and DIEA (610 mg, 4.72 mmol, 4.00 equiv.). The mixture was cooled to 0° C., and added with AcCl (0.25 g, 2.68 equiv.) dropwise with stirring. The resulting mixture was stirred for 10 min at room temperature and concentrated. The residue was purified by silica gel column chromatography eluting with ethyl acetate/petroleum ether (2:1) to give 1-[(1S,4S,5R)-5-[[5-cyclopropyl-3-(2,6-dichlorophenyl)-1,2-oxazol-4-yl]methoxy]-2-azabicyclo[2.2.1]heptan-2-yl]ethan-1-one 180a (0.34 g, 68%) as a red oil.

Step 2

To a 10 mL sealed tube was added 1-[(1S,4S,5R)-5-[[5-cyclopropyl-3-(2,6-dichlorophenyl)-1,2-oxazol-4-yl]methoxy]-2-azabicyclo[2.2.1]heptan-2-yl]ethan-1-one 180a (500 mg, 1.19 mmol, 1.00 equiv.), diethyl oxalate (693.7 mg, 4.75 mmol, 4.00 equiv.), and a 2M solution of EtONa in ethanol (0.770 mL). The resulting mixture was stirred at 80° C., overnight. After cooling to room temperature, the mixture was diluted with 50 mL of $H_2O$, extracted with ethyl acetate (30 mL×3), and the combined organic extracts were dried over anhydrous sodium sulfate and concentrated in vacuum. The residue was purified by silica gel column chromatography eluting with ethyl acetate/petroleum ether (1:10-1:5) to give ethyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2,4-dioxobutanoate 180b (350 mg, 57%) as a light yellow oil.

Step 3

To a 50 mL round-bottom flask was added ethyl 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2,4-dioxobutanoate 180b (60 mg, 0.12 mmol, 1.00 equiv.), TFA (1.5 mL), methyl hydrazine (0.015 mL), and $CF_3CH_2OH$ (5 mL). The resulting mixture was stirred at room temperature overnight and concentrated under vacuum to give ethyl (2Z)-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-(2-methylhydrazin-1-ylidene)-4-oxobutanoate 180c (60 mg, 95%) as a light yellow crude oil.

Step 4

To a 100 mL round-bottom flask was added ethyl (2E)-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-2-(2-methylhydrazin-1-ylidene)-4-oxobutanoate 180c (320 mg, 0.58 mmol, 1.00 equiv.), $CF_3CH_2OH$ (5 mL), and Lawesson's reagent (306.5 mg, 0.76 mmol, 1.3 equiv.). The resulting mixture was stirred at 65° C., for 1 h and concentrated under vacuum. The residue was purified by silica gel column chromatography eluting with ethyl acetate/petroleum ether (1:10-1:5-1:2). Removal of solvents gave ethyl 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1-methyl-1H-pyrazole-3-carboxylate 180d (200 mg, 65%) as a light yellow solid.

Step 5

To a 25 mL round-bottom flask was added ethyl 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1-methyl-1H-pyrazole-3-carboxylate 180d (80 mg, 0.15 mmol, 1.00 equiv.), ethanol (3 mL), water (0.5 mL), and sodium hydroxide (35 mg, 0.88 mmol, 5.81 equiv.). The resulting mixture was stirred at 60° C., for 2 h. After cooling to room temperature, the pH value of the solution was adjusted to 7 using a 1M hydrogen chloride aqueous solution. The mixture was concentrated under vacuum. The crude product was purified by Prep-HPLC using the following conditions Column, XBridge Prep OBD C18 Column, 19*250 mm, 5 um; mobile phase, Water (0.05% TFA) and ACN (48.0% ACN up to 63.0% in 8 min); Detector, uv 220 nm. After purification 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1-methyl-1H-pyrazole-3-carboxylic acid I-180 (32 mg, 42%) as a blue color solid. $^1$H-NMR (300 MHz, $CDCl_3$): δ 7.41 (q, J=7.2 Hz, 3H), 6.12 (s, 1H), 4.28 (s, 2H), 3.96 (s, 6H), 3.79 (s, 2H), 3.63 (s, 2H), 3.23 (s, 1H), 2.53 (d, J=46.3 Hz, 1H), 2.13 (s, 1H), 2.02 (s, 1H), 1.31-1.10 (m, 4H); MS (ES, m/z): [M+1]=503.0.

Example 174: N-(cyclohexanesulfonyl)-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]benzamide (I-181)

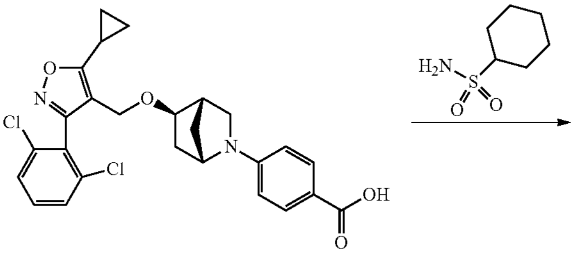

I-52

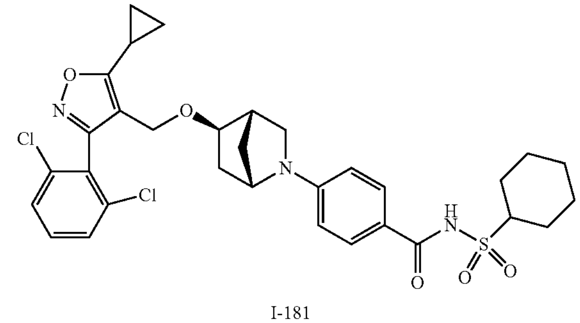

I-181

To a 25 mL round-bottom flask purged with and maintained under an inert atmosphere of nitrogen was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl] benzoic acid I-52 (100 mg, 0.20 mmol, 1.00 equiv.), dichloromethane (1 mL), 4-dimethylaminopyridine (73 mg, 0.60 mmol, 3.00 equiv.), cyclohexanesulfonamide (98 mg, 0.60 mmol, 3.00 equiv.), and EDCI (57 mg, 0.30 mmol, 1.50 equiv.). The resulting mixture was stirred at room temperature overnight and quenched with the addition of 2 mL of water. The aqueous mixture was extracted with 100 mL of ethyl acetate; the organic layer was washed with a 1M hydrogen chloride aqueous solution (10 mL×2), brine (20 mL×2), dried over anhydrous sodium sulfate, and concentrated under vacuum. The residue was dissolved in 1 mL of DMF and purified by Prep-HPLC using the following conditions: Column, XBridge Prep OBD C18 Column, 19*250 mm, 5 um; mobile phase, Water (0.05% TFA) and ACN (69.0% ACN up to 84.0% in 8 min); Detector, UV 220 nm. After purification N-(cyclohexanesulfonyl)-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzamide I-181 (29.5 mg, 23%) as a gray solid. $^1$H-NMR (300 MHz, $CD_3OD$): δ 7.70 (d, J=9.0 Hz, 4H), 7.53-7.40 (m, 4H), 6.49 (d, J=8.8 Hz, 4H), 4.28 (s, 4H), 4.15 (s, 2H), 3.32 (s, 1H), 2.57 (s, 1H), 2.48 (s, 2H), 2.09 (s, 2H), 1.86 (s, 2H), 1.54 (s, 3H), 1.28 (d, J=12.8 Hz, 5H), 1.13 (d, J=6.8 Hz, 7H), 0.17 (s, 1H); MS (ES, m/z): [M+1]=644.35.

Example 175: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(oxane-4-sulfonyl) benzamide (I-182)

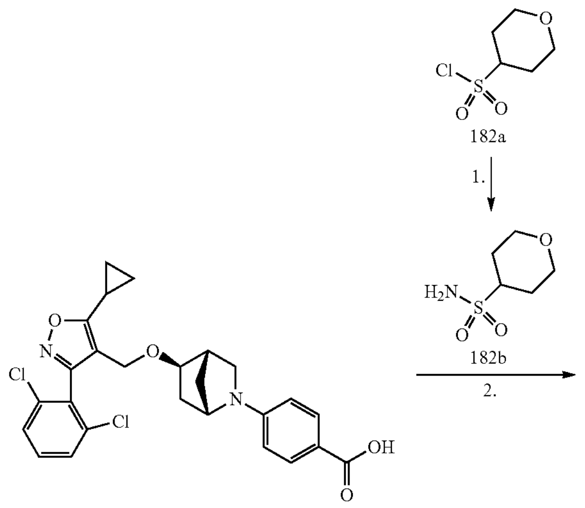

182a

182b

I-52

-continued

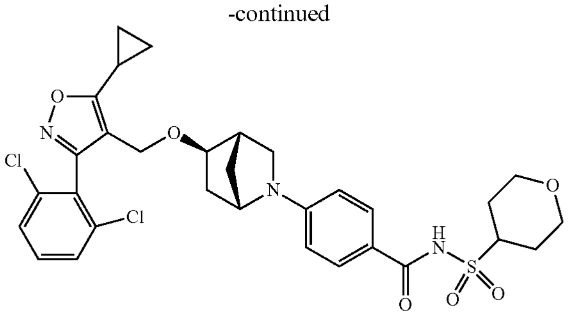

I-182

Step 1

To a 250 mL round-bottom flask was added oxane-4-sulfonyl chloride 182a (1 g, 5.42 mmol, 1.00 equiv.) followed by a 0.5 M solution of $NH_3$ in tetrahydrofuran (20 mL). The resulting mixture was stirred at room temperature for 30 min and concentrated under vacuum. The residue was purified by silica gel column chromatography eluting with dichloromethane/ethyl acetate (2:1) to give oxane-4-sulfonamide 182b (400 mg, 45%) as a light yellow solid.

Step 2

To a 8 mL vial was added oxane-4-sulfonamide 182b (150 mg, 0.91 mmol, 2.00 equiv.), 4-[(1S,4S)-5-[5-cyclopropyl-3-(2,6-dichlorophenyl)-1,2-oxazol-4-yl]methoxy-2-azabicyclo[2.2.1]heptan-2-yl]benzoic acid I-52 (220 mg, 0.44 mmol, 1.00 equiv.), dichloromethane (2 mL), 4-dimethylaminopyridine (162 mg, 1.33 mmol, 3.00 equiv.), and EDCI (127 mg, 0.66 mmol, 1.50 equiv.). The resulting mixture was stirred at room temperature overnight. The mixture was diluted with $H_2O$ (10 mL). The pH value of the solution was adjusted to 7 using a 1M HCl aqueous solution, and the aqueous mixture was extracted with dichloromethane (20 mL×3). The combined organic extracts were washed with brine (20 mL), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (54.0% ACN up to 60.0% in 8 min); Detector, uv 254 nm. Removal of solvents afforded 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-(oxane-4-sulfonyl)benzamide I-182 (125.2 mg, 44%) as a colorless solid. $^1$HNMR (300 MHz, $CD_3OD$): δ 7.74 (d, J=8.8 Hz, 2H), 7.60-7.41 (m, 3H), 6.53 (d, J=8.9 Hz, 2H), 4.31 (s, 2H), 4.18 (s, 1H), 4.12-3.85 (m, 3H), 3.55-3.31 (m, 4H), 2.62 (d, J=9.6 Hz, 1H), 2.52 (s, 1H), 2.26 (p, J=6.7 Hz, 1H), 2.04-1.74 (m, 5H), 1.59 (q, J=10.0 Hz, 2H), 1.32 (d, J=13.2 Hz, 1H), 1.17 (d, J=6.7 Hz, 4H); MS (ES, m/z): [M+1]=646.15.

Example 176: Synthesis of I-183 to I-207

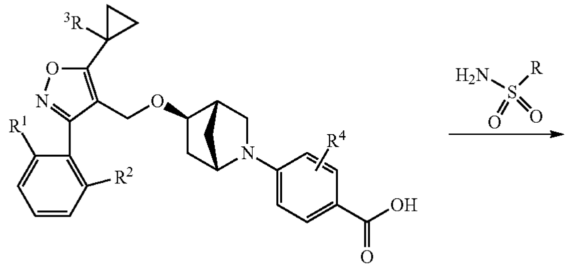

I-Acids

-continued

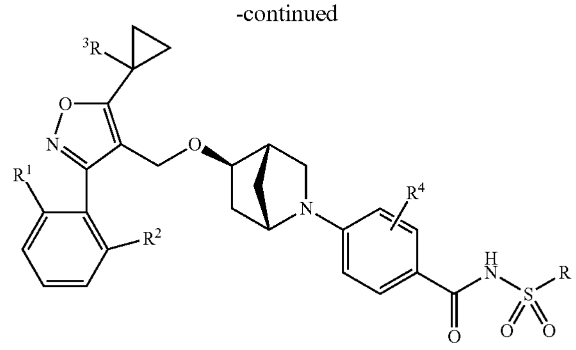

I-x

Acyl-sulfonamide compounds of I-183 to I-207 were prepared from the corresponding acids (I-Acids) and sulfonamides following the procedure described in either Preparative Example 174 if the sulfonamide reagent is commercially available or Preparative Example 175 when the sulfonamide needs to be converted from a commercially available sulfonyl chloride. The data for compounds I-183 to 1-207 is summarized in Table 9.

TABLE 9

| Acid SM | Cmpd Structure | Cmpd No. | MS/$^1$H NMR |
|---|---|---|---|
| I-52 | 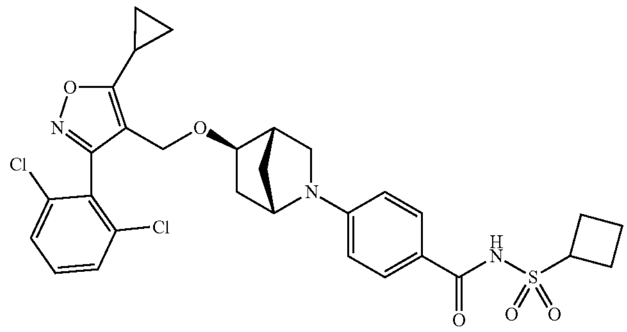 [SMILES: O=C(NS(=O)(=O)C1CCC1)c1ccc(N2C[C@@H]3C[C@H]2C[C@H]3OCc2c(-c3c(Cl)cccc3Cl)noc2C2CC2)cc1] | I-183 | MS (ES, m/z): [M + 1] = 616.5. $^1$H NMR (300 MHz, $CDCl_3$) δ: 8.27 (s, 1H), 7.67 (d, J = 8.8 Hz, 2H), 7.49-7.27 (m, 3H), 6.50-6.39 (m, 2H), 4.62 (p, J = 8.5 Hz, 1H), 4.28 (d, J = 0.9 Hz, 2H), 4.11 (s, 1H), 3.49 (d, J = 5.9 Hz, 1H), 3.39 (dd, J = 9.4, 4.0 Hz, 1H), 2.75-2.57 (m, 3H), 2.53 (s, 1H), 2.38 (ddt, J = 13.1, 8.7, 6.3 Hz, 2H), 2.09 (dddd, J = 22.3, 9.3, 5.8, 3.0 Hz, 3H), 1.92-1.78 (m, 1H), 1.63 (q, J = 10.2 Hz, 2H), 1.36 (d, J = 13.4 Hz, 1H), 1.31-1.24 (m, 2H), 1.19-1.09 (m, 2H). |
| I-52 | 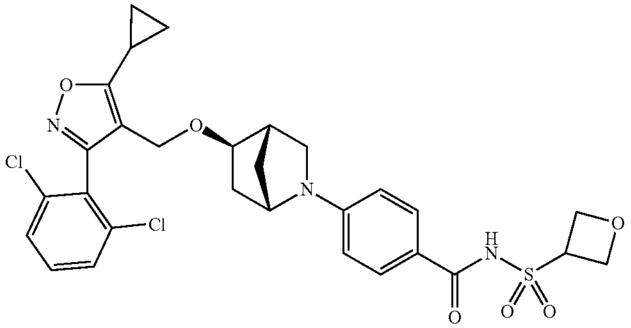 [SMILES: O=C(NS(=O)(=O)C1COC1)c1ccc(N2C[C@@H]3C[C@H]2C[C@H]3OCc2c(-c3c(Cl)cccc3Cl)noc2C2CC2)cc1] | I-184 | MS (ES, m/z): [M + 1] = 618.5. $^1$H NMR (300 MHz, $CDCl_3$) δ: 8.51 (s, 1H), 7.65 (d, J = 8.8 Hz, 2H), 7.49-7.27 (m, 3H), 6.43 (t, J = 8.8 Hz, 2H), 5.17-5.04 (m, 2H), 5.01-4.87 (m, 2H), 4.28 (d, J = 0.8 Hz, 2H), 4.12 (s, 1H), 3.55-3.46 (m, 1H), 3.39 (dd, J = 9.4, 4.0 Hz, 1H), 2.61 (d, J = 9.4 Hz, 1H), 2.54 (d, J = 3.7 Hz, 1H), 2.20-2.00 (m, 1H), 1.91-1.78 (m, 1H), 1.64 (q, J = 10.1 Hz, 2H), 1.45-1.32 (m, 1H), 1.28 (dt, J = 5.9, 3.0 Hz, 2H), 1.19-1.06 (m, 2H). |

TABLE 9-continued

| Acid SM | Cmpd Structure | Cmpd No. | MS/$^1$H NMR |
|---|---|---|---|
| I-52 | 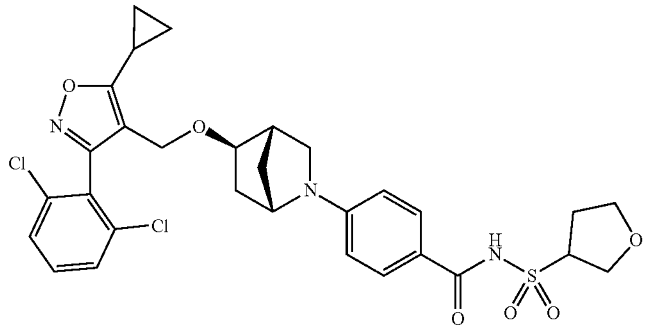 [SMILES: O=C(NS(=O)(=O)C1CCOC1)c1ccc(N2C[C@@H]3C[C@H]2C[C@H]3OCc2c(-c3c(Cl)cccc3Cl)noc2C2CC2)cc1] | I-185 | MS (ES, m/z): [M + 1] = 631.95. $^1$H NMR (400 MHz, DMSO-d6) δ: 11.57 (s, 1H), 7.73 (d, J = 8.1 Hz, 2H), 7.64-7.55 (m, 3H), 6.50 (d, J = 8.6 Hz, 2H), 4.50-4.37 (m, 1H), 4.25-4.20 (m, 4H), 4.08-3.83 (m, 3H), 3.69 (t, J = 6.9 Hz, 1H), 3.44 (d, J = 5.3 Hz, 1H), 3.30 (d, J = 6.2 Hz, 1H), 2.50-2.49 (m, 1H), 2.26 (dt, J = 13.9 & 5.8 Hz, 2H), 1.78-1.56 (m, 1H), 1.44 (dd, J = 24.4 & 10.1 Hz, 2H), 1.28-0.96 (m, 6H) |
| I-52 | 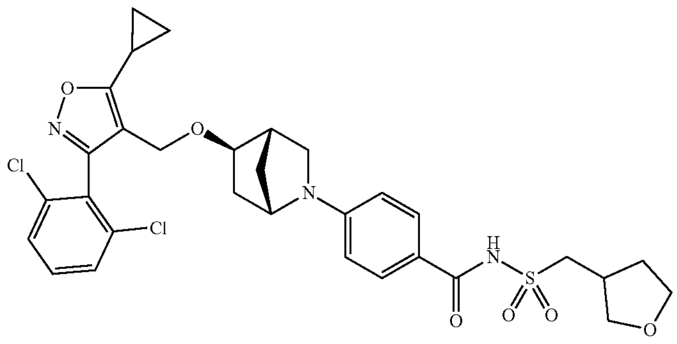 [SMILES: O=C(NS(=O)(=O)CC1CCOC1)c1ccc(N2C[C@@H]3C[C@H]2C[C@H]3OCc2c(-c3c(Cl)cccc3Cl)noc2C2CC2)cc1] | I-186 | MS (ES, m/z): [M + 1] = 645.90. $^1$H NMR (400 MHz, DMSO-d6) δ: 11.54 (s, 1H), 7.72 (d, J = 8.5 Hz, 2H), 7.66-7.56 (m, 3H), 6.50 (d, J = 8.8 Hz, 2H), 4.26-4.21 (m, 4H), 3.93-3.79 (m, 1H), 3.76-3.64 (m, 3H), 3.45 (d, J = 5.3 Hz, 1H), 3.38 (t, J = 7.9 Hz, 1H), 3.31 (dd, J = 9.6 & 3.9 Hz, 1H), 2.62-2.50 (m, 2H), 2.43-2.27 (m, 1H), 2.10 (dt, J = 10.6 & 3.7 Hz, 1H), 1.78-1.56 (m, 2H), 1.45 (dd, J = 23.1 & 9.4 Hz, 2H), 1.26-1.06 (m, 6H) |
| I-52 | 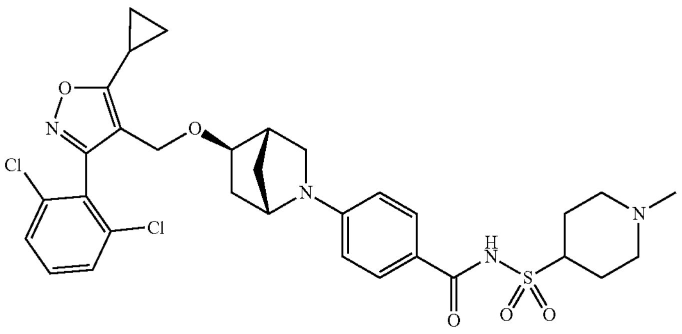 [SMILES: CN1CCC(S(=O)(=O)NC(=O)c2ccc(N3C[C@@H]4C[C@H]3C[C@H]4OCc3c(-c4c(Cl)cccc4Cl)noc3C3CC3)cc2)CC1] | I-187 | MS (ES, m/z): [M + 1] = 659.2. $^1$H NMR (400 MHz, $CD_3OD$) δ: 7.79 (d, J = 8.6 Hz, 2H), 7.61-7.46 (m, 3H), 6.51 (d, J = 8.7 Hz, 2H), 4.32 (s, 2H), 4.17 (s, 1H), 3.94 (s, 1H), 3.59 (d, J = 12.9 Hz, 2H), 3.50 (d, J = 6.2 Hz, 1H), 3.38 (dd, J = 9.5, 4.0 Hz, 1H), 3.07 (s, 2H), 2.86 (s, 3H), 2.61 (d, J = 9.5 Hz, 1H), 2.52 (s, 1H), 2.41-2.33 (m, 2H), 2.33-2.21 (m, 1H), 2.16 (s, 2H), 1.81 (dd, J = 13.3, 6.6 Hz, 1H), 1.67-1.53 (m, 3H), 1.32 (d, J = 11.1 Hz, 4H), 1.22-1.15 (m, 5H), 0.12 (s, 1H). |
| I-52 | 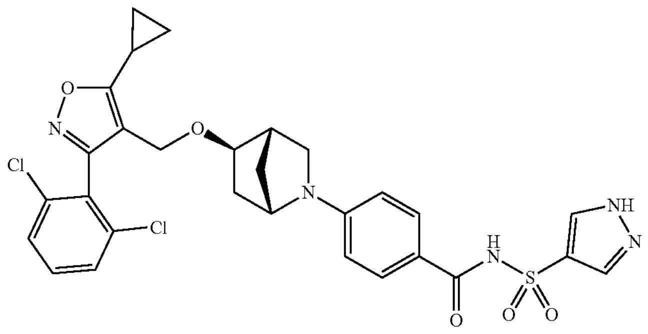 [SMILES: O=C(NS(=O)(=O)c1cn[nH]c1)c1ccc(N2C[C@@H]3C[C@H]2C[C@H]3OCc2c(-c3c(Cl)cccc3Cl)noc2C2CC2)cc1] | I-188 | MS (ES, m/z): [M + 1] = 481.10. $^1$H NMR (300 MHz, DMSO-d6) δ: 8.71 (d, J = 0.8 Hz, 1H), 8.12 (d, J = 0.8 Hz, 1H), 8.01 (d, J = 8.9 Hz, 2H), 7.70-7.50 (m, 5H), 6.59 (d, J = 8.7 Hz, 2H), 4.26 (s, 2H), 3.53-3.44 (m, 1H), 2.64 (d, J = 9.9 Hz, 1H), 2.41-2.25 (m, 1H), 1.71 (dd, J = 13.2, 6.7 Hz, 1H), 1.54-1.31 (m, 2H), 1.26-1.02 (m, 6H). |

TABLE 9-continued

| Acid SM | Cmpd Structure | Cmpd No. | MS/$^1$H NMR |
|---|---|---|---|
| I-52 | 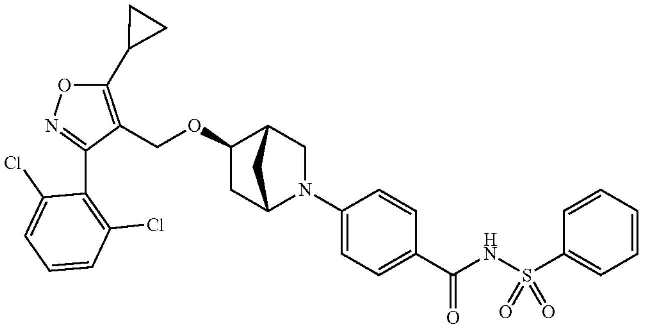 [SMILES: O=C(NS(=O)(=O)c1ccccc1)c1ccc(N2C[C@@H]3C[C@H]2C[C@H]3OCc2c(-c3c(Cl)cccc3Cl)noc2C2CC2)cc1] | I-189 | MS (ES, m/z): [M + 1] = 638.2. $^1$H NMR (300 MHz, $CD_3OD$) δ: 8.14-8.04 (m, 2H), 7.72-7.59 (m, 5H), 7.59-7.54 (m, 1H), 7.53-7.48 (m, 2H), 6.51 (d, J = 8.9 Hz, 2H), 4.32 (s, 2H), 4.18 (s, 1H), 3.34 (p, J = 1.7 Hz, 1H), 2.61 (d, J = 9.6 Hz, 1H), 2.53 (s, 1H), 2.29 (q, J = 7.0 Hz, 1H), 1.80 (dd, J = 12.8, 7.1 Hz, 1H), 1.60 (q, J = 10.0 Hz, 2H), 1.32 (d, J = 13.0 Hz, 2H), 1.19 (d, J = 6.7 Hz, 4H). |
| I-53 | 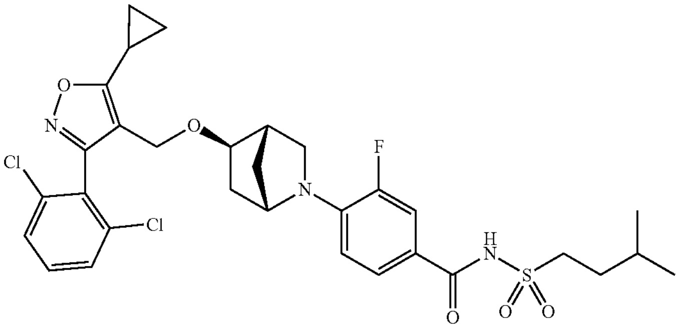 [SMILES: CC(C)CCS(=O)(=O)NC(=O)c1ccc(N2C[C@@H]3C[C@H]2C[C@H]3OCc2c(-c3c(Cl)cccc3Cl)noc2C2CC2)c(F)c1] | I-190 | MS (ES, m/z): [M + 1] = 650.5. $^1$H NMR (400 MHz, DMSO-d6) δ: 11.65 (s, 1H), 7.72-7.52 (m, 5H), 6.66 (t, J = 8.8 Hz, 1H), 4.24 (d, J = 10.1 Hz, 3H), 3.51 (d, J = 5.7 Hz, 4H), 2.71 (dd, J = 9.8, 3.6 Hz, 1H), 2.46-2.40 (m, 1H), 2.39-2.27 (m, 1H), 1.80 (ddd, J = 13.3, 6.7, 2.3 Hz, 1H), 1.74-1.44 (m, 4H), 1.40 (d, J = 9.7 Hz, 1H), 1.31-1.04 (m, 5H), 0.86 (d, J = 6.5 Hz, 6H). |
| I-53 | 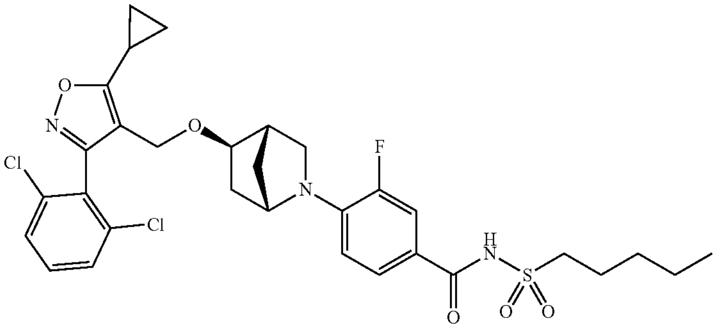 [SMILES: CCCCCS(=O)(=O)NC(=O)c1ccc(N2C[C@@H]3C[C@H]2C[C@H]3OCc2c(-c3c(Cl)cccc3Cl)noc2C2CC2)c(F)c1] | I-191 | MS (ES, m/z): [M + 1] = 650.5. $^1$H NMR (400 MHz, DMSO-d6) δ: 11.65 (s, 1H), 7.69-7.52 (m, 5H), 6.67 (t, J = 8.8 Hz, 1H) 4.24 (d, J = 9.9 Hz, 3H), 3.48 (dt, J = 9.6, 6.7 Hz, 4H), 2.71 (dd, J = 9.7, 3.6 Hz, 1H), 2.46-2.40 (m, 1H), 2.39-2.27 (m, 1H), 1.80 (ddd, J = 13.1, 7.3, 2.3 Hz, 1H), 1.73-1.61 (m, 2H), 1.48 (d, J = 9.9 Hz, 1H), 1.44-1.04 (m, 10H), 0.84 (t, J = 7.2 Hz, 3H). |
| I-53 | 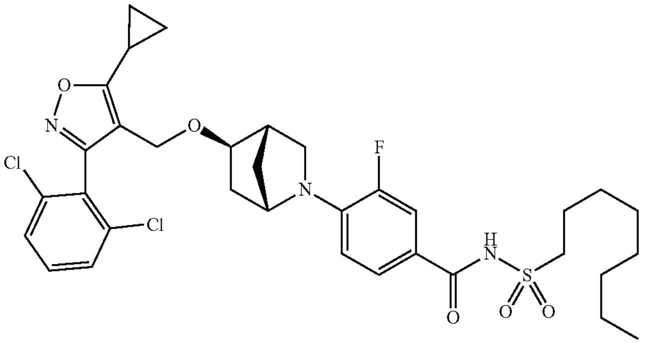 [SMILES: CCCCCCCCS(=O)(=O)NC(=O)c1ccc(N2C[C@@H]3C[C@H]2C[C@H]3OCc2c(-c3c(Cl)cccc3Cl)noc2C2CC2)c(F)c1] | I-192 | MS (ES, m/z): [M + 1] = 692.2. $^1$H NMR (300 MHz, DMSO-d6) δ: 11.65 (s, 1H), 7.81-7.44 (m, 5H), 6.69 (d, J = 8.9 Hz, 1H), 4.25 (d, J = 8.0 Hz, 3H), 3.48 (dd, J = 9.0, 6.5 Hz, 4H), 2.71 (dd, J = 9.9, 3.7 Hz, 1H), 2.34 (dd, J = 6.2, 4.4 Hz, 1H), 1.88-1.75 (m, 1H), 1.67 (t, J = 7.6 Hz, 1H), 1.49 (d, J = 10.0 Hz, 2H), 1.39 (dd, J = 13.1, 7.5 Hz, 4H), 1.32-1.14 (m, 9H), 1.10 (dt, J = 5.1, 2.7 Hz, 4H), 0.84 (td, J = 7.2, 4.5 Hz, 3H). |

TABLE 9-continued

| Acid SM | Cmpd Structure | Cmpd No. | MS/$^1$H NMR |
|---|---|---|---|
| I-53 | 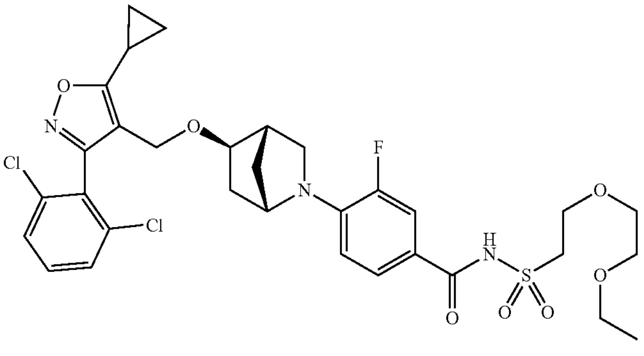 [SMILES: CCOCCOCCS(=O)(=O)NC(=O)c1ccc(N2C[C@@H]3C[C@H]2C[C@H]3OCc2c(-c3c(Cl)cccc3Cl)noc2C2CC2)c(F)c1] | I-193 | MS (ES, m/z): [M + 1] = 696.20. $^1$H NMR (400 MHz, DMSO-d6) δ: 7.68-7.51 (m, 5H), 7.33-6.86 (m, 1H), 6.64 (t, J = 8.9 Hz, 1H), 4.29-4.17 (m, 3H), 3.81-3.67 (m, 4H), 3.33-3.25 (m, 3H), 2.67 (dd, J = 10.1, 3.6 Hz, 1H), 2.41 (d, J = 3.9 Hz, 1H), 2.31 (tt, J = 8.3, 5.1 Hz, 1H), 1.82-1.72 (m, 1H), 1.50-1.35 (m, 2H), 1.24-1.02 (m, 6H), 0.97 (t, J = 7.0 Hz, 3H). |
| I-103 | 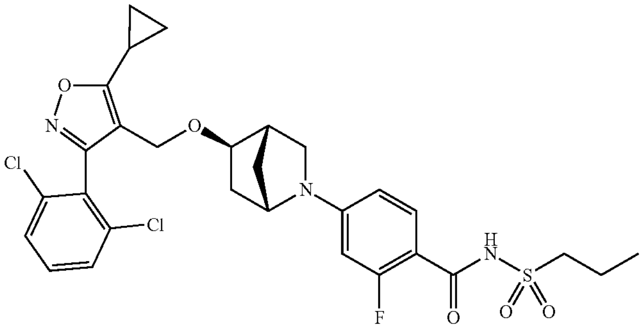 [SMILES: CCCS(=O)(=O)NC(=O)c1ccc(N2C[C@@H]3C[C@H]2C[C@H]3OCc2c(-c3c(Cl)cccc3Cl)noc2C2CC2)cc1F] | I-194 | MS (ES, m/z): [M + 1] = 622.10. $^1$H NMR (400 MHz, DMSO-d6) δ: 11.31 (s, 1H), 7.67-7.41 (m, 4H), 6.28 (t, J = 12.1 Hz, 2H), 4.24 (s, 2H), 4.17 (s, 1H), 3.47-3.31 (m, 3H), 3.26 (dd, J = 9.9, 4.1 Hz, 1H), 2.52 (d, J = 9.7 Hz, 1H), 2.44 (d, J = 3.6 Hz, 1H), 2.37-2.25 (m, 1H), 1.75-1.60 (m, 3H), 1.49-1.34 (m, 2H), 1.19-1.02 (m, 5H), 0.96 (t, J = 7.4 Hz, 3H). |
| I-103 | 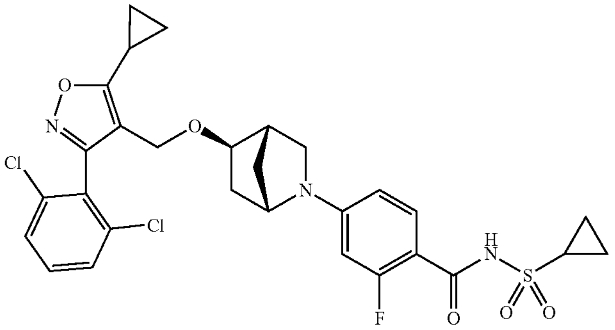 [SMILES: O=C(NS(=O)(=O)C1CC1)c1ccc(N2C[C@@H]3C[C@H]2C[C@H]3OCc2c(-c3c(Cl)cccc3Cl)noc2C2CC2)cc1F] | I-195 | MS (ES, m/z): [M + 1] = 620.05. $^1$H NMR (400 MHz, DMSO-d6) δ: 11.30 (s, 1H), 7.66-7.44 (m, 4H), 6.33-6.21 (m, 2H), 4.24 (s, 2H), 4.16 (d, J = 2.5 Hz, 1H), 3.43 (dd, J = 6.6, 2.3 Hz, 1H), 3.33-3.22 (m, 4H), 3.00 (tt, J = 8.1, 4.7 Hz, 1H), 2.51 (d, J = 9.5 Hz, 1H), 2.47-2.41 (m, 1H), 2.37-2.25 (m, 1H), 1.66 (ddd, J = 13.2, 6.8, 2.4 Hz, 1H), 1.48-1.34 (m, 2H), 1.25-0.92 (m, 10H). |
| I-56 | 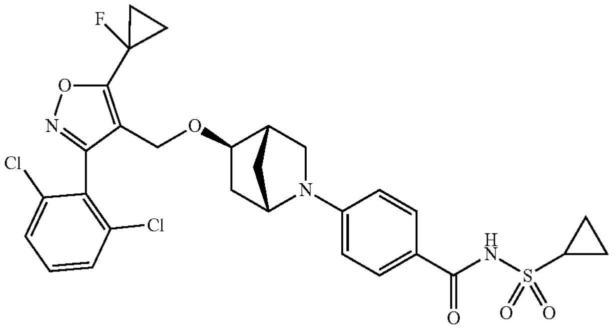 [SMILES: O=C(NS(=O)(=O)C1CC1)c1ccc(N2C[C@@H]3C[C@H]2C[C@H]3OCc2c(-c3c(Cl)cccc3Cl)noc2C2(F)CC2)cc1] | I-196 | MS (ES, m/z): [M + 1] = 620.20. $^1$H NMR (400 MHz, $CD_3OD$) δ: 7.71 (d, J = 9.0 Hz, 2H), 7.61-7.45 (m, 3H), 6.56-6.47 (m, 2H), 4.42 (t, J = 1.3 Hz, 2H), 4.16 (s, 1H), 3.49 (d, J = 2.4 Hz, 1H), 3.36 (dd, J = 9.6, 4.1 Hz, 1H), 3.18-3.06 (m, 1H), 2.60 (d, J = 9.6 Hz, 1H), 2.49 (s, 1H), 1.85-1.75 (m, 1H), 1.68-1.49 (m, 4H), 1.47-1.36 (m, 2H), 1.26 (dt, J = 6.5, 4.4 Hz, 3H), 1.17-1.05 (m, 2H). |

TABLE 9-continued

| Acid SM | Cmpd Structure | Cmpd No. | MS/$^1$H NMR |
|---|---|---|---|
| I-57 | 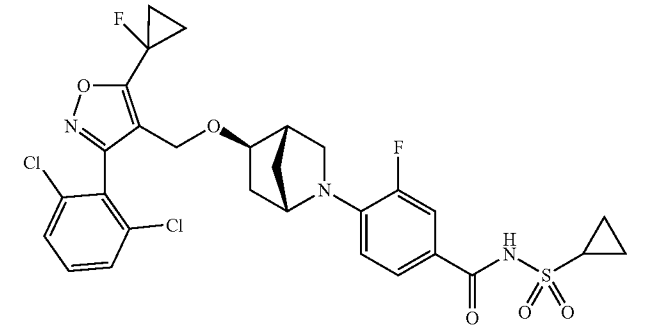 [SMILES: O=C(NS(=O)(=O)C1CC1)c1ccc(N2C[C@@H]3C[C@H]2C[C@H]3OCc2c(-c3c(Cl)cccc3Cl)noc2C2(F)CC2)c(F)c1] | I-197 | MS (ES, m/z): [M + 1] = 638.15. $^1$H NMR (300 MHz, $CD_3OD$) δ: 7.65-7.47 (m, 5H), 6.66 (t, J = 8.8 Hz, 1H), 4.45 (t, J = 1.3 Hz, 2H), 4.29 (s, 1H), 3.64-3.47 (m, 2H), 3.22-3.05 (m, 1H), 2.77 (dd, J = 10.0, 3.4 Hz, 1H), 2.47 (s, 1H), 1.93 (dd, J = 13.4, 6.7 Hz, 1H), 1.74-1.50 (m, 3H), 1.52-1.37 (m, 2H), 1.29 (dd, J = 7.5, 4.9 Hz, 5H), 1.20-1.07 (m, 2H). |
| I-57 | 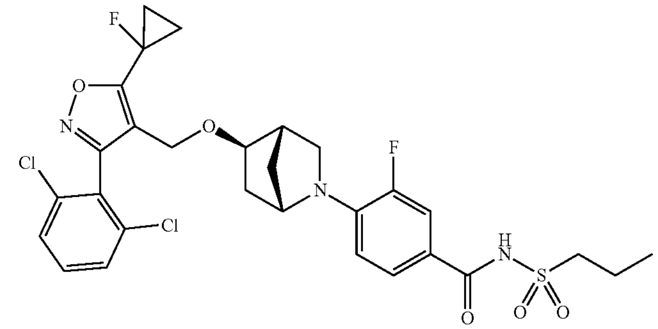 [SMILES: CCCS(=O)(=O)NC(=O)c1ccc(N2C[C@@H]3C[C@H]2C[C@H]3OCc2c(-c3c(Cl)cccc3Cl)noc2C2(F)CC2)c(F)c1] | I-198 | MS (ES, m/z): [M + 1] = 640.15. $^1$H NMR (400 MHz, $CD_3OD$) δ: 7.63-7.48 (m, 5H), 6.65 (t, J = 8.8 Hz, 1H), 4.44 (t, J = 1.6 Hz, 2H), 4.28 (s, 1H), 3.62-3.45 (m, 4H), 3.36 (s, 1H), 2.76 (dd, J = 10.1, 3.3 Hz, 1H), 2.47 (s, 1H), 1.97-1.78 (m, 3H), 1.71-1.53 (m, 4H), 1.49-1.38 (m, 2H), 1.31 (t, J = 16.6 Hz, 2H), 1.09 (t, J = 7.5 Hz, 3H |
| I-44 | 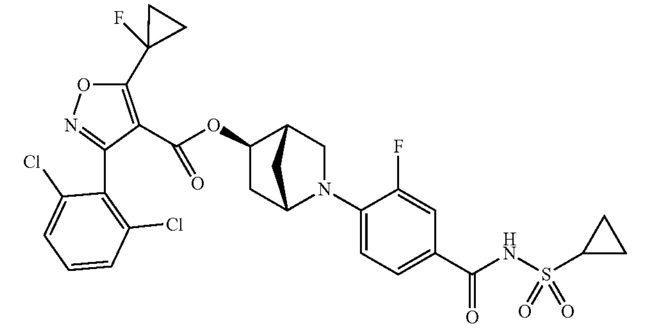 [SMILES: O=C(NS(=O)(=O)C1CC1)c1ccc(N2C[C@@H]3C[C@H]2C[C@H]3OC(=O)c2c(-c3c(Cl)cccc3Cl)noc2C2(F)CC2)c(F)c1] | I-199 | MS (ES, m/z): [M + 1] = 652.2. $^1$H NMR (400 MHz, $CD_3OD$) δ: 7.62-7.48 (m, 5H), 6.67 (t, J = 8.8 Hz, 1H), 4.87 (s, 10H), 4.33 (s, 1H), 3.62 (dt, J = 10.1, 3.8 Hz, 1H), 3.17-3.05 (m, 1H), 2.98-2.90 (m, 1H), 2.49 (s, 1H), 2.19 (ddd, J = 14.0, 7.1, 2.6 Hz, 1H), 1.73-1.51 (m, 5H), 1.40-1.22 (m, 4H), 1.15-1.05 (m, 2H). |
| I-121 | 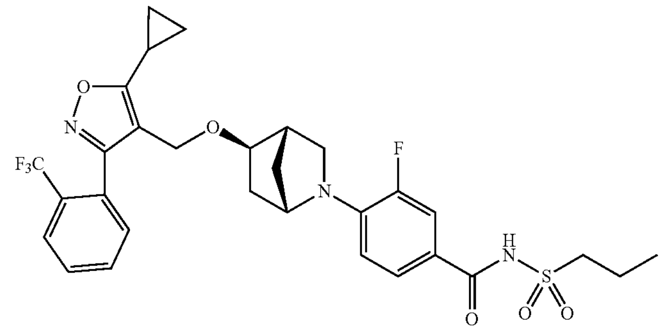 [SMILES: CCCS(=O)(=O)NC(=O)c1ccc(N2C[C@@H]3C[C@H]2C[C@H]3OCc2c(-c3ccccc3C(F)(F)F)noc2C2CC2)c(F)c1] | I-200 | MS (ES, m/z): [M + 1] = 622.5. $^1$H NMR (300 MHz, $CD_3OD$) δ: 7.87 (dd, J = 7.1, 2.1 Hz, 1H), 7.81-7.65 (m, 2H), 7.62-7.46 (m, 3H), 6.65 (t, J = 8.7 Hz, 1H), 4.29 (dd, J = 11.9, 4.9 Hz, 3H), 3.63-3.43 (m, 3H), 2.75 (dd, J = 10.0, 3.3 Hz, 1H), 2.50 (s, 1H), 2.33-2.17 (m, 1H), 1.96 (dd, J = 13.7, 6.9 Hz, 1H), 1.91-1.76 (m, 2H), 1.59 (d, J = 13.7 Hz, 2H), 1.43-1.26 (m, 1H), 1.20-1.12 (m, 4H), 1.07 (t, J = 7.5 Hz, 3H). |

TABLE 9-continued

| Acid SM | Cmpd Structure | Cmpd No. | MS/$^1$H NMR |
|---|---|---|---|
| I-121 | 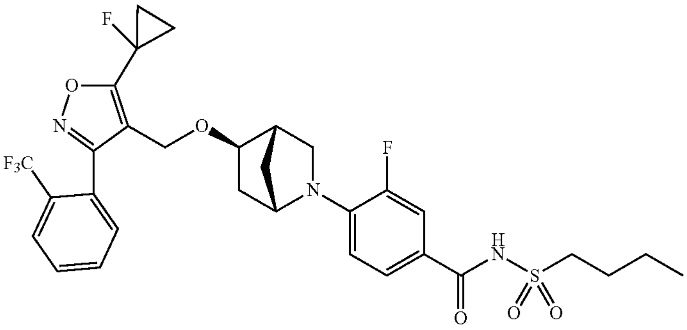 [SMILES: CCCCS(=O)(=O)NC(=O)c1ccc(N2C[C@@H]3C[C@H]2C[C@H]3OCc2c(-c3ccccc3C(F)(F)F)noc2C2(F)CC2)c(F)c1] | I-201 | MS (ES, m/z): [M + 1] = 636.6. $^1$H NMR (300 MHz, $CD_3OD$) δ: 7.92-7.80 (m, 1H), 7.80-7.65 (m, 2H), 7.63-7.46 (m, 3H), 6.65 (t, J = 8.7 Hz, 1H), 4.35-4.19 (m, 3H), 3.63-3.45 (m, 4H), 2.75 (dd, J = 10.0, 3.3 Hz, 1H), 2.51 (s, 1H), 2.33-2.17 (m, 1H), 1.96 (dd, J = 13.5, 6.8 Hz, 1H), 1.78 (tt, J = 7.8, 6.4 Hz, 2H), 1.61 (s, 2H), 1.53-1.41 (m, 2H), 1.36 (d, J = 13.4 Hz, 1H), 1.22-1.08 (m, 4H), 0.95 (t, J = 7.3 Hz, 3H). |
| I-121 | 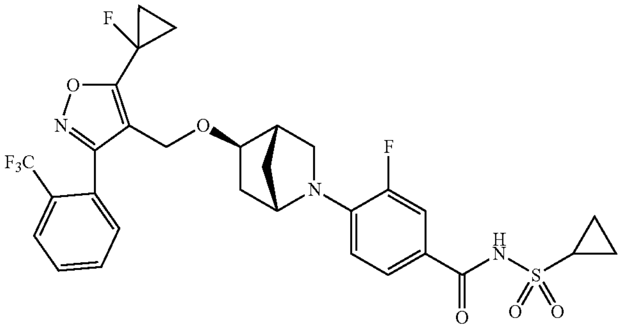 [SMILES: O=C(NS(=O)(=O)C1CC1)c1ccc(N2C[C@@H]3C[C@H]2C[C@H]3OCc2c(-c3ccccc3C(F)(F)F)noc2C2(F)CC2)c(F)c1] | I-202 | MS (ES, m/z): [M + 1] = 620.5. $^1$H NMR (300 MHz, $CD_3OD$) δ: 8.04-7.83 (m, 1H), 7.81-7.65 (m, 2H), 7.66-7.46 (m, 3H), 6.65 (t, J = 8.7 Hz, 1H), 4.41-4.15 (m, 3H), 3.54 (dd, J = 17.7, 8.4 Hz, 2H), 3.12 (tt, J = 8.0, 4.8 Hz, 1H), 2.75 (d, J = 9.3 Hz, 1H), 2.51 (s, 1H), 2.25 (p, J = 6.9 Hz, 1H), 2.07-1.83 (m, 1H), 1.59 (d, J = 13.5 Hz, 2H), 1.36 (d, J = 13.6 Hz, 1H), 1.27 (tt, J = 5.1, 3.0 Hz, 2H), 1.22-1.05 (m, 6H). |
| I-114 | 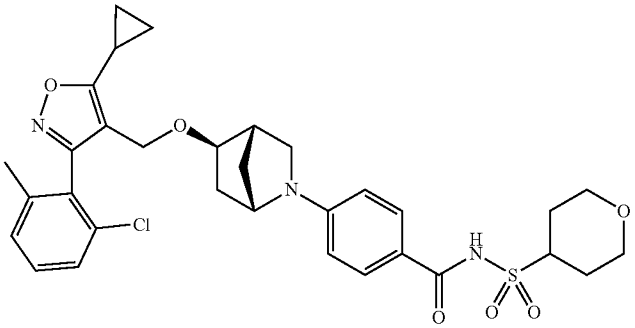 [SMILES: Cc1cccc(Cl)c1-c1noc(C2CC2)c1CO[C@@H]1C[C@@H]2C[C@H]1CN2c1ccc(C(=O)NS(=O)(=O)C2CCOCC2)cc1] | I-203 | MS (ES, m/z): [M + 1] = 626.4. $^1$H NMR (400 MHz, $CD_3OD$) δ: 7.75 (d, J = 8.7 Hz, 2H), 7.44-7.35 (m, 2H), 7.32-7.22 (m, 1H), 6.54 (dd, J = 9.1, 2.6 Hz, 2H), 4.35 (dd, J = 11.7, 1.6 Hz, 1H), 4.24-4.13 (m, 2H), 4.13-4.05 (m, 2H), 4.01-3.90 (m, 1H), 3.51-3.33 (m, 4H), 2.67-2.41 (m, 2H), 2.28 (dd, J = 7.4, 6.0 Hz, 1H), 2.17 (d, J = 3.0 Hz, 3H), 2.04-1.75 (m, 5H), 1.63 (t, J = 8.9 Hz, 1H), 1.53 (s, 1H), 1.38 (d, J = 13.1 Hz, 1H), 1.24-1.15 (m, 5H). |
| I-55 | 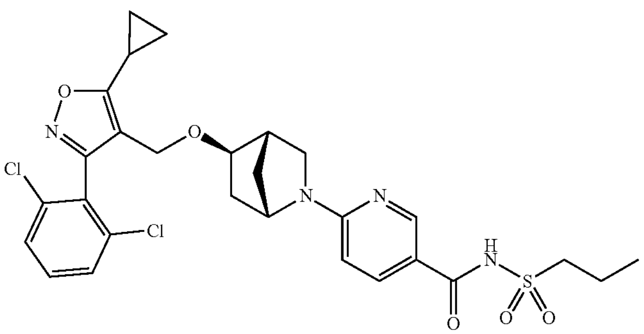 [SMILES: CCCS(=O)(=O)NC(=O)c1ccc(N2C[C@@H]3C[C@H]2C[C@H]3OCc2c(-c3c(Cl)cccc3Cl)noc2C2CC2)nc1] | I-204 | MS (ES, m/z): [M + 1] = 605. $^1$H NMR (400 MHz, $CD_3OD$) δ: 8.50 (d, J = 2.0 Hz, 1H), 8.16 (d, J = 9.4 Hz, 1H), 7.61-7.47 (m, 3H), 4.58 (s, 1H), 4.43-4.30 (m, 2H), 3.67 (d, J = 6.4 Hz, 1H), 3.56-3.48 (m, 3H), 3.04 (s, 1H), 2.69 (s, 1H), 2.29 (p, J = 6.8 Hz, 1H), 1.88 (dp, J = 15.1, 7.8 Hz, 3H), 1.74 (d, J = 10.5 Hz, 1H), 1.67 (d, J = 10.2 Hz, 1H), 1.44 (d, J = 13.8 Hz, 1H), 1.20 (d, J = 6.7 Hz, 4H), 1.10 (t, J = 7.5 Hz, 3H). |

TABLE 9-continued
| Acid SM | Cmpd Structure | Cmpd No. | MS/$^1$H NMR |
| --- | --- | --- | --- |
| I-55 | 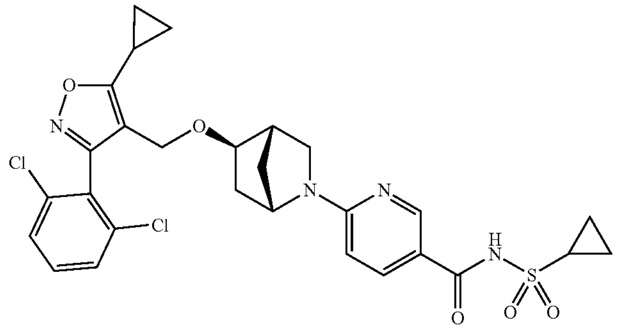 [SMILES: O=C(NS(=O)(=O)C1CC1)c1ccc(N2C[C@@H]3C[C@H]2C[C@H]3OCc2c(-c3c(Cl)cccc3Cl)noc2C2CC2)nc1] | I-205 | MS (ES, m/z): [M + 1] = 603. $^1$H NMR (400 MHz, $CD_3OD$) δ: 8.50 (d, J = 2.1 Hz, 1H), 8.15 (s, 1H), 7.62-7.47 (m, 3H), 4.58 (s, 1H), 4.43-4.30 (m, 2H), 3.67 (d, J = 6.5 Hz, 1H), 3.34 (s, 1H), 3.03 (s, 1H), 2.68 (s, 1H), 2.29 (p, J = 6.9 Hz, 1H), 1.94 (d, J = 10.2 Hz, 1H), 1.74 (d, J = 10.2 Hz, 1H), 1.66 (d, J = 10.6 Hz, 1H), 1.44 (d, J = 13.9 Hz, 1H), 1.36-1.26 (m, 2H), 1.17 (dd, J = 20.2, 7.3 Hz, 6H). |
| I-129 | 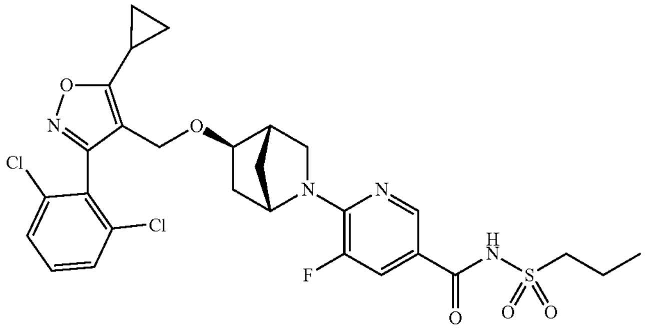 [SMILES: CCCS(=O)(=O)NC(=O)c1cnc(N2C[C@@H]3C[C@H]2C[C@H]3OCc2c(-c3c(Cl)cccc3Cl)noc2C2CC2)c(F)c1] | I-206 | MS (ES, m/z): [M + 1] = 623.30. $^1$H NMR (400 MHz, $CD_3OD$) δ: 8.44-8.36 (m, 1H), 7.72 (dd, J = 14.1, 2.1 Hz, 1H), 7.61-7.43 (m, 3H), 4.67 (s, 1H), 4.40-4.25 (m, 2H), 3.67-3.43 (m, 4H), 3.13 (dd, J = 11.1, 3.4 Hz, 1H), 2.53 (s, 1H), 2.27 (p, J = 6.8 Hz, 1H), 1.99-1.75 (m, 3H), 1.59 (q, J = 10.2 Hz, 2H), 1.35 (d, J = 13.3 Hz, 1H), 1.22-1.02 (m, 7H). |
| I-129 | 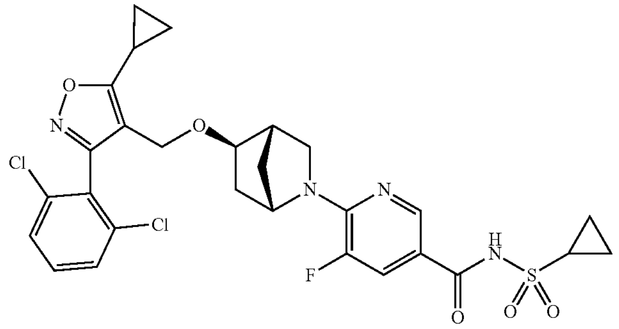 [SMILES: O=C(NS(=O)(=O)C1CC1)c1cnc(N2C[C@@H]3C[C@H]2C[C@H]3OCc2c(-c3c(Cl)cccc3Cl)noc2C2CC2)c(F)c1] | I-207 | MS (ES, m/z): [M + 1] = 621.25. $^1$H NMR (300 MHz, $CD_3OD$) δ: 8.43-8.36 (m, 1H), 7.71 (dd, J = 14.1, 2.0 Hz, 1H), 7.61-7.43 (m, 3H), 4.67 (s, 1H), 4.40-4.25 (m, 2H), 3.66-3.54 (m, 2H), 3.19-3.06 (m, 2H), 2.54 (s, 1H), 2.27 (p, J = 6.8 Hz, 1H), 1.92 (dd, J = 12.9, 6.9 Hz, 1H), 1.59 (q, J = 10.2 Hz, 2H), 1.41-1.06 (m, 9H). |

Example 177: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(oxane-4-sulfonyl) benzamide (I-208)

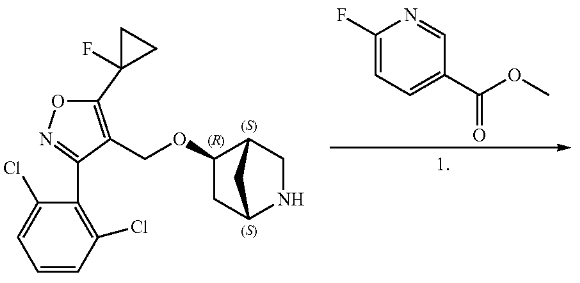

24d

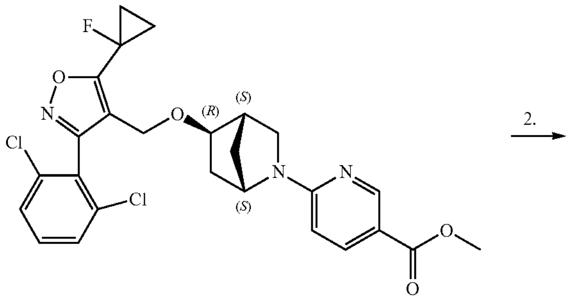

208a

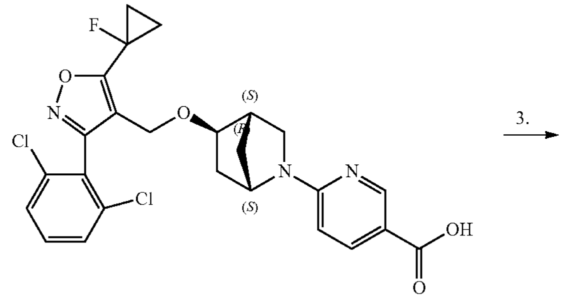

208b

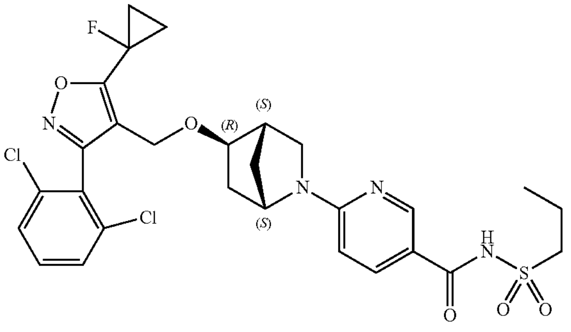

I-208

Step 1

To a 25 mL round bottom flask purged with and maintained under an inert atmosphere of nitrogen was added (1S,4S,5R)-5-[[3-(2,6-dichlorophenyl)-5-(1-fluorocyclopropyl)-1,2-oxazol-4-yl]methoxy]-2-azabicyclo[2.2.1]heptane 24d (140 mg, 0.35 mmol, 1.00 equiv.), MeCN (1.5 mL), methyl 6-bromopyridine-3-carboxylate (70 mg, 0.32 mmol, 1.20 equiv.), and TEA (70 mg, 0.69 mmol, 2.00 equiv.). The resulting mixture was heated at 80° C., overnight. Upon cooling to room temperature, the mixture was concentrated under vacuum. The residue was purified by silica gel column chromatography eluting with ethyl acetate/petroleum ether (1:3) to give methyl 6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]pyridine-3-carboxylate 208a (100 mg, 53%) as a light yellow solid.

Step 2

To a 25 mL round-bottom flask was added methyl 6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]pyridine-3-carboxylate 208a (190 mg, 0.36 mmol, 1.00 equiv.), methanol (3 mL), and a solution of LiOH (152 mg, 6.35 mmol, 10.00 equiv.) in water (0.3 mL). The resulting mixture was stirred at 50° C., for 2 h, then quenched by the addition of 5 mL of $H_2O$. The pH value of the solution was adjusted to 5 using a 1M hydrogen chloride aqueous solution. The mixture was extracted with ethyl acetate (100 mL×2). The combined organic extracts were washed with brine (50 mL×2), dried over sodium sulfate and concentrated under vacuum to afford 6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]pyridine-3-carboxylic acid 208b (110 mg, 59%) as a light yellow solid.

Step 3

To a 25 mL round-bottom flask was added 6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]pyridine-3-carboxylic Acid 208b (110 mg, 0.21 mmol, 1.00 equiv.), EDCI (60 mg, 0.31 mmol, 1.50 equiv.), 4-dimethylaminopyridine (78 mg, 0.64 mmol, 3.00 equiv.), dichloromethane (1.5 mL), and propane-1-sulfonamide (77 mg, 0.63 mmol, 3.00 equiv.). The resulting mixture was stirred overnight at room temperature. 10 mL of water was added, the pH value of the solution was adjusted to 6 using a 1M HCl aqueous solution. The aqueous mixture was extracted with ethyl acetate (50 mL×3); and the combined organic extracts were washed with brine (30 mL×2), dried over anhydrous sodium sulfate and concentrated under vacuum. The crude product was purified by Prep-HPLC using the following conditions: Column, XBridge C18 OBD Prep Column, 19 mm×250 mm; mobile phase, Water (0.05% TFA) and ACN (42.0% ACN up to 62.0% in 8 min); Detector, uv 254 nm. After purification 6-[(1S,4S,5R)-5-[[3-(2,6-dichlorophenyl)-5-(1 I-fluorocyclopropyl)-1,2-oxazol-4-yl]methoxy]-2-azabicyclo[2.2.1]heptan-2-yl]-N-(propane-1-sulfonyl)pyridine-3-carboxamide I-208 (56.7 mg, 43%) was obtained as an off-white solid. $^{1}$HNMR (300 MHz, $CD_3OD$): δ 8.48 (d, J=2.3 Hz, 1H), 8.19-8.09 (m, 1H), 7.63-7.46 (m, 3H), 4.61-4.39 (m, 3H), 3.66 (d, J=6.5 Hz, 1H), 3.56-3.44 (m, 3H), 3.03 (s, 1H), 2.65 (d, J=3.9 Hz, 1H), 2.00-1.76 (m, 3H), 1.73-1.55 (m, 4H), 1.54-1.34 (m, 3H), 1.08 (t, J=7.4 Hz, 3H); MS (ES, m/z): [M+1]=623.20.

Example 178: N-(cyclopropanesulfonyl)-6-[(1S,4S,5R)-5-{[3-(2,6-dichlorophenyl)-5-(1-fluorocyclopropyl)-1,2-oxazol-4-yl]methoxy}-2-azabicyclo[2.2.1]heptan-2-yl]pyridine-3-carboxamide (I-209)

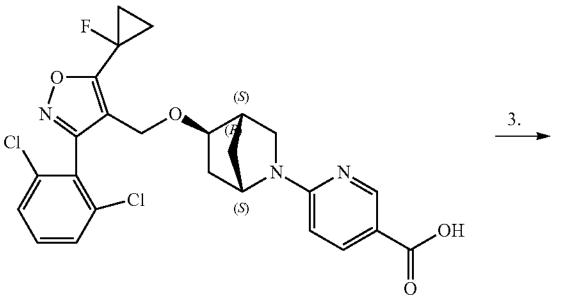

208b

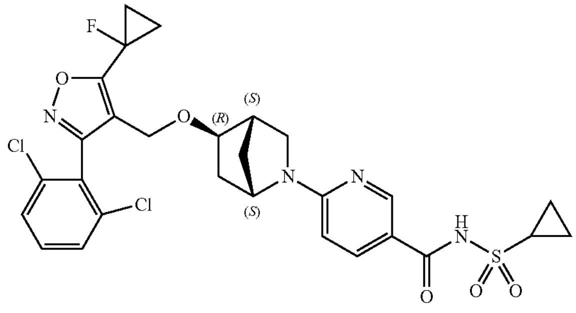

I-209

To a 25 mL round bottom flask was added 6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]pyridine-3-carboxylic Acid 208b (110 mg, 0.21 mmol, 1.00 equiv.), EDCI (60 mg, 0.31 mmol, 1.50 equiv.), 4-dimethylaminopyridine (78 mg, 0.64 mmol, 3.00 equiv.), dichloromethane (1.5 mL), and cyclopropanesulfonamide (77 mg, 0.64 mmol, 3.00 equiv.). The resulting mixture was stirred at room temperature overnight. The mixture was diluted with 10 mL of water, and the pH value of the solution was adjusted to 6 using a 1M HCl aqueous solution. The aqueous mixture was extracted with ethyl acetate (50 mL×3). The combined organic extracts were washed with brine (20 mL×2), dried over anhydrous sodium sulfate, and concentrated under vacuum. The crude product was purified by Prep-HPLC using the following conditions: Column, XBridge Prep C18 OBD Column, 19$_{i}$ Á150 mm 5 um; mobile phase, Water (0.05% TFA) and ACN (48.0% ACN up to 62.0% in 8 min); Detector, 254 nm. After purification N-(cyclopropanesulfonyl)-6-[(1S,4S,5R)-5-[[3-(2,6-dichlorophenyl)-5-(1-fluorocyclopropyl)-1,2-oxazol-4-yl]methoxy]-2-azabicyclo[2.2.1]heptan-2-yl]pyridine-3-carboxamide I-209 (41.2 mg, 31%) was obtained as an off-white solid. $^{1}$HNMR (300 MHz, $CD_3OD$): δ 8.47 (d, J=2.2 Hz, 1H), 8.15 (dd, J=9.4, 2.3 Hz, 1H), 7.63-7.46 (m, 3H), 4.60-4.39 (m, 3H), 3.66 (d, J=6.7 Hz, 1H), 3.50 (dd, J=10.5, 4.1 Hz 1H), 3.19-3.01 (m, 2H), 2.67 (d, J=3.0 Hz, 1H), 1.94 (dd, J=13.7, 6.7 Hz, 1H), 1.73-1.55 (m, 4H), 1.54-1.06 (m, 7H); MS (ES, m/z): [M+1]=621.20.

Example 179: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(2-hydroxyethanesulfonyl)benzamide (I-210)

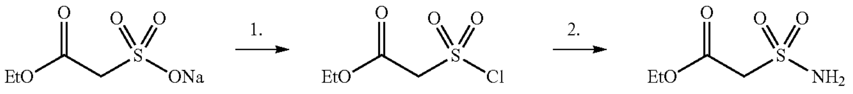

210a 210b 210c

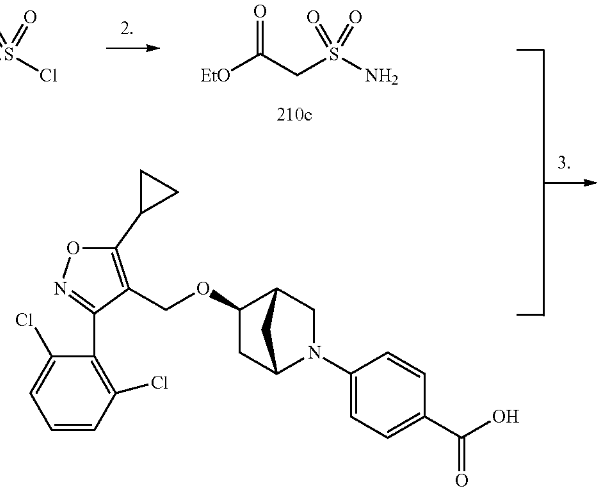

I-52

-continued

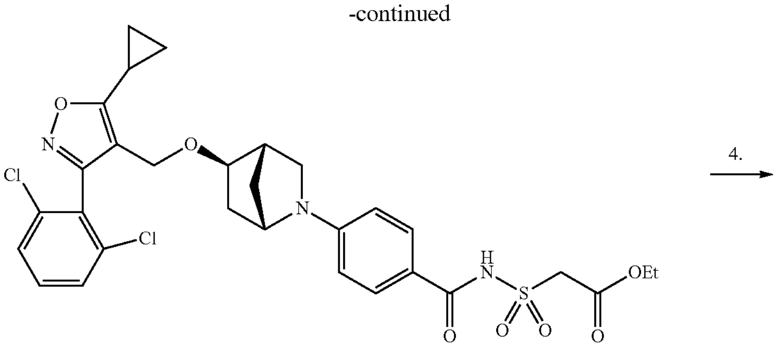

210d

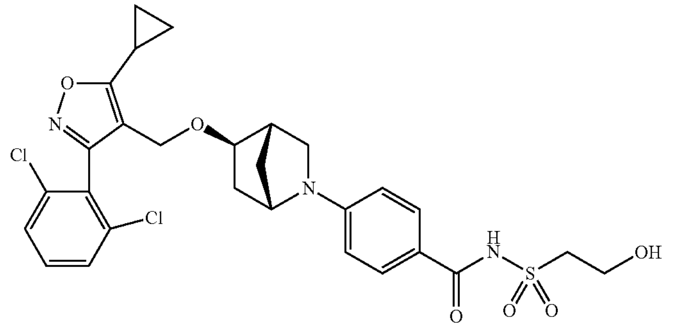

I-210

Step 1

To a 50 mL round-bottom flask was added ethyl 2-[(sodiooxy)sulfonyl]acetate 210a (5 g, 26.30 mmol, 1.00 equiv.) followed by phosphorous pentachloride (13.6 g, 65.31 mmol, 2.50 equiv.). The resulting mixture was stirred at room temperature for 20 min. The mixture was washed with toluene (40 mL×3) and concentrated under vacuum to give of ethyl 2-(chlorosulfonyl)acetate 210b (3.2 g, 65%/0) as a yellow oil.

Step 2

To a 250 mL round-bottom flask was added ethyl 2-(chlorosulfonyl)acetate 210b (3.2 g, 17.15 mmol, 1.00 equiv.) and a 0.5M solution of $NH_3$ in tetrahydrofuran (80 mL). The resulting solution was stirred at room temperature for 30 min and then concentrated under vacuum. The residue was treated with 5 mL of DCM and purified by silica gel column chromatography eluting with dichloromethane/ethyl acetate (2:1) to afford ethyl 2-sulfamoylacetate 210c (300 mg, 10%) as a yellow oil.

Step 3

To a 8 mL sealed tube was added ethyl 2-sulfamoylacetate 210c (140 mg, 0.84 mmol, 2.00 equiv.), 4-[(1S,4S,5R)-5-[5-cyclopropyl-3-(2,6-dichlorophenyl)-1,2-oxazol-4-yl] methoxy-2-azabicyclo[2.2.1]heptan-2-yl]benzoic acid I-52 (206 mg, 0.41 mmol, 1.00 equiv.), dichloromethane (2 mL), 4-dimethylaminopyridine (152 mg, 1.24 mmol, 3.00 equiv.), and EDCI (120 mg, 0.63 mmol, 1.50 equiv.). The resulting mixture was stirred at room temperature overnight. The mixture was diluted with 50 mL of DCM, washed with $H_2O$ (30 mL×2) and brine (30 mL×2), and concentrated. The residue was purified by silica gel column chromatography eluting with dichloromethane/methanol (10:1) to give ethyl 2-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]acetate 210d (160 mg, 60%) as a white solid.

Step 4

To a 8 mL sealed tube purged with and maintained under an inert atmosphere of nitrogen was added ethyl 2-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl] methane)sulfonyl]acetate 210d (100 mg, 0.15 mmol, 1.00 equiv.) and tetrahydrofuran (2 mL). A 4M solution of $LiBH_4$ in THF (0.08 mL, 2.00 equiv.) was added dropwise with stirring. The reaction mixture was stirred at room temperature for 4 h. Water was added to quench the reaction, the mixture was extracted with ethyl acetate (30 mL×3). The combined organic extracts were washed with brine (30 mL×2), dried over anhydrous sodium sulfate, and concentrated under vacuum. The crude product was purified by Prep-HPLC using the following conditions: Column, XBridge Shield RP18 OBD Column, 5 um, 19*150 mm; mobile phase, Water (0.05% TFA) and ACN (43.0% ACN up to 60.0% in 8 min); Detector, UV 254 nm. After purification 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[(2-hydroxyethane)sulfonyl]benzamide I-210 (27.7 mg, 30%) was obtained as a colorless solid. $^1$HNMR (300 MHz, $CD_3OD$): δ 7.69 (d, J=8.9 Hz, 2H), 7.56-7.40 (m, 3H), 6.49 (d, J=8.9 Hz, 2H), 4.83 (s, 18H), 4.28 (s, 2H), 4.14 (s, 1H), 3.94 (t, J=6.2 Hz, 2H), 3.67 (t, J=6.2 Hz, 2H), 3.46 (d, J=6.4 Hz, 1H), 3.34 (dd, J=9.5, 4.0 Hz, 1H), 2.58 (d, J=9.5 Hz, 1H), 2.48 (s, 1H), 2.21 (q, J=6.7 Hz, 1H), 1.81-1.70 (m, 1H), 1.61-1.47 (m, 2H), 1.28 (d, J=12.6 Hz, 2H), 1.18-1.09 (m, 4H); MS (ES, m/z): [M+1]=606.25.

Example 180: 2-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]ethyl Acetate (I-211)

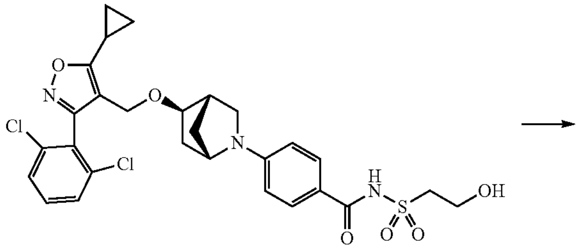

I-210

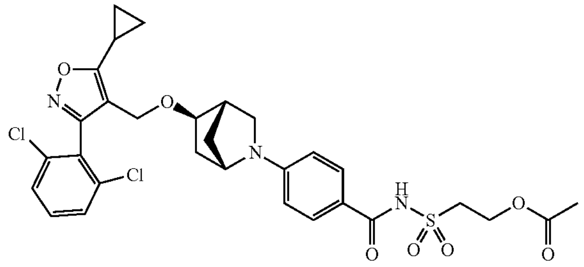

I-211

To a 25 mL round bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[(2-hydroxyethane)sulfonyl]benzamide I-210 (60 mg, 0.10 mmol, 1.00 equiv.), AcOH (6 mg, 0.10 mmol, 1.00 equiv.), 4-dimethylaminopyridine (1.2 mg, 0.01 mmol, 0.10 equiv.), dichloromethane (1 mL), and EDCI (21 mg, 0.11 mmol, 1.10 equiv.). The reaction mixture was stirred at room temperature for 1 h and concentrated under vacuum. The crude product was purified by Prep-HPLC using the following conditions: Column, XBridge Prep C18 OBD Column, 19, Á150 mm 5 um; mobile phase, Water (0.05% TFA) and ACN (48.0% ACN up to 62.0% in 8 min); Detector, uv 254 nm. After purification 2-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]ethyl acetate I-211 (23.5 mg, 37%) was obtained as an off-white solid. $^1$HNMR (400 MHz, DMSO-$d_6$): δ 11.63 (s, 1H), 7.77 (d, J=8.8 Hz, 2H), 7.69-7.52 (m, 3H), 6.51 (d, J=8.6 Hz, 2H), 4.38-4.18 (m, 5H), 3.85 (t, J=5.5 Hz, 2H), 3.31 (dd, J=9.7, 4.0 Hz, 1H), 2.56 (d, J=9.7 Hz, 1H), 2.47 (s, 1H), 2.33 (ddd, J=13.3, 8.2, 5.1 Hz, 1H), 1.99 (s, 1H), 1.77 (s, 3H), 1.68 (dd, J=12.8, 6.8 Hz, 1H), 1.51-1.37 (m, 2H), 1.27-1.05 (m, 6H); MS (ES, m/z): [M+1]=648.25.

Example 181: 2-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]ethyl Cyclopropanecarboxylate (I-212)

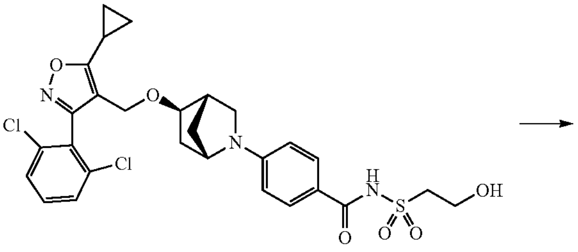

I-210

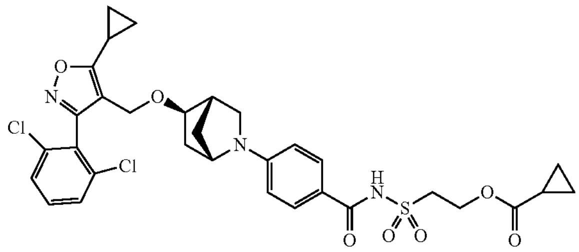

I-212

To a 25 mL round bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[(2-hydroxyethane)sulfonyl]benzamide I-210 (140 mg, 0.23 mmol, 1.00 equiv.), 4-dimethylaminopyridine (3 mg, 0.02 mmol, 0.10 equiv.), dichloromethane (2 mL), cyclopropanecarboxylic acid (20 mg, 0.23 mmol, 1.00 equiv.), and EDCI (48 mg, 0.25 mmol, 1.10 equiv.). The reaction mixture was stirred at room temperature for 1 h and then concentrated under vacuum. The crude product was purified by Prep-HPLC using the following conditions: Column, XBridge Prep OBD C18 Column, 19*250 mm, 5 um; mobile phase, Water (0.05% TFA) and ACN (60.0% ACN up to 66.0% in 10 min); Detector, UV 220 nm. After purification 2-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]ethyl cyclopropanecarboxylate I-212 (51.4 mg, 33%) was obtained as an off-white solid. $^1$HNMR (300 MHz, DMSO-d6): δ 11.63 (s, 1H), 7.75 (d, J=8.7 Hz, 2H), 7.68-7.48 (m, 3H), 6.48 (d, J=8.6 Hz, 2H), 4.35 (t, J=5.5 Hz, 2H), 4.22 (d, J=14.0 Hz, 3H), 3.93 (s, 2H), 3.84 (t, J=5.6 Hz, 2H), 3.43 (d, J=6.2 Hz, 2H), 3.29 (dd, J=9.6, 4.0 Hz, 1H), 2.50 (d, J=28.4 Hz, 2H), 2.32 (td, J=8.2, 4.2 Hz, 2H), 1.65 (dd, J=13.5, 6.7 Hz, 1H), 1.51-1.27 (m, 3H), 1.26-1.01 (m, 5H), 0.81-0.64 (m, 4H); MS (ES, m/z): [M+1]=674.30.

Example 182: 2-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]ethyl 2-methylpropanoate (I-213)

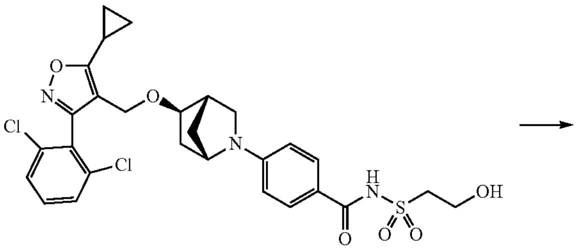

I-210

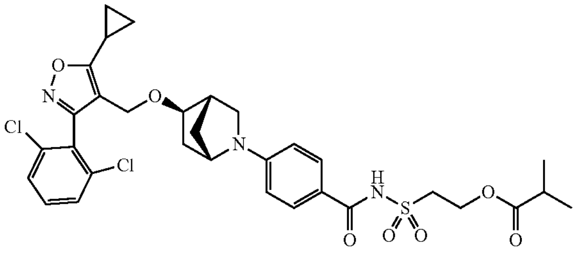

I-213

To a 8 mL sealed tube was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[(2-hydroxyethane)sulfonyl]benzamide I-210 (80 mg, 0.13 mmol, 1.00 equiv.), 2-methylpropanoic acid (11 mg, 0.12 mmol, 1.00 equiv.), dichloromethane (1 mL), 4-dimethylaminopyridine (2 mg, 0.02 mmol, 0.10 equiv), and EDCI (28 mg, 0.15 mmol, 1.10 equiv.). The reaction mixture was stirred at room temperature overnight, quenched with water, and extracted with ethyl acetate (30 mL×3). The combined organic extracts were washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (53.0% ACN up to 69.0% in 9 min); Detector, uv 254 nm. After purification 2-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]ethyl 2-methylpropanoate 1-213 (21.4 mg, 24%) was obtained as a white solid. $^1$HNMR (300 MHz, $CD_3OD$): δ 7.76 (d, J=9.0 Hz, 2H), 7.62-7.44 (m, 3H), 6.60-6.50 (m, 2H), 4.97-4.89 (m, 2H), 4.56-4.46 (m, 2H), 4.34 (s, 2H), 4.21 (s, 1H), 3.94-3.84 (m, 2H), 3.52 (d, J=6.4 Hz, 1H), 3.39 (dd, J=9.6, 4.1 Hz, 1H), 2.64 (d, J=9.6 Hz, 1H), 2.54 (d, J=3.8 Hz, 1H), 2.32 (dp, J=20.4, 6.8 Hz, 2H), 1.82 (dd, J=12.7, 6.7 Hz, 1H), 1.69-1.53 (m, 2H), 1.40-1.28 (m, 1H), 1.24-1.15 (m, 4H), 1.03 (d, J=7.0 Hz, 6H); MS (ES, m/z): [M+1]=676.15.

Example 183: 3-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]propyl Acetate (I-214)

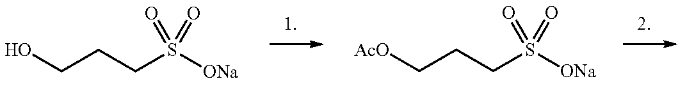

214a 214b

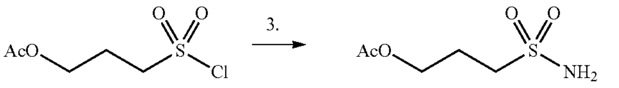

214c 214d

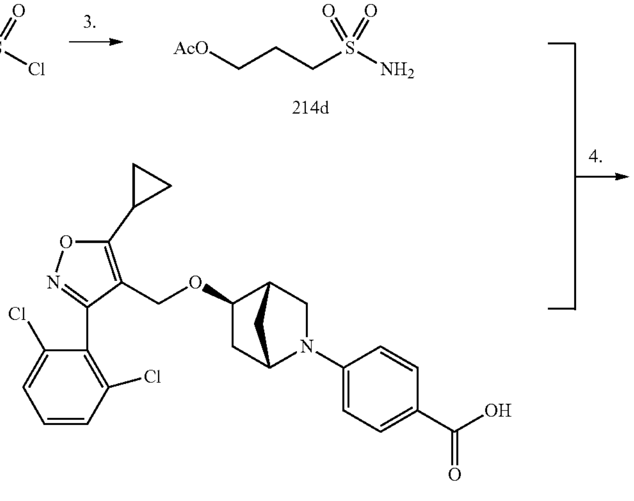

I-52

-continued

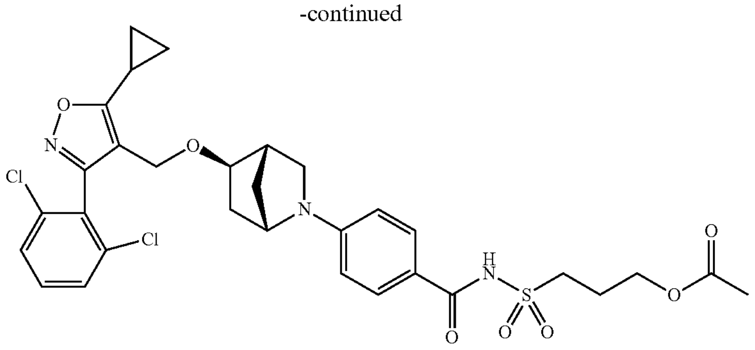

I-214

Step 1

To a 250 mL round bottom flask purged with and maintained under an inert atmosphere of nitrogen was added sodium 3-hydroxypropane-1-sulfonate 214a (10 g, 61.68 mmol, 1.00 equiv.) and acetic anhydride (15 mL). The reaction mixture was heated at 140° C., for 5 h with stirring and then concentrated under vacuum. The residue was washed with ether (100 mL×5) to give 3-[(sodiooxy)sulfonyl]propyl acetate 214b (12 g, 95%) as an off-white crude solid.

Step 2

To a 50 mL round-bottom flask was added 3-[(sodiooxy) sulfonyl]propyl acetate 214b (1 g, 4.90 mmol, 1.00 equiv.) and phosphorous pentachloride (3 g, 14.41 mmol, 3.00 equiv.). The resulting mixture was stirred for 10 min at room temperature, then washed with toluene (30 mL×3), and concentrated under vacuum to provide 3-(chlorosulfonyl) propyl acetate 214c (760 mg, 77%) as a colorless oil.

Step 3

To a 250 mL round bottom flask was added 3-(chlorosulfonyl)propyl acetate 214c (760 mg, 3.79 mmol, 1.00 equiv.) and a 0.5 M solution of $NH_3$ in tetrahydrofuran (30 mL). The resulting mixture was stirred at room temperature for 30 min and then concentrated under vacuum. The residue was diluted with of DCM and purified by silica gel column chromatography eluting with dichloromethane/ethyl acetate (2:1) to provide 3-sulfamoylpropyl acetate 214d (270 mg, 39%) as a light yellow oil.

Step 4

To a 8 mL vial was added 3-sulfamoylpropyl acetate 214d (230 mg, 1.27 mmol, 3.00 equiv.), 4-[(1S,4S,5R)-5-[5-cyclopropyl-3-(2,6-dichlorophenyl)-1,2-oxazol-4-yl]methoxy-2-azabicyclo[2.2.1]heptan-2-yl]benzoic acid I-52 (210 mg, 0.42 mmol, 1.00 equiv.), dichloromethane (2 mL), 4-dimethylaminopyridine (155 mg, 1.27 mmol, 3.00 equiv), and EDCI (122 mg, 0.64 mmol, 1.50 equiv.). The resulting mixture was stirred at room temperature overnight. The mixture was diluted with DCM, washed with brine (30 mL) and a 0.5 M hydrogen chloride aqueous solution (10 mL), dried over anhydrous sodium sulfate and concentrated. The residue was purified by silica gel column chromatography eluting with dichloromethane-methanol (5:1). Removal of solvents afforded 3-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]propyl acetate I-214 (131.3 mg, 47%) as a colorless solid. $^1$HNMR (300 MHz, $CD_3OD$): δ 7.75 (d, J=9.0 Hz, 2H), 7.61-7.43 (m, 3H), 6.54 (d, J=8.9 Hz, 2H), 5.03-4.75 (m, 3H), 4.33 (s, 2H), 4.20 (t, J=6.2 Hz, 3H), 3.69-3.58 (m, 2H), 3.52 (d, J=6.1 Hz, 1H), 3.39 (dd, J=9.5, 4.0 Hz, 1H), 2.63 (d, J=9.6 Hz, 1H), 2.54 (s, 1H), 2.35-2.07 (m, 3H), 2.03 (s, 3H), 1.82 (dd, J=12.4, 8.0 Hz, 1H), 1.61 (q, J=10.0 Hz, 2H), 1.33 (d, J=12.7 Hz, 2H), 1.23-1.13 (m, 4H); MS (ES, m/z): [M+1]=662.25.

Example 184: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(3-hydroxypropanesulfonyl)benzamide (I-215)

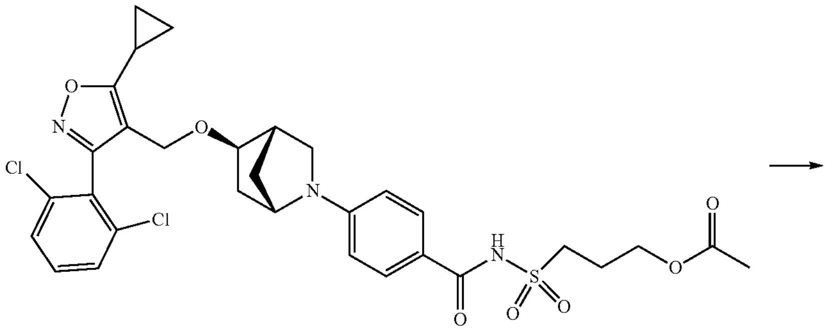

I-214

-continued

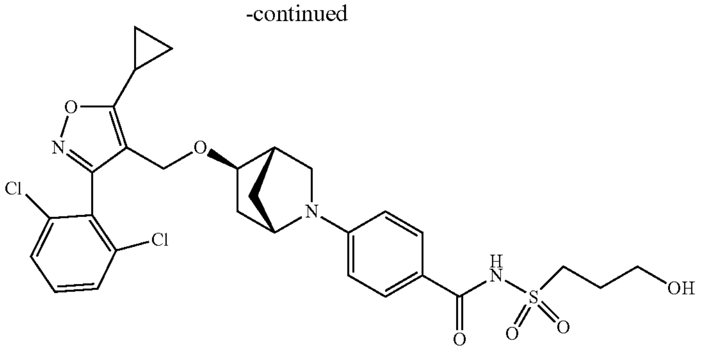

I-215

To a 50 mL round bottom flask was added 3-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]propyl acetate I-214 (100 mg, 0.15 mmol, 1.00 equiv.), methanol (5 mL), water (0.5 mL), and LiOH (70 mg, 2.92 mmol, 10.00 equiv.). The resulting mixture was stirred at room temperature for 4 h. The mixture was diluted with water. The pH value of the solution was adjusted to 4 using a 1.0M aqueous hydrogen chloride solution. The aqueous mixture was extracted with ethyl acetate (40 mL×3); and the combined organic extracts were washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase. Water (0.05% TFA) and ACN (43.0% ACN up to 60.0% in 8 min); Detector, UV 254 nm. After purification 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[(3-hydroxypropane)sulfonyl]benzamide I-215 (39 mg, 42%) was obtained as a colorless solid. $^1$HNMR (300 MHz, $CD_3OD$): δ 7.75 (d, J=9.0 Hz, 2H), 7.63-7.43 (m, 3H), 6.59-6.49 (m, 2H), 5.04-4.83 (m, 2H), 4.33 (s, 2H), 4.20 (s, 1H), 3.73-3.47 (m, 5H), 3.39 (dd, J=9.5, 4.1 Hz, 1H), 2.63 (d, J=9.5 Hz, 1H), 2.54 (s, 1H), 2.28 (p, J=6.8 Hz, 1H), 2.10-1.94 (m, 3H), 1.81 (dd, J=13.3, 6.8 Hz, 1H), 1.60 (q, J=9.9 Hz, 2H), 1.33 (d, J=12.6 Hz, 2H), 1.23-1.14 (m, 4H); MS (ES, m/z): [M+1]=620.25.

Example 185: 4-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]butan-2-yl Acetate (I-216)

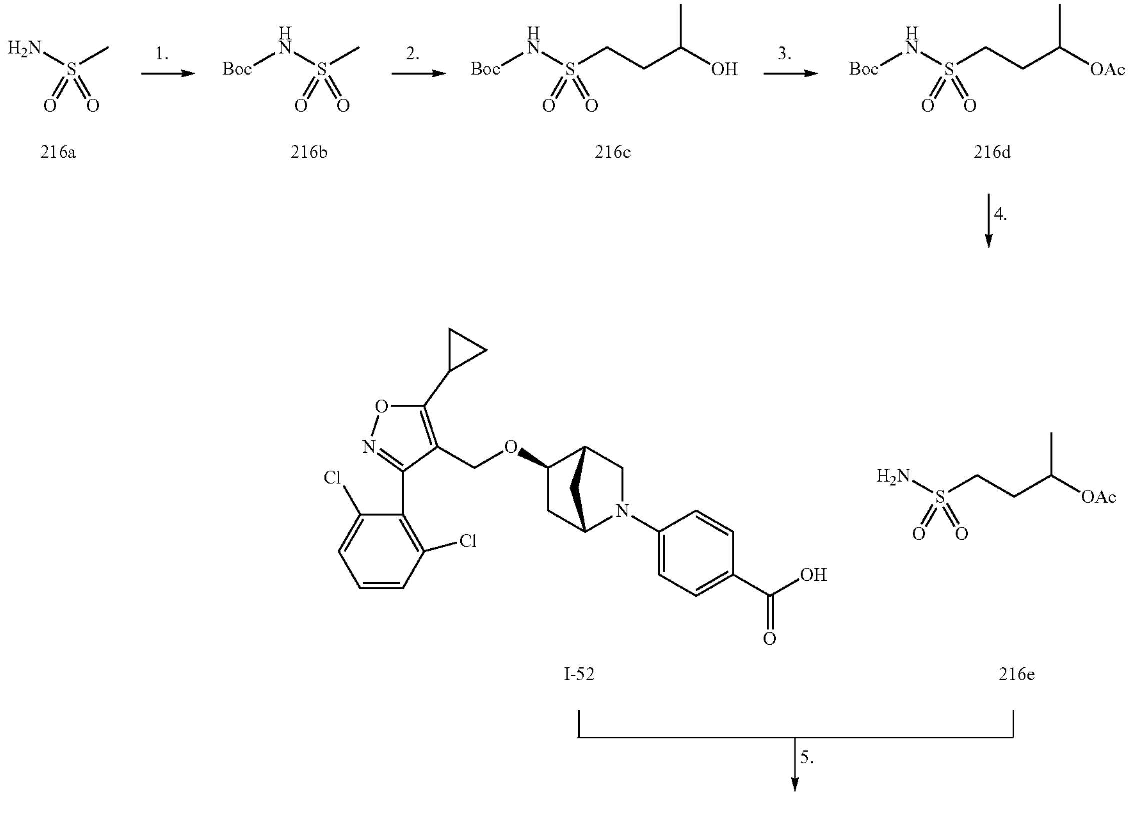

-continued

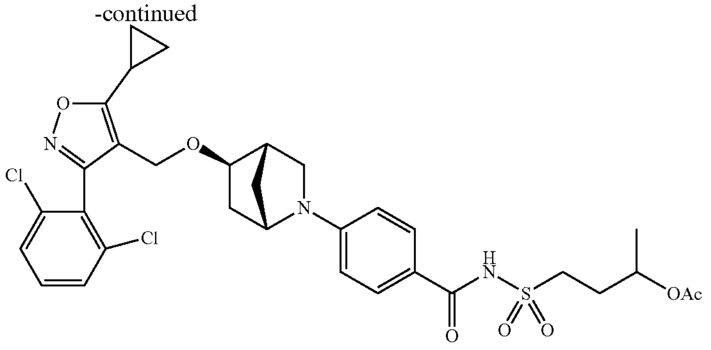

I-216

Step 1

To a 500 mL round bottom flask was added a solution of methanesulfonamide (10 g, 105.13 mmol, 1.00 equiv.) in dichloromethane (300 mL) followed by TEA (22 g, 217.41 mmol, 1.50 equiv.), $Boc_2O$ (27.5 g, 126.00 mmol, 1.20 equiv.), and 4-dimethylaminopyridine (1.28 g, 10.48 mmol, 0.10 equiv.). The reaction mixture was stirred at room temperature overnight and then concentrated under vacuum. 200 mL of $H_2O$ was added, the pH value of the solution was adjusted to 3 using a 1M hydrogen chloride aqueous solution, and the mixture was extracted with ethyl acetate (200 mL×3). The combined organic extracts were washed with brine (300 mL×2), dried over anhydrous sodium sulfate and concentrated under vacuum to give of tert-butyl N-methanesulfonylcarbamate 216b (10.06 g, 49%) as a white solid.

Step 2

To a 100 mL 3-necked round bottom flask purged with and maintained under an inert atmosphere of nitrogen was added a solution of diisopropylamine (1.03 g, 10.18 mmol, 2.00 equiv.) in tetrahydrofuran (20 mL), the solution was cooled to −78° C. A 2.5M solution of n-BuLi in THF (4.1 mL, 2.00 equiv.) was added dropwise with stirring during a 10 min period. The mixture was stirred for another 10 min at this temperature. A solution of tert-butyl N-methanesulfonylcarbamate 216b (1 g, 5.12 mmol, 1.00 equiv.) in tetrahydrofuran (10 mL) was added dropwise with stirring at −78° C., during a 10 min period. The reaction was continued for 20 min. Then, a solution of 2-methyloxirane (298 mg, 5.13 mmol, 1.00 equiv.) in tetrahydrofuran (10 mL) was added dropwise with stirring at −78° C., in a 15 min period. The reaction was continued for 30 min at this low temperature. Cooling bath was removed, and the reaction mixture was stirred at room temperature overnight. The mixture was cooled in an ice/salt bath, quenched by the addition of 40 mL of a saturated $NH_4Cl$ aqueous solution. The pH value of the solution was adjusted to 3 using a 2M hydrogen chloride aqueous solution. The aqueous mixture was extracted with ethyl acetate (100 mL×2), and the combined organic extracts were washed with brine (100 mL×3), dried over anhydrous sodium sulfate and concentrated under vacuum. The residue was purified by silica gel column chromatography eluting with ethyl acetate/petroleum ether (1:2) to furnish tert-butyl N-[(3-hydroxybutane)sulfonyl]carbamate 216c (320 mg, 25%) as a light yellow oil.

Step 3

To a 50 mL round bottom flask was added a solution of tert-butyl N-[(3-hydroxybutane)sulfonyl]carbamate 216c (10) mg, 0.39 mmol, 1.00 equiv.) in dichloromethane (3 mL) followed by AcOH (23.7 mg, 0.39 mmol, 1.00 equiv.), 4-dimethylaminopyridine (4.8 mg, 0.04 mmol, 0.10 equiv.), and EDCI (83.5 mg, 0.44 mmol, 1.10 equiv). The resulting mixture was stirred at room temperature for 2 h. The mixture was diluted with 100 mL of EA, washed with a 1M hydrogen chloride aqueous solution (100 mL) then brine (100 mL), dried over anhydrous sodium sulfate, and concentrated under vacuum to provide 4-([[(tert-butoxy)carbonyl]amino]sulfonyl)butan-2-yl acetate 216d (96 mg, 82%) as a light yellow oil.

Step 4

To a 50 mL round-bottom flask was added a solution of 4-([[(tert-butoxy) carbonyl]amino]sulfonyl) butan-2-yl acetate 216d (146 mg, 0.49 mmol, 1.00 equiv) in dichloromethane (2 mL) followed by trifluoroacetic acid (1 mL). The reaction mixture was stirred at room temperature for 30 min. The mixture was diluted with 10 mL of water. The pH value of the solution was adjusted to 8 with $NH_4HCO_3$. The aqueous mixture was extracted with ethyl acetate (20 mL×2). The combined organic extracts were washed with brine, dried over anhydrous sodium sulfate and concentrated under vacuum to give 4-sulfamoylbutan-2-yl acetate 216e (60 mg, 62%) as a light yellow oil.

Step 5

To a 50 mL round bottom flask was added a solution of 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-52 (350 mg, 0.70 mmol, 1.00 equiv.) in dichloromethane (10 mL), 4-sulfamoylbutan-2-yl acetate 216e (342 mg, 1.75 mmol, 2.50 equiv.), 4-dimethylaminopyridine (357 mg, 2.92 mmol, 3.00 equiv), and EDCI (202 mg, 1.05 mmol, 1.50 equiv). The resulting mixture was stirred at room temperature overnight. The mixture was diluted with 50 mL of EA and washed with a 1M HCl aqueous solution (1M). The aqueous layer was back extracted with 200 mL of ethyl acetate. The organic extracts were combined, washed with brine (200 mL), dried over anhydrous sodium sulfate and concentrated under vacuum. The crude product was purified by Prep-HPLC using the following conditions (mobile phase, Water (0.05° % TFA) and ACN (52.0% ACN up to 63.0% in 10 min); Detector, uv 254 nm. After purification 4-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]butan-2-yl acetate I-216 (350 mg, 70%) was obtained as a yellow oil. $^{1}$HNMR (300 MHz, $CD_3OD$): δ 7.70 (d, J=8.9 Hz, 2H), 7.56-7.38 (m, 3H), 6.49 (d, J=8.9 Hz, 2H), 5.02-4.81 (m, 1H), 4.28 (s, 2H), 4.15 (s, 1H), 3.61-3.42 (m, 3H), 3.34 (dd, J=9.6, 4.1 Hz, 1H), 2.64-2.54 (m, 1H), 2.48 (s, 1H), 2.22 (p, J=6.7 Hz, 1H), 2.12-1.92 (m, 5H), 1.83-1.70 (m, 1H), 1.56 (q, J=10.0 Hz, 2H), 1.28 (d, J=13.4 Hz, 2H), 1.21 (d, J=6.3 Hz, 3H), 1.17-1.10 (m, 4H); MS (ES, m/z): [M+1]=676.35.

Example 186: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(3-hydroxybutanesulfonyl)benzamide (I-217)

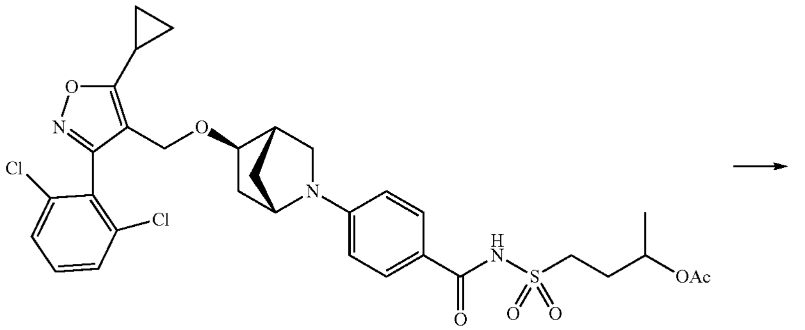

I-216

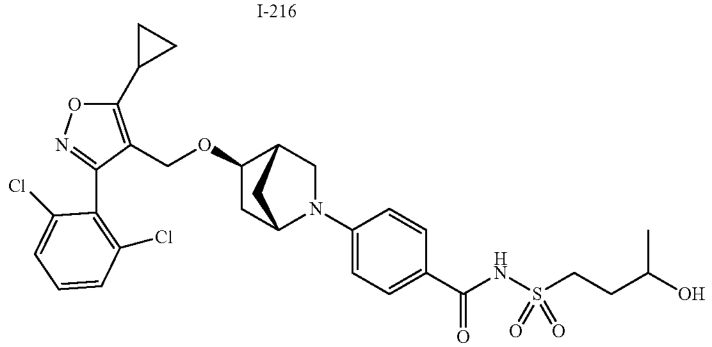

I-217

To a 50 mL round-bottom flask was added a solution of 4-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]butan-2-yl acetate I-216 (200 mg, 0.30 mmol, 1.00 equiv.) in methanol (2 mL), and LiOH (71 mg, 2.96 mmol, 10.00 equiv) in $H_2O$ (0.2 mL). The resulting mixture was stirred at 50° C., overnight. The mixture was diluted with 10 mL of water. The pH value of the solution was adjusted to 3 using a 1M hydrogen chloride aqueous solution. The aqueous mixture was extracted with ethyl acetate (100 mL), and the organic extract was washed with brine (50 mL×2), dried over anhydrous sodium sulfate and concentrated under vacuum. The crude product was purified by Prep-HPLC using the following conditions (mobile phase. Water (0.05% TFA) and ACN (46.0% ACN up to 64.0% in 8 min); Detector, uv 254 nm. After purification 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[(3-hydroxybutane)sulfonyl]benzamide I-217 (52.4 mg, 28%) was obtained as a white solid. $^{1}$HNMR (400 MHz, $CDCl_3$): δ 7.71 (d, J=8.7 Hz, 2H), 7.547-7.464 (m, 3H), 6.526-6.503 (m, 2H), 4.303 (d, J=0.9 Hz, 2H), 4.17 (s, 1H), 3.845 (m, 1H), 3.658-3.485 (m, 3H), 3.303 (m, 1H), 2.62 (d, J=9.5 Hz, 1H), 2.59-2.50 (m, 1H), 2.25 (p, J=6.7 Hz, 1H), 1.91-1.85 (m, 3H), 1.62-1.56 (m, 2H), 5.30-5.20 (m, 1H), 1.32-1.28 (m, 7H); MS (ES, m/z): [M+1]=634.30.

Example 187: 4-({4-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]phenyl}formamido)sulfonyl]butan-2-yl}oxy)-4-oxobutanoic Acid (I-218)

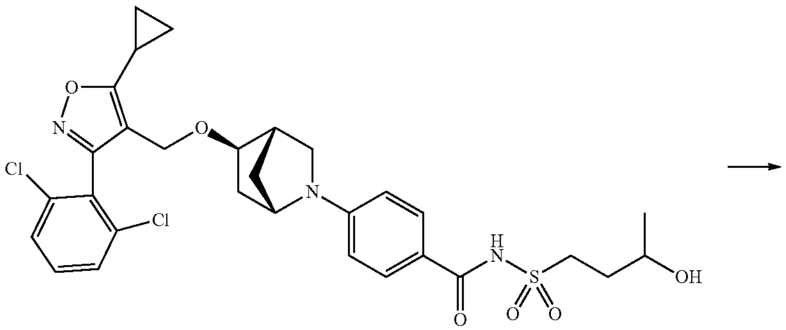

I-217

-continued

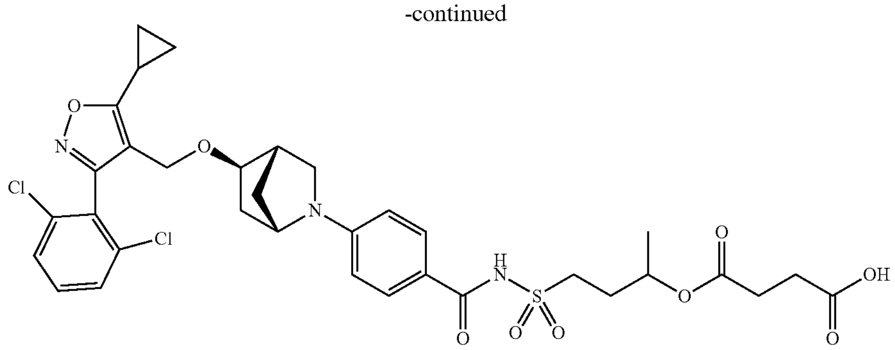

I-218

To a 5 mL sealed tube purged with and maintained under an inert atmosphere of nitrogen was added a solution of 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[(3-hydroxybutane)sulfonyl]benzamide I-217 (90 mg, 0.14 mmol, 1.00 equiv.) in dichloromethane (2 mL), succinic anhydride (56.8 mg, 0.57 mmol, 4.00 equiv.), 4-dimethylaminopyridine (52 mg, 0.43 mmol, 3.00 equiv.), and TEA (0.12 mL, 4.00 equiv.). The resulting mixture was stirred at room temperature overnight and concentrated under vacuum. The crude product was purified by Prep-HPLC using the following conditions (mobile phase, Water (0.05% TFA) and ACN (hold 5.0% ACN in 2 min, up to 60.0% in 8 min); Detector, uv 254 nm. After purification 4-([4-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]butan-2-yl]oxy)-4-oxobutanoic acid I-218 (19 mg, 18%) was obtained as a white solid. $^1$HNMR (400 MHz. $CD_3OD$): δ 7.75 (d, J=8.9 Hz, 2H), 7.63-7.43 (m, 3H), 6.59-6.49 (m, 2H), 5.12-4.95 (m, 1H), 4.33 (s, 2H), 4.20 (s, 1H), 3.69-3.47 (m, 3H), 3.37 (s, 2H), 2.64 (d, J=9.6 Hz, 1H), 2.57 (s, 5H), 2.27 (p, J=6.8 Hz, 1H), 2.18-1.95 (m, 2H), 1.89-1.75 (m, 1H), 1.61 (q, J=10.0 Hz, 2H), 1.39-1.11 (m, 9H); MS (ES, m/z): [M+1]=734.10.

Example 188: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(3,4-dihydroxybutanesulfonyl)benzamide (I-219)

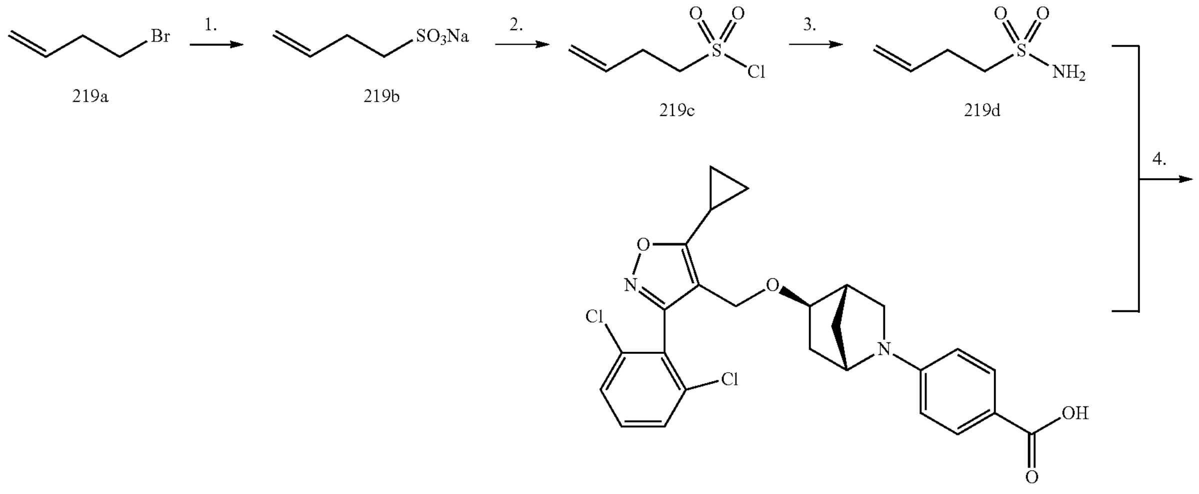

219a 219b 219c 219d

I-52

-continued

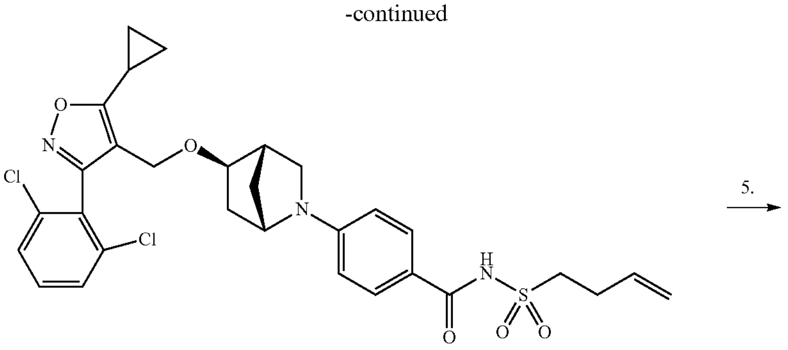

219e

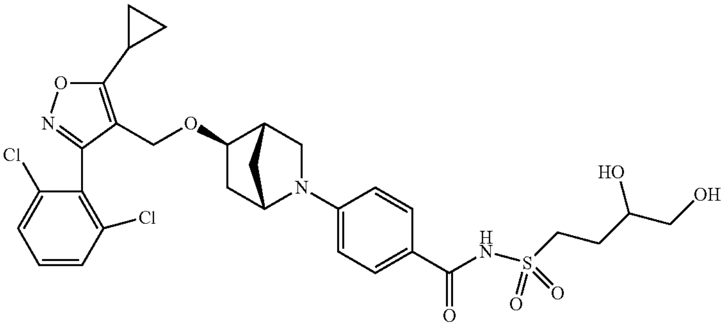

I-219

Step 1

To a 500 mL round bottom flask was added 4-bromobut-1-ene 219a (10 g, 74.07 mmol, 1.00 equiv.) and ethanol (50 mL). A solution of $Na_2SO_3$ (18.8 g, 149.21 mmol, 2.00 equiv.) in water (50 mL) was added dropwise with stirring. The reaction mixture was heated at 80° C., overnight. The mixture was concentrated under vacuum. The residue was dissolved in EA, and washed with water then brine. The organic phase was dried over $Na_2SO_4$ and concentrated to give sodium but-3-ene-1-sulfonate 219b (10 g, 85%) as a white solid.

Step 2

To a 50 mL round bottom flask was added sodium but-3-ene-1-sulfonate 219b (5 g, 31.62 mmol, 1.00 equiv.), and $PCl_5$ (16 g, 76.83 mmol, 2.50 equiv.). The resulting mixture was stirred at room temperature for 10 min. The mixture was diluted with EA. The solids were filtered out. The filtrate was dried over anhydrous sodium sulfate and concentrated under vacuum to a residue which was purified by silica gel column chromatography eluting with ethyl acetate/petroleum ether (0%-5%) to afford but-3-ene-1-sulfonyl chloride 219c (1 g, 20%) as yellow oil.

Step 3

To a 100 mL round-bottom flask was added but-3-ene-1-sulfonyl chloride 219c (1 g, 6.47 mmol, 1.00 equiv.) and a 0.5M solution of $NH_3$ in tetrahydrofuran (10 mL). The resulting mixture was stirred at room temperature for 30 min and concentrated under vacuum. The residue was purified by silica gel column chromatography eluting with dichloromethane/ethyl acetate (2:1) to give but-3-ene-1-sulfonamide 219d (188 mg, 22%) as a yellow oil.

Step 4

To a 8 mL sealed tube was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzoic acid I-52 (160 mg, 0.32 mmol, 1.00 equiv.), but-3-ene-1-sulfonamide 219d (85 mg, 0.63 mmol, 2.00 equiv.), dichloromethane (2 mL), 4-dimethylaminopyridine (115 mg, 0.94 mmol, 3.00 equiv.), and EDCI (91 mg, 0.47 mmol, 1.50 equiv.). The resulting mixture was stirred at room temperature overnight. The mixture was diluted with EA, washed with brine, dried over anhydrous sodium sulfate and concentrated. The residue was purified by silica gel column chromatography eluting with dichloromethane/methanol (15:1) to provide N-(but-3-ene-1-sulfonyl)-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzamide 219e (100 mg, 51%) as a white solid.

Step 5

To a 8 mL sealed tube was added N-(but-3-ene-1-sulfonyl)-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzamide 219e (60 mg, 0.10 mmol, 1.00 equiv.), a solution of NMO (60 mg, 0.51 mmol, 1.00 equiv.) in tetrahydrofuran (4 mL), and osmium tetroxide (20 mg, 0.08 mmol, 0.10 equiv.). The resulting mixture was stirred at room temperature overnight, then diluted EA, washed with $H_2O$ and brine. The organic phase was dried over anhydrous sodium sulfate and concentrated under vacuum. The crude product was purified by Prep-HPLC using the following conditions: Column, XBridge Prep OBD C18 Column, 19*250 mm, 5 um; mobile phase, Water (0.05% $NH_3H_2O$) and ACN (26.0% ACN up to 44.0% in 10 min); Detector, UV 220 nm. After purification 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[(3,4-dihydroxybutane)sulfonyl]benzamide I-219 (18.8 mg, 30%) was obtained as a white solid. $^1$HNMR (300 MHz, $CD_3OD$): δ 7.87 (d, J=8.5 Hz, 2H), 7.61-7.44 (m, 3H), 6.45 (d, J=8.6 Hz, 2H), 4.32 (s, 2H), 4.12 (s, 1H), 3.73 (t, J=6.7 Hz, 1H), 3.54-3.33 (m, 5H), 2.61-2.45 (m, 2H), 2.27 (q, J=6.6 Hz, 1H), 2.06 (s, 1H), 1.86 (dt, J=14.1, 7.6 Hz, 2H), 1.60 (s, 2H), 1.35-1.14 (m, 6H); MS (ES, m/z): [M+1]=650.15.

Example 189: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-{[(1s,4s)-4-hydroxycyclohexyl]sulfonyl}benzamide (I-220) and 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-{[(1r,4r)-4-hydroxycyclohexyl]sulfonyl}benzamide (I-221)

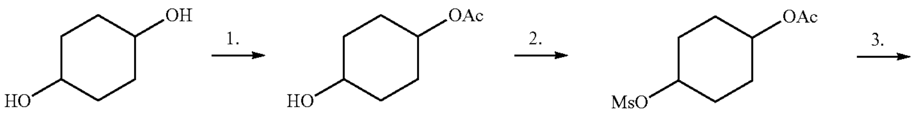

220a 220b 220c

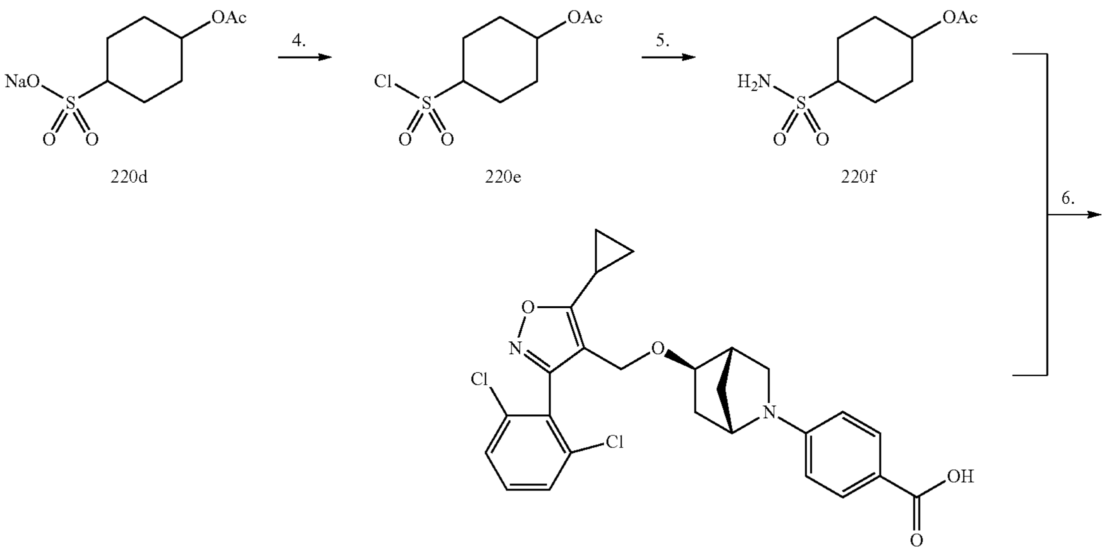

220d 220e 220f

I-52

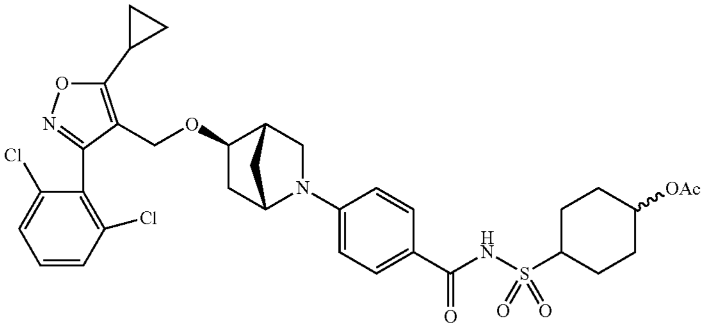

220g

7.

-continued

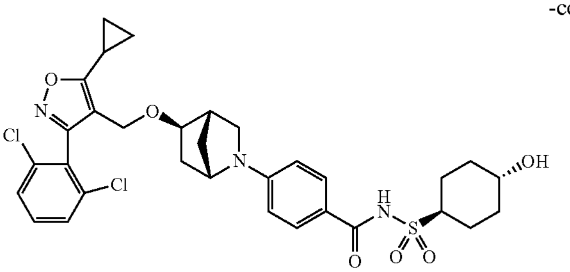

I-221

+

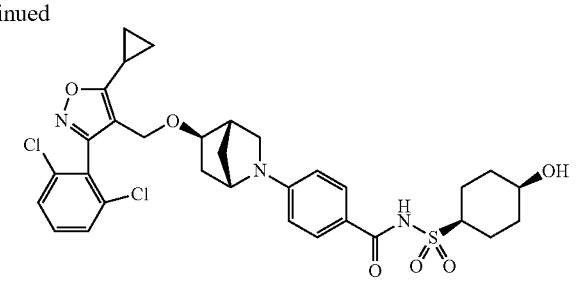

I-220

Step 1

To a 1000 mL round bottom flask was added cyclohexane-1,4-diol 220a (10 g, 86.09 mmol, 1.00 equiv.), dichloromethane (200 mL), and TEA (17.4 g, 171.95 mmol, 2.00 equiv.). Acetyl chloride (6.7 g, 85.35 mmol, 1.00 equiv.) was added dropwise at 0° C., with stirring. The resulting mixture was stirred at 0° C., for 1 h, and then diluted with 100 mL of DCM. The mixture was washed with $H_2O$ (500 mL×2) and brine (500 mL×2), dried over anhydrous sodium sulfate and concentrated under vacuum. The residue was purified by silica gel column chromatography eluting with ethyl acetate/petroleum ether (0-50%) to give 4-hydroxycyclohexyl acetate 220b (5 g, 37%) as a colorless oil.

Step 2

To a 500 mL round bottom flask was added a solution of 4-hydroxycyclohexyl acetate 220b (7 g, 44.25 mmol, 1.00 equiv.) in dichloromethane (140 mL) and TEA (4.9 g, 48.42 mmol, 1.10 equiv.), the mixture was cooled at 0° C. Methanesulfonyl chloride (5.5 g, 48.01 mmol, 1.10 equiv.) was added dropwise with stirring. Cooling bath was removed, and the reaction mixture was stirred at room temperature for 2 h. The reaction was quenched by the addition of 20 mL of water/ice. The mixture was diluted with 100 mL of DCM, washed with brine (300 mL), dried over anhydrous sodium sulfate, and concentrated under vacuum. The residue was purified by silica gel column chromatography eluting with ethyl acetate/petroleum ether (0-50%) to provide 4-(methanesulfonyloxy)cyclohexyl acetate 220c (7 g, 66%) as a colorless oil.

Step 3

To a 1 L round bottom flask was added 4-(methanesulfonyloxy)cyclohexyl acetate 220c (5.2 g, 22.01 mmol, 1.00 equiv.) and ethanol (300 mL). A solution of $Na_2SO_3$ (5.6 g, 44.44 mmol, 2.00 equiv.) in water (300 mL) was added dropwise with stirring at 0° C. Cooling bath was removed, the resulting mixture was heated at 80° C., overnight and concentrated under vacuum to afford 4-[(sodiooxy)sulfonyl]cyclohexyl acetate 220d (8 g, crude) as a white solid.

Step 4

To a 500 mL round-bottom flask was added 4-[(sodiooxy)sulfonyl]cyclohexyl acetate 220d (8 g, 32.75 mmol, 1.00 equiv.) and a solution of phosphorous pentachloride (34 g, 163.27 mmol, 5.00 equiv.) in toluene (150 mL). The resulting mixture was heated at 100° C., for 2 h. The solids were filtered out, the filtrate was concentrated under vacuum to a residue which was purified by silica gel column chromatography eluting with ethyl acetate/petroleum ether (0-100%) to give 4-(chlorosulfonyl)cyclohexyl acetate 220e (1.9 g, 24%) as a light yellow oil.

Step 5

To a 100 mL round bottom flask was added 4-(chlorosulfonyl)cyclohexyl acetate 220e (900 mg, 3.74 mmol, 1.00 equiv.) and a 0.5M solution of $NH_3$ in tetrahydrofuran (20 mL). The resulting mixture was stirred at room temperature for 30 min and then concentrated under vacuum. The residue was purified by silica gel column chromatography eluting with dichloromethane/ethyl acetate (2:1) to give 4-sulfamoylcyclohexyl acetate 220f (180 mg, 22%) as a light yellow oil.

Step 6

To a 8 mL vial was added 4-sulfamoylcyclohexyl acetate 220f (200 mg, 0.90 mmol, 3.00 equiv.), 4-[(1S,4S,5R)-5-[5-cyclopropyl-3-(2,6-dichlorophenyl)-1,2-oxazol-4-yl]methoxy-2-azabicyclo[2.2.1]heptan-2-yl]benzoic acid I-52 (150 mg, 0.30 mmol, 1.00 equiv.), dichloromethane (2 mL), 4-dimethylaminopyridine (110 mg, 0.90 mmol, 3.00 equiv.), and EDCI (87 mg, 0.45 mmol, 1.50 equiv.). The resulting mixture was stirred at room temperature for 4 h. The mixture was diluted with 100 mL of DCM, washed with $H_2O$ (40 mL) and brine (40 mL), dried over anhydrous sodium sulfate and concentrated under vacuum. The residue was purified by silica gel column chromatography eluting with dichloromethane/methanol (20:1) to give 4-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane)sulfonyl]cyclohexyl acetate 220g (80 mg, 38%) as a light yellow solid.

Step 7

To a 50 mL round bottom flask was added 4-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]phenyl]methane) sulfonyl]cyclohexyl acetate 220g (70 mg, 0.10 mmol, 1.00 equiv.), methanol (10 mL), water (1 mL), and LiOH (42 mg, 1.75 mmol, 1.00 equiv.). The resulting mixture was heated at 60° C., for 2 h. After cooling to room temperature, the mixture was diluted with EA, the pH value of the solution was adjusted to 2 using a 1 M HCl aqueous solution, and further partitioned with 30 mL of brine. The separated organic layer was dried over anhydrous sodium sulfate and concentrated under vacuum. The crude product was purified by Prep-HPLC with the following conditions:

Column, XBridge Shield RP18 OBD Column, 5 um, 19*150 mm; mobile phase, Water (0.05% TFA) and ACN (48.0% ACN up to 63.0% in 8 min); Detector, uv 254 nm. After purification two isomers were obtained: the cis isomer (the absolute stereo configuration of the hydroxycyclohexane moiety was arbitrary assigned) 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-[[(1s,4s)-4-hydroxycyclohexane]sulfonyl]benzamide I-220 (6.9 mg, 10%) as a light yellow solid, $^{1}$HNMR (300 MHz, $CDCl_3$): δ 8.10 (s, 1H), 7.63 (d, J=8.3 Hz, 2H), 7.45-7.25 (m, 3H), 6.41 (d, J=8.3 Hz, 2H), 4.24 (s, 2H), 4.07 (s, 1H), 3.68 (dt, J=35.0, 11.7 Hz, 2H), 3.50-3.41 (m, 1H), 3.35 (dd, J=9.5, 4.0 Hz, 1H), 2.53 (dd, J=20.2, 6.4 Hz, 2H), 2.30-2.19 (m, 2H), 2.09 (td, J=9.0, 8.6, 4.7 Hz, 3H), 1.88-1.75 (m, 1H), 1.60 (q, J=10.3 Hz, 2H), 1.39-1.18 (m, 5H), 1.09 (dq, J=7.4, 4.3 Hz, 2H); MS (ES, m/z): [M+1]=660.1; and the trans isomer (the absolute stereo configuration of the hydroxycyclohexane moiety was arbitrary assigned) 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-{[(1r,4r)-4-hydroxycyclohexyl]sulfonyl}benzamide I-221 (11.8 mg, 18%) as a light yellow solid. $^{1}$HNMR (300 MHz, $CDCl_3$): δ 8.57 (s, 1H), 7.67 (d, J=7.4 Hz, 3H), 7.44-7.25 (m, 4H), 6.41 (t, J=4.3 Hz, 3H), 4.24 (s, 3H), 4.07 (s, 2H), 3.80 (d, J=11.8 Hz, 2H), 3.65 (s, 1H), 3.46 (s, 1H), 3.34 (d, J=8.2 Hz, 1H), 2.49 (td, J=26.0, 25.0, 9.7 Hz, 4H), 2.20-1.74 (m, 15H), 1.56 (d, J=10.2 Hz, 4H), 1.38-1.03 (m, 12H); MS (ES, m/z): [M+1]=660.1.

Example 190: 4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-N-(dodecane-1-sulfonyl)-3-fluorobenzamide (I-222)

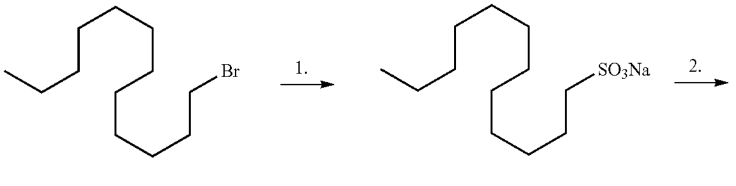

222a

222b

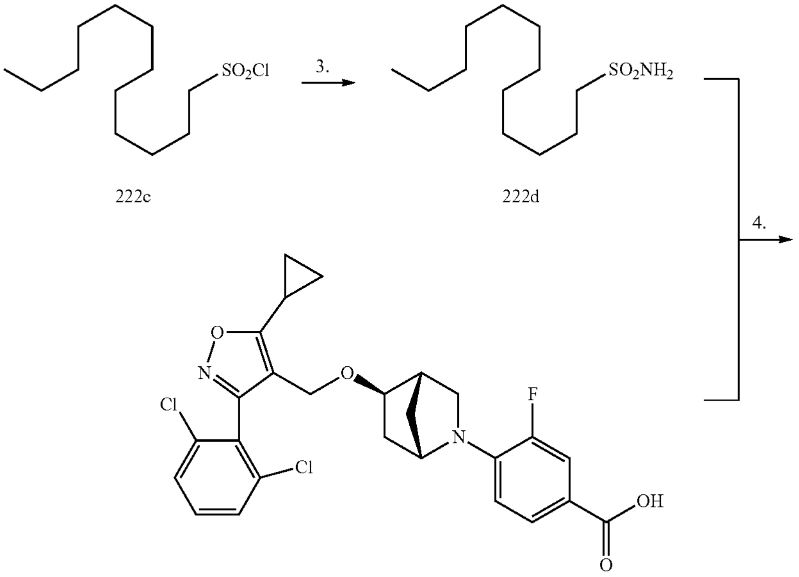

222c

222d

I-53

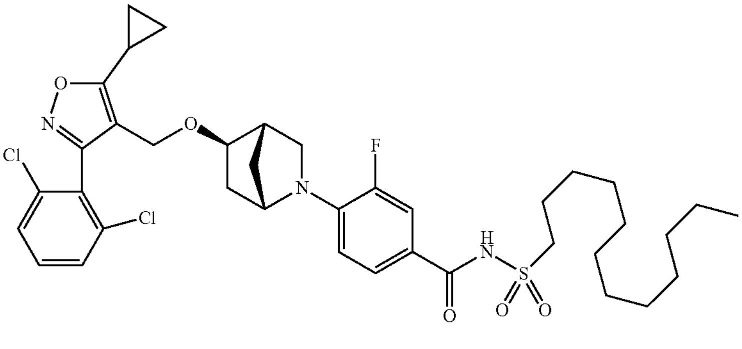

I-222

Step 1

To a 250 mL round bottom flask was added a solution of 1-bromododecane 222a (5 g, 20.06 mmol, 1.00 equiv.) in ethanol (40 mL) and a solution of $Na_2SO_3$ (5.2 g, 2.00 equiv.) in water (40 mL). The resulting mixture was heated at 80° C., overnight. After cooling to room temperature, the mixture was extracted with ethyl acetate (100 mL×2). The combined organic extracts were washed with brine (30 mL×2), dried over anhydrous sodium sulfate and concentrated to a residue which was triturated with hexanes (20 mL×3) to give sodium dodecane-1-sulfonate 222b (5.2 g, 92%) as a white solid.

Step 2

To a 100 mL mortar was added sodium dodecane-1-sulfonate 222b (1 g, 3.67 mmol, 1.00 equiv.) and phosphorous pentachloride (3.03 g, 14.55 mmol, 4.00 equiv.). The resulting mixture was stirred at room temperature for 10 min. The mixture was washed with ether (50 mL×3), the solids were filtered out, and the filtrate was concentrated under vacuum to give dodecane-1-sulfonyl chloride 222c (500 mg, 51%) as a white solid.

Step 3

To a 250 mL round bottom flask was added dodecane-1-sulfonyl chloride 222c (500 mg, 1.86 mmol, 1.00 equiv.) and a 7M solution of $NH_3$ in methanol. The resulting mixture was stirred at room temperature for 2 h. The solids were filtered out, the filtrate was concentrated under vacuum to a residue which was purified by silica gel column chromatography eluting with $CH_3CN:H_2O$ (0%-100%). Removal of solvents afforded dodecane-1-sulfonamide 222d (220 mg, 47%) as a white solid.

Step 4

To a 50 mL round bottom flask was added dodecane-1-sulfonamide 222d (80 mg, 0.32 mmol, 2.00 equiv.), 4-[(1S,4S,5R)-5-[5-cyclopropyl-3-(2,6-dichlorophenyl)-1,2-oxazol-4-yl]methoxy-2-azabicyclo[2.2.1]heptan-2-yl]-3-fluorobenzoic acid I-53 (80 mg, 0.15 mmol, 1.00 equiv.), dichloromethane (2 mL), EDCI (45 mg, 0.23 mmol, 1.50 equiv.), and 4-dimethylaminopyridine (57 mg, 0.47 mmol, 3.00 equiv.). The resulting mixture was stirred at room temperature overnight. The mixture was diluted 50 mL of DCM, washed with $H_2O$ (30 mL×2) and brine (30 mL×2), dried over anhydrous sodium sulfate and concentrated. The crude product was purified by Prep-HPLC using the following conditions: Column, XBridge C18 OBD Prep Column, 100� 5 μm, 19 mm×250 mm; mobile phase, Water (0.05% TFA) and ACN (hold 96.0% ACN in 8 min); Detector, UV 254 nm. After purification 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-N-(dodecane-1-sulfonyl)-3-fluorobenzamide I-222 (23.4 mg, 20%) was obtained as a colorless solid. $^1$HNMR (300 MHz, $CD_3OD$): δ 7.59-7.41 (m, 5H), 6.60 (t, J=8.7 Hz, 1H), 4.26 (d, J=11.1 Hz, 3H), 3.59-3.41 (m, 4H), 2.71 (dd, J=9.9, 3.4 Hz, 1H), 2.48-2.40 (m, 1H), 2.23 (p, J=6.7 Hz, 1H), 1.94-1.68 (m, 3H), 1.62-1.34 (m, 4H), 1.24 (d, J=8.6 Hz, 18H), 1.13 (d, J=6.7 Hz, 4H), 0.91-0.80 (m, 3H); MS (ES, m/z): [M+1] =748.30.

Example 191: (2R,3S,4R,5R)—N-{10-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}formamido)sulfonyl]decyl}-2,3,4,5,6-pentahydroxyhexanamide (I-223)

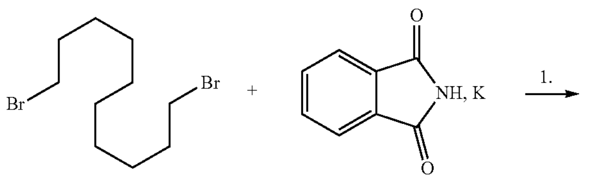

223a 223b

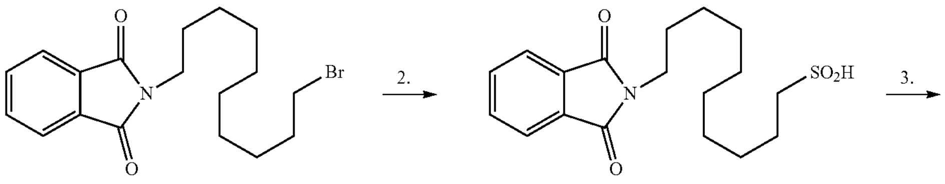

223c 223d

-continued
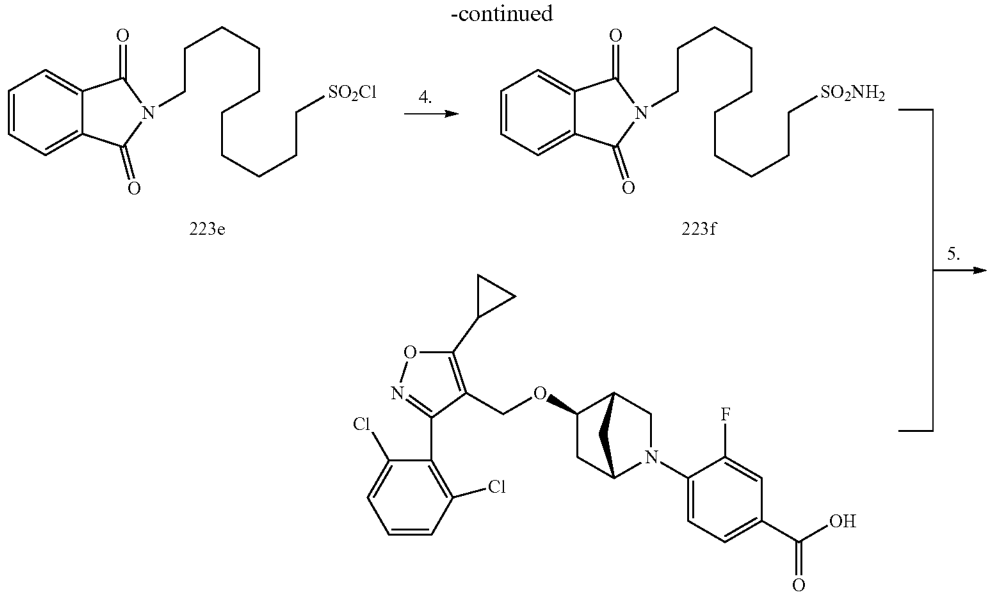
223e
223f
I-53
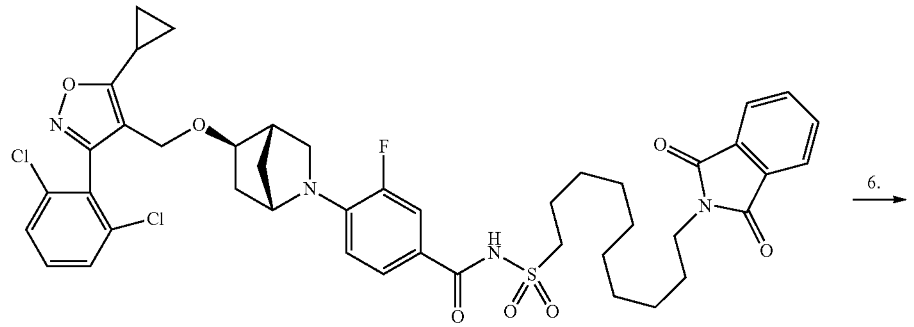
223g
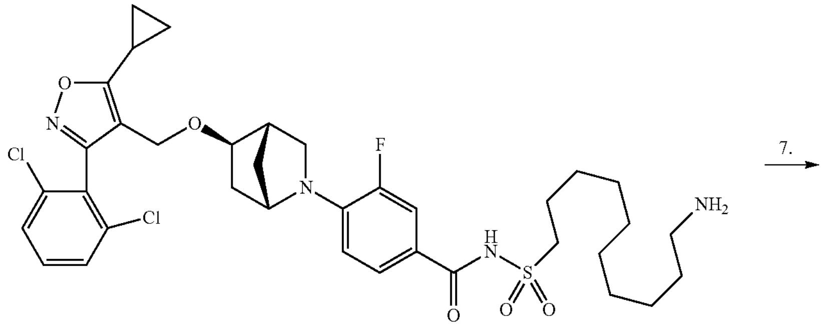
223h

-continued

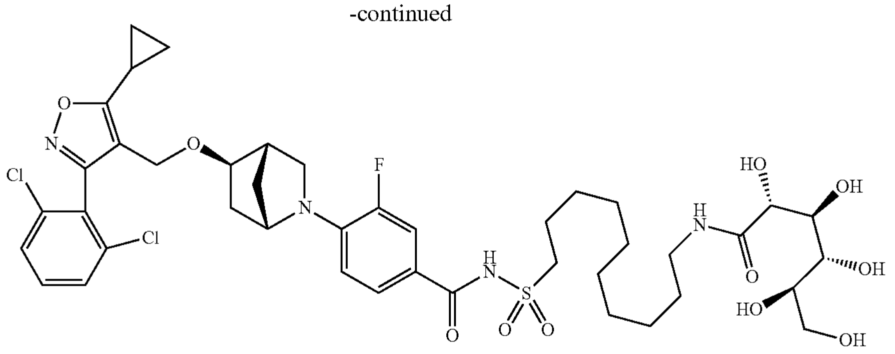

I-223

Step 1

To a 500 mL round-bottom flask was added 1,10-dibromodecane 223a (24.2 g, 80.65 mmol, 3.00 equiv.), acetone (150 mL), 2-potassio-2,3-dihydro-1H-isoindole-1,3-dione 223b (5 g, 26.99 mmol, 1.00 equiv.), and potassium carbonate (11.2 g, 81.04 mmol, 3.00 equiv.). The resulting mixture was stirred at 60° C., for 16 h and concentrated. The residue was purified by silica gel column chromatography eluting with ethyl acetate/petroleum ether (1:10) to give 2-(10-bromodecyl)-2,3-dihydro-1H-isoindole-1,3-dione 223c (8.5 g, 86%) as a white solid.

Step 2

To a 250 mL round bottom flask was added 2-(10-bromodecyl)-2,3-dihydro-1H-isoindole-1,3-dione 223c (3.5 g, 9.56 mmol, 1.00 equiv.), ethanol (20 mL), $Na_2SO_3$ (2.4 g, 2.00 equiv), and water (20 mL). The resulting mixture was heated at 80° C., for 16 h. Solids were filtered out. The filtrate was allowed to cool and solids precipitated out which was collected by filtration to give 10-(1,3-dioxo-2,3-dihydro-1H-isoindol-2-yl)decane-1-sulfonic acid 223d (2.5 g, 71%) as a white solid.

Step 3

To a 90 mL mortar was added sodium 10-(1,3-dioxo-2,3-dihydro-1H-isoindol-2-yl)decane-1-sulfonate 223d (1 g, 2.57 mmol, 1.00 equiv) and phosphorus pentachloride (2.12 g, 10.18 mmol, 4.00 equiv.). The mixture was grounded for 3 min at room temperature. The resulting mixture was diluted with toluene (100 mL), filtered, and the toluene filtrate was concentrated under vacuum. The residue was dissolved in 100 mL of EA, washed with a saturated sodium bicarbonate aqueous solution (100 mL×2) and brine (100 mL×2), dried over anhydrous sodium sulfate, and concentrated under vacuum to provide 10-(1,3-dioxo-2,3-dihydro-1H-isoindol-2-yl)decane-1-sulfonyl chloride 223e (620 mg, 63%) as a white solid.

Step 4

To a 500 mL round bottom flask was added 10-(1,3-dioxo-2,3-dihydro-1H-isoindol-2-yl)decane-1-sulfonyl chloride 223e (3.5 g, 9.07 mmol, 1.00 equiv.), tetrahydrofuran (50 mL), and a saturated solution of $NH_3$ in THF (300 mL). The resulting mixture was stirred at room temperature for 3 h. The mixture was concentrated under vacuum to a residue which was purified by silica gel column chromatography eluting with dichloromethane/methanol (10:1) to give 10-(1,3-dioxo-2,3-dihydro-1H-isoindol-2-yl)decane-1-sulfonamide 223f (1.5 g, 45%) as a white solid.

Step 5

To a 50 mL round bottom flask purged with and maintained under an inert atmosphere of nitrogen was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzoic acid I-53 (520 mg, 1.01 mmol, 1.00 equiv.), 10-(1,3-dioxo-2,3-dihydro-1H-isoindol-2-yl)decane-1-sulfonamide 223f (552 mg, 1.51 mmol, 1.50 equiv.), dichloromethane (10 mL), EDCI (480 mg, 2.50 mmol, 2.50 equiv.), and 4-dimethylaminopyridine (307 mg, 2.51 mmol, 2.50 equiv.). The reaction mixture was stirred at room temperature for 16 h, then quenched by the addition of a 1M hydrogen chloride aqueous solution (10 mL). 100 mL of brine was added, the aqueous mixture was extracted with chloromethane (100 mL×3). The combined organic extracts were dried over anhydrous sodium sulfate and concentrated under vacuum. The residue was dissolved in 3 mL of DMF and purified by reverse phase column chromatography eluting with ACN:$H_2O$ (52:48) to afford 4-[(1S,4S,5R)-5-[[5-cyclopropyl-3-(2,6-dichlorophenyl)-1,2-oxazol-4-yl] methoxy]-2-azabicyclo[2.2.1]heptan-2-yl]-N-[[10-(1,3-dioxo-2,3-dihydro-1H-isoindol-2-yl)decane]sulfonyl]-3-fluorobenzamide 223g (420 mg, 48%) as a white solid.

Step 6

To a 30 mL vial was added 4-[(1S,4S,5R)-5-[[5-cycloprorpyl-3-(2,6-dichlorophenyl)-1,2-oxazol-4-yl]methoxy]-2-azabicyclo[2.2.1]heptan-2-yl]-N-[[10-(1,3-dioxo-2,3-dihydro-1H-isoindol-2-yl)decane]sulfonyl]-3-fluorobenzamide 223g (420 mg, 0.49 mmol, 1.00 equiv.), chloroform (3 mL), ethanol (3 mL), and hydrazine (0.5 mL). The resulting mixture was stirred at 70° C., for 3 h and concentrated under vacuum. The residue was dissolved in 3 mL of DMF and purified by reverse phase column chromatography eluting with $CH_3CN$:$H_2O$ (4:6) to afford N-[(10-aminodecane)sulfonyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzamide 223h (280 mg, 78%) as a white solid.

Step 7

To a 10 mL vial was added N-[(10-aminodecane)sulfonyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzamide 223h (70 mg, 0.10 mmol, 1.00 equiv.), methanol (3 mL), (3R,4S,5S,6R)-3,4,5-trihydroxy-6-(hydroxymethyl)oxan-2-one (34 mg, 0.19 mmol, 2.00 equiv), and TEA (0.1 mL). The resulting mixture was heated at 70° C., for 3 h and concentrated under vacuum. The crude product was purified by Prep-HPLC using the following conditions: Column, XBridge Prep C18 OBD Column, 19?? 150 mm 5 um; mobile phase: Water (0.05% $NH_3H_2O$) and ACN (35.0% ACN up to 45.0% in 7 min); Detector, UV 254/220 nm. After purification (2R,3S,4R,5R)—N-[10-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]methane)sulfonyl]decyl]-2,3,4,5,6-pentahydroxy hexanamide 1-223 (10.2 mg, 12%) was obtained as a white solid. $^1$HNMR (400 MHz, DMSO-$d_6$): δ 7.66-7.49 (m, 6H), 7.07 (s, 1H), 6.58 (t, J=9.0 Hz, 1H), 5.32 (d, J=5.0 Hz, 1H), 4.51 (d, J=4.9 Hz, 1H), 4.44 (d, J=5.4 Hz, 1H), 4.40-4.27 (m, 2H), 4.22 (s, 2H), 4.13 (s, 1H), 3.98-3.83 (m, 2H), 3.60-3.50 (m, 1H), 3.51-3.30 (m, 5H), 3.23 (s, 2H), 3.03 (dp, J=19.3, 6.3 Hz, 2H), 2.62 (d, J=8.9 Hz, 1H), 2.41-2.25 (m, 2H), 1.79 (dd, J=13.7, 6.6 Hz, 1H), 1.58 (p, J=7.4 Hz, 2H), 1.44 (d, J=9.6 Hz, 1H), 1.40-1.26 (m, 5H), 1.22-1.02 (m, 15H); MS (ES, m/z): [M+1]=915.30.

Example 192: N-{10-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}formamido)sulfonyl]decyl}acetamide (I-224)

To a 8 mL vial was added N-[(10-aminodecane)sulfonyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzamide 223h (100 mg, 0.14 mmol, 1.00 equiv.), tetrahydrofuran (5 mL), acetyl chloride (11.7 mg, 0.15 mmol, 1.10 equiv.), and TEA (28 mg, 0.28 mmol, 2.00 equiv.). The resulting mixture was stirred at room temperature for 1 h and concentrated under vacuum. The residue was dissolved in 3 mL of DMF. The crude product was purified by Prep-HPLC using the following conditions: Column, XBridge C18 OBD Prep Column, 19 mm×250 mm; mobile phase, Water (0.05% TFA) and ACN (60.0% ACN up to 66.0% in 10 min); Detector, uv 254 nm. After purification N-[10-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]methane)sulfonyl]decyl]acetamide I-224 (29.4 mg, 28%) as a white solid. $^1$HNMR (400 MHz, $CD_3OD$): δ 7.61-7.43 (m, 5H), 6.63 (t, J=8.8 Hz, 1H), 4.33-4.24 (m, 3H), 3.60-3.45 (m, 4H), 3.12 (t, J=7.1 Hz, 2H), 2.74 (dd, J=10.0, 3.3 Hz, 1H), 2.46 (d, J=3.8 Hz, 1H), 2.25 (p, J=6.8 Hz, 1H), 1.91 (s, 4H), 1.57 (q, J=10.0 Hz, 2H), 1.50-1.39 (m, 5H), 1.28 (s, 11H), 1.20-1.12 (m, 4H); MS (ES, m/z): [M+1]=777.25-

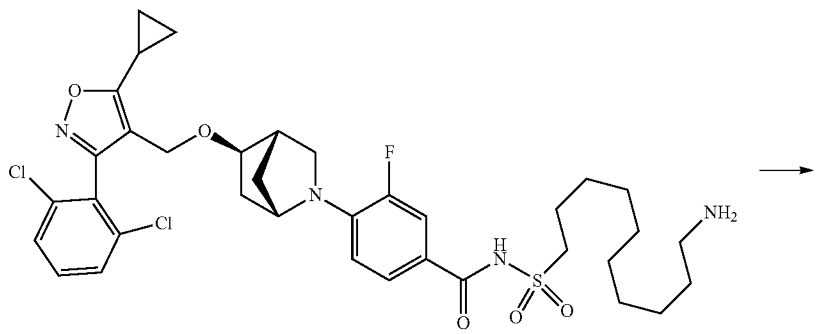

223h

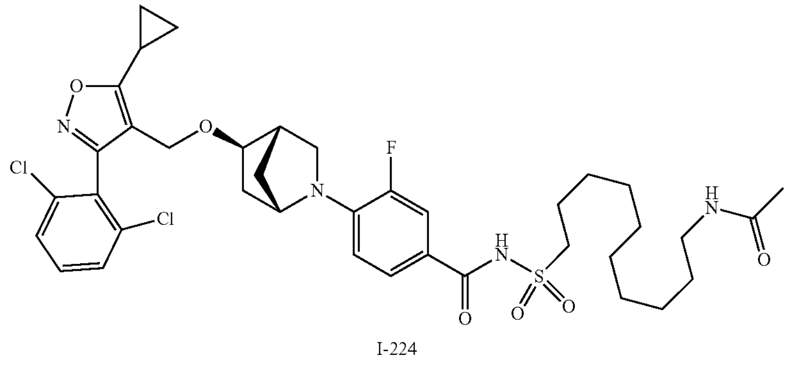

I-224

Example 193: N-{10-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}formamido)sulfonyl]decyl}-2-methoxyacetamide (I-225)

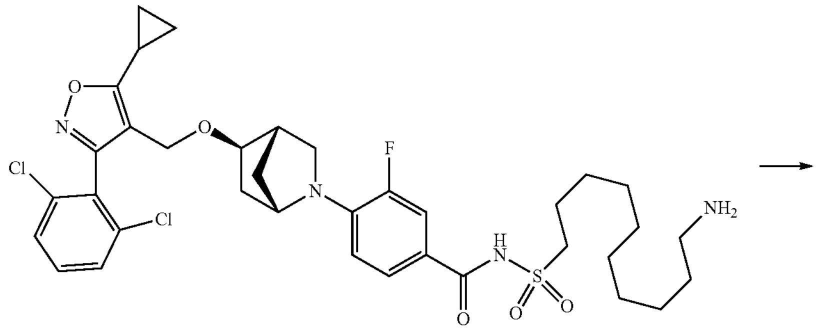

223h

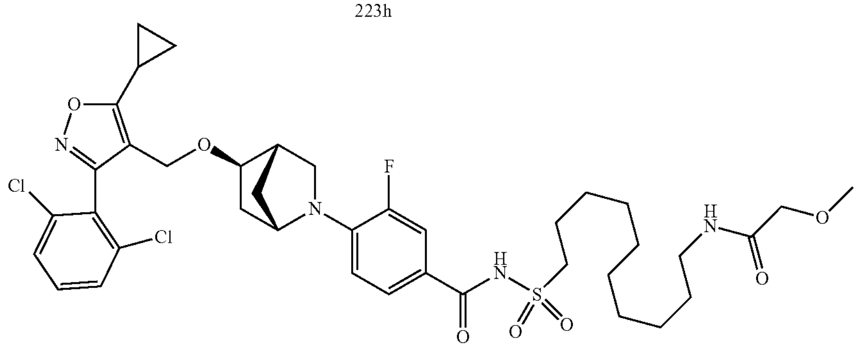

I-225

To a 8 mL sealed tube was added a solution of N-[(10-aminodecane)sulfonyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzamide 223h (60 mg, 0.08 mmol, 1.00 equiv.) in tetrahydrofuran (1 mL) followed by TEA (25 mg, 0.25 mmol, 3.00 equiv.). 2-Methoxyacetyl chloride (8.8 mg, 0.08 mmol, 1.00 equiv.) was added dropwise with stirring. The resulting mixture was stirred at room temperature overnight. The mixture was diluted with EA (50 mL), washed with brine (50 mL), and concentrated. The crude product was purified by Prep-HPLC using the following conditions: Column, XBridge Prep OBD C18 Column, 19*250 mm, 5 um; mobile phase, Water (0.05% TFA) and ACN (65% ACN up to 76% in 10 min); Detector, uv 220 nm. After purification N-[10-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]methane)sulfonyl]decyl]-2-methoxyacetamide 1-225 (28.2 mg, 43%) was obtained as a white solid. $^{1}$HNMR (400 MHz, $CD_3OD$): δ 7.63-7.45 (m, 5H), 6.66 (t, J=8.8 Hz, 1H), 4.35-4.27 (m, 3H), 3.88 (s, 2H), 3.62-3.47 (m, 4H), 3.42 (s, 3H), 3.22 (t, J=7.2 Hz, 2H), 2.77 (dd, J=9.9, 3.2 Hz, 1H), 2.49 (s, 1H), 2.28 (p, J=6.8 Hz, 1H), 1.92 (dd, J=13.0, 6.9 Hz, 1H), 1.82 (p, J=7.6 Hz, 2H), 1.53 (ddt, J=38.0, 14.8, 8.7 Hz, 6H), 1.31 (s, 12H), 1.22-1.15 (n, 4H); MS (ES, m/z): [M+1]=807.30.

Example 194: {10-[({4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorophenyl}formamido)sulfonyl]decyl}diethylmethylazanium (I-226)

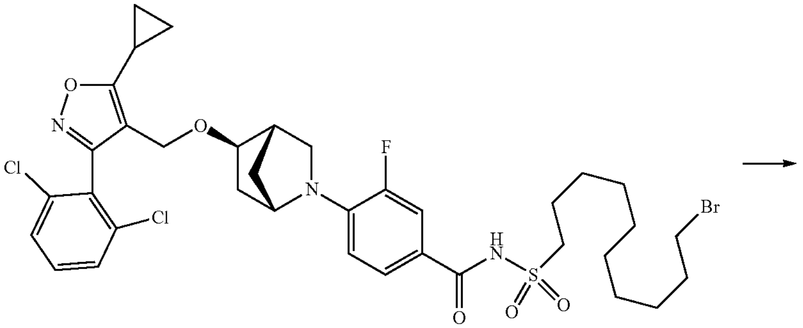

227d

-continued

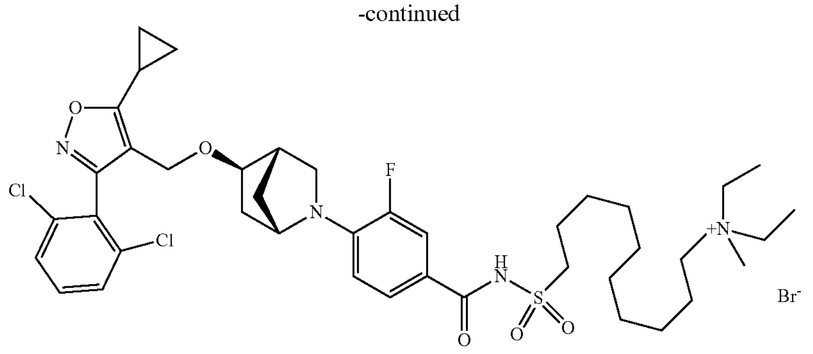

I-226

To a 8 mL sealed tube was added a solution of N-[(10-bromodecane)sulfonyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzamide 227d (68 mg, 0.09 mmol, 1.00 equiv.) in toluene (1 mL) followed by diethyl(methyl)amine (111 mg, 1.27 mmol, 15.00 equiv.). The resulting mixture was heated at 85° C., for 2 d and concentrated under vacuum. The crude product was purified by Prep-HPLC using the following conditions: Column, XBridge Shield RP18 OBD Column, 5 um, 19*150 mm; mobile phase, Water (0.05% TFA) and ACN (45% ACN up to 54% in 10 min); Detector, uv 254 nm. After purification [10-[([4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorophenyl]methane)sulfonyl]decyl]diethylmethylazanium bromide I-226 (23.7 mg, 31%) was obtained as a grayish semi-solid. $^1$HNMR (400 MHz. $CD_3OD$): δ 7.64-7.46 (m, 5H), 6.66 (t, J=8.7 Hz, 1H), 4.31 (d, J=11.8 Hz, 3H), 3.64-3.46 (m, 8H), 3.43-3.18 (m, 2H), 2.99 (s, 3H), 2.76 (dd, J=10.0, 3.3 Hz, 1H), 2.49 (d, J=3.1 Hz, 1H), 2.28 (p, J=6.8 Hz, 1H), 1.81 (ddt, J=31.7, 24.0, 7.3 Hz, 7H), 1.64-1.27 (m, 20H), 1.19 (d, J=6.7 Hz, 4H); MS (ES, m/z): $[M+Br]^+$=805.

Example 195: N-[10-(azetidin-1-yl)decanesulfonyl]-4-[(1S,4S,5R)-5-{[5-cyclopropyl-3-(2,6-dichlorophenyl)-1,2-oxazol-4-yl]methoxy}-2-azabicyclo[2.2.1]heptan-2-yl]-3-fluorobenzamide (I-227)

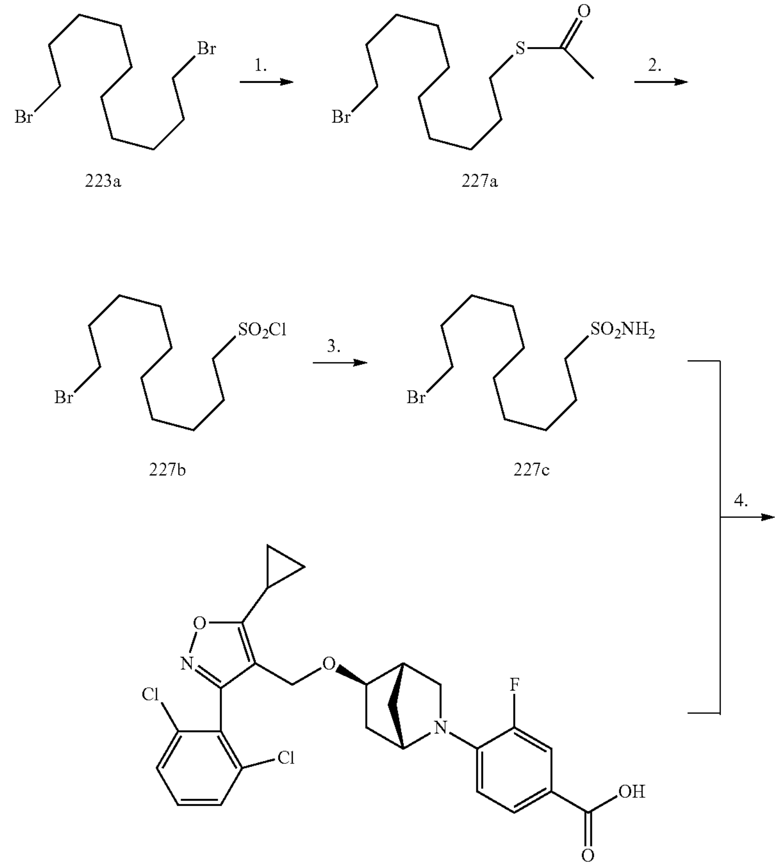

223a 227a 227b 227c

I-53

-continued

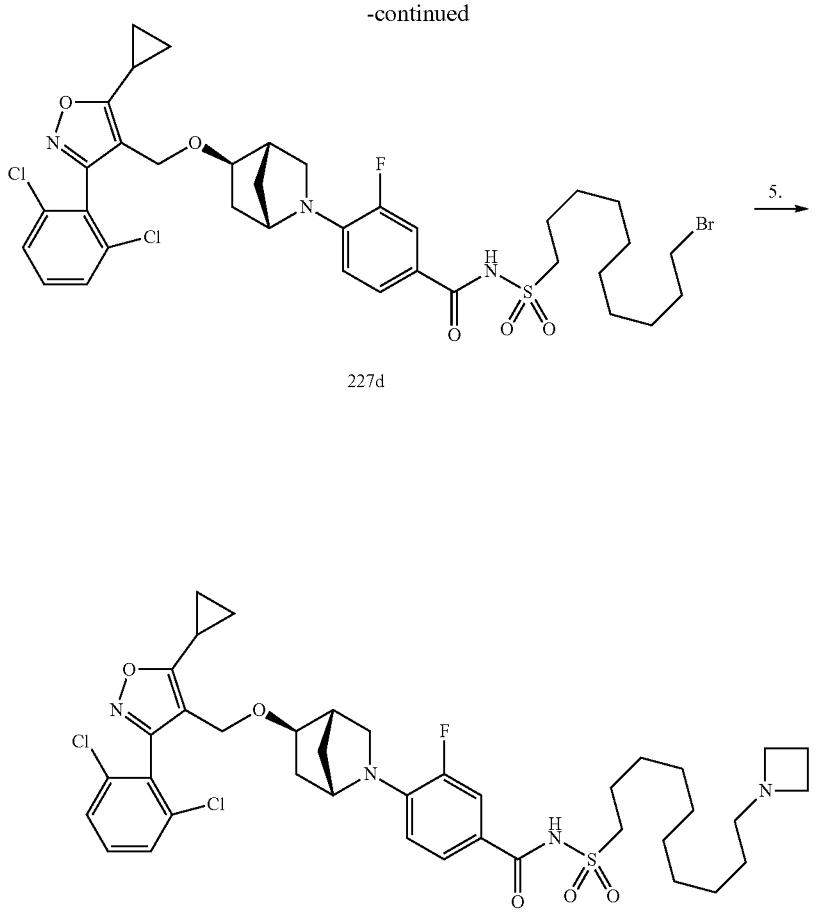

227d

I-227

Step 1

To a 1000 mL round-bottom flask was added a solution of 1,10-dibromodecane 223a (20 g, 66.65 mmol, 1.00 equiv.) in tetrahydrofuran (300 mL). Potassium ethanethioate (4.2 g, 36.78 mmol, 0.55 equiv.) was added in several batches. The resulting mixture was stirred at room temperature overnight. The mixture was diluted with 500 mL of EA, washed with brine (500 mL×2), dried over anhydrous sodium sulfate, and concentrated under vacuum. The residue was purified by silica gel column chromatography eluting with ethyl acetate/petroleum ether (0-20%) to give 1-[(10-bromodecyl)sulfanyl]ethan-1-one 227a (18 g, 91%) as a yellow oil.

Step 2

To a 250 mL round-bottom flask was added MeCN (8 mL) and a 2M hydrogen chloride aqueous solution (7 mL, 0.53 equiv, 2M). NCS (15.2 g, 113.83 mmol, 4.30 equiv.) was added in several batches at 10° C. A solution of 1-[(10-bromodecyl)sulfanyl]ethan-1-one 227a (7.8 g, 26.42 mmol, 1.00 equiv.) in $CH_3CN$ (8 mL) was added dropwise with stirring at 10° C. The resulting mixture was stirred at room temperature overnight, diluted with EA (200 mL), and washed with a saturated sodium carbonate aqueous solution (200 mL×2). The organic layer was dried over anhydrous sodium sulfate and concentrated under vacuum. The residue was purified by silica gel column chromatography eluting with ethyl acetate/petroleum ether (0-20%) to give 10-bromodecane-1-sulfonyl chloride 227b (6 g, 71%) as colorless oil.

Step 3

To a 250 mL round bottom flask was added 10-bromodecane-1-sulfonyl chloride 227b (3 g, 9.38 mmol, 1.00 equiv.) and a saturated solution of $NH_3$ in THF (50 mL). The reaction mixture was stirred at room temperature for 30 min and concentrated under vacuum. The residue was purified by silica gel column chromatography eluting with dichloromethane/ethyl acetate (100%-75%) to give 10-bromodecane-1-sulfonamide 227c (1.5 gm 53%) as a white solid.

Step 4

To a 25 mL round bottom flask was added 4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzoic acid I-53 (310 mg, 0.60 mmol, 1.00 equiv.), a solution of 10-bromodecane-1-sulfonamide 227c (450 mg, 1.50 mmol, 2.50 equiv.) in dichloromethane (5 mL), EDCI (173 mg, 0.90 mmol, 1.50 equiv.), and 4-dimethylaminopyridine (220 mg, 1.80 mmol, 3.00 equiv.). The resulting mixture was stirred at room temperature overnight. The mixture was diluted with 30 mL of DCM, washed with brine (30 mL), dried over anhydrous sodium sulfate, and concentrated under vacuum. The residue was purified by silica gel column chromatography eluting with dichloromethane/methanol (15:1) to afford N-[(10-bromodecane)sulfonyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzamide 227d (260 mg, 54%) as a yellow solid.

Step 5

To a 25 mL round-bottom flask was added a solution of N-[(10-chlorodecane)sulfonyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzamide 227d (260 mg, 0.34 mmol, 1.00 equiv.) in N,N-dimethylformamide (2 mL), DIEA (84 mg, 0.65 mmol, 3.00 equiv), and azetidine (56 mg, 0.98 mmol, 2.00 equiv.). The resulting mixture was stirred at 50° C. overnight. Solids were filtered out and the filtrate was concentrated under vacuum. The crude product was purified by Prep-HPLC using the following conditions: Column, XBridge Shield RP18 OBD Column, 5 um, 19*150 mm; mobile phase, Water (0.05% NH3H2O) and ACN (45.0% ACN up to 65.0% in 10 min); Detector, uv 220 nm. After purification N-[[10-(azetidin-1-yl)decane]sulfonyl]-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]-3-fluorobenzamide I-227 (41.5 mg, 16%) was obtained as a white solid. $^1$HNMR (400 MHz, $CD_3OD$): δ 7.71-7.43 (m, 5H), 6.56 (t, J=8.8 Hz, 1H), 4.31 (s, 2H), 4.18 (s, 1H), 4.10 (t, J=8.2 Hz, 4H), 3.59-3.51 (m, 1H), 3.47 (d, J=6.6 Hz, 1H), 3.18-3.09 (m, 2H), 2.70-2.63 (m, 1H), 2.52-2.41 (m, 3H), 2.27 (p, J=6.8 Hz, 1H), 1.95-1.87 (m, 1H), 1.79 (q, J=7.8 Hz, 2H), 1.51 (dd, J=36.9, 10.5 Hz, 6H), 1.32 (d, J=14.0 Hz, 8H), 1.22-1.14 (m, 4H); MS (ES, m/z): [M+1]=775.3.

Example 196: Synthesis of I-228 to I-230

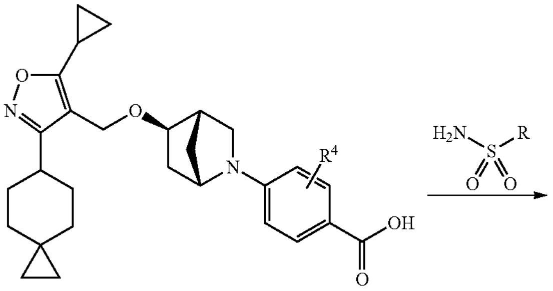

I-Acids

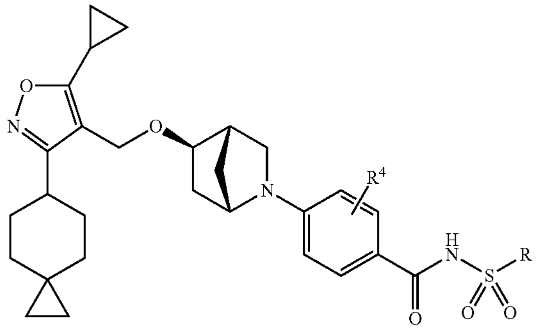

I-x

Acyl-sulfonamide compounds of I-228 to I-230 were prepared from the corresponding acids (I-Acids) and sulfonamides following the procedure described in Preparative Example 174. The data for compounds I-228 to I-230 is summarized in Table 10.

TABLE 10

| Acid SM | Cmpd Structure | Cmpd. No. | MS/$^1$H NMR |
|---|---|---|---|
| I-125 | 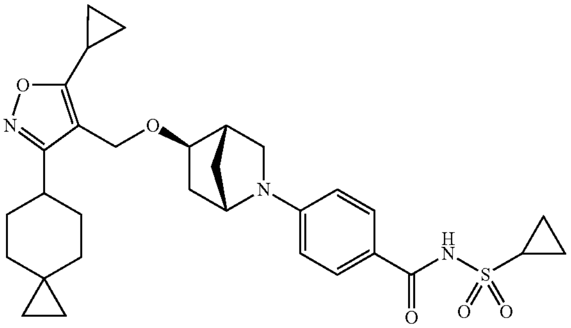 [SMILES: O=C(NS(=O)(=O)C1CC1)c1ccc(N2C[C@@H]3C[C@H]2C[C@H]3OCc2c(C3CCC4(CC3)CC4)noc2C2CC2)cc1] | I-228 | MS (ES, m/z): [M + 1] = 566. $^1$H NMR (400 MHz, $CDCl_3$) δ: 8.22 (s, 1H), 7.67 (m, 2H), 6.54-6.47 (m, 2H), 4.37 (q, J = 11.7 Hz, 2H), 4.25 (s, 1H), 3.67 (d, J = 6.4 Hz, 1H), 3.50 (dd, J = 9.4, 4.0 Hz, 1H), 3.20-3.11 (m, 1H), 2.82 (s, 1H), 2.76-2.64 (m, 2H), 2.09 (dd, J = 14.8, 5.5 Hz, 1H), 2.02-1.88 (m, 4H), 1.87-1.70 (m, 5H), 1.67 (d, J = 13.4 Hz, 1H), 1.45-1.39 (m, 2H), 1.18-1.09 (m, 4H), 1.06-0.95 (m, 4H), 0.35-0.21 (m, 4H). |
| I-126 | 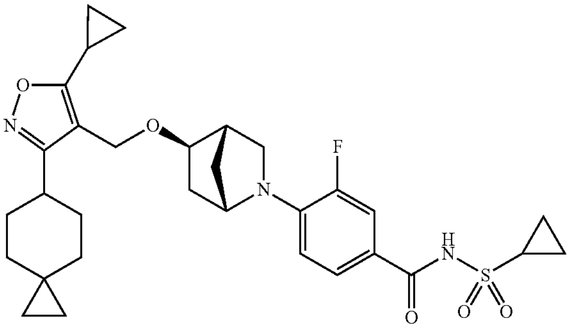 [SMILES: O=C(NS(=O)(=O)C1CC1)c1ccc(N2C[C@@H]3C[C@H]2C[C@H]3OCc2c(C3CCC4(CC3)CC4)noc2C2CC2)c(F)c1] | I-229 | MS (ES, m/z): [M + 1] = 584. $^1$H NMR (400 MHz, $CDCl_3$) δ: 8.23 (s, 1H), 7.48 (dd, J = 14.6, 2.2 Hz, 1H), 7.41 (dd, J = 8.6, 2.2 Hz, 1H), 6.55 (t, J = 8.7 Hz, 1H), 4.37 (dd, J = 18.0, 11.7 Hz, 3H), 3.68 (d, J = 6.2 Hz, 2H), 3.19-3.08 (m, 1H), 2.89-2.80 (m, 1H), 2.77 (s, 1H), 2.73-2.63 (m, 1H), 2.17 (dd, J = 13.5, 4.5 Hz, 1H), 2.03-1.86 (m, 4H), 1.79 (dd, J = 20.7, 12.1 Hz, 5H), 1.68 (d, J = 13.8 Hz, 1H), 1.48-1.37 (m, 2H), 1.19-1.09 (m, 4H), 1.06-0.96 (m, 4H), 0.36-0.20 (m, 4H), 1.19-1.06 (m, 2H). |

TABLE 10-continued

| Acid SM | Cmpd Structure | Cmpd. No. | MS/$^1$H NMR |
|---|---|---|---|
| I-126 | 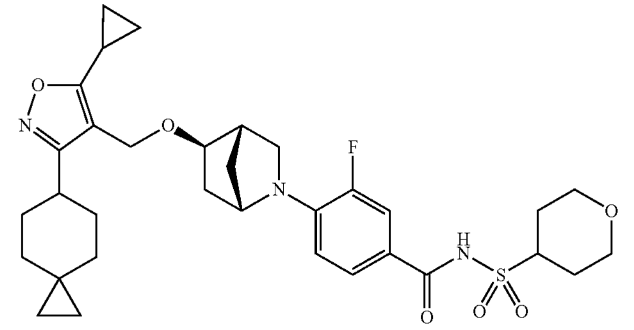 [SMILES: O=C(NS(=O)(=O)C1CCOCC1)c1ccc(N2C[C@@H]3C[C@H]2C[C@H]3OCc2c(C3CCC4(CC3)CC4)noc2C2CC2)c(F)c1] | I-230 | MS(ES, m/z): [M + 1] = 628. $^1$H NMR (400 MHz, $CDCl_3$) δ: 8.18 (s, 1H), 7.49 (dd, J = 14.6, 2.2 Hz, 1H), 7.43 (dd, J = 8.6, 2.2 Hz, 1H), 6.55 (t, J = 8.7 Hz, 1H), 4.37 (q, J = 11.7 Hz, 3H), 4.16-4.07 (m, 2H), 4.03 (s, 1H), 3.72-3.63 (m, 2H), 3.44 (td, J = 11.6, 3.4 Hz, 2H), 2.86 (dd, J = 9.8, 2.8 Hz, 1H), 2.80-2.62 (m, 3H), 2.17 (dd, J = 12.3, 5.5 Hz, 1H), 2.08-2.02 (m, 3H), 2.02-1.87 (m, 4H), 1.79 (m, 4H), 1.68 (d, J = 131. Hz, 1H), 1.17-1.09 (m, 2H), 1.03 (m, 4H), 0.37-0.20 (m, 4H). |

Example 197: Synthesis of I-231 and I-232

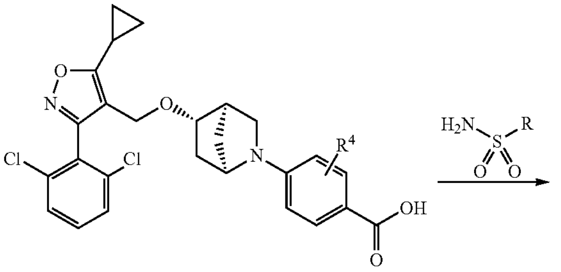

I-Acids

-continued

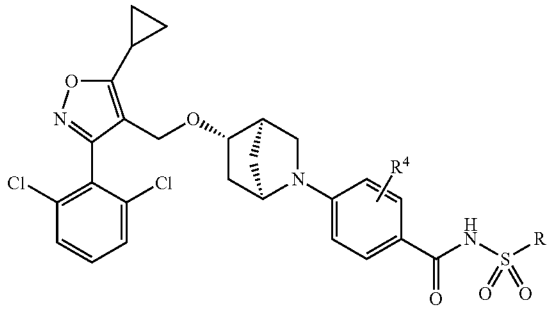

I-x

Acyl-sulfonamide compounds of I-231 and I-232 were prepared from the corresponding acids (I-Acids) and sulfonamides following the procedure described in Preparative Example 174. The data for compounds I-231 and I-232 is summarized in Table 11.

TABLE 11

| Acid SM | Cmpd Structure | Cmpd No. | MS/$^1$H NMR |
|---|---|---|---|
| I-131 | 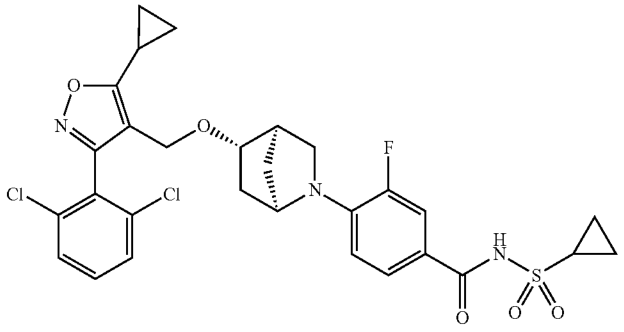 [SMILES: O=C(NS(=O)(=O)C1CC1)c1ccc(N2C[C@H]3C[C@@H]2C[C@@H]3OCc2c(-c3c(Cl)cccc3Cl)noc2C2CC2)c(F)c1] | I-231 | MS (ES, m/z): [M + 1] = 620. $^1$H NMR (400 MHz, $CD_3OD$) δ: 7.59-7.52 (m, 3H), 7.52-7.44 (m, 3H), 6.63 (t, J = 8.8 Hz, 1H), 4.30 (d, J = 1.4 Hz, 2H), 4.27 (s, 1H), 3.54 (m, 2H), 3.15-3.07 (m, 1H), 2.74 (dd, J = 9.9, 3.0 Hz, 1H), 2.47 (s, 1H), 2.25 (dq, J = 13.5, 6.7 HZ, 1H), 1.94-1.86 (m, 1H), 1.62-1.52 (m, 2H), 1.35-1.23 (m, 4H), 1.19-1.14 (m, 4H), 1.14-1.07 (m, 2H). |

TABLE 11-continued

| Acid SM | Cmpd Structure | Cmpd No. | MS/$^1$H NMR |
| --- | --- | --- | --- |
| I-132 | 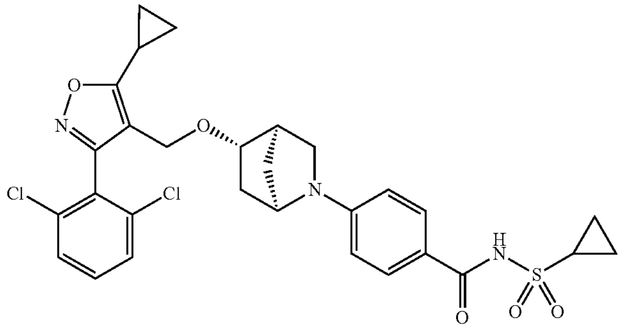 [SMILES: O=C(NS(=O)(=O)C1CC1)c1ccc(N2C[C@H]3C[C@@H]2C[C@@H]3OCc2c(-c3c(Cl)cccc3Cl)noc2C2CC2)cc1] | I-232 | MS (ES, m/z): [M + 1] = 602. $^1$H NMR (400 MHz, $CD_3OD$) δ: 7.72 (d, J = 9.0 Hz, 2H), 7.56-7.51 (m, 1H), 7.50-7.44 (m, 2H), 6.50 (d, J = 8.9 Hz, 2H), 4.30 (s, 2H), 4.17 (s, 1H), 3.49 (d, J = 5.6 Hz, 1H), 3.36 (dd, J = 9.4, 4.1 Hz, 1H), 3.16-3.06 (m, 1H), 2.61 (d, J = 9.6 Hz, 1H), 2.50 (s, 1H), 2.30-2.19 (m, 1H), 1.80 (dd, J = 14.5, 5.7 Hz, 1H), 1.58 (dd, J = 24.5, 9.8 Hz, 2H), 1.35-1.23 (m, 3H), 1.16 (d, J = 6.6 Hz, 4H), 1.13-1.05 (m, 2H). |

Example 198: N-(cyclopropanesulfonyl)-5-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1-methyl-1H-pyrazole-3-carboxamide (I-233)

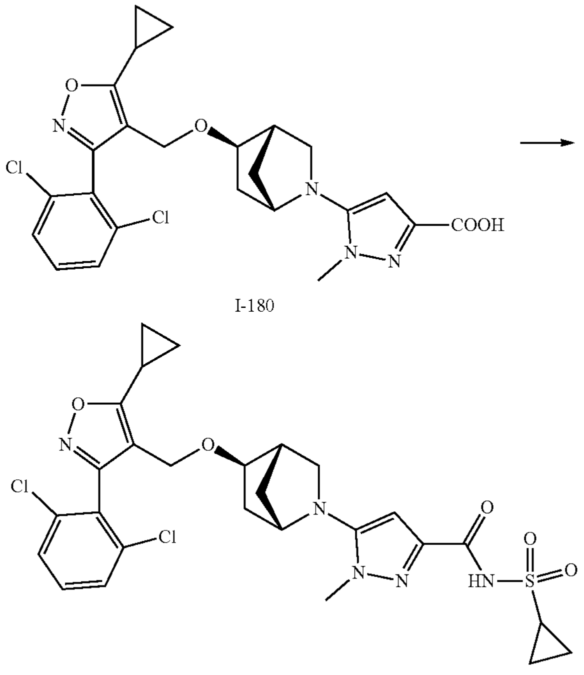

I-180

I-233

To a 100 mL round bottom flask was added 5-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1-methyl-1H-pyrazole-3-carboxylic acid I-180 (70 mg, 0.14 mmol, 1.00 equiv.), dichloromethane (10 mL), cyclopropanesulfonamide (52.6 mg, 0.43 mmol, 3.12 equiv.), 4-dimethylaminopyridine (51 mg, 0.42 mmol, 3.00 equiv.), and EDCI (80 mg, 0.42 mmol, 3.00) equiv.). The resulting mixture was stirred at 10-25° C., overnight. The reaction was quenched by the addition of 10 mL of water. The mixture was extracted with dichloromethane (30 mL×3), the combined organic layers were washed with brine and concentrated under vacuum. The crude product was purified by Prep-HPLC using the following conditions Column, XBridge Shield RP18 OBD Column, 5 um, 19*150 mm; mobile phase, Water (0.05% $NH_3H_2O$) and ACN (20.0% ACN up to 45.0% in 8 min); Detector, UV 254 nm. After purification N-(cyclopropanesulfonyl)-5-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1-methyl-1H-pyrazole-3-carboxamide I-233 (6.5 mg, 8%) was obtained as a white solid. $^1$HNMR (300 MHz, $CDCl_3$): δ 8.98 (s, 1H), 7.48-7.30 (m, 3H), 6.10 (s, 1H), 4.26 (d, J=1.1 Hz, 2H), 3.69 (s, 3H), 3.59 (s, 1H), 3.52-3.41 (m, 1H), 3.19 (dd, J=9.2, 4.2 Hz, 1H), 3.02 (tt, J=8.1, 4.8 Hz, 1H), 2.56 (d, J=9.1 Hz, 1H), 2.43 (s, 1H), 2.12 (tt, J=8.4, 5.1 Hz, 1H), 1.97 (dd, J=13.7, 6.8 Hz, 1H), 1.58 (s, 2H), 1.52-1.37 (m, 2H), 1.34-1.21 (m, 3H), 1.20-1.06 (m, 4H); MS (ES, m/z): [M+1]=606.1.

Example 199: (1S,4S,5R)-2-{4-[(cyclopropanesulfonyl)carbamoyl]phenyl}-5-{[5-cyclopropyl-3-(2,6-dichlorophenyl)-1,2-oxazol-4-yl]methoxy}-2-azabicyclo[2.2.1]heptan-2-ium-2-olate (I-234)

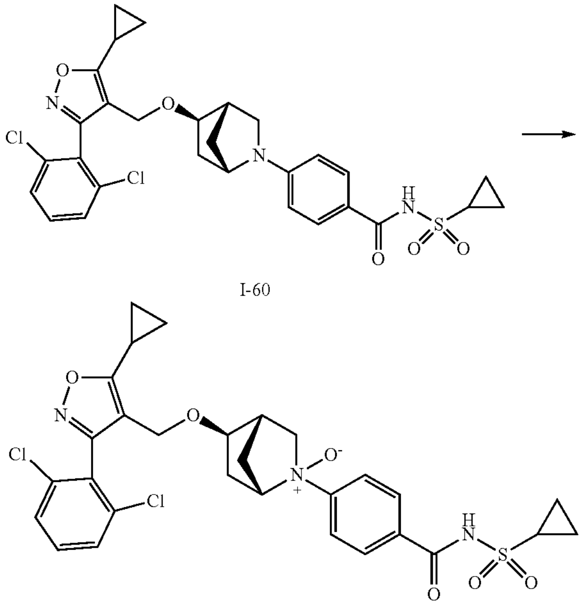

I-60

I-234

To a 25 mL round-bottom flask was added N-(cyclopropanesulfonyl)-4-[(1S,4S,5R)-5-[[5-cyclopropyl-3-(2,6-dichlorophenyl)-1,2-oxazol-4-yl]methoxy]-2-azabicyclo[2.2.1]heptan-2-yl]benzamide I-60 (150 mg, 0.25 mmol, 1.00 equiv.), methanol (2 mL), and a solution of Oxone (306 mg, 0.50 mmol, 2.00 equiv.) in water (2 mL). The resulting mixture was stirred at 25° C., for 2 h. Solids were filtered out and the filtrate was concentrated. The crude product was purified by Prep-HPLC using the following conditions: Column, XBridge Shield RP18 OBD Column, 5 um, 19*150 mm; mobile phase, Water (0.05% TFA) and ACN (30.0% ACN up to 39.0% in 10 min); Detector, UV 254 nm. After purification (1S,4S,5R)-2-[4-[(cyclopropanesulfonyl)carbamoyl]phenyl]-5-[[5-cyclopropyl-3-(2,6-dichlorophenyl)-1,2-oxazol-4-yl]methoxy]-2-azabicyclo[2.2.1]heptan-2-ium-2-olate I-234 (49.4 mg, 32%) was obtained as a light yellow solid. $^1$HNMR (400 MHz, $CD_3OD$): δ 8.21-8.10 (m, 2H), 7.91-7.81 (m, 2H), 7.61-7.43 (m, 3H), 5.51 (s, 1H), 4.37-4.08 (m, 4H), 3.70-3.58 (m, 1H), 3.12 (tt, J=8.0, 4.8 Hz, 1H), 2.84 (s, 1H), 2.68 (d, J=12.0 Hz, 1H), 2.25 (p, J=6.7 Hz, 1H), 2.09-1.97 (m, 1H), 1.82-1.68 (m, 1H), 1.59 (d, J=16.4 Hz, 2H), 1.34-1.00 (m, 11H), 0.91 (d, J=7.6 Hz, 3H); MS (ES, m/z): [M+1]=618.25.

Example 200: 3-{4-[(1S,4S,5R)-5-{[3-(2-chloro-6-fluorophenyl)-5-cyclopropyl-1,2-oxazol-4-yl]methoxy}-2-azabicyclo[2.2.1]heptan-2-yl]-3-fluorophenyl}-N-(oxane-4-sulfonyl)propanamide (I-235)

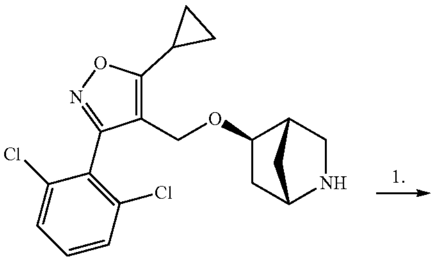

118h

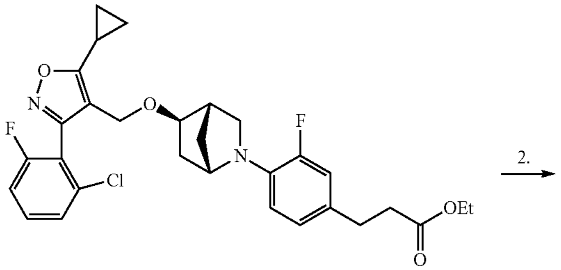

235a

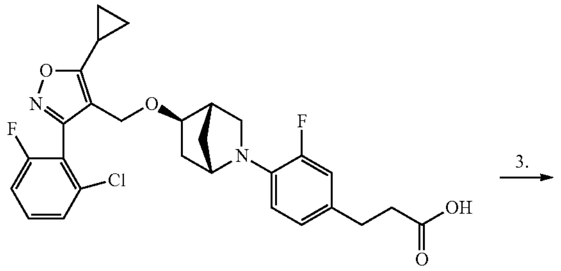

235b

-continued

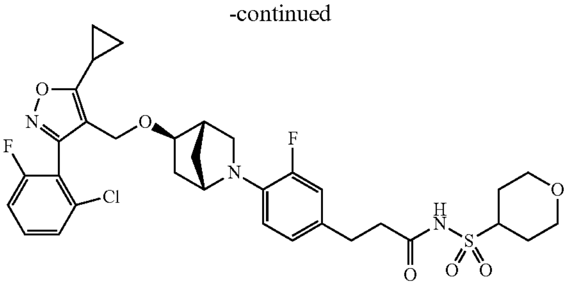

I-235

Step 1

To a 8 mL sealed tube purged with and maintained under an inert atmosphere of nitrogen was added a solution of (1S,4S,5R)-5-[[3-(2-chloro-6-fluorophenyl)-5-cyclopropyl-1,2-oxazol-4-yl]methox]-2-azabicyclo[2.2.1]heptane 118h (600 mg, 1.65 mmol, 1.00 equiv.) in toluene (3 mL), ethyl 3-(4-bromo-3-fluorophenyl)propanoate (681 mg, 2.48 mmol, 1.50 equiv), Ruphos (155 mg, 0.33 mmol, 0.20 equiv), Ruphos precatalyst (282 mg, 0.33 mmol, 0.20 equiv), and $Cs_2CO_3$ (1.08 g, 3.31 mmol, 2.00 equiv.). The resulting mixture was heated at 110° C., overnight. After cooling to room temperature, the mixture was diluted with EA (50 mL), washed with water (50 mL) and brine (50 mL), dried over anhydrous sodium sulfate, and concentrated under vacuum. The residue was purified by silica gel column chromatography eluting with ethyl acetate/petroleum ether (1:3) to give ethyl 3-[4-(1S,4S,5R)-5-[[3-(2-chloro-6-fluorophenyl)-5-cyclopropyl-1,2-oxazol-4-yl]methoxy-2-azabicyclo[2.2.1]heptan-2-yl]-3-fluorophenyl]propanoate 235a (240 mg, 26%) as a yellow oil.

Step 2

To a 250 mL round bottom flask was added a solution of ethyl 3-[4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-3-fluorophenyl]propanoate 235a (240 mg, 0.43 mmol, 1.00 equiv.) in ethanol/$H_2O$ (5/1 mL), and LiOH (104 mg, 4.34 mmol, 10.00 equiv.). The resulting mixture was heated at 60° C., for 1 h. The pH value of the solution was adjusted to 2 using a 1M HCl aqueous solution. The mixture was extracted with ethyl acetate (20 mL×2); the combined organic extracts were washed with brine (20 mL×2), dried over anhydrous sodium sulfate and concentrated under vacuum to give 3-[4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-3-fluorophenyl]propanoic acid 235b (200 mg, 88%) as a light yellow solid.

Step 3

To a 50 mL round bottom flask was added 3-[4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-3-fluorophenyl]propanoic acid 235b (80 mg, 0.15 mmol, 1.00 equiv.), oxane-4-sulfonamide (50 mg, 0.30 mmol, 2.00 equiv.), dichloromethane (2 mL), 4-dimethylaminopyridine (56 mg, 0.46 mmol, 3.00 equiv.), and EDCI (44 mg, 0.23 mmol, 1.50 equiv.). The resulting mixture was stirred at room temperature overnight. The mixture was diluted with EA (100 mL), washed with brine (40 mL), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (52.0% ACN up to 67.0% in 8 min); Detector, UV 254 nm. After purification 3-[4-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-3-fluorophenyl]-N-(oxane-4-sulfonyl)propanamide 1-235 (24 mg, 23%) was obtained as a colorless solid. $^1$HNMR (300 MHz, $CD_3OD$): δ 7.54 (td, J=8.3, 5.9 Hz, 1H), 7.41 (d, J=8.0 Hz, 1H), 7.23 (t, J=8.6 Hz, 1H), 6.91-6.78 (m, 2H), 6.61-6.49 (m, 1H), 4.33 (s, 2H), 4.07-3.91 (m, 3H), 3.68-3.26 (m, 4H), 2.83 (t, J=7.1 Hz, 2H), 2.66-2.45 (m, 3H), 2.40 (d, J=4.0 Hz, 1H), 2.26 (p, J=6.8 Hz, 1H), 1.97-1.67 (m, 5H), 1.53 (s, 2H), 1.39-1.12 (m, 5H); MS (ES, m/z): [M+1]=676.20.

Example 201: Synthesis of I-236 and I-243

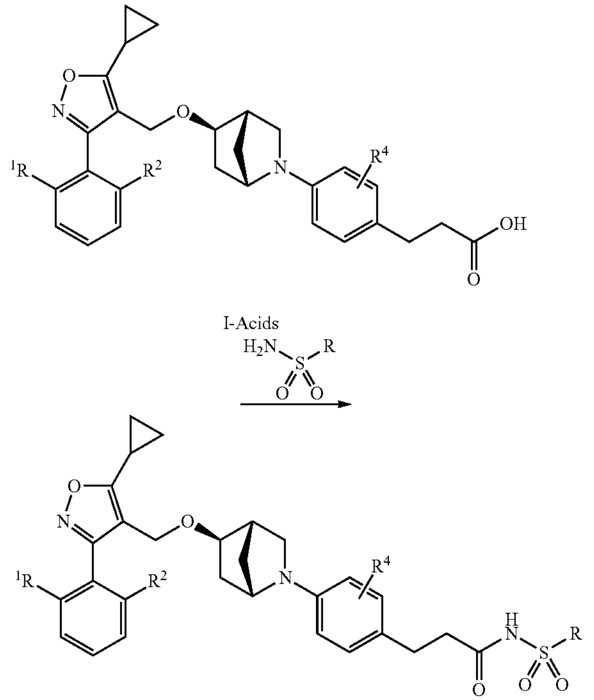

I-x

Acyl-sulfonamide compounds of I-236 and I-243 were prepared from the corresponding acids (I-Acids) and sulfonamides following the procedure described in Preparative Example 174. The data for compounds I-236 and I-243 is summarized in Table 12.

TABLE 12

| Acid SM | Cmpd Structure | Cmpd No. | MS/$^1$H NMR |
|---|---|---|---|
| I-154 | 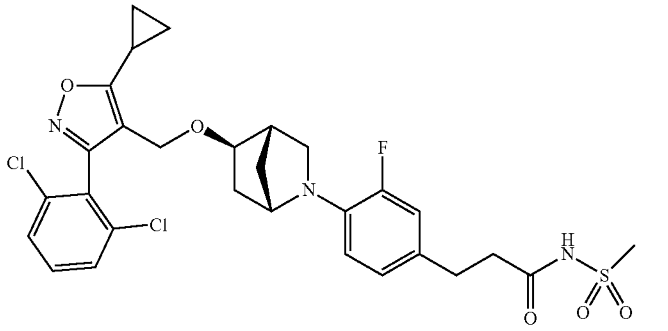 [SMILES: CS(=O)(=O)NC(=O)CCc1ccc(N2C[C@@H]3C[C@H]2C[C@H]3OCc2c(-c3c(Cl)cccc3Cl)noc2C2CC2)c(F)c1] | I-236 | MS (ES, m/z): [M + 1] = 623. $^1$H NMR (400 MHz, $CD_3OD$) δ: 7.58-7.42 (m, 3H), 6.95-6.84 (m, 2H), 6.71 (t, J = 8.5 Hz, 1H), 4.29 (d, J = 1.3 Hz, 2H), 4.07 (s, 1H), 3.48 (ddd, J = 16.1, 6.6, 3.0 Hz, 2H), 3.17 (s, 3H), 2.84 (t, J = 7.5 Hz, 2H), 2.65 (dd, J = 10.2, 3.0 Hz, 1H), 2.56 (t, J = 7.4 Hz, 2H), 2.46-2.40 (m, 1H), 2.25 (p, J = 6.7 Hz, 1H), 1.93 (dd, J = 13.9, 6.8 Hz, 1H), 1.58 (s, 2H), 1.26 (d, J = 14.0 Hz, 1H), 1.16 (d, J = 6.8 Hz, 4H). |
| I-154 | 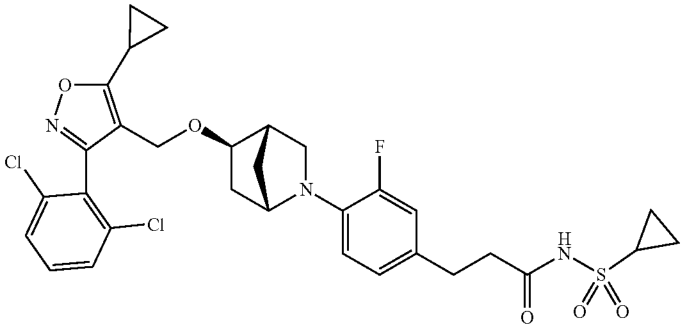 [SMILES: O=C(CCc1ccc(N2C[C@@H]3C[C@H]2C[C@H]3OCc2c(-c3c(Cl)cccc3Cl)noc2C2CC2)c(F)c1)NS(=O)(=O)C1CC1] | I-237 | MS (ES, m/z): [M + 1] = 648. $^1$H NMR (400 MHz, $CD_3OD$) δ: 1.124 (10H, m), 1.580 (2H, m), 1.898 (H, m), 2.228 (1H, m), 2.559 (1H, m), 2.625 (3H, m), 2.902 (3H, m), 3.494 (2H, m), 4.069 (1H, m), 4.296 (2H, m), 6.874 (1H, m), 6.923 (2H, m), 7.509 (3H, m). |

TABLE 12-continued

| Acid SM | Cmpd Structure | Cmpd No. | MS/$^1$H NMR |
|---|---|---|---|
| I-154 | 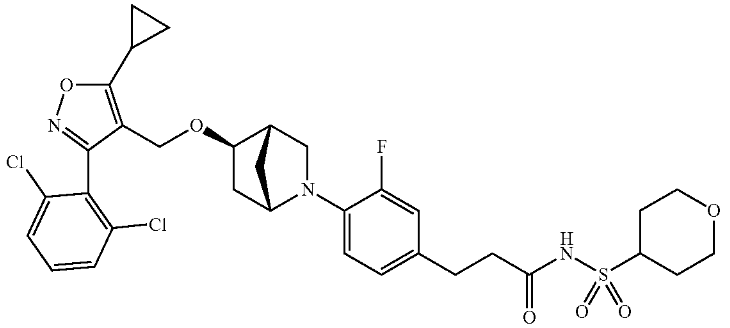 [SMILES: O=C(CCc1ccc(N2C[C@@H]3C[C@H]2C[C@H]3OCc2c(-c3c(Cl)cccc3Cl)noc2C2CC2)c(F)c1)NS(=O)(=O)C1CCOCC1] | I-238 | MS (ES, m/z): [M + 1] = 693. $^1$H NMR (400 MHz, $CD_3OD$) δ: 7.58-7.50 (m, 1H), 7.48 (d, J = 3.7 Hz, 2H), 6.93-6.82 (m, 2H), 6.65 (t, J = 8.9 Hz, 1H), 4.29 (d, J = 1.9 Hz, 2H), 4.06 (s, 1H), 3.96 (dt, J = 11.4, 3.4 Hz, 2H), 3.58 (p, J = 8.3 Hz, 1H), 3.47 (ddt, J = 16.2, 6.8, 3.0 Hz, 2H), 3.39-3.24 (m, 2H), 2.83 (t, J = 7.1 Hz, 2H), 2.60 (t, J = 7.2 Hz, 3H), 2.46-2.39 (m, 1H), 2.24 (p, J = 6.7 Hz, 1H), 1.96-1.86 (m, 1H), 1.72 (tt, J = 7.6, 3.9 Hz, 4H), 1.56 (s, 2H), 1.25 (d, J = 13.8 Hz, 2H), 1.16 (d, J = 6.8 Hz, 4H). |
| 235b | 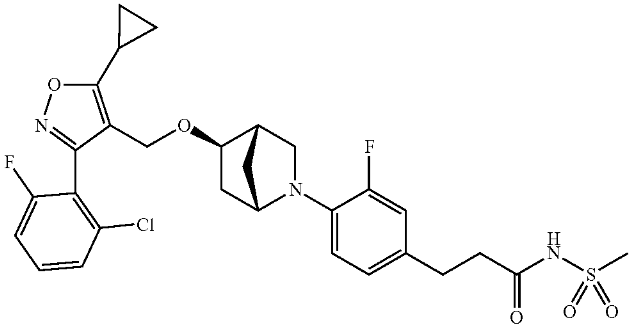 [SMILES: CS(=O)(=O)NC(=O)CCc1ccc(N2C[C@@H]3C[C@H]2C[C@H]3OCc2c(-c3c(F)cccc3Cl)noc2C2CC2)c(F)c1] | I-239 | MS (ES, m/z): [M + 1] = 606.25. $^1$H NMR (300 MHz, $CD_3OD$) δ: 7.54 (td, J = 8.3, 6.0 Hz, 1H), 7.41 (d, J = 8.2 Hz, 1H), 7.23 (t, J = 8.7 Hz, 1H), 6.91-6.78 (m, 2H), 6.56 (t, J = 9.0 Hz, 1H), 4.33 (s, 2H), 4.03 (s, 1H), 3.55-3.35 (m, 3H), 3.18 (s, 3H), 2.83 (t, J = 7.4 Hz, 2H), 2.62-2.44 (m, 3H), 2.39 (d, J = 4.0 Hz, 1H), 2.26 (p, J = 6.8 Hz, 1H), 1.90 (dd, J = 13.6, 6.9 Hz, 1H), 1.53 (d, J = 1.8 Hz, 2H), 1.39-1.13 (m, 6H). |
| 235b | 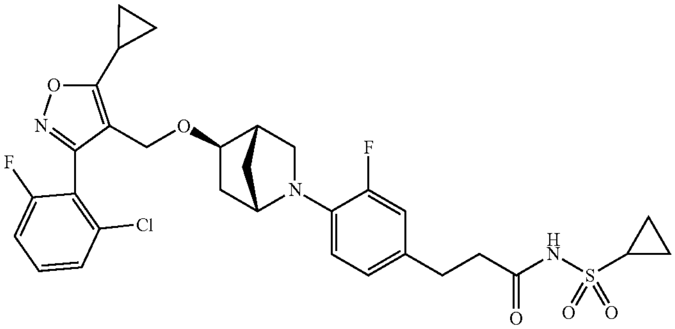 [SMILES: O=C(CCc1ccc(N2C[C@@H]3C[C@H]2C[C@H]3OCc2c(-c3c(F)cccc3Cl)noc2C2CC2)c(F)c1)NS(=O)(=O)C1CC1] | I-240 | MS (ES, m/z): [M + 1] = 632.35. $^1$H NMR (300 MHz, $CD_3OD$) δ: 7.54 (td, J = 8.3, 6.0 Hz, 1H), 7.41 (d, J = 8.1 Hz, 1H), 7.23 (t, J = 8.7 Hz, 1H), 6.91-6.79 (m, 2H), 6.62-6.50 (m, 1H), 4.33 (s, 2H), 4.03 (s, 1H), 3.55-3.35 (m, 2H), 2.98-2.78 (m, 3H), 2.62-2.44 (m, 3H), 2.40 (s, 1H), 2.26 (p, J = 6.8 Hz, 1H), 1.90 (dd, J = 13.5, 6.9 Hz, 1H), 1.53 (d, J = 1.8 Hz, 2H), 1.39-1.10 (m, 8H), 1.05 (dddd, J = 8.2, 6.6, 4.6, 1.4 Hz, 2H). |
| I-159 | 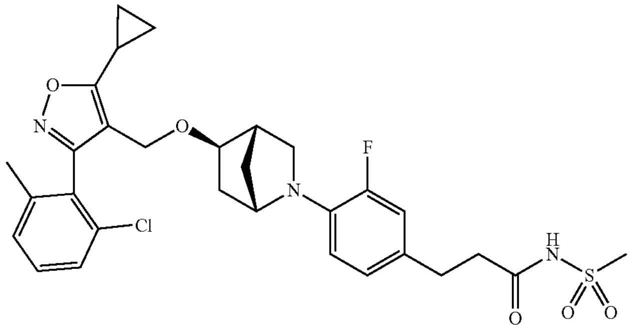 | I-241 | MS (ES, m/z): [M + 1] = 602.2. $^1$H NMR (300 MHz, $CD_3OD$) δ: 7.45-7.33 (m, 2H), 7.32-7.21 (m, 1H), 6.99-6.85 (m, 2H), 6.74 (td, J = 8 8, 3.0 Hz, 1H), 4.33 (dd, J = 11.7, 3.4 Hz, 1H), 4.25-4.03 (m, 2H), 3.56-3.39 (m, 2H), 3.18 (s, 3H), 2.85 (t, J = 7.4 Hz, 2H), 2.68 (dt, J = 10.1, 2.9 Hz, 1H), 2.61-2.33 (m, 3H), 2.26 (p, J = 6.8 Hz, 1H), 2.15 (d, J = 2.2 Hz, 3H), 1.96 (td, J = 16.3, 14.3, 6.8 Hz, 1H), 1.65-1.44 (m, 2H), 1.33 (d, J = 14.0 Hz, 1H), 1.17 (d, J = 7.2 Hz, 5H). |

TABLE 12-continued

| Acid SM | Cmpd Structure | Cmpd No. | MS/$^1$H NMR |
|---|---|---|---|
| I-159 | 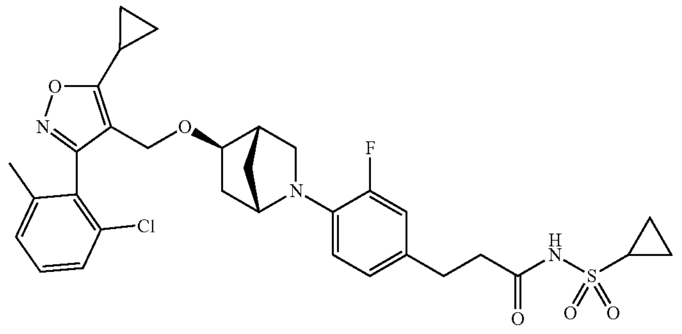 [SMILES: Cc1cccc(Cl)c1-c1noc(C2CC2)c1CO[C@@H]1C[C@@H]2C[C@H]1CN2c1ccc(CCC(=O)NS(=O)(=O)C2CC2)cc1F] | I-242 | MS (ES, m/z): [M + 1] = 628.2. $^1$H NMR (300 MHz, $CD_3OD$) δ: 7.42-7.33 (m, 2H), 7.33-7.22 (m, 1H), 6.97-6.84 (m, 2H), 6.72 (d, J = 9.0 Hz, 1H), 4.33 (dd, J = 11.8, 3.5 Hz, 1H), 4.16 (dd, J = 19.6, 11.7 Hz, 1H), 4.07 (d, J = 9.1 Hz, 1H), 3.46 (dt, J = 16.1, 6.4 Hz, 2H), 2.97-2.79 (m, 3H), 2.58 (q, J = 7.7 Hz, 3H), 2.43 (d, J = 41.4 Hz, 1H), 2.26 (p, J = 6.7 Hz, 1H), 2.15 (d, J = 2.4 Hz, 3H), 2.05-1.86 (m, 1H), 1.60 (s, 1H), 1.50 (t, J = 8.4 Hz, 1H), 1.32 (d, J = 13.9 Hz, 1H), 1.22-1.09 (m, 7H), 1.09-1.00 (m, 2H). |
| I-159 | 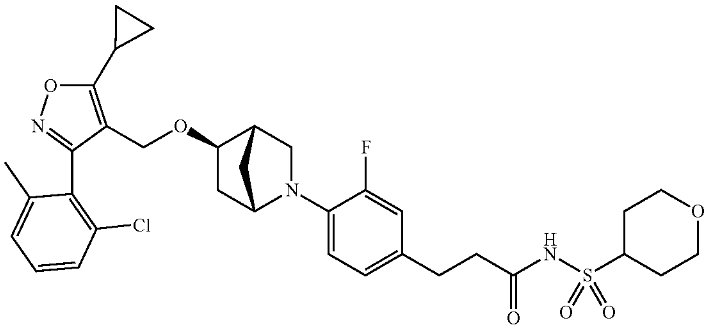 [SMILES: Cc1cccc(Cl)c1-c1noc(C2CC2)c1CO[C@@H]1C[C@@H]2C[C@H]1CN2c1ccc(CCC(=O)NS(=O)(=O)C2CCOCC2)cc1F] | I-243 | MS (ES, m/z): [M + 1] = 672.2. $^1$H NMR (300 MHz, $CD_3OD$) δ: 7.44-7.34 (m, 2H), 7.31-7.23 (m, 1H), 6.97-6.83 (m, 2H), 6.69 (td, J = 8.8, 3.2 Hz, 1H), 4.33 (dd, J = 11.7, 4.0 Hz, 1H), 4.24-4.42 (m, 1H), 4.11-4.03 (m, 1H), 3.97 (dt, J = 11.4, 3.4 Hz, 2H), 3.59 (p, J = 8.6 Hz, 1H), 3.52-3.34 (m, 3H), 2.85 (t, J = 7.0 Hz, 2H), 2.62 (q, J = 7.8, 7.2 Hz, 3H), 2.44 (d, J = 43.8 Hz, 1H), 2.25 (q, J = 6.8 Hz, 1H), 2.15 (d, J = 2.3 Hz, 3H), 2.07-1.85 (m, 1H), 1.74 (dq, J = 9.7, 4.4 Hz, 4H), 1.60 (s, 1H), 1.56-1.41 (m, 1H), 1.32 (d, J = 13.3 Hz, 1H), 1.17 (d, J = 7.1 Hz, 5H). |

Example 202: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic Acid (I-244)

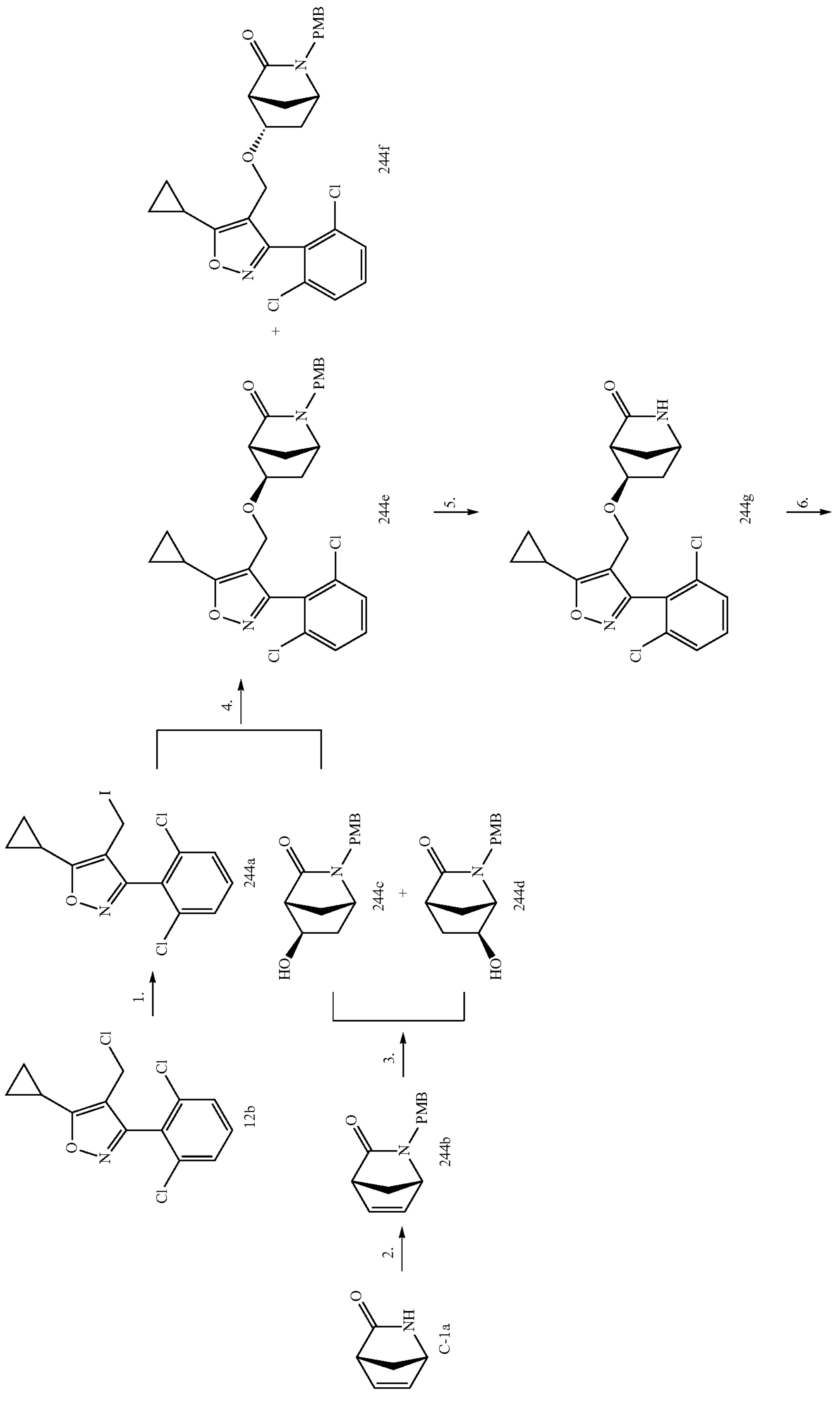
12b
1.
244a
244b
2.
C-1a
3.
244c
+
244d
4.
244e
5.
+
244f
244g
6.

-continued
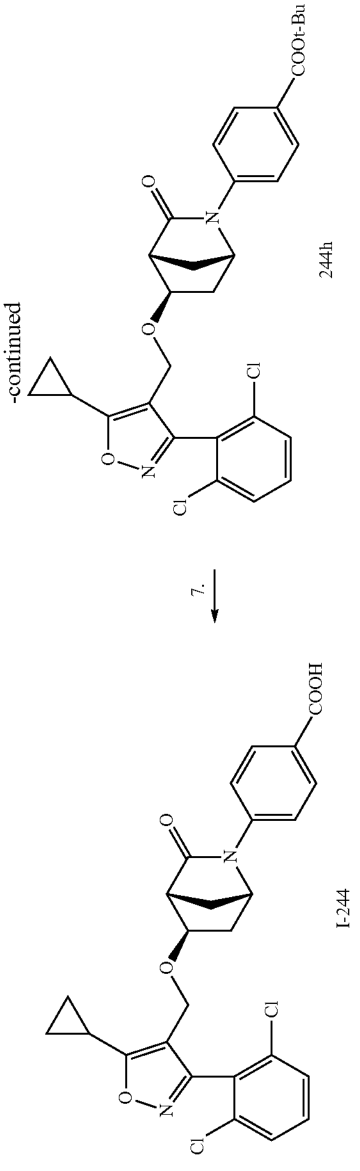
244h
I-244

Step 1

To a 1 L round bottom flask purged with and maintained under an inert atmosphere of nitrogen was added a solution of 4-(chloromethyl)-5-cyclopropyl-3-(2,6-dichlorophenyl) isoxazole 12b (30 g, 99.15 mmol, 1 equiv.) in acetone (400 mL). Solid sodium iodide (29.7 g, 198.15 mmol, 2 equiv.) was added followed by tetrabutylammonium iodide (TBAI, 9.2 g, 24.9 mmol, 0.25 equiv.). The mixture was heated to reflux for 2 hours. After cooling down, the mixture was concentrated to dryness under vacuum. The crude product was purified by Flash chromatograph using the following conditions: Column, silica gel; mobile phase, EA:PE=0%6 increasing to EA:PE=20% within 30 min; Detector. UV 254 nm. Removal of solvents provided 5-cyclopropyl-3-(2,6-dichlorophenyl)-4-(iodomethyl)isoxazole 244a (36.5 g, 93%) as a light yellow solid.

Step 2

To a 1 L round bottom flask was added a solution of (1S,4R)-2-azabicyclo[2.2.1]hept-5-en-3-one C-1a (30 g, 274.9 mmol, 1.00 equiv.) in N,N-dimethylformamide (500 mL). The solution was cooled to 0° C. Sodium hydride (12 g, 300.0 mmol, 1.10 equiv., 60% dispersion in mineral oil) was added in several batches at 0° C. The reaction mixture was stirred for another 30 min at 0° C. To this mixture was added TBAI (10 g, 27.1 mmol, 0.10 equiv.). 1-(chloromethyl)-4-methoxybenzene (47 g, 300.1 mmol, 1.10 equiv.) was added dropwise with stirring at 0° C. The resulting mixture was stirred overnight at room temperature. The reaction was then quenched by the addition of 300 mL of chilled water. The aqueous mixture was extracted with ethyl acetate (400 mL×3). The combined organic extracts were washed with brine (200 mL×2), dried over anhydrous sodium sulfate and concentrated under vacuum. The residue was purified by silica gel column chromatography eluting with PE:EA (5:1) to afford (1S,4R)-2-[(4-methoxyphenyl) methyl]-2-azabicyclo[2.2.1]hept-5-en-3-one 244b (56.6 g, 90%) as a yellow oil. $^1H$ NMR (400 MHz, $CD_3OD$): δ 7.14 (dd, J=8.5, 1.4 Hz, 2H), 6.88 (dq, J=9.4, 2.6, 2.1 Hz, 2H), 6.62-6.50 (m, 2H), 4.87-4.79 (m, OH), 4.26 (d, J=14.5 Hz, 1H), 4.19-4.05 (m 2H), 3.77 (d, J=2.8 Hz, 3H), 2.98 (q, J=2.5, 1.7 Hz, 1H), 2.86 (d, J=2.9 Hz, 1H), 2.25 (ddd, J=7.3, 4.0, 1.8 Hz, 1H), 2.07 (tt, J=7.2, 1.8 Hz, 1H).

Step 3

To a 500 mL round bottom flask purged with and maintained under an inert atmosphere of nitrogen was added a solution of (1S,4R)-2-[(4-methoxyphenyl)methyl]-2-azabicyclo[2.2.1]hept-5-en-3-one 244b (12.2 g, 53.21 mmol, 1.00 equiv.) in anhydrous dimethoxyethane (120 mL). The solution was cooled to 0° C. A solution of borane-dimethyl sulfide complex (11.6 mL, 10 M in DMS, 2.18 equiv.) was added dropwise with stirring at 0° C. After addition, the mixture was stirred at room temperature for 2 h, and then cooled to 0° C. An aqueous solution of sodium hydroxide (5.4 mL, 3 M aq, 0.30 equiv.) was added dropwise with stirring at 0° C., followed by dropwise addition of an aqueous solution of $H_2O_2$ (21.2 g, 3.50 equiv, 30%). The reaction was allowed to continue at room temperature overnight. The mixture was diluted with EA (500 mL), washed successively with water (500 mL×2) and brine (500 mL×2), dried over anhydrous sodium sulfate, and concentrated under vacuum. The crude product was purified by high pressure (maximum: 20 MPa) Prep-flash using the following conditions: Column. Welch Ultimate® XB-C18 OBD Column, 10 um, 50*250 mm (300 g); mobile phase, Water (0.05% TFA) and ACN (5.0% ACN up to 30.0% in 40 min); Detector, UV 254 nm, to provide the desired isomer (1S,4R,5R)-5-hydroxy-2-[(4-methoxyphenyl)methyl]-2-azabicyclo[2.2.1]heptan-3-one 244c (4.6 g, 35%, with a longer retention time than isomer 244d) as a white solid. $^1H$ NMR (300 MHz, $CD_3OD$): δ 7.26-7.14 (m, 2H), 6.97-6.85 (m, 2H), 4.42 (d, J=14.8 Hz, 1H), 4.16-3.98 (m, 2H), 3.80 (s, 4H), 2.73 (d, J=1.8 Hz, 1H), 2.08-1.84 (m, 3H), 1.46 (dt, J=13.2, 2.5 Hz, 1H).

Step 4

To a 250 mL round bottom flask purged with and maintained under an inert atmosphere of nitrogen was added a solution of 5-cyclopropyl-3-(2,6-dichlorophenyl)-4-(iodomethyl)isoxazole 244a (16.9 g, 40.4 mmol, 2.00 equiv.) in N,N-dimethylformamide (50 mL), followed by (1S,4R,5R)-5-hydroxy-2-[(4-methoxyphenyl)methyl]-2-azabicyclo[2.2.1]heptan-3-one 244c (5 g, 20.2 mmol, 1.00 equiv.). The mixture was cooled down to −20° C., and sodium hydride (1.6 g, 40.0 mmol, 2.00 equiv., 60% dispersion in mineral oil) was added in one batch. The resulting mixture was stirred for 2 h while the temperature was maintained between −20° C., and −10° C. The resulting mixture was diluted with 100 mL of EA, and then quenched with the addition of 100 mL of chilled water. The aqueous mixture was extracted with ethyl acetate (150 mL×2). The combined mixture organic extracts were washed with brine (200 mL×2), dried over anhydrous sodium sulfate and concentrated under vacuum. The crude product was purified by Flash column chromatograph using the following conditions: silica gel column; eluents EA in PE from 0% increasing to 50% within 25 min; Detector, UV 254 nm. Removal of solvents afforded (1S,4R,5R)-5-[[5-cyclopropyl-3-(2,6-dichlorophenyl)-1,2-oxazol-4-yl]methoxy]-2-[(4-methoxyphenyl)methyl]-2-azabicyclo[2.2.1]heptan-3-one 244e (8.7 g, 84%) as a light yellow semi-solid (contaminated with trace diasteroisomer 244f). The ratio of 244e and 244f is approximately 12 to 1.

Step 5

To a 250 mL round bottom flask was added a solution of (1S,4R,5R)-5-[[5-cyclopropyl-3-(2,6-dichlorophenyl)-1,2-oxazol-4-yl]methoxy]-2-[(4-methoxyphenyl)methyl]-2-azabicyclo[2.2.1]heptan-3-one 244e (8.7 g, 16.94 mmol, 1.00 equiv.) in $CH_3CN$ (21 mL). A solution of $(NH_4)_2Ce(NO_3)_6$ (37.1 g, 67.92 mmol, 4.00 equiv.) in water (73 mL) was added in one portion at room temperature. The reaction mixture was stirred for 30 min, and quenched with a saturated $Na_2SO_3$ aqueous solution (50 mL). The aqueous mixture was extracted with ethyl acetate (100 mL×3). The combined organic extracts were washed with brine (200 mL), dried over anhydrous sodium sulfate and concentrated under vacuum. The residue was purified by silica gel column chromatography eluting with PE/EA (2/3, v/v) to provide (1S,4R,5R)-5-[[5-cyclopropyl-3-(2,6-dichlorophenyl)-1,2-oxazol-4-yl]methoxy]-2-azabicyclo[2.2.1]heptan-3-one 244g (5 g, 75%) as a light yellow solid, containing trace diasteromeric isomer derived from 244f.

Step 6

To a 250 mL round bottom flask purged with and maintained under an inert atmosphere of nitrogen was added a solution of (1S,4R,5R)-5-[[5-cyclopropyl-3-(2,6-dichlorophenyl)-1,2-oxazol-4-yl]methoxy]-2-azabicyclo[2.2.1]heptan-3-one 244g (5 g, 12.74 mmol, 1.00 equiv.) in 1,4-dioxane (100 mL), tert-butyl 4-bromobenzoate (4 g, 15.56 mmol, 1.22 equiv), Xantphos (1.11 g, 1.92 mmol, 0.15 equiv), $Pd_2(dba)_3$ (586 mg, 0.64 mmol, 0.05 equiv.), and $Cs_2CO_3$ (6.23 g, 19.12 mmol, 1.50 equiv.). The resulting mixture was heated at 105° C., overnight with stirring. After cooling down, the mixture was diluted with 500 mL of EA, washed with brine (300 mL×2), dried over anhydrous sodium sulfate, and concentrated under vacuum. The residue was purified by silica gel column chromatography eluting with ethyl acetate/petroleum ether (1:3) to afford tert-butyl 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]benzoate 244h (6 g, 83%) as a yellow solid.

Step 7

To a 500 mL round bottom flask was added tert-butyl 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]benzoate 244h (6 g, 10.50 mmol, 1.00 equiv.), dichloromethane (120 mL), and trifluoroacetic acid (60 mL). The resulting mixture was stirred at room temperature for 1 h, then quenched by the addition of 100 mL of water. The pH value of the solution was adjusted to 7 using sodium bicarbonate. The aqueous mixture was extracted with dichloromethane (200 mL×3). The combined organic layers were washed with brine, dried over anhydrous sodium sulfate and concentrated under vacuum. The crude product was purified by high pressure (maximum: 20 MPa) Prep-flash using the following conditions: Column, Welch Ultimate® XB-C18 OBD Column, 10 um, 50*250 mm (~300 g); mobile phase, Water (0.1% FA) and ACN (45.0% ACN up to 65.0% in 30 min); Detector, UV 254 nm. After purification 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]benzoic acid I-244 (3.15 g, 58%) was obtained as an off-white solid. $^1$HNMR (300 MHz, $CD_3OD$): δ 8.06-7.95 (m, 2H), 7.64-7.45 (m, 5H), 4.62-4.54 (m, 1H), 4.40 (d, J=1.0 Hz, 2H), 3.87 (d, J=6.7 Hz, 1H), 2.86 (s, 1H), 2.38-2.11 (m, 2H), 2.09-1.94 (m, 1H), 1.79 (dt, J=10.0, 1.4 Hz, 1H), 1.62 (dt, J=13.6, 2.6 Hz, 1H), 1.28-1.14 (m, 4H); MS (ES, m/z): [M+1]=513.10.

Example 203: 4-[(1S,4R,5S)-5-{[5-cyclopropyl-3-(2,6-dichlorophenyl)-1,2-oxazol-4-yl]methoxy}-3-oxo-2-azabicyclo[2.2.1]heptan-2-yl]benzoic Acid (I-245)

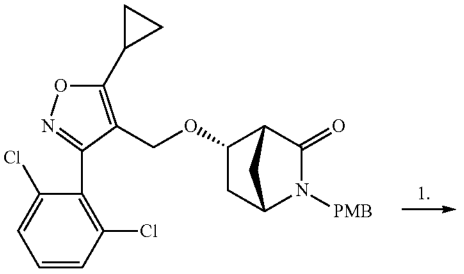

244f

-continued

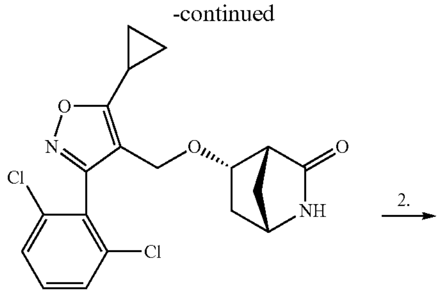

245a

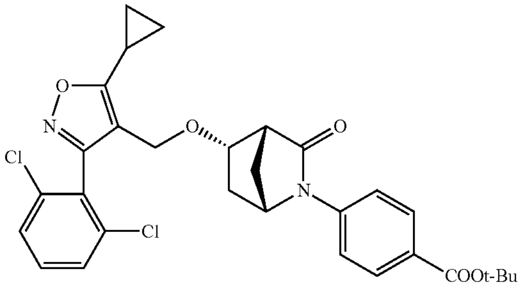

245b

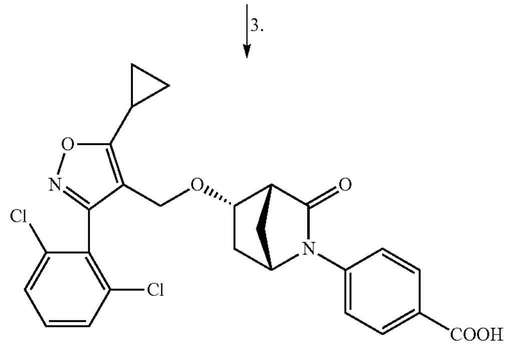

I-245

Step 1

To a 50 mL round bottom flask was added a solution of (1S,4R,5S)-5-[[5-cyclopropyl-3-(2,6-dichlorophenyl)-1,2-oxazol-4-yl]methoxy]-2-[(4-methoxyphenyl)methyl]-2-azabicyclo[2.2.1]heptan-3-one 244f (320 mg, contaminated with 244e, 0.62 mmol, 1.00 equiv.) in $CH_3CN$ (6 mL), and a solution of $(NH_4)_2Ce(NO_3)_6$ (1.025 g, 3.00 equiv.) in water (3 mL). The resulting mixture was stirred for 1 h at room temperature, diluted with 100 mL of EA, and washed with brine (100 mL). The organic layer was dried over anhydrous sodium sulfate and concentrated under vacuum. The residue was purified by silica gel column chromatography eluting with dichloromethane/methanol (15:1) to afford (1S,4R,5S)-5-[[5-cyclopropyl-3-(2,6-dichlorophenyl)-1,2-oxazol-4-yl]methoxy]-2-azabicyclo[2.2.1]heptan-3-one 245a (103 mg, 42%, mixed with isomer 244g in a ratio of ca. 1/2) as a light yellow solid.

Step 2

To a 50 mL round bottom flask purged with and maintained under an inert atmosphere of nitrogen was added a solution of (1S,4R,5S)-5-[[5-cyclopropyl-3-(2,6-dichlorophenyl)-1,2-oxazol-4-yl]methoxy]-2-azabicyclo[2.2.1]heptan-3-one 245a (100 mg, mixed with 244g, 0.25 mmol, 1.00 equiv.) in 1,4-dioxane (3 mL), tert-butyl 4-bromobenzoate (78.5 mg, 0.31 mmol, 1.20 equiv.). Xantphos (4.5 mg, 0.01 mmol, 0.03 equiv.), $Pd_2(dba)_3$ (3 mg, 0.01 equiv.), and $Cs_2CO_3$ (125 mg, 0.38 mmol, 1.50 equiv.). The resulting mixture was heated at 110° C., overnight. After cooling to room temperature, the mixture was diluted with EA (100 mL), washed with brine (100 mL), dried over anhydrous sodium sulfate and concentrated under vacuum. The residue was purified by silica gel column chromatography eluting with ethyl acetate/petroleum ether (4:1) to provide tert-butyl 4-[(1S,4R,5S)-5-[[5-cyclopropyl-3-(2,6-dichlorophenyl)-1,2-oxazol-4-yl]methoxy]-3-oxo-2-azabicyclo[2.2.1]heptan-2-yl]benzoate 245b (90 mg, 62%, mixed with isomer 244h in a ratio of ca. 1/2) as yellow oil.

Step 3

To a 50 mL round bottom flask was added a solution of tert-butyl 4-[(1S,4R,5S)-5-[[5-cyclopropyl-3-(2,6-dichlorophenyl)-1,2-oxazol-4-yl]methoxy]-3-oxo-2-azabicyclo[2.2.1]heptan-2-yl]benzoate 245b (90 mg, mixed with 244h, 0.16 mmol, 1.00 equiv.) in dichloromethane (2 mL), and trifluoroacetic acid (1 mL). The resulting mixture was stirred at room temperature for 2 h and concentrated under vacuum. The crude product was purified by Prep-HPLC using the following conditions (mobile phase, Water (0.05% TFA) and ACN (48.0% ACN up to 68.0% in 8 min); Detector, UV 254 nm. After purification 4-[(1S,4R,5S)-5-[[5-cyclopropyl-3-(2,6-dichlorophenyl)-1,2-oxazol-4-yl]methoxy]-3-oxo-2-azabicyclo[2.2.1]heptan-2-yl]benzoic acid I-245 (26.1 mg, 32%) was obtained as a colorless solid. $^1$HNMR (300 MHz, $CD_3OD$): δ 8.09-7.98 (m, 2H), 7.69-7.57 (m, 2H), 7.50-7.30 (m, 3H), 4.59-4.47 (m, 2H), 4.37 (dt, J=8.5, 3.3 Hz, 1H), 4.19 (d, J=12.0 Hz, 1H), 3.16 (dq. J=3.1, 1.5 Hz, 1H), 2.35-2.17 (m, 2H), 2.13-2.01 (m, 1H), 1.74-1.64 (m, 1H), 1.45 (dt, J=13.4, 3.1 Hz, 1H), 1.21-0.96 (m, 4H); MS (ES, m/z): [M+1]=513.10.

Example 204: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-ethyl-1,3-benzothiazole-6-carboxylic Acid (I-246)

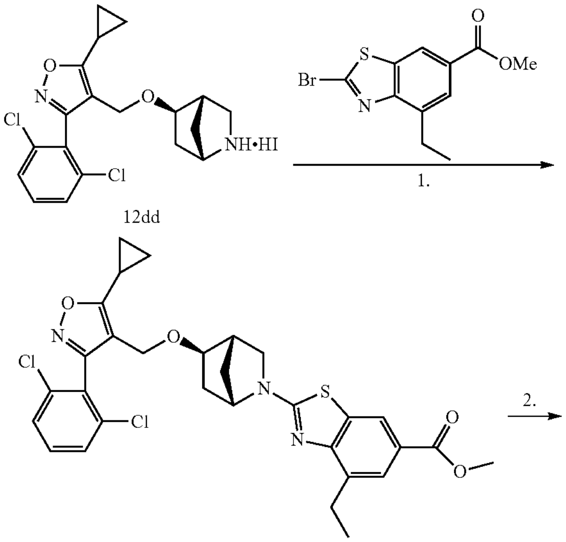

12dd

246a

-continued

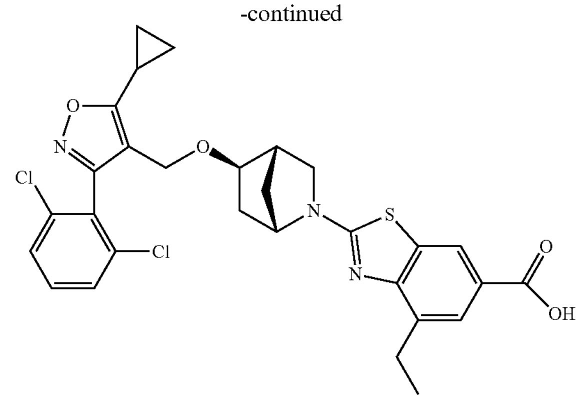

I-246

Step 1

To a 100 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (110 mg, 0.217 mmol, 1.00 equiv.), methyl 2-bromo-4-ethyl-1,3-benzothiazole-6-carboxylate (104 mg, 0.35 mmol, 1.61 equiv.), DMA (100 mL), and $Cs_2CO_3$ (285 mg, 0.87 mmol, 4.00 equiv.). The resulting mixture was heated at 60° C., overnight with stirring. After cooling to room temperature, 50 mL of $H_2O$ was added, and the aqueous mixture was extracted with ethyl acetate (100 mL×2). The combined organic extracts were washed with brine (100 mL×2), dried over anhydrous sodium sulfate, and concentrated under vacuum. The residue was purified by silica gel column chromatography eluting with ethyl acetate/petroleum ether (1:2) to give methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-ethyl-1,3-benzothiazole-6-carboxylate 246a (97 mg, 73.7%) as a light yellow oil.

Step 2

To a 100 mL round bottom flask was added a solution of methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-ethyl-1,3-benzothiazole-6-carboxylate 246a (97 mg, 0.16 mmol, 1.00 equiv.) in 12 mL of a solution of methanol and $H_2O$ (5:1, v/v)). Solid LiOH (39 mg, 1.63 mmol, 10.00 equiv.) was added. The reaction mixture was stirred overnight at room temperature, then diluted with 50 mL of $H_2O$, the pH value of the solution was adjusted to 3-4 using a 1M HCl aqueous solution. The aqueous mixture was extracted with ethyl acetate (100 mL×2); the combined organic extracts were washed with brine (100 mL×2), dried over anhydrous sodium sulfate and concentrated under vacuum. The crude product was purified by Prep-HPLC using the following conditions: Column, XBridge C18 OBD Prep Column, 19 mm×250 mm; mobile phase, Water (0.05% TFA) and ACN (63.0% ACN up to 83.0% in 8 min); Detector, uv 254 nm. After purification 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-ethyl-1,3-benzothiazole-6-carboxylic acid I-246 (28.3 mg, 30%) was obtained as an off-white solid. $^1$HNMR (300 MHz, $CD_3OD$): δ 8.14 (d, J=1.7 Hz, 1H), 7.80 (d, J=1.6 Hz, 1H), 7.58-7.38 (m, 3H), 4.31 (d, J=1.6 Hz, 3H), 3.63 (dd, J=6.9, 2.4 Hz, 1H), 3.55-3.44 (m, 1H), 3.05-2.85 (m, 3H), 2.60 (s, 1H), 2.24 (p, J=6.8 Hz, 1H), 1.98 (dd, J=13.5, 6.7 Hz, 1H), 1.66 (s, 2H), 1.45-1.22 (m, 4H), 1.15 (d, J=6.7 Hz, 4H); MS (ES, m/z): [M+1]=584.

Example 205: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(propan-2-yl)-1,3-benzothiazole-6-carboxylic Acid (I-247)

Step 1

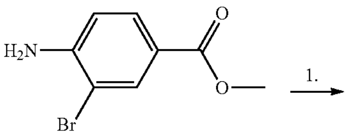

247a

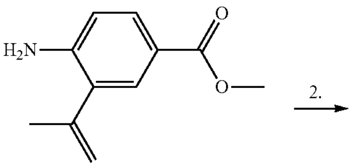

247b

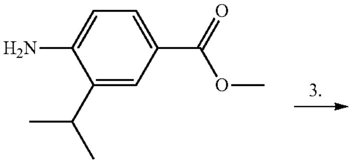

247c

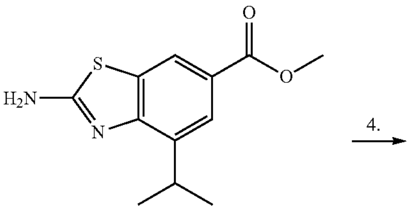

247d

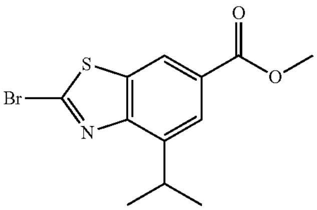
247e

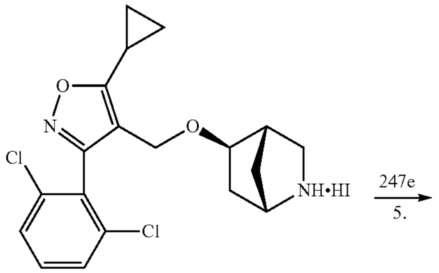

12dd

-continued

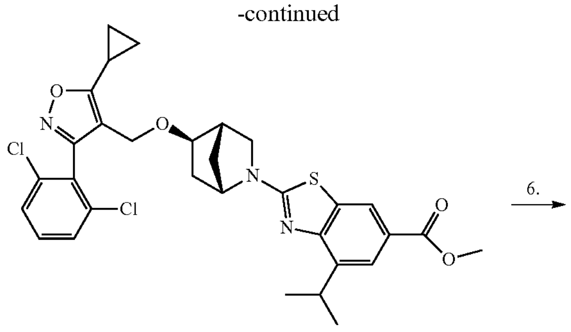

247f

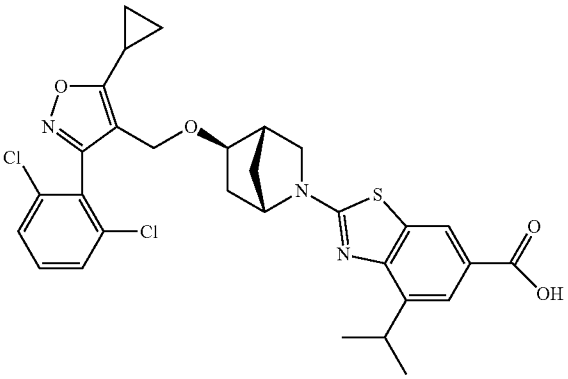
I-247

To a 250 mL round bottom flask purged with and maintained under an inert atmosphere of nitrogen was added methyl 4-amino-3-bromobenzoate 247a (2.29 g, 9.95 mmol, 1.00 equiv.), tetrahydrofuran (90 mL), Potassium trifluoro(isopropenyl)borate(1-) (4.44 g, 30.00 mmol, 3.00 equiv.), $Cs_2CO_3$ (19.56 g, 60.03 mmol, 6.00 equiv.), water (10 mL), and $Pd(PPh_3)_2Cl_2$ (700 mg, 1.00) mmol, 0.10 equiv.). The resulting mixture was stirred at 80° C., overnight. After cooling to room temperature, 150 mL of water was added, and the aqueous mixture was extracted with ethyl acetate (150 mL×3). The combined organic extracts were washed with brine (300 mL×2), dried over anhydrous sodium sulfate and concentrated in vacuo to afford methyl 4-amino-3-(prop-1-en-2-yl)benzoate 247b (1.12 g, 59%) as a yellow oil.

Step 2

To a 100 mL round bottom flask was added methyl 4-amino-3-(prop-1-en-2-yl)benzoate 247b (1.15 g, 6.01 mmol, 1.00 equiv.), methanol (20 mL), and Palladium on carbon (1.2 g, 10% wt). The mixture was flushed with nitrogen and then placed under a hydrogen atmosphere, the reaction mixture was stirred 30° C. for 16 h. Solids were filtered out, the filtrate was concentrated under vacuum to give methyl 4-amino-3-(propan-2-yl) benzoate 247c (1.0 g, 86%) as a white solid.

Step 3

To a 100 mL round-bottom flask was added methyl 4-amino-3-(propan-2-yl) benzoate 247c (1 g, 5.17 mmol, 1.00 equiv.), AcOH (20 mL), NaSCN (1.67 g, 4.00 equiv), and a solution of $Br_2$ (1.64 g, 10.26 mmol, 2.00 equiv.) in AcOH (20 mL). The resulting mixture was stirred at 30° C., for 16 h. The reaction was quenched by the addition of 150 mL of water. The pH value of the solution was adjusted to 10 using sodium hydroxide pellets. The solids were collected by filtration, and further dried in an oven under reduced pressure to provide methyl 2-amino-4-(propan-2-yl)-1,3-benzothiazole-6-carboxylate 247d (1.2 g, 93%) as a yellow solid.

Step 4

To a 250 mL round-bottom flask was added methyl 2-amino-4-(propan-2-yl)-1,3-benzothiazole-6-carboxylate 247d (1.2 g, 4.79 mmol, 1.00 equiv.), $CuBr_2$ (1.5 g, 1.50 equiv.), MeCN (100 mL), and t-BuONO (1.42 g, 2.26 equiv.). The resulting mixture was stirred at 30° C., for 16 h. The solids were filtered, and the filtrate was concentrated. The residue was purified by silica gel column chromatography eluting with ethyl acetate/petroleum ether (1:15) to afford methyl 2-bromo-4-(propan-2-yl)-1,3-benzothiazole-6-carboxylate 247e (1.23 g, 82%) as a white solid.

Step 5

To a 50 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (100 mg, 0.197 mmol, 1.00 equiv.), DMA (8 mL), methyl 2-bromo-4-(propan-2-yl)-1,3-benzothiazole-6-carboxylate 247e (100 mg, 0.32 mmol, 1.60 equiv.), $Cs_2CO_3$ (258 mg, 0.79 mmol, 4.00 equiv.). The resulting mixture was stirred at 60° C., for 16 h. The reaction was then quenched by the addition of 80 mL of water upon cooling to room temperature. The aqueous mixture was extracted with ethyl acetate (100 mL×3). The combined organic extracts were washed with brine (200 mL×2), dried over anhydrous sodium sulfate, and concentrated to give methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(propan-2-yl)-1,3-benzothiazole-6-carboxylate 247f (85 mg, 71%) as a white solid.

Step 6

To a 25 mL round bottom flask was added methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(propan-2-yl)-1,3-benzothiazole-6-carboxylate 247f (85 mg, 0.14 mmol, 1.00 equiv.), LiOH (34 mg, 1.42 mmol, 10.00 equiv.), methanol (10 mL), and water (1 mL). The resulting mixture was heated at 50° C., for 3 h with stirring. The reaction was quenched by the addition of 50 mL of water upon cooling to room temperature. The pH value of the solution was adjusted to 6 using a hydrogen chloride aqueous solution (3 M). The aqueous mixture was extracted with ethyl acetate (100 mL×3); and the combined organic extracts were dried over anhydrous sodium sulfate and concentrated under vacuum. The residue was dissolved in 2 mL of DMF and purified by Prep-HPLC using the following conditions: Column, XBridge C18 OBD Prep Column, 19 mm×250 mm; mobile phase, Water (0.05% TFA) and ACN (68.0% ACN up to 85.0% in 8 min); Detector, uv 254 nm. 100 mL product was obtained. After purification 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(propan-2-yl)-1,3-benzothiazole-6-carboxylic Acid I-247 (43.7 mg, 53%) was obtained as a white solid. $^1$HNMR (300 MHz, $CD_3OD$): δ 8.17 (d, J=1.7 Hz, 1H), 7.90 (d, J=1.7 Hz, 1H), 7.61-7.42 (m, 3H), 4.35 (d, J=1.3 Hz, 2H), 3.71-3.47 (m, 3H), 3.06 (d, J=10.2 Hz, 1H), 2.63 (s, 1H), 2.28 (p, J=6.8 Hz, 1H), 2.02 (dd, J=13.7, 6.7 Hz, 1H), 1.69 (s, 2H), 1.47-1.26 (m, 7H), 1.18 (d, J=6.7 Hz, 4H); MS (ES, m/z): [M+1]=598.10.

Example 206: 4-tert-butyl-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic Acid (I-248)

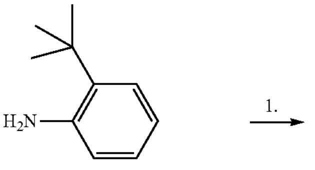

248a

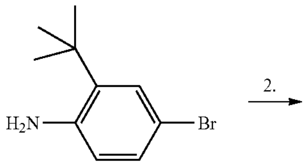

248b

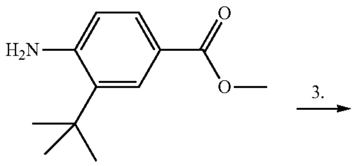

248c

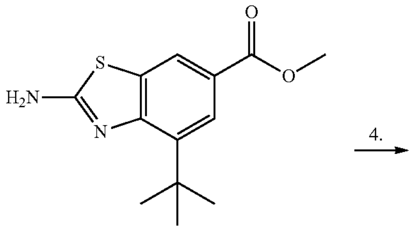

248d

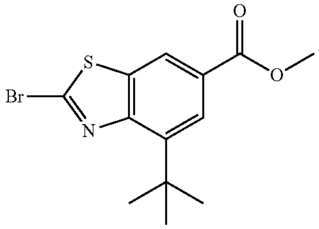
248e

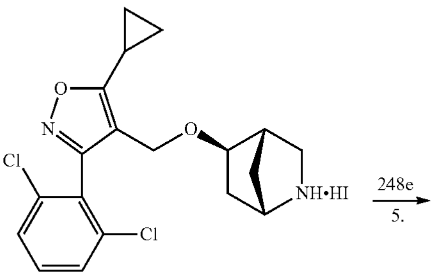

12dd

-continued

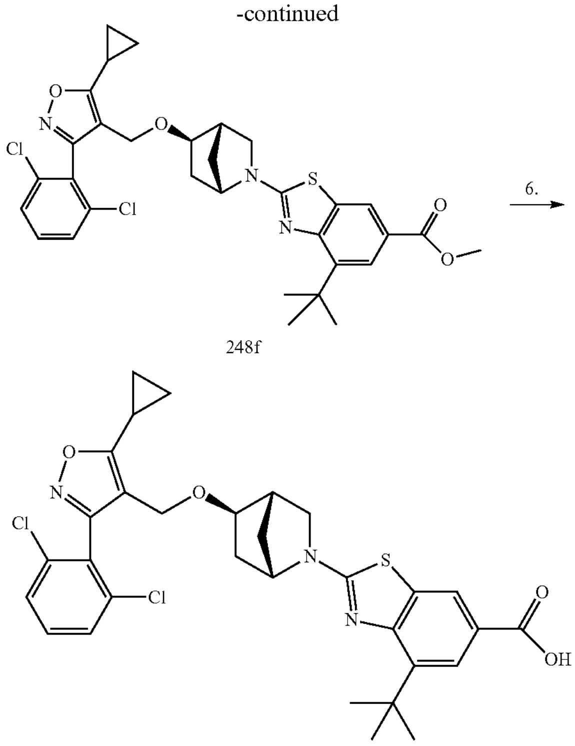

248f

I-248

Step 1

To a 100 mL round bottom flask was added 2-tert-butylaniline 247a (2.5 g, 16.75 mmol, 1.00 equiv.), tetrahydrofuran (25 mL), and tetrabutylammoniumtribromide (8.1 g, 16.80 mmol, 1.00 equiv.). The resulting mixture was stirred at 0-5° C., for 10 minutes, and then at room temperature overnight. The mixture was diluted with 50 mL of EA, washed successively with $Na_2S_2O_5$ (30 mL×3) and brine (30 mL), dried over anhydrous sodium sulfate, and concentrated under vacuum. The crude product was purified by Flash-Prep-HPLC using the following conditions (IntelFlash-1): Column, silica gel; mobile phase: PE:EA=100:0 increasing to PE:EA=30:70 within 30 min; Detector, UV 254 nm. Removal of solvents gave 4-bromo-2-tert-butylaniline 248b (3.2 g, 84%) as a colorless oil.

Step 2

To a 100 mL round-bottom flask was added 4-bromo-2-tert-butylaniline 248b (1.5 g, 6.58 mmol, 1.00 equiv), MeOH (5 mL), TEA (4.0 g, 39.53 mmol, 6.00 equiv), and Pd(dppf)$Cl_2$—$CH_2Cl_2$ complex (540 mg, 0.10 equiv.). CO (g) was introduced in. The resulting mixture was heated at 100° C., overnight with stirring. The mixture was concentrated under vacuum. The crude product was purified by Flash-Prep-HPLC using the following conditions (IntelFlash-1): Column, silica gel; mobile phase: PE:EA=100:0 increasing to PE:EA=90:10 within 20 min; Detector, UV 254 nm. Removal of solvent provided methyl 4-amino-3-tert-butylbenzoate 248c (1.3 g, 95%) as a colorless oil.

Step 3

To a 100 mL round-bottom flask was added methyl 4-amino-3-tert-butylbenzoate 248c (1.3 g, 6.27 mmol, 1.00 equiv.), AcOH (10 mL), NaSCN (2.08 g, 25.68 mmol, 4.00 equiv.), and $Br_2$ (1.01 g, 6.32 mmol, 1.00 equiv.). The resulting mixture was stirred at 30° C., overnight. The reaction was quenched by the addition of 500 mL of water/ice. The pH value of the solution was adjusted to 10.0 using sodium hydroxide pellets. The solids were collected by filtration, further dried to provide methyl 2-amino-4-tert-butyl-1,3-benzothiazole-6-carboxylate 248d (1.67 g, crude) as a light yellow solid.

Step 4

To a 100 mL round-bottom flask was added methyl 2-amino-4-tert-butyl-1,3-benzothiazole-6-carboxylate 248d (1.66 g, 6.28 mmol, 1.00 equiv.), $CH_3CN$ (35 mL), $CuBr_2$ (2.1 g, 9.42 mmol, 1.50 equiv.), and t-BuONO (1.47 g, 14.27 mmol, 2.26 equiv). The resulting mixture was stirred at 30° C., overnight, and concentrated under vacuum. The crude product was purified by Flash-Prep-HPLC using the following conditions (IntelFlash-1): Column, silica gel; mobile phase: PE:EA=100:0 increasing to PE:EA=95:5 within 30 min; Detector, UV 254 nm. Removal of solvents provided methyl 2-bromo-4-tert-butyl-1,3-benzothiazole-6-carboxylate 248e (1.76 g, 85%) as a yellow solid.

Step 5

To a 100 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (100 mg, 0.197 mmol, 1.00 equiv.), DMA (5 mL), methyl 2-bromo-4-tert-butyl-1,3-benzothiazole-6-carboxylate (174 mg, 0.53 mmol, 2.7 equiv.), and $Cs_2CO_3$ (173 mg, 0.53 mmol, 2.7 equiv.). The resulting mixture was stirred at 60° C. overnight. Upon cooling to room temperature, 50 mL of water was added, and the mixture was extracted with ethyl acetate (100 mL×3). The combined organic layers were dried over anhydrous sodium sulfate and concentrated under vacuum. The crude product was purified by Flash-Prep-HPLC using the following conditions (IntelFlash-1): Column, silica gel; mobile phase: PE:EA=100:0 increasing to PE:EA=80:20 within 20 min; Detector, UV 254 nm. Removal of solvents afforded methyl 4-tert-butyl-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylate 248f (115 mg, 91%) as a white solid.

Step 6

To a 25 mL round-bottom flask was added methyl 4-tert-butyl-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylate 248f (115 mg, 0.18 mmol, 1.00 equiv.), methanol (4 mL), water (2 mL), tetrahydrofuran (2 mL), and LiOH (100 mg, 4.18 mmol, 10.00 equiv). The resulting mixture was stirred at room temperature overnight. The reaction was quenched by the addition of 10 mL of water. The pH value of the solution was adjusted to 5.0 using a 1M HCl aqueous solution. The aqueous mixture was extracted with ethyl acetate (100 mL×2); the combined organic extracts were washed with brine (50 mL×2), dried over anhydrous sodium sulfate and concentrated under vacuum. The crude product was purified by Prep-HPLC using the following conditions: Mobile phase—water (0.05% TFA) and ACN (85% ACN up to 95% in 8 min); Detector, UV 254 nm. After purification 4-tert-butyl-2-[(1S,4S,5R)-5-[[5-cyclopropyl-3-(2,6-dichlorophenyl)-1, 2-oxazol-4-yl]methoxy]-2-azabicyclo[2.2.1]heptan-2-yl]-1,3-benzothiazole-6-carboxylic Acid I-248 (56.7 mg, 50%) was obtained as a colorless solid. $^1$HNMR (400 MHz, $CD_3OD$): δ 8.17 (d, J=1.7 Hz, 1H), 7.91 (d, J=1.7 Hz, 1H), 7.55 (dd, J=7.3, 2.0 Hz, 1H), 7.53-7.41 (m, 2H), 4.33 (s, 2H), 4.29 (s, 1H), 3.62 (dd, J=6.9, 2.4 Hz, 1H), 3.53-3.44 (m, 1H), 2.98 (d, J=9.9 Hz, 1H), 2.57 (s, 1H), 2.27 (p, J=6.8 Hz, 1H), 1.97 (dd, J=13.5, 6.6 Hz, 1H), 1.66 (s, 2H), 1.52 (s, 9H), 1.38 (d, J=13.2 Hz, 1H), 1.21-1.14 (m, 4H); MS (ES, m/z): [M+1]=613.

Example 207: 4-cyclobutyl-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic Acid (I-249)

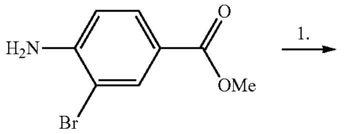

249a

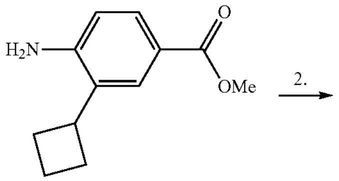

249b

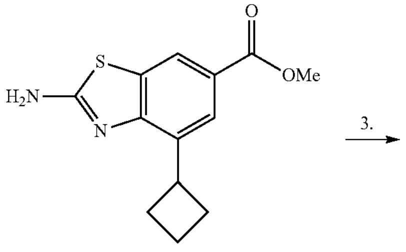

249c

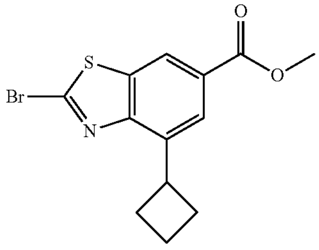

249d

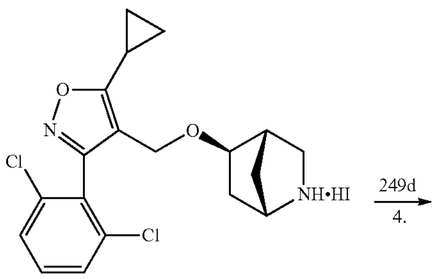

12dd

-continued

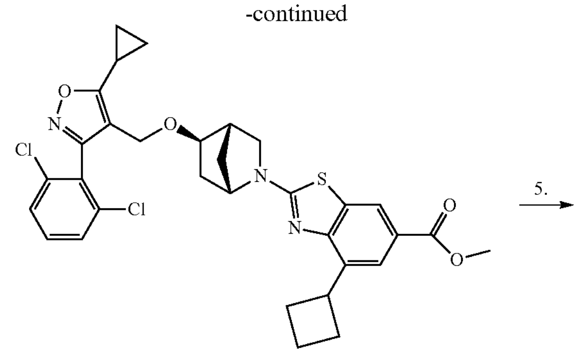

249e

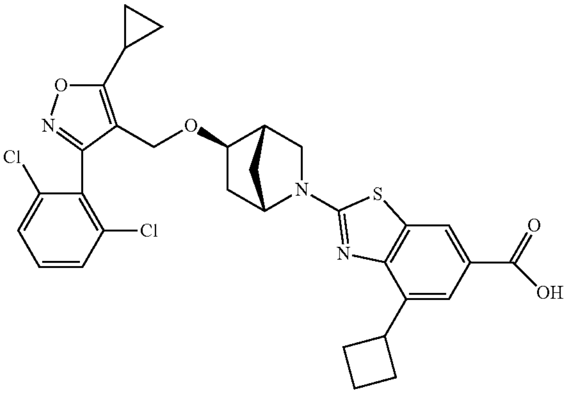

I-249

Step 1

To a 250 mL round-bottom flask was added methyl 4-amino-3-bromobenzoate 249a (6 g, 26.08 mmol, 1.00 equiv.), Toluene (80 mL), cyclobutylboronic acid (5.4 g, 54.04 mmol, 2.00 equiv.), a solution of $Cs_2CO_3$ (13.67 g, 41.96 mmol, 1.60 equiv.) in water (21 mL), and Pd(dppf)$Cl_2$.DCM (2.14 g, 2.62 mmol, 0.10 equiv.). The resulting mixture was stirred at 90° C., for 2 days. After cooling to room temperature, the mixture was diluted with 750 mL of brine, and extracted with ethyl acetate (200 mL×2). The combined organic extracts were dried over anhydrous sodium sulfate and concentrated under vacuum. The crude product was purified by Flash-Prep-HPLC using the following conditions (IntelFlash-1): Column, silica gel, mobile phase, EA:PE increasing to EA:PE=100 within 30 min; Detector, UV 254 nm. Removal of solvents gave methyl 4-amino-3-cyclobutylbenzoate 249b (2.384 g, 45%) as a light yellow oil.

Step 2

To a 100 mL round-bottom flask was added methyl 4-amino-3-cyclobutylbenzoate 249b (1 g, 4.87 mmol, 1.00 equiv.), AcOH (10 mL), NaSCN (1.6 g), and a solution of $Br_2$ (780 mg, 4.88 mmol, 1.00 equiv.) in AcOH (10 mL). The resulting mixture was stirred at 10-25° C., overnight, then diluted with 200 mL of $H_2O$, and the pH value of the solution was adjusted to 8-9 using sodium carbonate. The solids were collected by filtration, dried, to afford methyl 2-amino-4-cyclobutyl-1,3-benzothiazole-6-carboxylate 249c (0.7 g, 55%) as a light yellow solid.

Step 3

To a 250 mL round-bottom flask was added methyl 2-amino-4-cyclobutyl-1,3-benzothiazole-6-carboxylate 249c (1 g, 3.81 mmol, 1.00 equiv.), MeCN (20 mL), and $CuBr_2$ (1.28 g), t-BuONO (0.89 g) was added dropwise at 15-25° C., with stirring. The resulting mixture was stirred at 30° C., overnight and then concentrated under vacuum. The residue was purified by silica gel column chromatography eluting with ethyl acetate/petroleum ether (1:10-1:5-1:3) to afford methyl 2-bromo-4-cyclobutyl-1,3-benzothiazole-6-carboxylate 249d (0.79 g, 64%) as a yellow solid.

Step 4

To a 100 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (100 mg, 0.197 mmol, 1.00 equiv.), DMA (10 mL), methyl 2-bromo-4-cyclobutyl-1,3-benzothiazole-6-carboxylate 249d (129 mg, 0.40 mmol, 2.0 equiv), and $Cs_2CO_3$ (257.8 mg, 0.79 mmol, 4.00 equiv.). The resulting mixture was stirred at 10-25° C., overnight. The reaction was quenched by the addition of 100 mL of water. The aqueous mixture was extracted with ethyl acetate (50 mL×3), and the combined organic extracts were dried and concentrated under vacuum. The residue was purified by silica gel column chromatography eluting with ethyl acetate/petroleum ether (1:10-1:5) to afford methyl 4-cyclobutyl-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylate 249e (78 mg, 61%) as an off-white solid.

Step 5

To a 100 mL round bottom flask was added methyl 4-cyclobutyl-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylate 249e (78 mg, 0.12 mmol, 1.00 equiv.), EtOH (5 mL), water (I mL), and sodium hydroxide (25 mg, 0.62 mmol, 5.00 equiv.). The resulting mixture was stirred at 60° C., for 3 h. Upon cooling to room temperature, the pH value of the mixture was adjusted to 7 using a 1M aqueous hydrogen chloride solution. The aqueous mixture was extracted with ethyl acetate (50 mL×3), and the combined organic extracts were washed with brine, dried and concentrated under vacuum. The crude product was purified by Prep-HPLC using the following conditions Column, XBridge C18 OBD Prep Column, 19 mm×250 mm; mobile phase, Water (0.05% TFA) and ACN (80.0% ACN up to 90.0% in 8 min); Detector, uv 254 nm. After purification 4-cyclobutyl-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylic acid I-249 (46.5 mg, 61%) was obtained as a white solid. $^1$HNMR (300 MHz, $CD_3OD$): δ 8.19 (d, J=1.7 Hz, 1H), 7.96 (dd, J=1.6, 0.8 Hz, 1H), 7.62-7.42 (m, 3H), 4.35 (d, J=1.5 Hz, 3H), 4.06 (q, J=8.9 Hz, 1H), 3.67 (d, J=5.7 Hz, 1H), 3.60-3.48 (m, 1H), 3.16-3.00 (m, 1H), 2.64 (s, 1H), 2.44 (t, J=7.0 Hz, 2H), 2.36-1.89 (m, 6H), 1.71 (s, 2H), 1.42 (d, J=13.5 Hz, 1H), 1.19 (d, J=6.7 Hz, 4H); MS (ES, m/z): [M+1]=610.0.

Example 208: 4-cyclopentyl-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic Acid (I-250)

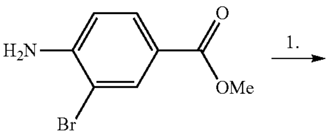

249a

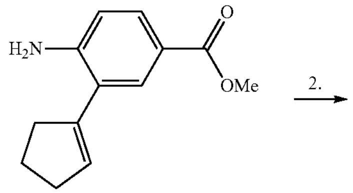

250a

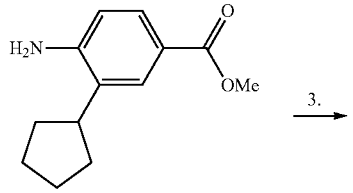

250b

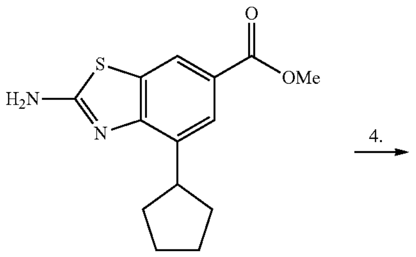

250c

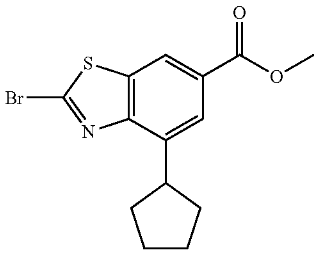

250d

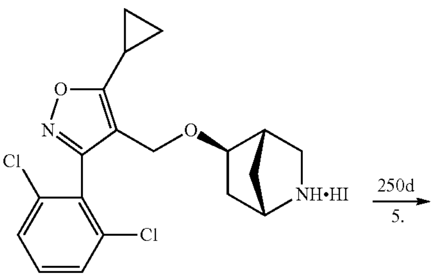

12dd

-continued

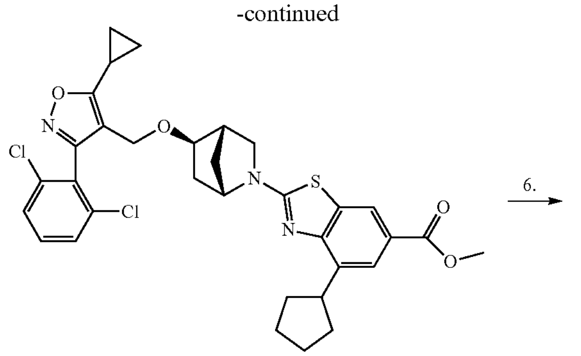

250e

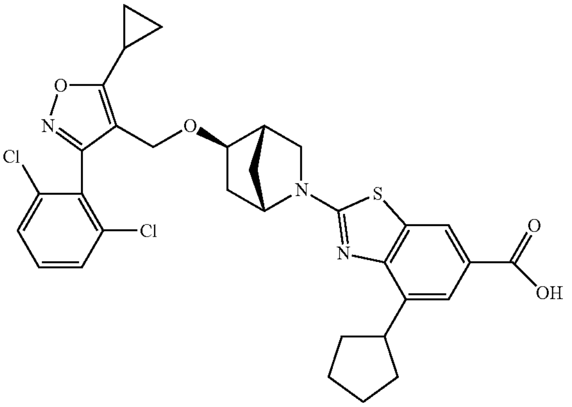 [SMILES: CC(C)c1cc(C(=O)O)cc2sc(N3C[C@@H]4C[C@H]3C[C@H]4OCc3c(-c4c(Cl)cccc4Cl)noc3C3CC3)nc12]

I-250

Step 1

To a 250 mL round-bottom flask purged with and maintained under an inert atmosphere of nitrogen was added methyl 4-amino-3-bromobenzoate 249a (2.2 g, 9.56 mmol, 1.00 equiv.), toluene (50 mL), water (10 mL), (cyclopent-1-en-1-yl)boronic acid (3.36 g, 30.02 mmol, 3.00 equiv), $K_3PO_4$ (6.36 g, 29.96 mmol, 3.00 equiv.), $Pd(OAc)_2$ (224 mg, 1.00 mmol, 0.10 equiv.), and $P(Cy)_3$ (0.280 g, 0.10 equiv.). The resulting mixture was heated at 110° C., for 16 h. The reaction was quenched by the addition of water/ice upon cooling to room temperature. The aqueous mixture was extracted with ethyl acetate (150 mL×3), and the combined organic extracts were washed with brine (300 mL), dried over anhydrous sodium sulfate, and concentrated. The residue was purified by silica gel column chromatography eluting with ethyl acetate/petroleum ether (1:10) to give methyl 4-amino-3-(cyclopent-1-en-1-yl)benzoate 250a (1.45 g, 70%) as a yellow solid.

Step 2

To a 100 mL round-bottom flask was added methyl 4-amino-3-(cyclopent-1-en-1-yl)benzoate 250a (1.56 g, 7.18 mmol, 1.00 equiv.) and methanol (30 mL). Palladium on carbon (2 g, 10 wt %) was added. Hydrogen gas was introduced via a balloon. The reaction mixture was stirred at room temperature for 16 h under a hydrogen atmosphere. Solids were filtered out, the filtrate was concentrated under vacuum to give methyl 4-amino-3-cyclopentylbenzoate 250b (1.6 g, Q) as a white solid.

Step 3

To a 250 mL round-bottom flask was added methyl 4-amino-3-cyclopentylbenzoate 250b (1.6 g, 7.30 mmol, 1.00 equiv.), NaSCN (25 mL), and AcOH (2.4 g, 39.97 mmol, 4.00 equiv.). A solution of $Br_2$ (2.3 g, 14.39 mmol, 2.00 equiv.) in AcOH (25 mL) was added dropwise with stirring at 0° C. The resulting mixture was stirred at 30° C., for 16 h, then quenched by the addition of 200 mL of water. The pH value of the solution was adjusted to 10 using sodium hydroxide pellets. The solids were collected by filtration, further dried in an oven under reduced pressure to give methyl 2-amino-4-cyclopentyl-1,3-benzothiazole-6-carboxylate 250c (2.5 g, crude) as a yellow solid.

Step 4

To a 250 mL round-bottom flask was added methyl 2-amino-4-cyclopentyl-1,3-benzothiazole-6-carboxylate 250c (2.15 g, 7.78 mmol, 1.00 equiv.), MeCN (100 mL), $CuBr_2$ (2.58 g, 1.50 equiv.), and t-BuONO (2.3 g, 2.26 equiv.). The resulting mixture was stirred at 30° C., for 16 h and concentrated. The residue was purified by silica gel column chromatography eluting with ethyl acetate/petroleum ether (1:10) to give methyl 2-bromo-4-cyclopentyl-1,3-benzothiazole-6-carboxylate 250d (1.6 g, 60%) as a white solid.

Step 5

To a 50 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (100 mg, 0.197 mmol, 1.00 equiv.), DMA (8 mL), methyl 2-bromo-4-cyclopentyl-1,3-benzothiazole-6-carboxylate 250d (108 mg, 0.32 mmol, 1.62 equiv.), and $Cs_2CO_3$ (259 mg, 0.79 mmol, 4.00 equiv.). The resulting mixture was heated at 60° C., for 16 h. The mixture was cooled to room temperature and quenched by the addition of 80 mL of water. The aqueous mixture was extracted with ethyl acetate (100 mL×3); the combined organic extracts were washed with brine (100 mL×2), dried over anhydrous sodium sulfate, and concentrated to give methyl 4-cyclopentyl-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylate 250e (101 mg, 81.2%) as a yellow oil.

Step 6

To a 50 mL round-bottom flask was added methyl 4-cyclopentyl-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylate 250e (101 mg, 0.16 mmol, 1.00 equiv.), methanol (10 mL), LiOH (38 mg, 1.6 mmol, 10.00 equiv), and water (1 mL). The resulting mixture was stirred at 50° C., for 3 h. The reaction was quenched by the addition of 50 mL of water after cooling to room temperature. The pH value of the solution was adjusted to 6 using a 3M hydrogen chloride aqueous solution. The aqueous mixture was extracted with ethyl acetate (100 mL×5); the combined organic extracts were dried and concentrated under vacuum. The residue was dissolved in 3 mL of DMF, and purified by Prep-HPLC using the following conditions: Column, XBridge C18 OBD Prep Column, 19 mm×250 mm; mobile phase, Water (0.05% TFA) and ACN (73.0% ACN up to 90.0% in 8 min); Detector, UV 254 nm. After purification 4-cyclopentyl-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylic acid I-250 (42.6 mg, 43%) was obtained as a colorless solid. $^1$HNMR (300 MHz, $CD_3OD$): δ 8.17 (d, J=1.7 Hz, 1H), 7.90 (d, J=1.7 Hz, 1H), 7.62-7.42 (m, 3H), 4.34 (d, J=1.4 Hz, 2H), 3.72-3.47 (m, 3H), 3.06 (d, J=10.2 Hz, 1H), 2.63 (s, 1H), 2.28 (p, J=6.8 Hz, 1H), 2.13 (s, 2H), 2.08-1.85 (m, 3H), 1.86-1.66 (m, 6H), 1.41 (d, J=13.6 Hz, 1H), 1.18 (d, J=6.7 Hz, 4H); MS (ES, m/z): [M+1]=624.10.

Example 209: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(oxolan-3-yl)-1,3-benzothiazole-6-carboxylic Acid (I-251)

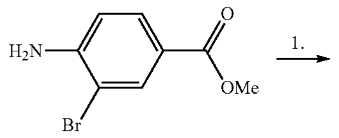

249a

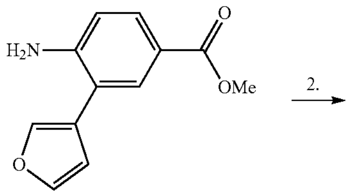

251a

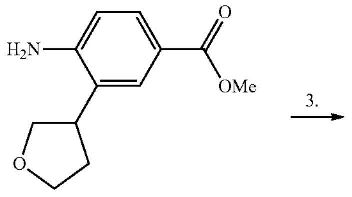

251b

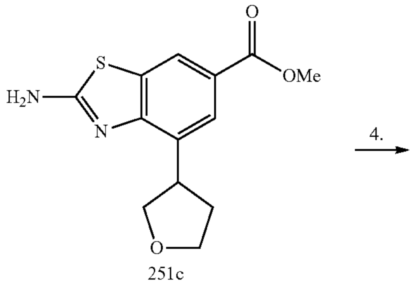

251c

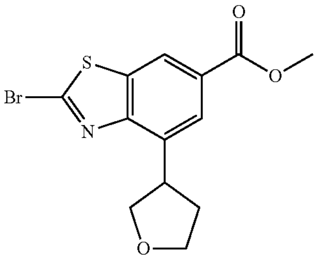

251d

-continued

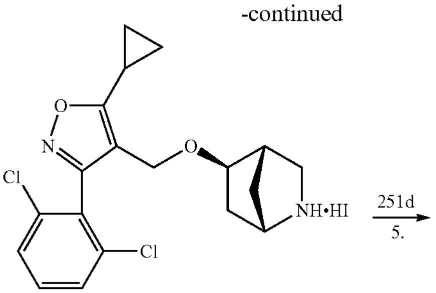

12dd

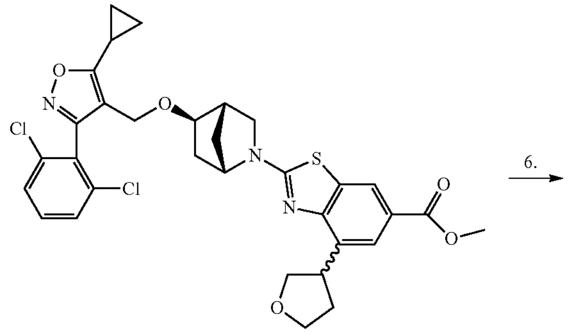

251e

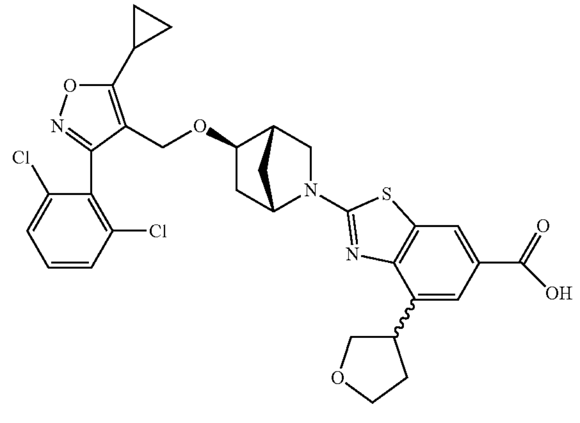

I-251

Step 1

To a 1 L round-bottom flask purged with and maintained under an inert atmosphere of nitrogen was added methyl 4-amino-3-bromobenzoate 249a (13.6 g, 59.12 mmol, 1.00 equiv.), (furan-3-yl)boronic acid (10 g, 89.37 mmol, 1.50 equiv.), 1,4-dioxane (500 mL), 1M aq. $NaHCO_3$ (17.5 g, 3.50 equiv.), and tetrakis(triphenylphosphine) palladium (6.86 g, 5.94 mmol, 0.10 equiv.). The resulting mixture was heated at 110° C., overnight with stirring. After cooling to room temperature, the mixture was diluted with 200 mL of water, and extracted with ethyl acetate (500 mL×2). The combined organic extracts were washed successively with $H_2O$ (500 mL) and brine (500 mL×2), dried over anhydrous sodium sulfate, and concentrated under vacuum. The crude product was purified by Flash-Prep-HPLC using the following conditions (IntelFlash-1): Column, silica gel; mobile phase: EA:PE=0:100 increasing to EA:PE=50:50 within 20 min; Detector, UV 254 nm. Removal of solvents gave methyl 4-amino-3-(furan-3-yl)benzoate 251a (8.345 g, 65%) as a yellow oil.

Step 2

To a 25 mL round-bottom flask was added methyl 4-amino-3-(furan-3-yl) benzoate 251a (7.1 g, 32.69 mmol, 1.00 equiv.), Palladium on carbon (3 g, 10 wt %), tetrahydrofuran (30 mL), and methanol (30 mL). Hydrogen gas was introduced via a gas balloon. The resulting mixture was stirred at 30° C., overnight. The solids were filtered out. The filtrate was concentrated under vacuum to give methyl 4-amino-3-(oxolan-3-yl)benzoate 251b (6.9 g, 95%) as a white solid.

Step 3

To a 500 mL round-bottom flask was added methyl 4-amino-3-(oxolan-3-yl) benzoate 251b (11.7 g, 52.88 mmol, 1.00 equiv.), AcOH (150 mL), NaSCN (17.2 g, 212.35 mmol, 4.00 equiv.), and $Br_2$ (8.5 g, 53.19 mmol, 1.00 equiv.). The resulting mixture was stirred at 30° C., overnight. The reaction was quenched by the addition of 100 mL of water/ice. The pH value of the solution was adjusted to 10 using sodium hydroxide. The solids were collected by filtration and dried to afford methyl 2-amino-4-(oxolan-3-yl)-1,3-benzothiazole-6-carboxylate 251c (12.4 g, 84%) as a yellow solid.

Step 4

To a 50 mL round-bottom flask was added methyl 2-amino-4-(oxolan-3-yl)-1,3-benzothiazole-6-carboxylate 251c (589 mg, 2.12 mmol, 1.00 equiv.). MeCN (10 mL), t-BuONO (494 mg, 2.26 equiv), and $CuBr_2$ (710 mg, 1.50 equiv). The resulting mixture was stirred at 30° C., overnight and concentrated under vacuum. The crude product was purified by Flash-Prep-HPLC using the following conditions (IntelFlash-1): Column, silica gel; mobile phase: PE:EA=100:0 increasing to PE:EA=95:5 within 30 min; Detector, UV 254 nm. Removal of solvents afforded methyl 2-bromo-4-(oxolan-3-yl)-1,3-benzothiazole-6-carboxylate 251d (497 mg, 69%) as a yellow solid.

Step 5

To a 25 mL round-bottom flask was added (1S,4S,5R)-5-[[5-cyclopropyl-3-(2,6-dichlorophenyl)-1,2-oxazol-4-yl] methoxy]-2-azabicyclo[2.2.1]heptane hydroiodide salt 12dd (150 mg, 0.296 mmol, 1.00 equiv.), DMA (5 mL), $Cs_2CO_3$ (259 mg, 0.79 mmol, 2.66 equiv.), and methyl 2-bromo-4-(oxolan-3-yl)-1,3-benzothiazole-6-carboxylate 251d (205 mg, 0.60 mmol, 2.02 equiv.). The resulting mixture was heated at 60° C., overnight. After cooling to room temperature, the mixture was diluted with 200 mL of EA, washed with brine (150 mL×2), dried over anhydrous sodium sulfate, and concentrated under vacuum. The residue was purified by silica gel column eluting with ethyl acetate/petroleum ether (1:3) to afford methyl 2-[(1S,4S,5R)-5-[[5-cyclopropyl-3-(2,6-dichlorophenyl)-1,2-oxazol-4-yl] methoxy]-2-azabicyclo[2.2.1]heptan-2-yl]-4-(oxolan-3-yl)-1,3-benzothiazole-(6-carboxylate 251e (115 mg, 61%) as a white solid.

Step 6

To a 25 mL round-bottom flask was added methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(oxolan-3-yl)-1,3-benzothiazole-6-carboxylate (260 mg, 0.41 mmol, 1.00 equiv.), methanol (4 mL), water (2 mL), and $LiOH.H_2O$ (170 mg, 4.05 mmol, 10.00 equiv.). The resulting mixture was stirred at room temperature overnight. The pH value of the solution was adjusted to 7.0 using a 1M HCl aqueous solution. The aqueous mixture was extracted with ethyl acetate (20 mL×3). The combined organic extracts were washed with brine, dried over anhydrous sodium sulfate and concentrated under vacuum. The crude product was purified by Prep-HPLC using following conditions: Mobile phase: Water (0.05% TFA) and ACN (37.0% ACN up to 50.0% in 8 min); Detector, UV 254 nm. After purification 2-[(1S,4S,5R)-5-[[5-cyclopropyl-3-(2,6-dichlorophenyl)-1,2-oxazol-4-yl]methoxy]-2-azabicyclo[2.2.1] heptan-2-yl]-4-(oxolan-3-yl)-1,3-benzothiazole-6-carboxylic acid I-251 (106.3 mg, 42%) was obtained as a colorless solid. $^1$HNMR (400 MHz, $CD_3OD$): δ 8.20 (d, J=1.7 Hz, 1H), 7.90 (d, J=1.6 Hz, 1H), 7.55 (dd, J=7.2, 2.1 Hz, 1H), 7.52-7.43 (m, 2H), 4.34 (d, J=2.9 Hz, 3H), 4.21-4.07 (m, 2H), 4.07-3.90 (m, 2H), 3.82 (q, J=8.0 Hz, 1H), 3.64 (d, J=6.1 Hz, 1H), 3.54-3.46 (m, 1H), 3.03 (s, 1H), 2.61 (s, 1H), 2.41 (dt, J=12.4, 4.4 Hz, 1H), 2.25 (tt, J=18.6, 8.2 Hz, 2H), 1.99 (dd, J=13.6, 6.7 Hz, 1H), 1.68 (s, 2H), 1.40 (d, J=13.5 Hz, 1H), 1.17 (d, J=6.7 Hz, 4H); MS (ES, m/z): [M+1]=627.

Example 210: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(3S)-oxolan-3-yl]-1,3-benzothiazole-6-carboxylic Acid (I-252) and 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(3R)-oxolan-3-yl]-1,3-benzothiazole-6-carboxylic Acid (I-253)

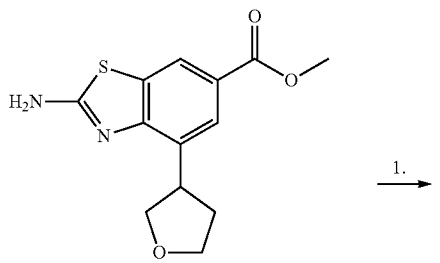

251c

-continued

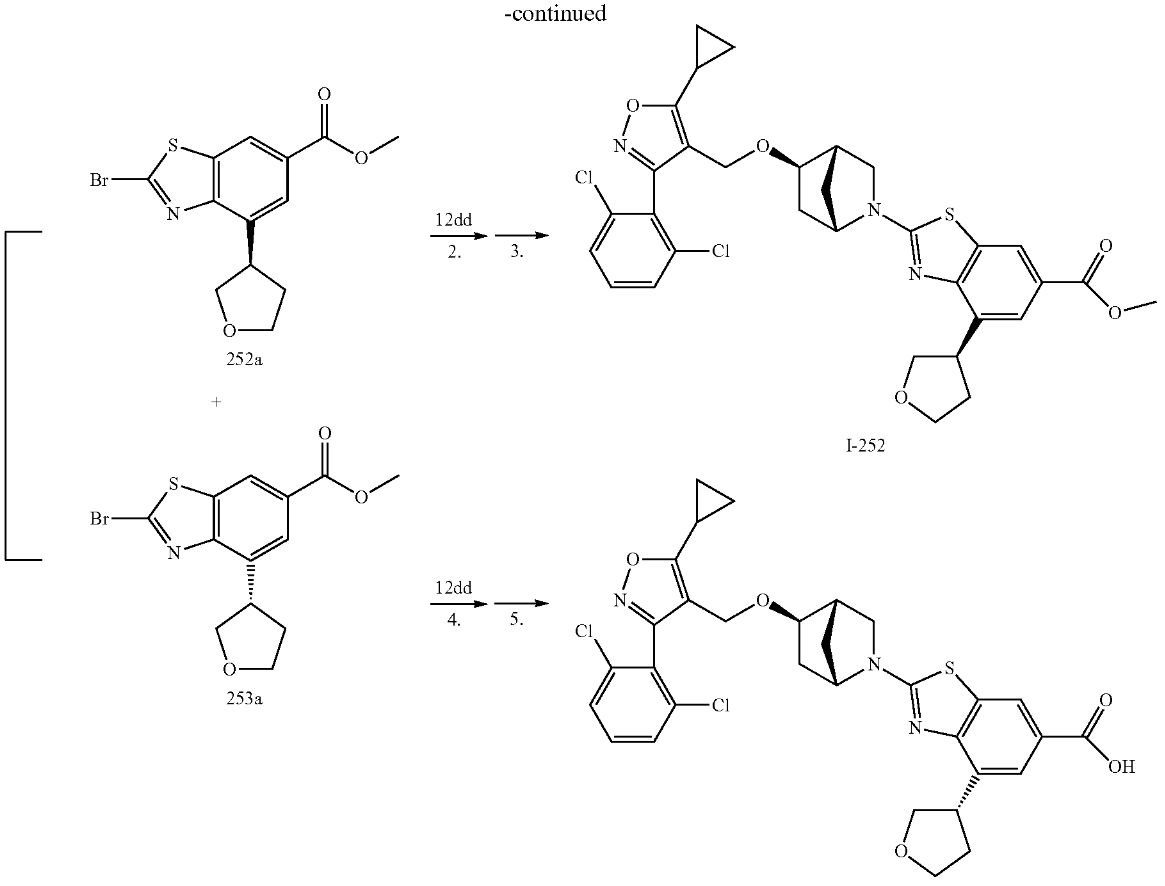

252a

253a

I-252

I-253

Step 1

To a 50 mL round-bottom flask was added methyl 2-amino-4-(oxolan-3-yl)-1,3-benzothiazole-6-carboxylate 251c (600 mg, 2.16 mmol, 1.00 equiv.), MeCN (10 mL), t-BuONO (502 mg, 4.87 mmol, 2.26 equiv.), $CuBr_2$ (722 mg, 3.24 mmol, 1.50 equiv.). The resulting mixture was stirred at 30° C., overnight and concentrated under vacuum. The residue was purified by silica gel column chromatography eluting with ethyl acetate in hexanes (0% to 5%) to give a racemic mixture 251d (~500 mg). This racemic mixture was separated by chiral HPLC under following conditions: Column, CHIRALPAK IF, 2*25 cm, 5 um; mobile phase, Hex- and ethanol-(hold 30.0% ethanol—in 14 min); Detector, UV 254/220 nm. After separation, methyl 2-bromo-4-[(3R)-oxolan-3-yl]-1,3-benzothiazole-6-carboxylate 252a (201.8 mg, 27%) and methyl 2-bromo-4-[(3S)-oxolan-3-yl]-1,3-benzothiazole-6-carboxylate 253a (202.3 mg, 27%) were obtained, both are light yellow solids. 252a: $^1$HNMR (300 MHz, $CDCl_3$): δ 2.124 (1H, m), 2.496 (1H, m), 3.862 (1H, m), 4.032 (4H, m), 4.128 (1H, m), 4.328 (2H, m), 8.060 (1H, s), 8.400 (1H, s); MS (ES, m/z): [M+1]=343; 253a: $^1$HNMR (300 MHz, $CDCl_3$): δ 2.124 (1H, m), 2.496 (1H, m), 3.862 (1H, m), 4.032 (4H, m), 4.128 (1H, m), 4.328 (2H, m), 8.060 (1H, s), 8.400 (1H, s); MS (ES, m/z): [M+1]=343.

Step 2

To a 50 mL round-bottom flask purged with and maintained under an inert atmosphere of nitrogen was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (44 mg, 0.087 mmol, 1.00 equiv.), DMA (1.5 mL), methyl 2-bromo-4-[(3S)-oxolan-3-yl]-1,3-benzothiazole-6-carboxylate 252a (40 mg, 0.12 mmol, 1.37 equiv), and $Cs_2CO_3$ (114 mg, 0.35 mmol, 4.00 equiv.). The resulting mixture was heated at 60° C., overnight, cooled to room temperature, and diluted with 10 mL of $H_2O$. The aqueous mixture was extracted with ethyl acetate (50 mL×2); and the combined organic extracts were washed with brine (20 mL×4), dried over anhydrous sodium sulfate and concentrated under vacuum. The residue was purified by silica gel column chromatography eluting with ethyl acetate/petroleum ether (1/3) to give methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3S)-oxolan-3-yl]-1,3-benzothiazole-6-carboxylate 252b (54 mg, 92%) as a light yellow solid.

Step 3

Following the procedure described in Preparative Example 209 step 6, methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3S)-oxolan-3-yl]-1,3-benzothiazole-6-carboxylate 252b (54 mg, 0.08 mmol, 1.00 equiv.) was hydrolyzed to give 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3S)-oxolan-3-yl]-1,3-benzothiazole-6-carboxylic acid I-252 (22.8 mg, 43%) as an off-white solid. $^1$HNMR (300 MHz, $CD_3OD$): δ 8.22 (d, J=1.7 Hz, 1H), 7.92 (d, J=1.7 Hz, 1H), 7.70-7.38 (m, 3H), 4.51-4.25 (m, 3H), 4.27-3.74 (m, 5H), 3.78-3.42 (m, 2H), 3.05 (d, J=10.2 Hz, 1H), 2.64 (s, 1H), 2.51-1.88 (m, 4H), 1.71 (s, 2H), 1.53-1.07 (m, 5H); MS (ES, m/z): [M+1]=626.45.

Step 4

To a 50 mL round-bottom flask purged with and maintained under an inert atmosphere of nitrogen was added methyl 2-bromo-4-[(3R)-oxolan-3-yl]-1,3-benzothiazole-6-carboxylate 253a (60 mg, 0.18 mmol, 1.38 equiv.). DMA (1.5 mL). (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (66 mg, 0.13 mmol, 1.00 equiv.), and $Cs_2CO_3$ (171 mg, 0.52 mmol, 4.00 equiv.). The resulting mixture was heated at 60° C., overnight, upon cooling to room temperature, diluted with 10 mL of $H_2O$. The aqueous mixture was extracted with ethyl acetate (30 mL×2); and the combined organic were washed with brine (20 mL×2), dried over anhydrous sodium sulfate and concentrated under vacuum. The residue was purified by silica gel column chromatography eluting with ethyl acetate/petroleum ether (1/3) to give methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3R)-oxolan-3-yl]-1,3-benzothiazole-6-carboxylate 253b (75 mg, 92%) as a light yellow solid.

Step 5

Following the procedure described in Preparative Example 209 step 6, methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3R)-oxolan-3-yl]-1,3-benzothiazole-6-carboxylate 253b (75 mg, 0.12 mmol, 1.00 equiv.) was hydrolyzed to give 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3R)-oxolan-3-yl]-1,3-benzothiazole-6-carboxylic acid I-253 (36 mg, 49%) as an off-white solid. $^1$HNMR (400 MHz, $CD_3OD$): δ 8.22 (d, J=1.7 Hz, 1H), 7.92 (d, J=1.6 Hz, 1H), 7.65-7.43 (m, 3H), 4.85 (s, 30H), 4.36 (d, J=1.6 Hz, 4H), 4.29-4.09 (m, 2H), 4.12-3.93 (m, 2H), 3.83 (dd, J=8.1, 7.1 Hz, 1H), 3.66 (dd, J=6.9, 2.4 Hz, 1H), 3.05 (d, J=10.1 Hz, 1H), 2.63 (d, J=3.7 Hz, 1H), 2.34-2.20 (m, 2H), 2.08-1.95 (m, 1H), 1.70 (s, 2H), 1.49-1.37 (m, 1H), 1.19 (d, J=6.8 Hz, 4H); MS (ES, m/z): [M+1]=626.35.

Example 211: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(oxan-4-yl)-1,3-benzothiazole-6-carboxylic Acid (I-254)

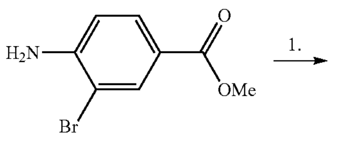

249a

-continued

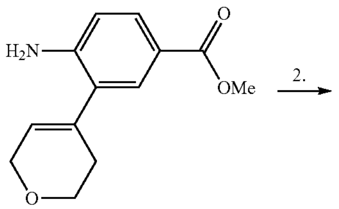

254a

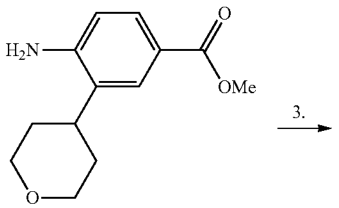

254b

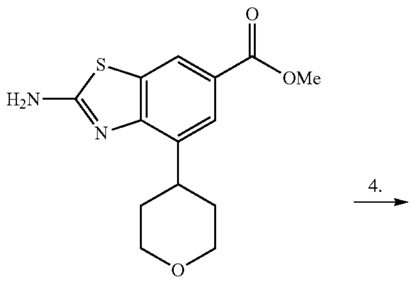

254c

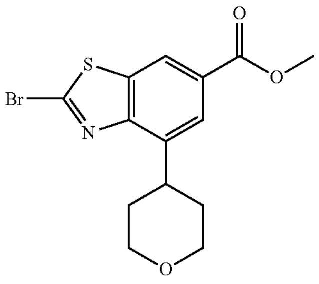

254d

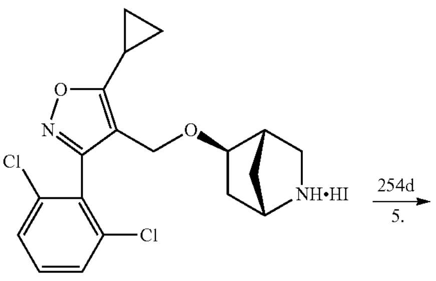

12dd

-continued

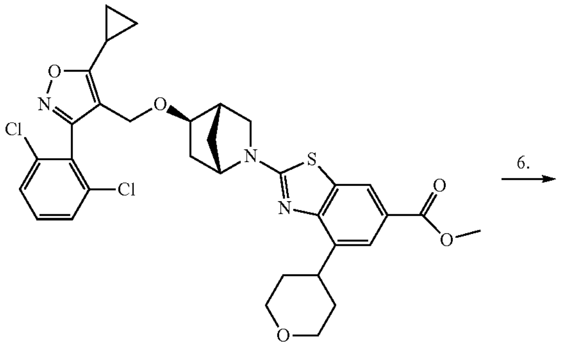

254e

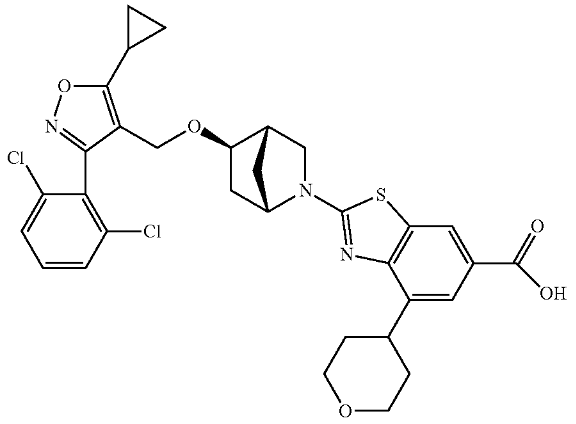

I-254

Step 1

To a 250 mL round-bottom flask was added methyl 4-amino-3-bromobenzoate 249a (2.4 g, 10.43 mmol, 1.00 equiv.), 2-(3,6-dihydro-2H-pyran-4-yl)-4,4,5,5-tetramethyl-1,3,2-dioxaborolane (2.6 g, 12.38 mmol, 1.20 equiv.), dioxane (100 mL), aq, sodium bicarbonate (37 mL, 3.50 equiv, 1M), and $Pd(PPh_3)_4$ (1.21 g, 1.05 mmol, 0.10 equiv.). The resulting mixture was heated at 100° C., overnight. After cooling to room temperature, the mixture was diluted with 300 mL of EA and washed with brine (200 mL×2). The organic phase was dried over anhydrous sodium sulfate and concentrated under vacuum. The crude product was purified by Flash-Prep-HPLC using the following conditions (IntelFlash-1): Column, silica gel; mobile phase, PE:EA=100:0 increasing to PE:EA=50:50 within 30 min; Detector, UV 254 nm. Removal of solvents afforded methyl 4-amino-3-(3,6-dihydro-2H-pyran-4-yl)benzoate 254a (2.4 g, 99% as a white solid.

Step 2

To a 50 mL round-bottom flask was added methyl 4-amino-3-(3,6-dihydro-2H-pyran-4-yl)benzoate 254a (1.2 g, 5.14 mmol, 1.00 equiv.), methanol (24 mL), and Palladium on carbon (1.2 g, 10 wt %). Hydrogen gas was introduced in. The resulting mixture was stirred at room temperature under an atmosphere of hydrogen. The solids were filtered out, and the filtrate was concentrated under vacuum to give methyl 4-amino-3-(oxan-4-yl)benzoate 254b (1.14 g, 94%) as a white solid.

Step 3

To a 50 mL round bottom flask was added methyl 4-amino-3-(oxan-4-yl)benzoate 254b (1.14 g, 4.85 mmol, 1.00 equiv.), AcOH (10 mL), NaSCN (1.58 g, 19.51 mmol, 4.00 equiv.), and $Br_2$ (772 mg, 4.83 mmol, 1.00 equiv.). The resulting mixture was stirred at 30° C., overnight. The mixture was quenched by the addition of 200 mL of water/ice. The pH value of the solution was adjusted to 10 using sodium hydroxide pellets. The solids were filtered out. The resulting mixture was concentrated under vacuum to give methyl 2-amino-4-(oxan-4-yl)-1,3-benzothiazole-6-carboxylate 254c (1.15 g, 81%) as an orange color solid.

Step 4

To a 50 mL round-bottom flask was added methyl 2-amino-4-(oxan-4-yl)-1,3-benzothiazole-6-carboxylate 254c (1.15 g, 3.93 mmol, 1.00 equiv.), MeCN (20 mL), t-BuONO (920 mg, 9.02 mmol, 2.26 equiv.), and $CuBr_2$ (1.32 g, 5.92 mmol, 1.50 equiv.). The resulting mixture was stirred at 30° C., overnight, and then concentrated under vacuum. The crude product was purified by Flash-Prep-HPLC using the following conditions (IntelFlash-1): Column, silica gel; mobile phase, EA:PE=0:100 increasing to EA:PE=5:95 within 30 min; Detector, UV 254 nm. Removal of solvents afforded methyl 2-bromo-4-(oxan-4-yl)-1,3-benzothiazole-6-carboxylate 254d (1.08 g, 77%) as a yellow solid.

Step 5

To a 25 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (150 mg, 0.296 mmol, 1.00 equiv.), DMA (5 mL), methyl 2-bromo-4-(oxan-4-yl)-1,3-benzothiazole-6-carboxylate 254d (211 mg, 0.59 mmol, 2.0 equiv.), and $Cs_2CO_3$ (259 mg, 0.79 mmol, 2.66 equiv.). The resulting mixture was heated at 60° C., overnight. After cooling to room temperature, the mixture was diluted with 100 mL of EA, washed with brine (100 mL×3), dried over anhydrous sodium sulfate and concentrated under vacuum. The residue was purified by silica gel column chromatography eluting with ethyl acetate/petroleum ether (1:3) to give methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(oxan-4-yl)-1,3-benzothiazole-6-carboxylate 254e (190 mg, 98%) as a white solid.

Step 6

To a 25-mL round-bottom flask, was placed methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(oxan-4-yl)-1,3-benzothiazole-6-carboxylate 254e (190 mg, 0.29 mmol, 1.00 equiv), methanol (4 mL), water (2 mL), and $LiOHH_2O$ (140 mg, 3.33 mmol, 12 equiv.). The resulting mixture was stirred at room temperature overnight. The pH value of the solution was adjusted to 7.0 using a 1M aqueous HCl solution. The mixture was extracted with ethyl acetate (20 mL×3); the combined organic extracts were dried over anhydrous sodium sulfate and concentrated under vacuum. The crude product was purified by Prep-HPLC using the following conditions: Column, XBridge Prep C18 OBD Column, 5 um, 19*150 mm; mobile phase, Waters (0.05% TFA) and ACN (37.0% ACN up to 50.0% in 8 min);

Detector, 254 nm. After purification 2-[(1S,4S,5R)-5-[[5-cyclopropyl-3-(2,6-dichlorophenyl)-1,2-oxazol-4-yl] methoxy]-2-azabicyclo[2.2.1]heptan-2-yl]-4-(oxan-4-yl)-1, 3-benzothiazole-6-carboxylic acid I-254 (120.5 mg, 57%) was obtained as a white solid. $^1$HNMR (400 MHz, $CD_3OD$): δ 1.163 (4H, m), 1.384 (1H, m), 1.673 (2H, m), 1.966 (5H, m), 2.232 (1H, m), 2.603 (1H, m), 3.021 (1H, m), 3.314 (2H, m), 33655 (3H, m), 4.085 (2H, m), 4.302 (3H, m), 7.415 (3H, m), 7.857 (1H, m), 8.175 (1H, m); MS (ES, m/z): [M+1]=640.

Example 212: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(1R,3R,5S)-8-oxabicyclo[3.2.1]octan-3-yl]-1,3-benzothiazole-6-carboxylic Acid (I-255) and 2-[(1S,4S,5R)-5-{[5-cyclopropyl-3-(2,6-dichlorophenyl)-1,2-oxazol-4-yl] methoxy}-2-azabicyclo[2.2.1]heptan-2-yl]-4-[(1R, 3S,5S)-8-oxabicyclo[3.2.1]octan-3-yl]-1,3-benzothiazole-6-carboxylic Acid (I-256)

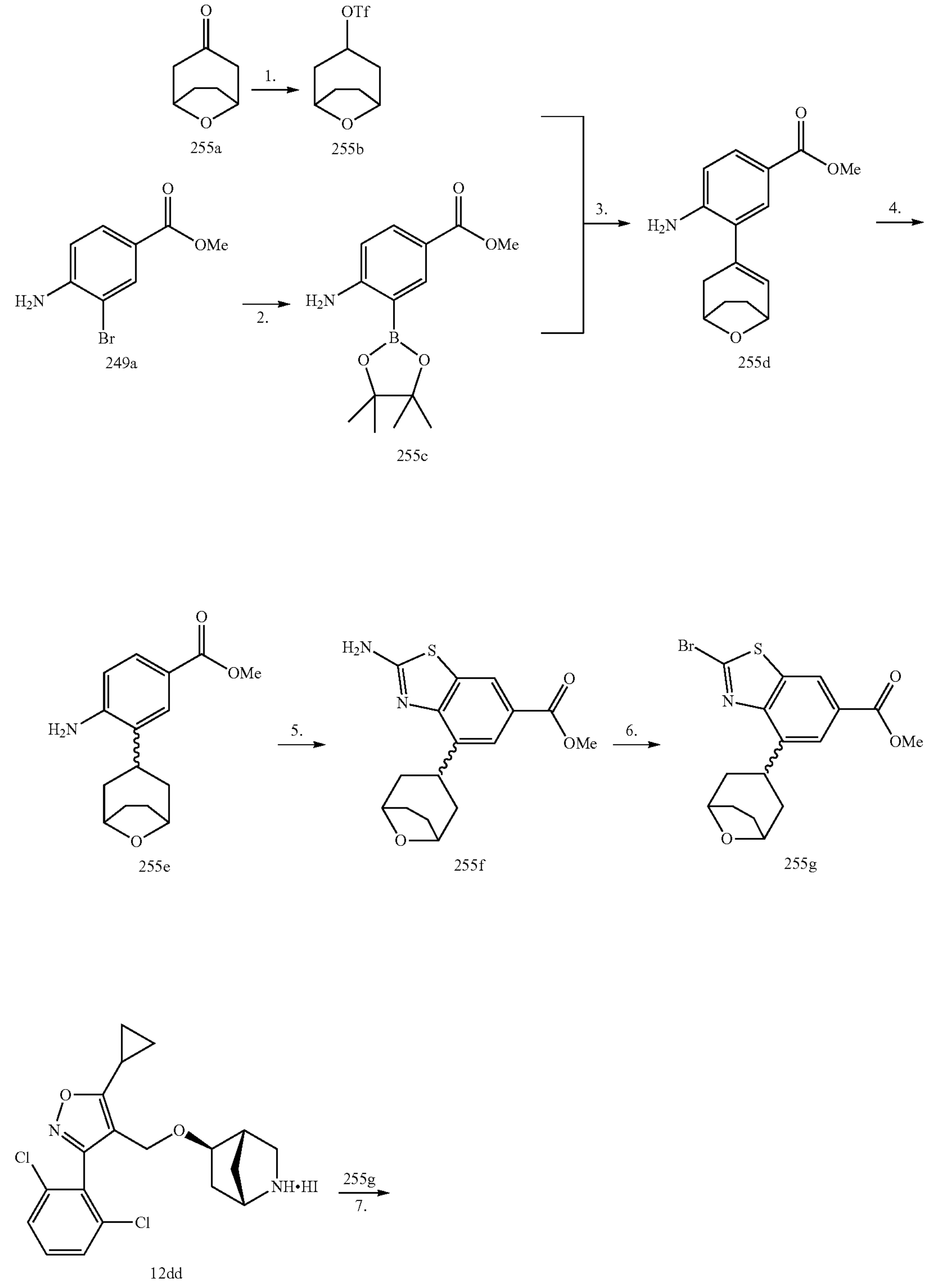

-continued

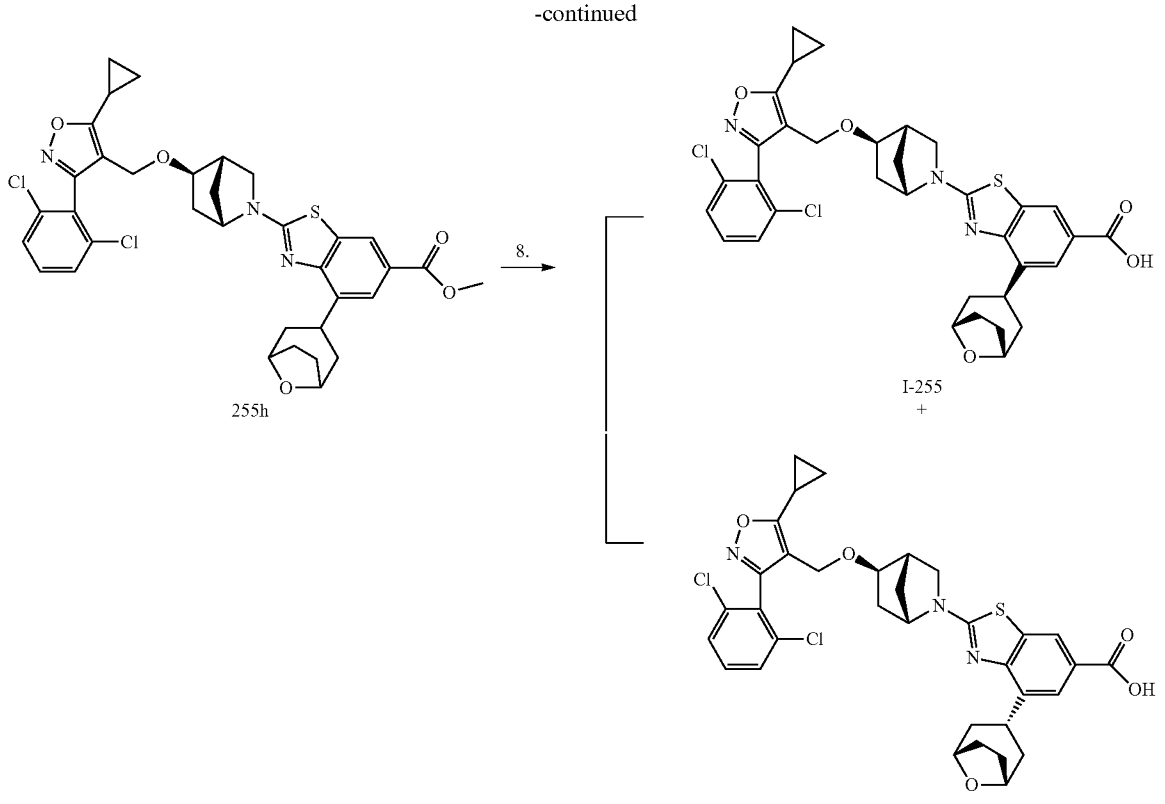

255h

I-255

+

I-256

Step 1

To a 100 mL 3-necked round-bottom flask purged with and maintained under an inert atmosphere of nitrogen was added a solution of N,N-diisopropylamine (481 mg, 4.75 mmol, 1.20 equiv.) in tetrahydrofuran (7 mL). The solution was cooled to −78° C., and a 2.27 M solution of the n-BuLi (1.83 mL, 4.16 mmol, 1.05 equiv.) was added dropwise with stirring. The mixture was stirred for 35 min at −78° C.; a solution of 8-oxabicyclo[3.2.1]octan-3-one 255a (500 mg, 3.96 mmol, 1.00 equiv.) in tetrahydrofuran (3 mL) was added dropwise. Reaction was continued at the same temperature for 30 min. A solution of 1,1,1-trifluoro-N-phenyl-N-[(trifluoromethane) sulfonyl]methanesulfonamide (1.4 g, 3.92 mmol, 1.00 equiv.) in tetrahydrofuran (3 mL) was added dropwise at −78° C. Cooling bath was removed, and the mixture was stirred overnight at room temperature. The mixture was diluted with 50 mL of EA, quenched by the addition of 10 mL of water/ice, and separated. The organic layer was washed with water (50 mL) and brine (50 mL×2), dried over anhydrous sodium sulfate, and concentrated under vacuum to give 8-oxabicyclo[3.2.1]oct-2-en-3-yl trifluoromethanesulfonate 255b (900 mg, 88%) as a yellow oil.

Step 2

To a 250 mL round-bottom flask purged with and maintained under an inert atmosphere of nitrogen was added methyl 4-amino-3-bromobenzoate 249a (1 g, 4.35 mmol, 1.00 equiv.), DMSO (20 mL), 4,4,5,5-tetramethyl-2-(tetramethyl-1,3,2-dioxaborolan-2-yl)-1,3,2-dioxaborolane (2 g, 7.88 mmol, 1.81 equiv.), KOAc (760 mg, 7.74 mmol, 1.78 equiv.), and Pd(dppf)$Cl_2$ (120 mg, 0.16 mmol, 0.04 equiv.). The resulting mixture was heated at 100° C., overnight. After cooling to room temperature, 200 mL of $H_2O$ was added, the aqueous mixture was extracted with ethyl acetate (50 mL×3). The combined organic extracts were washed with brine, dried, and concentrated under vacuum. The residue was purified by silica gel column chromatography eluting with ethyl acetate/petroleum ether (1:10-1:5-1:3-1:0) to afford methyl 4-amino-3-(tetramethyl-1,3,2-dioxaborolan-2-yl)benzoate 255c (400 mg, 33%) as an off-white solid.

Step 3

To a 100 mL round-bottom flask purged with and maintained under an inert atmosphere of nitrogen was added 8-oxabicyclo[3.2.1]oct-2-en-3-yl trifluoromethanesulfonate 255b (1 g, 3.87 mmol, 1.20 equiv.), a solution of methyl 4-amino-3-(tetramethyl-1,3,2-dioxaborolan-2-yl)benzoate 255c (895 mg, 3.23 mmol, 1.00 equiv.) in ethylene glycol dimethyl ether (27 mL), a saturated sodium bicarbonate aqueous solution (5.4 mL), and $Pd(PPh)_4$ (374 mg, 0.32 mmol, 0.10 equiv.). The resulting mixture was heated at 85° C., overnight. After cooling to room temperature, the mixture was diluted with 100 mL of EA, washed with water (100 mL×2) and brine (100 mL×2), dried, and concentrated. The residue was purified by silica gel column chromatography eluting with EA:PE (0-50%) to give methyl 4-amino-3-[8-oxabicyclo[3.2.1]oct-2-en-3-yl]benzoate 255d (610 mg, 73%) as a yellow oil.

Step 4

To a 100 mL round-bottom flask was added a solution of methyl 4-amino-3-[8-oxabicyclo[3.2.1]oct-2-en-3-yl]benzoate 255d (560 mg, 2.16 mmol, 1.00 equiv.) in methanol (8 mL), and Palladium on carbon (560 mg, 10 wt %). Hydrogen gas was introduced. The resulting mixture was stirred at room temperature overnight under a hydrogen atmosphere. Solids were filtered out and the filtrate was concentrated under vacuum. The residue was purified by silica gel column chromatography eluting with EA:PE (1:1) to give methyl 4-amino-3-[8-oxabicyclo[3.2.1]octan-3-yl]benzoate 255e (364 mg, 64%) as a yellow solid.

Step 5

To a 250-mL round-bottom flask was added methyl 4-amino-3-[8-oxabicyclo[3.2.1]octan-3-yl]benzoate 255e (364 mg, 1.39 mmol, 1.00 equiv.), AcOH (6 mL), NaSCN (452 mg, 4.00 equiv.), and $Br_2$ (333 mg, 2.08 mmol, 1.50 equiv.). The resulting mixture was stirred at 30° C., overnight, and quenched by the addition of 10 mL of water/ice. The pH value of the solution was adjusted to 8 using a 1M sodium hydroxide aqueous solution. Solids were collected by filtration to give methyl 2-amino-4-[8-oxabicyclo[3.2.1]octan-3-yl]-1,3-benzothiazole-6-carboxylate 255f (589 mg, crude, >100%) as a yellow solid.

Step 6

To a 250 mL round-bottom flask was added a solution of methyl 2-amino-4-[8-oxabicyclo[3.2.1]octan-3-yl]-1,3-benzothiazole-6-carboxylate 255f (589 mg, ~1.85 mmol, 1.00 equiv) in $CH_3CN$ (12 mL), $CuBr_2$ (620 mg, 2.78 mmol, 1.50 equiv.), and tert-butyl nitrite (431 mg, 4.18 mmol, 2.26 equiv.). The resulting mixture was stirred at 30° C., overnight and concentrated under vacuum. The residue was purified by silica gel column chromatography eluting with ethyl acetate/petroleum ether (0-10%) to yield methyl 2-bromo-4-[8-oxabicyclo[3.2.1]octan-3-yl]-1,3-benzothiazole-6-carboxylate 255g (370 mg, 52%) as a yellow solid.

Step 7

To a 50 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (100 mg, 0.197 mmol, 1.00 equiv.), a solution of methyl 2-bromo-4-[8-oxabicyclo[3.2.1]octan-3-yl]-1,3-benzothiazole-6-carboxylate 255g (101 mg, 0.26 mmol, 1.32 equiv.) in DMA (3 mL), and $Cs_2CO_3$ (173 mg, 0.53 mmol, 2.69 equiv.). The resulting mixture was heated at 60° C., overnight. After cooling to room temperature, the mixture was diluted with EA (50 mL), washed with $H_2O$ (30 mL) and brine (30 mL), dried over anhydrous sodium sulfate and concentrated under vacuum. The residue was purified by silica gel column chromatography eluting with ethyl acetate/petroleum ether (1:3) to furnish methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[8-oxabicyclo[3.2.1]octan-3-yl]-1,3-benzothiazole-6-carboxylate 255h (135 mg, Q) as a light yellow solid.

Step 8

To a 100 mL round-bottom flask was added methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[8-oxabicyclo[3.2.1]octan-3-yl]-1,3-benzothiazole-6-carboxylate 255h (135 mg, 0.20 mmol, 1.00 equiv.), methanol (5 mL), water (0.5 mL), and LiOH (84 mg, 3.51 mmol, 10.00 equiv.). The resulting mixture was heated at 60° C., overnight. After cooling to room temperature, the mixture was diluted with $H_2O$, the pH value of the solution was adjusted to 2 using a 1M HCl aqueous solution. The aqueous mixture was extracted with EA (40 mL), and the organic extract was washed with brine (40 mL), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (62.0% ACN up to 80.0% in 8 min); Detector, UV 254 nm. After purification the cis-isomer 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(1R,3S,5S)-8-oxabicyclo[3.2.1]octan-3-yl]-1,3-benzothiazole-6-carboxylic acid I-255 (34.2 mg, 26%) was obtained as a white solid, the major product, and the trans-isomer 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(1R,3R,5S)-8-oxabicyclo[3.2.1]octan-3-yl]-1,3-benzothiazole-6-carboxylic acid I-256 (4.63 mg, 4%) was also obtained as a white solid, the minor product. I-255: $^1$HNMR (400 MHz DMSO-d6) δ: 8.17 (d, J=1.7 Hz, 1H), 7.73-7.52 (m, 4H), 4.39 (t, J=6.5 Hz, 2H), 4.34-4.22 (m, 2H), 3.61 (dd, J=6.4, 2.2 Hz, 1H), 3.49-3.30 (m, 2H), 2.94 (s, 1H), 2.55 (d, J=3.5 Hz, 1H), 2.41-2.20 (m, 3H), 1.95-1.45 (m, 10H), 1.31-1.21 (m, 2H), 1.20-1.05 (m, 4H); MS (ES, m/z): [M+1]=666.20. I-256: $^1$HNMR (300 MHz, $CD_3OD$): δ 8.15 (d, J=1.6 Hz, 3H), 7.86 (s, 2H), 7.62-7.45 (m, 7H), 4.52 (s, 6H), 4.36 (s, 5H), 3.65 (d, J=5.2 Hz, 2H), 3.01 (s, 1H), 2.60 (s, 3H), 2.35-2.24 (m, 2H), 2.06 (d, J=2.4 Hz, 12H), 1.82 (s, 3H), 1.69 (s, 6H), 1.44 (s, 2H), 1.20 (d, J=6.7 Hz, 10H), 0.22 (s, 1H), −0.17 (s, 1H); MS (ES, m/z): [M+1]=666.25.

Example 213: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-{7-oxaspiro[3.5]nonan-2-yl}-1,3-benzothiazole-6-carboxylic Acid (I-257)

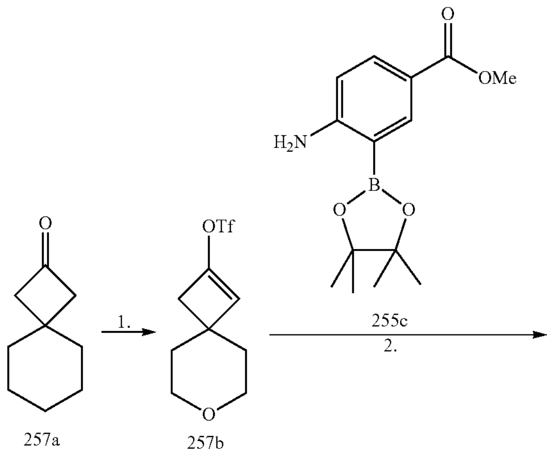

257a
257b

-continued

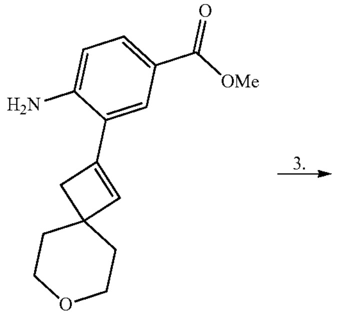

257c

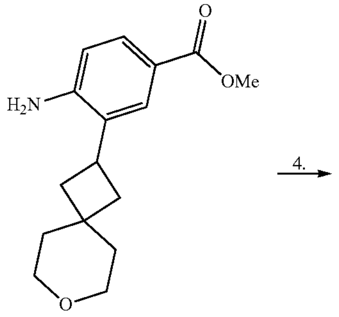

257d

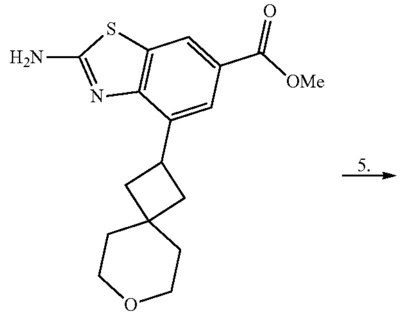

257e

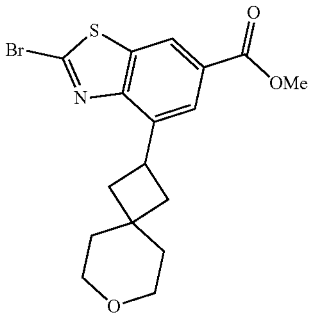

257f

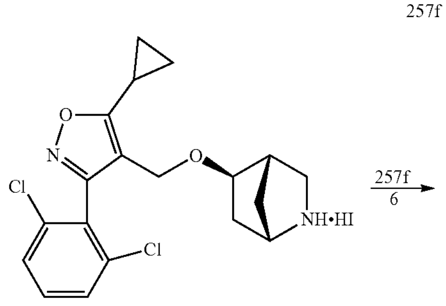

12dd

-continued

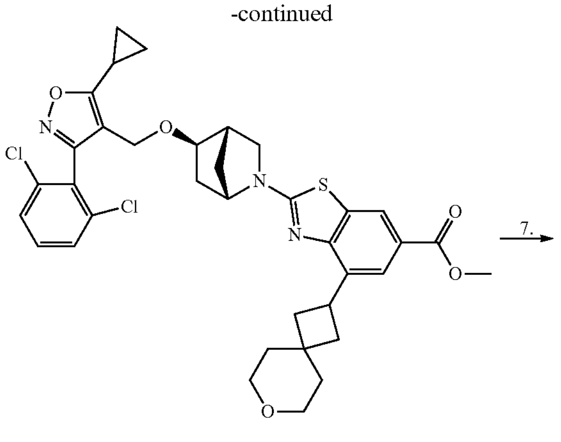

257g

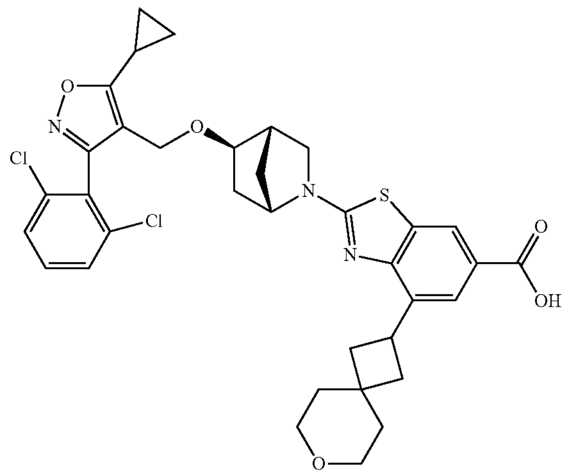

I-257

Step 1

To a 100 mL 3-necked round-bottom flask purged with and maintained under an inert atmosphere of nitrogen was added a solution of N,N-diisopropyl amine (433 mg, 4.28 mmol, 1.20 equiv.) in tetrahydrofuran (1 mL). The solution was cooled in a −78° C., bath, a 2.5 M solution of n-BuLi (2.2 mL, 1.50 equiv.) was added dropwise with stirring, and the mixture was stirred for 35 min. A solution of 7-oxaspiro [3.5]nonan-2-one 257a (500 mg, 3.57 mmol, 1.00 equiv.) in tetrahydrofuran (3 mL) was added dropwise, reaction was continued for 30 min at −78° C. A solution of N-Phenyl-bis(trifluoromethanesulfonimide) (1.27 g, 3.55 mmol, 1.00 equiv.) in tetrahydrofuran (3 mL) was added dropwise with stirring at −78° C. The temperature was then allowed to gradually warmed up to room temperature, and the reaction continued at room temperature overnight. The mixture was diluted with 50 mL of EA, washed with water (50 mL) and brine (50 mL) successively, dried over anhydrous sodium sulfate, and concentrated under vacuum to provide 7-oxaspiro[3.5]non-1-en-2-yl trifluoromethanesulfonate 257b (900 mg, 93%) as a crude yellow oil.

Step 2

To a 100 mL round-bottom flask purged with and maintained under an inert atmosphere of nitrogen was added 7-oxaspiro[3.5]non-1-en-2-yl trifluoromethanesulfonate 257b (900 mg, 3.31 mmol, 1.00 equiv.), a solution of methyl 4-amino-3-(tetramethyl-1,3,2-dioxaborolan-2-yl)benzoate 255c (1.1 g, 3.97 mmol, 1.20 equiv.) in ethylene glycol dimethyl ether (27 mL), a saturated aqueous solution of sodium bicarbonate (5.4 mL), and $Pd(PPh_3)_4$ (382 mg, 0.33 mmol, 0.10 equiv.). The resulting mixture was heated at 85° C., overnight. After cooling to room temperature, the mixture was diluted with 100 mL of EA, washed successively with water (100 mL) and brine (100 mL×2), and concentrated. The residue was purified by silica gel column chromatography eluting with EA in PE (0 to 50%) to afford methyl 4-amino-3-[7-oxaspiro[3.5]non-1-en-2-yl]benzoate 257c (510 mg, 56%) as a light yellow oil.

Step 3

To a 250 mL round-bottom flask was added a solution of methyl 4-amino-3-[7-oxaspiro[3.5]non-1-en-2-yl]benzoate 257c (510 mg, 1.87 mmol, 1.00 equiv.) in methanol (8 mL), and Palladium on carbon (510 mg, 10 wt %). Hydrogen gas was introduced. The resulting mixture was stirred at room temperature overnight under a hydrogen atmosphere. Solids were filtered out, and the filtrate was concentrated under vacuum. The residue was purified by silica gel column chromatography eluting with ethyl acetate/petroleum ether (1:1) to give methyl 4-amino-3-[7-oxaspiro[3.5]nonan-2-yl] benzoate 257d (405 mg, 79%) as a yellow solid.

Step 4

To a 250 mL round-bottom flask was added methyl 4-amino-3-[7-oxaspiro[3.5]nonan-2-yl]benzoate 257d (405 mg, 1.47 mmol, 1.00 equiv), AcOH (6 mL), NaSCN (477 mg, 5.89 mmol, 4.00 equiv.), and $Br_2$ (351 mg, 2.20 mmol, 1.50 equiv.). The resulting mixture was stirred at 30° C., overnight. The reaction was quenched by the addition of 10 mL of water/ice. The pH value of the solution was adjusted to 8 using a 1M sodium hydroxide aqueous solution. The solids were collected by filtration to afford methyl 2-amino-4-[7-oxaspiro[3.5]nonan-2-yl]-1,3-benzothiazole-6-carboxylate 257e (600 mg, crude) as a yellow solid.

Step 5

To a 250 mL round-bottom flask was added a solution of methyl 2-amino-4-[7-oxaspiro[3.5]nonan-2-yl]-1,3-benzothiazole-6-carboxylate 257e (600 mg, 1.80 mmol, 1.00 equiv.) in $CH_3CN$ (15 mL). $CuBr_2$ (605 mg, 2.71 mmol, 1.50 equiv.), and t-BuONO (421 mg, 4.09 mmol, 2.26 equiv.). The resulting mixture was stirred at 30° C., overnight and concentrated under vacuum. The residue was purified by silica gel column chromatography eluting with ethyl acetate in petroleum ether (0-20%) to provide methyl 2-bromo-4-[7-oxaspiro[3.5]nonan-2-yl]-1,3-benzothiazole-6-carboxylate 257f (347 mg, 49%) as a yellow oil.

Step 6

To a 50 mL round-bottom flask was added (1S,4S,5R)-5-[[5-cyclopropyl-3-(2,6-dichlorophenyl)-1,2-oxazol-4-yl] methoxy]-2-azabicyclo[2.2.1]heptane hydroiodide salt 12dd (100 mg, 0.197 mmol, 1.00 equiv.), a solution of methyl 2-bromo-4-[7-oxaspiro[3.5]nonan-2-yl]-1,3-benzothiazole-6-carboxylate 257f (104 mg, 0.26 mmol, 1.32 equiv.) in DMA (2 mL), and $Cs_2CO_3$ (173 mg, 0.53 mmol, 2.00 equiv.). The resulting mixture was stirred at 60° C., overnight. After cooling to room temperature, the mixture was diluted with 30 mL of EA, washed with water (30 mL×2) and brine (30 mL×2), dried over anhydrous sodium sulfate and concentrated under vacuum. The residue was purified by silica gel column chromatography eluting with ethyl acetate: petroleum ether (1:3) to give methyl 2-[(1S,4S,5R)-5-[[5-cyclopropyl-3-(2,6-dichlorophenyl)-1,2-oxazol-4-yl] methoxy]-2-azabicyclo[2.2.1]heptan-2-yl]-4-[7-oxaspiro [3.5]nonan-2-yl]-1,3-benzothiazole-6-carboxylate 257g (120 mg, 86%) as a light yellow solid.

Step 7

To a 50 mL round-bottom flask was added a solution of methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[7-oxaspiro[3.5]nonan-2-yl]-1,3-benzothiazole-6-carboxylate 257g (120 mg, 0.17 mmol, 1.00 equiv.) in methanol/$H_2O$ (5/0.5 mL), and LiOH (41 mg, 1.71 mmol, 10.00 equiv.). The resulting mixture was heated at 60° C., for 3 h. After cooling to room temperature, the mixture was diluted with 10 mL of water. The pH value of the solution was adjusted to 2 using a 1M hydrogen chloride aqueous solution. The aqueous mixture was extracted with ethyl acetate (15 mL×3). The combined organic extracts were washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (62.0% ACN up to 80.0% in 8 min); Detector, UV 254 nm. After purification 2-[(1S,4S,5R)-5-[[5-cyclopropyl-3-(2,6-dichlorophenyl)-1,2-oxazol-4-yl]methoxy]-2-azabicyclo[2.2.1] heptan-2-yl]-4-[7-oxaspiro[3.5]nonan-2-yl]-1,3-benzothiazole-6-carboxylic acid I-257 (66.9 mg, 57%) was obtained as a white solid. $^1$HNMR (300 MHz, $CD_3OD$): δ 8.14 (d, J=1.7 Hz, 1H), 7.87 (d, J=1.6 Hz, 1H), 7.57-7.38 (m, 3H), 4.31 (d, J=1.1 Hz, 3H), 3.99 (t, J=9.0 Hz, 1H), 3.75-3.43 (m, 6H), 3.03 (s, 1H), 2.58 (s, 1H), 2.37 (d, J=8.5 Hz, 2H), 2.30-2.18 (m, 1H), 2.16-1.93 (m 3H), 1.82 (t, J=5.3 Hz, 2H), 1.62 (dd, J=1.9, 6.4 Hz, 4H), 1.38 (d, J=13.5 Hz, 1H), 1.15 (d, J=6.7 Hz, 4H); MS (ES, m/z): [M+1]=680.15.

Example 214: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-(oxepan-4-yl)-1,3-benzothiazole-6-carboxylic Acid (I-258)

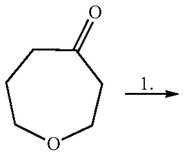

258a

-continued

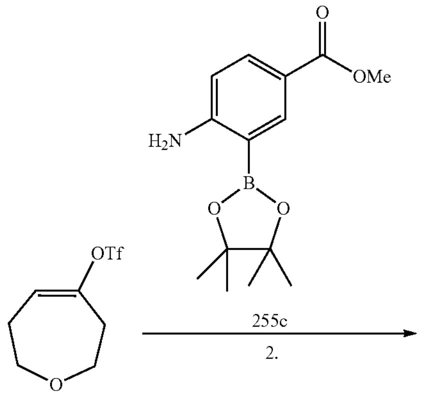

258b

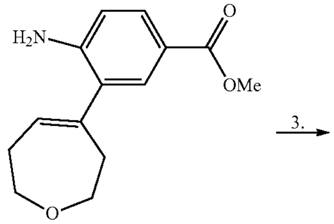

258c

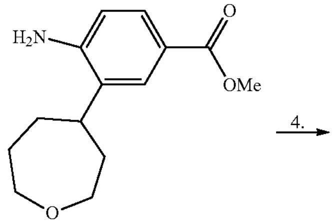

258d

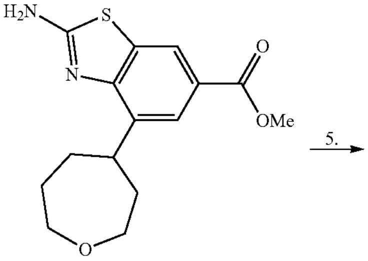

258e

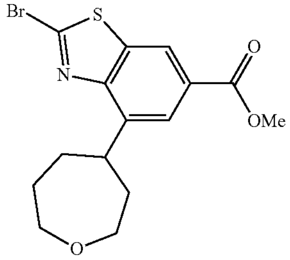

258f

-continued

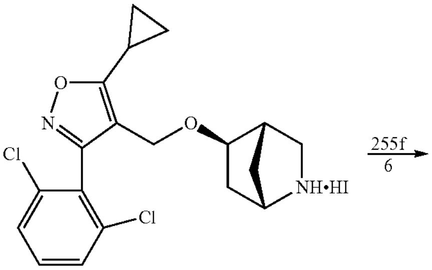

12dd

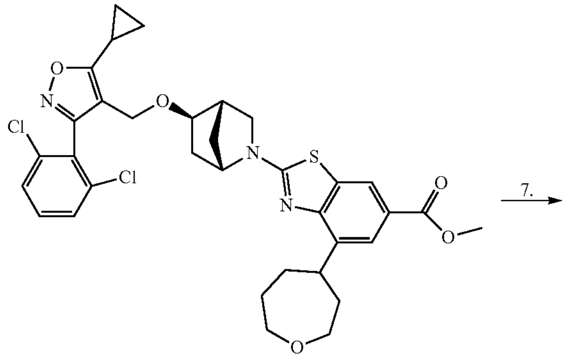

255g

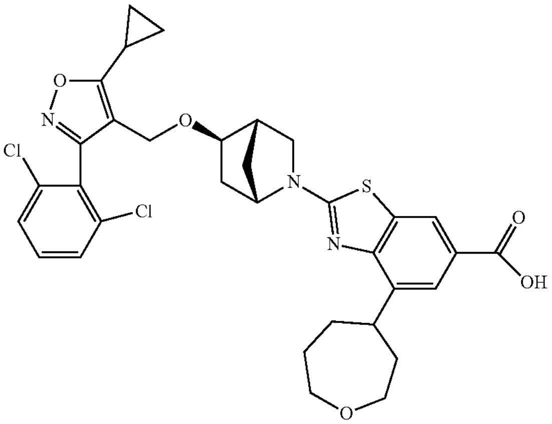

I-258

Step 1

To a 100 mL 3-necked round-bottom flask purged with and maintained under an inert atmosphere of nitrogen was added a solution of diisopropylamine (522 mg, 5.16 mmol, 1.20 equiv.) in tetrahydrofuran (2 mL). The solution was cooled to −78° C., and a 2.5M solution of n-BuLi (2.6 mL, 6.5 mmol, 1.50 equiv.) was added dropwise with stirring. After 30 min, a solution of oxepan-4-one 258a (500 mg, 4.38 mmol, 1.00 equiv.) in tetrahydrofuran (3 mL) was added dropwise at −78° C. Reaction was continued for 30 min at this temperature. A solution of 1,1,1-trifluoro-N-phenyl-N-[(trifluoromethane)sulfonyl]methanesulfonamide (1.54 g, 4.31 mmol, 1.00 equiv.) in tetrahydrofuran (2 mL) was added dropwise. The temperature was allowed to increase gradually to room temperature, and the reaction mixture was stirred overnight. The resulting mixture was diluted with 100 mL of EA, washed with water (100 mL×2) and brine (100 mL×2) successively, dried over anhydrous sodium sulfate, and concentrated under vacuum to give 2,3,6,7-tetrahydrooxepin-4-yl trifluoromethanesulfonate 258b (1 g, 93%) as a yellow oil.

Step 2

To a 100 mL round-bottom flask purged with and maintained under an inert atmosphere of nitrogen was added methyl 4-amino-3-(tetramethyl-1,3,2-dioxaborolan-2-yl) benzoate 255c (1 g, 3.61 mmol, 1.00 equiv.), a solution of 2,3,6,7-tetrahydrooxepin-4-yl trifluoromethanesulfonate 258b (900 mg, 3.66 mmol, 1.00 equiv.) in ethylene glycol dimethyl ether (27 mL), a saturated sodium bicarbonate aqueous solution (5.4 mL), and $Pd(PPh_3)_4$ (420 mg, 0.36 mmol, 0.10 equiv.). The resulting mixture was heated at 85° C., overnight. After cooling to room temperature, the mixture was diluted with 100 mL of EA, washed with $H_2O$ (100 mL×2) and brine (100 mL×2), and concentrated. The residue was purified by silica gel column chromatography eluting with EA in PE (11%) to afford methyl 4-amino-3-(2,3,6,7-tetrahydrooxepin-4-yl)benzoate 258c (500 mg, 56%) as a yellow oil.

Step 3

To a 500 mL round-bottom flask was added a solution of methyl 4-amino-3-(2,3,6,7-tetrahydrooxepin-4-yl)benzoate 258c (500 mg, 2.02 mmol, 1.00 equiv.) in methanol (200 mL), and Palladium on carbon (500 mg, 10 wt %). Hydrogen gas was introduced, and the reaction mixture was stirred at 25° C., overnight under a hydrogen atmosphere. Solids were filtered out, and the filtrate was concentrated under vacuum. The residue was purified by silica gel column chromatography eluting with ethyl acetate/petroleum ether (1:5) to provide methyl 4-amino-3-(oxepan-4-yl)benzoate 258d (110 mg, 22%) as a yellow oil.

Step 4

To a 50 mL round-bottom flask was added methyl 4-amino-3-(oxepan-4-yl)benzoate 258d (110 mg, 0.44 mmol, 1.00 equiv.), AcOH (3 mL), NaSCN (143 mg, 1.77 mmol, 4.00 equiv.), and $Br_2$ (105 mg, 0.66 mmol, 1.50 equiv.). The resulting mixture was stirred at 30° C., overnight. The reaction was quenched by the addition of 10 mL of water/ice. The pH value of the solution was adjusted to 8 using a 1M sodium hydroxide aqueous solution. The solids were collected by filtration, dried to afford methyl 2-amino-4-(oxepan-4-yl)-1,3-benzothiazole-6-carboxylate 258e (180 mg, crude) as a yellow solid.

Step 5

To a 25 mL round-bottom flask was added a solution of methyl 2-amino-4-(oxepan-4-yl)-1,3-benzothiazole-6-carboxylate 258e (180 mg, 0.59 mmol, 1.00 equiv.) in MeCN (4 mL), t-BuONO (137 mg, 1.33 mmol, 2.26 equiv.), and $CuBr_2$ (197 mg, 0.88 mmol, 1.50 equiv.). The resulting mixture was stirred at 30° C., overnight and concentrated under vacuum. The residue was purified by silica gel column chromatography eluting with ethyl acetate in petroleum ether (0 to 10%) to afford methyl 2-bromo-4-(oxepan-4-yl)-1,3-benzothiazole-6-carboxylate 258f (90 mg, 41%) as a colorless oil.

Step 6

To a 25 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt 12dd (111 mg, 0.22 mmol, 0.9 equiv.), a solution of methyl 2-bromo-4-(oxepan-4-yl)-1,3-benzothiazole-6-carboxylate 258f (90 mg, 0.24 mmol, 1.00 equiv.) in DMA (3 mL), and $Cs_2CO_3$ (159 mg, 0.49 mmol, 2.00 equiv.). The resulting mixture was heated at 60° C., overnight. After cooling to room temperature, the mixture was diluted with 20 mL of EA, washed with brine (20 mL×2), dried over anhydrous sodium sulfate and concentrated under vacuum. The residue was purified by silica gel column chromatography eluting with ethyl acetate/petroleum ether (1:3) to give methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(oxepan-4-yl)-1,3-benzothiazole-6-carboxylate 258g (90 mg, 59%) as a light yellow solid.

Step 7

To a 25 mL round-bottom flask was added a solution of methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(oxepan-4-yl)-1,3-benzothiazole-6-carboxylate 258g (90 mg, 0.13 mmol, 1.00 equiv.) in methanol/$H_2O$ (5/1 mL), and LiOH (32 mg, 1.34 mmol, 10.00 equiv.). The resulting mixture was heated at 50° C., overnight. The mixture was cooled to room temperature, diluted with water, and the pH value of the solution was adjusted to 2 using a 1M hydrogen chloride aqueous solution. The aqueous mixture was extracted with ethyl acetate (20 mL×2); the combined organic extracts were washed with brine (20 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (5.0% ACN up to 64.0% in 1 min, up to 77.0%, in 7 min); Detector, uv 254 nm. After purification 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-(oxepan-4-yl)-1,3-benzothiazole-6-carboxylic acid I-258 (48.9 mg, 55%) was obtained as a white solid. $^1$HNMR (300 MHz, $CD_3OD$): δ 8.17 (d, J=1.7 Hz, 1H), 7.88 (d, J=1.7 Hz, 1H), 7.62-7.43 (m, 3H), 4.36 (d, J=1.4 Hz, 3H), 4.00-3.73 (m, 2H), 3.66 (d, J=5.0 Hz, 2H), 3.52 (d, J=7.2 Hz, 1H), 3.37 (s, 2H), 3.05 (d, J=10.3 Hz, 1H), 2.63 (s, 1H), 2.29 (p, J=6.8 Hz, 1H), 2.10-1.94 (m, 7H), 1.70 (s, 2H), 1.42 (d, J=13.7 Hz, 1H), 1.19 (d, J=6.7 Hz, 4H); MS (ES, m/z): [M+1]=680.15.

Example 215: 4-cyclopropoxy-2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic Acid (I-259)

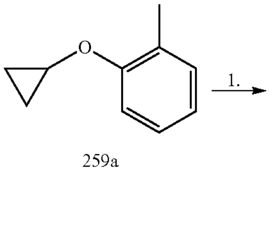

259a

-continued

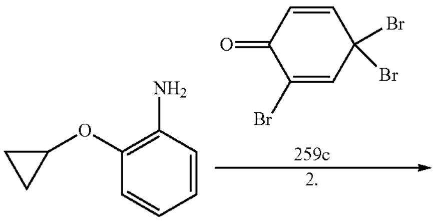

259b

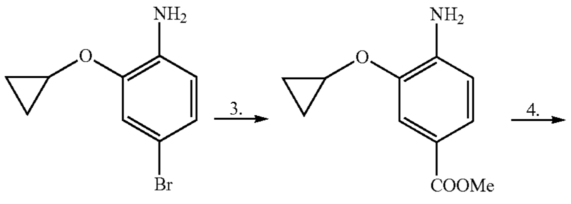

259d

259e

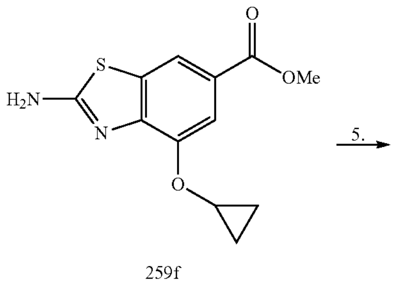

259f

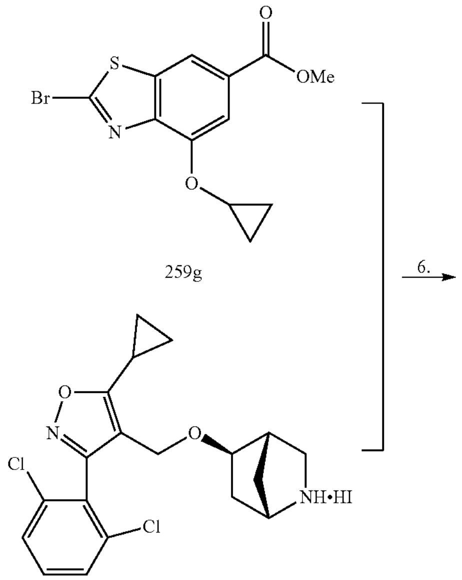

259g

12dd

-continued

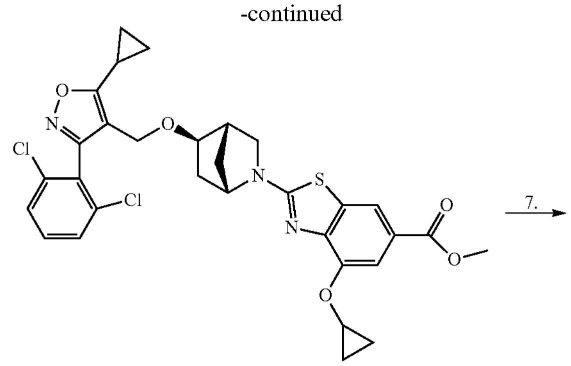

259h

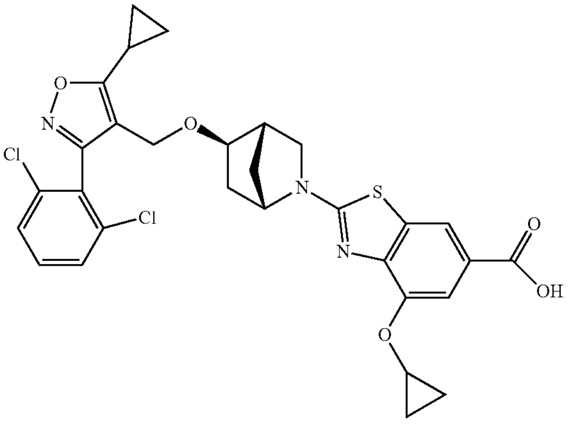

I-259

Step 1

To a 100 mL sealed tube was added 1-cyclopropoxy-2-iodobenzene 259a (7 g, 26.92 mmol, 1.00 equiv.), Acetone/$H_2O$ (40 mL, 1:1), CuI (525 mg, 2.76 mmol, 0.10 equiv.), and D-glucosamine hydrochloride (610 mg, 2.80 mmol, 0.10 equiv.). Potassium carbonate (7.7 g, 55.71 mmol, 2.00 equiv.) was added. The mixture was heated at 90° C., for 10 min. A saturated aqueous ammonia solution (30 mL) was added. The resulting mixture was heated at 90° C., overnight, and concentrated under vacuum. The crude product was purified by Flash-Prep-HPLC using the following conditions (IntelFlash-1): Column, silica gel: mobile phase, PE:EA=100:0 increasing to PE:EA=70:30 within 30 min; Detector, UV 254 nm. Removal of solvents afforded 2-cyclopropoxyaniline 259b (1.8 g, 45%) as a brown oil.

Step 2

To a 100 mL round-bottom flask was added 2-cyclopropoxyaniline 259b (1.8 g, 12.07 mmol, 1.00 equiv.), tetrahydrofuran (40 mL), and tetrabutylammonium tribromide (5.8 g, 12.03 mmol, 1.00 equiv.). The resulting mixture was stirred for 30 min in a water/ice bath, and concentrated under vacuum. The crude product was purified by Flash-Prep-HPLC using the following conditions (IntelFlash-1): Column, silica gel; mobile phase, PE:EA=100:0 increasing to PE:EA=95:5 within 20 min; Detector, UV 254 nm. Removal of solvents afforded 4-bromo-2-cyclopropoxyaniline 259c (1.2 g, 44%) as a brown oil.

Step 3

To a 100 mL pressure tank reactor was added 4-bromo-2-cyclopropoxyaniline 259c (1.0 g, 4.38 mmol, 1.00 equiv.), methanol (60 mL), TEA (2.67 g, 26.39 mmol, 6.00 equiv.), and $Pd(dppf)Cl_2$—$CH_2Cl_2$ (360 mg, 0.44 mmol, 0.10 equiv.). To the above mixture, CO gas was introduced in. The resulting mixture was heated at 100° C., overnight with stirring, and concentrated under vacuum. The crude product was purified by Flash-Prep-HPLC using the following conditions (IntelFlash-1): Column, silica gel; mobile phase, PE:EA=100:0 increasing to PE:EA=90:10 within 30 min; Detector, UV 254 nm. Removal of solvents provided methyl 4-amino-3-cyclopropoxybenzoate 259d (655 mg, 72%) as a brown oil.

Step 4

To a 250 mL round-bottom flask was added methyl 4-amino-3-cyclopropoxybenzoate 259d (2.1 g, 10.13 mmol, 1.00 equiv.), AcOH (100 mL), NaSCN (3.29 g, 40.62 mmol, 4.00 equiv.), and $Br_2$ (1.62 g, 10.14 mmol, 1.00 equiv.). The resulting mixture was stirred at 30° C., overnight. The reaction was quenched by the addition of 50 mL of water/ice. The pH value of the solution was adjusted to 10.0 using a 1M sodium hydroxide aqueous solution. The solids were collected by filtration to give methyl 2-amino-4-cyclopropoxy-1,3-benzothiazole-6-carboxylate 259e (2.0 g, 75%) as a reddish solid.

Step 5

To a 250 mL round-bottom flask was added methyl 2-amino-4-cyclopropoxy-1,3-benzothiazole-6-carboxylate 259e (2.0 g, 7.57 mmol, 1.00 equiv.), t-BuONO (1.76 g, 17.09 mmol, 2.26 equiv.), $CuBr_2$ (2.53 g, 11.35 mmol, 1.50 equiv.), and MeCN (60 mL). The resulting mixture was stirred at 30° C., overnight, and concentrated under vacuum. The crude product was purified by Flash-Prep-HPLC using the following conditions (IntelFlash-1): Column, silica gel; mobile phase, PE:EA=100:0 increasing to PE:EA=95:5 within 25 min; Detector, UV 254 nm. Removal of solvent gave methyl 2-bromo-4-cyclopropoxy-1,3-benzothiazole-6-carboxylate 259f (2.1 g, 85%) as a gray solid.

Step 6

To a 25 mL round-bottom flask was added (1S,4S,5R)-5-[[5-cyclopropyl-3-(2,6-dichlorophenyl)-1,2-oxazol-4-yl]methoxy]-2-azabicyclo[2.2.1]heptane hydroiodide salt (100 mg, 0.197 mmol, 1.00 equiv.), DMA (5 mL), methyl 2-bromo-4-cyclopropoxy-1,3-benzothiazole-6-carboxylate 259f (174 mg, 0.53 mmol, 2.69 equiv.), and $Cs_2CO_3$ (173 mg, 0.53 mmol, 2.69 equiv.). The resulting mixture was stirred at 60° C., overnight. After cooling to room temperature, the reaction was quenched by the addition of 50 mL of water. The mixture was extracted with ethyl acetate (100 mL×3). The combined organic extracts were dried over anhydrous sodium sulfate and concentrated under vacuum. The crude product was purified by Flash-Prep-HPLC using the following conditions (IntelFlash-1): Column, silica gel; mobile phase, PE:EA=100:0 increasing to PE:EA=80:20 within 30 min; Detector, UV 254 nm. Removal of solvents afforded methyl 4-cyclopropoxy-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylate 259g (120 mg, 95%) as a light yellow oil.

Step 7

To a 25 mL round-bottom flask was added methyl 4-cyclopropoxy-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylate 259g (165 mg, 0.26 mmol, 1.00 equiv.), methanol (4 mL), water (2 mL), and LiOH (100 mg, 4.18 mmol, 10.00 equiv.). The resulting mixture was stirred at room temperature overnight. The pH value of the solution was adjusted to 5.0 using a 1M HCl aqueous solution. The aqueous mixture was extracted with dichloromethane (30 mL×3); the combined organic extracts were washed with brine, dried over anhydrous sodium sulfate, and concentrated under vacuum. The crude product was purified by Prep-HPLC using the following conditions: Column, XBridge Prep C18 OBD Column, 5 um, 19*150 mm; mobile phase, Water (0.05% TFA) and ACN (50.0% ACN up to 72.0% in 8 min); Detector, UV 254 nm. After purification 4-cyclopropoxy-2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-1,3-benzothiazole-6-carboxylic acid I-259 (54.8 mg, 34%) was obtained as a colorless solid. $^1$HNMR (300 MHz, $CD_3OD$): δ 0.869 (4H, m), 1.135 (4H, m), 1.406 (1H, m), 1.672 (2H, m), 2.026 (1H, m), 2.216 (1H, m), 2.620 (1H, m), 3.018 (1H, m), 3.484 (1H, m), 3.626 (1H, m), 4.003 (1H, m), 4.358 (3H, m), 7.486 (3H, m), 7.982 (2H, m); MS (ES, m/z): [M+1]=612.

Example 216: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(3S)-oxolan-3-yloxy]-1,3-benzothiazole-6-carboxylic Acid (I-260)

Step 1

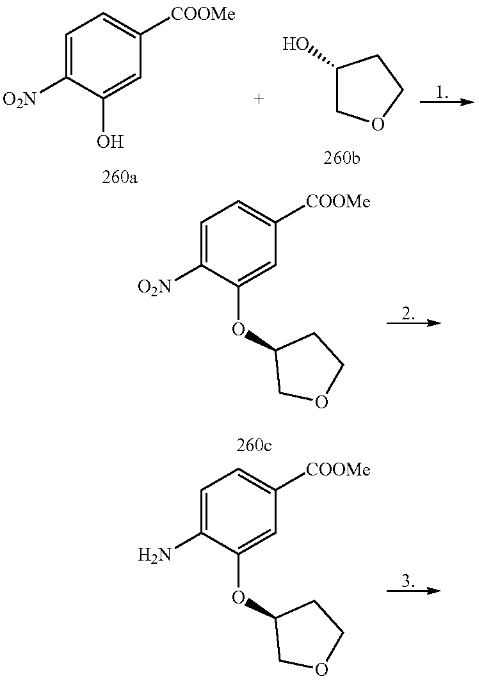

260a 260b 260c 260d

-continued

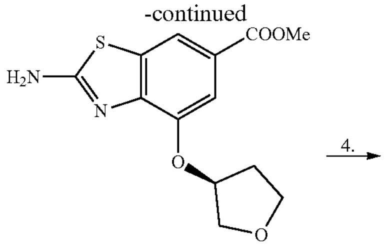

260e

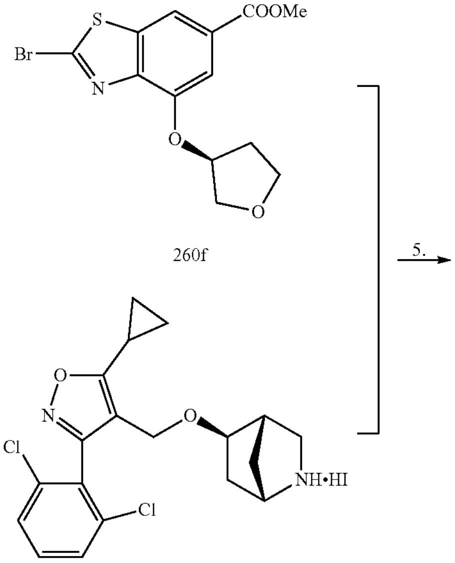

260f

12dd

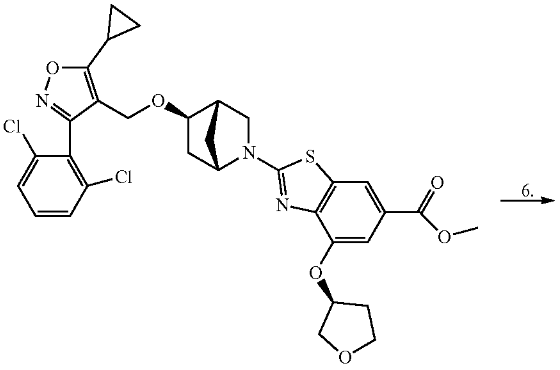

260g

-continued

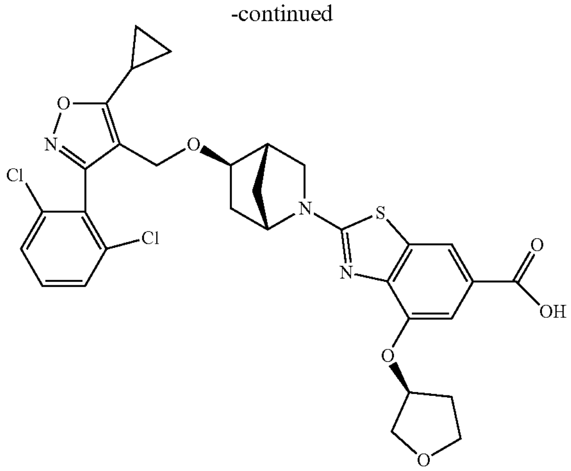

I-260

To a 1000 mL round-bottom flask purged with and maintained under an inert atmosphere of nitrogen was added methyl 3-hydroxy-4-nitrobenzoate 260a (10 g, 50.72 mmol, 1.00 equiv.), $PPh_3$ (19.9 g, 75.87 mmol, 1.50 equiv), tetrahydrofuran (240 mL), and (3R)-oxolan-3-ol 260b (5.4 g, 61.29 mmol, 1.20 equiv.). DIAD (15.4 g, 76.16 mmol, 1.50 equiv) was added. The resulting mixture was heated at 50° C., overnight with stirring. The mixture was concentrated under vacuum and the residue was purified by silica gel column chromatography eluting with ethyl acetate in petroleum ether (0% to 20%) to give methyl 4-nitro-3-[(3S)-oxolan-3-yloxy]benzoate 260c (7.7 g, 57%) as a light yellow solid.

Step 2

To a 250 mL round-bottom flask was added methyl 4-nitro-3-[(3S)-oxolan-3-yloxy]benzoate 260c (7.7 g, 28.81 mmol, 1.00 equiv.), methanol (100 mL), and Palladium on carbon (7.7 g, 10 wt %). Hydrogen gas was introduced. The reaction mixture was stirred at 30° C., for 1 h. Solids were filtered out, and the filtrate was concentrated under vacuum to afford methyl 4-amino-3-[(3S)-oxolan-3-yloxy]benzoate 260d (7.4 g, crude) as a colorless oil.

Step 3

To a 250 mL round-bottom flask was added methyl 4-amino-3-[(3S)-oxolan-3-yloxy]benzoate 260d (7.4 g, 31.19 mmol, 1.00 equiv.), AcOH (128 mL), NaSCN (10.4 g, 4.00 equiv.), and $Br_2$ (7.7 g, 48.18 mmol, 1.50 equiv.). The resulting mixture was stirred at 30° C., overnight, quenched by the addition of 50 mL of water/ice. The pH value of the solution was adjusted to 10.0 using a 1M sodium hydroxide aqueous solution. Solids were collected by filtration to afford methyl 2-amino-4-[(3S)-oxolan-3-yloxy]-1,3-benzothiazole-6-carboxylate 260e (11 g, crude) as a reddish solid.

Step 4

To a 250 mL round-bottom flask was added methyl 2-amino-4-[(3S)-oxolan-3-yloxy]-1,3-benzothiazole-6-carboxylate 260e (2.5 g, 8.49 mmol, 1.00 equiv.), $CuBr_2$ (2.8 g, 12.73 mmol, 1.50 equiv.), t-BuONO (2.2 g, 21.36 mmol, 2.50 equiv.), and MeCN (100 mL). The resulting mixture was stirred at 30° C., overnight and concentrated under vacuum. The residue was purified by silica gel column chromatography eluting with ethyl acetate in petroleum ether (0% to 20%) to produce methyl 2-bromo-4-[(3S)-oxolan-3-yloxy]-1,3-benzothiazole-6-carboxylate 260f (670 mg, 22%) as a light yellow solid.

Step 5

To a 50 mL round-bottom flask purged with and maintained under an inert atmosphere of nitrogen was added methyl 2-bromo-4-[(3S)-oxolan-3-yloxy]-1,3-benzothiazole-6-carboxylate 260f (184 mg, 0.51 mmol, 1.7 equiv.), $Cs_2CO_3$ (387 g, 1.19 mol, 4.00 equiv.), DMA (3 mL), and (1S,4S,5R)-5-[5-cyclopropyl-3-(2,6-dichlorophenyl)-1,2-oxazol-4-yl]methoxy-2-azabicyclo[2.2.1]heptane hydroiodide salt 12dd (150 mg, 0.296 mmol, 1.00 equiv.). The reaction mixture was heated at 60° C., overnight. After cooling to room temperature, the mixture was diluted with 200 mL of EA, washed with brine (50 mL×3), dried over anhydrous sodium sulfate and concentrated under vacuum to yield methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3S)-oxolan-3-yloxy]-1,3-benzothiazole-6-carboxylate 260g (200 mg) as a light yellow crude oil.

Step 6

To a 25 mL round-bottom flask was added methyl 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3S)-oxolan-3-yloxy]-1,3-benzothiazole-6-carboxylate 260g (260 mg, 0.40 mmol, 1.00 equiv.), LiOH (158 mg, 6.60 mmol, 10.00) equiv.), and methanol (10 mL). The resulting mixture was stirred at 35° C., overnight. The mixture was diluted with 10 mL of $H_2O$, extracted with ethyl acetate (100 mL×2). The combined organic extracts were washed with brine, dried, and concentrated to a crude product which was purified by Prep-HPLC using the following conditions: Column, XBridge Prep C18 OBD Column 19*150 mm 5umc-0013; mobile phase; Detector, 254 nm. After purification 2-[(1S,4S,5R)-5-[[5-cyclopropyl-3-(2,6-dichlorophenyl)-1,2-oxazol-4-yl]methoxy]-2-azabicyclo[2.2.1]heptan-2-yl]-4-[(3S)-oxolan-3-yloxy]-1,3-benzothiazole-6-carboxylic acid I-260 (101.7 mg, 40%) was obtained as an off-white solid. $^1$HNMR (300 MHz, $CD_3OD$): δ 8.03 (q, J=1.3 Hz, 1H), 7.63-7.44 (m, 4H), 5.31 (d, J=5.2 Hz, 1H), 4.44-4.28 (m, 2H), 4.17-3.84 (m, 4H), 3.69 (d, J=5.7 Hz, 1H), 3.57 (dd, J=10.3, 4.0 Hz, 1H), 3.09 (d, J=10.3 Hz, 1H), 2.68 (s, 1H), 2.45-2.16 (m, 3H), 2.12-1.98 (m, 1H), 1.73 (s, 2H), 1.44 (d, J=13.7 Hz, 1H), 1.24-1.15 (m, 4H); MS (ES, m/z): [M+1]=642.15.

Example 217: 2-[(1S,4S,5R)-5-{[5-cyclopropyl-3-(2,6-dichlorophenyl)-1,2-oxazol-4-yl]methoxy}-2-azabicyclo[2.2.1]heptan-2-yl]-4-[(3R)-oxolan-3-yloxy]-1,3-benzothiazole-6-carboxylic Acid (I-261)

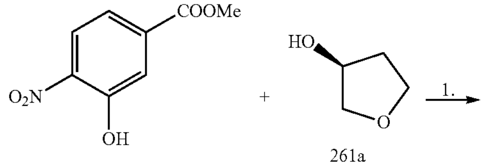

260a

261a

-continued

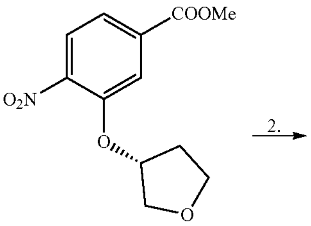

261b

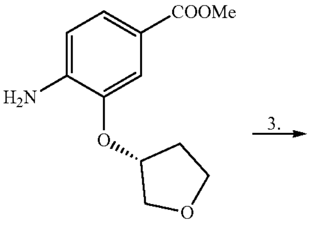

261c

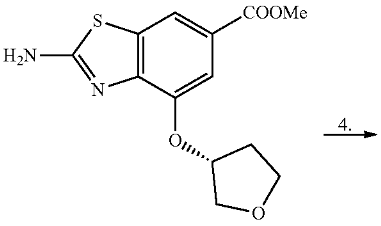

261d

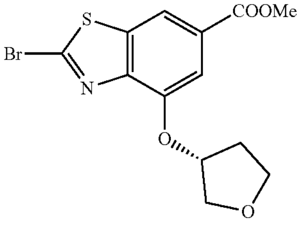

261e

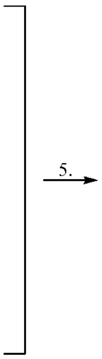

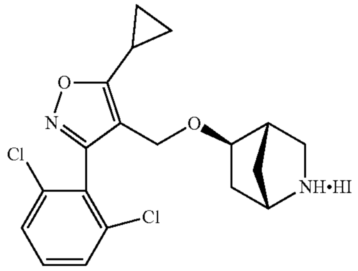

12dd

-continued

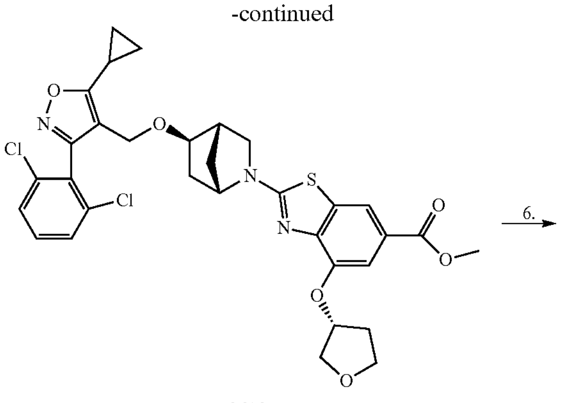

261f

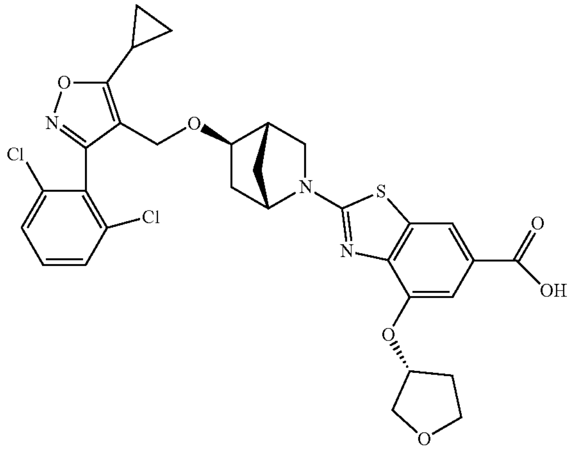

I-261

Step 1

To a 1000 mL round-bottom flask was added methyl 3-hydroxy-4-nitrobenzoate 260a (10 g, 50.72 mmol, 1.00 equiv.), tetrahydrofuran (400 mL), and $PPh_3$ (20 g, 76.25 mmol, 1.50 equiv.). (3S)-Oxolan-3-ol 261a (4.5 g, 51.08 mmol, 1.00 equiv.) was added. The mixture was cooled to 0° C., and added DIAD (15.4 g, 76.16 mmol, 1.50 equiv.). The reaction mixture was heated at 50° C., overnight, and concentrated under vacuum. The residue was purified by silica gel column chromotography eluting with ethyl acetate in hexanes (0% to 25%) to afford methyl 4-nitro-3-[(3R)-oxolan-3-yloxy]benzoate 261b (10 g, 80%) as a red oil.

Step 2

To a 1000 mL round-bottom flask was added methyl 4-nitro-3-[(3R)-oxolan-3-yloxy]benzoate 261b (10.9 g, 40.79 mmol, 1.00 equiv.), methanol (200 mL), tetrahydrofuran (200 mL), and Palladium on carbon (11 g, 10 wt %). Hydrogen gas was introduced in. The resulting mixture was stirred under an atmosphere of hydrogen overnight. Solids were filtered out, and the filtrate was concentrated under vacuum to give methyl 4-amino-3-[(3R)-oxolan-3-yloxy] benzoate 261c (9.5 g, 98%) as a reddish oil.

Step 3

To a 500 mL round-bottom flask was added methyl 4-amino-3-[(3R)-oxolan-3-yloxy]benzoate 261c (9.5 g, 40.04 mmol, 1.00 equiv.) AcOH (300 mL), NaSCN (13.0 g, 160.49 mmol, 4.00 equiv.), and $Br_2$ (6.4 g, 40.05 mmol, 1.00 equiv.). The resulting mixture was stirred at 30° C., overnight. The mixture was diluted with 500 mL of $H_2O$/ice. The pH value of the solution was adjusted to 10.0 using sodium hydroxide. The solids were collected by filtration, dried, to afford methyl 2-amino-4-[(3R)-oxolan-3-yloxy]-1,3-benzothiazole-6-carboxylate 261d (10.2 g, 87%) as a red solid.

Step 4

To a 250 mL round-bottom flask was added methyl 2-amino-4-[(3R)-oxolan-3-yloxy]-1,3-benzothiazole-6-carboxylate 261d (10.2 g, 34.66 mmol, 1.00 equiv.), $CH_3CN$ (150 mL), $CuBr_2$ (11.6 g, 52.02 mmol, 1.50 equiv), and t-BuONO (8 g, 78.43 mmol, 2.26 equiv). The resulting mixture was stirred at 30° C., overnight. The mixture was concentrated under vacuum, and the residue was purified by silica gel column chromatography eluting with ethyl acetate in hexanes (0% to 5%). Removal of solvents afforded methyl 2-bromo-4-[(3R)-oxolan-3-yloxy]-1,3-benzothiazole-6-carboxylate 261e (3.4 g, 27%) as a light yellow solid.

Step 5

To a 25 mL round-bottom flask was added (1S,4S,5R)-5-[[5-cyclopropyl-3-(2,6-dichlorophenyl)-1,2-oxazol-4-yl] methoxy]-2-azabicyclo[2.2.1]heptane hydroiodide salt 12dd (150 mg, 0.296 mmol, 1.00 equiv), methyl 2-bromo-4-[(3R)-oxolan-3-yloxy]-1,3-benzothiazole-6-carboxylate 261e (185 mg, 0.52 mmol, 1.75 equiv.), DMA (5 mL), and $Cs_2CO_3$ (259 mg, 0.79 mmol, 2.67 equiv.). The resulting mixture was heated at 60° C., overnight. After cooling to room temperature, the mixture was diluted with EA (100 mL), washed with brine (30 mL×3), dried over anhydrous sodium sulfate, and concentrated under vacuum. The residue was purified by silica gel column chromatography eluting with ethyl acetate in hexanes (1:3). Removal of solvents gave methyl 2-[(1S,4S,5R)-5-[[5-cyclopropyl-3-(2,6-dichlorophenyl)-1,2-oxazol-4-yl]methoxy]-2-azabicyclo [2.2.1]heptan-2-yl]-4-[(3R)-oxolan-3-yloxy]-1,3-benzothiazole-6-carboxylate 261f (150 mg, 78%) as a colorless oil.

Step 6

To a 25 mL round-bottom flask was added methyl 2-[(1S, 4S,5R)-5-[[5-cyclopropyl-3-(2,6-dichlorophenyl)-1,2-oxazol-4-yl]methoxy]-2-azabicyclo[2.2.1]heptan-2-yl]-4-[(3R)-oxolan-3-yloxy]-1,3-benzothiazole-6-carboxylate 261f (150 mg, 0.23 mmol, 1.00 equiv.), methanol (4 mL), water (2 mL), and $LiOH.H_2O$ (100 mg, 2.38 mmol, 10.00 equiv.). The resulting mixture was stirred at room temperature overnight. The pH value of the solution was adjusted to 7.0 using a 1M HCl aqueous solution. The aqueous mixture was extracted with ethyl acetate (30 mL×3). The combined organic extracts were dried over anhydrous sodium sulfate and concentrated under vacuum. The crude product was purified by Prep-HPLC using the following conditions: Column, XBridge Prep C18 OBD Column, 5 um 19*150 mm; mobile phase, Water (0.05% TFA) and ACN (52.0% ACN up to 72.0% in 8 min); Detector, UV 220 nm. After purification 2-[(1S,4S,5R)-5-[[5-cyclopropyl-3-(2,6-dichlorophenyl)-1,2-oxazol-4-yl]methoxy]-2-azabicyclo[2.2.1] heptan-2-yl]-4-[(3R)-oxolan-3-yloxy]-1,3-benzothiazole-6-carboxylic acid I-261 (87.8 mg, 60%) was obtained as a pink solid. $^1$HNMR (300 MHz, $CD_3OD$): δ 1.133 (4H, m), 1.673 (1H, m), 1.963 (2H, m), 2.009 (1H, m), 2.193 (3H, m), 2.611

(1H, m), 3.020 (1H, m), 3.516 (1H, m), 3.644 (1H, m), 3.872 (1H, m), 4.084 (3H, m), 4.267 (3H, m), 5.247 (1H, m), 7.449 (4H, m), 7.978 (1H, m); MS (ES, m/z): [M+1]=642.

Example 218: 2-[(1S,4S,5R)-5-{[3-(2-chloro-6-fluorophenyl)-5-cyclopropyl-1,2-oxazol-4-yl]methoxy}-2-azabicyclo[2.2.1]heptan-2-yl]-4-methyl-1,3-benzothiazole-6-carboxylic Acid (I-262)

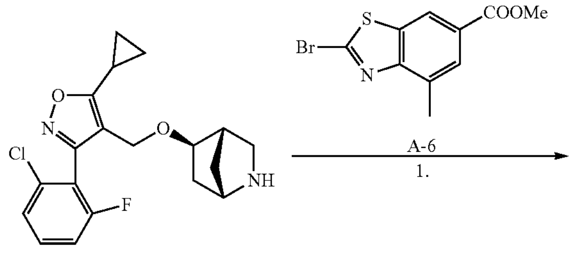

118h

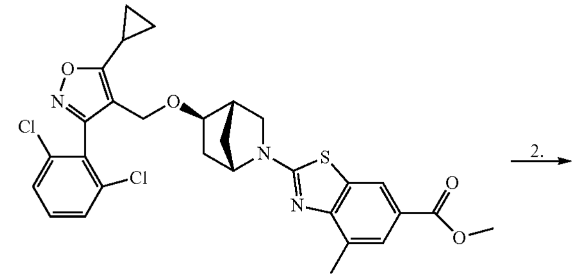

262a

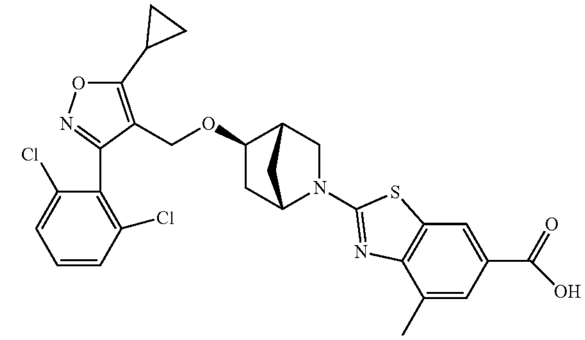

I-262

Step 1

To a 100 mL round-bottom flask was added (1S,4S,5R)-5-[[3-(2-chloro-6-fluorophenyl)-5-cyclopropyl-1,2-oxazol-4-yl]methoxy]-2-azabicyclo[2.2.1]heptane 118h (150 mg, 0.41 mmol, 1.00 equiv.), methyl 2-bromo-4-methyl-1,3-benzothiazole-6-carboxylate A-6 (142 mg, 0.50 mmol, 1.20 equiv.), DMA (2 mL), and $Cs_2CO_3$ (270 mg, 0.83 mmol, 2.00 equiv.). The resulting mixture was stirred at 60° C., overnight. After cooling to room temperature, the mixture was diluted with of $H_2O$ (30 mL), extracted with ethyl acetate (30 mL×3), and the combined organic extracts were washed with brine (30 mL×2), then dried, concentrated. The residue was purified by silica gel column chromatography eluting with ethyl acetate/petroleum ether (1:3) to give methyl 2-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-4-methyl-1,3-benzothiazole-6-carboxylate 262a (150 mg, 64%) as colorless oil.

Step 2

To a 50 mL round-bottom flask was added methyl 2-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-4-methyl-1,3-benzothiazole-6-carboxylate 262a (150 mg, 0.26 mmol, 1.00 equiv.), methanol (4 mL), water (2 mL), and lithium hydroxide (63.5 mg, 2.65 mmol, 10.00 equiv.). The resulting mixture was stirred at room temperature overnight. The mixture was diluted with 20 mL of $H_2O$, extracted with ethyl acetate (50 mL×2). The combined organic extracts were washed with brine (50 mL×2), dried over anhydrous sodium sulfate, and concentrated. The residue was purified by Prep-HPLC using the following conditions (Column, XBridge C18 OBD Prep Column, 19 mm×250 mm; mobile phase, Water (0.05% TFA) and ACN (60.0% ACN up to 80.0% in 8 min); Detector, uv 254 nm. After purification 2-[(1S,4S,5R)-5-[[3-(2-chloro-6-fluorophenyl)-5-cyclopropyl-1,2-oxazol-4-yl]methoxy]-2-azabicyclo[2.2.1]heptan-2-yl]-4-methyl-1,3-benzothiazole-6-carboxylic Acid I-262 (83.2 mg, 57%) was obtained as a colorless solid. $^1$HNMR (300 MHz, $CD_3OD$): δ 8.18 (d, J=1.6 Hz, 1H), 7.82 (s, 1H), 7.55 (td, J=8.2, 5.9 Hz, 1H), 7.43 (d, J=8.1 Hz, 1H), 7.26 (t, J=8.6 Hz, 1H), 4.38 (d, J=2.6 Hz, 3H), 3.66 (d, J=6.4 Hz, 1H), 3.53 (s, 1H), 3.09 (s, 1H), 2.65 (s, 1H), 2.58-2.51 (m, 3H), 2.34-2.20 (m, 1H), 2.03 (q, J=6.6 Hz, 1H), 1.70 (s, 2H), 1.43 (d, J=14.0 Hz, 1H), 1.18 (d, J=6.7 Hz, 4H); MS (ES, m/z): [M+1]=554.15.

Example 219: Synthesis of I-263 to I-268

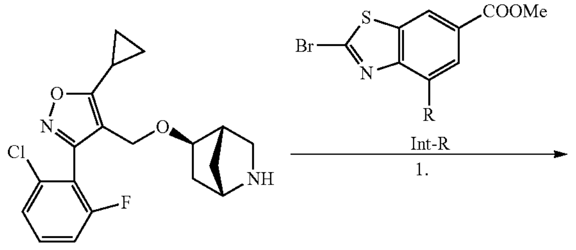

118h

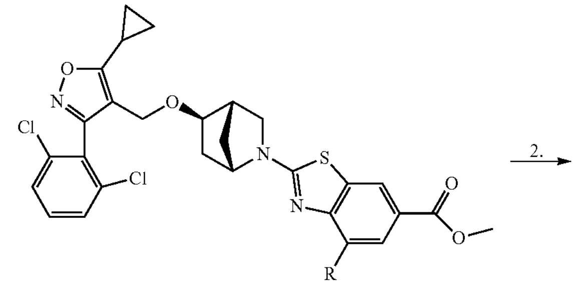

263-x

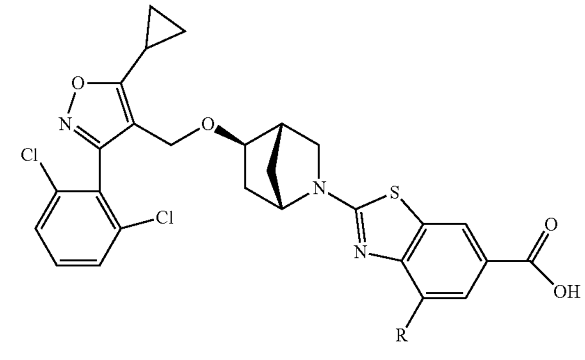

I-x

Bicyclic aryl compounds of 1-263 to 1-268 were prepared from intermediate 118h and the corresponding bicyclic arylbromide Int-R following the two-step procedure described in Preparative Example 218. The data for compounds I-263 to I-268 is summarized in Table 13.

TABLE 13

| Int-R | Cmpd Structure | Cmpd No. | MS/$^1$H NMR |
|---|---|---|---|
| 259g | 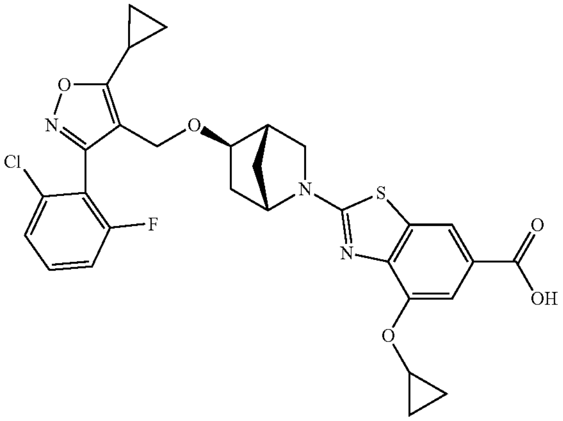 [SMILES: O=C(O)c1cc(OC2CC2)c2nc(N3C[C@@H]4C[C@H]3C[C@H]4OCc3c(-c4c(F)cccc4Cl)noc3C3CC3)sc2c1] | I-263 | MS (ES, m/z): [M + 1] = 596. $^1$H NMR (300 MHz, $CD_3OD$) δ: 8.04 (d, J = 1.5 Hz, 1H), 7.95 (d, J = 1.5 Hz, 1H), 7.57 (td, J = 8.3, 6.0 Hz, 1H), 7.45 (d, J = 8.2 Hz, 1H), 7.28 (t, J = 8.7 Hz, 1H), 4.41 (t, J = 8.5 Hz, 3H), 4.04 (tt, J = 6.0, 3.2 Hz, 1H), 3.68 (dd, J = 6.7, 2.4 Hz, 1H), 3.57 (dd, J = 10.4, 4.0 Hz, 1H), 3.09 (d, J = 10.2 Hz, 1H), 2.68 (s, 1H), 2.29 (p, J = 6.9 Hz, 1H), 2.12-1.98 (m, 1H), 1.72 (s, 2H), 1.45 (d, J = 13.7 Hz, 1H), 1.20 (d, J = 6.7 Hz, 4H), 1.02-0.82 (m, 4H). |
| 254d | 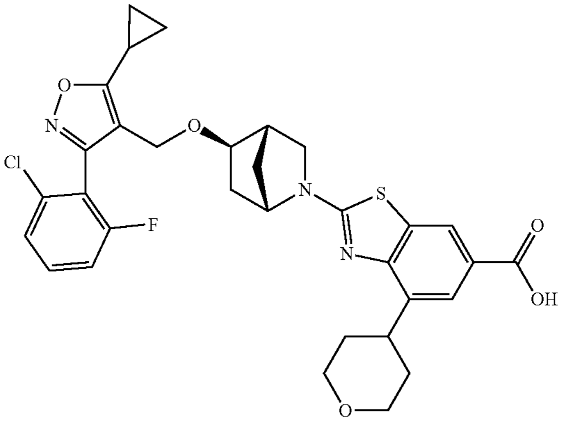 [SMILES: O=C(O)c1cc(C2CCOCC2)c2nc(N3C[C@@H]4C[C@H]3C[C@H]4OCc3c(-c4c(F)cccc4Cl)noc3C3CC3)sc2c1] | I-264 | MS (ES, m/z): [M + 1] = 624.25. $^1$H NMR (300 MHz, $CD_3OD$) δ: 8.20 (d, J = 1.7 Hz, 1H), 7.88 (d, J = 1.7 Hz, 1H), 7.55 (td, J = 8.3, 5.9 Hz, 1H), 7.43 (dt, J = 8.1, 1.0 Hz, 1H), 7.32-7.19 (m, 1H), 4.46-4.31 (m, 2H), 4.15-4.03 (m, 2H), 3.65 (td, J = 11.3, 2.6 Hz, 3H), 3.52 (dtd, J = 12.1, 8.5, 4.0 Hz, 2H), 3.05 (d, J = 10.2 Hz, 1H), 2.63 (s, 1H), 2.28 (p, J = 6.8 Hz, 1H), 2.08-1.80 (m, 5H), 1.69 (d, J = 1.9 Hz, 2H), 1.50-1.37 (m, 1H), 1.24-1.13 (m, 4H). |
| 252a | 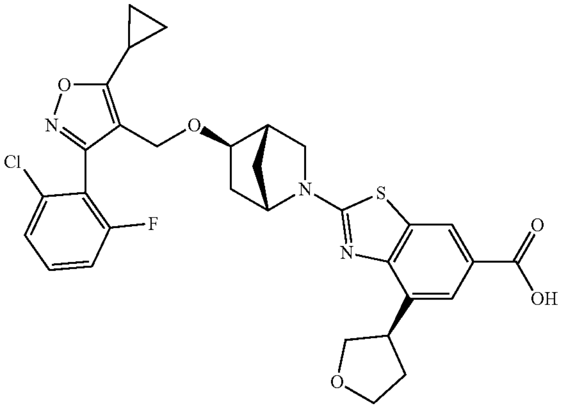 [SMILES: O=C(O)c1cc([C@H]2CCOC2)c2nc(N3C[C@@H]4C[C@H]3C[C@H]4OCc3c(-c4c(F)cccc4Cl)noc3C3CC3)sc2c1] | I-265 | MS (ES, m/z): [M + 1] = 610.20. $^1$H NMR (300 MHz, $CD_3OD$) δ: 8.21 (d, J = 1.7 Hz, 1H), 7.95-7.88 (m, 1H), 7.55 (td, J = 8.2, 5.9 Hz, 1H), 7.43 (d, J = 8.3 Hz, 1H), 7.26 (t, J = 8.6 Hz, 1H), 4.38 (d, J = 1.5 Hz, 3H), 4.24 (t, J = 7.7 Hz, 1H), 4.15 (td, J = 8.2, 4.9 Hz, 1H), 4.08-3.93 (m, 2H), 3.88-3.76 (m, 1H), 3.65 (d, J = 4.7 Hz, 1H), 3.52 (dd, J = 10.1, 4.1 Hz, 1H), 3.04 (d, J = 10.2 Hz, 1H), 2.63 (s, 1H), 2.51-2.34 (m, 1H), 2.36-2.15 (m, 2H), 2.01 (dd, J = 13.6, 6.7 Hz, 1H), 1.69 (s, 2H), 1.43 (d, J = 13.5 Hz, 1H), 1.19 (d, J = 6.7 Hz, 4H). |

TABLE 13-continued

| Int-R | Cmpd Structure | Cmpd No. | MS/$^1$H NMR |
|---|---|---|---|
| 253a | 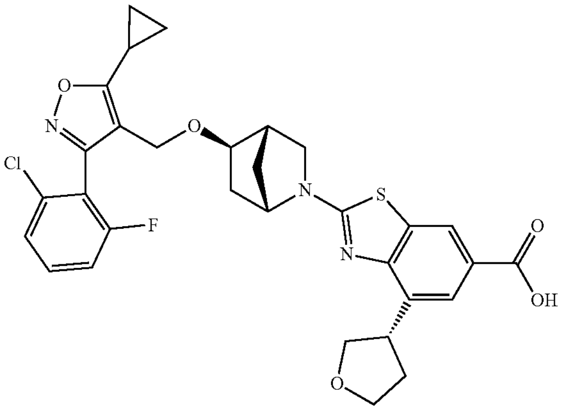 [SMILES: O=C(O)c1cc([C@@H]2CCOC2)c2nc(N3C[C@@H]4C[C@H]3C[C@H]4OCc3c(-c4c(F)cccc4Cl)noc3C3CC3)sc2c1] | I-266 | MS (ES, m/z): [M + 1] = 610.25. $^1$H NMR (300 MHz, $CD_3OD$) δ: 8.22 (d, J = 1.7 Hz, 1H), 7.92 (d, J = 1.6 Hz, 1H), 7.55 (td, J = 8.3, 5.9 Hz, 1H), 7.43 (d, J = 8.0 Hz, 1H), 7.32-7.20 (m, 1H), 4.46-4.31 (m, 2H), 4.27-4.10 (m, 2H), 4.09-3.93 (m, 2H), 3.89-3.78 (m, 1H), 3.65 (dd, J = 6.9, 2.5 Hz, 1H), 3.52 (dd, J = 10.1, 4.0 Hz, 1H), 3.05 (d, J = 10.1 Hz, 1H), 2.64 (s, 1H), 2.44 (dtd, J = 12.6, 7.7, 4.8 Hz, 1H), 2.32-2.14 (m, 2H), 2.08-1.94 (m, 1H), 1.70 (s, 2H), 1.43 (d, J = 13.4 Hz, 1H), 1.19 (d, J = 6.7 Hz, 4H). |
| 260f | 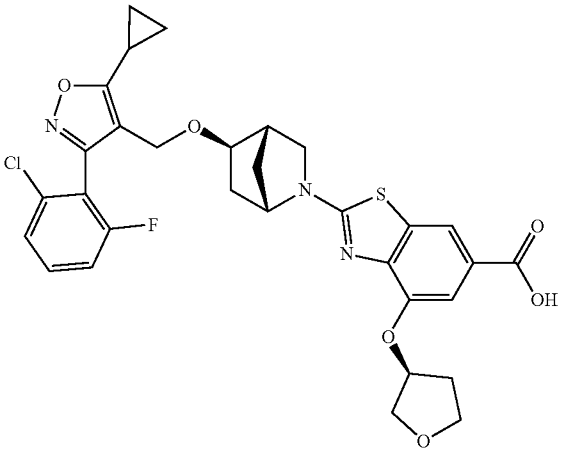 [SMILES: O=C(O)c1cc(O[C@H]2CCOC2)c2nc(N3C[C@@H]4C[C@H]3C[C@H]4OCc3c(-c4c(F)cccc4Cl)noc3C3CC3)sc2c1] | I-267 | MS (ES, m/z): [M + 1] = 626.1. $^1$H NMR (300 MHz, $CD_3OD$) δ: 8.04 (s, 1H), 7.61-7.50 (m, 2H), 7.45 (d, J = 8.2 Hz, 1H), 7.30 (d, J = 8.6 Hz, 1H), 5.32 (d, J = 5.3 Hz, 1H), 4.40 (d, J = 3.2 Hz, 3H), 4.14-4.02 (m, 3H), 3.93 (d, J = 4.9 Hz, 1H), 3.67 (s, 1H), 3.57 (s, 1H), 2.67 (s, 1H), 2.29 (d, J = 7.8 Hz, 3H), 1.72 (s, 2H), 1.20 (d, J = 6.6 Hz, 4H). |
| 261e | 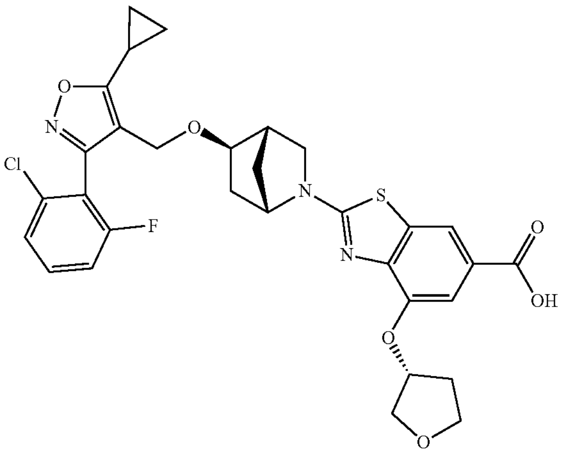 [SMILES: O=C(O)c1cc(O[C@@H]2CCOC2)c2nc(N3C[C@@H]4C[C@H]3C[C@H]4OCc3c(-c4c(F)cccc4Cl)noc3C3CC3)sc2c1] | I-268 | MS (ES, m/z): [M + 1] = 626.1. $^1$H NMR (300 MHz, $CD_3OD$) δ: 8.04 (d, J = 1.4 Hz, 1H), 7.64-7.50 (m, 2H), 7.45 (d, J = 8.2 Hz, 1H), 7.28 (t, J = 8.6 Hz, 1H), 5.31 (s, 1H), 4.40 (d, J = 2.9 Hz, 3H), 4.18-4.00 (m, 3H), 3.94 (dd, J = 8.2, 4.9 Hz, 1H), 3.69 (d, J = 7.0 Hz, 1H), 3.56 (s, 1H), 3.10 (s, 1H), 2.68 (s, 1H), 2.42-2.24 (m, 3H), 2.09 (s, 1H) 1.73 (s, 2H), 1.46 (d, J = 13.5 Hz, 1H), 1.20 (d, J = 6.6 Hz, 4H). |

Example 220: Synthesis of I-269 to I-275

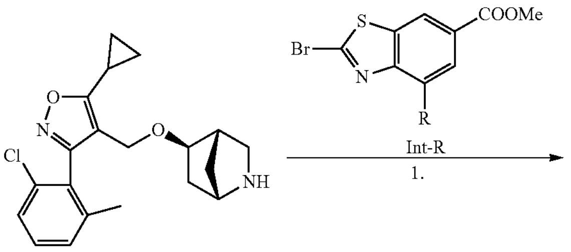

113h

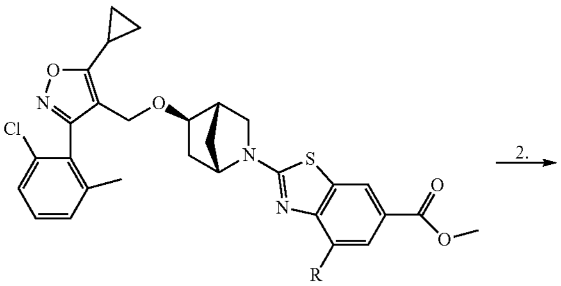

269-x

-continued

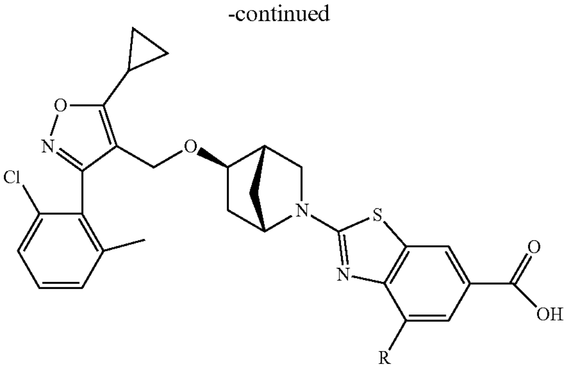

I-x

Bicyclic aryl compounds of 1-269 to 1-275 were prepared from intermediate 113h and the corresponding bicyclic arylbromide Int-R following the two-step procedure described in Preparative Example 218. The data for compounds I-269 to I-275 is summarized in Table 14.

TABLE 14

| Int-R | Cmpd Structure | Cmpd No. | MS/$^{1}$H NMR |
|---|---|---|---|
| A-6 | 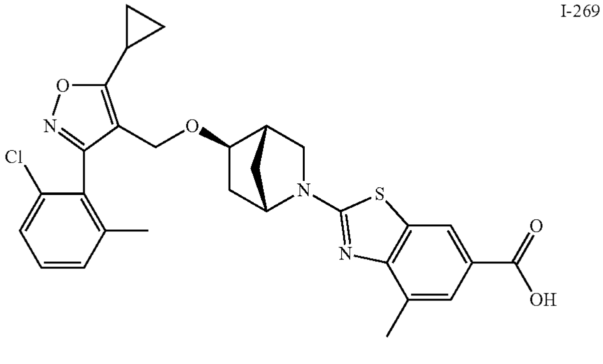 | I-269 | MS (ES, m/z): [M + 1] = 550.5. $^{1}$H NMR (300 MHz, $CD_3OD$) δ: 8.21 (d, J = 1.6 Hz, 1H), 7.90-7.83 (m, 1H), 7.49-7.38 (m, 2H), 7.37-7.12 (m, 1H), 4.39 (dd, J = 11.7, 6.2 Hz, 2H), 4.23 (dd, J = 23.3, 11.7 Hz, 1H), 3.75-3.65 (m, 1H), 3.57 (td, J = 6.4, 3.4 Hz, 1H), 3.12 (d, J = 10.6 Hz, 1H), 2.56 (s, 4H), 2.35-2.23 (m, 1H), 2.19 (d, J = 1.3 Hz, 3H), 2.05 (ddd, J = 13.6, 10.1, 6.7 Hz, 1H), 1.78-1.58 (m, 2H), 1.39-1.25 (m, 1H), 1.25-1.16 (m, 4H). |
| 259g | 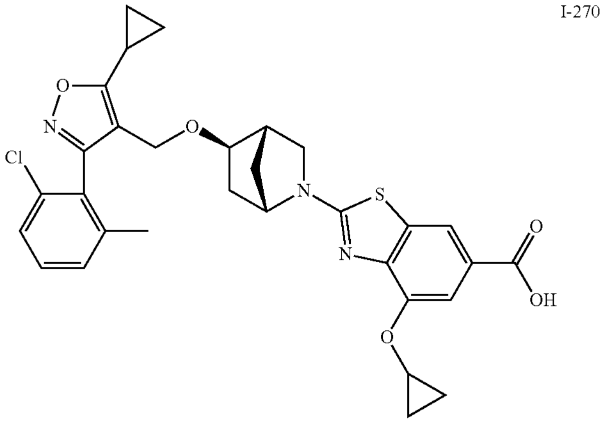 | I-270 | MS (ES, m/z): [M + 1] = 592.3. $^{1}$H NMR (300 MHz, $CD_3OD$) δ: 8.05 (d, J = 1.4 Hz, 1H), 7.95 (d, J = 1.5 Hz, 1H), 7.44-7.38 (m, 2H), 7.32 (s, 1H), 4.39 (dd, J = 11.7, 5.9 Hz, 2H), 4.23 (dd, J = 22.8. 11.7 Hz, 1H), 4.11-3.98 (m, 1H), 3.72-3.62 (m, 1H), 3.61-3.50 (m, 1H), 3.15-3.04 (m, 1H), 2.66 (d, J = 46.0 Hz, 1H), 2.35-2.24 (m, 1H), 2.19 (t, J = 0.9 Hz, 3H), 2.06 (ddd, J = 20.4, 13.8, 6.8 Hz, 1H), 1.78-1.58 (m, 2H), 1.55-1.25 (m, 1H), 1.24-1.17 (m, 4H), 0.92 (dt, J = 12.5, 4.2 Hz, 4H). |

TABLE 14-continued
| Int-R | Cmpd Structure | Cmpd No. | MS/$^1$H NMR |
|---|---|---|---|
| 254d | 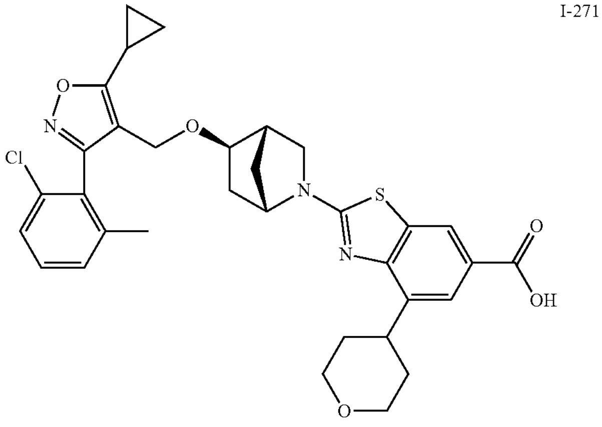 | I-271 | MS (ES, m/z): [M + 1] = 620.2. $^1$H NMR (300 MHz, $CDCl_3$) δ: 8.11 (s, 1H), 7.98 (s, 1H), 7.33 (d, J = 6.2 Hz, 2H), 7.23 (d, J = 2.0 Hz, 1H), 4.37-4.09 (m, 4H), 3.71 (d, J = 19.1 Hz, 5H), 3.30 (s, 1H), 2.67 (d, J = 39.3 Hz, 1H), 2.21 (s, 5H), 1.90 (s, 5H), 1.80 (d, J = 9.4 Hz, 1H), 1.70 (s, 1H), 1.64-1.42 (m, 1H), 1.29 (d, J = 4.0 Hz, 2H), 1.18 (d, J = 8.2 Hz, 2H). |
| 252a | 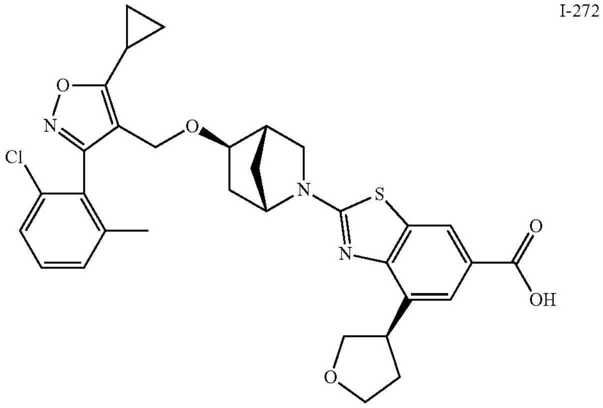 | I-272 | MS (ES. m/z): [M + 1] = 606.2. $^1$H NMR (300 MHz, $CDCl_3$) δ: 8.15 (s, 1H), 8.00 (s, 1H), 7.39-7.27 (m, 2H), 7.20 (t, J = 6.3 Hz, 1H), 4.34-4.11 (m, 5H), 3.99 (s, 1H), 3.88 (s, 1H), 3.63 (s, 2H), 3.18 (s, 1H), 2.63 (d, J = 38.8 Hz, 1H), 2.48 (s, 1H), 2.19 (s, 6H), 1.71 (d, J = 29.0 Hz, 2H), 1.57-1.34 (m, 1H), 1.27 (s, 2H), 1.25 (s, 1H), 1.20-1.10 (m, 2H). |
| 253a | 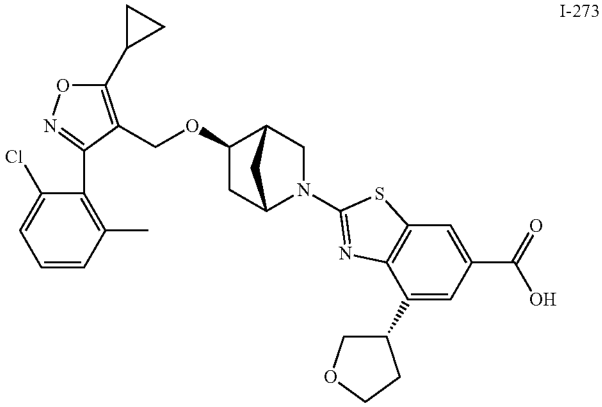 | I-273 | MS (ES, m/z): [M + 1] = 606.2. $^1$H NMR (300 MHz, $CDCl_3$) δ: 8.17 (d, J = 1.4 Hz, 1H), 8.00 (s, 1H), 7.38-7.26 (m, 2H), 7.20 (t, J = 6.7 Hz, 1H), 4.34-4.11 (m, 5H), 3.94 (dt, J = 38.6, 7.2 Hz, 2H), 3.60 (s, 2H), 3.15 (s, 1H), 2.72-2.39 (m, 2H), 2.22-2.06 (m, 6H), 1.70 (d, J = 29.2 Hz, 2H), 1.57-1.33 (m, 1H), 1.32-1.22 (m, 3H), 1.16 (td, J = 8.1, 3.6 Hz, 2H). |

TABLE 14-continued

| Int-R | Cmpd Structure | Cmpd No. | MS/$^1$H NMR |
|---|---|---|---|
| 260f | 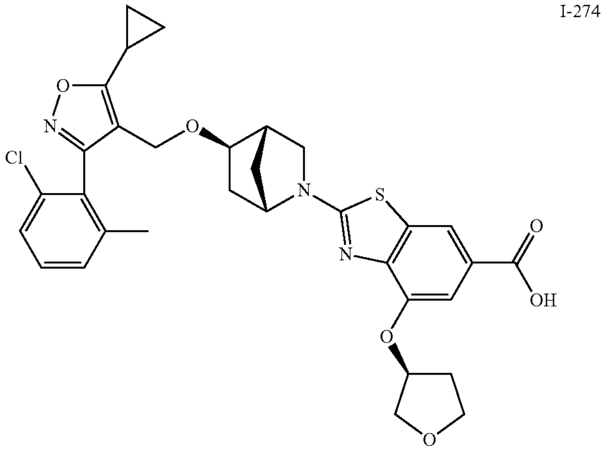 | I-274 | MS (ES. m/z): [M + 1] = 622.5. $^1$H NMR (400 MHz, $CD_3OD$) δ: 8.04 (d, J = 1.4 Hz, 1H), 7.57 (d, J = 1.4 Hz, 1H), 7.40 (dd, J = 6.2, 2.2 Hz, 2H), 7.35-7.27 (m, 1H), 5.30 (t, J = 5.3 Hz, 1H), 4.38 (dd, J = 11.7, 8.4 Hz, 2H), 4.23 (dd, J = 30.7, 11.7 Hz, 1H), 4.17-4.00 (m, 3H), 3.97-3.86 (m, 1H), 3.72-3.63 (m, 1H), 3.57 (s, 1H), 3.10 (s, 1H), 2.76-2.54 (m, 1H), 2.43-2.21 (m, 3H), 2.21-2.15 (m, 3H), 2.06 (ddd, J = 26.9, 14.0, 6.8 Hz, 1H), 1.74 (s, 1H), 1.64 (t, J = 9.5 Hz, 1H), 1.40 (dd, J = 73.5, 13.5 Hz, 1H), 1.23-1.16 (m, 4H). |
| 261e | 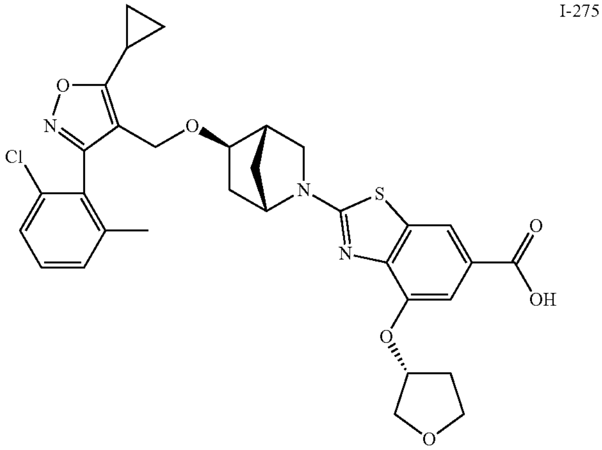 | I-275 | MS (ES, m/z): [M + 1] = 622.3 $^1$H NMR (400 MHz, $CD_3OD$) δ: 8.03 (t, J = 1.7 Hz, 1H), 7.56 (t, J = 1.6 Hz, 1H), 7.39 (dt, J = 5.9, 1.5 Hz, 2H), 7.30 (ddd, J = 9.0, 6.4, 2.8 Hz, 1H), 5.30 (tt, J = 4.3, 1.8 Hz, 1H), 4.38 (ddd, J = 11.5, 9.3, 1.6 Hz, 2H), 4.29-4.16 (m, 1H), 4.13-4.00 (m, 3H), 3.96-3.86 (m, 1H), 3.71-3.61 (m, 1H), 3.61-3.50 (m, 1H), 3.10 (s, 1H), 2.66 (dd, J = 61.2. 2.3 Hz, 1H), 2.42-2.21 (m, 3H), 2.20-2.13 (m, 3H), 2.05 (ddd, J = 26.9, 13.9, 6.9 Hz, 1H), 1.74 (s, 1H), 1.64 (t, J = 9.7 Hz, 1H), 1.54-1.25 (m, 1H), 1.23-1.14 (m, 4H). |

Example 221: 2-[(1S,4S,5R)-5-{[5-cyclopropyl-3-(2,6-dimethylphenyl)-1,2-oxazol-4-yl]methoxy}-2-azabicyclo[2.2.1]heptan-2-yl]-4-methyl-1,3-benzothiazole-6-carboxylic Acid (I-276)

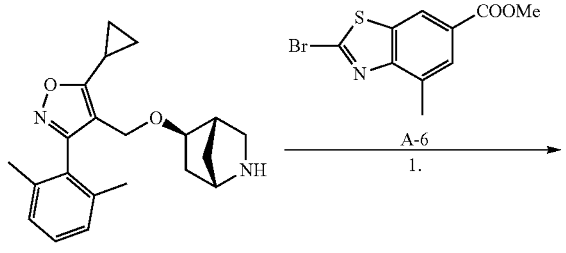

116h

-continued

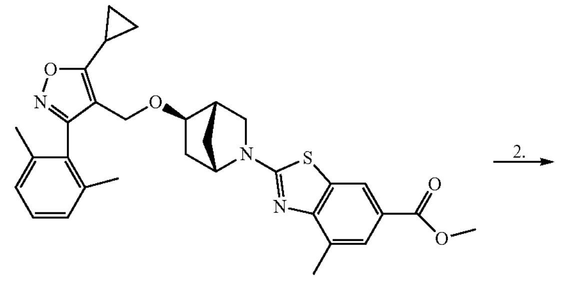

276a

-continued

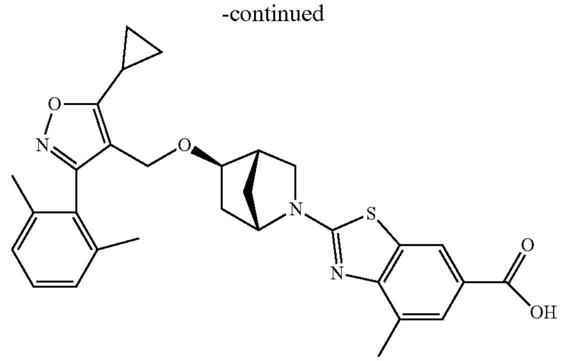

I-276

-continued

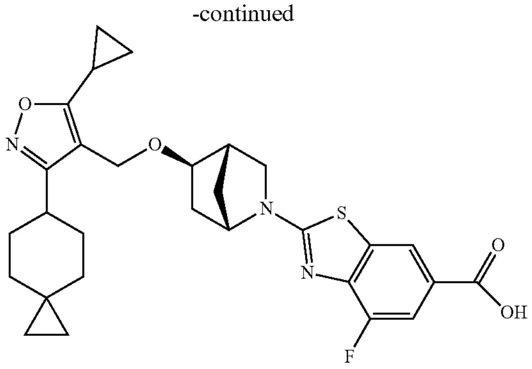

I-277

Bicyclic aryl compound I-276 was prepared from intermediates 16h (120 mg, 0.35 mmol, 1.00 equiv.) and bicyclic arylbromide A-6 (131.5 mg, 0.46 mmol, 1.30 equiv.) following the two-step procedure described in Preparative Example 218. After purification 2-[(1S,4S,5R)-5-[[5-cyclopropyl-3-(2,6-dimethylphenyl)-1,2-oxazol-4-yl]methoxy]-2-azabicyclo[2.2.1]heptan-2-yl]-4-methyl-1,3-benzothiazole-6-carboxylic acid I-276 (84.6 mg, 45%) was obtained as a white solid. $^1$HNMR (300 MHz, $CD_3OD$): δ 8.14 (dd, J=1.6, 0.7 Hz, 1H), 7.79 (dd, J=1.7, 0.9 Hz, 1H), 7.24 (t, J=7.5 Hz, 1H), 7.11 (dd, J=7.4, 4.6 Hz, 2H), 4.36 (s, 1H), 4.16 (q, J=11.4 Hz, 2H), 3.64-3.44 (m, 2H), 3.03 (d, J=10.1 Hz, 1H), 2.58 (s, 1H), 2.50 (s, 3H), 2.24 (p, J=6.8 Hz, 1H), 2.10-1.93 (m, 7H), 1.66 (d, J=1.8 Hz, 2H), 1.30 (dd, J=13.4, 10.4 Hz, 1H), 1.14 (d, J=6.8 Hz, 4H); MS (ES, m/z): [M+1]=530.2.

Example 222: 2-[(1S,4S,5R)-5-[(5-cyclopropyl-3-{spiro[2.5]octan-6-yl}-1,2-oxazol-4-yl)methoxy]-2-azabicyclo[2.2.1]heptan-2-yl]-4-fluoro-1,3-benzothiazole-6-carboxylic Acid (I-277)

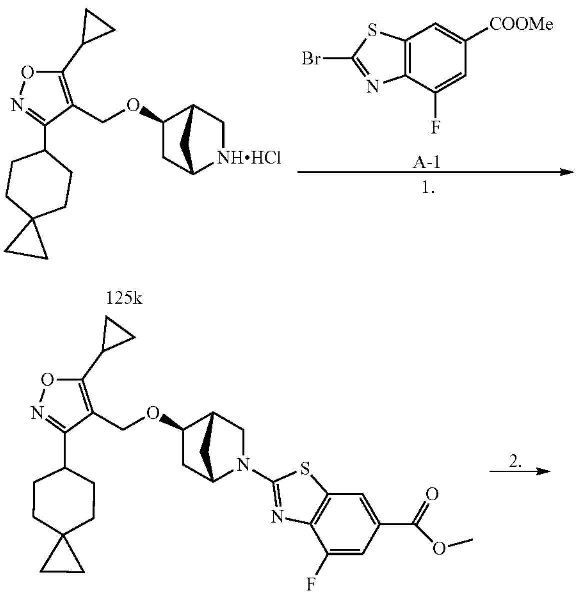

125k

277a

Step 1

To a solution of 4-((((1S,4S,5R)-2-azabicyclo[2.2.1]heptan-5-yl)oxy)methyl)-5-cyclopropyl-3-(spiro[2.5]octan-6-yl)isoxazole hydrochloride 125k (53.0 mg, 0.14 mmol) and methyl 2-bromo-4-fluorobenzo[d]thiazole-6-carboxylate A-1 (48.0 mg, 0.17 mmol) in DMA (2 mL) was added $Et_3N$ (40.0 μL, 0.28 mmol). The mixture was heated at 80° C., overnight. After cooling to room temperature, the mixture was partitioned between EtOAc and water. The organic layer was separated, dried ($MgSO_4$) and concentrated. The residue was purified by silica gel column chromatography to give methyl 2-((1S,4S,5R)-5-((5-cyclopropyl-3-(spiro[2.5]octan-6-yl)isoxazol-4-yl)methoxy)-2-azabicyclo[2.2.1]heptan-2-yl)-4-fluorobenzo[d]thiazole-6-carboxylate 277a (30 mg) as a clear oil.

Step 2

To a solution of methyl 2-((1S,4S,5R)-5-((5-cyclopropyl-3-(spiro[2.5]octan-6-yl)isoxazol-4-yl)methoxy)-2-azabicyclo[2.2.1]heptan-2-yl)-4-fluorobenzo[d]thiazole-6-carboxylate 277a (30.0 mg, 0.054 mmol) in MeOH (2 mL) was added NaOH (0.11 mL, 0.11 mmol, 1M in water). The mixture was stirred at room temperature overnight. The mixture was cooled to 0° C., and neutralized with a 1M aqueous HCl solution. The mixture was purified with prep-HPLC to give 2-((1S,4S,5R)-5-((5-cyclopropyl-3-(spiro[2.5]octan-6-yl)isoxazol-4-yl)methoxy)-2-azabicyclo[2.2.1]heptan-2-yl)-4-fluorobenzo[d]thiazole-6-carboxylic acid I-277 as a white solid (10.1 mg) after lyophilization. $^1$HNMR (400 MHz, $CD_3OD$): δ 8.15 (d, J=1.5 Hz, 1H), 7.67 (dd, J=11.5, 1.5 Hz, 1H), 4.48 (dd, J=24.9, 11.8 Hz, 2H), 3.86 (t, J=12.4 Hz, 1H), 3.63 (d, J=6.3 Hz, 1H), 3.23-3.08 (m, 1H), 2.96 (s, 1H), 2.76 (tt, J=11.9, 3.3 Hz, 1H), 2.29-2.10 (m, 2H), 1.99-1.82 (m, 6H), 1.78-1.67 (m, 3H), 1.10-0.96 (m, 6H), 0.35-0.23 (m, 4H); MS (ES, m/z): [M+1]=538.

Example 223: Synthesis of I-278 to I-283

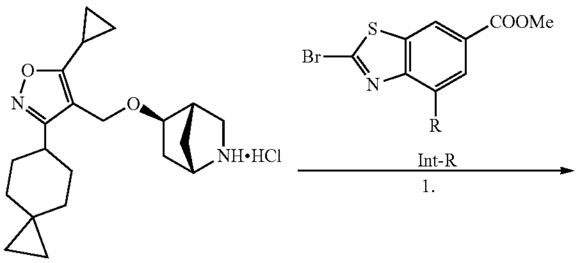

125k

-continued

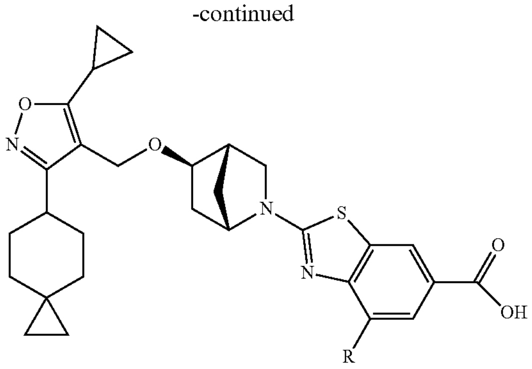

I-x

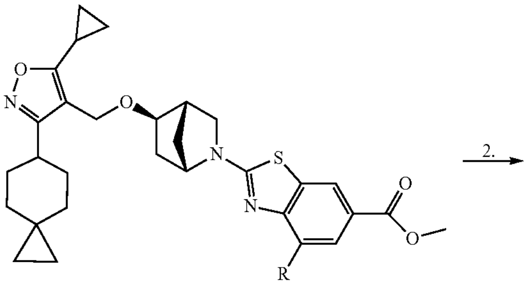

223a

Bicyclic aryl compounds of I-278 to I-283 were prepared from intermediate 125k and the corresponding bicyclic arylbromide Int-R following the two-step procedure described in Preparative Example 222. The data for compounds I-278 to I-283 is summarized in Table 15.

TABLE 15

| Int-R | Cmpd Structure | Cmpd No. | MS/$^1$H NMR |
|---|---|---|---|
| 259g | 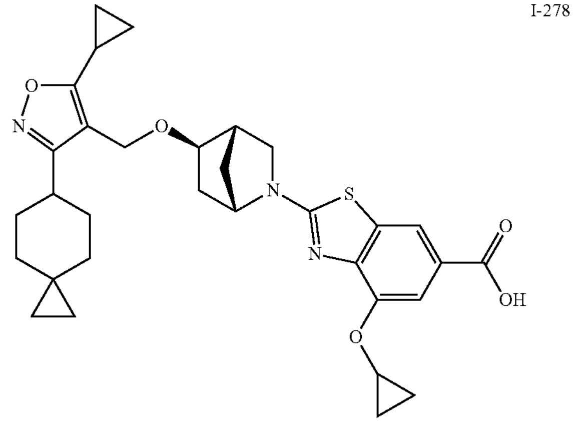 | I-278 | MS (ES, m/z): [M + 1] = 576. $^1$H NMR (300 MHz, $CD_3OD$) δ: 8.05 (d, J = 1.4 Hz, 1H), 7.95 (d, J = 1.5 Hz, 1H), 7.44-7.38 (m, 2H), 7.32 (s, 1H), 4.39 (dd, J = 11.7, 5.9 Hz, 2H), 4.23 (dd, J = 22.8, 11.7 Hz, 1H), 4.11-3.98 (m, 1H), 3.72-3.62 (m, 1H), 3.61-3.50 (m, 1H), 3.15-3.04 (m, 1H), 2.66 (d, J = 46.0 Hz, 1H), 2.35-2.24 (m, 1H), 2.19 (t, J = 0.9 Hz, 3H), 2.06 (ddd, J = 20.4, 13.8, 6.8 Hz, 1H), 1.78-1.58 (m, 2H), 1.55-1.25 (m, 1H), 1.24-1.17 (m, 4H), 0.92 (dt, J = 12.5, 4.2 Hz, 4H). |
| 254d | 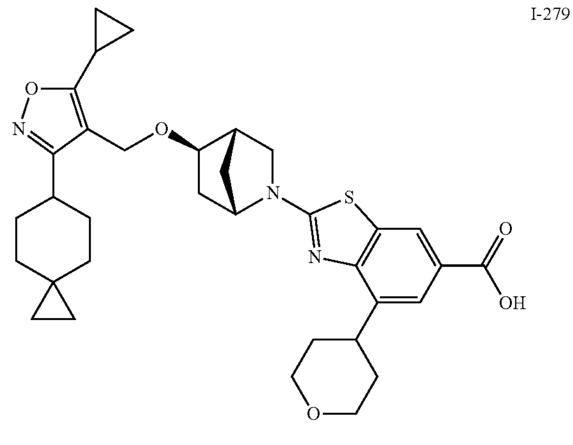 | I-279 | MS (ES, m/z): [M + 1] = 604. $^1$H NMR (400 MHz, $CD_3OD$) δ: 7.97 (d, J = 1.4 Hz, 1H), 7.85 (d, J = 1.4 Hz, 1H), 4.46 (m, 3H), 4.01-3.91 (m, 1H), 3.85 (d, J = 5.5 Hz, 1H), 3.59 (dd, J = 10.0, 3.9 Hz, 1H), 3.12 (d, J = 9.3 Hz, 1H), 2.92 (s, 1H), 2.80-2.70 (m, 1H), 2.17 (tdd, J = 13.5, 9.9, 4.9 Hz, 2H), 1.93 (m, 3H), 1.84 (m, 2H), 1.79-1.66 (m, 3H), 1.10-0.97 (m, 6H), 0.91-0.82 (m, 4H), 0.37-0.22 (m, 4H). |

TABLE 15-continued

| Int-R | Cmpd Structure | Cmpd No. | MS/$^1$H NMR |
|---|---|---|---|
| 252a | 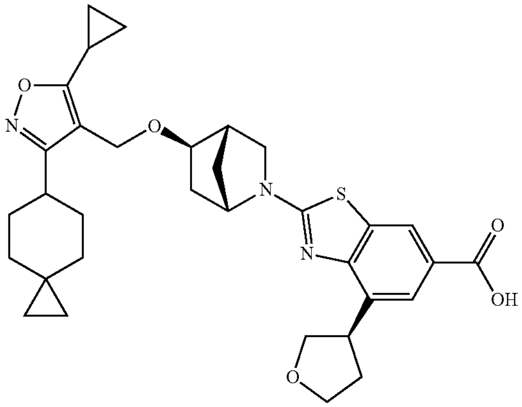 [SMILES: O=C(O)c1cc([C@H]2CCOC2)c2nc(N3C[C@@H]4C[C@H]3C[C@H]4OCc3c(C4CCC5(CC4)CC5)noc3C3CC3)sc2c1] | I-280 | MS (ES, m/z): [M + 1] = 590. $^1$H NMR (400 MHz, $CD_3OD$) δ: 8.19 (d, J = 1.7 Hz, 1H), 7.88 (d, J = 1.5 Hz, 1H), 4.47 (m, 3H), 4.24 (t, J = 7.8 Hz, 1H), 4.12 (td, J = 8.3, 5.0 Hz, 1H), 4.08-4.02 (m, 1H), 3.97 (dd, J = 15.6, 7.4 Hz, 1H), 3.86 (d, J = 6.2 Hz, 1H), 3.80 (t, J = 7.8 Hz, 1H), 3.61 (d, J = 6.2 Hz, 1H), 3.13 (s, 1H), 2.93 (s, 1H), 2.76 (t, J = 11.8 Hz, 1H), 2.40 (dd, J = 12.5, 4.5 Hz, 1H), 2.29-2.09 (m, 3H), 2.00-1.81 (m, 5H), 1.74 (t, J = 12.3 Hz, 3H), 1.11-0.96 (m, 6H), 0.35-0.22 (m, 4H). |
| 253a | 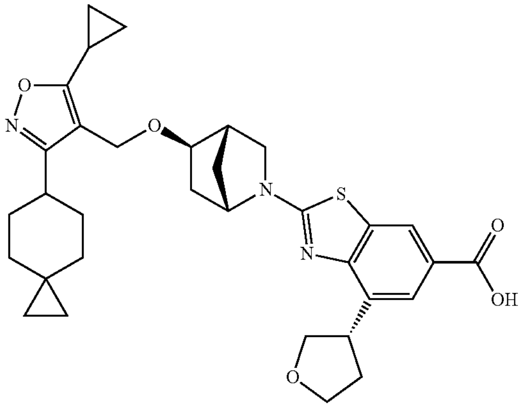 [SMILES: O=C(O)c1cc([C@@H]2CCOC2)c2nc(N3C[C@@H]4C[C@H]3C[C@H]4OCc3c(C4CCC5(CC4)CC5)noc3C3CC3)sc2c1] | I-281 | MS (ES, m/z): [M + 1] = 590. $^1$H NMR (400 MHz, $CD_3OD$) δ: 8.18 (d, J = 1.7 Hz, 1H), 7.88 (d, J = 1.6 Hz, 1H), 4.47 (m, 3H), 4.23 (t, J = 7.8 Hz, 1H), 4.12 (dt, J = 8.1, 4.0 Hz, 1H), 4.08-4.01 (m, 1H), 3.97 (dd, J = 15.6, 7.4 Hz, 1H), 3.86 (d, J = 6.0 Hz, 1H), 3.81 (t, J = 7.8 Hz, 1H), 3.66-3.55 (m, 1H), 3.13 (s, 1H), 2.93 (s, 1H), 2.76 (dd, J = 13.4, 10.2 Hz, 1H), 2.39 (dt, J = 15.3, 6.2 Hz, 1H), 2.29-2.10 (m, 3H), 1.91 (m, 5H), 1.74 (t, J = 12.2 Hz, 3H), 1.11-0.96 (m, 6H), 0.31 (dt, J = 14.1, 5.3 Hz, 4H). |
| 249d | 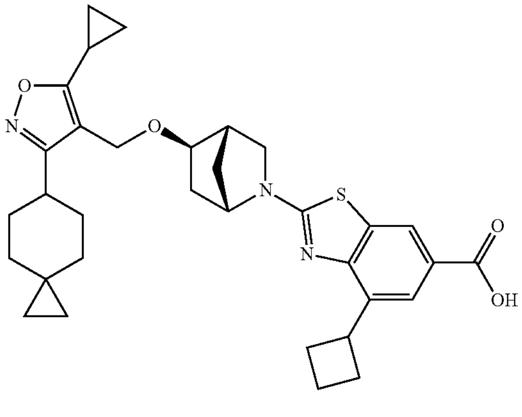 [SMILES: O=C(O)c1cc(C2CCC2)c2nc(N3C[C@@H]4C[C@H]3C[C@H]4OCc3c(C4CCC5(CC4)CC5)noc3C3CC3)sc2c1] | I-282 | MS (ES, m/z): [M + 1] = 574. $^1$H NMR (400 MHz, $CDCl_3$) δ: 8.21 (s, 1H), 7.97 (s, 1H), 4.38 (m, 3H), 4.11 (p, J = 8.9 Hz, 1H), 3.78 (d, J = 6.3 Hz, 1H), 3.60 (d, J = 5.9 Hz, 1H), 3.13 (s, 1H), 2.85 (s, 1H), 2.68 (t, J = 9.6 Hz, 1H), 2.43 (dd, J = 9.8, 5.8 Hz, 2H), 2.30 (dt, J = 21.0, 12.3 Hz, 3H), 2.09 (dt, J = 18.6, 9.2 Hz, 1H), 2.03-1.88 (m, 4H), 1.79 (dt, J = 29.1, 11.5 Hz, 6H), 1.25 (s, 1H), 1.16-1.08 (m, 2H), 1.08-0.94 (m, 4H), 0.37-0.19 (m, 4H). |

TABLE 15-continued

| Int-R | Cmpd Structure | Cmpd No. | MS/$^1$H NMR |
| --- | --- | --- | --- |
| 250d | 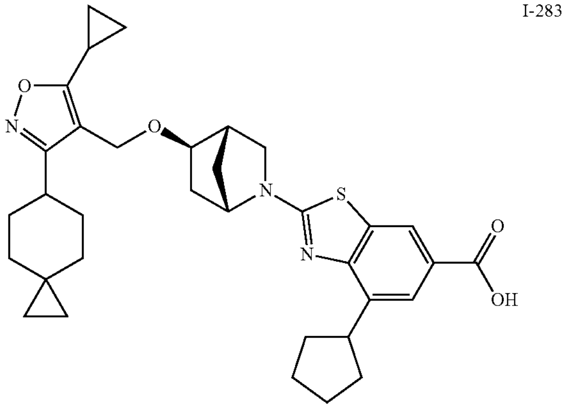 | I-283 | MS (ES, m/z): [M + 1] = 588. $^1$H NMR (400 MHz, $CDCl_3$) δ: 8.20 (s, 1H), 7.94 (s, 1H), 4.38 (m, 3H), 3.78 (d, J = 5.3 Hz, 1H), 3.73-3.53 (m, 2H), 3.12 (d, J = 8.9 Hz, 1H), 2.85 (s, 1H), 2.68 (dt, J = 11.3, 5.7 Hz, 1H), 2.27 (dd, J = 12.5, 5.7 Hz, 1H), 2.14 (s, 2H), 2.04-1.65 (m, 13H), 1.28 (d, J = 18.9 Hz, 3H), 1.17-1.09 (m, 2H), 1.07-0.96 (m, 5H), 0.38-0.20 (m, 4H). |

Example 224: 4-cyclobutyl-2-[(1R,4R,5S)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic Acid (I-284)

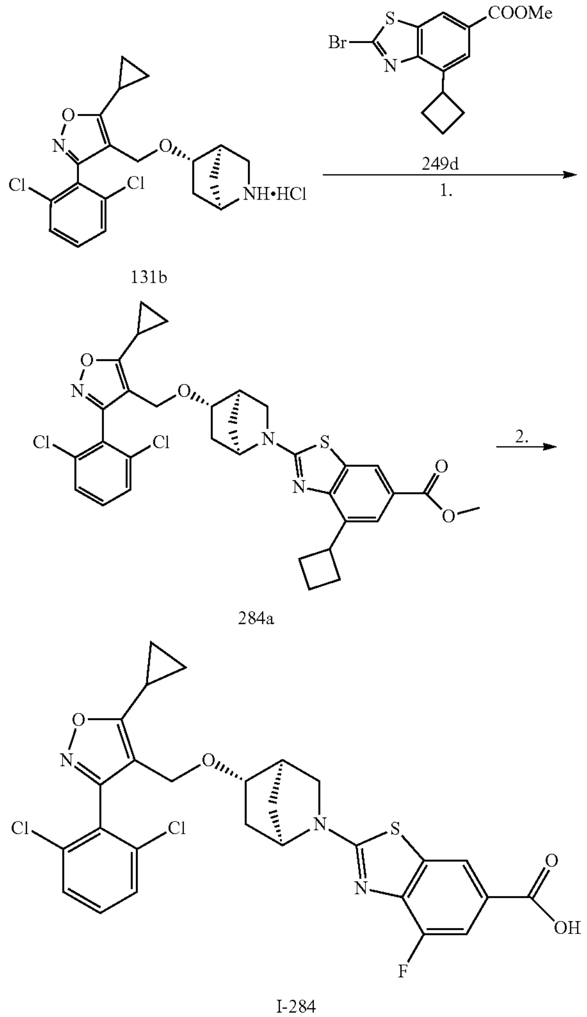

131b

284a

I-284

Step 1

Cesium carbonate (0.196 g, 0.60 mmol) was added to a stirred solution of 4-((((1R,4R,5S)-2-azabicyclo[2.2.1]heptan-5-yl)oxy)methyl)-5-cyclopropyl-3-(2,6-dichlorophenyl)isoxazole hydrochloride 131b (0.10 g, 0.24 mmol) and methyl 2-bromo-4-cyclobutylbenzo[d]thiazole-6-carboxylate 249d (0.078 g, 0.24 mmol) in DMA (2 mL). The mixture was heated at 60° C., under $N_2$ overnight. The mixture was cooled to room temperature and partitioned between EtOAc and water. The organic layer was separated, dried with $MgSO_4$, and concentrated. The residue was purified by silica gel column chromatography eluting with 20% EtOAc in hexanes to give methyl 4-cyclobutyl-2-((1R,4R,5S)-5-((5-cyclopropyl-3-(2,6-dichlorophenyl)isoxazol-4-yl)methoxy)-2-azabicyclo[2.2.1]heptan-2-yl)benzo[d]thiazole-6-carboxylate 284a (0.11 g) as a clear oil.

Step 2

A 1M aqueous solution of NaOH (0.35 mL, 0.35 mmol) was added to a solution of methyl 4-cyclobutyl-2-((1R,4R,5S)-5-((5-cyclopropyl-3-(2,6-dichlorophenyl)isoxazol-4-yl)methoxy)-2-azabicyclo[2.2.1]heptan-2-yl)benzo[d]thiazole-6-carboxylate 284a (0.11 g, 0.17 mmol) in MeOH (3 mL). The mixture was stirred at room temperature overnight, then neutralized with a 1M aqueous HCl solution, purified by prep-HPLC to afford 4-Cyclobutyl-2-((1R,4R,5S)-5-((5-cyclopropyl-3-(2,6-dichlorophenyl)isoxazol-4-yl)methoxy)-2-azabicyclo[2.2.1]heptan-2-yl)benzo[d]thiazole-6-carboxylic Acid I-284 (83.2 mg) as a colorless solid after lyophilization. $^1$HNMR (400 MHz, $CD_3OD$): δ 8.12 (d, J=1.7 Hz, 1H), 7.87 (dd, J=1.7, 0.8 Hz, 1H), 7.58-7.52 (m, 1H), 7.51-7.43 (m, 2H), 4.33 (t, J=6.6 Hz, 2H), 4.30 (m 1H), 4.14-4.01 (m, 1H), 3.61 (dd, J=6.8, 2.3 Hz, 1H), 3.46 (dd, J=9.9, 3.9 Hz, 1H), 2.99 (d, J=10.1 Hz, 1H), 2.56 (s, 1H), 2.47-2.36 (m, 2H), 2.32-2.16 (m, 3H), 2.08 (tdd, J=18.1, 9.9, 8.1 Hz, 1H), 1.92 (ddd, J=20.2, 12.4, 7.3 Hz, 2H), 1.65 (s, 2H), 1.37 (d, J=13.3 Hz, 1H), 1.20-1.12 (m, 4H); MS (ES, m/z): [M+1]=610.

Example 225: 4-cyclopentyl-2-[(1R,4R,5S)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic Acid (I-285)

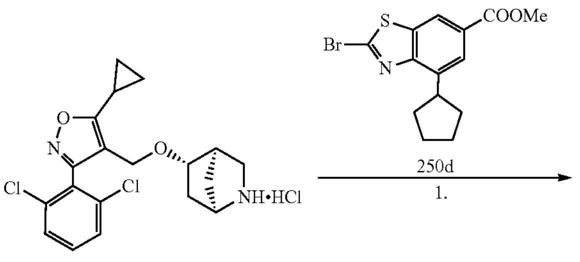

131b

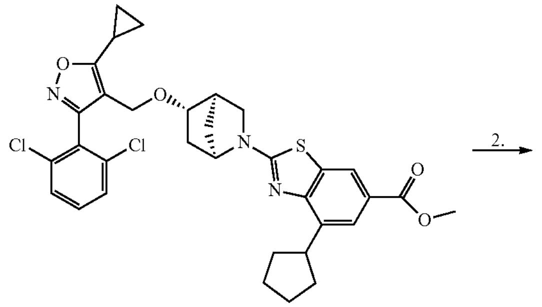

285a

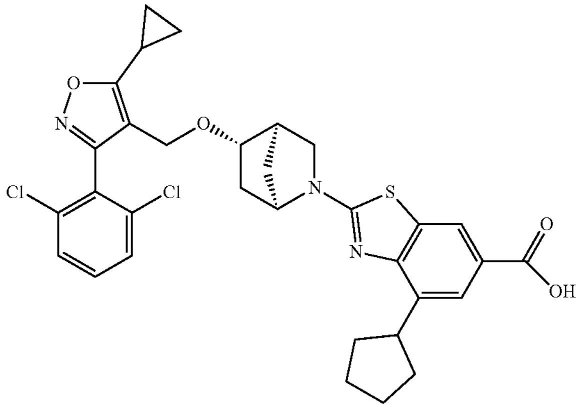

I-285

Following the procedure described in Preparative Example 224, by reacting with methyl 2-bromo-4-cyclopentyllbenzo[d]thiazole-6-carboxylate 250d, 4-((((1R,4R,5S)-2-azabicyclo[2.2.1]heptan-5-yl)oxy)methyl)-5-cyclopropyl-3-(2,6-dichlorophenyl)isoxazole hydrochloride 131 b was converted to 4-cyclopentyl-2-[(1R,4R,5S)-5-{[5-cyclopropyl-3-(2,6-dichlorophenyl)-1,2-oxazol-4-yl]methoxy}-2-azabicyclo[2.2.1]heptan-2-yl]-1,3-benzothiazole-6-carboxylic acid I-285. $^1$HNMR (400 MHz, $CD_3OD$): δ 8.10 (d, J=1.7 Hz, 1H), 7.85 (d, J=1.4 Hz, 1H), 7.55 (dd, J=7.1, 2.2 Hz, 1H), 7.50-7.42 (m, 2H), 4.33 (d, J=0.6 Hz, 2H), 4.28 (d, J=9.1 Hz, 1H), 3.63 (dd, J=14.1, 6.3 Hz, 2H), 3.47 (dd, J=9.9, 3.9 Hz, 1H), 2.99 (d, J=10.0 Hz, 1H), 2.57 (s, 1H), 2.32-2.20 (m, 1H), 2.10 (s, 2H), 1.97 (dd, J=13.5, 6.7 Hz, 1H), 1.89 (s, 2H), 1.73 (s, 4H), 1.65 (s, 2H), 1.37 (d, J=12.8 Hz, 1H), 1.22-1.12 (m, 4H); MS (ES, m/z): [M+1]=624.

Example 226: 2-[(1S,4S,5R)-5-{[5-cyclopropyl-3-(2,6-dichloro-4-methoxyphenyl)-1,2-oxazol-4-yl]methoxy}-2-azabicyclo[2.2.1]heptan-2-yl]-4-fluoro-1,3-benzothiazole-6-carboxylic Acid (I-286)

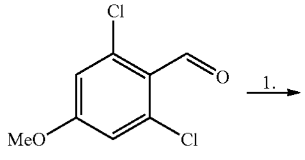

286a

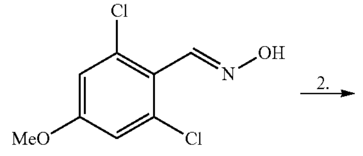

286b

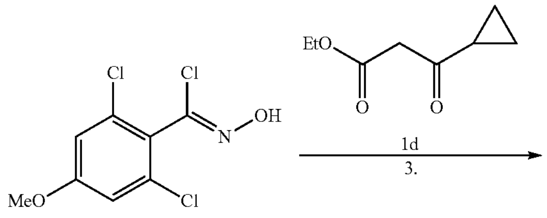

286c

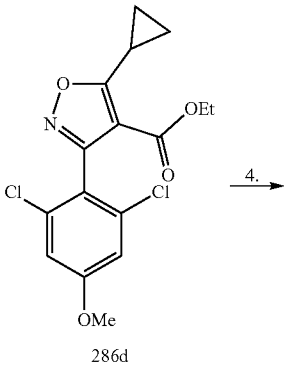

286d

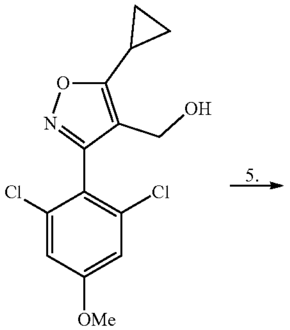

286e

-continued

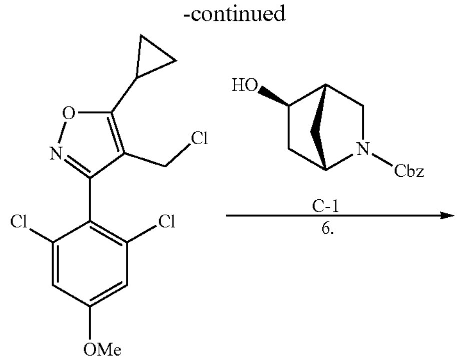

286f

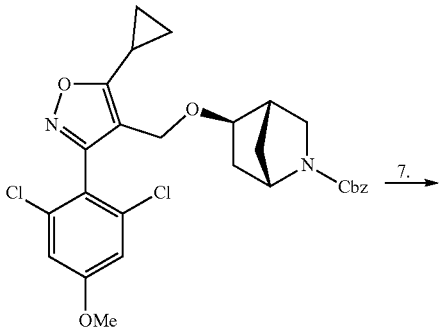

286g

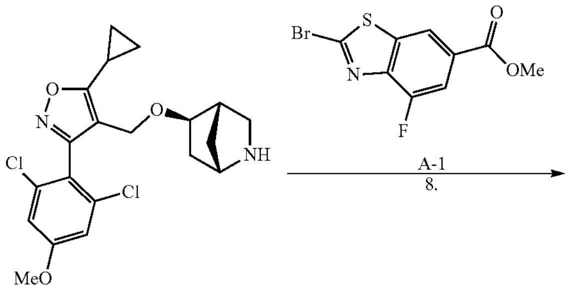

286h

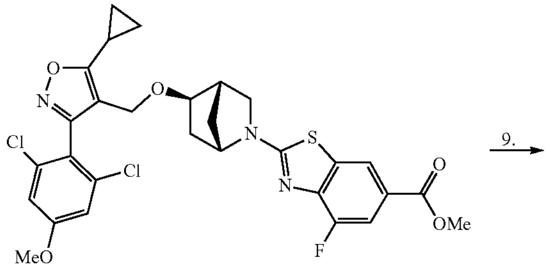

286i

-continued

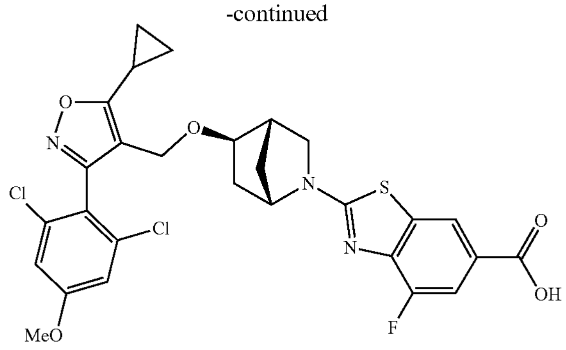

I-286

Step 1

To a solution of 2,3-dichloro-4-methoxybenzaldehyde 286a (7.5 g, 1 equiv.) in ethanol (120 mL) was added hydroxylamine hydrochloride (3.7 g, 1.2 equiv.) and sodium hydroxide (2.2 gm, 1.2 equiv.) in water (40 mL). The reaction was heated at 80° C., for 16 h, then ethanol was removed under reduced pressure. Additional water was added to the reaction mixture. The white solid was collected by filtration and washed with water, further dried to give oxime 286b (7.8 g), used as such in the next step.

Step 2

To a solution of the oxime 286b (7.8 gm, 1 equiv.) from step 1 above in DMF (80 mL) was added NCS (6.8 g, 1.5 equiv.) and the reaction mixture was stirred at room temperature for 16 h. The reaction mixture was diluted with ethyl acetate (200 mL) and washed with brine (100 mL×2). The organic layer was dried over sodium sulfate, filtered and concentrated under reduced pressure to give chloro oxime 286c (10.5 g, crude), which was used as such for next step.

Step 3

To a solution of chloro oxime 286c (10.5 g, 1 equiv.) in triethylamine (40 mL) was added ethyl 3-cyclopropyl-3-oxopropanoate 1d (9.6 g, 1.5 equiv.). The reaction mixture was stirred at room temperature for 16 h. Solvent was removed under reduced pressure and the residue was taken in ethyl acetate, washed with water, saline, dried over sodium sulfate, filtered and concentrated under the reduced pressure. The crude material was purified on ISCO eluting with 10-15% ethyl acetate in hexanes to give the ethyl 5-cyclopropyl-3-(2,6-dichloro-4-methoxyphenyl)isoxazole-4-carboxylate 286d (22 g). $^1$H-NMR (400 MHz, DMSO-d6) δ: 7.20 (s, 2H), 4.04 (q, J=7.1 Hz, 2H), 3.82 (s, 3H), 2.87-2.68 (m, 1H), 1.32-1.13 (m, 4H), 0.97 (t, J=7.1 Hz, 3H).

Step 4

To a solution of ethyl 5-cyclopropyl-3-(2,6-dichloro-4-methoxyphenyl)isoxazole-4-carboxylate 286d (7.5 g, 1.0 equiv.) in THF (75 mL) was added a 1M solution of DIBAL in $CH_2Cl_2$ (63 mL, 3 equiv.) dropwise. The reaction mixture was stirred at room temperature for 16 h, and quenched by the addition of MeOH (30 mL) and a 2M aqueous HCl solution at 0° C. The mixture was diluted with ethyl acetate and filtered through a pad of Celite. The organic layer was washed with saline, dried over sodium sulfate, filtered and concentrates to give (5-cyclopropyl-3-(2,6-dichloro-4-methoxyphenyl)isoxazol-4-yl)methanol 286e (6.5 g) as a white solid after treatment with ether. $^1$H-NMR (400 MHz, DMSO-d6) δ: 7.24 (s, 2H), 4.93 (t, J=5.1 Hz, 1H), 4.20 (d, J=5.1 Hz, 2H), 3.87 (s, 3H), 2.42-2.21 (m, 1H), 1.17-1.02 (m, 4H).

Step 5

To a solution of benzotriazole (2.5 gm, 1 equiv.) in $CH_2Cl_2$ (20 mL) was added $SOCl_2$ (1.5 mL, 0.4 equiv.) at 0° C., and the mixture was warmed to room temperature and continued to stir for 1 hr. A solution of (5-cyclopropyl-3-(2,6-dichloro-4-methoxyphenyl)isoxazol-4-yl)methanol 286e (6.5 g) in $CH_2Cl_2$ (30 mL) was added at 0° C. After addition, the reaction mixture was warmed to room temperature and stirred for another 2 h. Water (150 mL) was added, the organic layer was separated and washed with a saturated aq. $NaHCO_3$ solution, saline, dried over sodium sulfate, filtered and concentrated under the reduced pressure. The crude residue was purified by silica gel chromatography using 10-15% ethyl acetate in hexanes as eluent to give the 4-(chloromethyl)-5-cyclopropyl-3-(2,6-dichloro-4-methoxyphenyl)isoxazole 286f (5.3 g). $^1$H-NMR (400 MHz, DMSO-d6) δ: 7.28 (s, 2H), 4.54 (s, 2H), 3.88 (s, 3H), 2.47-2.34 (m, 1H), 1.27-1.07 (m, 4H).

Step 6

Sodium hydride (0.2 g, 60% oil in emulsion, 1.2 equiv.) was added to a stirred solution of (1S,4S,5R)-benzyl 5-hydroxy-2 azabicyclo[2.2.1]heptane-2-carboxylate C-1 (1.0 g, 1.0 equiv.) in DMF (10 mL) at 0° C. The reaction mixture was stirred at the same temperature for 0.5 h and 4-(chloromethyl)-5-cyclopropyl-3-(2,6-dichloro-4-methoxyphenyl)isoxazole 286f (1.5 g, 1.2 equiv.) in DMF (5.0 mL) was added dropwise to the reaction mixture. The reaction mixture was warmed to room temperature and heated at 60° C. for 16 h. Upon cooling to room temperature, the mixture was diluted with ethyl acetate, washed with cold water, saline, dried over $Na_2SO_4$, filtered and concentrated under the reduced pressure. The crude material was purified by Isco silica gel column chromatography and the desired compound was eluted with 30-35% ethyl acetate in hexanes to afford (1S,4S,5R)-benzyl 5-((5-cyclopropyl-3-(2,6-dichloro-4-methoxyphenyl)isoxazol-4-yl)methoxy)-2-azabicyclo[2.2.1]heptane-2-carboxylate 286g (1.2 g) $^1$H-NMR (400 MHz. DMSO-d6) δ: 7.33 (d, J=7.8 Hz, 5H), 7.28-7.14 (m, 2H), 5.01 (s, 2H), 4.21 (s, 2H), 4.03 (d, J=14.8 Hz, 1H), 3.85 (s, 3H), 3.51 (s, 1H), 3.13 (dd, J=23.9 & 10.1 Hz, 1H), 2.73 (dd, J=23.1&8.5 Hz, 1H), 2.39 (s, 1H), 2.30 (dd, J=8.2 & 4.7 Hz, 1H), 1.74 (bs, 1H), 1.36 (s, 2H), 1.22-1.04 (m, 5H).

Step 7

To a solution of (1S,4S,5R)-benzyl 5-((5-cyclopropyl-3-(2,6-dichloro-4-methoxyphenyl)isoxazol-4 yl)methoxy)-2-azabicyclo[2.2.1]heptane-2-carboxylate 286g (1.2 g, 1 equiv.) in $CH_2Cl_2$ (20 mL) was added a 1M solution of trimethylsilyl iodide in DCM (4.0 mL, 2 equiv.). The mixture was stirred at room temperature for 1 h and concentrated under vacuum. The residue was treated with a 2M solution of HCl in ether (20.0 mL) to give a sticky hydroiodide compound. It was triturated with anhydrous ether (×3) and dried under high vacuum to give crude (((1S,4S,5R)-2-azabicyclo[2.2.1]heptan-5-yloxy)methyl)-5-cyclopropyl-3-(2,6-dichloro-4-methoxyphenyl)isoxazole hydroiodide salt 286h (1.1 g, purity ~90%) as a light yellow amorphous solid. MS (ES, m/z): [M+1]=409.18.

Step 8

A suspension of 4-(((1S,4S,5R)-2-azabicyclo[2.2.1]heptan-5-yloxy)methyl)-5-cyclopropyl-3-(2,6-dichlorophenyl) isoxazole hydroiodide 286h (0.45 g, 1 equiv.), methyl 2-bromo-4-fluorobenzo[d]thiazole-6-carboxylate A-1 (0.3 g, 1 equiv.) and cesium carbonate (0.82 gm, 2 equiv.) in DMA (10 mL) was heated at 65° C., for 16 h. The reaction mixture was cooled to room temperature and diluted with ethyl acetate. The organic layer was washed with water, saline, dried over sodium sulfate, filtered and concentrated under reduced pressure. The crude material was purified by silica gel column chromatography using 30-40% ethyl acetate in hexanes as gradient to give the methyl 2-((1S,4S,5R)-5-((5-cyclopropyl-3-(2,6-dichloro-4-methoxyphenyl)isoxazol-4-yl)methoxy)-2-azabicyclo[2.2.1]heptan-2-yl)-4-fluorobenzo[d]thiazole-6-carboxylate 286i (0.51 g). $^1$H-NMR (400 MHz, DMSO-d6) δ: 8.25 (d, J=1.6 Hz, 1H), 7.61 (dd, J=11.5 & 1.6 Hz, 1H), 7.23 (dd, J=12.5 & 2.5 Hz, 2H), 4.26 (s, 2H), 3.86 (s, 4H), 3.84 (s, 3H), 3.62 (d, J=5.8 Hz, 1H), 3.46-3.44 (m, 1H), 2.59 (s, 1H), 2.33 (td, J=8.4 & 4.2 Hz, 1H), 191 (dd, J=13.2 & 6.9 Hz, 1H), 1.59 (dd, J=34.9 & 9.7 Hz, 2H), 1.35 (d, J=13.2 Hz, 1H), 1.23-1.01 (m, 5H).

Step 9

Methyl carboxylate 286i (0.15 g) from step 8 above was dissolved in methanol (10 mL) and treated with a 1M NaOH aqueous solution (0.5 mL). The mixture was heated at 60° C., for 3 h; then, it was neutralized with IR-120 (H+) resin, filtered and concentrated under the reduced pressure. The residue was purified on Semi-prep HPLC using 30-90% acetonitrile in 30 min, method. The fractions corresponding to the desired product were lyophilized to afford 2-((1S,4S,5R)-5-((5-cyclopropyl-3-(2,6-dichloro-4-methoxyphenyl) isoxazol-4-yl)methoxy)-2-azabicyclo[2.2.1]heptan-2-yl)-4-fluorobenzo[d]thiazole-6-carboxylic acid I-286 (87 mg). $^1$H-NMR (400 MHz, DMSO-$d_6$) δ: 8.20 (d, J=1.5 Hz, 1H), 7.58 (dd, J=11.5 & 1.5 Hz, 1H), 7.24 (dd, J=16.2 & 2.5 Hz, 2H), 4.26 (s, 3H), 3.85 (s, 3H), 3.62 (d, J=5.8 Hz, 1H), 3.45 (d, J=6.4 Hz, 1H), 2.59 (s, 1H), 2.33 (td, J=8.3 & 5.2 Hz, 1H), 1.91 (dd, J=12.4 & 5.8 Hz, 1H), 1.59 (dd, J=34.7 & 9.9 Hz, 2H), 1.35 (d, J=13.3 Hz, 1H), 1.23-0.99 (m, 5H). MS (ES, m/z): [M+1]=604.27.

Example 227: 2-[(1S,4S,5R)-5-{[5-cyclopropyl-3-(2,6-dichloro-4-hydroxyphenyl)-1,2-oxazol-4-yl]methoxy}-2-azabicyclo[2.2.1]heptan-2-yl]-4-fluoro-1,3-benzothiazole-6-carboxylic Acid (I-287)

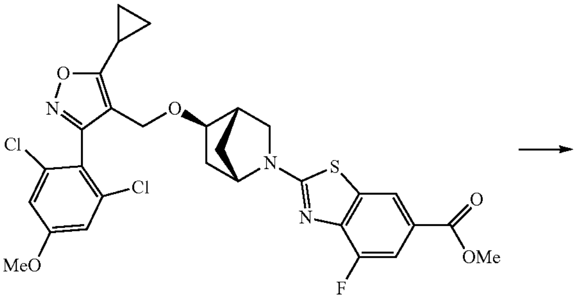

286i

-continued

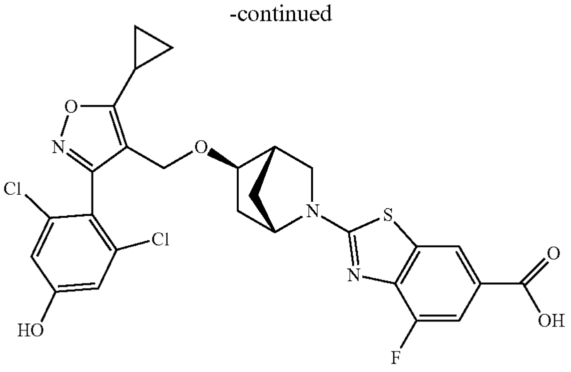

I-287

Boron tribromide was added to a stirred solution of methyl 2-((1S,4S,5R)-5-((5-cyclopropyl-3-(2,6-dichloro-4-methoxy phenyl)isoxazol-4-yl)methoxy)-2-azabicyclo [2.2.1]heptan-2-yl)-4-fluorobenzo[d]thiazole-6-carboxylate 286i (0.25 g, 1 equiv.) in $CH_2Cl_2$ (15 mL) at 0° C. The reaction mixture was warmed to room temperature and continued to stir for another 2 h. The excess reagent was quenched with methanol and the mixture was concentrated under the reduced pressure. The residue was dissolved in ethyl acetate, washed with saline, aq. $NaHCO_3$ solution, water successively, dried over $Na_2SO_4$, filtered and concentrated in vacuo to a residue which was used in the next step.

The above residue was dissolved in methanol (10 mL) and treated with a 1M aqueous NaOH (1.0 mL) solution. The mixture was heated at 70° C., for 16 h, then neutralized with IR-120 (H+) resin, filtered and concentrated under the reduced pressure. The residue was purified on Semi-prep HPLC using 30-90% acetonitrile in 30 min, method. The fractions corresponding to the desired product were lyophilized to afford 2-((1S,4S,5R)-5-((5-cyclopropyl-3-(2,6-dichloro-4-hydroxyphenyl)isoxazol-4-yl)methoxy)-2-azabicyclo[2.2.1]heptan-2-yl)-4-fluorobenzo[d]thiazole-6-carboxylic Acid I-287 (116 mg). $^1$H-NMR (400 MHz, DMSO-d6) δ: 8.19 (d, J=1.5 Hz, 1H), 7.57 (dd, J=11.5 & 1.5 Hz, 1H), 6.98 (dd, J=11.5 & 2.3 Hz, 2H), 4.23 (bs, 3H), 3.62

(d, J=5.8 Hz, 1H), 3.45 (d, J=6.3 Hz, 1H), 2.59 (s, 1H), 2.33-2.23 (m, 1H), 1.91 (dd, J=13.4 & 6.4 Hz, 1H), 1.59 (dd, J=26.3 & 9.8 Hz, 2H), 1.33 (d, J=13.4 Hz, 1H), 1.18-0.97 (m, 5H); MS (ES, m/z): [M+1]=590.16.

Example 228: Synthesis of I-288 to I-290

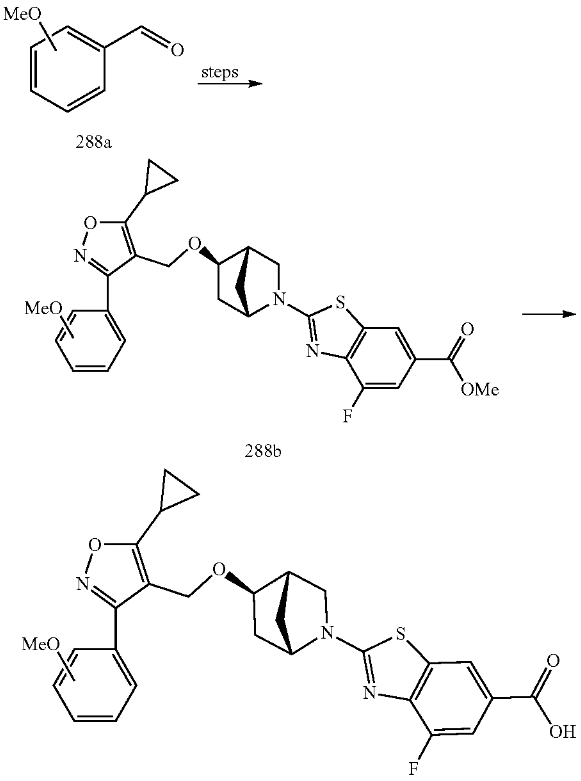

288a

288b

I-x

Following the procedures described in Preparative Example 226, by using appropriately substituted methoxyphenyl aldehyde 288a, compounds of I-288 to I-290 were prepared. The data is summarized in Table 16.

TABLE 16

| 288a | Cmpd Structure | Cmpd No. | MS/$^1$H NMR |
|---|---|---|---|
| 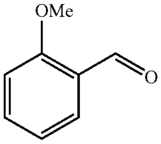 | 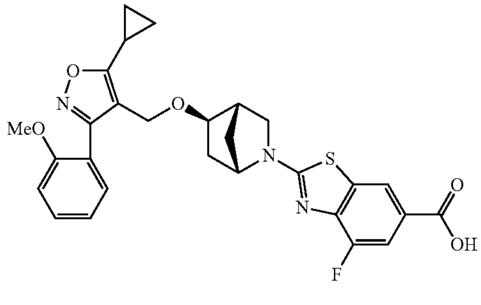 [SMILES: COc1ccccc1-c1noc(C2CC2)c1CO[C@@H]1C[C@@H]2C[C@H]1CN2c1nc2c(F)cc(C(=O)O)cc2s1] | I-289 | MS (ES, m/z): [M + 1] = 536. $^1$H NMR (400 MHz, DMSO-d6, $D_2O$) δ: 8.20 (d, J = 1.4 Hz, 1H), 7.58 (dd, J = 11.5, 1.5 Hz, 1H), 7.51-7.45 (m, 1H), 7.29 (dd, J = 7.5, 1.7 Hz, 1H), 7.15 (d, J = 8.4 Hz, 1H), 7.02 (dd, J = 7.9, 7.1 Hz, 1H), 4.30 (dd, J = 24.7, 11.9 Hz, 3H), 3.78 (s, 3H), 3.60 (d, J = 6.0 Hz, 1H), 3.43 (s, 1H), 2.58 (s, 1H), 2.26 (td, J = 8.5, 4.3 Hz, 1H), 1.87 (d, J = 8.2 Hz, 1H), 1.61 (d, J = 10.3 Hz, 1H), 1.52 (d, J = 9.7 Hz, 1H), 1.36 (d, J = 13.9 Hz, 1H), 1.14-1.00 (m, 4H). |

TABLE 16-continued

| 288a | Cmpd Structure | Cmpd No. | MS/$^1$H NMR |
|---|---|---|---|
| 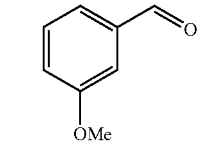 | 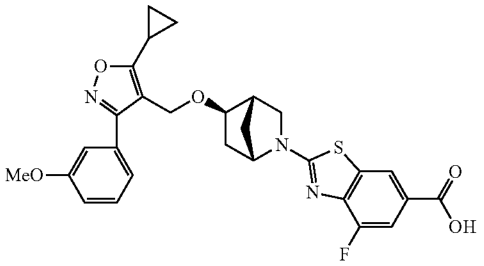 [SMILES: COc1cccc(-c2noc(C3CC3)c2CO[C@@H]2C[C@@H]3C[C@H]2CN3c2nc3c(F)cc(C(=O)O)cc3s2)c1] | I-289 | MS (ES, m/z): [M + 1] = 536. $^1$H NMR (400 MHz, $CD_3OD$) δ: 8.15 (d, J = 1.5 Hz, 1H), 7.71-7.65 (m, 1H), 7.43-7.37 (m, 1H), 7.30 (tt, J = 2.5, 1.3 Hz, 2H), 7.09-7.03 (m, 1H), 4.51 (dd, J = 24.7, 11.8 Hz, 3H), 3.88 (d, J = 6.2 Hz, 1H), 3.84 (s, 3H), 3.60 (d, J = 7.0 Hz, 1H), 3.13 (s, 1H), 2.93 (s, 1H), 2.31-2.14 (m, 2H), 1.96 (t, J = 9.0 Hz, 1H), 1.84 (d, J = 10.0 Hz, 1H), 1.74 (d, J = 13.9 Hz, 1H), 1.20-1.10 (m, 4H). |
| 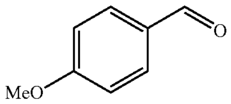 | 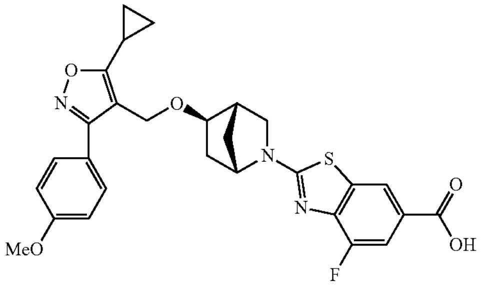 [SMILES: COc1ccc(-c2noc(C3CC3)c2CO[C@@H]2C[C@@H]3C[C@H]2CN3c2nc3c(F)cc(C(=O)O)cc3s2)cc1] | I-290 | MS (ES, m/z): [M + 1] = 536. $^1$H NMR (400 MHz, $CD_3OD$) δ: 8.15 (d, J = 1.5 Hz, 1H), 7.71-7.63 (m, 3H), 7.07-7.00 (m, 2H), 4.50 (q, J = 11.9 Hz, 3H), 3.88 (d, J = 5.9 Hz, 1H), 3.84 (s, 3H), 3.60 (d, J = 6.9 Hz, 1H), 3.13 (s, 1H), 2.92 (s, 1H), 2.29-2.14 (m, 2H), 1.96 (d, J = 10.0 Hz, 1H), 1.85 (d, J = 10.6 Hz, 1H), 1.74 (d, J = 13.9 Hz, 1H), 1.18-1.06 (m, 4H). |

Example 229: Synthesis of I-291 to I-293

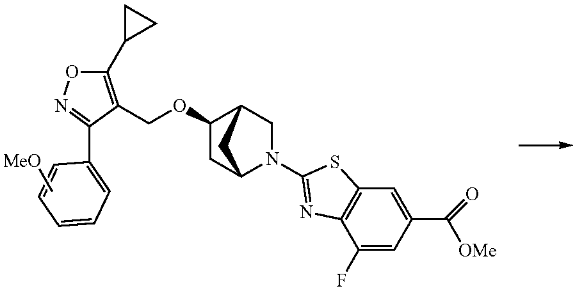

288b

-continued

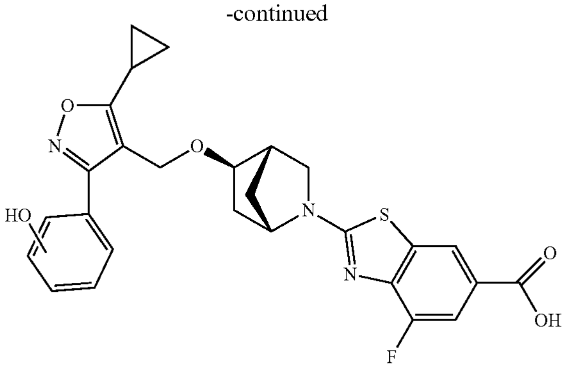

I-x

Following the procedures described in Preparative Example 227, by using appropriately substituted methoxyphenyl intermediate 288b, available from Preparative Example 228, compounds of I-291 to I-293 were prepared. The data is summarized in Table 17.

TABLE 17

| 288b | Cmpd Structure | Cmpd No. | MS/$^1$H NMR |
|---|---|---|---|
| 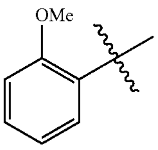 [SMILES: *c1ccccc1OC] | 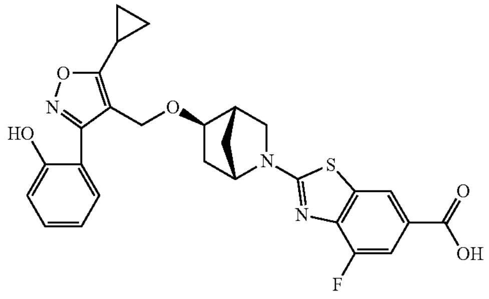 [SMILES: O=C(O)c1cc(F)c2nc(N3C[C@@H]4C[C@H]3C[C@H]4OCc3c(-c4ccccc4O)noc3C3CC3)sc2c1] | I-291 | MS (ES, m/z): [M + 1] = 522. $^1$H NMR (400 MHz, DMSO-d6, $D_2O$) δ: 8.13 (d, J = 1.5 Hz, 1H), 7.66 (dd, J = 11.5, 1.5 Hz, 1H), 7.40 (dd, J = 7.7, 1.7 Hz, 1H), 7.33-7.26 (m, 1H), 6.96-6.88 (m, 2H), 4.51 (q, J = 12.0 Hz, 3H), 3.73 (d, J = 5.4 Hz, 1H), 3.49 (s, 1H), 3.0 (m, 1H), 2.72 (s, 1H), 2.25 (dd, J = 13.4, 6.8 Hz, 1H), 2.05 (d, J = 12.9 Hz, 1H), 1.76 (t, J = 12.2 Hz, 2H), 1.57 (d, J = 13.2 Hz, 1H), 1.16-1.00 (m, 4H). |

TABLE 17-continued

| 288b | Cmpd Structure | Cmpd No. | MS/$^1$H NMR |
|---|---|---|---|
| 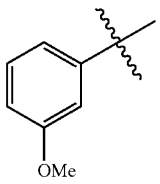 [SMILES: *c1cccc(OC)c1] | 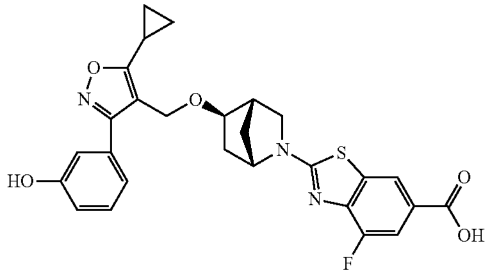 [SMILES: O=C(O)c1cc(F)c2nc(N3C[C@@H]4C[C@H]3C[C@H]4OCc3c(-c4cccc(O)c4)noc3C3CC3)sc2c1] | I-292 | MS (ES, m/z): [M + 1] = 522. $^1$H NMR (400 MHz, $CD_3OD$) δ: 8.14 (d, J = 1.5 Hz, 1H), 7.67 (dd, J = 11.5, 1.5 Hz, 1H), 7.30 (t, J = 7.8 Hz, 1H), 7.20-7.09 (m, 2H), 6.91 (ddd, J = 8.2, 2.5, 1.0 Hz, 1H), 4.49 (dd, J = 22.6, 11.7 Hz, 3H), 3.87 (d, J = 6.2 Hz, 1H), 3.58 (s, 1H), 3.13 (s, 1H), 2.91 (s, 1H), 2.31-2.13 (m, 2H), 2.01-1.91 (m, 1H), 1.78 (dd, J = 35.7, 12.3 Hz, 2H), 1.14 (ddd, J = 5.1, 4.3, 1.9 Hz, 4H). |
| 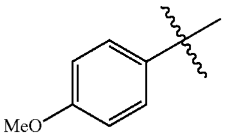 [SMILES: *c1ccc(OC)cc1] | 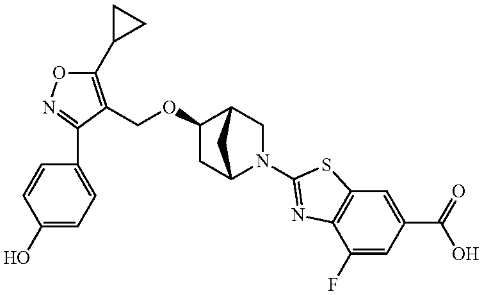 [SMILES: O=C(O)c1cc(F)c2nc(N3C[C@@H]4C[C@H]3C[C@H]4OCc3c(-c4ccc(O)cc4)noc3C3CC3)sc2c1] | I-293 | MS (ES, m/z): [M + 1] = 522. $^1$H NMR (400 MHz, $CD_3OD$) δ: 8.18 (d, J = 1.5 Hz, 1H), 7.71 (dd, J = 11.4, 1.5 Hz, 1H), 7.60-7.54 (m, 2H), 6.92-6.85 (m, 2H), 4.59-4.43 (m, 3H), 3.89 (d, J = 6.1 Hz, 1H), 3.62 (s, 1H), 3.21-3.09 (m, 1H), 2.95 (s, 1H), 2.23 (dd, J = 13.5, 5.6 Hz, 3H), 1.98 (d, J = 10.2 Hz, 1H), 1.87 (d, J = 1.11 Hz, 1H), 1.75 (d, J = 13.3 Hz, 1H), 1.13 (td, J = 4.8. 1.9 Hz, 4H). |

Example 230: 2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-4-ethyl-1,3-benzothiazole-6-carboxylic Acid (I-294)

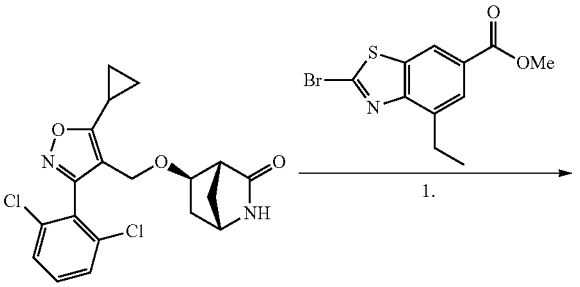

244g

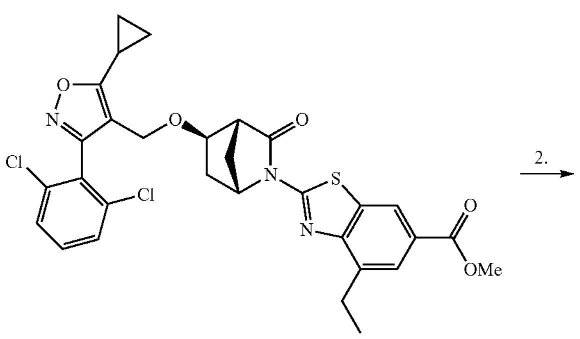

294a

-continued

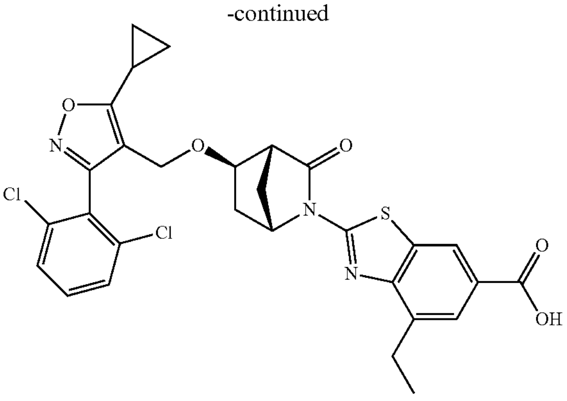

I-294

Step 1

To a 100 mL round-bottom flask purged with and maintained under an inert atmosphere of nitrogen was added methyl 2-bromo-4-ethyl-1,3-benzothiazole-6-carboxylate (128 mg, 0.43 mmol, 1.75 equiv.), a solution of (1S,4R,5R)-5-[5-cyclopropyl-3-(2,6-dichlorophenyl)-1,2-oxazol-4-yl] methoxy-2-azabicyclo[2.2.1]heptan-3-one 244g (100 mg, 0.25 mmol, 1.00 equiv.) in p-xylene (30 mL), CuCl (25 mg, 0.26 mmol, 1.00 equiv.), potassium carbonate (59 mg, 0.43 mmol, 1.66 equiv.), and TDA-1 (Tris(dioxa-3,6-heptyl) amine, 24 mg, 0.07 mmol, 0.29 equiv.). The resulting mixture was heated at 145° C., overnight. After cooling to room temperature, the mixture was diluted with 40 mL of EA, washed with brine (30 mL×2), dried over anhydrous sodium sulfate and concentrated under vacuum. The residue was purified by silica gel column chromatography eluting with ethyl acetate/petroleum ether (1:4) to afford methyl 2-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-4-ethyl-1,3-benzothiazole-6-carboxylate 294a (70 mg, 45%) as a yellow oil.

Step 2

To a 50 mL round-bottom flask purged with and maintained under an inert atmosphere of nitrogen was added methyl 2-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-4-ethyl-1,3-benzothiazole-6-carboxylate 294a (100 mg, 0.16 mmol, 1.00 equiv.), pyridine (4 mL), and LiI (220 mg, 1.64 mmol, 10.00 equiv.). The resulting mixture was heated overnight at 125° C. The mixture was diluted with 40 mL of EA after cooling to room temperature, and the pH value of the solution was adjusted to 2 using a 2M hydrogen chloride aqueous solution. The mixture was washed with brine (30 mL×2), dried over anhydrous sodium sulfate and concentrated under vacuum. The crude product was purified by Prep-HPLC using the following conditions: Column, XBridge Prep OBD C18 Column, 19*250 mm, 5 um; mobile phase, Water (0.05% TFA) and ACN (47.0% ACN up to 65.0% in 8 min); Detector, uv 220 nm. After purification 2-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-4-ethyl-1,3-benzothiazole-6-carboxylic acid I-294 (53.8 mg, 55%) was obtained as a yellow solid. $^1$H-NMR (400 MHz, $CD_3OD$) δ: 8.38 (d, J=1.7 Hz, 1H), 7.93 (d, J=1.7 Hz, 1H), 7.64-7.45 (m, 3H), 5.21 (s, 1H), 4.42 (s, 2H), 3.91 (d, J=6.8 Hz, 1H), 3.17-2.98 (m, 3H), 2.36-2.23 (m, 1H), 2.24-2.06 (m, 2H), 1.93 (d, J=10.2 Hz, 1H), 1.68 (d, J=13.6 Hz, 1H), 1.36 (t, J=7.5 Hz, 3H), 1.26-1.16 (m, 4H). MS (ES, m/z): [M+1]=598.20.

Example 231: Synthesis of I-295 to I-302

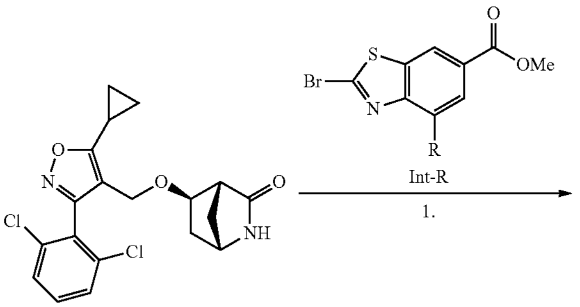

Int-R

244g

-continued

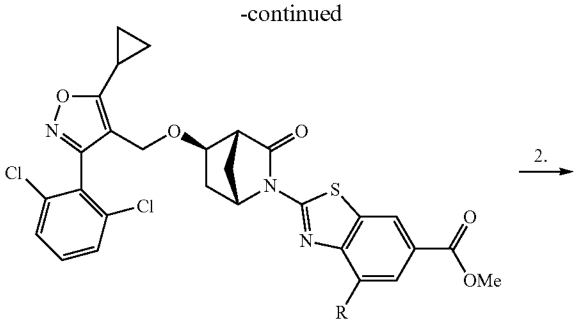

295a

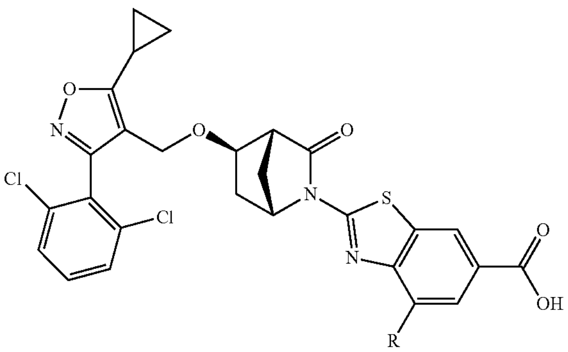

I-x

Bicyclic aryl compounds of 1-295 to 1-302 were prepared from intermediate 244g and the corresponding bicyclic arylbromide Int-R following the two-step procedure described in Preparative Example 230. The data for compounds I-295 to I-302 is summarized in Table 18.

TABLE 18

| Int-R | Cmpd Structure | Cmpd No. | MS/$^1$H NMR |
|---|---|---|---|
| A-7 | 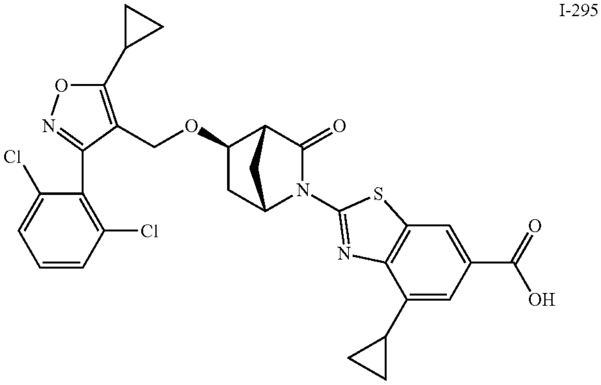 | I-295 | MS (ES, m/z): [M + 1] = 610.15. $^1$H NMR (300 MHz, $CD_3OD$) δ: 8.26 (d, J = 1.6 Hz, 1H), 7.59-7.40 (m, 4H), 5.17 (s, 1H), 4.37 (s, 2H), 3.87 (d, J = 6.4 Hz, 1H), 2.96 (s, 1H), 2.66 (ddd, J = 13.8, 8.7, 5.3 Hz, 1H), 2.34-2.14 (m, 1H), 2.19-2.02 (m, 2H), 1.88 (d, J = 10.2 Hz, 1H), 1.62 (d, J = 13.6 Hz, 1H), 1.21-1.02 (m, 5H), 0.97-0.85 (m, 0H), 0.90 (s, 1H). |

TABLE 18-continued
| Int-R | Cmpd Structure | Cmpd No. | MS/$^1$H NMR |
|---|---|---|---|
| 249d | 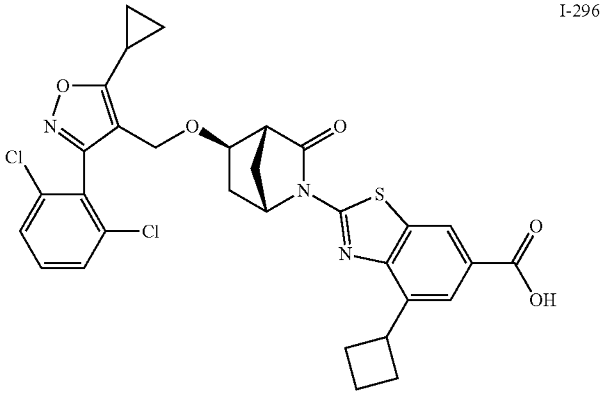 | I-296 | MS (ES, m/z): [M + 1] = 624.20. $^1$H NMR (300 MHz, $CDCl_3$) δ: 8.33 (d, J = 1.7 Hz, 1H), 7.95 (s, 1H), 7.59-7.40 (m, 3H), 5.15 (s, 1H), 4.37 (s, 2H), 4.23-4.11 (m, 1H), 3.86 (d, J = 6.4 Hz, 1H), 2.96 (s, 1H), 2.44 (s, 2H), 2.36-2.18 (m, 2H), 2.19-2.01 (m, 2H), 2.00-1.83 (m, 2H), 1.63 (d, J = 13.4 Hz, 1H), 1.26 (s, 0H), 1.16 (d, J = 8.7 Hz, 4H). |
| 259g | 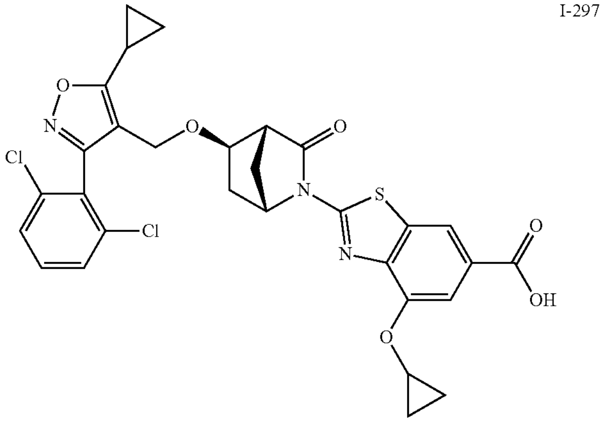 | I-297 | MS (ES, m/z): [M + 1] = 626. $^1$H NMR (400 MHz, $CD_3OD$) δ: 8.19 (d, J = 1.5 Hz, 1H), 7.95 (d, J = 1.5 Hz, 1H), 7.64-7.46 (m, 3H), 5.23 (s, 1H), 4.41 (s, 2H), 4.12-4.03 (m, 1H), 3.90 (d, J = 6.5 Hz, 1H), 3.01 (s, 1H), 2.36-2.23 (m, 1H), 2.10 (d, J = 11.9 Hz, 2H), 1.91 (d, J = 10.2 Hz, 1H), 1.64 (d, J = 13.6 Hz, 1H), 1.26-1.16 (m, 4H), 1.06-0.87 (m, 4H). |
| 254d | 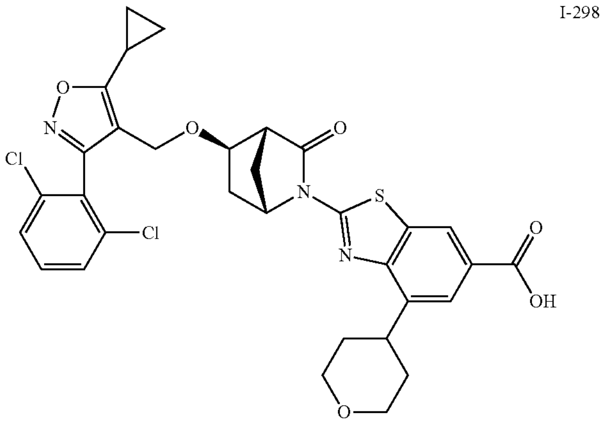 | I-298 | MS (ES, m/z): [M + 1] = 652.25. $^1$H NMR (300 MHz, $CD_3OD$) δ: 8.36 (d, J = 1.6 Hz, 1H), 7.93 (d, J = 1.6 Hz, 1H), 7.59-7.40 (m, 3H), 5.18 (s, 1H), 4.37 (s, 2H), 4.07 (d, J = 11.5 Hz, 3H), 3.87 (d, J = 6.5 Hz, 1H), 3.62 (q, J = 11.5 Hz, 3H), 2.97 (s, 1H), 2.34-2.18 (m, 1H), 2.19-1.91 (m, 4H), 1.86 (t, J = 11.2 Hz, 3H), 1.64 (d, J = 13.6 Hz, 1H), 1.21-1.11 (m, 4H). |

TABLE 18-continued

| Int-R | Cmpd Structure | Cmpd No. | MS/$^1$H NMR |
|---|---|---|---|
| 251d | 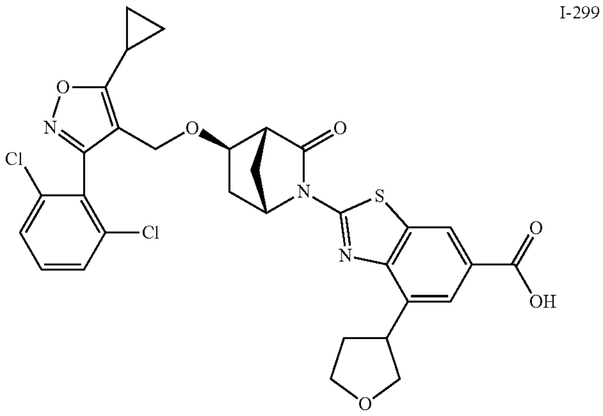 | I-299 | MS (ES, m/z): [M + 1] = 640.05. $^1$H NMR (400 MHz, $CD_3OD$) δ: 8.43 (d, J = 1.6 Hz, 1H), 8.03 (d, J = 1.6 Hz, 1H), 7.62-7.47 (m, 3H), 5.21 (s, 1H), 4.42 (s, 2H), 4.35-4.11 (m, 3H), 4.02 (qd, J = 7.4, 2.0 Hz, 1H), 3.95-3.81 (m, 2H), 3.02 (s, 1H), 2.47 (td, J = 7.9, 4.5 Hz, 1H), 2.36-2.22 (m, 2H), 2.15 (dd, J = 24.5, 12.4 Hz, 2H), 1.94 (d, J = 10.2 Hz, 1H), 1.72-1.64 (m, 1H), 1.20 (ddt, J = 5.9, 4.2, 2.2 Hz, 4H). |
| 257f | 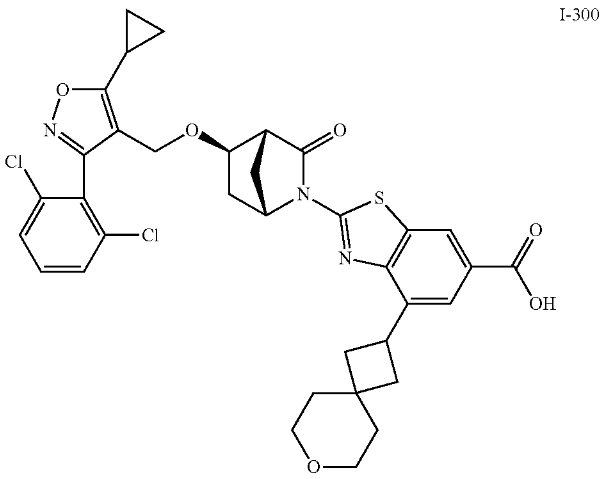 | I-300 | MS (ES, m/z): [M + 1] = 694. $^1$H NMR (300 MHz, DMSO-d6) δ: 8.18 (d, J = 1.7 Hz, 1H), 7.88 (d, J = 1.6 Hz, 1H), 4.47 (m, 3H), 4.23 (t, J = 7.8 Hz, 1H), 4.12 (dt, J = 8.1, 4.0 Hz, 1H), 4.08-4.01 (m, 1H), 3.97 (dd, J = 15.6, 7.4 Hz, 1H), 3.86 (d, J = 6.0 Hz, 1H), 3.81 (t, J = 7.8 Hz, 1H), 3.66-3.55 (m, 1H), 3.13 (s, 1H), 2.93 (s, 1H), 2.76 (dd, J = 13.4, 10.2 Hz, 1H), 2.39 (dt, J = 15.3, 6.2 Hz, 1H), 2.29-2.10 (m, 3H), 1.91 (m, 5H), 1.74 (t, J = 12.2 Hz, 3H), 1.11-0.96 (m, 6H), 0.31 (dt, J = 14.1, 5.3 Hz, 4H 8.44 (d, J = 1.6 Hz, 1H), 7.87 (dd, J = 1.7, 0.8 Hz, 1H), 7.73-7.53 (m, 3H), 5.09 (s, 1H), 4.45-4.29 (m, 2H), 4.07 (p, J = 9.1 Hz, 1H), 3.88 (d, J = 6.1 Hz, 1H), 3.64 (t, J = 5.2 Hz, 3H), 3.03 (d, J = 1.8 Hz, 1H), 2.49-2.32 (m, 4H), 2.15 (d, J = 6.3 Hz, 1H), 2.13-2.07 (m, 2H), 2.07-1.97 (m, 1H), 1.83-1.70 (m, 3H), 1.62-1.51 (m, 3H), 1.28-1.07 (m, 4H). |
| 261e | 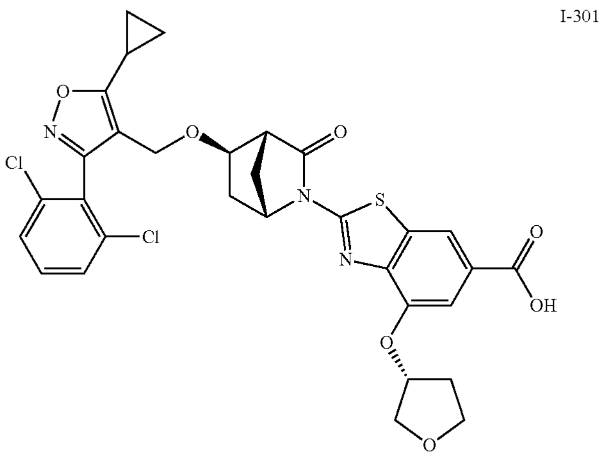 | I-301 | MS (ES, m/z): [M + 1] = 656.15. $^1$H NMR (300 MHz, $CD_3OD$) δ: 8.19 (d, J = 1.4 Hz, 1H), 7.64-7.46 (m, 4H), 5.38 (s, 1H), 5.24 (s, 1H), 4.42 (s, 2H), 4.18-4.01 (m, 3H), 3.94 (td, J = 8.3, 5.0 Hz, 2H), 3.02 (s, 1H), 2.44-2.06 (m, 5H), 1.93 (d, J = 10.2 Hz, 1H), 1.72-1.60 (m, 1H), 1.27-1.16 (m, 4H). |

TABLE 18-continued

| Int-R | Cmpd Structure | Cmpd No. | MS/$^1$H NMR |
|---|---|---|---|
| 260f | 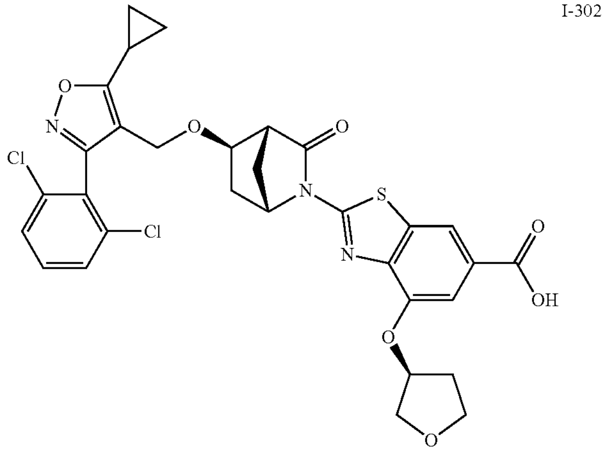 | I-302 | MS (ES, m/z): [M + 1] = 656.10. $^1$H NMR (300 MHz, $CD_3OD$) δ: 8.19 (d, J = 1.5 Hz, 1H), 7.64-7.46 (m, 4H), 5.38 (s, 1H), 5.24 (s, 1H), 4.42 (s, 2H), 4.17-3.87 (m, 5H), 3.02 (s, 1H), 2.44-2.06 (m, 5H), 1.03 (d, J = 10.2 Hz, 1H), 1.66 (d, J = 13.9 Hz, 1H), 1.27-1.16 (m, 4H). |

Example 232: 3-{4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]phenyl}propanoic Acid (I-303)

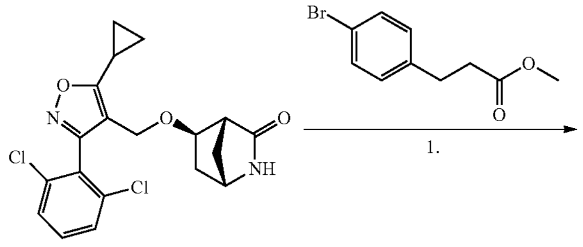

244g

-continued

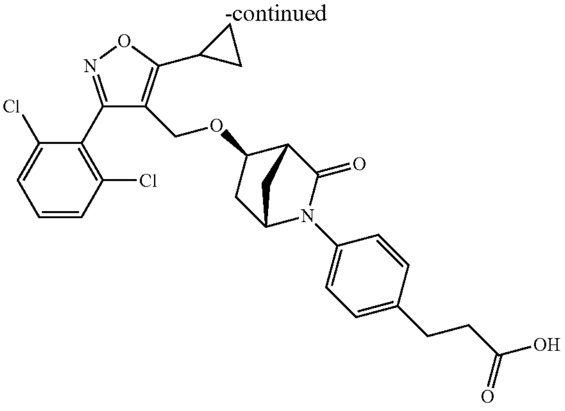

I-303

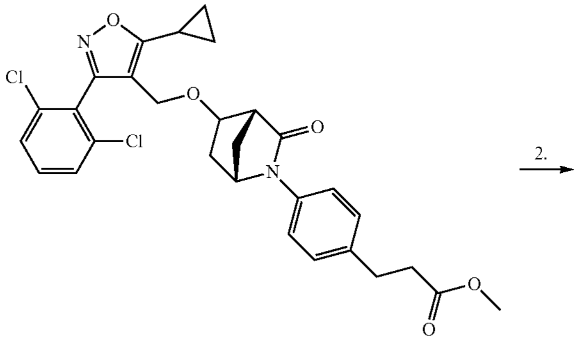

303a

Step 1

To a 8 mL sealed tube purged with and maintained under an inert atmosphere of nitrogen was added (1S,4R,5R)-5-[[5-cyclopropyl-3-(2,6-dichlorophenyl)-1,2-oxazol-4-yl]methoxy]-2-azabicyclo[2.2.1]heptan-3-one 244g (100 mg, 0.25 mmol, 1.00 equiv.), a solution of methyl 3-(4-bromophenyl)propanoate (93 mg, 0.38 mmol, 1.50 equiv.) in dioxane (2 mL), Xant-Phos (22 mg, 0.04 mmol, 0.15 equiv.), $Pd_2(dba)_3$ (12 mg, 0.01 mmol, 0.05 equiv.), and $Cs_2CO_3$ (125 mg, 0.38 mmol, 1.50 equiv.). The resulting mixture was heated at 105° C., overnight. After cooling to room temperature, the mixture was diluted with 20 mL of EA, washed with brine (20 mL×2), dried over anhydrous sodium sulfate, and concentrated under vacuum. The residue was purified by silica gel column chromatography eluting with ethyl acetate/petroleum ether (1:3) to give methyl 3-[4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]phenyl]propanoate 303a (100 mg, 71%) as a light yellow oil.

Step 2

To a 250 mL round-bottom flask was added a solution of methyl 3-[4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]phenyl]propanoate 303a (100 mg, 0.18 mmol, 1.00 equiv.) in ethanol (5 mL) and $H_2O$ (1 mL), and LiOH (43 mg, 1.80 mmol, 10.00 equiv.). The resulting mixture was stirred at 30° C., for 1 h. The pH value of the solution was adjusted to 2 using a 1M hydrogen chloride aqueous solution. The resulting mixture was extracted with ethyl acetate (30 mL×2); the combined organic extracts were washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (44.00% ACN up to 62.0% in 8 min); Detector, UV 254 nm. After purification 3-[4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]phenyl]propanoic acid I-303 (58.3 mg, 60%) was obtained as a colorless solid. $^1$H-NMR (300 MHz, $CD_3OD$) δ: 7.60-7.47 (m, 3H), 7.40-7.30 (m, 2H), 7.22 (d, J=8.5 Hz, 2H), 4.46-4.36 (m, 3H), 3.86 (d, J=6.8 Hz, 1H), 2.95-2.77 (m, 3H), 2.59 (t, J=7.5 Hz, 2H), 2.22-2.09 (m, 2H), 1.97 (d, J=10.0 Hz, 1H), 1.75 (d, J=9.8 Hz, 1H), 1.25-1.15 (m, 5H). MS (ES, m/z): [M+1]=541.2.

Example 233: 3-{4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluorophenyl}propanoic Acid (I-304)

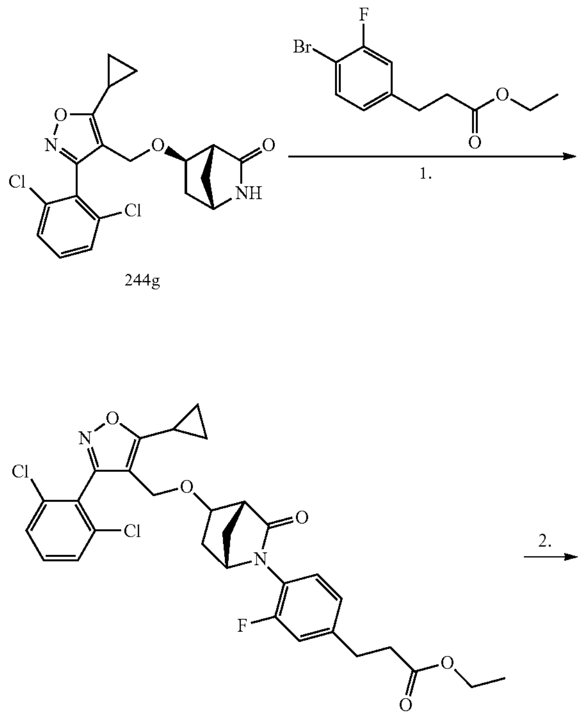

244g

304a

-continued

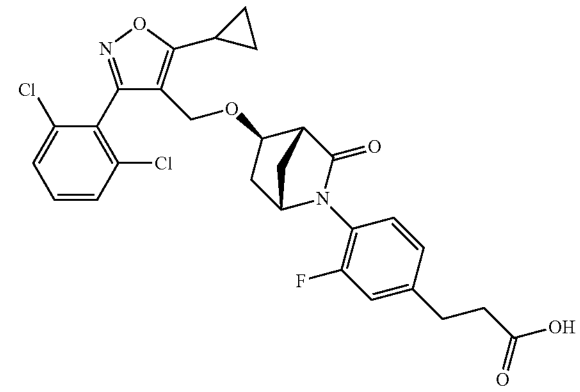

I-304

Following the procedure described in Preparative Example 232, by reacting with ethyl 3-(4-bromo-3-fluorophenyl)propanoate (105 mg, 0.38 mmol, 1.50 equiv.), (1S,4R,5R)-5-[[5-cyclopropyl-3-(2,6-dichlorophenyl)-1,2-oxazol-4-yl]methoxy]-2-azabicyclo[2.2.1]heptan-3-one 244g (100 mg, 0.25 mmol, 1.00 equiv) was converted in two steps to 3-[4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-3-fluorophenyl]propanoic acid I-304 (28.3 mg) as a colorless solid. $^1$H-NMR (300 MHz, $CD_3OD$) δ: 7.63-7.45 (m, 3H), 7.28-7.03 (m, 3H), 4.41 (s, 2H), 4.17 (s, 1H), 3.95 (d, J=6.6 Hz, 1H), 2.93 (t, J=7.5 Hz, 2H), 2.81 (s, 1H), 2.62 (t, J=7.5 Hz, 2H), 2.39-2.02 (m, 3H), 1.78 (d, J=9.7 Hz, 1H), 1.49 (d, J=13.4 Hz, 1H), 1.26-1.15 (m, 4H). MS (ES, m/z): [M+1]=559.2.

Example 234: 3-{4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorophenyl}propanoic Acid (I-305)

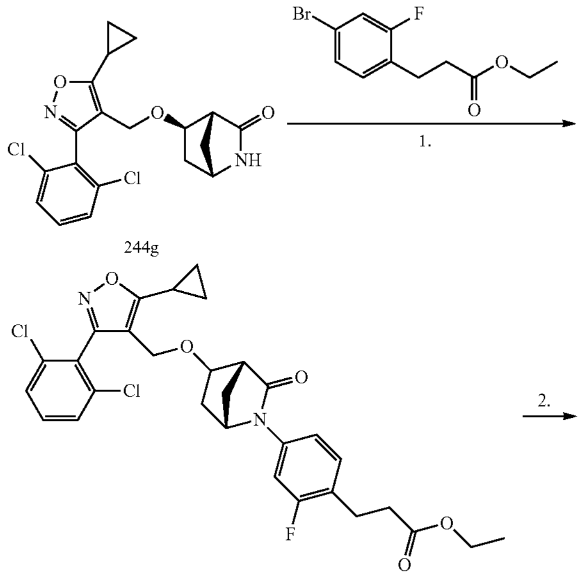

244g

305a

-continued

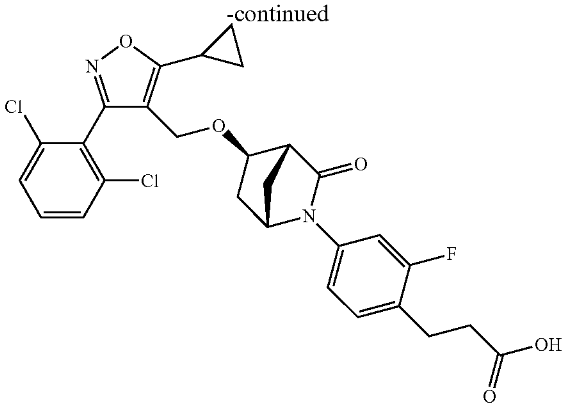

I-305

Following the procedure described in Preparative Example 232, by reacting with ethyl 3-(4-bromo-2-fluorophenyl)propanoate (105 mg, 0.38 mmol, 1.50 equiv.), (1S,4R,5R)-5-[[5-cyclopropyl-3-(2,6-dichlorophenyl)-1,2-oxazol-4-yl]methoxy]-2-azabicyclo[2.2.1]heptan-3-one 244g (100 mg, 0.25 mmol, 1.00 equiv) was converted in two steps to 3-[4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2-fluorophenyl]propanoic acid I-305 (53.1 mg) as a white solid. $^1$H-NMR (300 MHz, $CD_3OD$) δ: 7.63-7.45 (m, 3H), 7.41-7.20 (m, 2H), 7.12 (dd, J=8.4, 2.2 Hz, 1H), 4.43 (dd, J=27.0, 1.9 Hz, 3H), 3.85 (d, J=6.8 Hz, 1H), 2.91 (t, J=7.6 Hz, 2H), 2.82 (s, 1H), 2.64-2.53 (m, 2H), 2.29 (tt, J=8.4, 5.5 Hz, 1H), 2.13 (ddd, J=13.4, 6.9, 2.6 Hz, 1H), 1.96 (d, J=10.1 Hz, 1H), 1.75 (dt, J=9.9, 1.4 Hz, 1H), 1.58 (dt, J=13.5, 2.5 Hz, 1H), 1.26-1.14 (m, 4H). MS (ES, m/z): [M+1]=559.15.

Example 235: 4-[(1S,4R,5R)-5-{[3-(2-chloro-6-fluorophenyl)-5-cyclopropyl-1,2-oxazol-4-yl]methoxy}-3-oxo-2-azabicyclo[2.2.1]heptan-2-yl]benzoic Acid (I-306)

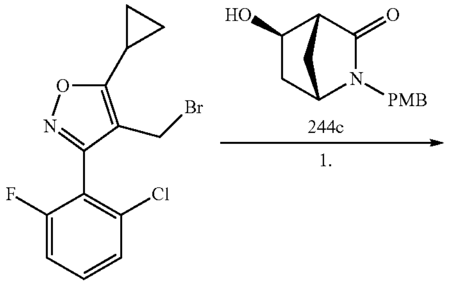

118f

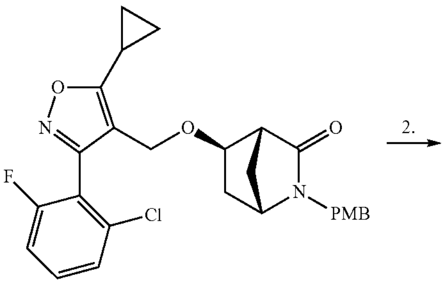

306a

-continued

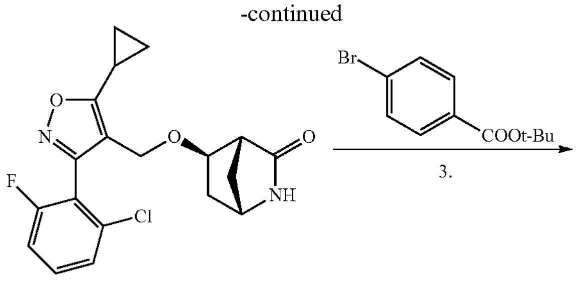

306b

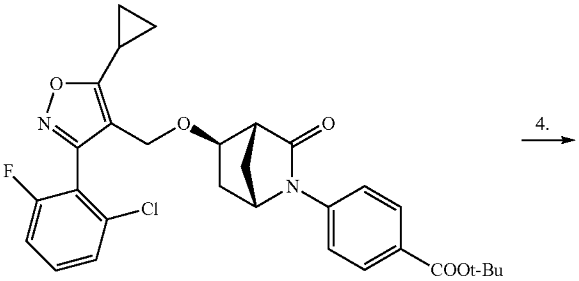

306c

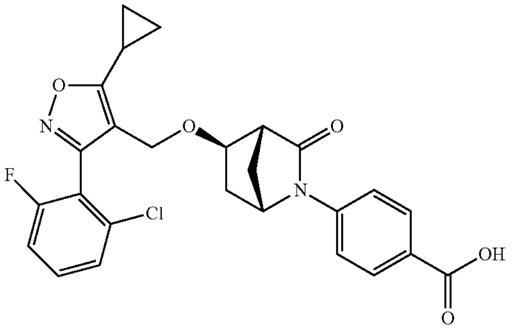

I-306

Step 1

To a 100 mL round-bottom flask was added a solution of 4-(bromomethyl)-3-(2-chloro-6-fluorophenyl)-5-cyclopropyl-1,2-oxazole 118f (590 mg, 1.78 mmol, 2.00 equiv.) in N,N-dimethylformamide (12 mL), (1S,4R,5R)-5-hydroxy-2-[(4-methoxyphenyl)methyl]-2-azabicyclo[2.2.1]heptan-3-one 244c (221 mg, 0.89 mmol, 1.00 equiv.), and sodium hydride (144 mg, 6.00 mmol, 4.00 equiv.). The resulting mixture was stirred for 2 h at room temperature, then quenched by the addition of water/ice. The aqueous mixture was extracted with ethyl acetate (200 mL). The organic extract was washed with brine (100 mL), dried over anhydrous sodium sulfate and concentrated under vacuum. The residue was purified by silica gel column chromatography eluting with ethyl acetate/petroleum ether (1:3) to give (1S,4R,5R)-5-[[3-(2-chloro-6-fluorophenyl)-5-cyclopropyl-1,2-oxazol-4-yl]methoxy]-2-[(4-methoxyphenyl)methyl]-2-azabicyclo[2.2.1]heptan-3-one 306a (474 mg, Q) as a crude light yellow oil.

Step 2

To a 100 mL round-bottom flask was added a solution of (1S,4R,5R)-5-[[3-(2-chloro-6-fluorophenyl)-5-cyclopropyl-1,2-oxazol-4-yl]methoxy]-2-[(4-methoxyphenyl)methyl]-2-azabicyclo[2.2.1]heptan-3-one 306a (474 mg, 0.95 mmol, 1.00 equiv.) in $CH_3CN$ (12 mL), and a solution of $(NH_4)_2Ce(NO_3)_6$ (2.094 g, 4.00 equiv.) in water (4 mL). The resulting mixture was stirred at room temperature of 30 min, and quenched with a saturated $Na_2SO_3$ aqueous solution (10 mL). The resulting mixture was further diluted with 50 mL of $H_2O$, extracted with ethyl acetate (200 mL). The organic extract was washed with brine (100 mL), dried over anhydrous sodium sulfate and concentrated under vacuum. The residue was purified by silica gel column chromatography eluting with ethyl acetate/petroleum ether (1.2:1) to afford (1S,4R,5R)-5-[[3-(2-chloro-6-fluorophenyl)-5-cyclopropyl-1,2-oxazol-4-yl]methoxy]-2-azabicyclo[2.2.1]heptan-3-one 306b (220 mg, 61%) as a yellow oil.

Step 3

To a 100 mL round-bottom flask purged with and maintained under an inert atmosphere of nitrogen was added a solution of (1S,4R,5R)-5-[[3-(2-chloro-6-fluorophenyl)-5-cyclopropyl-1,2-oxazol-4-yl]methoxy]-2-azabicyclo[2.2.1]heptan-3-one 306b (220 mg, 0.58 mmol, 1.00 equiv.) in 1,4-dioxane (8 mL), tert-butyl 4-bromobenzoate (180 mg, 0.70 mmol, 1.20 equiv.), Xantphos (51 mg, 0.09 mmol, 0.15 equiv), $Pd_2(dba)_3$ (27 mg, 0.03 mmol, 0.05 equiv.), and $Cs_2CO_3$ (286 mg, 0.88 mmol, 1.50 equiv.). The resulting mixture was heated at 105° C., overnight. After cooling to room temperature, the mixture was diluted with 50 mL of water, and extracted with 200 mL of ethyl acetate. The organic extract was washed with brine (100 mL), dried over anhydrous sodium sulfate and concentrated under vacuum. The residue was purified by silica gel column chromatography eluting with ethyl acetate/petroleum ether (1:4) to afford tert-butyl 4-[(1S,4R,5R)-5-[[3-(2-chloro-6-fluorophenyl)-5-cyclopropyl-1,2-oxazol-4-yl]methoxy]-3-oxo-2-azabicyclo[2.2.1]heptan-2-yl]benzoate 306c (250 mg, 77%) as a yellow oil.

Step 4

To a 50 mL round-bottom flask was added a solution of tert-butyl 4-[(1S,4R,5R)-5-[[3-(2-chloro-6-fluorophenyl)-5-cyclopropyl-1,2-oxazol-4-yl]methoxy]-3-oxo-2-azabicyclo[2.2.1]heptan-2-yl]benzoate 306c (220 mg, 0.40 mmol, 1.00 equiv.) in dichloromethane (4 mL), and trifluoroacetic acid (2 mL). The resulting mixture was stirred at room temperature for 30 min and concentrated under vacuum. The crude product was purified by Prep-HPLC using the following conditions: Column, XBridge Shield RP18 OBD Column, 5 um, 19*150 mm; mobile phase, Water (0.05% TFA) and ACN (44.0% ACN up to 62.0% in 8 min); Detector, UV 254/220 nm. After purification 4-[(1S,4R,5R)-5-[[3-(2-chloro-6-fluorophenyl)-5-cyclopropyl-1,2-oxazol-1,2-oxazol-4-yl]methoxy]-3-oxo-2-azabicyclo[2.2.1]heptan-2-yl]benzoic acid I-306 (100.9 mg, 51%) was obtained as a colorless solid. $^1$H-NMR (300 MHz, $CD_3OD$) δ: 8.11-7.87 (m, 2H), 7.64-7.50 (m, 3H), 7.48-7.39 (m, 1H), 7.33-7.21 (m, 1H), 4.58 (s, 1H), 4.42 (s, 2H), 3.87 (d, J=6.7 Hz, 1H), 2.87 (s, 1H), 2.35-2.24 (m, 1H), 2.18 (dd, J=13.5, 6.9 Hz, 1H), 1.99 (d, J=10.2 Hz, 1H), 1.77 (d, J=10.0 Hz, 1H), 1.68-1.55 (m, 1H), 1.28-1.08 (m, 4H); MS (ES, m/z): [M+1]=497.05.

Example 236: 4-[(1S,4R,5R)-5-{[5-cyclopropyl-3-(2-fluoro-6-methylphenyl)-1,2-oxazol-4-yl]methoxy}-3-oxo-2-azabicyclo[2.2.1]heptan-2-yl]benzoic Acid (I-307)

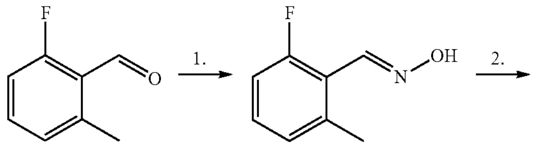

307a 307b

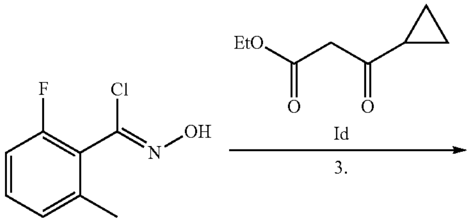

307c

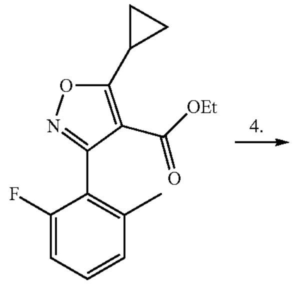

307d

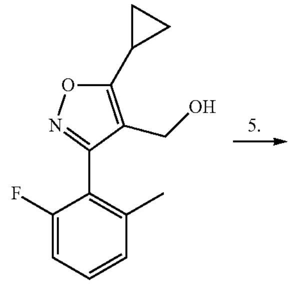

307e

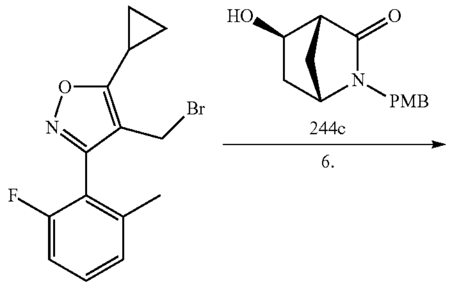

244c

307f

-continued

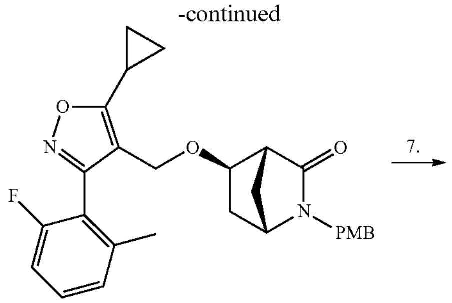

307g

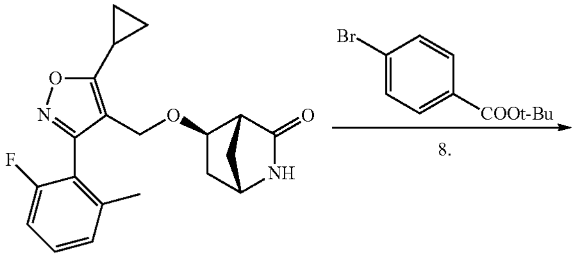

307h

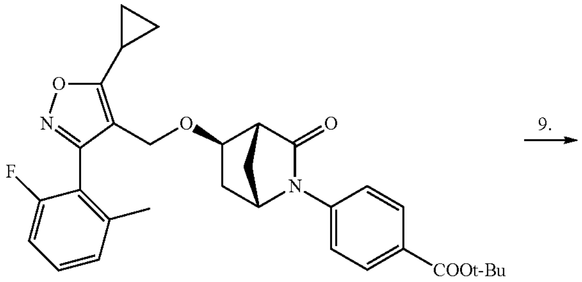

307i

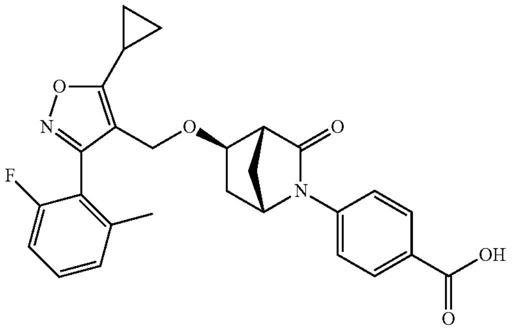

I-307

Step 1

To a 250 mL round-bottom flask was added a solution of sodium hydroxide (2.26 g, 56.50 mmol, 1.30 equiv.) in water (12 mL), $NH_2OH$—HCl (3.9 g, 1.30 equiv.), and a solution of 2-fluoro-6-methylbenzaldehyde 307a (6 g, 43.43 mmol, 1.00 equiv.) in ethanol (30 mL). The resulting mixture was heated at 90° C., overnight with stirring, and concentrated under vacuum to remove most of EtOH. The solids were collected by filtration and dried in an oven at 50° C., overnight to afford N-[(2-fluoro-6-methylphenyl)methylidene]hydroxylamine 307b (6 g, 90%) as a colorless solid.

Step 2

To a 250 mL round-bottom flask was added N-[(2-fluoro-6-methylphenyl)methylidene]hydroxylamine 307b (4 g, 26.12 mmol, 1.00 equiv.) and N,N-dimethylformamide (50 mL). The mixture was cooled at 0° C., for 10 min, and added NCS (3.5 g, 26.21 mmol, 1.0 equiv.) at 0° C., with stirring. The reaction mixture was stirred at room temperature for 2 h, then diluted with 50 mL of $H_2O$. The aqueous mixture was extracted with ethyl acetate (200 mL×2); the combined organic extracts were washed with brine (100 mL×2), dried over anhydrous sodium sulfate and concentrated under vacuum to give 2-fluoro-N-hydroxy-6-methylbenzene-1-carbonimidoyl chloride 307c (3.3 g, 67%) as a light yellow crude oil.

Step 3

To a 50 mL round bottom flask was added a solution of t-BuOK (2.912 g, 25.95 mmol, 1.00 equiv.) in tetrahydrofuran (40 mL), followed by the addition of ethyl 3-cyclopropyl-3-oxopropanoate 1d (4.056 g, 25.97 mmol, 1.00 equiv.). The mixture was stirred at 0° C., for 30 min. A solution of 2-fluoro-N-hydroxy-6-methylbenzene-1-carbonimidoyl chloride 307c (4.862 g, 25.92 mmol, 1.00 equiv.) in tetrahydrofuran (40 mL) was added. The resulting mixture was stirred at room temperature overnight, and quenched by the addition of 10 mL of water, and extracted with ethyl acetate (200 mL×2). The combined organic extracts were washed with brine (100 mL×2), dried over anhydrous sodium sulfate and concentrated under vacuum. The residue was purified by silica gel column chromatography eluting with ethyl acetate/petroleum ether (1:5) to afford ethyl 5-cyclopropyl-3-(2-fluoro-6-methylphenyl)-1,2-oxazole-4-carboxylate 307d (1.83 g, 24%) as a light yellow solid.

Step 4

To a 100 mL round-bottom flask was added ethyl 5-cyclopropyl-3-(2-fluoro-6-methylphenyl)-1,2-oxazole-4-carboxylate 307d (1 g, 3.46 mmol, 1.00 equiv.) and tetrahydrofuran (12 mL). The mixture was cooled to 0° C., and stirred for 10 min. Solid $LiAlH_4$ (145 mg, 3.82 mmol, 1.10 equiv.) was added in several batches at 0° C. Reaction was continued at 0° C., for 2 h. Solid $NaSO_4.10H_2O$ (350 mg) was added. The resulting mixture was stirred at room temperature for 2 h, solids were filtered out, and the filtrate was concentrated under vacuum. The residue was purified by silica gel column chromatography eluting with ethyl acetate/petroleum ether (1:5) to afford [5-cyclopropyl-3-(2-fluoro-6-methylphenyl)-1,2-oxazol-4-yl]methanol 307e (760 mg, 81.8%) as a light yellow oil.

Step 5

To a 100 mL round-bottom flask was added [5-cyclopropyl-3-(2-fluoro-6-methylphenyl)-1,2-oxazol-4-yl]methanol 307e (720 mg, 2.91 mmol, 1.00 equiv.), dichloromethane (6 mL), tetrahydrofuran (6 mL), NBS (778 mg, 4.37 mmol, 1.50 equiv.), and $PPh_3$ (1.146 g, 4.37 mmol, 1.50 equiv.). The resulting mixture was stirred for 1 h at room temperature and quenched with water. The aqueous mixture was extracted with ethyl acetate (100 mL×2); the combined organic extracts were washed with brine (50 mL×2), dried over anhydrous sodium sulfate and concentrated under vacuum. The residue was purified by silica gel column chromatography eluting with ethyl acetate and petroleum ether (1:5) to provide 4-(bromomethyl)-5-cyclopropyl-3-(2-fluoro-6-methylphenyl)-1,2-oxazole 307f (770 mg, 85%) as a light yellow oil.

Step 6

To a 100 mL round-bottom flask was added 4-(bromomethyl)-5-cyclopropyl-3-(2-fluoro-6-methylphenyl)-1,2-oxazole 307f (750 mg, 2.42 mmol, 2.00 equiv.) and N,N-dimethylformamide (6 mL). (1S,4R,5R)-5-hydroxy-2-[(4-methoxyphenyl)methyl]-2-azabicyclo[2.2.1]heptan-3-one 244c (280 mg, 1.13 mmol, 1.00 equiv.) was added. The mixture was stirred at −20° C., for 10 min, and sodium hydride (91 mg, 3.79 mmol, 2.00 equiv., 60%6 suspension in mineral oil) was added. The resulting mixture was stirred at −20° C., to −5° C., for 2 h, then quenched by the addition of 10 mL of water/ice. The aqueous mixture was extracted with ethyl acetate (100 mL×2); the combined organic extracts were washed with brine (50 mL×4), dried over anhydrous sodium sulfate and concentrated under vacuum. The residue was purified by silica gel column chromatography eluting with ethyl acetate/petroleum ether (1:3) to afford (1S,4R,5R)-5-[[5-cyclopropyl-3-(2-fluoro-6-methylphenyl)-1,2-oxazol-4-yl]methoxy]-2-[(4-methoxyphenyl)methyl]-2-azabicyclo[2.2.1]heptan-3-one 307g (510 mg, 95%) as a light yellow solid.

Step 7

To a 50 mL round-bottom flask was added a solution of (1S,4R,5R)-5-[[5-cyclopropyl-3-(2-fluoro-6-methylphenyl)-1,2-oxazol-4-yl]methoxy]-2-[(4-methoxyphenyl)methyl]-2-azabicyclo[2.2.1]heptan-3-one 307g (510 mg, 1.07 mmol, 1.00 equiv.) in MeCN (13 mL), and a solution of $(NH_4)_2Ce(NO_3)_6$ (2.35 g, 4.00 equiv.) in water (5 mL). The resulting mixture was stirred at room temperature for 30 min, then quenched by the addition of 1 g of $Na_2SO_3$. The mixture was diluted with $H_2O$, extracted with ethyl acetate (100 mL×2), and the combined organic extracts were washed with brine (50 mL×2), dried over anhydrous sodium sulfate and concentrated under vacuum to provide (1S,4R,5R)-5-[[5-cyclopropyl-3-(2-fluoro-6-methylphenyl)-1,2-oxazol-4-yl]methoxy]-2-azabicyclo[2.2.1]heptan-3-one 307h (285 mg, 75%) as an off-white solid.

Step 8

To a 50 mL round-bottom flask was added a solution of (1S,4R,5R)-5-[[5-cyclopropyl-3-(2-fluoro-6-methylphenyl)-1,2-oxazol-4-yl]methoxy]-2-azabicyclo[2.2.1]heptan-3-one 307h (150 mg, 0.42 mmol, 1.00 equiv.) in dioxane (4 mL), tert-butyl 4-bromobenzoate (120 mg, 0.47 mmol, 1.20 equiv.), $Pd_2(dba)_3$ (11 mg, 0.05 equiv.), XantPhos (34 mg, 0.06 mmol, 0.15 equiv.), and $Cs_2CO_3$ (191 mg, 1.50 equiv.). The resulting mixture was heated at 105° C., overnight with stirring. After cooling to room temperature, water was added, the aqueous mixture was extracted with ethyl acetate (50 mL×2). The combined organic extracts were washed with brine (50 mL×2), dried over anhydrous sodium sulfate and concentrated under vacuum. The residue was purified by silica gel column chromatography eluting with ethyl acetate/petroleum ether (1:3) to afford tert-butyl 4-[(1S,4R,5R)-5-[[5-cyclopropyl-3-(2-fluoro-6-methylphenyl)-1,2-oxazol-4-yl]methoxy]-3-oxo-2-azabicyclo[2.2.1]heptan-2-yl]benzoate 307i (200 mg, 89%) as a yellow solid.

Step 9

To a 25 mL round bottom flask was added tert-butyl 4-[(1S,4R,5R)-5-[[5-cyclopropyl-3-(2-fluoro-6-methylphenyl)-1,2-oxazol-4-yl]methoxy]-3-oxo-2-azabicyclo[2.2.1]heptan-2-yl]benzoate 307i (200 mg, 0.38 mmol, 1.00 equiv.), dichloromethane (2 mL), and trifluoroacetic acid (1 mL). The resulting mixture was stirred at room temperature for 1 h. The pH value of the solution was adjusted to 5 using a saturated sodium bicarbonate aqueous solution. The aqueous mixture was extracted with ethyl acetate (50 mL×2). The combined organic extracts was washed with brine (50 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (44.0% ACN up to 62.0% in 8 min); Detector, UV 254/220 nm. After purification 4-[(1S,4R,5R)-5-[[5-cyclopropyl-3-(2-fluoro-6-methylphenyl)-1,2-oxazol-4-yl]methoxy]-3-oxo-2-azabicyclo[2.2.1]heptan-2-yl]benzoic acid I-307 (86.5 mg, 48%) as a colorless solid. $^1$H-NMR (300 MHz, $CD_3OD$) δ: 8.06-7.95 (m, 2H), 7.70 (s, OH), 7.64-7.52 (m, 2H), 7.43 (td, J=8.1, 5.9 Hz, 1H), 7.18 (d, J=7.7 Hz, 1H), 7.15-7.03 (m, 1H), 4.57 (s, 1H), 4.35 (s, 2H), 3.85 (d, J=6.7 Hz, 1H), 2.83 (d, J=1.8 Hz, 1H), 2.37-2.21 (m, 1H), 2.21 (s, 3H), 2.22-2.10 (m, 1H), 1.98 (d, J=10.0 Hz, 1H), 1.75 (d, J=10.0 Hz, 1H), 1.61 (dt, J=13.5, 2.6 Hz, 1H), 1.27-1.14 (m, 4H); MS (ES, m/z): [M+1]=477.

Example 237: 4-[(1S,4R,5R)-5-{[5-cyclopropyl-3-(2,6-dimethylphenyl)-1,2-oxazol-4-yl]methoxy}-3-oxo-2-azabicyclo[2.2.1]heptan-2-yl]benzoic Acid (I-308)

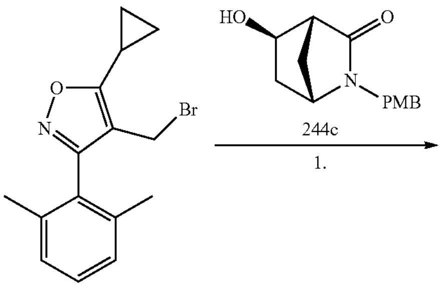

116f

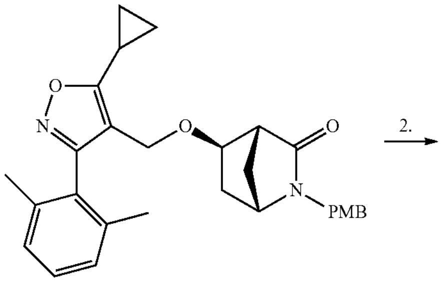

308a

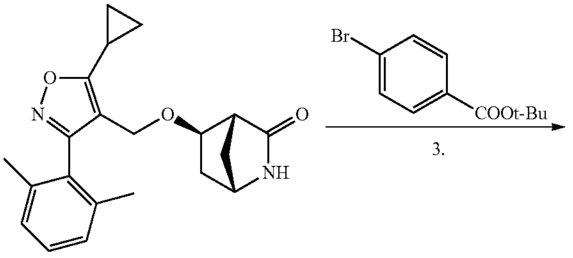

308b

-continued

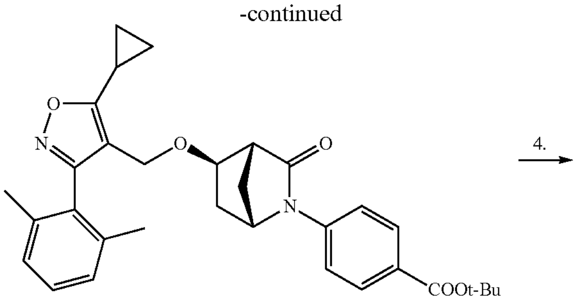

308c

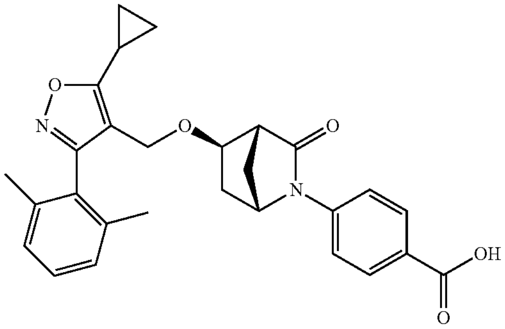

I-308

Step 1

To a 100 mL round-bottom flask was added a solution of 4-(bromomethyl)-5-cyclopropyl-3-(2,6-dimethylphenyl)-1,2-oxazole 116f (450 mg, 1.47 mmol, 2.00 equiv.) in N,N-dimethylformamide (10 mL), (1S,4R,5R)-5-hydroxy-2-[(4-methoxyphenyl)methyl]-2-azabicyclo[2.2.1]heptan-3-one 244c (182 mg, 0.74 mmol, 1.00 equiv.), and sodium hydride (120 mg, 5.00 mmol, 4.00 equiv., 60% dispersion in oil). The resulting mixture was stirred at room temperature for 1 h, and quenched by the addition of $H_2O$. The aqueous mixture was diluted with of EA, extracted with ethyl acetate (200 mL), and the combined organic extracts were washed with brine (100 mL), dried over anhydrous sodium sulfate and concentrated under vacuum. The residue was purified by silica gel column chromatography eluting with ethyl acetate/petroleum ether (1:3) to provide (1S,4R,5R)-5-[[5-cyclopropyl-3-(2,6-dimethylphenyl)-1,2-oxazol-4-yl]methoxy]-2-[(4-methoxyphenyl)methyl]-2-azabicyclo[2.2.1]heptan-3-one 308a (400 mg, Q) as a crude yellow oil.

Step 2

To a 100 mL round-bottom flask was added a solution of (1S,4R,5R)-5-[[5-cyclopropyl-3-(2,6-dimethylphenyl)-1,2-oxazol-4-yl]methoxy]-2-[(4-methoxyphenyl)methyl]-2-azabicyclo[2.2.1]heptan-3-one 308a (400 mg, 0.85 mmol, 1.00 equiv.) in $CH_3CN$ (9.6 mL), and a solution of $(NH_4)_2Ce(NO_3)_6$ (1.857 g, 4.00 equiv.) in water (3.2 mL). The resulting mixture was stirred for 0.5 h at room temperature, and diluted with 100 mL of EA. The mixture was washed with brine (100 mL), dried over anhydrous sodium sulfate and concentrated under vacuum. The residue was purified by silica gel column chromatography eluting with ethyl acetate/petroleum ether (1.2:1) to afford (1S,4R,5R)-5-[[5-cyclopropyl-3-(2,6-dimethylphenyl)-1,2-oxazol-4-yl]methoxy]-2-azabicyclo[2.2.1]heptan-3-one 308b (152 mg, 51%) as a light yellow solid.

Step 3

To a 100 mL round-bottom flask purged with and maintained under an inert atmosphere of nitrogen was added a solution of (1S,4R,5R)-5-[[5-cyclopropyl-3-(2,6-dimethylphenyl)-1,2-oxazol-4-yl]methoxy]-2-azabicyclo[2.2.1]heptan-3-one 308b (152 mg, 0.43 mmol, 1.00 equiv.) in 1,4-dioxane (5 mL), tert-butyl 4-bromobenzoate (133 mg, 0.52 mmol, 1.20 equiv.), Xantphos (37 mg, 0.06 mmol, 0.15 equiv.). $Pd_2(dba)_3$ (20 mg, 0.02 mmol, 0.05 equiv.), and $Cs_2CO_3$ (211 mg, 0.65 mmol, 1.50 equiv.). The resulting mixture was stirred at 105° C., overnight. After cooling to room temperature, the reaction mixture was diluted with 100 mL of EA and washed with brine (100 mL). The organic layer was dried over anhydrous sodium sulfate and concentrated under vacuum. The residue was purified by silica gel column chromatography eluting with ethyl acetate/petroleum ether (1:4) to give tert-butyl 4-[(1S,4R,5R)-5-[[5-cyclopropyl-3-(2,6-dimethylphenyl)-1,2-oxazol-4-yl]methoxy]-3-oxo-2-azabicyclo[2.2.1]heptan-2-yl]benzoate 308c (240 mg, Q) as a crude yellow oil.

Step 4

To a 50 mL round-bottom flask was added a solution of tert-butyl 4-[(1S,4R,5R)-5-[[5-cyclopropyl-3-(2,6-dimethylphenyl)-1,2-oxazol-4-yl]methoxy]-3-oxo-2-azabicyclo[2.2.1]heptan-2-yl]benzoate 308c (200 mg, 0.38 mmol, 1.00 equiv.) in dichloromethane (4 mL), and trifluoroacetic acid (2 mL). The resulting mixture was stirred for 0.5 h at room temperature and concentrated under vacuum. The crude product was purified by Prep-HPLC using the following conditions (2#-Analyse HPLC-SHIMADZU(HPLC-10)): Column, XBridge Prep OBD C18 Column, 19*250 mm, 5 um; mobile phase, Water (0.05% TFA) and ACN (62.0% ACN up to 80.0% in 8 min); Detector, uv 220 nm. After purification 4-[(1S,4R,5R)-5-[[5-cyclopropyl-3-(2,6-dimethylphenyl)-1,2-oxazol-4-yl]methoxy]-3-oxo-2-azabicyclo[2.2.1]heptan-2-yl]benzoic acid I-308 (108 mg, 60%) was obtained as a colorless solid. $^1H$-NMR (300 MHz, $CD_3OD$) δ: 8.05-7.95 (m, 2H), 7.63-7.54 (m, 2H), 7.29 (t, J=7.6 Hz, 1H), 7.16 (t, J=7.3 Hz, 2H), 4.57 (s, 1H), 4.25 (s, 2H), 3.83 (d, J=6.7 Hz, 1H), 2.79 (s, 1H), 2.37-2.22 (m, 1H), 2.25-2.02 (m, 7H), 1.97 (d, J=10.1 Hz, 1H), 1.76 (d, J=10.0 Hz, 1H), 1.63-1.52 (m, 1H), 1.25-1.15 (m, 4H); MS (ES, m/z): [M+1]=473.25.

Example 238: 4-[(1S,4R,5R)-5-{[3-(2-chloro-6-methylphenyl)-5-cyclopropyl-1,2-oxazol-4-yl]methoxy}-3-oxo-2-azabicyclo[2.2.1]heptan-2-yl]benzoic Acid (I-309)

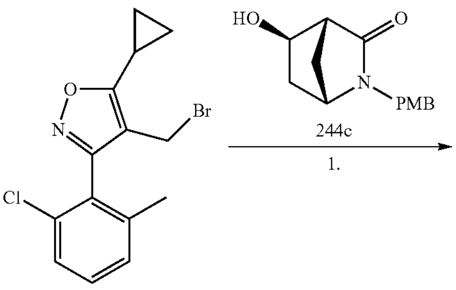

113h

-continued

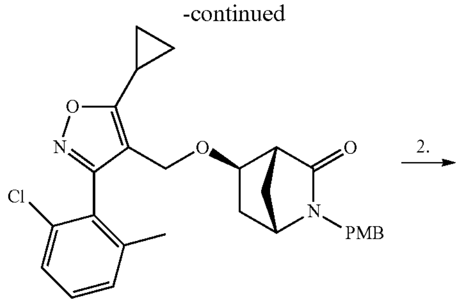

309a

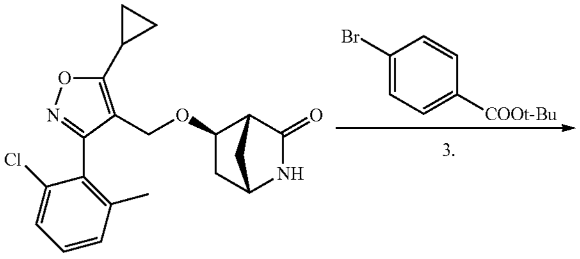

309b

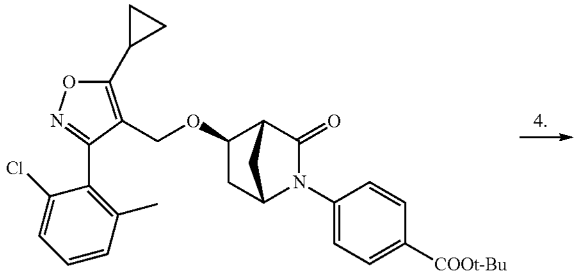

309c

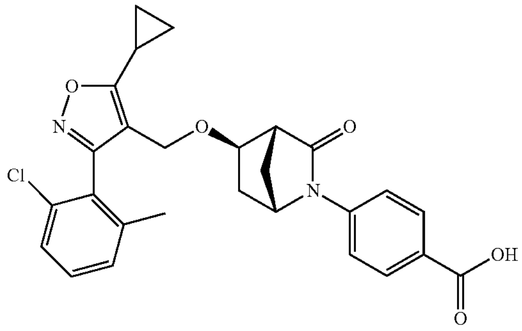

I-309

Step 1

To a 100 mL round-bottom flask was added 4-(bromomethyl)-3-(2-chloro-6-methylphenyl)-5-cyclopropyl-1,2-oxazole 113h (1.056 g, 3.23 mmol, 1.00 equiv.), N,N-dimethylformamide (20 mL), and (1S,4R,5R)-5-hydroxy-2-[(4-methoxyphenyl)methyl]-2-azabicyclo[2.2.1]heptan-3-one 244c (400 mg, 1.62 mmol, 0.50 equiv.). The mixture was cooled to −20 to −5° C., and sodium hydride (130 mg, 5.42 mmol, 1.68 equiv., 60% dispersion in mineral oil) was added. The reaction mixture was stirred for 1 h at this temperature in a water/ice bath, then diluted with 100 mL of EA, and quenched by the addition of 100 mL of water/ice. The aqueous mixture was extracted with ethyl acetate (50 mL×3); the combined organic extracts were dried and concentrated under vacuum. The residue was purified by silica gel column chromatography eluting with ethyl acetate/petroleum ether (1:3) to give (1S,4R,5R)-5-[[3-(2-chloro-6-methylphenyl)-5-cyclopropyl-1,2-oxazol-4-yl]methoxy]-2-[(4-methoxyphenyl)methyl]-2-azabicyclo[2.2.1]heptan-3-one 309a (760 mg, 48%) as a colorless oil.

Step 2

To a 100 mL round-bottom flask was added (1S,4R,5R)-5-[[3-(2-chloro-6-methylphenyl)-5-cyclopropyl-1,2-oxazol-4-yl]methoxy]-2-[(4-methoxyphenyl)methyl]-2-azabicyclo[2.2.1]heptan-3-one 309a (710 mg, 1.44 mmol, 1.00 equiv.), $CH_3CN$ (18 mL), water (6 mL), and $(NH_4)_2Ce(NO_3)_6$ (3.16 g). The resulting mixture was stirred at 10-25° C., for 30 min. The mixture was diluted with 30 mL of a saturated $Na_2SO_3$ aqueous solution, and extracted with ethyl acetate (50 mL×3). The combined organic extracts were dried and concentrated under vacuum. The residue was purified by silica gel column chromatography eluting with ethyl acetate/petroleum ether (1:10-1:0) to give (1S,4R,5R)-5-[[3-(2-chloro-6-methylphenyl)-5-cyclopropyl-1,2-oxazol-4-yl]methoxy]-2-azabicyclo[2.2.1]heptan-3-one 309b (420 mg, 78%) as an off-white solid.

Step 3

To a 100 mL round-bottom flask purged with and maintained under an inert atmosphere of nitrogen was added (1S,4R,5R)-5-[[3-(2-chloro-6-methylphenyl)-5-cyclopropyl-1,2-oxazol-4-yl]methoxy]-2-azabicyclo[2.2.1]heptan-3-one 309b (180 mg, 0.48 mmol, 1.00 equiv.), Tol (10 mL), tert-butyl 4-bromobenzoate (186 mg, 0.72 mmol, 1.50 equiv.), $Cs_2CO_3$ (236 mg, 0.72 mmol, 1.50 equiv.), $Pd_2(dba)_3$ (22.1 mg, 0.02 mmol, 0.05 equiv.), and Xantphos (28 mg, 0.05 mmol, 0.10 equiv.). The resulting mixture was stirred at 100° C., overnight. After cooling to room temperature, solids were filtered out and the filtrate was concentrated under vacuum. The residue was purified by silica gel column chromatography eluting with ethyl acetate/petroleum ether (1:1) to afford tert-butyl 4-[(1S,4R,5R)-5-[[3-(2-chloro-6-methylphenyl)-5-cyclopropyl-1,2-oxazol-4-yl]methoxy]-3-oxo-2-azabicyclo[2.2.1]heptan-2-yl]benzoate 309c (216 mg, 81%) as a light yellow solid.

Step 4

To a 50 mL round-bottom flask was added tert-butyl 4-[(1S,4R,5R)-5-[[3-(2-chloro-6-methylphenyl)-5-cyclopropyl-1,2-oxazol-4-yl]methoxy]-3-oxo-2-azabicyclo[2.2.1]heptan-2-yl]benzoate 309c (216 mg, 0.39 mmol, 1.00 equiv.), dichloromethane (1 mL), and trifluoroacetic acid (1 mL). The resulting mixture was stirred at 10-25° C., for 2 h, diluted with 100 mL of $H_2O$, and extracted with dichloromethane (50 mL×3). The combined organic extracts were dried and concentrated under vacuum. The crude product was purified by Prep-HPLC using the following conditions Column, XBridge Prep OBD C18 Column, 19*250 mm, 5 um; mobile phase, Water (0.05% TFA) and ACN (49.0% ACN up to 60.0% in 8 min); Detector, uv 220 nm. After purification 4-[(1S,4R,5R)-5-[[3-(2-chloro-6-methylphenyl)-5-cyclopropyl-1,2-oxazol-4-yl]methoxy]-3-oxo-2-azabicyclo[2.2.1]heptan-2-yl]benzoic acid I-309 (150 mg, 77%) was obtained as a colorless solid. $^1H$-NMR (300 MHz, $CD_3OD$) δ: 8.04-7.94 (m, 2H), 7.57 (d, J=8.8 Hz, 2H), 7.44-7.34 (m, 2H), 7.39-7.24 (m, 1H), 4.56 (s, 1H), 4.41 (dd, J=11.7, 8.0 Hz, 1H), 4.24 (dd, J=11.7, 5.8 Hz, 1H), 3.83 (t, J=8.6 Hz, 1H), 2.81 (d, J=44.6 Hz, 1H), 2.36-2.08 (m, 5H), 1.96 (dd, J=26.6, 9.9 Hz, 1H), 1.65 (td, J=44.1, 11.6 Hz, 2H), 1.18 (d, J=7.6 Hz, 4H); MS (ES, m/z): [M+1]=493.
Example 239: 4-[(1S,4R,5R)-5-({5-cyclopropyl-3-[2-fluoro-6-(propan-2-yl)phenyl]-1,2-oxazol-4-yl}methoxy)-3-oxo-2-azabicyclo[2.2.1]heptan-2-yl]benzoic Acid (I-310)
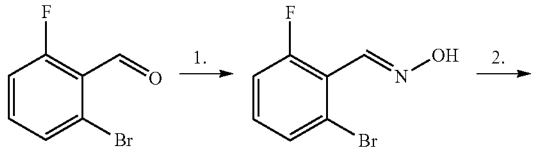
310a 310b
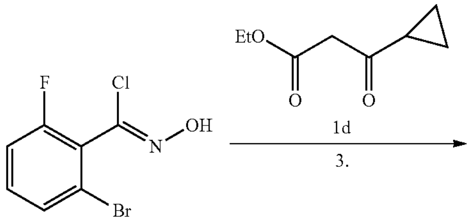
310c
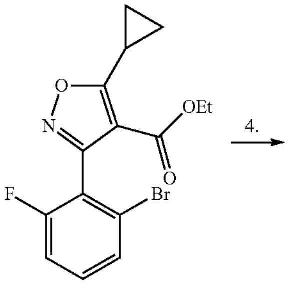
310d
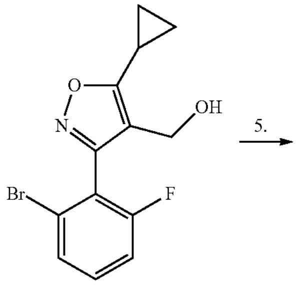
310e
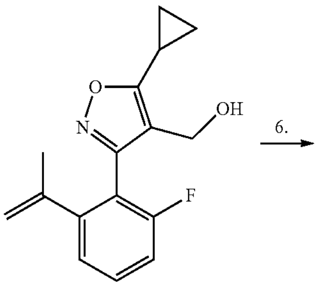
310f
-continued
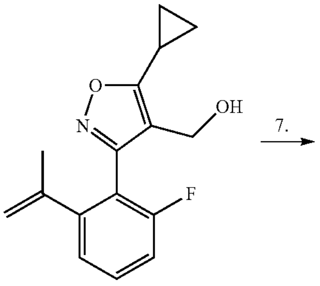
310g
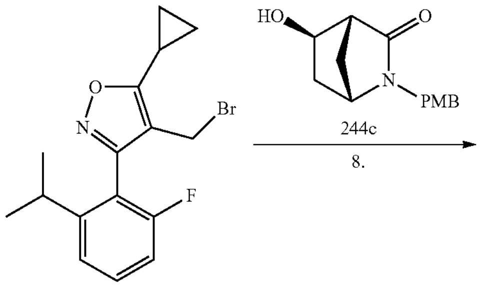
310h
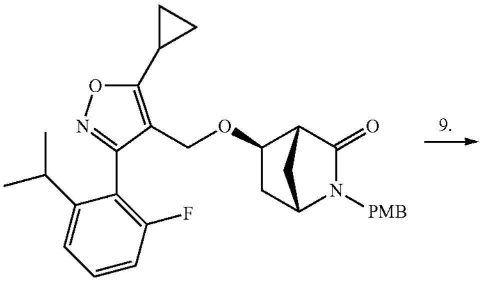
310i
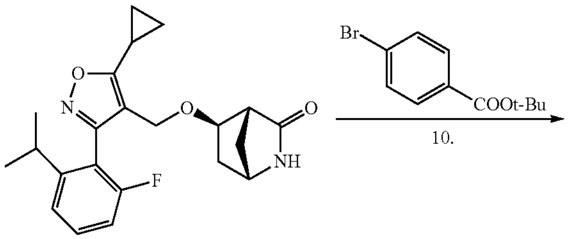
310j
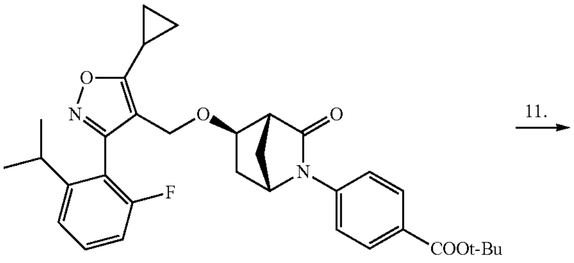
310k -continued

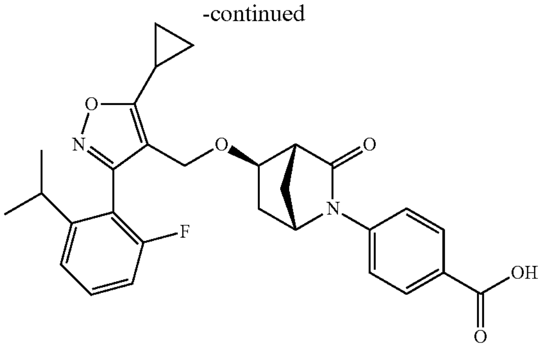

I-310

Step 1

To a 1000 mL round-bottom flask was added sodium hydroxide (10.3 g, 257.50 mmol, 1.30 equiv., 60% dispersed in mineral oil), water (200 mL), hydroxylamine hydrochloride (17.8 g, 256.15 mmol, 1.30 equiv.), 2-bromo-6-fluorobenzaldehyde 310a (40 g, 197.04 mmol, 1.00 equiv.), and ethanol (400 mL). The resulting mixture was stirred at 90° C., overnight. Solids were collected by filtration, dried, to afford N-[(2-bromo-6-fluorophenyl)methylidene]hydroxylamine 310b (42 g, 98%) as an off-white solid.

Step 2

To a 1000 mL round-bottom flask was added N-[(2-bromo-6-fluorophenyl)methylidene]hydroxylamine 310b (42 g, 192.64 mmol, 1.00 equiv.) and N,N-dimethylformamide (500 mL). NCS (26 g, 194.71 mmol, 1.00 equiv.) was added in several batches at 0° C. The resulting solution was stirred at room temperature for 2 h, and diluted with 1 L of $H_2O$. The aqueous mixture was extracted with ethyl acetate (2 L×2); and the combined organic extracts were washed with brine (1 L×4), dried over anhydrous sodium sulfate and concentrated under vacuum to give 2-bromo-6-fluoro-N-hydroxybenzene-1-carbonimidoyl chloride 310c (46 g, 95%) as a red oil.

Step 3

To a 1000 mL round-bottom flask was added 2-bromo-6-fluoro-N-hydroxybenzene-1-carbonimidoyl chloride 310c (46 g, 182.20 mmol, 1.00 equiv.) and ethyl 3-cyclopropyl-3-oxopropanoate 1d (43 g, 275.32 mmol, 1.50 equiv.). Triethyl amine (500 mL) was added in several batches at 0° C. The resulting mixture was stirred at room temperature overnight and concentrated under vacuum. The residue was diluted with 1 L of $H_2O$, extracted with ethyl acetate (1 L×2), and the combined organic extracts were washed with brine (1 L×2), dried over anhydrous sodium sulfate and concentrated under vacuum to afford ethyl 3-(2-bromo-6-fluorophenyl)-5-cyclopropyl-1,2-oxazole-4-carboxylate 310d (38 g, 59%) as an off-white solid.

Step 4

To a 1000 mL round-bottom flask was added ethyl 3-(2-bromo-6-fluorophenyl)-5-cyclopropyl-1,2-oxazole-4-carboxylate 310d (20 g, 56.47 mmol, 1.00 equiv.) and tetrahydrofuran (250 mL). A 1.5M solution of DIBAL in toluene (76 mL, 2.00 equiv.) was added dropwise with stirring at 0° C. The resulting mixture was stirred at room temperature overnight, and quenched by the successive addition of 76 mL of $H_2O$, 228 mL of a 1M sodium hydroxide aqueous solution, and 76 mL of $H_2O$. The aqueous mixture was extracted with ethyl acetate (1 L×2), the combined organic extracts were washed with brine (1 L×2), dried over anhydrous sodium sulfate and concentrated under vacuum. The residue was purified by silica gel column chromatography eluting with ethyl acetate in petroleum ether (0% to 28%). Removal of solvents gave [3-(2-bromo-6-fluorophenyl)-5-cyclopropyl-1,2-oxazol-4-yl]methanol 310e (13.6 g, 77%) as a colorless oil.

Step 5

To a 100 mL round-bottom flask was added a solution of [3-(2-bromo-6-fluorophenyl)-5-cyclopropyl-1,2-oxazol-4-yl]methanol 310e (2 g, 6.41 mmol, 1.00 equiv.) in dioxane: EtOH:$H_2O$ (12:4:4 mL), Pd(dppf)$Cl_2$ (520 mg, 0.71 mmol, 0.10 equiv.), sodium carbonate (2 g, 18.87 mmol, 3.00 equiv.), and potassium trifluoro(isopropenyl)borate (2.86 g, 19.33 mmol, 3.00) equiv.). The resulting mixture was stirred at 80° C. overnight. After cooling to room temperature, the mixture was diluted with 150 mL of $H_2O$, and extracted with ethyl acetate (200 mL×2). The combined organic extracts were washed with brine (200 mL×2), dried over anhydrous sodium sulfate and concentrated under vacuum. The crude product was purified by Flash-Prep-HPLC using the following conditions (IntelFlash-1): Column, C18 silica gel; mobile phase, MeCN:$H_2O$=0:100 increasing to MeCN:$H_2O$=50:50 within 40 min; Detector, UV 254 nm. Removal of solvents gave [5-cyclopropyl-3-[2-fluoro-6-(prop-1-en-2-yl)phenyl]-1,2-oxazol-4-yl]methanol 310f (0.66 g, 38%) as a yellow oil.

Step 6

To a 25 mL round-bottom flask was added [5-cyclopropyl-3-[2-fluoro-6-(prop-1-en-2-yl)phenyl]-1,2-oxazol-4-yl] methanol 310f (460 mg, 1.68 mmol, 1.00 equiv.), methanol (6 mL), Palladium on carbon (0.46 g, 10 wt %). Hydrogen gas was introduced. The resulting mixture was stirred at room temperature for 2 h under an atmosphere of hydrogen. Solids were filtered out, and the filtrate was concentrated under vacuum. The residue was purified by silica gel column chromatography eluting with ethyl acetate/petroleum ether (1:3) to afford [5-cyclopropyl-3-[2-fluoro-6-(propan-2-yl) phenyl]-1,2-oxazol-4-yl]methanol 310g (0.354 g, 76%) as a yellow oil.

Step 7

To a 100 mL round-bottom flask was added [5-cyclopropyl-3-[2-fluoro-6-(propan-2-yl)phenyl]-1,2-oxazol-4-yl] methanol 310g (434 mg, 1.58 mmol, 1.00 equiv.), tetrahydrofuran (8 mL), and dichloromethane (8 mL). NBS (421 mg, 2.37 mmol, 1.50 equiv.) was added in several batches followed by triphenyl phosphine (620 mg, 2.36 mmol, 1.50 equiv.) at 0° C. The resulting mixture was stirred for 1 h at room temperature and concentrated under vacuum. The residue was purified by silica gel column chromatography eluting with ethyl acetate/petroleum ether (1:3) to afford 4-(bromomethyl)-5-cyclopropyl-3-[2-fluoro-6-(propan-2-yl)phenyl]-1,2-oxazole 310h (0.266 g, 50%) as an off-white solid.

Step 8

To a 50 mL round-bottom flask was added 4-(bromomethyl)-5-cyclopropyl-3-[2-fluoro-6-(propan-2-yl)phenyl]-1, 2-oxazole 310h (210 mg, 0.62 mmol, 2.00 equiv.), (1S,4R,5R)-5-hydroxy-2-[(4-methoxyphenyl)methyl]-2-azabicyclo[2.2.1]heptan-3-one 244c (77 mg, 0.31 mmol, 1.00 equiv.), and N,N-dimethylformamide (6 mL). The mixture was cooled to −20° C., and sodium hydride (15 mg, 0.62 mmol, 2.00 equiv., 60% dispersion in mineral oil) was added in several batches. The reaction mixture was stirred at −20° C., for 2 h, then quenched by the addition of water/ice. The aqueous mixture was extracted with ethyl acetate (100 mL×2); and the combined organic extracts were washed with brine (100 mL×2), dried, and concentrated. The residue was purified by silica gel column chromatography eluting with ethyl acetate/petroleum ether (1:2) to give (1S,4R,5R)-5-([5-cyclopropyl-3-[2-fluoro-6-(propan-2-yl)phenyl]-1,2-oxazol-4-yl]methoxy)-2-[(4-methoxyphenyl)methyl]-2-azabicyclo[2.2.1]heptan-3-one 310i (0.2 g, Q) as a crude green oil.

Step 9

To a 50 mL round-bottom flask was added (1S,4R,5R)-5-([5-cyclopropyl-3-[2-fluoro-6-(propan-2-yl)phenyl]-1,2-oxazol-4-yl]methoxy)-2-[(4-methoxyphenyl)methyl]-2-azabicyclo[2.2.1]heptan-3-one 310i (200 mg, 0.40 mmol, 1.00 equiv.), $CH_3CN$ (4.8 mL), $(NH_4)_2Ce(NO_3)_6$ (870 mg, 1.59 mmol, 4.00 equiv.), and water (1.6 mL). The resulting mixture was stirred at room temperature for 30 min. The reaction was quenched by the addition of $Na_2SO_3$, and 100 mL of $H_2O$ was added. The aqueous mixture was extracted with ethyl acetate (100 mL×2), and the combined organic extracts were washed with brine (100 mL×2), dried, and concentrated under reduced pressure. The residue was purified by silica gel column chromatography eluting with ethyl acetate/petroleum ether (1:1) to afford (1S,4R,5R)-5-([5-cyclopropyl-3-[2-fluoro-6-(propan-2-yl)phenyl]-1,2-oxazol-4-yl]methoxy)-2-azabicyclo[2.2.1]heptan-3-one 310j (0.15 g, 98%) as a crude greenish oil.

Step 10

To a 25 mL round-bottom flask was added (1S,4R,5R)-5-([5-cyclopropyl-3-[2-fluoro-6-(propan-2-yl)phenyl]-1,2-oxazol-4-yl]methoxy)-2-azabicyclo[2.2.1]heptan-3-one 310j (150 mg, 0.39 mmol, 1.00 equiv.), $Pd_2(dba)_3$ (18 mg, 0.02 mmol, 0.05 equiv.), Xantphos (23 mg, 0.04 mmol, 0.10 equiv.), $Cs_2CO_3$ (190 mg, 0.58 mmol, 1.50 equiv.), tert-butyl 4-bromobenzoate (150 mg, 0.58 mmol, 1.50 equi.), and dioxane (3 mL). The resulting mixture was stirred at 110° C., overnight. After cooling to room temperature, water was added, the mixture was extracted with ethyl acetate (100 mL×2), and the combined organic extracts were washed with brine (100 mL×2), dried, and concentrated in vacuo. The residue was purified by silica gel column chromatography eluting with ethyl acetate/petroleum ether (1:3) to afford tert-butyl 4-[(1S,4R,5R)-5-([5-cyclopropyl-3-[2-fluoro-6-(propan-2-yl)phenyl]-1,2-oxazol-4-yl]methoxy)-3-oxo-2-azabicyclo[2.2.1]heptan-2-yl]benzoate 310k (0.2 g, 91%) as a reddish oil.

Step 11

To a 25 mL round-bottom flask was added tert-butyl 4-[(1S,4R,5R)-5-([5-cyclopropyl-3-[2-fluoro-6-(propan-2-yl)phenyl]-1,2-oxazol-4-yl]methoxy)-3-oxo-2-azabicyclo[2.2.1]heptan-2-yl]benzoate 310k (200 mg, 0.36 mmol, 1.00 equiv.), dichloromethane (4 mL), and trifluoroacetic acid (2 mL). The reaction mixture was stirred for 1 h at room temperature, diluted with 50 mL of DCM, and the pH value of the solution was adjusted to 7 using a saturated sodium bicarbonate aqueous solution. The aqueous mixture was extracted with ethyl acetate (100 mL×2), and the combined organic extracts were washed with brine (100 mL), dried over anhydrous sodium sulfate and concentrated under vacuum. The crude product was purified by Prep-HPLC using the following conditions: Column, XBridge Prep C18 OBD Column, 5 um, 19*150 mm; mobile phase, Water (10 MMOL/L NH4HCO3+0.1% NH3.H2O) and ACN (47.0% ACN up to 61.0% in 8 min); Detector, UV 254/220 nm. After purification 4-[(1S,4R,5R)-5-([5-cyclopropyl-3-[2-fluoro-6-(propan-2-yl)phenyl]-1,2-oxazol-4-yl]methoxy)-3-oxo-2-azabicyclo[2.2.1]heptan-2-yl]benzoic acid I-310 (68.1 mg, 38%) was obtained as an off-white solid. $^1$H-NMR (400 MHz, DMSO-$d_6$) δ: 12.76 (s, 1H), 7.94-7.85 (m, 2H), 7.63-7.49 (m, 3H), 7.33 (d, J=7.8 Hz, 1H), 7.18 (t, J=8.9 Hz, 1H), 4.61 (s, 1H), 3.79 (d, J=6.5 Hz, 1H), 2.86 (s, 1H), 2.75-2.65 (m, 1H), 2.35 (ddd, J=13.0, 8.3, 5.3 Hz, 1H), 2.06 (dd, J=13.8, 6.5 Hz, 1H), 1.91 (d, J=9.8 Hz, 1H), 1.48 (d, J=13.2 Hz, 1H), 1.13 (q, J=7.1, 6.6 Hz, 10H); MS (ES, m/z): [M+1]=505.

Example 240: 4-[(1S,4R,5R)-5-{[5-cyclopropyl-3-(2-cyclopropyl-6-fluorophenyl)-1,2-oxazol-4-yl]methoxy}-3-oxo-2-azabicyclo[2.2.1]heptan-2-yl]benzoic Acid (I-311)

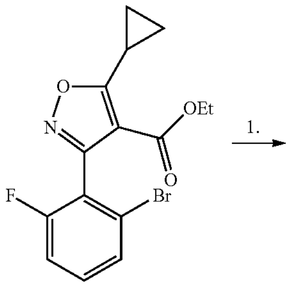

310d

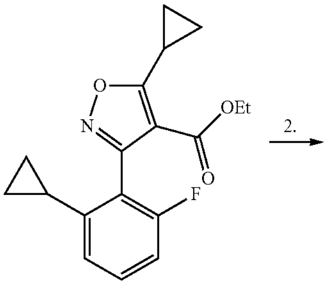

311a

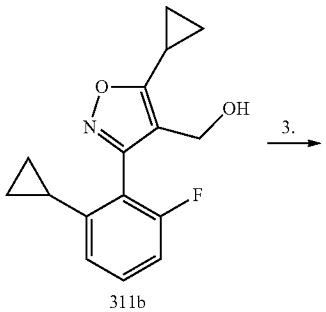

311b

-continued

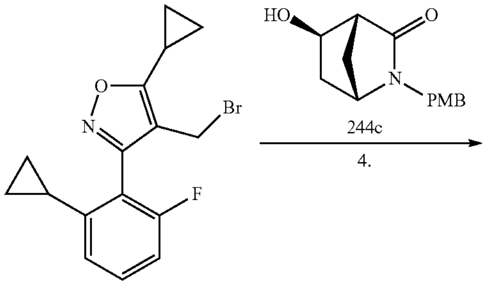

311c

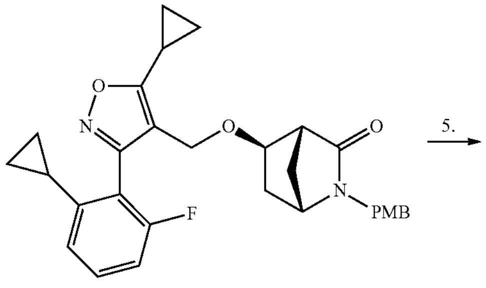

311d

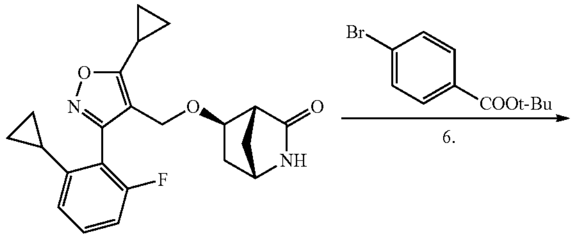

311e

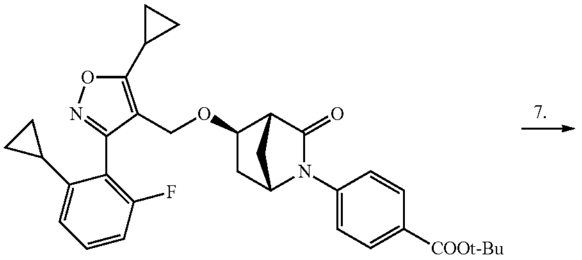

311f

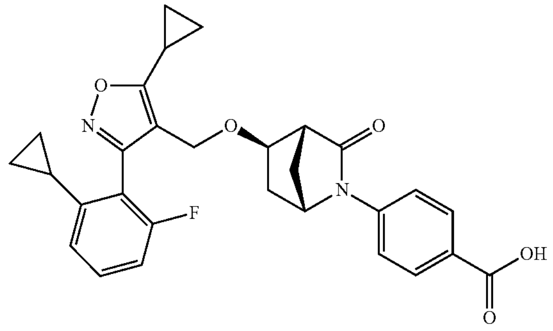

I-311

Step 1

To a 250 mL round-bottom flask was added ethyl 3-(2-bromo-6-fluorophenyl)-5-cyclopropyl-1,2-oxazole-4-carboxylate 310d (200 mg, 0.56 mmol, 1.00 equiv.), $Pd_2(dba)_3$ (25.8 mg, 0.03 mmol, 0.05 equiv.), $K_3PO_4$ (360 mg, 1.70 mmol, 3.00 equiv.), S-Phos (46.3 mg, 0.20 equiv.), tol (10 mL), and cyclopropylboronic acid (97 mg, 1.13 mmol, 2.00 equiv.). The resulting mixture was heated at 100° C. overnight. After cooling to room temperature, 100 mL of $H_2O$ was added, the aqueous mixture was extracted with ethyl acetate (50 mL×2), and the combined organic extracts were washed with brine (100 mL×2), dried and concentrated under vacuum. The residue was purified by silica gel column chromatography eluting with ethyl acetate/hexane (1:3) to give ethyl 5-cyclopropyl-3-(2-cyclopropyl-6-fluorophenyl)-1,2-oxazole-4-carboxylate 311a (80 mg, 45%) as a colorless oil.

Step 2

To a 250 mL round-bottom flask was added ethyl 5-cyclopropyl-3-(2-cyclopropyl-6-fluorophenyl)-1,2-oxazole-4-carboxylate 311a (1.17 g, 3.71 mmol, 1.00 equiv.), $LiAlH_4$ (170 mg, 4.48 mmol, 1.20 equiv.), and tetrahydrofuran (50 mL). The resulting mixture was stirred at room temperature for 3 h. The reaction was quenched by the addition of $Na_2SO_4.10H_2O$. Solids were filtered out, the filtrate was concentrated under vacuum. The residue was purified by silica gel column chromatography eluting with ethyl acetate in hexanes (0% to 28%). Removal of solvents afforded [5-cyclopropyl-3-(2-cyclopropyl-6-fluorophenyl)-1,2-oxazol-4-yl]methanol 311b (0.55 g, 54%) as a yellow oil.

Step 3

To a 250 mL round-bottom flask was added [5-cyclopropyl-3-(2-cyclopropyl-6-fluorophenyl)-1,2-oxazol-4-yl]methanol 311b (550 mg, 2.01 mmol, 1.00 equiv.), NBS (540 mg, 3.03 mmol, 1.50 equiv.), $PPh_3$ (790 mg, 3.01 mmol, 1.50 equiv.), and tetrahydrofuran/DCM (15/15 mL). The resulting mixture was stirred at room temperature for 1 h, and 50 mL of $H_2O$ was added. The aqueous mixture was extracted with ethyl acetate (100 mL×2), and the combined organic extracts were washed with brine (100 mL×2), dried, and concentrated. The residue was purified by silica gel column chromatography eluting with ethyl acetate/hexane (10:1) to give 4-(bromomethyl)-5-cyclopropyl-3-(2-cyclopropyl-6-fluorophenyl)-1,2-oxazole 311c (0.5 g, 74%) as a yellow oil.

Step 4

To a 250 mL round-bottom flask was added 4-(bromomethyl)-5-cyclopropyl-3-(2-cyclopropyl-6-fluorophenyl)-1,2-oxazole 311c (54.3 mg, 0.16 mmol, 2.00 equiv.), (1S,4R,5R)-5-hydroxy-2-[(4-methoxyphenyl)methyl]-2-azabicyclo[2.2.1]heptan-3-one 244c (20 mg, 0.08 mmol, 1.00 equiv.), and N,N-dimethylformamide (1.4 mL). The mixture was cooled at −20° C., and added with sodium hydride (7 mg, 60% dispersion in mineral oil, 0.17 mmol, 1.20 equiv.) The resulting solution was stirred at −20° C., for 2 h, then quenched by the addition of water/ice. The aqueous mixture was extracted with ethyl acetate, and the combined organic extracts were washed with brine, dried, and concentrated. The residue was purified by silica gel column chromatography eluting with ethyl acetate/petroleum ether (1:2) to give (1S,4R,5R)-5-[[5-cyclopropyl-3-(2-cyclopropyl-6-fluorophenyl)-1,2-oxazol-4-yl]methoxy]-2-[(4-methoxyphenyl)methyl]-2-azabicyclo[2.2.1]heptan-3-one 311d (50 mg) as a crude green oil.

Step 5

To a 250 mL round-bottom flask was added (1S,4R,5R)-5-[[5-cyclopropyl-3-(2-cyclopropyl-6-fluorophenyl)-1,2- oxazol-4-yl]methoxy]-2-[(4-methoxyphenyl)methyl]-2-azabicyclo[2.2.1]heptan-3-one 311d (500 mg, 0.99 mmol, 1.00 equiv.), $(NH_4)_2Ce(NO_3)_6$ (2 g, 3.65 mmol, 4.00 equiv.), MeCN (6 mL), and water (2 mL). The resulting mixture was stirred for 30 min at room temperature. The reaction was quenched by the addition of 3 g of $Na_2SO_3$. The resulting solution was diluted with 50 mL of water, extracted with ethyl acetate (100 mL×2), and the combined organic extracts were dried and concentrated under vacuum. The residue was purified by silica gel column chromatography eluting with ethyl acetate/hexane (4:1). Removal of solvents gave (1S,4R,5R)-5-[[5-cyclopropyl-3-(2-cyclopropyl-6-fluorophenyl)-1,2-oxazol-4-yl]methoxy]-2-azabicyclo[2.2.1]heptan-3-one 311e (300 mg, 79%) as a yellow solid.

Step 6

To a 250 mL round-bottom flask was added (1S,4R,5R)-5-[[5-cyclopropyl-3-(2-cyclopropyl-6-fluorophenyl)-1,2-oxazol-4-yl]methoxy]-2-azabicyclo[2.2.2]heptan-3-one 311e (300 mg, 0.78 mmol, 1.00 equiv.), $Pd_2(dba)_3$ (36 mg, 0.04 mmol, 0.05 equiv.), XantPhos (46 mg, 0.08 mmol, 0.10 equiv.), $Cs_2CO_3$ (384 mg, 1.18 mmol, 1.50 equiv.), tol (5 mL), and tert-butyl 4-bromobenzoate (301 mg, 1.17 mmol, 1.50 equiv.). The resulting mixture was heated at 110° C., overnight with stirring. After cooling to room temperature, the mixture was diluted with 50 mL of $H_2O$, extracted with ethyl acetate (100 mL×2), and the combined organic extracts were washed with brine (100 mL×2), dried, and concentrated. The residue was purified by silica gel column chromatography eluting with ethyl acetate/hexane (2:1) to give tert-butyl 4-[(1S,4R,5R)-5-[[5-cyclopropyl-3-(2-cyclopropyl-6-fluorophenyl)-1,2-oxazol-4-yl]methoxy]-3-oxo-2-azabicyclo[2.2.1]heptan-2-yl]benzoate 311f (300 mg, 68%) as a yellow oil.

Step 7

To a 250 mL round-bottom flask was added tert-butvl 4-[(1S,4R,5R)-5-[[5-cyclopropyl-3-(2-cyclopropyl-6-fluorophenyl)-1,2-oxazol-4-yl]methoxy]-3-oxo-2-azabicyclo[2.2.1]heptan-2-yl]benzoate 311f (160 mg, 0.29 mmol, 1.00 equiv.), trifluoroacetic acid (2 mL), and dichloromethane (4 mL). The resulting mixture was stirred for 1 h at room temperature. The mixture was diluted with 50 mL of $H_2O$, extracted with ethyl acetate (100 mL×2), and the combined organic extracts were washed with brine, dried, and concentrated. The residue was purified by silica gel column chromatography eluting with ethyl acetatehexane (1:1) to afford 4-[(1S,4R,5R)-5-[[5-cyclopropyl-3-(2-cyclopropyl-6-fluorophenyl)-1,2-oxazol-4-yl]methoxy]-3-oxo-2-azabicyclo[2.2.1]heptan-2-yl]benzoic acid I-311 (32.8 mg, 23%) as a colorless solid. $^1$H-NMR (400 MHz, $CD_3OD$) δ: 8.06-7.95 (m, 2H), 7.59 (d, J=8.9 Hz, 2H), 7.43 (td, J=8.1, 5.9 Hz, 1H), 7.04 (t, J=8.7 Hz, 1H), 6.84 (d, J=8.0 Hz, 1H), 4.57 (s, 1H), 4.40 (s, 2H), 3.86 (d, J=6.5 Hz, 1H), 2.84 (s, 1H), 2.30 (p, J=7.0 Hz, 1H), 2.15 (dd, J=13.1, 6.4 Hz, 1H), 1.98 (d, J=10.2 Hz, 1H), 1.83-1.66 (m, 2H), 1.64 (t, J=12.8 Hz, 1H), 1.19 (d, J=6.8 Hz, 4H), 0.95-0.85 (m, 2H), 0.72 (d, J=5.3 Hz, 2H); MS (ES, m/z): [M+1]=503.

Example 241: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2,3-dihydro-1H-indene-1-carboxylic Acid (I-312)

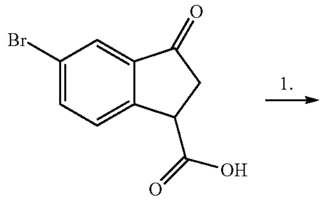

312a

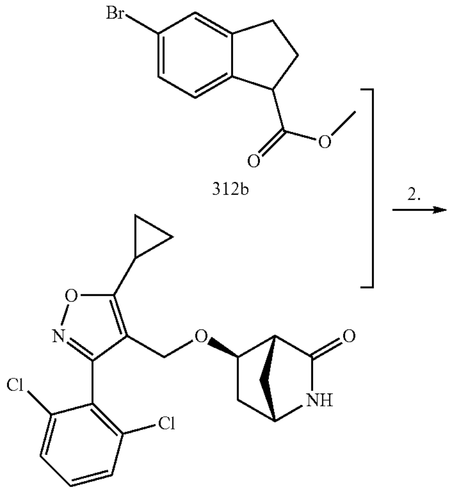

312b

244g

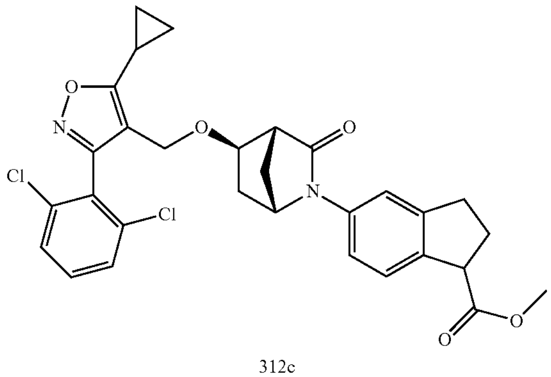

312c

-continued

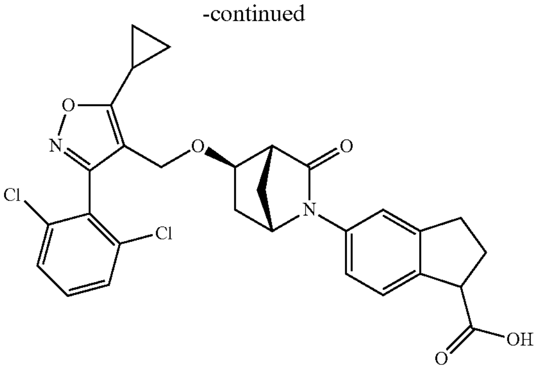

I-312

Step 1

To a 8 mL tube was added 5-bromo-2,3-dihydro-H-indene-1-carboxylic acid 312a (200 mg, 0.83 mmol, 1.00 equiv.), tetrahydrofuran (1 mL), methanol (1 mL), and a 2M solution of $TMSCHN_2$ in n-hexane (7 mL, 4.00 equiv.). The resulting mixture was stirred at room temperature for 1 h and concentrated under vacuum. The residue was purified by silica gel column chromatography eluting with ethyl acetate/petroleum ether (1:5) to give methyl 5-bromo-2,3-dihydro-1H-indene-1-carboxylate 312b (205 mg, 97%) as a colorless oil.

Step 2

To a 8 mL sealed tube was added (1S,4R,5R)-5-[[5-cyclopropyl-3-(2,6-dichlorophenyl)-1,2-oxazol-4-yl]methoxy]-2-azabicyclo[2.2.1]heptan-3-one 244g (150 mg, 0.38 mmol, 1.00 equiv.), methyl 5-bromo-2,3-dihydro-1H-indene-1-carboxylate 312b (200 mg, 0.78 mmol, 1.20 equiv.), XantPhos (0.15 equiv.) (34 mg, 0.15 equiv.), $Pd_2(dba)_3$ (18 mg, 0.05 equiv.). $Cs_2CO_3$ (188 mg, 1.50 equiv.), and dioxane (2 mL). The resulting mixture was heated at 105° C., overnight. After cooling to room temperature, 50 mL of $H_2O$ was added, the mixture was extracted with ethyl acetate (50 mL×2), and the combined organic extracts were washed with brine (100 mL×2), dried over sodium sulfate, and concentrated under vacuum. The residue was purified by silica gel column chromatography eluting with ethyl acetate/petroleum ether (1:3) to give methyl 5-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2,3-dihydro-1H-indene-1-carboxylate 312c (77 mg, 36%) as a light yellow oil.

Step 3

To a 8 mL sealed tube was added methyl 5-[(1S,4R,5R)-5-[5-cyclopropyl-3-(2,6-dichlorophenyl)-1,2-oxazol-4-yl]methoxy-3-oxo-2-azabicyclo[2.2.1]heptan-2-yl]-2,3-dihydro-1H-indene-1-carboxylate 312c (77 mg, 0.14 mmol, 1.00 equiv.), pyridine (1 mL), and LiI (182 mg, 10.00 equiv.). The resulting mixture was heated at 125° C., overnight. After cooling, the pH value of the solution was adjusted to 7 using a 1M aqueous hydrogen chloride solution, and the aqueous mixture was extracted with ethyl acetate (100 mL×2). The combined organic extracts were washed with brine, dried over anhydrous sodium sulfate, and concentrated under vacuum. The crude product was purified by Prep-HPLC using the following conditions: Column, XBridge Shield RP18 OBD Column, 5 um, 19*150 mm; mobile phase, Water (0.05% TFA) and ACN (48.0% ACN up to 66.0% in 8 min); Detector, uv 254/220 nm. After purification 5-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2,3-dihydro-1H-indene-1-carboxylic acid I-312 (16 mg, 21%) was obtained as a colorless solid. $^1$H-NMR (400 MHz, $CD_3OD$) δ: 7.62-7.45 (m, 3H), 7.40-7.30 (m, 2H), 7.28-7.18 (m, 1H), 4.41 (dd, J=11.3, 1.8 Hz, 3H), 4.00 (t, J=7.3 Hz, 1H), 3.86 (d, J=6.7 Hz, 1H), 3.16-2.99 (m, 1H), 2.91 (dt, J=15.6, 7.4 Hz, 1H), 2.81 (s, 1H), 2.49-2.28 (m, 3H), 2.28-2.10 (m, 1H), 1.97 (d, J=10.1 Hz, 1H), 1.75 (d, J=9.8 Hz, 1H), 1.57 (d, J=13.4 Hz, 1H), 1.25-1.14 (m, 4H); MS (ES, m/z): [M+1]=553.12.

Example 242: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2,3-dihydro-1H-indene-2-carboxylic Acid (I-313)

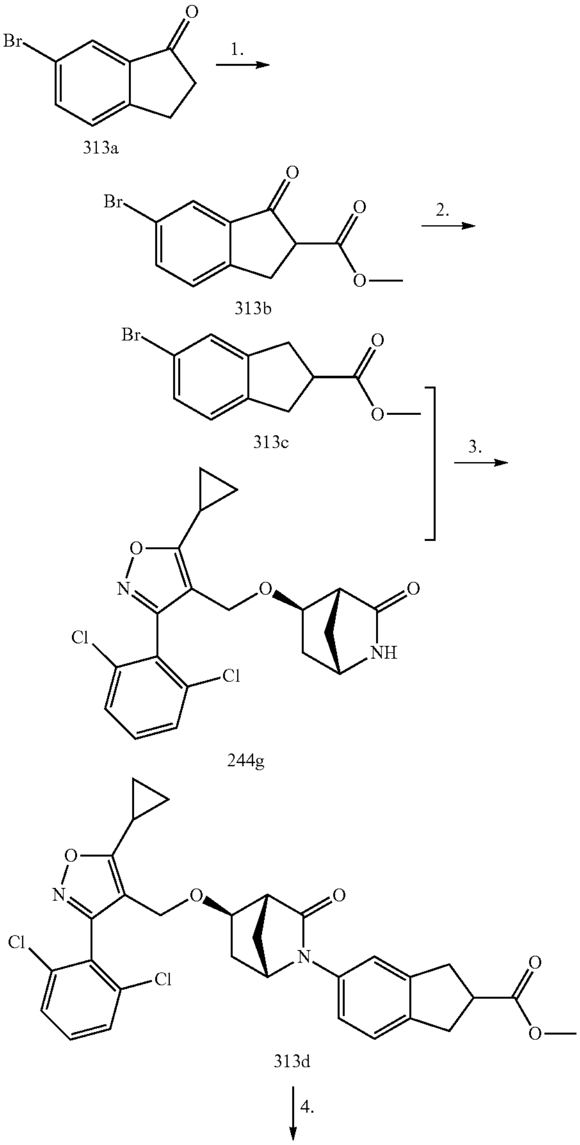

313a

313b

313c

244g

313d

-continued

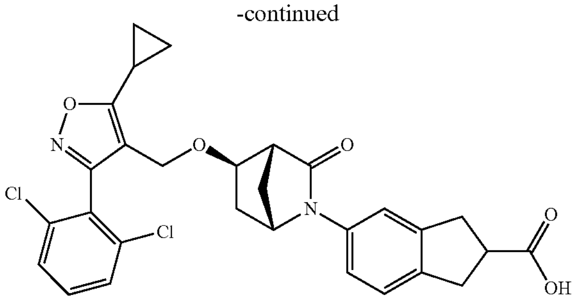

I-313

Step 1

To a 250 mL round-bottom flask was added 6-bromo-2,3-dihydro-1H-inden-1-one 313a (5 g, 23.69 mmol, 1.00 equiv.), sodium hydride (1.84 g, 60% dispersed in mineral oil, 76.67 mmol, 2.00 equiv.), tetrahydrofuran (20 mL), and dimethyl carbonate (3.2 g, 35.52 mmol, 1.50 equiv.). The resulting mixture was stirred at 30° C., for 1 h. The reaction was quenched by the addition of 50 mL of water. The aqueous mixture was extracted with ethyl acetate (100 mL×2), and the combined organic extracts were washed with brine (100 mL×2), dried, and concentrated under reduced pressure. The residue was purified by silica gel column chromatography eluting with ethyl acetate/hexane (2:1) to afford methyl 6-bromo-1-oxo-2,3-dihydro-1H-indene-2-carboxylate 313b (7.1 g, Q) as a crude yellowish oil.

Step 2

To a 50 mL round-bottom flask was added methyl 6-bromo-1-oxo-2,3-dihydro-1H-indene-2-carboxylate 313b (3.5 g, 13.01 mmol, 1.00 equiv.), $Et_3SiH$ (10 mL), and trifluoroacetic acid (25 mL). The resulting mixture was stirred overnight at room temperature and concentrated under vacuum. The residue was purified by silica gel column chromatography eluting with ethyl acetate/hexane (2:1) to give methyl 5-bromo-2,3-dihydro-1H-indene-2-carboxylate 313c (1.37 g, 41%) as a yellow crystal.

Step 3

To a 50 mL round-bottom flask was added methyl 5-bromo-2,3-dihydro-1H-indene-2-carboxylate 313c (116 mg, 0.45 mmol, 1.20 equiv), $Pd_2(dba)_3$ (18 mg, 0.02 mmol, 0.05 equiv.), XantPhos (22 mg, 0.04 mmol, 0.10 equiv.). $Cs_2CO_3$ (185 mg, 0.57 mmol, 1.50 equiv.), dioxane (5 mL), and (1S,4R,5R)-5-[5-cyclopropyl-3-(2,6-dichlorophenyl)-1,2-oxazol-4-yl]methoxy-2-azabicyclo[2.2.1]heptan-3-one 244g (150 mg, 0.38 mmol, 1.00 equiv.). The resulting mixture was heated at 110° C., overnight. The mixture was diluted with 50 mL of $H_2O$ upon cooling to room temperature, and extracted with ethyl acetate (100 mL×2). The combined organic extracts were washed with brine (100 mL×2), dried, and concentrated. The residue was purified by silica gel column chromatography eluting with ethyl acetate/hexane (2:1) to give methyl 5-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2,3-dihydro-1H-indene-2-carboxylate 313d (200 mg, 92%) as a yellow oil.

Step 4

To a 250 mL round-bottom flask was added methyl 5-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2,3-dihydro-1H-indene-2-carboxylate 313d (170 mg, 0.30 mmol, 1.00 equiv.), pyridine (3 mL), and LiI (402 mg, 3.00 mmol, 10.00 equiv.). The resulting mixture was heated at 125° C., overnight. After cooling to room temperature, the pH value of the solution was adjusted to 3 using a 1M hydrogen chloride aqueous solution. The mixture was extracted with ethyl acetate (100 mL×2), and the combined organic extracts were washed with brine (100 mL×2), dried over anhydrous $Na_2SO_4$, and concentrated to dryness under vacuum. The crude product was purified by Prep-HPLC using the following conditions: Column, XBridge Shield RP18 OBD Column, 5 um, 19*150 mm; mobile phase, Water (0.05% TFA) and ACN (56.0% ACN up to 85.0% in 8 min); Detector, UV 254/220 nm. After purification 5-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2,3-dihydro-1H-indene-2-carboxylic Acid I-313 (19 mg, 11%) was obtained as a colorless solid. $^1$H-NMR (300 MHz, $CD_3OD$) δ: 7.62-7.44 (m, 3H), 7.28 (s, 1H), 7.17 (s, 2H), 4.38 (d, J=1.4 Hz, 3H), 3.85 (d, J=6.8 Hz, 1H), 3.28 (t, J=8.0 Hz, 1H), 3.18 (t, J=8.0 Hz, 4H), 2.79 (s, 1H), 2.37-2.21 (m, 1H), 2.16 (dd, J=13.5, 7.0 Hz, 1H), 2.08-1.91 (m, 1H), 1.73 (d, J=9.7 Hz, 1H), 1.55 (d, J=13.3 Hz, 1H), 1.24-1.14 (m, 4H); MS (ES, m/z): [M+1]=553.

Example 243: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorobenzoic Acid (I-314)

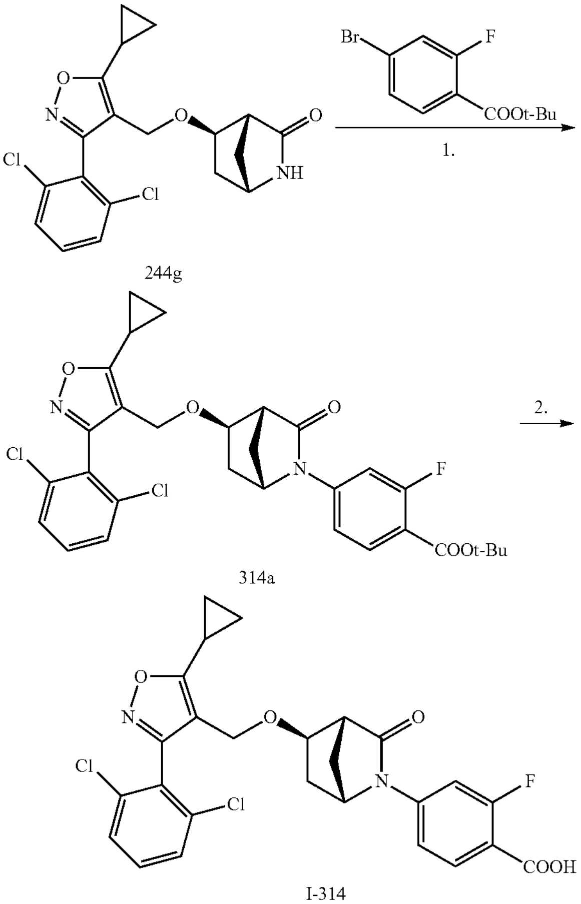

244g

314a

I-314

Step 1

To a 5 mL sealed tube purged with and maintained under an inert atmosphere of nitrogen was added a solution of (1S,4R,5R)-5-[[5-cyclopropyl-3-(2,6-dichlorophenyl)-1,2-oxazol-4-yl]methoxy]-2-azabicyclo[2.2.1]heptan-3-one 244g (180 mg, 0.46 mmol, 1.00 equiv.) in 1,4-dioxane (3 mL), tert-butyl 4-bromo-2-fluorobenzoate (151 mg, 0.55 mmol, 1.20 equiv.), Xant-Phos (39.8 mg, 0.15 equiv.), $Pd_2(dba)_3$ (21 mg, 0.02 mmol, 0.05 equiv.), and $Cs_2CO_3$ (224.5 mg, 0.69 mmol, 1.50 equiv.). The resulting mixture was heated at 90° C., overnight. After cooling to room temperature, 20 mL of $H_2O$ was added, the mixture was extracted with ethyl acetate (50 mL×2), and the combined organic extracts were washed with brine (50 mL), dried over anhydrous sodium sulfate and concentrated under vacuum. The residue was purified by silica gel column chromatography eluting with ethyl acetate/petroleum ether (1:3) to afford tert-butyl 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2-fluorobenzoate 314a (180 mg, 67%) as a yellow oil.

Step 2

To a 25 mL round-bottom flask was added a solution of tert-butyl 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2-fluorobenzoate 314a (40 mg, 0.07 mmol, 1.00 equiv.) in dichloromethane (2 mL), and trifluoroacetic acid (1 mL). The resulting mixture was stirred at room temperature for 3 h and concentrated. The residue was diluted with DCM (30 mL) and washed with brine (30 mL), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (46.0% ACN up to 64.0% in 8 min); Detector, UV 254 nm. After purification 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2-fluorobenzoic acid I-314 (28.2 mg, 78%) was obtained as a colorless solid. $^1$H-NMR (300 MHz, $CD_3OD$) δ: 7.94 (s, 1H), 7.55 (t, J=9.7 Hz, 4H), 7.34 (s, 1H), 4.61 (s, 1H), 4.40 (s, 2H), 3.87 (s, 1H), 2.87 (s, 1H), 2.31 (s, 1H), 2.11-2.09 (m, 1H), 1.97 (s, 1H), 1.82 (s, 1H), 1.65 (s, 1H), 1.20 (s, 4H); MS (ES, m/z): [M+1]=531.1.

Example 244: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluorobenzoic Acid (I-315)

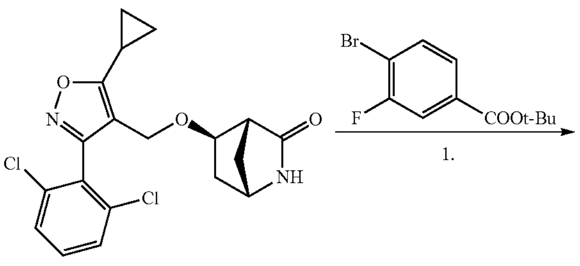

244g

-continued

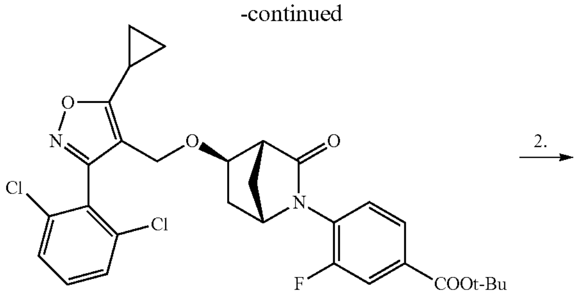

315a

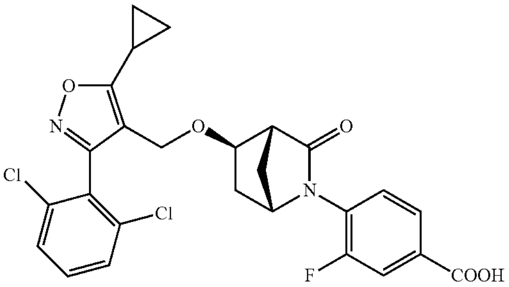

I-315

Step 1

To a 50 mL round-bottom flask purged with and maintained under an inert atmosphere of nitrogen was added tert-butyl 4-bromo-3-fluorobenzoate (126 mg, 0.46 mmol, 1.20 equiv.), a solution of (1S,4R,5R)-5-[[5-cyclopropyl-3-(2,6-dichlorophenyl)-1,2-oxazol-4-yl]methoxy]-2-azabicyclo[2.2.1]heptan-3-one 244g (100 mg, 0.25 mmol, 1.00 equiv.) in dioxane (3 mL), $Pd_2(dba)_3$ (18.9 mg, 0.02 mmol, 0.05 equiv.). Xant-Phos (36 mg, 0.15 equiv.), and $Cs_2CO_3$ (202 mg, 0.62 mmol, 1.50 equiv.). The resulting mixture was heated at 110° C., for 3 h. After cooling to room temperature, the mixture was diluted with EA (100 mL), washed with brine (50 mL×2), dried over anhydrous sodium sulfate and concentrated under vacuum. The residue was purified by silica gel column chromatography eluting with ethyl acetate/petroleum ether (1:3). Removal of solvents gave tert-butyl 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-3-fluorobenzoate 315a (110 mg, 74%) as a light yellow foam.

Step 2

To a 25 mL round-bottom flask was added a solution of tert-butyl 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-3-fluorobenzoate 315a (110 mg, 0.19 mmol, 1.00 equiv.) in dichloromethane (2 mL), and trifluoroacetic acid (1 mL). The resulting mixture was stirred for 1 h at room temperature. The mixture was diluted with dichloromethane (100 mL), and washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (5.0% ACN up to 48.0% in 1 min, up to 63.0% in 7 min); Detector, UV 254 nm. After purification 4-[(1S,4R,5R)-5-[[5-cyclopropyl-3-(2,6-dichlorophenyl)-1,2-oxazol-4-yl]methoxy]-3-oxo-2- azabicyclo[2.2.1]heptan-2-yl]-3-fluorobenzoic acid I-315 (66.9 mg, 67%) was obtained as a colorless solid. $^{1}$H-NMR (300) MHz. $CD_3OD$) δ: 7.84-7.68 (m, 2H), 7.58-7.41 (m, 4H), 4.33 (d, J=19.7 Hz, 3H), 3.91 (d, J=6.7 Hz, 1H), 2.80 (s, 1H), 2.34-2.15 (m, 2H), 2.06 (d, J=10.0 Hz, 1H), 1.77 (d, J=9.9 Hz, 1H), 1.51 (d, J=13.5 Hz, 1H), 1.24-1.12 (m, 4H); MS (ES, m/z): [M+1]=531.08.

Example 245: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-methylbenzoic Acid (I-316)

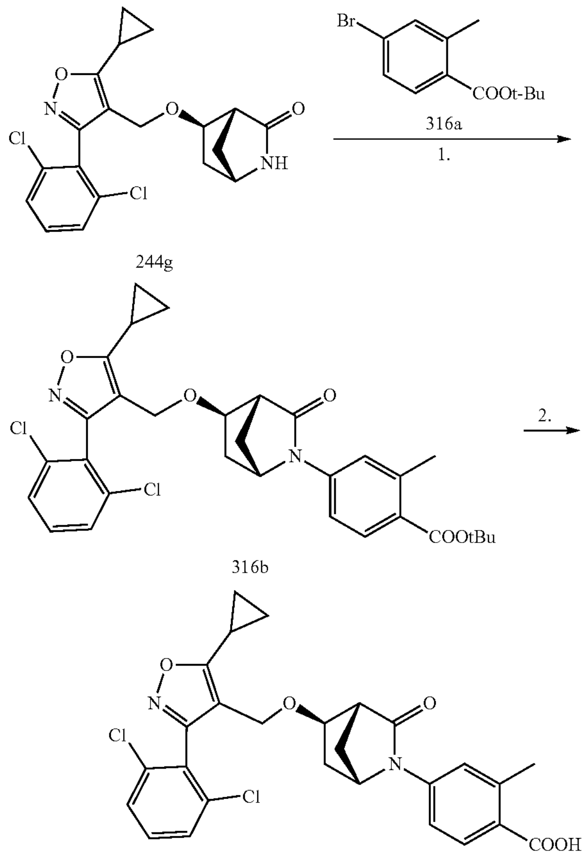

244g
316a
316b
I-316

Following the two step procedures described in Preparative Example 244, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (191 mg, 1.00 equiv.) with tert-butyl 4-bromo-2-methylbenzoate 316a (200 mg, 1.5 equiv.), the desired product 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-methylbenzoic acid I-316 (138 mg) was obtained as an off-white solid. $^{1}$H-NMR (400 MHz, DMSO-d6) δ: 7.73 (d, J=8.6 Hz, 1H), 7.45-7.24 (m, 3H), 7.18-7.01 (m, 2H), 4.30 (s, 1H), 4.10-3.93 (m, 2H), 3.49 (d, J=6.1 Hz, 1H), 2.79 (s, 1H), 2.38 (s, 3H), 2.36-2.34 (m, 1H), 2.11 (dd, J=13.3 & 6.8 Hz, 1H), 1.76 (d, J=9.8 Hz, 1H), 1.44 (d, J=13.3 Hz, 1H), 1.31 (d, J=9.8 Hz, 1H), 1.17-1.08 (m, 4H); MS (ES, m/z): [M+1]=527.06.

Example 246: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-methylbenzoic Acid (I-317)

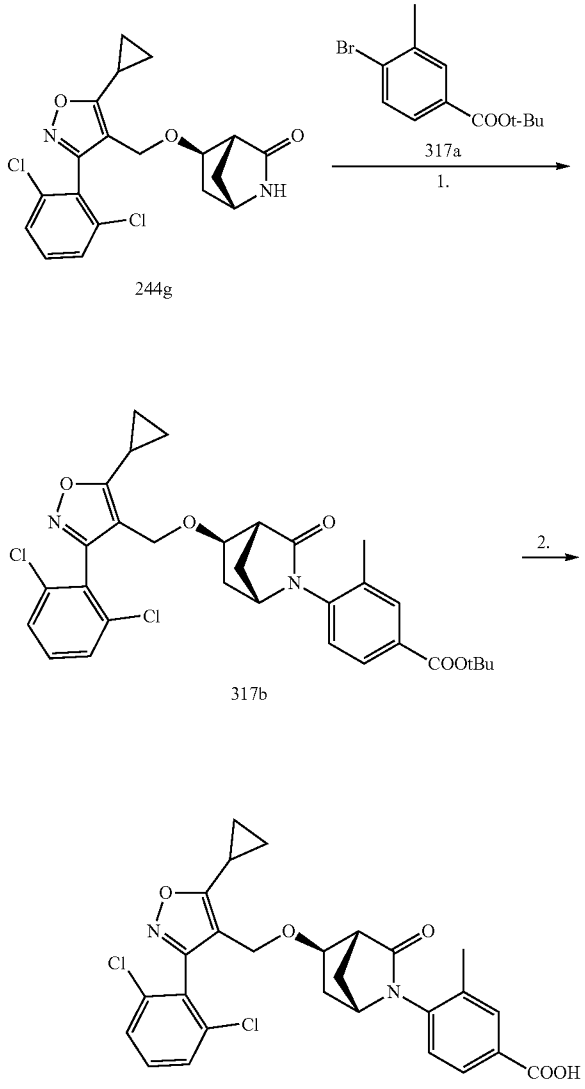

244g
317a
317b
I-317

Following the two step procedures described in Preparative Example 244, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (191 mg, 1.00 equiv.) with tert-butyl 4-bromo-3-methylbenzoate 317a (200 mg, 1.5 equiv.), the desired product 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-methylbenzoic acid I-317 (97 mg) was obtained as an off-white solid. $^{1}$H-NMR (400 MHz, DMSO-d6) δ: 7.82 (s, 1H), 7.72 (dd, J=15.4 & 13.7 Hz, 1H), 7.67-7.52 (m, 3H), 7.13 (d, J=8.3 Hz, 1H), 4.35 (d, J=5.1 Hz, 2H), 4.13 (s, 1H), 3.91 (d, J=5.8 Hz, 1H), 2.74 (s, 1H), 2.44-2.31 (m, 1H), 2.17 (bs, 4H), 2.05 (d, J=9.5 Hz, 1H), 1.58 (d, J=9.6 Hz, 1H), 1.35 (d, J=13.3 Hz, 1H), 1.18-1.09 (m, 4H); MS (ES, m/z): [M+1]=527.04.

Example 247: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-ethylbenzoic Acid (I-318)

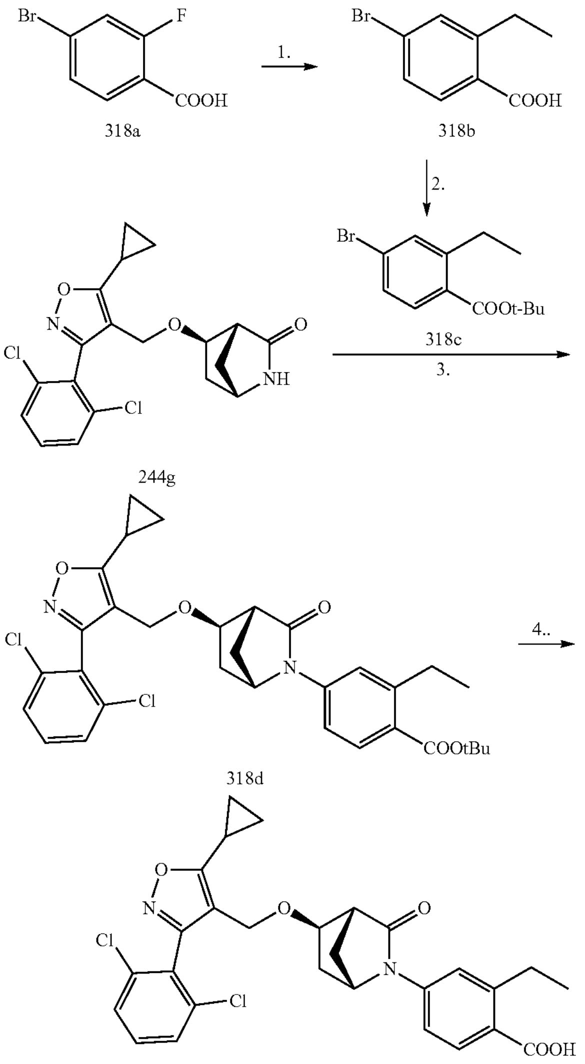

318a 318b 318c 244g 318d

I-318

Step 1

To a stirred solution of 4-bromo-2-fluorobenzoic acid 318a (6.0 g, 27.6 mmol, 1 equiv.) in THF (48 mL) was added a 1.0 M solution of ethyl magnesium bromide in THF (96 mL, 96 mmol) dropwise at 0° C. The reaction mixture was stirred at room temperature for 16 h, then diluted with water (200 mL) and washed with ethyl acetate. The water layer was acidified using a 2N HCl aqueous solution and extract with ethyl acetate. The combined ethyl acetate layers were washed with brine, dried over sodium sulfate, filter and concentrated under reduced pressure to afford 4-bromo-2-ethylbenzoic acid 318b (crude, 2.1 g) which was used in the next step without purification. $^1$HNMR (400 MHz. DMSO-d6) δ: 13.0 (s, 1H), 7.70 (d, J=8.3 Hz 1H), 7.55 (d, J=2.0 Hz, 1H), 7.49 (dd, J=8.3 & 2.0 Hz, 1H), 2.91 (q, J=7.5 Hz, 2H), 1.23-1.02 (m, 3H); MS (ES, m/z): [M+1]=228.93.

Step 2

To a stirred solution of the above acid 318b (2.1 g, 1 equiv.) in THF (20 mL) was added di-tert-butyl dicarbonate (3.5 g; 1.5 equiv.), TEA (3.5 mL; 2.5 equiv.), and DMAP (0.6 g, 0.5 equiv.). The reaction mixture was stirred at room temperature for 16 h. It was diluted with ethyl acetate and washed with water, saline, dried over sodium sulfate and concentrated under reduced pressure. The crude material was purified by silica gel column chromatography eluting with 2-5% ethyl acetate in hexanes to give the desired ester 318c (0.49 g) as a liquid. $^1$HNMR (400 MHz, DMSO-d6) δ: 7.60 (d, J=8.3 Hz, 1H), 7.55 (d, J=2.0 Hz, 1H), 7.48 (dd, J=8.3 & 2.0 Hz, 1H), 2.84 (q, J=7.5 Hz, 2H), 1.54 (bs, 9H), 1.14 (q. J=7.3 Hz, 3H).

Steps 3 and 4

Following the two step procedures described in Preparative Example 244, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (191 mg, 1.00 equiv.) with tert-butyl 4-bromo-2-ethylbenzoate 318c (210 mg, 1.5 equiv.), the desired product 4-[(1S,4R,5R)-5-{([5-cyclopropyl-3-(2,6-dichlorophenyl)-1,2-oxazol-4-yl]methoxy}-3-oxo-2-azabicyclo[2.2.1]heptan-2-yl]-2-ethylbenzoic acid I-318 (126 mg) was obtained as an off-white solid. $^1$H-NMR (400 MHz, DMSO-d6) δ: 7.79 (d, J=8.5 Hz, 1H), 7.69-7.50 (m, 3H), 7.46-7.32 (m, 2H), 4.59 (s, 1H), 4.42-4.22 (m, 2H), 3.78 (d, J=6.1 Hz, 1H), 2.92 (q, J=7.4 Hz, 2H), 2.79 (s, 1H), 2.44-2.25 (m, 1H), 2.17-1.94 (m, 1H), 1.88 (d, J=9.5 Hz, 1H), 1.56 (d, J=9.7 Hz, 1H), 1.44 (d, J=13.3 Hz, 1H), 1.21-1.04 (m, 7H); MS (ES, m/z): [M+1]=541.03.

Example 248: 2-cyclopropyl-4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic Acid (I-319) and 4-cyclopropyl-2-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic Acid (I-320)

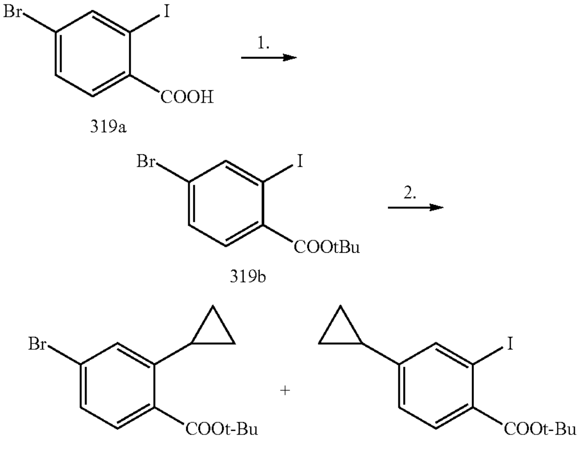

319a 319b

319c + 319d

-continued

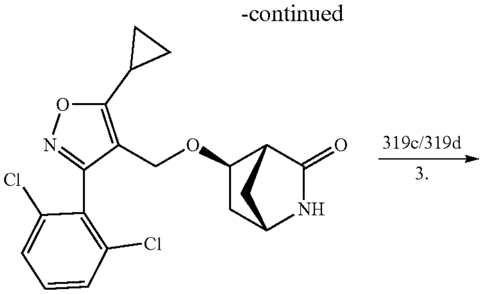

244g

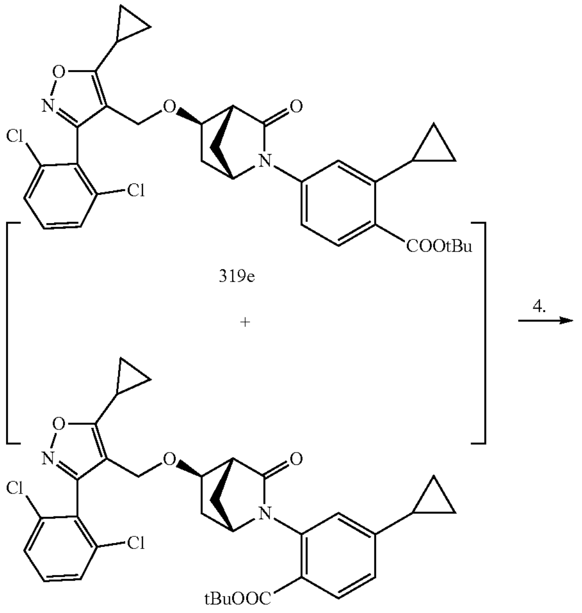

319e

+

319f

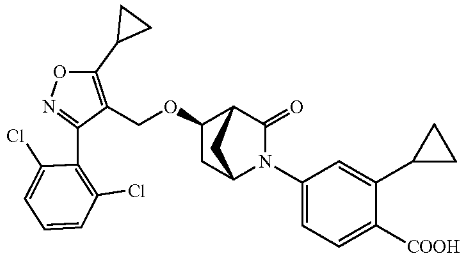

I-319

+

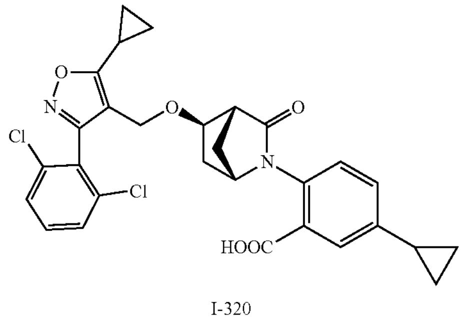

I-320

Step 1

To a stirred solution of 4-bromo2-iodobenzoic acid 319a (3.0 g, 1 equiv.) in THF (40 mL) was added di-tert-butyl dicarbonate (3.0 g, 1.5 equiv.), TEA (3.2 mL, 2.5 equiv.) and DMAP (1.1 g, 1.0 equiv.). The reaction mixture was stirred at room temperature for 16 h, diluted with ethyl acetate, and washed with water, brine, dried over sodium sulfate, filtered and concentrated under reduced pressure. The residue was purified by silica gel chromatography eluting with 3-5% ethyl acetate in hexanes to give the tert-butyl 4-bromo-2-iodobenzoate 319b (0.9 g) as a liquid. $^{1}$HNMR (400 MHz, DMSO-d6) δ: 8.18 (d, J=1.9 Hz, 1H), 7.76-7.60 (m, 1H), 7.54 (d, J=8.3 Hz, 1H), 1.56 (bs, 9H).

Step 2

To a stirred solution of tert-butyl 4-bromo-2-iodobenzoate 319b (0.38 g, 1 equiv.), cyclopropyl-boronic acid (0.12 g, 1.3 equiv.) and potassium phosphate tribasic (0.43 g, 2.5 equiv.) in toluene-water (10:1; 11.0 mL) was added $PdCl_2$(dppf).$CH_2Cl_2$ (83 mg, 0.1 equiv.) under nitrogen atmosphere. The reaction mixture was heated at 80° C., for 16 h. After cooling to room temperature, the mixture was diluted with ethyl acetate and filtered through a pad of Celite, the filtrate was separated. The isolated organic layer was washed with saline, dried over sodium sulfate, filtered and concentrated under the reduced pressure. The crude material was purified by silica gel column chromatography eluting with 3-5 ethyl acetate in hexanes to afford a mixture of tert-butytyl 4-bromo-2-cyclopropylbenzoate 319c and tert-butyl 4-cyclopropyl-2-iodo-benzoate 319d in 4:1 ratio (0.24 g). $^{1}$HNMR (400 MHz DMSO-d6) δ: 7.83-7.78 (m, 0.2H), 7.72 (dd, J=6.3 & 4.8 Hz, 0.2H), 7.53 (d, J=8.3 Hz, 0.8H), 7.44 (dd, J=8.3 & 2.0 Hz, 0.8H), 7.18 (d, J=1.9 Hz, 1H), 2.47-2.37 (m, 1H), 1.55 (bs, 9H), 1.01-0.92 (m, 2H), 0.72 (dd, J=5.3 & 1.8 Hz, 2H).

Steps 3 and 4

Following the two step procedures described in Preparative Example 244, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (191 mg, 1.00 equiv.) with the mixture of tert-butyl 4-bromo-2-cyclopropylbenzoate 319c and tert-butyl 4-cyclopropyl-2-iodo-benzoate 319d (0.21 g, 4:1 ratio, 1.5 equiv.), the titled products were obtained after Semi-prep HPLC purification employing 40-95% ACN (0.1% TFA) in 30 min, method afforded 2-cyclopropyl-4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoic acid I-319 (56 mg) as an off-white solid and 4-cyclopropyl-2-((1S,4R,5R)-5-((5-cyclopropyl-3-(2,6-dichlorophenyl)isoxazol-4-yl)methoxy)-3-oxo-2-azabicyclo[2.2.1]heptan-2-yl)benzoic acid I-320 (5.8 mg) also an off-white solid.

I-319: $^{1}$HNMR (400 MHz, DMSO-d6) δ: 7.73 (d, J=8.6 Hz, 1H), 7.69-7.50 (m, 3H), 7.26 (dd, J=8.71 & 2.1 Hz, 1H), 7.08 (d, J=2.1 Hz, 1H), 4.58 (s, 1H), 4.33-4.28 (m, 2H), 3.77 (d, J=6.1 Hz, 1H), 2.89-2.66 (m, 2H), 2.46-2.25 (m, 1H), 2.01 (dd, J=13.2 & 6.6 Hz, 1H), 1.86 (d, J=9.8 Hz, 1H), 1.54 (d, J=9.7 Hz, 1H), 1.43 (d, J=13.3 Hz, 1H), 1.16-1.08 (m, 4H), 0.95 (dd, J=8.5 & 2.0 Hz, 2H), 0.72-0.52 (m 2H); MS (ES, m/z): [M+1]=553.09.

I-320: $^{1}$HNMR (400 MHz. DMSO-d6) δ: 7.86-7.73 (m, 2H), 7.69-7.52 (m, 4H), 4.66 (d, J=15.1 Hz, 1H), 4.33 (bs, 2H), 3.81 (d, J=6.2 Hz, 1H), 2.85 (bs, 2H), 2.41-2.28 (m, 1H), 2.18-2.03 (m, 2H), 1.93 (d, J=9.7 Hz, 1H), 1.72 (dt, J=14.5 & 7.2 Hz, 1H), 1.61-1.31 (m, 2H), 1.22-1.03 (m 4H), 0.86 (q, J=7.1 Hz, 2H); MS (ES, m/z): [M+1]=553.01.

Example 249: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridine-2-carboxylic Acid (I-321)

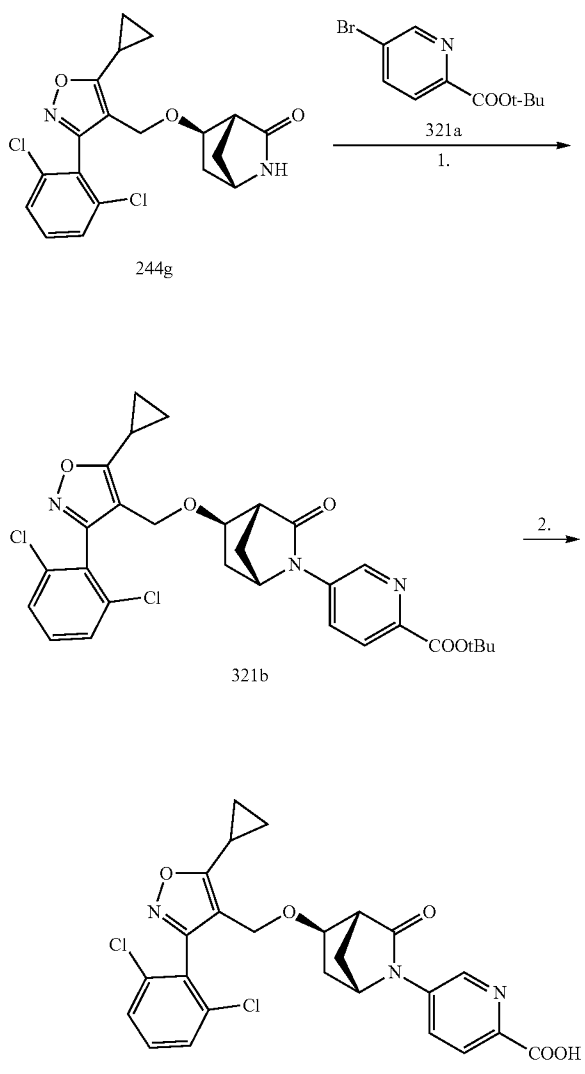

244g
321b
I-321

Following the two step procedures described in Preparative Example 244, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (98 mg, 1.00 equiv.) with tert-butyl 5-bromonicotinate 321a (130 mg, 1.5 equiv.), the desired product 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridine-2-carboxylic acid I-321 (37 mg) was obtained as an off-white solid. $^{1}$H-NMR (400 MHz, DMSO-$d_6$) δ: 8.91-8.69 (m, 1H), 8.21 (dd, J=8.8 & 2.3 Hz, 1H), 8.02 (d, J=8.8 Hz, 1H), 7.75-7.48 (m, 3H), 4.99 (s, 1H), 4.33-4.22 (m, 2H), 3.81 (d, J=6.1 Hz, 1H), 2.84 (s, 1H), 2.43-2.24 (m, 1H), 2.00 (dd, J=13.3 & 6.8 Hz, 1H), 1.91 (d, J=9.8 Hz, 1H), 1.59 (d, J=9.7 Hz, 1H), 1.42 (d, J=13.4 Hz, 1H), 1.24-0.99 (m, 4H); MS (ES, m/z): [M+1]=514.13.

Example 250: 6-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yll]pyridine-3-carboxylic Acid (I-322)

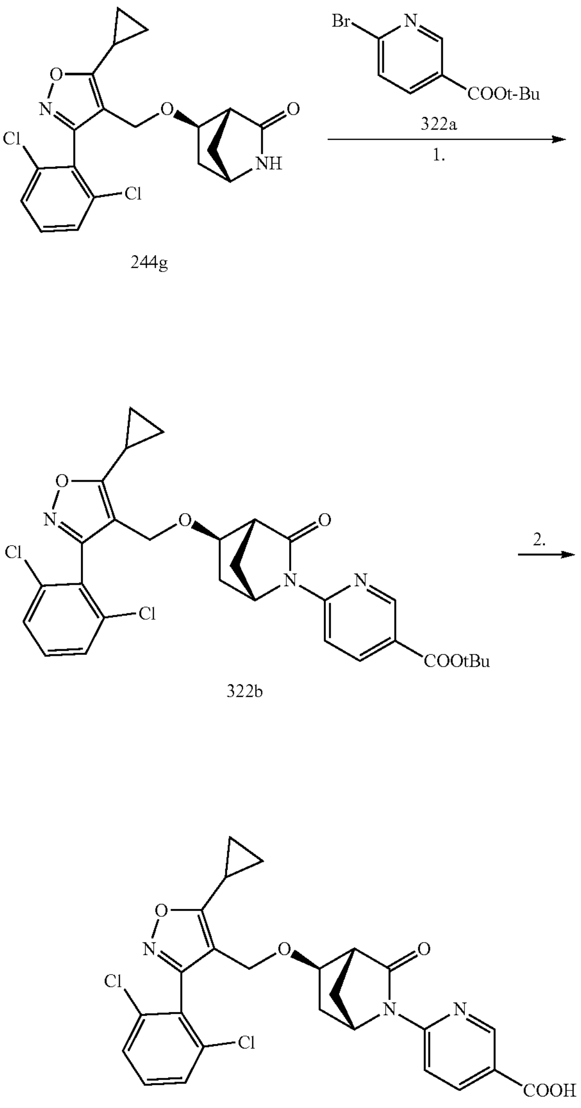

244g
322b
I-322

Following the two step procedures described in Preparative Example 244, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (98 mg, 1.00 equiv.) with tert-butyl 6-bromonicotinate 322a (130 mg, 1.5 equiv.), the desired product 6-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridine-3-carboxylic acid I-322 (106 mg) was obtained as an off-white solid. $^{1}$H-NMR (400 MHz, DMSO-d6) δ: 8.03 (s, 1H), 7.78-7.46 (m, 3H), 4.71 (s, 1H), 4.44-4.22 (m, 2H), 3.81 (d, J=5.9 Hz, 1H), 2.85 (s, 1H), 2.37 (dt, J=13.0 & 4.5 Hz, 1H), 2.10 (dd, J=13.4 & 6.7 Hz, 1H), 1.95 (d, J=9.7 Hz, 1H), 1.61 (d, J=9.7 Hz, 1H), 1.45 (d, J=13.3 Hz, 1H), 1.27-1.06 (m, 4H); MS (ES, m/z): [M+1]=514.13.

Example 251: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyrimidine-2-carboxylic Acid (I-323)

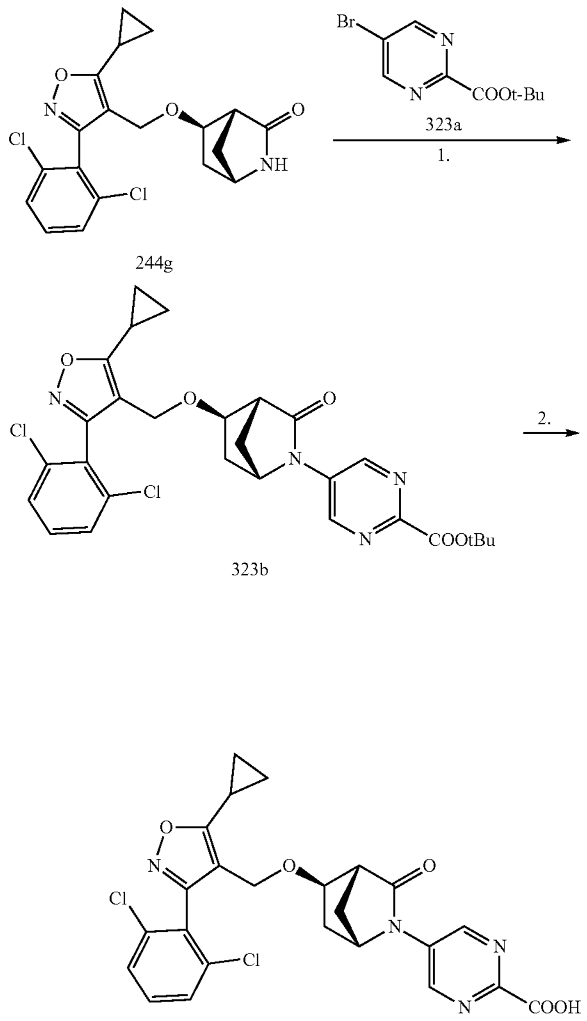

244g

323b

I-323

Following the two step procedures described in Preparative Example 244, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (98 mg, 1.00 equiv.) with tert-butyl 5-bromopyrimidine-2-carboxylate 323a (130 mg, 1.5 equiv.), the desired product 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyrimidine-2-carboxylic acid I-323 (106 mg) was obtained as an off-white solid. $^1$H-NMR (400 MHz, DMSO-d6) δ: 9.08 (d, J=1.2 Hz, 2H), 7.67-7.57 (m, 3H), 4.79 (s, 1H), 4.35-4.34 (m, 2H), 3.81 (d, J=6.0 Hz, 1H), 2.89 (s, 1H), 2.44-2.28 (m, 1H), 2.16 (dd, J=13.3 & 6.4 Hz, 1H), 1.98 (d, J=9.3 Hz, 1H), 1.64 (d, J=10.1 Hz, 1H), 1.44 (d, J=13.9 Hz, 1H), 1.29-0.97 (m, 4H); MS (ES, m/z): [M+1]=514.13.

Example 252: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyrazine-2-carboxylic Acid (I-324)

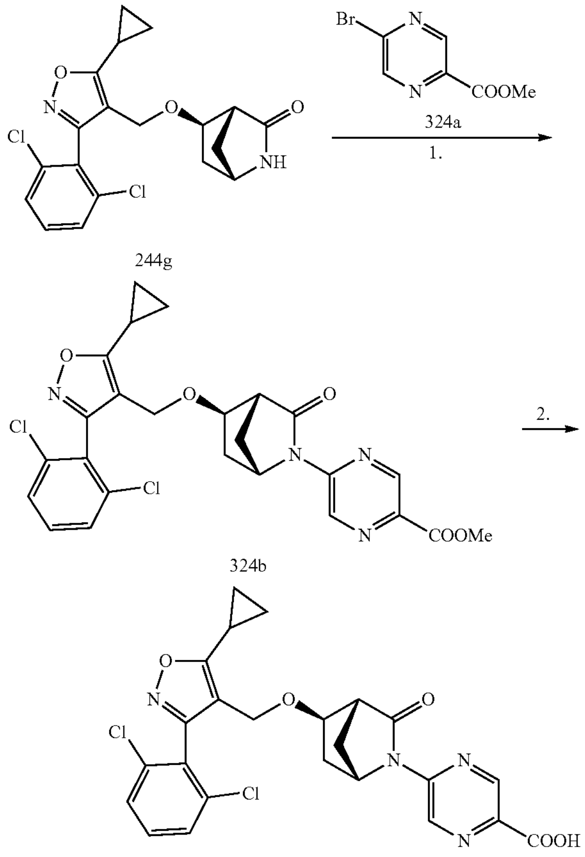

244g

324b

I-324

Following the procedures described in Preparative Example 244 step 1, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (200 mg, 1.00 equiv.) with methyl-5-bromopyrazine-2-carboxylate 324a (220 mg, 2.0 equiv.), the methyl ester intermediate 324b was obtained. Following the procedures described in Preparative Example 242 step 4, the methyl ester intermediate 324b from above was hydrolyzed under the conditions of LiI in pyridine at 100° C., for 3 h, and after semi-prep HPLC purification using 10-90% ACN (0.1% TFA) in 30 min, method afforded 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyrazine-2-carboxylic acid I-324 (70 mg) as an off-white solid. $^1$H-NMR (400 MHz, DMSO-$d_6$) δ: 9.27 (s, 1H), 8.93 (s, 1H), 7.65-7.59 (m, 3H), 4.93 (s, 1H), 4.34 (s, 2H), 3.84 (bs, 1H), 2.91 (s, 1H), 2.39-2.33 (m, 1H), 2.01 (dd, J=13.3 & 6.4 Hz, 1H), 1.66 (d, J=9.5 Hz, 1H), 1.43 (d, J=12.3 Hz, 1H), 1.43 (d, J=12.3 Hz, 1H), 1.15-1.10 (m, 4H); MS (ES, m/z): [M+1]=515.06.

Example 253: 6-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridazine-3-carboxylic Acid (I-325)

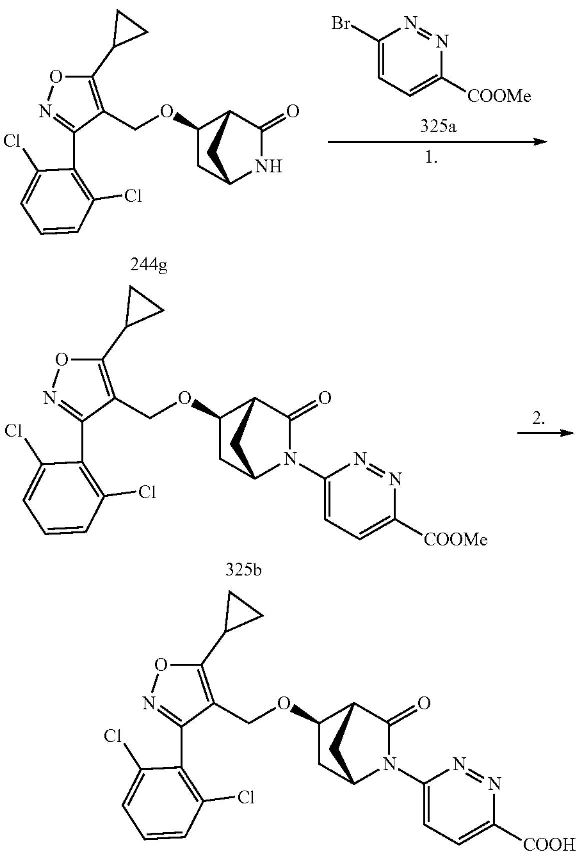

244g, 325a, 325b, I-325

Following the procedures described in Preparative Example 244 step 1, by reacting (1S,4R,5R)-5-[[5-cyclopropyl-3-(2,6-dichlorophenyl)-1,2-oxazol-4-yl]methoxy]-2-azabicyclo[2.2.1]heptan-3-one 244g (98 mg, 1.00 equiv.) with methyl-6-bromopyridazine-3-carboxylate 325a (110 mg, 1.5 equiv.), the methyl ester intermediate 325b was obtained.

Following the procedures described in Preparative Example 242 step 4, the methyl ester intermediate 325b from above was hydrolyzed under the conditions of LiI in pyridine at 100° C., for 3 h, and after semi-prep HPLC purification using 10-90% ACN (0.1% TFA) in 30 min, method afforded 6-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridazine-3-carboxylic Acid I-325 (34 mg) as an off-white solid. $^{1}$H-NMR (400 MHz, DMSO-$d_6$) δ: 8.32 (d, J=9.3 Hz, 1H), 8.16 (d, J=9.3 Hz, 1H), 7.70-7.50 (m, 3H), 5.18 (s, 1H), 4.36-4.34 (m, 2H), 3.85 (d, J=5.8 Hz, 1H), 2.92 (s, 1H), 2.37 (td, J=8.6 & 4.3 Hz, 1H), 2.11 (dd, J=13.4 & 7.0 Hz, 1H), 2.00 (d, J=9.6 Hz, 1H), 1.68 (d, J=9.8 Hz, 1H), 1.49 (d, J=13.4 Hz, 1H), 1.17-1.10 (m, 4H); MS (ES, m/z): [M+1]=515.13.

Example 253: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluoropyridine-2-carboxylic Acid (I-326)

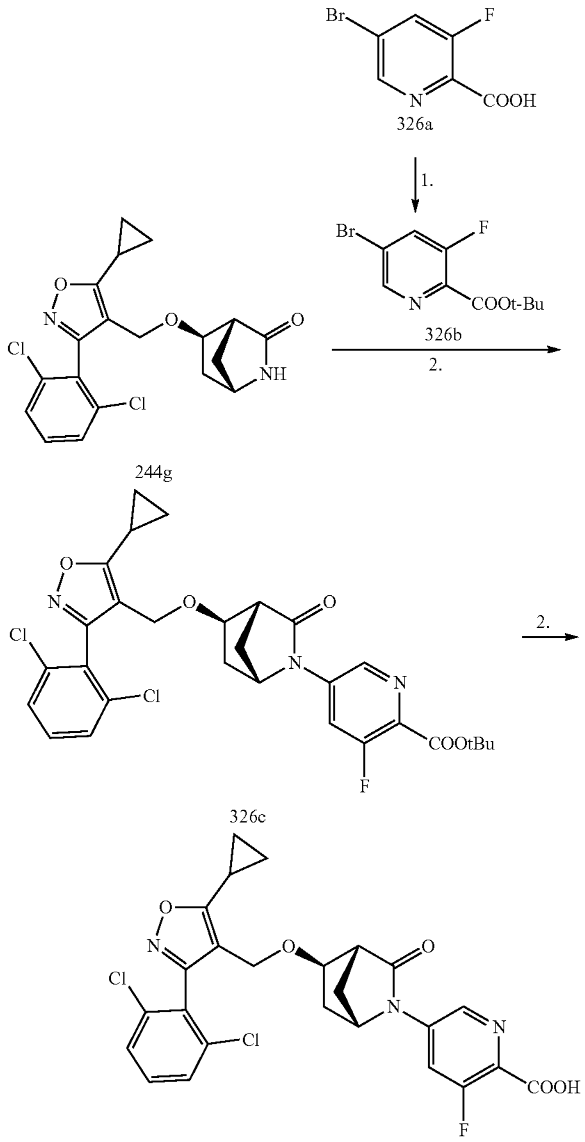

326a, 326b, 244g, 326c, I-326

Step 1

DMAP (1.38 g, 11.3 mmol) was added to a solution of 5-bromo-3-fluoropicolinic acid 326a (2.5 g, 11.3 mmol) and di-tert-butyl dicarbonate (4.93 g, 22.6 mmol) in THF (50 mL). The mixture was heated at 65° C., for 2 hours. The mixture was cooled to RT, quenched with a sat. $NaHCO_3$ aqueous solution, and extracted with EtOAc. The combined EtOAc extracts were dried, filtered, concentrated under vacuum to a residue, which was purified by silica gel column chromatography to give tert-Butyl 5-bromo-3-fluoropicolinate 326b (2.8 g) as a yellow oil.

Step 2

To a solution of (1S,4R,5R)-5-((5-cyclopropyl-3-(2,6-dichlorophenyl)isoxazol-4-yl)methoxy)-2-azabicyclo[2.2.2.1]heptan-3-one 244g (1.0 g, 2.54 mmol) and tert-butyl 5-bromo-3-fluoropicolinate 326b (1.05 g, 3.81 mmol) in dioxane (20 mL) was added $Cs_2CO_3$ (1.65 g, 5.08 mmol), $Pd_2(dba)_3$ (0.232 g, 0.254 mmol) and Xantphos (0.293 mmol, 0.508 mmol). The mixture was degassed and heated at 100° C., under $N_2$ for 16 hours. The mixture was cooled to RT and partitioned between water and EtOAc. The organic layer was dried, filtered and concentrated. The residue was purified by silica gel column chromatography eluting with 30-50% EtOAc in hexanes to give tert-Butyl 5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoropicolinate 326c (1.5 g) as a yellow foam.

Step 3

TFA (10 mL) was added to a solution of tert-butyl 5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoropicolinate 326c (1.5 g, 2.54 mmol) in DCM (20 mL). The mixture was stirred at RT for 2 hours. DCM and TFA were removed under vacuum to give 5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoropicolinic acid I-326 (1.2 g, crude) as a yellow foam. $^1H$ NMR (400 MHz, $CDCl_3$) δ: 8.52 (s, 1H), 7.92 (dd, J=11.9, 2.0 Hz, 1H), 7.47-7.33 (m, 3H), 4.48 (s, 1H), 4.40-4.27 (m, 2H), 3.90 (d, J=6.9 Hz, 1H), 2.97 (s, 1H), 2.21-1.99 (m, 3H), 1.90 (d, J=10.2 Hz, 1H), 1.75-1.65 (m, 1H), 1.31-1.23 (m, 2H), 1.20-1.11 (m, 2H); MS (ES, m/z): [M+1]=532.

Example 254: 3-{5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]pyridin-2-yl}propanoic Acid (I-327)

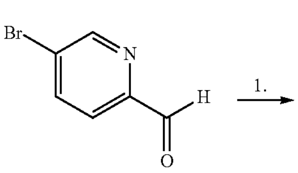

327a

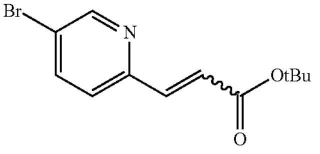

327b

-continued

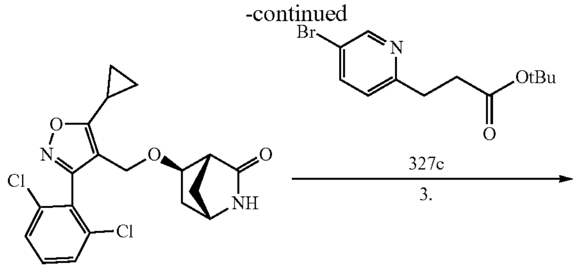

244g

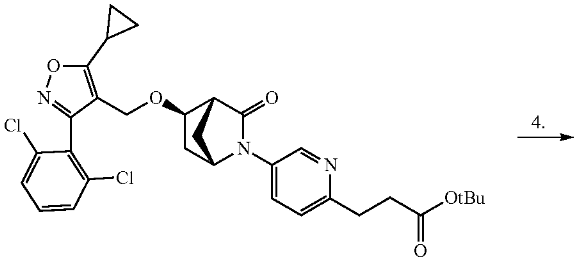

327d

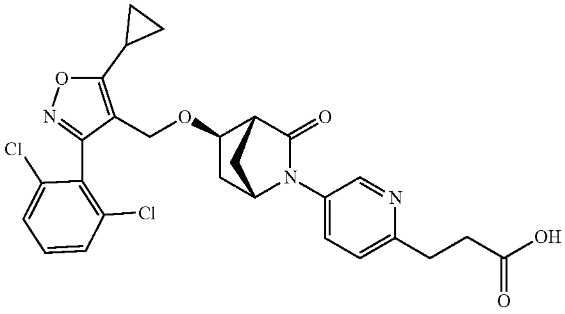

I-327

Step 1

To a solution of 5-bromopicolinaldehyde 327a (3.0 g, 16.1 mmol) in DCM (30 mL) was added tert-butyl 2-(triphenylphosphoranylidene)acetate (6.06 g, 16.1 mmol) in small portions at 0° C. The mixture was stirred at room temperature overnight. Solvent was removed under reduced pressure and the residue was purified by silica gel column chromatography eluting with 10% EtOAc in hexanes to afford tert-Butyl 3-(5-bromopyridin-2-yl)acrylate 327b (3.92 g) as a colorless solid. $^1H$ NMR (400 MHz, $CDCl_3$) δ: 8.65 (d, J=2.4 Hz, 1H), 7.80 (dd, J=8.3, 2.4 Hz, 1H), 7.50 (d, J=15.7 Hz, 1H), 7.28 (dd, J=8.3, 0.5 Hz, 1H), 6.79 (t, J=8.5 Hz, 1H), 1.51 (d, J=2.2 Hz, 9H).

Step 2

A solution of tert-butyl 3-(5-bromopyridin-2-yl)acrylate 327b (1.0 g, 3.51 mmol) in MeOH (20 mL) was cooled to 0° C. $CoCl_2.6H_2O$ (83.5 mg, 351 μmol) was added followed by $NaBH_4$ (198 mg, 5.26 mmol). The mixture was stirred at room temperature for 3 hours. The reaction was quenched with water, extracted with EtOAc. The organic extracts were dried, filtered and concentrated. The residue was purified by silica gel column chromatography eluting with 10% EtOAc in hexanes to give tert-Butyl 3-(5-bromopyridin-2-yl)propanoate 327c (0.8 g) as a clear oil. $^1H$ NMR (400 MHz, $CDCl_3$) δ: 8.54 (d, J=2.4 Hz, 1H), 7.67 (dd, J=8.3, 2.4 Hz, 1H), 7.07 (d, J=8.3 Hz, 1H), 2.99 (t, J=7.4 Hz, 2H), 2.66 (t, J=7.4 Hz, 2H), 1.40-1.36 (m, 9H).

Step 3

To a solution of (1S,4R,5R)-5-((5-cyclopropyl-3-(2,6-dichlorophenyl)isoxazol-4-yl)methoxy)-2-azabicyclo[2.2.1]heptan-3-one 244g (0.20 g, 0.508 mmol) and tert-butyl 3-(5-bromopyridin-2-yl)propanoate 327c (0.218 g, 0.762 mmol) in dioxane (6 mL), was added $Pd_2(dba)_3$ (46.5 mg, 50.8 μmol), Xantphos (58.4 mg, 101 μmol) and $cs_2CO_3$ (0.329 g, 1.01 mmol). The mixture was heated at 100° C., under $N_2$ overnight. After cooling to room temperature, the mixture was partitioned between water and EtOAc. The EtOAc layer was washed with brine, dried, concentrated, and purified by silica gel column chromatography eluting with 40-50% EtOAc in hexanes to afford tert-Butyl 3-(5-((1S,4R,5R)-5-((5-cyclopropyl-3-(2,6-dichlorophenyl)isoxazol-4-yl)methoxy)-3-oxo-2-azabicyclo[2.2.1]heptan-2-yl)pyridin-2-yl)propanoate 327d (0.22 g) as a yellow oil.

Step 4

TFA (3 mL) was added to a solution of tert-butyl 3-(5-((1S,4R,5R)-5-((5-cyclopropyl-3-(2,6-dichlorophenyl)isoxazol-4-yl)methoxy)-3-oxo-2-azabicyclo[2.2.1]heptan-2-yl)pyridin-2-yl)propanoate 327d (0.22 g, 0.367 mmol) in DCM (6 mL). The reaction mixture was stirred at room temperature for 1 hour. TFA and DCM were removed under vacuum. The residue was purified by prep-HPLC to give 3-(5-((1S,4R,5R)-5-((5-cyclopropyl-3-(2,6-dichlorophenyl)isoxazol-4-yl)methoxy)-3-oxo-2-azabicyclo[2.2.1]heptan-2-yl)pyridin-2-yl)propanoic acid I-327 (163.4 mg) as a white solid after lyophilization. $^1$HNMR (400 MHz, DMSO-d6) δ: 8.69 (d, J=2.5 Hz, 1H), 8.03 (dd, J=8.6, 2.5 Hz, 1H), 7.62 (ddt, J=19.9, 15.9, 4.8 Hz, 3H), 7.50 (d, J=8.7 Hz, 1H), 4.61 (s, 1H), 4.33 (q, J=12.2 Hz, 2H), 3.78 (d, J=6.4 Hz, 1H), 2.99 (t, J=7.3 Hz, 2H), 2.82 (s, 1H), 2.68 (t, J=7.3 Hz, 2H), 2.37 (dq, J=8.3, 5.2 Hz, 1H), 2.12-2.03 (m, 1H), 1.91 (d, J=9.8 Hz, 1H), 1.59 (d, J=9.8 Hz, 1H), 1.42 (d, J=13.4 Hz, 1H), 1.20-1.05 (m, 4H); MS (ES, m/z): [M+1]=542.

Example 255: 3-{5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluoropyridin-2-yl}propanoic Acid (I-328)

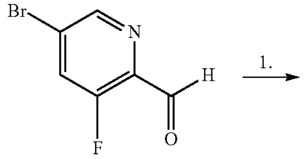

328a

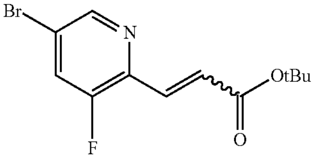

328b

-continued

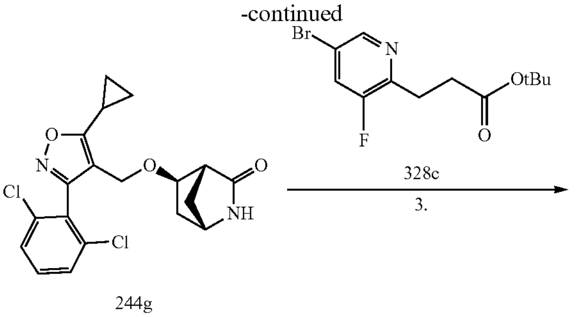

244g

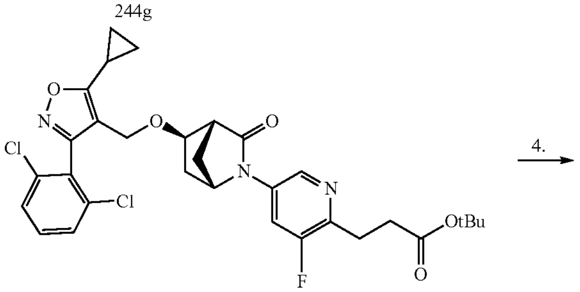

328d

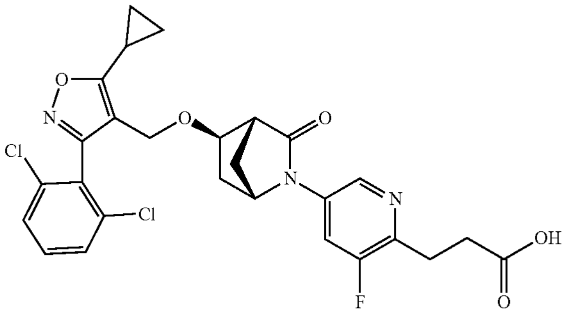

I-328

Step 1

5-Bromo-3-fluoropicolinaldehyde 328a (1.0 g, 4.90 mmol) was dissolved in DCM (20 mL) and cooled to 0° C. 2-(triphenylphosphoranylidene)acetate (1.84 g, 4.90 mmol) was added in small portions. The mixture was stirred at room temperature overnight. Solvent was removed and the residue was purified by silica gel column chromatography eluting with 10% EtOAc in hexanes to give tert-Butyl 3-(5-bromo-3-fluoropyridin-2-yl)acrylate 328b (1.31 g) as a white solid. $^1$HNMR (400 MHz, $CDCl_3$) δ: 8.51-8.44 (m, 1H), 7.70 (dd, J=15.7, 1.4 Hz, 1H), 7.60 (dd, J=9.2, 1.9 Hz, 1H), 6.99-6.90 (m, 1H), 1.53-1.50 (m, 9H).

Step 2

A solution of tert-butyl 3-(5-bromo-3-fluoropyridin-2-yl)acrylate 328b (1.31 g, 4.33 mmol) in MeOH (20 mL) was cooled to 0° C. $CoCl_2.6H_2O$ (0.103 g, 0.433 mmol) was added at 0° C., followed by $NaBH_4$ (0.245 g, 6.49 mmol). The mixture was stirred at room temperature for 3 hours, then partitioned between EtOAc and water. The organic layer was washed with brine, dried and concentrated. The residue was purified by silica gel column chromatography eluting with 10% EtOAc in hexanes to afford tert-Butyl 3-(5-bromo-3-fluoropyridin-2-yl)propanoate 328c (1.0 g) as a clear oil. $^1$HNMR (400 MHz, $CDCl_3$) δ: 8.37 (dd, J=1.8, 0.9 Hz, 1H), 7.49 (dd, J=8.7, 1.9 Hz, 1H), 3.05 (td, J=7.3, 2.1 Hz, 3H), 2.69 (t, J=7.3 Hz, 3H), 1.43-1.33 (m, 9H).

Step 3

To a solution of (1S,4R,5R)-5-((5-cyclopropyl-3-(2,6-dichlorophenyl)isoxazol-4-yl)methoxy)-2-azabicyclo[2.2.1]heptan-3-one 244g (0.2 g, 0.508 mmol) and tert-butyl 3-(5-bromo-3-fluoropyridin-2-yl)propanoate 328c (0.231 g, 0.762 mmol) in dioxane (6 mL), was added $Pd_2(dba)_3$ (0.046 g, 0.051 mmol), Xantphos (0.058 g, 0.101 mmol) and $Cs_2CO_3$ (0.329 g, 1.01 mmol). The mixture was degassed and heated at 100° C., under $N_2$ overnight. After cooling to room temperature, the mixture was partitioned between EtOAc and water. The EtOAc layer was washed with brine, dried, and concentrated. The residue was purified by silica gel column chromatography eluting with EtOAc in hexanes (30-50%) to give tert-Butyl 3-(5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoropyridin-2-yl)propanoate 328d (0.24 g) as a light yellow oil.

Step 4

TFA (5 mL) was added to a solution of tert-butyl 3-(5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoropyridin-2-yl)propanoate 328d (0.24 g, 0.389 mmol) in DCM (10 mL). The mixture was stirred at room temperature for 2 hours. DCM and TFA were removed under vacuum. The residue was purified using prep-HPLC to give 3-(5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoropyridin-2-yl)propanoic acid I-328 (170.5 mg) as an off white solid after lyophilization. $^1$HNMR (400 MHz, $CDCl_3$) δ: 8.44 (s, 1H), 8.38 (dd, J=10.8, 2.0 Hz, 1H), 7.46-7.32 (m, 3H), 4.49 (s, 1H), 4.38-4.25 (m, 2H), 3.87 (d, J=6.2 Hz, 1H), 3.25 (t, J=6.7 Hz, 2H), 2.96 (s, 1H), 2.84 (t, J=6.9 Hz, 2H), 2.18-2.05 (m, 2H), 2.04-1.97 (m, 1H), 1.88 (d, J=10.2 Hz, 1H), 1.66 (d, J=13.7 Hz, 1H), 1.30-1.23 (m, 2H), 1.19-1.11 (m, 2H); MS (ES, m/z): [M+1]=560.

Example 256: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[(2,2-dimethyloxan-4-yl)sulfonyl]benzamide (I-329)

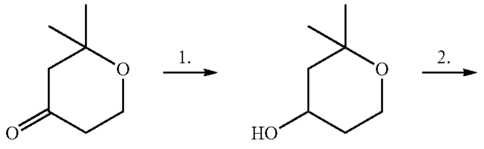

329a 329b

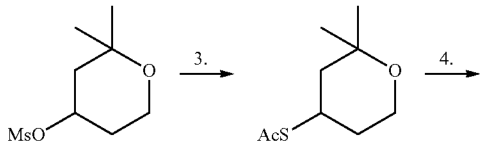

329c 329d

-continued

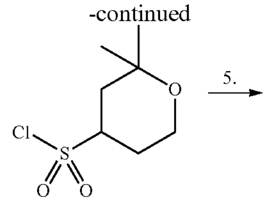

329e

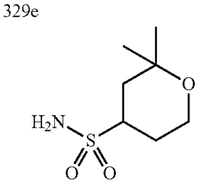

329f

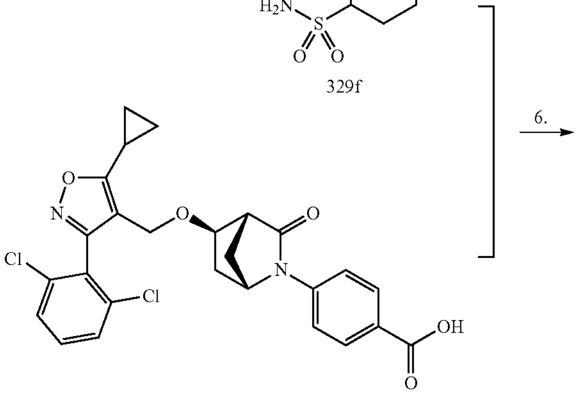

I-244

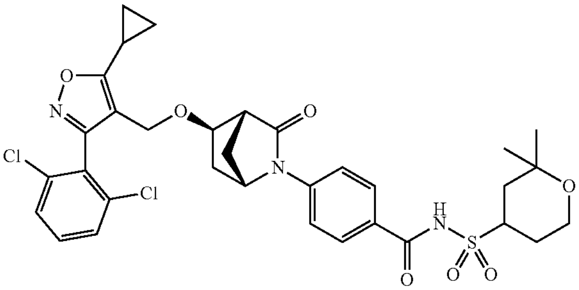

I-329

Step 1

To a 500 mL round-bottom flask was added 2,2-dimethyloxan-4-one 329a (10 g, 78.02 mmol, 1.00 equiv.) and methanol (100 mL). $NaBH_4$ (5.9 g, 155.96 mmol, 2.00 equiv.) was added in several batches at 0° C. The resulting mixture was stirred at room temperature for 3 h, then diluted with 200 mL of EA, washed with brine (100 mL×2), dried over anhydrous sodium sulfate, and concentrated under vacuum. The residue was purified by silica gel column chromatography eluting with ethyl acetate in petroleum ether (0% to 100%) to give 2,2-dimethyloxan-4-ol 329b (9 g, 89%) as a light yellow oil.

Step 2

To a 500 mL round-bottom flask purged with and maintained under an inert atmosphere of nitrogen was added a solution of 2,2-dimethyloxan-4-ol 329b (9 g, 69.13 mmol, 1.00 equiv.) in dichloromethane (200 mL) followed by TEA (7.69 g, 76.00 mmol, 1.10 equiv.). The mixture was cooled to 0° C., MsCl (8.68 g, 76.14 mmol, 1.10 equiv.) was added dropwise with stirring. The resulting mixture was stirred at room temperature for 2 h. The mixture was diluted with DCM (200 mL), washed with brine (100 mL×2), dried over anhydrous sodium sulfate, and concentrated under vacuum. The residue was purified by silica gel column chromatography eluting with ethyl acetate in petroleum ether (0% to 30%) to give 2,2-dimethyloxan-4-yl methanesulfonate 329c (14 g, 97%) as a white solid.

Step 3

To a 250 mL round-bottom flask purged with and maintained under an inert atmosphere of nitrogen was added 2,2-dimethyloxan-4-yl methanesulfonate 329c (2 g, 9.60 mmol, 1.00 equiv.), N,N-dimethylformamide (50 mL), and AcSK (3.4 g, 3.00 equiv.). The resulting mixture was heated at 80° C., for 2 h. After cooling to room temperature, the mixture was diluted with EA (200 mL), washed with brine (50 mL×5), dried over anhydrous sodium sulfate, and concentrated under vacuum. The residue was purified by silica gel column chromatography eluting with ethyl acetate/petroleum ether (1/5) to afford 1-[(2,2-dimethyloxan-4-yl)sulfanyl]ethan-1-one 329d (1 g, 55%) as a red crude oil.

Step 4

To a 250 mL round-bottom flask was added a solution of NCS (2.8 g, 20.97 mmol, 4.00 equiv.) in MeCN (21 mL) followed by the addition of a 12M hydrogen chloride solution (5.3 mL, 63.6 mmol, 12.0 eq.). The mixture was cooled at 0° C., for 10 min, a solution of 1-[(2,2-dimethyloxan-4-yl)sulfanyl]ethan-1-one 329d (1 g, 5.31 mmol, 1.00 equiv.) in MeCN (5.3 mL) was added dropwise with stirring. The resulting mixture was stirred for 10 min at 0° C., and diluted with EA (200 mL). The organic mixture was washed with brine (50 mL×3), dried over anhydrous sodium sulfate and concentrated under vacuum. The residue was purified by silica gel column chromatography eluting with ethyl acetate/petroleum ether (5/1) to afford 2,2-dimethyloxane-4-sulfonyl chloride 329e (600 mg, 53%) as a crude red solid.

Step 5

To a 100 mL round-bottom flask was added 2,2-dimethyloxane-4-sulfonyl chloride 329e (700 mg, 3.29 mmol, 1.00 equiv.) and a saturated solution of $NH_3$ in tetrahydrofuran (20 mL). The resulting mixture was stirred at 0° C., for 2 h and concentrated under vacuum. The residue was diluted with 30 mL of ether. The precipitated solids were filtered out. The filtrate was concentrated under vacuum to give 2,2-dimethyloxane-4-sulfonamide 329f (530 mg, 83%) as a light yellow crude solid, which was used in the next step without further purification.

Step 6

To a 8 mL tube was added 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]benzoic acid I-244 (100 mg, 0.19 mmol, 1.00 equiv.), 2,2-dimethyloxane-4-sulfonamide (120 mg, 0.62 mmol, 4.00 equiv.), 4-dimethylaminopyridine (75 mg, 3.00 equiv.), dichloromethane (4 mL), and EDCI (60 mg, 1.50 equiv.). The resulting mixture was stirred at room temperature overnight. A 1M HCl aqueous solution (50 mL) was add, the aqueous mixture was extracted with dichloromethane (100 mL×2), and the combined organic layers were dried over sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (46% ACN up to 66% in 8 min); Detector, uv 254/220 nm. After purification 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-N-(2,2-dimethyloxane-4-sulfonyl)benzamide I-329 (65.6 mg, 49%) was obtained as a white solid. $^1$HNMR (300 MHz, $CD_3OD$) δ: 7.93 (d, J=8.9 Hz, 2H), 7.72-7.61 (m, 2H), 7.64-7.46 (m, 3H), 4.61 (s, 1H), 4.41 (d, J=1.2 Hz, 2H), 4.13 (ddd, J=12.7, 9.0, 3.8 Hz, 1H), 4.02-3.58 (m, 3H), 2.88 (s, 1H), 2.39-2.23 (m, 1H), 2.18 (dd, J=13.3, 7.3 Hz, 1H), 2.02 (d, J=24.0 Hz, 3H), 1.93-1.58 (m, 4H), 1.28 (d, J=8.2 Hz, 6H), 1.24-1.16 (m, 4H); MS (ES, m/z): [M+1]=688.16.

Example 257: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-[(2,2-dimethyloxan-4-yl)sulfonyl]-2-fluorobenzamide (I-330)

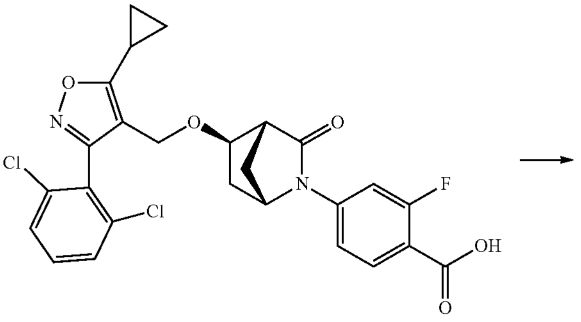

I-314

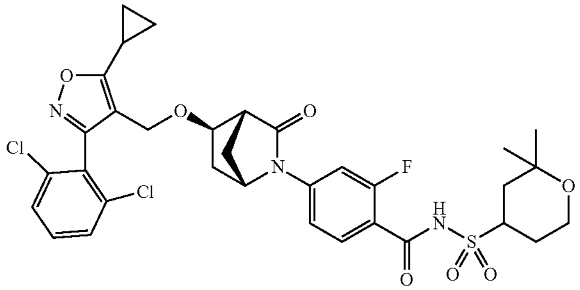

I-330

To a 8 mL tube was added 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-2-fluorobenzoic acid I-314 (100 mg, 0.19 mmol, 1.00 equiv.), 2,2-dimethyloxane-4-sulfonamide 329f (110 mg, 0.57 mmol, 4.00 equiv.), 4-dimethylaminopyridine (70 mg, 3.00 equiv.), dichloromethane (4 mL), and EDCI (54.4 mg, 1.50 equiv.). The resulting mixture was stirred at room temperature overnight. A 1M HCl aqueous solution (50 mL) was added, the mixture was extracted with dichloromethane (100 mL×2), and the combined organic extracts were dried over sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (48% ACN up to 68% in 8 min); Detector, uv 254/220 nm. After purification 4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]-N-(2,2-dimethyloxane-4-sulfonyl)-2- fluorobenzamide I-330 (43.4 mg, 33%) was obtained as a white solid. $^{1}$HNMR (300 MHz, $CD_3OD$) δ: 7.72 (t, J=8.4 Hz, 1H), 7.67-7.46 (m, 4H), 7.38 (dd, J=8.7, 2.1 Hz, 1H), 4.62 (s, 1H), 4.40 (d, J=1.4 Hz, 2H), 4.16-4.04 (m, 1H), 3.84-3.45 (m, 3H), 2.88 (s, 1H), 2.38-2.23 (m, 1H), 2.21-1.94 (m, 1H), 1.92-1.76 (m, 3H), 1.76-1.57 (m, 4H), 1.33-1.22 (m, 6H), 1.20 (d, J=4.3 Hz, 4H); MS (ES, m/z): [M+1]=706.15.

Example 258: Synthesis of I-331 to I-336

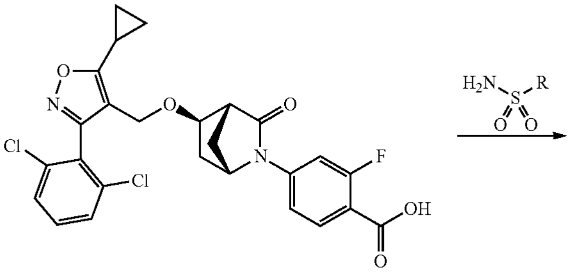

I-314

-continued

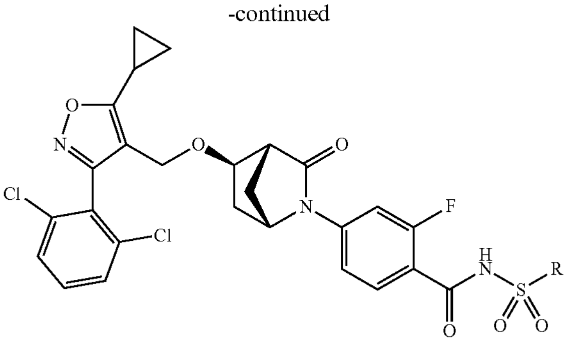

I-x

Acyl-sulfonamides I-331 to I-336 were prepared from acid I-314 and the corresponding sulfonamide $RSO_2NH_2$ following the procedure described in Preparative Example 257. The data for compounds I-331 to I-336 is summarized in Table 19.

TABLE 19

| $RSO_2NH_2$ | Cmpd Structure | Cmpd No. | MS/$^{1}$H NMR |
|---|---|---|---|
| 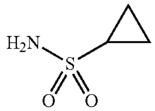 | 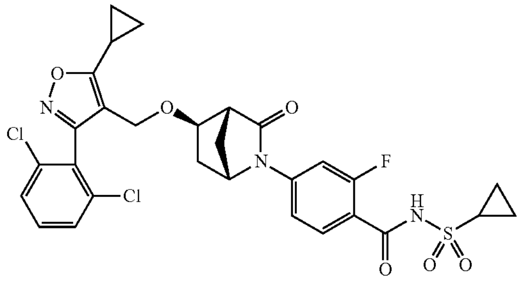 [SMILES: O=C(NS(=O)(=O)C1CC1)c1ccc(N2C(=O)[C@@H]3C[C@H]2C[C@H]3OCc2c(-c3c(Cl)cccc3Cl)noc2C2CC2)cc1F] | I-331 | MS (ES, m/z): [M + 1] = 634.09. $^{1}$H NMR (300 MHz, $CD_3OD$) δ: 7.73 (t, J = 8.4 Hz, 1H), 7.65-7.45 (m, 4H), 7.36 (dd, J = 8.7, 2.1 Hz, 1H), 4.61 (s, 1H), 4.39 (d, J = 1.4 Hz, 2H), 3.86 (d, J = 6.6 Hz, 1H), 3.20-3.04 (m, 1H), 2.87 (s, 1H), 2.37-2.22 (m, 1H), 2.14 (dd, J = 15.0, 7.7 Hz, 1H), 1.98 (d, J = 10.4 Hz, 1H), 1.80 (d, J = 10.0 Hz, 1H), 1.62 (d, J = 13.4 Hz, 1H), 1.38-1.26 (m, 2H), 1.25-1.10 (m, 6H). |
| 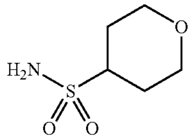 | 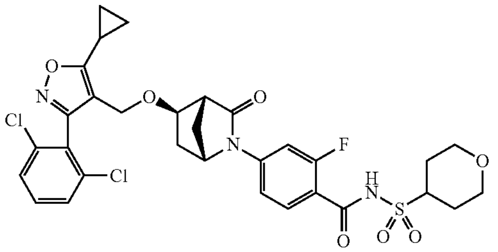 [SMILES: O=C(NS(=O)(=O)C1CCOCC1)c1ccc(N2C(=O)[C@@H]3C[C@H]2C[C@H]3OCc2c(-c3c(Cl)cccc3Cl)noc2C2CC2)cc1F] | I-332 | MS (ES, m/z): [M + 1] = 678.20. $^{1}$H NMR (300 MHz, $CD_3OD$) δ: 7.71 (t, J = 8.4, 2.1 Hz, 1H), 7.63-7.45 (m, 4H), 7.36 (dd, J = 8.7, 2.1 Hz, 1H), 4.61 (d, J = 2.4 Hz, 1H), 4.39 (d, J = 1.4 Hz, 2H), 4.14-4.02 (m, 2H), 3.98-3.82 (m, 2H), 3.47 (td, J = 11.7, 2.5 Hz, 2H), 2.87 (s, 1H), 2.37-2.24 (m, 1H), 2.21-1.85 (m, 7H), 1.80 (dt, J = 10.0, 1.4 Hz, 1H), 1.62 (dt, J = 13.6. 2.6 Hz, 1H), 1.26-1.14 (m, 4H). |
| 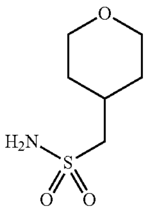 [SMILES: NS(=O)(=O)CC1CCOCC1] | 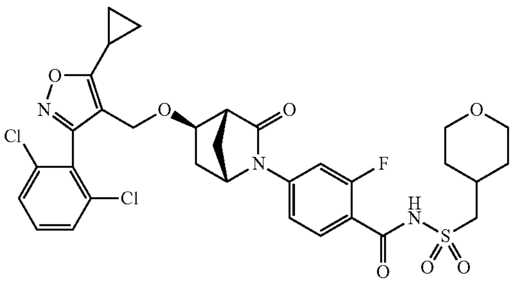 [SMILES: O=C(NS(=O)(=O)CC1CCOCC1)c1ccc(N2C(=O)[C@@H]3C[C@H]2C[C@H]3OCc2c(-c3c(Cl)cccc3Cl)noc2C2CC2)cc1F] | I-333 | MS (ES, m/z): [M + 1] = 692. $^{1}$H NMR (400 MHz, DMSO-d6) δ: 7.73 (d, J = 8.6 Hz, 1H), 7.69-7.50 (m, 3H), 7.26 (dd, J = 8.71 & 2.1 Hz, 1H), 7.08 (d, J = 2.1 Hz, 1H), 4.58 (s, 1H), 4.33-4.28 (m, 2H), 3.77 (d, J = 6.1 Hz, 1H), 2.89-2.66 (m, 2H), 2.46-2.25 (m, 1H), 2.01 (dd, J = 13.2 & 6.6 Hz, 1H), 1.86 (d, J = 9.8 Hz, 1H), 1.54 (d, J = 9.7 Hz, 1H), 1.43 (d, J = 13.3 Hz, 1H), 1.16-1.08 (m, 4H), 0.95 (dd, J = 8.5 & 2.0 Hz, 2H), 0.72-0.52 (m, 2H). |

TABLE 19-continued

| $RSO_2NH_2$ | Cmpd Structure | Cmpd No. | MS/$^1$H NMR |
|---|---|---|---|
| 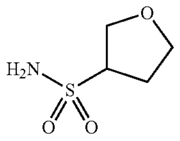 | 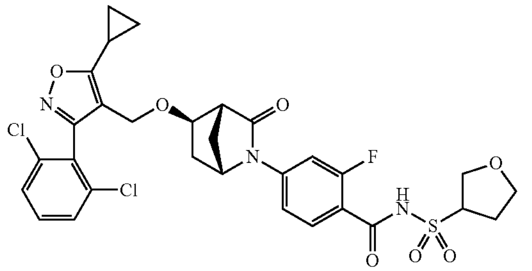 [SMILES: O=C(NS(=O)(=O)C1CCOC1)c1ccc(N2C(=O)[C@@H]3C[C@H]2C[C@H]3OCc2c(-c3c(Cl)cccc3Cl)noc2C2CC2)cc1F] | I-334 | MS (ES, m/z): [M + 1] = 664.10. $^1$H NMR (300 MHz, $CD_3OD$) δ: 7.66 (t, J = 8 4 Hz, 1H), 7.61-7.40 (m, 4H), 7.31 (dd, J = 8.7, 2.1 Hz, 1H), 4.56 (s, 1H), 4.52-4.38 (m, 1H), 4.34 (d, J = 1.4 Hz, 2H), 4.22 (dd, J = 10.2, 4.6 Hz, 1H), 4.07-3.70 (m, 5H), 2.82 (d, J = 1.8 Hz, 1H), 2.49-2.17 (m, 2H), 2.09 (ddd, J = 13.5, 6.9, 2.5 Hz, 1H), 1.96 (d, J = 26.5 Hz, 2H), 1.80-1.70 (m, 1H), 1.63-1.50 (m, 1H), 1.15 (tdd, J = 5.5, 4.6, 4.2, 2.2 Hz, 4H)). |
| 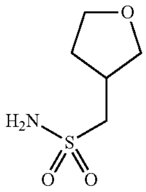 | 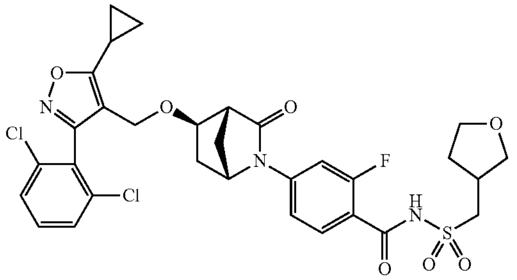 [SMILES: O=C(NS(=O)(=O)CC1CCOC1)c1ccc(N2C(=O)[C@@H]3C[C@H]2C[C@H]3OCc2c(-c3c(Cl)cccc3Cl)noc2C2CC2)cc1F] | I-335 | MS (ES, m/z): [M + 1] = 678.12. $^1$H NMR (300 MHz, $CD_3OD$) δ: 7.68 (t, J = 8.4 Hz, 1H), 7.61-7.40 (m, 4H), 7.32 (dd, J = 8.7, 2.1 Hz, 1H), 4.56 (s, 1H), 4.35 (d, J = 1.4 Hz, 2H), 3.97 (dd, J = 8.7, 7.1 Hz, 1H), 3.84 (td, J = 8.3, 4.9 Hz, 2H), 3.80-3.47 (m, 4H), 2.82 (s, 1H), 2.73 (dt, J = 14.6, 7.4 Hz, 1H), 2.30-2.17 (m, 2H), 2.17-2.06 (m, 1H), 2.05-1.86 (m, 1H), 1.85-1.66 (m, 2H), 1.57 (d, J = 13.5 Hz, 1H), 1.21-1.10 (m, 4H). |
| 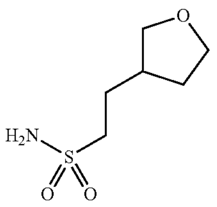 [SMILES: NS(=O)(=O)CCC1CCOC1] | 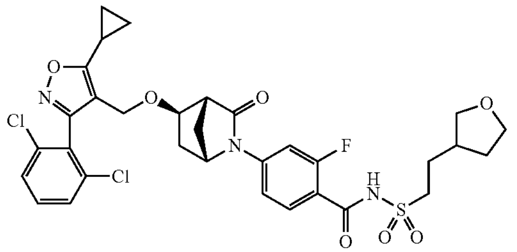 [SMILES: O=C(NS(=O)(=O)CCC1CCOC1)c1ccc(N2C(=O)[C@@H]3C[C@H]2C[C@H]3OCc2c(-c3c(Cl)cccc3Cl)noc2C2CC2)cc1F] | I-336 | MS (ES, m/z): [M + 1] = 692. $^1$H NMR (400 MHz, DMSO-d6) δ: 12.03 (s, 1H), 7.69-7.55 (m, 4H), 7.52 (dd, J = 13.3, 2.0 Hz, 1H), 7.42 (dd, J = 8.7, 2.1 Hz, 1H), 4.66 (s, 1H), 4.33 (q, J = 12.2 Hz, 2H), 3.81-3.67 (m, 3H), 3.65-3.56 (m, 1H), 3.56-3.46 (m, 2H), 3.25 (dd, J = 8.4, 6.5 Hz, 1H), 2.84 (s, 1H), 2.37 (ddd, J = 16.9, 8.3, 5.2 Hz, 1H), 2.26 (dq, J = 14.2, 7.1 Hz, 1H), 2.07-1.95 (m, 2H), 1.91 (d, J = 9.9 Hz, 1H), 1.83-1.67 (m, 2H), 1.58 (d, J = 9.8 Hz, 1H), 1.45 (dq, J = 12.2, 7.2 Hz, 2H), 1.19-1.05 (m, 4H). |

Example 259: Synthesis of I-337 to I-343

-continued

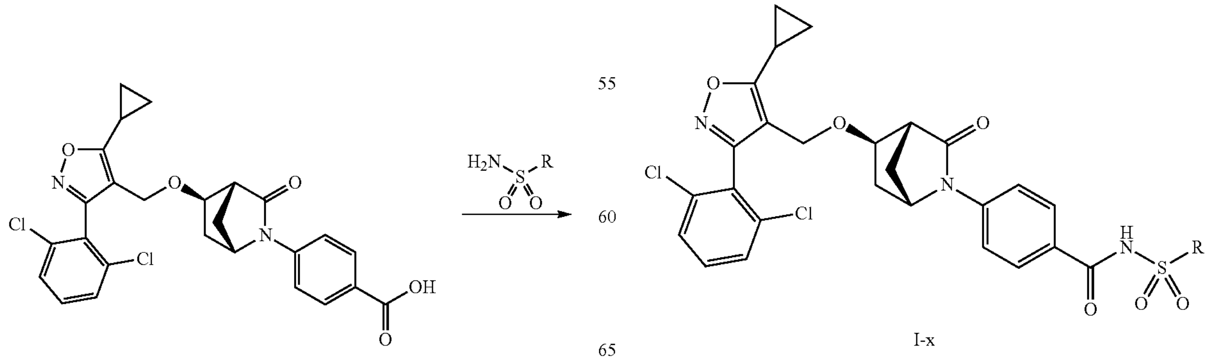

I-244

I-x

Acyl-sulfonamides I-337 to I-343 were prepared from acid I-244 and the corresponding sulfonamide $RSO_2NH_2$ following the procedure described in Preparative Example 257. The data for compounds I-337 to I-343 is summarized in Table 20.

TABLE 20

| $RSO_2NH_2$ | Cmpd Structure | Cmpd No. | MS/$^1$H NMR |
|---|---|---|---|
| 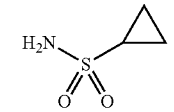 | 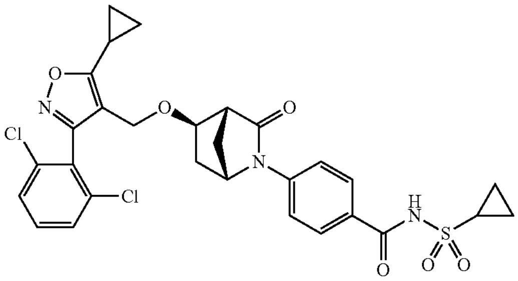 [SMILES: O=C(NS(=O)(=O)C1CC1)c1ccc(N2C(=O)[C@@H]3C[C@H]2C[C@H]3OCc2c(-c3c(Cl)cccc3Cl)noc2C2CC2)cc1] | I-337 | MS (ES, m/z): [M + 1] = 616.10. $^1$H NMR (400 MHz, $CD_3OD$) δ: 7.91 (d, J = 8.9 Hz, 2H), 7.69-7.57 (m, 2H), 7.57-7.45 (m, 2H), 4.60 (s, 1H), 4.40 (d, J = 1.2 Hz, 2H), 3.87 (d, J = 6.5 Hz, 1H), 3.23-3.09 (m, 1H), 2.87 (s, 1H), 2.38-2.22 (m, 1H), 2.17 (dd, J = 14.3, 7.4 Hz, 1H), 1.99 (d, J = 9.8 Hz, 1H), 1.80 (d, J = 9.9 Hz, 1H), 1.63 (d, J = 13.5 Hz, 1H), 1.31 (dt, J = 6.9, 3.2 Hz, 2H), 1.25-1.08 (m, 6H). |
| 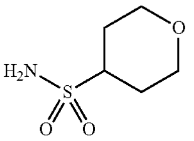 | 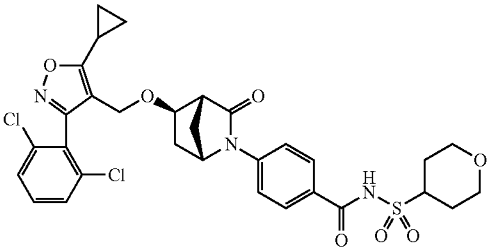 [SMILES: O=C(NS(=O)(=O)C1CCOCC1)c1ccc(N2C(=O)[C@@H]3C[C@H]2C[C@H]3OCc2c(-c3c(Cl)cccc3Cl)noc2C2CC2)cc1] | I-338 | MS (ES, m/z): [M + 1] = 660.20. $^1$H NMR (300 MHz, $CD_3OD$) δ: 7.91 (d, J = 8.8 Hz, 2H), 7.69-7.44 (m, 5H), 4.59 (s, 1H), 4.39 (d, J = 1.2 Hz, 2H), 4.06 (d, J = 11.5 Hz, 2H), 3.85 (d, J = 6.4 Hz, 1H), 3.52-3.39 (m, 2H), 2.86 (s, 1H), 2.15 (s, 1H), 2.07-1.88 (m, 5H), 1.79 (d, J = 10.1 Hz, 1H), 1.62 (d, J = 13.7 Hz, 1H), 1.24-1.14 (m, 4H). |
| 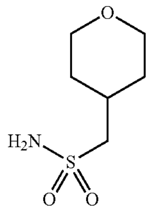 [SMILES: NS(=O)(=O)CC1CCOCC1] | 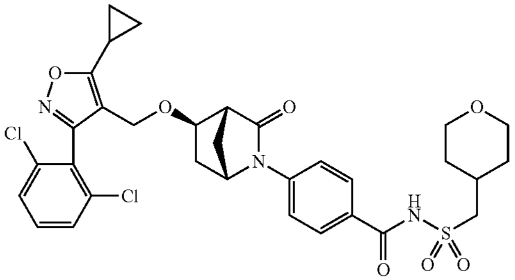 [SMILES: O=C(NS(=O)(=O)CC1CCOCC1)c1ccc(N2C(=O)[C@@H]3C[C@H]2C[C@H]3OCc2c(-c3c(Cl)cccc3Cl)noc2C2CC2)cc1] | I-339 | MS (ES, m/z): [M + 1] = 674. $^1$H NMR (400 MHz, DMSO-d6) δ: 12.01 (s, 1H), 7.92 (d, J = 9.0 Hz, 2H), 7.68-7.55 (m, 5H), 4.63 (s, 1H), 4.33 (q, J = 12.2 Hz, 2H), 3.83-3.73 (m, 3H), 3.50 (d, J = 6.5 Hz, 2H), 3.29 (td, J = 11.6, 2.0 Hz, 2H), 2.82 (s, 1H) 2.42-2.29 (m, 1H), 2.20-1.99 (m, 2H), 1.90 (d, J = 10.1 Hz, 1H), 1.74 (d, J = 13.2 Hz, 2H), 1.58 (d, J = 9.9 Hz, 1H), 1.49-1.28 (m, 3H), 1.20-1.04 ((m, 4H). |
| 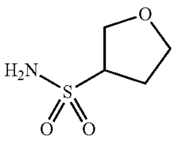 | 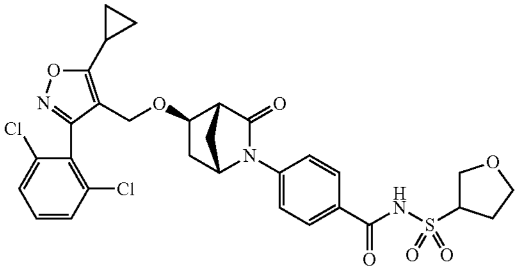 [SMILES: O=C(NS(=O)(=O)C1CCOC1)c1ccc(N2C(=O)[C@@H]3C[C@H]2C[C@H]3OCc2c(-c3c(Cl)cccc3Cl)noc2C2CC2)cc1] | I-340 | MS (ES, m/z): [M + 1] = 646.11. $^1$H NMR (300 MHz, $CD_3OD$) δ: 7.91-7.81 (m, 2H), 7.65-7.55 (m, 2H), 7.58-7.40 (m, 3H), 4.59-4.42 (m, 2H), 4.35 (d, J = 1.2 Hz, 2H), 4.21 (dd, J = 10.1, 4.6 Hz, 1H), 4.06-3.87 (m, 2H), 3.79 (dt, J = 15.2, 6.9 Hz, 2H), 2.82 (s, 1H), 2.49-2.05 (m, 4H), 1.94 (d, J = 10.2 Hz, 1H), 1.75 (d, J = 9.9 Hz, 1H), 1.58 (d, J = 13.4 Hz, 1H), 1.21-1.10 (m, 4H). |
| 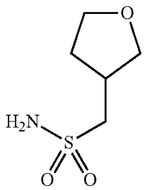 | 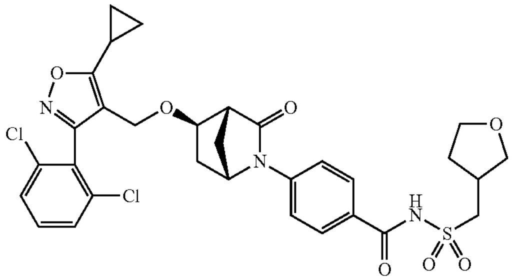 [SMILES: O=C(NS(=O)(=O)CC1CCOC1)c1ccc(N2C(=O)[C@@H]3C[C@H]2C[C@H]3OCc2c(-c3c(Cl)cccc3Cl)noc2C2CC2)cc1] | I-341 | MS (ES, m/z): [M + 1] = 660.13. $^1$H NMR (300 MHz, $CD_3OD$) δ: 7.92-7.81 (m, 2H), 7.65-7.55 (m, 2H), 7.58-7.40 (m, 3H), 4.55 (s, 1H), 4.35 (d, J = 1.2 Hz, 2H), 3.96 (dd, J = 8.7, 7.2 Hz, 1H), 3.83 (td, J = 8.4, 4.8 Hz, 2H), 3.79-3.62 (m, 2H), 3.65-3.46 (m, 2H), 2.82 (s, 1H), 2.72 (dt, J = 14.6, 7.4 Hz, 1H), 2.33-2.05 (m, 3H), 1.94 (d, J = 10.1 Hz, 1H), 1.84-1.65 (m, 2H), 1.58 (d, J = 13.5 Hz, 1H), 1.21-1.09 (m, 4H). |

TABLE 20-continued

| $RSO_2NH_2$ | Cmpd Structure | Cmpd No. | MS/$^1$H NMR |
|---|---|---|---|
| 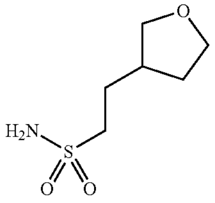 [SMILES: NS(=O)(=O)CCC1CCOC1] | 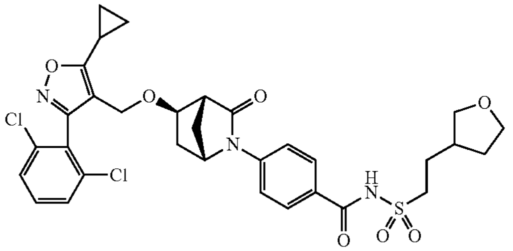 [SMILES: O=C(NS(=O)(=O)CCC1CCOC1)c1ccc(N2C(=O)[C@@H]3C[C@H]2C[C@H]3OCc2c(-c3c(Cl)cccc3Cl)noc2C2CC2)cc1] | I-342 | MS (ES, m/z): [M + 1] = 674. $^1$H NMR (400 MHz, DMSO-d6) δ: 11.97 (s, 1H), 8.08-7.80 (m, 2H), 7.78-7.47 (m, 5H), 4.63 (s, 1H), 4.33 (q, J = 12.1 Hz, 2H), 3.84-3.63 (m, 3H), 3.59-3.51 (m, 3H), 3.23 (dd, J = 8.4, 6.6 Hz, 1H), 2.82 (s, 1H), 2.36 (ddd, J = 16.9, 8.3, 5.2 Hz, 1H), 2.26 (dt, J = 14.4, 7.4 Hz, 1H), 1.99 (m, 3H), 1.83-1.66 (m, 2H), 1.58 (d, J = 9.8 Hz, 1H), 1.49-1.37 (m, 2H), 1.20-1.04 (m, 4H). |
| 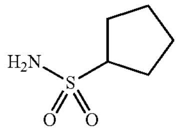 | 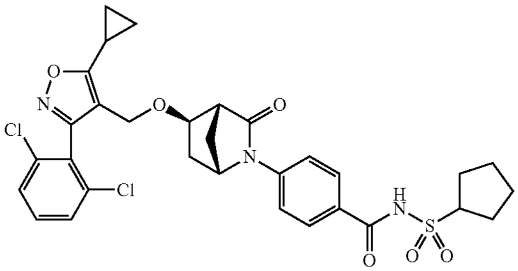 | I-343 | MS (ES, m/z): [M + 1] = 644.13. $^1$H NMR (300 MHz, $CD_3OD$) δ: 7.91-7.82 (m, 2H), 7.63-7.40 (m, 5H), 4.55 (s, 1H), 4.35 (d, J = 1.2 Hz, 2H), 4.28-4.10 (m, 1H), 3.82 (d, J = 6.6 Hz, 1H), 2.81 (s, 1H), 2.33-2.17 (m, 1H), 2.17-1.89 (m, 6H), 1.82-1.52 (m, 6H), 1.21-1.10 (m, 4H). |

Example 260: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-{[(1R,2R)-2-hydroxycyclopentyl]sulfonyl}benzamide (I-344) and (1R,2R)-2-sulfamoylcyclopentyl 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]benzoate (I-345)

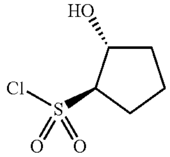

344a

1.

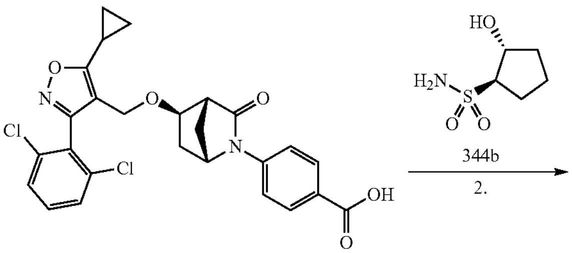

I-244

-continued

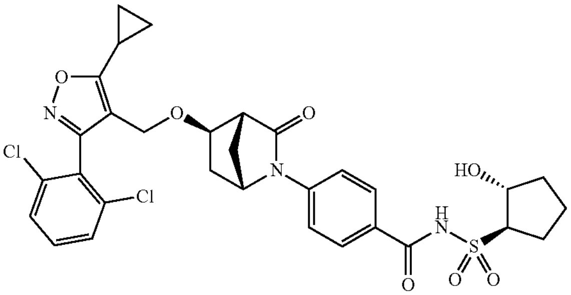

I-344

+

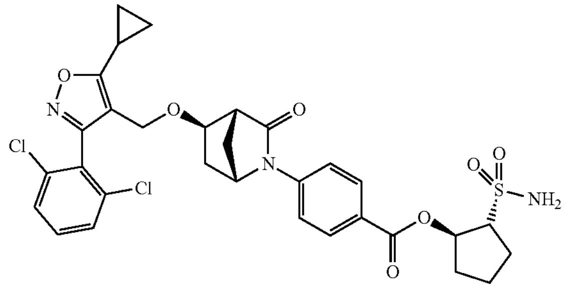

I-345

Step 1

(1R,2R)-2-hydroxycyclopentane-1-sulfonyl chloride 344a (1.0 g, 5.41 mmol) was dissolved in a 0.5 M solution of ammonia in THF (100 mL, 0.5M). The mixture was stirred at room temperature overnight. TLC (iodine stain) showed the starting material disappeared. The solids were filtered off. The filtrate was concentrated to give (1R,2R)-

2-hydroxycyclopentane-1-sulfonamide 344b (0.72 g, crude) as a brown oil. The crude product was used without further purification.

Step 2

To a solution of 4-((1S,4R,5R)-5-((5-cyclopropyl-3-(2,6-dichlorophenyl)isoxazol-4-yl)methoxy)-3-oxo-2-azabicyclo [2.2.1]heptan-2-yl)benzoic acid I-244 (100 mg, 194 μmol) and (1R,2R)-2-hydroxycyclopentane-1-sulfonamide 344b (48.0 mg, 291 μmol) in DCM (5 mL) was added EDCI (74.3 mg, 388 μmol), DMAP (24 mg, 196 μmol) and $Et_3N$ (80.9 μL, 582 μmol). The mixture was stirred at room temperature for 16 hours. The mixture was diluted with DCM, washed with water, dried and concentrated. The crude material was purified by prep-HPLC to give 4-((1S,4R,5R)-5-((5-cyclopropyl-3-(2,6-dichlorophenyl)isoxazol-4-yl)methoxy)-3-oxo-2-azabicyclo[2.2.1]heptan-2-yl)-N-(((1R,2R)-2-hydroxycyclopentyl)sulfonyl)benzamide I-344 (20.2 mg) as an off white solid, and also (1R,2R)-2-sulfamoylcyclopentyl 4-((1S,4R,5R)-5-((5-cyclopropyl-3-(2,6-dichlorophenyl) isoxazol-4-yl)methoxy)-3-oxo-2-azabicyclo[2.2.1]heptan-2-yl)benzoate I-345 (16 mg) as an off white solid.

I-344: $^1$HNMR (400 MHz, DMSO-$d_6$): δ 12.02 (s, 1H), 8.01-7.85 (m, 2H), 7.69-7.53 (m, 5H), 7.02 (s, 1H), 4.62 (s, 1H), 4.39-4.27 (m, 2H), 3.79 (d, J=5.6 Hz, 1H), 3.67 (m, 1H), 2.81 (s, 1H), 2.65-2.53 (m, 2H), 2.41-2.31 (m, 1H), 2.20 (m, 1H), 2.12-1.96 (m, 3H), 1.90 (d, J=9.0 Hz, 2H), 1.82-1.69 (m, 1H), 1.58 (d, J=9.3 Hz, 1H), 1.45 (d, J=13.3 Hz, 1H), 1.20-1.04 (m, 4H); MS (ES, m/z): [M+1]=660.

I-345: $^1$HNMR (400 MHz, DMSO-$d_6$): δ 11.88 (s, 1H), 11.69 (s, 1H), 7.91 (d, J=9.0 Hz, 2H), 7.69-7.52 (m, 5H), 4.62 (s, 1H), 4.38-4.27 (m, 2H), 3.98-3.89 (m, 2H), 3.79 (d, J=6.1 Hz, 1H), 2.80 (s, 1H), 2.42-2.30 (m, 1H), 1.93 (dd, J=17.5, 10.0 Hz, 2H), 1.87-1.62 (m, 3H), 1.59 (m, 2H), 1.46 (d, J=13.4 Hz, 1H), 1.20-1.05 (m, 4H); MS (ES, m/z): [M+1]=660.

Example 261: 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-{[(1R,2R)-2-hydroxycyclopentyl] sulfonyl}benzamide (I-346) and (1R,2R)-2-sulfamoylcyclopentyl 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluorobenzoate (I-347)

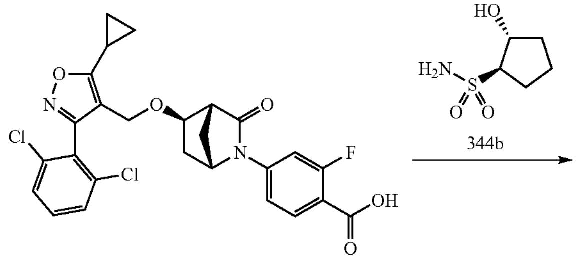

I-314

-continued

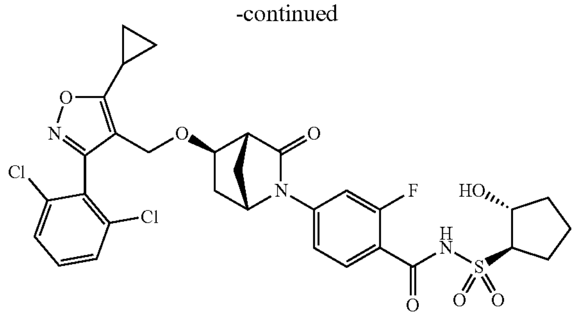

I-346

+

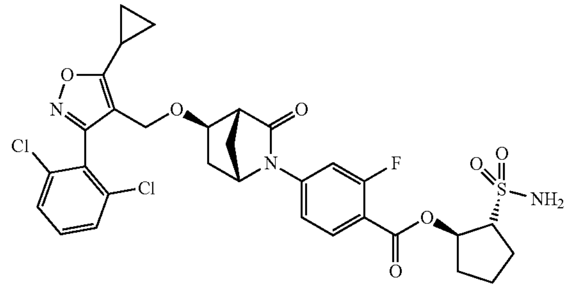

I-347

To a solution of 4-((1S,4R,5R)-5-((5-cyclopropyl-3-(2,6-dichlorophenyl)isoxazol-4-yl)methoxy)-3-oxo-2-azabicyclo [2.2.1]heptan-2-yl)-2-fluorobenzoic acid I-314 (200 mg, 376 μmol) and (1R,2R)-2-hydroxycyclopentane-1-sulfonamide 344b (93.1 mg, 564 μmol) in DCM (10 mL) was added EDCI (144 mg, 752 μmol), DMAP (45.9 mg, 376 μmol) and $Et_3N$ (155 μL, 1.12 mmol). The mixture was stirred at room temperature overnight. The mixture was diluted with DCM, washed with water, dried and concentrated. The crude material was purified with prep-HPLC to afford 4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-2-fluoro-N-{[(1R,2R)-2-hydroxycyclopentyl] sulfonyl}benzamide I-346 (43.1 mg) as a white solid and also (1R,2R)-2-sulfamoylcyclopentyl 4-[(1S,4R,5R)-5-{[5-cyclopropyl-3-(2,6-dichlorophenyl)-1,2-oxazol-4-yl] methoxy}-3-oxo-2-azabicyclo[2.2.1]heptan-2-yl]-2-fluorobenzoate I-347 (32.0 mg) an off-white solid.

I-346: $^1$HNMR (400 MHz, DMSO-d6+$CD_3OD$): δ 7.88 (t, J=8.7 Hz, 1H), 7.68-7.54 (m, 3H), 7.51 (dd, J=13.5, 7.8 Hz, 1H), 7.40 (t, J=8.2 Hz, 1H), 4.66 (s, 1H), 4.39-4.26 (m, 2H), 3.79 (d, J=6.2 Hz, 1H), 3.67-3.57 (m, 1H), 2.83 (s, 1H), 2.59 (d, J=18.1 Hz, 1H), 2.41-2.29 (m, 1H), 2.18 (s, 1H), 2.12-1.97 (m, 3H), 1.91 (d, J=9.7 Hz, 2H), 1.76 (s, 2H), 1.58 (d, J=9.5 Hz, 1H), 1.44 (d, J=13.1 Hz, 1H), 1.13 (ddd, J=17.7, 8.1, 2.8 Hz, 4H); MS (ES, m/z): [M+1]=678.

I-347: $^1$HNMR (400 MHz, DMSO-d6+$CD_3OD$): δ 7.68-7.54 (m, 4H), 7.51 (d, J=13.3 Hz, 1H), 7.40 (d, J=8.8 Hz, 1H), 4.65 (s, 1H), 4.42 (dd, J=10.0, 4.6 Hz, 1H), 4.33 (q, J=12.2 Hz, 2H), 3.92-3.83 (m, 1H), 3.79 (d, J=5.9 Hz, 1H), 2.82 (d, J=7.3 Hz, 1H), 2.36 (dq, J=8.3, 5.2 Hz, 1H), 2.14-1.98 (m, 2H), 1.96-1.86 (m, 2H), 1.86-1.71 (m, 2H), 1.70-1.53 (m, 3H), 1.44 (d, J=13.4 Hz, 1H), 1.19-1.06 (m, 4H); MS (ES, m/z): [M+1]=678.

Example 262: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluoro-N-{[(1R,2R)-2-methoxycyclopentyl]sulfonyl}pyridine-2-carboxamide (I-348)

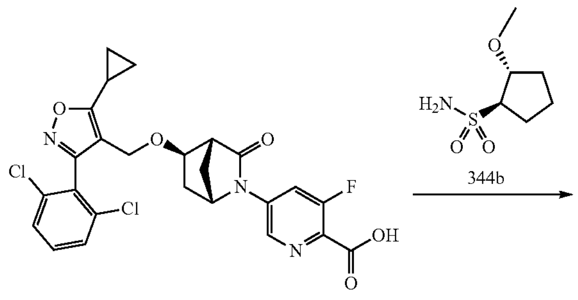

I-326

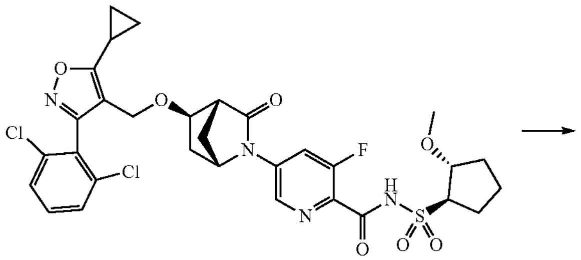

I-348

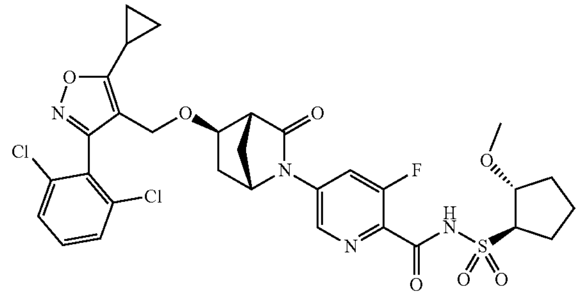

I-348

Following the procedures described in Preparative Example 257, by reacting 5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoropicolinic acid I-326 with (1R,2R)-2-methoxycyclopentane-1-sulfonamide 344b, 5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoro-N-(((1R,2R)-2-methoxycyclopentyl)sulfonyl)picolinamide I-348 was prepared (152 mg) as a clear oil. $^1$HNMR (400 MHz, DMSO-d6+$CD_3OD$): δ 8.47 (d, J=11.1 Hz, 1H), 7.93-7.84 (m, 1H), 7.42 (ddt, J=16.3, 15.8, 4.9 Hz, 3H), 4.50 (s, 1H), 4.39-4.25 (m, 3H), 4.19-4.07 (m, 1H), 3.90 (d, J=6.5 Hz, 1H), 3.30 (d, J=0.7 Hz, 3H), 2.96 (s, 1H), 2.31-2.06 (m, 4H), 2.00 (dt, J=13.3, 8.5 Hz, 2H), 1.90 (d, J=10.2 Hz, 1H), 1.87-1.75 (m, 3H), 1.70 (d, J=13.7 Hz, 1H), 1.30-1.24 (m, 2H), 1.20-1.13 (m, 2H); MS (ES, m/z): [M+1]=693.

Example 263: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-3-fluoro-N-{[(1R,2R)-2-hydroxycyclopentyl]sulfonyl}pyridine-2-carboxamide (I-349)

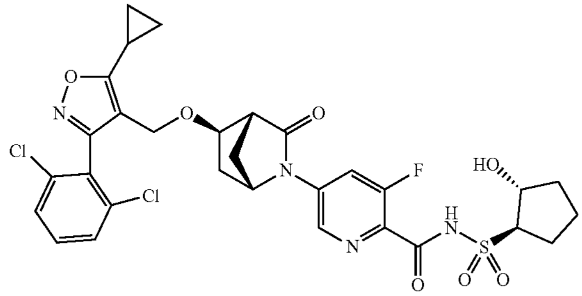

I-349

$BBr_3$ (216 μL, 216 μmol, 1M in DCM) was added to a solution of 5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoro-N-(((1R,2R)-2-methoxycyclopentyl)sulfonyl)picolinamide I-348 (100 mg, 144 μmol) in DCM (3 mL). The mixture was stirred at room temperature overnight. The mixture was quenched with water, extracted with DCM. The organic layer was dried, filtered and concentrated. The residue was purified by prep-HPLC to give 5-((1S,4R,5R)-5-((5-cyclopropyl-3-(2,6-dichlorophenyl)isoxazol-4-yl)methoxy)-3-oxo-2-azabicyclo[2.2.1]heptan-2-yl)-3-fluoro-N-(((1R,2R)-2-hydroxycyclopentyl)sulfonyl)picolinamide I-349 (6.7 mg) as a white solid after lyophilization. $^1$HNMR (400 MHz, $CDCl_3$): δ 8.48 (d, J=5.8 Hz, 1H), 7.95 (dd, J=40.2, 12.4 Hz, 1H), 7.49-7.36 (m, 3H), 4.73-4.63 (m, 1H), 4.52 (s, 1H), 4.40-4.28 (m, 2H), 4.08-3.94 (m, 1H), 3.88 (s, 1H), 2.95 (s, 1H), 2.35-1.61 (m, 11H), 1.26 (t, J=4.2 Hz, 2H), 1.18 (d, J=8.3 Hz, 2H); MS (ES, m/z): [M+1]=679.

Example 264: 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-{[(1R,2R)-2-hydroxycyclopentyl]sulfonyl}pyridine-2-carboxamide (I-350)

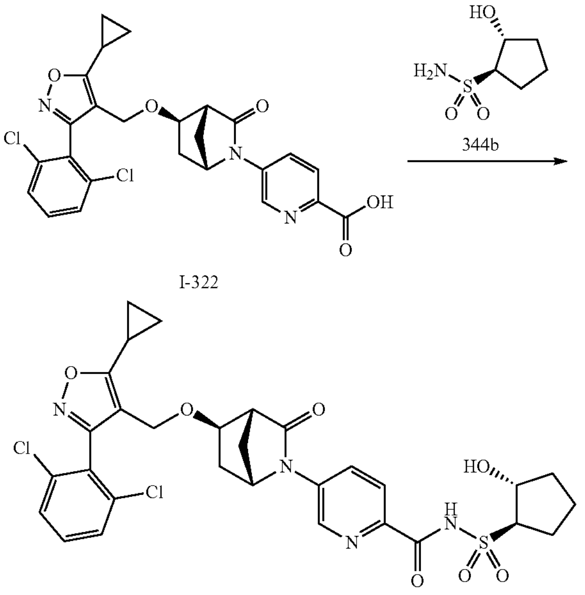

I-322

I-350

To a solution of 5-((1S,4R,5R)-5-((5-cyclopropyl-3-(2,6-dichlorophenyl)isoxazol-4-yl)methoxy-3-oxo-2-azabicyclo[2.2.1]heptan-2-yl)picolinic acid trifluoroacetic acid salt I-322 (126 mg, 1 equiv.) and (1R,2R)-2-hydroxycyclopentane-1-sulfonamide 344b (68 mg, 2.0 equiv) in $CH_2Cl_2$ (10.0 mL) was added DIEA (0.084 mL, 3.0 equiv.), DMAP (48 mg, 2.0 equiv.) and EDCI (76 mg, 2.0 equiv.). The mixture was stirred at room temperature for 16 h and washed with 5% aq Citric acid, brine, dried over $Na_2SO_4$ and concentrated under the reduced pressure. The crude material was purified by Semi-prep HPLC using 10-90% acetonitrile in 30 min, gradient to give 5-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]-N-{[(1R,2R)-2-hydroxycyclopentyl]sulfonyl}pyridine-2-carboxamide I-350 (18 mg) as trifluoroacetic acid salt after lyophilization. $^1$H-NMR (400 MHz, DMSO-$d_6$) δ: 8.83 (s, 1H), 8.02 (bs, 2H), 7.63-7.54 (m, 3H), 4.65 (s, 1H), 4.35-4.25 (m, 3H), 3.74 (bs, 1H), 2.78 (s, 1H), 2.31-2.29 (m, 1H), 2.07 (bs, 2H), 1.93 (d, J=9.9 Hz, 2H), 1.76-1.60 (m, 2H), 1.59 (d, J=9.6 Hz, 2H), 1.46 (d, J=12.8 Hz, 1H), 1.15-1.06 (m, 6H); MS (ES, m/z): [M+1]=660.96.

Example 265: Synthesis of I-351 to I-354

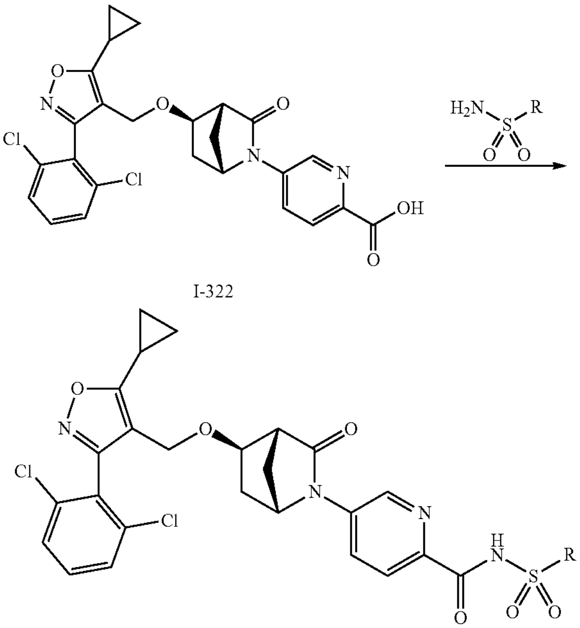

I-322

I-x

Acyl-sulfonamides I-351 to I-354 were prepared from acid I-322 and the corresponding sulfonamide $RSO_2NH_2$ following the procedure described in Preparative Example 264. The data for compounds I-351 to 1-354 is summarized in Table 21.

TABLE 21

| $RSO_2NH_2$ | Cmpd Structure | Cmpd No. | MS/$^1$H NMR |
|---|---|---|---|
| 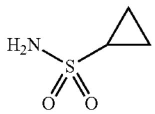 | 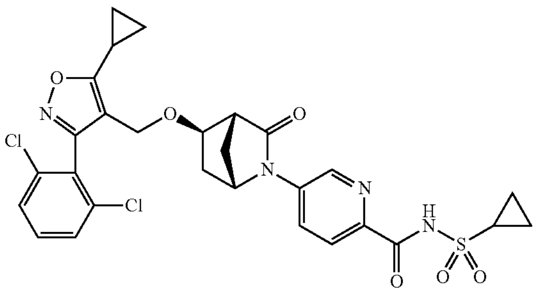 [SMILES: O=C(NS(=O)(=O)C1CC1)c1ccc(N2C(=O)[C@@H]3C[C@H]2C[C@H]3OCc2c(-c3c(Cl)cccc3Cl)noc2C2CC2)cn1] | I-351 | MS (ES, m/z): [M + 1] = 617.01 $^1$H NMR (400 MHz, DMSO-d6) δ: 8.87 (d, J = 2.3 Hz, 1H), 8.17-7.95 (m, 2H), 7.73-7.51 (m, 3H), 4.75 (s, 1H), 4.35-4.33 (m, 2H), 3.81 (d, J = 6.3 Hz, 1H), 3.18-3.01 (m, 1H), 2.87 (s, 1H), 2.43-2.27 (m, 1H), 2.09 (dd, J = 13.5 & 7.0 Hz, 1H), 1.97 (d, J = 9.5 Hz, 1H), 1.62 (d, J = 9.8 Hz, 1H), 1.46 (d, J = 13.6 Hz, 1H), 1.23-1.00 (m, 8H). |

TABLE 21-continued

| $RSO_2NH_2$ | Cmpd Structure | Cmpd No. | MS/$^1$H NMR |
|---|---|---|---|
| 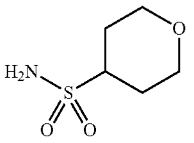 | 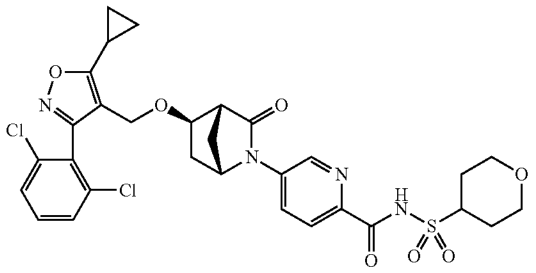 [SMILES: O=C(NS(=O)(=O)C1CCOCC1)c1ccc(N2C(=O)[C@@H]3C[C@H]2C[C@H]3OCc2c(-c3c(Cl)cccc3Cl)noc2C2CC2)cn1] | I-352 | MS (ES, m/z): [M + 1] = 660.94. $^1$H NMR (400 MHz, DMSO-d6) δ: 8.86 (d, J = 2.5 Hz, 1H), 8.11-8.04 (m, 2H), 7.67-7.47 (m, 3H), 4.75 (s, 1H), 4.35-4.33 (m, 2H), 3.94 (dd, J = 11.3 & 3.5 Hz, 1H), 3.89-3.76 (m, 2H), 3.35 (t, J = 10.9 Hz, 2H), 2.87 (s, 1H), 2.43-2.30 (m, 1H), 2.09 (dd, J = 13.5 & 7.2 Hz, 1H), 1.93 (dd, J = 25.2 & 10.5 Hz, 3H), 1.73 (qd, J = 12.4 & 4.6 Hz, 2H), 1.62 (d, J = 9.9 Hz, 1H), 1.46 (d, J = 13.4 Hz, 1H), 1.23-1.01 (m, 4H). |
| 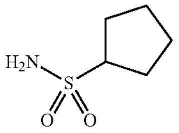 | 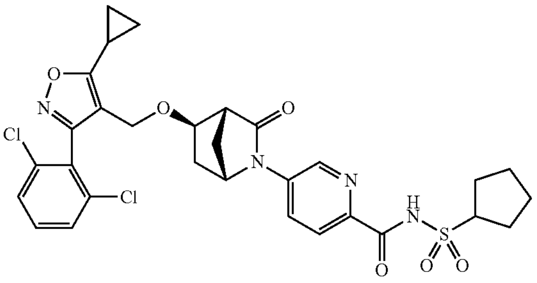 [SMILES: O=C(NS(=O)(=O)C1CCCC1)c1ccc(N2C(=O)[C@@H]3C[C@H]2C[C@H]3OCc2c(-c3c(Cl)cccc3Cl)noc2C2CC2)cn1] | I-353 | MS (ES, m/z): [M + 1] = 644.94. $^1$H NMR (300 MHz, DMSO-d6) δ: 8.86 (d, J = 2.4 Hz, 1H), 8.11-8.03 (m, 2H), 7.75-7.50 (m, 3H), 4.75 (s, 1H), 4.38-4.30 (m, 2H), 4.10 (t, J = 7.7 Hz, 1H), 3.81 (d, J = 5.6 Hz, 1H), 2.87 (s, 1H), 2.43-2.27 (m, 1H), 2.10 (dd, J = 13.2 & 6.6 Hz, 1H), 2.05-1.88 (m, 5H), 1.65 (dd, J = 22.0 & 8.4 Hz, 5H), 1.46 (d, J = 13.4 Hz, 1H), 1.20-0.99 (m, 4H). |
| 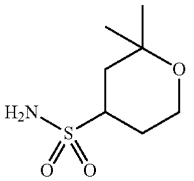 | 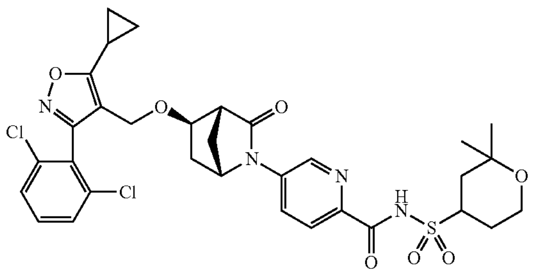 [SMILES: CC1(C)CC(S(=O)(=O)NC(=O)c2ccc(N3C(=O)[C@@H]4C[C@H]3C[C@H]4OCc3c(-c4c(Cl)cccc4Cl)noc3C3CC3)cn2)CCO1] | I-354 | MS (ES, m/z): [M + 1] = 689.03. $^1$H NMR (400 MHz, DMSO-d6) δ: 8.85 (s, 1H), 8.08-8.03 (m, 2H), 7.70-7.55 (m, 3H), 4.74 (s, 1H), 4.37-4.29 (m, 2H), 4.01-3.88 (m, 1H), 3.80 (d, J = 5.9 Hz, 1H), 3.71 (dd, J = 12.0 & 4.5 Hz, 1H), 3.58 (t, J = 11.1 Hz, 1H), 2.86 (s, 1H), 2.37-2.34 (m, 1H), 2.08 (dd, J = 13.5 & 7.0 Hz, 1H), 1.90 (dd, J = 38.7 & 9.9 Hz, 1H), 1.60 (dd, J = 11.3 & 6.0 Hz, 1H), 1.55-1.39 (m, 1H), 1.21-1.05 (m, 14H). |

Example 266: Synthesis of I-355 to I-357

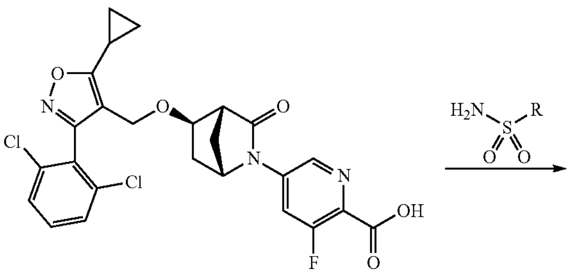

I-326

-continued

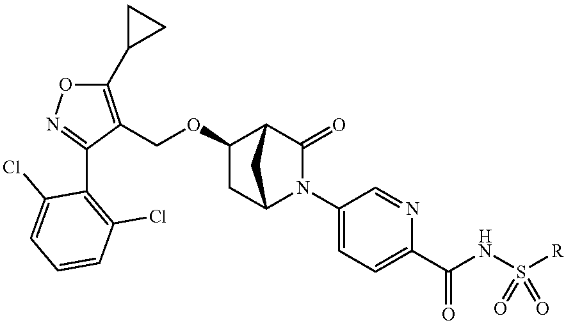

I-x

Acyl-sulfonamides I-355 to I-357 were prepared from acid I-326 and the corresponding sulfonamide $RSO_2NH_2$ following the procedure described in Preparative Example 264. The data for compounds I-355 to I-357 is summarized in Table 22.

TABLE 22

| $RSO_2NH_2$ | Cmpd Structure | Cmpd No. | MS/$^1$H NMR |
|---|---|---|---|
| 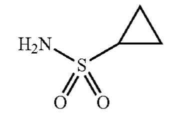 | 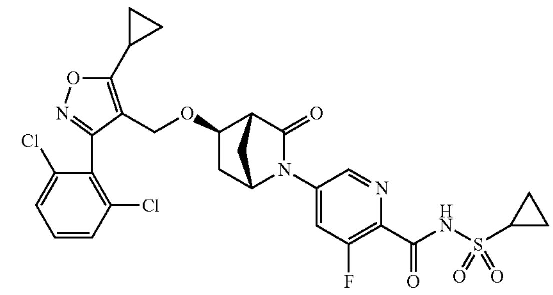 [SMILES: O=C(NS(=O)(=O)C1CC1)c1ncc(N2C(=O)[C@@H]3C[C@H]2C[C@H]3OCc2c(-c3c(Cl)cccc3Cl)noc2C2CC2)cc1F] | I-355 | MS (ES, m/z): [M + 1] = 635. $^1$H NMR (400 MHz, $CDCl_3$) δ: 9.97 (s, 1H), 8.42 (s, 1H), 7.92 (dd, J = 12.4, 2.1 Hz, 1H), 7.48-7.32 (m, 3H), 4.48 (s, 1H), 4.39-4.26 (m, 2H), 3.90 (d, J = 6.2 Hz, 1H), 3.04 (dt, J = 12.9, 4.1 Hz, 1H), 2.96 (s, 1H), 2.09-2.15 (m, 3H), 1.90 (d, J = 10.2 Hz, 1H), 1.70 (d, J = 13.6 Hz, 1H), 1.53-1.44 (m, 2H), 1.32-1.24 (m, 2H), 1.20-1.10 (m, 4H). |
| 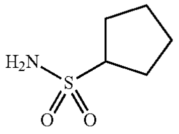 | 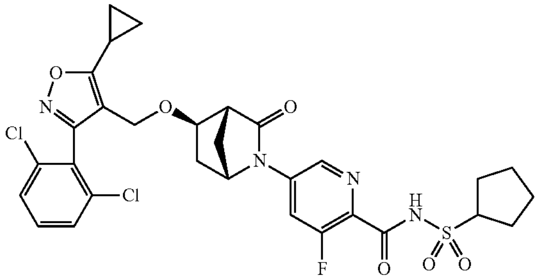 [SMILES: O=C(NS(=O)(=O)C1CCCC1)c1ncc(N2C(=O)[C@@H]3C[C@H]2C[C@H]3OCc2c(-c3c(Cl)cccc3Cl)noc2C2CC2)cc1F] | I-356 | MS (ES, m/z): [M + 1] = 663. $^1$H NMR (400 MHz, $CDCl_3$) δ: 9.87 (s, 1H), 8.44-8.38 (m, 1H), 7.91 (dd, J = 12.4, 2.1 Hz, 1H), 7.47-7.33 (m, 3H), 4.48 (s, 1H), 4.39-4.28 (m, 2H), 4.28-4.19 (m, 1H), 3.89 (d, J = 6.8 Hz, 1H), 2.96 (s, 1H), 2.21-1.99 (m, 7H), 1.93-1.80 (m, 3H), 1.74-1.62 (m, 3H), 1.31-1.23 (m, 2H), 1.21-1.12 (m, 2H). |
| 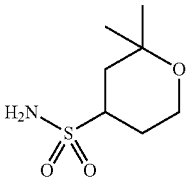 | 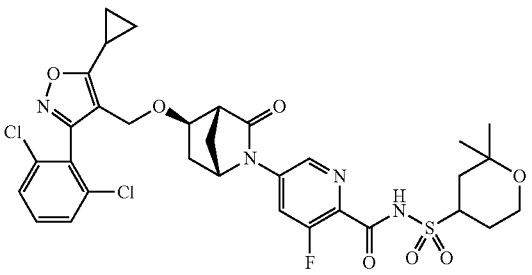 [SMILES: CC1(C)CC(S(=O)(=O)NC(=O)c2ncc(N3C(=O)[C@@H]4C[C@H]3C[C@H]4OCc3c(-c4c(Cl)cccc4Cl)noc3C3CC3)cc2F)CCO1] | I-357 | MS (ES, m/z): [M + 1] = 707. $^1$H NMR (400 MHz, $CDCl_3$) δ: 9.81 (s, 1H), 8.43 (d, J = 2.0 Hz, 1H), 7.98-7.87 (m, 1H), 7.48-7.33 (m, 3H), 4.48 (s, 1H), 4.40-4.22 (m, 2H), 4.05 (tt, J = 12.7, 3.9 Hz, 1H), 3.94-3.83 (m, 2H), 3.68 (td, J = 12.2, 2.6 Hz, 1H), 2.96 (s, 1H), 2.18-2.06 (m, 2H), 2.02 (t, J = 11.5 Hz, 3H), 1.96-1.87 (m, 2H), 1.82 (t, J = 13.0 Hz, 1H), 1.70 (d, J = 13.5 Hz, 1H), 1.30 (d, J = 4.0 Hz, 3H), 1.29-1.25 (m, 2H), 1.23 (s, 3H), 1.19-1.12 (m, 2H). |

Example 267: 2-({4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl]phenyl}formamido)acetic Acid (I-358)

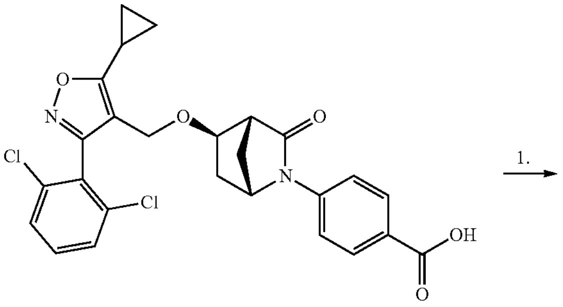

I-244

-continued

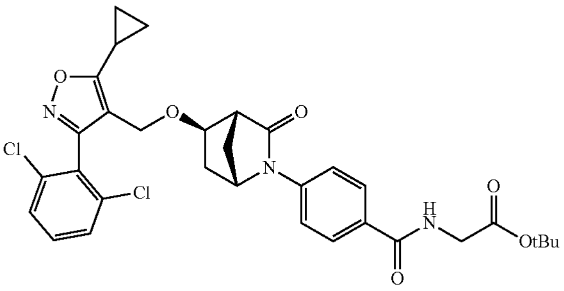

358a

-continued

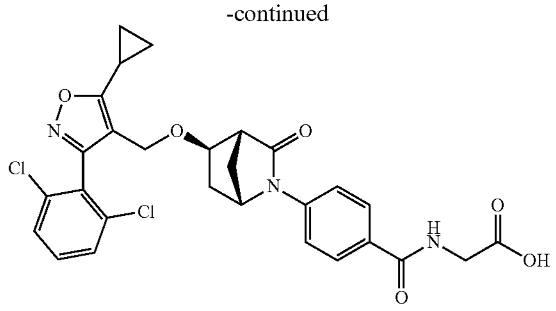

I-358

Step 1

To a 25 mL round-bottom flask was added 4-[(1S,4R,5R)-5-[[5-cyclopropyl-3-(2,6-dichlorophenyl)-1,2-oxazol-4-yl] methoxy]-3-oxo-2-azabicyclo[2.2.1]heptan-2-yl]benzoic acid I-244 (90 mg, 0.18 mmol, 1.00 equiv.), tert-butyl 2-aminoacetate hydrochloride (59 mg, 0.35 mmol, 2.00 equiv.). N,N-dimethylformamide (3 mL), HATU (133 mg, 0.35 mmol, 2.00 equiv.), and DIEA (91 mg, 0.70 mmol, 4.00) equiv.). The resulting solution was stirred for 1 h at room temperature. The mixture was diluted with 100 mL of $H_2O$, extracted with ethyl acetate (100 mL×2), and combined organic extracts were washed with brine (100 mL×2), dried over anhydrous sodium sulfate and concentrated under vacuum. The residue was purified by silica gel column chromatography eluting with ethyl acetate/petroleum ether (1:1) to give tert-butyl 2-([4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]phenyl]formamido)acetate 358a (148 mg) as a crude colorless oil Step 2

To a 25 mL round-bottom flask was added tert-butyl 2-([4-[(1S,4R,5R)-5-[[5-cyclopropyl-3-(2,6-dichlorophenyl)-1,2-oxazol-4-yl]methoxy]-3-oxo-2-azabicyclo[2.2.1] heptan-2-yl]phenyl]formamido) acetate 358a (148 mg, 0.24 mmol, 1.00 equiv.), dichloromethane (4 mL), and trifluoroacetic acid (2 mL). The resulting mixture was stirred for 1 h at room temperature, diluted with 20 mL of DCM. The pH value of the solution was adjusted to 7 using a saturated sodium bicarbonate aqueous solution. The aqueous mixture was extracted with ethyl acetate (200 mL×2), and the combined organic extracts were washed with brine (200 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (38.0% ACN up to 56.0% in 8 min); Detector, uv 254/220 nm. After purification 2-([4-[(1S,4R,5R)-5-[[5-cyclopropyl-3-(2,6-dichlorophenyl)-1,2-oxazol-4-yl]methoxy]-3-oxo-2-azabicyclo [2.2.1]heptan-2-yl]phenyl]formamido) acetic acid I-358 (12.7 mg, 79%) was obtained as a white solid. $^1$HNMR (300 MHz, $CDCl_3$) δ: 7.92-7.82 (m, 2H), 7.65-7.45 (m, 5H), 4.58 (s, 1H), 4.40 (d, J=1.5 Hz, 2H), 4.10 (s, 2H), 3.87 (d, J=6.6 Hz, 1H), 2.85 (s, 1H), 2.38-2.23 (m, 1H), 2.23-2.11 (m, 1H), 1.99 (d, J=10.1 Hz, 1H), 1.79 (d, J=9.9 Hz, 1H), 1.62 (d, J=13.5 Hz, 1H), 1.25-1.16 (m, 4H); MS (ES, m/z): [M+1]=570.

Example 268: 2-({4-[(1S,4R,5R)-5-{[5-cyclopropyl-3-(2,6-dichlorophenyl)-1,2-oxazol-4-yl]methoxy}-3-oxo-2-azabicyclo[2.2.1]heptan-2-yl] phenyl}formamido)ethane-1-sulfonic Acid (I-359)

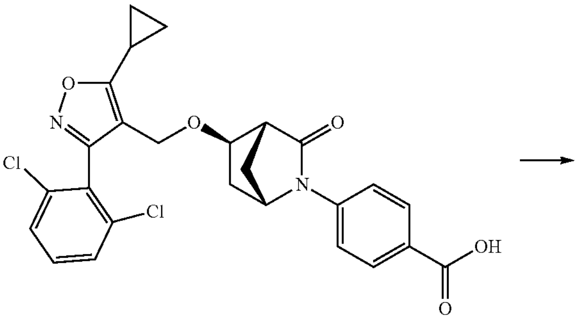

I-244

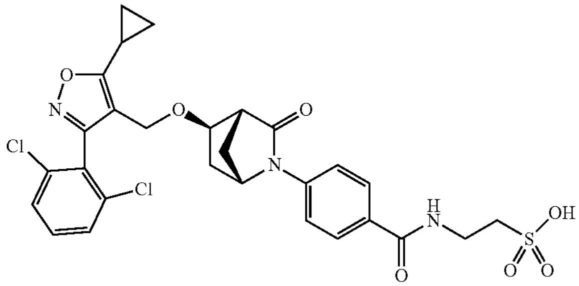

I-359

To a 25 mL round-bottom flask was added 4-[(1S,4R,5R)-5-[[5-cyclopropyl-3-(2,6-dichlorophenyl)-1,2-oxazol-4-yl] methoxy]-3-oxo-2-azabicyclo[2.2.1]heptan-2-yl]benzoic acid I-244 (100 mg, 0.19 mmol, 1.00 equiv.), 2-aminoethane-1-sulfonic acid (36.7 mg, 0.29 mmol, 1.50 equiv.), PyBOP (133 mg, 1.30 equiv.), N,N-dimethylformamide (3 mL), and DIEA (0.14 mL, 4.00 equiv.). The resulting mixture was heated at 80° C., for 3 h, cooled to room temperature, and concentrated. The crude product was purified by Flash-Prep-HPLC using the following conditions (IntelFlash-1): Column, C18 silica gel; mobile phase, $CH_3CN$:$H_2O$ increasing from 0% to 60% within 30 min; Detector, UV 220 nm, 80 mg of crude product was obtained. The crude product was repurified by Prep-HPLC with the following conditions: Column, XBridge Shield RP18 OBD Column, 5 um, 19*150 mm; mobile phase, Water (0.05% TFA) and ACN (36.0% ACN up to 55.0% in 8 min); Detector, uv 254/220 nm. After purification 2-([4-[(1S,4R,5R)-5-[[5-cyclopropyl-3-(2,6-dichlorophenyl)-1,2-oxazol-4-yl]methoxy]-3-oxo-2-azabicyclo[2.2.1]heptan-2-yl]phenyl]formamido) ethane-1-sulfonic acid I-359 (54.1 mg, 45%) was obtained as a white solid. $^1$HNMR (400 MHz, $CD_3OD$) δ: 7.83 (d, J=8.7 Hz, 2H), 7.63-7.45 (m, 5H), 4.57 (s, 1H), 4.39 (d, J=1.4 Hz, 2H), 3.91-3.76 (m, 3H), 3.10 (t, J=6.6 Hz, 2H), 2.84 (s, 1H), 2.38-2.22 (m, 1H), 2.24-2.10 (m, 1H), 1.98 (d, J=10.1 Hz, 1H), 1.78 (d, J=9.9 Hz, 1H), 1.61 (d, J=13.4 Hz, 1H), 1.25-1.15 (m, 4H); MS (ES, m/z): [M+1]=620.09.

Example 269: 4-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]benzoic Acid (I-360) and 4-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]benzoic Acid (I-361)

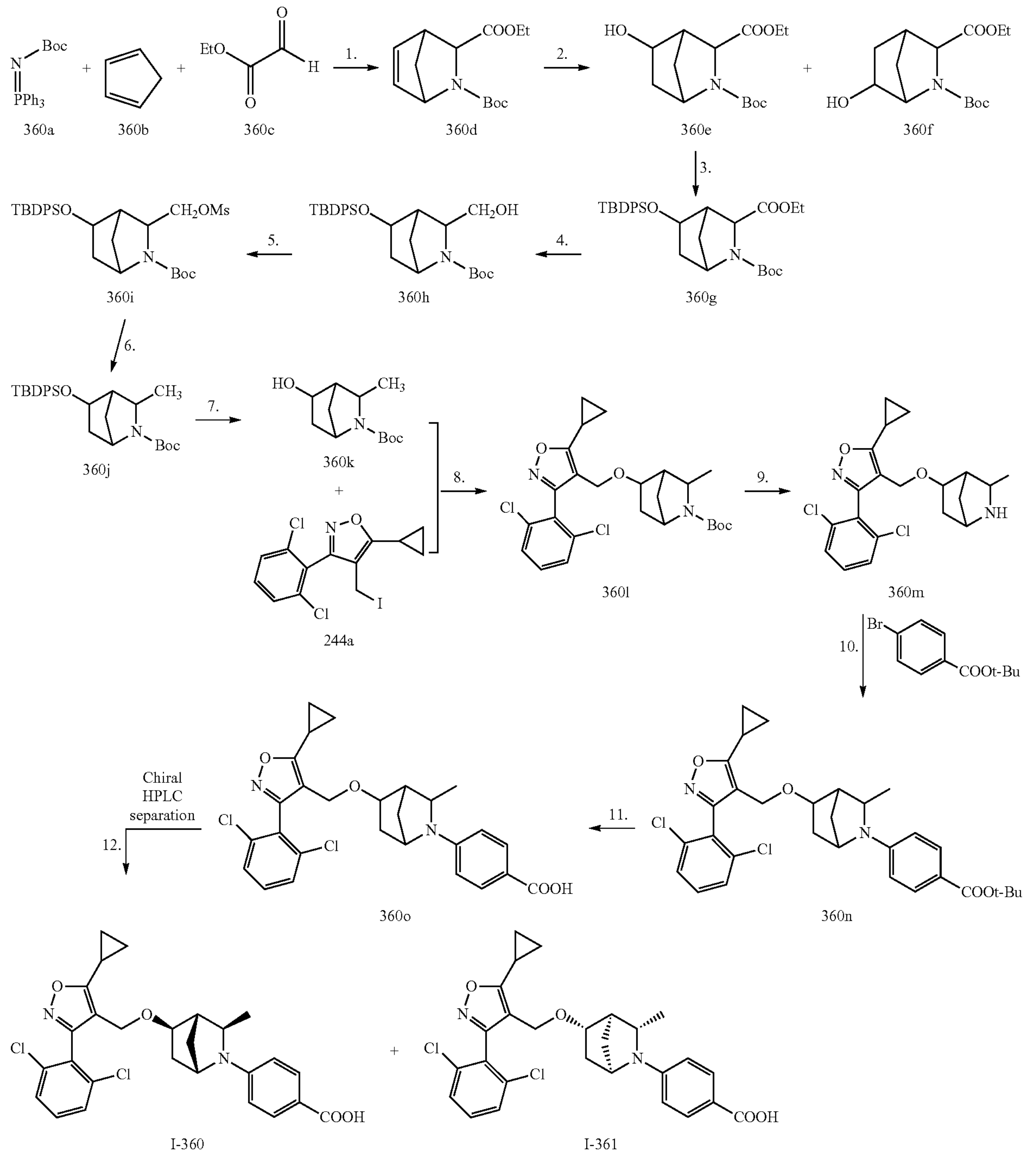

Step 1

Ethyl 2-oxoacetate 360c was predistilled at 120 to 130° C. Cyclopenta-1,3-diene 360b was freshly cracked at 175° C. To a 2000 mL round-bottom flask was added tert-butyl N-(triphenyl-[5]-phosphanylidene)carbamate 360a (56.6 g, 149.97 mmol, 1.00 equiv.), toluene (500 mL), cyclopenta-1,3-diene 360b (19.8 g, 299.54 mmol, 2.00 equiv.), and ethyl 2-oxoacetate 360c (30.6 g, 299.74 mmol, 2.00 equiv.). The resulting mixture was stirred at room temperature for 2 days and concentrated under vacuum. The residue was purified by Flash-Prep-HPLC using the following conditions (Intel-Flash-1): Column, C18 silica gel; mobile phase, MeCN/$H_2O$=0:1 increasing to MeCN/$H_2O$=1:0 within 60 min; Detector, UV 220 nm. Removal of solvents afforded 2-tert-butyl 3-ethyl 2-azabicyclo[2.2.1]hept-5-ene-2,3-dicarboxylate 360d (32 g, 80%) as a light yellow oil.

Step 2

To a 2000 mL 3-necked round-bottom flask purged with and maintained under an inert atmosphere of nitrogen was added 2-tert-butyl 3-ethyl 2-azabicyclo[2.2.1]hept-5-ene-2,3-dicarboxylate 360d (26.7 g, 99.88 mmol, 1.00 equiv.) and tetrahydrofuran (400 mL, 1.00 equiv.). A 1M solution of $BH_3$ in THF (110 mL, 1.10 equiv.) was added dropwise with stirring at −78° C., and the mixture was stirred at this temperature for 15 min. The mixture was then allowed to warm to room temperature and stirred for 1 more hour. A 2M sodium hydroxide aqueous solution (175 mL, 3.50 equiv.) was added dropwise followed by the addition of a 30% $H_2O_2$ aqueous solution (50 mL, 5.00 equiv.) dropwise with stirring at 0° C. The resulting mixture was stirred for 30 min at room temperature. The mixture was cooled in an ice/water bath, carefully quenched by the addition of 100 mL of a sat. $NaHCO_3$ aqueous solution, and further diluted with 400 mL of brine. The aqueous mixture was extracted with ethyl acetate (300 mL×4). The combined organic extracts were washed with brine (400 mL×2), dried over anhydrous sodium sulfate and concentrated under vacuum. The crude product was purified by Flash-Prep-HPLC using the following conditions (High pressure IntelFlash-1.20 MPa): Column, C18 silica gel; mobile phase, $MeCN/H_2O$ with 0.05% $NH_4HCO_3$=15%:85% increasing to $MeCN/H_2O$ with 0.05% $NH_4HCO_3$=45%:55% within 30 min; Detector, UV 210 nm. Removal of solvents afforded 2-tert-butyl 3-ethyl 5-hydroxy-2-azabicyclo[2.2.1]heptane-2,3-dicarboxylate 360e (9.4 g, 33%) as a light yellow oil.

Step 3

To a 250 mL round-bottom flask was added 2-tert-butyl 3-ethyl 5-hydroxy-2-azabicyclo[2.2.1]heptane-2,3-dicarboxylate 360e (5 g, 17.52 mmol, 1.00 equiv.), N,N-dimethylformamide (50 mL), imidazole (4.8 g, 4.00 equiv.), and TBDPSCl (9.6 g, 2.00 equiv.). The resulting mixture was stirred at 40° C., overnight. After cooling to room temperature, the mixture was diluted with brine (300 mL), extracted with ethyl acetate (150 mL×4), and the combined organic extracts were washed brine (200 mL×2), dried over anhydrous sodium sulfate, and concentrated under vacuum. The residue was purified by silica gel column chromatography eluting with ethyl acetate/petroleum ether (1:5) to give 2-tert-butyl 3-ethyl 5-[(tert-butyldiphenylsilyl)oxy]-2-azabicyclo[2.2.1]heptane-2,3-dicarboxylate 360g (8.5 g, 93%) as a light yellow solid.

Step 4

To a 250 mL round-bottom flask was added 2-tert-butyl 3-ethyl 5-[(tert-butyldiphenylsilyl)oxy]-2-azabicyclo[2.2.1]heptane-2,3-dicarboxylate 360g (8.5 g, 16.23 mmol, 1.00 equiv.) and tetrahydrofuran (90 mL). Solid $LiBH_4$ (245 mg, 2.50 equiv.) was added in small portions at 0° C. The resulting mixture was stirred overnight at room temperature. The mixture was diluted with EA (100 mL), cooled in an ice bath, and quenched by the addition of a chilled sat. $NH_4Cl$ aqueous solution (100 mL). The aqueous mixture was extracted with ethyl acetate (100 mL×4). The combined organic extracts were washed with brine (200 mL×2), dried over anhydrous sodium sulfate, and concentrated under vacuum to afford tert-butyl 5-[(tert-butyldiphenylsilyl)oxy]-3-(hydroxymethyl)-2-azabicyclo[2.2.1]heptane-2-carboxylate 360h (7.8 g, Q) as a light yellow crude oil.

Step 5

To a 250 mL round bottom flask was added tert-butyl 5-[(tert-butyldiphenylsilyl)oxy]-3-(hydroxymethyl)-2-azabicyclo[2.2.1]heptane-2-carboxylate 360h (8 g, 16.61 mmol, 1.00 equiv.), tetrahydrofuran (100 mL), and TEA (7.5 mL, 3.00 equiv.). MsCl (3.8 g, 2.00 equiv.) was added dropwise with stirring at 0° C. The resulting mixture was stirred at room temperature for 30 min, and quenched by the addition of 100 mL of water. The aqueous mixture was extracted with ethyl acetate (100 mL×3), and the combined organic extracts were washed with brine (100 mL×2), dried over anhydrous sodium sulfate and concentrated under vacuum. The residue was purified by silica gel column chromatography eluting with ethyl acetate/petroleum ether (1:5) to give tert-butyl 5-[(tert-butyldiphenylsilyl)oxy]-3-[(methanesulfonyloxy)methyl]-2-azabicyclo[2.2.1]heptane-2-carboxylate 360i (8.2 g, 88%) as a light yellow oil.

Step 6

To a 250 mL round-bottom flask was added tert-butyl 5-[(tert-butyldiphenylsilyl)oxy]-3-[(methanesulfonyloxy)methyl]-2-azabicyclo[2.2.1]heptane-2-carboxylate 360i (5.6 g, 10.00 mmol, 1.00 equiv.) and tetrahydrofuran (60 mL). Solid $LiBH_4$ (1.3 g, 6.00 equiv.) was added in portions at room temperature. The resulting mixture was heated at 60° C., for 2 days. The mixture was cooled to room temperature, diluted with ether (100 mL), and quenched by the addition of a cold sat. $NH_4Cl$ aqueous solution. The aqueous mixture was extracted with ethyl acetate (100 mL×3), and the combined organic extracts were washed with brine (200 mL×2), dried over anhydrous sodium sulfate, and concentrated under vacuum. The residue was purified by silica gel column chromatography eluting with ethyl acetate/petroleum ether (1:10) to give tert-butyl 5-[(tert-butyldiphenylsilyl)oxy]-3-methyl-2-azabicyclo[2.2.1]heptane-2-carboxylate 360j (4.2 g, 90%) as a light yellow oil.

Step 7

To a 25 mL round-bottom flask was added tert-butyl 5-[(tert-butyldiphenylsilyl)oxy]-3-methyl-2-azabicyclo[2.2.1]heptane-2-carboxylate 360j (380 mg, 0.82 mmol, 1.00 equiv.), tetrahydrofuran (2.2 mL), and TBAF (1.63 mL, 2.00 equiv.). The resulting mixture was stirred at room temperature for 1 h, quenched with $H_2O$ (100 mL). The aqueous mixture was extracted with ethyl acetate (100 mL×2), and the combined organic extracts were washed with brine (150 mL×2), dried over anhydrous sodium sulfate and concentrated under vacuum to afford tert-butyl 5-hydroxy-3-methyl-2-azabicyclo[2.2.1]heptane-2-carboxylate 360k (450 mg, crude, Q) as a light yellow oil.

Step 8

To a 25 mL round-bottom flask was added 5-cyclopropyl-3-(2,6-dichlorophenyl)-4-(iodomethyl)-1,2-oxazole 360k (700 mg, 1.78 mmol, 2.00 equiv.), N,N-dimethylformamide (3 mL), and tert-butyl 5-hydroxy-3-methyl-2-azabicyclo[2.2.1]heptane-2-carboxylate 244a (210 mg, 0.92 mmol, 1.0 equiv.). Sodium hydride (72 mg, 1.80 mmol, 2.0 equiv., 60%6 dispersed in mineral oil) was added in portions at 0° C. The resulting mixture was stirred at room temperature overnight, diluted with 50 mL of EA, and quenched by the addition of 50 mL of water. The aqueous mixture was extracted with ethyl acetate (200 mL×2). The combined organic extracts were washed with brine (200 mL×3), dried over anhydrous sodium sulfate and concentrated under vacuum. The residue was purified by silica gel column chromatography eluting with ethyl acetate/petroleum ether (1:3) to afford tert-butyl 5-[[5-cyclopropyl-3-(2,6-dichlorophenyl)-1,2-oxazol-4-yl]methoxy]-3-methyl-2-azabicyclo[2.2.1]heptane-2-carboxylate 360l (180 mg, 39%) as a light yellow oil.

Step 9

To a 25 mL round bottom flask was added tert-butyl 5-[[5-cyclopropyl-3-(2,6-dichlorophenyl)-1,2-oxazol-4-yl]methoxy]-3-methyl-2-azabicyclo[2.2.1]heptane-2-carboxylate 360l (380 mg, 0.77 mmol, 1.00 equiv.), dichloromethane (12 mL), and trifluoroacetic acid (6 mL). The resulting mixture was stirred at room temperature for 1 h. The mixture was extracted with ethyl acetate (150 mL×2), and the combined organic extracts were washed with brine (200 mL×2), dried over anhydrous sodium sulfate and concentrated under vacuum. The residue was purified by silica gel column chromatography eluting with dichloromethane/methanol (15:1) to give 5-[[5-cyclopropyl-3-(2,6-dichlorophenyl)-1,2-oxazol-4-yl]methoxy]-3-methyl-2-azabicyclo[2.2.21]heptane trifluoroacetic acid salt 360m (210 mg, 54%) as an off-white foam.

Step 10

To a 25 mL sealed tube was added 5-[[5-cyclopropyl-3-(2,6-dichlorophenyl)-1,2-oxazol-4-yl]methoxy]-3-methyl-2-azabicyclo[2.2.1]heptane trifluoroacetic acid salt 360m (250 mg, 0.49 mmol, 1.00 equiv.), tert-butyl 4-bromobenzoate (196 mg, 0.76 mmol, 1.50 equiv.), Ruphos precatalyst (105 mg, 0.20 equiv.), Ruphos (59.5 mg, 0.20 equiv.), tol (6 mL), and $Cs_2CO_3$ (595 mg, 1.83 mmol, 3.00 equiv.). The resulting mixture was heated at 110° C., overnight. After cooling to room temperature, $H_2O$ (100 mL) was added, the mixture was extracted with ethyl acetate (100 mL×2). The combined organic extracts were washed with brine (200 mL×2), dried over anhydrous sodium sulfate, and concentrated under vacuum. The residue was purified by silica gel column chromatography eluting with ethyl acetate/petroleum ether (1:3) to give tert-butyl 4-(5-[[5-cyclopropyl-3-(2,6-dichlorophenyl)-1,2-oxazol-4-yl]methoxy]-3-methyl-2-azabicyclo[2.2.1]heptan-2-yl)benzoate 360n (230 mg, 81%) as a light yellow foam.

Step 11

To a 25 mL round-bottom flask was added tert-butyl 4-(5-[[5-cyclopropyl-3-(2,6-dichlorophenyl)-1,2-oxazol-4-yl]methoxy]-3-methyl-2-azabicyclo[2.2.1]heptan-2-yl)benzoate 360n (255 mg, 0.45 mmol, 1.00 equiv.), dichloromethane (5 mL), and trifluoroacetic acid (2.5 mL). The resulting mixture was stirred at room temperature for 1 h. The mixture was concentrated under vacuum. The crude product was purified by Prep-HPLC using the following conditions: Column, XBridge Shield RP18 OBD Column, 5 um, 19*150 mm; mobile phase, Water (10 mM $NH_4HCO_3$+0.1% $NH_3.H_2O$) and ACN (28.0% ACN up to 44.0% in 8 min); Detector, uv 254/220 nm. After purification 4-(5-[[5-cyclopropyl-3-(2,6-dichlorophenyl)-1,2-oxazol-4-yl]methoxy]-3-methyl-2-azabicyclo[2.2.1]heptan-2-yl)benzoic acid 360o (160 mg, 70%) was obtained as an off-white foam.

Step 12

The racemic acid mixture 360o from the step above was purified by Chiral-Prep-HPLC using the following conditions: Column, CHIRALPAK IC, 2*25 cm, 5 um; mobile phase, Hex- and ethanol-(hold 5.0% ethanol—in 13 min); Detector, UV 220/254 nm. After purification, 4-[(1S,3R,4S,5R)-5-[[5-cyclopropyl-3-(2,6-dichlorophenyl)-1,2-oxazol-4-yl]methoxy]-3-methyl-2-azabicyclo[2.2.1]heptan-2-yl]benzoic acid I-360 (Ret time: 1.213 min; 44.5 mg, 28%) was obtained as an off-white solid, and 4-[(1R,3S,4R,5S)-5-[[5-cyclopropyl-3-(2,6-dichlorophenyl)-1,2-oxazol-4-yl]methoxy]-3-methyl-2-azabicyclo[2.2.1]heptan-2-yl]benzoic acid I-361 (Ret time: 1.884 min; 40.1 mg, 25%) also off-white solid.

I-360: d (+), $[\alpha]_D$=+90.7° ($CHCl_3$, 25.5° C.). $^1$HNMR (300 MHz, $CD_3OD$) δ: 7.86-7.75 (m, 2H), 7.60-7.43 (m, 3H), 6.63-6.53 (m, 2H), 4.36 (s, 2H), 3.97 (s, 1H), 3.29 (s, 1H), 3.11-2.99 (m, 1H), 2.38-2.20 (m, 1H), 2.18 (d, J=4.1 Hz, 1H), 1.79 (d, J=10.3 Hz 1H), 1.65-1.52 (m, 1H), 1.46 (d, J=10.1 Hz, 1H), 1.28 (td, J=9.6, 9.2, 4.2 Hz, 1H), 1.27-1.07 (m, 9H), MS (ES, m/z): [M+1]=513.13.

I-361: 1 (−), $[\alpha]_D$=−94.2° ($CHCl_3$, 25.1° C.). $^1$HNMR (300 MHz, $CD_3OD$) δ: 7.86-7.76 (m, 2H), 7.60-7.43 (m, 3H), 6.58 (d, J=8.8 Hz, 2H), 4.36 (s, 2H), 3.95 (dt, J=12.3, 6.2 Hz, 2H), 3.10-2.99 (m, 1H), 2.36-2.22 (m, 1H), 2.20 (d, J=18.2 Hz, 1H), 1.79 (d, J=10.4 Hz, 1H), 1.59 (dd, J=13.3, 6.6 Hz, 1H), 1.46 (d, J=10.2 Hz, 1H), 1.34-1.27 (m, 1H), 1.27-1.08 (m, 10H). MS (ES, m/z): [M+1]=513.13.

Example 270: 4-[(1S,3R,4S,5R)-5-{([5-cyclopropyl-3-(2,6-dichlorophenyl)-1,2-oxazol-4-yl]methoxy}-3-methyl-2-azabicyclo[2.2.1]heptan-2-yl]-2-fluorobenzoic Acid (I-362)

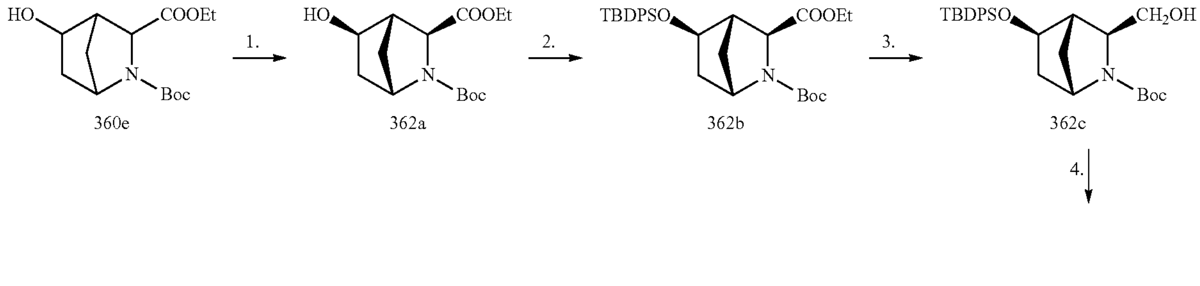

360e 362a 362b 362c

-continued

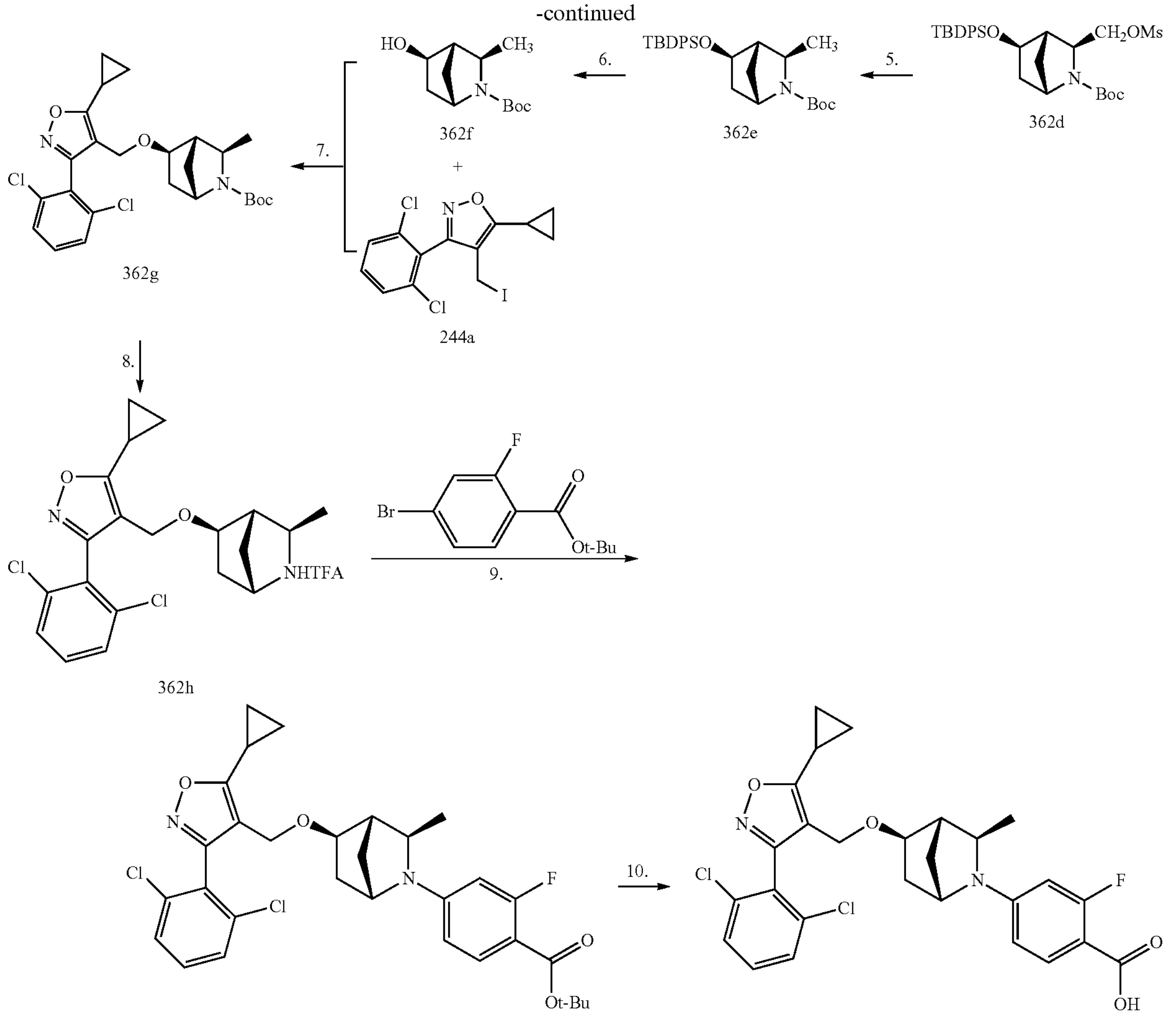

362d, 362e, 362f, 244a, 362g, 362h, 362i, I-362

Step 1

2-tert-butyl 3-ethyl 5-hydroxy-2-azabicyclo[2.2.1]heptane-2,3-dicarboxylate 360e (5 g, 17.52 mmol, 1.00 equiv.) was resolved by Chiral HPLC using the following condition: Column, Chiralpak IC, 2*25 cm, 5 um; mobile phase, Hex- and ethanol-(hold 5.0% ethanol—in 13 min); Detector, UV 220/254 nm. After separation 2-tert-butyl 3-ethyl (1S,3S,4S,5R)-5-hydroxy-2-azabicyclo[2.2.1]heptane-2,3-dicarboxylate 362a (2 g, 40%) was obtained as a light yellow oil.

Step 2

To a 100 mL round-bottom flask was added 2-tert-butyl 3-ethyl (1S,3S,4S,5R)-5-hydroxy-2-azabicyclo[2.2.1]heptane-2,3-dicarboxylate 362a (2.2 g, 7.71 mmol, 1.00 equiv.), N,N-dimethylformamide (20 mL), imidazole (2.1 g, 4.00 equiv), and TBDPSCl (4.2 g, 2.00 equiv). The resulting mixture was stirred at 40° C., overnight. The mixture was diluted with 50 mL of brine, and extracted with ethyl acetate (250 mL×3). The combined organic extracts were washed with brine (250 mL×4), dried over anhydrous sodium sulfate, and concentrated under vacuum. The residue was purified by silica gel column chromatography eluting with ethyl acetate/petroleum ether (1:5) to give 2-tert-butyl 3-ethyl (1S,3S,4S,5R)-5-[(tert-butyldiphenylsilyl)oxy]-2-azabicyclo[2.2.1]heptane-2,3-dicarboxylate 362b (3.8 g, 94%) as a light yellow solid.

Step 3

To a 250 mL round-bottom flask was added 2-tert-butyl 3-ethyl (1S,3S,4S,5R)-5-[(tert-butyldiphenylsilyl)oxy]-2-azabicyclo[2.2.1]heptane-2,3-dicarboxylate 362b (3.73 g, 7.12 mmol, 1.00 equiv.), tetrahydrofuran (26 mL), and $LiBH_4$ (389 mg, 2.00 equiv). The resulting mixture was stirred at room temperature overnight, diluted with 50 mL of EA, and then quenched by the addition of 100 mL of a saturated $NH_4Cl$ aqueous solution. The aqueous mixture was extracted with ethyl acetate (200 mL×2). The combined organic extracts were washed with brine (250 mL×2), dried over anhydrous sodium sulfate, and concentrated under vacuum. The crude product was purified by Flash-Prep-HPLC using the following conditions: Column, silica gel; mobile phase, EA:PE increasing to EA:PE=15% within 15 min; Detector. UV 254 nm. Removal of solvents afforded tert-butyl (1S,3S,4S,5R)-5-[(tert-butyldiphenylsilyl)oxy]-3-(hydroxymethyl)-2-azabicyclo[2.2.1]heptane-2-carboxylate 362c (3.31 g, 96%) as a light yellow oil.

Step 4

To a 100 mL round-bottom flask was added tert-butyl (1S,3S,4S,5R)-5-[(tert-butyldiphenylsilyl)oxy]-3-(hydroxy methyl)-2-azabicyclo[2.2.1]heptane-2-carboxylate 362c (3.31 g, 6.87 mmol, 1.00 equiv.), tetrahydrofuran (42 mL), TEA (3.1 mL, 3.00 equiv.), and methanesulfonyl chloride (1.6 g, 13.97 mmol, 2.00 equiv.). The resulting mixture was stirred for 1 h at room temperature, and quenched with water. The aqueous mixture was extracted with ethyl acetate (200 mL×2), and the combined organic extracts were washed with brine (250 mL×3), dried over anhydrous sodium sulfate and concentrated under vacuum. The crude product was purified by Flash-Prep-HPLC using the following conditions: Column, silica gel; mobile phase, EA:PE increasing to EA:PE=50% within 30 min; Detector, UV 254 nm. Removal of solvents afforded tert-butyl (1S,3S,4S,5R)-5-[(tert-butyldiphenylsilyl)oxy]-3-[(methanesulfonyloxy) methyl]-2-azabicyclo[2.2.1]heptane-2-carboxylate 362d (3.44 g, 89%) as a white foam.

Step 5

To a 100 mL round-bottom flask was added tert-butyl (1S,3S,4S,5R)-5-[(tert-butyldiphenylsilyl)oxy]-3-[(methanesulfonyloxy)methyl]-2-azabicyclo[2.2.1]heptane-2-carboxylate 362d (3.44 g, 6.15 mmol, 1.00 equiv.), tetrahydrofuran (28 mL), and $LiBH_4$ (1.1 g, 8.00 equiv.). The resulting mixture was heated at 60° C., overnight. After cooling to room temperature, the mixture was diluted with 100 mL of EA, and quenched with 150 mL of a sat. $NH_4Cl$ aqueous solution. The aqueous mixture was extracted with ethyl acetate (150 mL×2), and the combined organic extracts were washed with brine (250 mL×2), dried over anhydrous sodium sulfate and concentrated under vacuum. The crude product was purified by Flash-Prep-HPLC with the following conditions: Column, silica gel; mobile phase, EA:PE increasing to EA:PE=10% within 10 min; Detector, UV 254 nm. Removal of solvents afforded tert-butyl (1S,3R,4S,5R)-5-[(tert-butyldiphenylsilyl)oxy]-3-methyl-2-azabicyclo [2.2.1]heptane-2-carboxylate 362e (2.39 g, 84%) as a colorless oil.

Step 6

To a 100 mL round-bottom flask was added tert-butyl (1S,3R,4S,5R)-5-[(tert-butyldiphenylsilyl)oxy]-3-methyl-2-azabicyclo[2.2.1]heptane-2-carboxylate 362e (2.39 g, 5.13 mmol, 1.00 equiv.), tetrahydrofuran (14 mL), and TBAF (10.3 mL, 2.00 equiv.). The resulting mixture was stirred at room temperature overnight, and diluted with water. The aqueous mixture was extracted with ethyl acetate (200 mL×2); and the combined organic extracts were washed with brine (250 mL×3), dried over anhydrous sodium sulfate and concentrated under vacuum to give tert-butyl (1S,3R,4S,5R)-5-hydroxy-3-methyl-2-azabicyclo[2.2.1]heptane-2-carboxylate 362f (3.21 g, 99%) as a light yellow oil.

Step 7

To a 25 mL round-bottom flask was added 5-cyclopropyl-3-(2,6-dichlorophenyl)-4-(iodomethyl)-1,2-oxazole 244a (844 mg, 2.14 mmol, 1.00 equiv.), tert-butyl (1S,3R,4S,5R)-5-hydroxy-3-methyl-2-azabicyclo[2.2.1]heptane-2-carboxylate 362f (900 mg, 1.43 mmol, 1.50 equiv, 36%), N,N-dimethylformamide (8 mL), and sodium hydride (115 mg, 2.88 mmol, 1.00 equiv, 60% dispersed in mineral oil). The resulting mixture was stirred at room temperature overnight, diluted with 100 mL of EA, quenched by the addition of 100 mL of water. The aqueous mixture was extracted with ethyl acetate (200 mL×2); the combined organic extracts were washed with brine (250 mL×3), dried over anhydrous sodium sulfate and concentrated under vacuum. The residue was purified by silica gel column chromatography eluting with ethyl acetate/petroleum ether (1:3) to afford tert-butyl (1S,3R,4S,5R)-5-[[5-cyclopropyl-3-(2,6-dichlorophenyl)-1,2-oxazol-4-yl]methoxy]-3-methyl-2-azabicyclo[2.2.1]heptane-2-carboxylate 362g (320 mg, 30%) as a yellow oil.

Step 8

To a 25 mL round-bottom flask was added tert-butyl (1S,3R,4S,5R)-5-[[5-cyclopropyl-3-(2,6-dichlorophenyl)-1,2-oxazol-4-yl]methoxy]-3-methyl-2-azabicyclo[2.2.1]heptane-2-carboxylate 362g (320 mg, 0.65 mmol, 1.00 equiv.), dichloromethane (6 mL), and trifluoroacetic acid (3 mL). The resulting mixture was stirred for 1 h at room temperature and concentrated under vacuum. The crude product was purified by Flash-Prep-HPLC using the following conditions: Column, silica gel; mobile phase, EA:PE increasing to EA:PE=100% within 5 min; Detector, UV 254 nm. Removal of solvents afforded (1S,3R,4S,5R)-5-[[5-cyclopropyl-3-(2,6-dichlorophenyl)-1,2-oxazol-4-yl]methoxy]-3-methyl-2-azabicyclo[2.2.1]heptane trifluoroacetic acid salt 362h (280 mg, 85%) as an off-white foam.

Step 9

To a 5 mL sealed tube was added (1S,3R,4S,5R)-5-[[5-cyclopropyl-3-(2,6-dichlorophenyl)-1,2-oxazol-4-yl] methoxy]-3-methyl-2-azabicyclo[2.2.1]heptane trifluoroacetic acid salt 362h (100 mg, 0.20 mmol, 1.00 equiv.), tert-butyl 4-bromo-2-fluorobenzoate (104 mg, 0.38 mmol, 1.50 equiv.). Ruphos precatalyst (42 mg, 0.20 equiv.), Ruphos (24 mg, 0.20 equiv.), $Cs_2CO_3$ (245 mg, 0.75 mmol, 3.00 equiv.), and tol (1.5 mL). The resulting mixture was heated at 110° C., overnight. The mixture was cooled to room temperature, diluted with water, and extracted with ethyl acetate (100 mL×3). The combined organic extracts were washed with brine (150 mL×3), dried, and concentrated. The residue was purified by silica gel column chromatography eluting with ethyl acetate/petroleum ether (1:3) to give tert-butyl 4-[(1S,3R,4S,5R)-5-[[5-cyclopropyl-3-(2,6-dichlorophenyl)-1,2-oxazol-4-yl]methoxy]-3-methyl-2-azabicyclo[2.2.1]heptan-2-yl]-2-fluorobenzoate 362i (100 mg, 86%) as a light yellow foam.

Step 10

To a 25 mL round bottom flask was added tert-butyl 4-[(1S,3R,4S,5R)-5-[[5-cyclopropyl-3-(2,6-dichlorophenyl)-1,2-oxazol-4-yl]methoxy]-3-methyl-2-azabicyclo [2.2.1]heptan-2-yl]-2-fluorobenzoate 362i (100 mg, 0.17 mmol, 1.00 equiv.), dichloromethane (2 mL), and trifluoroacetic acid (1 mL). The resulting mixture was stirred for 1 h at room temperature and concentrated. The crude product was purified by Prep-HPLC using the following conditions: Column, XBridge Shield RP18 OBD Column, 5 um, 19*150 mm; mobile phase, Water (0.05% TFA) and ACN (55.0%

ACN up to 75.0% in 8 min); Detector, UV 254/220 nm. After purification 4-[(1S,3R,4S,5R)-5-[[5-cyclopropyl-3-(2,6-dichlorophenyl)-1,2-oxazol-4-yl]methoxy]-3-methyl-2-azabicyclo[2.2.1]heptan-2-yl]-2-fluorobenzoic acid I-362 (42 mg, 46%) was obtained as a white solid. $^1$HNMR (300 MHz, $CD_3OD$) δ: 7.74 (t, J=8.8 Hz, 1H), 7.60-7.43 (m, 3H), 6.40 (dd, J=8.9, 2.4 Hz, 1H), 6.28 (dd, J=14.7, 2.3 Hz, 1H), 4.36 (s, 2H), 3.95 (s, 1H), 3.29 (s, 1H), 3.06 (t, J=6.2 Hz, 1H), 2.43-2.16 (m, 2H), 1.81 (d, J=10.6 Hz, 1H), 1.67-1.53 (m, 1H), 1.48 (d, J=10.4 Hz, 1H), 1.29 (dd, J=13.4, 4.3 Hz, 1H), 1.22-1.09 (m, 7H). MS (ES, m/z): [M+1]=531.12.

Example 271: 4-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]-3-fluorobenzoic Acid (I-363) and 4-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]-3-fluorobenzoic Acid (I-364)

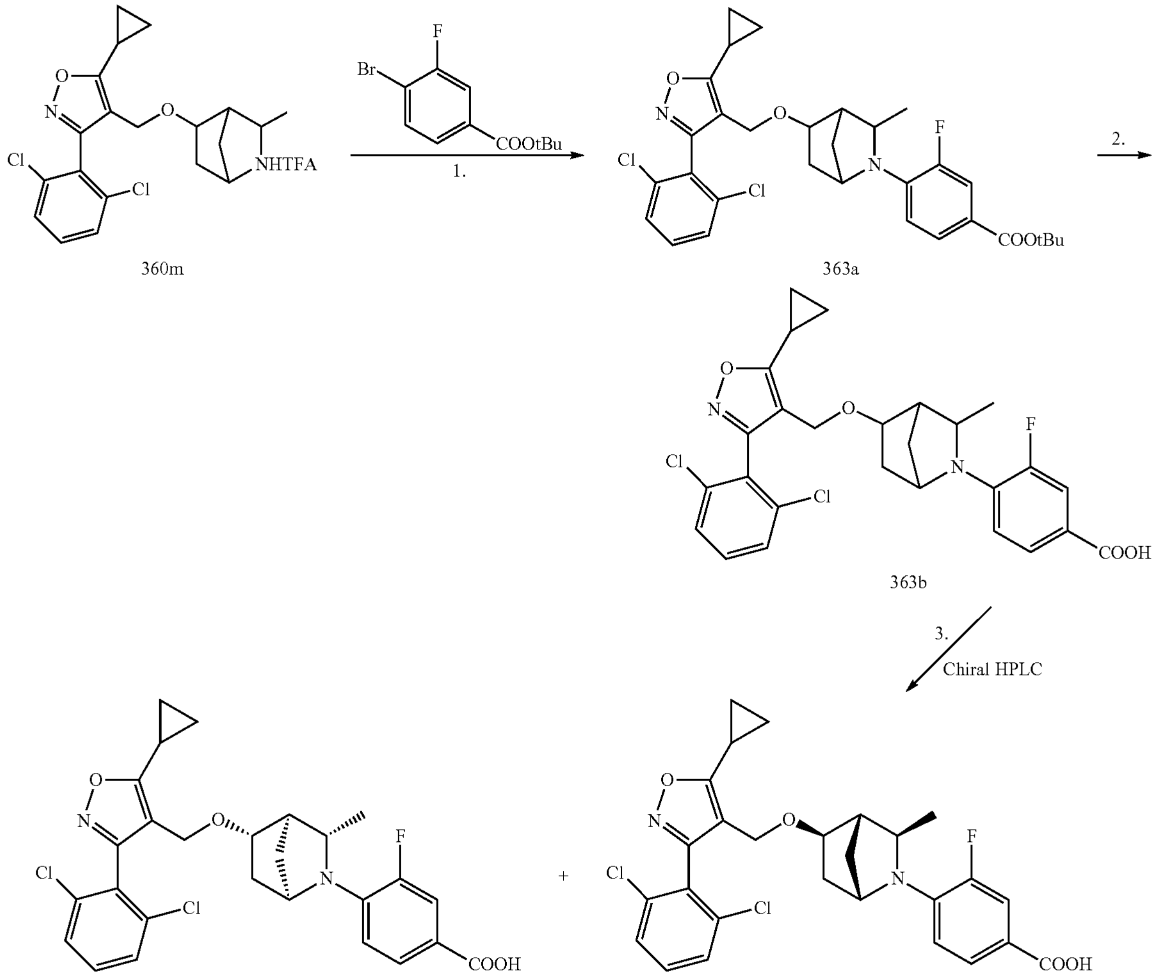

360m

363a

363b

I-364

+

I-363

Step 1

To a 25 mL round-bottom flask was added 5-[[5-cyclopropyl-3-(2,6-dichlorophenyl)-1,2-oxazol-4-yl]methoxy]-3-methyl-2-azabicyclo[2.2.1]heptane trifluoroacetic acid salt 360m (180 mg, 0.37 mmol, 1.00 equiv.), Ruphos precatalyst (34 mg, 0.20 equiv.), Ruphos (61.4 mg, 0.20 equiv.), $Cs_2CO_3$ (360 mg, 1.10 mmol, 1.00 equiv.), tol (2 mL), and tert-butyl 4-bromo-3-fluorobenzoate (121 mg, 0.44 mmol, 1.20 equiv.). The resulting mixture was heated at 110° C., overnight. After cooling to room temperature, the mixture was diluted with 100 mL of $H_2O$, extracted with ethyl acetate (100 mL×3). The combined organic extracts were washed with brine (100 mL×2), dried over anhydrous sodium sulfate, and concentrated. The residue was purified by silica gel column chromatography eluting with ethyl acetate/hexane (1:4) to afford 5-[2-[2-cyclopropyl-5-(2,6-dimethylphenyl)cyclopenta-1,4-dien-1-yl]ethyl]-2-(2,4-dimethylphenyl)-3-methylbicyclo[2.2.1]heptane 363a (160 mg, 97%) as a yellow oil.

Step 2

To a 25 mL round-bottom flask was added 5-[2-[2-cyclopropyl-5-(2,6-dimethylphenyl)cyclopenta-1,4-dien-1-yl]ethyl]-2-(2,4-dimethylphenyl)-3-methylbicyclo[2.2.1]heptane 363a (160 mg, 0.36 mmol, 1.00 equiv.), trifluoroacetic acid (2 mL), and dichloromethane (4 mL). The resulting mixture was stirred for 1 h at room temperature. The mixture was diluted with $H_2O$ (100 mL), extracted with ethyl acetate (100 mL×2), and the combined organic extracts were washed with brine (100 mL×2), dried over anhydrous sodium sulfate and concentrated. The residue was purified by silica gel column chromatography eluting with ethyl acetate/hexane (1:3) to afford 4-(5-[[5-cyclopropyl-3-(2,6-dichlorophenyl)-1,2-oxazol-4-yl]methoxy]-3-methyl-2-azabicyclo[2.2.1]heptan-2-yl)-3-fluorobenzoic acid 363b (144 mg, 76%) as a yellow oil.

Step 3

The racemic acid 363b was separated by Chiral-Prep-HPLC using the following conditions: Column, CHIRALPAK IE, 2*25 cm, 5 um; mobile phase, Hex:DCM=5:1 (0.1% TFA)- and ethanol-(hold 50.0% ethanol—in 20 min); Detector, UV 220/254 nm. After chiral separation, 4-[(1S,3R,4S,5R)-5-[[5-cyclopropyl-3-(2,6-dichlorophenyl)-1,2-oxazol-4-yl]methoxy]-3-methyl-2-azabicyclo[2.2.1]heptan-2-yl]-3-fluorobenzoic acid I-363 (38.1, 24%, Retention time: 1.246 min) was obtained as a colorless solid and also 4-[(1S,3R,4S,5R)-5-[[5-cyclopropyl-3-(2,6-dichlorophenyl)-1,2-oxazol-4-yl]methoxy]-3-methyl-2-azabicyclo[2.2.1]heptan-2-yl]-3-fluorobenzoic acid I-364 (38.1 mg, 24%, Retention time: 1.571 min) as a colorless solid.

I-363: 1 (−), $[\alpha]_D$=−64.1° ($CHCl_3$, 27.7° C.). $^1$HNMR (300 MHz, $CD_3OD$) δ: 7.64 (dd, J=8.7, 2.0 Hz, 1H), 7.60-7.41 (m 4H), 6.72 (t, J=8.9 Hz, 1H), 4.40-4.26 (m, 3H), 3.23 (q, J=6.2 Hz, 1H), 2.29-2.12 (m, 1H), 1.76 (d, J=10.4 Hz, 1H), 1.67-1.54 (m, 1H), 1.49-1.34 (m 1H), 1.34-1.21 (m, 1H), 1.27-1.03 (m, 7H), 0.91 (s, 1H). MS (ES, m/z): [M+1]=531.

I-364: d (+), $[\alpha]_D$=+38.10 ($CHCl_3$, 27.1° C.). $^1$HNMR (300 MHz, $CD_3OD$) δ: 8.09 (s, OH), 7.69-7.41 (m, 8H), 6.72 (t, J=8.9 Hz, 2H), 4.40-4.26 (m, 5H), 3.23 (q, J=6.2 Hz, 2H), 2.31-2.11 (m, 2H), 2.05 (s, 1H), 1.76 (d, J=10.6 Hz, 2H), 1.67-1.54 (m, 1H), 1.39 (d, J=10.4 Hz, 2H), 1.34-1.24 (m, 1H), 1.30-1.03 (m, 12H). MS (ES, m/z): [M+1]=531.

Example 272: 4-[(1S,3R,4S,5R)-5-{([5-cyclopropyl-3-(2,6-dichlorophenyl)-1,2-oxazol-4-yl]methoxy}-3-ethyl-2-azabicyclo[2.2.1]heptan-2-yl]benzoic Acid (I-365) and 4-[(1R,3S,4R,5S)-5-{[5-cyclopropyl-3-(2,6-dichlorophenyl)-1,2-oxazol-4-yl]methoxy}-3-ethyl-2-azabicyclo[2.2.1]heptan-2-yl]benzoic Acid (I-366)

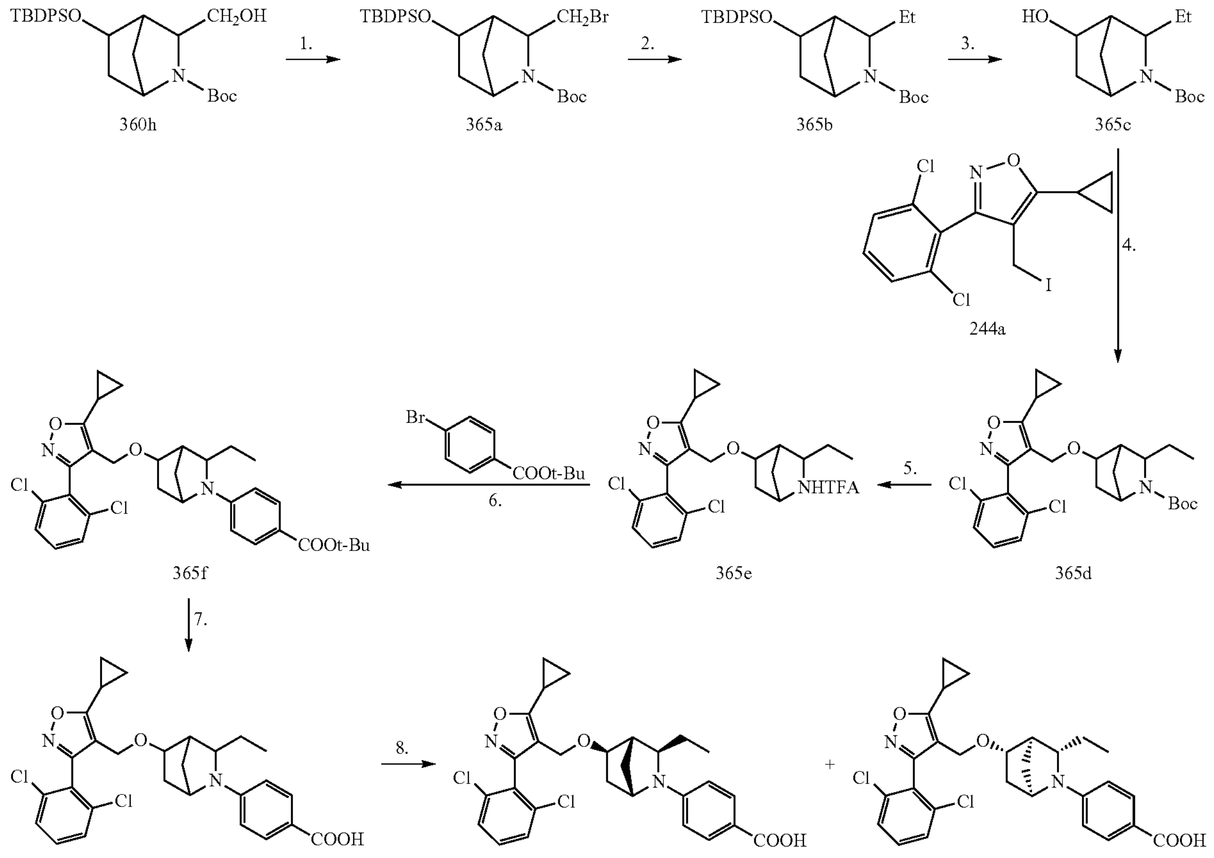

360h, 365a, 365b, 365c, 244a, 365d, 365e, 365f, 365g, I-365, I-366

Step 1

To a 50 mL round-bottom flask was added tert-butyl 5-[(tert-butyldiphenylsilyl)oxy]-3-(hydroxymethyl)-2-azabicyclo[2.2.1]heptane-2-carboxylate 360h (963 mg, 2.00 mmol, 1.00 equiv.), tetrahydrofuran (5 mL), dichloromethane (5 mL), and NBS (534 mg, 3.00 mmol, 1.50 equiv). The mixture was cooled to 0° C., and $PPh_3$ (787 mg, 3.00 mmol, 1.50 equiv.) was added in portions. The resulting mixture was stirred at room temperature for 24 h and concentrated under vacuum. The residue was purified by silica gel column chromatography eluting with ethyl acetate/petroleum ether (1:5) to give tert-butyl 3-(bromomethyl)-5-[(tert-butyldiphenylsilyl)oxy]-2-azabicyclo[2.2.1]heptane-2-carboxylate 365a (817 mg, 75%) as a light yellow solid.

Step 2

To a 24 mL sealed tube purged with and maintained under an inert atmosphere of nitrogen was added tert-butyl 3-(bromomethyl)-5-[(tert-butyldiphenylsilyl)oxy]-2-azabicyclo[2.2.1]heptane-2-carboxylate 365a (700 mg, 1.29 mmol, 1.00 equiv.), ether (2.4 mL), and $Me_2CuLi$ (4.7 mL, 0.5 M, 2.00 equiv.). The resulting mixture was stirred at room temperature overnight. The reaction was quenched by the addition of 100 mL of a saturated $NH_4Cl$ aqueous solution. The aqueous mixture was extracted with ethyl acetate (100 mL×3), and the combined organic extracts were washed with brine (50 mL×3), dried over sodium sulfate and concentrated under vacuum. The residue was purified by silica gel column chromatography eluting with PE % EA (5/1) to afford tert-butyl 5-[(tert-butyldiphenylsilyl)oxy]-3-ethyl-2-azabicyclo[2.2.1]heptane-2-carboxylate 365b (500 mg, 81%) as a light yellow oil.

Step 3

To a 50 mL round-bottom flask was added tert-butyl 5-[(tert-butyldiphenylsilyl)oxy]-3-ethyl-2-azabicyclo[2.2.1]heptane-2-carboxylate 365b (500 mg, 1.04 mmol, 1.00 equiv.), TBAF (2 mL, 1.0M in THF, 2.00 equiv.), and THF (8 mL). The resulting mixture was stirred at 25° C., overnight, diluted with EA (100 mL), washed with brine (50 mL×5), dried over anhydrous sodium sulfate and concentrated under vacuum to give tert-butyl 3-ethyl-5-hydroxy-2-azabicyclo[2.2.1]heptane-2-carboxylate 365c (685 mg, Q, crude) as a light yellow oil.

Step 4

To a 100 mL round-bottom flask purged with and maintained under an inert atmosphere of nitrogen was added tert-butyl 3-ethyl-5-hydroxy-2-azabicyclo[2.2.1]heptane-2-carboxylate 365c (340 mg, 1.41 mmol, 1.00 equiv.), 5-cyclopropyl-3-(2,6-dichlorophenyl)-4-(iodomethyl)-1,2-oxazole 244a (1.1 g, 2.79 mmol, 2.00 equiv.), N,N-dimethylformamide (3 mL), and sodium hydride (118 mg, 4.92 mmol, 2.00 equiv., 60% dispersion in mineral oil). The resulting mixture was stirred overnight at room temperature. The mixture was diluted with 20 mL of EA, quenched by the addition of 10 mL of water, and extracted with ethyl acetate (50 mL×2). The combined organic extracts were washed with brine (50 mL×3), dried over anhydrous sodium sulfate and concentrated under vacuum. The residue was purified by silica gel column chromatography eluting with ethyl acetate/petroleum ether (1/5) to afford tert-butyl 5-[[5-cyclopropyl-3-(2,6-dichlorophenyl)-1,2-oxazol-4-yl]methoxy]-3-ethyl-2-azabicyclo[2.2.1]heptane-2-carboxylate 365d (230 mg, 32%) as a light yellow oil.

Step 5

To a 50 mL round-bottom flask was added tert-butyl 5-[[5-cyclopropyl-3-(2,6-dichlorophenyl)-1,2-oxazol-4-yl]methoxy]-3-ethyl-2-azabicyclo[2.2.1]heptane-2-carboxylate 365d (230 mg, 0.45 mmol, 1.00 equiv.), dichloromethane (2 mL), and trifluoroacetic acid (1 mL). The resulting mixture was stirred for 1 h at 25° C., and concentrated under vacuum. The residue was purified by silica gel column chromatography eluting with dichloromethane/methanol (10/1) to give 5-[[5-cyclopropyl-3-(2,6-dichlorophenyl)-1,2-oxazol-4-yl]methoxy]-3-ethyl-2-azabicyclo[2.2.1]heptane trifluoro acetic acid salt 365e (150 mg, 66%) as a light yellow oil.

Step 6

To a 50 mL round-bottom flask purged with and maintained under an inert atmosphere of nitrogen was added give 5-[[5-cyclopropyl-3-(2,6-dichlorophenyl)-1,2-oxazol-4-yl]methoxy]-3-ethyl-2-azabicyclo[2.2.1]heptane trifluoro acetic acid salt 365e (150 mg, 0.30 mmol, 1.00 equiv.), tert-butyl 4-bromobenzoate (150 mg, 0.58 mmol, 1.50 equiv.), Ruphos (34 mg, 0.07 mmol, 0.20 equiv), Ruphos-precatalyst (62 mg, 0.07 mmol, 0.20 equiv.), $Cs_2CO_3$ (358 mg, 1.10 mmol, 3.00 equiv.), and tol. (2.5 mL). The resulting mixture was heated at 110° C., overnight, and concentrated under vacuum. The residue was purified by silica gel column chromatography eluting with ethyl acetate/petroleum ether (1/5) to afford tert-butyl 4-(5-[[5-cyclopropyl-3-(2,6-dichlorophenyl)-1,2-oxazol-4-yl]methoxy]-3-ethyl-2-azabicyclo[2.2.1]heptan-2-yl)benzoate 365f (140 mg, 81%) as a light yellow oil.

Step 7

To a 25 mL round-bottom flask was added tert-butyl 4-(5-[[5-cyclopropyl-3-(2,6-dichlorophenyl)-1,2-oxazol-4-yl]methoxy]-3-ethyl-2-azabicyclo[2.2.1]heptan-2-yl)benzoate 365f (140 mg, 0.24 mmol, 1.00 equiv.), dichloromethane (1 mL), and trifluoroacetic acid (0.5 mL). The resulting solution was stirred at room temperature for 1 h and concentrated under vacuum. The crude product was purified by Flash-Prep-HPLC using the following conditions: Column, C18 silica gel; mobile phase, $ACN/H_2O$=5% increasing to $ACN/H_2O$=65% within 35 min; Detector, UV 254 nm. After purification 4-(5-[[5-cyclopropyl-3-(2,6-dichlorophenyl)-1,2-oxazol-4-yl]methoxy]-3-ethyl-2-azabicyclo[2.2.1]heptan-2-yl)benzoic acid 365g (85 mg, 67%) was obtained as a light yellow solid.

Step 8

The racemic acid 365g (70 mg) from step 7 above was further purified by Chiral-Prep-HPLC using the following conditions (Prep-HPLC-009): Column, (R,R) WHELK-014.6*50 mm, 3.5 um; 1-780220-30056749; mobile phase, Hex (0.1% TFA):ethanol=70:30; Detector, UV 220/254 nm. After separation, 4-[(1S,3R,4S,5R)-5-[[5-cyclopropyl-3-(2,6-dichlorophenyl)-1,2-oxazol-4-yl]methoxy]-3-ethyl-2-azabicyclo[2.2.1]heptan-2-yl]benzoic acid I-365 (20.2 mg, 29%; retention time: 1.314 min) was obtained as a light yellow solid, also obtained was 4-[(1R,3S,4R,5S)-5-[[5-cyclopropyl-3-(2,6-dichlorophenyl)-1,2-oxazol-4-yl]methoxy]-3-ethyl-2-azabicyclo[2.2.1]heptan-2-yl]benzoic acid I-366 (20.3 mg, 29%; retention time: 1.822 min) as a light yellow solid.

I-365: d (+), $[\alpha]_D$=+45.90 ($CHCl_3$, 26.7° C.). $^1$HNMR (300 MHz, $CDCl_3$) δ: 7.92 (d, J=8.8 Hz, 2H), 7.49-7.30 (m, 3H), 6.48 (d, J=8.9 Hz, 2H), 4.30 (s, 2H), 3.88 (s, 1H), 3.33 (d, J=6.5 Hz, 1H), 2.71 (d, J=9.7 Hz, 1H), 2.35 (d, J=4.2 Hz, 1H), 2.12 (tt, J=8.4, 5.1 Hz, 1H), 1.74 (dd, J=22.9, 9.1 Hz, 2H), 1.63-1.49 (m, 1H), 1.42 (d, J=10.4 Hz, 1H), 1.38-1.17 (m, 5H), 1.13 (ddd, J=8.3, 5.6, 3.0 Hz, 2H), 0.98 (t, J=7.4 Hz, 3H). MS (ES, m/z): [M+1]=526.95.

I-366: 1 (−), $[\alpha]_D$=−36.0° ($CHCl_3$, 26.9° C.). $^1$HNMR (300 MHz, $CDCl_3$) δ: 7.91 (d, J=8.9 Hz, 2H), 7.49-7.30 (m, 3H), 6.48 (d, J=9.0 Hz, 2H), 4.29 (s, 2H), 3.88 (s, 1H), 3.33

(d, J=6.4 Hz, 1H), 2.71 (d, J=9.5 Hz, 1H), 2.35 (d, J=4.2 Hz, 1H), 2.12 (tt, J=8.4, 5.1 Hz, 1H), 1.80-1.65 (m, 1H), 1.63-1.49 (m, 1H), 1.42 (d, J=10.2 Hz, 1H), 1.30 (s, 3H), 1.38-1.21 (m, 3H), 1.26-1.03 (m, 2H), 0.98 (t, J=7.4 Hz, 3H). MS (ES, m/z): [M+1]=526.95.

Example 273: 5-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]pyridine-2-carboxylic Acid (I-367) and 5-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]pyridine-2-carboxylic Acid (I-368)

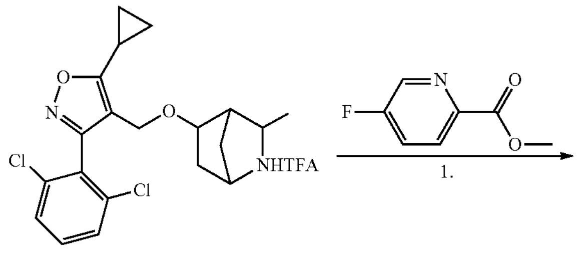

360m

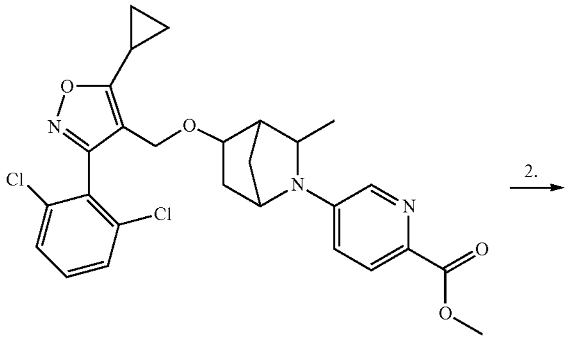

367a

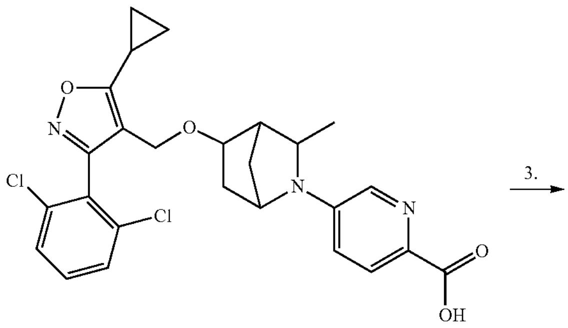

367b

-continued

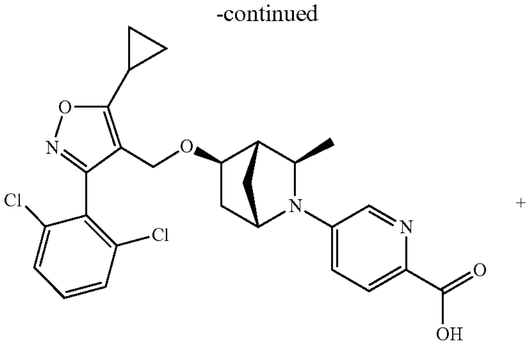

I-367

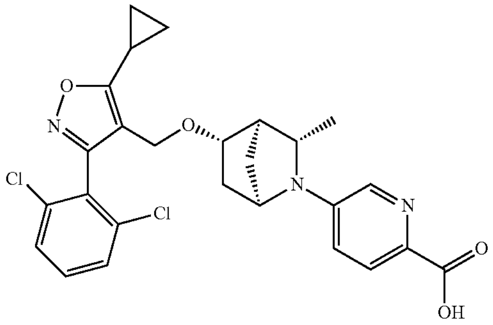

I-368

Step 1

To a 8 mL sealed tube was added 5-[[5-cyclopropyl-3-(2,6-dichlorophenyl)-1,2-oxazol-4-yl]methoxy]-3-methyl-2-azabicyclo[2.2.1]heptane trifluoroacetic acid salt 360m (400 mg, 0.79 mmol, 1.00 equiv.), methyl 5-fluoropyridine-2-carboxylate (256 mg, 1.65 mmol, 2.00 equiv.), DMSO (4.8 mL), and DIEA (416 mg, 3.22 mmol, 4.00 equiv.). The resulting mixture was heated at 120° C., overnight. After cooling to room temperature, the mixture was diluted with water (100 mL), extracted with ethyl acetate (100 mL×2), and the combined organic extracts were washed with brine (150 mL×2), dried over sodium sulfate and concentrated under vacuum. The residue was purified by silica gel column chromatography eluting with ethyl acetate/petroleum ether (1:1) to give methyl 5-(5-[[5-cyclopropyl-3-(2,6-dichlorophenyl)-1,2-oxazol-4-yl]methoxy]-3-methyl-2-azabicyclo[2.2.1]heptan-2-yl)pyridine-2-carboxylate 367a (350 mg, 84%) as a light yellow oil.

Step 2

To a 25 mL round-bottom flask was added methyl 5-(5-[[5-cyclopropyl-3-(2,6-dichlorophenyl)-1,2-oxazol-4-yl]methoxy]-3-methyl-2-azabicyclo[2.2.1]heptan-2-yl)pyridine-2-carboxylate 367a (350 mg, 0.66 mmol, 1.00 equiv.), methanol (4 mL), water (2 mL), and $LiOH.H_2O$ (279 mg, 6.64 mmol, 10.00 equiv.). The resulting mixture was heated at 60° C., for h. The pH value of the solution was adjusted to 4 using a 1M hydrogen chloride aqueous solution. The aqueous mixture was extracted with ethyl acetate (100 mL×2) and the combined organic extracts were washed with brine (100 mL×2), dried over anhydrous sodium sulfate and concentrated under vacuum. The crude product was purified by Flash-Prep-HPLC using the following conditions (Intel-Flash-1): Column, silica gel; mobile phase, EA:PE=1 increasing to EA:PE=60% within 30 min; Detector, UV 254 nm. After purification 5-(5-[[5-cyclopropyl-3-(2,6-dichlorophenyl)-1,2-oxazol-4-yl]methoxy]-3-methyl-2-azabicyclo[2.2.1]heptan-2-yl)pyridine-2-carboxylic Acid 367b (100 mg, 32%) as an off-white foam.

Step 3

The racemic acid 367a from step 2 above was separated by Chiral HPLC using the following condition: Column: CHIRALPAK ID-3; Size: 0.46*10 cm; 3 um; Mobile phase: Hex(0.1% TFA):EtOH:DCM=70:10:20; Pressure: MPA Flow: 1.0 mL/min Instrument: LC-37; Detector: UV-330 nm; Temperature: 25° C. After separation, 5-[(1S,3R,4S,5R)-5-[[5-cyclopropyl-3-(2,6-dichlorophenyl)-1,2-oxazol-4-yl]methoxy]-3-methyl-2-azabicyclo[2.2.1]heptan-2-yl]pyridine-2-carboxylic Acid I-367 (38.6 mg, 43%, retention time: 1.456 min) as a solid, and also 5-[(1R,3S,4R,5S)-5-[[5-cyclopropyl-3-(2,6-dichlorophenyl)-1,2-oxazol-4-yl]methoxy]-3-methyl-2-azabicyclo[2.2.1]heptan-2-yl]pyridine-2-carboxylic acid I-368 (36.4 mg, 40%) as a yellow green foam.

I-367: d (+), $[\alpha]_D$=+28.20 ($CHCl_3$, 26.3° C.). $^1$HNMR (300 MHz, $CDCl_3$) δ: 8.10-7.71 (m, 2H), 7.50-7.32 (m, 3H), 6.89 (d, J=8.6 Hz, 1H), 5.33 (s, 1H), 4.31 (s, 2H), 3.96 (s, 1H), 3.32 (d, J=6.3 Hz, 1H), 3.09 (d, J=6.0 Hz, 1H), 2.25 (d, J=4.3 Hz, 1H), 1.81 (d, J=10.5 Hz, 1H), 1.68-1.59 (m, 1H), 1.56 (d, J=13.4 Hz, 2H), 1.32-0.85 (m, 10H). MS (ES, m/z): [M+1]=514.12.

I-368: 1 (−), $[\alpha]_D$=−36.20 ($CHCl_3$, 26.7° C.). $^1$HNMR (300 MHz, $CD_3OD$) δ: 7.92 (d, J=10.8 Hz, 2H), 7.49 (q, J=5.5 Hz, 3H), 7.05 (d, J=9.0 Hz, 1H), 4.43-4.25 (m, 2H), 4.06 (s, 1H), 3.34 (s, 1H), 3.25 (s, 1H), 3.11 (d, J=5.6 Hz, 1H), 2.33-2.17 (m, 2H), 1.80 (d, J=10.5 Hz, 1H), 1.64-1.51 (m, 1H), 1.48 (d, J=10.4 Hz, 1H), 1.28 (d, J=4.6 Hz, 1H), 1.20 (d, J=6.2 Hz, 3H), 1.15-1.07 (m, 3H). MS (ES, m/z): [M+1]=514.12.

Example 274: 6-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]pyridine-3-carboxylic Acid (I-369) and 6-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]pyridine-3-carboxylic Acid (I-370)

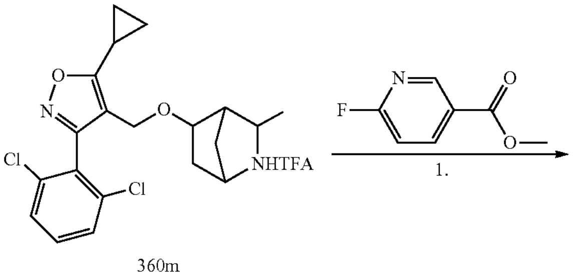

360m

-continued

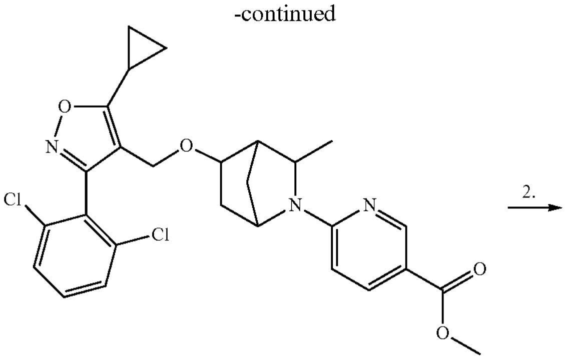

369a

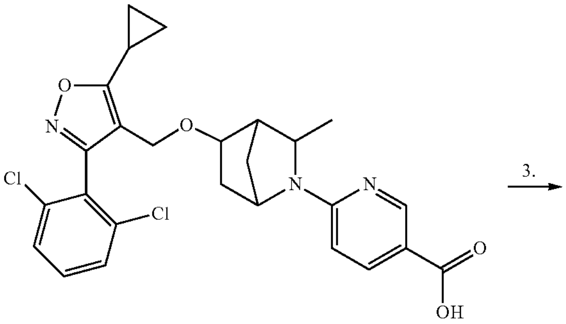

369b

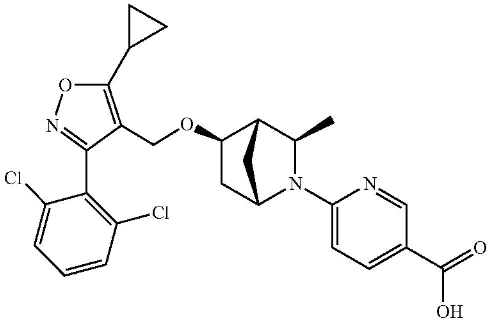

I-369

+

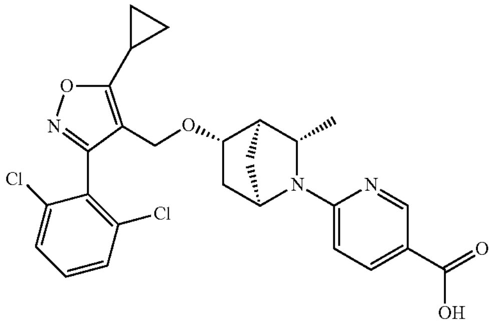

I-370

Step 1

To a 20 mL sealed tube was added 5-[[5-cyclopropyl-3-(2,6-dichlorophenyl)-1,2-oxazol-4-yl]methoxy]-3-methyl-2-azabicyclo[2.2.1]heptane trifluoroacetic acid salt 360m (400 mg, 0.82 mmol, 1.00 equiv.), methyl 6-fluoropyridine-3-carboxylate (384 mg, 2.48 mmol, 3.00 equiv.), ACN (3.2 mL), and DIEA (416 mg, 3.22 mmol, 4.00 equiv.). The resulting mixture was heated at 90° C., overnight. After cooling to room temperature, the mixture was treated with water (100 mL), extracted with ethyl acetate (100) mL×2), and the organic extracts were combined, wished with brine (50 mL×3), dried over sodium sulfate and concentrated under vacuum. The residue was purified by silica gel column chromatography eluting with PE/EA (3/1) to give methyl 6-(5-[[5-cyclopropyl-3-(2,6-dichlorophenyl)-1,2-oxazol-4-yl]methoxy]-3-methyl-2-azabicyclo[2.2.1]heptan-2-yl)pyridine-3-carboxylate 369a (380 mg, 88%) as a light yellow oil.

Step 2

To a 25 mL round-bottom flask was added methyl 6-(5-[[5-cyclopropyl-3-(2,6-dichlorophenyl)-1,2-oxazol-4-yl] methoxy]-3-methyl-2-azabicyclo[2.2.1]heptan-2-yl)pyridine-3-carboxylate 369a (380 mg, 0.72 mmol, 1.00) equiv.), methanol (4 mL), $LiOH.H_2O$ (302 mg, 7.55 mmol, 10.00 equiv.), and water (0.4 mL). The resulting mixture was heated at 60° C., for 1 h. After cooling to room temperature, a 10% aqueous hydrogen chloride solution was added to adjust the pH to 6. The aqueous mixture was extracted with ethyl acetate (100 mL×3), and the combined organic extracts were washed with brine (50 mL×3), dried over anhydrous sodium sulfate and concentrated under vacuum. The crude product was re-crystallized from ethyl acetate to afford 6-(5-[[5-cyclopropyl-3-(2,6-dichlorophenyl)-1,2-oxazol-4-yl]methoxy]-3-methyl-2-azabicyclo[2.2.1]heptan-2-yl)pyridine-3-carboxylic acid 369b (260 mg, 70%) as a light yellow solid.

Step 3

The racemic acid 369b (90 mg) was purified by Chiral-Prep-HPLC using the following conditions: mobile phase, Hex (0.1% TFA):ethanol=70:30 Total Run Time (20 min); Detector, 254 nm. After separation 6-[(1S,3R,4S,5R)-5-[[5-cyclopropyl-3-(2,6-dichlorophenyl)-1,2-oxazol-4-yl] methoxy]-3-methyl-2-azabicyclo[2.2.1]heptan-2-yl]pyridine-3-carboxylic acid I-369 (42.3 mg, 47%, retention time: 1.489 min) was obtained as an off-white solid and 6-[(1R,3S,4R,5S)-5-[[5-cyclopropyl-3-(2,6-dichlorophenyl)-1,2-oxazol-4-yl]methoxy]-3-methyl-2-azabicyclo[2.2.1]heptan-2-yl]pyridine-3-carboxylic acid I-370 (39.1 mg, 44%, retention time: 2.162 min) as an off-white solid.

I-369: d (+), $[\alpha]_D$=+91.50 ($CHCl_3$, 28.3° C.). $^1$HNMR (300 MHz, $CDCl_3$) δ: 8.81-8.74 (m, 1H), 7.97 (dd, J=8.9, 2.3 Hz, 1H), 7.44-7.26 (m, 3H), 6.28 (d, J=9.0 Hz, 1H), 5.30 (s, 1H), 4.40 (s, 1H), 4.31 (d, J=11.0 Hz, 1H), 3.32 (d, J=6.7 Hz, 1H), 3.09 (s, 1H), 2.23-2.16 (m, 2H), 1.75 (d, J=10.5 Hz, 1H), 1.62 (dd, J=13.5, 6.8 Hz, 1H), 1.45 (d, J=10.4 Hz 1H), 1.41-1.18 (m, 7H), 1.17-1.01 (m, 2H). MS (ES, m/z): [M+1]=514.15.

I-370: 1 (−), $[\alpha]_D$=−105.30 ($CHCl_3$, 28.9° C.). $^1$HNMR (300 MHz, $CDCl_3$) δ: 8.78 (s, 1H), 7.97 (dd, J=8.9, 2.3 Hz, 1H), 7.44-7.23 (m, 3H), 6.28 (d, J=8.9 Hz, 1H), 5.30 (s, 1H), 4.40 (s, 1H), 4.31 (d, J=11.1 Hz, 1H), 3.54 (s, 1H), 3.32 (d, J=6.6 Hz, 1H), 3.09 (s, 1H), 2.21 (s, 1H), 1.80-1.69 (m, 1H), 1.62 (dd, J=13.9, 7.1 Hz, 1H), 1.50-1.34 (m, 1H), 1.35-1.18 (m 6H), 1.19-1.01 (m, 2H). MS (ES, m/z): [M+1]=514.15.

Example 275: 5-[(1S,3R,4S,5R)-5-{[5-cyclopropyl-3-(2,6-dichlorophenyl)-1,2-oxazol-4-yl]methoxy}-3-methyl-2-azabicyclo[2.2.1]heptan-2-yl]-N-(oxane-4-sulfonyl)pyridine-2-carboxamide (I-371) and 5-[(1R,3S,4R,5S)-5-({[5-cyclopropyl-3-(2,6-dichlorophenyl)-1,2-oxazol-4-yl]methoxy)}-3-methyl-2-azabicyclo[2.2.1]heptan-2-yl]-N-(oxane-4-sulfonyl) pyridine-2-carboxamide (I-372)

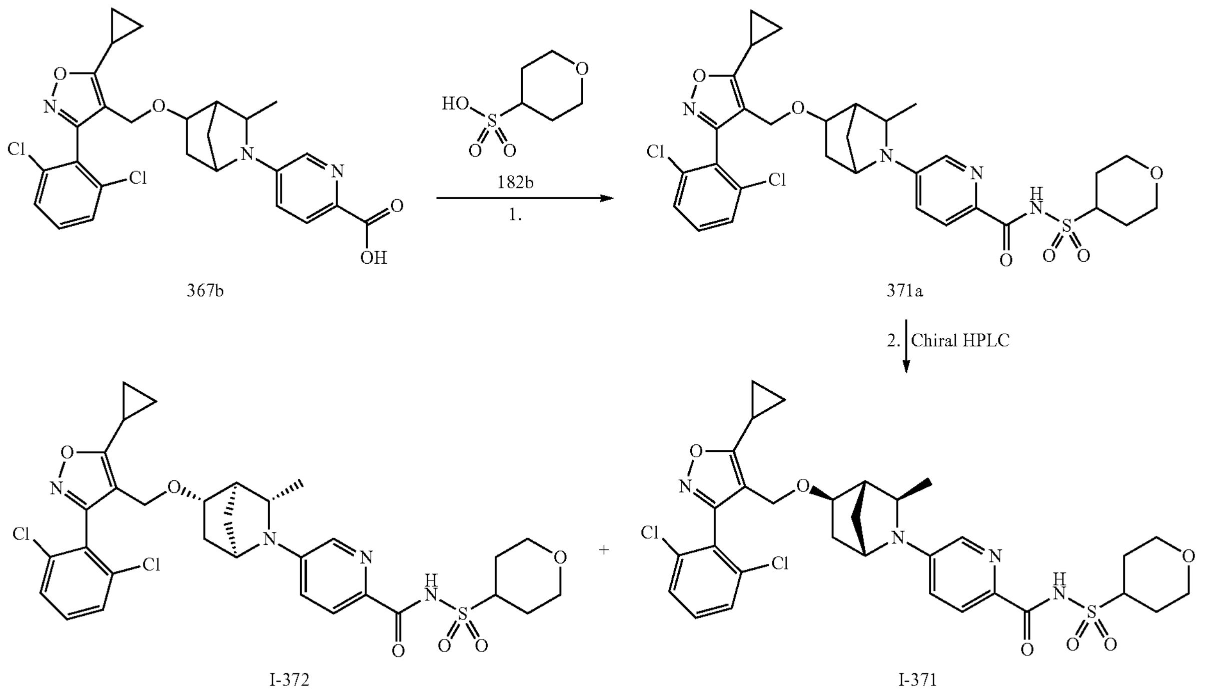 [SMILES: CC1C2CC(CC2OCc2c(-c3c(Cl)cccc3Cl)noc2C2CC2)N1c1ccc(C(=O)O)nc1 ; O=S(=O)(O)C1CCOCC1 ; CC1C2CC(CC2OCc2c(-c3c(Cl)cccc3Cl)noc2C2CC2)N1c1ccc(C(=O)NS(=O)(=O)C2CCOCC2)nc1 ; C[C@H]1[C@H]2C[C@H](C[C@@H]2OCc2c(-c3c(Cl)cccc3Cl)noc2C2CC2)N1c1ccc(C(=O)NS(=O)(=O)C2CCOCC2)nc1 ; C[C@@H]1[C@@H]2C[C@@H](C[C@H]2OCc2c(-c3c(Cl)cccc3Cl)noc2C2CC2)N1c1ccc(C(=O)NS(=O)(=O)C2CCOCC2)nc1]

367b

371a

I-372

+

I-371

Step 1

To a 25 mL round-bottom flask was added 5-(5-[[5-cyclopropyl-3-(2,6-dichlorophenyl)-1,2-oxazol-4-yl]

methoxy]-3-methyl-2-azabicyclo[2.2.1]heptan-2-yl)pyridine-2-carboxylic acid 367b (240 mg, 0.47 mmol, 1.00 equiv.), oxane-4-sulfonamide 182b (155 mg, 0.94 mmol, 2.00 equiv.), EDCI (136 mg, 0.71 mmol, 1.50 equiv), 4-dimethylaminopyridine (174 mg, 1.42 mmol, 3.00 equiv.), and dichloromethane (7 mL). The resulting mixture was stirred at room temperature overnight and quenched by the addition of water (100 mL). The aqueous mixture was extracted with ethyl acetate (150 mL×2), and the combined organic extracts were washed with brine (200 mL×2), dried, and concentrated. The crude product was purified by Prep-HPLC using the following conditions: Column, XBridge Shield RP18 OBD Column, 5 um, 19*150 mm; mobile phase, Water (0.05% TFA) and ACN (5.0% ACN up to 60.0% in 1 min, up to 74.0% in 7 min); Detector, UV 254/220 nm. After purification 5-(5-[[5-cyclopropyl-3-(2,6-dichlorophenyl)-1,2-oxazol-4-yl]methoxy]-3-methyl-2-azabicyclo[2.2.1]heptan-2-yl)-N-(oxane-4-sulfonyl)pyridine-2-carboxamide 371a (90 mg, 29%) was obtained as a light yellow foam.

Step 2

The racemic compound 371a was separated by Chiral-Prep-HPLC using the following conditions (Prep-HPLC-004): Column, Chiralpak ID-2, 2*25 cm, 5 um; mobile phase, Hex(0.1% TFA)- and ethanol:DCM=1:1—(hold 30.0% ethanol:DCM=1:1—in 20 min); Detector, UV 220/254 nm. After separation 5-[(1S,3R,4S,5R)-5-[[5-cyclopropyl-3-(2,6-dichlorophenyl)-1,2-oxazol-4-yl]methoxy]-3-methyl-2-azabicyclo[2.2.1]heptan-2-yl]-N-(oxane-4-sulfonyl)pyridine-2-carboxamide I-371 (18.2 mg, 20%, retention time: 8.128 min) as a light yellow solid, and also 5-[(1R,3S,4R,5S)-5-[[5-cyclopropyl-3-(2,6-dichlorophenyl)-1,2-oxazol-4-yl]methoxy]-3-methyl-2-azabicyclo[2.2.1]heptan-2-yl]-N-(oxane-4-sulfonyl)pyridine-2-carboxamide I-372 (27 mg, 30%, retention time: 7.324 min) as a light yellow foam.

I-371: d (+), $[\alpha]_D$=+38.40 ($CHCl_3$, 26.1° C.). $^1$HNMR (300 MHz, $CD_3OD$) δ: 8.02 (d, J=2.7 Hz, 1H), 7.93 (d, J=8.9 Hz, 1H), 7.53 (q, J=5.1 Hz, 3H), 7.05 (dd, J=8.9, 2.9 Hz, 1H), 4.46-4.29 (m, 2H), 4.09 (d, J=18.1 Hz, 3H), 3.99-3.83 (m, 2H), 3.65 (d, J=15.0 Hz, 2H), 3.53-3.39 (m, 1H), 3.33 (s, 1H), 2.37-2.21 (m, 2H), 2.05 (d, J=13.6 Hz, 5H), 2.02-1.91 (m, 1H), 1.84 (d, J=10.9 Hz, 1H), 1.64-1.47 (m, 2H), 1.32 (d, J=2.4 Hz, 2H), 1.23 (d, J=6.2 Hz, 3H), 1.17 (dd, J=6.0, 4.3 Hz, 4H), 0.94 (d, J=6.3 Hz, 1H). MS (ES, m/z): [M+1]=661.16.

I-372: 1 (−), $[\alpha]_D$=−34.0° ($CHCl_3$, 25.6° C.). $^1$HNMR (300 MHz, $CD_3OD$) δ: 8.02 (d, J=2.7 Hz, 1H), 7.93 (d, J=8.9 Hz, 1H), 7.60-7.44 (m, 3H), 7.06 (dd, J=9.0, 2.8 Hz, 1H), 4.46-4.29 (m, 2H), 4.16-4.03 (m, 3H), 3.97-3.83 (m, 1H), 3.47 (td, J=11.5, 2.6 Hz, 2H), 3.50-3.00 (m, 2H), 2.37-2.21 (m, 1H), 2.10-1.79 (m, 5H), 1.68-1.59 (m, 1H), 1.59-1.47 (m, 1H), 1.38-1.28 (m, 2H), 1.24 (d, J=6.2 Hz, 3H), 1.19 (s, 1H), 1.17-1.12 (m, 3H). MS (ES, m/z): [M+1]=661.16.

Example 276: 6-[(1S,3R,4S,5R)-5-{([5-cyclopropyl-3-(2,6-dichlorophenyl)-1,2-oxazol-4-yl]methoxy}-3-methyl-2-azabicyclo[2.2.1]heptan-2-yl]-N-(oxane-4-sulfonyl)pyridine-3-carboxamide (I-373) and 6-[(1R,3S,4R,5S)-5-{[5-cyclopropyl-3-(2,6-dichlorophenyl)-1,2-oxazol-4-yl]methoxy}-3-methyl-2-azabicyclo[2.2.1]heptan-2-yl]-N-(oxane-4-sulfonyl)pyridine-3-carboxamide (I-374)

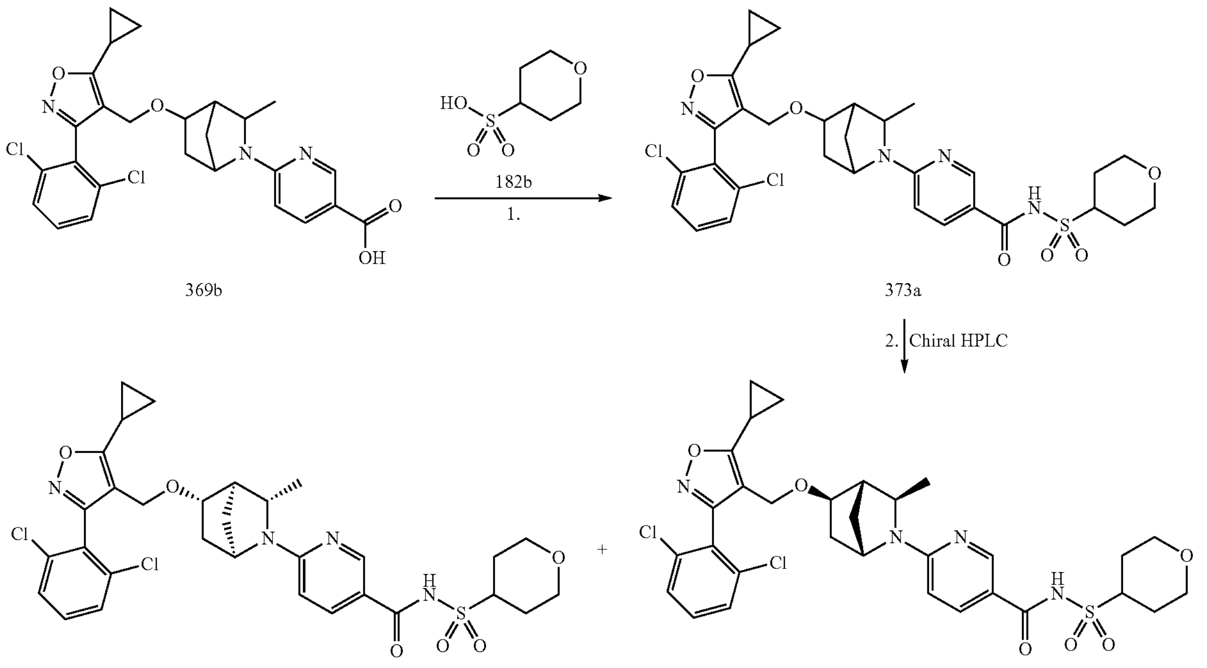

369b

373a

I-374

I-373

Step 1

To a 25 mL round-bottom flask was added 6-(5-[[5-cyclopropyl-3-(2,6-dichlorophenyl)-1,2-oxazol-4-yl]methoxy]-3-methyl-2-azabicyclo[2.2.1]heptan-2-yl)pyridine-3-carboxylic acid 369b (100 mg, 0.19 mmol, 1.00 equiv.), oxane-4-sulfonamide 182b (64 mg, 0.39 mmol, 2.00 equiv.), 4-dimethylaminopyridine (71 mg, 0.58 mmol, 3.00 equiv.), dichloromethane (2 mL), and EDCI (56 mg, 0.29 mmol, 1.50 equiv.). The resulting mixture was stirred overnight at 25° C., and diluted with EA (100 mL). The pH value of the solution was adjusted to 6 using a 10% aqueous hydrogen chloride solution. The mixture was washed with brine (50 mL×3), dried over anhydrous sodium sulfate and concentrated under vacuum. The residue was purified by silica gel column chromatography eluting with dichloromethane/methanol (15/1) to give 6-(5-[[5-cyclopropyl-3-(2,6-dichlorophenyl)-1,2-oxazol-4-yl]methoxy]-3-methyl-2-azabicyclo[2.2.1]heptan-2-yl)-N-(oxane-4-sulfonyl) pyridine-3-carboxamide 373a (110 mg, 86%) as a light yellow solid.

Step 2

The racemic compound 373a was separated by Chiral-Prep-HPLC using the following conditions: Column, CHIRALPAK IE, 2*25 cm, 5 um; mobile phase, Hex:DCM=5:1 (0.1% TFA)- and ethanol-(hold 50.0% ethanol—in 20 min); Detector, UV 220/254 nm. After separation 6-[(1S,3R,4S,5R)-5-[[5-cyclopropyl-3-(2,6-dichlorophenyl)-1,2-oxazol-4-yl]methoxy]-3-methyl-2-azabicyclo[2.2.1]heptan-2-yl]-N-(oxane-4-sulfonyl)pyridine-3-carboxamide I-373 (40.4 mg, 40%, retention time: 2.425 min) was obtained as a light yellow solid and 6-[(1R,3S,4R,5S)-5-[[5-cyclopropyl-3-(2,6-dichlorophenyl)-1,2-oxazol-4-yl]methoxy]-3-methyl-2-azabicyclo[2.2.1]heptan-2-yl]-N-(oxane-4-sulfonyl)pyridine-3-carboxamide I-374 (42.6 mg, 43%, retention time: 2.843 min) also a light yellow solid.

I-373: d (+), $[\alpha]_D$=+83.10 ($CHCl_3$, 25.4° C.). $^1$HNMR (300 MHz, $CDCl_3$) δ: 9.15 (s, 1H), 8.25 (s, 1H), 7.56-7.28 (m, 3H), 6.74 (t, J=11.1 Hz, 1H), 4.99 (s, 1H), 4.72 (d, J=12.0 Hz, 1H), 4.40 (d, J=12.3 Hz, 1H), 4.26 (t, J=9.1 Hz, 1H), 4.07 (s, 2H), 3.81 (s, 1H), 3.38 (s, 3H), 2.42-2.30 (m, 1H), 2.21 (s, 1H), 1.90 (s, 4H), 1.75-1.50 (m, 1H), 1.44-1.06 (m, 10H), 0.86 (d, J=8.7 Hz, 1H). MS (ES, m/z): [M+1]=661.20.

I-374: 1 (−), $[\alpha]_D$=−111.7° ($CHCl_3$, 25.5° C.). $^1$HNMR (300 MHz, $CDCl_3$) δ: 9.07 (s, 1H), 8.26 (s, 1H), 7.36 (t, J=20.3 Hz, 3H), 6.75 (t, J=11.1 Hz, 1H), 4.95 (s, 1H), 4.70 (d, J=11.9 Hz, 1H), 4.42-4.18 (m, 1H), 4.08 (s, 1H), 3.81 (s, 2H), 3.39 (s, 4H), 2.36 (d, J=13.3 Hz, 1H), 2.19 (s, 1H), 1.92 (s, 4H), 1.74-1.54 (m, 1H), 1.37-1.08 (m, 10H), 0.86 (d, J=9.1 Hz, 1H). MS (ES, m/z): [M+1]=661.10.

Example 277: FXR Ligand Binding Assay

The affinity of FXR ligands for the ligand binding domain of FXR was determined using a commercially available human FXR ligand binding assay (LanthaScreen, Thermofisher Cat # PV4833). The purified ligand binding domain of human FXR tagged with GST (glutathiones-S-transferase) is incubated with a terbium labelled anti-GLT antibody and a fluorescein-labelled SRC2-2 peptide (LKEKHKILHRLLQDSSSPV (SEQ ID NO.: 1)). Binding of FXR ligands to the FXR ligand binding domain promotes binding of the fluorescein-labelled SRC2-2 peptide. This causes a FRET signal between the terbium-labelled anti-GST antibody and the fluorescein-labelled SRC peptide which are both bound to the FXR ligand binding domain.

Test compounds are dissolved in DMSO and a 3-fold serial dilution series is generated, then further diluted into assay buffer. The compounds are mixed with 5 nM GST-tagged FXR ligand binding domain, 5 nM Tb-labelled anti-GST antibody and 500 nM fluorescein-labelled SRC2-2 peptide in a pH7.4 buffer. The reaction is incubated at room temperature for 1 hour, then the FRET signal is measured as the ratio of the 520 nm/495 nm emission following excitation at 340 nm. The change in FRET signal is plotted against the test article concentration and fit to a 3-parameter logistical equation. The concentration required to produce 50% activation is expressed as $pEC_{50}$ ($-\log EC_{50}$), and the extent of activation is expressed relative to GW4064 as % activation. The data for the compounds of the invention in the ligand binding assay are shown in Table 23.

TABLE 23

FXR activity of compounds of the present invention in the FXR ligand binding assay.

| Cmpd No. | $pEC_{50}$ | % Efficacy |
|---|---|---|
| I-1 | 7.4 | 148 |
| I-2 | 7.3 | 138 |
| I-3 | 7.6 | 153 |
| I-4 | 7.3 | 166 |
| I-5 | 7.2 | 139 |
| I-6 | 7.7 | 173 |
| I-7 | 7.4 | 162 |
| I-8 | 7.6 | 137 |
| I-9 | 7.1 | 172 |
| I-10 | 7 | 145 |
| I-11 | 7.7 | 15 |
| I-12 | 9 | 153 |
| I-13 | 8.6 | 174 |
| I-14 | 8.6 | 146 |
| I-15 | 7.8 | 150 |
| I-16 | 8.8 | 174 |
| I-17 | 8.2 | 162 |
| I-18 | 8.8 | 135 |
| I-19 | 8 | 178 |
| I-20 | 8.4 | 191 |
| I-21 | 7 | 123 |
| I-22 | 6.5 | 85 |
| I-23 | 5.5 | 85 |
| I-24 | 7.9 | 180 |
| I-25 | 8.4 | 172 |
| I-26 | 8.4 | 137 |
| I-27 | 7.9 | 130 |
| I-28 | 8.9 | 153 |
| I-29 | 7.8 | 194 |
| I-30 | 8.6 | 160 |
| I-31 | 7.4 | 117 |
| I-32 | 7.6 | 148 |
| I-33 | 7.6 | 136 |
| I-34 | >4.5 | — |
| I-35 | >4.5 | — |
| I-36 | 5.4 | 86 |
| I-37 | >4.5 | 0.0 |
| I-38 | 6.3 | 56 |
| I-39 | 7.8 | 96 |
| I-40 | >4.5 | — |
| I-41 | >4.5 | — |
| I-42 | 7.6 | 166 |
| I-43 | 7.8 | 176 |
| I-44 | 7.6 | 152 |
| I-45 | 7.5 | 152 |
| I-46 | 7.9 | 174 |
| I-47 | 7.8 | 174 |
| I-48 | 7.6 | 199 |
| I-49 | 8 | 188 |
| I-50 | 6.8 | 184 |
| I-51 | 6.7 | 269 |
| I-52 | 8.8 | 148 |
| I-53 | 8.7 | 145 |
| I-54a | 7.0 | 162 |
| I-54 | 8.8 | 158 |
| I-55 | 7.9 | 121 |
| I-56 | 8.5 | 137 |
| I-57 | 7.9 | 146 |
| I-58 | 8.4 | 153 |
| I-59 | 8.2 | 176 |

TABLE 23-continued

FXR activity of compounds of the present invention in the FXR ligand binding assay.

| Cmpd No. | $pEC_{50}$ | % Efficacy |
|---|---|---|
| I-60 | 8.2 | 170 |
| I-61 | 8.7 | 174 |
| I-62 | 7.9 | 188 |
| I-63 | 8.7 | 13 |
| I-64 | >4.5 | — |
| I-65 | 6.9 | 45 |
| I-101 | 9.8 | 137 |
| I-102 | 8.6 | 112 |
| I-103 | 8.7 | 135 |
| I-104 | 9.4 | 156 |
| I-105 | 9.4 | 142 |
| I-106 | 8.6 | 126 |
| I-107 | 8.6 | 122 |
| I-108 | 9.1 | 117 |
| I-109 | 9.4 | 117 |
| I-110 | 10 | 132 |
| I-111 | 9.3 | 132 |
| I-112 | 9.4 | 116 |
| I-113 | 8.8 | 126 |
| I-114 | 8.4 | 124 |
| I-115 | 9.6 | 144 |
| I-116 | 8.6 | 131 |
| I-117 | 8.2 | 113 |
| I-118 | 8.6 | 145 |
| I-119 | 8.7 | 145 |
| I-120 | 8 | 188 |
| I-121 | 8.5 | 174 |
| I-122 | 9.6 | 137 |
| I-123 | 8.6 | 160 |
| I-124 | 9.7 | 143 |
| I-125 | 6.8 | 92 |
| I-126 | 7.1 | 114 |
| I-127 | 9.3 | 136 |
| I-128 | 7.8 | 110 |
| I-129 | 8.4 | 152 |
| I-130 | 8 | 152 |
| I-131 | 8 | 108 |
| I-132 | 7.3 | 98 |
| I-133 | 7.4 | 79 |
| I-134 | 8.2 | 156 |
| I-135 | 9.4 | 152 |
| I-136 | 9 | 154 |
| I-137 | 8 | 132 |
| I-138 | 7.6 | 132 |
| I-13 | 9.2 | 132 |
| I-140 | 9.1 | 142 |
| I-141 | 7 | 137 |
| I-142 | 7.8 | 78 |
| I-143 | 8 | 132 |
| I-144 | 8.2 | 128 |
| I-145 | 8 | 118 |
| I-146 | 7.9 | 134 |
| I-147 | 8.1 | 142 |
| I-148 | 7.8 | 136 |
| I-149 | 8.2 | 106 |
| I-150 | 8.9 | 102 |
| I-151 | 8.6 | 134 |
| I-152 | 8.4 | 132 |
| I-153 | 9.2 | 130 |
| I-154 | 8.6 | 158 |
| I-155 | 8.3 | 136 |
| I-156 | 7.6 | 128 |
| I-157 | 8.2 | 134 |
| I-158 | 7.6 | 126 |
| I-159 | 8.2 | 144 |
| I-160 | 6.9 | 93 |
| I-161 | 6.9 | 134 |
| I-162 | 8.1 | 140 |
| I-163 | 7.5 | 154 |
| I-164 | 9.7 | 148 |
| I-165 | 8.4 | 140 |
| I-166 | 8.7 | 154 |
| I-167 | 8.7 | 152 |
| I-168 | 8.6 | 164 |
| I-169 | 8.4 | 160 |
| I-170 | 9.4 | 142 |
| I-171 | 8.6 | 147 |
| I-172 | 8.4 | 160 |
| I-173 | 9.2 | 144 |
| I-174 | 8.8 | 161 |
| I-175 | 8.2 | 120 |
| I-176 | 7.5 | 120 |
| I-177 | 7.4 | 130 |
| I-178 | 6.9 | 86 |
| I-179 | 6.2 | 83 |
| I-180 | >6.5 | — |
| I-181 | 8.8 | 166 |
| I-182 | 8.9 | 156 |
| I-183 | 8.6 | 163 |
| I-184 | 7.7 | 161 |
| I-185 | 8.9 | 155 |
| I-186 | 8.9 | 134 |
| I-187 | 9.2 | 156 |
| I-188 | 8.6 | 150 |
| I-18 | 8.8 | 154 |
| I-190 | 8.4 | 163 |
| I-191 | 8.4 | 163 |
| I-192 | 7.9 | 152 |
| I-193 | 8.2 | 138 |
| I-194 | 9 | 141 |
| I-195 | 8.8 | 144 |
| I-196 | 8.5 | 154 |
| I-197 | 8.5 | 167 |
| I-198 | 8.5 | 178 |
| I-199 | 7.4 | 146 |
| I-200 | 8.6 | 215 |
| I-201 | 8.4 | 208 |
| I-202 | 8.5 | 215 |
| I-203 | 9 | 157 |
| I-204 | 8.4 | 136 |
| I-205 | 8.4 | 142 |
| I-206 | 8.4 | 159 |
| I-207 | 8.6 | 152 |
| I-208 | 8 | 166 |
| I-209 | 7.8 | 160 |
| I-210 | 8.6 | 148 |
| I-211 | 8.4 | 152 |
| I-212 | 9.2 | 136 |
| I-213 | 9.4 | 131 |
| I-214 | 8.6 | 138 |
| I-215 | 8.6 | 142 |
| I-216 | 9.4 | 145 |
| I-217 | 9.9 | 142 |
| I-218 | 8.6 | 146 |
| I-219 | 8.6 | 144 |
| I-220 | 8.7 | 154 |
| I-221 | 8.8 | 147 |
| I-222 | 7.5 | 143 |
| I-223 | 8.6 | 144 |
| I-224 | 8.1 | 155 |
| I-225 | 9.5 | 166 |
| I-226 | 9.6 | 148 |
| I-227 | 8.1 | 163 |
| I-228 | 7 | 134 |
| I-229 | 7.4 | 150 |
| I-230 | 8 | 150 |
| I-231 | 8.4 | 110 |
| I-232 | 8.1 | 126 |
| I-233 | 7.8 | 77 |
| I-234 | 8.1 | 146 |
| I-235 | 8.2 | 176 |
| I-236 | 8.4 | 156 |
| I-237 | 8.7 | 162 |
| I-238 | 8.6 | 176 |
| I-239 | 8.2 | 176 |
| I-240 | 8.1 | 162 |
| I-241 | 8 | 176 |
| I-242 | 8.2 | 182 |

TABLE 23-continued

FXR activity of compounds of the present invention in the FXR ligand binding assay.

| Cmpd No. | $pEC_{50}$ | % Efficacy |
|---|---|---|
| I-243 | 8.4 | 182 |
| I-244 | 8.4 | 130 |
| I-245 | >5.5 | — |
| I-246 | 8.5 | 136 |
| I-247 | 8.5 | 128 |
| I-248 | 7.8 | 116 |
| I-249 | 8.4 | 134 |
| I-250 | 7.8 | 128 |
| I-251 | 9.1 | 133 |
| I-252 | 8.6 | 135 |
| I-253 | 8.6 | 140 |
| I-254 | 9 | 143 |
| I-255 | 8.4 | 150 |
| I-256 | 8.4 | 157 |
| I-257 | 8.6 | 148 |
| I-258 | 8.6 | 146 |
| I-259 | 8.5 | 124 |
| I-260 | 8.8 | 148 |
| I-261 | 8.6 | 161 |
| I-262 | 8.6 | 144 |
| I-263 | 8.6 | 150 |
| I-264 | 8.5 | 142 |
| I-265 | 8.4 | 146 |
| I-266 | 8.6 | 139 |
| I-267 | 8.6 | 146 |
| I-268 | 8.6 | 146 |
| I-269 | 8.5 | 137 |
| I-270 | 8.7 | 150 |
| I-271 | 8.6 | 132 |
| I-272 | 8.4 | 132 |
| I-273 | 8.4 | 132 |
| I-274 | 8.8 | 150 |
| I-275 | 8.8 | 140 |
| I-276 | 8.2 | 124 |
| I-277 | 8.1 | 106 |
| I-278 | 7.7 | 96 |
| I-279 | 7.2 | 112 |
| I-280 | 7.3 | 115 |
| I-281 | 7.4 | 104 |
| I-282 | 7.4 | 100 |
| I-283 | 7 | 114 |
| I-284 | 9 | 116 |
| I-285 | 8.9 | 116 |
| I-286 | 8.7 | 130 |
| I-287 | 9.2 | 134 |
| I-288 | 8 | 188 |
| I-289 | 6.9 | 70 |
| I-290 | >4.5 | — |
| I-291 | 6.1 | 120 |
| I-292 | 6.5 | 120 |
| I-293 | >4.5 | — |
| I-294 | 8.2 | 82 |
| I-295 | 8.2 | 98 |
| I-296 | 7.6 | 90 |
| I-297 | 9 | 77 |
| I-298 | 7.9 | 133 |
| I-299 | 8 | 112 |
| I-300 | 1 | 82 |
| I-301 | 8.2 | 89 |
| I-302 | 8.4 | 106 |
| I-303 | 7.4 | 132 |
| I-304 | 6.6 | 118 |
| I-305 | 7.5 | 121 |
| I-306 | 8.2 | 171 |
| I-307 | 7.4 | 154 |
| I-308 | 7.6 | 150 |
| I-309 | 8.2 | 157 |
| I-310 | 7.6 | 155 |
| I-311 | 7.8 | 148 |
| I-312 | 7 | 149 |
| I-313 | 7 | 140 |
| I-314 | 8.4 | 145 |
| I-315 | 7.4 | 157 |
| I-316 | 7.6 | 152 |

TABLE 23-continued

FXR activity of compounds of the present invention in the FXR ligand binding assay.

| Cmpd No. | $pEC_{50}$ | % Efficacy |
|---|---|---|
| I-317 | 6.7 | 131 |
| I-318 | 7.2 | 127 |
| I-319 | 7.4 | 118 |
| I-320 | 7.5 | 114 |
| I-321 | 7.6 | 146 |
| I-322 | 7.4 | 132 |
| I-323 | 6.4 | 103 |
| I-324 | 7.1 | 140 |
| I-325 | 6.6 | 104 |
| I-326 | 7.1 | 132 |
| I-327 | >5.5 | — |
| I-328 | 6.9 | 87 |
| I-329 | 9 | 162 |
| I-330 | 8.8 | 156 |
| I-331 | 8.7 | 180 |
| I-332 | 8.8 | 150 |
| I-333 | 8.8 | 158 |
| I-334 | 9 | 180 |
| I-335 | 8.8 | 172 |
| I-336 | 8.6 | 182 |
| I-337 | 8.6 | 174 |
| I-338 | 8.9 | 158 |
| I-339 | 8.6 | 198 |
| I-340 | 8.8 | 182 |
| I-341 | 8.7 | 164 |
| I-342 | 8.6 | 139 |
| I-343 | 9 | 176 |
| I-344 | 8.4 | 203 |
| I-345 | 8.6 | 203 |
| I-346 | 8.2 | 188 |
| I-347 | 8.5 | 203 |
| I-348 | 8 | 171 |
| I-349 | 8.2 | 171 |
| I-350 | 8.1 | 170 |
| I-351 | 7.6 | 132 |
| I-352 | 8 | 154 |
| I-353 | 8.3 | 159 |
| I-354 | 8.1 | 138 |
| I-355 | 7.9 | 157 |
| I-356 | 8.6 | 168 |
| I-357 | 8.4 | 166 |
| I-358 | 8 | 155 |
| I-359 | 8.4 | 148 |
| I-360 | 8.6 | 117 |
| I-361 | 6 | 52 |
| I-362 | 7.2 | 72 |
| I-363 | 7.1 | 61 |
| I-364 | 6.3 | 47 |
| I-365 | 6.4 | 67 |
| I-366 | 6.2 | 56 |
| I-367 | 6.4 | 61 |
| I-368 | 5.8 | 22 |
| I-369 | 6.8 | 50 |
| I-370 | 4.5 | 79 |
| I-371 | 6.7 | 57 |
| I-372 | 6.1 | 22 |
| I-373 | 7.2 | 62 |
| I-374 | 6 | 48 |

Example 278: Cell-Based Assay of FXR Activation

FXR activation was measured using a cell line and procedure obtained from Life Technologies (Cat # K1691). FXR-UAS-bla HEK 293T cells contain a human Farnesoid X receptor ligand-binding domain/Gal4 DNA binding domain chimera stably integrated into the CellSensor® UAS-bla HEK 293T cell line. The CellSensor® UAS-bla HEK 293T contains a beta-lactamase reporter gene under control of a UAS response element stably integrated into HEK 293T cells. Activation of FXR by bound ligands results in transcriptional activation of the beta-lactamase reporter gene, which is detected via assay of beta-lactamase activity.

Cells are harvested and diluted into assay medium containing phenol red-free DMEM supplemented with 2% Charcoal-stripped FBS, pyruvate, non-essential amino acids. Cells are then transferred to a 384 well assay plate. Test compounds are dissolved in DMSO and a 3-fold serial dilution series is generated, then further diluted into assay medium. Compounds in assay medium are added to cells in the 384 well plate and allowed to incubate 16 h at 37 C in the presence of 5% $CO_2$.

Following incubation, FXR activity is detected via measurement of beta-lactamase that is produced under its transcriptional control. A FRET-based beta-lactamase (CCF4) is loaded into cells as its acetomethoxy ester. Intracellular esterases liberate free CCF4, a cephalosporin core linking 7-hydroxycoumarin to fluorescein. In the presence of beta-lactamase activity produced in the presence of FXR agonists, cleavage of CCF4 spatially separates the two dyes and disrupts FRET, so that exciting the coumarin at 409 nm now produces a blue fluorescence signal at 447 nm. The change in FRET signal is plotted against the test compound concentration and fit to a 3-parameter logistical equation. The concentration required to produce 50% activation is expressed as $pEC_{50}$ ($-\log EC_{50}$), and the extent of activation is expressed relative to GW4064 as % activation. The data for the compounds of the invention in the cell-based assay are shown in Table 24.

TABLE 24

The activity of compounds of the present invention in the cellular FXR beta-lactamase reporter assay.

| Cmpd No. | $pEC_{50}$ | % Efficacy |
|---|---|---|
| I-1 | 8 | 126 |
| I-2 | 8 | 120 |
| I-3 | 8.3 | 123 |
| I-4 | 8.5 | 112 |
| I-5 | 7.4 | 102 |
| I-6 | 8.4 | 112 |
| I-7 | 8.3 | 119 |
| I-8 | 8.6 | 106 |
| I-9 | 8.3 | 107 |
| I-10 | 7.6 | 111 |
| I-11 | 6.6 | 28 |
| I-12 | 10 | 122 |
| I-13 | 9.8 | 116 |
| I-14 | 10 | 111 |
| I-15 | 9.6 | 104 |
| I-16 | 10.4 | 109 |
| I-17 | 10.0 | 102 |
| I-18 | 10.0 | 109 |
| I-19 | 8.7 | 114 |
| I-20 | 9.2 | 113 |
| I-21 | 7.1 | 110 |
| I-22 | 6.9 | 113 |
| I-23 | 6.2 | 100 |
| I-24 | 9.2 | 102 |
| I-25 | 9.4 | 102 |
| I-26 | 7.6 | 106 |
| I-27 | 8.7 | 94 |
| I-28 | 8.7 | 122 |
| I-29 | 8.8 | 118 |
| I-30 | 8.6 | 114 |
| I-31 | 6.8 | 115 |
| I-32 | 6.9 | 110 |
| I-33 | 6.9 | 112 |
| I-34 | 6.4 | 15 |
| I-35 | 6.2 | 19 |
| I-36 | 5.2 | 50 |
| I-37 | 5.8 | 82 |
| I-38 | 6.7 | 96 |

TABLE 24-continued

The activity of compounds of the present invention in the cellular FXR beta-lactamase reporter assay.

| Cmpd No. | $pEC_{50}$ | % Efficacy |
|---|---|---|
| I-39 | 7.3 | 105 |
| I-40 | >4.5 | — |
| I-41 | 5.6 | 40 |
| I-42 | 7.4 | 110 |
| I-43 | 8.2 | 124 |
| I-44 | 8 | 107 |
| I-45 | 7.6 | 107 |
| I-46 | 7.9 | 110 |
| I-47 | 7.8 | 106 |
| I-48 | 8.2 | 119 |
| I-49 | 8.4 | 118 |
| I-50 | 7.8 | 109 |
| I-51 | 7.7 | 104 |
| I-52 | 9 | 111 |
| I-53 | 9.4 | 113 |
| I-54a | 7.5 | 112 |
| I-54 | 9.5 | 101 |
| I-55 | 8.5 | 104 |
| I-56 | 8.7 | 125 |
| I-57 | 9.0 | 109 |
| I-58 | 9.3 | 104 |
| I-59 | 10 | 103 |
| I-60 | 9.7 | 105 |
| I-61 | 10.2 | 106 |
| I-62 | 9.8 | 112 |
| I-63 | >4.5 | — |
| I-64 | 6.3 | 55 |
| I-65 | 7 | 52 |
| I-101 | 9 | 113 |
| I-102 | 9.1 | 106 |
| I-103 | 9.1 | 103 |
| I-104 | 8.5 | 104 |
| I-105 | 8.9 | 112 |
| I-106 | 9.2 | 106 |
| I-107 | 9 | 102 |
| I-108 | 8.4 | 101 |
| I-109 | 8.8 | 100 |
| I-110 | 9 | 111 |
| I-111 | 8.9 | 100 |
| I-112 | 8.3 | 100 |
| I-113 | 9.1 | 101 |
| I-114 | 8.6 | 103 |
| I-115 | 8.7 | 108 |
| I-116 | 8.4 | 102 |
| I-117 | 8.1 | 100 |
| I-118 | 8.1 | 108 |
| I-119 | 9.2 | 104 |
| I-120 | 8.7 | 112 |
| I-121 | 8.9 | 107 |
| I-122 | 8.8 | 102 |
| I-123 | 9.3 | 99 |
| I-124 | 8.4 | 105 |
| I-125 | 6.6 | 106 |
| I-126 | 7.4 | 106 |
| I-127 | 8.6 | 104 |
| I-128 | 8 | 93 |
| I-129 | 8.4 | 101 |
| I-130 | 8.1 | 99 |
| I-131 | 7.5 | 94 |
| I-132 | >6.5 | — |
| I-133 | >7.4 | 106 |
| I-134 | 9.1 | 104 |
| I-135 | 9 | 102 |
| I-136 | 8.4 | 114 |
| I-137 | 8 | 106 |
| I-138 | 7.8 | 106 |
| I-13 | 8.6 | 112 |
| I-140 | 7.7 | 121 |
| I-141 | 7.2 | 106 |
| I-142 | 7.7 | 104 |
| I-143 | 9 | 105 |
| I-144 | >7.5 | — |
| I-145 | 7.2 | 108 |
| I-146 | 8.1 | 101 |

TABLE 24-continued

The activity of compounds of the present invention in the cellular FXR beta-lactamase reporter assay.

| Cmpd No. | $pEC_{50}$ | % Efficacy |
|---|---|---|
| I-147 | 9.2 | 112 |
| I-148 | 7.7 | 117 |
| I-149 | 7.2 | 101 |
| I-150 | 7.6 | 96 |
| I-151 | 7.6 | 106 |
| I-152 | 8.3 | 105 |
| I-153 | 8 | 100 |
| I-154 | 9.3 | 105 |
| I-155 | 9 | 102 |
| I-156 | 7.4 | 105 |
| I-157 | 8.6 | 100 |
| I-158 | 8.2 | 104 |
| I-159 | 8.8 | 100 |
| I-160 | 6 | 110 |
| I-161 | 7.9 | 102 |
| I-162 | 8.2 | 105 |
| I-163 | 8.9 | 99 |
| I-164 | 7.1 | 118 |
| I-165 | 7.7 | 107 |
| I-166 | 7.3 | 114 |
| I-167 | 8.1 | 106 |
| I-168 | 7 | 107 |
| I-169 | 8.8 | 106 |
| I-170 | 8.9 | 103 |
| I-171 | 9.1 | 104 |
| I-172 | 9 | 110 |
| I-173 | 7 | 114 |
| I-174 | 6.6 | 152 |
| I-175 | 6.2 | 101 |
| I-176 | 6.2 | 92 |
| I-177 | 7.9 | 109 |
| I-178 | 6.8 | 70 |
| I-179 | >7.5 | — |
| I-180 | >6.5 | — |
| I-181 | 10.2 | 110 |
| I-182 | 9.8 | 106 |
| I-183 | 10 | 119 |
| I-184 | 8.5 | 108 |
| I-185 | 10 | 105 |
| I-186 | 9.8 | 107 |
| I-187 | 8 | 104 |
| I-188 | 8.2 | 100 |
| I-18 | 9.7 | 100 |
| I-190 | 10.2 | 113 |
| I-191 | 10.4 | 111 |
| I-192 | 9.7 | 106 |
| I-193 | 8.8 | 114 |
| I-194 | 9.7 | 104 |
| I-195 | 9.5 | 109 |
| I-196 | 9.1 | 110 |
| I-197 | 9.3 | 111 |
| I-198 | 9.3 | 112 |
| I-199 | 8 | 110 |
| I-200 | 9.6 | 110 |
| I-201 | 9.8 | 115 |
| I-202 | 9.4 | 114 |
| I-203 | 9.8 | 102 |
| I-204 | 8.6 | 104 |
| I-205 | 8 | 104 |
| I-206 | 8.8 | 104 |
| I-207 | 8.4 | 104 |
| I-208 | 8.3 | 104 |
| I-209 | 7.8 | 104 |
| I-210 | >7.5 | — |
| I-211 | 9 | 105 |
| I-212 | 8.6 | 107 |
| I-213 | >7.5 | — |
| I-214 | 8.6 | 105 |
| I-215 | 8.8 | 107 |
| I-216 | 9.4 | 112 |
| I-217 | 9 | 111 |
| I-218 | 8.3 | 101 |
| I-219 | 7.4 | 104 |
| I-220 | 9.6 | 108 |

TABLE 24-continued

The activity of compounds of the present invention in the cellular FXR beta-lactamase reporter assay.

| Cmpd No. | $pEC_{50}$ | % Efficacy |
|---|---|---|
| I-221 | 9.5 | 108 |
| I-222 | 7.7 | 114 |
| I-223 | >7.5 | — |
| I-224 | 8.6 | 104 |
| I-225 | 8.7 | 103 |
| I-226 | 6.6 | 152 |
| I-227 | 9 | 97 |
| I-228 | 7.7 | 105 |
| I-229 | 7.4 | 101 |
| I-230 | 8.2 | 104 |
| I-231 | 7.8 | 106 |
| I-232 | 7.6 | 93 |
| I-233 | >7.5 | — |
| I-234 | 8.8 | 102 |
| I-235 | 8.4 | 94 |
| I-236 | 8.6 | 95 |
| I-237 | 8.6 | 94 |
| I-238 | 8.6 | 95 |
| I-239 | 8.1 | 94 |
| I-240 | 8.2 | 92 |
| I-241 | 8 | 98 |
| I-242 | 8 | 97 |
| I-243 | 8.2 | 98 |
| I-244 | 8.7 | 102 |
| I-245 | >7.5 | 0.0 |
| I-246 | 9.6 | 113 |
| I-247 | 8.7 | 114 |
| I-248 | 9.2 | 112 |
| I-249 | 9.8 | 114 |
| I-250 | 9.3 | 114 |
| I-251 | 9.7 | 110 |
| I-252 | 9.7 | 107 |
| I-253 | 9.8 | 107 |
| I-254 | 9.5 | 106 |
| I-255 | 9.3 | 104 |
| I-256 | 9.7 | 107 |
| I-257 | 10 | 108 |
| I-258 | 9.9 | 106 |
| I-259 | 10 | 114 |
| I-260 | 9.4 | 103 |
| I-261 | 9.4 | 110 |
| I-262 | 8.7 | 114 |
| I-263 | 10 | 109 |
| I-264 | 9.2 | 105 |
| I-265 | 9.3 | 110 |
| I-266 | 9.6 | 105 |
| I-267 | 9 | 102 |
| I-268 | 8.8 | 102 |
| I-269 | 9.2 | 106 |
| I-270 | 10 | 106 |
| I-271 | 9.4 | 108 |
| I-272 | 9.3 | 105 |
| I-273 | 9.4 | 106 |
| I-274 | 9.2 | 100 |
| I-275 | 9.2 | 106 |
| I-276 | 8.4 | 114 |
| I-277 | 6.8 | 123 |
| I-278 | 8 | 98 |
| I-279 | 7.4 | 104 |
| I-280 | 7.6 | 105 |
| I-281 | 7.8 | 105 |
| I-282 | 7.6 | 117 |
| I-283 | 7.6 | 104 |
| I-284 | 8.5 | 100 |
| I-285 | 8.6 | 100 |
| I-286 | 7.4 | 108 |
| I-287 | 7.2 | 113 |
| I-288 | 8.4 | 112 |
| I-289 | >7.5 | — |
| I-290 | >7.5 | — |
| I-291 | >7.5 | — |
| I-292 | >7.5 | — |
| I-293 | >7.5 | — |
| I-294 | 8.6 | 104 |

TABLE 24-continued

The activity of compounds of the present invention in the cellular FXR beta-lactamase reporter assay.

| Cmpd No. | $pEC_{50}$ | % Efficacy |
|---|---|---|
| I-295 | 9 | 105 |
| I-296 | 8 | 109 |
| I-297 | 9.5 | 110 |
| I-298 | 8.1 | 112 |
| I-299 | 8.4 | 108 |
| I-300 | 7 | 117 |
| I-301 | 7.4 | 96 |
| I-302 | 7.4 | 114 |
| I-303 | 8.2 | 98 |
| I-304 | 7 | 107 |
| I-305 | 8.5 | 98 |
| I-306 | 8.6 | 108 |
| I-307 | 8 | 110 |
| I-308 | 8.4 | 99 |
| I-309 | 8.8 | 104 |
| I-310 | 8.1 | 115 |
| I-311 | 8.4 | 105 |
| I-312 | 7.7 | 134 |
| I-313 | 7.6 | 112 |
| I-314 | 8.6 | 103 |
| I-315 | 7.6 | 106 |
| I-316 | 8.1 | 109 |
| I-317 | 7 | 126 |
| I-318 | 8.2 | 116 |
| I-319 | 8 | 113 |
| I-320 | 7.7 | 110 |
| I-329 | 9.1 | 117 |
| I-330 | 9.8 | 120 |
| I-331 | 9.5 | 107 |
| I-332 | 9.5 | 100 |
| I-333 | 9.3 | 112 |
| I-334 | 9 | 104 |
| I-335 | 9 | 108 |
| I-336 | 8.6 | 125 |
| I-337 | 8.7 | 110 |
| I-338 | 7.8 | 106 |
| I-339 | 8.3 | 118 |
| I-340 | 8.1 | 110 |
| I-341 | 8 | 109 |
| I-342 | 7.5 | 125 |
| I-343 | 10 | 105 |
| I-344 | 8.8 | 132 |
| I-345 | 8.4 | 121 |
| I-346 | 9.1 | 133 |
| I-347 | 9 | 135 |
| I-358 | 6.2 | 124 |
| I-359 | 6.4 | 126 |
| I-360 | 9.1 | 102 |

Example 279: Restoration of Epithelial Barrier Integrity in Colitis

Colonic histopathology was assessed in mice administered dextran sodium sulfate (DSS) to assess the ability of selected example compounds to restore epithelial barrier integrity in a model of colitis presenting with epithelial erosions. Approximately seven-week old, female, C57Bl/6 mice were purchased from Envigo (Livermore, Calif.), were housed 6 per cage and acclimated for at least 2 weeks before study initiation. Animals were fed standard laboratory rodent chow Harlan Teklad Global 2018 (Maddison, Wis.). Mice had ad libitum access to food and water for the duration of the study and were maintained in a temperature and humidity controlled room on a standard light/dark cycle of 6 AM to 6 PM. DSS was prepared at 1.5% (MW 35-50 kDa, Lot # M7191, MP Biomedical) in filtered drinking water and provided to the mice from Day 0 to Day 7 (n=12/group). The DSS water was replaced once during the study on Day 3 or 4 with fresh DSS water. One cohort of mice (n=6) was provided drinking water without DSS and severed as the non-diseased control group. Vehicle (1% methylcellulose in water, 10 mL/kg) or varying doses of test compound were administered once daily by oral gavage beginning on Day −3 through Day 8. FXR agonist compounds of the invention, FXR1 and FXR2, were tested at doses of 0.3 and 1 mg/kg and compared to known FXR agonist obeticholic acid (OCA) administered at 30 mg/kg. Body weight and food and water intake were measured daily from the initiation of DSS administration. Disease activity index (DAI) scoring was performed on Day 9 prior to necropsy. Stool consistency, blood in stool, incidence of rectal prolapse, and body condition was assessed according to the scoring system in Table 25 and summed to a total DAI score:

TABLE 25

DAI scoring criteria

| Stool score | Stool blood score | Rectal prolapse | Body condition |
|---|---|---|---|
| 0 Normal | 0 No blood | 0 Negative | 0 Normal |
| 1 Moist/ sticky stool | 1 Evidence of blood in stool or around anus | 1 Positive | 1 Ruffled fur or altered gait |
| 2 Soft stool | 2 Severe bleeding | | 2 Lethargic or moribund |
| 3 Diarrhea | | | |

Following DAI scoring on Day 9 and under isoflurane anesthesia mice were exsanguinated via cardiac puncture and euthanized by thoracotomy, followed by cervical dislocation. The entire colon (from the cecum to the anus) was removed, and the length recorded. The luminal contents were removed by flushing with ice-cold PBS using a blunt needle attached to a syringe and the colon was blotted dry and weighed. For each treatment group, half of the distal colon samples were prepared for cytokine analysis and half were prepared for histological evaluation. For cytokine measurement, the distal ⅓ of the colon was excised and weighed, placed into 5 mL Eppendorf tubes, frozen on dry ice and stored at −80° C., until analysis. Inflammatory cytokines were measured in colon tissue using a V-Plex custom kit (Proinflammatory Panel 1 (mouse), Mesoscale Technology). For histology, the colon was rolled by grasping the distal end and rotating to generate a spiral with a third dimension. The colon was then placed in a tissue cassette, and into a jar of 10/o buffered formalin phosphate at room temperature for at least 24 hours to ensure tissue fixation, at which point the formalin was replaced with 70% ethanol. The tissue was processed in paraffin, sectioned in cross-section (5 μm) and stained with hematoxylin and eosin (H&E) stain. A blinded, board-certified Veterinary pathologist, graded the severity of colitis according to the criteria described in Table 26. Three levels of the distal colon were assigned a colitis score and the average colitis score for each animal was derived by summing the colitis scores for the three levels of colon evaluated and dividing the sum by three. The average colitis score for each treatment group was derived by summing the colitis scores for all levels of colon evaluated in the group and dividing the sum by the total number of levels of colon evaluated for that group. The presence or absence of mucosal defects (erosions or ulcerations) was also recorded for each level of colon. Statistical analysis was performed on continuous variables by one-way analysis of variance (ANOVA) with post-hoc multiple comparison with Dunnetts correction to compare all groups to DSS colitis mice treated with vehicle control. Statistical analysis was performed on ordinal variables using a Fisher's Exact Test. A $p<0.05$ was considered statistically significant.

TABLE 26

| Histological colitis grading criteria |
|---|
| 0 = Within Normal Limits |
| 1 = focal to multifocal (segmental) infiltrates in mucosa, no to minimal epithelial changes |
| 2 = coalescing infiltrates in mucosa, some loss of goblet cells but mucosal architecture generally intact; mild to moderate inflammatory infiltrates with/without occasional multinucleate giant cells |
| 3 = mucosa diffusely expanded by severe inflammatory cell infiltrates, limited inflammation in submucosa, crypt atrophy + loss of goblet cells, limited effacement of architecture; mild edema may be present; with/without multinucleate giant cells |
| 4 = severe inflammation: may expand into muscularis; severe edema may be present; loss of goblet cells; crypt abnormalities such as branching may be present; significant architectural effacement |

Figure 2:
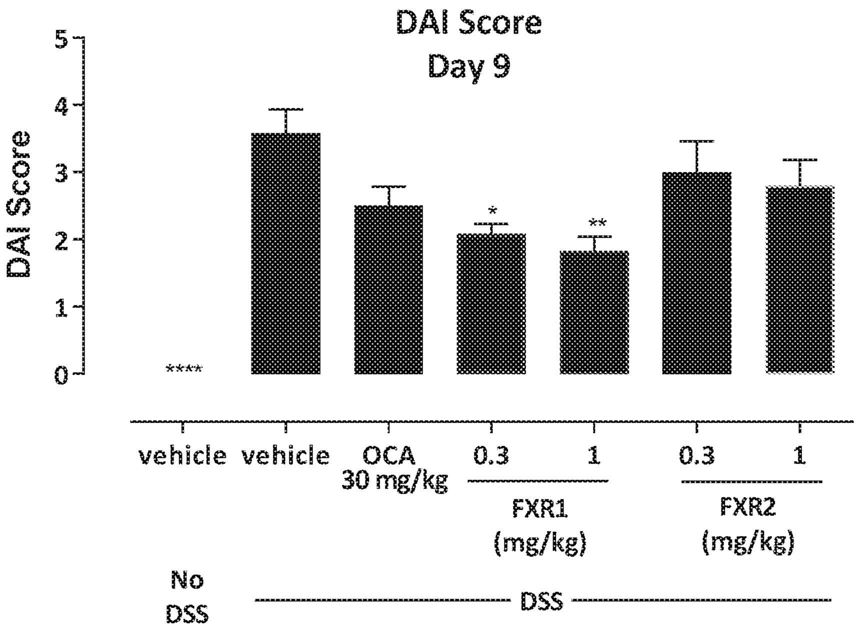
FIG. 2: DAI score measured on Day 9 immediately prior to terminal necropsy. DSS significantly increased DAI score compared to no DSS control mice. FXR1 significantly attenuated the DSS-induced increase in DAI score at both 0.3 and 1 mg/kg
Figure 3:
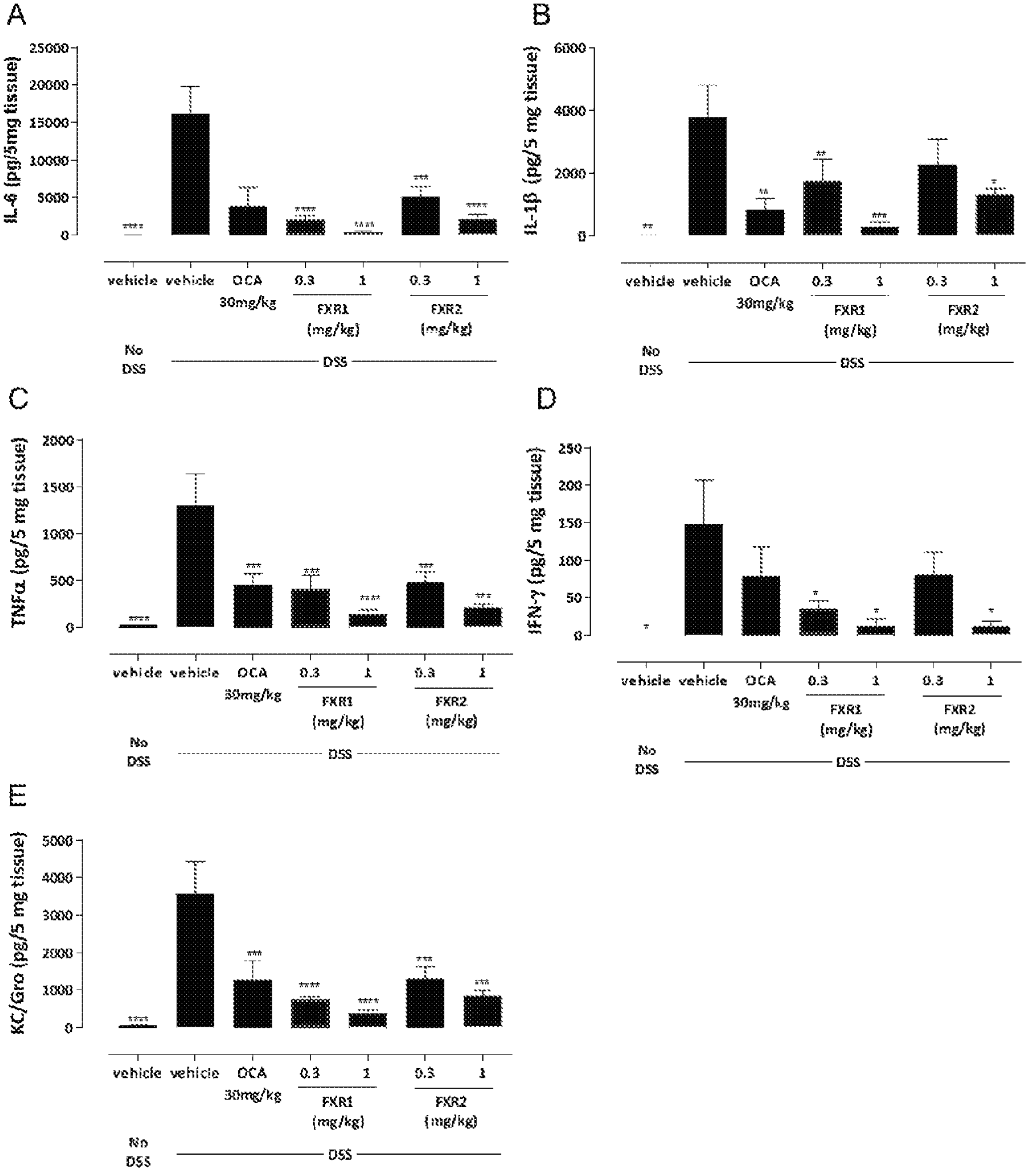
FIG. 3: Pro-inflammatory cytokine measurements in the colon on Day 9. DSS administration significantly increased the content of inflammatory cytokines IL-6 (FIG. 3*a*), IL-1β (FIG. 3*b*), TNFα (FIG. 3*c*), IFNγ (FIG. 3*d*) and KC/Gro (FIG. 3*e*) in the colon compared to no DSS control mice. FXR agonist compounds of the invention, FXR1 and FXR2, significantly reduced the levels of all of these pro-inflammatory cytokines in the colon of DSS mice at 1 mg/kg.
Figure 4:
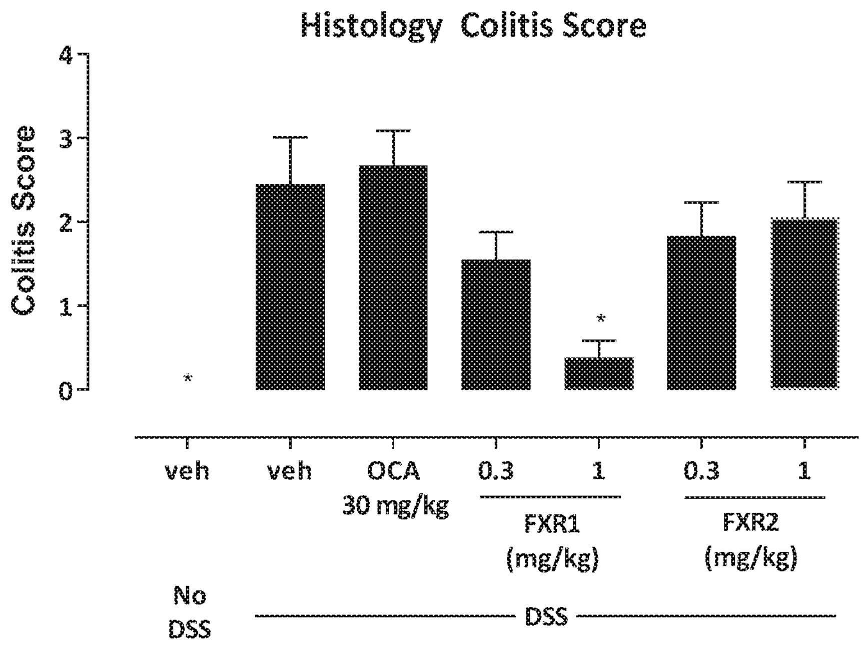
FIG. 4: Histology colitis score on Day 9. Histology colitis score was significantly increased by DSS administration compared to no DSS control mice which significantly reduced by FXR1 at 1 mg/kg.
Figure 5:
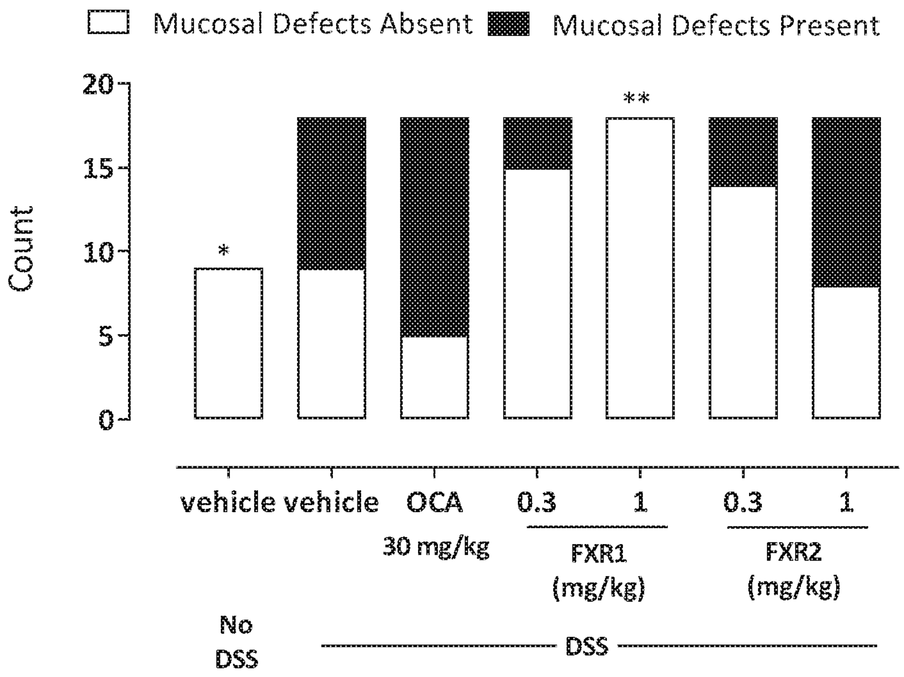
FIG. 5: The histological presence of epithelial erosions in the colon on Day 9. DSS administration significantly increased the presence of epithelial erosions (mucosal defects) observed histologically which was significantly prevented by FXR1 at 1 mg/kg.

DSS administration significantly decreased body weight (FIG. 1) and significantly increased DAI score (FIG. 2) compared to no DSS control mice. Only FXR1 significantly attenuated the DSS-induced reduction in body weight at 1 mg/kg (FIG. 1) and significantly attenuated the DSS-induced increase in DAI score at both 0.3 and 1 mg/kg (FIG. 2). Known FXR agonist OCA did not significantly affect body weight nor DAI score. DSS administration significantly increased the content of inflammatory cytokines IL-6 (FIG. 3*a*), IL-1β (FIG. 3*b*), TNFα (FIG. 3*c*), IFNγ (FIG. 3*d*) and KC/Gro (FIG. 3*e*) in the colon compared to no DSS control mice. FXR1 and FXR2 significantly reduced the levels of all of these pro-inflammatory cytokines in the colon of DSS mice at 1 mg/kg, with FXR1 also significantly reducing the levels of all of these cytokines at 0.3 mg/kg. Whereas known FXR agonist OCA only significantly reduced the levels of IL-1β, TNFα and KC/Gro at 30 mg/kg. (FIG. 3). Histology colitis score was significantly increased by DSS administration compared to no DSS control mice (FIG. 4). Only FXR1 at 1 mg/kg significantly reduced histology colitis score in DSS mice (FIG. 4). Known FXR agonist OCA did not significantly affect histology colitis score (FIG. 4). DSS administration significantly increased the presence of epithelial erosions (mucosal defects) observed histologically (FIG. 5). Only FXR1 at 1 mg/kg significantly prevented the development of epithelial erosions in DSS mice (FIG. 5). Known FXR agonist OCA did not reduce the number of epithelial erosions observed in DSS mice. FXR1 was unique in its effect to attenuate body weight loss, reduce DAI severity and provide histological protection to the colon including the prevention of DSS-induced epithelial erosions

Figure 6:
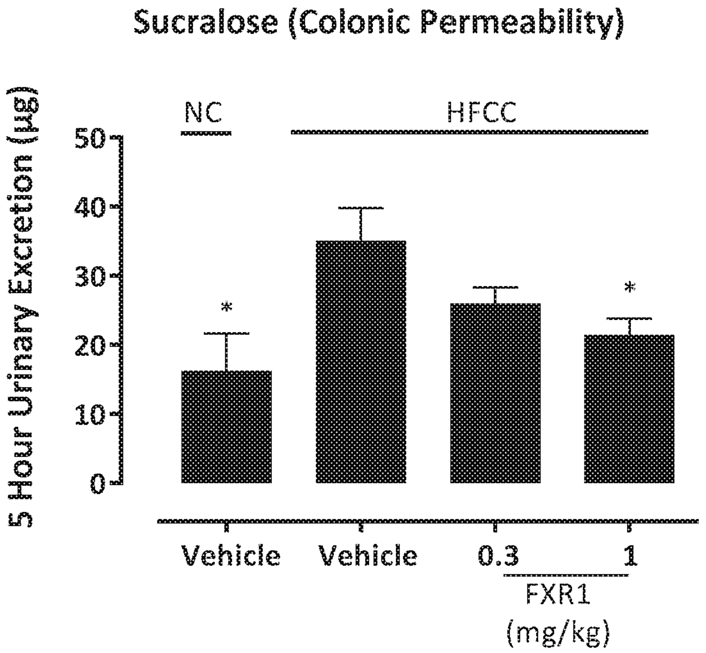
FIG. 6: Urinary sucralose excretion as a marker of colonic permeability in HFCC mice. Colonic permeability was increased in HFCC fed mice, compared to NC control mice as indicated by a significant increase in urinary sucralose excretion. FXR1 dose-dependently normalized urinary sucralose excretion in HFCC fed mice, indicating restoration of colonic permeability.

Example 280: Restoration of Colonic Permeability in High Fat, High Cholesterol and High Carbohydrate Fed Mice Urinary excretion of an oral bolus of sucralose was measured as a marker of colonic permeability in mice acclimated to a high fat, high cholesterol, high carbohydrate (HFCC) diet to assess the ability of selected example compounds to restore colonic permeability in vivo. Urinary excretion of an oral bolus of sucralose has been established as a method to assess colonic permeability in vivo and mouse models of obesity created by the administration of high fat diets have been shown to demonstrate increased colonic permeability (Bischoff et al. BMC Gastroenterology 2014, 14:189). Approximately five-week old, male, C57Bl/6 mice purchased from Taconic (Albany, N.Y.), were housed 5 per cage and acclimated for at least 48 hours before study initiation. Animals were then acclimated to a high fat, high cholesterol, high carbohydrate diet (HFCC) containing 20% protein, 43% carbohydrate, and 23% fat (6.6% trans-fat) (TD.130885, TEKLAD Diets) and were provided drinking water containing 55:45 fructose:dextrose, 42 g/L) for 18-weeks. Mice had ad libitum access to food and water for the duration of the study and were maintained in a temperature and humidity controlled room on a standard light/dark cycle of 6 AM to 6 PM. C57Bl/6 male mice ($n=5$) fed standard rodent diet (NC) (2018, TEKLAD Diets), were used as normal control mice. Vehicle (2.5% HPCD/0.1% Tween 80+HCl, 10 mL/kg) or varying doses of test compound were administered once daily by oral gavage following the 18-week acclimation period for 3-weeks ($n=10$/group). FXR1 was tested at doses of 0.3 and 1 mg/kg. Following 3-weeks of treatment, each mouse was administered a 200 μL oral bolus containing 0.45 mg of sucralose in distilled water. Immediately following the sucralose bolus, mice were given a subcutaneous injection of 2 mL of sterile saline to increase urine volume. Mice were then placed individually in metabolic cages with free access to food and water. Urine was collected for 5-hours following the oral sucralose bolus and urine volume was measured and recorded. Urinary sucralose concentration was then quantified by liquid chromatography/mass spectrometry (LC/MS). Urinary sucralose excretion (μg) was calculated as urine sucralose concentration (μg/mL) multiplied by 5-hour urine volume (mL). Statistical analysis was performed by one-way analysis of variance (ANOVA) with post-hoc multiple comparison with Dunnetts correction to compare all groups to HFCC mice treated with vehicle control. A $p<0.05$ was considered statistically significant. Colonic permeability was increased in HFCC fed mice, compared to NC control mice as indicated by a significant increase in urinary sucralose excretion (FIG. 6). FXR1 dose-dependently normalized urinary sucralose excretion in HFCC fed mice, indicating restoration of colonic permeability (FIG. 6).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:
1. A compound of Formula (Ix):
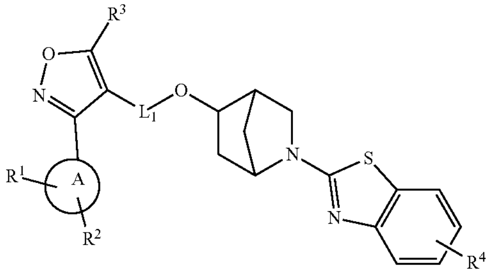
or a salt thereof,
wherein:
$L_1$ is —$(CH_2)_p$— and p is 1;
A is phenyl;
$R^1$ and $R^2$ are both a Cl;
$R^3$ is cyclopropyl;
$R^4$ is $COOR^{6a}$; and
$R^{6a}$ is H.
* * * * *